US012133852B2

(12) United States Patent
Nakache et al.

(10) Patent No.: US 12,133,852 B2
(45) Date of Patent: Nov. 5, 2024

(54) ACSS2 INHIBITORS AND METHODS OF USE THEREOF

(71) Applicant: EpiVario, Inc., Philadelphia, PA (US)

(72) Inventors: Philippe Nakache, Ness Ziona (IL); Omri Erez, Rehovot (IL); Simone Botti, Rehovot (IL); Andreas Goutopoulos, Boston, MA (US)

(73) Assignee: EpiVario, Inc., Philadelphia, PA (US)

( * ) Notice: Subject to any disclaimer, the term of this patent is extended or adjusted under 35 U.S.C. 154(b) by 816 days.

(21) Appl. No.: 17/088,613

(22) Filed: Nov. 4, 2020

(65) Prior Publication Data

US 2022/0305010 A1  Sep. 29, 2022

Related U.S. Application Data

(63) Continuation-in-part of application No. 16/411,168, filed on May 14, 2019, now Pat. No. 10,851,064, which is a continuation-in-part of application No. PCT/IL2018/051232, filed on Nov. 15, 2018, application No. 17/088,613 is a continuation-in-part of application No. PCT/IL2020/050526, filed on May 14, 2020, which is a continuation-in-part of application No. 16/411,168, filed on May 14, 2019, now Pat. No. 10,851,064.

(60) Provisional application No. 62/847,348, filed on May 14, 2019, provisional application No. 62/586,195, filed on Nov. 15, 2017.

(51) Int. Cl.
| | |
|---|---|
| *A61K 31/501* | (2006.01) |
| *A61K 31/4152* | (2006.01) |
| *A61K 31/4155* | (2006.01) |
| *A61K 31/4184* | (2006.01) |
| *A61K 31/422* | (2006.01) |
| *A61K 31/4245* | (2006.01) |
| *A61K 31/4439* | (2006.01) |
| *A61K 31/497* | (2006.01) |
| *A61K 31/498* | (2006.01) |
| *A61K 31/635* | (2006.01) |
| *A61P 35/04* | (2006.01) |

(52) U.S. Cl.
CPC ........ *A61K 31/501* (2013.01); *A61K 31/4152* (2013.01); *A61K 31/4155* (2013.01); *A61K 31/4184* (2013.01); *A61K 31/422* (2013.01); *A61K 31/4245* (2013.01); *A61K 31/4439* (2013.01); *A61K 31/497* (2013.01); *A61K 31/498* (2013.01); *A61K 31/635* (2013.01); *A61P 35/04* (2018.01)

(58) Field of Classification Search
CPC ..... A61P 35/04; A61K 31/498; A61K 31/497; A61K 31/4245; A61K 31/4184; A61K 31/422; A61K 31/501; A61K 31/4152; A61K 31/4155; A61K 31/4439; A61K 31/635
See application file for complete search history.

(56) References Cited

U.S. PATENT DOCUMENTS

| | | | |
|---|---|---|---|
| 3,905,997 A | 9/1975 | Zinnes et al. | |
| 4,207,317 A * | 6/1980 | Walker ................ | C07D 231/26 548/369.7 |
| 2017/0190689 A1 | 7/2017 | Sparks et al. | |

FOREIGN PATENT DOCUMENTS

| | | |
|---|---|---|
| DE | 2324893 A1 | 12/1974 |
| DE | 140966 A1 | 4/1980 |
| JP | H11291635 A | 10/1999 |
| WO | WO 03/013484 A2 | 2/2003 |
| WO | WO 03/024448 A2 | 3/2003 |
| WO | WO 2007/026215 A1 | 3/2007 |
| WO | WO 2011/143425 A2 | 11/2011 |
| WO | WO 2013/159224 A1 | 10/2013 |
| WO | WO 2015/175845 A1 | 11/2015 |
| WO | WO 2019/097515 A1 | 5/2019 |
| WO | WO 2020/230134 A1 | 11/2020 |

OTHER PUBLICATIONS

Björnson et al. "Stratification of hepatocellular carcinoma patients based on acetate utilization" Cell reports. Dec. 1, 2015;13(9):2014-26.
Bulusu et al. "Acetate recapturing by nuclear acetyl-CoA synthetase 2 prevents loss of histone acetylation during oxygen and serum limitation" Cell reports. Jan. 17, 2017;18(3):647-58.
CAS Registry No. 1808705-10-3, CA Index Name: 1H-Pyrazole-4-carboxamide, 1-(4,6-dimethyl-2-pyrimidinyl)-4,5-dihydro-3-methyl-N-[2-(1-methylethyl)phenyl]-5-oxo-, Entered STN: Sep. 30, 2015.
CAS Registry No. 1791350-17-8, CA Index Name: 1H-Pyrazole-4-carboxamide, 1-(2,4-dimethylphenyl)-4,5-dihydro-3-methyl-N-[1-(1-methylethyl)-1H-pyrazol-5-yl]-5-oxo-, Entered STN: Jun. 30, 2015.
CAS Registry No. 1787906-31-3, CA Index Name: 1H-Pyrazole-4-carboxamide, 4,5-dihydro-3-methyl-N-[3-methyl-1-(phenylmethyl)-1H-pyrazol-5-yl]-5-oxo-1-phenyl-, Entered STN: Jun. 25, 2015.
CAS Registry No. 1444619-19-5, CA Index Name: 1H-Pyrazole-4-carboxamide, 1-(4-fluorophenyl)-4,5-dihydro-3-methyl-5-oxo-N-(tetrahydro-1,1-dioxido-3-thienyl)-, Entered STN: Jul. 16, 2013.

(Continued)

*Primary Examiner* — Erich A Leeser
(74) *Attorney, Agent, or Firm* — Meunier Carlin & Curfman LLC

(57) ABSTRACT

The present invention relates to novel ACSS2 inhibitors having activity as anti-cancer therapy, treatment of alcoholism, and viral infection (e.g., CMV), composition and methods of preparation thereof, and uses thereof for treating viral infection, alcoholism, alcoholic steatohepatitis (ASH), non-alcoholic steatohepatitis (NASH), obesity/weight gain, anxiety, depression, post-traumatic stress disorder, inflammatory/autoimmune conditions and cancer, including metastatic cancer, advanced cancer, and drug resistant cancer of various types.

17 Claims, 5 Drawing Sheets

(56) References Cited

OTHER PUBLICATIONS

CAS Registry No. 1444612-86-5, CA Index Name: 1H-Pyrazole-4-carboxamide, 1-(3-chlorophenyl)-4,5-dihydro-3-methyl-5-oxo-N-(tetrahydro-1,1-dioxido-3-thienyl)-, Entered STN: Jun. 16, 2013.
CAS Registry No. 1444608-50-7, CA Index Name: 1H-Pyrazole-4-carboxamide, 1-(2,4-dimethylphenyl)-4,5-dihydro-3-methyl-5-oxo-N-(tetrahydro-1,1-dioxido-3-thienyl)-, Entered STN: Jul. 16, 2013.
CAS Registry No. 1427938-63-3, CA Index Name: 1H-Pyrazole-4-carboxamide, 4,5-dihydro-3-methyl-5-oxo-N-2-pyridinyl-1-(tetrahydro-1,1-dioxido-3-thienyl)-, Entered STN: Apr. 11, 2013.
CAS Registry No. 1424277-15-5, CA Index Name: 1H-Pyrazole-4-carboxamide, 4,5-dihydro-3-methyl-5-oxo-1-(tetrahydro-1,1-dioxido-3-thienyl)-N-2-thiazolyl, Entered STN: Mar. 15, 2013.
CAS Registry No. 1424179-52-1, CA Index Name: 1H-Pyrazole-4-carboxamide, 4,5-dihydro-3-methyl-5-oxo-1-(tetrahydro-1,1-dioxido-3-thienyl)-N-1,3,4-thiadiazol-2-yl, Entered STN: Mar. 15, 2013.
CAS Registry No. 1424083-43-1, CA Index Name: 1H-Pyrazole-4-carboxamide, 4,5-dihydro-3-methyl-5-oxo-N-3-pyridinyl-1-(tetrahydro-1,1-dioxido-3-thienyl), Entered STN: Mar. 15, 2013.
CAS Registry No. 1423725-39-6, CA Index Name: 1H-Pyrazole-4-carboxamide, N-1,3-benzodioxol-5-yl-4,5-dihydro-3-methyl-5-oxo-1-(tetrahydro-1,1-dioxido-3-thienyl)—Entered STN: Mar. 14, 2013.
CAS Registry No. 1423670-51-2, CA Index Name: 1H-Pyrazole-4-carboxamide, 4,5-dihydro-3-methyl-5-oxo-N-phenyl-1-(tetrahydro-1,1-dioxido-3-thienyl), Entered STN: Mar. 14, 2013.
CAS Registry No. 1423624-35-4, CA Index Name: 1H-Pyrazole-4-carboxamide, N-(2-chloro-3-pyridinyl)-4,5-dihydro-3-methyl-5-oxo-1-(tetrahydro-1,1-dioxido-3-thienyl)-, Entered STN: Mar. 14, 2013.
CAS Registry No. 1376380-77-6, CA Index Name: 1H-Pyrazole-4-carboxamide, N-[4-(3-fluorophenyl)-2-thiazolyl]-4,5-dihydro-3-methyl-5-oxo-1-(tetrahydro-1,1-dioxido-3-thienyl)-, Entered STN: Jun. 7, 2012.
CAS Registry No. 1375980-06-5, CA Index Name: 1H-Pyrazole-4-carboxamide, N-(6-ethyl-2-benzothiazolyl)-4,5-dihydro-3-methyl-5-oxo-1-(tetrahydro-1,1-dioxido-3-thienyl)-, Entered STN: Jun. 7, 2012.
CAS Registry No. 483276-32-0, CA Index Name: 1H-Pyrazole-4-carbothioamide, 1-[4-(4-chlorophenyl)-2-thiazolyl]-4,5-dihydro-5-oxo-N,3-diphenyl-, Entered STN: Jan. 30, 2003.
CAS Registry No. 483276-31-9, CA Index Name: 1H-Pyrazole-4-carboxamide, N-(4-chlorophenyl)-1-[4-(4-chlorophenyl)-2-thiazolyl]-4,5-dihydro-5-oxo-3-phenyl-, Entered STN: Jan. 30, 2003.
CAS Registry No. 97635-51-3; CA Index Name: Benzamide, 3-amino-N-[2,5-dihydro-5-oxo-1-(2,4,5-trichlorophenyl)-1H-pyrazol-4-yl]-; Entered STN: Aug. 18, 1985.
Chen et al. "Coordinate regulation of stress signaling and epigenetic events by Acss2 and HIF-2" in cancer cells. PloS one. Dec. 27, 2017;12(12):e0190241.
Chen et al. "The acetate/ACSS2 switch regulates HIF-2 stress signaling in the tumor cell microenvironment" PloS one. Feb. 17, 2015;10(2):e0116515.
Chen et al. "TM6SF2 E167K variant, a novel genetic susceptibility variant, contributing to nonalcoholic fatty liver disease" Journal of clinical and translational hepatology. Dec. 28, 2015;3(4):265.
Comerford et al. "Acetate dependence of tumors" Cell. Dec. 18, 2014;159(7):1591-602.
El-Desoky et al. "Utility of isothiocyanates in heterocyclic synthesis" Sulfur Letters. Jan. 1, 2002;25(5):199-205.
Gaffer et al. "Synthesis and antioxidant activity of some new thiazolyl-pyrazolone derivatives" Journal of Heterocyclic Chemistry. Jan. 2017;54(1):331-40.
Gao et al. "Acetate functions as an epigenetic metabolite to promote lipid synthesis under hypoxia. Nature communications" Jun. 30, 2016;7:11960.
Gräff et al. "Histone acetylation: molecular mnemonics on the chromatin" Nature Reviews Neuroscience. Feb. 2013;14(2):97.
Harriman et al. "Acetyl-CoA carboxylase inhibition by ND-630 reduces hepatic steatosis, improves insulin sensitivity, and modulates dyslipidemia in rats" Proceedings of the National Academy of Sciences. Mar. 29, 2016;113(13):E1796-805.
Hosios et al. "Acetate metabolism in cancer cells" Cancer & metabolism. Dec. 2014;2(1):27.
Huang et al. "ACSS2 promotes systemic fat storage and utilization through selective regulation of genes involved in lipid metabolism" Proceedings of the National Academy of Sciences. Oct. 2, 2018;115(40):E9499-506.
International Search Report for PCT Application No. PCT/IL2018/051232 dated Jan. 30, 2019.
International Search Report for PCT Application No. PCT/IL2020/050524 dated May 14, 2020.
Kamphorst et al. "Quantitative analysis of acetyl-CoA production in hypoxic cancer cells reveals substantial contribution from acetate" Cancer & metabolism. Dec. 2014;2(1):23.
Kort, M. E., Atkinson, R. N., Thomas, J. B., Drizin, I., Johnson, M. S., Secrest, M. A., . & Matulenko, M. A. (2010). Subtype-selective Nav1. 8 sodium channel blockers: Identification of potent, orally active nicotinamide derivatives. Bioorganic & medicinal chemistry letters, 20(22), 6812-6815.
Lakhter et al. "Glucose—independent acetate metabolism promotes melanoma cell survival and tumor growth" Journal of Biological Chemistry. Oct. 14, 2016;291(42):21869-79.
Li et al. "Nucleus-translocated ACSS2 promotes gene transcription for lysosomal biogenesis and autophagy" Molecular cell. Jun. 1, 2017;66(5):684-97.
Linchenko et al. "Cyclizations in the reactions of isocyanates with compounds containing active methylene groups in the presence of triethylamine" Russian chemical bulletin. May 2006;55(5):873-8.
Lyssiotis et al. "Acetate fuels the cancer engine. Cell" Dec. 18, 2014;159(7):1492-4.
Márquez et al. "Tricarboxylic Acid Cycle Activity and Remodeling of Glycerophosphocholine Lipids Support Cytokine Induction in Response to Fungal Patterns" Cell reports. Apr. 9, 2019;27(2):525-36.
Marzouk et al. "Synthesis and characterization of novel pyrazolone derivatives" European Journal of Chemistry. Mar. 31, 2014;5(1):24-32.
Mashimo et al. "Acetate is a bioenergetic substrate for human glioblastoma and brain metastases" Cell. Dec. 18, 2014;159(7):1603-14.
McKnight SL. "A hypothetical means of treating or preventing cancer" Cancer & metabolism. May 2014;2(1):O7.
Mews et al. "Acetyl-CoA synthetase regulates histone acetylation and hippocampal memory" Nature. Jun. 2017;546(7658):381.
Ribeiro et al. "Possible involvement of ACSS2 gene in alcoholism" Journal of Neural Transmission. Sep. 1, 2017;124(9):1151-8.
Saeed, A., Ejaz, S. A., Khurshid, A., Hassan, S., al-Rashida, M., Latif, M., . . . & Iqbal, J. (2015). Synthesis, characterization and biological evaluation of N-(2, 3-dimethyl-5-oxo- 1-phenyl-2, 5-dihydro-1 H-pyrazol-4-yl) benzamides. RSC advances, 5(105), 86428-86439.
Santeusanio et al. "Divergent approach to thiazolylidene derivatives: a perspective on the synthesis of a heterocyclic skeleton from B-amidothioamides reactivity" The Journal of organic chemistry. Sep. 15, 2017;82(18):9773-8.
Schug et al. "Acetyl-CoA synthetase 2 promotes acetate utilization and maintains cancer cell growth under metabolic stress" Cancer cell. Jan. 12, 2015;27(1):57-71.
Schug et al. "The metabolic fate of acetate in cancer" Nature Reviews Cancer. Nov. 2016;16(11):708.
Vysochan et al. "ACSS2-mediated acetyl-CoA synthesis from acetate is necessary for human cytomegalovirus infection" Proceedings of the National Academy of Sciences. Feb. 21, 2017;114(8):E1528-35.
Wakil et al. "Fatty acid metabolism: target for metabolic syndrome" Journal of lipid research. Apr. 1, 2009;50(Supplement):S138-43.
Yoshii et al. "Cytosolic acetyl-CoA synthetase affected tumor cell survival under hypoxia: the possible function in tumor acetyl-CoA/acetate metabolism" Cancer science. May 2009;100(5):821-7.

(56) References Cited

OTHER PUBLICATIONS

Yoshii et al. "Tumor uptake of radiolabeled acetate reflects the expression of cytosolic acetyl-CoA synthetase: implications for the mechanism of acetate PET" Nuclear medicine and biology. Oct. 1, 2009;36(7):771-7.

Yoshii et al. "Acetate/acetyl-CoA metabolism associated with cancer fatty acid synthesis: overview and application" Cancer letters. Jan. 28, 2015;356(2):211-6.

Yun et al. "The importance of acetyl coenzyme A synthetase for 11C-acetate uptake and cell survival in hepatocellular carcinoma" Journal of nuclear medicine. Aug. 1, 2009;50(8):1222-8.

Zhao et al. "ATP-citrate lyase controls a glucose-to-acetate metabolic switch" Cell reports. Oct. 18, 2016;17(4):1037-52.

Zlotorynski E. "Gene expression: ACSS2 boosts local histone acetylation" Nature Reviews Molecular Cell Biology. Jun. 7, 2017;18(7):405.

Banerjee et al. "Small molecule ACSS2 inhibitors target acetate metabolizing tumor cells in hypoxic conditions" [abstract]. In: Proceedings of the American Association for Cancer Research Annual Meeting 2018; Apr. 14-18, 2018; Chicago, IL. Philadelphia (PA): AACR. Cancer Research (Jul. 2018), vol. 78, Issue: 13—Suppl. Abstract No. 3510. DOI: <10.1158/1538-7445.AM2018-3510>. Retrieved from URL: <https://cancerres.aacrjournals.org/content/78/13_Supplement/3510>. Also see: <https://www.curadev.in/images/AACR_2018_Annual_Meeting.jpg>. Jul. 31, 2018 (Jul. 31, 2018).

Ertel et al. Synthese von 1-Hydroxyimidazolen und 1-Hydroxyimidazol-3-oxiden. Liebigs Ann. Chem. (1974), vol. 1974, issue 9, pp. 1399-1406. First published: Oct. 17, 1974. DOI: <10.1002/jlac.197419740904>. URL: <https://booksc.org/book/1592532/9b03fe>. Oct. 17, 1974 (Oct. 17, 1974) p. 1399.

Nikitina et al. "Synthesis and antiviral activity of 1-hydroxy-2-(2-hydroxyphenyl) imidazoles against vaccinia virus" Russian Chemical Bulletin. Mar. 2019;68(3):634-7.

PubChem Compound CID 137186565. National Center for Biotechnology Information. Create date: Jan. 25, 2019. URL: <https://pubchem.ncbi.nlm.nih.gov/compound/137186565>. & ZINC604419253. URL: <http://zinc.docking.org/substances/ZINC000604419253/>. Jan. 25, 2019 (Jan. 25, 2019).

Wen et al. "Glucose-derived acetate and ACSS2 as key players in cisplatin resistance in bladder cancer" Biochimica et Biophysica Acta (BBA)—Molecular and Cell Biology of Lipids. Mar. 1, 2019;1864(3):413-21.

* cited by examiner

ACSS2 INHIBITORS AND METHODS OF USE THEREOF

CROSS-REFERENCE TO RELATED APPLICATIONS

This application is a Continuation-In-Part of U.S. application Ser. No. 16/411,168, filed May 14, 2019, which is a Continuation-In-Part of PCT Application Number PCT/IL2018/051232, filed Nov. 15, 2018; which claims priority of U.S. Provisional Application Ser. No. 62/586,195, filed Nov. 15, 2017. This application is a Continuation-In-Part of PCT Application Number PCT/IL2020/050526, filed May 14, 2020; which claims priority of U.S. Provisional Application Ser. No. 62/847,348, filed May 14, 2019 and from U.S. application Ser. No. 16/411,168, filed May 14, 2019; all of these applications are herein incorporated by reference in their entirely.

FIELD OF THE INVENTION

The present invention relates to novel ACSS2 inhibitors, composition and methods of preparation thereof, and uses thereof for treating viral infection (e.g. CMV), alcoholism, alcoholic steatohepatitis (ASH), non-alcoholic steatohepatitis (NASH), metabolic disorders including: obesity, weight gain and hepatic steatosis, neuropsychiatric diseases including: anxiety, depression, schizophrenia, autism and post-traumatic stress disorder, inflammatory/autoimmune conditions and cancer, including metastatic cancer, advanced cancer, and drug resistant cancer of various types.

BACKGROUND OF THE INVENTION

Cancer is the second most common cause of death in the United States, exceeded only by heart disease. In the United States, cancer accounts for 1 of every 4 deaths. The 5-year relative survival rate for all cancer patients diagnosed in 1996-2003 is 66%, up from 50% in 1975-1977 (*Cancer Facts & Figures* American Cancer Society: Atlanta, GA (2008)). The rate of new cancer cases decreased by an average 0.6% per year among men between 2000 and 2009 and stayed the same for women. From 2000 through 2009, death rates from all cancers combined decreased on average 1.8% per year among men and 1.4% per year among women. This improvement in survival reflects progress in diagnosing at an earlier stage and improvements in treatment. Discovering highly effective anticancer agents with low toxicity is a primary goal of cancer research.

Cell growth and proliferation are intimately coordinated with metabolism. Potentially distinct differences in metabolism between normal and cancerous cells have sparked a renewed interest in targeting metabolic enzymes as an approach to the discovery of new anticancer therapeutics.

It is now appreciated that cancer cells within metabolically stressed microenvironments, herein defined as those with low oxygen and low nutrient availability (i.e., hypoxia conditions), adopt many tumor-promoting characteristics, such as genomic instability, altered cellular bioenergetics and invasive behaviour. In addition, these cancer cells are often intrinsically resistant to cell death and their physical isolation from the vasculature at the tumor site can compromise successful immune responses, drug delivery and therapeutic efficiency, thereby promoting relapse and metastasis, which ultimately translates into drastically reduced patient survival. Therefore, there is an absolute requirement to define therapeutic targets in metabolically stressed cancer cells and to develop new delivery techniques to increase therapeutic efficacy. For instance, the particular metabolic dependence of cancer cells on alternative nutrients (such as acetate) to support energy and biomass production may offer opportunities for the development of novel targeted therapies.

Acetyl-CoA Synthetase Enzyme, ACSS2 as a Target for Cancer Treatment

Acetyl-CoA represents a central node of carbon metabolism that plays a key role in bioenergetics, cell proliferation, and the regulation of gene expression. Highly glycolytic or hypoxic tumors must produce sufficient quantities of this metabolite to support cell growth and survival under nutrient-limiting conditions. Acetate is an important source of acetyl-CoA in hypoxia. Inhibition of acetate metabolism may impair tumor growth. The nucleocytosolic acetyl-CoA synthetase enzyme, ACSS2, supplies a key source of acetyl-CoA for tumors by capturing acetate as a carbon source. Despite exhibiting no gross deficits in growth or development, adult mice lacking ACSS2 exhibit a significant reduction in tumor burden in two different models of hepatocellular carcinoma. ACSS2 is expressed in a large proportion of human tumors, and its activity is responsible for the majority of cellular acetate uptake into both lipids and histones. Further, ACSS2 was identified in an unbiased functional genomic screen as a critical enzyme for the growth and survival of breast and prostate cancer cells cultured in hypoxia and low serum. High expression of ACSS2 is frequently found in invasive ductal carcinomas of the breast, triple-negative breast cancer, glioblastoma, ovarian cancer, pancreatic cancer and lung cancer, and often directly correlates with higher-grade tumors and poorer survival compared with tumors that have low ACSS2 expression. These observations may qualify ACSS2 as a targetable metabolic vulnerability of a wide spectrum of tumors.

Due to the nature of tumorigenesis, cancer cells constantly encounter environments in which nutrient and oxygen availability is severely compromised. In order to survive these harsh conditions, cancer cell transformation is often coupled with large changes in metabolism to satisfy the demands for energy and biomass imposed by continued cellular proliferation. Several recent reports discovered that acetate is used as an important nutritional source by some types of breast, prostate, liver and brain tumors in an acetyl-CoA synthetase 2 (ACSS2)-dependent manner. It was shown that acetate and ACSS2 supplied a significant fraction of the carbon within the fatty acid and phospholipid pools (Comerford et. al. Cell 2014; Mashimo et. al. Cell 2014; Schug et al Cancer Cell 2015*). High levels of ACSS2 due to copy-number gain or high expression were found to correlate with disease progression in human breast prostate and brain tumors. Furthermore, ACSS2, which is essential for tumor growth under hypoxic conditions, is dispensable for the normal growth of cells, and mice lacking ACSS2 demonstrated normal phenotype (Comerford et. al. 2014). The switch to increased reliance on ACSS2 is not due to genetic alterations, but rather due to metabolic stress conditions in the tumor microenvironment. Under normal oxidative conditions, acetyl-CoA is typically produced from citrate via citrate lyase activity. However, under hypoxia, when cells adapt to anaerobic metabolism, acetate becomes a key source for acetyl-CoA and hence, ACSS2 becomes essential and is, defacto, synthetically lethal with hypoxic conditions (see Schug et. al., *Cancer Cell*, 2015, 27:1, pp. 57-71). The accumulative evidences from several studies suggest that ACSS2 may be a targetable metabolic vulnerability of a wide spectrum of tumors.

In certain tumors expressing ACSS2, there is a strict dependency on acetate for their growth or survival, then selective inhibitors of this nonessential enzyme might represent an unusually ripe opportunity for the development of new anticancer therapeutics. If the normal human cells and tissues are not heavily reliant on the activity of the ACSS2 enzyme, it is possible that such agents might inhibit the growth of ACSS2-expressing tumors with a favorable therapeutic window.

Non-alcoholic steatohepatitis (NASH) and alcoholic steatohepatitis (ASH) have a similar pathogenesis and histopathology but a different etiology and epidemiology. NASH and ASH are advanced stages of non-alcoholic fatty liver disease (NAFLD) and alcoholic fatty liver disease (AFLD). NAFLD is characterized by excessive fat accumulation in the liver (steatosis), without any other evident causes of chronic liver diseases (viral, autoimmune, genetic, etc.), and with an alcohol consumption ≤20-30 g/day. On the contrary, AFLD is defined as the presence of steatosis and alcohol consumption >20-30 g/day.

Hepatocyte ethanol metabolism produces free acetate as its endproduct which, largely in other tissues, can be incorporated into acetyl-coenzyme A (acetylcoA) for use in Krebs cycle oxidation, fatty acid synthesis, or as a substrate for protein acetylation. This conversion is catalyzed by the acyl-coenzyme A synthetase short-chain family members 1 and 2 (ACSS1 and ACSS2). The role of acetyl-coA synthesis in control of inflammation opens a novel field of study into the relationship between cellular energy supply and inflammatory disease. It has been shown that ethanol enhances macrophage cytokine production by uncoupling gene transcription from its normal regulatory mechanisms through increased histone acetylation, and that the conversion of the ethanol metabolite acetate to acetyl-coA is crucial to this process.

It was suggested that inflammation is enhanced in acute alcoholic hepatitis in which acetyl-coA synthetases are up-regulated and convert the ethanol metabolite acetate to an excess of acetyl-coA which increases proinflammatory cytokine gene histone acetylation by increased substrate concentration and histone deacetylases (HDAC) inhibition, leading to enhanced gene expression and perpetuation of the inflammatory response. The clinical implication of these findings is that modulation of HDAC or ACSS activity might affect the clinical course of alcoholic liver injury in humans. If inhibitors of ACSS1 and 2 can modulate ethanol-associated histone changes without affecting the flow of acetyl-coA through the normal metabolic pathways, then they have the potential to become much needed effective therapeutic options in acute alcoholic hepatitis. Therefore, synthesis of metabolically available acetyl-coA from acetate is critical to the increased acetylation of proinflammatory gene histones and consequent enhancement of the inflammatory response in ethanol-exposed macrophages. This mechanism is a potential therapeutic target in acute alcoholic hepatitis.

Cytosolic acetyl-CoA is the precursor of multiple anabolic reactions including de-novo fatty acids (FA) synthesis. Inhibition of FA synthesis may favorably affect the morbidity and mortality associated with Fatty-liver metabolic syndromes (Wakil S J, Abu-Elheiga L A. 2009. 'Fatty acid metabolism: Target for metabolic syndrome'. *J. Lipid Res.*) and because of the pivotal role of Acetyl-CoA Carboxylase (ACC) in regulating fatty acid metabolism, ACC inhibitors are under investigation as clinical drug targets in several metabolic diseases, including nonalcoholic fatty liver disease (NAFLD) and nonalcoholic steatohepatitis (NASH). Inhibition of ACSS2 is expected to directly reduce fatty-acid accumulation in the liver through its effect on Acetyl-CoA flux from acetate that is present in the liver at high levels due to the hepatocyte ethanol metabolism. Furthermore, ACSS2 inhibitors are expected to have a better safety profile than ACC inhibitors since they are expected only to affect the flux from Acetate that is not a major source for Ac-CoA in normal conditions (Harriman G et. al., 2016. "Acetyl-CoA carboxylase inhibition by ND-630 reduces hepatic steatosis, improves insulin sensitivity, and modulates dyslipidemia in rats" *PNAS*). In addition, mice lacking ACSS2 showed reduced body weight and hepatic steatosis in a diet-induced obesity model (Z. Huang et al., ACSS2 promotes systemic fat storage and utilization through selective regulation of genes involved in lipid metabolism PNAS 115, (40), E9499-E9506, 2018).

ACSS2 is also shown to enter the nucleus under certain condition (hypoxia, high fat etc.) and to affect histone acetylation and crotonylation by making available acetyl-CoA and crotonyl-CoA and thereby regulate gene expression. For example, ACSS2 decrease is shown to lower levels of nuclear acetyl-CoA and histone acetylation in neurons affecting the expression of many neuronal genes. In the hippocampus such reductions in ACSS2 lead to effects on memory and neuronal plasticity (Mews P, et al., Nature, Vol 546, 381, 2017). Such epigenetic modifications are implicated in neuropsychiatric diseases such as anxiety, PTSD, depression etc. (Graff, J et al. Histone acetylation: molecular mnemonics on chromatin. Nat Rev. Neurosci. 14, 97-111 (2013)). Thus, an inhibitor of ACSS2 may find useful application in these conditions.

Nuclear ACSS2 is also shown to promote lysosomal biogenesis, autophagy and to promote brain tumorigenesis by affecting Histone H3 acetylation (Li, X et al.: Nucleus-Translocated ACSS2 Promotes Gene Transcription for Lysosomal Biogenesis and Autophagy, Molecular Cell 66, 1-14, 2017). In addition, nuclear ACSS2 is shown to activate HIF-2alpha by acetylation and thus accelerate growth and metastasis of HIF2alpha-driven cancers such as certain Renal Cell Carcinoma and Glioblastomas (Chen, R. et al. Coordinate regulation of stress signaling and epigenetic events by ACSS2 and HIF-2 in cancer cells, Plos One, 12 (12) 1-31, 2017).

SUMMARY OF THE INVENTION

This invention provides a method of treating, suppressing, reducing the severity, reducing the risk of developing or inhibiting cancer comprising administering a compound represented by the structure of formula (I)-(V), and by the structures listed in Table 1, as defined herein below, to a subject suffering from cancer under conditions effective to treat, suppress, reduce the severity, reduce the risk of developing, or inhibit said cancer. In various embodiments, the cancer is selected from the list of: hepatocellular carcinoma, melanoma (e.g., BRAF mutant melanoma), glioblastoma, breast cancer (e.g., invasive ductal carcinomas of the breast, triple-negative breast cancer), prostate cancer, liver cancer, brain cancer, ovarian cancer, lung cancer, Lewis lung carcinoma (LLC), colon carcinoma, pancreatic cancer, renal cell carcinoma and mammary carcinoma. In various embodiments, the cancer is early cancer, advanced cancer, invasive cancer, metastatic cancer, drug resistant cancer or any combination thereof. In various embodiments, the subject has been previously treated with chemotherapy, immunotherapy, radiotherapy, biological therapy, surgical intervention, or any combination thereof. In various embodiments, the compound is administered in combination with an anti-cancer therapy. In various embodiments, the anti-cancer therapy is chemotherapy, immunotherapy, radiotherapy, biological therapy, surgical intervention, or any combination thereof.

This invention further provides a method of suppressing, reducing or inhibiting tumor growth in a subject, comprising administering a compound represented by the structure of formula (I)-(V), and by the structures listed in Table 1, as defined herein below, to a subject, under conditions effective to suppress, reduce or inhibit said tumor growth in said subject. In various embodiments, the subject is suffering from cancer. In various embodiments, the tumor is cancerous. In various embodiments, the tumor growth is enhanced by increased acetate uptake by cancer cells of said tumor. In various embodiments, the increased acetate uptake is mediated by ACSS2. In various embodiments, the cancer cells are under hypoxic stress. In various embodiments, the tumor growth is suppressed due to suppression of lipid (e.g., fatty acid) synthesis and/or histones synthesis induced by ACSS2 mediated acetate metabolism to acetyl-CoA. In various embodiments, the tumor growth is suppressed due to suppressed regulation of histones acetylation and function induced by ACSS2 mediated acetate metabolism to acetyl-CoA.

This invention further provides a method of binding an ACSS2 inhibitor compound to an ACSS2 enzyme, comprising the step of contacting an ACSS2 enzyme with an ACSS2 inhibitor compound represented by the structure of formula (I)-(V), and by the structures listed in Table 1, as defined herein below, in an amount effective to bind the ACSS2 inhibitor compound to the ACSS2 enzyme.

This invention further provides a method of suppressing, reducing or inhibiting acetyl-CoA synthesis from acetate in a cell, comprising contacting a compound represented by the structure of formula (I)-(V), and by the structures listed in Table 1, as defined herein below, with a cell, under conditions effective to suppress, reduce or inhibit acetyl-CoA synthesis from acetate in said cell. In various embodiments, the cell is a cancer cell. In various embodiments, the synthesis is mediated by ACSS2.

This invention further provides a method of treating, suppressing, reducing the severity, reducing the risk of developing or inhibiting human alcoholism in a subject, comprising administering a compound represented by the structure of formula (I)-(V), and by the structures listed in Table 1, as defined herein below, to a subject suffering from alcoholism under conditions effective to treat, suppress, reduce the severity, reduce the risk of developing, or inhibit alcoholism in said subject.

This invention further provides a method of treating, suppressing, reducing the severity, reducing the risk of developing or inhibiting a viral infection in a subject, comprising administering a compound represented by the structure of formula (I)-(V), and by the structures listed in Table 1, as defined herein below, to a subject suffering from a viral infection under conditions effective to treat, suppress, reduce the severity, reduce the risk of developing, or inhibit the viral infection in said subject. In various embodiments, the viral infection is human cytomegalovirus (HCMV) infection.

This invention further provides a method of treating, suppressing, reducing the severity, reducing the risk of developing or inhibiting a non-alcoholic steatohepatitis (NASH) in a subject, comprising administering a compound represented by the structure of formula (I)-(V), and by the structures listed in Table 1, as defined herein below, to a subject suffering from non-alcoholic steatohepatitis (NASH) under conditions effective to treat, suppress, reduce the severity, reduce the risk of developing, or inhibit the non-alcoholic steatohepatitis (NASH) in said subject.

This invention further provides a method of treating, suppressing, reducing the severity, reducing the risk of developing or inhibiting an alcoholic steatohepatitis (ASH) in a subject, comprising administering a compound represented by the structure of formula (I)-(V), and by the structures listed in Table 1, as defined herein below, to a subject suffering from an alcoholic steatohepatitis (ASH) under conditions effective to treat, suppress, reduce the severity, reduce the risk of developing, or inhibit the alcoholic steatohepatitis (ASH) in said subject.

This invention further provides a method of treating, suppressing, reducing the severity, reducing the risk of developing or inhibiting a metabolic disorder in a subject, comprising administering a compound represented by the structure of formula (I)-(V), and by the structures listed in Table 1, as defined herein below, to a subject suffering from metabolic disorder under conditions effective to treat, suppress, reduce the severity, reduce the risk of developing, or inhibit metabolic disorder in said subject. In various embodiment, the metabolic disorder is selected from: obesity, weight gain, hepatic steatosis and fatty liver disease.

This invention further provides a method of treating, suppressing, reducing the severity, reducing the risk of developing or inhibiting a neuropsychiatric disease or disorder in a subject, comprising administering a compound represented by the structure of formula (I)-(V), and by the structures listed in Table 1, as defined herein below, to a subject suffering from neuropsychiatric disease or disorder under conditions effective to treat, suppress, reduce the severity, reduce the risk of developing, or inhibit neuropsychiatric disease or disorder in said subject. In some embodiments, the neuropsychiatric disease or disorder is selected from: anxiety, depression, schizophrenia, autism and post-traumatic stress disorder.

This invention further provides a method of treating, suppressing, reducing the severity, reducing the risk of developing or inhibiting inflammatory condition in a subject, comprising administering a compound represented by the structure of formula (I)-(V), and by the structures listed in Table 1, as defined herein below, to a subject suffering from inflammatory condition under conditions effective to treat, suppress, reduce the severity, reduce the risk of developing, or inhibit inflammatory condition in said subject.

This invention further provides a method of treating, suppressing, reducing the severity, reducing the risk of developing or inhibiting an autoimmune disease or disorder in a subject, comprising administering a compound represented by the structure of formula (I)-(V), and by the structures listed in Table 1, as defined herein below, to a subject suffering from an autoimmune disease or disorder under conditions effective to treat, suppress, reduce the severity, reduce the risk of developing, or inhibit the autoimmune disease or disorder in said subject.

BRIEF DESCRIPTION OF THE DRAWINGS

The subject matter regarded as the invention is particularly pointed out and distinctly claimed in the concluding portion of the specification. The invention, however, both as to organization and method of operation, together with objects, features, and advantages thereof, may best be understood by reference to the following detailed description when read with the accompanying drawings in which:

Figure 1:
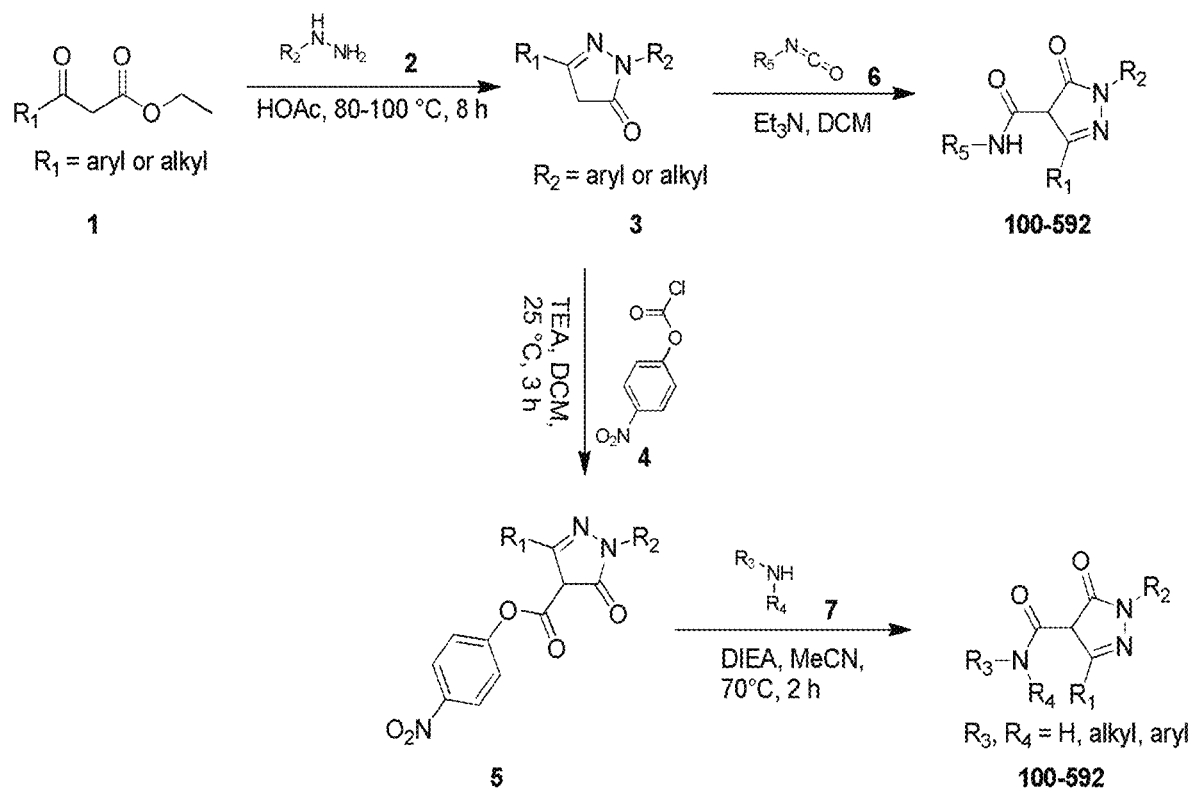
FIG. 1 depicts a general synthetic scheme for compounds of the invention.

It will be appreciated that for simplicity and clarity of illustration, elements shown in the figures have not necessarily been drawn to scale. For example, the dimensions of some of the elements may be exaggerated relative to other elements for clarity. Further, where considered appropriate, reference numerals may be repeated among the figures to indicate corresponding or analogous elements.

DETAILED DESCRIPTION OF THE INVENTION

In various embodiments, this invention is directed to a compound represented by the structure of formula (I):

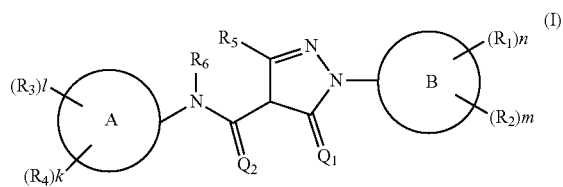

wherein
- A and B rings are each independently a single or fused aromatic (e.g., phenyl) or heteroaromatic (e.g., indole, 2-, 3- or 4-pyridine, naphthalene, thiazole, benzimidazole, thiophene, imidazole, 1-methylimidazole, benzofuran, B: quinoline, indole, benzothiophene, indazole, benzimidazole, 1H-pyrrolo[3,2-c]pyridine, quinoxaline, cinnoline, pyrazine, pyridazine, benzofurane) ring system, or a single fused or bridged $C_3$-$C_{10}$ cycloalkyl (e.g. cyclohexyl, bicyclo[2.1.1]hexane, bicyclo[2.2.1]heptane, bicyclo[3.1.1]heptane, cubane, bicyclo[2.2.2]octane) or a single or fused $C_3$-$C_{10}$ heterocyclic ring (e.g., benzofuran-2(3H)-one, benzo[d][1,3]dioxole, tetrahydrothiophene 1,1-dioxide, piperidine, 1-methylpiperidine, isoquinoline and 1,3-dihydroisobenzofuran);
- $R_1$ and $R_2$ are each independently H, D, F, Cl, Br, I, OH, SH, $R_8$—OH (e.g., $CH_2$—OH), $R_8$—SH, —$R_8$—O—$R_{10}$, (e.g., —$CH_2$—O—$CH_3$), $R_8$-aryl (e.g., $CH_2$-3-methoxy-phenyl, benzyl, $CH_2$-1-methoxy-phenyl, $CH_2$-4-chloro-phenyl, $CH_2CH_2$-phenyl), $CF_3$, $CD_3$, $OCD_3$, CN, $NO_2$, —$CH_2CN$, —$R_8CN$, $NH_2$, NHR, $N(R)_2$, $R_8$—N($R_{10}$)($R_{11}$) (e.g., $CH_2$—$NH_2$, $CH_2$—N($CH_3$)$_2$), $R_9$—$R_8$—N($R_{10}$)($R_{11}$) (e.g., C≡C—$CH_2$—$NH_2$), B(OH)$_2$, —OC(O)$CF_3$, —$OCH_2Ph$, NHC(O)—$R_{10}$ (e.g., NHC(O)$CH_3$), NHCO—N($R_{10}$)($R_{11}$) (e.g., NHC(O)N($CH_3$)$_2$), COOH, —C(O)Ph, —C(O)-aryl (e.g., C(O)-1-methyl-phenyl, C(O)-4-methyl-phenyl, C(O)-3-methyl-phenyl, C(O)-phenol, C(O)-4-hydroxy-phenyl, C(O)-3-hydroxy-phenyl), C(O)-2-hydroxy-phenyl, C(O)O—$R_{10}$ (e.g. C(O)O—$CH_3$, C(O)O—CH($CH_3$)$_2$, C(O)O—$CH_2CH_3$), $R_8$—C(O)—$R_{10}$ (e.g., $CH_2C(O)CH_3$), C(O)H, C(O)—$R_{10}$ (e.g., C(O)—$CH_3$, C(O)—$CH_2CH_3$, C(O)—$CH_2CH_2CH_3$), $C_1$-$C_5$ linear or branched C(O)-haloalkyl (e.g., C(O)—$CF_3$), —C(O)$NH_2$, C(O)NHR, C(O)N($R_{10}$)($R_{11}$) (e.g., C(O)N($CH_3$)$_2$), $SO_2R$ (e.g., $SO_2$-Ph, $SO_2$-toluene, $SO_2$—$CH_3$), $SO_2N(R_{10})(R_{11})$ (e.g., $SO_2N(CH_3)_2$, $SO_2NHC(O)CH_3$), substituted or unsubstituted $C_1$-$C_5$ linear or branched or $C_3$-$C_8$ cyclic alkyl (e.g., methyl, 2, 3, or 4-$CH_2$—$C_6H_4$—Cl, ethyl, propyl, iso-propyl, cyclopropyl, t-Bu, iso-butyl, pentyl, benzyl, C($CH_3$)(OH)Ph, $CH_2$-3-methoxy-phenyl, $CH_2$-1-methoxy-phenyl, $CH_2$-4-chloro-phenyl, $CH_2CH_2$-phenyl), $C_1$-$C_5$ linear or branched haloalkyl (e.g., $CF_3$, $CF_2CH_3$, $CH_2CF_3$, $CF_2CH_2CH_3$, $CH_2CH_2CF_3$, $CF_2CH(CH_3)_2$, $CF(CH_3)$—CH($CH_3$)$_2$, $CF_2$CH-cyclopropyl), substituted or unsubstituted $C_1$-$C_5$ linear or branched or $C_3$-$C_8$ cyclic alkoxy (e.g. methoxy, ethoxy, propoxy, isopropoxy, O—$CH_2$-cyclopropyl, O-cyclobutyl, O-cyclopentyl, O-cyclohexyl, 1-butoxy, 2-butoxy, O-tBu), optionally wherein at least one methylene group ($CH_2$) in the alkoxy is replaced with an oxygen atom (e.g., O-1-oxacyclobutyl, 0-2-oxacyclobutyl), $C_1$-$C_5$ linear or branched thioalkoxy (e.g., S—$CH_3$), $C_1$-$C_5$ linear or branched haloalkoxy (e.g., $OCF_3$, $OCHF_2$), $C_1$-$C_5$ linear or branched alkoxyalkyl, substituted or unsubstituted $C_3$-$C_8$ cycloalkyl (e.g., cyclopropyl, cyclopentyl), substituted or unsubstituted $C_3$-$C_8$ heterocyclic ring (e.g., 3-methyl-4H-1,2,4-triazole, 5-methyl-1,2,4-oxadiazole, thiophene, oxazole, oxadiazole, imidazole, furane, triazole, tetrazole, pyridine (2, 3, or 4-pyridine), 2-methyl-4-pyridine, 2,6-dimethyl-4-pyridine, 3,5-dimethyl-4-pyridine, 2,5-dimethyl-4-pyridine, 3-methyl-4-pyridine, 5-methyl-2-pyridine, 3-methyl-2-pyridine, 3-ethyl-2-pyridine, 3-isopropyl-2-pyridine, 3-propyl-2-pyridine, 3-phenyl-2-pyridine, 4-methyl-2-pyridine, 6-methyl-2-pyridine, 5-methyl-2-pyridine, pyrimidine, 5-methyl-pyrimidine, pyrazine, oxacyclobutane (1 or 2-oxacyclobutane), indole, protonated or deprotonated pyridine oxide), substituted or unsubstituted aryl (e.g., phenyl) (wherein substitutions include: F, Cl, Br, I, $C_1$-$C_5$ linear or branched alkyl (e.g. methyl, ethyl, propyl, isopropyl), OH, alkoxy, N(R)$_2$, $CF_3$, aryl, phenyl, halophenyl, (benzyloxy)phenyl, CN, $NO_2$ or any combination thereof), CH($CF_3$)(NH—$R_{10}$);
- or $R_2$ and $R_1$ are joint together to form a 5 or 6 membered substituted or unsubstituted, aliphatic or aromatic, carbocyclic or heterocyclic single or fused ring (e.g., [1,3]dioxole, furan-2(3H)-one, benzene, pyridine, pyrrol, 1-methyl-1H-pyrrole, 1-benzyl-1H-pyrrole, 7,8-dihydro-5H-pyrano[4,3-b]pyridine);
- $R_3$ and $R_4$ are each independently H, F, Cl, Br, I, OH, SH, $R_8$—OH (e.g., $CH_2$—OH), $R_8$—SH, —$R_8$—O—$R_{10}$, (e.g., $CH_2$—O—$CH_3$) $CF_3$, $CD_3$, $OCD_3$, CN, $NO_2$, —$CH_2CN$, —$R_8CN$, $NH_2$, NHR, $N(R)_2$, $R_8$—N($R_{10}$)($R_{11}$) (e.g., $CH_2$—$NH_2$, $CH_2$—N($CH_3$)$_2$), $R_8$—C(O)N($R_{10}$)($R_{11}$) (e.g., $CF_2C(O)N[(CH_3)(OCH_3)]$) $R_9$—$R_8$—N($R_{10}$)($R_{11}$), B(OH)$_2$, —OC(O)$CF_3$, —$OCH_2Ph$, —NHCO—$R_{10}$ (e.g., NHC(O)$CH_3$), NHCO—N($R_{10}$)($R_{11}$) (e.g., NHC(O)N($CH_3$)$_2$), COOH, —C(O)Ph, C(O)O—$R_{10}$ (e.g. C(O)O—$CH_3$, C(O)O—$CH_2CH_3$), $R_8$—C(O)—$R_{10}$ (e.g., $CH_2C(O)CH_3$), C(O)H, C(O)—$R_{10}$ (e.g., C(O)—$CH_3$, C(O)—$CH_2CH_3$, C(O)—$CH_2CH_2CH_3$), $C_1$-$C_5$ linear or branched C(O)-haloalkyl (e.g., C(O)—CF$_3$), —C(O)NH$_2$, C(O)NHR, C(O)N(R$_{10}$)(R$_{11}$) (e.g., C(O)N(CH$_3$)$_2$), SO$_2$R, SO$_2$N(R$_{10}$)(R$_{11}$) (e.g., SO$_2$N(CH$_3$)$_2$), substituted or unsubstituted C$_1$-C$_5$ linear or branched or C$_3$-C$_8$ cyclic alkyl (e.g., methyl, C(OH)(CH$_3$)(Ph), ethyl, propyl, iso-propyl, t-Bu, iso-butyl, 2-butyl, pentyl, tert-pentyl, 1-ethylcyclopropyl, C(CH$_3$)(OH)Ph), C$_1$-C$_5$ linear or branched or C$_3$-C$_8$ cyclic haloalkyl (e.g., CF$_3$, CF$_2$CH$_3$, CH$_2$CF$_3$, CF$_2$CH$_2$CH$_3$, CF$_2$CHFCH$_3$, CHFCHFCH$_3$, CH$_2$CH$_2$CF$_3$, CF$_2$CH(CH$_3$)$_2$, CF(CH$_3$)—CH(CH$_3$)$_2$, CF$_2$-cyclopropyl, CF$_2$-cyclopentyl), substituted or unsubstituted C$_1$-C$_5$ linear or branched or C$_3$-C$_8$ cyclic cyclic haloalkenyl (e.g. CF=CH—CH$_3$ E, Z, CF=C—(CH$_3$)$_2$), substituted or unsubstituted C$_1$-C$_5$ linear or branched or C$_3$-C$_8$ cyclic alkoxy (e.g. methoxy, ethoxy, propoxy, isopropoxy, O—CH$_2$-cyclopropyl), C$_1$-C$_5$ linear or branched thioalkoxy, C$_1$-C$_5$ linear or branched haloalkoxy, C$_1$-C$_5$ linear or branched alkoxyalkyl, substituted or unsubstituted C$_3$-C$_8$ cycloalkyl (e.g., cyclopropyl, cyclopentyl), substituted or unsubstituted C$_3$-C$_8$ heterocyclic ring (e.g., 3-methyl-4H-1,2,4-triazole, 5-methyl-1,2,4-oxadiazole, thiophene, oxazole, isoxazole, imidazole, furane, pyrrole, 1-methyl-pyrrol, imidazole, 1-methyl-imidazole, triazole, pyridine (2, 3, or 4-pyridine), pyrimidine, pyrazine, oxacyclobutane (1 or 2-oxacyclobutane), indole), substituted or unsubstituted aryl (e.g., phenyl), (wherein substitutions include: F, Cl, Br, I, C$_1$-C$_5$ linear or branched alkyl, OH, alkoxy, N(R)$_2$, CF$_3$, aryl, phenyl, halophenyl, (benzyloxy)phenyl, CN, NO$_2$ or any combination thereof), CH(CF$_3$)(NH—R$_{10}$);

or R$_3$ and R$_4$ are joint together to form a 5 or 6 membered substituted or unsubstituted, aliphatic or aromatic, carbocyclic or heterocyclic ring (e.g., [1,3]dioxole, furan-2(3H)-one, benzene, cyclopentane, imidazole, pyrrol);

R$_5$ is H, C$_1$-C$_5$ linear or branched, substituted or unsubstituted alkyl (e.g., methyl, CH$_2$SH, ethyl, iso-propyl), C$_1$-C$_5$ linear or branched haloalkyl (e.g., CF$_3$, CF$_2$CH$_3$, CH$_2$CF$_3$, CF$_2$CH$_2$CH$_3$, CH$_2$CH$_2$CF$_3$, CF$_2$CH(CH$_3$)$_2$, CF(CH$_3$)—CH(CH$_3$)$_2$), R$_8$-aryl (e.g., CH$_2$-Ph), C(O)—R$_{10}$ (e.g., C(O)—CH$_3$), substituted or unsubstituted aryl (e.g., phenyl), substituted or unsubstituted heteroaryl (e.g., pyridine (2, 3, and 4-pyridine), (wherein substitutions include: F, Cl, Br, I, C$_1$-C$_5$ linear or branched alkyl, OH, alkoxy, N(R)$_2$, CF$_3$, phenyl, halophenyl, (benzyloxy)phenyl, CN, NO$_2$ or any combination thereof);

R$_6$ is H, C$_1$-C$_5$ linear or branched alkyl (e.g., methyl), C(O)R, or S(O)$_2$R;

R$_8$ is [CH$_2$]$_p$ or [CF$_2$]$_p$
wherein p is between 1 and 10;

R$_9$ is [CH]$_q$, [C]$_q$
wherein q is between 2 and 10;

R$_{10}$ and Ru are each independently H, C$_1$-C$_5$ linear or branched alkyl (e.g., methyl, ethyl), C(O)R, or S(O)$_2$R;

R is H, C$_1$-C$_5$ linear or branched alkyl (e.g., methyl, ethyl), C$_1$-C$_5$ linear or branched alkoxy, phenyl, aryl (e.g., toluene) or heteroaryl, or two gem R substituents are joint together to form a 5 or 6 membered heterocyclic ring;

m, n, l and k are each independently an integer between 0 and 4;

Q$_1$ and Q$_2$ are each independently S, O, N—OH, CH$_2$, C(R)$_2$ or N—OMe;

or its pharmaceutically acceptable salt, optical isomer, tautomer, hydrate, N-oxide, reverse amide analog, prodrug, isotopic variant (e.g., deuterated analog), PROTAC, pharmaceutical product or any combination thereof.

In various embodiments, if rings A and B are each independently a phenyl or a fused aromatic ring system (e.g. naphtyl), then R$_1$, R$_2$, R$_3$ and R$_4$ cannot be H, alkyl, alkoxy, halide, or CF$_3$. In some embodiments, if rings A and B are both phenyls, then R$_1$ and R$_2$ cannot be both H. In some embodiments, if rings A and B are both phenyls, then R$_3$ and R$_4$ cannot be both H. In some embodiments, if rings A and B are each independently a phenyl or a fused aromatic ring system, then R$_5$ cannot be aryl. In some embodiments, ring B is not tetrahydrothiophene 1,1-dioxide. In some embodiments, ring A is not tetrahydrothiophene 1,1-dioxide.

In various embodiments, this invention is directed to a compound represented by the structure of formula (I):

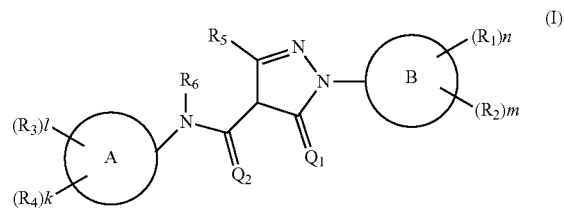

wherein

A and B rings are each independently a single or fused aromatic (e.g., phenyl) or heteroaromatic (e.g., indole, 2-, 3- or 4-pyridine, naphthalene, thiazole, benzimidazole, thiophene, imidazole, 1-methylimidazole, benzofuran, B: quinoline, indole, benzothiophene, indazole, benzimidazole, 1H-pyrrolo[3,2-c]pyridine, quinoxaline, cinnoline, pyrazine, pyridazine, benzofurane) ring system, or a single fused or bridged C$_3$-C$_{10}$ cycloalkyl (e.g. cyclohexyl, bicyclo[2.1.1]hexane, bicyclo[2.2.1]heptane, bicyclo[3.1.1]heptane, cubane, bicyclo [2.2.2]octane) or a single or fused C$_3$-C$_{10}$ heterocyclic ring (e.g., benzofuran-2(3H)-one, benzo[d][1,3]dioxole, tetrahydrothiophene 1,1-dioxide, piperidine, 1-methylpiperidine, isoquinoline and 1,3-dihydroisobenzofuran);

R$_1$ and R$_2$ are each independently H, D, F, Cl, Br, I, OH, SH, R$_8$—OH (e.g., CH$_2$—OH), R$_8$—SH, —R$_8$—O—R$_{10}$, (e.g., —CH$_2$—O—CH$_3$), R$_8$-aryl (e.g., CH$_2$-3-methoxy-phenyl, benzyl, CH$_2$-1-methoxy-phenyl, CH$_2$-4-chloro-phenyl, CH$_2$CH$_2$-phenyl), CF$_3$, CD$_3$, OCD$_3$, CN, NO$_2$, —CH$_2$CN, —R$_8$CN, NH$_2$, NHR, N(R)$_2$, R$_8$—N(R$_{10}$)(R$_{11}$) (e.g., CH$_2$—NH$_2$, CH$_2$—N(CH$_3$)$_2$), R$_9$—R$_8$—N(R$_{10}$)(R$_{11}$) (e.g., C≡C—CH$_2$—NH$_2$), B(OH)$_2$, —OC(O)CF$_3$, —OCH$_2$Ph, NHC(O)—R$_{10}$ (e.g., NHC(O)CH$_3$), NHCO—N(R$_{10}$)(R$_{11}$) (e.g., NHC(O)N(CH$_3$)$_2$), COOH, —C(O)Ph, —C(O)-aryl (e.g., C(O)-1-methyl-phenyl, C(O)-4-methyl-phenyl, C(O)-3-methyl-phenyl, C(O)-phenol, C(O)-4-hydroxy-phenyl, C(O)-3-hydroxy-phenyl), C(O)-2-hydroxy-phenyl, C(O)O—R$_{10}$ (e.g. C(O)O—CH$_3$, C(O)O—CH(CH$_3$)$_2$, C(O)O—CH$_2$CH$_3$), R$_8$—C(O)—R$_{10}$ (e.g., CH$_2$C(O)CH$_3$), C(O)H, C(O)—R$_{10}$ (e.g., C(O)—CH$_3$, C(O)—CH$_2$CH$_3$, C(O)—CH$_2$CH$_2$CH$_3$), C$_1$-C$_5$ linear or branched C(O)-haloalkyl (e.g., C(O)—CF$_3$), —C(O)NH$_2$, C(O)NHR, C(O)N(R$_{10}$)(R$_{11}$) (e.g., C(O)N(CH$_3$)$_2$), SO$_2$R (e.g., SO$_2$-Ph, SO$_2$-toluene, SO$_2$—CH$_3$), SO$_2$N(R$_{10}$)(R$_{11}$) (e.g., SO$_2$N(CH$_3$)$_2$, SO$_2$NHC(O)CH$_3$), C$_1$-C$_5$ linear or branched, substituted or unsubstituted alkyl (e.g., methyl, 2, 3, or 4-CH$_2$—

$C_6H_4$—Cl, ethyl, propyl, iso-propyl, cyclopropyl, t-Bu, iso-butyl, pentyl, benzyl, $C(CH_3)(OH)Ph$, $CH_2$-3-methoxy-phenyl, $CH_2$-1-methoxy-phenyl, $CH_2$-4-chloro-phenyl, $CH_2CH_2$-phenyl), $C_1$-$C_5$ linear or branched haloalkyl (e.g., $CF_3$, $CF_2CH_3$, $CH_2CF_3$, $CF_2CH_2CH_3$, $CH_2CH_2CF_3$, $CF_2CH(CH_3)_2$, $CF(CH_3)$—$CH(CH_3)_2$, $CF_2CH$-cyclopropyl), substituted or unsubstituted $C_1$-$C_5$ linear or branched or $C_3$-$C_8$ cyclic alkoxy (e.g. methoxy, ethoxy, propoxy, isopropoxy, O—$CH_2$-cyclopropyl, O-cyclobutyl, O-cyclopentyl, O-cyclohexyl, 1-butoxy, 2-butoxy, O-tBu), optionally wherein at least one methylene group ($CH_2$) in the alkoxy is replaced with an oxygen atom (e.g., O-1-oxacyclobutyl, O-2-oxacyclobutyl), $C_1$-$C_5$ linear or branched thioalkoxy (e.g., S—$CH_3$), $C_1$-$C_5$ linear or branched haloalkoxy (e.g., $OCF_3$, $OCHF_2$), $C_1$-$C_5$ linear or branched alkoxyalkyl, substituted or unsubstituted $C_3$-$C_8$ cycloalkyl (e.g., cyclopropyl, cyclopentyl), substituted or unsubstituted $C_3$-$C_8$ heterocyclic ring (e.g., 3-methyl-4H-1,2,4-triazole, 5-methyl-1,2,4-oxadiazole, thiophene, oxazole, oxadiazole, imidazole, furane, triazole, tetrazole, pyridine (2, 3, or 4-pyridine), 2-methyl-4-pyridine, 2,6-dimethyl-4-pyridine, 3,5-dimethyl-4-pyridine, 2,5-dimethyl-4-pyridine, 3-methyl-4-pyridine, 5-methyl-2-pyridine, 3-methyl-2-pyridine, 3-ethyl-2-pyridine, 3-isopropyl-2-pyridine, 3-propyl-2-pyridine, 3-phenyl-2-pyridine, 4-methyl-2-pyridine, 6-methyl-2-pyridine, 5-methyl-2-pyridine, pyrimidine, 5-methyl-pyrimidine, pyrazine, oxacyclobutane (1 or 2-oxacyclobutane), indole, protonated or deprotonated pyridine oxide), substituted or unsubstituted aryl (e.g., phenyl) (wherein substitutions include: F, Cl, Br, I, $C_1$-$C_5$ linear or branched alkyl (e.g. methyl, ethyl, propyl, isopropyl), OH, alkoxy, $N(R)_2$, $CF_3$, aryl, phenyl, halophenyl, (benzyloxy)phenyl, CN, $NO_2$ or any combination thereof), $CH(CF_3)(NH$—$R_{10})$;

or $R_2$ and $R_1$ are joint together to form a 5 or 6 membered substituted or unsubstituted, aliphatic or aromatic, carbocyclic or heterocyclic single or fused ring (e.g., [1,3]dioxole, furan-2(3H)-one, benzene, pyridine, pyrrol, 1-methyl-1H-pyrrole, 1-benzyl-1H-pyrrole, 7,8-dihydro-5H-pyrano[4,3-b]pyridine);

$R_3$ is $C_2$-$C_5$ linear, branched or cyclic haloalkyl, (e.g., $CF_2CH_3$, $CH_2CF_3$, $CF_2CH_2CH_3$, $CF_2CHFCH_3$, $CHFCHFCH_3$, $CH_2CH_2CF_3$, $CF_2CH(CH_3)_2$, $CF(CH_3)$—$CH(CH_3)_2$, $CF_2$-cyclopropyl, $CF_2$-cyclopentyl) or substituted or unsubstituted $C_1$-$C_5$ linear or branched or $C_3$-$C_8$ cyclic haloalkenyl (e.g. CF=CH—$CH_3$ E, Z, CF=C—$(CH_3)_2$);

$R_4$ is H, F, Cl, Br, I, OH, SH, $R_8$—OH (e.g., $CH_2$—OH), $R_8$—SH, —$R_8$—O—$R_{10}$, (e.g., $CH_2$—O—$CH_3$)$CF_3$, $CD_3$, $OCD_3$, CN, $NO_2$, —$CH_2CN$, —$R_8CN$, $NH_2$, $NHR$, $N(R)_2$, $R_8$—$N(R_{10})(R_{11})$ (e.g., $CH_2$—$NH_2$, $CH_2$—$N(CH_3)_2$), $R_8$—$C(O)N(R_{10})(R_{11})$ (e.g., $CF_2C(O)N[(CH_3)(OCH_3)])$ $R_9$—$R_8$—$N(R_{10})(R_{11})$, $B(OH)_2$, —$OC(O)CF_3$, —$OCH_2Ph$, —$NHCO$—$R_{10}$ (e.g., $NHC(O)CH_3$), $NHCO$—$N(R_{10})(R_{11})$ (e.g., $NHC(O)N(CH_3)_2$), COOH, —$C(O)Ph$, $C(O)O$—$R_{10}$ (e.g. $C(O)O$—$CH_3$, $C(O)O$—$CH_2CH_3$), $R_8$—$C(O)$—$R_{10}$ (e.g., $CH_2C(O)CH_3$), $C(O)H$, $C(O)$—$R_{10}$ (e.g., $C(O)$—$CH_3$, $C(O)$—$CH_2CH_3$, $C(O)$—$CH_2CH_2CH_3$), $C_1$-$C_5$ linear or branched C(O)-haloalkyl (e.g., $C(O)$—$CF_3$), —$C(O)NH_2$, $C(O)NHR$, $C(O)N(R_{10})(R_{11})$ (e.g., $C(O)N(CH_3)_2$), $SO_2R$, $SO_2N(R_{10})(R_{11})$ (e.g., $SO_2N(CH_3)_2$), substituted or unsubstituted $C_1$-$C_5$ linear or branched or $C_3$-$C_8$ cyclic alkyl (e.g., methyl, $C(OH)(CH_3)(Ph)$, ethyl, propyl, iso-propyl, t-Bu, iso-butyl, 2-butyl, pentyl, tert-pentyl, 1-ethylcyclopropyl, $C(CH_3)(OH)Ph$), substituted or unsubstituted $C_1$-$C_5$ linear or branched or $C_3$-$C_8$ cyclic haloalkyl (e.g., $CF_3$, $CF_2CH_3$, $CH_2CF_3$, $CF_2CH_2CH_3$, $CF_2CHFCH_3$, $CHFCHFCH_3$, $CH_2CH_2CF_3$, $CF_2CH(CH_3)_2$, $CF(CH_3)$—$CH(CH_3)_2$, $CF_2$-cyclopropyl, $CF_2$-cyclopentyl), substituted or unsubstituted $C_1$-$C_5$ linear or branched or $C_3$-$C_8$ cyclic haloalkenyl (e.g. CF=CH—$CH_3$ E, Z, CF=C—$(CH_3)_2$), substituted or unsubstituted $C_1$-$C_5$ linear or branched or $C_3$-$C_8$ cyclic alkoxy (e.g. methoxy, ethoxy, propoxy, isopropoxy, O—$CH_2$-cyclopropyl), $C_1$-$C_5$ linear or branched thioalkoxy, $C_1$-$C_5$ linear or branched haloalkoxy, $C_1$-$C_5$ linear or branched alkoxyalkyl, substituted or unsubstituted $C_3$-$C_8$ cycloalkyl (e.g., cyclopropyl, cyclopentyl), substituted or unsubstituted $C_3$-$C_8$ heterocyclic ring (e.g., 3-methyl-4H-1,2,4-triazole, 5-methyl-1,2,4-oxadiazole, thiophene, oxazole, isoxazole, imidazole, furane, pyrrole, 1-methyl-pyrrol, imidazole, 1-methyl-imidazole, triazole, pyridine (2, 3, or 4-pyridine), pyrimidine, pyrazine, oxacyclobutane (1 or 2-oxacyclobutane), indole), substituted or unsubstituted aryl (e.g., phenyl), (wherein substitutions include: F, Cl, Br, I, $C_1$-$C_5$ linear or branched alkyl, OH, alkoxy, $N(R)_2$, $CF_3$, aryl, phenyl, halophenyl, (benzyloxy)phenyl, CN, $NO_2$ or any combination thereof), $CH(CF_3)(NH$—$R_{10})$;

$R_5$ is H, $C_1$-$C_5$ linear or branched, substituted or unsubstituted alkyl (e.g., methyl, $CH_2SH$, ethyl, iso-propyl), $C_1$-$C_5$ linear or branched haloalkyl (e.g., $CF_3$, $CF_2CH_3$, $CH_2CF_3$, $CF_2CH_2CH_3$, $CH_2CH_2CF_3$, $CF_2CH(CH_3)_2$, $CF(CH_3)$—$CH(CH_3)_2$), $R_8$-aryl (e.g., $CH_2$-Ph), $C(O)$—$R_{10}$ (e.g., $C(O)$—$CH_3$), substituted or unsubstituted aryl (e.g., phenyl), substituted or unsubstituted heteroaryl (e.g., pyridine (2, 3, and 4-pyridine), (wherein substitutions include: F, Cl, Br, I, $C_1$-$C_5$ linear or branched alkyl, OH, alkoxy, $N(R)_2$, $CF_3$, phenyl, halophenyl, (benzyloxy)phenyl, CN, $NO_2$ or any combination thereof);

$R_6$ is H, $C_1$-$C_5$ linear or branched alkyl (e.g., methyl), $C(O)R$, or $S(O)_2R$;

$R_8$ is $[CH_2]_p$ or $[CF_2]_p$ wherein p is between 1 and 10;

$R_9$ is $[CH]_q$, $[C]_q$ wherein q is between 2 and 10;

$R_{10}$ and $R_{11}$ are each independently H, $C_1$-$C_5$ linear or branched alkyl (e.g., methyl, ethyl), $C(O)R$, or $S(O)_2R$;

R is H, $C_1$-$C_5$ linear or branched alkyl (e.g., methyl, ethyl), $C_1$-$C_5$ linear or branched alkoxy, phenyl, aryl (e.g., toluene) or heteroaryl, or two gem R substituents are joint together to form a 5 or 6 membered heterocyclic ring;

m, n, l and k are each independently an integer between 0 and 4;

$Q_1$ and $Q_2$ are each independently S, O, N—OH, $CH_2$, $C(R)_2$ or N—OMe; or its pharmaceutically acceptable salt, optical isomer, tautomer, hydrate, N-oxide, reverse amide analog, prodrug, isotopic variant (e.g., deuterated analog), PROTAC, pharmaceutical product or any combination thereof.

In various embodiments, this invention is directed to a compound represented by the structure of formula (II)

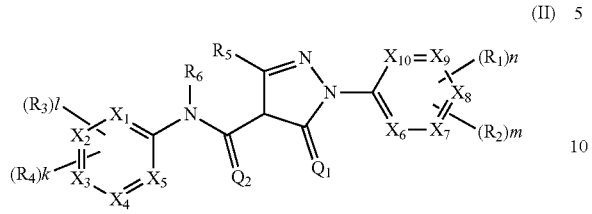

(II)

wherein $R_1$ and $R_2$ are each independently H, D, F, Cl, Br, I, OH, SH, $R_8$—OH (e.g., $CH_2$—OH), $R_8$—SH, —$R_8$—O—$R_{10}$, (e.g., —$CH_2$—O—$CH_3$), $R_8$-aryl (e.g., $CH_2$-3-methoxy-phenyl, benzyl, $CH_2$-1-methoxy-phenyl, $CH_2$-4-chloro-phenyl, $CH_2CH_2$-phenyl), $CF_3$, $CD_3$, $OCD_3$, CN, $NO_2$, —$CH_2CN$, —$R_8CN$, $NH_2$, NHR, $N(R)_2$, $R_8$—$N(R_{10})(R_{11})$ (e.g., $CH_2$—$NH_2$, $CH_2$—N$(CH_3)_2$), $R_9$—$R_8$—$N(R_{10})(R_{11})$ (e.g., C≡C—$CH_2$—$NH_2$), $B(OH)_2$, —OC(O)$CF_3$, —$OCH_2Ph$, NHC(O)—$R_{10}$ (e.g., NHC(O)$CH_3$), NHCO—$N(R_{10})(R_{11})$ (e.g., NHC(O)N$(CH_3)_2$), COOH, —C(O)Ph, —C(O)-aryl (e.g., C(O)-1-methyl-phenyl, C(O)-4-methyl-phenyl, C(O)-3-methyl-phenyl, C(O)-phenol, C(O)-4-hydroxy-phenyl, C(O)-3-hydroxy-phenyl), C(O)-2-hydroxy-phenyl), C(O)O—$R_{10}$ (e.g. C(O)O—$CH_3$, C(O)O—CH$(CH_3)_2$, C(O)O—$CH_2CH_3$), $R_8$—C(O)—$R_{10}$ (e.g., $CH_2$C(O)$CH_3$), C(O)H, C(O)—$R_{10}$ (e.g., C(O)—$CH_3$, C(O)—$CH_2CH_3$, C(O)—$CH_2CH_2CH_3$), $C_1$-$C_5$ linear or branched C(O)-haloalkyl (e.g., C(O)—$CF_3$), —C(O)$NH_2$, C(O)NHR, C(O)$N(R_{10})(R_{11})$ (e.g., C(O)N$(CH_3)_2$), $SO_2R$ (e.g., $SO_2$-Ph, $SO_2$-toluene, $SO_2$—$CH_3$), $SO_2N(R_{10})(R_{11})$ (e.g., $SO_2N(CH_3)_2$, $SO_2$NHC(O)$CH_3$), $C_1$-$C_5$ linear or branched, substituted or unsubstituted alkyl (e.g., methyl, 2, 3, or 4-$CH_2$—$C_6H_4$—Cl, ethyl, propyl, iso-propyl, cyclopropyl, t-Bu, iso-butyl, pentyl, benzyl, C$(CH_3)$(OH)Ph, $CH_2$-3-methoxy-phenyl, $CH_2$-1-methoxy-phenyl, $CH_2$-4-chloro-phenyl, $CH_2CH_2$-phenyl), $C_1$-$C_5$ linear or branched haloalkyl (e.g., $CF_3$, $CF_2CH_3$, $CH_2CF_3$, $CF_2CH_2CH_3$, $CH_2CH_2CF_3$, $CF_2CH(CH_3)_2$, CF$(CH_3)$—CH$(CH_3)_2$, $CF_2$CH-cyclopropyl), substituted or unsubstituted $C_1$-$C_5$ linear or branched or $C_3$-$C_8$ cyclic alkoxy (e.g. methoxy, ethoxy, propoxy, isopropoxy, O—$CH_2$-cyclopropyl, O-cyclobutyl, O-cyclopentyl, O-cyclohexyl, 1-butoxy, 2-butoxy, O-tBu), optionally wherein at least one methylene group ($CH_2$) in the alkoxy is replaced with an oxygen atom (e.g., O-1-oxacyclobutyl, O-2-oxacyclobutyl), $C_1$-$C_5$ linear or branched thioalkoxy (e.g., S—$CH_3$), $C_1$-$C_5$ linear or branched haloalkoxy (e.g., $OCF_3$, $OCHF_2$), $C_1$-$C_5$ linear or branched alkoxyalkyl, substituted or unsubstituted $C_3$-$C_8$ cycloalkyl (e.g., cyclopropyl, cyclopentyl), substituted or unsubstituted $C_3$-$C_8$ heterocyclic ring (e.g., 3-methyl-4H-1,2,4-triazole, 5-methyl-1,2,4-oxadiazole, thiophene, oxazole, oxadiazole, imidazole, furane, triazole, tetrazole, pyridine (2, 3, or 4-pyridine), 2-methyl-4-pyridine, 2,6-dimethyl-4-pyridine, 3,5-dimethyl-4-pyridine, 2,5-dimethyl-4-pyridine, 3-methyl-4-pyridine, 5-methyl-2-pyridine, 3-methyl-2-pyridine, 3-ethyl-2-pyridine, 3-isopropyl-2-pyridine, 3-propyl-2-pyridine, 3-phenyl-2-pyridine, 4-methyl-2-pyridine, 6-methyl-2-pyridine, 5-methyl-2-pyridine, pyrimidine, 5-methyl-pyrimidine, pyrazine, oxacyclobutane (1 or 2-oxacyclobutane), indole, protonated or deprotonated pyridine oxide), substituted or unsubstituted aryl (e.g., phenyl) (wherein substitutions include: F, Cl, Br, I, $C_1$-$C_5$ linear or branched alkyl (e.g. methyl, ethyl, propyl, isopropyl), OH, alkoxy, $N(R)_2$, $CF_3$, aryl, phenyl, halophenyl, (benzyloxy)phenyl, CN, $NO_2$ or any combination thereof), CH$(CF_3)$(NH—$R_{10}$);

or $R_2$ and $R_1$ are joint together to form a 5 or 6 membered substituted or unsubstituted, aliphatic or aromatic, carbocyclic or heterocyclic single or fused ring (e.g., [1,3]dioxole, furan-2(3H)-one, benzene, pyridine, pyrrol, 1-methyl-1H-pyrrole, 1-benzyl-1H-pyrrole, 7,8-dihydro-5H-pyrano[4,3-b]pyridine);

$R_3$ and $R_4$ are each independently H, F, Cl, Br, I, OH, SH, $R_8$—OH (e.g., $CH_2$—OH), $R_8$—SH, —$R_8$—O—$R_{10}$, (e.g., $CH_2$—O—$CH_3$) $CF_3$, $CD_3$, $OCD_3$, CN, $NO_2$, —$CH_2CN$, —$R_8CN$, $NH_2$, NHR, $N(R)_2$, $R_8$—$N(R_{10})(R_{11})$ (e.g., $CH_2$—$NH_2$, $CH_2$—N$(CH_3)_2$), $R_8$—C(O)N$(R_{10})(R_{11})$ (e.g., $CF_2$C(O)N[$(CH_3)(OCH_3)$]) $R_9$—$R_8$—$N(R_{10})(R_{11})$, $B(OH)_2$, —OC(O)$CF_3$, —$OCH_2Ph$, —NHCO—$R_{10}$ (e.g., NHC(O)$CH_3$), NHCO—$N(R_{10})(R_{11})$ (e.g., NHC(O)N$(CH_3)_2$), COOH, —C(O)Ph, C(O)O—$R_{10}$ (e.g. C(O)O—$CH_3$, C(O)O—$CH_2CH_3$), $R_8$—C(O)—$R_{10}$ (e.g., $CH_2$C(O)$CH_3$), C(O)H, C(O)—$R_{10}$ (e.g., C(O)—$CH_3$, C(O)—$CH_2CH_3$, C(O)—$CH_2CH_2CH_3$), $C_1$-$C_5$ linear or branched C(O)-haloalkyl (e.g., C(O)—$CF_3$), —C(O)$NH_2$, C(O)NHR, C(O)$N(R_{10})(R_{11})$ (e.g., C(O)N$(CH_3)_2$), $SO_2R$, $SO_2N(R_{10})(R_{11})$ (e.g., $SO_2N(CH_3)_2$), substituted or unsubstituted $C_1$-$C_5$ linear or branched or $C_3$-$C_8$ cyclic alkyl (e.g., methyl, C$(OH)(CH_3)$(Ph), ethyl, propyl, iso-propyl, t-Bu, iso-butyl, 2-butyl, pentyl, tert-pentyl, 1-ethylcyclopropyl, C$(CH_3)$(OH)Ph), substituted or unsubstituted $C_1$-$C_5$ linear or branched or $C_3$-$C_8$ cyclic haloalkyl (e.g., $CF_3$, $CF_2CH_3$, $CH_2CF_3$, $CF_2CH_2CH_3$, $CF_2$CHF$CH_3$, CHFCHF$CH_3$, $CH_2CH_2CF_3$, $CF_2$CH$(CH_3)_2$, CF$(CH_3)$—CH$(CH_3)_2$, $CF_2$-cyclopropyl, $CF_2$-cyclopentyl), substituted or unsubstituted $C_1$-$C_5$ linear or branched or $C_3$-$C_8$ cyclic haloalkenyl (e.g. CF=CH—$CH_3$ E, Z, CF=C—$(CH_3)_2$), substituted or unsubstituted $C_1$-$C_5$ linear or branched or $C_3$-$C_8$ cyclic alkoxy (e.g. methoxy, ethoxy, propoxy, isopropoxy, O—$CH_2$-cyclopropyl), $C_1$-$C_5$ linear or branched thioalkoxy, $C_1$-$C_5$ linear or branched haloalkoxy, $C_1$-$C_5$ linear or branched alkoxyalkyl, substituted or unsubstituted $C_3$-$C_8$ cycloalkyl (e.g., cyclopropyl, cyclopentyl), substituted or unsubstituted $C_3$-$C_8$ heterocyclic ring (e.g., 3-methyl-4H-1,2,4-triazole, 5-methyl-1,2,4-oxadiazole, thiophene, oxazole, isoxazole, imidazole, furane, pyrrole, 1-methyl-pyrrol, imidazole, 1-methyl-imidazole, triazole, pyridine (2, 3, or 4-pyridine), pyrimidine, pyrazine, oxacyclobutane (1 or 2-oxacyclobutane), indole), substituted or unsubstituted aryl (e.g., phenyl), (wherein substitutions include: F, Cl, Br, I, $C_1$-$C_5$ linear or branched alkyl, OH, alkoxy, $N(R)_2$, $CF_3$, aryl, phenyl, halophenyl, (benzyloxy)phenyl, CN, $NO_2$ or any combination thereof), CH$(CF_3)$(NH—$R_{10}$);

or $R_3$ and $R_4$ are joint together to form a 5 or 6 membered substituted or unsubstituted, aliphatic or aromatic, carbocyclic or heterocyclic ring (e.g., [1,3]dioxole, furan-2(3H)-one, benzene, cyclopentane, imidazole, pyrrol);

$R_5$ is H, $C_1$-$C_5$ linear or branched, substituted or unsubstituted alkyl (e.g., methyl, $CH_2SH$, ethyl, iso-propyl), $C_1$-$C_5$ linear or branched haloalkyl (e.g., $CF_3$, $CF_2CH_3$, $CH_2CF_3$, $CF_2CH_2CH_3$, $CH_2CH_2CF_3$, $CF_2$CH$(CH_3)_2$, CF$(CH_3)$—CH$(CH_3)_2$), $R_8$-aryl (e.g., $CH_2$-Ph), C(O)—$R_{10}$ (e.g., C(O)—$CH_3$), substituted or unsubstituted aryl (e.g., phenyl), substituted or unsubstituted heteroaryl (e.g., pyridine (2, 3, and 4-pyridine), (wherein substitutions include: F, Cl, Br, I, $C_1$-$C_5$ linear or branched alkyl, OH, alkoxy, $N(R)_2$, $CF_3$, phenyl, halophenyl, (benzyloxy)phenyl, CN, $NO_2$ or any combination thereof);

$R_6$ is H, $C_1$-$C_5$ linear or branched alkyl (e.g., methyl), C(O)R, or $S(O)_2R$;

$R_8$ is $[CH_2]_p$ or $[CF_2]_p$ wherein p is between 1 and 10;

$R_9$ is $[CH]_q$, $[C]_q$ wherein q is between 2 and 10;

$R_{10}$ and $R_{11}$ are each independently H, $C_1$-$C_5$ linear or branched alkyl (e.g., methyl, ethyl), C(O)R, or $S(O)_2R$;

R is H, $C_1$-$C_5$ linear or branched alkyl (e.g., methyl, ethyl), $C_1$-$C_5$ linear or branched alkoxy, phenyl, aryl (e.g., toluene) or heteroaryl, or two gem R substituents are joint together to form a 5 or 6 membered heterocyclic ring;

m, n, l and k are each independently an integer between 0 and 4;

$Q_1$ and $Q_2$ are each independently S, O, N—OH, $CH_2$, $C(R)_2$ or N—OMe;

$X_1$, $X_2$, $X_3$, $X_4$, $X_5$, $X_6$, $X_7$, $X_8$, $X_9$ or $X_{10}$ are each independently C or N;

or its pharmaceutically acceptable salt, optical isomer, tautomer, hydrate, N-oxide, reverse amide analog, prodrug, isotopic variant (e.g., deuterated analog), PROTAC, pharmaceutical product or any combination thereof.

In various embodiments, if $X_1$, $X_2$, $X_3$, $X_4$, $X_5$, $X_6$, $X_7$, $X_8$, $X_9$ or $X_{10}$ are all C, then $R_1$, $R_2$, $R_3$ and $R_4$ cannot be H, alkyl, alkoxy, halide, or $CF_3$. In some embodiments, $R_1$ and $R_2$ cannot be both H. In some embodiments, $R_3$ and $R_4$ cannot be both H. In some embodiments, if $X_1$, $X_2$, $X_3$, $X_4$, $X_5$, $X_6$, $X_7$, $X_8$, $X_9$ or $X_{10}$ are all C, then R cannot be aryl.

In various embodiments, this invention is directed to a compound represented by the structure of formula (III)

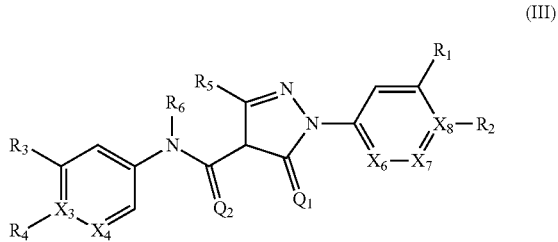

(III)

wherein $R_1$ and $R_2$ are each independently H, D, F, Cl, Br, I, OH, SH, $R_8$—OH (e.g., $CH_2$—OH), $R_8$—SH, —$R_8$—O—$R_{10}$, (e.g., —$CH_2$—O—$CH_3$), $R_8$-aryl (e.g., $CH_2$-3-methoxy-phenyl, benzyl, $CH_2$-1-methoxy-phenyl, $CH_2$-4-chloro-phenyl, $CH_2CH_2$-phenyl), $CF_3$, $CD_3$, $OCD_3$, CN, $NO_2$, —$CH_2CN$, —$R_8CN$, $NH_2$, NHR, $N(R)_2$, $R_8$—$N(R_{10})(R_{11})$ (e.g., $CH_2$—$NH_2$, $CH_2$—N$(CH_3)_2$), $R_9$—$R_8$—$N(R_{10})(R_{11})$ (e.g., C≡C—$CH_2$—$NH_2$), $B(OH)_2$, —$OC(O)CF_3$, —$OCH_2Ph$, NHC(O)—$R_{10}$ (e.g., $NHC(O)CH_3$), NHCO—$N(R_{10})(R_{11})$ (e.g., $NHC(O)N(CH_3)_2$), COOH, —C(O)Ph, —C(O)-aryl (e.g., C(O)-1-methyl-phenyl, C(O)-4-methyl-phenyl, C(O)-3-methyl-phenyl, C(O)-phenol, C(O)-4-hydroxyphenyl, C(O)-3-hydroxy-phenyl), C(O)-2-hydroxyphenyl, C(O)O—$R_{10}$ (e.g. C(O)O—$CH_3$, C(O)O—CH$(CH_3)_2$, C(O)O—$CH_2CH_3$), $R_8$—C(O)—$R_{10}$ (e.g., $CH_2C(O)CH_3$), C(O)H, C(O)—$R_{10}$ (e.g., C(O)—$CH_3$, C(O)—$CH_2CH_3$, C(O)—$CH_2CH_2CH_3$), $C_1$-$C_5$ linear or branched C(O)-haloalkyl (e.g., C(O)—$CF_3$), —C(O)$NH_2$, C(O)NHR, C(O)$N(R_{10})(R_{11})$ (e.g., C(O)N$(CH_3)_2$), $SO_2R$ (e.g., $SO_2$-Ph, $SO_2$-toluene, $SO_2$—$CH_3$), $SO_2N(R_{10})(R_{11})$ (e.g., $SO_2N(CH_3)_2$, $SO_2NHC(O)CH_3$), $C_1$-$C_5$ linear or branched, substituted or unsubstituted alkyl (e.g., methyl, 2, 3, or 4-$CH_2$—$C_6H_4$—Cl, ethyl, propyl, iso-propyl, cyclopropyl, t-Bu, iso-butyl, pentyl, benzyl, $C(CH_3)(OH)Ph$, $CH_2$-3-methoxy-phenyl, $CH_2$-1-methoxy-phenyl, $CH_2$-4-chloro-phenyl, $CH_2CH_2$-phenyl), $C_1$-$C_5$ linear or branched haloalkyl (e.g., $CF_3$, $CF_2CH_3$, $CH_2CF_3$, $CF_2CH_2CH_3$, $CH_2CH_2CF_3$, $CF_2CH(CH_3)_2$, $CF(CH_3)$—$CH(CH_3)_2$, $CF_2CH$-cyclopropyl), substituted or unsubstituted $C_1$-$C_5$ linear or branched or $C_3$-$C_8$ cyclic alkoxy (e.g. methoxy, ethoxy, propoxy, isopropoxy, O—$CH_2$-cyclopropyl, O-cyclobutyl, O-cyclopentyl, O-cyclohexyl, 1-butoxy, 2-butoxy, O-tBu), optionally wherein at least one methylene group ($CH_2$) in the alkoxy is replaced with an oxygen atom (e.g., O-1-oxacyclobutyl, O-2-oxacyclobutyl), $C_1$-$C_5$ linear or branched thioalkoxy (e.g., S—$CH_3$), $C_1$-$C_5$ linear or branched haloalkoxy (e.g., $OCF_3$, $OCHF_2$), $C_1$-$C_5$ linear or branched alkoxyalkyl, substituted or unsubstituted $C_3$-$C_8$ cycloalkyl (e.g., cyclopropyl, cyclopentyl), substituted or unsubstituted $C_3$-$C_8$ heterocyclic ring (e.g., 3-methyl-4H-1,2,4-triazole, 5-methyl-1,2,4-oxadiazole, thiophene, oxazole, oxadiazole, imidazole, furane, triazole, tetrazole, pyridine (2, 3, or 4-pyridine), 2-methyl-4-pyridine, 2,6-dimethyl-4-pyridine, 3,5-dimethyl-4-pyridine, 2,5-dimethyl-4-pyridine, 3-methyl-4-pyridine, 5-methyl-2-pyridine, 3-methyl-2-pyridine, 3-ethyl-2-pyridine, 3-isopropyl-2-pyridine, 3-propyl-2-pyridine, 3-phenyl-2-pyridine, 4-methyl-2-pyridine, 6-methyl-2-pyridine, 5-methyl-2-pyridine, pyrimidine, 5-methyl-pyrimidine, pyrazine, oxacyclobutane (1 or 2-oxacyclobutane), indole, protonated or deprotonated pyridine oxide), substituted or unsubstituted aryl (e.g., phenyl) (wherein substitutions include: F, Cl, Br, I, $C_1$-$C_5$ linear or branched alkyl (e.g. methyl, ethyl, propyl, isopropyl), OH, alkoxy, $N(R)_2$, $CF_3$, aryl, phenyl, halophenyl, (benzyloxy)phenyl, CN, $NO_2$ or any combination thereof), $CH(CF_3)(NH$—$R_{10})$;

or $R_2$ and $R_1$ are joint together to form a 5 or 6 membered substituted or unsubstituted, aliphatic or aromatic, carbocyclic or heterocyclic single or fused ring (e.g., [1,3]dioxole, furan-2(3H)-one, benzene, pyridine, pyrrol, 1-methyl-1H-pyrrole, 1-benzyl-1H-pyrrole, 7,8-dihydro-5H-pyrano[4,3-b]pyridine);

$R_3$ and $R_4$ are each independently H, F, Cl, Br, I, OH, SH, $R_8$—OH (e.g., $CH_2$—OH), $R_8$—SH, —$R_8$—O—$R_{10}$, (e.g., $CH_2$—O—$CH_3$) $CF_3$, $CD_3$, $OCD_3$, CN, $NO_2$, —$CH_2CN$, —$R_8CN$, $NH_2$, NHR, $N(R)_2$, $R_8$—$N(R_{10})(R_{11})$ (e.g., $CH_2$—$NH_2$, $CH_2$—$N(CH_3)_2$), $R_8$—C(O)N$(R_{10})(R_{11})$ (e.g., $CF_2C(O)N[(CH_3)(OCH_3)]$) $R_9$—$R_8$—$N(R_{10})(R_{11})$, $B(OH)_2$, —$OC(O)CF_3$, —$OCH_2Ph$, —NHCO—$R_{10}$ (e.g., $NHC(O)CH_3$), NHCO—$N(R_{10})(R_{11})$ (e.g., $NHC(O)N(CH_3)_2$), COOH, —C(O)Ph, C(O)O—$R_{10}$ (e.g. C(O)O—$CH_3$, C(O)O—$CH_2CH_3$), $R_8$—C(O)—$R_{10}$ (e.g., $CH_2C(O)CH_3$), C(O)H, C(O)—$R_{10}$ (e.g., C(O)—$CH_3$, C(O)—$CH_2CH_3$, C(O)—$CH_2CH_2CH_3$), $C_1$-$C_5$ linear or branched C(O)-haloalkyl (e.g., C(O)—$CF_3$), —C(O)$NH_2$, C(O)NHR, C(O)$N(R_{10})(R_{11})$ (e.g., C(O)N$(CH_3)_2$), $SO_2R$, $SO_2N(R_{10})$ ($R_{11}$) (e.g., $SO_2N(CH_3)_2$), substituted or unsubstituted $C_1$-$C_5$ linear or branched or $C_3$-$C_8$ cyclic alkyl (e.g., methyl, $C(OH)(CH_3)(Ph)$, ethyl, propyl, iso-propyl, t-Bu, iso-butyl, 2-butyl, pentyl, tert-pentyl, 1-ethylcyclopropyl, $C(CH_3)(OH)Ph$), substituted or unsubstituted $C_1$-$C_5$ linear or branched or $C_3$-$C_8$ cyclic haloalkyl (e.g., $CF_3$, $CF_2CH_3$, $CH_2CF_3$, $CF_2CH_2CH_3$, $CF_2CHFCH_3$, $CHFCHFCH_3$, $CH_2CH_2CF_3$, $CF_2CH(CH_3)_2$, $CF(CH_3)$—$CH(CH_3)_2$, $CF_2$-cyclopropyl, $CF_2$-cyclopentyl), substituted or unsubstituted $C_1$-$C_5$ linear or branched or $C_3$-$C_8$ cyclic haloalkenyl (e.g. CF=CH—$CH_3$ E, Z, CF=C—$(CH_3)_2$), substituted or unsubstituted $C_1$-$C_5$ linear or branched or $C_3$-$C_8$ cyclic alkoxy (e.g. methoxy, ethoxy, propoxy, isopropoxy, O—$CH_2$-cyclopropyl), $C_1$-$C_5$ linear or branched thioalkoxy, $C_1$-$C_5$ linear or branched haloalkoxy, $C_1$-$C_5$ linear or branched alkoxyalkyl, substituted or unsubstituted $C_3$-$C_8$ cycloalkyl (e.g., cyclopropyl, cyclopentyl), substituted or unsubstituted $C_3$-$C_8$ heterocyclic ring (e.g., 3-methyl-4H-1,2,4-triazole, 5-methyl-1,2,4-oxadiazole, thiophene, oxazole, isoxazole, imidazole, furane, pyrrole, 1-methyl-pyrrol, imidazole, 1-methyl-imidazole, triazole, pyridine (2, 3, or 4-pyridine), pyrimidine, pyrazine, oxacyclobutane (1 or 2-oxacyclobutane), indole), substituted or unsubstituted aryl (e.g., phenyl), (wherein substitutions include: F, Cl, Br, I, $C_1$-$C_5$ linear or branched alkyl, OH, alkoxy, $N(R)_2$, $CF_3$, aryl, phenyl, halophenyl, (benzyloxy)phenyl, CN, $NO_2$ or any combination thereof), $CH(CF_3)(NH$—$R_{10})$; or $R_3$ and $R_4$ are joint together to form a 5 or 6 membered substituted or unsubstituted, aliphatic or aromatic, carbocyclic or heterocyclic ring (e.g., [1,3]dioxole, furan-2(3H)-one, benzene, cyclopentane, imidazole, pyrrol);

$R_5$ is H, $C_1$-$C_5$ linear or branched, substituted or unsubstituted alkyl (e.g., methyl, $CH_2SH$, ethyl, iso-propyl), $C_1$-$C_5$ linear or branched haloalkyl (e.g., $CF_3$, $CF_2CH_3$, $CH_2CF_3$, $CF_2CH_2CH_3$, $CH_2CH_2CF_3$, $CF_2CH(CH_3)_2$, $CF(CH_3)$—$CH(CH_3)_2$), $R_8$-aryl (e.g., $CH_2$-Ph), $C(O)$—$R_{10}$ (e.g., $C(O)$—$CH_3$), substituted or unsubstituted aryl (e.g., phenyl), substituted or unsubstituted heteroaryl (e.g., pyridine (2, 3, and 4-pyridine), (wherein substitutions include: F, Cl, Br, I, $C_1$-$C_5$ linear or branched alkyl, OH, alkoxy, $N(R)_2$, $CF_3$, phenyl, halophenyl, (benzyloxy)phenyl, CN, $NO_2$ or any combination thereof);

$R_6$ is H, $C_1$-$C_5$ linear or branched alkyl (e.g., methyl), $C(O)R$, or $S(O)_2R$;

$R_8$ is $[CH_2]_p$ or $[CF_2]_p$
wherein p is between 1 and 10;

$R_9$ is $[CH]_q$, $[C]_q$
wherein q is between 2 and 10;

$R_{10}$ and Ru are each independently H, $C_1$-$C_5$ linear or branched alkyl (e.g., methyl, ethyl), $C(O)R$, or $S(O)_2R$;

R is H, $C_1$-$C_5$ linear or branched alkyl (e.g., methyl, ethyl), $C_1$-$C_5$ linear or branched alkoxy, phenyl, aryl (e.g., toluene) or heteroaryl, or two gem R substituents are joint together to form a 5 or 6 membered heterocyclic ring;

$Q_1$ and $Q_2$ are each independently S, O, N—OH, $CH_2$, $C(R)_2$ or N—OMe;

$X_3$ and $X_4$ are each independently C or N, wherein if $X_3$ is N, then $R_4$ is absent;

$X_6$, $X_7$ and $X_8$ are each independently C or N, wherein if $X_8$ is N, then $R_2$ is absent;

or its pharmaceutically acceptable salt, optical isomer, tautomer, hydrate, N-oxide, reverse amide analog, prodrug, isotopic variant (e.g., deuterated analog), PROTAC, pharmaceutical product or any combination thereof.

In various embodiments, if $X_3$, $X_4$, $X_6$, $X_7$, or $X_8$ are all C, then $R_1$, $R_2$, $R_3$ and $R_4$ cannot be H, alkyl, alkoxy, halide, or $CF_3$. In some embodiments, $R_1$ and $R_2$ cannot be both H. In some embodiments, $R_3$ and $R_4$ cannot be both H. In some embodiments, if $X_3$, $X_4$, $X_6$, $X_7$, or $X_8$ are all C, then $R_5$ cannot be aryl.

In various embodiments, this invention is directed to a compound represented by the structure of formula (IV)

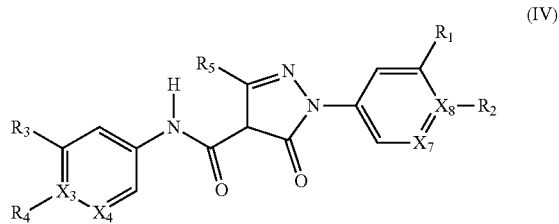

(IV)

wherein $R_1$ and $R_2$ are each independently H, D, F, Cl, Br, I, OH, SH, $R_8$—OH (e.g., $CH_2$—OH), $R_8$—SH, —$R_8$—O—$R_{10}$, (e.g., —$CH_2$—O—$CH_3$), $R_8$-aryl (e.g., $CH_2$-3-methoxy-phenyl, benzyl, $CH_2$-1-methoxy-phenyl, $CH_2$-4-chloro-phenyl, $CH_2CH_2$-phenyl), $CF_3$, $CD_3$, $OCD_3$, CN, $NO_2$, —$CH_2CN$, —$R_8CN$, $NH_2$, NHR, $N(R)_2$, $R_8$—$N(R_{10})(R_{11})$ (e.g., $CH_2$—$NH_2$, $CH_2$—N$(CH_3)_2$), $R_9$—$R_8$—$N(R_{10})(R_{11})$ (e.g., C≡C—$CH_2$—$NH_2$), $B(OH)_2$, —$OC(O)CF_3$, —$OCH_2Ph$, $NHC(O)$—$R_{10}$ (e.g., $NHC(O)CH_3$), NHCO—$N(R_{10})(R_{11})$ (e.g., $NHC(O)N(CH_3)_2$), COOH, —$C(O)Ph$, —$C(O)$-aryl (e.g., C(O)-1-methyl-phenyl, C(O)-4-methyl-phenyl, C(O)-3-methyl-phenyl, C(O)-phenol, C(O)-4-hydroxy-phenyl, C(O)-3-hydroxy-phenyl), C(O)-2-hydroxy-phenyl, C(O)O—$R_{10}$ (e.g. C(O)O—$CH_3$, C(O)O—CH$(CH_3)_2$, C(O)O—$CH_2CH_3$), $R_8$—C(O)—$R_{10}$ (e.g., $CH_2C(O)CH_3$), C(O)H, C(O)—$R_{10}$ (e.g., C(O)—$CH_3$, C(O)—$CH_2CH_3$, C(O)—$CH_2CH_2CH_3$), $C_1$-$C_5$ linear or branched C(O)-haloalkyl (e.g., C(O)—$CF_3$), —C(O)$NH_2$, C(O)NHR, C(O)N$(R_{10})(R_{11})$ (e.g., C(O)N$(CH_3)_2$), $SO_2R$ (e.g., $SO_2$-Ph, $SO_2$-toluene, $SO_2$—$CH_3$), $SO_2N(R_{10})(R_{11})$ (e.g., $SO_2N(CH_3)_2$, $SO_2NHC(O)CH_3$), $C_1$-$C_5$ linear or branched, substituted or unsubstituted alkyl (e.g., methyl, 2, 3, or 4-$CH_2$—$C_6H_4$—Cl, ethyl, propyl, iso-propyl, cyclopropyl, t-Bu, iso-butyl, pentyl, benzyl, $C(CH_3)(OH)Ph$, $CH_2$-3-methoxy-phenyl, $CH_2$-1-methoxy-phenyl, $CH_2$-4-chloro-phenyl, $CH_2CH_2$-phenyl), $C_1$-$C_5$ linear or branched haloalkyl (e.g., $CF_3$, $CF_2CH_3$, $CH_2CF_3$, $CF_2CH_2CH_3$, $CH_2CH_2CF_3$, $CF_2CH(CH_3)_2$, $CF(CH_3)$—$CH(CH_3)_2$, $CF_2CH$-cyclopropyl), substituted or unsubstituted $C_1$-$C_5$ linear or branched or $C_3$-$C_8$ cyclic alkoxy (e.g. methoxy, ethoxy, propoxy, isopropoxy, O—$CH_2$-cyclopropyl, O-cyclobutyl, O-cyclopentyl, O-cyclohexyl, 1-butoxy, 2-butoxy, O-tBu), optionally wherein at least one methylene group ($CH_2$) in the alkoxy is replaced with an oxygen atom (e.g., O-1-oxacyclobutyl, O-2-oxacyclobutyl), $C_1$-$C_5$ linear or branched thioalkoxy (e.g., S—$CH_3$), $C_1$-$C_5$ linear or branched haloalkoxy (e.g., $OCF_3$, $OCHF_2$), $C_1$-$C_5$ linear or branched alkoxyalkyl, substituted or unsubstituted $C_3$-$C_8$ cycloalkyl (e.g., cyclopropyl, cyclopentyl), substituted or unsubstituted $C_3$-$C_8$ heterocyclic ring (e.g., 3-methyl-4H-1,2,4-triazole, 5-methyl-1,2,4-oxadiazole, thiophene, oxazole, oxadiazole, imidazole, furane, triazole, tetrazole, pyridine (2, 3, or 4-pyridine), 2-methyl-4-pyridine, 2,6-dimethyl-4-pyridine, 3,5-dimethyl-4-pyridine, 2,5-dimethyl-4-pyridine, 3-methyl-4-pyridine, 5-methyl-2-pyridine, 3-methyl-2-pyridine, 3-ethyl-2-pyridine, 3-isopropyl-2-pyridine, 3-propyl-2-pyridine, 3-phenyl-2-pyridine, 4-methyl-2-pyridine, 6-methyl-2-pyridine, 5-methyl-2-pyridine, pyrimidine, 5-methyl-pyrimidine, pyrazine, oxacyclobutane (1 or 2-oxacyclobutane), indole, protonated or deprotonated pyridine oxide), substituted or unsubstituted aryl (e.g., phenyl) (wherein substitutions include: F, Cl, Br, I, $C_1$-$C_5$ linear or branched alkyl (e.g. methyl, ethyl, propyl, isopropyl), OH, alkoxy, $N(R)_2$, $CF_3$, aryl, phenyl, halophenyl, (benzyloxy)phenyl, CN, $NO_2$ or any combination thereof), $CH(CF_3)(NH-R_{10})$;

or $R_2$ and $R_1$ are joint together to form a 5 or 6 membered substituted or unsubstituted, aliphatic or aromatic, carbocyclic or heterocyclic single or fused ring (e.g., [1,3]dioxole, furan-2(3H)-one, benzene, pyridine, pyrrol, 1-methyl-1H-pyrrole, 1-benzyl-1H-pyrrole, 7,8-dihydro-5H-pyrano[4,3-b]pyridine);

$R_3$ and $R_4$ are each independently H, F, Cl, Br, I, OH, SH, $R_8$—OH (e.g., $CH_2$—OH), $R_8$—SH, —$R_8$—O—$R_{10}$, (e.g., $CH_2$—O—$CH_3$) $CF_3$, $CD_3$, $OCD_3$, CN, $NO_2$, —$CH_2CN$, —$R_8CN$, $NH_2$, NHR, $N(R)_2$, $R_8$—$N(R_{10})(R_{11})$ (e.g., $CH_2$—$NH_2$, $CH_2$—$N(CH_3)_2$), $R_8$—$C(O)N(R_{10})(R_{11})$ (e.g., $CF_2C(O)N[(CH_3)(OCH_3)])$ $R_9$—$R_8$—$N(R_{10})(R_{11})$, $B(OH)_2$, —$OC(O)CF_3$, —$OCH_2Ph$, —NHCO—$R_{10}$ (e.g., $NHC(O)CH_3$), NHCO—$N(R_{10})(R_{11})$ (e.g., $NHC(O)N(CH_3)_2$), COOH, —$C(O)Ph$, $C(O)O$—$R_{10}$ (e.g. $C(O)O$—$CH_3$, $C(O)O$—$CH_2CH_3$), $R_8$—$C(O)$—$R_{10}$ (e.g., $CH_2C(O)CH_3$), $C(O)H$, $C(O)$—$R_{10}$ (e.g., $C(O)$—$CH_3$, $C(O)$—$CH_2CH_3$, $C(O)$—$CH_2CH_2CH_3$), $C_1$-$C_5$ linear or branched C(O)-haloalkyl (e.g., $C(O)$—$CF_3$), —$C(O)NH_2$, C(O)NHR, $C(O)N(R_{10})(R_{11})$ (e.g., $C(O)N(CH_3)_2$), $SO_2R$, $SO_2N(R_{10})(R_{11})$ (e.g., $SO_2N(CH_3)_2$), substituted or unsubstituted $C_1$-$C_5$ linear or branched or $C_3$-$C_8$ cyclic alkyl (e.g., methyl, $C(OH)(CH_3)(Ph)$, ethyl, propyl, iso-propyl, t-Bu, iso-butyl, 2-butyl, pentyl, tert-pentyl, 1-ethylcyclopropyl, $C(CH_3)(OH)Ph)$, substituted or unsubstituted $C_1$-$C_5$ linear or branched or $C_3$-$C_8$ cyclic haloalkyl (e.g., $CF_3$, $CF_2CH_3$, $CH_2CF_3$, $CF_2CH_2CH_3$, $CF_2CHFCH_3$, $CHFCHFCH_3$, $CH_2CH_2CF_3$, $CF_2CH(CH_3)_2$, $CF(CH_3)$—$CH(CH_3)_2$, $CF_2$-cyclopropyl, $CF_2$-cyclopentyl), substituted or unsubstituted $C_1$-$C_5$ linear or branched or $C_3$-$C_8$ cyclic haloalkenyl (e.g. CF=CH—$CH_3$ E, Z, CF=C—$(CH_3)_2$), substituted or unsubstituted $C_1$-$C_5$ linear or branched or $C_3$-$C_8$ cyclic alkoxy (e.g. methoxy, ethoxy, propoxy, isopropoxy, O—$CH_2$-cyclopropyl), $C_1$-$C_5$ linear or branched thioalkoxy, $C_1$-$C_5$ linear or branched haloalkoxy, $C_1$-$C_5$ linear or branched alkoxyalkyl, substituted or unsubstituted $C_3$-$C_8$ cycloalkyl (e.g., cyclopropyl, cyclopentyl), substituted or unsubstituted $C_3$-$C_8$ heterocyclic ring (e.g., 3-methyl-4H-1,2,4-triazole, 5-methyl-1,2,4-oxadiazole, thiophene, oxazole, isoxazole, imidazole, furane, pyrrole, 1-methyl-pyrrol, imidazole, 1-methyl-imidazole, triazole, pyridine (2, 3, or 4-pyridine), pyrimidine, pyrazine, oxacyclobutane (1 or 2-oxacyclobutane), indole, substituted or unsubstituted aryl (e.g., phenyl), (wherein substitutions include: F, Cl, Br, I, $C_1$-$C_5$ linear or branched alkyl, OH, alkoxy, $N(R)_2$, $CF_3$, aryl, phenyl, halophenyl, (benzyloxy)phenyl, CN, $NO_2$ or any combination thereof), $CH(CF_3)(NH-R_{10})$;

or $R_3$ and $R_4$ are joint together to form a 5 or 6 membered substituted or unsubstituted, aliphatic or aromatic, carbocyclic or heterocyclic ring (e.g., [1,3]dioxole, furan-2(3H)-one, benzene, cyclopentane, imidazole, pyrrol);

$R_5$ is H, $C_1$-$C_5$ linear or branched, substituted or unsubstituted alkyl (e.g., methyl, $CH_2SH$, ethyl, iso-propyl), $C_1$-$C_5$ linear or branched haloalkyl (e.g., $CF_3$, $CF_2CH_3$, $CH_2CF_3$, $CF_2CH_2CH_3$, $CH_2CH_2CF_3$, $CF_2CH(CH_3)_2$, $CF(CH_3)$—$CH(CH_3)_2$), $R_8$-aryl (e.g., $CH_2$-Ph), $C(O)$—$R_{10}$ (e.g., $C(O)$—$CH_3$), substituted or unsubstituted aryl (e.g., phenyl), substituted or unsubstituted heteroaryl (e.g., pyridine (2, 3, and 4-pyridine), (wherein substitutions include: F, Cl, Br, I, $C_1$-$C_5$ linear or branched alkyl, OH, alkoxy, $N(R)_2$, $CF_3$, phenyl, halophenyl, (benzyloxy)phenyl, CN, $NO_2$ or any combination thereof);

$R_8$ is $[CH_2]_p$ or $[CF_2]_p$
wherein p is between 1 and 10;

$R_9$ is $[CH]_q$, $[C]_q$
wherein q is between 2 and 10;

$R_{10}$ and Ru are each independently H, $C_1$-$C_5$ linear or branched alkyl (e.g., methyl, ethyl), C(O)R, or $S(O)_2R$;

R is H, $C_1$-$C_5$ linear or branched alkyl (e.g., methyl, ethyl), $C_1$-$C_5$ linear or branched alkoxy, phenyl, aryl (e.g., toluene) or heteroaryl, or two gem R substituents are joint together to form a 5 or 6 membered heterocyclic ring;

$X_3$ and $X_4$ are each independently C or N, wherein if $X_3$ is N, then $R_4$ is absent;

$X_7$ and $X_8$ are each independently C or N, wherein if $X_8$ is N, then $R_2$ is absent;

or its pharmaceutically acceptable salt, optical isomer, tautomer, hydrate, N-oxide, reverse amide analog, prodrug, isotopic variant (e.g., deuterated analog), PROTAC, pharmaceutical product or any combination thereof.

In various embodiments, if $X_3$, $X_4$, $X_7$, or $X_8$ are all C, then $R_1$, $R_2$, $R_3$ and $R_4$ cannot be H, alkyl, alkoxy, halide, or $CF_3$. In some embodiments, $R_1$ and $R_2$ cannot be both H. In some embodiments, $R_3$ and $R_4$ cannot be both H. In some embodiments, if $X_3$, $X_4$, $X_7$, or $X_8$ are all C, then $R_5$ cannot be aryl.

In various embodiments, this invention is directed to a compound represented by the structure of formula (V)

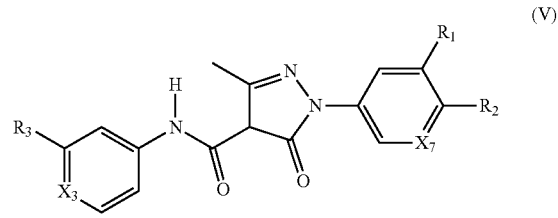

wherein
$R_1$ and $R_2$ are each independently H, D, F, Cl, Br, I, OH, SH, $R_8$—OH (e.g., $CH_2$—OH), $R_8$—SH, —$R_8$—O—$R_{10}$, (e.g., —$CH_2$—O—$CH_3$), $R_8$-aryl (e.g., $CH_2$-3-methoxy-phenyl, benzyl, $CH_2$-1-methoxy-phenyl, $CH_2$-4-chloro-phenyl, $CH_2CH_2$-phenyl), $CF_3$, $CD_3$, $OCD_3$, CN, $NO_2$, —$CH_2CN$, —$R_8CN$, $NH_2$, NHR, $N(R)_2$, $R_8$—$N(R_{10})(R_{11})$ (e.g., $CH_2$—$NH_2$, $CH_2$—$N(CH_3)_2$), $R_9$—$R_8$—$N(R_{10})(R_{11})$ (e.g., C≡C—$CH_2$—$NH_2$), $B(OH)_2$, —$OC(O)CF_3$, —$OCH_2Ph$, NHC(O)—$R_{10}$ (e.g., $NHC(O)CH_3$), NHCO—$N(R_{10})(R_{11})$ (e.g., NHC(O)N(CH$_3$)$_2$), COOH, —C(O)Ph, —C(O)-aryl (e.g., C(O)-1-methyl-phenyl, C(O)-4-methyl-phenyl, C(O)-3-methyl-phenyl, C(O)-phenol, C(O)-4-hydroxyphenyl, C(O)-3-hydroxy-phenyl), C(O)-2-hydroxyphenyl, C(O)O—R$_{10}$ (e.g. C(O)O—CH$_3$, C(O)O—CH(CH$_3$)$_2$, C(O)O—CH$_2$CH$_3$), R$_8$—C(O)—R$_{10}$ (e.g., CH$_2$C(O)CH$_3$), C(O)H, C(O)—R$_{10}$ (e.g., C(O)—CH$_3$, C(O)—CH$_2$CH$_3$, C(O)—CH$_2$CH$_2$CH$_3$), C$_1$-C$_5$ linear or branched C(O)-haloalkyl (e.g., C(O)—CF$_3$), —C(O)NH$_2$, C(O)NHR, C(O)N(R$_{10}$)(R$_{11}$) (e.g., C(O)N(CH$_3$)$_2$), SO$_2$R (e.g., SO$_2$-Ph, SO$_2$-toluene, SO$_2$—CH$_3$), SO$_2$N(R$_{10}$)(R$_{11}$) (e.g., SO$_2$N(CH$_3$)$_2$, SO$_2$NHC(O)CH$_3$), C$_1$-C$_5$ linear or branched, substituted or unsubstituted alkyl (e.g., methyl, 2, 3, or 4-CH$_2$—C$_6$H$_4$—Cl, ethyl, propyl, iso-propyl, cyclopropyl, t-Bu, iso-butyl, pentyl, benzyl, C(CH$_3$)(OH)Ph, CH$_2$-3-methoxy-phenyl, CH$_2$-1-methoxy-phenyl, CH$_2$-4-chloro-phenyl, CH$_2$CH$_2$-phenyl), C$_1$-C$_5$ linear or branched haloalkyl (e.g., CF$_3$, CF$_2$CH$_3$, CH$_2$CF$_3$, CF$_2$CH$_2$CH$_3$, CH$_2$CH$_2$CF$_3$, CF$_2$CH(CH$_3$)$_2$, CF(CH$_3$)—CH(CH$_3$)$_2$, CF$_2$CH-cyclopropyl), substituted or unsubstituted C$_1$-C$_5$ linear or branched or C$_3$-C$_8$ cyclic alkoxy (e.g. methoxy, ethoxy, propoxy, isopropoxy, O—CH$_2$-cyclopropyl, O-cyclobutyl, O-cyclopentyl, O-cyclohexyl, 1-butoxy, 2-butoxy, O-tBu), optionally wherein at least one methylene group (CH$_2$) in the alkoxy is replaced with an oxygen atom (e.g., O-1-oxacyclobutyl, O-2-oxacyclobutyl), C$_1$-C$_5$ linear or branched thioalkoxy (e.g., S—CH$_3$), C$_1$-C$_5$ linear or branched haloalkoxy (e.g., OCF$_3$, OCHF$_2$), C$_1$-C$_5$ linear or branched alkoxyalkyl, substituted or unsubstituted C$_3$-C$_8$ cycloalkyl (e.g., cyclopropyl, cyclopentyl), substituted or unsubstituted C$_3$-C$_8$ heterocyclic ring (e.g., 3-methyl-4H-1,2,4-triazole, 5-methyl-1,2,4-oxadiazole, thiophene, oxazole, oxadiazole, imidazole, furane, triazole, tetrazole, pyridine (2, 3, or 4-pyridine), 2-methyl-4-pyridine, 2,6-dimethyl-4-pyridine, 3,5-dimethyl-4-pyridine, 2,5-dimethyl-4-pyridine, 3-methyl-4-pyridine, 5-methyl-2-pyridine, 3-methyl-2-pyridine, 3-ethyl-2-pyridine, 3-isopropyl-2-pyridine, 3-propyl-2-pyridine, 3-phenyl-2-pyridine, 4-methyl-2-pyridine, 6-methyl-2-pyridine, 5-methyl-2-pyridine, pyrimidine, 5-methyl-pyrimidine, pyrazine, oxacyclobutane (1 or 2-oxacyclobutane), indole, protonated or deprotonated pyridine oxide), substituted or unsubstituted aryl (e.g., phenyl) (wherein substitutions include: F, Cl, Br, I, C$_1$-C$_5$ linear or branched alkyl (e.g. methyl, ethyl, propyl, isopropyl), OH, alkoxy, N(R)$_2$, CF$_3$, aryl, phenyl, halophenyl, (benzyloxy)phenyl, CN, NO$_2$ or any combination thereof), CH(CF$_3$)(NH—R$_{10}$);

or R$_2$ and R$_1$ are joint together to form a 5 or 6 membered substituted or unsubstituted, aliphatic or aromatic, carbocyclic or heterocyclic single or fused ring (e.g., [1,3]dioxole, furan-2(3H)-one, benzene, pyridine, pyrrol, 1-methyl-1H-pyrrole, 1-benzyl-1H-pyrrole, 7,8-dihydro-5H-pyrano[4,3-b]pyridine);

R$_3$ is H, F, Cl, Br, I, OH, SH, R$_8$—OH (e.g., CH$_2$—OH), R$_8$—SH, —R$_8$—O—R$_{10}$, (e.g., CH$_2$—O—CH$_3$) CF$_3$, CD$_3$, OCD$_3$, CN, NO$_2$, —CH$_2$CN, —R$_8$CN, NH$_2$, NHR, N(R)$_2$, R$_8$—N(R$_{10}$)(R$_{11}$) (e.g., CH$_2$—NH$_2$, CH$_2$—N(CH$_3$)$_2$), R$_8$—C(O)N(R$_{10}$)(R$_{11}$) (e.g., CF$_2$C(O)N[(CH$_3$)(OCH$_3$)]) R$_9$—R$_8$—N(R$_{10}$)(R$_{11}$), B(OH)$_2$, —OC(O)CF$_3$, —OCH$_2$Ph, —NHCO—R$_{10}$ (e.g., NHC(O)CH$_3$), NHCO—N(R$_{10}$)(R$_{11}$) (e.g., NHC(O)N(CH$_3$)$_2$), COOH, —C(O)Ph, C(O)O—R$_{10}$ (e.g. C(O)O—CH$_3$, C(O)O—CH$_2$CH$_3$), R$_8$—C(O)—R$_{10}$ (e.g., CH$_2$C(O)CH$_3$), C(O)H, C(O)—R$_{10}$ (e.g., C(O)—CH$_3$, C(O)—CH$_2$CH$_3$, C(O)—CH$_2$CH$_2$CH$_3$), C$_1$-C$_5$ linear or branched C(O)-haloalkyl (e.g., C(O)—CF$_3$), —C(O)NH$_2$, C(O)NHR, C(O)N(R$_{10}$)(R$_{11}$) (e.g., C(O)N(CH$_3$)$_2$), SO$_2$R, SO$_2$N(R$_{10}$)(R$_{11}$) (e.g., SO$_2$N(CH$_3$)$_2$), substituted or unsubstituted C$_1$-C$_5$ linear or branched or C$_3$-C$_8$ cyclic alkyl (e.g., methyl, C(OH)(CH$_3$)(Ph), ethyl, propyl, iso-propyl, t-Bu, iso-butyl, 2-butyl, pentyl, tert-pentyl, 1-ethylcyclopropyl, C(CH$_3$)(OH)Ph), substituted or unsubstituted C$_1$-C$_5$ linear or branched or C$_3$-C$_8$ cyclic haloalkyl (e.g., CF$_3$, CF$_2$CH$_3$, CH$_2$CF$_3$, CF$_2$CH$_2$CH$_3$, CF$_2$CHFCH$_3$, CHFCHFCH$_3$, CH$_2$CH$_2$CF$_3$, CF$_2$CH(CH$_3$)$_2$, CF(CH$_3$)—CH(CH$_3$)$_2$, CF$_2$-cyclopropyl, CF$_2$-cyclopentyl), substituted or unsubstituted C$_1$-C$_5$ linear or branched or C$_3$-C$_8$ cyclic haloalkenyl (e.g. CF═CH—CH$_3$ E, Z, CF═C—(CH$_3$)$_2$), substituted or unsubstituted C$_1$-C$_5$ linear or branched or C$_3$-C$_8$ cyclic alkoxy (e.g. methoxy, ethoxy, propoxy, isopropoxy, O—CH$_2$-cyclopropyl), C$_1$-C$_5$ linear or branched thioalkoxy, C$_1$-C$_5$ linear or branched haloalkoxy, C$_1$-C$_5$ linear or branched alkoxyalkyl, substituted or unsubstituted C$_3$-C$_8$ cycloalkyl (e.g., cyclopropyl, cyclopentyl), substituted or unsubstituted C$_3$-C$_8$ heterocyclic ring (e.g., 3-methyl-4H-1,2,4-triazole, 5-methyl-1,2,4-oxadiazole, thiophene, oxazole, isoxazole, imidazole, furane, pyrrole, 1-methyl-pyrrol, imidazole, 1-methyl-imidazole, triazole, pyridine (2, 3, or 4-pyridine), pyrimidine, pyrazine, oxacyclobutane (1 or 2-oxacyclobutane), indole), substituted or unsubstituted aryl (e.g., phenyl), (wherein substitutions include: F, Cl, Br, I, C$_1$-C$_5$ linear or branched alkyl, OH, alkoxy, N(R)$_2$, CF$_3$, aryl, phenyl, halophenyl, (benzyloxy)phenyl, CN, NO$_2$ or any combination thereof), CH(CF$_3$)(NH—R$_{10}$);

R$_8$ is [CH$_2$]$_p$ or [CF$_2$]$_p$ wherein p is between 1 and 10;

R$_9$ is [CH]$_q$, [C]$_q$ wherein q is between 2 and 10;

R$_{10}$ and Ru are each independently H, C$_1$-C$_5$ linear or branched alkyl (e.g., methyl, ethyl), C(O)R, or S(O)$_2$R;

R is H, C$_1$-C$_5$ linear or branched alkyl (e.g., methyl, ethyl), C$_1$-C$_5$ linear or branched alkoxy, phenyl, aryl (e.g., toluene) or heteroaryl, or two gem R substituents are joint together to form a 5 or 6 membered heterocyclic ring;

X$_3$ and X$_7$ are each independently C or N;

or its pharmaceutically acceptable salt, optical isomer, tautomer, hydrate, N-oxide, reverse amide analog, prodrug, isotopic variant (e.g., deuterated analog), PROTAC, pharmaceutical product or any combination thereof.

In various embodiments, if X$_3$ and X$_7$ are both C, then R$_1$, R$_2$, and R$_3$ cannot be H, alkyl, alkoxy, halide, or CF$_3$. In some embodiments, R$_1$ and R$_2$ cannot be both H. In some embodiments, R$_1$, R$_2$ and R$_3$ cannot be all H. In some embodiments, R$_3$ is C$_2$-C$_5$ haloalkyl.

In some embodiments, A of compound of formula I is a phenyl. In other embodiments, A is pyridinyl. In other embodiments, A is 2-pyridinyl. In other embodiments, A is 3-pyridinyl. In other embodiments, A is 4-pyridinyl. In other embodiments, A is naphthyl. In other embodiments, A is benzothiazolyl. In other embodiments, A is benzimidazolyl. In other embodiments, A is quinolinyl. In other embodiments, A is isoquinolinyl. In other embodiments, A is indolyl. In other embodiments, A is tetrahydronaphthyl. In other embodiments, A is indenyl. In other embodiments, A is benzofuran-2(3H)-one. In other embodiments, A is benzo[d][1,3]dioxole. In other embodiments, A is naphthalene. In other embodiments, A is tetrahydrothiophene1,1-dioxide. In other embodiments, A is thiazole. In other embodiments, A is benzimidazole. In others embodiment, A is piperidine. In other embodiments, A is 1-methylpiperidine. In other embodiments, A is imidazole. In other embodiments, A is 1-methylimidazole. In other embodiments, A is thiophene. In other embodiments, A is isoquinoline. In other embodiments, A is indole. In other embodiments, A is 1,3-dihydroisobenzofuran. In other embodiments, A is benzofuran. In other embodiments, A is benzothiophene. In other embodiments, A is indazole. In other embodiments, A is benzimidazole. In other embodiments, A is 1H-pyrrolo[3,2-c]pyridine. In other embodiments, A is quinoxaline. In other embodiments, A is cinnoline. In other embodiments, A is pyrazine. In other embodiments, A is single fused or bridged $C_3$-$C_{10}$ cycloalkyl. In other embodiments, A is cyclohexyl. In other embodiments, A is bicyclo[2.1.1]hexane. In other embodiments, A is bicyclo[2.2.1]heptane. In other embodiments, A is bicyclo[3.1.1]heptane. In other embodiments, A is cubane. In other embodiments, A is bicyclo [2.2.2]octane.

In some embodiments, B of compound of formula I is a phenyl ring. In other embodiments, B is pyridinyl. In other embodiments, B is 2-pyridinyl. In other embodiments, B is 3-pyridinyl. In other embodiments, B is 4-pyridinyl. In other embodiments, B is naphthyl. In other embodiments, B is indolyl. In other embodiments, B is benzimidazolyl. In other embodiments, B is benzothiazolyl. In other embodiments, B is quinoxalinyl. In other embodiments, B is tetrahydronaphthyl. In other embodiments, B is quinolinyl. In other embodiments, B is isoquinolinyl. In other embodiments, B is indenyl. In other embodiments, B is naphthalene. In other embodiments, B is tetrahydrothiophene1,1-dioxide. In other embodiments, B is thiazole. In other embodiments, B is benzimidazole. In other embodiments, B is piperidine. In other embodiments, B is 1-methylpiperidine. In other embodiments, B is imidazole. In other embodiments, B is 1-methylimidazole. In other embodiments, B is thiophene. In other embodiments, B is isoquinoline. In other embodiments, B is 1,3-dihydroisobenzofuran. In other embodiments, B is benzofuran. In other embodiments, B is benzothiophene. In other embodiments, B is indazole. In other embodiments, B is 1H-pyrrolo[3,2-c]pyridine. In other embodiments, B is cinnoline. In other embodiments, B is pyrazine. In other embodiments, B is single fused or bridged $C_3$-$C_{10}$ cycloalkyl. In other embodiments, B is cyclohexyl. In other embodiments, B is bicyclo [2.1.1]hexane. In other embodiments, B is bicyclo[2.2.1]heptane. In other embodiments, B is bicyclo[3.1.1]heptane. In other embodiments, B is cubane. In other embodiments, B is bicyclo [2.2.2]octane.

In some embodiments, $R_1$ of compound of formula I-V is H. In other embodiments, $R_1$ is D. In other embodiments, $R_1$ is F. In other embodiments, $R_1$ is Cl. In other embodiments, $R_1$ is Br. In other embodiments, $R_1$ is I. In other embodiments, $R_1$ is $R_8$-aryl. In other embodiments, $R_1$ is $CH_2$-3-methoxy-phenyl. In other embodiments, $R_1$ is benzyl. In other embodiments, $R_1$ is $CH_2$-1-methoxy-phenyl. In other embodiments, $R_1$ is $CH_2$-4-chloro-phenyl. In other embodiments, $R_1$ is $CH_2CH_2$-phenyl. In other embodiments, $R_1$ is $C_1$-$C_5$ linear or branched haloalkyl. In other embodiments, $R_1$ is $CF_3$. In other embodiments, $R_1$ is $CF_2CH_3$. In other embodiments, $R_1$ is $CF_2CH_2CH_3$. In other embodiments, $R_1$ is $CH_2CH_2CF_3$. In other embodiments, $R_1$ is $CF_2CH(CH_3)_2$. In other embodiments, $R_1$ is $CF(CH_3)$—$CH(CH_3)_2$. In other embodiments, $R_1$ is $OCD_3$. In other embodiments, $R_1$ is CN. In other embodiments, $R_1$ is $NO_2$. In other embodiments, $R_1$ is $NH_2$. In other embodiments, $R_1$ is $N(R)_2$. In other embodiments, $R_1$ is $R_8$—$N(R_{10})(R_{11})$. In other embodiments, $R_1$ is $CH_2$—$NH_2$. In other embodiments, $R_1$ is $CH_2$—$N(CH_3)_2$). In other embodiments, $R_1$ is $R_9$—$R_8$—$N(R_{10})(R_{11})$. In other embodiments, $R_1$ is C≡C—$CH_2$—$NH_2$. In other embodiments, $R_1$ is $B(OH)_2$. In other embodiments, $R_1$ is NHC(O)—$R_{10}$. In other embodiments, $R_1$ is $NHC(O)CH_3$. In other embodiments, $R_1$ is NHCO—$N(R_{10})(R_{11})$. In other embodiments, $R_1$ is $NHC(O)N(CH_3)_2$. In other embodiments, $R_1$ is COOH. In other embodiments, $R_1$ is —C(O)Ph. In other embodiments, $R_1$ is —C(O)-aryl. In other embodiments, $R_1$ is C(O)-1-methyl-phenyl. In other embodiments, $R_1$ is C(O)-4-methyl-phenyl. In other embodiments, $R_1$ is C(O)-3-methyl-phenyl. In other embodiments, $R_1$ is C(O)-phenol. In other embodiments, $R_1$ is C(O)-4-hydroxy-phenyl. In other embodiments, $R_1$ is C(O)-3-hydroxy-phenyl. In other embodiments, $R_1$ is C(O)-2-hydroxy-phenyl. In other embodiments, $R_1$ is C(O)O—$R_{10}$. In other embodiments, $R_1$ is C(O)—$R_{10}$. In other embodiments, $R_1$ is C(O)—$CH_3$. In other embodiments, $R_1$ is C(O)—$CH_2CH_2CH_3$. In other embodiments, $R_1$ is C(O)O—$CH(CH_3)_2$. In other embodiments, $R_1$ is C(O)O—$CH_3$. In other embodiments, $R_1$ is $SO_2R$. In other embodiments, $R_1$ is $SO_2$-Ph. In other embodiments, $R_1$ is $SO_2$-toluene. In other embodiments, $R_1$ is $SO_2$—$CH_3$. In other embodiments, $R_1$ is $SO_2N(R_{10})(R_{11})$. In other embodiments, $R_1$ is $SO_2N(CH_3)_2$. In other embodiments, $R_1$ is $SO_2NHC(O)CH_3$. In other embodiments, $R_1$ is substituted or unsubstituted $C_1$-$C_5$ linear or branched or $C_3$-$C_8$ cyclic alkyl. In other embodiments, $R_1$ is methyl. In other embodiments, $R_1$ is 2-$CH_2$—$C_6H_4$—Cl. In other embodiments, $R_1$ is 3-$CH_2$—$C_6H_4$—Cl. In other embodiments, $R_1$ is 4-$CH_2$—$C_6H_4$—Cl. In other embodiments, $R_1$ is ethyl. In other embodiments, $R_1$ is propyl. In other embodiments, $R_1$ is iso-propyl. In other embodiments, $R_1$ is cyclopropyl. In other embodiments, $R_1$ is t-Bu. In other embodiments, $R_1$ is iso-butyl. In other embodiments, $R_1$ is pentyl. In other embodiments, $R_1$ is benzyl. In other embodiments, $R_1$ is $CH_2$-3-methoxy-phenyl. In other embodiments, $R_1$ is $CH_2$-1-methoxy-phenyl. In other embodiments, $R_1$ is $CH_2$-4-chloro-phenyl. In other embodiments, $R_1$ is $CH_2CH_2$-phenyl. In other embodiments, $R_1$ is $C_1$-$C_5$ linear or branched haloalkyl. In other embodiments, $R_1$ is $CF_2CH_2CH_3$. In other embodiments, $R_1$ is $C(CH_3)(OH)Ph$. In other embodiments, $R_1$ is substituted or unsubstituted $C_3$-$C_8$ cycloalkyl (e.g., cyclopropyl, cyclopentyl). In other embodiments, $R_1$ is substituted or unsubstituted $C_1$-$C_5$ linear or branched or $C_3$-$C_8$ cyclic alkoxy. In other embodiments, $R_1$ is methoxy. In other embodiments, $R_1$ is ethoxy. In other embodiments, $R_1$ is propoxy. In other embodiments, $R_1$ is isopropoxy. In other embodiments, $R_1$ is O—$CH_2$-cyclopropyl. In other embodiments, $R_1$ is O-cyclobutyl. In other embodiments, $R_1$ is O-cyclopentyl. In other embodiments, $R_1$ is O-cyclohexyl. In other embodiments, $R_1$ is O-1-oxacyclobutyl. In other embodiments, $R_1$ is O-2-oxacyclobutyl. In other embodiments, $R_1$ is 1-butoxy. In other embodiments, $R_1$ is 2-butoxy. In other embodiments, $R_1$ is O-tBu. In other embodiments, $R_1$ is substituted or unsubstituted $C_1$-$C_5$ linear or branched or $C_3$-$C_8$ cyclic alkoxy wherein at least one methylene group ($CH_2$) in the alkoxy is replaced with an oxygen atom (O). In other embodiments, $R_1$ is O-1-oxacyclobutyl. In other embodiments, $R_1$ is O-2-oxacyclobutyl. In other embodiments, $R_1$ is $C_1$-$C_5$ linear or branched thioalkoxy. In other embodiments, $R_1$ is S—$CH_3$. In other embodiments, $R_1$ is $C_1$-$C_5$ linear or branched haloalkoxy. In other embodiments, $R_1$ is $OCF_3$. In other embodiments, $R_1$ is $OCHF_2$. In other embodiments, $R_1$ is substituted or unsubstituted $C_3$—C cycloalkyl. In other embodiments, $R_1$ is cyclopropyl. In other embodiments, $R_1$ is substituted or unsubstituted $C_3$-$C_8$ heterocyclic ring. In other embodiments, $R_1$ is oxazole. In other embodiments, $R_1$ is methyl substituted oxazole. In other embodiments, $R_1$ is oxadiazole. In other embodiments, $R_1$ is methyl substituted oxadiazole. In other embodiments, $R_1$ is imidazole. In other embodiments, $R_1$ is methyl substituted imidazole. In other embodiments, $R_1$ is thiophene. In other embodiments, $R_1$ is triazole. In other embodiments, $R_1$ is pyridine. In other embodiments, $R_1$ is 2-pyridine. In other embodiments, $R_1$ is 3-pyridine. In other embodiments, $R_1$ is 4-pyridine. In other embodiments, $R_1$ is 2-methyl-4-pyridine. In other embodiments, $R_1$ is 2,6-dimethyl-4-pyridine. In other embodiments, $R_1$ is 3,5-dimethyl-4-pyridine. In other embodiments, $R_1$ is 2,5-dimethyl-4-pyridine. In other embodiments, $R_1$ is 3-methyl-4-pyridine. In other embodiments, $R_1$ is 5-methyl-2-pyridine. In other embodiments, $R_1$ is 3-methyl-2-pyridine. In other embodiments, $R_1$ is 3-ethyl-2-pyridine. In other embodiments, $R_1$ is 3-isopropyl-2-pyridine. In other embodiments, $R_1$ is 3-propyl-2-pyridine. In other embodiments, $R_1$ is 3-phenyl-2-pyridine. In other embodiments, $R_1$ is 4-methyl-2-pyridine. In other embodiments, $R_1$ is 6-methyl-2-pyridine. In other embodiments, $R_1$ is 5-methyl-2-pyridine. In other embodiments, $R_1$ is tetrazole. In other embodiments, $R_1$ is pyrimidine. In other embodiments, $R_1$ is 5-methyl-pyrimidine. In other embodiments, $R_1$ is pyrazine. In other embodiments, $R_1$ is oxacyclobutane. In other embodiments, $R_1$ is 1-oxacyclobutane. In other embodiments, $R_1$ is 2-oxacyclobutane. In other embodiments, $R_1$ is indole. In other embodiments, $R_1$ is pyridine oxide. In other embodiments, $R_1$ is protonated pyridine oxide. In other embodiments, $R_1$ is deprotonated pyridine oxide. In other embodiments, $R_1$ is 3-methyl-4H-1,2,4-triazole. In other embodiments, $R_1$ is 5-methyl-1,2,4-oxadiazole. In other embodiments, $R_1$ is substituted or unsubstituted aryl. In other embodiments, $R_1$ is phenyl. In other embodiments, $R_1$ is bromophenyl. In other embodiments, $R_1$ is 2-bromophenyl. In other embodiments, $R_1$ is 3-bromophenyl. In other embodiments, $R_1$ is 4-bromophenyl. In other embodiments, $R_1$ is $R_8$—$N(R_{10})(R_{11})$. In other embodiments, $R_1$ is $CH_2$—$NH_2$. In other embodiments, substitutions include: F, Cl, Br, I, $C_1$-$C_5$ linear or branched alkyl (e.g. methyl, ethyl, propyl, isopropyl), OH, alkoxy, $N(R)_2$, $CF_3$, aryl, phenyl, halophenyl, (benzyloxy)phenyl, CN, $NO_2$ or any combination thereof; each is a separate embodiment according to this invention.

In some embodiments, $R_2$ of compound of formula I-V is H. In other embodiments, $R_2$ is D. In other embodiments, $R_2$ is F. In other embodiments, $R_2$ is Cl. In other embodiments, $R_2$ is Br. In other embodiments, $R_2$ is I. In other embodiments, $R_2$ is $R_8$-aryl. In other embodiments, $R_2$ is $CH_2$-3-methoxy-phenyl. In other embodiments, $R_2$ is benzyl. In other embodiments, $R_2$ is $CH_2$-1-methoxy-phenyl. In other embodiments, $R_2$ is $CH_2$-4-chloro-phenyl. In other embodiments, $R_2$ is $CH_2CH_2$-phenyl. In other embodiments, $R_2$ is $C_1$-$C_5$ linear or branched haloalkyl. In other embodiments, $R_2$ is $CF_3$. In other embodiments, $R_2$ is $CF_2CH_3$. In other embodiments, $R_2$ is $CF_2CH_2CH_3$. In other embodiments, $R_2$ is $CH_2CH_2CF_3$. In other embodiments, $R_2$ is $CF_2CH(CH_3)_2$. In other embodiments, $R_2$ is $CF(CH_3)$—$CH(CH_3)_2$. In other embodiments, $R_2$ is $OCD_3$. In other embodiments, $R_2$ is CN. In other embodiments, $R_2$ is $NO_2$. In other embodiments, $R_2$ is $NH_2$. In other embodiments, $R_2$ is $N(R)_2$. In other embodiments, $R_2$ is $R_8$—$N(R_{10})(R_{11})$. In other embodiments, $R_2$ is $CH_2$—$NH_2$. In other embodiments, $R_2$ is $CH_2$—$N(CH_3)_2$). In other embodiments, $R_2$ is $R_9$—$R_8$—$N(R_{10})(R_{11})$. In other embodiments, $R_2$ is C≡C—$CH_2$—$NH_2$. In other embodiments, $R_2$ is $B(OH)_2$. In other embodiments, $R_2$ is NHC(O)—$R_{10}$. In other embodiments, $R_2$ is $NHC(O)CH_3$. In other embodiments, $R_2$ is NHCO—$N(R_{10})(R_{11})$. In other embodiments, $R_2$ is $NHC(O)N(CH_3)_2$. In other embodiments, $R_2$ is COOH. In other embodiments, $R_1$ is —C(O)Ph. In other embodiments, $R_2$ is —C(O)-aryl. In other embodiments, $R_2$ is C(O)-1-methyl-phenyl. In other embodiments, $R_2$ is C(O)-4-methyl-phenyl. In other embodiments, $R_2$ is C(O)-3-methyl-phenyl. In other embodiments, $R_2$ is C(O)-phenol. In other embodiments, $R_2$ is C(O)-4-hydroxy-phenyl. In other embodiments, $R_2$ is C(O)-3-hydroxy-phenyl. In other embodiments, $R_2$ is C(O)-2-hydroxy-phenyl. In other embodiments, $R_2$ is C(O)O—$R_{10}$. In other embodiments, $R_2$ is C(O)—$R_{10}$. In other embodiments, $R_2$ is C(O)—$CH_3$. In other embodiments, $R_1$ is C(O)—$CH_2CH_2CH_3$. In other embodiments, $R_2$ is C(O)O—$CH(CH_3)_2$. In other embodiments, $R_2$ is C(O)O—$CH_3$. In other embodiments, $R_1$ is $SO_2R$. In other embodiments, $R_2$ is $SO_2$-Ph. In other embodiments, $R_2$ is $SO_2$-toluene. In other embodiments, $R_2$ is $SO_2$—$CH_3$. In other embodiments, $R_2$ is $SO_2N(R_{10})(R_{11})$. In other embodiments, $R_2$ is $SO_2N(CH_3)_2$. In other embodiments, $R_2$ is $SO_2NHC(O)CH_3$. In other embodiments, $R_2$ is substituted or unsubstituted $C_1$-$C_5$ linear or branched or $C_3$-$C_8$ cyclic alkyl. In other embodiments, $R_2$ is methyl. In other embodiments, $R_2$ is 2-$CH_2$—$C_6H_4$—Cl. In other embodiments, $R_2$ is 3-$CH_2$—$C_6H_4$—Cl. In other embodiments, $R_2$ is 4-$CH_2$—$C_6H_4$—Cl. In other embodiments, $R_2$ is ethyl. In other embodiments, $R_2$ is propyl. In other embodiments, $R_2$ is iso-propyl. In other embodiments, $R_2$ is cyclopropyl. In other embodiments, $R_2$ is t-Bu. In other embodiments, $R_2$ is iso-butyl. In other embodiments, $R_2$ is pentyl. In other embodiments, $R_2$ is benzyl. In other embodiments, $R_2$ is $CH_2$-3-methoxy-phenyl. In other embodiments, $R_2$ is $CH_2$-1-methoxy-phenyl. In other embodiments, $R_2$ is $CH_2$-4-chloro-phenyl. In other embodiments, $R_2$ is $CH_2CH_2$-phenyl. In other embodiments, $R_2$ is $C_1$-$C_5$ linear or branched haloalkyl. In other embodiments, $R_1$ is $CF_2CH_2CH_3$. In other embodiments, $R_2$ is $C(CH_3)(OH)Ph$. In other embodiments, $R_2$ is substituted or unsubstituted $C_3$-$C_8$ cycloalkyl (e.g., cyclopropyl, cyclopentyl). In other embodiments, $R_2$ is substituted or unsubstituted $C_1$-$C_5$ linear or branched or $C_3$-$C_8$ cyclic alkoxy. In other embodiments, $R_2$ is methoxy. In other embodiments, $R_2$ is ethoxy. In other embodiments, $R_2$ is propoxy. In other embodiments, $R_2$ is isopropoxy. In other embodiments, $R_2$ is O—$CH_2$-cyclopropyl. In other embodiments, $R_2$ is O-cyclobutyl. In other embodiments, $R_2$ is O-cyclopentyl. In other embodiments, $R_2$ is O-cyclohexyl. In other embodiments, $R_2$ is O-1-oxacyclobutyl. In other embodiments, $R_2$ is O-2-oxacyclobutyl. In other embodiments, $R_2$ is 1-butoxy. In other embodiments, $R_2$ is 2-butoxy. In other embodiments, $R_2$ is O-tBu. In other embodiments, $R_2$ is substituted or unsubstituted $C_1$-$C_5$ linear or branched or $C_3$-$C_8$ cyclic alkoxy wherein at least one methylene group ($CH_2$) in the alkoxy is replaced with an oxygen atom (O). In other embodiments, $R_2$ is O-1-oxacyclobutyl. In other embodiments, $R_2$ is O-2-oxacyclobutyl. In other embodiments, $R_2$ is $C_1$-$C_5$ linear or branched thioalkoxy. In other embodiments, $R_2$ is S—$CH_3$. In other embodiments, $R_2$ is $C_1$-$C_5$ linear or branched haloalkoxy. In other embodiments, $R_2$ is $OCF_3$. In other embodiments, $R_2$ is $OCHF_2$. In other embodiments, $R_2$ is substituted or unsubstituted $C_3$—C cycloalkyl. In other embodiments, $R_2$ is cyclopropyl. In other embodiments, $R_2$ is substituted or unsubstituted $C_3$-$C_8$ heterocyclic ring. In other embodiments, $R_2$ is oxazole or methyl substituted oxazole. In other embodiments, $R_2$ is oxadiazole or methyl substituted oxadiazole. In other embodiments, $R_2$ is imidazole or methyl substituted imidazole. In other embodiments, $R_2$ is thiophene. In other embodiments, $R_2$ is triazole. In other embodiments, $R_2$ is pyridine. In other embodiments, $R_2$ is 2-pyridine. In other embodiments, $R_2$ is 3-pyridine. In other embodiments, $R_2$ is 4-pyridine. In other embodiments, $R_2$ is 2-methyl-4-pyridine. In other embodiments, $R_2$ is 2,6-dimethyl-4-pyridine. In other embodiments, $R_2$ is 3,5-dimethyl-4-pyridine. In other embodiments, $R_2$ is 2,5-dimethyl-4-pyridine. In other embodiments, $R_2$ is 3-methyl-4-pyridine. In other embodiments, $R_2$ is 5-methyl-2-pyridine. In other embodiments, $R_2$ is 3-methyl-2-pyridine. In other embodiments, $R_2$ is 3-ethyl-2-pyridine. In other embodiments, $R_2$ is 3-isopropyl-2-pyridine. In other embodiments, $R_2$ is 3-propyl-2-pyridine. In other embodiments, $R_2$ is 3-phenyl-2-pyridine. In other embodiments, $R_2$ is 4-methyl-2-pyridine. In other embodiments, $R_2$ is 6-methyl-2-pyridine. In other embodiments, $R_2$ is 5-methyl-2-pyridine. In other embodiments, $R_2$ is tetrazole. In other embodiments, $R_2$ is pyrimidine. In other embodiments, $R_2$ is 5-methyl-pyrimidine. In other embodiments, $R_2$ is pyrazine. In other embodiments, $R_2$ is oxacyclobutane. In other embodiments, $R_2$ is 1-oxacyclobutane. In other embodiments, $R_2$ is 2-oxacyclobutane. In other embodiments, $R_2$ is indole. In other embodiments, $R_2$ is pyridine oxide. In other embodiments, $R_2$ is protonated pyridine oxide. In other embodiments, $R_2$ is deprotonated pyridine oxide. In other embodiments, $R_2$ is 3-methyl-4H-1,2,4-triazole. In other embodiments, $R_2$ is 5-methyl-1,2,4-oxadiazole. In other embodiments, $R_2$ is substituted or unsubstituted aryl. In other embodiments, $R_2$ is phenyl. In other embodiments, $R_2$ is bromophenyl. In other embodiments, $R_2$ is 2-bromophenyl. In other embodiments, $R_2$ is 3-bromophenyl. In other embodiments, $R_2$ is 4-bromophenyl. In other embodiments, $R_2$ is $R_8$—N($R_{10}$)($R_{11}$). In other embodiments, $R_2$ is $CH_2$—$NH_2$. In other embodiments, substitutions include: F, Cl, Br, I, $C_1$-$C_5$ linear or branched alkyl (e.g. methyl, ethyl, propyl, isopropyl), OH, alkoxy, $N(R)_2$, $CF_3$, aryl, phenyl, halophenyl, (benzyloxy) phenyl, CN, $NO_2$ or any combination thereof; each is a separate embodiment according to this invention.

In some embodiments, $R_1$ and $R_2$ of compound of formula I-V are joint together to form a 5 or 6 membered substituted or unsubstituted, aliphatic or aromatic, carbocyclic or heterocyclic single or fused ring. In some embodiments, $R_1$ and $R_2$ are joint together to form a heterocyclic single ring. In some embodiments, $R_1$ and $R_2$ are joint together to form a [1,3]dioxole ring. In some embodiments, $R_1$ and $R_2$ are joint together to form a furanone ring (e.g., furan-2(3H)-one). In some embodiments, $R_1$ and $R_2$ are joint together to form a benzene ring. In some embodiments, $R_1$ and $R_2$ are joint together to form a pyridine ring. In some embodiments, $R_1$ and $R_2$ are joint together to form a pyrrol ring. In some embodiments, $R_1$ and $R_2$ are joint together to form a 1-methyl-1H-pyrrole. In some embodiments, $R_1$ and $R_2$ are joint together to form a 1-benzyl-1H-pyrrole ring. In some embodiments, $R_1$ and $R_2$ are joint together to form a 5 or 6 membered substituted or unsubstituted, aliphatic or aromatic, carbocyclic or heterocyclic ring fused to another 5 or 6 membered substituted or unsubstituted, aliphatic or aromatic, carbocyclic or heterocyclic ring. In some embodiments, $R_1$ and $R_2$ are joint together to form a 7,8-dihydro-5H-pyrano[4,3-b]pyridine.

In some embodiments, $R_1$ and $R_2$ of compound of formula I-V are both H. In some embodiments, at least one of $R_1$ and $R_2$ is not H.

In some embodiments, $R_3$ of compound of formula I-V is H. In other embodiments, $R_3$ is Cl. In other embodiments, $R_3$ is I. In other embodiments, $R_3$ is F. In other embodiments, $R_3$ is Br. In other embodiments, $R_3$ is OH. In other embodiments, $R_3$ is $CD_3$. In other embodiments, $R_3$ is $OCD_3$. In other embodiments, $R_3$ is CN. In other embodiments, $R_3$ is $R_8$—OH. In other embodiments, $R_3$ is $CH_2$—OH. In other embodiments, $R_3$ is —$R_8$—O—$R_{10}$. In other embodiments, $R_3$ is $CH_2$—O—$CH_3$. In other embodiments, $R_3$ is $R_8$—N($R_{10}$)($R_{11}$). In other embodiments, $R_3$ is $CH_2$—$NH_2$. In other embodiments, $R_3$ is $CH_2$—$N(CH_3)_2$. In other embodiments, $R_3$ is $R_8$—C(O)N($R_{10}$)($R_{11}$). In other embodiments, $R_3$ is $CF_2C(O)N[(CH_3)(OCH_3)]$. In other embodiments, $R_3$ is COOH. In other embodiments, $R_3$ is C(O)O—$R_{10}$. In other embodiments, $R_3$ is C(O)O—$CH_2CH_3$. In other embodiments, $R_3$ is $R_8$—C(O)—$R_{10}$. In other embodiments, $R_3$ is $CH_2C(O)CH_3$. In other embodiments, $R_3$ is C(O)—$R_{10}$. In other embodiments, $R_3$ is C(O)—$CH_3$. In other embodiments, $R_3$ is C(O)—$CH_2CH_3$. In other embodiments, $R_3$ is C(O)—$CH_2CH_2CH_3$. In other embodiments, $R_3$ is $C_1$-$C_5$ linear or branched C(O)-haloalkyl. In other embodiments, $R_3$ is C(O)—$CF_3$. In other embodiments, $R_3$ is C(O)N($R_{10}$)($R_{11}$). In other embodiments, $R_3$ is C(O)N($CH_3)_2$). In other embodiments, $R_3$ is $SO_2N(R_{10})(R_{11})$. In other embodiments, $R_3$ is $SO_2N(CH_3)_2$. In other embodiments, $R_3$ is linear, branched or cyclic, substituted or unsubstituted alkyl. In other embodiments, $R_3$ is methyl. In other embodiments, $R_3$ is C(OH)($CH_3$)(Ph). In other embodiments, $R_3$ is ethyl. In other embodiments, $R_3$ is propyl. In other embodiments, $R_3$ is iso-propyl. In other embodiments, $R_3$ is t-Bu. In other embodiments, $R_3$ is iso-butyl. In other embodiments, $R_3$ is 2-butyl. In other embodiments, $R_3$ is tert-pentyl. In other embodiments, $R_3$ is 1-ethylcyclopropyl. In other embodiments, $R_3$ is pentyl. In other embodiments, $R_3$ is $C(CH_3)(OH)Ph$. In other embodiments, $R_3$ is substituted or unsubstituted $C_1$-$C_5$ linear or branched or $C_3$-$C_8$ cyclic haloalkyl. In other embodiments, $R_3$ is $C_2$-$C_5$ linear, branched or cyclic haloalkyl. In other embodiments, $R_3$ is $C_2$-$C_6$ linear or branched or cyclic haloalkyl. In other embodiments, $R_3$ is $C_2$-$C_7$ linear, branched or cyclic haloalkyl. In other embodiments, $R_3$ is $C_3$-$C_8$ linear, branched or cyclic haloalkyl. In other embodiments, $R_3$ is $CF_2CH_3$. In other embodiments, $R_3$ is $CH_2CF_3$. In other embodiments, $R_3$ is $CF_2CH_2CH_3$. In other embodiments, $R_3$ is $CF_2CHFCH_3$. In other embodiments, $R_3$ is $CHFCHFCH_3$. In other embodiments, $R_3$ is $CF_3$. In other embodiments, $R_3$ is $CH_2CF_2CH_3$. In other embodiments, $R_3$ is $CH_2CH_2CF_3$. In other embodiments, $R_3$ is $CF_2CH(CH_3)_2$. In other embodiments, $R_3$ is $CF(CH_3)$—$CH(CH_3)_2$. In other embodiments, $R_3$ is $CF_2$-cyclopropyl. In other embodiments, $R_3$ is $CF_2$-cyclopentyl. In other embodiments, $R_3$ is substituted or unsubstituted $C_1$-$C_5$ linear or branched or $C_3$-$C_8$ cyclic haloalkenyl. In other embodiments, $R_3$ is CF=CH—$CH_3$ E, Z or combination thereof. In other embodiments, $R_3$ is CF=C—$(CH_3)_2$). In other embodiments, $R_3$ is substituted or unsubstituted $C_1$-$C_5$ linear or branched or $C_3$-$C_8$ cyclic alkoxy. In other embodiments, $R_3$ is $C_1$-$C_5$ linear, branched or cyclic alkoxy. In other embodiments, $R_3$ is methoxy. In other embodiments, $R_3$ is isopropoxy. In other embodiments, $R_3$ is substituted or unsubstituted $C_3$-$C_8$ cycloalkyl. In other embodiments, $R_3$ is cyclopropyl. In other embodiments, $R_3$ is cyclopentyl. In other embodiments, $R_3$ is substituted or unsubstituted $C_3$-$C_8$ heterocyclic ring. In other embodiments, $R_3$ is thiophene. In other embodiments, $R_3$ is oxazole. In other embodiments, $R_3$ is isoxazole. In other embodiments, $R_3$ is imidazole. In other embodiments, $R_3$ is furane. In other embodiments, $R_3$ is pyrrole. In other embodiments, $R_3$ is 1-methyl-pyrrol. In other embodiments, $R_3$ is imidazole. In other embodiments, $R_3$ is 1-methyl-imidazole. In other embodiments, $R_3$ is triazole. In other embodiments, $R_3$ is pyridine. In other embodiments, $R_3$ is 2-pyridine. In other embodiments, $R_3$ is 3-pyridine. In other embodiments, $R_3$ is 4-pyridine. In other embodiments, $R_3$ is pyrimidine. In other embodiments, $R_3$ is pyrazine. In other embodiments, $R_3$ is oxacyclobutane. In other embodiments, $R_3$ is 1-oxacyclobutane. In other embodiments, $R_3$ is 2-oxacyclobutane. In other embodiments, $R_3$ is indole. In other embodiments, $R_3$ is 3-methyl-4H-1,2,4-triazole. In other embodiments, $R_3$ is 5-methyl-1,2,4-oxadiazole. In other embodiments, $R_3$ is substituted or unsubstituted aryl. In other embodiments, $R_3$ is phenyl. In other embodiments, $R_3$ is $CH(CF_3)(NH-R_{10})$. In other embodiments, substitutions include: F, Cl, Br, I, $C_1$-$C_5$ linear or branched alkyl, OH, alkoxy, $N(R)_2$, $CF_3$, aryl, phenyl, halophenyl, (benzyloxy)phenyl, CN, $NO_2$ or any combination thereof; each is a separate embodiment according to this invention.

In some embodiments, $R_4$ of compound of formula I-IV is H. In other embodiments, $R_4$ is Cl. In other embodiments, $R_4$ is I. In other embodiments, $R_4$ is F. In other embodiments, $R_4$ is Br. In other embodiments, $R_4$ is OH. In other embodiments, $R_4$ is $CD_3$. In other embodiments, $R_4$ is $OCD_3$. In other embodiments, $R_4$ is CN. In other embodiments, $R_4$ is $R_8$—OH. In other embodiments, $R_4$ is $CH_2$—OH. In other embodiments, $R_4$ is —$R_8$—O—$R_{10}$. In other embodiments, $R_4$ is $CH_2$—O—$CH_3$. In other embodiments, $R_4$ is $R_8$—N($R_{10}$)($R_{11}$). In other embodiments, $R_4$ is $CH_2$—$NH_2$. In other embodiments, $R_4$ is $CH_2$—$N(CH_3)_2$. In other embodiments, $R_4$ is $R_8$—C(O)N($R_{10}$)($R_{11}$). In other embodiments, $R_4$ is $CF_2C(O)N[(CH_3)(OCH_3)]$. In other embodiments, $R_4$ is COOH. In other embodiments, $R_4$ is C(O)O—$R_{10}$. In other embodiments, $R_4$ is C(O)O—$CH_2CH_3$. In other embodiments, $R_4$ is $R_8$—C(O)—$R_{10}$. In other embodiments, $R_4$ is $CH_2C(O)CH_3$. In other embodiments, $R_4$ is C(O)—$R_{10}$. In other embodiments, $R_4$ is C(O)—$CH_3$. In other embodiments, $R_4$ is C(O)—$CH_2CH_3$. In other embodiments, $R_4$ is C(O)—$CH_2CH_2CH_3$. In other embodiments, $R_4$ is $C_1$-$C_5$ linear or branched C(O)-haloalkyl. In other embodiments, $R_4$ is C(O)—$CF_3$. In other embodiments, $R_4$ is C(O)N($R_{10}$)($R_{11}$). In other embodiments, $R_4$ is $C(O)N(CH_3)_2$. In other embodiments, $R_4$ is $SO_2N(R_{10})(R_{11})$. In other embodiments, $R_4$ is $SO_2N(CH_3)_2$. In other embodiments, $R_4$ is substituted or unsubstituted $C_1$-$C_5$ linear or branched or $C_3$-$C_8$ cyclic alkyl. In other embodiments, $R_4$ is methyl. In other embodiments, $R_4$ is $C(OH)(CH_3)(Ph)$. In other embodiments, $R_4$ is ethyl. In other embodiments, $R_4$ is propyl. In other embodiments, $R_4$ is iso-propyl. In other embodiments, $R_4$ is t-Bu. In other embodiments, $R_4$ is iso-butyl. In other embodiments, $R_4$ is 2-butyl. In other embodiments, $R_4$ is tert-pentyl. In other embodiments, $R_4$ is 1-ethylcyclopropyl. In other embodiments, $R_4$ is pentyl. In other embodiments, $R_4$ is $C(CH_3)(OH)Ph$. In other embodiments, $R_4$ is substituted or unsubstituted $C_1$-$C_5$ linear or branched or $C_3$-$C_8$ cyclic haloalkyl. In other embodiments, $R_4$ is $C_2$-$C_5$ linear, branched or cyclic haloalkyl. In other embodiments, $R_4$ is $C_2$-$C_6$ linear or branched or cyclic haloalkyl. In other embodiments, $R_4$ is $C_2$-$C_7$ linear, branched or cyclic haloalkyl. In other embodiments, $R_4$ is $C_3$-$C_8$ linear, branched or cyclic haloalkyl. In other embodiments, $R_4$ is $CF_2CH_3$. In other embodiments, $R_4$ is $CH_2CF_3$. In other embodiments, $R_4$ is $CF_2CH_2CH_3$. In other embodiments, $R_4$ is $CF_2CHFCH_3$. In other embodiments, $R_4$ is $CHFCHFCH_3$, In other embodiments, $R_4$ is $CF_3$. In other embodiments, $R_4$ is $CH_2CF_2CH_3$. In other embodiments, $R_4$ is $CH_2CH_2CF_3$. In other embodiments, $R_4$ is $CF_2CH(CH_3)_2$. In other embodiments, $R_4$ is $CF(CH_3)$—$CH(CH_3)_2$. In other embodiments, $R_4$ is $CF_2$-cyclopropyl. In other embodiments, $R_4$ is $CF_2$-cyclopentyl. In other embodiments, $R_4$ is substituted or unsubstituted $C_1$-$C_5$ linear or branched or $C_3$-$C_8$ cyclic haloalkenyl. In other embodiments, $R_4$ is $CF=CH-CH_3$ E, Z or combination thereof. In other embodiments, $R_4$ is $CF=C-(CH_3)_2$. In other embodiments, $R_4$ is substituted or unsubstituted $C_1$-$C_5$ linear or branched or $C_3$-$C_8$ cyclic alkoxy. In other embodiments, $R_4$ is $C_1$-$C_5$ linear, branched or cyclic alkoxy. In other embodiments, $R_4$ is methoxy. In other embodiments, $R_4$ is isopropoxy. In other embodiments, $R_4$ is substituted or unsubstituted $C_3$-$C_8$ cycloalkyl. In other embodiments, $R_4$ is cyclopropyl. In other embodiments, $R_4$ is cyclopentyl. In other embodiments, $R_4$ is substituted or unsubstituted $C_3$-$C_8$ heterocyclic ring. In other embodiments, $R_4$ is thiophene. In other embodiments, $R_4$ is oxazole. In other embodiments, $R_4$ is isoxazole. In other embodiments, $R_4$ is imidazole. In other embodiments, $R_4$ is furane. In other embodiments, $R_4$ is pyrrole. In other embodiments, $R_4$ is 1-methyl-pyrrol. In other embodiments, $R_4$ is imidazole. In other embodiments, $R_4$ is 1-methyl-imidazole. In other embodiments, $R_4$ is triazole. In other embodiments, $R_4$ is pyridine. In other embodiments, $R_4$ is 2-pyridine. In other embodiments, $R_4$ is 3-pyridine. In other embodiments, $R_4$ is 4-pyridine. In other embodiments, $R_4$ is pyrimidine. In other embodiments, $R_4$ is pyrazine. In other embodiments, $R_4$ is oxacyclobutane. In other embodiments, $R_4$ is 1-oxacyclobutane. In other embodiments, $R_4$ is 2-oxacyclobutane. In other embodiments, $R_4$ is indole. In other embodiments, $R_4$ is 3-methyl-4H-1,2,4-triazole. In other embodiments, $R_4$ is 5-methyl-1,2,4-oxadiazole. In other embodiments, $R_4$ is substituted or unsubstituted aryl. In other embodiments, $R_4$ is phenyl. In other embodiments, $R_4$ is $CH(CF_3)(NH-R_{10})$. In other embodiments, substitutions include: F, Cl, Br, I, $C_1$-$C_5$ linear or branched alkyl, OH, alkoxy, $N(R)_2$, $CF_3$, aryl, phenyl, halophenyl, (benzyloxy)phenyl, CN, $NO_2$ or any combination thereof; each is a separate embodiment according to this invention.

In some embodiments, $R_3$ and $R_4$ of compound of formula I-IV are joint together to form a [1,3]dioxole ring. In some embodiments, $R_3$ and $R_4$ are joint together to form a furanone ring (e.g., furan-2(3H)-one). In some embodiments, $R_3$ and $R_4$ are joint together to form a benzene ring. In some embodiments, $R_3$ and $R_4$ are joint together to form a cyclopentene ring. In some embodiments, $R_3$ and $R_4$ are joint together to form an imidazole ring. In some embodiments, $R_3$ and $R_4$ are joint together to form a pyrrol ring.

In some embodiments, $R_3$ and $R_4$ of compound of formula I-V are both H. In some embodiments, at least one of $R_3$ and $R_4$ is not H. In some embodiments, if $R_3$ is H, then $R_4$ is not H. In some embodiments, if $R_4$ is H, then $R_3$ is not H.

In some embodiments, $R_5$ of compound of formula I-IV is H. In other embodiments, $R_5$ is $C_1$-$C_5$ linear or branched, substituted or unsubstituted alkyl. In other embodiments, $R_5$ is methyl. In other embodiments, $R_5$ is $CH_2SH$. In other embodiments, $R_5$ is ethyl. In other embodiments, $R_5$ is iso-propyl. In other embodiments, $R_5$ is $C_1$-$C_5$ linear or branched haloalkyl. In other embodiments, $R_5$ is $CF_2CH_3$. In other embodiments, $R_5$ is $CH_2CF_3$. In other embodiments, $R_5$ is $CF_2CH_2CH_3$. In other embodiments, $R_5$ is $CF_3$. In other embodiments, $R_5$ is $CF_2CH_2CH_3$. In other embodiments, $R_5$ is $CH_2CH_2CF_3$. In other embodiments, $R_5$ is $CF_2CH(CH_3)_2$. In other embodiments, $R_5$ is $CF(CH_3)-CH(CH_3)_2$. In other embodiments, $R_5$ is $R_8$-aryl. In other embodiments, $R_5$ is $CH_2$-Ph (i.e., benzyl). In other embodiments, $R_5$ is C(O)—$R_{10}$. In other embodiments, $R_5$ is C(O)—$CH_3$. In other embodiments, $R_5$ is substituted or unsubstituted aryl. In other embodiments, $R_5$ is phenyl. In other embodiments, $R_5$ is substituted or unsubstituted heteroaryl. In other embodiments, $R_5$ is pyridine. In other embodiments, $R_5$ is 2-pyridine. In other embodiments, $R_5$ is 3-pyridine. In other embodiments, $R_5$ is 4-pyridine.

In some embodiments, $R_6$ of compound of formula I-III is H. In other embodiments, $R_6$ is $C_1$-$C_5$ linear or branched alkyl. In other embodiments, $R_6$ is methyl.

In some embodiments, $R_8$ of compound of formula I-V is $CH_2$. In other embodiments, $R_8$ is $CH_2CH_2$. In other embodiments, $R_8$ is $CH_2CH_2CH_2$. In other embodiments, $R_8$ is $CF_2$. In other embodiments, $R_8$ is $CF_2CF_2$.

In some embodiments, p of compound of formula I-V is 1. In other embodiments, p is 2. In other embodiments, p is 3.

In some embodiments, $R_9$ of compound of formula I-V is C≡C.

In some embodiments, q of compound of formula I-V is 2.

In some embodiments, $R_{10}$ of compound of formula I-V is $C_1$-$C_5$ linear or branched alkyl. In other embodiments, $R_{10}$ is H. In other embodiments, $R_{10}$ is $CH_3$. In other embodiments, $R_{10}$ is $CH_2CH_3$. In other embodiments, $R_{10}$ is $CH_2CH_2CH_3$.

In some embodiments, $R_{11}$ of compound of formula I-V is $C_1$-$C_5$ linear or branched alkyl. In other embodiments, $R_{10}$ is H. In other embodiments, $R_1$ is $CH_3$.

In some embodiments, R of compound of formula I-V is H. In other embodiments, R is $C_1$-$C_5$ linear or branched alkyl. In other embodiments, R is methyl. In other embodiments, R is ethyl. In other embodiments, R is phenyl. In other embodiments, R is aryl. In other embodiments, R is toluene.

In some embodiments, m of compound of formula I-II is 1. In other embodiments, m is 0.

In some embodiments, n of compound of formula I-II is 1. In other embodiments, n is 0.

In some embodiments, k of compound of formula I-II is 1. In other embodiments, k is 0.

In some embodiments, l of compound of formula I-II is 1. In other embodiments, l is 0.

In some embodiments, $Q_1$ of compound of formula I-III is O.

In some embodiments, $Q_2$ of compound of formula I-III is O.

In some embodiments, $X_1$ of compound of formula II is C. In other embodiments, $X_1$ is N.

In some embodiments, $X_2$ of compound of formula II is C. In other embodiments, $X_2$ is N.

In some embodiments, $X_3$ of compound of formula II-V is C. In other embodiments, $X_3$ is N.

In some embodiments, $X_4$ of compound of formula II-IV is C. In other embodiments, $X_4$ is N.

In some embodiments, $X_5$ of compound of formula II is C. In other embodiments, $X_5$ is N.

In some embodiments, $X_6$ of compound of formula II-III is C. In other embodiments, $X_6$ is N.

In some embodiments, $X_7$ of compound of formula II-V is C. In other embodiments, $X_7$ is N.

In some embodiments, $X_8$ of compound of formula II-IV is C. In other embodiments, $X_8$ is N.

In some embodiments, $X_9$ of compound of formula II is C. In other embodiments, $X_9$ is N.

In some embodiments, $X_{10}$ of compound of formula II is C. In other embodiments, $X_{10}$ is N.

In various embodiments, this invention is directed to the compounds presented in Table 1, pharmaceutical compositions and/or method of use thereof:

TABLE 1

| Compound name | Structure |
| --- | --- |
| 100 | 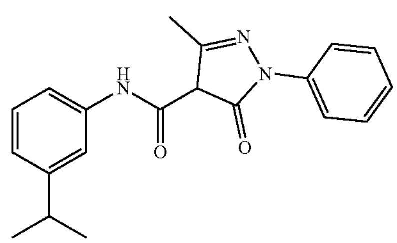 [SMILES: CC1=NN(c2ccccc2)C(=O)C1C(=O)Nc1cccc(C(C)C)c1] |
| 101 | 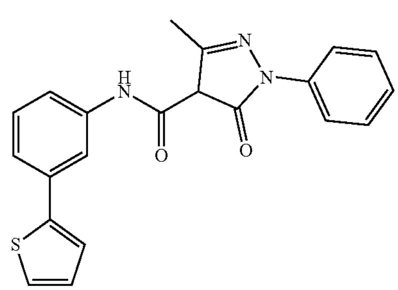 [SMILES: CC1=NN(c2ccccc2)C(=O)C1C(=O)Nc1cccc(-c2cccs2)c1] |

TABLE 1-continued
| Compound name | Structure |
|---|---|
| 102 | 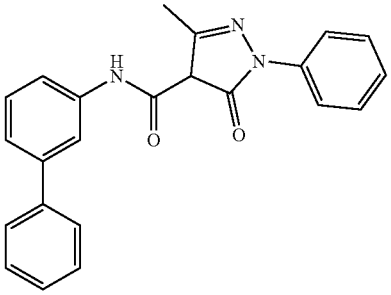 [SMILES: CC1=NN(c2ccccc2)C(=O)C1C(=O)Nc1cccc(-c2ccccc2)c1] |
| 103 | 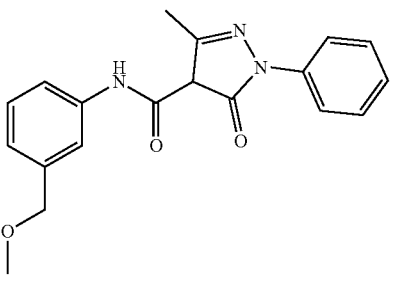 [SMILES: COCc1cccc(NC(=O)C2C(=O)N(c3ccccc3)N=C2C)c1] |
| 104 | 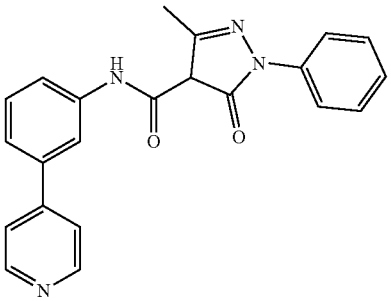 [SMILES: CC1=NN(c2ccccc2)C(=O)C1C(=O)Nc1cccc(-c2ccncc2)c1] |
| 105 | 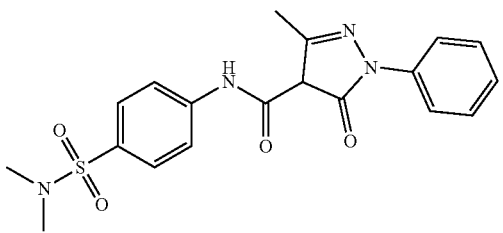 [SMILES: CC1=NN(c2ccccc2)C(=O)C1C(=O)Nc1ccc(S(=O)(=O)N(C)C)cc1] |
| 106 | 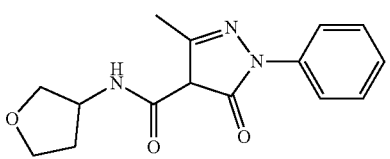 [SMILES: CC1=NN(c2ccccc2)C(=O)C1C(=O)NC1CCOC1] |

TABLE 1-continued

| Compound name | Structure |
|---|---|
| 107 | 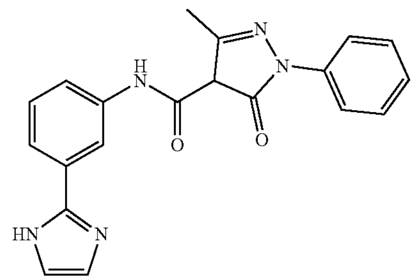 [SMILES: CC1=NN(c2ccccc2)C(=O)C1C(=O)Nc1cccc(-c2ncc[nH]2)c1] |
| 108 | 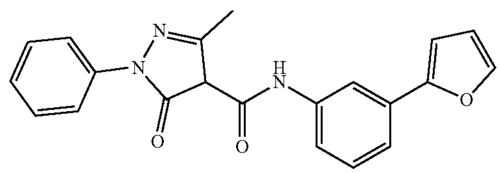 [SMILES: CC1=NN(c2ccccc2)C(=O)C1C(=O)Nc1cccc(-c2ccco2)c1] |
| 109 | 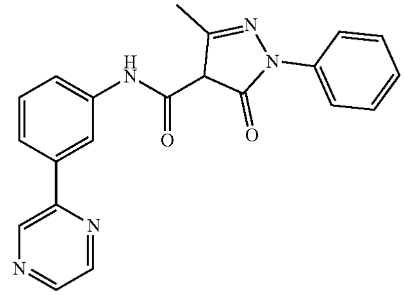 [SMILES: CC1=NN(c2ccccc2)C(=O)C1C(=O)Nc1cccc(-c2cnccn2)c1] |
| 110 | 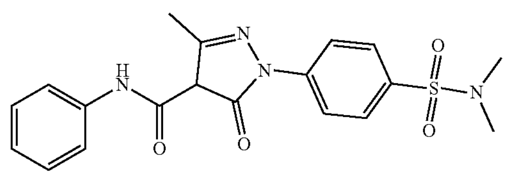 [SMILES: CC1=NN(c2ccc(S(=O)(=O)N(C)C)cc2)C(=O)C1C(=O)Nc1ccccc1] |
| 111 | 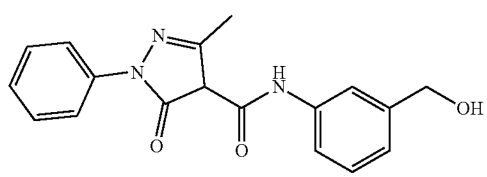 [SMILES: CC1=NN(c2ccccc2)C(=O)C1C(=O)Nc1cccc(CO)c1] |
| 112 | 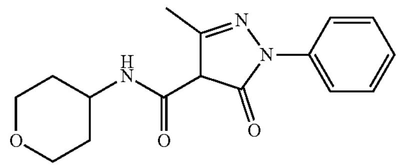 [SMILES: CC1=NN(c2ccccc2)C(=O)C1C(=O)NC1CCOCC1] |

TABLE 1-continued

| Compound name | Structure |
|---|---|
| 113 | ethyl 3-[[(5-oxo-3-methyl-1-phenyl-4,5-dihydro-1H-pyrazol-4-yl)carbonyl]amino]benzoate |
| 114 | N-[3-butanoylphenyl]-3-methyl-5-oxo-1-phenyl-4,5-dihydro-1H-pyrazole-4-carboxamide |
| 115 | N-[3-tert-butylphenyl]-3-methyl-5-oxo-1-phenyl-4,5-dihydro-1H-pyrazole-4-carboxamide |
| 116 | 3-[[(5-oxo-3-methyl-1-phenyl-4,5-dihydro-1H-pyrazol-4-yl)carbonyl]amino]benzoic acid |
| 117 | N-[3-propanoylphenyl]-3-methyl-5-oxo-1-phenyl-4,5-dihydro-1H-pyrazole-4-carboxamide |
| 118 | N-[3-pentylphenyl]-3-methyl-5-oxo-1-phenyl-4,5-dihydro-1H-pyrazole-4-carboxamide |
| 119 | N-[3-cyclopropylphenyl]-3-methyl-5-oxo-1-phenyl-4,5-dihydro-1H-pyrazole-4-carboxamide |

TABLE 1-continued

| Compound name | Structure |
|---|---|
| 120 | *(3-acetylphenyl)-NH-C(=O)-[4-methyl-5-oxo-pyrazoline]-N-(4-carboxyphenyl)* |
| 121 | *1-phenyl-3-methyl-5-oxo-pyrazoline-4-carboxamide-N-(piperidin-4-yl)* |
| 122 | *(3-oxo-1,3-dihydroisobenzofuran-5-yl)-NH-C(=O)-[3-methyl-5-oxo-1-phenyl-pyrazoline]* |
| 123 | *(3-acetylphenyl)-NH-C(=O)-[3-methyl-5-oxo-pyrazoline]-N-(3-carboxyphenyl)* |
| 124 | *[3-(oxazol-2-yl)phenyl]-NH-C(=O)-[3-methyl-5-oxo-1-phenyl-pyrazoline]* |
| 125 | *(3-ethylphenyl)-NH-C(=O)-[3-methyl-5-oxo-1-phenyl-pyrazoline]* |

TABLE 1-continued

| Compound name | Structure |
|---|---|
| 126 | (structure) |
| 127 | (structure) |
| 128 | (structure) |
| 129 | (structure) |
| 130 | (structure) |
| 131 | (structure) |

TABLE 1-continued

| Compound name | Structure |
|---|---|
| 132 | 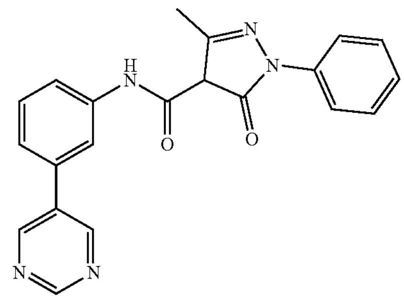 [SMILES: CC1=NN(c2ccccc2)C(=O)C1C(=O)Nc1cccc(-c2cncnc2)c1] |
| 133 | 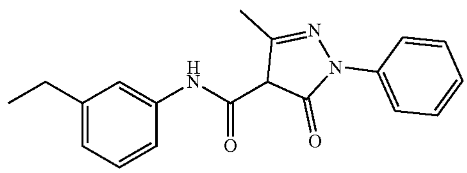 [SMILES: CCc1cccc(NC(=O)C2C(=O)N(c3ccccc3)N=C2C)c1] |
| 134 | 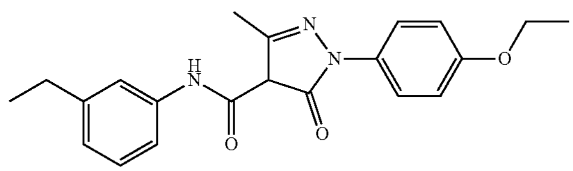 [SMILES: CCOc1ccc(N2N=C(C)C(C(=O)Nc3cccc(CC)c3)C2=O)cc1] |
| 135 | 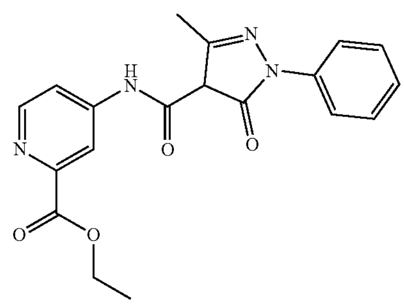 [SMILES: CCOC(=O)c1cc(NC(=O)C2C(=O)N(c3ccccc3)N=C2C)ccn1] |
| 136 | 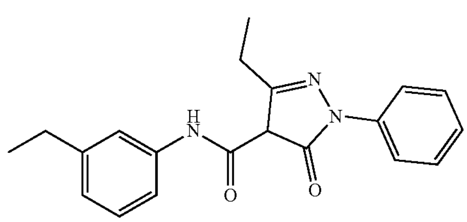 [SMILES: CCC1=NN(c2ccccc2)C(=O)C1C(=O)Nc1cccc(CC)c1] |
| 137 | 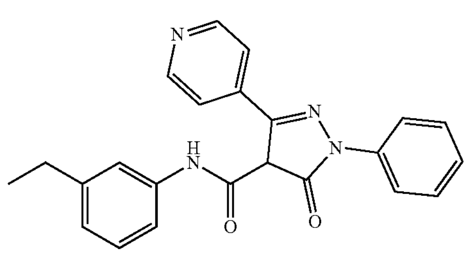 [SMILES: CCc1cccc(NC(=O)C2C(=O)N(c3ccccc3)N=C2c2ccncc2)c1] |

TABLE 1-continued

| Compound name | Structure |
|---|---|
| 138 | 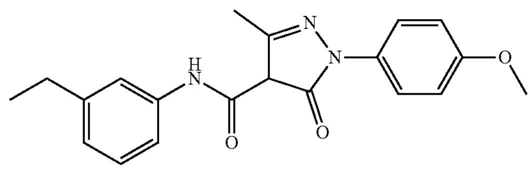 [SMILES: CCc1cccc(NC(=O)C2C(=O)N(c3ccc(OC)cc3)N=C2C)c1] |
| 139 | 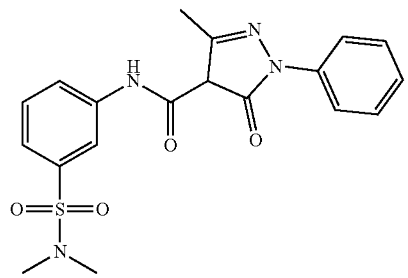 [SMILES: CC1=NN(c2ccccc2)C(=O)C1C(=O)Nc1cccc(S(=O)(=O)N(C)C)c1] |
| 140 | 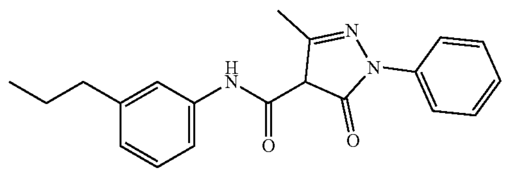 [SMILES: CCCc1cccc(NC(=O)C2C(=O)N(c3ccccc3)N=C2C)c1] |
| 141 | 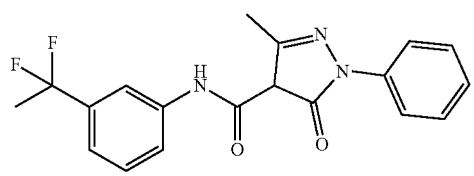 [SMILES: CC1=NN(c2ccccc2)C(=O)C1C(=O)Nc1cccc(C(C)(F)F)c1] |
| 142 | 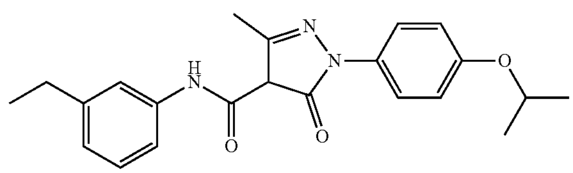 [SMILES: CCc1cccc(NC(=O)C2C(=O)N(c3ccc(OC(C)C)cc3)N=C2C)c1] |
| 143 | 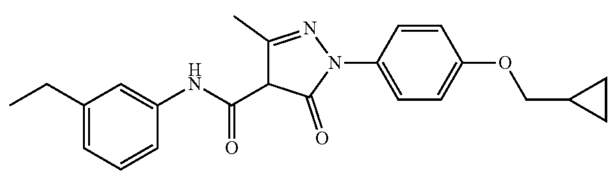 [SMILES: CCc1cccc(NC(=O)C2C(=O)N(c3ccc(OCC4CC4)cc3)N=C2C)c1] |
| 144 | 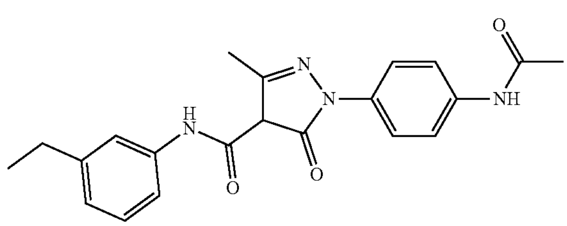 [SMILES: CCc1cccc(NC(=O)C2C(=O)N(c3ccc(NC(C)=O)cc3)N=C2C)c1] |
| 145 | 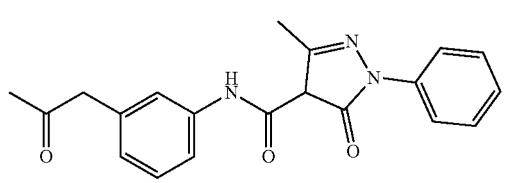 [SMILES: CC(=O)Cc1cccc(NC(=O)C2C(=O)N(c3ccccc3)N=C2C)c1] |

TABLE 1-continued

| Compound name | Structure |
|---|---|
| 146 | *3-cyclopentylphenyl N-(3-methyl-5-oxo-1-phenyl-4,5-dihydro-1H-pyrazole-4-carboxamide)* |
| 147 | *3-isobutylphenyl N-(3-methyl-5-oxo-1-phenyl-4,5-dihydro-1H-pyrazole-4-carboxamide)* |
| 148 | *N-(3-(1H-imidazol-2-yl)phenyl)-3-methyl-5-oxo-1-(4-(trifluoromethyl)phenyl)-4,5-dihydro-1H-pyrazole-4-carboxamide* |
| 149 | *N-(3-(1H-imidazol-2-yl)phenyl)-3-methyl-5-oxo-1-(3-(trifluoromethyl)phenyl)-4,5-dihydro-1H-pyrazole-4-carboxamide* |
| 150 | *3-methyl-5-oxo-N-(3-(pyrazin-2-yl)phenyl)-1-(4-(trifluoromethyl)phenyl)-4,5-dihydro-1H-pyrazole-4-carboxamide* |
| 152 | *N-(3-(2,2,2-trifluoroacetyl)phenyl)-3-methyl-5-oxo-1-phenyl-4,5-dihydro-1H-pyrazole-4-carboxamide* |
| 153 | *N-(3-ethylphenyl)-3-methyl-1-(4-nitrophenyl)-5-oxo-4,5-dihydro-1H-pyrazole-4-carboxamide* |

TABLE 1-continued

| Compound name | Structure |
|---|---|
| 154 | 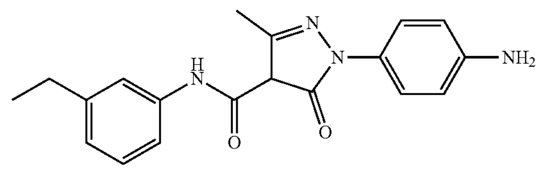 [SMILES: CCc1cccc(NC(=O)C2C(=O)N(c3ccc([N+](=O)[O-])cc3)N=C2C)c1] |
| 155 | 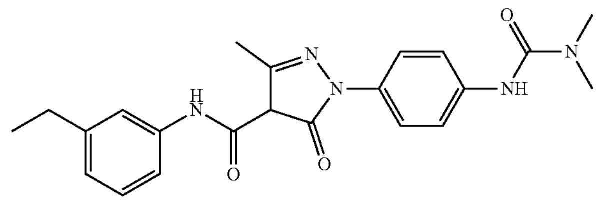 [SMILES: CCc1cccc(NC(=O)C2C(=O)N(c3ccc(NC(=O)N(C)C)cc3)N=C2C)c1] |
| 156 | 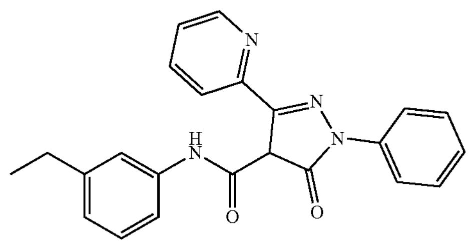 [SMILES: CCc1cccc(NC(=O)C2C(=O)N(c3ccccc3)N=C2c2ccccn2)c1] |
| 157 | 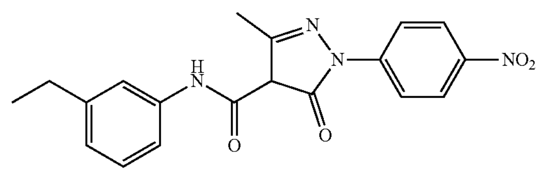 [SMILES: CCc1cccc(NC(=O)C2C(=O)N(c3ccc([N+](=O)[O-])cc3)N=C2C)c1] |
| 158 | 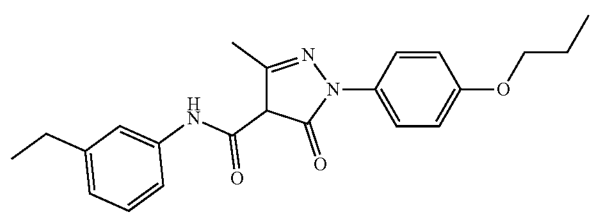 [SMILES: CCCOc1ccc(N2N=C(C)C(C(=O)Nc3cccc(CC)c3)C2=O)cc1] |
| 159 | 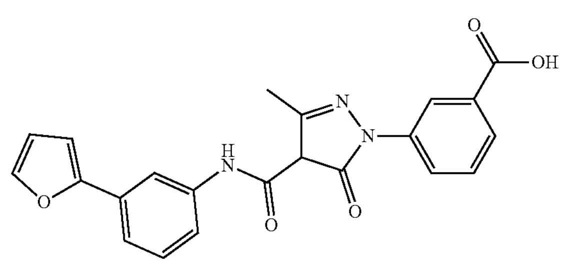 |
| 160 | 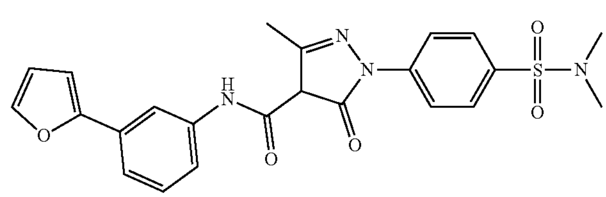 |

TABLE 1-continued

| Compound name | Structure |
|---|---|
| 161 | 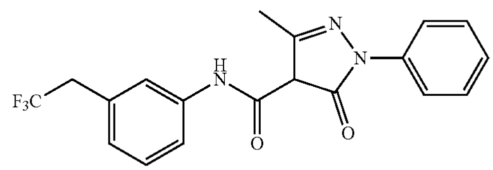 [SMILES: CC1=NN(c2ccccc2)C(=O)C1C(=O)Nc1cccc(CC(F)(F)F)c1] |
| 162 | 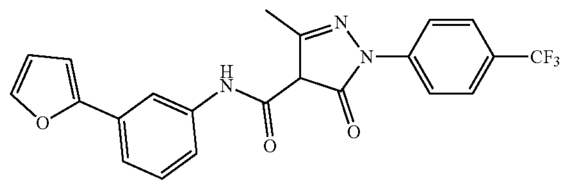 [SMILES: CC1=NN(c2ccc(C(F)(F)F)cc2)C(=O)C1C(=O)Nc1cccc(-c2ccco2)c1] |
| 164 | 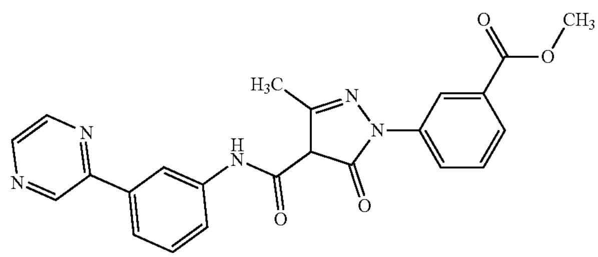 [SMILES: COC(=O)c1cccc(N2N=C(C)C(C(=O)Nc3cccc(-c4cnccn4)c3)C2=O)c1] |
| 165 | 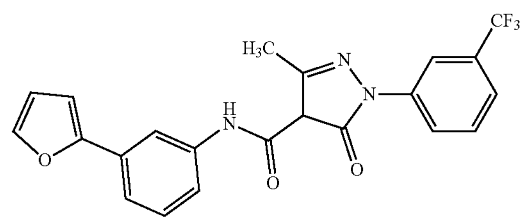 [SMILES: CC1=NN(c2cccc(C(F)(F)F)c2)C(=O)C1C(=O)Nc1cccc(-c2ccco2)c1] |
| 166 | 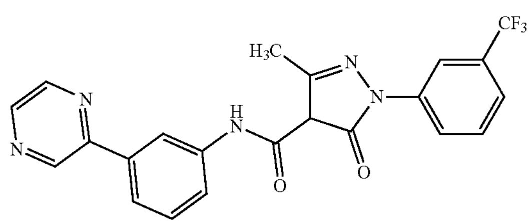 [SMILES: CC1=NN(c2cccc(C(F)(F)F)c2)C(=O)C1C(=O)Nc1cccc(-c2cnccn2)c1] |
| 167 | 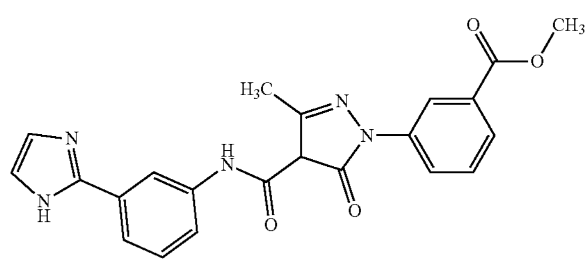 [SMILES: COC(=O)c1cccc(N2N=C(C)C(C(=O)Nc3cccc(-c4ncc[nH]4)c3)C2=O)c1] |
| 168 | 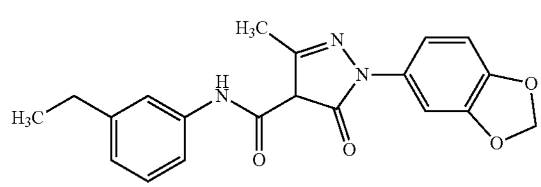 [SMILES: CCc1cccc(NC(=O)C2C(=O)N(c3ccc4c(c3)OCO4)N=C2C)c1] |

TABLE 1-continued
| Compound name | Structure |
|---|---|
| 169 | 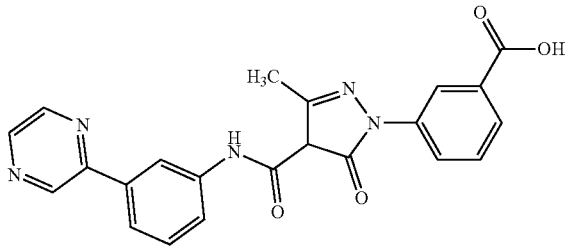 [SMILES: CC1=NN(c2cccc(C(=O)O)c2)C(=O)C1C(=O)Nc1cccc(-c2cnccn2)c1] |
| 170 | 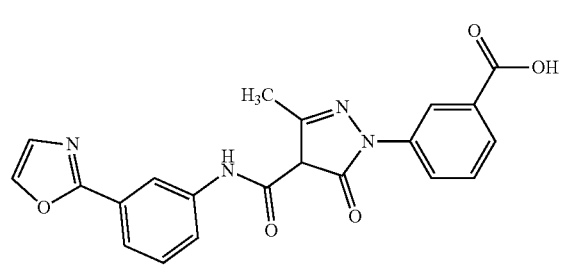 [SMILES: CC1=NN(c2cccc(C(=O)O)c2)C(=O)C1C(=O)Nc1cccc(-c2ncco2)c1] |
| 171 | 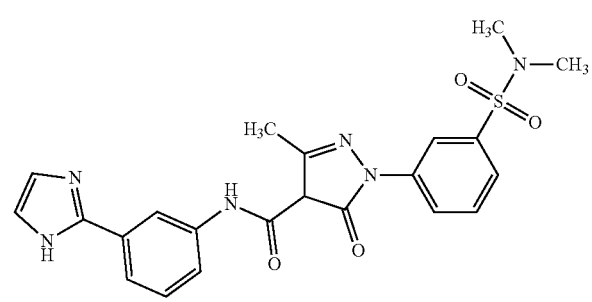 [SMILES: CC1=NN(c2cccc(S(=O)(=O)N(C)C)c2)C(=O)C1C(=O)Nc1cccc(-c2ncc[nH]2)c1] |
| 172 | 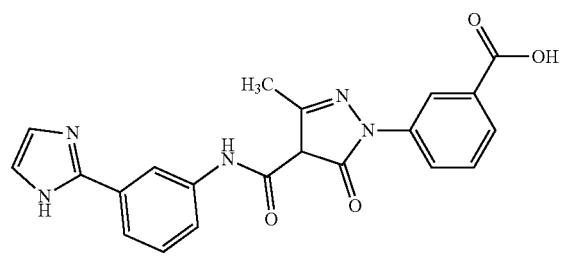 [SMILES: CC1=NN(c2cccc(C(=O)O)c2)C(=O)C1C(=O)Nc1cccc(-c2ncc[nH]2)c1] |
| 173 | 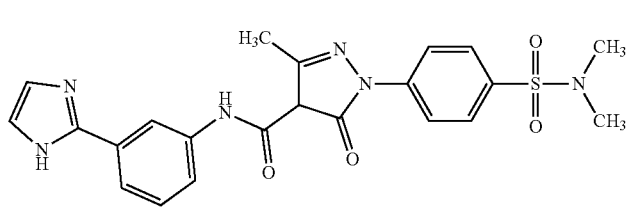 [SMILES: CC1=NN(c2ccc(S(=O)(=O)N(C)C)cc2)C(=O)C1C(=O)Nc1cccc(-c2ncc[nH]2)c1] |
| 174 | 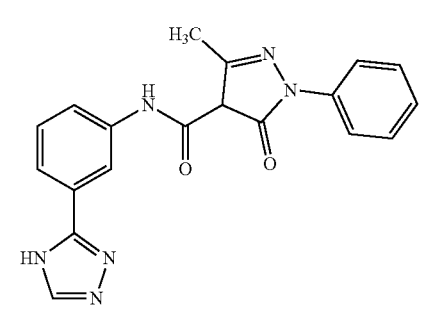 [SMILES: CC1=NN(c2ccccc2)C(=O)C1C(=O)Nc1cccc(-c2nnc[nH]2)c1] |

TABLE 1-continued

| Compound name | Structure |
|---|---|
| 176 | 3-methyl-N-(3-(2,2,2-trifluoro-1-(ethylamino)ethyl)phenyl)-5-oxo-1-phenyl-4,5-dihydro-1H-pyrazole-4-carboxamide |
| 182 | 3-methyl-5-oxo-N,1-diphenyl-4,5-dihydro-1H-pyrazole-4-carboxamide |
| 183 | N-(3-acetylphenyl)-3-methyl-5-oxo-1-phenyl-4,5-dihydro-1H-pyrazole-4-carboxamide |
| 184 | N-(3-ethylphenyl)-3-methyl-5-oxo-1-phenyl-4,5-dihydro-1H-pyrazole-4-carboxamide |
| 185 | 3-methyl-N-(naphthalen-1-yl)-5-oxo-1-phenyl-4,5-dihydro-1H-pyrazole-4-carboxamide |
| 186 | N-benzyl-3-methyl-5-oxo-1-phenyl-4,5-dihydro-1H-pyrazole-4-carboxamide |
| 187 | 1-isopropyl-3-methyl-5-oxo-N-phenyl-4,5-dihydro-1H-pyrazole-4-carboxamide |

TABLE 1-continued

| Compound name | Structure |
|---|---|
| 188 | 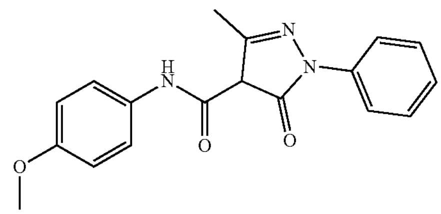 [SMILES: COc1ccc(NC(=O)C2C(=O)N(c3ccccc3)N=C2C)cc1] |
| 189 | 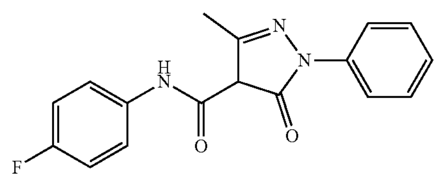 [SMILES: CC1=NN(c2ccccc2)C(=O)C1C(=O)Nc1ccc(F)cc1] |
| 190 | 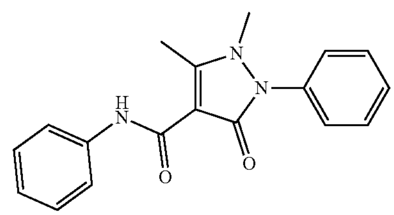 [SMILES: Cc1c(C(=O)Nc2ccccc2)c(=O)n(-c2ccccc2)n1C] |
| 191 | 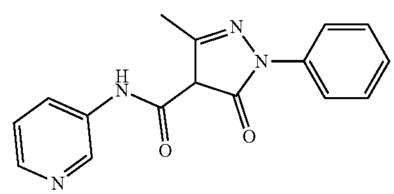 [SMILES: CC1=NN(c2ccccc2)C(=O)C1C(=O)Nc1cccnc1] |
| 192 | 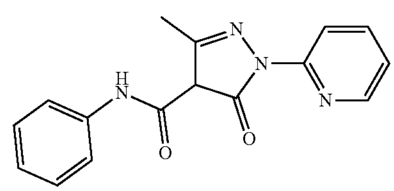 [SMILES: CC1=NN(c2ccccn2)C(=O)C1C(=O)Nc1ccccc1] |
| 193 | 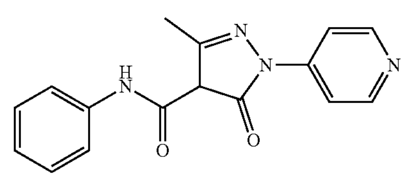 |
| 194 | 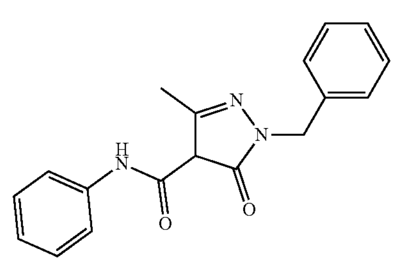 [SMILES: CC1=NN(Cc2ccccc2)C(=O)C1C(=O)Nc1ccccc1] |

TABLE 1-continued

| Compound name | Structure |
|---|---|
| 195 | 3-methyl-5-oxo-1-(pyridin-3-yl)-N-phenyl-4,5-dihydro-1H-pyrazole-4-carboxamide |
| 196 | 1,3-dimethyl-5-oxo-N-phenyl-4,5-dihydro-1H-pyrazole-4-carboxamide |
| 197 | 1-(4-methoxyphenyl)-3-methyl-5-oxo-N-phenyl-4,5-dihydro-1H-pyrazole-4-carboxamide |
| 198 | 3-methyl-1-(naphthalen-2-yl)-5-oxo-N-phenyl-4,5-dihydro-1H-pyrazole-4-carboxamide |
| 199 | N,3-dimethyl-5-oxo-1-phenyl-4,5-dihydro-1H-pyrazole-4-carboxamide |
| 200 | N-isopropyl-3-methyl-5-oxo-1-phenyl-4,5-dihydro-1H-pyrazole-4-carboxamide |
| 201 | 3-methyl-5-oxo-N-phenyl-1-(4-(trifluoromethyl)phenyl)-4,5-dihydro-1H-pyrazole-4-carboxamide |
| 202 | 1-(1,1-dioxidotetrahydrothiophen-3-yl)-3-methyl-5-oxo-N-phenyl-4,5-dihydro-1H-pyrazole-4-carboxamide |

TABLE 1-continued

| Compound name | Structure |
|---|---|
| 203 | 4-acetylphenyl derivative of 3-methyl-5-oxo-1-phenyl-4,5-dihydro-1H-pyrazole-4-carboxamide |
| 204 | N-methyl-N-phenyl 3-methyl-5-oxo-1-phenyl-4,5-dihydro-1H-pyrazole-4-carboxamide |
| 205 | N-(4-hydroxyphenyl) 3-methyl-5-oxo-1-phenyl-4,5-dihydro-1H-pyrazole-4-carboxamide |
| 206 | N-(3-(methoxycarbonyl)phenyl) 3-methyl-5-oxo-1-phenyl-4,5-dihydro-1H-pyrazole-4-carboxamide |
| 207 | N-benzoyl 3-methyl-5-oxo-1-phenyl-4,5-dihydro-1H-pyrazole-4-carboxamide |
| 208 | N-(3-(trifluoromethyl)phenyl) 3-methyl-5-oxo-1-phenyl-4,5-dihydro-1H-pyrazole-4-carboxamide |
| 209 | N-(2,3-dihydro-1H-inden-5-yl) 3-methyl-5-oxo-1-phenyl-4,5-dihydro-1H-pyrazole-4-carboxamide |
| 210 | N-(3-chlorophenyl) 3-methyl-5-oxo-1-phenyl-4,5-dihydro-1H-pyrazole-4-carboxamide |

TABLE 1-continued

| Compound name | Structure |
|---|---|
| 211 | *N-(3-methoxyphenyl)-3-methyl-5-oxo-1-phenyl-4,5-dihydro-1H-pyrazole-4-carboxamide* |
| 212 | *3-methyl-5-oxo-1-phenyl-N-(m-tolyl)-4,5-dihydro-1H-pyrazole-4-carboxamide* |
| 213 | *N-(2-acetylphenyl)-3-methyl-5-oxo-1-phenyl-4,5-dihydro-1H-pyrazole-4-carboxamide* |
| 214 | *3-methyl-5-oxo-1-phenyl-N-(pyridin-2-yl)-4,5-dihydro-1H-pyrazole-4-carboxamide* |
| 215 | *N-(3-bromophenyl)-3-methyl-5-oxo-1-phenyl-4,5-dihydro-1H-pyrazole-4-carboxamide* |
| 216 | *3-methyl-5-oxo-1-phenyl-N-(pyridin-4-yl)-4,5-dihydro-1H-pyrazole-4-carboxamide* |
| 217 | *3-methyl-5-oxo-1-phenyl-N-(thiazol-2-yl)-4,5-dihydro-1H-pyrazole-4-carboxamide* |
| 218 | *(S)-2-(3-methyl-5-oxo-1-phenyl-4,5-dihydro-1H-pyrazole-4-carboxamido)propanoic acid* |

TABLE 1-continued

| Compound name | Structure |
|---|---|
| 219 | 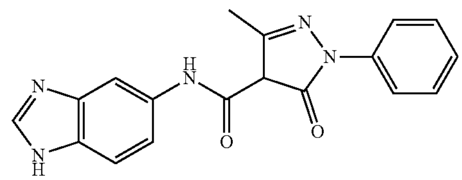 [SMILES: CC1=NN(c2ccccc2)C(=O)C1C(=O)Nc1ccc2[nH]cnc2c1] |
| 220 | 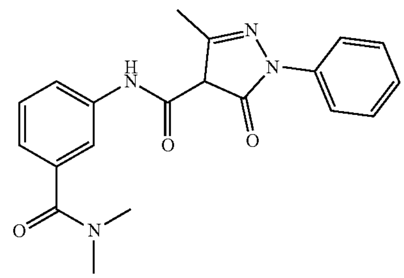 [SMILES: CC1=NN(c2ccccc2)C(=O)C1C(=O)Nc1cccc(C(=O)N(C)C)c1] |
| 221 | 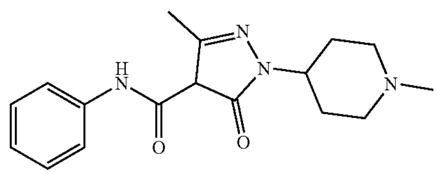 [SMILES: CC1=NN(C2CCN(C)CC2)C(=O)C1C(=O)Nc1ccccc1] |
| 222 | 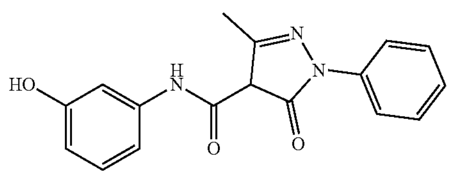 [SMILES: CC1=NN(c2ccccc2)C(=O)C1C(=O)Nc1cccc(O)c1] |
| 223 | 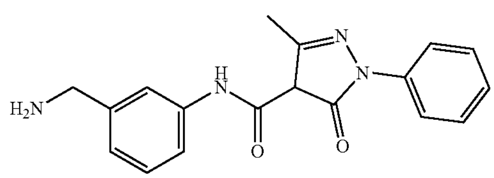 [SMILES: CC1=NN(c2ccccc2)C(=O)C1C(=O)Nc1cccc(CN)c1] |
| 224 | 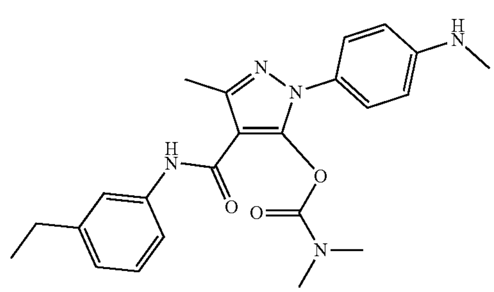 [SMILES: CCc1cccc(NC(=O)c2c(C)nn(-c3ccc(NC)cc3)c2OC(=O)N(C)C)c1] |
| 226 | 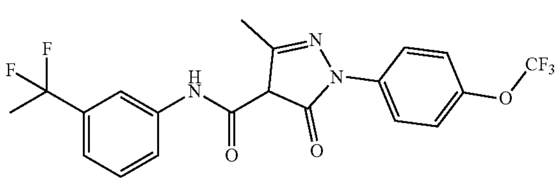 [SMILES: CC1=NN(c2ccc(OC(F)(F)F)cc2)C(=O)C1C(=O)Nc1cccc(C(C)(F)F)c1] |

TABLE 1-continued

| Compound name | Structure |
|---|---|
| 227 | 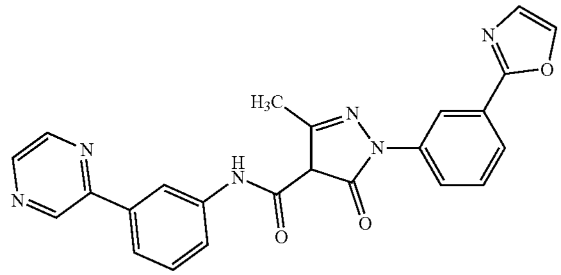 [SMILES: CC1=NN(c2cccc(-c3ncco3)c2)C(=O)C1C(=O)Nc1cccc(-c2cnccn2)c1] |
| 228 | 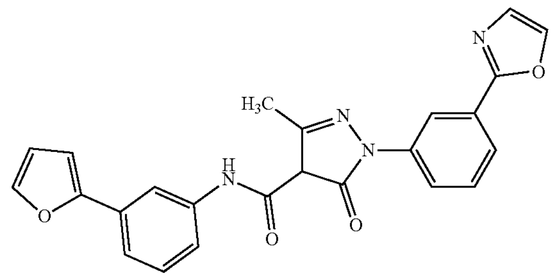 [SMILES: CC1=NN(c2cccc(-c3ncco3)c2)C(=O)C1C(=O)Nc1cccc(-c2ccco2)c1] |
| 229 | 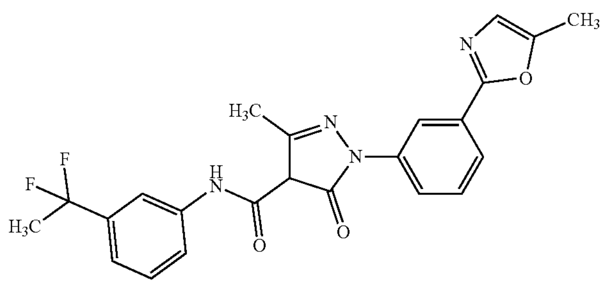 [SMILES: CC1=NN(c2cccc(-c3ncc(C)o3)c2)C(=O)C1C(=O)Nc1cccc(C(C)(F)F)c1] |
| 230 | 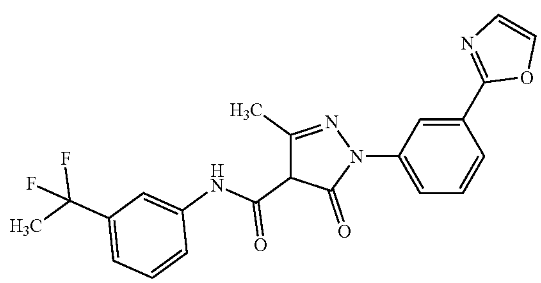 [SMILES: CC1=NN(c2cccc(-c3ncco3)c2)C(=O)C1C(=O)Nc1cccc(C(C)(F)F)c1] |
| 231 | 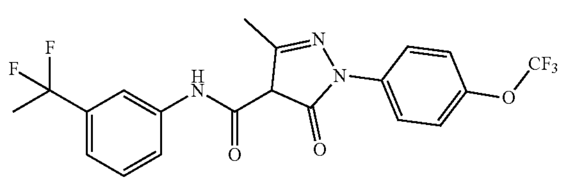 [SMILES: CC1=NN(c2ccc(OC(F)(F)F)cc2)C(=O)C1C(=O)Nc1cccc(C(C)(F)F)c1] |
| 232 | 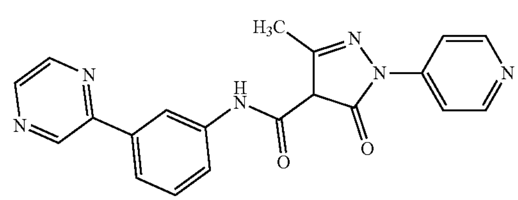 [SMILES: CC1=NN(c2ccncc2)C(=O)C1C(=O)Nc1cccc(-c2cnccn2)c1] |

TABLE 1-continued
| Compound name | Structure |
|---|---|
| 233 | 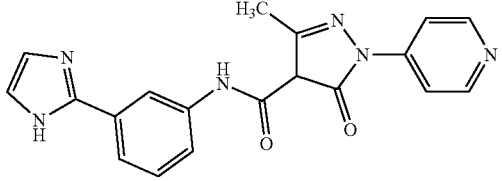 |
| 234 | 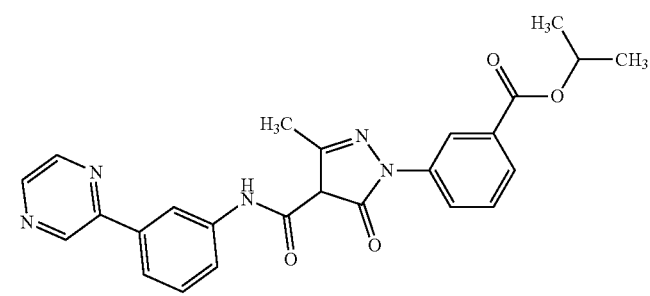 [SMILES: CC1=NN(c2cccc(C(=O)OC(C)C)c2)C(=O)C1C(=O)Nc1cccc(-c2cnccn2)c1] |
| 235 | 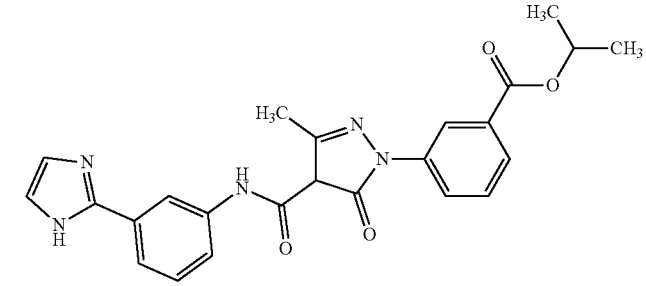 [SMILES: CC1=NN(c2cccc(C(=O)OC(C)C)c2)C(=O)C1C(=O)Nc1cccc(-c2ncc[nH]2)c1] |
| 236 | 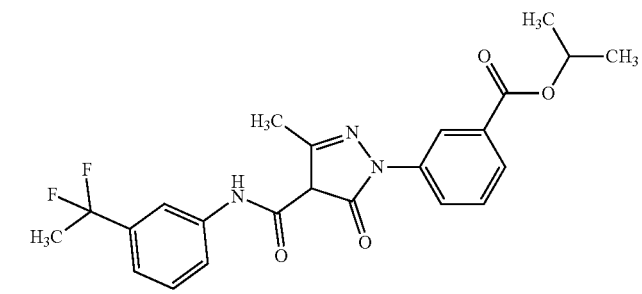 [SMILES: CC1=NN(c2cccc(C(=O)OC(C)C)c2)C(=O)C1C(=O)Nc1cccc(C(C)(F)F)c1] |
| 237 | 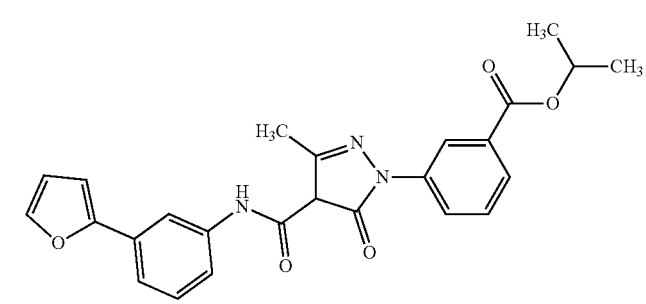 [SMILES: CC1=NN(c2cccc(C(=O)OC(C)C)c2)C(=O)C1C(=O)Nc1cccc(-c2ccco2)c1] |

TABLE 1-continued

| Compound name | Structure |
|---|---|
| 238 | 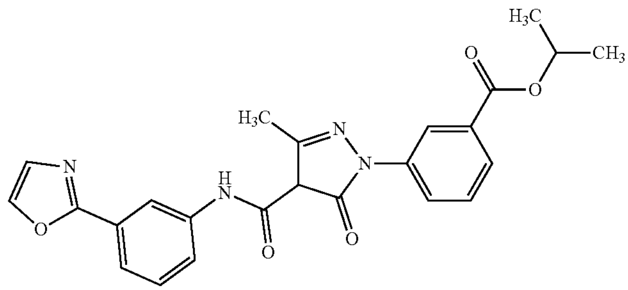 [SMILES: CC1=NN(c2cccc(C(=O)OC(C)C)c2)C(=O)C1C(=O)Nc1cccc(-c2ncco2)c1] |
| 239 | 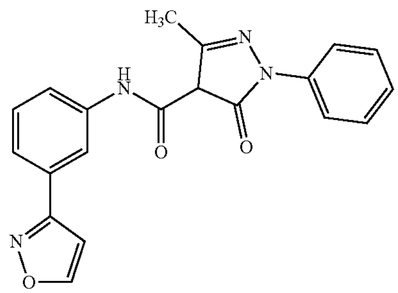 [SMILES: CC1=NN(c2ccccc2)C(=O)C1C(=O)Nc1cccc(-c2ccon2)c1] |
| 240 | 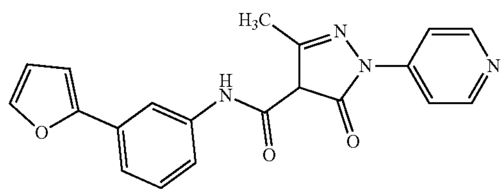 [SMILES: CC1=NN(c2ccncc2)C(=O)C1C(=O)Nc1cccc(-c2ccco2)c1] |
| 241 | 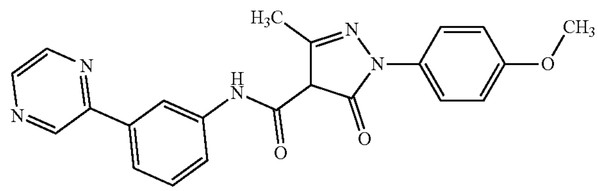 [SMILES: COc1ccc(N2N=C(C)C(C(=O)Nc3cccc(-c4cnccn4)c3)C2=O)cc1] |
| 242 | 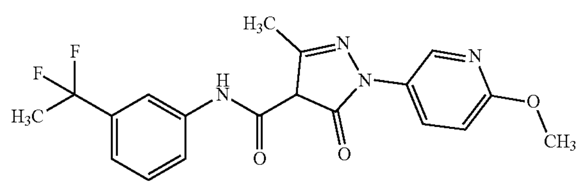 [SMILES: COc1ccc(N2N=C(C)C(C(=O)Nc3cccc(C(C)(F)F)c3)C2=O)cn1] |
| 243 | 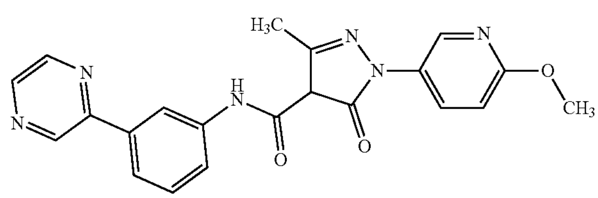 [SMILES: COc1ccc(N2N=C(C)C(C(=O)Nc3cccc(-c4cnccn4)c3)C2=O)cn1] |
| 244 | 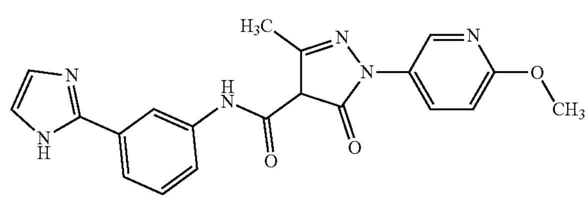 [SMILES: COc1ccc(N2N=C(C)C(C(=O)Nc3cccc(-c4ncc[nH]4)c3)C2=O)cn1] |

TABLE 1-continued

| Compound name | Structure |
|---|---|
| 245 | (oxazol-2-yl)phenyl-NH-C(=O)- pyrazolone with 3-methyl and N-(6-methoxypyridin-3-yl) |
| 246 | (furan-2-yl)phenyl-NH-C(=O)- pyrazolone with 3-methyl and N-(6-methoxypyridin-3-yl) |
| 247 | (furan-2-yl)phenyl-NH-C(=O)- pyrazolone with 3-methyl and N-(3-methoxyphenyl) |
| 248 | (1H-imidazol-2-yl)phenyl-NH-C(=O)- pyrazolone with 3-methyl and N-(3-methoxyphenyl) |
| 249 | (pyrazin-2-yl)phenyl-NH-C(=O)- pyrazolone with 3-methyl and N-(3-methoxyphenyl) |
| 250 | (1,1-difluoroethyl)phenyl-NH-C(=O)- pyrazolone with 3-methyl and N-(3-methoxyphenyl) |

TABLE 1-continued

| Compound name | Structure |
|---|---|
| 251 | (structure) |
| 252 | (structure) |
| 253 | (structure) |
| 254 | (structure) |
| 255 | (structure) |
| 256 | (structure) |
| 257 | (structure) |

TABLE 1-continued

| Compound name | Structure |
|---|---|
| 258 | (3-methyl-5-oxo-1-(3-carboxyphenyl)-4,5-dihydro-1H-pyrazol-4-yl)-N-(3-(1,1-difluoroethyl)phenyl)carboxamide |
| 259 | methyl 3-(3-methyl-4-((3-(oxazol-2-yl)phenyl)carbamoyl)-5-oxo-4,5-dihydro-1H-pyrazol-1-yl)benzoate |
| 260 | N-(5-ethylthiophen-2-yl)-3-methyl-5-oxo-1-phenyl-4,5-dihydro-1H-pyrazole-4-carboxamide |
| 261 | methyl 3-(4-((3-(1,1-difluoroethyl)phenyl)carbamoyl)-3-methyl-5-oxo-4,5-dihydro-1H-pyrazol-1-yl)benzoate |
| 252 | 4-(4-((3-(pyrazin-2-yl)phenyl)carbamoyl)-3-methyl-5-oxo-4,5-dihydro-1H-pyrazol-1-yl)-N,N-dimethylbenzenesulfonamide |
| 263 | 3-(4-((3-(furan-2-yl)phenyl)carbamoyl)-3-methyl-5-oxo-4,5-dihydro-1H-pyrazol-1-yl)-N,N-dimethylbenzenesulfonamide |

TABLE 1-continued

| Compound name | Structure |
|---|---|
| 264 | (structure) |
| 265 | (structure) |
| 266 | (structure) |
| 267 | (structure) |
| 268 | (structure) |
| 269 | (structure) |
| 270 | (structure) |

TABLE 1-continued

| Compound name | Structure |
|---|---|
| 271 | *[structure: 4-((3-(1,1-difluoroethyl)phenyl)carbamoyl)-3-methyl-1-(3-(trifluoromethyl)phenyl)-5-oxo-4,5-dihydro-1H-pyrazole]* |
| 272 | *[structure: N-(3-(pyrazin-2-yl)phenyl)-3-methyl-1-(3-(N,N-dimethylsulfamoyl)phenyl)-5-oxo-4,5-dihydro-1H-pyrazole-4-carboxamide]* |
| 273 | *[structure: 3-(4-((3-(1H-imidazol-2-yl)phenyl)carbamoyl)-3-methyl-5-oxo-4,5-dihydro-1H-pyrazol-1-yl)benzoic acid]* |
| 274 | *[structure: 3-(3-methyl-4-((3-(oxazol-2-yl)phenyl)carbamoyl)-5-oxo-4,5-dihydro-1H-pyrazol-1-yl)benzoic acid]* |
| 275 | *[structure: methyl 3-(3-methyl-4-((3-(pyrazin-2-yl)phenyl)carbamoyl)-5-oxo-4,5-dihydro-1H-pyrazol-1-yl)benzoate]* |
| 276 | *[structure: methyl 3-(4-((3-(1H-imidazol-2-yl)phenyl)carbamoyl)-3-methyl-5-oxo-4,5-dihydro-1H-pyrazol-1-yl)benzoate]* |

TABLE 1-continued
| Compound name | Structure |
|---|---|
| 277 | 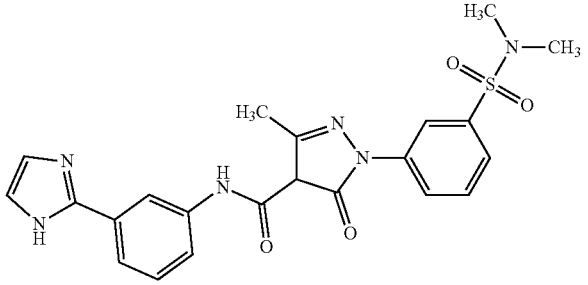 [SMILES: CC1=NN(c2cccc(S(=O)(=O)N(C)C)c2)C(=O)C1C(=O)Nc1cccc(-c2ncc[nH]2)c1] |
| 278 | 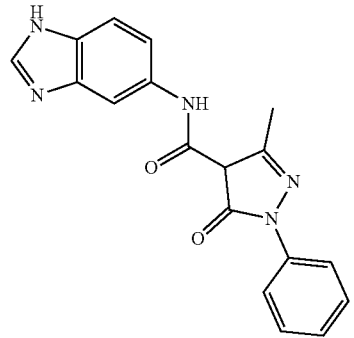 [SMILES: CC1=NN(c2ccccc2)C(=O)C1C(=O)Nc1ccc2[nH]cnc2c1] |
| 279 | 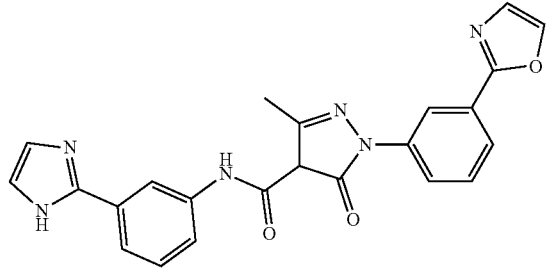 [SMILES: CC1=NN(c2cccc(-c3ncco3)c2)C(=O)C1C(=O)Nc1cccc(-c2ncc[nH]2)c1] |
| 280 | 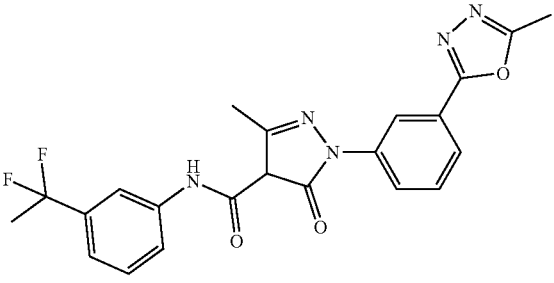 [SMILES: CC1=NN(c2cccc(-c3nnc(C)o3)c2)C(=O)C1C(=O)Nc1cccc(C(C)(F)F)c1] |
| 281 | 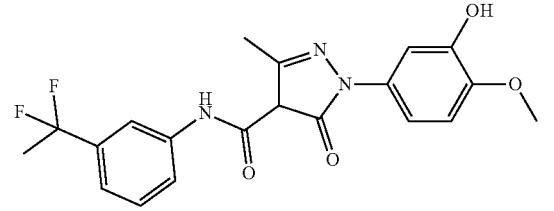 [SMILES: COc1ccc(N2N=C(C)C(C(=O)Nc3cccc(C(C)(F)F)c3)C2=O)cc1O] |

TABLE 1-continued

| Compound name | Structure |
|---|---|
| 282 | 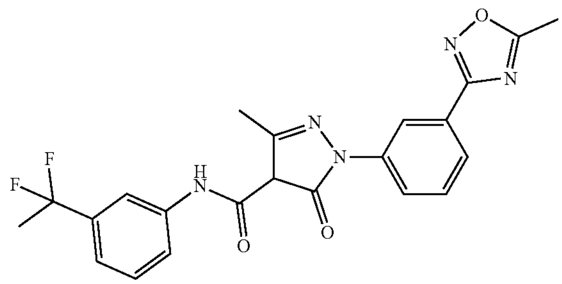 [SMILES: CC1=NN(c2cccc(-c3noc(C)n3)c2)C(=O)C1C(=O)Nc1cccc(C(C)(F)F)c1] |
| 283 | 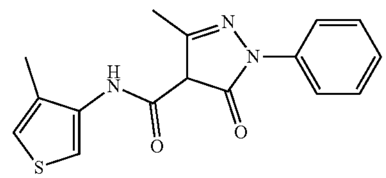 [SMILES: CC1=NN(c2ccccc2)C(=O)C1C(=O)Nc1cscc1C] |
| 284 | 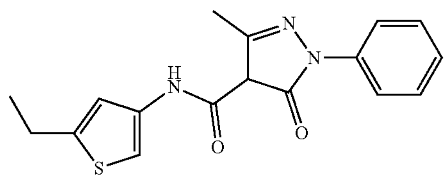 [SMILES: CCc1cc(NC(=O)C2C(=O)N(c3ccccc3)N=C2C)cs1] |
| 285 | 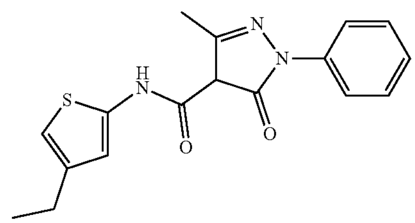 [SMILES: CCc1csc(NC(=O)C2C(=O)N(c3ccccc3)N=C2C)c1] |
| 286 | 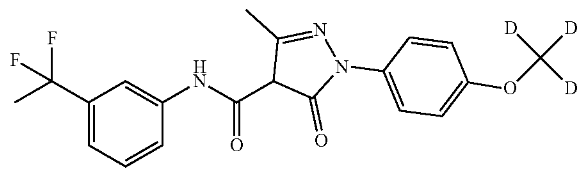 [SMILES: [2H]C([2H])([2H])Oc1ccc(N2N=C(C)C(C(=O)Nc3cccc(C(C)(F)F)c3)C2=O)cc1] |
| 287 | 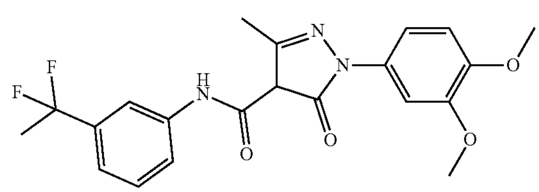 [SMILES: COc1ccc(N2N=C(C)C(C(=O)Nc3cccc(C(C)(F)F)c3)C2=O)cc1OC] |
| 288 | 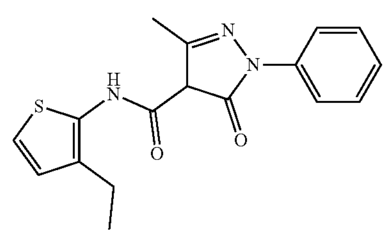 [SMILES: CCc1ccsc1NC(=O)C1C(=O)N(c2ccccc2)N=C1C] |

TABLE 1-continued

| Compound name | Structure |
|---|---|
| 289 | 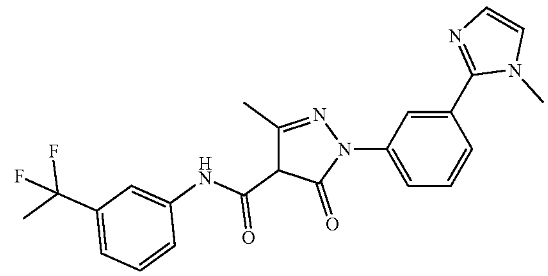 [SMILES: CC1=NN(c2cccc(-c3nccn3C)c2)C(=O)C1C(=O)Nc1cccc(C(C)(F)F)c1] |
| 290 | 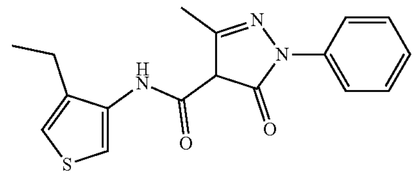 [SMILES: CCc1cscc1NC(=O)C1C(=O)N(c2ccccc2)N=C1C] |
| 291 | 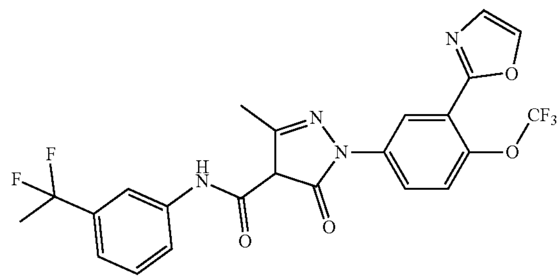 [SMILES: CC1=NN(c2ccc(OC(F)(F)F)c(-c3ncco3)c2)C(=O)C1C(=O)Nc1cccc(C(C)(F)F)c1] |
| 292 | 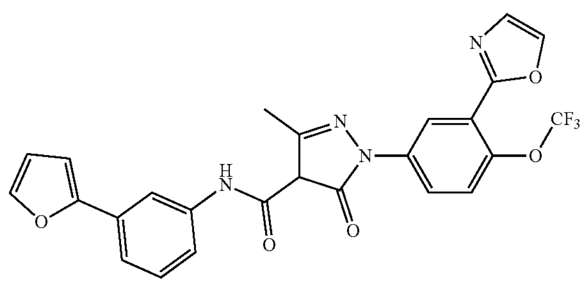 [SMILES: CC1=NN(c2ccc(OC(F)(F)F)c(-c3ncco3)c2)C(=O)C1C(=O)Nc1cccc(-c2ccco2)c1] |
| 293 | 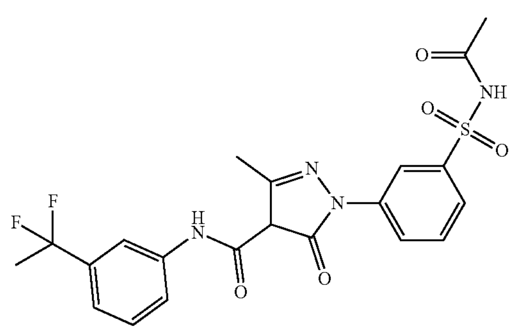 [SMILES: CC(=O)NS(=O)(=O)c1cccc(N2N=C(C)C(C(=O)Nc3cccc(C(C)(F)F)c3)C2=O)c1] |

TABLE 1-continued

| Compound name | Structure |
|---|---|
| 294 | 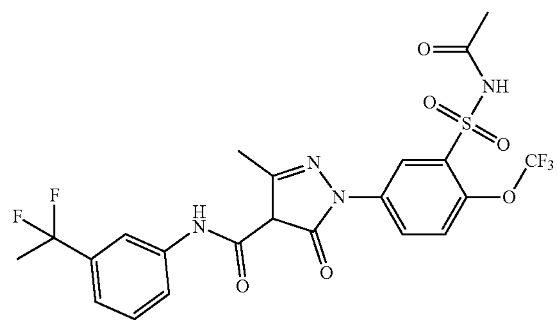 [SMILES: CC(=O)NS(=O)(=O)c1cc(N2N=C(C)C(C(=O)Nc3cccc(C(C)(F)F)c3)C2=O)ccc1OC(F)(F)F] |
| 295 | 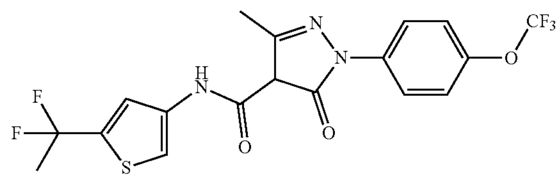 [SMILES: CC1=NN(c2ccc(OC(F)(F)F)cc2)C(=O)C1C(=O)Nc1csc(C(C)(F)F)c1] |
| 296 | 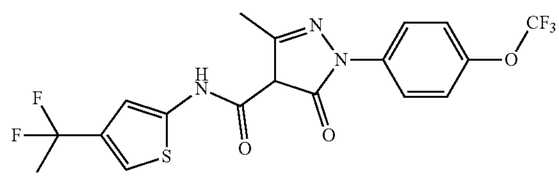 [SMILES: CC1=NN(c2ccc(OC(F)(F)F)cc2)C(=O)C1C(=O)Nc1cc(C(C)(F)F)cs1] |
| 297 | 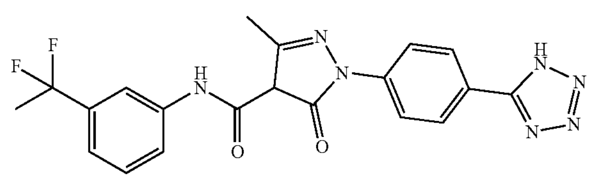 [SMILES: CC1=NN(c2ccc(-c3nnn[nH]3)cc2)C(=O)C1C(=O)Nc1cccc(C(C)(F)F)c1] |
| 298 | 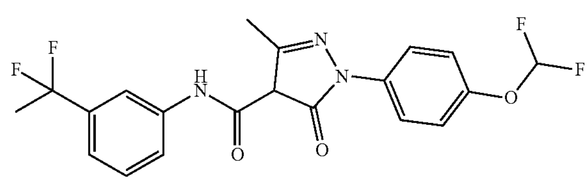 [SMILES: CC1=NN(c2ccc(OC(F)F)cc2)C(=O)C1C(=O)Nc1cccc(C(C)(F)F)c1] |
| 299 | 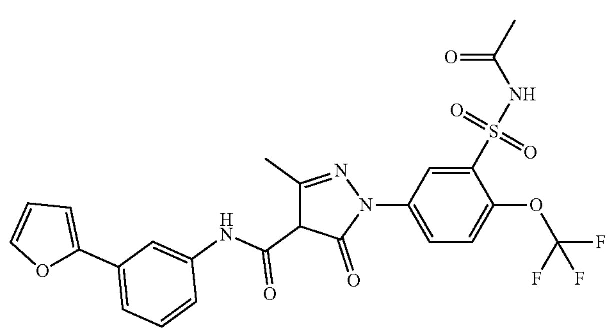 [SMILES: CC(=O)NS(=O)(=O)c1cc(N2N=C(C)C(C(=O)Nc3cccc(-c4ccco4)c3)C2=O)ccc1OC(F)(F)F] |

TABLE 1-continued

| Compound name | Structure |
|---|---|
| 300 | 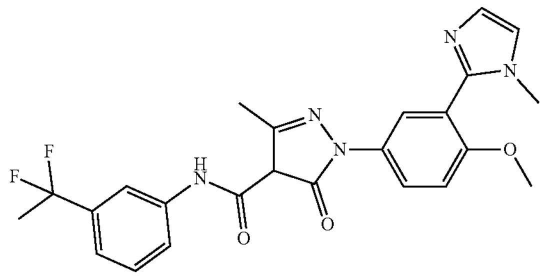 [SMILES: COc1ccc(N2N=C(C)C(C(=O)Nc3cccc(C(C)(F)F)c3)C2=O)cc1-c1nccn1C] |
| 301 | 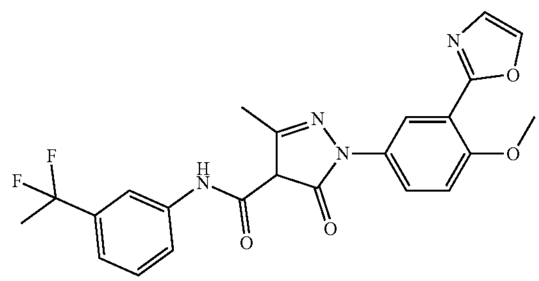 [SMILES: COc1ccc(N2N=C(C)C(C(=O)Nc3cccc(C(C)(F)F)c3)C2=O)cc1-c1ncco1] |
| 302 | 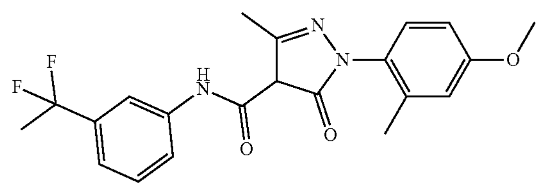 [SMILES: COc1ccc(N2N=C(C)C(C(=O)Nc3cccc(C(C)(F)F)c3)C2=O)c(C)c1] |
| 303 | 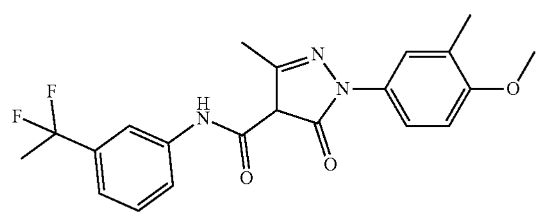 [SMILES: COc1ccc(N2N=C(C)C(C(=O)Nc3cccc(C(C)(F)F)c3)C2=O)cc1C] |
| 304 | 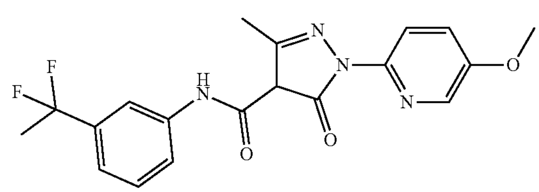 [SMILES: COc1ccc(N2N=C(C)C(C(=O)Nc3cccc(C(C)(F)F)c3)C2=O)nc1] |
| 305 | 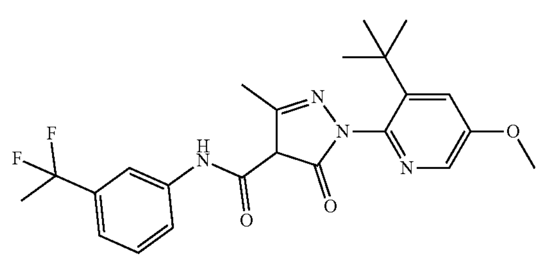 |

TABLE 1-continued
| Compound name | Structure |
|---|---|
| 306 | 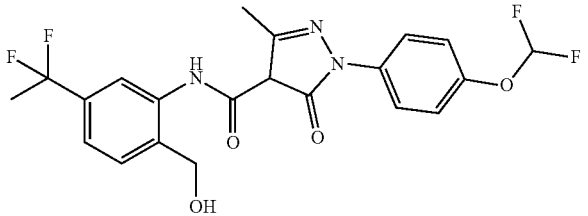 [SMILES: CC1=NN(c2ccc(OC(F)F)cc2)C(=O)C1C(=O)Nc1cc(C(C)(F)F)ccc1CO] |
| 307 | 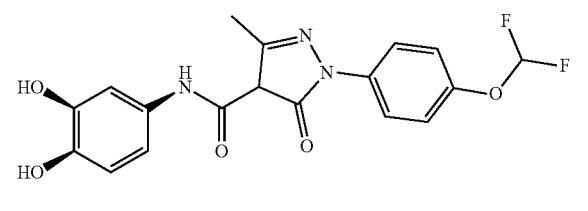 |
| 308 | 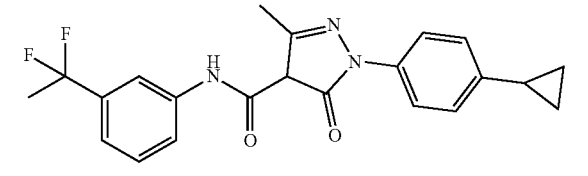 [SMILES: CC1=NN(c2ccc(C3CC3)cc2)C(=O)C1C(=O)Nc1cccc(C(C)(F)F)c1] |
| 309 | 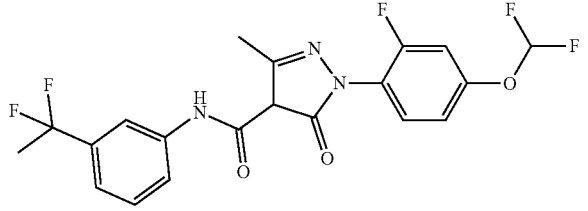 [SMILES: CC1=NN(c2ccc(OC(F)F)cc2F)C(=O)C1C(=O)Nc1cccc(C(C)(F)F)c1] |
| 310 | 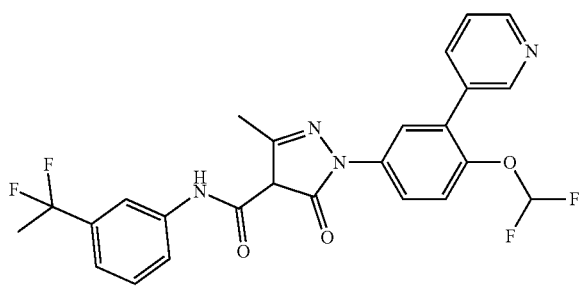 |
| 311 | 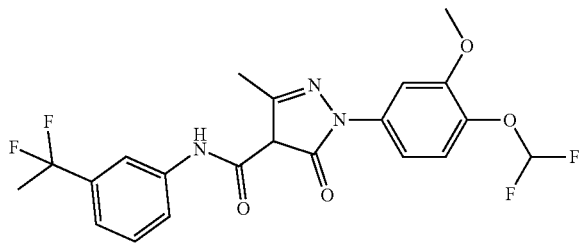 [SMILES: COc1cc(N2N=C(C)C(C(=O)Nc3cccc(C(C)(F)F)c3)C2=O)ccc1OC(F)F] |

TABLE 1-continued

| Compound name | Structure |
|---|---|
| 312 | 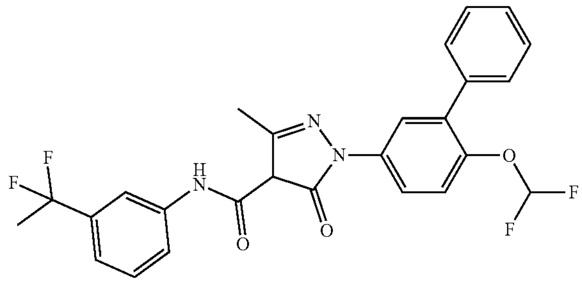 |
| 313 | 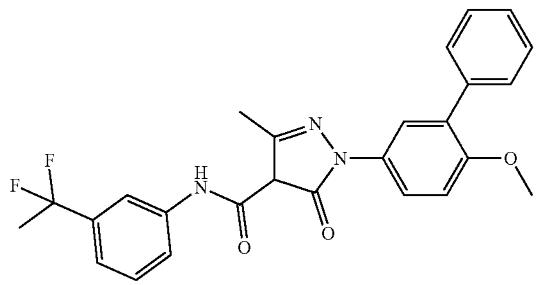 |
| 314 | 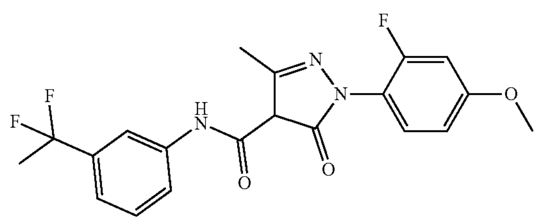 [SMILES: COc1ccc(N2N=C(C)C(C(=O)Nc3cccc(C(C)(F)F)c3)C2=O)c(F)c1] |
| 315 | 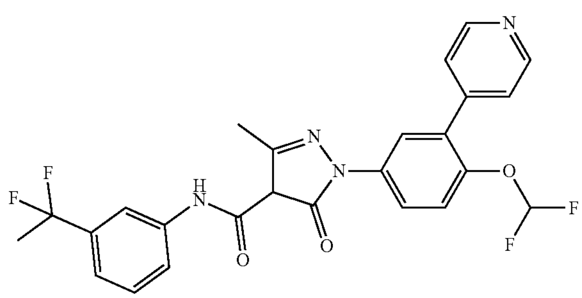 |
| 316 | 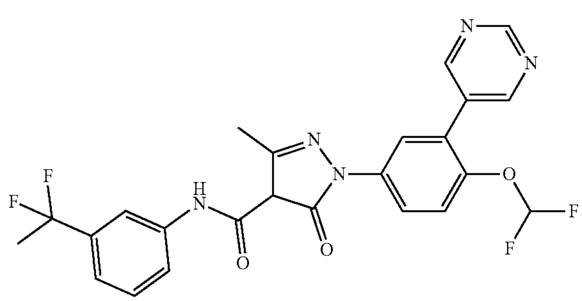 |

TABLE 1-continued

| Compound name | Structure |
|---|---|
| 317 | 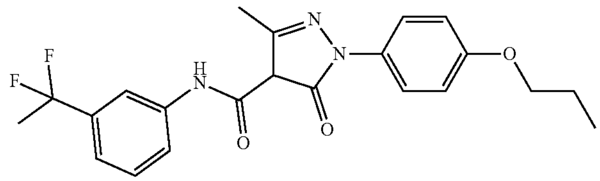 [SMILES: CCCOc1ccc(N2N=C(C)C(C(=O)Nc3cccc(C(C)(F)F)c3)C2=O)cc1] |
| 318 | 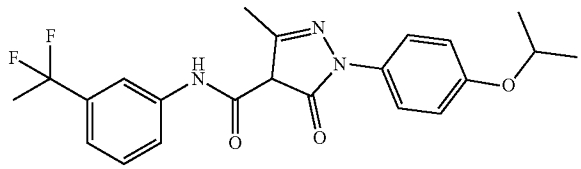 [SMILES: CC1=NN(c2ccc(OC(C)C)cc2)C(=O)C1C(=O)Nc1cccc(C(C)(F)F)c1] |
| 319 | 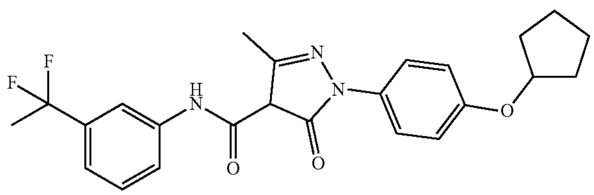 [SMILES: CC1=NN(c2ccc(OC3CCCC3)cc2)C(=O)C1C(=O)Nc1cccc(C(C)(F)F)c1] |
| 320 | 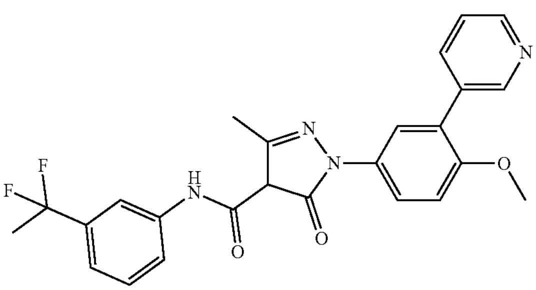 [SMILES: COc1ccc(N2N=C(C)C(C(=O)Nc3cccc(C(C)(F)F)c3)C2=O)cc1-c1cccnc1] |
| 321 | 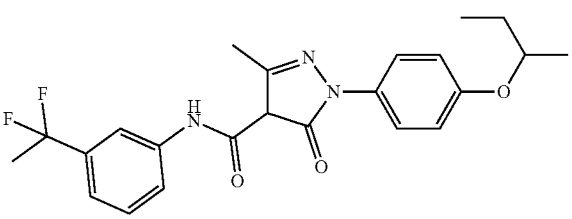 [SMILES: CCC(C)Oc1ccc(N2N=C(C)C(C(=O)Nc3cccc(C(C)(F)F)c3)C2=O)cc1] |
| 322 | 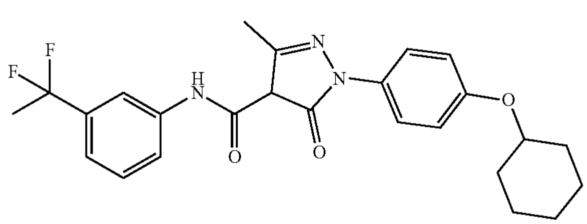 [SMILES: CC1=NN(c2ccc(OC3CCCCC3)cc2)C(=O)C1C(=O)Nc1cccc(C(C)(F)F)c1] |

TABLE 1-continued

| Compound name | Structure |
|---|---|
| 323 | 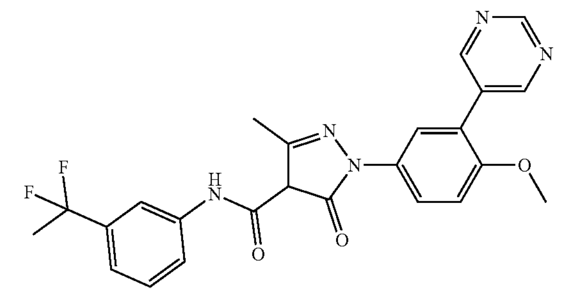 [SMILES: COc1ccc(N2N=C(C)C(C(=O)Nc3cccc(C(C)(F)F)c3)C2=O)cc1-c1cncnc1] |
| 324 | 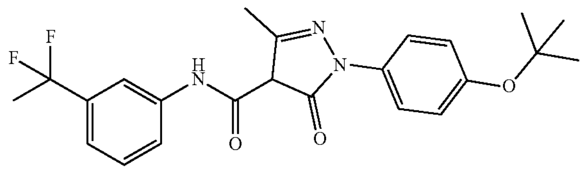 [SMILES: CC1=NN(c2ccc(OC(C)(C)C)cc2)C(=O)C1C(=O)Nc1cccc(C(C)(F)F)c1] |
| 325 | 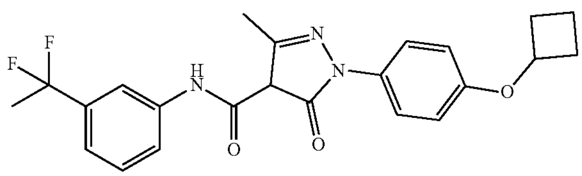 [SMILES: CC1=NN(c2ccc(OC3CCC3)cc2)C(=O)C1C(=O)Nc1cccc(C(C)(F)F)c1] |
| 326 | 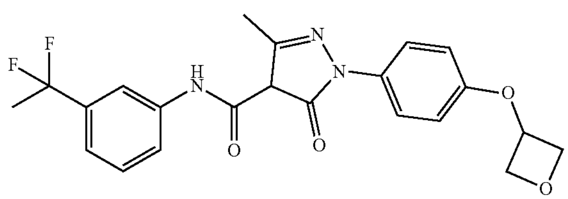 [SMILES: CC1=NN(c2ccc(OC3COC3)cc2)C(=O)C1C(=O)Nc1cccc(C(C)(F)F)c1] |
| 327 | 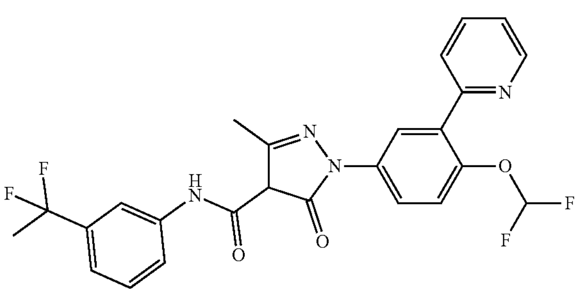 [SMILES: CC1=NN(c2ccc(OC(F)F)c(-c3ccccn3)c2)C(=O)C1C(=O)Nc1cccc(C(C)(F)F)c1] |
| 328 | 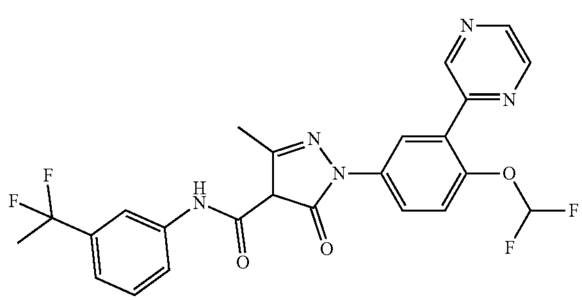 [SMILES: CC1=NN(c2ccc(OC(F)F)c(-c3cnccn3)c2)C(=O)C1C(=O)Nc1cccc(C(C)(F)F)c1] |

TABLE 1-continued

| Compound name | Structure |
|---|---|
| 329 | 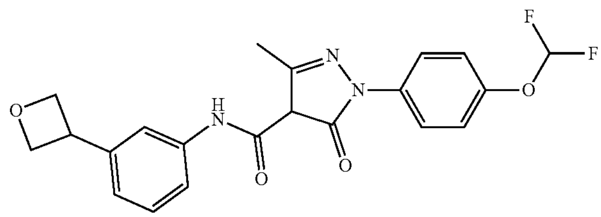 [SMILES: CC1=NN(c2ccc(OC(F)F)cc2)C(=O)C1C(=O)Nc1cccc(C2COC2)c1] |
| 330 | 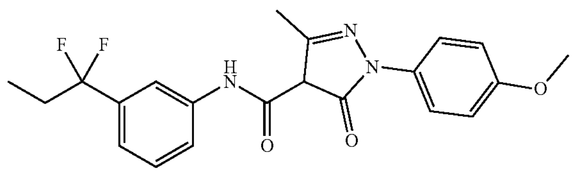 [SMILES: CCC(F)(F)c1cccc(NC(=O)C2C(=O)N(c3ccc(OC)cc3)N=C2C)c1] |
| 331 | 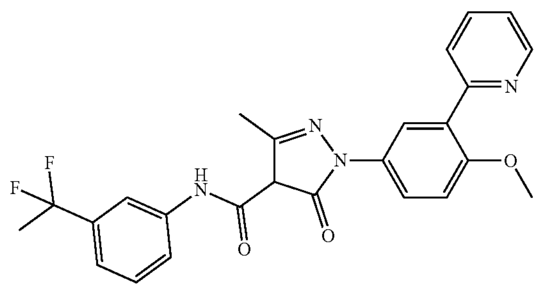 |
| 332 | 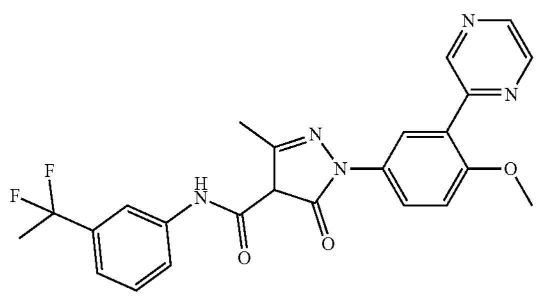 [SMILES: COc1ccc(N2N=C(C)C(C(=O)Nc3cccc(C(C)(F)F)c3)C2=O)cc1-c1cnccn1] |
| 333 | 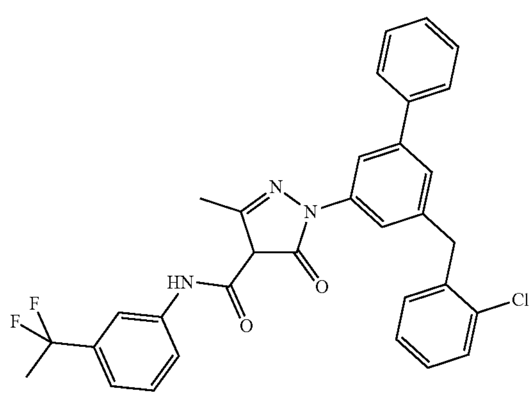 [SMILES: CC1=NN(c2cc(Cc3ccccc3Cl)cc(-c3ccccc3)c2)C(=O)C1C(=O)Nc1cccc(C(C)(F)F)c1] |

TABLE 1-continued

| Compound name | Structure |
|---|---|
| 334 | 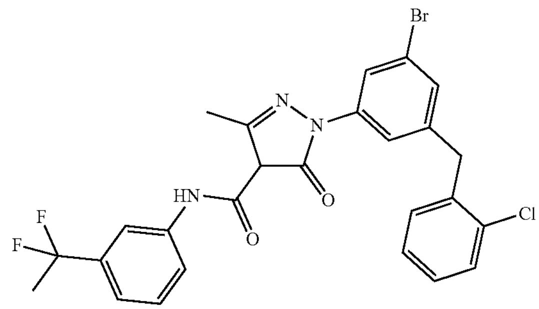 [SMILES: CC1=NN(c2cc(Br)cc(Cc3ccccc3Cl)c2)C(=O)C1C(=O)Nc1cccc(C(C)(F)F)c1] |
| 335 | 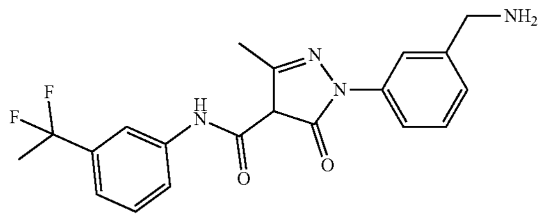 [SMILES: CC1=NN(c2cccc(CN)c2)C(=O)C1C(=O)Nc1cccc(C(C)(F)F)c1] |
| 336 | 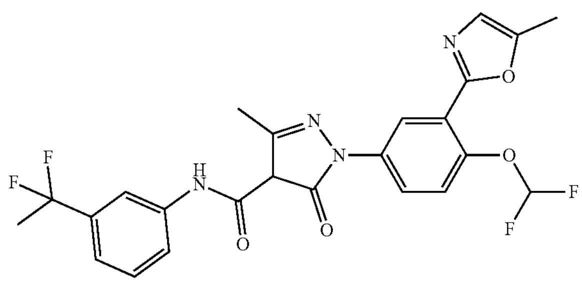 [SMILES: CC1=NN(c2ccc(OC(F)F)c(-c3ncc(C)o3)c2)C(=O)C1C(=O)Nc1cccc(C(C)(F)F)c1] |
| 337 | 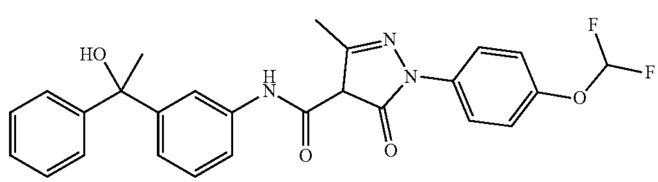 [SMILES: CC1=NN(c2ccc(OC(F)F)cc2)C(=O)C1C(=O)Nc1cccc(C(C)(O)c2ccccc2)c1] |
| 339 | 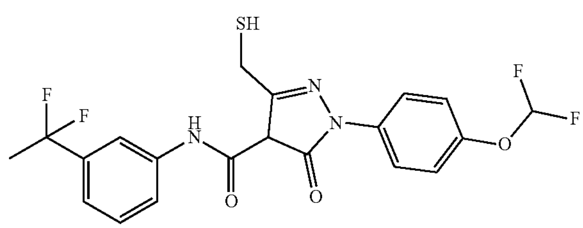 [SMILES: CC(F)(F)c1cccc(NC(=O)C2C(=O)N(c3ccc(OC(F)F)cc3)N=C2CS)c1] |
| 340 | 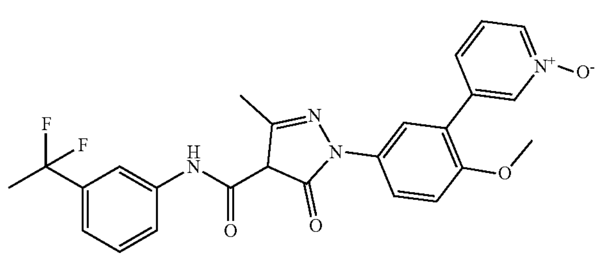 [SMILES: COc1ccc(N2N=C(C)C(C(=O)Nc3cccc(C(C)(F)F)c3)C2=O)cc1-c1ccc[n+]([O-])c1] |

TABLE 1-continued

| Compound name | Structure |
|---|---|
| 341 | 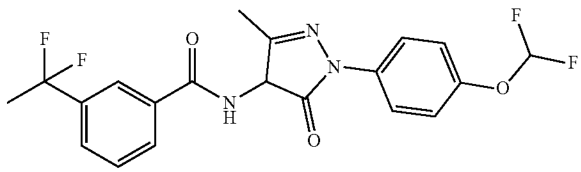 [SMILES: CC1=NN(c2ccc(OC(F)F)cc2)C(=O)C1NC(=O)c1cccc(C(C)(F)F)c1] |
| 342 | 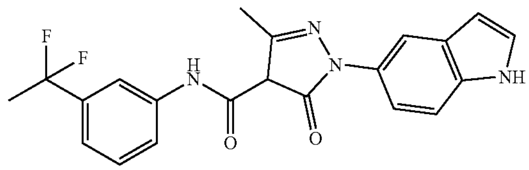 [SMILES: CC1=NN(c2ccc3[nH]ccc3c2)C(=O)C1C(=O)Nc1cccc(C(C)(F)F)c1] |
| 343 | 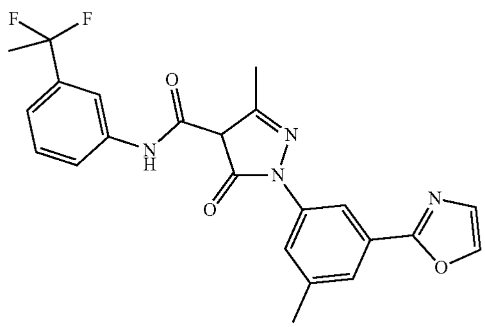 [SMILES: CC1=NN(c2cc(C)cc(-c3ncco3)c2)C(=O)C1C(=O)Nc1cccc(C(C)(F)F)c1] |
| 344 | 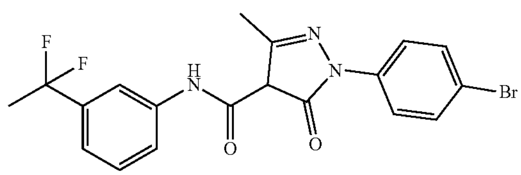 [SMILES: CC1=NN(c2ccc(Br)cc2)C(=O)C1C(=O)Nc1cccc(C(C)(F)F)c1] |
| 345 | 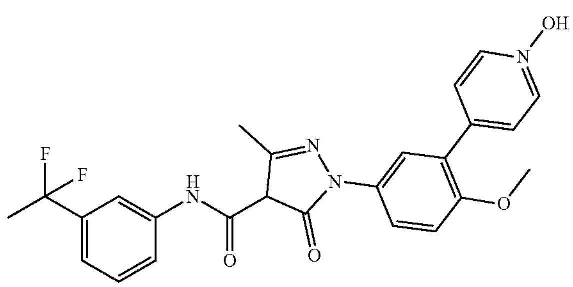 |
| 346 | 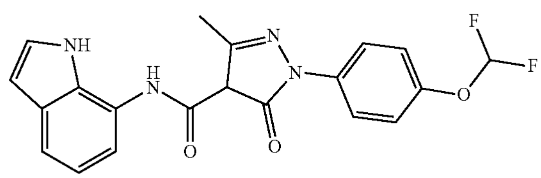 [SMILES: CC1=NN(c2ccc(OC(F)F)cc2)C(=O)C1C(=O)Nc1cccc2cc[nH]c12] |
| 347 | 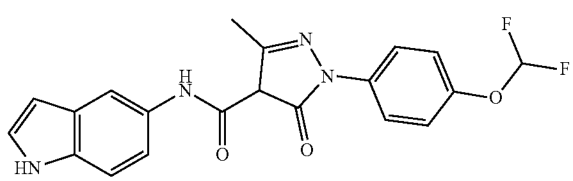 [SMILES: CC1=NN(c2ccc(OC(F)F)cc2)C(=O)C1C(=O)Nc1ccc2[nH]ccc2c1] |

TABLE 1-continued

| Compound name | Structure |
|---|---|
| 348 | 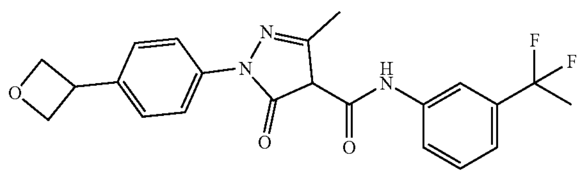 [SMILES: CC1=NN(c2ccc(C3COC3)cc2)C(=O)C1C(=O)Nc1cccc(C(C)(F)F)c1] |
| 349 | 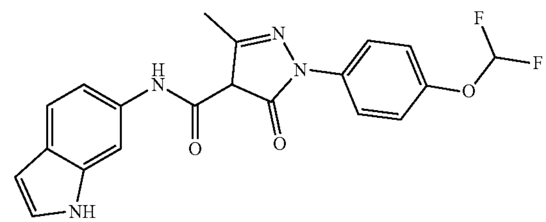 [SMILES: CC1=NN(c2ccc(OC(F)F)cc2)C(=O)C1C(=O)Nc1ccc2cc[nH]c2c1] |
| 350 | 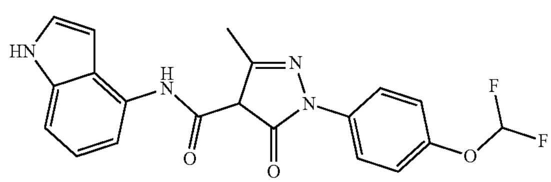 [SMILES: CC1=NN(c2ccc(OC(F)F)cc2)C(=O)C1C(=O)Nc1cccc2[nH]ccc12] |
| 351 | 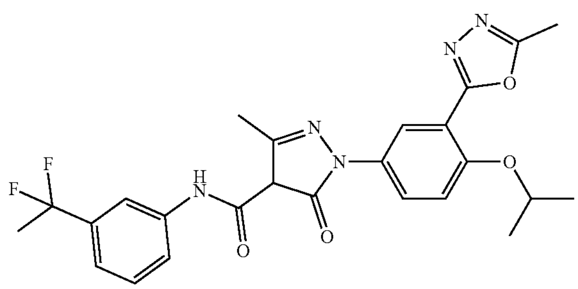 [SMILES: CC1=NN(c2ccc(OC(C)C)c(-c3nnc(C)o3)c2)C(=O)C1C(=O)Nc1cccc(C(C)(F)F)c1] |
| 352 | 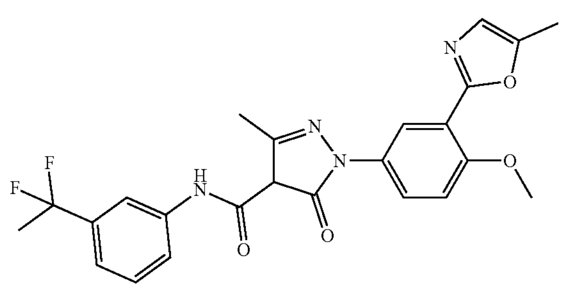 |
| 353 | 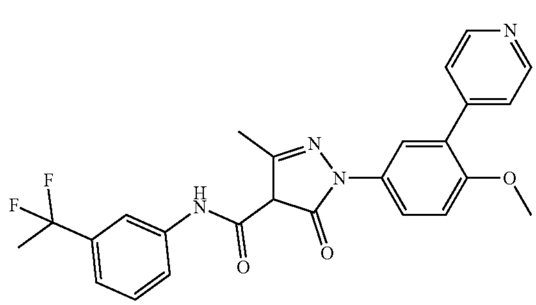 [SMILES: COc1ccc(N2N=C(C)C(C(=O)Nc3cccc(C(C)(F)F)c3)C2=O)cc1-c1ccncc1] |

TABLE 1-continued

| Compound name | Structure |
|---|---|
| 354 | 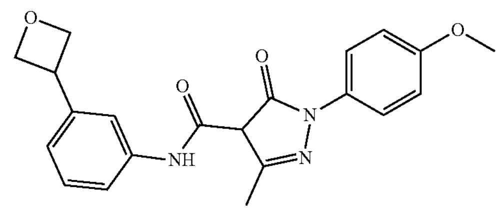 [SMILES: COc1ccc(N2N=C(C)C(C(=O)Nc3cccc(C4COC4)c3)C2=O)cc1] |
| 355 | 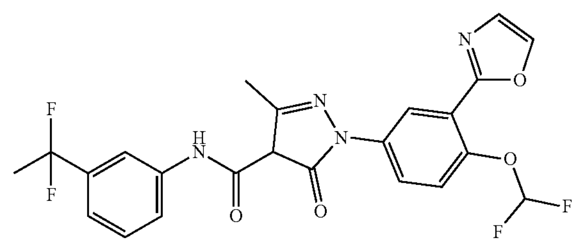 [SMILES: CC1=NN(c2ccc(OC(F)F)c(-c3ncco3)c2)C(=O)C1C(=O)Nc1cccc(C(C)(F)F)c1] |
| 356 | 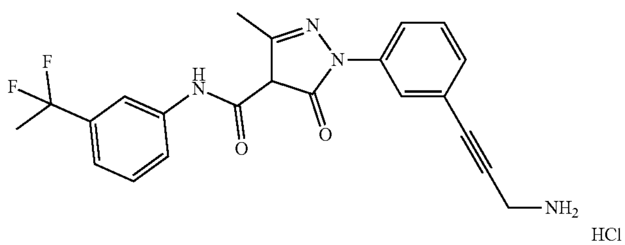 [SMILES: CC1=NN(c2cccc(C#CCN)c2)C(=O)C1C(=O)Nc1cccc(C(C)(F)F)c1 ; Cl] |
| 357 | 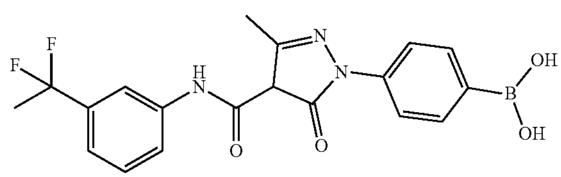 [SMILES: CC1=NN(c2ccc(B(O)O)cc2)C(=O)C1C(=O)Nc1cccc(C(C)(F)F)c1] |
| 358 | 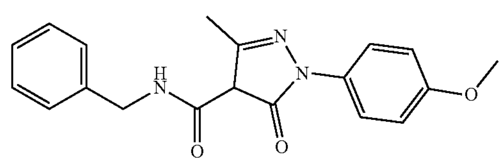 [SMILES: COc1ccc(N2N=C(C)C(C(=O)NCc3ccccc3)C2=O)cc1] |
| 359 | 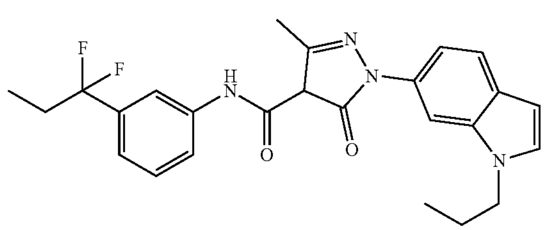 [SMILES: CCCn1ccc2ccc(N3N=C(C)C(C(=O)Nc4cccc(C(F)(F)CC)c4)C3=O)cc21] |
| 360 | 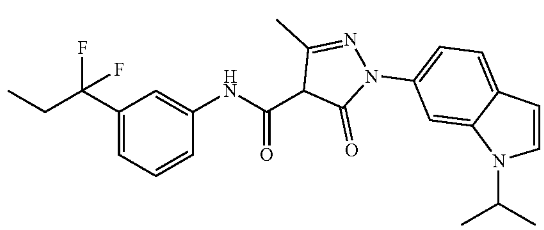 [SMILES: CCC(F)(F)c1cccc(NC(=O)C2C(=O)N(c3ccc4ccn(C(C)C)c4c3)N=C2C)c1] |

TABLE 1-continued

| Compound name | Structure |
|---|---|
| 361 | 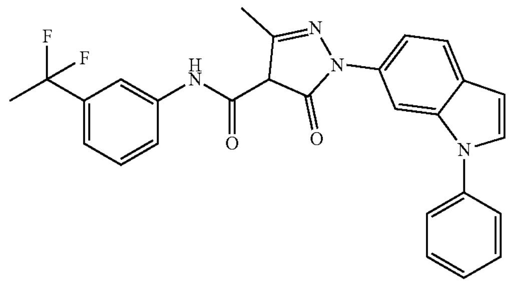 [SMILES: CC1=NN(c2ccc3ccn(-c4ccccc4)c3c2)C(=O)C1C(=O)Nc1cccc(C(C)(F)F)c1] |
| 362 | 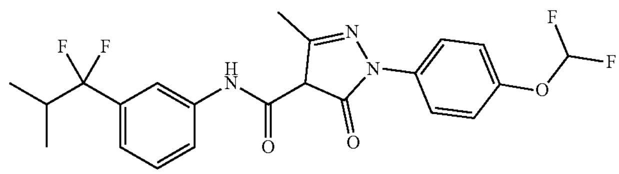 [SMILES: CC1=NN(c2ccc(OC(F)F)cc2)C(=O)C1C(=O)Nc1cccc(C(F)(F)C(C)C)c1] |
| 363 | 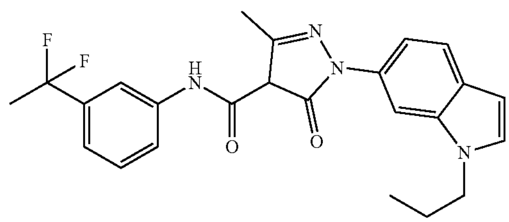 [SMILES: CCCn1ccc2ccc(N3N=C(C)C(C(=O)Nc4cccc(C(C)(F)F)c4)C3=O)cc21] |
| 364 | 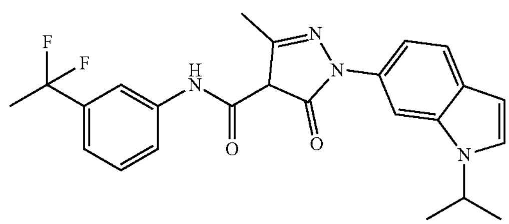 [SMILES: CC1=NN(c2ccc3ccn(C(C)C)c3c2)C(=O)C1C(=O)Nc1cccc(C(C)(F)F)c1] |
| 365 | 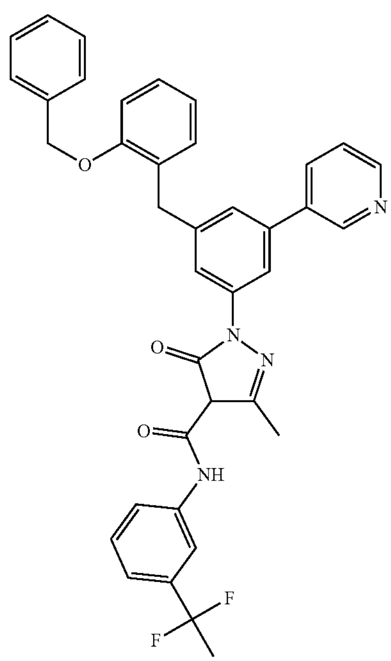 [SMILES: CC1=NN(c2cc(Cc3ccccc3OCc3ccccc3)cc(-c3cccnc3)c2)C(=O)C1C(=O)Nc1cccc(C(C)(F)F)c1] |

US 12,133,852 B2
113                                                             114
TABLE 1-continued
| Compound name | Structure |
|---|---|
| 366 | 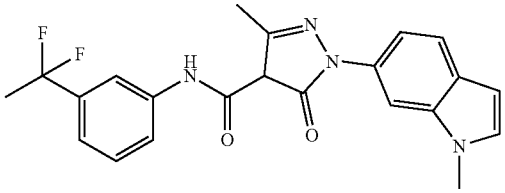 [SMILES: CC1=NN(c2ccc3ccn(C)c3c2)C(=O)C1C(=O)Nc1cccc(C(C)(F)F)c1] |
| 367 | 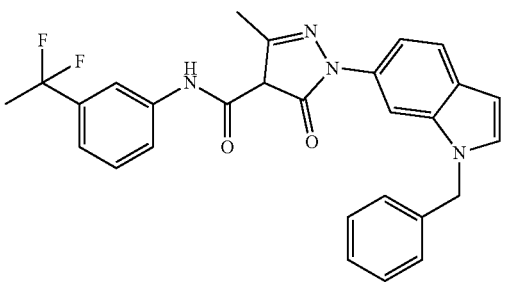 [SMILES: CC1=NN(c2ccc3ccn(Cc4ccccc4)c3c2)C(=O)C1C(=O)Nc1cccc(C(C)(F)F)c1] |
| 368 | 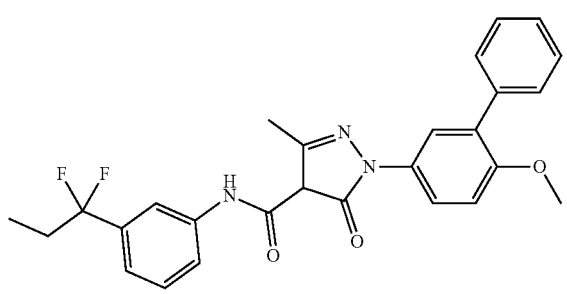 [SMILES: CCC(F)(F)c1cccc(NC(=O)C2C(=O)N(c3ccc(OC)c(-c4ccccc4)c3)N=C2C)c1] |
| 369 | 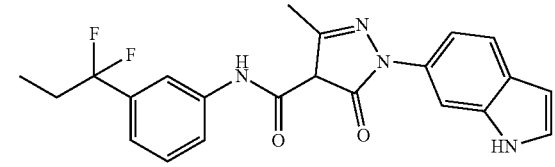 [SMILES: CCC(F)(F)c1cccc(NC(=O)C2C(=O)N(c3ccc4cc[nH]c4c3)N=C2C)c1] |
| 370 | 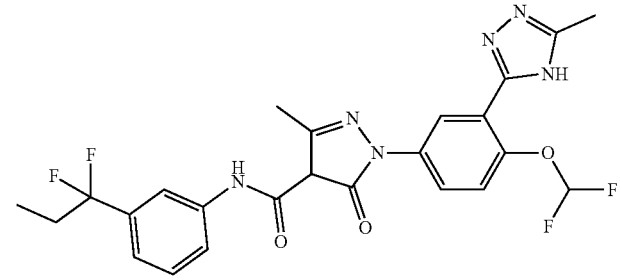 [SMILES: CCC(F)(F)c1cccc(NC(=O)C2C(=O)N(c3ccc(OC(F)F)c(-c4nnc(C)[nH]4)c3)N=C2C)c1] |
| 371 | 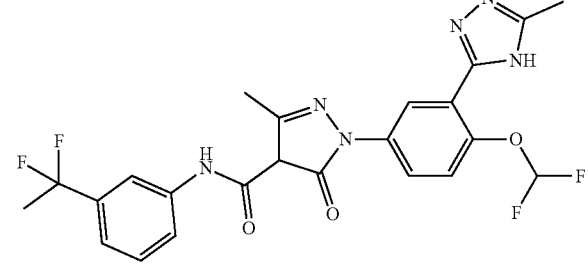 |

TABLE 1-continued
| Compound name | Structure |
|---|---|
| 372 | 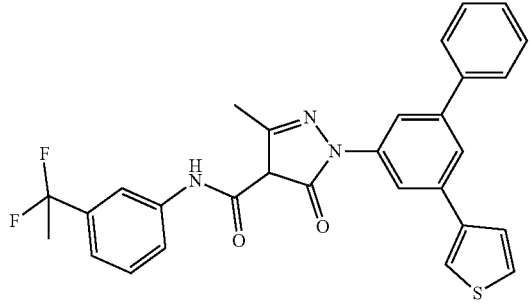 [SMILES: CC1=NN(c2cc(-c3ccccc3)cc(-c3ccsc3)c2)C(=O)C1C(=O)Nc1cccc(C(C)(F)F)c1] |
| 373 | 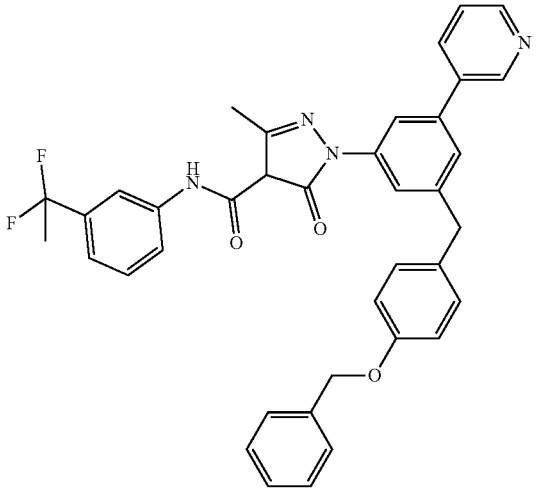 [SMILES: CC1=NN(c2cc(Cc3ccc(OCc4ccccc4)cc3)cc(-c3cccnc3)c2)C(=O)C1C(=O)Nc1cccc(C(C)(F)F)c1] |
| 374 | 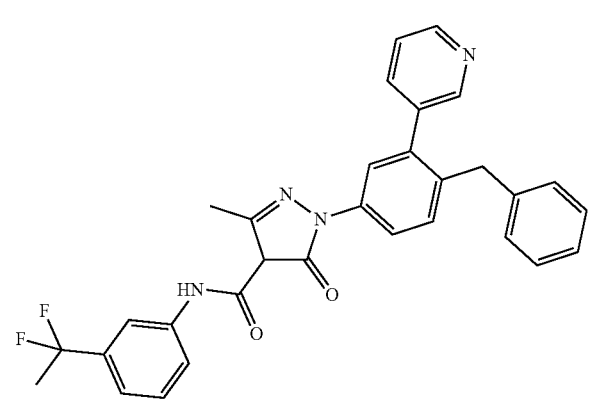 [SMILES: CC1=NN(c2ccc(Cc3ccccc3)c(-c3cccnc3)c2)C(=O)C1C(=O)Nc1cccc(C(C)(F)F)c1] |

TABLE 1-continued

| Compound name | Structure |
|---|---|
| 375 | 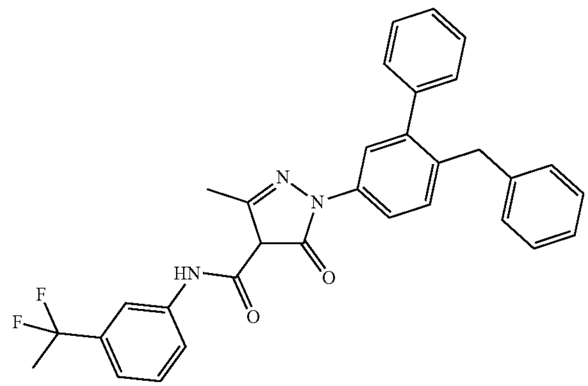 [SMILES: CC1=NN(c2ccc(Cc3ccccc3)c(-c3ccccc3)c2)C(=O)C1C(=O)Nc1cccc(C(C)(F)F)c1] |
| 376 | 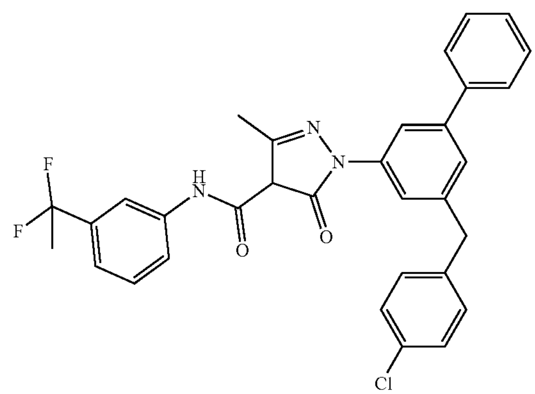 [SMILES: CC1=NN(c2cc(Cc3ccc(Cl)cc3)cc(-c3ccccc3)c2)C(=O)C1C(=O)Nc1cccc(C(C)(F)F)c1] |
| 377 | 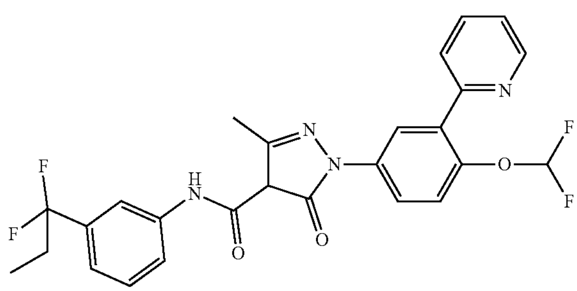 [SMILES: CCC(F)(F)c1cccc(NC(=O)C2C(=O)N(c3ccc(OC(F)F)c(-c4ccccn4)c3)N=C2C)c1] |
| 378 | 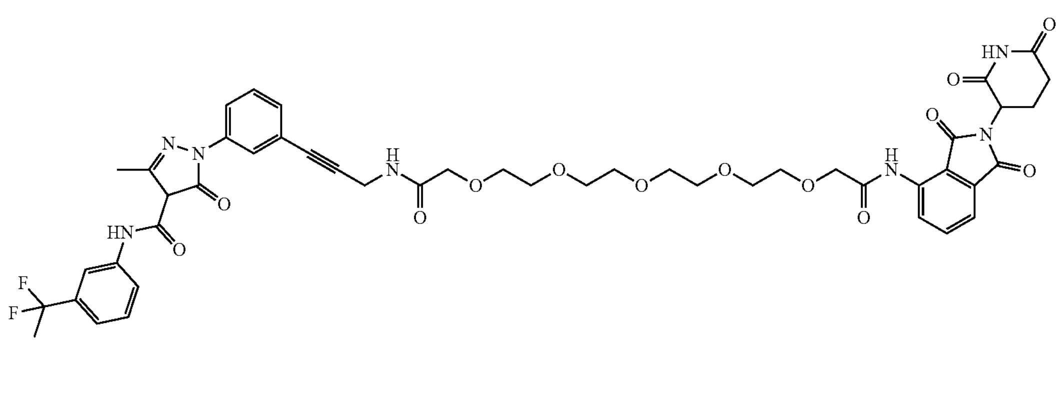 [SMILES: CC1=NN(c2cccc(C#CCNC(=O)COCCOCCOCCOCCOCC(=O)Nc3cccc4c3C(=O)N(C3CCC(=O)NC3=O)C4=O)c2)C(=O)C1C(=O)Nc1cccc(C(C)(F)F)c1] |

| Compound name | Structure |
|---|---|
| 379 | 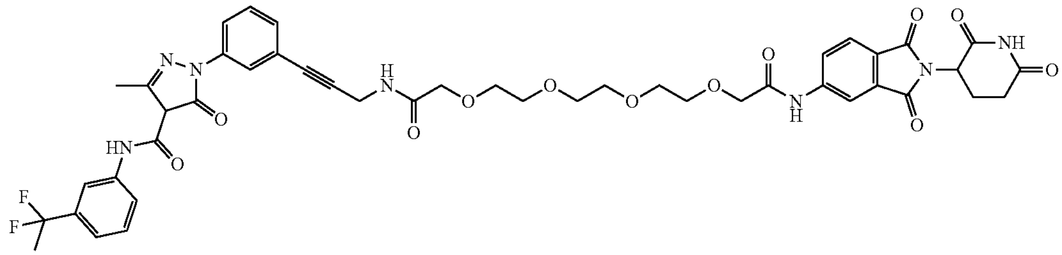 [SMILES: CC1=NN(c2cccc(C#CCNC(=O)COCCOCCOCCOCC(=O)Nc3ccc4c(c3)C(=O)N(C3CCC(=O)NC3=O)C4=O)c2)C(=O)C1C(=O)Nc1cccc(C(C)(F)F)c1] |
| 380 | 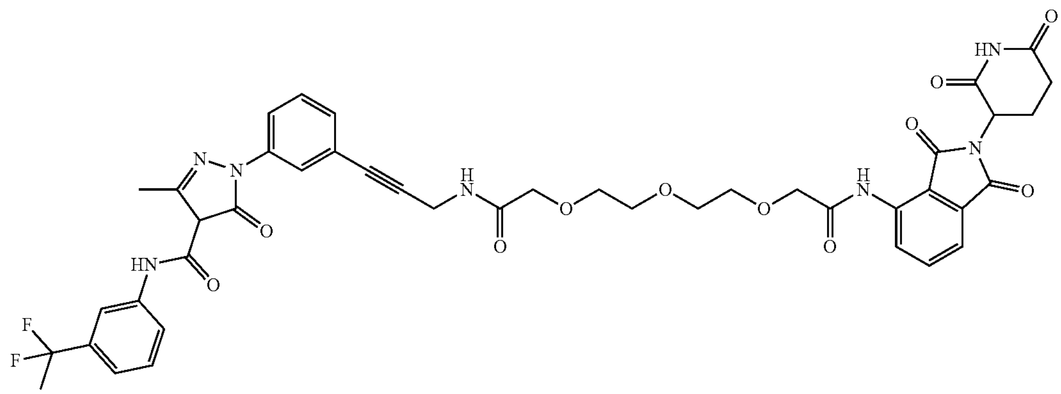 [SMILES: CC1=NN(c2cccc(C#CCNC(=O)COCCOCCOCC(=O)Nc3cccc4c3C(=O)N(C3CCC(=O)NC3=O)C4=O)c2)C(=O)C1C(=O)Nc1cccc(C(C)(F)F)c1] |
| 381 | 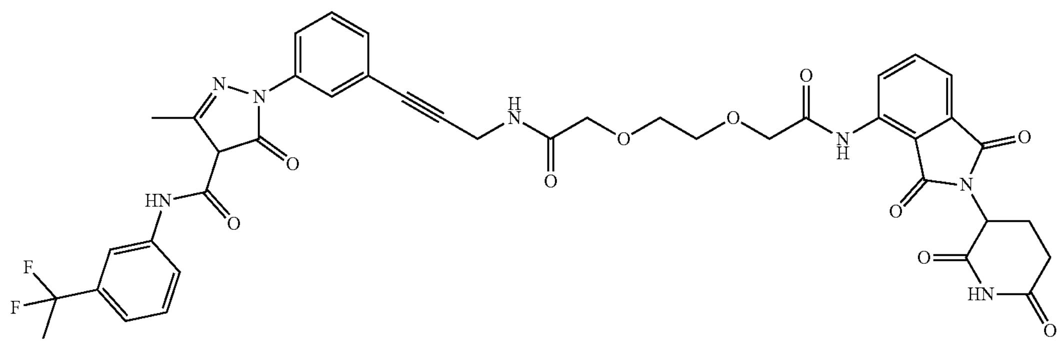 [SMILES: CC1=NN(c2cccc(C#CCNC(=O)COCCOCC(=O)Nc3cccc4c3C(=O)N(C3CCC(=O)NC3=O)C4=O)c2)C(=O)C1C(=O)Nc1cccc(C(C)(F)F)c1] |
| 382 | 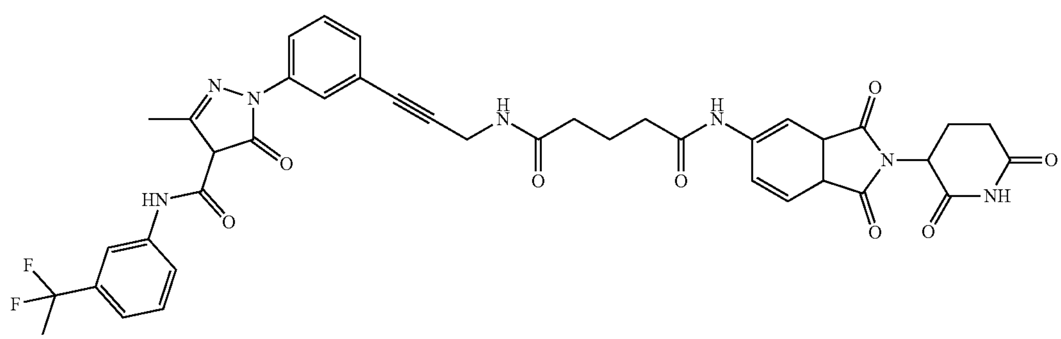 [SMILES: CC1=NN(c2cccc(C#CCNC(=O)CCCC(=O)NC3=CC4C(=O)N(C5CCC(=O)NC5=O)C(=O)C4C=C3)c2)C(=O)C1C(=O)Nc1cccc(C(C)(F)F)c1] |
| 383 | 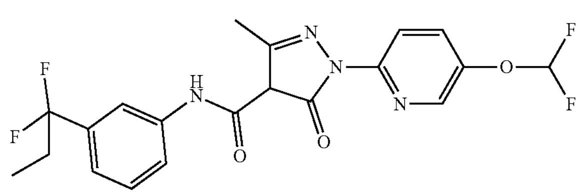 [SMILES: CCC(F)(F)c1cccc(NC(=O)C2C(=O)N(c3ccc(OC(F)F)cn3)N=C2C)c1] |

TABLE 1-continued

| Compound name | Structure |
|---|---|
| 384 | 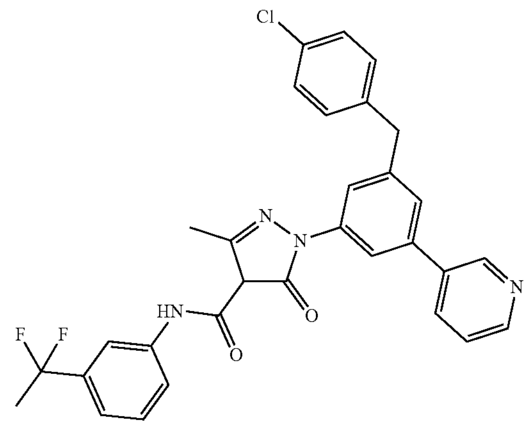 [SMILES: CC1=NN(c2cc(Cc3ccc(Cl)cc3)cc(-c3cccnc3)c2)C(=O)C1C(=O)Nc1cccc(C(C)(F)F)c1] |
| 385 | 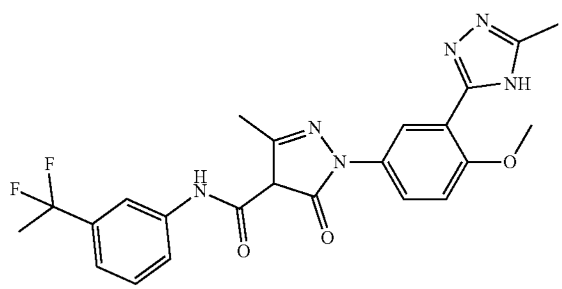 [SMILES: COc1ccc(N2N=C(C)C(C(=O)Nc3cccc(C(C)(F)F)c3)C2=O)cc1-c1nnc(C)[nH]1] |
| 386 | 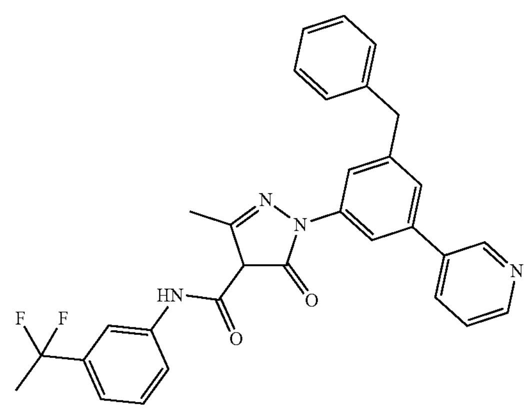 [SMILES: CC1=NN(c2cc(Cc3ccccc3)cc(-c3cccnc3)c2)C(=O)C1C(=O)Nc1cccc(C(C)(F)F)c1] |
| 387 | 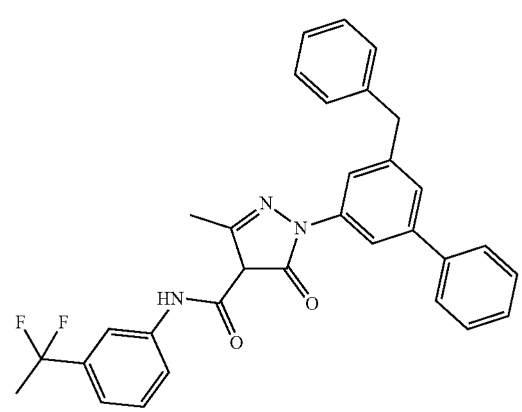 [SMILES: CC1=NN(c2cc(Cc3ccccc3)cc(-c3ccccc3)c2)C(=O)C1C(=O)Nc1cccc(C(C)(F)F)c1] |

TABLE 1-continued
| Compound name | Structure |
|---|---|
| 388 | 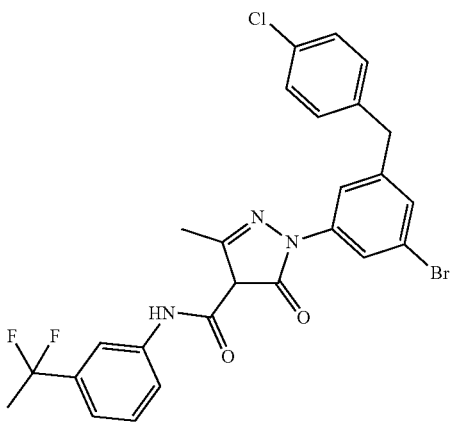 [SMILES: CC1=NN(c2cc(Br)cc(Cc3ccc(Cl)cc3)c2)C(=O)C1C(=O)Nc1cccc(C(C)(F)F)c1] |
| 389 | 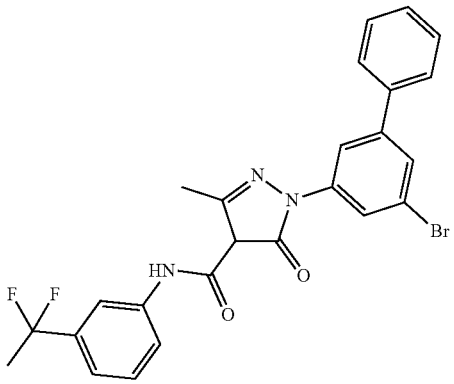 [SMILES: CC1=NN(c2cc(Br)cc(-c3ccccc3)c2)C(=O)C1C(=O)Nc1cccc(C(C)(F)F)c1] |
| 390 | 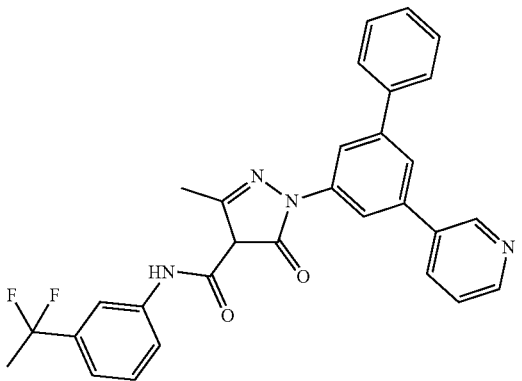 [SMILES: CC1=NN(c2cc(-c3ccccc3)cc(-c3cccnc3)c2)C(=O)C1C(=O)Nc1cccc(C(C)(F)F)c1] |
| 391 | 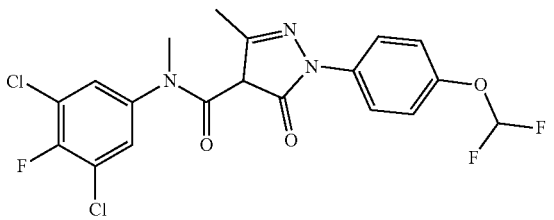 [SMILES: CC1=NN(c2ccc(OC(F)F)cc2)C(=O)C1C(=O)N(C)c1cc(Cl)c(F)c(Cl)c1] |

TABLE 1-continued

| Compound name | Structure |
|---|---|
| 392 | 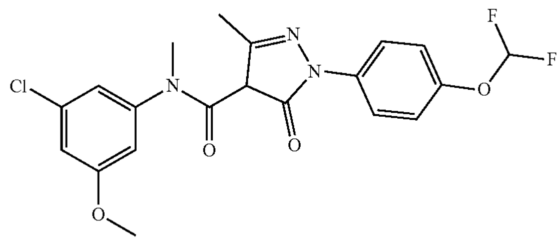 [SMILES: COc1cc(Cl)cc(N(C)C(=O)C2C(=O)N(c3ccc(OC(F)F)cc3)N=C2C)c1] |
| 393 | 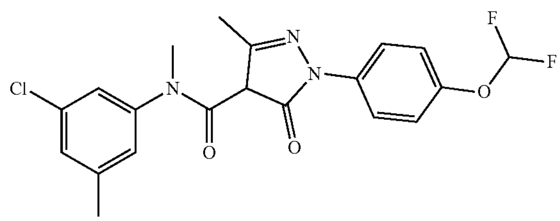 [SMILES: CC1=NN(c2ccc(OC(F)F)cc2)C(=O)C1C(=O)N(C)c1cc(C)cc(Cl)c1] |
| 394 | 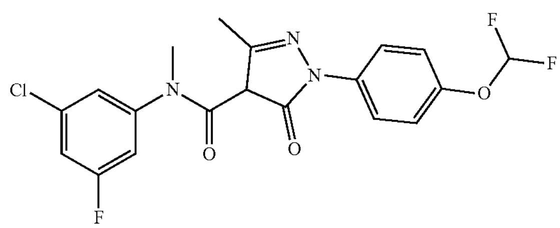 [SMILES: CC1=NN(c2ccc(OC(F)F)cc2)C(=O)C1C(=O)N(C)c1cc(F)cc(Cl)c1] |
| 395 | 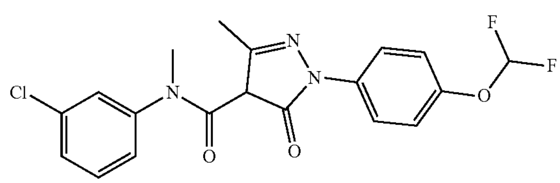 [SMILES: CC1=NN(c2ccc(OC(F)F)cc2)C(=O)C1C(=O)N(C)c1cccc(Cl)c1] |
| 396 | 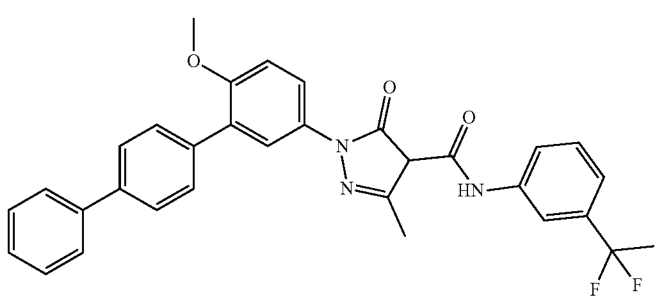 [SMILES: COc1ccc(N2N=C(C)C(C(=O)Nc3cccc(C(C)(F)F)c3)C2=O)cc1-c1ccc(-c2ccccc2)cc1] |
| 397 | 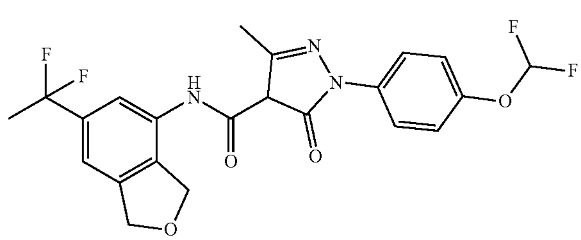 [SMILES: CC1=NN(c2ccc(OC(F)F)cc2)C(=O)C1C(=O)Nc1cc(C(C)(F)F)cc2c1COC2] |

TABLE 1-continued

| Compound name | Structure |
|---|---|
| 398 | 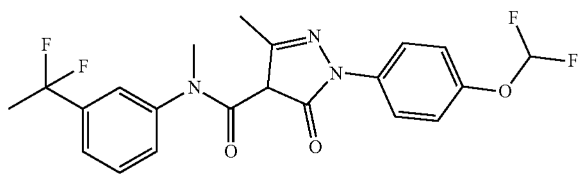 [SMILES: CC1=NN(c2ccc(OC(F)F)cc2)C(=O)C1C(=O)N(C)c1cccc(C(C)(F)F)c1] |
| 399 | 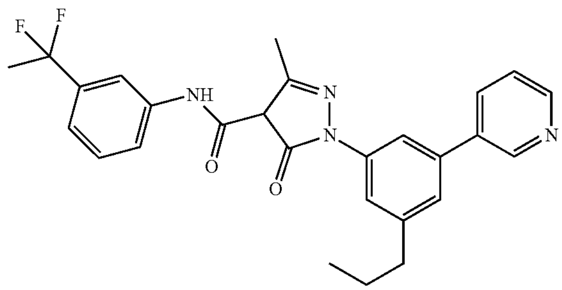 [SMILES: CCCc1cc(-c2cccnc2)cc(N2N=C(C)C(C(=O)Nc3cccc(C(C)(F)F)c3)C2=O)c1] |
| 400 | 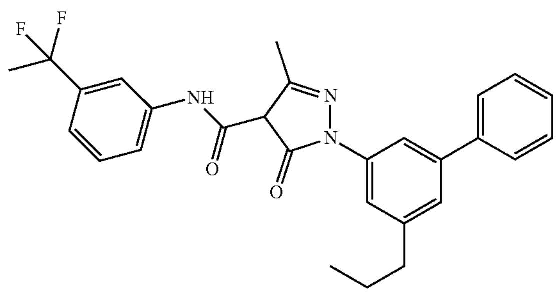 [SMILES: CCCc1cc(-c2ccccc2)cc(N2N=C(C)C(C(=O)Nc3cccc(C(C)(F)F)c3)C2=O)c1] |
| 401 | 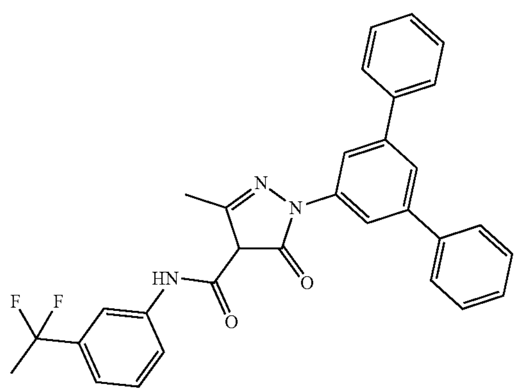 [SMILES: CC1=NN(c2cc(-c3ccccc3)cc(-c3ccccc3)c2)C(=O)C1C(=O)Nc1cccc(C(C)(F)F)c1] |
| 402 | 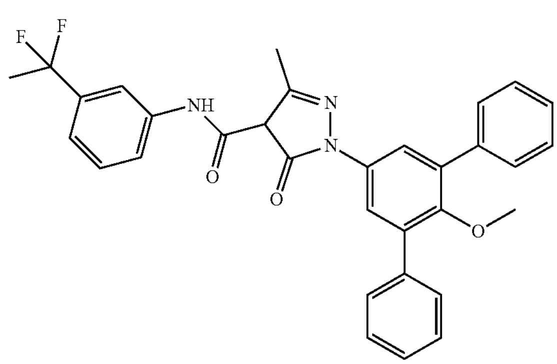 [SMILES: COc1c(-c2ccccc2)cc(N2N=C(C)C(C(=O)Nc3cccc(C(C)(F)F)c3)C2=O)cc1-c1ccccc1] |

TABLE 1-continued

| Compound name | Structure |
|---|---|
| 403 | 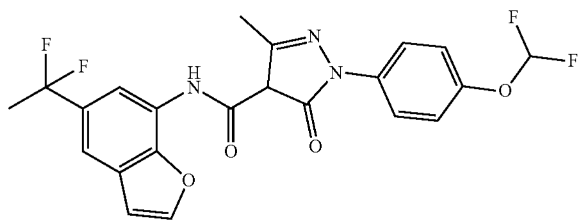 [SMILES: CC1=NN(c2ccc(OC(F)F)cc2)C(=O)C1C(=O)Nc1cc(C(C)(F)F)cc2ccoc12] |
| 404 | 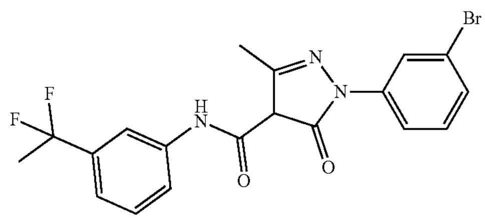 [SMILES: CC1=NN(c2cccc(Br)c2)C(=O)C1C(=O)Nc1cccc(C(C)(F)F)c1] |
| 405 | 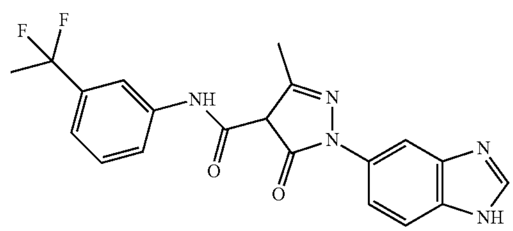 [SMILES: CC1=NN(c2ccc3[nH]cnc3c2)C(=O)C1C(=O)Nc1cccc(C(C)(F)F)c1] |
| 406 | 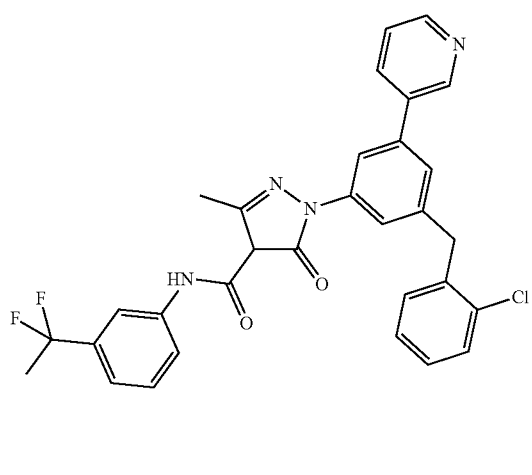 [SMILES: CC1=NN(c2cc(Cc3ccccc3Cl)cc(-c3cccnc3)c2)C(=O)C1C(=O)Nc1cccc(C(C)(F)F)c1] |
| 407 | 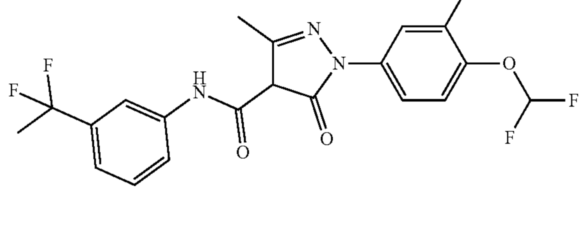 |

TABLE 1-continued

| Compound name | Structure |
|---|---|
| 408 | 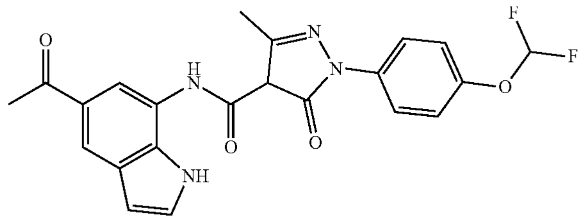 [SMILES: CC(=O)c1cc(NC(=O)C2C(=O)N(c3ccc(OC(F)F)cc3)N=C2C)c2[nH]ccc2c1] |
| 409 | 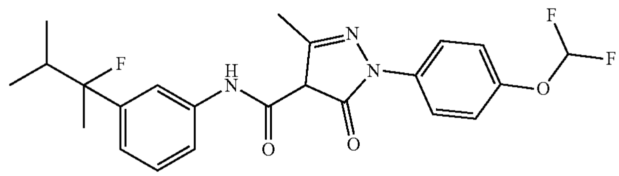 [SMILES: CC1=NN(c2ccc(OC(F)F)cc2)C(=O)C1C(=O)Nc1cccc(C(C)(F)C(C)C)c1] |
| 410 | 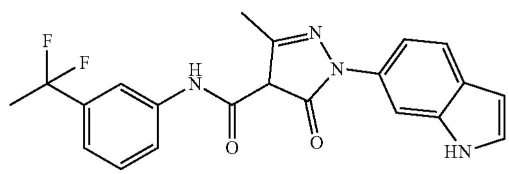 [SMILES: CC1=NN(c2ccc3cc[nH]c3c2)C(=O)C1C(=O)Nc1cccc(C(C)(F)F)c1] |
| 461 | 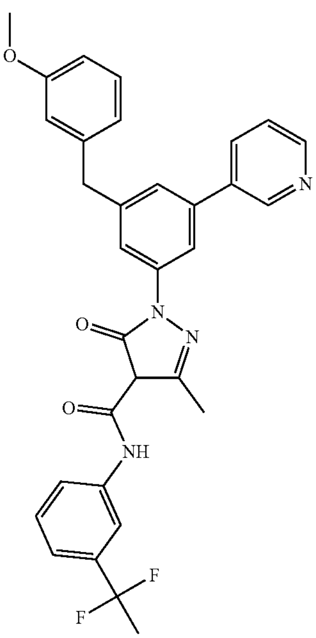 [SMILES: COc1cccc(Cc2cc(-c3cccnc3)cc(N3N=C(C)C(C(=O)Nc4cccc(C(C)(F)F)c4)C3=O)c2)c1] |
| 462 | 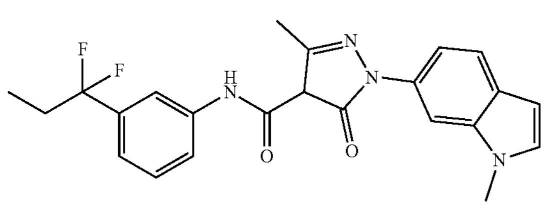 [SMILES: CCC(F)(F)c1cccc(NC(=O)C2C(=O)N(c3ccc4ccn(C)c4c3)N=C2C)c1] |

TABLE 1-continued
| Compound name | Structure |
|---|---|
| 463 | 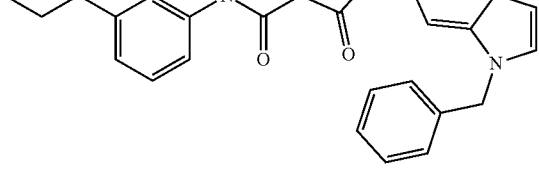 |
| 464 | 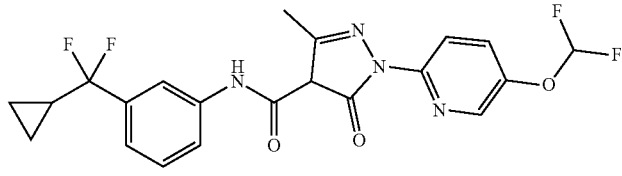 [SMILES: CC1=NN(c2ccc(OC(F)F)cn2)C(=O)C1C(=O)Nc1cccc(C(F)(F)C2CC2)c1] |
| 465 | 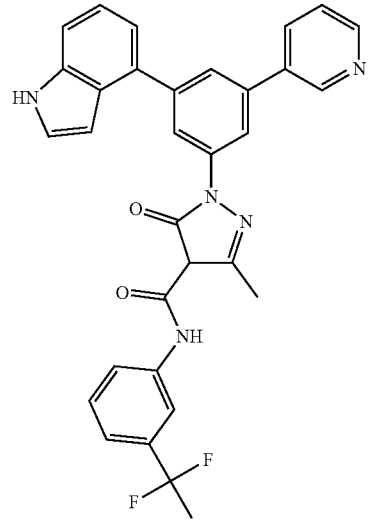 [SMILES: CC1=NN(c2cc(-c3cccnc3)cc(-c3cccc4[nH]ccc34)c2)C(=O)C1C(=O)Nc1cccc(C(C)(F)F)c1] |
| 466 | 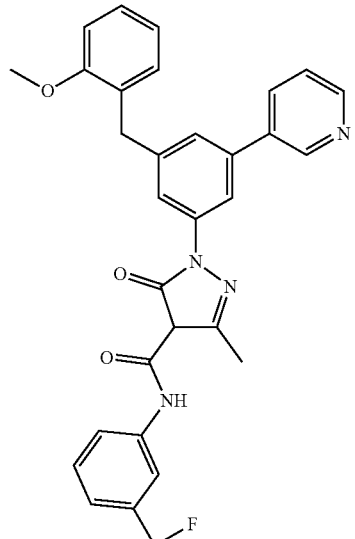 |

TABLE 1-continued

| Compound name | Structure |
|---|---|
| 467 | 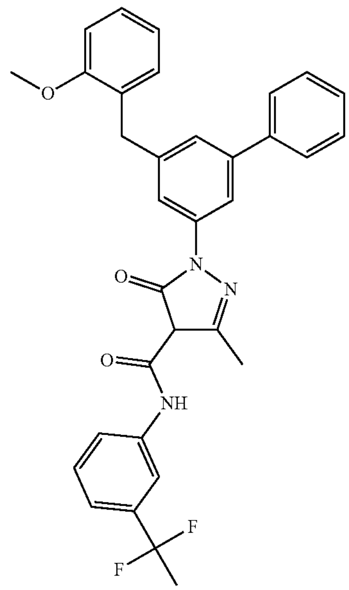 [SMILES: COc1ccccc1Cc1cc(-c2ccccc2)cc(N2N=C(C)C(C(=O)Nc3cccc(C(C)(F)F)c3)C2=O)c1] |
| 468 | 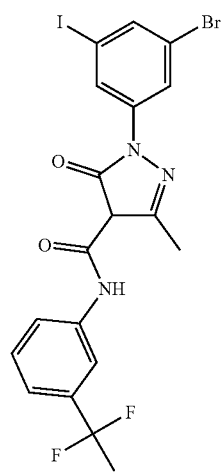 [SMILES: CC1=NN(c2cc(Br)cc(I)c2)C(=O)C1C(=O)Nc1cccc(C(C)(F)F)c1] |
| 470 | 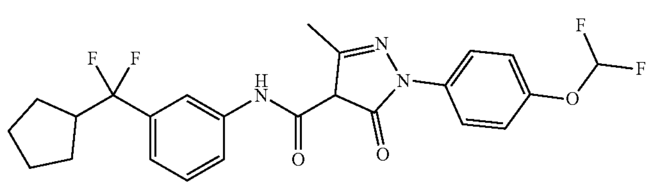 [SMILES: CC1=NN(c2ccc(OC(F)F)cc2)C(=O)C1C(=O)Nc1cccc(C(F)(F)C2CCCC2)c1] |
| 471 | 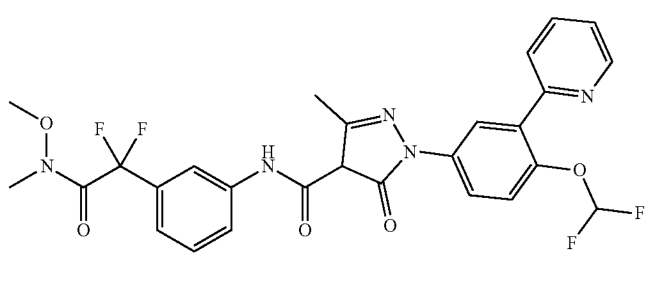 [SMILES: CON(C)C(=O)C(F)(F)c1cccc(NC(=O)C2C(=O)N(c3ccc(OC(F)F)c(-c4ccccn4)c3)N=C2C)c1] |

TABLE 1-continued
| Compound name | Structure |
|---|---|
| 472 | 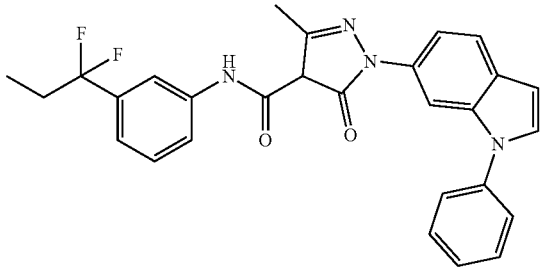 [SMILES: CCC(F)(F)c1cccc(NC(=O)C2C(=O)N(c3ccc4ccn(-c5ccccc5)c4c3)N=C2C)c1] |
| 473 | 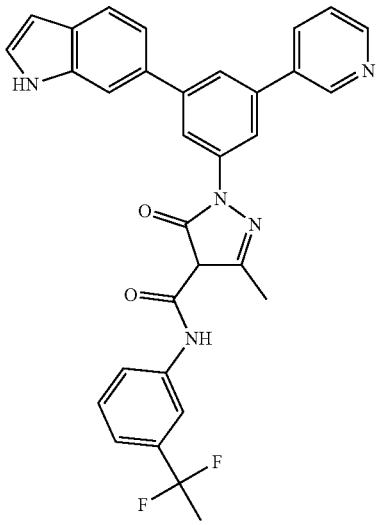 [SMILES: CC1=NN(c2cc(-c3cccnc3)cc(-c3ccc4cc[nH]c4c3)c2)C(=O)C1C(=O)Nc1cccc(C(C)(F)F)c1] |
| 474 | 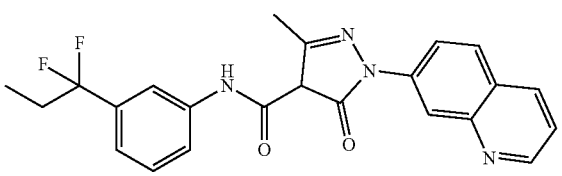 [SMILES: CCC(F)(F)c1cccc(NC(=O)C2C(=O)N(c3ccc4cccnc4c3)N=C2C)c1] |
| 475 | 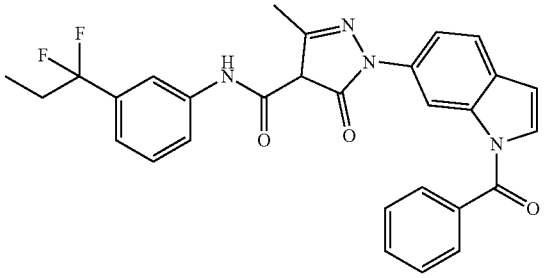 [SMILES: CCC(F)(F)c1cccc(NC(=O)C2C(=O)N(c3ccc4ccn(C(=O)c5ccccc5)c4c3)N=C2C)c1] |

TABLE 1-continued
| Compound name | Structure |
|---|---|
| 476 | 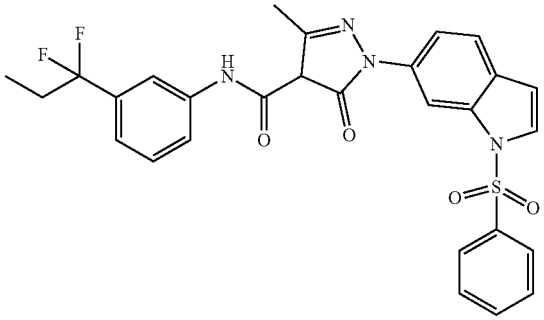 [SMILES: CCC(F)(F)c1cccc(NC(=O)C2C(=O)N(c3ccc4ccn(S(=O)(=O)c5ccccc5)c4c3)N=C2C)c1] |
| 477 | 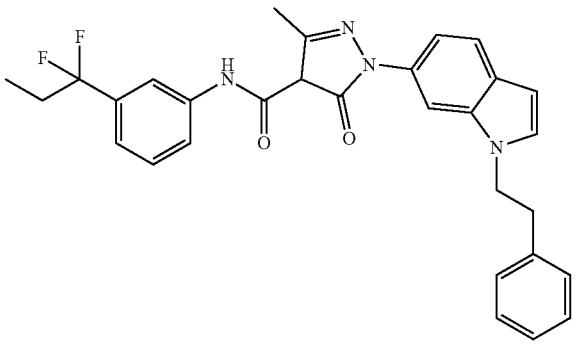 [SMILES: CCC(F)(F)c1cccc(NC(=O)C2C(=O)N(c3ccc4ccn(CCc5ccccc5)c4c3)N=C2C)c1] |
| 478 | 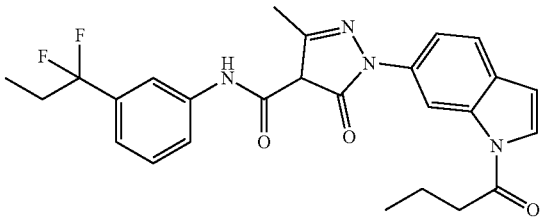 [SMILES: CCCC(=O)n1ccc2ccc(N3N=C(C)C(C(=O)Nc4cccc(C(F)(F)CC)c4)C3=O)cc21] |
| 479 | 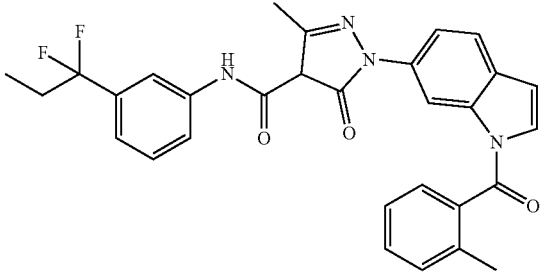 [SMILES: CCC(F)(F)c1cccc(NC(=O)C2C(=O)N(c3ccc4ccn(C(=O)c5ccccc5C)c4c3)N=C2C)c1] |
| 480 | 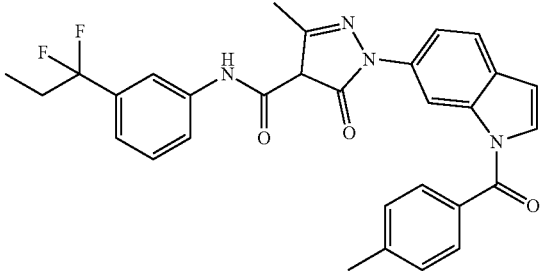 [SMILES: CCC(F)(F)c1cccc(NC(=O)C2C(=O)N(c3ccc4ccn(C(=O)c5ccc(C)cc5)c4c3)N=C2C)c1] |

TABLE 1-continued

| Compound name | Structure |
|---|---|
| 481 | 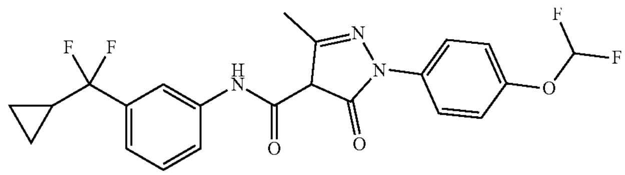 [SMILES: CC1=NN(c2ccc(OC(F)F)cc2)C(=O)C1C(=O)Nc1cccc(C(F)(F)C2CC2)c1] |
| 482 | 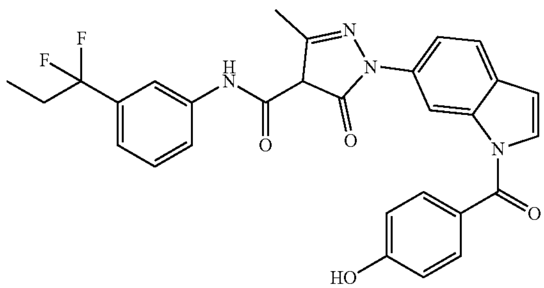 [SMILES: CCC(F)(F)c1cccc(NC(=O)C2C(=O)N(c3ccc4ccn(C(=O)c5ccc(O)cc5)c4c3)N=C2C)c1] |
| 483 | 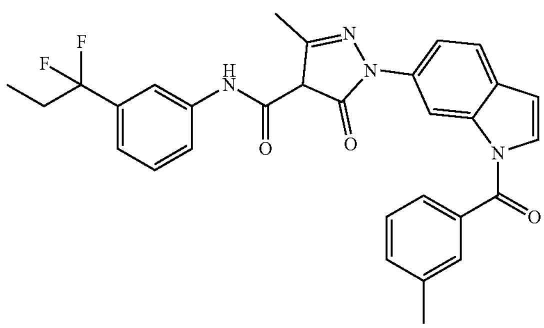 [SMILES: CCC(F)(F)c1cccc(NC(=O)C2C(=O)N(c3ccc4ccn(C(=O)c5cccc(C)c5)c4c3)N=C2C)c1] |
| 484 | 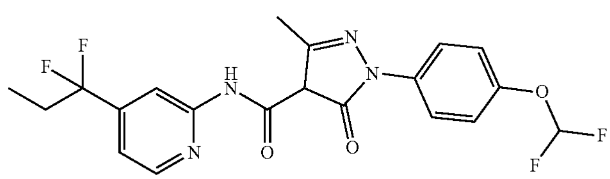 [SMILES: CCC(F)(F)c1ccnc(NC(=O)C2C(=O)N(c3ccc(OC(F)F)cc3)N=C2C)c1] |
| 485 | 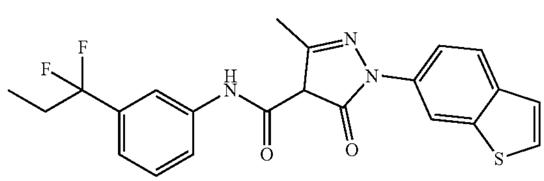 |
| 486 | 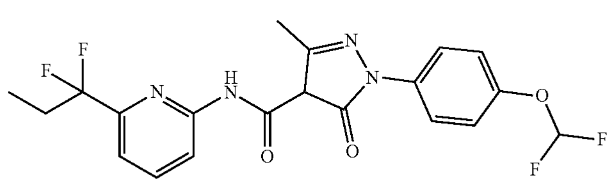 [SMILES: CCC(F)(F)c1cccc(NC(=O)C2C(=O)N(c3ccc(OC(F)F)cc3)N=C2C)n1] |

TABLE 1-continued

| Compound name | Structure |
|---|---|
| 487 | 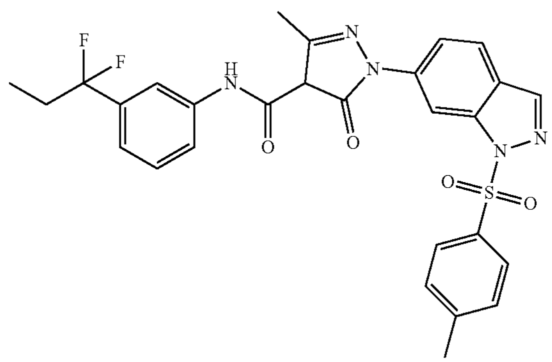 [SMILES: CCC(F)(F)c1cccc(NC(=O)C2C(=O)N(c3ccc4cnn(S(=O)(=O)c5ccc(C)cc5)c4c3)N=C2C)c1] |
| 488 | 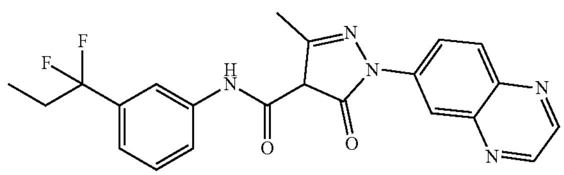 [SMILES: CCC(F)(F)c1cccc(NC(=O)C2C(=O)N(c3ccc4nccnc4c3)N=C2C)c1] |
| 489 | 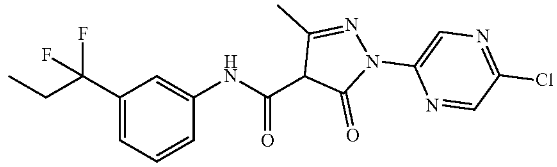 [SMILES: CCC(F)(F)c1cccc(NC(=O)C2C(=O)N(c3cnc(Cl)cn3)N=C2C)c1] |
| 490 | 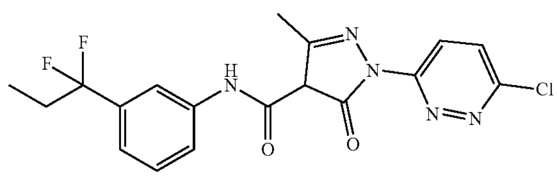 [SMILES: CCC(F)(F)c1cccc(NC(=O)C2C(=O)N(c3ccc(Cl)nn3)N=C2C)c1] |
| 491 | 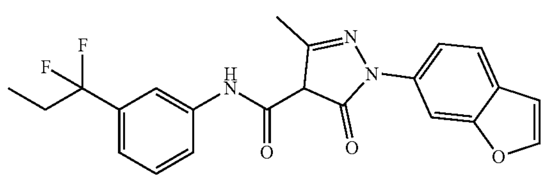 [SMILES: CCC(F)(F)c1cccc(NC(=O)C2C(=O)N(c3ccc4ccoc4c3)N=C2C)c1] |
| 492 | 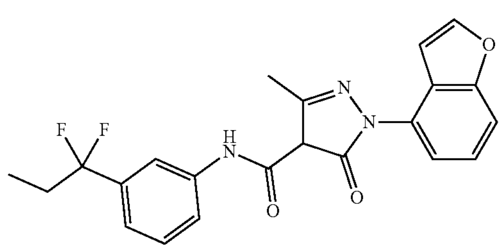 [SMILES: CCC(F)(F)c1cccc(NC(=O)C2C(=O)N(c3cccc4occc34)N=C2C)c1] |

US 12,133,852 B2
145                                                                 146
TABLE 1-continued
| Compound name | Structure |
|---|---|
| 493 | 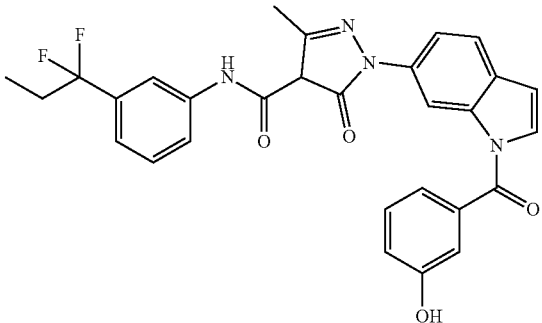 [SMILES: CCC(F)(F)c1cccc(NC(=O)C2C(=O)N(c3ccc4ccn(C(=O)c5cccc(O)c5)c4c3)N=C2C)c1] |
| 494 | 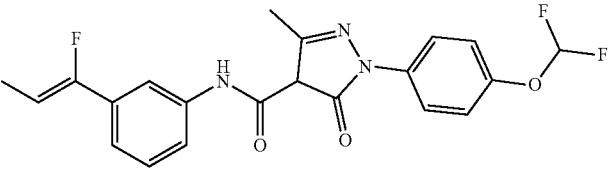 [SMILES: C/C=C(\F)c1cccc(NC(=O)C2C(=O)N(c3ccc(OC(F)F)cc3)N=C2C)c1] |
| 495 | 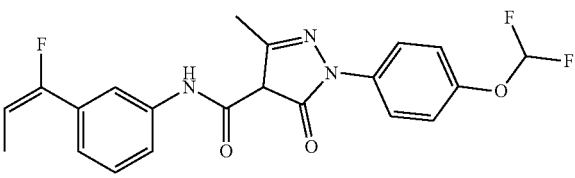 [SMILES: C/C=C(/F)c1cccc(NC(=O)C2C(=O)N(c3ccc(OC(F)F)cc3)N=C2C)c1] |
| 496 | 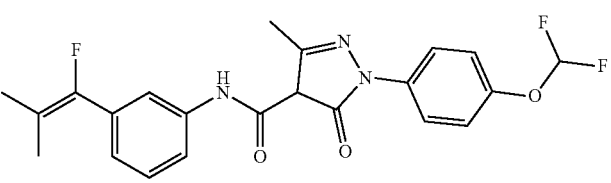 [SMILES: CC1=NN(c2ccc(OC(F)F)cc2)C(=O)C1C(=O)Nc1cccc(C(F)=C(C)C)c1] |
| 497 | 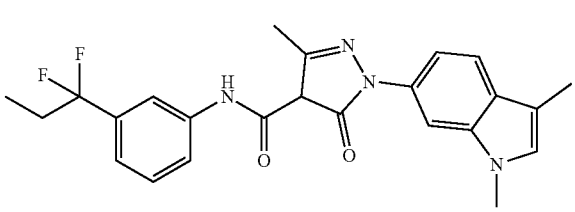 [SMILES: CCC(F)(F)c1cccc(NC(=O)C2C(=O)N(c3ccc4c(C)cn(C)c4c3)N=C2C)c1] |
| 498 | 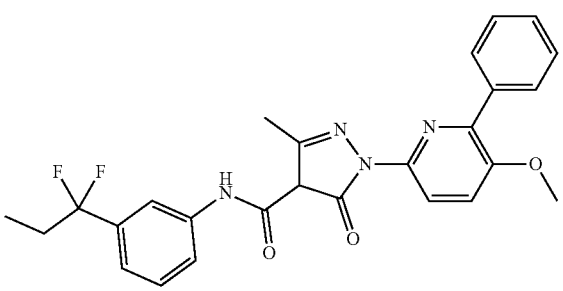 [SMILES: CCC(F)(F)c1cccc(NC(=O)C2C(=O)N(c3ccc(OC)c(-c4ccccc4)n3)N=C2C)c1] |
| 499 | 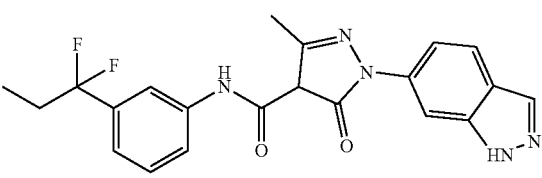 [SMILES: CCC(F)(F)c1cccc(NC(=O)C2C(=O)N(c3ccc4cn[nH]c4c3)N=C2C)c1] |

TABLE 1-continued

| Compound name | Structure |
|---|---|
| 500 | 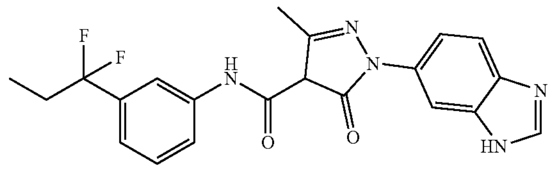 [SMILES: CCC(F)(F)c1cccc(NC(=O)C2C(=O)N(c3ccc4nc[nH]c4c3)N=C2C)c1] |
| 501 | 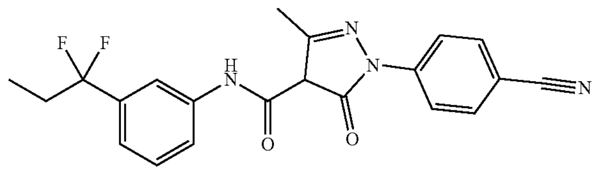 [SMILES: CCC(F)(F)c1cccc(NC(=O)C2C(=O)N(c3ccc(C#N)cc3)N=C2C)c1] |
| 502 | 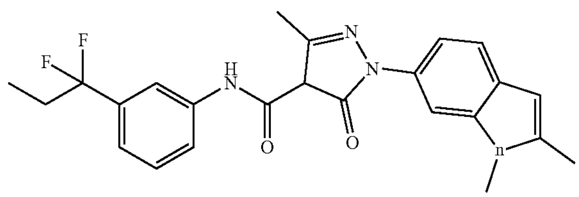 |
| 503 | 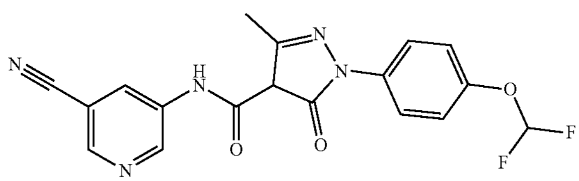 [SMILES: CC1=NN(c2ccc(OC(F)F)cc2)C(=O)C1C(=O)Nc1cncc(C#N)c1] |
| 504 | 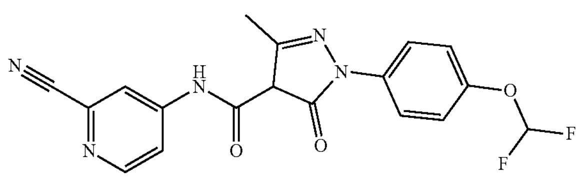 [SMILES: CC1=NN(c2ccc(OC(F)F)cc2)C(=O)C1C(=O)Nc1ccnc(C#N)c1] |
| 505 | 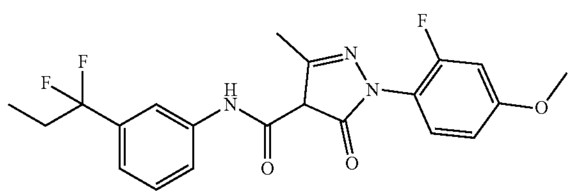 [SMILES: CCC(F)(F)c1cccc(NC(=O)C2C(=O)N(c3ccc(OC)cc3F)N=C2C)c1] |
| 506 | 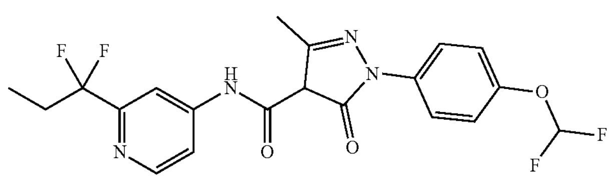 [SMILES: CCC(F)(F)c1cc(NC(=O)C2C(=O)N(c3ccc(OC(F)F)cc3)N=C2C)ccn1] |
| 507 | 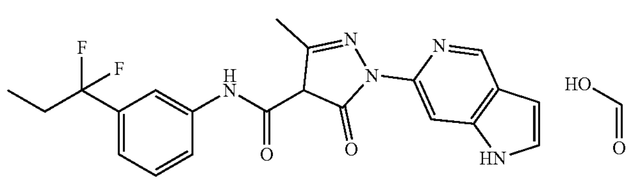 |

TABLE 1-continued

| Compound name | Structure |
|---|---|
| 508 | 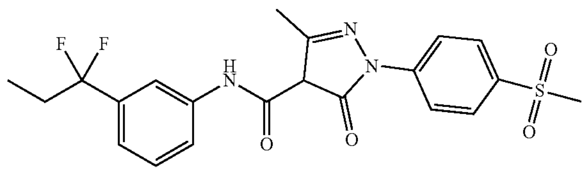 [SMILES: CCC(F)(F)c1cccc(NC(=O)C2C(=O)N(c3ccc(S(C)(=O)=O)cc3)N=C2C)c1] |
| 509 | 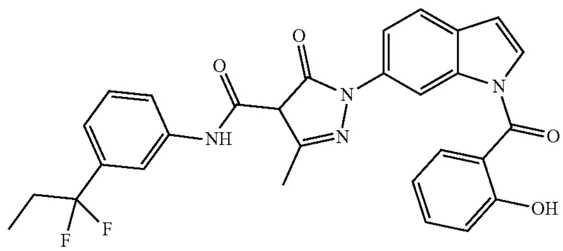 [SMILES: CCC(F)(F)c1cccc(NC(=O)C2C(=O)N(c3ccc4ccn(C(=O)c5ccccc5O)c4c3)N=C2C)c1] |
| 510 | 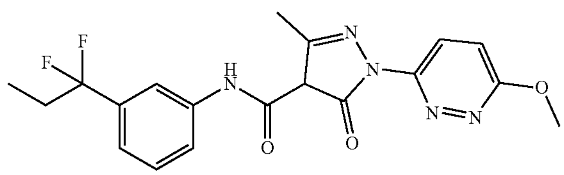 [SMILES: CCC(F)(F)c1cccc(NC(=O)C2C(=O)N(c3ccc(OC)nn3)N=C2C)c1] |
| 511 | 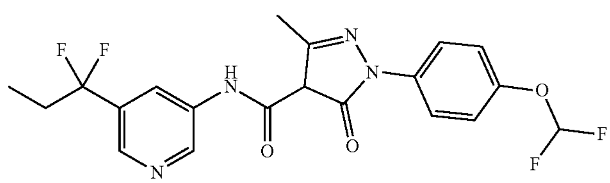 [SMILES: CCC(F)(F)c1cncc(NC(=O)C2C(=O)N(c3ccc(OC(F)F)cc3)N=C2C)c1] |
| 512 | 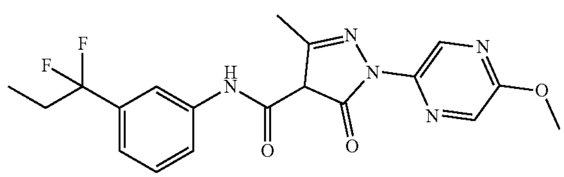 [SMILES: CCC(F)(F)c1cccc(NC(=O)C2C(=O)N(c3cnc(OC)cn3)N=C2C)c1] |
| 516 | 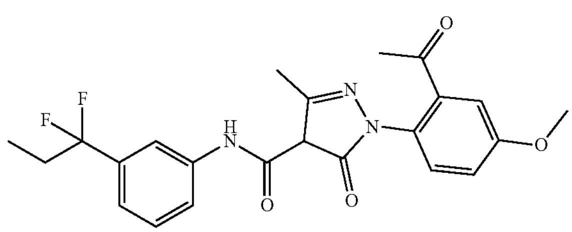 [SMILES: CCC(F)(F)c1cccc(NC(=O)C2C(=O)N(c3ccc(OC)cc3C(C)=O)N=C2C)c1] |
| 524 | 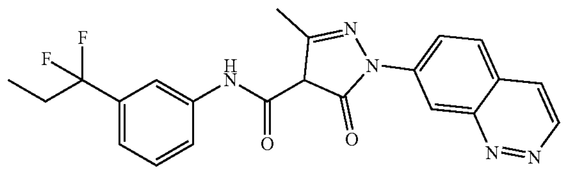 [SMILES: CCC(F)(F)c1cccc(NC(=O)C2C(=O)N(c3ccc4ccnnc4c3)N=C2C)c1] |

TABLE 1-continued

| Compound name | Structure |
|---|---|
| 529 | 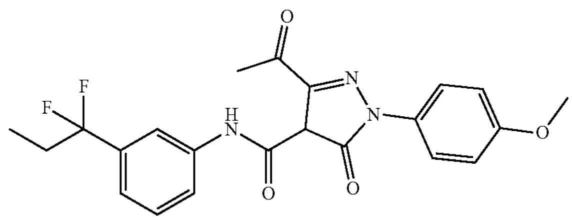 [SMILES: CCC(F)(F)c1cccc(NC(=O)C2C(=O)N(c3ccc(OC)cc3)N=C2C(C)=O)c1] |
| 530 | 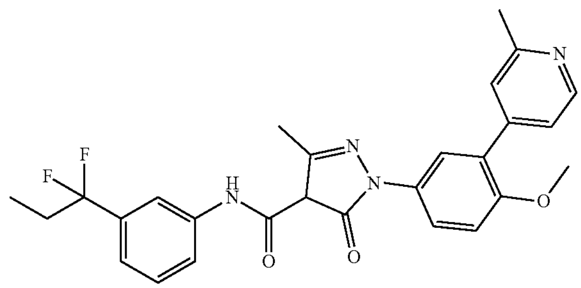 [SMILES: CCC(F)(F)c1cccc(NC(=O)C2C(=O)N(c3ccc(OC)c(-c4ccnc(C)c4)c3)N=C2C)c1] |
| 531 | 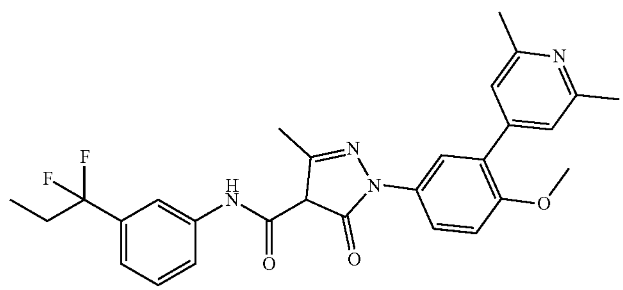 [SMILES: CCC(F)(F)c1cccc(NC(=O)C2C(=O)N(c3ccc(OC)c(-c4cc(C)nc(C)c4)c3)N=C2C)c1] |
| 532 | 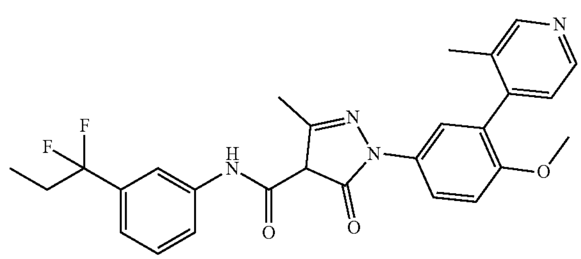 [SMILES: CCC(F)(F)c1cccc(NC(=O)C2C(=O)N(c3ccc(OC)c(-c4ccncc4C)c3)N=C2C)c1] |
| 534 | 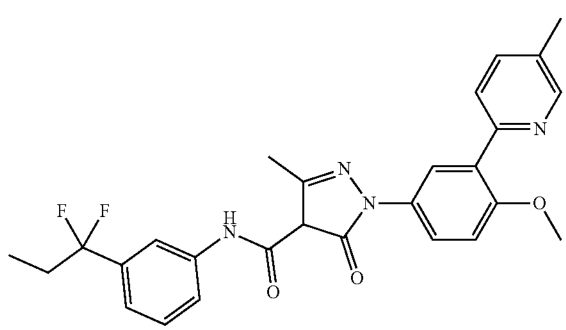 [SMILES: CCC(F)(F)c1cccc(NC(=O)C2C(=O)N(c3ccc(OC)c(-c4ccc(C)cn4)c3)N=C2C)c1] |

TABLE 1-continued

| Compound name | Structure |
|---|---|
| 535 | 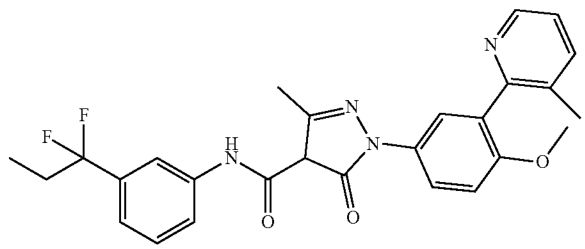 [SMILES: CCC(F)(F)c1cccc(NC(=O)C2C(=O)N(c3ccc(OC)c(-c4ncccc4C)c3)N=C2C)c1] |
| 536 | 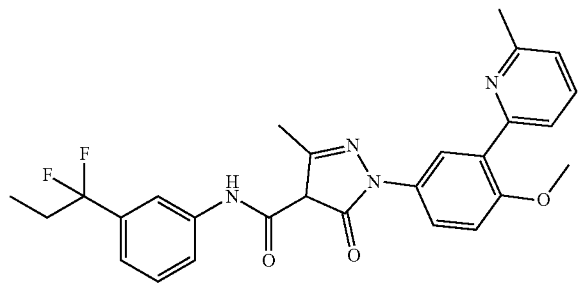 [SMILES: CCC(F)(F)c1cccc(NC(=O)C2C(=O)N(c3ccc(OC)c(-c4cccc(C)n4)c3)N=C2C)c1] |
| 537 | 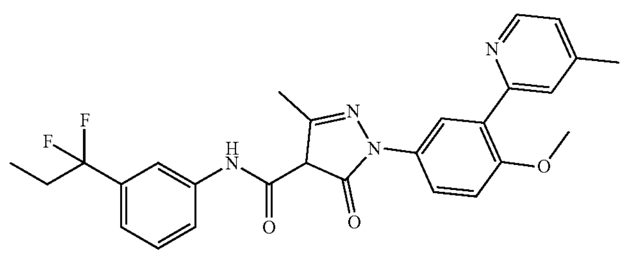 [SMILES: CCC(F)(F)c1cccc(NC(=O)C2C(=O)N(c3ccc(OC)c(-c4cc(C)ccn4)c3)N=C2C)c1] |
| 538 | |
| 539 | |
| 540 | |
| 541 | 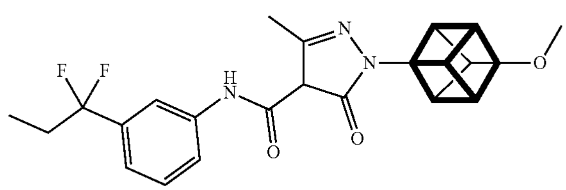 |
| 542 | 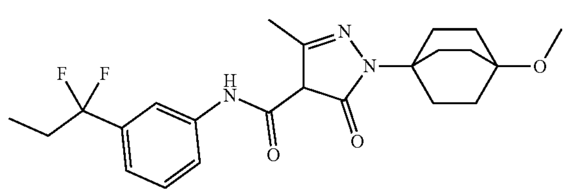 [SMILES: CCC(F)(F)c1cccc(NC(=O)C2C(=O)N(C34CCC(OC)(CC3)CC4)N=C2C)c1] |
| 543 | 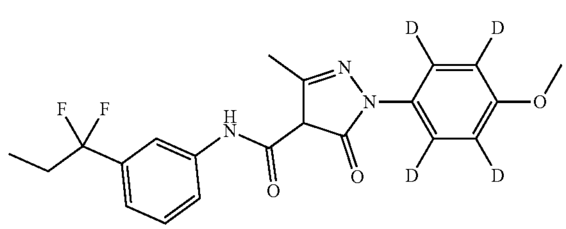 [SMILES: [2H]c1c([2H])c(N2N=C(C)C(C(=O)Nc3cccc(C(F)(F)CC)c3)C2=O)c([2H])c([2H])c1OC] |

TABLE 1-continued

| Compound name | Structure |
|---|---|
| 544 | 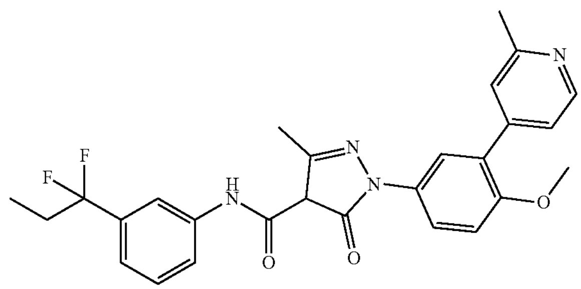 [SMILES: CCC(F)(F)c1cccc(NC(=O)C2C(=O)N(c3ccc(OC)c(-c4ccnc(C)c4)c3)N=C2C)c1] |
| 545 | 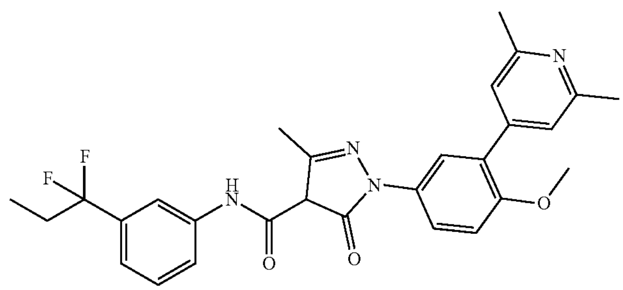 [SMILES: CCC(F)(F)c1cccc(NC(=O)C2C(=O)N(c3ccc(OC)c(-c4cc(C)nc(C)c4)c3)N=C2C)c1] |
| 546 | 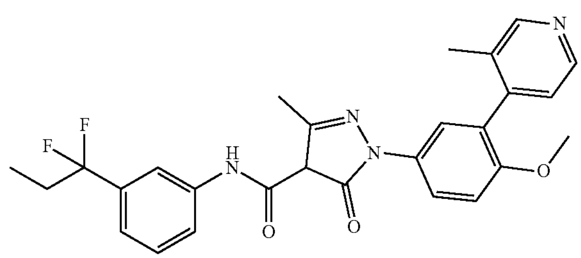 [SMILES: CCC(F)(F)c1cccc(NC(=O)C2C(=O)N(c3ccc(OC)c(-c4ccncc4C)c3)N=C2C)c1] |
| 547 | 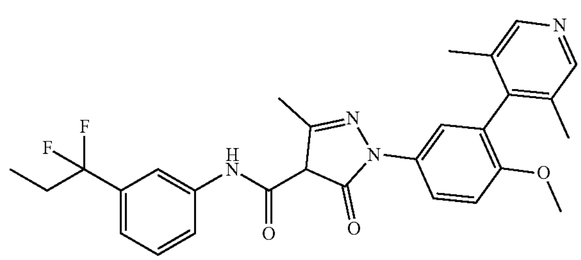 [SMILES: CCC(F)(F)c1cccc(NC(=O)C2C(=O)N(c3ccc(OC)c(-c4c(C)cncc4C)c3)N=C2C)c1] |
| 548 | 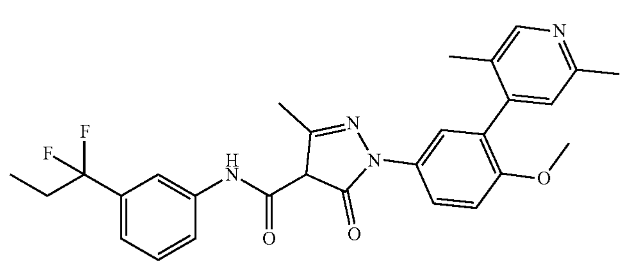 [SMILES: CCC(F)(F)c1cccc(NC(=O)C2C(=O)N(c3ccc(OC)c(-c4cc(C)ncc4C)c3)N=C2C)c1] |

TABLE 1-continued
| Compound name | Structure |
|---|---|
| 549 | 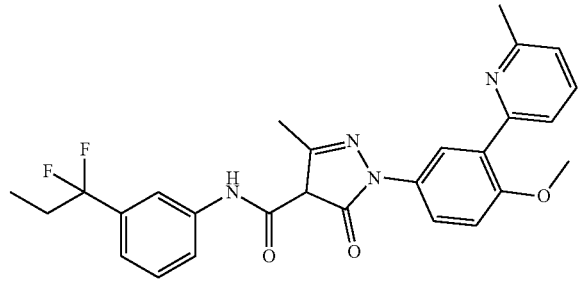 [SMILES: CCC(F)(F)c1cccc(NC(=O)C2C(=O)N(c3ccc(OC)c(-c4cccc(C)n4)c3)N=C2C)c1] |
| 550 | 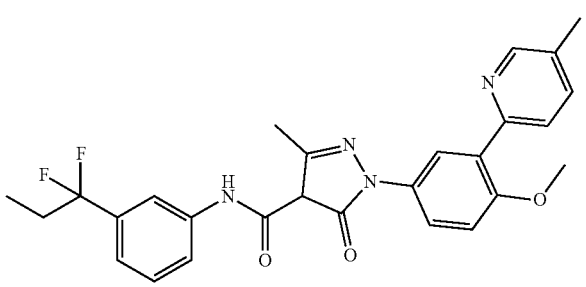 [SMILES: CCC(F)(F)c1cccc(NC(=O)C2C(=O)N(c3ccc(OC)c(-c4ccc(C)cn4)c3)N=C2C)c1] |
| 551 | 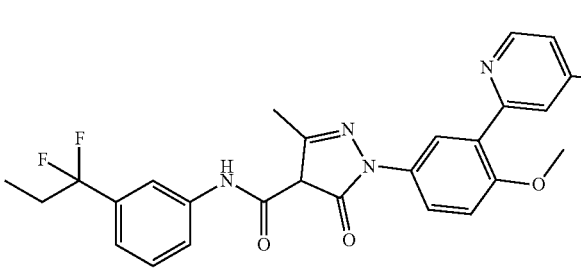 |
| 552 | 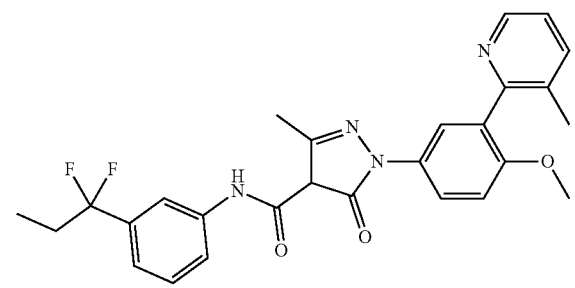 [SMILES: CCC(F)(F)c1cccc(NC(=O)C2C(=O)N(c3ccc(OC)c(-c4ncccc4C)c3)N=C2C)c1] |
| 553 | 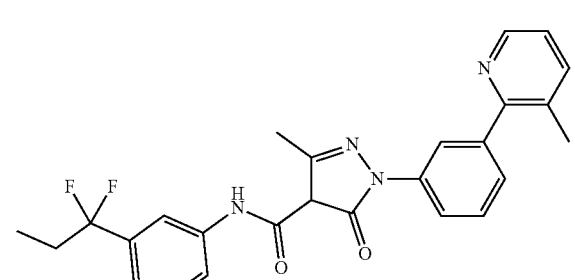 |

TABLE 1-continued

| Compound name | Structure |
|---|---|
| 554 | 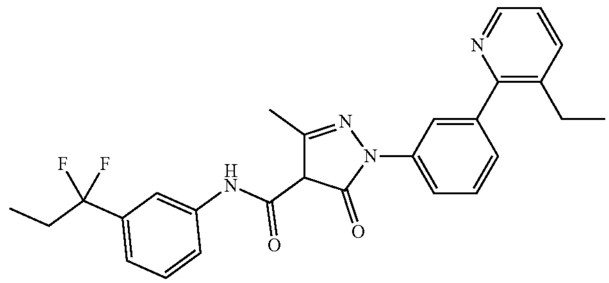 [SMILES: CCc1cccnc1-c1cccc(N2N=C(C)C(C(=O)Nc3cccc(C(F)(F)CC)c3)C2=O)c1] |
| 555 | 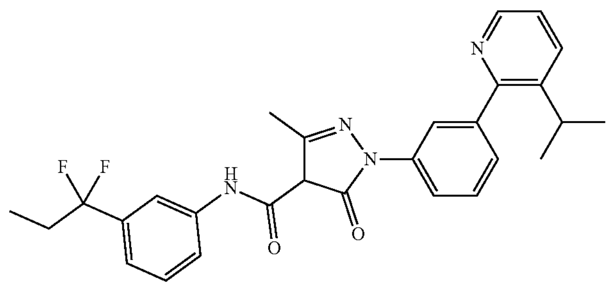 [SMILES: CCC(F)(F)c1cccc(NC(=O)C2C(=O)N(c3cccc(-c4ncccc4C(C)C)c3)N=C2C)c1] |
| 556 | 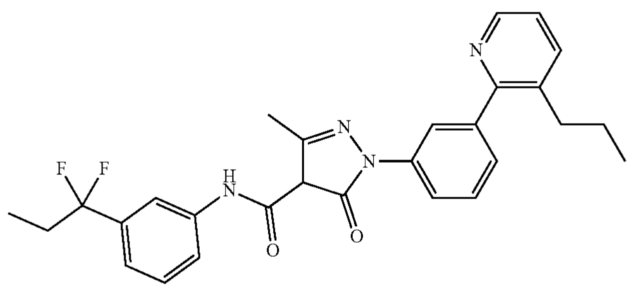 [SMILES: CCCc1cccnc1-c1cccc(N2N=C(C)C(C(=O)Nc3cccc(C(F)(F)CC)c3)C2=O)c1] |
| 557 | 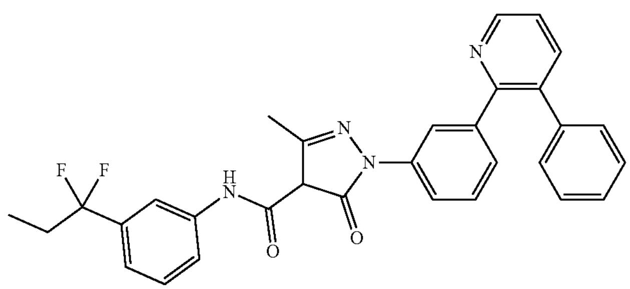 [SMILES: CCC(F)(F)c1cccc(NC(=O)C2C(=O)N(c3cccc(-c4ncccc4-c4ccccc4)c3)N=C2C)c1] |
| 558 | 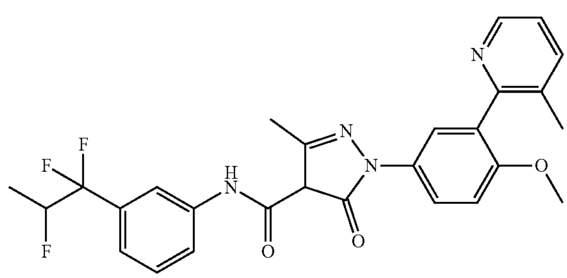 [SMILES: COc1ccc(N2N=C(C)C(C(=O)Nc3cccc(C(F)(F)C(C)F)c3)C2=O)cc1-c1ncccc1C] |

TABLE 1-continued

| Compound name | Structure |
|---|---|
| 559 | 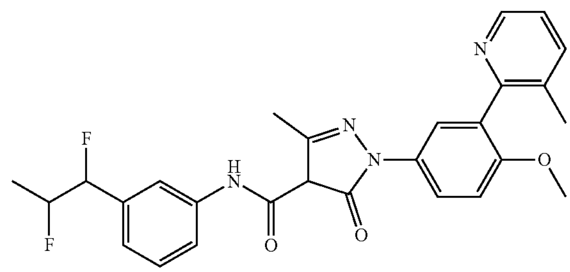 [SMILES: COc1ccc(N2N=C(C)C(C(=O)Nc3cccc(C(F)C(C)F)c3)C2=O)cc1-c1ncccc1C] |
| 560 | 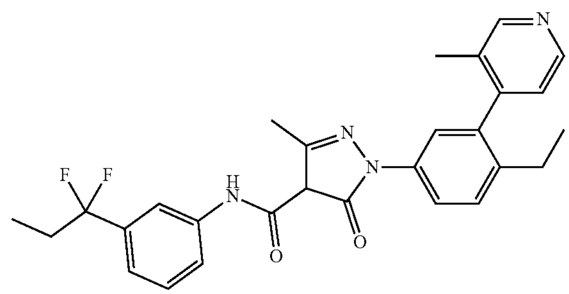 [SMILES: CCc1ccc(N2N=C(C)C(C(=O)Nc3cccc(C(F)(F)CC)c3)C2=O)cc1-c1ccncc1C] |
| 561 | 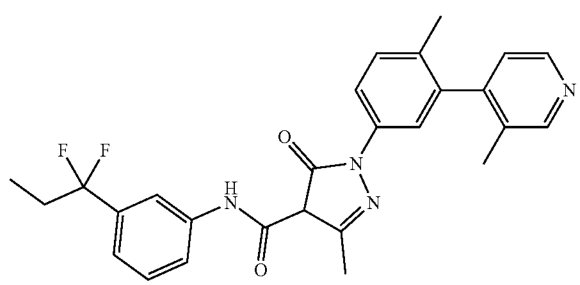 [SMILES: CCC(F)(F)c1cccc(NC(=O)C2C(=O)N(c3ccc(C)c(-c4ccncc4C)c3)N=C2C)c1] |
| 562 | 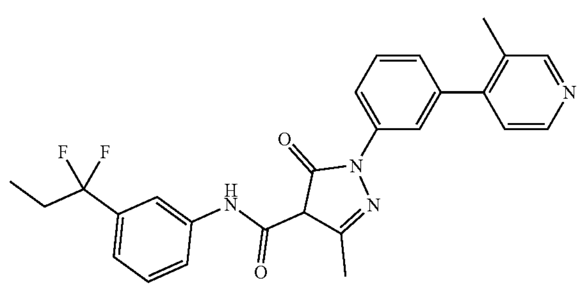 [SMILES: CCC(F)(F)c1cccc(NC(=O)C2C(=O)N(c3cccc(-c4ccncc4C)c3)N=C2C)c1] |
| 563 | 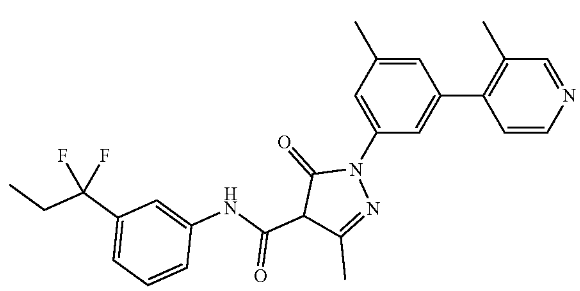 [SMILES: CCC(F)(F)c1cccc(NC(=O)C2C(=O)N(c3cc(C)cc(-c4ccncc4C)c3)N=C2C)c1] |

TABLE 1-continued

| Compound name | Structure |
|---|---|
| 564 | 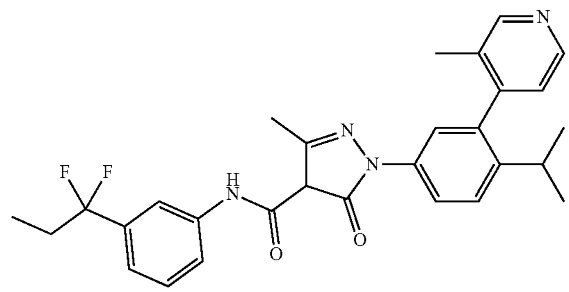 [SMILES: CCC(F)(F)c1cccc(NC(=O)C2C(=O)N(c3ccc(C(C)C)c(-c4ccncc4C)c3)N=C2C)c1] |
| 565 | 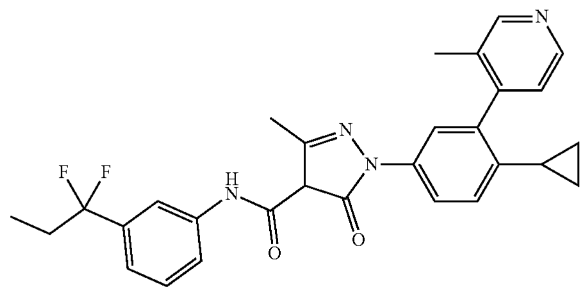 [SMILES: CCC(F)(F)c1cccc(NC(=O)C2C(=O)N(c3ccc(C4CC4)c(-c4ccncc4C)c3)N=C2C)c1] |
| 566 | 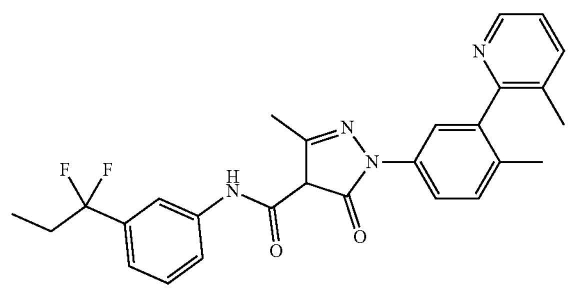 [SMILES: CCC(F)(F)c1cccc(NC(=O)C2C(=O)N(c3ccc(C)c(-c4ncccc4C)c3)N=C2C)c1] |
| 567 | 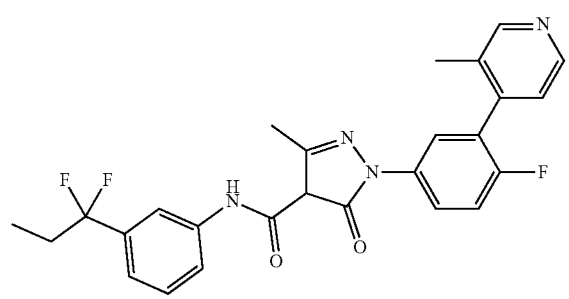 [SMILES: CCC(F)(F)c1cccc(NC(=O)C2C(=O)N(c3ccc(F)c(-c4ccncc4C)c3)N=C2C)c1] |
| 568 | 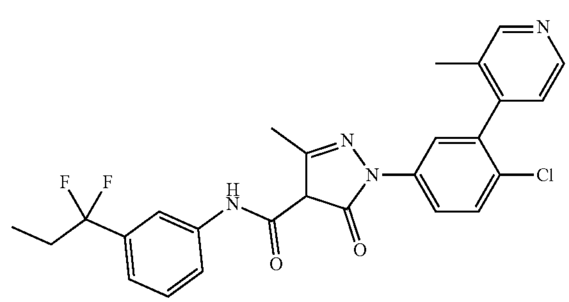 [SMILES: CCC(F)(F)c1cccc(NC(=O)C2C(=O)N(c3ccc(Cl)c(-c4ccncc4C)c3)N=C2C)c1] |

TABLE 1-continued

| Compound name | Structure |
|---|---|
| 569 | (structure: N-[3-(1,1-difluoropropyl)phenyl]-3-methyl-5-oxo-1-[3-(pyrimidin-2-yl)phenyl]-4,5-dihydro-1H-pyrazole-4-carboxamide) |
| 570 | (structure: N-[3-(1,1-difluoropropyl)phenyl]-3-methyl-5-oxo-1-[3-(pyrazin-2-yl)phenyl]-4,5-dihydro-1H-pyrazole-4-carboxamide) |
| 571 | (structure: N-[3-(1,1-difluoropropyl)phenyl]-3-methyl-5-oxo-1-(5H-chromeno[4,3-b]pyridin-yl)-4,5-dihydro-1H-pyrazole-4-carboxamide) |
| 572 | (structure: N-[3-(1,1-difluoropropyl)phenyl]-3-methyl-1-[4-methyl-3-(3-methylpyridin-2-yl)phenyl]-5-oxo-4,5-dihydro-1H-pyrazole-4-carboxamide) |
| 573 | (structure: N-[3-(1,1-difluoropropyl)phenyl]-3-methyl-5-oxo-1-[3-(pyrimidin-4-yl)phenyl]-4,5-dihydro-1H-pyrazole-4-carboxamide) |

TABLE 1-continued

| Compound name | Structure |
|---|---|
| 574 | 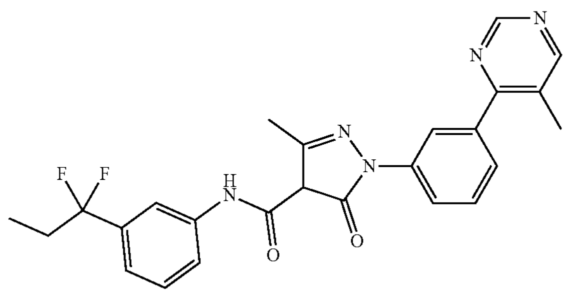 [SMILES: CCC(F)(F)c1cccc(NC(=O)C2C(=O)N(c3cccc(-c4ncncc4C)c3)N=C2C)c1] |
| 575 | 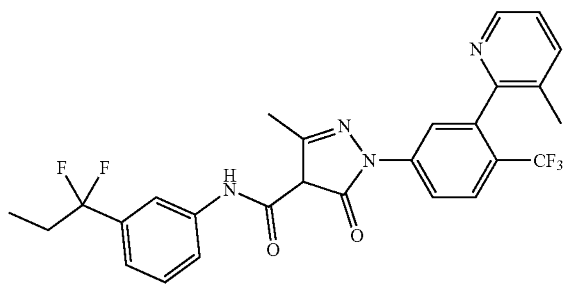 [SMILES: CCC(F)(F)c1cccc(NC(=O)C2C(=O)N(c3ccc(C(F)(F)F)c(-c4ncccc4C)c3)N=C2C)c1] |
| 576 | 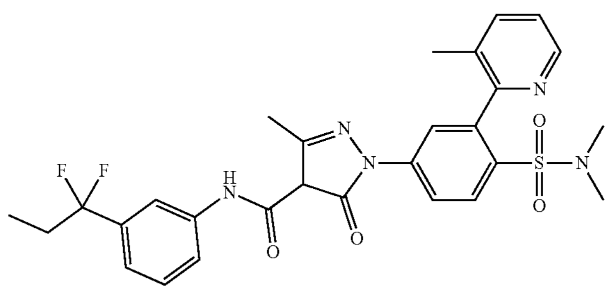 [SMILES: CCC(F)(F)c1cccc(NC(=O)C2C(=O)N(c3ccc(S(=O)(=O)N(C)C)c(-c4ncccc4C)c3)N=C2C)c1] |
| 577 | 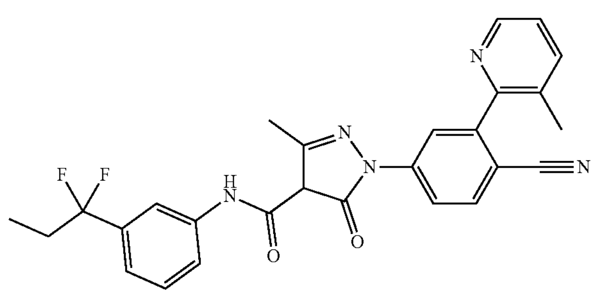 [SMILES: CCC(F)(F)c1cccc(NC(=O)C2C(=O)N(c3ccc(C#N)c(-c4ncccc4C)c3)N=C2C)c1] |
| 578 | 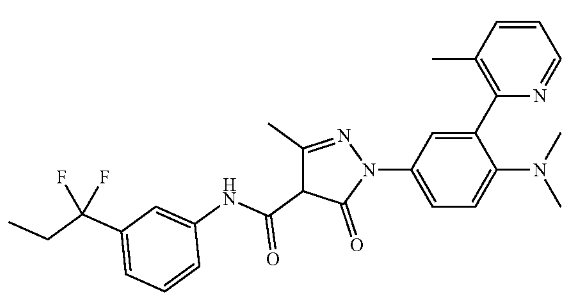 [SMILES: CCC(F)(F)c1cccc(NC(=O)C2C(=O)N(c3ccc(N(C)C)c(-c4ncccc4C)c3)N=C2C)c1] |

TABLE 1-continued

| Compound name | Structure |
|---|---|
| 579 | 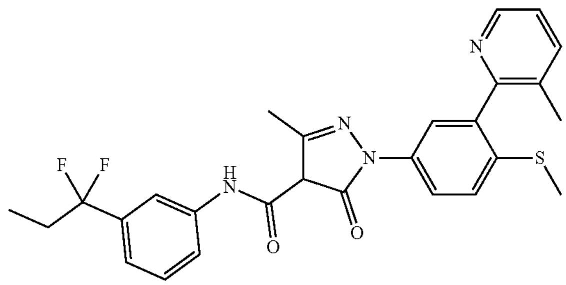 [SMILES: CCC(F)(F)c1cccc(NC(=O)C2C(=O)N(c3ccc(SC)c(-c4ncccc4C)c3)N=C2C)c1] |
| 580 | 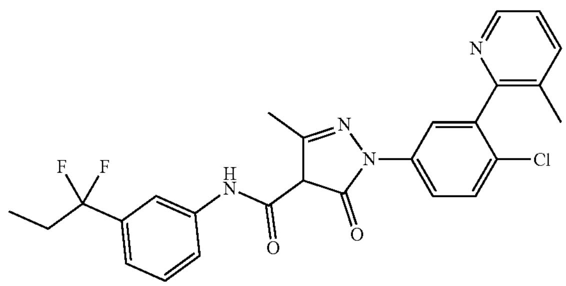 [SMILES: CCC(F)(F)c1cccc(NC(=O)C2C(=O)N(c3ccc(Cl)c(-c4ncccc4C)c3)N=C2C)c1] |
| 581 | 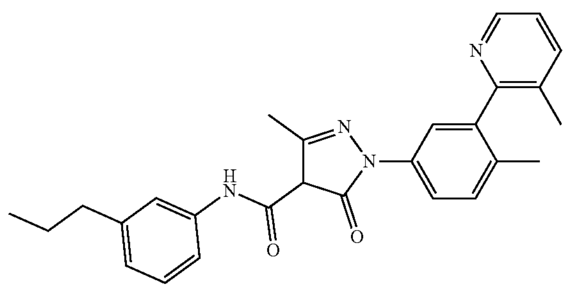 [SMILES: CCCc1cccc(NC(=O)C2C(=O)N(c3ccc(C)c(-c4ncccc4C)c3)N=C2C)c1] |
| 582 | 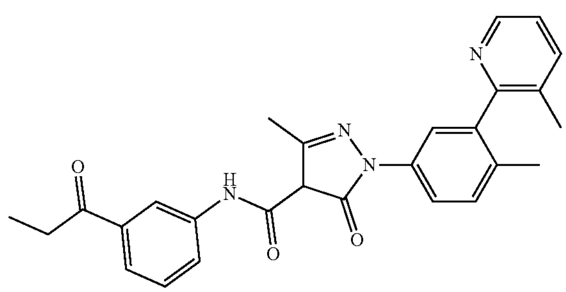 [SMILES: CCC(=O)c1cccc(NC(=O)C2C(=O)N(c3ccc(C)c(-c4ncccc4C)c3)N=C2C)c1] |
| 583 | 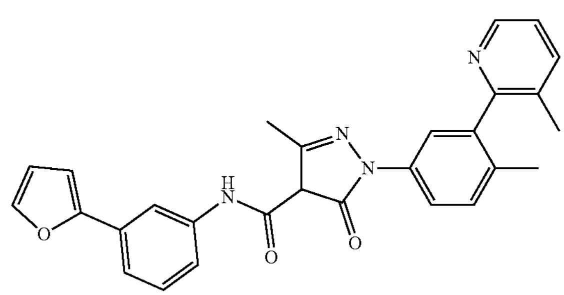 [SMILES: CC1=NN(c2ccc(C)c(-c3ncccc3C)c2)C(=O)C1C(=O)Nc1cccc(-c2ccco2)c1] |

TABLE 1-continued

| Compound name | Structure |
|---|---|
| 584 | 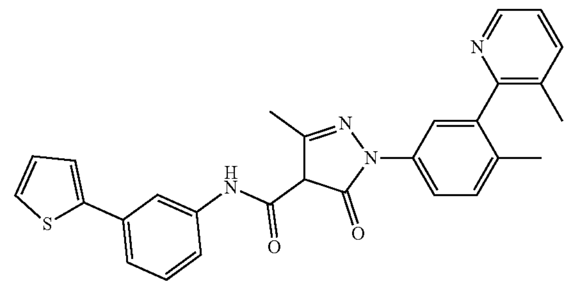 |
| 585 | 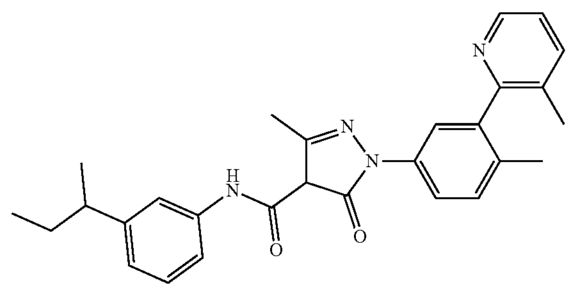 [SMILES: CCC(C)c1cccc(NC(=O)C2C(=O)N(c3ccc(C)c(-c4ncccc4C)c3)N=C2C)c1] |
| 586 | 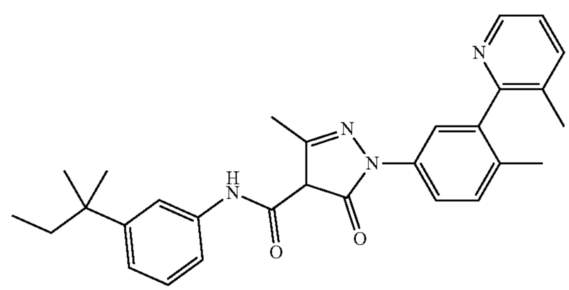 [SMILES: CCC(C)(C)c1cccc(NC(=O)C2C(=O)N(c3ccc(C)c(-c4ncccc4C)c3)N=C2C)c1] |
| 587 | 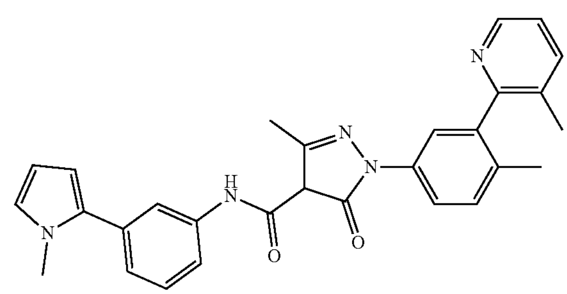 [SMILES: CC1=NN(c2ccc(C)c(-c3ncccc3C)c2)C(=O)C1C(=O)Nc1cccc(-c2cccn2C)c1] |
| 588 | 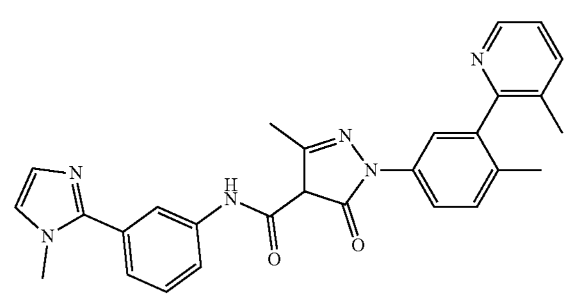 [SMILES: CC1=NN(c2ccc(C)c(-c3ncccc3C)c2)C(=O)C1C(=O)Nc1cccc(-c2nccn2C)c1] |

TABLE 1-continued

| Compound name | Structure |
|---|---|
| 589 | 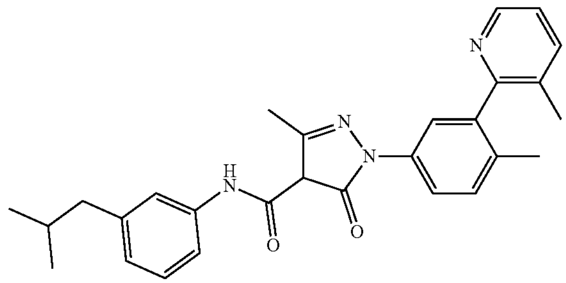 [SMILES: CC1=NN(c2ccc(C)c(-c3ncccc3C)c2)C(=O)C1C(=O)Nc1cccc(CC(C)C)c1] |
| 590 | 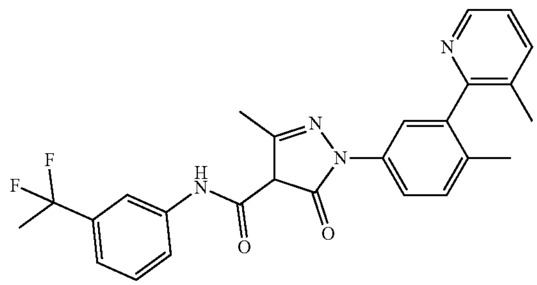 [SMILES: CC1=NN(c2ccc(C)c(-c3ncccc3C)c2)C(=O)C1C(=O)Nc1cccc(C(C)(F)F)c1] |
| 591 | 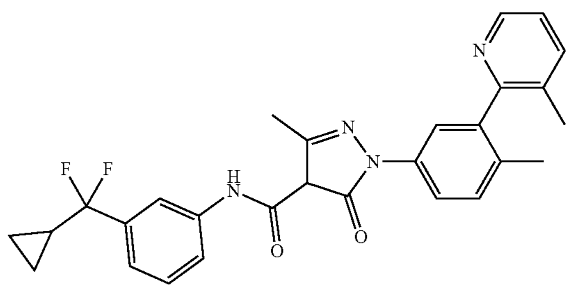 [SMILES: CC1=NN(c2ccc(C)c(-c3ncccc3C)c2)C(=O)C1C(=O)Nc1cccc(C(F)(F)C2CC2)c1] |
| 592 | 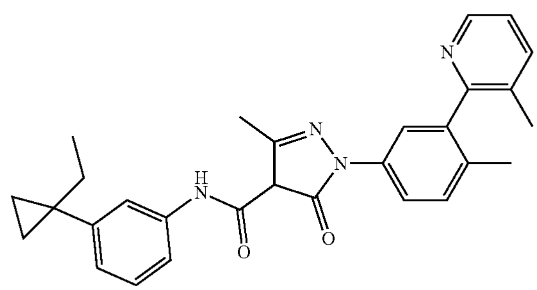 [SMILES: CCC1(c2cccc(NC(=O)C3C(=O)N(c4ccc(C)c(-c5ncccc5C)c4)N=C3C)c2)CC1] |

It is well understood that in structures presented in this invention wherein the nitrogen atom has less than 3 bonds, H atoms are present to complete the valence of the nitrogen.

In some embodiments, this invention is directed to the compounds listed hereinabove, pharmaceutical compositions and/or method of use thereof, wherein the compound is pharmaceutically acceptable salt, optical isomer, tautomer, hydrate, N-oxide, reverse amide analog, prodrug, isotopic variant (deuterated analog), PROTAC, pharmaceutical product or any combination thereof. In some embodiments, the compounds are Acyl-CoA Synthetase Short-Chain Family Member 2 (ACSS2) inhibitors.

In various embodiments, the A ring of formula I is phenyl, naphthyl, pyridinyl, pyrimidinyl, pyridazinyl, pyrazinyl, triazinyl, tetrazinyl, thiazolyl, isothiazolyl, oxazolyl, isoxazolyl, imidazolyl, 1-methylimidazole, isoquinoline, pyrazolyl, pyrrolyl, furanyl, thiophene-yl, isoquinolinyl, indolyl, 1H-indole, isoindolyl, naphthyl, anthracenyl, benzimidazolyl, indazolyl, benzothiophene, 2H-indazole, triazolyl, 4,5,6,7-tetrahydro-2H-indazole, 3H-indol-3-one, purinyl, benzoxazolyl, 1,3-benzoxazolyl, benzisoxazolyl, benzothiazolyl, 1,3-benzothiazole, 4,5,6,7-tetrahydro-1,3-benzothiazole, quinazolinyl, quinoxalinyl, cinnolinyl, phthalazinyl, quinolinyl, isoquinolinyl, 2,3-dihydroindenyl, indenyl, tetrahydronaphthyl, 3,4-dihydro-2H-benzo[b][1,4]dioxepine, benzo[d][1,3]dioxole, acridinyl, benzofuranyl, 1-benzofuran, isobenzofuranyl, benzofuran-2(3H)-one, benzothiophenyl, benzoxadiazole, benzo[c][1,2,5]oxadiazolyl, benzo[c]thiophenyl, benzodioxolyl, benzo[d][1,3]dioxole, thiadiazolyl, [1,3]oxazolo[4,5-b]pyridine, oxadiaziolyl, imidazo[2,1-b][1,3]thiazole, 4H,5H,6H-cyclopenta[d][1,3]thiazole, 5H,6H,7H,8H-imidazo[1,2-a]pyridine, 7-oxo-6H,7H-[1,3]thiazolo[4,5-d]pyrimidine, [1,3]thiazolo[5,4-b]pyridine, 2H,3H-imidazo[2,1-b][1,3]thiazole, thieno[3,2-d]pyrimidin-4(3H)-one, 4-oxo-4H-thieno[3,2-d][1,3]thiazin, imidazo[1,2-a]pyridine, 1H-imidazo[4,5-b]pyridine, 1H-imidazo[4,5-c]pyridine, 3H-imidazo[4,5-c]pyridine, pyrazolo[1,5-a]pyridine, imidazo[1,2-a]pyrazine, imidazo[1,2-a]pyrimidine, 1H-pyrrolo[2,3-b]pyridine, pyrido[2,3-b]pyrazine, pyrido[2,3-b]pyrazin-3(4H)-one, 4H-thieno[3,2-b]pyrrole, quinoxalin-2(1H)-one, 1H-pyrrolo[3,2-b]pyridine, 1H-pyrrolo[3,2-c]pyridine, 7H-pyrrolo[2,3-d]pyrimidine, oxazolo[5,4-b]pyridine, thiazolo[5,4-b]pyridine, thieno[3,2-c]pyridine, 1,3-dihydroisobenzofuran each definition is a separate embodiment according to this invention; or A is single fused or bridged $C_3$-$C_8$ cycloalkyl (e.g. cyclohexyl, bicyclo [2.1.1]hexane, bicyclo [2.2.1]heptane, bicyclo [3.1.1]heptane, cubane, bicyclo[2.2.2]octane) or $C_3$-$C_8$ heterocyclic ring including but not limited to: tetrahydropyran, piperidine, 1-methylpiperidine, tetrahydrothiophene 1,1-dioxide, 1-(piperidin-1-yl)ethanone or morpholine.

In various embodiments, the A ring of formula I is phenyl. In some embodiments, the A ring is naphtyl. In some embodiments, the A ring is pyridinyl. In some embodiments, the A ring is pyrimidinyl. In some embodiments, the A ring is pyridazinyl. In some embodiments, A is pyrazinyl. In some embodiments, the A ring is triazinyl. In some embodiments, the A ring is tetrazinyl. In some embodiments, the A ring is thiazolyl. In some embodiments, the A ring is isothiazolyl. In some embodiments, the A ring is oxazolyl. In some embodiments, the A ring is isoxazolyl. In some embodiments, the A ring is imidazolyl. In some embodiments, the A ring is 1-methylimidazole. In some embodiments, the A ring is pyrazolyl. In some embodiments, the A ring is pyrrolyl. In some embodiments, the A ring is furanyl. In some embodiments, the A ring is thiophene-yl. In some embodiments, the A ring is indolyl. In some embodiments, the A ring is indenyl. In some embodiments, the A ring is 2,3-dihydroindenyl. In some embodiments, the A ring is tetrahydronaphthyl. In some embodiments, the A ring is isoindolyl. In some embodiments, the A ring is naphthyl. In some embodiments, the A ring is anthracenyl. In some embodiments, the A ring is benzimidazolyl. In some embodiments, the A ring is indazolyl. In some embodiments, the A ring is purinyl. In some embodiments, the A ring is benzoxazolyl. In some embodiments, the A ring is benzisoxazolyl. In some embodiments, the A ring is benzothiazolyl. In some embodiments, the A ring is quinazolinyl. In some embodiments, the A ring is quinoxalinyl. In some embodiments, the A ring is cinnolinyl. In some embodiments, the A ring is phthalazinyl. In some embodiments, the A ring is quinolinyl. In some embodiments, the A ring is isoquinolinyl. In some embodiments, the A ring is 3,4-dihydro-2H-benzo[b][1,4]dioxepine. In some embodiments, the A ring is benzo[d][1,3]dioxole. In some embodiments, the A ring is benzofuran-2(3H)-one. In some embodiments, the A ring is benzodioxolyl. In some embodiments, the A ring is acridinyl. In some embodiments, the A ring is benzofuranyl. In some embodiments, the A ring is isobenzofuranyl. In some embodiments, the A ring is benzothiophenyl. In some embodiments, the A ring is benzo[c]thiophenyl. In some embodiments, the A ring is benzodioxolyl. In some embodiments, the A ring is thiadiazolyl. In some embodiments, the A ring is oxadiazolyl. In some embodiments, the A ring is 7-oxo-6H,7H-[1,3]thiazolo[4,5-d]pyrimidine. In some embodiments, the A ring is [1,3]thiazolo[5,4-b]pyridine. In some embodiments, the A ring is thieno[3,2-d]pyrimidin-4(3H)-one. In some embodiments, the A ring is 4-oxo-4H-thieno[3,2-d][1,3]thiazin. In some embodiments, the A ring is pyrido[2,3-b]pyrazin or pyrido[2,3-b]pyrazin-3(4H)-one. In some embodiments, the A ring is quinoxalin-2(1H)-one. In some embodiments, the A ring is 1H-indole. In some embodiments, the A ring is 2H-indazole. In some embodiments, the A ring is 4,5,6,7-tetrahydro-2H-indazole. In some embodiments, the A ring is 3H-indol-3-one. In some embodiments, the A ring is 1,3-benzoxazolyl. In some embodiments, the A ring is 1,3-benzothiazole. In some embodiments, the A ring is 4,5,6,7-tetrahydro-1,3-benzothiazole. In some embodiments, the A ring is 1-benzofuran. In some embodiments, the A ring is [1,3]oxazolo[4,5-b]pyridine. In some embodiments, the A ring is imidazo[2,1-b][1,3]thiazole. In some embodiments, the A ring is 4H,5H,6H-cyclopenta[d][1,3]thiazole. In some embodiments, the A ring is 5H,6H,7H,8H-imidazo[1,2-a]pyridine. In some embodiments, the A ring is 2H,3H-imidazo[2,1-b][1,3]thiazole. In some embodiments, the A ring is imidazo[1,2-a]pyridine. In some embodiments, the A ring is pyrazolo[1,5-a]pyridine. In some embodiments, the A ring is imidazo[1,2-a]pyrazine. In some embodiments, the A ring is imidazo[1,2-a]pyrimidine. In some embodiments, the A ring is 4H-thieno[3,2-b]pyrrole. In some embodiments, the A ring is 1H-pyrrolo[2,3-b]pyridine. In some embodiments, the A ring is 1H-pyrrolo[3,2-b]pyridine. In some embodiments, the A ring is 7H-pyrrolo[2,3-d]pyrimidine. In some embodiments, the A ring is oxazolo[5,4-b]pyridine. In some embodiments, the A ring is thiazolo[5,4-b]pyridine. In some embodiments, the A ring is triazolyl. In some embodiments, the A ring is benzoxadiazole. In some embodiments, the A ring is benzo[c][1,2,5]oxadiazolyl. In some embodiments, the A ring is 1H-imidazo[4,5-b]pyridine. In some embodiments, the A ring is 3H-imidazo[4,5-c]pyridine. In some embodiments, the A ring is a $C_3$-$C_8$ cycloalkyl. In some embodiments, the A ring is $C_3$—C heterocyclic ring. In some embodiments, the A ring is tetrahydropyran. In some embodiments, the A ring is piperidine. In some embodiments, the A ring is 1-(piperidin-1-yl)ethanone. In some embodiments, the A ring is morpholine. In some embodiments, the A ring is thieno[3,2-c]pyridine. In some embodiments, the A ring is 1-methylpiperidine. In some embodiments, the A ring is tetrahydrothiophene 1,1-dioxide. In some embodiments, the A ring is cyclohexyl. In some embodiments, the A ring is indole. In some embodiments, the A ring is 1,3-dihydroisobenzofuran. In some embodiments, the A ring is benzofuran. In some embodiments, the A ring is 1,3-dihydroisobenzofuran. In other embodiments, A is single fused or bridged $C_3$-$C_{10}$ cycloalkyl. In other embodiments, A is cyclohexyl. In other embodiments, A is bicyclo[2.1.1]hexane. In other embodiments, A is bicyclo[2.2.1]heptane. In other embodiments, A is bicyclo[3.1.1]heptane. In other embodiments, A is cubane. In other embodiments, A is bicyclo [2.2.2]octane.

In various embodiments, the B ring of formula I is phenyl, naphthyl, pyridinyl, pyrimidinyl, pyridazinyl, pyrazinyl, triazinyl, tetrazinyl, thiazolyl, isothiazolyl, oxazolyl, isoxazolyl, imidazolyl, 1-methylimidazole, isoquinoline, pyrazolyl, pyrrolyl, furanyl, thiophene-yl, isoquinolinyl, indolyl, 1H-indole, isoindolyl, naphthyl, anthracenyl, benzimidazolyl, indazolyl, benzothiophene, 2H-indazole, triazolyl, 4,5,6,7-tetrahydro-2H-indazole, 3H-indol-3-one, purinyl, benzoxazolyl, 1,3-benzoxazolyl, benzisoxazolyl, benzothiazolyl, 1,3-benzothiazole, 4,5,6,7-tetrahydro-1,3-benzothiazole, quinazolinyl, quinoxalinyl, cinnolinyl, phthalazinyl, quinolinyl, isoquinolinyl, 2,3-dihydroindenyl, indenyl, tetrahydronaphthyl, 3,4-dihydro-2H-benzo[b][1,4]dioxepine, benzo[d][1,3]dioxole, acridinyl, benzofuranyl, 1-benzofuran, isobenzofuranyl, benzofuran-2(3H)-one, benzothiophenyl, benzoxadiazole, benzo[c][1,2,5]oxadiazolyl, benzo[c]thiophenyl, benzodioxolyl, benzo[d][1,3]dioxole, thiadiazolyl, [1,3]oxazolo[4,5-b]pyridine, oxadiaziolyl, imidazo[2,1-b][1,3]thiazole, 4H,5H,6H-cyclopenta[d][1,3]thiazole, 5H,6H,7H,8H-imidazo[1,2-a]pyridine, 7-oxo-6H,7H-[1,3]thiazolo[4,5-d]pyrimidine, [1,3]thiazolo[5,4-b]pyridine, 2H,3H-imidazo[2,1-b][1,3]thiazole, thieno[3,2-d]pyrimidin-4(3H)-one, 4-oxo-4H-thieno[3,2-d][1,3]thiazin, imidazo[1,2-a]pyridine, 1H-imidazo[4,5-b]pyridine, 1H-imidazo[4,5-c]pyridine, 3H-imidazo[4,5-c]pyridine, pyrazolo[1,5-a]pyridine, imidazo[1,2-a]pyrazine, imidazo[1,2-a]pyrimidine, 1H-pyrrolo[2,3-b]pyridine, pyrido[2,3-b]pyrazine, pyrido[2,3-b]pyrazin-3(4H)-one, 4H-thieno[3,2-b]pyrrole, quinoxalin-2(1H)-one, 1H-pyrrolo[3,2-b]pyridine, 1H-pyrrolo[3,2-c]pyridine, 7H-pyrrolo[2,3-d]pyrimidine, oxazolo[5,4-b]pyridine, thiazolo[5,4-b]pyridine, thieno[3,2-c]pyridine, 1,3-dihydroisobenzofuran each definition is a separate embodiment according to this invention.

In various embodiments, the B ring of formula I is phenyl. In some embodiments, the B ring is naphthyl. In some embodiments, the B ring is pyridinyl. In some embodiments, the B ring is pyrimidinyl. In some embodiments, the B ring is pyridazinyl. In some embodiments, the B ring is pyrazinyl. In some embodiments, the B ring is triazinyl. In some embodiments, the B ring is tetrazinyl. In some embodiments, the B ring is thiazolyl. In some embodiments, the B ring is isothiazolyl. In some embodiments, the B ring is oxazolyl. In some embodiments, the B ring is isoxazolyl. In some embodiments, the B ring is imidazolyl. In some embodiments, the B ring is 1-methylimidazole. In some embodiments, the B ring is pyrazolyl. In some embodiments, the B ring is pyrrolyl. In some embodiments, the B ring is furanyl. In some embodiments, the B ring is thiophene-yl. In some embodiments, the B ring is isoquinolinyl. In some embodiments, the B ring is indolyl. In some embodiments, the B ring is isoindolyl. In some embodiments, the B ring is naphthyl. In some embodiments, the B ring is anthracenyl. In some embodiments, the B ring is benzimidazolyl. In some embodiments, the B ring is 2,3-dihydro-1H-benzo[d]imidazole. In some embodiments, the B ring is indazolyl. In some embodiments, the B ring is purinyl. In some embodiments, the B ring is benzoxazolyl. In some embodiments, the B ring is benzisoxazolyl. In some embodiments, the B ring is benzothiazolyl. In some embodiments, the B ring is quinazolinyl. In some embodiments, the B ring is quinoxalinyl. In some embodiments, the B ring is 1,2,3,4-tetrahydroquinoxaline. In other embodiments, B is 1-(pyridin-1(2H)-yl)ethanone. In some embodiments, the B ring is benzo[d][1,3]dioxole. In some embodiments, the B ring is benzofuran-2(3H)-one. In some embodiments, the B ring is benzodioxolyl. In some embodiments, the B ring is tetrahydronaphthyl. In some embodiments, the B ring is cinnolinyl. In some embodiments, the B ring is phthalazinyl. In some embodiments, the B ring is quinolinyl. In some embodiments, the B ring is isoquinolinyl. In some embodiments, the B ring is acridinyl. In some embodiments, the B ring is benzofuranyl. In some embodiments, the B ring is isobenzofuranyl. In some embodiments, the B ring is benzothiophenyl. In some embodiments, the B ring is benzo[c]thiophenyl. In some embodiments, the B ring is benzodioxolyl. In some embodiments, the B ring is thiadiazolyl. In some embodiments, the B ring is oxadiaziolyl. In some embodiments, the B ring is 7-oxo-6H,7H-[1,3]thiazolo[4,5-d]pyrimidine. In some embodiments, the B ring is [1,3]thiazolo[5,4-b]pyridine. In some embodiments, the C ring is thieno[3,2-d]pyrimidin-4(3H)-one. In some embodiments, the B ring is 4-oxo-4H-thieno[3,2-d][1,3]thiazin. In some embodiments, the B ring is pyrido[2,3-b]pyrazin or pyrido[2,3-b]pyrazin-3(4H)-one. In some embodiments, the B ring is quinoxalin-2(1H)-one. In some embodiments, the B ring is 1H-indole. In some embodiments, the B ring is 2H-indazole. In some embodiments, the B ring is 4,5,6,7-tetrahydro-2H-indazole. In some embodiments, the B ring is 3H-indol-3-one. In some embodiments, the B ring is 1,3-benzoxazolyl. In some embodiments, the B ring is 1,3-benzothiazole. In some embodiments, the B ring is 4,5,6,7-tetrahydro-1,3-benzothiazole. In some embodiments, the B ring is 1-benzofuran. In some embodiments, the C ring is [1,3]oxazolo[4,5-b]pyridine. In some embodiments, the B ring is imidazo[2,1-b][1,3]thiazole. In some embodiments, the B ring is 4H,5H,6H-cyclopenta[d][1,3]thiazole. In some embodiments, the C ring is 5H,6H,7H,8H-imidazo[1,2-a]pyridine. In some embodiments, the B ring is 2H,3H-imidazo[2,1-b][1,3]thiazole. In some embodiments, the B ring is imidazo[1,2-a]pyridine. In some embodiments, the B ring is pyrazolo[1,5-a]pyridine. In some embodiments, the B ring is imidazo[1,2-a]pyrazine. In some embodiments, the B ring is imidazo[1,2-a]pyrimidine. In some embodiments, the B ring is 4H-thieno[3,2-b]pyrrole. In some embodiments, the B ring is 1H-pyrrolo[2,3-b]pyridine, In some embodiments, the B ring is 1H-pyrrolo[3,2-b]pyridine. In some embodiments, the B ring is 7H-pyrrolo[2,3-d]pyrimidine. In some embodiments, the B ring is oxazolo[5,4-b]pyridine. In some embodiments, the B ring is thiazolo[5,4-b]pyridine. In some embodiments, the B ring is triazolyl. In some embodiments, the B ring is benzoxadiazole. In some embodiments, the B ring is benzo[c][1,2,5]oxadiazolyl. In some embodiments, the B ring is 1H-imidazo[4,5-b]pyridine. In some embodiments, the B ring is 3H-imidazo[4,5-c]pyridine. In some embodiments, the B ring is a $C_3$-$C_8$ cycloalkyl. In some embodiments, the B ring is $C_3$-$C_8$ heterocyclic ring. In some embodiments, the B ring is tetrahydropyran. In some embodiments, the B ring is piperidine. In some embodiments, the B ring is 1-(piperidin-1-yl)ethanone. In some embodiments, the B ring is morpholine. In some embodiments, the B ring is thieno[3,2-c]pyridine. In some embodiments, the B ring is 1-methylpiperidine. In some embodiments, the B ring is tetrahydrothiophene 1,1-dioxide. In some embodiments, the B ring is indole. In some embodiments, the B ring is 1,3-dihydroisobenzofuran. In some embodiments, the B ring is benzofuran. In some embodiments, the B ring is cyclohexyl. In some embodiments, the B ring is 1,3-dihydroisobenzofuran. In other embodiments, B is bicyclo[2.1.1]hexane. In other embodiments, B is bicyclo[2.2.1]heptane. In other embodiments, B is bicyclo[3.1.1]heptane. In other embodiments, B is cubane. In other embodiments, B is bicyclo [2.2.2]octane.

In various embodiments, compound of formula I is substituted by $R_1$ and $R_2$. Single substituents can be present at the ortho, meta, or para positions.

In various embodiments, $R_1$ of formula I-V is H. In other embodiments, $R_1$ is D. In some embodiments, $R_1$ is F. In some embodiments, $R_1$ is Cl. In some embodiments, $R_1$ is Br. In some embodiments, $R_1$ is I. In some embodiments, $R_1$ is OH. In some embodiments, $R_1$ is SH. In some embodiments, $R_1$ is $R_8$—OH. In some embodiments, $R_1$ is $CH_2$—OH. In some embodiments, $R_1$ is $R_8$—SH. In some embodiments, $R_1$ is —$R_8$—O—$R_{10}$. In some embodiments, $R_1$ is —$CH_2$—O—$CH_3$. In other embodiments, $R_1$ is $R_8$-aryl. In other embodiments, $R_1$ is $CH_2$-3-methoxy-phenyl. In other embodiments, $R_1$ is benzyl. In other embodiments, $R_1$ is $CH_2$-1-methoxy-phenyl. In other embodiments, $R_1$ is $CH_2$-

4-chloro-phenyl. In other embodiments, $R_1$ is $CH_2CH_2$-phenyl. In other embodiments, $R_1$ is $C_1$-$C_5$ linear or branched haloalkyl. In other embodiments, $R_1$ is $CF_3$. In other embodiments, $R_1$ is $CF_2CF_3$. In other embodiments, $R_1$ is $CF_2CH_2CH_3$. In other embodiments, $R_1$ is $CH_2CH_2CF_3$. In other embodiments, $R_1$ is $CF_2CH(CH_3)_2$. In other embodiments, $R_1$ is $CF(CH_3)$—$CH(CH_3)_2$. In other embodiments, $R_1$ is $CD_3$. In other embodiments, $R_1$ is $OCD_3$. In some embodiments, $R_1$ is CN. In some embodiments, $R_1$ is $NO_2$. In some embodiments, $R_1$ is —$CH_2CN$. In some embodiments, $R_1$ is —$R_8CN$. In some embodiments, $R_1$ is $NH_2$. In some embodiments, $R_1$ is NHR. In some embodiments, $R_1$ is $N(R)_2$. In some embodiments, $R_1$ is $R_8$—$N(R_{10})(R_{11})$. In other embodiments, $R_1$ is $CH_2$—$NH_2$. In other embodiments, $R_1$ is $CH_2$—$N(CH_3)_2$. In other embodiments, $R_1$ is $R_9$—$R_8$—$N(R_{10})(R_{11})$. In other embodiments, $R_1$ is C≡C—$CH_2$—$NH_2$. In other embodiments, $R_1$ is $B(OH)_2$. In some embodiments, $R_1$ is —OC(O)$CF_3$. In some embodiments, $R_1$ is —$OCH_2Ph$. In some embodiments, $R_1$ is NHC(O)—$R_{10}$. In some embodiments, $R_1$ is NHC(O)$CH_3$. In some embodiments, $R_1$ is NHCO—$N(R_{10})(R_{11})$. In some embodiments, $R_1$ is NHC(O)N($CH_3)_2$. In some embodiments, $R_1$ is COOH. In some embodiments, $R_1$ is —C(O)Ph. In other embodiments, $R_1$ is —C(O)-aryl. In other embodiments, $R_1$ is C(O)-1-methyl-phenyl. In other embodiments, $R_1$ is C(O)-4-methyl-phenyl. In other embodiments, $R_1$ is C(O)-3-methyl-phenyl. In other embodiments, $R_1$ is C(O)-phenol. In other embodiments, $R_1$ is C(O)-4-hydroxy-phenyl. In other embodiments, $R_1$ is C(O)-3-hydroxy-phenyl. In other embodiments, $R_1$ is C(O)-2-hydroxy-phenyl. In some embodiments, $R_1$ is C(O)O—$R_{10}$. In some embodiments, $R_1$ is C(O)O—$CH_3$. In some embodiments, $R_1$ is C(O)—$R_{10}$. In some embodiments, $R_1$ is C(O)—$CH_3$. In other embodiments, $R_1$ is C(O)—$CH_2CH_2CH_3$. In some embodiments, $R_1$ is C(O)O—CH($CH_3)_2$. In some embodiments, $R_1$ is C(O)O—$CH_2CH_3$). In some embodiments, $R_1$ is $R_8$—C(O)—$R_{10}$. In some embodiments, $R_1$ is $CH_2C(O)CH_3$). In some embodiments, $R_1$ is C(O)H. In some embodiments, $R_1$ is C(O)—$R_{10}$. In some embodiments, $R_1$ is C(O)—$CH_3$. In some embodiments, $R_1$ is C(O)—$CH_2CH_3$. In some embodiments, $R_1$ is C(O)—$CH_2CH_2CH_3$). In some embodiments, $R_1$ is $C_1$-$C_5$ linear or branched C(O)-haloalkyl. In some embodiments, $R_1$ is C(O)—$CF_3$. In some embodiments, $R_1$ is —C(O)$NH_2$. In some embodiments, $R_1$ is C(O)NHR. In some embodiments, $R_1$ is C(O)N($R_{10})(R_{11})$. In some embodiments, $R_1$ is C(O)N($CH_3)_2$. In some embodiments, $R_1$ is $SO_2R$. In other embodiments, $R_1$ is $SO_2$-Ph. In other embodiments, $R_1$ is $SO_2$-toluene. In other embodiments, $R_1$ is $SO_2$—$CH_3$. In some embodiments, $R_1$ is $SO_2N(R_{10})(R_{11})$. In some embodiments, $R_1$ is $SO_2N(CH_3)_2$. In some embodiments, $R_1$ is $C_1$-$C_5$ linear or branched, substituted or unsubstituted alkyl. In some embodiments, $R_1$ is methyl, 2, 3, or 4-$CH_2$—$C_6H_4$—Cl, ethyl, propyl, iso-propyl, t-Bu, iso-butyl, pentyl, benzyl, or C($CH_3$)(OH)Ph, each represents a separate embodiment according to this invention. In other embodiments, $R_1$ is $CH_2$-3-methoxy-phenyl. In other embodiments, $R_1$ is $CH_2$-1-methoxy-phenyl. In other embodiments, $R_1$ is $CH_2$-4-chloro-phenyl. In other embodiments, $R_1$ is $CH_2CH_2$-phenyl. In some embodiments, $R_1$ is $C_1$-$C_5$ linear or branched haloalkyl. In other embodiments, $R_1$ is $CF_2CH_3$. In other embodiments, $R_1$ is $CH_2CF_3$. In other embodiments, $R_1$ is $CF_2CH_2CH_3$. In other embodiments, $R_1$ is $CF_3$. In other embodiments, $R_1$ is $CF_2CH_2CH_3$. In other embodiments, $R_1$ is $CH_2CH_2CF_3$. In other embodiments, $R_1$ is $CF_2CH(CH_3)_2$. In other embodiments, $R_1$ is $CF(CH_3)$—CH($CH_3)_2$. In some embodiments, $R_1$ is substituted or unsubstituted $C_1$-$C_5$ linear or branched or $C_3$-$C_8$ cyclic alkoxy. In some embodiments, $R_1$ is methoxy, ethoxy, propoxy, iso-propoxy or O—$CH_2$-cyclopropyl, O-cyclobutyl, O-cyclopentyl, O-cyclohexyl, 1-butoxy, 2-butoxy, 0-tBu, each represents a separate embodiment according to this invention. In other embodiments, $R_1$ is substituted or unsubstituted $C_1$-$C_5$ linear or branched or $C_3$-$C_8$ cyclic alkoxy wherein at least one methylene group ($CH_2$) in the alkoxy is replaced with an oxygen atom (O). In some embodiments, $R_1$ is O-1-oxacyclobutyl, O-2-oxacyclobutyl, each represents a separate embodiment according to this invention. In some embodiments, $R_1$ is $C_1$-$C_5$ linear or branched thioalkoxy. In other embodiments, $R_1$ is S—$CH_3$. In some embodiments, $R_1$ is $C_1$-$C_5$ linear or branched haloalkoxy. In some embodiments, $R_1$ is $OCF_3$. In some embodiments, $R_1$ is $OCHF_2$. In some embodiments, $R_1$ is $C_1$-$C_5$ linear or branched alkoxyalkyl. In some embodiments, $R_1$ is substituted or unsubstituted $C_3$-$C_8$ cycloalkyl. In some embodiments, $R_1$ is cyclopropyl. In some embodiments, $R_1$ is cyclopentyl. In some embodiments, $R_1$ is substituted or unsubstituted $C_3$-$C_8$ heterocyclic ring. In some embodiments, $R_1$ is thiophene, oxazole, oxadiazole, imidazole, furane, triazole, tetrazole, pyridine (2, 3, or 4-pyridine), pyrimidine, pyrazine, 1 or 2-oxacyclobutane, indole, protonated or deprotonated pyridine oxide, 3-methyl-4H-1,2,4-triazole, 5-methyl-1,2,4-oxadiazole, each represents a separate embodiment according to this invention. In other embodiments, $R_1$ is 2-methyl-4-pyridine. In other embodiments, $R_1$ is 2,6-dimethyl-4-pyridine. In other embodiments, $R_1$ is 3,5-dimethyl-4-pyridine. In other embodiments, $R_1$ is 2,5-dimethyl-4-pyridine. In other embodiments, $R_1$ is 3-methyl-4-pyridine. In other embodiments, $R_1$ is 5-methyl-2-pyridine. In other embodiments, $R_1$ is 3-methyl-2-pyridine. In other embodiments, $R_1$ is 3-ethyl-2-pyridine. In other embodiments, $R_1$ is 3-isopropyl-2-pyridine. In other embodiments, $R_1$ is 3-propyl-2-pyridine. In other embodiments, $R_1$ is 3-phenyl-2-pyridine. In other embodiments, $R_1$ is 4-methyl-2-pyridine. In other embodiments, $R_1$ is 6-methyl-2-pyridine. In other embodiments, $R_1$ is 5-methyl-2-pyridine. In other embodiments, $R_1$ is pyrimidine. In other embodiments, $R_1$ is 5-methyl-pyrimidine. In other embodiments, $R_1$ is pyrazine. In some embodiments, $R_1$ is methyl substituted oxazole. In some embodiments, $R_1$ is methyl substituted oxadiazole. In some embodiments, $R_1$ is methyl substituted imidazole. In other embodiments, $R_1$ is thiophene. In other embodiments, $R_1$ is triazole. In other embodiments, $R_1$ is tetrazole. In other embodiments, $R_1$ is indole. In some embodiments, $R_1$ is substituted aryl. In some embodiments, $R_1$ is phenyl. In some embodiments, substitutions include: F, Cl, Br, I, $C_1$-$C_5$ linear or branched alkyl (e.g. methyl, ethyl), OH, alkoxy, $N(R)_2$, $CF_3$, phenyl, halophenyl, (benzyloxy)phenyl, CN, $NO_2$ or any combination thereof. In some embodiments, $R_1$ is CH($CF_3$)(NH—$R_{10}$). In some embodiments, $R_1$ is 2,3, or 4 bromophenyl, each is a separate embodiment according to this invention. In other embodiments, substitutions include: F, Cl, Br, I, $C_1$-$C_5$ linear or branched alkyl (e.g. methyl, ethyl, propyl, isopropyl), OH, alkoxy, $N(R)_2$, $CF_3$, aryl, phenyl, halophenyl, (benzyloxy)phenyl, CN, $NO_2$ or any combination thereof; each is a separate embodiment according to this invention.

In some embodiments, $R_1$ and $R_2$ are joint together to form a 5 or 6 membered substituted or unsubstituted, aliphatic or aromatic, carbocyclic or heterocyclic single or fused ring. In some embodiments, $R_1$ and $R_2$ are joined together to form a 5 or 6 membered heterocyclic ring. In some embodiments, $R_1$ and $R_2$ are joint together to form a heterocyclic single ring. In some embodiments, $R_1$ and $R_2$ are joined together to form a [1,3]dioxole ring. In some embodiments, $R_1$ and $R_2$ are joined together to form a furan-2(3H)-one ring. In some embodiments, $R_1$ and $R_2$ are joint together to form a benzene ring. In some embodiments, $R_1$ and $R_2$ are joined together to form a pyridine ring. In some embodiments, $R_1$ and $R_2$ are joined together to form a morpholine ring. In some embodiments, $R_1$ and $R_2$ are joined together to form a piperazine ring. In some embodiments, $R_1$ and $R_2$ are joined together to form an imidazole ring. In some embodiments, $R_1$ and $R_2$ are joined together to form a pyrrole ring. In some embodiments, $R_1$ and $R_2$ are joined together to form a cyclohexene ring. In some embodiments, $R_1$ and $R_2$ are joined together to form a pyrazine ring. In some embodiments, $R_1$ and $R_2$ are joint together to form a pyrrol ring. In some embodiments, $R_1$ and $R_2$ are joint together to form a 1-methyl-H-pyrrole. In some embodiments, $R_1$ and $R_2$ are joint together to form a 1-benzyl-1H-pyrrole ring. In some embodiments, $R_1$ and $R_2$ are joint together to form a 5 or 6 membered substituted or unsubstituted, aliphatic or aromatic, carbocyclic or heterocyclic ring fused to another 5 or 6 membered substituted or unsubstituted, aliphatic or aromatic, carbocyclic or heterocyclic ring. In some embodiments, $R_1$ and $R_2$ are joint together to form a 7,8-dihydro-5H-pyrano[4,3-b]pyridine.

In various embodiments, $R_2$ of formula I-V is H. In other embodiments, $R_2$ is D. In some embodiments, $R_2$ is F. In some embodiments, $R_2$ is Cl. In some embodiments, $R_2$ is Br. In some embodiments, $R_2$ is I. In other embodiments, $R_2$ is $R_8$-aryl. In other embodiments, $R_2$ is $CH_2$-3-methoxy-phenyl. In other embodiments, $R_2$ is benzyl. In other embodiments, $R_2$ is $CH_2$-1-methoxy-phenyl. In other embodiments, $R_2$ is $CH_2$-4-chloro-phenyl. In other embodiments, $R_2$ is $CH_2CH_2$-phenyl. In some embodiments, $R_2$ is OH. In some embodiments, $R_2$ is SH. In some embodiments, $R_2$ is $R_8$—OH. In some embodiments, $R_2$ is $CH_2$—OH. In some embodiments, $R_2$ is $R_8$—SH. In some embodiments, $R_1$ is —$R_8$—O—$R_{10}$. In some embodiments, $R_2$ is —$CH_2$—O—$CH_3$. In other embodiments, $R_2$ is $C_1$-$C_5$ linear or branched haloalkyl. In other embodiments, $R_2$ is $CF_3$. In other embodiments, $R_2$ is $CF_2CH_3$. In other embodiments, $R_2$ is $CF_2CH_3$. In other embodiments, $R_2$ is $CH_2CF_3$. In other embodiments, $R_2$ is $CF_2CH_2CH_3$. In other embodiments, $R_2$ is $CF_3$. In other embodiments, $R_2$ is $CF_2CH_2CH_3$. In other embodiments, $R_2$ is $CH_2CH_2CF_3$. In other embodiments, $R_2$ is $CF_2CH(CH_3)_2$. In other embodiments, $R_2$ is $CF(CH_3)$—$CH(CH_3)_2$. In other embodiments, $R_2$ is $CD_3$. In other embodiments, $R_2$ is $OCD_3$. In some embodiments, $R_2$ is CN. In some embodiments, $R_2$ is $NO_2$. In some embodiments, $R_2$ is —$CH_2CN$. In some embodiments, $R_2$ is —$R_8CN$. In some embodiments, $R_2$ is $NH_2$. In some embodiments, $R_2$ is NHR. In some embodiments, $R_2$ is $N(R)_2$. In some embodiments, $R_2$ is $R_8$—$N(R_{10})(R_{11})$. In other embodiments, $R_2$ is $CH_2$—$NH_2$. In some embodiments, $R_2$ is $CH_2$—$N(CH_3)_2$. In other embodiments, $R_2$ is $R_9$—$R_8$—$N(R_{10})(R_{11})$. In other embodiments, $R_2$ is C≡C—$CH_2$—$NH_2$. In other embodiments, $R_2$ is $B(OH)_2$. In some embodiments, $R_2$ is —$OC(O)CF_3$. In some embodiments, $R_2$ is —$OCH_2Ph$. In some embodiments, $R_2$ is NHC(O)—$R_{10}$. In some embodiments, $R_2$ is $NHC(O)CH_3$. In some embodiments, $R_2$ is NHCO—$N(R_{10})(R^{11})$. In some embodiments, $R_2$ is $NHC(O)N(CH_3)_2$. In some embodiments, $R_2$ is COOH. In some embodiments, $R_2$ is —C(O)Ph. In other embodiments, $R_2$ is —C(O)-aryl. In other embodiments, $R_2$ is C(O)-1-methyl-phenyl. In other embodiments, $R_2$ is C(O)-4-methyl-phenyl. In other embodiments, $R_2$ is C(O)-3-methyl-phenyl. In other embodiments, $R_2$ is C(O)-phenol. In other embodiments, $R_2$ is C(O)-4-hydroxy-phenyl. In other embodiments, $R_2$ is C(O)-3-hydroxy-phenyl. In other embodiments, $R_2$ is C(O)-2-hydroxy-phenyl. In some embodiments, $R_2$ is C(O)O—$R_{10}$. In some embodiments, $R_2$ is C(O)O—$CH(CH_3)_2$. In some embodiments, $R_2$ is C(O)O—$CH_3$. In some embodiments, $R_2$ is C(O)O—$CH_2CH_3$). In some embodiments, $R_2$ is $R_8$—C(O)—$R_{10}$. In some embodiments, $R_2$ is $CH_2C(O)CH_3$). In some embodiments, $R_2$ is C(O)H. In some embodiments, $R_2$ is C(O)—$R_{10}$. In some embodiments, $R_2$ is C(O)—$CH_3$. In some embodiments, $R_2$ is C(O)—$CH_2CH_3$. In some embodiments, $R_2$ is C(O)—$CH_2CH_2CH_3$). In some embodiments, $R_2$ is $C_1$-$C_5$ linear or branched C(O)-haloalkyl. In some embodiments, $R_2$ is C(O)—$CF_3$. In some embodiments, $R_2$ is —$C(O)NH_2$. In some embodiments, $R_2$ is C(O)NHR. In some embodiments, $R_2$ is $C(O)N(R_{10})(R_1)$. In some embodiments, $R_2$ is $C(O)N(CH_3)_2$. In some embodiments, $R_2$ is $SO_2R$. In other embodiments, $R_2$ is $SO_2$-Ph. In other embodiments, $R_2$ is $SO_2$-toluene. In other embodiments, $R_2$ is $SO_2$—$CH_3$. In some embodiments, $R_2$ is $SO_2N(R_{10})(R_{11})$. In some embodiments, $R_2$ is $SO_2N(CH_3)_2$. In some embodiments, $R_2$ is $C_1$-$C_5$ linear or branched, substituted or unsubstituted alkyl. In some embodiments, $R_2$ is methyl, 2, 3, or 4-$CH_2$—$C_6H_4$—Cl, ethyl, propyl, iso-propyl, t-Bu, iso-butyl, pentyl, benzyl or $C(CH_3)(OH)Ph$; each represents a separate embodiment according to this invention. In other embodiments, $R_2$ is benzyl. In other embodiments, $R_2$ is $CH_2$-3-methoxy-phenyl. In other embodiments, $R_2$ is $CH_2$—I-methoxy-phenyl. In other embodiments, $R_2$ is $CH_2$-4-chloro-phenyl. In other embodiments, $R_2$ is $CH_2CH_2$-phenyl. In some embodiments, $R_2$ is $C_1$-$C_5$ linear or branched haloalkyl In other embodiments, $R_2$ is $CF_2CH_3$. In other embodiments, $R_2$ is $CH_2CF_3$. In other embodiments, $R_2$ is $CF_2CH_2CH_3$. In other embodiments, $R_2$ is $CF_3$. In other embodiments, $R_2$ is $CF_2CH_2CH_3$. In other embodiments, $R_2$ is $CH_2CH_2CF_3$. In other embodiments, $R_2$ is $CF_2CH(CH_3)_2$. In other embodiments, $R_2$ is $CF(CH_3)$—CH$(CH_3)_2$. In other embodiments, $R_2$ is substituted or unsubstituted $C_1$-$C_5$ linear or branched or $C_3$-$C_8$ cyclic alkoxy. In some embodiments, $R_2$ is methoxy, ethoxy, propoxy, iso-propoxy or O—$CH_2$-cyclopropyl, O-cyclobutyl, O-cyclopentyl, O-cyclohexyl, O-1-oxacyclobutyl, 0-2-oxacyclobutyl, 1-butoxy, 2-butoxy, 0-tBu, each represents a separate embodiment according to this invention. In other embodiments, $R_2$ is substituted or unsubstituted $C_1$-$C_5$ linear or branched or $C_3$-$C_8$ cyclic alkoxy wherein at least one methylene group (CH) in the alkoxy is replaced with an oxygen atom (0). In some embodiments, $R_2$ is O-1-oxacyclobutyl or O-2-oxacyclobutyl, each represents a separate embodiment according to this invention. In some embodiments, $R_2$ is $C_1$-$C_5$ linear or branched thioalkoxy. In other embodiments, $R_2$ is S—$CH_3$. In some embodiments, $R_2$ is $C_1$-$C_5$ linear or branched haloalkoxy. In some embodiments, $R_2$ is $OCF_3$. In some embodiments, $R_2$ is $OCHF_2$. In some embodiments, $R_2$ is $C_1$-$C_5$ linear or branched alkoxyalkyl. In some embodiments, $R_2$ is substituted or unsubstituted $C_3$-$C_8$ cycloalkyl. In some embodiments, $R_2$ is cyclopropyl. In some embodiments, $R_2$ is cyclopentyl. In some embodiments, $R_2$ is substituted or unsubstituted $C_3$-$C_8$ heterocyclic ring. In some embodiments, $R_2$ is thiophene, oxazole, oxadiazole, imidazole, furane, triazole, tetrazole, pyridine (2, 3, or 4-pyridine), pyrimidine, pyrazine, 1 or 2-oxacyclobutane, indole, protonated or deprotonated pyridine oxide, 3-methyl-4H-1,2,4-triazole, 5-methyl-1,2,4-oxadiazole, each represents a separate embodiment according to this invention. In other embodiments, $R_2$ is 2-methyl-4-pyridine. In other embodiments, $R_2$ is 2,6-dimethyl-4-pyridine. In other embodiments, $R_2$ is 3,5-dimethyl-4-pyridine. In other embodiments, $R_2$ is 2,5-dimethyl-4-pyridine. In other embodiments, $R_2$ is 3-methyl-4-pyridine. In other embodiments, $R_2$ is 5-methyl-2-pyridine. In other embodiments, $R_2$ is 3-methyl-2-pyridine. In other embodiments, $R_2$ is 3-ethyl-2-pyridine. In other embodiments, $R_2$ is 3-isopropyl-2-pyridine. In other embodiments, $R_2$ is 3-propyl-2-pyridine. In other embodiments, $R_2$ is 3-phenyl-2-pyridine. In other embodiments, $R_2$ is 4-methyl-2-pyridine. In other embodiments, $R_2$ is 6-methyl-2-pyridine. In other embodiments, $R_2$ is 5-methyl-2-pyridine. In other embodiments, $R_2$ is pyrimidine. In other embodiments, $R_2$ is 5-methyl-pyrimidine. In other embodiments, $R_2$ is pyrazine. In some embodiments, $R_2$ is methyl substituted oxazole. In some embodiments, $R_2$ is methyl substituted oxadiazole. In some embodiments, $R_2$ is methyl substituted imidazole. In some embodiments, $R_2$ is thiophene. In some embodiments, $R_2$ is triazole. In other embodiments, $R_2$ is tetrazole. In some embodiments, $R_2$ is substituted aryl. In some embodiments, $R_2$ is phenyl. In some embodiments, substitutions include: F, Cl, Br, I, $C_1$-$C_5$ linear or branched alkyl (e.g. methyl, ethyl, propyl, isopropyl), OH, alkoxy, $N(R)_2$, $CF_3$, aryl, phenyl, halophenyl, (benzyloxy)phenyl, CN, $NO_2$ or any combination thereof. In some embodiments, $R_2$ is $CH(CF_3)(NH-R_{10})$. In some embodiments, $R_2$ is 2, 3, or 4 bromophenyl, each represents a separate embodiment according to this invention. In other embodiments, substitutions include: F, Cl, Br, I, $C_1$-$C_5$ linear or branched alkyl (e.g. methyl, ethyl), OH, alkoxy, $N(R)_2$, $CF_3$, aryl, phenyl, halophenyl, (benzyloxy)phenyl, CN, $NO_2$ or any combination thereof; each is a separate embodiment according to this invention.

In some embodiments, $R_1$ and $R_2$ of compound of formula I-V are both H. In some embodiments, at least one of $R_1$ and $R_2$ is not H.

In various embodiments, compound of formula I-V is substituted by $R_3$ and $R_4$. Single substituents can be present at the ortho, meta, or para positions.

In various embodiments, $R_3$ of formula I-V is H. In some embodiments, $R_3$ is F. In some embodiments, $R_3$ is Cl. In some embodiments, $R_3$ is Br. In some embodiments, $R_3$ is I. In some embodiments, $R_3$ is OH. In some embodiments, $R_3$ is SH. In some embodiments, $R_3$ is $R_8$—OH. In some embodiments, $R_3$ is $CH_2$—OH. In some embodiments, $R_3$ is $R_8$—SH. In some embodiments, $R_3$ is —$R_8$—O—$R_{10}$. In some embodiments, $R_3$ is $CH_2$—O—$CH_3$. In other embodiments, $R_3$ is $C_1$-$C_5$ linear or branched haloalkyl. In other embodiments, $R_3$ is $C_2$-$C_5$ linear or branched haloalkyl. In other embodiments, $R_3$ is $C_3$-$C_8$ linear or branched haloalkyl. In other embodiments, $R_3$ is $C_2$-$C_6$ linear or branched haloalkyl. In other embodiments, $R_3$ is $C_2$-$C_7$ linear or branched haloalkyl. In other embodiments, $R_3$ is $CF_2CH_3$. In other embodiments, $R_3$ is $CH_2CF_3$. In other embodiments, $R_3$ is $CF_2CH_2CH_3$. In other embodiments, $R_3$ is $CF_3$. In other embodiments, $R_3$ is $CF_2CH_2CH_3$. In other embodiments, $R_3$ is $CH_2CH_2CF_3$. In other embodiments, $R_3$ is $CF_2CH(CH_3)_2$. In other embodiments, $R_3$ is $CF(CH_3)$—$CH(CH_3)_2$. In other embodiments, $R_3$ is $CD_3$. In other embodiments, $R_3$ is $OCD_3$. In other embodiments, $R_3$ is CN. In some embodiments, $R_3$ is $NO_2$. In some embodiments, $R_3$ is —$CH_2CN$. In some embodiments, $R_3$ is —$R_8CN$. In some embodiments, $R_3$ is $NH_2$. In some embodiments, $R_3$ is NHR. In some embodiments, $R_3$ is $N(R)_2$. In some embodiments, $R_3$ is $R_8$—$N(R_{10})(R_{11})$. In some embodiments, $R_3$ is $CH_2$—$NH_2$. In some embodiments, $R_3$ is $CH_2$—$N(CH_3)_2$. In other embodiments, $R_3$ is $R_9$—$R_8$—$N(R_{10})(R_{11})$. In other embodiments, $R_3$ is C≡C—$CH_2$—$NH_2$. In other embodiments, $R_3$ is $B(OH)_2$. In some embodiments, $R_3$ is —OC(O)$CF_3$. In some embodiments, $R_3$ is —$OCH_2Ph$. In some embodiments, $R_3$ is —NHCO—$R_{10}$. In some embodiments, $R_3$ is $NHC(O)CH_3$). In some embodiments, $R_3$ is NHCO—$N(R_{10})(R_{11})$. In some embodiments, $R_3$ is $NHC(O)N(CH_3)_2$. In other embodiments, $R_3$ is $R_8$—$C(O)N(R_{10})(R_{11})$. In other embodiments, $R_3$ is $CF_2C(O)N[(CH_3)(OCH_3)]$. In some embodiments, $R_3$ is COOH. In some embodiments, $R_3$ is —C(O)Ph. In some embodiments, $R_3$ is $C(O)O$—$R_{10}$. In some embodiments, $R_3$ is $C(O)O$—$CH_3$. In some embodiments, $R_3$ is $C(O)O$—$CH_2CH_3$. In some embodiments, $R_3$ is $R_8$—$C(O)$—$R_{10}$. In some embodiments, $R_3$ is $CH_2C(O)CH_3$. In some embodiments, $R_3$ is C(O)H. In some embodiments, $R_3$ is $C_1$-$C_5$ linear or branched C(O)—$R_{10}$. In some embodiments, $R_3$ is $C(O)$—$CH_3$. In some embodiments, $R_3$ is $C(O)$—$CH_2CH_3$. In some embodiments, $R_3$ is $C(O)$—$CH_2CH_2CH_3$. In some embodiments, $R_3$ is $C_1$-$C_5$ linear or branched C(O)-haloalkyl. In some embodiments, $R_3$ is $C(O)$—$CF_3$. In some embodiments, $R_3$ is —$C(O)NH_2$. In some embodiments, $R_3$ is C(O)NHR. In some embodiments, $R_3$ is $C(O)N(R_{10})(R_{11})$. In some embodiments, $R_3$ is $C(O)N(CH_3)_2$. In some embodiments, $R_3$ is $SO_2R$. In some embodiments, $R_3$ is $SO_2N(R_{10})(R_{11})$. In some embodiments, $R_3$ is $SO_2N(CH_3)_2$. In some embodiments, $R_3$ is substituted or unsubstituted $C_1$-$C_5$ linear or branched or $C_3$-$C_8$ cyclic alkyl. In some embodiments, $R_3$ is methyl, $C(OH)(CH_3)$ (Ph), ethyl, propyl, iso-propyl, t-Bu, iso-butyl, 2-butyl, pentyl, tert-pentyl, 1-ethylcyclopropyl, benzyl or $C(CH_3)(OH)Ph$; each represents a separate embodiment of this invention. In some embodiments, $R_3$ is $C_1$-$C_5$ linear branched or cyclic haloalkyl. In other embodiments, $R_3$ is $CF_3$. In other embodiments, $R_3$ is $CF_2CH_3$. In other embodiments, $R_3$ is $CF_2CH_2CH_3$. In other embodiments, $R_3$ is $CF_2CHFCH_3$. In other embodiments, $R_3$ is $CHFCHFCH_3$, In other embodiments, $R_3$ is $CH_2CH_2CF_3$. In other embodiments, $R_3$ is $CF_2CH(CH_3)_2$. In other embodiments, $R_3$ is $CF(CH_3)$—$CH(CH_3)_2$. In other embodiments, $R_3$ is $CF_2$-cyclopropyl. In other embodiments, $R_3$ is $CF_2$-cyclopentyl. In other embodiments, $R_3$ is substituted or unsubstituted $C_1$-$C_5$ linear or branched or $C_3$-$C_8$ cyclic haloalkenyl. In other embodiments, $R_3$ is CF=CH—$CH_3$ E, Z or combination thereof. In other embodiments, $R_3$ is CF=C—$(CH_3)_2$). In some embodiments, $R_3$ is substituted or unsubstituted $C_1$-$C_5$ linear or branched or $C_3$-$C_8$ cyclic alkoxy. In some embodiments, $R_3$ is methoxy, ethoxy, propoxy, isopropoxy, O—$CH_2$-cyclopropyl; each represents a separate embodiment of this invention. In some embodiments, $R_3$ is $C_1$-$C_5$ linear or branched thioalkoxy. In some embodiments, $R_3$ is $C_1$-$C_5$ linear or branched haloalkoxy. In some embodiments, $R_3$ is $C_1$-$C_5$ linear or branched alkoxyalkyl. In some embodiments, $R_3$ is substituted or unsubstituted $C_3$-$C_8$ cycloalkyl. In some embodiments, $R_3$ is cyclopropyl. In some embodiments, $R_3$ is cyclopentyl. In some embodiments, $R_3$ is substituted or unsubstituted $C_3$-$C_8$ heterocyclic ring. In some embodiments, $R_3$ is thiophene, oxazole, isoxazole, imidazole, furane, pyrrole, 1-methyl-pyrrol, imidazole, 1-methyl-imidazole, triazole, pyridine (2, 3, or 4-pyridine), pyrimidine, pyrazine, oxacyclobutane (1 or 2-oxacyclobutane), indole, 3-methyl-4H-1,2,4-triazole, 5-methyl-1,2,4-oxadiazole; each represents a separate embodiment of this invention. In some embodiments, $R_3$ is substituted or unsubstituted aryl. In some embodiments, $R_3$ is phenyl. In some embodiments, substitutions include: F, Cl, Br, I, $C_1$-$C_5$ linear or branched alkyl, OH, alkoxy, $N(R)_2$, $CF_3$, phenyl, halophenyl, (benzyloxy)phenyl, CN, $NO_2$ or any combination thereof. In some embodiments, $R_3$ is $CH(CF_3)(NH-R_{10})$.

In some embodiments, $R_3$ and $R_4$ are joint together to form a 5 or 6 membered substituted or unsubstituted, aliphatic or aromatic, carbocyclic or heterocyclic ring. In some embodiments, $R_3$ and $R_4$ are joint together to form a 5 or 6 membered carbocyclic ring. In some embodiments, $R_3$ and $R_4$ are joined together to form a 5 or 6 membered heterocyclic ring. In some embodiments, $R_3$ and $R_4$ are joined together to form a dioxole ring. [1,3]dioxole ring. In some embodiments, $R_3$ and $R_4$ are joined together to form a dihydrofuran-2(3H)-one ring. In some embodiments, $R_3$ and $R_4$ are joined together to form a furan-2(3H)-one ring. In some embodiments, $R_3$ and $R_4$ are joined together to form a benzene ring. In some embodiments, $R_3$ and $R_4$ are joint together to form an imidazole ring. In some embodiments, $R_3$ and $R_4$ are joined together to form a pyridine ring. In some embodiments, $R_3$ and $R_4$ are joined together to form a pyrrole ring. In some embodiments, $R_3$ and $R_4$ are joined together to form a cyclohexene ring. In some embodiments, $R_3$ and $R_4$ are joined together to form a cyclopentene ring. In some embodiments, $R_4$ and $R_3$ are joint together to form a dioxepine ring.

In various embodiments, $R_4$ of formula I-IV is H. In some embodiments, $R_4$ is F. In some embodiments, $R_4$ is Cl. In some embodiments, $R_4$ is Br. In some embodiments, $R_4$ is I. In some embodiments, $R_4$ is OH. In some embodiments, $R_4$ is SH. In some embodiments, $R_4$ is $R_8$—OH. In some embodiments, $R_4$ is $CH_2$—OH. In some embodiments, $R_4$ is $R_8$—SH. In some embodiments, $R_4$ is —$R_8$—O—$R_{10}$. In some embodiments, $R_4$ is $CH_2$—O—$CH_3$. In other embodiments, $R_4$ is $CD_3$. In other embodiments, $R_4$ is $OCD_3$. In some embodiments, $R_4$ is CN. In some embodiments, $R_4$ is $NO_2$. In some embodiments, $R_4$ is —$CH_2CN$. In some embodiments, $R_4$ is —$R_8CN$. In some embodiments, $R_4$ is $NH_2$. In some embodiments, $R_4$ is NHR. In some embodiments, $R_4$ is $N(R)_2$. In some embodiments, $R_4$ is $R_8$—$N(R_{10})(R_{11})$. In other embodiments, $R_4$ is $CH_2$—$NH_2$. In some embodiments, $R_4$ is $CH_2$—$N(CH_3)_2$. In other embodiments, $R_4$ is $R_8$—$C(O)N(R_{10})(R_{11})$. In other embodiments, $R_4$ is $CF_2C(O)N[(CH_3)(OCH_3)]$. In other embodiments, $R_4$ is $R_9$—$R_8$—$N(R_{10})(R_{11})$. In other embodiments, $R_4$ is C≡C—$CH_2$—$NH_2$. In other embodiments, $R_4$ is $B(OH)_2$. In some embodiments, $R_4$ is —$OC(O)CF_3$. In some embodiments, $R_4$ is —$OCH_2Ph$. In some embodiments, $R_4$ is —NHCO—$R_{10}$. In some embodiments, $R_4$ is $NHC(O)CH_3$). In some embodiments, $R_4$ is NHCO—$N(R_{10})(R_{11})$. In some embodiments, $R_4$ is $NHC(O)N(CH_3)_2$. In some embodiments, $R_4$ is COOH. In some embodiments, $R_4$ is —C(O)Ph. In some embodiments, $R_4$ is C(O)O—$R_{10}$. In some embodiments, $R_4$ is C(O)O—$CH_3$. In some embodiments, $R_4$ is C(O)O—$CH_2CH_3$. In some embodiments, $R_4$ is $R_8$—C(O)—$R_{10}$. In some embodiments, $R_4$ is $CH_2C(O)CH_3$. In some embodiments, $R_4$ is C(O)H. In some embodiments, $R_4$ is $C_1$-$C_5$ linear or branched C(O)—$R_{10}$. In some embodiments, $R_4$ is C(O)—$CH_3$. In some embodiments, $R_4$ is C(O)—$CH_2CH_3$. In some embodiments, $R_4$ is C(O)—$CH_2CH_2CH_3$. In some embodiments, $R_4$ is $C_1$-$C_5$ linear or branched C(O)-haloalkyl. In some embodiments, $R_4$ is C(O)—$CF_3$. In some embodiments, $R_4$ is —$C(O)NH_2$. In some embodiments, $R_4$ is C(O)NHR. In some embodiments, $R_4$ is $C(O)N(R_{10})(R_1 1)$. In some embodiments, $R_4$ is $C(O)N(CH_3)_2$. In some embodiments, $R_4$ is $SO_2R$. In some embodiments, $R_4$ is $SO_2N(R_{10})(R_{11})$. In some embodiments, $R_4$ is $SO_2N(CH_3)_2$. In some embodiments, $R_4$ is substituted or unsubstituted $C_1$-$C_5$ linear or branched or $C_3$-$C_8$ cyclic alkyl. In some embodiments, $R_4$ is methyl, $C(OH)(CH_3)$(Ph), ethyl, propyl, iso-propyl, t-Bu, iso-butyl, 2-butyl, pentyl, tert-pentyl, 1-ethylcyclopropyl, benzyl or $C(CH_3)(OH)Ph$; each represents a separate embodiment of this invention. In other embodiments, $R_4$ is substituted or unsubstituted $C_1$-$C_5$ linear or branched or $C_3$-$C_8$ cyclic haloalkyl.

In other embodiments, $R_4$ is $C_2$-$C_5$ linear, branched or cyclic haloalkyl. In other embodiments, $R_4$ is $C_2$-$C_6$ linear or branched or cyclic haloalkyl. In other embodiments, $R_4$ is $C_2$-$C_7$ linear, branched or cyclic haloalkyl. In other embodiments, $R_4$ is $C_3$-$C_8$ linear, branched or cyclic haloalkyl. In other embodiments, $R_4$ is $CF_2CH_3$. In other embodiments, $R_4$ is $CH_2CF_3$. In other embodiments, $R_4$ is $CF_2CH_2CH_3$. In other embodiments, $R_4$ is $CF_2CHFCH_3$. In other embodiments, $R_4$ is $CHFCHFCH_3$, In other embodiments, $R_4$ is $CF_3$. In other embodiments, $R_4$ is $CF_2CH_2CH_3$. In other embodiments, $R_4$ is $CH_2CH_2CF_3$. In other embodiments, $R_4$ is $CF_2CH(CH_3)_2$. In other embodiments, $R_4$ is $CF(CH_3)$—$CH(CH_3)_2$. In other embodiments, $R_4$ is $CF_2$-cyclopropyl. In other embodiments, $R_4$ is $CF_2$-cyclopentyl. In other embodiments, $R_4$ is substituted or unsubstituted $C_1$-$C_5$ linear or branched or $C_3$-$C_8$ cyclic haloalkenyl. In other embodiments, $R_4$ is CF═CH—$CH_3$ E, Z or combination thereof. In other embodiments, $R_4$ is CF═C—$(CH_3)_2$). In some embodiments, $R_4$ is substituted or unsubstituted $C_1$-$C_5$ linear or branched or $C_3$-$C_8$ cyclic alkoxy. In some embodiments, $R_4$ is methoxy, ethoxy, propoxy, isopropoxy, O—$CH_2$-cyclopropyl; each represents a separate embodiment of this invention. In some embodiments, $R_4$ is $C_1$-$C_5$ linear or branched thioalkoxy. In some embodiments, $R_4$ is $C_1$-$C_5$ linear or branched haloalkoxy. In some embodiments, $R_4$ is $C_1$-$C_5$ linear or branched alkoxyalkyl. In some embodiments, $R_4$ is substituted or unsubstituted $C_3$-$C_8$ cycloalkyl. In some embodiments, $R_4$ is cyclopropyl. In some embodiments, $R_4$ is cyclopentyl. In some embodiments, $R_4$ is substituted or unsubstituted $C_3$-$C_8$ heterocyclic ring. In some embodiments, $R_4$ is thiophene, oxazole, isoxazole, imidazole, furane, pyrrole, 1-methyl-pyrrol, imidazole, 1-methyl-imidazole, triazole, pyridine (2, 3, or 4-pyridine), pyrimidine, pyrazine, oxacyclobutane (1 or 2-oxacyclobutane), indole, 3-methyl-4H-1,2,4-triazole, 5-methyl-1,2,4-oxadiazole; each represents a separate embodiment of this invention. In some embodiments, $R_4$ is substituted or unsubstituted aryl. In some embodiments, $R_4$ is phenyl. In some embodiments, substitutions include: F, Cl, Br, I, $C_1$-$C_5$ linear or branched alkyl, OH, alkoxy, $N(R)_2$, $CF_3$, aryl, phenyl, halophenyl, (benzyloxy)phenyl, CN, $NO_2$ or any combination thereof. In some embodiments, $R_4$ is $CH(CF_3)(NH$—$R_{10})$.

In some embodiments, $R_3$ and $R_4$ of compound of formula I-V are both H. In some embodiments, at least one of $R_3$ and $R_4$ is not H. In some embodiments, if $R_3$ is H, then $R_4$ is not H. In some embodiments, if $R_4$ is H, then $R_3$ is not H.

In various embodiments, $R_5$ of compound of formula I-IV is H. In some embodiments, $R_5$ is $C_1$-$C_5$ linear or branched, substituted or unsubstituted alkyl. In some embodiments, $R_5$ is methyl, $CH_2SH$, ethyl, iso-propyl; each represent a separate embodiment of this invention. In some embodiments, $R_5$ is $C_1$-$C_5$ linear or branched haloalkyl. In other embodiments, $R_5$ is $CF_2CH_3$. In other embodiments, $R_5$ is $CH_2CF_3$. In other embodiments, $R_5$ is $CF_2CH_2CH_3$. In other embodiments, $R_5$ is $CF_3$. In other embodiments, $R_5$ is $CF_2CH_2CH_3$. In other embodiments, $R_5$ is $CH_2CH_2CF_3$. In other embodiments, $R_5$ is $CF_2CH(CH_3)_2$. In other embodiments, $R_5$ is $CF(CH_3)$—$CH(CH_3)_2$. In some embodiments, $R_5$ is $R_8$-aryl. In some embodiments, $R_5$ is $CH_2$-Ph. In other embodiments, $R_5$ is C(O)—$R_{10}$. In other embodiments, $R_5$ is C(O)—$CH_3$. In some embodiments, $R_5$ is substituted or unsubstituted aryl. In some embodiments, $R_5$ is phenyl. In some embodiments, $R_5$ is substituted or unsubstituted heteroaryl. In some embodiments, $R_5$ is pyridine. In some embodiments, $R_5$ is 2-pyridine. In some embodiments, $R_5$ is 3-pyridine. In some embodiments, $R_5$ is 4-pyridine. In some embodiments, substitutions include: F, Cl, Br, I, $C_1$-$C_5$ linear or branched alkyl, OH, alkoxy, $N(R)_2$, $CF_3$, phenyl, halophenyl, (benzyloxy)phenyl, CN, $NO_2$ or any combination thereof.

In various embodiments, n of compound of formula I-II is 0. In some embodiments, n is 0 or 1. In some embodiments, n is between 1 and 3. In some embodiments, n is between 1 and 4. In some embodiments, n is between 0 and 2. In some embodiments, n is between 0 and 3. In some embodiments, n is between 0 and 4. In some embodiments, n is 1. In some embodiments, n is 2. In some embodiments, n is 3. In some embodiments, n is 4.

In various embodiments, m of compound of formula I-II is 0. In some embodiments, m is 0 or 1. In some embodiments, m is between 1 and 3. In some embodiments, m is between 1 and 4. In some embodiments, m is between 0 and 2. In some embodiments, m is between 0 and 3. In some embodiments, m is between 0 and 4. In some embodiments, m is 1. In some embodiments, m is 2. In some embodiments, m is 3. In some embodiments, m is 4.

In various embodiments, l of compound of formula I-II is 0. In some embodiments, l is 0 or 1. In some embodiments, l is between 1 and 3. In some embodiments, l is between 1 and 4. In some embodiments, l is between 0 and 2. In some embodiments, l is between 0 and 3. In some embodiments, l is between 0 and 4. In some embodiments, l is 1. In some embodiments, l is 2. In some embodiments, l is 3. In some embodiments, l is 4.

In various embodiments, k of compound of formula I-II is 0. In some embodiments, k is 0 or 1. In some embodiments, k is between 1 and 3. In some embodiments, k is between 1 and 4. In some embodiments, k is between 0 and 2. In some embodiments, k is between 0 and 3. In some embodiments, k is between 0 and 4. In some embodiments, k is 1. In some embodiments, k is 2. In some embodiments, k is 3. In some embodiments, k is 4.

It is understood that for heterocyclic rings, n, m, l and/or k are limited to the number of available positions for substitution, i.e. to the number of CH or NH groups minus one. Accordingly, if A and/or B rings are, for example, furanyl, thiophenyl or pyrrolyl, n, m, l and k are between 0 and 2; and if A and/or B rings are, for example, oxazolyl, imidazolyl or thiazolyl, n, m, l and k are either 0 or 1; and if A and/or B rings are, for example, oxadiazolyl or thiadiazolyl, n, m, l and k are 0.

In various embodiments, $R_6$ of compound of formula I-III is H. In some embodiments, $R_6$ is $C_1$-$C_5$ linear or branched alkyl. In some embodiments, $R_6$ is methyl. In some embodiments, $R_6$ is ethyl. In some embodiments, $R_6$ is C(O)R wherein R is $C_1$-$C_5$ linear or branched alkyl, $C_1$-$C_5$ linear or branched alkoxy, phenyl, aryl or heteroaryl. In some embodiments, $R_6$ is $S(O)_2R$ wherein R is $C_1$-$C_5$ linear or branched alkyl, $C_1$-$C_5$ linear or branched alkoxy, phenyl, aryl or heteroaryl.

In various embodiments, $R_8$ of compound of formula I-V is $CH_2$. In some embodiments, $R_8$ is $CH_2CH_2$. In some embodiments, $R_8$ is $CH_2CH_2CH_2$. In some embodiments, $R_8$ is $CH_2CH_2CH_2CH_2$. In other embodiments, $R_8$ is $CF_2$. In other embodiments, $R_8$ is $CF_2CF_2$.

In various embodiments, p is 1. In some embodiments, p is 2. In some embodiments, p is 3. In some embodiments, p is 4. In some embodiments, p is 5. In some embodiments, p is between 1 and 3. In some embodiments, p is between 1 and 5. In some embodiments, p is between 1 and 10.

In some embodiments, $R_9$ of compound of formula I-V is C≡C. In some embodiments, $R_9$ is C≡C—C≡C. In some embodiments, $R_9$ is CH=CH. In some embodiments, $R_9$ is CH=CH—CH=CH.

In some embodiments, q of compound of formula I-V is 2. In some embodiments, q is 4. In some embodiments, q is 6. In some embodiments, q is 8. In some embodiments, q is between 2 and 6.

In various embodiments, $R_{10}$ of compound of formula I-V is H. In some embodiments, $R_{10}$ is $C_1$-$C_5$ linear or branched alkyl. In some embodiments, $R_{10}$ is methyl. In some embodiments, $R_{10}$ is ethyl. In some embodiments, $R_{10}$ is propyl. In some embodiments, $R_{10}$ is isopropyl. In some embodiments, $R_{10}$ is butyl. In some embodiments, $R_{10}$ is isobutyl. In some embodiments, $R_{10}$ is t-butyl. In some embodiments, $R_{10}$ is cyclopropyl. In some embodiments, $R_{10}$ is pentyl. In some embodiments, $R_{10}$ is isopentyl. In some embodiments, $R_{10}$ is neopentyl. In some embodiments, $R_{10}$ is benzyl. In some embodiments, $R_{10}$ is C(O)R. In some embodiments, $R_{10}$ is $S(O)_2R$.

In various embodiments, $R_{11}$ of compound of formula I-V is H. In some embodiments, $R_{11}$ is $C_1$-$C_5$ linear or branched alkyl. In some embodiments, $R_{11}$ is methyl. In some embodiments, $R_{11}$ is ethyl. In some embodiments, $R_{10}$ is propyl. In some embodiments, Ra is isopropyl. In some embodiments, $R_{11}$ is butyl. In some embodiments, $R_{11}$ is isobutyl. In some embodiments, $R_{11}$ is t-butyl. In some embodiments, $R_{11}$ is cyclopropyl. In some embodiments, $R_{11}$ is pentyl. In some embodiments, $R_{11}$ is isopentyl. In some embodiments, $R_{11}$ is neopentyl. In some embodiments, $R_{11}$ is benzyl. In some embodiments, $R_{11}$ is C(O)R. In some embodiments, $R_{11}$ is $S(O)_2R$.

In various embodiments, R of compound of formula I-V is H. In other embodiments, R is $C_1$-$C_5$ linear or branched alkyl. In other embodiments, R is methyl. In other embodiments, R is ethyl. In other embodiments, R is $C_1$-$C_5$ linear or branched alkoxy. In other embodiments, R is phenyl. In other embodiments, R is aryl. In other embodiments, R is toluene. In other embodiments, R is heteroaryl. In other embodiments, two gem R substituents are joint together to form a 5 or 6 membered heterocyclic ring.

In various embodiments, $Q_1$ of compound of formula I-III is O. In other embodiments, $Q_1$ is S. In other embodiments, $Q_1$ is N—OH. In other embodiments, $Q_1$ is $CH_2$. In other embodiments, $Q_1$ is $C(R)_2$. In other embodiments, $Q_1$ is N—OMe.

In various embodiments, $Q_2$ of compound of formula I-III is O. In other embodiments, $Q_2$ is S. In other embodiments, $Q_2$ is N—OH. In other embodiments, $Q_2$ is $CH_2$. In other embodiments, $Q_2$ is $C(R)_2$. In other embodiments, $Q_2$ is N—OMe.

In various embodiments, $X_1$ of compound of formula II is C. In other embodiments, $X_1$ is N.

In various embodiments, $X_2$ of compound of formula II is C. In other embodiments, $X_2$ is N.

In various embodiments, $X_3$ of compound of formula II-V is C. In other embodiments, $X_3$ is N.

In various embodiments, $X_4$ of compound of formula II-IV is C. In other embodiments, $X_4$ is N.

In various embodiments, $X_5$ of compound of formula II is C. In other embodiments, $X_5$ is N.

In various embodiments, $X_6$ of compound of formula II-III is C. In other embodiments, $X_6$ is N.

In various embodiments, $X_7$ of compound of formula II-V is C. In other embodiments, $X_7$ is N.

In various embodiments, $X_8$ of compound of formula II-IV is C. In other embodiments, $X_8$ is N.

In various embodiments, $X_9$ of compound of formula II is C. In other embodiments, $X_9$ is N.

In various embodiments, $X_{10}$ of compound of formula II is C. In other embodiments, $X_{10}$ is N.

As used herein, "single or fused aromatic or heteroaromatic ring systems" can be any such ring, including but not limited to phenyl, naphthyl, pyridinyl, (2-, 3-, and 4-pyridinyl), quinolinyl, pyrimidinyl, pyridazinyl, pyrazinyl, triazinyl, tetrazinyl, thiazolyl, isothiazolyl, oxazolyl, isoxazolyl, imidazolyl, 1-methylimidazole, pyrazolyl, pyrrolyl, furanyl, thiophene-yl, quinolinyl, isoquinolinyl, 2,3-dihydroindenyl, indenyl, tetrahydronaphthyl, 3,4-dihydro-2H-benzo[b][1,4]dioxepine benzodioxolyl, benzo[d][1,3]dioxole, tetrahydronaphthyl, indolyl, 1H-indole, isoindolyl, anthracenyl, benzimidazolyl, 2,3-dihydro-1H-benzo[d]imidazolyl, indazolyl, 2H-indazole, triazolyl, 4,5,6,7-tetrahydro-2H-indazole, 3H-indol-3-one, purinyl, benzoxazolyl, 1,3-benzoxazolyl, benzisoxazolyl, benzothiazolyl, 1,3-benzothiazole, 4,5,6,7-tetrahydro-1,3-benzothiazole, quinazolinyl, quinoxalinyl, 1,2,3,4-tetrahydroquinoxaline, 1-(pyridin-1(2H)-yl)ethanone, cinnolinyl, phthalazinyl, quinolinyl, isoquinolinyl, acridinyl, benzofuranyl, 1-benzofuran, isobenzofuranyl, benzofuran-2(3H)-one, benzothiophenyl, benzoxadiazole, benzo[c][1,2,5]oxadiazolyl, benzo[c]thiophenyl, benzodioxolyl, thiadiazolyl, [1,3]oxazolo[4,5-b]pyridine, oxadiaziolyl, imidazo[2,1-b][1,3]thiazole, 4H,5H,6H-cyclopenta[d][1,3]thiazole, 5H,6H,7H,8H-imidazo[1,2-a]pyridine, 7-oxo-6H,7H-[1,3]thiazolo[4,5-d]pyrimidine, [1,3]thiazolo[5,4-b]pyridine, 2H,3H-imidazo[2,1-b][1,3]thiazole, thieno[3,2-d]pyrimidin-4(3H)-one, 4-oxo-4H-thieno[3,2-d][1,3]thiazin, imidazo[1,2-a]pyridine, 1H-imidazo[4,5-b]pyridine, 1H-imidazo[4,5-c]pyridine, 3H-imidazo[4,5-c]pyridine, pyrazolo[1,5-a]pyridine, imidazo[1,2-a]pyrazine, imidazo[1,2-a]pyrimidine, 1H-pyrrolo[2,3-b]pyridine, pyrido[2,3-b]pyrazine, pyrido[2,3-b]pyrazin-3(4H)-one, 4H-thieno[3,2-b]pyrrole, quinoxalin-2(1H)-one, 1H-pyrrolo[3,2-b]pyridine, 7H-pyrrolo[2,3-d]pyrimidine, oxazolo[5,4-b]pyridine, thiazolo[5,4-b]pyridine, thieno[3,2-c]pyridine, 3-methyl-4H-1,2,4-triazole, 5-methyl-1,2,4-oxadiazole, etc.

As used herein, the term "alkyl" can be any straight- or branched-chain alkyl group containing up to about 30 carbons unless otherwise specified. In various embodiments, an alkyl includes $C_1$-$C_5$ carbons. In some embodiments, an alkyl includes $C_1$-$C_6$ carbons. In some embodiments, an alkyl includes $C_1$-$C_8$ carbons. In some embodiments, an alkyl includes $C_1$-$C_{10}$ carbons. In some embodiments, an alkyl is a $C_1$-$C_{12}$ carbons. In some embodiments, an alkyl is a $C_1$-$C_{20}$ carbons. In some embodiments, branched alkyl is an alkyl substituted by alkyl side chains of 1 to 5 carbons. In various embodiments, the alkyl group may be unsubstituted. In some embodiments, the alkyl group may be substituted by a halogen, haloalkyl, hydroxyl, alkoxy, carbonyl, amido, alkylamido, dialkylamido, cyano, nitro, $CO_2H$, amino, alkylamino, dialkylamino, carboxyl, thio, thioalkyl, $C_1$-$C_5$ linear or branched haloalkoxy, $CF_3$, phenyl, halophenyl, (benzyloxy)phenyl, —$CH_2CN$, $NH_2$, NH-alkyl, N(alkyl)$_2$, —OC(O)CF$_3$, —OCH$_2$Ph, —NHCO-alkyl, —C(O)Ph, C(O)O-alkyl, C(O)H, —C(O)NH$_2$ or any combination thereof.

The alkyl group can be a sole substituent or it can be a component of a larger substituent, such as in an alkoxy, alkoxyalkyl, haloalkyl, arylalkyl, alkylamino, dialkylamino, alkylamido, alkylurea, etc. Preferred alkyl groups are methyl, ethyl, and propyl, and thus halomethyl, dihalomethyl, trihalomethyl, haloethyl, dihaloethyl, trihaloethyl, halopropyl, dihalopropyl, trihalopropyl, methoxy, ethoxy, propoxy, arylmethyl, arylethyl, arylpropyl, methylamino, ethylamino, propylamino, dimethylamino, diethylamino, methylamido, acetamido, propylamido, halomethylamido, haloethylamido, halopropylamido, methyl-urea, ethyl-urea, propyl-urea, 2, 3, or 4-CH$_2$—C$_6$H$_4$—Cl, C(OH)(CH$_3$)(Ph), etc.

As used herein, the term "alkenyl" can be any straight- or branched-chain alkenyl group containing up to about 30 carbons as defined hereinabove for the term "alkyl" and at least one carbon-carbon double bond. Accordingly, the term alkenyl as defined herein includes also alkadienes, alkatrienes, alkatetraenes, and so on. In some embodiments, the alkenyl group contains one carbon-carbon double bond. In some embodiments, the alkenyl group contains two, three, four, five, six, seven or eight carbon-carbon double bonds; each represents a separate embodiment according to this invention. Non limiting examples of alkenyl groups include: Ethenyl, Propenyl, Butenyl (i.e., 1-Butenyl, trans-2-Butenyl, cis-2-Butenyl, and Isobutylenyl), Pentene (i.e., 1-Pentenyl, cis-2-Pentenyl, and trans-2-Pentenyl), Hexene (e.g., 1-Hexenyl, (E)-2-Hexenyl, (Z)-2-Hexenyl, (E)-3-Hexenyl, (Z)-3-Hexenyl, 2-Methyl-1-Pentene, etc.), which may all be substituted as defined herein above for the term "alkyl".

As used herein, the term "alkynyl" can be any straight- or branched-chain alkynyl group containing up to about 30 carbons as defined hereinabove for the term "alkyl" and at least one carbon-carbon triple bond. Accordingly, the term alkynyl as defined herein includes also alkadiynes, alkatriynes, alkatetraynes, and so on. In some embodiments, the alkynyl group contains one carbon-carbon triple bond. In some embodiments, the alkynyl group contains two, three, four, five, six, seven or eight carbon-carbon triple bonds; each represents a separate embodiment according to this invention. Non limiting examples of alkynyl groups include: acetylenyl, Propynyl, Butynyl (i.e., 1-Butynyl, 2-Butynyl, and Isobutylynyl), Pentyne (i.e., 1-Pentynyl, 2-Pentenyl), Hexyne (e.g., 1-Hexynyl, 2-Hexeynyl, 3-Hexynyl, etc.), which may all be substituted as defined herein above for the term "alkyl".

As used herein, the term "aryl" refers to any aromatic ring that is directly bonded to another group and can be either substituted or unsubstituted. The aryl group can be a sole substituent, or the aryl group can be a component of a larger substituent, such as in an arylalkyl, arylamino, arylamido, etc. Exemplary aryl groups include, without limitation, phenyl, tolyl, xylyl, furanyl, naphthyl, pyridinyl, pyrimidinyl, pyridazinyl, pyrazinyl, triazinyl, thiazolyl, oxazolyl, isooxazolyl, pyrazolyl, imidazolyl, thiophene-yl, pyrrolyl, indolyl, phenylmethyl, phenylethyl, phenylamino, phenylamido, 3-methyl-4H-1,2,4-triazolyl, 5-methyl-1,2,4-oxadiazolyl, etc. Substitutions include but are not limited to: F, Cl, Br, I, $C_1$-$C_5$ linear or branched alkyl, $C_1$-$C_5$ linear or branched haloalkyl, $C_1$-$C_5$ linear or branched alkoxy, $C_1$-$C_5$ linear or branched haloalkoxy, $CF_3$, phenyl, halophenyl, (benzyloxy)phenyl, CN, $NO_2$, —$CH_2CN$, $NH_2$, NH-alkyl, N(alkyl)$_2$, hydroxyl, —OC(O)CF$_3$, —OCH$_2$Ph, —NHCO-alkyl, COOH, —C(O)Ph, C(O)O— alkyl, C(O)H, —C(O)NH$_2$ or any combination thereof.

As used herein, the term "alkoxy" refers to an ether group substituted by an alkyl group as defined above. Alkoxy refers both to linear and to branched alkoxy groups. Non-limiting examples of alkoxy groups are methoxy, ethoxy, propoxy, iso-propoxy, tert-butoxy.

As used herein, the term "aminoalkyl" refers to an amine group substituted by an alkyl group as defined above. Aminoalkyl refers to monoalkylamine, dialkylamine or trialkylamine. Nonlimiting examples of aminoalkyl groups are —N(Me)$_2$, —NHMe, —NH$_3$.

A "haloalkyl" group refers, in some embodiments, to an alkyl group as defined above, which is substituted by one or more halogen atoms, e.g. by F, Cl, Br or I. The term "haloalkyl" include but is not limited to fluoroalkyl, i.e., to an alkyl group bearing at least one fluorine atom. Nonlimiting examples of haloalkyl groups are $CF_3$, $CF_2CF_3$, $CF_2CH_3$, $CH_2CF_3$, $CF_2CH_2CH_3$, $CH_2CH_2CF_3$, $CF_2CH(CH_3)_2$ and $CF(CH_3)$—$CH(CH_3)_2$.

A "haloalkenyl" group refers, in some embodiments, to an alkenyl group as defined above, which is substituted by one or more halogen atoms, e.g. by F, Cl, Br or I. The term "haloalkenyl" include but is not limited to fluoroalkenyl, i.e., to an alkenyl group bearing at least one fluorine atom, as well as their respective isomers if applicable (i.e., E, Z and/or cis and trans). Nonlimiting examples of haloalkenyl groups are $CFCF_2$, $CF=CH$—$CH_3$, $CFCH_2$, $CHCF_2$, $CFCHCH_3$, $CHCHCF_3$, and $CF=C$—$(CH_3)_2$ (both E and Z isomers where applicable).

A "halophenyl" group refers, in some embodiments, to a phenyl substitutent which is substituted by one or more halogen atoms, e.g. by F, Cl, Br or I. In one embodiment, the halophenyl is 4-chlorophenyl.

An "alkoxyalkyl" group refers, in some embodiments, to an alkyl group as defined above, which is substituted by alkoxy group as defined above, e.g. by methoxy, ethoxy, propoxy, i-propoxy, t-butoxy etc. Nonlimiting examples of alkoxyalkyl groups are —$CH_2$—O—$CH_3$, —$CH_2$—O—$CH(CH_3)_2$, —$CH_2$—O—$C(CH_3)_3$, —$CH_2$—$CH_2$—O—$CH_3$, —$CH_2$—$CH_2$—O—$CH(CH_3)_2$, —$CH_2$—$CH_2$—O—$C(CH_3)_3$.

A "cycloalkyl" or "carbocyclic" group refers, In various embodiments, to a ring structure comprising carbon atoms as ring atoms, which may be either saturated or unsaturated, substituted or unsubstituted, single or fused. In some embodiments the cycloalkyl is a 3-10 membered ring. In some embodiments the cycloalkyl is a 3-12 membered ring. In some embodiments the cycloalkyl is a 6 membered ring. In some embodiments the cycloalkyl is a 5-7 membered ring. In some embodiments the cycloalkyl is a 3-8 membered ring. In some embodiments, the cycloalkyl group may be unsubstituted or substituted by a halogen, alkyl, haloalkyl, hydroxyl, alkoxy, carbonyl, amido, alkylamido, dialkylamido, cyano, nitro, $CO_2H$, amino, alkylamino, dialkylamino, carboxyl, thio, thioalkyl, $C_1$-$C_5$ linear or branched haloalkoxy, $CF_3$, phenyl, halophenyl, (benzyloxy)phenyl, —$CH_2CN$, $NH_2$, NH-alkyl, $N(alkyl)_2$, —$OC(O)CF_3$, —$OCH_2Ph$, —NHCO-alkyl, —$C(O)Ph$, $C(O)O$-alkyl, $C(O)H$, —$C(O)NH_2$ or any combination thereof. In some embodiments, the cycloalkyl ring may be fused to another saturated or unsaturated cycloalkyl or heterocyclic 3-8 membered ring. In some embodiments, the cycloalkyl ring is a saturated ring. In some embodiments, the cycloalkyl ring is an unsaturated ring. Non limiting examples of a cycloalkyl group comprise cyclohexyl, cyclohexenyl, cyclopropyl, cyclopropenyl, cyclopentyl, cyclopentenyl, cyclobutyl, cyclobutenyl, cyclooctyl, cyclooctadienyl (COD), cyclooctaene (COE) etc.

A "heterocycle" or "heterocyclic" group refers, in various embodiments, to a ring structure comprising in addition to carbon atoms, sulfur, oxygen, nitrogen or any combination thereof, as part of the ring. A "heteroaromatic ring" refers in various embodiments, to an aromatic ring structure comprising in addition to carbon atoms, sulfur, oxygen, nitrogen or any combination thereof, as part of the ring. In some embodiments the heterocycle or heteroaromatic ring is a 3-10 membered ring. In some embodiments the heterocycle or heteroaromatic ring is a 3-12 membered ring. In some embodiments the heterocycle or heteroaromatic ring is a 6 membered ring. In some embodiments the heterocycle or heteroaromatic ring is a 5-7 membered ring. In some embodiments the heterocycle or heteroaromatic ring is a 3-8 membered ring. In some embodiments, the heterocycle group or heteroaromatic ring may be unsubstituted or substituted by a halogen, alkyl, haloalkyl, hydroxyl, alkoxy, carbonyl, amido, alkylamido, dialkylamido, cyano, nitro, $CO_2H$, amino, alkylamino, dialkylamino, carboxyl, thio, thioalkyl, $C_1$-$C_5$ linear or branched haloalkoxy, $CF_3$, phenyl, halophenyl, (benzyloxy)phenyl, —$CH_2CN$, $NH_2$, NH-alkyl, $N(alkyl)_2$, —$OC(O)CF_3$, —$OCH_2Ph$, —NHCO-alkyl, —$C(O)Ph$, $C(O)O$-alkyl, $C(O)H$, —$C(O)NH_2$ or any combination thereof. In some embodiments, the heterocycle ring or heteroaromatic ring may be fused to another saturated or unsaturated cycloalkyl or heterocyclic 3-8 membered ring. In some embodiments, the heterocyclic ring is a saturated ring. In some embodiments, the heterocyclic ring is an unsaturated ring. Non limiting examples of a heterocyclic ring or heteroaromatic ring systems comprise pyridine, piperidine, morpholine, piperazine, thiophene, pyrrole, benzodioxole, benzofuran-2(3H)-one, benzo[d][1,3]dioxole, indole, oxazole, isoxazole, imidazole and 1-methylimidazole, furane, triazole, pyrimidine, pyrazine, oxacyclobutane (1 or 2-oxacyclobutane), naphthalene, tetrahydrothiophene 1,1-dioxide, thiazole, benzimidazole, piperidine, 1-methylpiperidine, isoquinoline, 1,3-dihydroisobenzofuran, benzofuran, 3-methyl-4H-1,2,4-triazole, 5-methyl-1,2,4-oxadiazole, or indole.

In various embodiments, this invention provides a compound of this invention or its isomer, metabolite, pharmaceutically acceptable salt, pharmaceutical product, tautomer, hydrate, N-oxide, reverse amide analog, prodrug, isotopic variant (deuterated analog), PROTAC, polymorph, or crystal or combinations thereof. In various embodiments, this invention provides an isomer of the compound of this invention. In some embodiments, this invention provides a metabolite of the compound of this invention. In some embodiments, this invention provides a pharmaceutically acceptable salt of the compound of this invention. In some embodiments, this invention provides a pharmaceutical product of the compound of this invention. In some embodiments, this invention provides a tautomer of the compound of this invention. In some embodiments, this invention provides a hydrate of the compound of this invention. In some embodiments, this invention provides an N-oxide of the compound of this invention. In some embodiments, this invention provides a reverse amide analog of the compound of this invention. In some embodiments, this invention provides a prodrug of the compound of this invention. In some embodiments, this invention provides an isotopic variant (including but not limited to deuterated analog) of the compound of this invention. In some embodiments, this invention provides a PROTAC (Proteolysis targeting chimera) of the compound of this invention. In some embodiments, this invention provides a polymorph of the compound of this invention. In some embodiments, this invention provides a crystal of the compound of this invention. In some embodiments, this invention provides composition comprising a compound of this invention, as described herein, or, In some embodiments, a combination of an isomer, metabolite, pharmaceutically acceptable salt, pharmaceutical product, tautomer, hydrate, N-oxide, reverse amide analog, prodrug, isotopic variant (deuterated analog), PROTAC, polymorph, or crystal of the compound of this invention. In another embodiment, compounds 378-382 of this invention are non limiting examples of PROTAC compounds. In another embodiment, compounds 378-382 of this invention are designed to be heterodimeric degrading compounds.

In various embodiments, the term "isomer" includes, but is not limited to, stereoisomers including optical isomers and analogs, structural isomers and analogs, conformational isomers and analogs, and the like. In some embodiments, the isomer is a stereoisomer. In another embodiment, the isomer is an optical isomer.

Certain compounds of the present invention may exist in particular geometric or stereoisomeric forms. The present invention contemplates all such compounds, including cis- and trans-isomers, R- and S-enantiomers, diastereomers, the racemic mixtures thereof, and other mixtures thereof, as falling within the scope of the invention. Additional asymmetric carbon atoms may be present in a substituent such as an alkyl group. All such isomers, as well as mixtures thereof, are included in this invention.

In various embodiments, this invention encompasses the use of various stereoisomers of the compounds of the invention. It will be appreciated by those skilled in the art that the compounds of the present invention may contain at least one chiral center. Accordingly, the compounds used in the methods of the present invention may exist in, and be isolated in, optically-active or racemic forms. The compounds according to this invention may further exist as stereoisomers which may be also optically-active isomers (e.g., enantiomers such as (R) or (S)), as enantiomerically enriched mixtures, racemic mixtures, or as single diastereomers, diastereomeric mixtures, or any other stereoisomers, including but not limited to: (R)(R), (R)(S), (S)(S), (S)(R), (R)(R)(R), (R)(R)(S), (R)(S)(R), (S)(R)(R), (R)(S)(S), (S)(R)(S), (S)(S)(R) or (S)(S)(S) stereoisomers. Some compounds may also exhibit polymorphism. It is to be understood that the present invention encompasses any racemic, optically-active, polymorphic, or sterereoisomeric form, or mixtures thereof, which form possesses properties useful in the treatment of the various conditions described herein.

It is well known in the art how to prepare optically-active forms (for example, by resolution of the racemic form by recrystallization techniques, by synthesis from optically-active starting materials, by chiral synthesis, or by chromatographic separation using a chiral stationary phase).

The compounds of the present invention can also be present in the form of a racemic mixture, containing substantially equivalent amounts of stereoisomers. In some embodiments, the compounds of the present invention can be prepared or otherwise isolated, using known procedures, to obtain a stereoisomer substantially free of its corresponding stereoisomer (i.e., substantially pure). By substantially pure, it is intended that a stereoisomer is at least about 95% pure, more preferably at least about 98% pure, most preferably at least about 99% pure.

Compounds of the present invention can also be in the form of a hydrate, which means that the compound further includes a stoichiometric or non-stoichiometric amount of water bound by non-covalent intermolecular forces.

As used herein, when some chemical functional group (e.g. alkyl or aryl) is said to be "substituted", it is herein defined that one or more substitutions are possible.

Compounds of the present invention may exist in the form of one or more of the possible tautomers and depending on the particular conditions it may be possible to separate some or all of the tautomers into individual and distinct entities. It is to be understood that all of the possible tautomers, including all additional enol and keto tautomers and/or isomers are hereby covered. For example the following tautomers, but not limited to these, are included:

Tautomerization of the Imidazole Ring

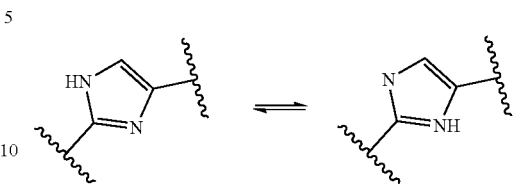

Tautomerization of the Pyrazolone Ring:

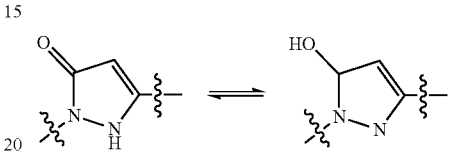

The invention includes "pharmaceutically acceptable salts" of the compounds of this invention, which may be produced, by reaction of a compound of this invention with an acid or base. Certain compounds, particularly those possessing acid or basic groups, can also be in the form of a salt, preferably a pharmaceutically acceptable salt. The term "pharmaceutically acceptable salt" refers to those salts that retain the biological effectiveness and properties of the free bases or free acids, which are not biologically or otherwise undesirable. The salts are formed with inorganic acids such as hydrochloric acid, hydrobromic acid, sulfuric acid, nitric acid, phosphoric acid and the like, and organic acids such as acetic acid, propionic acid, glycolic acid, pyruvic acid, oxylic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, N-acetylcysteine and the like. Other salts are known to those of skill in the art and can readily be adapted for use in accordance with the present invention.

Suitable pharmaceutically-acceptable salts of amines of compounds of this invention may be prepared from an inorganic acid or from an organic acid. In various embodiments, examples of inorganic salts of amines are bisulfates, borates, bromides, chlorides, hemisulfates, hydrobromates, hydrochlorates, 2-hydroxyethylsulfonates (hydroxyethanesulfonates), iodates, iodides, isothionates, nitrates, persulfates, phosphate, sulfates, sulfamates, sulfanilates, sulfonic acids (alkylsulfonates, arylsulfonates, halogen substituted alkylsulfonates, halogen substituted arylsulfonates), sulfonates and thiocyanates.

In various embodiments, examples of organic salts of amines may be selected from aliphatic, cycloaliphatic, aromatic, araliphatic, heterocyclic, carboxylic and sulfonic classes of organic acids, examples of which are acetates, arginines, aspartates, ascorbates, adipates, anthranilates, algenates, alkane carboxylates, substituted alkane carboxylates, alginates, benzenesulfonates, benzoates, bisulfates, butyrates, bicarbonates, bitartrates, citrates, camphorates, camphorsulfonates, cyclohexylsulfamates, cyclopentanepropionates, calcium edetates, camsylates, carbonates, clavulanates, cinnamates, dicarboxylates, digluconates, dodecylsulfonates, dihydrochlorides, decanoates, enanthuates, ethanesulfonates, edetates, edisylates, estolates, esylates, fumarates, formates, fluorides, galacturonates gluconates, glutamates, glycolates, glucorate, glucoheptanoates, glycerophosphates, gluceptates, glycollylarsanilates, glutarates, glutamate, heptanoates, hexanoates, hydroxymaleates, hydroxycarboxlic acids, hexylresorcinates, hydroxybenzoates, hydroxynaphthoates, hydrofluorates, lactates, lactobionates, laurates, malates, maleates, methylenebis(beta-oxynaphthoate), malonates, mandelates, mesylates, methane sulfonates, methylbromides, methylnitrates, methylsulfonates, monopotassium maleates, mucates, monocarboxylates, naphthalenesulfonates, 2-naphthalenesulfonates, nicotinates, nitrates, napsylates, N-methylglucamines, oxalates, octanoates, oleates, pamoates, phenylacetates, picrates, phenylbenzoates, pivalates, propionates, phthalates, phenylacetate, pectinates, phenylpropionates, palmitates, pantothenates, polygalacturates, pyruvates, quinates, salicylates, succinates, stearates, sulfanilate, subacetates, tartrates, theophyllineacetates, p-toluenesulfonates (tosylates), trifluoroacetates, terephthalates, tannates, teoclates, trihaloacetates, triethiodide, tricarboxylates, undecanoates and valerates.

In various embodiments, examples of inorganic salts of carboxylic acids or hydroxyls may be selected from ammonium, alkali metals to include lithium, sodium, potassium, cesium; alkaline earth metals to include calcium, magnesium, aluminium; zinc, barium, cholines, quaternary ammoniums.

In some embodiments, examples of organic salts of carboxylic acids or hydroxyl may be selected from arginine, organic amines to include aliphatic organic amines, alicyclic organic amines, aromatic organic amines, benzathines, t-butylamines, benethamines (N-benzylphenethylamine), dicyclohexylamines, dimethylamines, diethanolamines, ethanolamines, ethylenediamines, hydrabamines, imidazoles, lysines, methylamines, meglamines, N-methyl-D-glucamines, N,N'-dibenzylethylenediamines, nicotinamides, organic amines, ornithines, pyridines, picolies, piperazines, procain, tris(hydroxymethyl)methylamines, triethylamines, triethanolamines, trimethylamines, tromethamines and ureas.

In various embodiments, the salts may be formed by conventional means, such as by reacting the free base or free acid form of the product with one or more equivalents of the appropriate acid or base in a solvent or medium in which the salt is insoluble or in a solvent such as water, which is removed in vacuo or by freeze drying or by exchanging the ions of a existing salt for another ion or suitable ion-exchange resin.

Pharmaceutical Composition

Another aspect of the present invention relates to a pharmaceutical composition including a pharmaceutically acceptable carrier and a compound according to the aspects of the present invention. The pharmaceutical composition can contain one or more of the above-identified compounds of the present invention. Typically, the pharmaceutical composition of the present invention will include a compound of the present invention or its pharmaceutically acceptable salt, as well as a pharmaceutically acceptable carrier. The term "pharmaceutically acceptable carrier" refers to any suitable adjuvants, carriers, excipients, or stabilizers, and can be in solid or liquid form such as, tablets, capsules, powders, solutions, suspensions, or emulsions.

Typically, the composition will contain from about 0.01 to 99 percent, preferably from about 20 to 75 percent of active compound(s), together with the adjuvants, carriers and/or excipients. While individual needs may vary, determination of optimal ranges of effective amounts of each component is within the skill of the art. Typical dosages comprise about 0.01 to about 100 mg/kg body wt. The preferred dosages comprise about 0.1 to about 100 mg/kg body wt. The most preferred dosages comprise about 1 to about 100 mg/kg body wt. Treatment regimen for the administration of the compounds of the present invention can also be determined readily by those with ordinary skill in art. That is, the frequency of administration and size of the dose can be established by routine optimization, preferably while minimizing any side effects.

The solid unit dosage forms can be of the conventional type. The solid form can be a capsule and the like, such as an ordinary gelatin type containing the compounds of the present invention and a carrier, for example, lubricants and inert fillers such as, lactose, sucrose, or cornstarch. In some embodiments, these compounds are tabulated with conventional tablet bases such as lactose, sucrose, or cornstarch in combination with binders like acacia, cornstarch, or gelatin, disintegrating agents, such as cornstarch, potato starch, or alginic acid, and a lubricant, like stearic acid or magnesium stearate.

The tablets, capsules, and the like can also contain a binder such as gum tragacanth, acacia, corn starch, or gelatin; excipients such as dicalcium phosphate; a disintegrating agent such as corn starch, potato starch, alginic acid; a lubricant such as magnesium stearate; and a sweetening agent such as sucrose, lactose, or saccharin. When the dosage unit form is a capsule, it can contain, in addition to materials of the above type, a liquid carrier such as a fatty oil.

Various other materials may be present as coatings or to modify the physical form of the dosage unit. For instance, tablets can be coated with shellac, sugar, or both. A syrup can contain, in addition to active ingredient, sucrose as a sweetening agent, methyl and propylparabens as preservatives, a dye, and flavoring such as cherry or orange flavor.

For oral therapeutic administration, these active compounds can be incorporated with excipients and used in the form of tablets, capsules, elixirs, suspensions, syrups, and the like. Such compositions and preparations should contain at least 0.1% of active compound. The percentage of the compound in these compositions can, of course, be varied and can conveniently be between about 2% to about 60% of the weight of the unit. The amount of active compound in such therapeutically useful compositions is such that a suitable dosage will be obtained. Preferred compositions according to the present invention are prepared so that an oral dosage unit contains between about 1 mg and 800 mg of active compound.

The active compounds of the present invention may be orally administered, for example, with an inert diluent, or with an assimilable edible carrier, or they can be enclosed in hard or soft shell capsules, or they can be compressed into tablets, or they can be incorporated directly with the food of the diet.

The pharmaceutical forms suitable for injectable use include sterile aqueous solutions or dispersions and sterile powders for the extemporaneous preparation of sterile injectable solutions or dispersions. In all cases, the form should be sterile and should be fluid to the extent that easy syringability exists. It should be stable under the conditions of manufacture and storage and should be preserved against the contaminating action of microorganisms, such as bacteria and fungi. The carrier can be a solvent or dispersion medium containing, for example, water, ethanol, polyol (e.g., glycerol, propylene glycol, and liquid polyethylene glycol), suitable mixtures thereof, and vegetable oils.

The compounds or pharmaceutical compositions of the present invention may also be administered in injectable dosages by solution or suspension of these materials in a physiologically acceptable diluent with a pharmaceutical adjuvant, carrier or excipient. Such adjuvants, carriers and/or excipients include, but are not limited to, sterile liquids, such as water and oils, with or without the addition of a surfactant and other pharmaceutically and physiologically acceptable components. Illustrative oils are those of petroleum, animal, vegetable, or synthetic origin, for example, peanut oil, soybean oil, or mineral oil. In general, water, saline, aqueous dextrose and related sugar solution, and glycols, such as propylene glycol or polyethylene glycol, are preferred liquid carriers, particularly for injectable solutions.

These active compounds may also be administered parenterally. Solutions or suspensions of these active compounds can be prepared in water suitably mixed with a surfactant such as hydroxypropylcellulose. Dispersions can also be prepared in glycerol, liquid polyethylene glycols, and mixtures thereof in oils. Illustrative oils are those of petroleum, animal, vegetable, or synthetic origin, for example, peanut oil, soybean oil, or mineral oil. In general, water, saline, aqueous dextrose and related sugar solution, and glycols such as, propylene glycol or polyethylene glycol, are preferred liquid carriers, particularly for injectable solutions. Under ordinary conditions of storage and use, these preparations contain a preservative to prevent the growth of microorganisms.

For use as aerosols, the compounds of the present invention in solution or suspension may be packaged in a pressurized aerosol container together with suitable propellants, for example, hydrocarbon propellants like propane, butane, or isobutane with conventional adjuvants. The materials of the present invention also may be administered in a nonpressurized form such as in a nebulizer or atomizer.

In various embodiments, the compounds of this invention are administered in combination with an anti-cancer agent. In various embodiments, the anti-cancer agent is a monoclonal antibody. In some embodiments, the monoclonal antibodies are used for diagnosis, monitoring, or treatment of cancer. In various embodiments, monoclonal antibodies react against specific antigens on cancer cells. In various embodiments, the monoclonal antibody acts as a cancer cell receptor antagonist. In various embodiments, monoclonal antibodies enhance the patient's immune response. In various embodiments, monoclonal antibodies act against cell growth factors, thus blocking cancer cell growth. In various embodiments, anti-cancer monoclonal antibodies are conjugated or linked to anti-cancer drugs, radioisotopes, other biologic response modifiers, other toxins, or a combination thereof. In various embodiments, anti-cancer monoclonal antibodies are conjugated or linked to a compound of this invention as described hereinabove.

In various embodiments, the compounds of this invention are administered in combination with an agent treating Alzheimer's disease.

In various embodiments, the compounds of this invention are administered in combination with an anti-viral agent.

In various embodiments, the compounds of this invention are administered in combination with at least one of the following: chemotherapy, molecularly-targeted therapies, DNA damaging agents, hypoxia-inducing agents, or immunotherapy, each possibility represents a separate embodiment of this invention.

Yet another aspect of the present invention relates to a method of treating cancer that includes selecting a subject in need of treatment for cancer and administering to the subject a pharmaceutical composition comprising a compound according to the first aspect of the present invention and a pharmaceutically acceptable carrier under conditions effective to treat cancer.

When administering the compounds of the present invention, they can be administered systemically or, alternatively, they can be administered directly to a specific site where cancer cells or precancerous cells are present. Thus, administering can be accomplished in any manner effective for delivering the compounds or the pharmaceutical compositions to the cancer cells or precancerous cells. Exemplary modes of administration include, without limitation, administering the compounds or compositions orally, topically, transdermally, parenterally, subcutaneously, intravenously, intramuscularly, intraperitoneally, by intranasal instillation, by intracavitary or intravesical instillation, intraocularly, intraarterially, intralesionally, or by application to mucous membranes, such as, that of the nose, throat, and bronchial tubes.

Biological Activity

In various embodiments, the invention provides compounds and compositions, including any embodiment described herein, for use in any of the methods of this invention. In various embodiments, use of a compound of this invention or a composition comprising the same, will have utility in inhibiting, suppressing, enhancing or stimulating a desired response in a subject, as will be understood by one skilled in the art. In some embodiments, the compositions may further comprise additional active ingredients, whose activity is useful for the particular application for which the compound of this invention is being administered.

Acetate is an important source of acetyl-CoA in hypoxia. Inhibition of acetate metabolism may impair tumor growth. The nucleocytosolic acetyl-CoA synthetase enzyme, ACSS2, supplies a key source of acetyl-CoA for tumors by capturing acetate as a carbon source. Despite exhibiting no gross deficits in growth or development, adult mice lacking ACSS2 exhibit a significant reduction in tumor burden in two different models of hepatocellular carcinoma. ACSS2 is expressed in a large proportion of human tumors, and its activity is responsible for the majority of cellular acetate uptake into both lipids and histones. Further, ACSS2 was identified in an unbiased functional genomic screen as a critical enzyme for the growth and survival of breast and prostate cancer cells cultured in hypoxia and low serum. Indeed, high expression of ACSS2 is frequently found in invasive ductal carcinomas of the breast, triple-negative breast cancer, glioblastoma, ovarian cancer, pancreatic cancer and lung cancer, and often directly correlates with higher-grade tumors and poorer survival compared with tumors that have low ACSS2 expression. These observations may qualify ACSS2 as a targetable metabolic vulnerability of a wide spectrum of tumors.

Therefore, in various embodiments, this invention is directed to a method of treating, suppressing, reducing the severity, reducing the risk of developing or inhibiting cancer comprising administering a compound of this invention to a subject suffering from cancer under conditions effective to treat, suppress, reduce the severity, reduce the risk of developing, or inhibit the cancer. In some embodiments, the compound is an ACSS2 inhibitor. In some embodiments, the compound is selective to ACSS2. In some embodiments, the compound is selective to ACSS1. In some embodiments, the compound is selective to both ACSS2 and ACSS1. In some embodiments, the compound is selective to ACSS2, ACSS1, AACS, ACSF2 and ACSL5. In some embodiments, the cancer is early cancer. In some embodiments, the cancer is advanced cancer. In some embodiments, the cancer is invasive cancer. In some embodiments, the cancer is metastatic cancer. In some embodiments, the cancer is drug resistant cancer. In some embodiments, the cancer is selected from the list presented below:

---

Cancer, bladder (urothelial carcinoma)
Myelodysplasia
Cancer, breast (inflammatory)
Cancer, cervix
Cancer, endometrium
Cancer, esophagus
Cancer, head and neck (squamous cell carcinoma)
Cancer, kidney (renal cell carcinoma)
Cancer, kidney (renal cell carcinoma, clear cell)
Cancer, liver (hepatocellular carcinoma)
Cancer, lung (non-small cell) (NSCLC)
Cancer, metastatic (to brain)
Cancer, nasopharynx
Cancer, solid tumor
Cancer, stomach
Carcinoma, adrenocortical
Glioblastoma multiforme
Leukemia, acute myeloid
Leukemia, chronic lymphocytic
Lymphoma, Hodgkin's (classical)
Lymphoma, diffuse large B-cell
Lymphoma, primary central nervous system
Melanoma, malignant
Melanoma, uveal
Meningioma
Multiple myeloma
Cancer, breast
Cancer
Cancer, anus
Cancer, anus (squamous cell)
Cancer, biliary
Cancer, bladder, muscle invasive urothelial carcinoma
Cancer, breast metastatic
Cancer, colorectal
Cancer, colorectal metastatic
Cancer, fallopian tube
Cancer, gastroesophageal junction
Cancer, gastroesophageal junction (adenocarcinoma)
Cancer, larynx (squamous cell)
Cancer, lung (non-small cell) (NSCLC) (squamous cell carcinoma)
Cancer, lung (non-small cell) (NSCLC) metastatic
Cancer, lung (small cell) (SCLC)
Cancer, lung (small cell) (SCLC) (extensive)
Cancer, merkel cell
Cancer, mouth
Cancer, ovary
Cancer, ovary (epithelial)
Cancer, pancreas
Cancer, pancreas (adenocarcinoma)
Cancer, pancreas metastatic
Cancer, penis
Cancer, penis (squamous cell carcinoma)
Cancer, peritoneum
Cancer, prostate (castration-resistant)
Cancer, prostate (castration-resistant), metastatic
Cancer, rectum
Cancer, skin (basal cell carcinoma)
Cancer, skin (squamous cell carcinoma)
Cancer, small intestine (adenocarcinoma)
Cancer, testis
Cancer, thymus
Cancer, thyroid, anaplastic
Cholangiocarcinoma
Chordoma
Cutaneous T-cell lymphoma -continued Digestive-gastrointestinal cancer
Familial pheochromocytoma-paraganglioma
Glioma
HTLV-1-associated adult T-cell leukemia-lymphoma
Hematologic-blood cancer
Hepatitis C (HCV)
Infection, papillomaviral respiratory
Leiomyosarcoma, uterine
Leukemia, acute lymphocytic
Leukemia, chronic myeloid
Lymphoma, T-cell
Lymphoma, follicular
Lymphoma, primary mediastinal large B-cell
Lymphoma, testicular, diffuse large B-cell
Melanoma
Mesothelioma, malignant
Mesothelioma, pleural
Mycosis fungoides
Neuroendocrine cancer
Oral epithelial dysplasia
Sarcoma
Sepsis, severe
Sezary syndrome
Smoldering myeloma
Soft tissue sarcoma
T-cell lymphoma, nasal natural killer (NK) cell
T-cell lymphoma, peripheral

---

In some embodiments, the cancer is selected from the list of: hepatocellular carcinoma, melanoma (e.g., BRAF mutant melanoma), glioblastoma, breast cancer, prostate cancer, liver cancer, brain cancer, Lewis lung carcinoma (LLC), colon carcinoma, pancreatic cancer, renal cell carcinoma, and mammary carcinoma. In some embodiments, the cancer is selected from the list of: melanoma, non-small cell lung cancer, kidney cancer, bladder cancer, head and neck cancers, Hodgkin lymphoma, Merkel cell skin cancer (Merkel cell carcinoma), esophagus cancer; gastroesophageal junction cancer; liver cancer, (hepatocellular carcinoma); lung cancer, (small cell) (SCLC); stomach cancer; upper urinary tract cancer, (urothelial carcinoma); multiforme Glioblastoma; Multiple myeloma; anus cancer, (squamous cell); cervix cancer; endometrium cancer; nasopharynx cancer; ovary cancer; metastatic pancreas cancer; solid tumor cancer; adrenocortical Carcinoma; HTLV-1-associated adult T-cell leukemia-lymphoma; uterine Leiomyosarcoma; acute myeloid Leukemia; chronic lymphocytic Leukemia; diffuse large B-cell Lymphoma; follicular Lymphoma; uveal Melanoma; Meningioma; pleural Mesothelioma; Myelodysplasia; Soft tissue sarcoma; breast cancer; colon cancer; Cutaneous T-cell lymphoma; and peripheral T-cell lymphoma. In some embodiments, the cancer is selected from the list of: glioblastoma, melanoma, lymphoma, breast cancer, ovarian cancer, glioma, digestive system cancer, central nervous system cancer, hepatocellular cancer, hematological cancer, colon cancer or any combination thereof. In some embodiments, the compound is any one of the compounds listed in Table 1; each compound represents a separate embodiment according to this invention.

It has been shown that glucose-independent acetate metabolism promotes melanoma cell survival and tumor growth. Glucose-starved melanoma cells are highly dependent on acetate to sustain ATP levels, cell viability and proliferation. Conversely, depletion of ACSS1 or ACSS2 reduced melanoma tumor growth in mice. Collectively, this data demonstrates acetate metabolism as a liability in melanoma.

Accordingly, in various embodiments, this invention is directed to a method of treating, suppressing, reducing the severity, reducing the risk of developing or inhibiting melanoma comprising administering a compound of this invention to a subject suffering from melanoma under conditions effective to treat, suppress, reduce the severity, reduce the risk of developing, or inhibit the melanoma. In some embodiments, the melanoma is early melanoma. In some embodiments, the melanoma is advanced melanoma. In some embodiments, the melanoma is invasive melanoma. In some embodiments, the melanoma is metastatic melanoma. In some embodiments, the melanoma is drug resistant melanoma. In some embodiments, the melanoma is BRAF mutant melanoma. In some embodiments, the compound is an ACSS2 inhibitor. In some embodiments, the compound is selective to ACSS2. In some embodiments, the compound is selective to ACSS1. In some embodiments, the compound is selective to both ACSS2 and ACSS1. In some embodiments, the compound is selective to ACSS2, ACSS1, AACS, ACSF2 and ACSL5. In some embodiments, the compound is any one of the compounds listed in Table 1; each compound represents a separate embodiment according to this invention.

Acetyl-CoA synthetases that catalyse the conversion of acetate to acetyl-CoA have now been implicated in the growth of hepatocellular carcinoma, glioblastoma, breast cancer and prostate cancer.

Hepatocellular carcinoma (HCC) is a deadly form of liver cancer, and it is currently the second leading cause of cancer-related deaths worldwide (European Association For The Study Of The Liver; European Organisation For Research And Treatment Of Cancer, 2012). Despite a number of available treatment strategies, the survival rate for HCC patients is low. Considering its rising prevalence, more targeted and effective treatment strategies are highly desirable for HCC.

In various embodiments, this invention is directed to a method of treating, suppressing, reducing the severity, reducing the risk of developing or inhibiting hepatocellular carcinoma (HCC) comprising administering a compound of this invention to a subject suffering from hepatocellular carcinoma (HCC) under conditions effective to treat, suppress, reduce the severity, reduce the risk of developing, or inhibit the hepatocellular carcinoma (HCC). In some embodiments, the hepatocellular carcinoma (HCC) is early hepatocellular carcinoma (HCC). In some embodiments, the hepatocellular carcinoma (HCC) is advanced hepatocellular carcinoma (HCC). In some embodiments, the hepatocellular carcinoma (HCC) is invasive hepatocellular carcinoma (HCC). In some embodiments, the hepatocellular carcinoma (HCC) is metastatic hepatocellular carcinoma (HCC). In some embodiments, the hepatocellular carcinoma (HCC) is drug resistant hepatocellular carcinoma (HCC). In some embodiments, the compound is an ACSS2 inhibitor. In some embodiments, the compound is selective to ACSS2. In some embodiments, the compound is selective to ACSS1. In some embodiments, the compound is selective to both ACSS2 and ACSS1. In some embodiments, the compound is selective to ACSS2, ACSS1, AACS, ACSF2 and ACSL5. In some embodiments, the compound is any one of the compounds listed in Table 1; each compound represents a separate embodiment according to this invention.

ACSS2-mediated acetate metabolism contributes to lipid synthesis and aggressive growth in glioblastoma and breast cancer.

Nuclear ACSS2 is shown to activate HIF-2alpha by acetylation and thus accelerate growth and metastasis of HIF2alpha-driven cancers such as certain Renal Cell Carcinoma and Glioblastomas (Chen, R. et al. Coordinate regulation of stress signaling and epigenetic events by Acss2 and HIF-2 in cancer cells, Plos One, 12 (12) 1-31, 2017).

Therefore, and in various embodiments, this invention is directed to a method of treating, suppressing, reducing the severity, reducing the risk of developing or inhibiting glioblastoma comprising administering a compound of this invention to a subject suffering from glioblastoma under conditions effective to treat, suppress, reduce the severity, reduce the risk of developing, or inhibit the glioblastoma. In some embodiments, the glioblastoma is early glioblastoma. In some embodiments, the glioblastoma is advanced glioblastoma. In some embodiments, the glioblastoma is invasive glioblastoma. In some embodiments, the glioblastoma is metastatic glioblastoma. In some embodiments, the glioblastoma is drug resistant glioblastoma. In some embodiments, the compound is an ACSS2 inhibitor. In some embodiments, the compound is selective to ACSS2. In some embodiments, the compound is selective to ACSS1. In some embodiments, the compound is selective to both ACSS2 and ACSS1. In some embodiments, the compound is selective to ACSS2, ACSS1, AACS, ACSF2 and ACSL5. In some embodiments, the compound is any one of the compounds listed in Table 1; each compound represents a separate embodiment according to this invention.

Therefore, and in various embodiments, this invention is directed to a method of treating, suppressing, reducing the severity, reducing the risk of developing or inhibiting Renal Cell Carcinoma comprising administering a compound of this invention to a subject suffering from Renal Cell Carcinoma under conditions effective to treat, suppress, reduce the severity, reduce the risk of developing, or inhibit the Renal Cell Carcinoma. In some embodiments, the Renal Cell Carcinoma is early Renal Cell Carcinoma. In some embodiments, the Renal Cell Carcinoma is advanced Renal Cell Carcinoma. In some embodiments, the Renal Cell Carcinoma is invasive Renal Cell Carcinoma. In some embodiments, the Renal Cell Carcinoma is metastatic Renal Cell Carcinoma. In some embodiments, the Renal Cell Carcinoma is drug resistant Renal Cell Carcinoma. In some embodiments, the compound is an ACSS2 inhibitor. In some embodiments, the compound is selective to ACSS2. In some embodiments, the compound is selective to ACSS1. In some embodiments, the compound is selective to both ACSS2 and ACSS1. In some embodiments, the compound is selective to ACSS2, ACSS1, AACS, ACSF2 and ACSL5. In some embodiments, the compound is any one of the compounds listed in Table 1; each compound represents a separate embodiment according to this invention.

In various embodiments, this invention is directed to a method of treating, suppressing, reducing the severity, reducing the risk of developing or inhibiting breast cancer comprising administering a compound of this invention to a subject suffering from breast cancer under conditions effective to treat, suppress, reduce the severity, reduce the risk of developing, or inhibit the breast cancer. In some embodiments, the breast cancer is early breast cancer. In some embodiments, the breast cancer is advanced breast cancer. In some embodiments, the breast cancer is invasive breast cancer. In some embodiments, the breast cancer is metastatic breast cancer. In some embodiments, the breast cancer is drug resistant breast cancer. In some embodiments, the compound is an ACSS2 inhibitor. In some embodiments, the compound is selective to ACSS2. In some embodiments, the compound is selective to ACSS1. In some embodiments, the compound is selective to both ACSS2 and ACSS1. In some embodiments, the compound is selective to ACSS2, ACSS1, AACS, ACSF2 and ACSL5. In some embodiments, the compound is any one of the compounds listed in Table 1; each compound represents a separate embodiment according to this invention.

In various embodiments, this invention is directed to a method of treating, suppressing, reducing the severity, reducing the risk of developing or inhibiting prostate cancer comprising administering a compound of this invention to a subject suffering from prostate cancer under conditions effective to treat, suppress, reduce the severity, reduce the risk of developing, or inhibit the prostate cancer. In some embodiments, the prostate cancer is early prostate cancer. In some embodiments, the prostate cancer is advanced prostate cancer. In some embodiments, the prostate cancer is invasive prostate cancer. In some embodiments, the prostate cancer is metastatic prostate cancer. In some embodiments, the prostate cancer is drug resistant prostate cancer. In some embodiments, the compound is an ACSS2 inhibitor. In some embodiments, the compound is selective to ACSS2. In some embodiments, the compound is selective to ACSS1. In some embodiments, the compound is selective to both ACSS2 and ACSS1. In some embodiments, the compound is selective to ACSS2, ACSS1, AACS, ACSF2 and ACSL5. In some embodiments, the compound is any one of the compounds listed in Table 1; each compound represents a separate embodiment according to this invention.

In various embodiments, this invention is directed to a method of treating, suppressing, reducing the severity, reducing the risk of developing or inhibiting liver cancer comprising administering a compound of this invention to a subject suffering from liver cancer under conditions effective to treat, suppress, reduce the severity, reduce the risk of developing, or inhibit the liver cancer. In some embodiments, the liver cancer is early liver cancer. In some embodiments, the liver cancer is advanced liver cancer. In some embodiments, the liver cancer is invasive liver cancer. In some embodiments, the liver cancer is metastatic liver cancer. In some embodiments, the liver cancer is drug resistant liver cancer. In some embodiments, the compound is an ACSS2 inhibitor. In some embodiments, the compound is selective to ACSS2. In some embodiments, the compound is selective to ACSS1. In some embodiments, the compound is selective to both ACSS2 and ACSS1. In some embodiments, the compound is selective to ACSS2, ACSS1, AACS, ACSF2 and ACSL5. In some embodiments, the compound is any one of the compounds listed in Table 1; each compound represents a separate embodiment according to this invention.

Nuclear ACSS2 is also shown to promote lysosomal biogenesis, autophagy and to promote brain tumorigenesis by affecting Histone H3 acetylation (Li, X et al.: Nucleus-Translocated ACSS2 Promotes Gene Transcription for Lysosomal Biogenesis and Autophagy, *Molecular Cell* 66, 1-14, 2017).

In various embodiments, this invention is directed to a method of treating, suppressing, reducing the severity, reducing the risk of developing or inhibiting brain cancer comprising administering a compound of this invention to a subject suffering from brain cancer under conditions effective to treat, suppress, reduce the severity, reduce the risk of developing, or inhibit the brain cancer. In some embodiments, the brain cancer is early brain cancer. In some embodiments, the brain cancer is advanced brain cancer. In some embodiments, the brain cancer is invasive brain cancer. In some embodiments, the brain cancer is metastatic brain cancer. In some embodiments, the brain cancer is drug resistant brain cancer. In some embodiments, the compound is an ACSS2 inhibitor. In some embodiments, the compound is selective to ACSS2. In some embodiments, the compound is selective to ACSS1. In some embodiments, the compound is selective to both ACSS2 and ACSS1. In some embodiments, the compound is selective to ACSS2, ACSS1, AACS, ACSF2 and ACSL5. In some embodiments, the compound is any one of the compounds listed in Table 1; each compound represents a separate embodiment according to this invention.

In various embodiments, this invention is directed to a method of treating, suppressing, reducing the severity, reducing the risk of developing or inhibiting pancreatic cancer comprising administering a compound of this invention to a subject suffering from pancreatic cancer under conditions effective to treat, suppress, reduce the severity, reduce the risk of developing, or inhibit the pancreatic cancer. In some embodiments, the pancreatic cancer is early pancreatic cancer. In some embodiments, the pancreatic cancer is advanced pancreatic cancer. In some embodiments, the pancreatic cancer is invasive pancreatic cancer. In some embodiments, the pancreatic cancer is metastatic pancreatic cancer. In some embodiments, the pancreatic cancer is drug resistant pancreatic cancer. In some embodiments, the compound is an ACSS2 inhibitor. In some embodiments, the compound is selective to ACSS2. In some embodiments, the compound is selective to ACSS1. In some embodiments, the compound is selective to both ACSS2 and ACSS1. In some embodiments, the compound is selective to ACSS2, ACSS1, AACS, ACSF2 and ACSL5. In some embodiments, the compound is any one of the compounds listed in Table 1; each compound represents a separate embodiment according to this invention.

In various embodiments, this invention is directed to a method of treating, suppressing, reducing the severity, reducing the risk of developing or inhibiting Lewis lung carcinoma (LLC) comprising administering a compound of this invention to a subject suffering from Lewis lung carcinoma (LLC) under conditions effective to treat, suppress, reduce the severity, reduce the risk of developing, or inhibit the Lewis lung carcinoma (LLC). In some embodiments, the Lewis lung carcinoma (LLC) is early Lewis lung carcinoma (LLC). In some embodiments, the Lewis lung carcinoma (LLC) is advanced Lewis lung carcinoma (LLC). In some embodiments, the Lewis lung carcinoma (LLC) is invasive Lewis lung carcinoma (LLC). In some embodiments, the Lewis lung carcinoma (LLC) is metastatic Lewis lung carcinoma (LLC). In some embodiments, the Lewis lung carcinoma (LLC) is drug resistant Lewis lung carcinoma (LLC). In some embodiments, the compound is an ACSS2 inhibitor. In some embodiments, the compound is selective to ACSS2. In some embodiments, the compound is selective to ACSS1. In some embodiments, the compound is selective to both ACSS2 and ACSS1. In some embodiments, the compound is selective to ACSS2, ACSS1, AACS, ACSF2 and ACSL5. In some embodiments, the compound is any one of the compounds listed in Table 1; each compound represents a separate embodiment according to this invention.

In various embodiments, this invention is directed to a method of treating, suppressing, reducing the severity, reducing the risk of developing or inhibiting colon carcinoma comprising administering a compound of this invention to a subject suffering from colon carcinoma under conditions effective to treat, suppress, reduce the severity, reduce the risk of developing, or inhibit the colon carcinoma. In some embodiments, the colon carcinoma is early colon carcinoma. In some embodiments, the colon carcinoma is advanced colon carcinoma. In some embodiments, the colon carcinoma is invasive colon carcinoma. In some embodiments, the colon carcinoma is metastatic colon carcinoma. In some embodiments, the colon carcinoma is drug resistant colon carcinoma. In some embodiments, the compound is a 'program cell death receptor 1' (PD-1) modulator. In some embodiments, the compound is an ACSS2 inhibitor. In some embodiments, the compound is selective to ACSS2. In some embodiments, the compound is selective to ACSS1. In some embodiments, the compound is selective to both ACSS2 and ACSS1. In some embodiments, the compound is selective to ACSS2, ACSS1, AACS, ACSF2 and ACSL5. In some embodiments, the compound is any one of the compounds listed in Table 1; each compound represents a separate embodiment according to this invention.

In various embodiments, this invention is directed to a method of treating, suppressing, reducing the severity, reducing the risk of developing or inhibiting mammary carcinoma comprising administering a compound of this invention to a subject suffering from mammary carcinoma under conditions effective to treat, suppress, reduce the severity, reduce the risk of developing, or inhibit the mammary carcinoma. In some embodiments, the mammary carcinoma is early mammary carcinoma. In some embodiments, the mammary carcinoma is advanced mammary carcinoma. In some embodiments, the mammary carcinoma is invasive mammary carcinoma. In some embodiments, the mammary carcinoma is metastatic mammary carcinoma. In some embodiments, the mammary carcinoma is drug resistant mammary carcinoma. In some embodiments, the compound is an ACSS2 inhibitor. In some embodiments, the compound is selective to ACSS2. In some embodiments, the compound is selective to ACSS1. In some embodiments, the compound is selective to both ACSS2 and ACSS1. In some embodiments, the compound is selective to ACSS2, ACSS1, AACS, ACSF2 and ACSL5. In some embodiments, the compound is any one of the compounds listed in Table 1; each compound represents a separate embodiment according to this invention.

In various embodiments, this invention is directed to a method of suppressing, reducing or inhibiting tumor growth in a subject, comprising administering a compound according to this invention, to a subject under conditions effective to suppress, reduce or inhibit said tumor growth in said subject. In various embodiments, the subject is suffering from proliferative disorder. In some embodiments, the proliferative disorder is cancer. In various embodiments, the tumor is cancerous. In some embodiments, the tumor growth is enhanced by increased acetate uptake by cancer cells or said tumor. In some embodiments, the increase in acetate uptake is mediated by ACSS2. In some embodiments, the cancer cells are under hypoxic stress. In some embodiments, the compound is an ACSS2 inhibitor. In some embodiments, the compound is selective to ACSS2. In some embodiments, the compound is selective to ACSS1. In some embodiments, the compound is selective to both ACSS2 and ACSS1. In some embodiments, the compound is selective to ACSS2, ACSS1, AACS, ACSF2 and ACSL5. In some embodiments, the tumor growth is suppressed due to suppression of lipid synthesis (e.g., fatty acid) induced by ACSS2 mediated acetate metabolism to acetyl-CoA. In some embodiments, the tumor growth is suppressed due to suppression of the regulation of histones acetylation and function induced by ACSS2 mediated acetate metabolism to acetyl-CoA. In some embodiments, the synthesis is suppressed under hypoxia (hypoxic stress). In some embodiments, the compound is any one of the compounds listed in Table 1; each compound represents a separate embodiment according to this invention.

In various embodiments, this invention is directed to a method of suppressing, reducing or inhibiting lipid synthesis and/or regulating histones acetylation and function in a cell, comprising contacting a compound of this invention, with a cell under conditions effective to suppress, reduce or inhibit lipid synthesis and/or regulating histones acetylation and function in said cell. In various embodiments, the method is carried out in vitro. In various embodiments, the method is carried out in vivo. In various embodiments, the lipid synthesis is induced by ACSS2 mediated acetate metabolism to acetyl-CoA. In various embodiments, regulating histones acetylation and function is induced by ACSS2 mediated acetate metabolism to acetyl-CoA. In various embodiments, the cell is cancer cell. In various embodiments, the lipid is fatty acid. In various embodiments, the acetate metabolism to acetyl-CoA is carried out under hypoxia (i.e., hypoxic stress). In some embodiments, the compound is an ACSS2 inhibitor. In some embodiments, the compound is selective to ACSS2. In some embodiments, the compound is selective to ACSS1. In some embodiments, the compound is selective to both ACSS2 and ACSS1. In some embodiments, the compound is selective to ACSS2, ACSS1, AACS, ACSF2 and ACSL5. In some embodiments, the compound is any one of the compounds listed in Table 1; each compound represents a separate embodiment according to this invention.

In various embodiments, this invention is directed to a method of suppressing, reducing or inhibiting fatty-acid accumulation in the liver, comprising administering a compound of this invention to a subject in need thereof, under conditions effective to suppress, reduce or inhibit fatty-acid accumulation in the liver of said subject. In various embodiments, the fatty-acid accomulation is induced by ACSS2 mediated acetate metabolism to acetyl-CoA. In various embodiments, the subject suffers from a fatty liver condition. In various embodiments, the acetate metabolism to acetyl-CoA in the liver is carried out under hypoxia (i.e., hypoxic stress). In some embodiments, the compound is an ACSS2 inhibitor. In some embodiments, the compound is selective to ACSS2. In some embodiments, the compound is selective to ACSS1. In some embodiments, the compound is selective to both ACSS2 and ACSS1. In some embodiments, the compound is selective to ACSS2, ACSS1, AACS, ACSF2 and ACSL5. In some embodiments, the compound is any one of the compounds listed in Table 1; each compound represents a separate embodiment according to this invention.

In various embodiments, this invention is directed to a method of binding an ACSS2 inhibitor compound to an ACSS2 enzyme, comprising the step of contacting an ACSS2 enzyme with an ACSS2 inhibitor compound of this invention, in an amount effective to bind the ACSS2 inhibitor compound to the ACSS2 enzyme. In some embodiments, the method is carried out in vitro. In another embodiment, the method is carried out in vivo. In some embodiments, the compound is any one of the compounds listed in Table 1; each compound represents a separate embodiment according to this invention.

In various embodiments, this invention is directed to a method of suppressing, reducing or inhibiting acetyl-CoA synthesis from acetate in a cell, comprising contacting a compound according to this invention with a cell, under conditions effective to suppress, reduce or inhibit acetyl-CoA synthesis from acetate in said cell. In some embodiments, the cell is a cancer cell. In some embodiments, the method is carried out in vitro. In another embodiment, the method is carried out in vivo. In some embodiments, the synthesis is mediated by ACSS2. In some embodiments, the compound is an ACSS2 inhibitor. In some embodiments, the compound is selective to ACSS2. In some embodiments, the compound is selective to ACSS1. In some embodiments, the compound is selective to both ACSS2 and ACSS1. In some embodiments, the compound is selective to ACSS2, ACSS1, AACS, ACSF2 and ACSL5. In some embodiments, the cell is under hypoxic stress. In some embodiments, the compound is any one of the compounds listed in Table 1; each compound represents a separate embodiment according to this invention.

In various embodiments, this invention is directed to a method of suppressing, reducing or inhibiting acetate metabolism in a cancer cell, comprising contacting a compound according to this invention with a cancer cell, under conditions effective to suppress, reduce or inhibit acetate metabolism in said cell. In some embodiments, the acetate metabolism is mediated by ACSS2. In some embodiments, the compound is an ACSS2 inhibitor. In some embodiments, the compound is selective to ACSS2. In some embodiments, the compound is selective to ACSS1. In some embodiments, the compound is selective to both ACSS2 and ACSS1. In some embodiments, the compound is selective to ACSS2, ACSS1, AACS, ACSF2 and ACSL5. In some embodiments, the cancer cell is under hypoxic stress. In some embodiments, the compound is any one of the compounds listed in Table 1; each compound represents a separate embodiment according to this invention.

In various embodiments, this invention provides methods for treating, suppressing, reducing the severity, reducing the risk, or inhibiting metastatic cancer comprising the step of administering to said subject a compound of this invention and/or an isomer, metabolite, pharmaceutically acceptable salt, pharmaceutical product, tautomer, hydrate, N-oxide, reverse amide analog, prodrug, isotopic variant (e.g., deuterated analog), PROTAC, polymorph, or crystal of said compound, or any combination thereof. In some embodiments, the compound is an ACSS2 inhibitor. In some embodiments, the compound is selective to ACSS2. In some embodiments, the compound is selective to ACSS1. In some embodiments, the compound is selective to both ACSS2 and ACSS1. In some embodiments, the compound is selective to ACSS2, ACSS1, AACS, ACSF2 and ACSL5. In some embodiments, the cancer is melanoma. In some embodiments, the cancer is hepatocellular carcinoma. In some embodiments, the cancer is glioblastoma. In some embodiments, the cancer is breast cancer. In some embodiments, the cancer is prostate cancer. In some embodiments, the cancer is liver cancer. In some embodiments, the cancer is brain cancer. In some embodiments, the cancer is Lewis lung carcinoma. In some embodiments, the cancer is colon carcinoma. In some embodiments, the cancer is mammary carcinoma. In some embodiments, the cancer is pancreatic cancer.

In various embodiments, this invention provides methods for increasing the survival of a subject suffering from metastatic cancer comprising the step of administering to said subject a compound of this invention and/or an isomer, metabolite, pharmaceutically acceptable salt, pharmaceutical product, tautomer, hydrate, N-oxide, reverse amide analog, prodrug, isotopic variant (e.g., deuterated analog), PROTAC, polymorph, or crystal of said compound, or any combination thereof. In some embodiments, the compound is an ACSS2 inhibitor. In some embodiments, the compound is selective to ACSS2. In some embodiments, the compound is selective to ACSS1. In some embodiments, the compound is selective to both ACSS2 and ACSS1. In some embodiments, the compound is selective to ACSS2, ACSS1, AACS, ACSF2 and ACSL5. In some embodiments, the cancer is melanoma. In some embodiments, the cancer is hepatocellular carcinoma. In some embodiments, the cancer is glioblastoma. In some embodiments, the cancer is breast cancer. In some embodiments, the cancer is prostate cancer. In some embodiments, the cancer is liver cancer. In some embodiments, the cancer is brain cancer. In some embodiments, the cancer is Lewis lung carcinoma. In some embodiments, the cancer is colon carcinoma. In some embodiments, the cancer is mammary carcinoma. In some embodiments, the cancer is pancreatic cancer.

In various embodiments, this invention provides methods for treating, suppressing, reducing the severity, reducing the risk, or inhibiting advanced cancer comprising the step of administering to said subject a compound of this invention and/or an isomer, metabolite, pharmaceutically acceptable salt, pharmaceutical product, tautomer, hydrate, N-oxide, reverse amide analog, prodrug, isotopic variant (e.g., deuterated analog), PROTAC, polymorph, or crystal of said compound, or any combination thereof. In some embodiments, the compound is an ACSS2 inhibitor. In some embodiments, the compound is selective to ACSS2. In some embodiments, the compound is selective to ACSS1. In some embodiments, the compound is selective to both ACSS2 and ACSS1. In some embodiments, the compound is selective to ACSS2, ACSS1, AACS, ACSF2 and ACSL5. In some embodiments, the cancer is melanoma. In some embodiments, the cancer is hepatocellular carcinoma. In some embodiments, the cancer is glioblastoma. In some embodiments, the cancer is breast cancer. In some embodiments, the cancer is prostate cancer. In some embodiments, the cancer is liver cancer. In some embodiments, the cancer is brain cancer. In some embodiments, the cancer is Lewis lung carcinoma. In some embodiments, the cancer is colon carcinoma. In some embodiments, the cancer is mammary carcinoma. In some embodiments, the cancer is pancreatic cancer.

In various embodiments, this invention provides methods for increasing the survival of a subject suffering from advanced cancer comprising the step of administering to said subject a compound of this invention and/or an isomer, metabolite, pharmaceutically acceptable salt, pharmaceutical product, tautomer, hydrate, N-oxide, reverse amide analog, prodrug, isotopic variant (e.g., deuterated analog), PROTAC, polymorph, or crystal of said compound, or any combination thereof. In some embodiments, the compound is an ACSS2 inhibitor. In some embodiments, the compound is selective to ACSS2. In some embodiments, the compound is selective to ACSS1. In some embodiments, the compound is selective to both ACSS2 and ACSS1. In some embodiments, the compound is selective to ACSS2, ACSS1, AACS, ACSF2 and ACSL5. In some embodiments, the cancer is melanoma. In some embodiments, the cancer is hepatocellular carcinoma. In some embodiments, the cancer is glioblastoma. In some embodiments, the cancer is breast cancer. In some embodiments, the cancer is prostate cancer. In some embodiments, the cancer is liver cancer. In some embodiments, the cancer is brain cancer. In some embodiments, the cancer is Lewis lung carcinoma. In some embodiments, the cancer is colon carcinoma. In some embodiments, the cancer is mammary carcinoma. In some embodiments, the cancer is pancreatic cancer.

The compounds of the present invention are useful in the treatment, reducing the severity, reducing the risk, or inhibition of cancer, metastatic cancer, advanced cancer, drug resistant cancer, and various forms of cancer. In a preferred embodiment the cancer is hepatocellular carcinoma, melanoma (e.g., BRAF mutant melanoma), glioblastoma, breast cancer, prostate cancer, liver cancer, brain cancer, pancreatic cancer, Lewis lung carcinoma (LLC), colon carcinoma, renal cell carcinoma, and/or mammary carcinoma; each represents a separate embodiment according to this invention. Based upon their believed mode of action, it is believed that other forms of cancer will likewise be treatable or preventable upon administration of the compounds or compositions of the present invention to a patient. Preferred compounds of the present invention are selectively disruptive to cancer cells, causing ablation of cancer cells but preferably not normal cells. Significantly, harm to normal cells is minimized because the cancer cells are susceptible to disruption at much lower concentrations of the compounds of the present invention.

In various embodiments, other types of cancers that may be treatable with the ACSS2 inhibitors according to this invention include: adrenocortical carcinoma, anal cancer, bladder cancer, brain tumor, brain stem tumor, breast cancer, glioma, cerebellar astrocytoma, cerebral astrocytoma, ependymoma, medulloblastoma, supratentorial primitive neuroectodermal, pineal tumors, hypothalamic glioma, carcinoid tumor, carcinoma, cervical cancer, colon cancer, central nervous system (CNS) cancer, endometrial cancer, esophageal cancer, extrahepatic bile duct cancer, Ewing's family of tumors (Pnet), extracranial germ cell tumor, eye cancer, intraocular melanoma, gallbladder cancer, gastric cancer, germ cell tumor, extragonadal, gestational trophoblastic tumor, head and neck cancer, hypopharyngeal cancer, islet cell carcinoma, laryngeal cancer, leukemia, acute lymphoblastic, leukemia, oral cavity cancer, liver cancer, lung cancer, non-small cell lung cancer, small cell, lymphoma, AIDS-related lymphoma, central nervous system (primary), lymphoma, cutaneous T-cell, lymphoma, Hodgkin's disease, non-Hodgkin's disease, malignant mesothelioma, melanoma, Merkel cell carcinoma, metasatic squamous carcinoma, multiple myeloma, plasma cell neoplasms, mycosis fungoides, myelodysplastic syndrome, myeloproliferative disorders, nasopharyngeal cancer, neuroblastoma, oropharyngeal cancer, osteosarcoma, ovarian cancer, ovarian epithelial cancer, ovarian germ cell tumor, ovarian low malignant potential tumor, pancreatic cancer, exocrine, pancreatic cancer, islet cell carcinoma, paranasal sinus and nasal cavity cancer, parathyroid cancer, penile cancer, pheochromocytoma cancer, pituitary cancer, plasma cell neoplasm, prostate cancer, rhabdomyosarcoma, rectal cancer, renal cancer, renal cell cancer, salivary gland cancer, Sezary syndrome, skin cancer, cutaneous T-cell lymphoma, skin cancer, Kaposi's sarcoma, skin cancer, melanoma, small intestine cancer, soft tissue sarcoma, soft tissue sarcoma, testicular cancer, thymoma, malignant, thyroid cancer, urethral cancer, uterine cancer, sarcoma, unusual cancer of childhood, vaginal cancer, vulvar cancer, Wilms' tumor, hepatocellular cancer, hematological cancer or any combination thereof. In some embodiments the cancer is invasive. In some embodiments the cancer is metastatic cancer. In some embodiments the cancer is advanced cancer. In some embodiments the cancer is drug resistant cancer.

In various embodiments "metastatic cancer" refers to a cancer that spread (metastasized) from its original site to another area of the body. Virtually all cancers have the potential to spread. Whether metastases develop depends on the complex interaction of many tumor cell factors, including the type of cancer, the degree of maturity (differentiation) of the tumor cells, the location and how long the cancer has been present, as well as other incompletely understood factors. Metastases spread in three ways—by local extension from the tumor to the surrounding tissues, through the bloodstream to distant sites or through the lymphatic system to neighboring or distant lymph nodes. Each kind of cancer may have a typical route of spread. The tumor is called by the primary site (ex. breast cancer that has spread to the brain is called metastatic breast cancer to the brain).

In various embodiments "drug-resistant cancer" refers to cancer cells that acquire resistance to chemotherapy. Cancer cells can acquire resistance to chemotherapy by a range of mechanisms, including the mutation or overexpression of the drug target, inactivation of the drug, or elimination of the drug from the cell. Tumors that recur after an initial response to chemotherapy may be resistant to multiple drugs (they are multidrug resistant). In the conventional view of drug resistance, one or several cells in the tumor population acquire genetic changes that confer drug resistance. Accordingly, the reasons for drug resistance, inter alia, are: a) some of the cells that are not killed by the chemotherapy mutate (change) and become resistant to the drug. Once they multiply, there may be more resistant cells than cells that are sensitive to the chemotherapy; b) Gene amplification. A cancer cell may produce hundreds of copies of a particular gene. This gene triggers an overproduction of protein that renders the anticancer drug ineffective; c) cancer cells may pump the drug out of the cell as fast as it is going in using a molecule called p-glycoprotein; d) cancer cells may stop taking in the drugs because the protein that transports the drug across the cell wall stops working; e) the cancer cells may learn how to repair the DNA breaks caused by some anti-cancer drugs; f) cancer cells may develop a mechanism that inactivates the drug. One major contributor to multidrug resistance is overexpression of P-glycoprotein (P-gp). This protein is a clinically important transporter protein belonging to the ATP-binding cassette family of cell membrane transporters. It can pump substrates including anticancer drugs out of tumor cells through an ATP-dependent mechanism; g) Cells and tumors with activating RAS mutations are relatively resistant to most anti-cancer agents. Thus, the resistance to anticancer agents used in chemotherapy is the main cause of treatment failure in malignant disorders, provoking tumors to become resistant. Drug resistance is the major cause of cancer chemotherapy failure.

In various embodiments "resistant cancer" refers to drug-resistant cancer as described herein above. In some embodiments "resistant cancer" refers to cancer cells that acquire resistance to any treatment such as chemotherapy, radiotherapy or biological therapy.

In various embodiments, this invention is directed to treating, suppressing, reducing the severity, reducing the risk, or inhibiting cancer in a subject, wherein the subject has been previously treated with chemotherapy, radiotherapy or biological therapy.

In various embodiments "Chemotherapy" refers to chemical treatment for cancer such as drugs that kill cancer cells directly. Such drugs are referred as "anti-cancer" drugs or "antineoplastics." Today's therapy uses more than 100 drugs to treat cancer. To cure a specific cancer. Chemotherapy is used to control tumor growth when cure is not possible; to shrink tumors before surgery or radiation therapy; to relieve symptoms (such as pain); and to destroy microscopic cancer cells that may be present after the known tumor is removed by surgery (called adjuvant therapy). Adjuvant therapy is given to prevent a possible cancer reoccurrence.

In various embodiments, "Radiotherapy" (also referred herein as "Radiation therapy") refers to high energy x-rays and similar rays (such as electrons) to treat disease. Many people with cancer will have radiotherapy as part of their treatment. This can be given either as external radiotherapy from outside the body using x-rays or from within the body as internal radiotherapy. Radiotherapy works by destroying the cancer cells in the treated area. Although normal cells can also be damaged by the radiotherapy, they can usually repair themselves. Radiotherapy treatment can cure some cancers and can also reduce the chance of a cancer coming back after surgery. It may be used to reduce cancer symptoms.

In various embodiments "Biological therapy" refers to substances that occur naturally in the body to destroy cancer cells. There are several types of treatment including: monoclonal antibodies, cancer growth inhibitors, vaccines and gene therapy. Biological therapy is also known as immunotherapy.

When the compounds or pharmaceutical compositions of the present invention are administered to treat, suppress, reduce the severity, reduce the risk, or inhibit a cancerous condition, the pharmaceutical composition can also contain, or can be administered in conjunction with, other therapeutic agents or treatment regimen presently known or hereafter developed for the treatment of various types of cancer. Examples of other therapeutic agents or treatment regimen include, without limitation, radiation therapy, immunotherapy, chemotherapy, surgical intervention, and combinations thereof.

It is this kind of metabolic plasticity—the ability to exploit and survive on a variety of nutritional sources—that confers resistance to many of the current cancer metabolism drugs as monotherapies. Interestingly, ACSS2 is highly expressed in many cancer tissues, and its upregulation by hypoxia and low nutrient availability indicates that it is an important enzyme for coping with the typical stresses within the tumor microenvironment and, as such, a potential Achilles heel. Moreover, highly stressed regions of tumors have been shown to select for apoptotic resistance and promote aggressive behaviour, treatment resistance and relapse. In this way, the combination of ACSS2 inhibitors with a therapy that specifically targets well-oxygenated regions of tumors (for example, radiotherapy) could prove to be an effective regimen.

Accordingly, and in various embodiments, the compound according to this invention, is administered in combination with an anti-cancer therapy. Examples of such therapies include but are not limited to: chemotherapy, immunotherapy, radiotherapy, biological therapy, surgical intervention, and combinations thereof. In some embodiments, the compound according to this invention is administered in combination with a therapy that specifically targets well-oxygenated regions of tumors. In some embodiments, the compound according to this invention is administered in combination with radiotherapy.

In various embodiments, the compound is administered in combination with an anti-cancer agent by administering the compounds as herein described, alone or in combination with other agents.

In various embodiments, the composition for cancer treatment of the present invention can be used together with existing chemotherapy drugs or be made as a mixture with them. Such a chemotherapy drug includes, for example, alkylating agents, nitrosourea agents, antimetabolites, antitumor antibiotics, alkaloids derived from plant, topoisomerase inhibitors, hormone therapy medicines, hormone antagonists, aromatase inhibitors, P-glycoprotein inhibitors, platinum complex derivatives, other immunotherapeutic drugs, and other anticancer agents. Further, they can be used together with hypoleukocytosis (neutrophil) medicines that are cancer treatment adjuvant, thrombopenia medicines, antiemetic drugs, and cancer pain medicines for patient's QOL recovery or be made as a mixture with them.

In various embodiments, this invention is directed to a method of destroying a cancerous cell comprising: providing a compound of this invention and contacting the cancerous cell with the compound under conditions effective to destroy the contacted cancerous cell. According to various embodiments of destroying the cancerous cells, the cells to be destroyed can be located either in vivo or ex vivo (i.e., in culture).

In some embodiments, the cancer is selected from the group consisting of melanoma, non-small cell lung cancer, kidney cancer, bladder cancer, head and neck cancers, Hodgkin lymphoma, glioblastoma, renal cell carcinoma, Merkel cell skin cancer (Merkel cell carcinoma), and combinations thereof. In some embodiments, the cancer is selected from the group consisting of: melanoma, non-small cell lung cancer, kidney cancer, bladder cancer, head and neck cancers, Hodgkin lymphoma, glioblastoma, Merkel cell skin cancer (Merkel cell carcinoma), esophagus cancer; gastroesophageal junction cancer; liver cancer, (hepatocellular carcinoma); lung cancer, (small cell) (SCLC); stomach cancer; upper urinary tract cancer, (urothelial carcinoma); multiforme Glioblastoma; Multiple myeloma; anus cancer, (squamous cell); cervix cancer; endometrium cancer; nasopharynx cancer; ovary cancer; metastatic pancreas cancer; solid tumor cancer; adrenocortical Carcinoma; HTLV-1-associated adult T-cell leukemia-lymphoma; uterine Leiomyosarcoma; acute myeloid Leukemia; chronic lymphocytic Leukemia; diffuse large B-cell Lymphoma; follicular Lymphoma; uveal Melanoma; Meningioma; pleural Mesothelioma; Myelodysplasia; Soft tissue sarcoma; breast cancer; colon cancer; pancreatic cancer, Cutaneous T-cell lymphoma; peripheral T-cell lymphoma or any combination thereof.

A still further aspect of the present invention relates to a method of treating or preventing a cancerous condition that includes: providing a compound of the present invention and then administering an effective amount of the compound to a patient in a manner effective to treat or prevent a cancerous condition.

According to one embodiment, the patient to be treated is characterized by the presence of a precancerous condition, and the administering of the compound is effective to prevent development of the precancerous condition into the cancerous condition. This can occur by destroying the precancerous cell prior to or concurrent with its further development into a cancerous state.

According to other embodiments, the patient to be treated is characterized by the presence of a cancerous condition, and the administering of the compound is effective either to cause regression of the cancerous condition or to inhibit growth of the cancerous condition, i.e., stopping its growth altogether or reducing its rate of growth. This preferably occurs by destroying cancer cells, regardless of their location in the patient body. That is, whether the cancer cells are located at a primary tumor site or whether the cancer cells have metastasized and created secondary tumors within the patient body.

ACSS2 gene has recently been suggested to be associated with human alcoholism and ethanol intake. Accordingly, in various embodiments, this invention is directed to a method of treating, suppressing, reducing the severity, reducing the risk of developing or inhibiting human alcoholism in a subject, comprising administering a compound of this invention, to a subject suffering from alcoholism under conditions effective to treat, suppress, reduce the severity, reduce the risk of developing, or inhibit alcoholism in said subject. In some embodiments, the compound is an ACSS2 inhibitor. In some embodiments, the compound is selective to ACSS2. In some embodiments, the compound is selective to ACSS1. In some embodiments, the compound is selective to both ACSS2 and ACSS1. In some embodiments, the compound is selective to ACSS2, ACSS1, AACS, ACSF2 and ACSL5. In some embodiments, the compound is any one of the compounds listed in Table 1; each compound represents a separate embodiment according to this invention.

Non-alcoholic steatohepatitis (NASH) and alcoholic steatohepatitis (ASH) have a similar pathogenesis and histopathology but a different etiology and epidemiology. NASH and ASH are advanced stages of non-alcoholic fatty liver disease (NAFLD) and alcoholic fatty liver disease (AFLD). NAFLD is characterized by excessive fat accumulation in the liver (steatosis), without any other evident causes of chronic liver diseases (viral, autoimmune, genetic, etc.), and with an alcohol consumption ≤20-30 g/day. On the contrary, AFLD is defined as the presence of steatosis and alcohol consumption >20-30 g/day.

It has been shown that synthesis of metabolically available acetyl-coA from acetate is critical to the increased acetylation of proinflammatory gene histones and consequent enhancement of the inflammatory response in ethanol-exposed macrophages. This mechanism is a potential therapeutic target in acute alcoholic hepatitis.

Accordingly, in various embodiments, this invention is directed to a method of treating, suppressing, reducing the severity, reducing the risk of developing or inhibiting alcoholic steatohepatitis (ASH) in a subject, comprising administering a compound of this invention, to a subject suffering from alcoholic steatohepatitis (ASH) under conditions effective to treat, suppress, reduce the severity, reduce the risk of developing, or inhibit alcoholic steatohepatitis (ASH) in said subject. In some embodiments, the compound is an ACSS2 inhibitor. In some embodiments, the compound is selective to ACSS2. In some embodiments, the compound is selective to ACSS1. In some embodiments, the compound is selective to both ACSS2 and ACSS1. In some embodiments, the compound is selective to ACSS2, ACSS1, AACS, ACSF2 and ACSL5. In some embodiments, the compound is any one of the compounds listed in Table 1; each compound represents a separate embodiment according to this invention.

Accordingly, in various embodiments, this invention is directed to a method of treating, suppressing, reducing the severity, reducing the risk of developing or inhibiting non alcoholic fatty liver disease (NAFLD) in a subject, comprising administering a compound of this invention, to a subject suffering from non alcoholic fatty liver disease (NAFLD) under conditions effective to treat, suppress, reduce the severity, reduce the risk of developing, or inhibit non alcoholic fatty liver disease (NAFLD) in said subject. In some embodiments, the compound is an ACSS2 inhibitor. In some embodiments, the compound is selective to ACSS2. In some embodiments, the compound is selective to ACSS1. In some embodiments, the compound is selective to both ACSS2 and ACSS1. In some embodiments, the compound is selective to ACSS2, ACSS1, AACS, ACSF2 and ACSL5. In some embodiments, the compound is any one of the compounds listed in Table 1; each compound represents a separate embodiment according to this invention.

In various embodiments, this invention is directed to a method of treating, suppressing, reducing the severity, reducing the risk of developing or inhibiting non-alcoholic steatohepatitis (NASH) in a subject, comprising administering a compound of this invention, to a subject suffering from non-alcoholic steatohepatitis (NASH) under conditions effective to treat, suppress, reduce the severity, reduce the risk of developing, or inhibit non-alcoholic steatohepatitis (NASH) in said subject. In some embodiments, the compound is an ACSS2 inhibitor. In some embodiments, the compound is selective to ACSS2. In some embodiments, the compound is selective to ACSS1. In some embodiments, the compound is selective to both ACSS2 and ACSS1. In some embodiments, the compound is selective to ACSS2, ACSS1, AACS, ACSF2 and ACSL5. In some embodiments, the compound is any one of the compounds listed in Table 1; each compound represents a separate embodiment according to this invention.

ACSS2-mediated acetyl-CoA synthesis from acetate has also been shown to be necessary for human cytomegalovirus infection. It has been shown that glucose carbon can be converted to acetate and used to make cytosolic acetyl-CoA by acetyl-CoA synthetase short-chain family member 2 (ACSS2) for lipid synthesis, which is important for HCMV-induced lipogenesis and the viral growth. Accordingly, ACSS2 inhibitors are expected to be useful as an antiviral therapy, and in the treatment of HCMV infection.

Therefore, in various embodiments, this invention is directed to a method of treating, suppressing, reducing the severity, reducing the risk of developing or inhibiting a viral infection in a subject, comprising administering a compound of this invention, to a subject suffering from a viral infection under conditions effective to treat, suppress, reduce the severity, reduce the risk of developing, or inhibit the viral infection in said subject. In some embodiments, the viral infection is HCMV. In some embodiments, the compound is an ACSS2 inhibitor. In some embodiments, the compound is selective to ACSS2. In some embodiments, the compound is selective to ACSS1. In some embodiments, the compound is selective to both ACSS2 and ACSS1. In some embodiments, the compound is selective to ACSS2, ACSS1, AACS, ACSF2 and ACSL5. In some embodiments, the compound is any one of the compounds listed in Table 1; each compound represents a separate embodiment according to this invention.

It was found that mice lacking ACSS2 showed reduced body weight and hepatic steatosis in a diet-induced obesity model (Z. Huang et al., "ACSS2 promotes systemic fat storage and utilization through selective regulation of genes involved in lipid metabolism" *PNAS* 115, (40), E9499-E9506, 2018).

Accordingly, in various embodiments, this invention is directed to a method of treating, suppressing, reducing the severity, reducing the risk of developing or inhibiting a metabolic disorder in a subject, comprising administering a compound of this invention, to a subject suffering from a metabolic disorder under conditions effective to treat, suppress, reduce the severity, reduce the risk of developing, or inhibit the metabolic disorder in said subject. In some embodiments, the metabolic disorder is obesity. In other embodiments, the metabolic disorder is weight gain. In other embodiments, the metabolic disorder is hepatic steatosis. In other embodiments, the metabolic disorder is fatty liver disease. In some embodiments, the compound is an ACSS2 inhibitor. In some embodiments, the compound is selective to ACSS2. In some embodiments, the compound is selective to ACSS1. In some embodiments, the compound is selective to both ACSS2 and ACSS1. In some embodiments, the compound is selective to ACSS2, ACSS1, AACS, ACSF2 and ACSL5. In some embodiments, the compound is any one of the compounds listed in Table 1; each compound represents a separate embodiment according to this invention.

In various embodiments, this invention is directed to a method of treating, suppressing, reducing the severity, reducing the risk of developing or inhibiting obesity in a subject, comprising administering a compound of this invention, to a subject suffering from obesity under conditions effective to treat, suppress, reduce the severity, reduce the risk of developing, or inhibit the obesity in said subject. In some embodiments, the compound is an ACSS2 inhibitor. In some embodiments, the compound is selective to ACSS2. In some embodiments, the compound is selective to ACSS1. In some embodiments, the compound is selective to both ACSS2 and ACSS1. In some embodiments, the compound is selective to ACSS2, ACSS1, AACS, ACSF2 and ACSL5. In some embodiments, the compound is any one of the compounds listed in Table 1; each compound represents a separate embodiment according to this invention.

In various embodiments, this invention is directed to a method of treating, suppressing, reducing the severity, reducing the risk of developing or inhibiting weight gain in a subject, comprising administering a compound of this invention, to a subject suffering from weight gain under conditions effective to treat, suppress, reduce the severity, reduce the risk of developing, or inhibit the weight gain in said subject. In some embodiments, the compound is an ACSS2 inhibitor. In some embodiments, the compound is selective to ACSS2. In some embodiments, the compound is selective to ACSS1. In some embodiments, the compound is selective to both ACSS2 and ACSS1. In some embodiments, the compound is selective to ACSS2, ACSS1, AACS, ACSF2 and ACSL5. In some embodiments, the compound is any one of the compounds listed in Table 1; each compound represents a separate embodiment according to this invention.

In various embodiments, this invention is directed to a method of treating, suppressing, reducing the severity, reducing the risk of developing or inhibiting hepatic steatosis in a subject, comprising administering a compound of this invention, to a subject suffering from hepatic steatosis under conditions effective to treat, suppress, reduce the severity, reduce the risk of developing, or inhibit the hepatic steatosis in said subject. In some embodiments, the compound is an ACSS2 inhibitor. In some embodiments, the compound is selective to ACSS2. In some embodiments, the compound is selective to ACSS1. In some embodiments, the compound is selective to both ACSS2 and ACSS1. In some embodiments, the compound is selective to ACSS2, ACSS1, AACS, ACSF2 and ACSL5. In some embodiments, the compound is any one of the compounds listed in Table 1; each compound represents a separate embodiment according to this invention.

In various embodiments, this invention is directed to a method of treating, suppressing, reducing the severity, reducing the risk of developing or inhibiting fatty liver disease in a subject, comprising administering a compound of this invention, to a subject suffering from fatty liver disease under conditions effective to treat, suppress, reduce the severity, reduce the risk of developing, or inhibit the fatty liver disease in said subject. In some embodiments, the compound is an ACSS2 inhibitor. In some embodiments, the compound is selective to ACSS2. In some embodiments, the compound is selective to ACSS1. In some embodiments, the compound is selective to both ACSS2 and ACSS1. In some embodiments, the compound is selective to ACSS2, ACSS1, AACS, ACSF2 and ACSL5. In some embodiments, the compound is any one of the compounds listed in Table 1; each compound represents a separate embodiment according to this invention.

ACSS2 is also shown to enter the nucleus under certain condition (hypoxia, high fat etc.) and to affect histone acetylation and crotonylation by making available acetyl-CoA and crotonyl-CoA and thereby regulate gene expression. For example, ACSS2 decrease is shown to lower levels of nuclear acetyl-CoA and histone acetylation in neurons affecting the expression of many neuronal genes. In the hippocampus such redIt was found that uctions in ACSS2 lead to effects on memory and neuronal plasticity (Mews P, et al., Nature, Vol 546, 381, 2017). Such epigenetic modifications are implicated in neuropsychiatric diseases such as anxiety, PTSD, depression etc. (Graff, J et al. Histone acetylation: molecular mnemonics on chromatin. Nat Rev. Neurosci. 14, 97-111 (2013)). Thus, an inhibitor of ACSS2 may find useful application in these conditions.

Accordingly, in various embodiments, this invention is directed to a method of treating, suppressing, reducing the severity, reducing the risk of developing or inhibiting neuropsychiatric disease or disorder in a subject, comprising administering a compound of this invention, to a subject suffering from neuropsychiatric disease or disorder under conditions effective to treat, suppress, reduce the severity, reduce the risk of developing, or inhibit the neuropsychiatric disease or disorder in said subject. In some embodiments, the neuropsychiatric disease or disorder is selected from: anxiety, depression, schizophrenia, autism and/or or post-traumatic stress disorder; each represents a separate embodiment according to this invention. In some embodiments, the compound is an ACSS2 inhibitor. In some embodiments, the compound is selective to ACSS2. In some embodiments, the compound is selective to ACSS1. In some embodiments, the compound is selective to both ACSS2 and ACSS1. In some embodiments, the compound is selective to ACSS2, ACSS1, AACS, ACSF2 and ACSL5. In some embodiments, the compound is any one of the compounds listed in Table 1; each compound represents a separate embodiment according to this invention.

In various embodiments, this invention is directed to a method of treating, suppressing, reducing the severity, reducing the risk of developing or inhibiting anxiety in a subject, comprising administering a compound of this invention, to a subject suffering from anxiety under conditions effective to treat, suppress, reduce the severity, reduce the risk of developing, or inhibit the anxiety in said subject. In some embodiments, the compound is an ACSS2 inhibitor. In some embodiments, the compound is selective to ACSS2. In some embodiments, the compound is selective to ACSS1. In some embodiments, the compound is selective to both ACSS2 and ACSS1. In some embodiments, the compound is selective to ACSS2, ACSS1, AACS, ACSF2 and ACSL5. In some embodiments, the compound is any one of the compounds listed in Table 1; each compound represents a separate embodiment according to this invention.

In various embodiments, this invention is directed to a method of treating, suppressing, reducing the severity, reducing the risk of developing or inhibiting depression disorder in a subject, comprising administering a compound of this invention, to a subject suffering from depression under conditions effective to treat, suppress, reduce the severity, reduce the risk of developing, or inhibit the depression in said subject. In some embodiments, the compound is an ACSS2 inhibitor. In some embodiments, the compound is selective to ACSS2. In some embodiments, the compound is selective to ACSS1. In some embodiments, the compound is selective to both ACSS2 and ACSS1. In some embodiments, the compound is selective to ACSS2, ACSS1, AACS, ACSF2 and ACSL5. In some embodiments, the compound is any one of the compounds listed in Table 1; each compound represents a separate embodiment according to this invention.

In various embodiments, this invention is directed to a method of treating, suppressing, reducing the severity, reducing the risk of developing or inhibiting post-traumatic stress disorder disorder in a subject, comprising administering a compound of this invention, to a subject suffering from post-traumatic stress disorder under conditions effective to treat, suppress, reduce the severity, reduce the risk of developing, or inhibit the post-traumatic stress disorder in said subject. In some embodiments, the compound is an ACSS2 inhibitor. In some embodiments, the compound is selective to ACSS2. In some embodiments, the compound is selective to ACSS1. In some embodiments, the compound is selective to both ACSS2 and ACSS1. In some embodiments, the compound is selective to ACSS2, ACSS1, AACS, ACSF2 and ACSL5. In some embodiments, the compound is any one of the compounds listed in Table 1; each compound represents a separate embodiment according to this invention.

In some embodiments, this invention is directed to a method of treating, suppressing, reducing the severity, reducing the risk of developing or inhibiting inflammatory condition in a subject, comprising administering a compound of this invention, to a subject suffering from inflammatory condition under conditions effective to treat, suppress, reduce the severity, reduce the risk of developing, or inhibit the inflammatory condition in said subject. In some embodiments, the compound is an ACSS2 inhibitor. In some embodiments, the compound is selective to ACSS2. In some embodiments, the compound is selective to ACSS1. In some embodiments, the compound is selective to both ACSS2 and ACSS1. In some embodiments, the compound is selective to ACSS2, ACSS1, AACS, ACSF2 and ACSL5. In some embodiments, the compound is any one of the compounds listed in Table 1; each compound represents a separate embodiment according to this invention.

In some embodiments, this invention is directed to a method of treating, suppressing, reducing the severity, reducing the risk of developing or inhibiting an autoimmune disease or disorder in a subject, comprising administering a compound of this invention, to a subject suffering from an autoimmune disease or disorder under conditions effective to treat, suppress, reduce the severity, reduce the risk of developing, or inhibit the autoimmune disease or disorder in said subject. In some embodiments, the compound is an ACSS2 inhibitor. In some embodiments, the compound is selective to ACSS2. In some embodiments, the compound is selective to ACSS1. In some embodiments, the compound is selective to both ACSS2 and ACSS1. In some embodiments, the compound is selective to ACSS2, ACSS1, AACS, ACSF2 and ACSL5. In some embodiments, the compound is any one of the compounds listed in Table 1; each compound represents a separate embodiment according to this invention.

As used herein, subject or patient refers to any mammalian patient, including without limitation, humans and other primates, dogs, cats, horses, cows, sheep, pigs, rats, mice, and other rodents. In various embodiments, the subject is male. In some embodiments, the subject is female. In some embodiments, while the methods as described herein may be useful for treating either males or females.

When administering the compounds of the present invention, they can be administered systemically or, alternatively, they can be administered directly to a specific site where cancer cells or precancerous cells are present. Thus, administering can be accomplished in any manner effective for delivering the compounds or the pharmaceutical compositions to the cancer cells or precancerous cells. Exemplary modes of administration include, without limitation, administering the compounds or compositions orally, topically, transdermally, parenterally, subcutaneously, intravenously, intramuscularly, intraperitoneally, by intranasal instillation, by intracavitary or intravesical instillation, intraocularly, intraarterially, intralesionally, or by application to mucous membranes, such as, that of the nose, throat, and bronchial tubes.

The following examples are presented in order to more fully illustrate the preferred embodiments of the invention. They should in no way, however, be construed as limiting the broad scope of the invention.

EXAMPLES

Example 1

Figure 2:
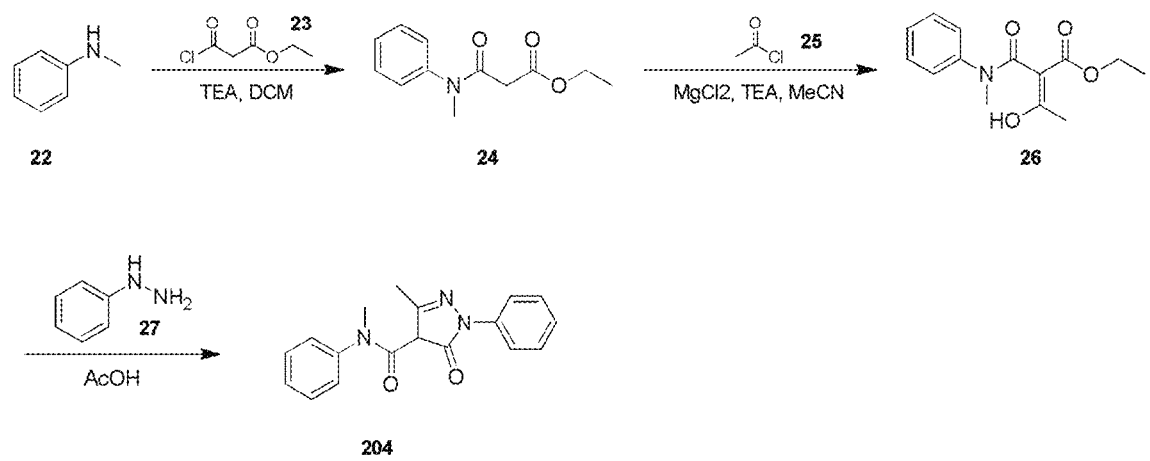
FIG. 2 depicts a synthetic scheme for compound 204.
Figure 3:
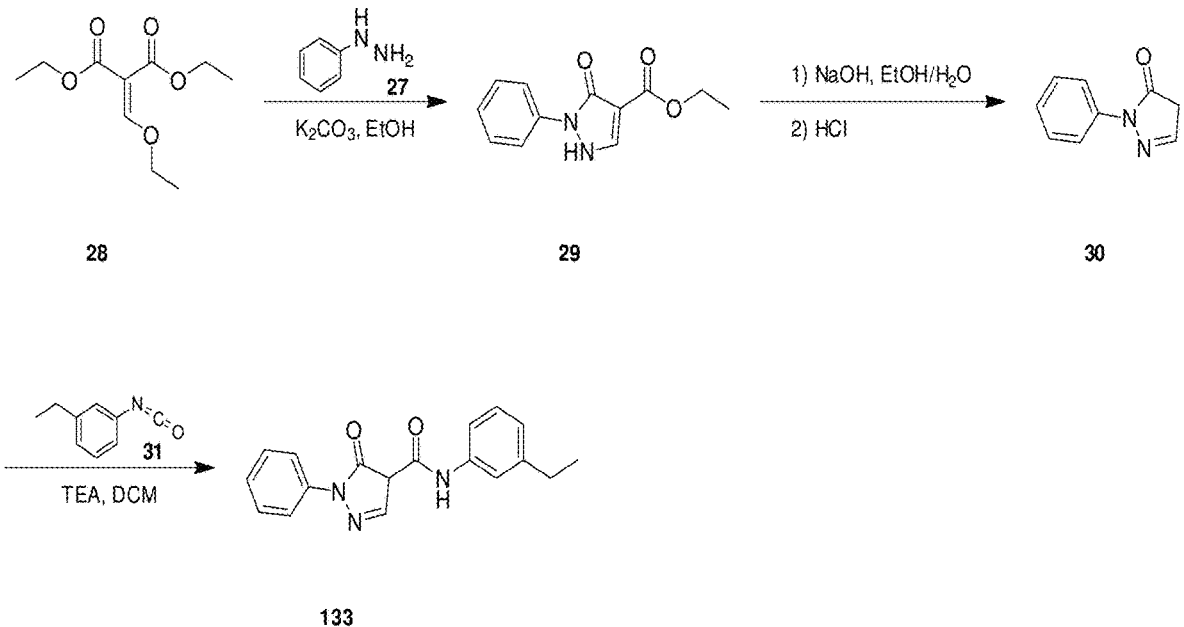
FIG. 3 depicts a synthetic scheme for compound 133.

Synthetic Details for Compounds of the Invention (FIGS. 1-3)

Experimental Procedure:
General Procedure I: Synthesis of Hydrazine 2

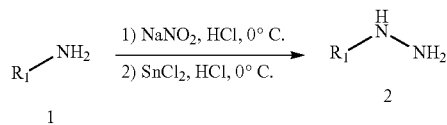

To a round-bottom flask equipped with a magnetic stir bar were added amine 1 (1.0 eq), water and hydrochloride acid (12 M, 10 eq). Then a saturated solution of sodium nitrite (1.2 eq) in water was added into the previous solution at 0° C. The mixture was stirred at 0~5° C. for 0.5 h. Then a solution of tin(II) chloride dihydrate (2.2 eq) in hydrochloride acid (12 M, 15.0 eq) was added at 0-5° C. dropwise. The mixture was stirred at 5° C. for 0.5 h. The resulting precipitate was collected by filtration to afford 2 as hydrochloride. Sometimes, the hydrazine was dissolved in water and needed to be extracted from the aqueous layer after neutralized the reaction solution.

General Procedure II: The General Synthesis of Pyrazol 4

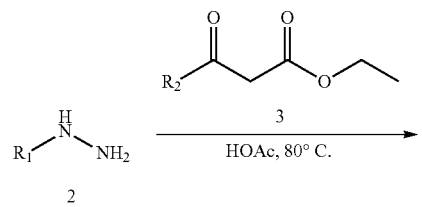

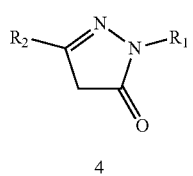

To a round-bottom flask equipped with a magnetic stir bar was added compound 3 (1.0 eq) followed by the addition of acetic acid. Then compound 2 (1.0 eq) was added into the mixture. The mixture was stirred at 80° C. under an atmosphere of nitrogen for 3~10 h. The solution was concentrated and the residue was triturated with ethyl acetate or ethanol to give compound 4.

General Procedure III: The General Synthesis of Active Ester 6

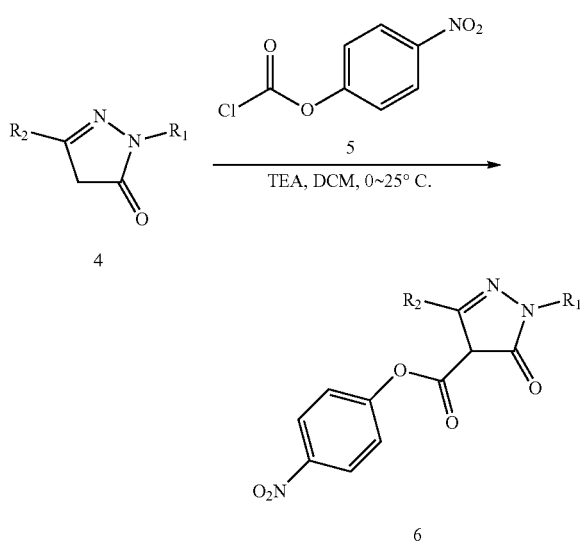

To a round-bottom flask equipped with a magnetic stir bar were added compound 4 (1.0 eq) and dichloromethane. Then triethylamine (2.0 eq) was added to the solution and the reaction mixture was stirred at 25° C. for 0.5 h. Compound 5 (1.0 eq) was added and the solution was stirred at 25° C. for 2.5 h under an atmosphere of nitrogen. The reaction solution was concentrated in vacuum to give compound 6 which was used directly for next step.

General Procedure IV: The General Synthesis of Final Compounds 100-592—(Method 1)

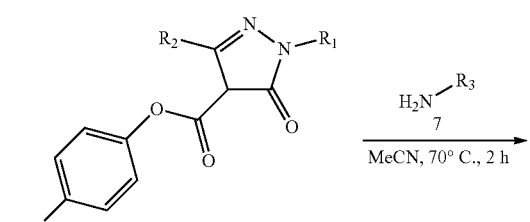

To a round-bottom flask equipped with a magnetic stir bar was added compound 6 (1.80 eq) in acetonitrile. Then benzotriazol-1-ol (2.0 eq), amine 7 (1.0 eq) and diisopropylethylamine (3.0 eq) were added. The mixture was stirred at 70° C. for 2 h before concentrated. The residue was purified by prep-HPLC to afford target compounds.

General Procedure V: The General Synthesis of Final Compounds 100-592—(Method 2)

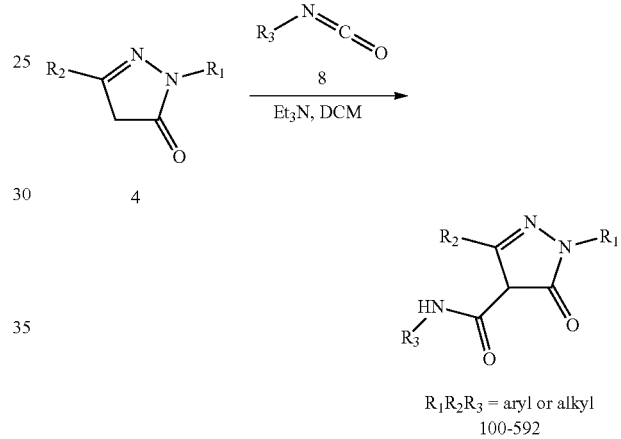

To a solution of compound 4 (1.0 eq) in dichloromethane (1~10 mL) was added triethylamine (2.0 eq) with stirring. Compound 8 (1.00 eq) was added and the mixture was stirred at 20° C. for 10 h. The reaction mixture was concentrated under vacuum, and the residue was purified by prep-HPLC to give the target compounds.

Compounds were synthesized according to the general schemes outlined above unless disclosed otherwise.

Synthetic Details and Analytical Data for Compound of the Invention

N-(3-hydroxyphenyl)-3-methyl-5-oxo-1-phenyl-4H-pyrazole-4-carboxamide

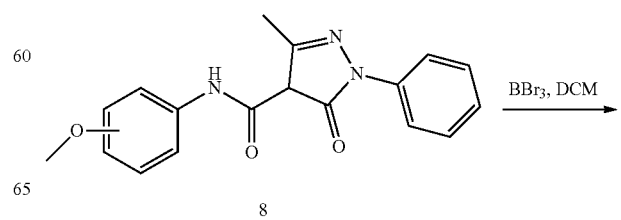

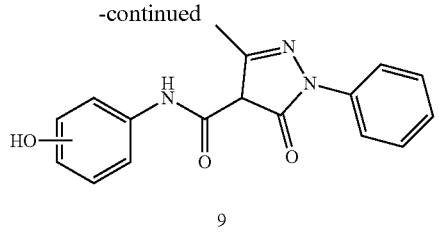

To a solution of N-(3-methoxyphenyl)-3-methyl-5-oxo-1-phenyl-4H-pyrazole-4-carboxamide (45 mg, 139.17 umol, 1.00 eq) in DCM (5 mL) was added BBr$_3$ (348 mg, 1.39 mmol, 10.00 eq) at 0° C. The mixture was stirred at 20° C. for 30 hours. It was quenched with MeOH (50 mL), and concentrated in vacuum. The residue was purified by prep-HPLC (column: Luna C18 150*25 5u; mobile phase: [water (0.225% FA)-ACN]; B %: 22%-49%, 10 min). N-(3-hydroxyphenyl)-3-methyl-5-oxo-1-phenyl-4H-pyrazole-4-carboxamide (15 mg, 48.13 umol, 34.59% yield, 99.26% purity) was obtained as a white solid.

N-(3-isopropylphenyl)-3-methyl-5-oxo-1-phenyl-4,5-dihydro-1H-pyrazole-4-carboxamide Compound ID: 100

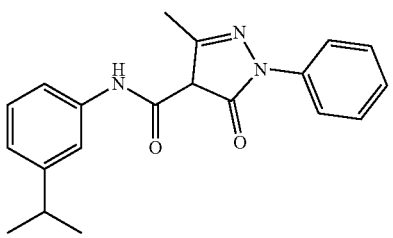 [SMILES: CC1=NN(c2ccccc2)C(=O)C1C(=O)Nc1cccc(C(C)C)c1]

LCMS: m/z 336.1 [M+H]$^+$;
$^1$H NMR (400 MHz, DMSO-d$_6$) δ 10.68 (s, 1H), 7.74 (d, J=7.6 Hz, 2H), 7.56-7.41 (m, 4H), 7.37-7.29 (m, 1H), 7.23 (t, J=7.6 Hz, 1H), 6.92 (d, J=8.0 Hz, 1H), 2.95-2.80 (m, 1H), 2.55 (s, 3H), 1.21 (d, J=6.8 Hz, 6H).

3-methyl-5-oxo-1-phenyl-N-(3-(thiophen-2-yl)phenyl)-4,5-dihydro-1H-pyrazole-4-carboxamide Compound ID: 101

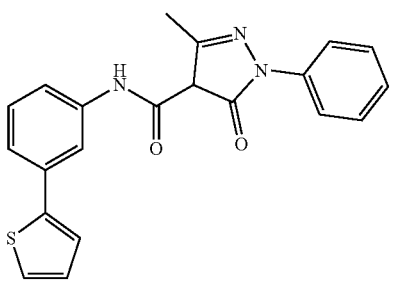 [SMILES: CC1=NN(c2ccccc2)C(=O)C1C(=O)Nc1cccc(-c2cccs2)c1]

LCMS: m/z 376.2 [M+H]$^+$;
$^1$H NMR (400 MHz, DMSO-d$_6$) δ 10.81 (s, 1H), 8.03 (s, 1H), 7.74 (d, J=7.6 Hz, 2H), 7.58-7.45 (m, 5H), 7.37-7.29 (m, 3H), 7.14 (dd, J=4.0, 5.2 Hz, 1H), 2.56 (s, 3H).

N-([1,1'-biphenyl]-3-yl)-3-methyl-5-oxo-1-phenyl-4,5-dihydro-1H-pyrazole-4-carboxamide Compound ID: 102

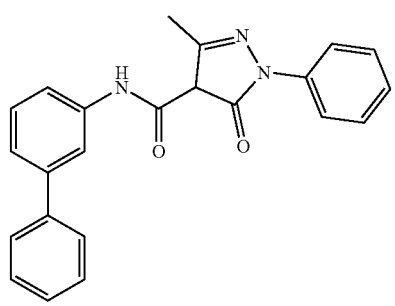 [SMILES: CC1=NN(c2ccccc2)C(=O)C1C(=O)Nc1cccc(-c2ccccc2)c1]

LCMS: m/z 370.1 [M+H]$^+$;
$^1$H NMR (400 MHz, DMSO-d$_6$) δ 10.84 (s, 1H), 7.99 (s, 1H), 7.75 (d, J=7.7 Hz, 2H), 7.65 (d, J=7.4 Hz, 2H), 7.56 (d, J=8.8 Hz, 1H), 7.54-7.45 (m, 4H), 7.43-7.35 (m, 2H), 7.34-7.28 (m, 2H), 2.55 (s, 3H)

N-(3-(methoxymethyl)phenyl)-3-methyl-5-oxo-1-phenyl-4,5-dihydro-1H-pyrazole-4-carboxamide Compound ID: 103

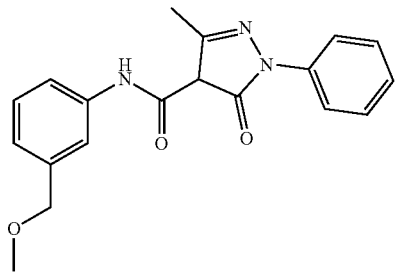 [SMILES: COCc1cccc(NC(=O)C2C(=O)N(c3ccccc3)N=C2C)c1]

LCMS: m/z 338.2 [M+H]$^+$;
$^1$H NMR (400 MHz, DMSO-d$_6$) δ 11.18 (s, 1H), 8.13 (s, 1H), 8.06 (s, 2H), 7.60 (s, 1H), 7.49 (d, J=8.0 Hz, 1H), 7.30 (s, 2H), 7.20 (t, J=7.6 Hz, 1H), 7.00 (s, 1H), 6.84 (d, J=7.6 Hz, 1H), 4.37 (s, 2H), 3.29 (s, 3H), 2.28 (s, 3H).

3-methyl-5-oxo-1-phenyl-N-(3-(pyridin-4-yl)phenyl)-4,5-dihydro-1H-pyrazole-4-carboxamide Compound ID: 104

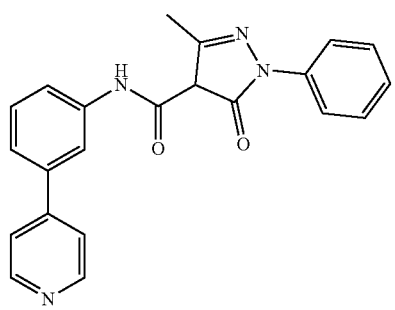 [SMILES: CC1=NN(c2ccccc2)C(=O)C1C(=O)Nc1cccc(-c2ccncc2)c1]

LCMS: m/z 371.3 [M+H]$^+$;
$^1$H NMR (400 MHz, DMSO-d$_6$) δ 10.99 (s, 1H), 8.71 (d, J=5.2 Hz, 2H), 8.16 (d, J=13.8 Hz, 1H), 7.88-7.78 (m, 4H), 7.77-7.65 (m, 1H), 7.53-7.45 (m, 4H), 7.27 (t, J=7.2 Hz, 1H), 2.49 (s, 3H).

N-(3-(aminomethyl)phenyl)-3-methyl-5-oxo-1-phenyl-4,5-dihydro-1H-pyrazole-4-carboxamide Compound ID: 223

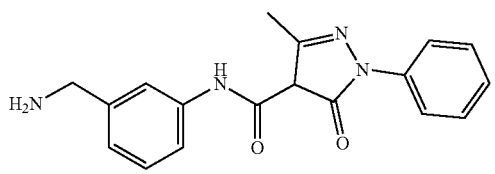 [SMILES: CC1=NN(c2ccccc2)C(=O)C1C(=O)Nc1cccc(CN)c1]

LCMS: m/z 323.2 [M+H]$^+$;

$^1$H NMR (400 MHz, DMSO-d$_6$) δ 10.81 (s, 1H), 8.35 (br s, 2H), 7.80-7.75 (m, 2H), 7.75-7.69 (m, 2H), 7.52 (t, J=8.0 Hz, 2H), 7.41-7.29 (m, 2H), 7.15 (d, J=7.6 Hz, 1H), 4.00 (d, J=5.6 Hz, 2H), 2.57 (s, 3H).

N-(4-(N,N-dimethylsulfamoyl)phenyl)-3-methyl-5-oxo-1-phenyl-4,5-dihydro-1H-pyrazole-4-carboxamide Compound ID: 105

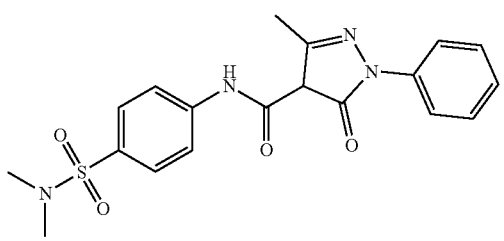 [SMILES: CC1=NN(c2ccccc2)C(=O)C1C(=O)Nc1ccc(S(=O)(=O)N(C)C)cc1]

LCMS: m/z 401.2 [M+H]$^+$;

$^1$H NMR (400 MHz, METHANOL-d$_4$) δ 8.16 (s, 1H), 7.87 (d, J=8.8 Hz, 2H), 7.77 (d, J=7.8 Hz, 2H), 7.71 (d, J=8.8 Hz, 2H), 7.43 (t, J=8.0 Hz, 2H), 7.27-7.18 (m, 1H), 2.68 (s, 6H), 2.47 (s, 3H).

3-methyl-5-oxo-1-phenyl-N-(tetrahydrofuran-3-yl)-4,5-dihydro-1H-pyrazole-4-carboxamide Compound ID: 106

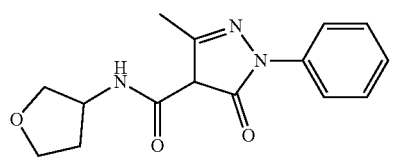 [SMILES: CC1=NN(c2ccccc2)C(=O)C1C(=O)NC1CCOC1]

LCMS: m/z 288.1 [M+H]$^+$;

$^1$H NMR (400 MHz, DMSO-d$_6$) δ 8.62 (br s, 1H), 7.71 (d, J=7.6 Hz, 2H), 7.48 (t, J=7.6 Hz, 2H), 7.28 (t, J=7.6 Hz, 1H), 4.43 (s, 1H), 3.85-3.77 (m, 2H), 3.76-3.69 (m, 1H), 3.49 (dd, J=3.6, 8.8 Hz, 1H), 2.47 (s, 3H), 2.23-2.13 (m, 1H), 1.78-1.68 (m, 1H)

N-(3-(1H-imidazol-2-yl)phenyl)-3-methyl-5-oxo-1-phenyl-4,5-dihydro-1H-pyrazole-4-carboxamide Compound ID: 107

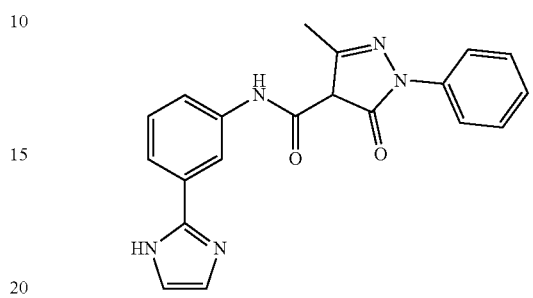

LCMS: m/z 360.1 [M+H]$^+$;

$^1$H NMR (400 MHz, METHANOL-d$_4$) δ 8.19 (s, 1H), 7.83-7.74 (d, J=8.4 Hz, 3H), 7.57-7.49 (m, 4H), 7.43 (t, J=7.6 Hz, 2H), 7.22 (t, J=7.2 Hz, 1H), 2.47 (s, 3H)

N-(3-(furan-2-yl)phenyl)-3-methyl-5-oxo-1-phenyl-4,5-dihydro-1H-pyrazole-4-carboxamide Compound ID: 108

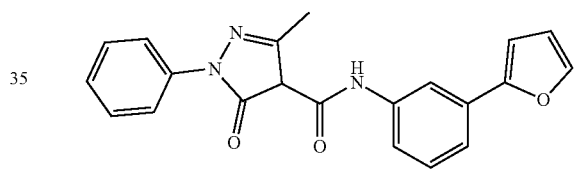

LCMS: m/z 360.2 [M+H]$^+$;

$^1$H NMR (400 MHz, DMSO-d$_6$) δ 10.82 (s, 1H), 8.10-7.96 (m, 1H), 7.86-7.67 (m, 3H), 7.61-7.43 (m, 3H), 7.41-7.34 (m, 2H), 7.33-7.27 (m, 1H), 6.94 (d, J=3.2 Hz, 1H), 6.60 (dd, J=1.6, 3.2 Hz, 1H), 2.54 (s, 3H)

3-methyl-5-oxo-1-phenyl-N-(3-(pyrazin-2-yl)phenyl)-4,5-dihydro-1H-pyrazole-4-carboxamide Compound ID: 109

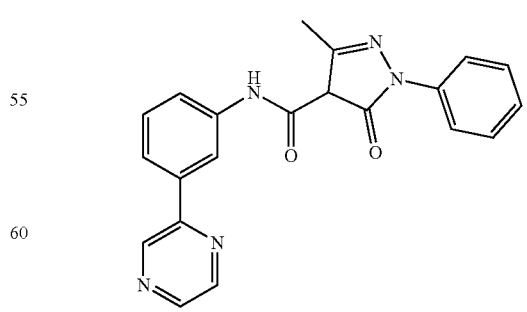

LCMS: m/z 372.1 [M+H]$^+$;

$^1$H NMR (400 MHz, DMSO-d$_6$) δ 10.86 (s, 1H), 9.24 (d, J=1.6 Hz, 1H), 8.74-8.73 (m, 1H), 8.63 (d, J=2.4 Hz, 1H), 8.44 (t, J=2.0 Hz, 1H), 7.81 (d, J=7.6 Hz, 1H), 7.77-7.73 (m, 3H), 7.56-7.47 (m, 3H), 7.34 (t, J=7.6 Hz, 1H), 2.58 (s, 3H).

1-(4-(N,N-dimethylsulfamoyl)phenyl)-3-methyl-5-oxo-N-phenyl-4,5-dihydro-1H-pyrazole-4-carboxamide Compound ID: 110

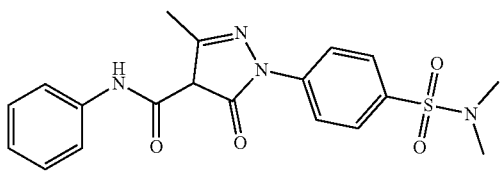 [SMILES: CC1=NN(c2ccc(S(=O)(=O)N(C)C)cc2)C(=O)C1C(=O)Nc1ccccc1]

LCMS: m/z 401.2 [M+H]$^+$;
$^1$H NMR (400 MHz, DMSO-d$_6$) δ=11.00 (s, 1H), 8.39 (d, J=8.8 Hz, 2H), 7.66 (d, J=8.8 Hz, 2H), 7.59 (d, J=7.6 Hz, 2H), 7.23 (t, J=7.6 Hz, 2H), 6.89 (t, J=7.2 Hz, 1H), 2.58 (s, 6H), 2.27 (s, 3H).

N-(3-(hydroxymethyl)phenyl)-3-methyl-5-oxo-1-phenyl-4,5-dihydro-1H-pyrazole-4-carboxamide Compound ID: 111

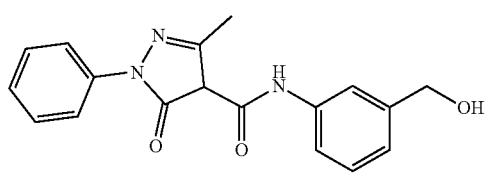 [SMILES: CC1=NN(c2ccccc2)C(=O)C1C(=O)Nc1cccc(CO)c1]

LCMS: m/z 324.1 [M+H]$^+$;
$^1$H NMR (400 MHz, DMSO-d$_6$) δ 10.69 (s, 1H), 7.72 (d, J=7.6 Hz, 2H), 7.57-7.54 (m, 1H), 7.52-7.50 (m, 3H), 7.34-7.25 (m, 1H), 7.25-7.23 (m, 1H), 6.98 (d, J=7.6 Hz, 1H), 4.48 (s, 2H), 2.55 (s, 3H).

3-methyl-5-oxo-1-phenyl-N-(tetrahydro-2H-pyran-4-yl)-4,5-dihydro-1H-pyrazole-4-carboxamide Compound ID: 112
LCMS: m/z 302.2 [M+H]$^+$;
$^1$H NMR (400 MHz, DMSO-d$_6$) δ 8.47 (s, 1H), 7.75 (d, J=8.0 Hz, 2H), 7.44 (t, J=7.6 Hz, 2H), 7.23 (t, J=7.2 Hz, 1H), 3.96-3.92 (m, 1H), 3.83-3.80 (m, 2H), 3.41 (t, J=10.4 Hz, 2H), 2.43 (s, 3H), 1.80 (d, J=10.8 Hz, 2H), 1.45-1.37 (m, 2H).

Ethyl 3-(3-methyl-5-oxo-1-phenyl-4,5-dihydro-1H-pyrazole-4-carboxamido)benzoate

Compound ID: 113

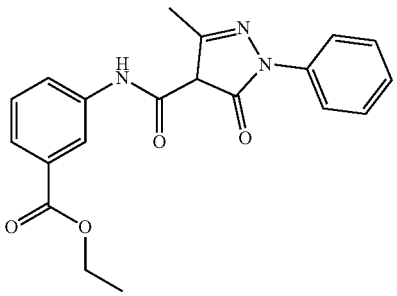 [SMILES: CCOC(=O)c1cccc(NC(=O)C2C(=O)N(c3ccccc3)N=C2C)c1]

LCMS: m/z 366.2 [M+H]$^+$;
$^1$H NMR (400 MHz, DMSO-d$_6$) δ 10.94 (s, 1H), 8.31 (t, J=2.0 Hz, 1H), 7.81-7.76 (m, 3H), 7.62 (d, J=7.6 Hz, 1H), 7.52-7.43 (m, 3H), 7.29 (t, J=7.6 Hz, 1H), 4.33 (q, J=7.2 Hz, 2H), 2.52 (s, 3H), 1.38 (t, J=7.2 Hz, 3H).

N-(3-butyrylphenyl)-3-methyl-5-oxo-1-phenyl-4,5-dihydro-1H-pyrazole-4-carboxamide Compound ID: 114

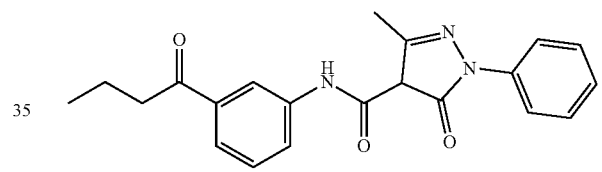

LCMS: m/z 364.1 [M+H]$^+$;
$^1$H NMR (400 MHz, DMSO-d$_6$) δ 10.93 (s, 1H), 8.25 (t, J=1.6 Hz, 1H), 7.82 (dd, J=1.2, 8.0 Hz, 3H), 7.62 (d, J=8.0 Hz, 1H), 7.51-7.44 (m, 3H), 7.32-7.26 (m, 1H), 2.99 (t, J=7.2 Hz, 2H), 2.52 (s, 3H), 1.64 (q, J=7.2 Hz, 2H), 0.94 (t, J=8.0 Hz, 3H).

N-(3-(tert-butyl)phenyl)-3-methyl-5-oxo-1-phenyl-4,5-dihydro-1H-pyrazole-4-carboxamide Compound ID: 115

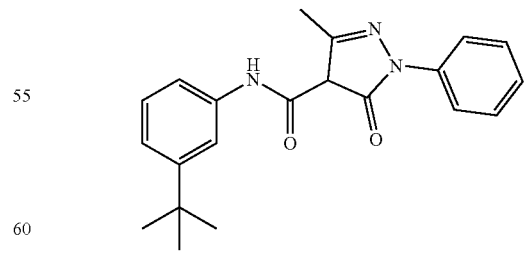

LCMS: m/z 350.3 [M+H]$^+$;
$^1$H NMR (400 MHz, DMSO-d$_6$) δ 10.72 (s, 1H), 7.76 (d, J=7.6 Hz, 2H), 7.58 (s, 1H), 7.50-7.45 (m, 3H), 7.27-7.21 (m, 1H), 7.20 (t, J=7.6 Hz, 1H), 7.03 (d, J=7.6 Hz, 1H), 2.49 (s, 3H), 1.27 (s, 9H).

3-(3-methyl-5-oxo-1-phenyl-4,5-dihydro-1H-pyrazole-4-carboxamido)benzoic acid Compound ID: 116

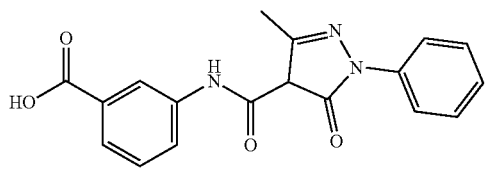 [SMILES: CC1=NN(c2ccccc2)C(=O)C1C(=O)Nc1cccc(C(=O)O)c1]

LCMS: m/z 338.2 [M+H]$^+$;

$^1$H NMR (400 MHz, DMSO-d$_6$) δ 13.12 (s, 1H), 10.84 (s, 1H), 8.31 (s, 1H), 7.79-7.70 (m, 3H), 7.64-7.59 (m, 1H), 7.57-7.49 (m, 2H), 7.44 (s, 1H), 7.33 (s, 1H), 2.56 (s, 3H).

3-methyl-5-oxo-1-phenyl-N-(3-propionylphenyl)-4,5-dihydro-1H-pyrazole-4-carboxamide Compound ID: 117

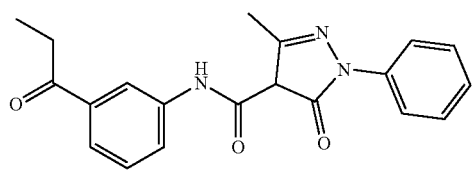 [SMILES: CCC(=O)c1cccc(NC(=O)C2C(=O)N(c3ccccc3)N=C2C)c1]

LCMS: m/z 350.2 [M+H]$^+$;

$^1$H NMR (400 MHz, DMSO-d$_6$) δ 10.86 (s, 1H), 8.21 (d, J=1.6 Hz, 1H), 7.80 (d, J=7.6 Hz, 1H), 7.74 (d, J=7.6 Hz, 2H), 7.60 (d, J=8.0 Hz, 1H), 7.49 (t, J=7.6 Hz, 2H), 7.44-7.42 (d, J=8.0 Hz, 1H), 7.26 (d, J=7.6 Hz, 1H), 3.05 (q, J=7.2 Hz, 2H), 2.54 (s, 3H), 1.10 (t, J=7.2 Hz, 3H).

3-methyl-5-oxo-N-(3-pentylphenyl)-1-phenyl-4,5-dihydro-1H-pyrazole-4-carboxamide Compound ID: 118

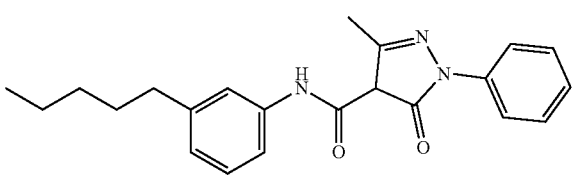 [SMILES: CCCCCc1cccc(NC(=O)C2C(=O)N(c3ccccc3)N=C2C)c1]

LCMS: m/z 364.3 [M+H]$^+$;

$^1$H NMR (400 MHz, DMSO-d$_6$) δ=10.66 (s, 1H), 7.74 (d, J=8.0 Hz, 2H), 7.52-7.51 (m, 2H), 7.51-7.49 (m, 2H), 7.45-7.43 (m, 1H), 7.24-7.15 (t, J=6.8 Hz, 1H), 6.88-6.81 (J=7.2 Hz, 1H), 2.57-2.52 (m, 5H), 1.62-1.51 (m, 2H), 1.35-1.23 (m, 4H), 0.86 (s, 3H).

N-(3-cyclopropylphenyl)-3-methyl-5-oxo-1-phenyl-4,5-dihydro-1H-pyrazole-4-carboxamide Compound ID: 119

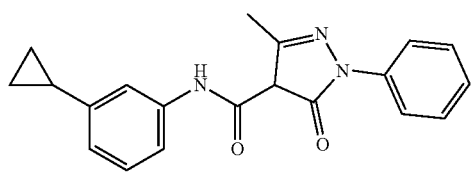 [SMILES: CC1=NN(c2ccccc2)C(=O)C1C(=O)Nc1cccc(C2CC2)c1]

LCMS: m/z 334.2 [M+H]$^+$;

$^1$H NMR (400 MHz, DMSO-d$_6$) δ 10.64 (s, 1H), 7.73 (d, J=7.6 Hz, 2H), 7.54-7.49 (m, 2H), 7.36-7.32 (m, 3H), 7.17 (t, J=8.0 Hz, 1H), 6.75 (d, J=7.6 Hz, 1H), 2.54 (s, 3H), 1.90-1.89 (m, 1H), 0.95-0.92 (m, 2H), 0.66-0.64 (m, 2H).

4-(4-((3-acetylphenyl)carbamoyl)-3-methyl-5-oxo-4,5-dihydro-1H-pyrazol-1-yl)benzoic acid Compound ID: 120

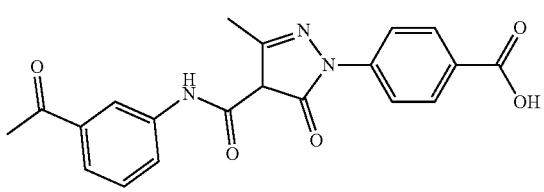 [SMILES: CC(=O)c1cccc(NC(=O)C2C(=O)N(c3ccc(C(=O)O)cc3)N=C2C)c1]

LCMS: m/z 380.2 [M+H]$^+$;

$^1$H NMR (400 MHz, METHANOL-d$_4$) δ 8.35 (s, 1H), 8.09-8.01 (m, 4H), 7.83-7.81 (m, 1H), 7.67 (d, J=4.4 Hz, 1H), 7.47-7.44 (m, 1H), 2.62 (s, 3H), 2.53 (s, 3H).

3-methyl-5-oxo-1-phenyl-N-(4-piperidyl)-4H-pyrazole-4-carboxamide

Compound ID: 121

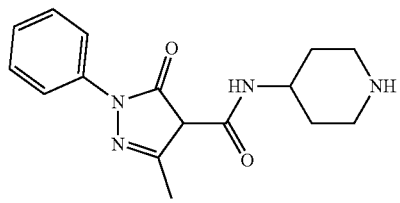 [SMILES: CC1=NN(c2ccccc2)C(=O)C1C(=O)NC1CCNCC1]

LCMS: m/z 301.2 [M+H]$^+$;

$^1$H NMR (400 MHz, METHANOL-d$_4$) δ=8.36 (s, 1H), 7.73 (d, J=8.0 Hz, 2H), 7.40 (t, J=7.6 Hz, 2H), 7.28-7.05 (m, 1H), 4.24-3.98 (m, 1H), 3.40-3.34 (m, 2H), 3.18-3.07 (m, 2H), 2.40 (s, 3H), 2.25-2.06 (m, 2H), 1.87-1.64 (m, 2H)

3-methyl-5-oxo-N-(3-oxo-1,3-dihydroisobenzofuran-5-yl)-1-phenyl-4,5-dihydro-1H-pyrazole-4-carboxamide Compound ID: 122

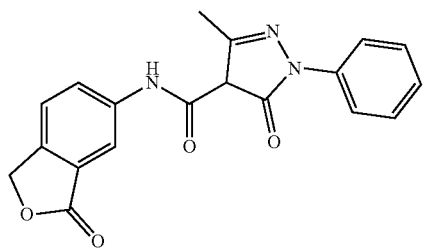 [SMILES: CC1=NN(c2ccccc2)C(=O)C1C(=O)Nc1ccc2c(c1)C(=O)OC2]

LCMS: m/z 350.0 [M+H]$^+$;
$^1$H NMR (400 MHz, DMSO-d$_6$) δ=10.99 (s, 1H), 8.37 (s, 1H), 7.80-7.77 (m, 3H), 7.75-7.69 (m, 1H), 7.54-7.49 (m, 2H), 7.38-7.31 (m, 1H), 5.36 (s, 2H), 2.54 (s, 3H).

3-(4-((3-acetylphenyl)carbamoyl)-3-methyl-5-oxo-4,5-dihydro-1H-pyrazol-1-yl)benzoic acid Compound ID: 123

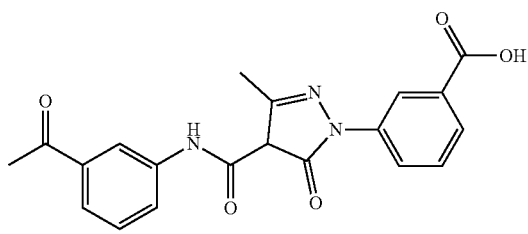 [SMILES: CC(=O)c1cccc(NC(=O)C2C(=O)N(c3cccc(C(=O)O)c3)N=C2C)c1]

LCMS: m/z 380.0 [M+H]$^+$;
$^1$H NMR (400 MHz, DMSO-d$_6$) δ 10.82 (s, 1H), 8.38 (s, 1H), 8.26 (t, J=2.0 Hz, 1H), 8.10-8.04 (m, 1H), 7.85 (d, J=8.0 Hz, 2H), 7.64-7.62 (m, 2H), 7.47 (d, J=8.0 Hz, 1H), 2.59 (s, 3H), 2.56 (s, 3H)

3-methyl-N-(3-(oxazol-2-yl)phenyl)-5-oxo-1-phenyl-4,5-dihydro-1H-pyrazole-4-carboxamide Compound ID: 124

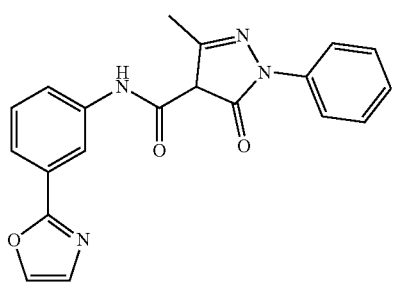 [SMILES: CC1=NN(c2ccccc2)C(=O)C1C(=O)Nc1cccc(-c2ncco2)c1]

LCMS: m/z 361.1 [M+H]$^+$;
$^1$H NMR (400 MHz, DMSO-d$_6$) δ 10.95 (s, 1H), 8.47 (s, 1H), 8.23 (s, 1H), 7.78 (d, J=8.0 Hz, 2H), 7.62 (dd, J=7.6, 18.4 Hz, 2H), 7.53-7.44 (m, 3H), 7.39 (s, 1H), 7.32-7.26 (m, 1H), 2.53 (s, 3H)

N-(3-ethylphenyl)-3-methyl-5-oxo-1-(pyridin-4-yl)-4,5-dihydro-1H-pyrazole-4-carboxamide Compound ID: 125

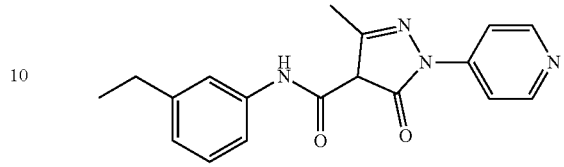

LCMS: m/z 323.1 [M+H]$^+$;
$^1$H NMR (400 MHz, METHANOL-d$_4$) δ 8.46-8.60 (m, 4H), 7.47 (s, 1H), 7.41 (d, J=8.0 Hz, 1H), 7.20 (t, J=8.0 Hz, 1H), 6.89 (d, J=7.6 Hz, 1H), 2.64 (q, J=7.6 Hz, 2H), 2.44 (s, 3H), 1.25 (t, J=7.6 Hz, 3H)

N-(3-ethylphenyl)-5-oxo-1,3-diphenyl-4,5-dihydro-1H-pyrazole-4-carboxamide

Compound ID: 126

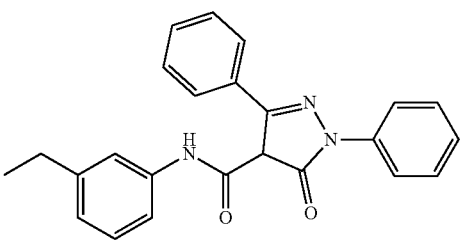 [SMILES: CCc1cccc(NC(=O)C2C(=O)N(c3ccccc3)N=C2c2ccccc2)c1]

LCMS: m/z 384.2 [M+H]$^+$;
$^1$H NMR (400 MHz, DMSO-d$_6$) δ 11.00-10.73 (s, 1H), 7.84 (d, J=7.6 Hz, 4H), 7.59-7.46 (m, 6H), 7.44-7.39 (m, 1H), 7.38-7.33 (m, 1H), 7.25-7.15 (m, 1H), 6.88 (d, J=8.0 Hz, 1H), 2.57 (d, J=7.6 Hz, 2H), 1.17 (t, J=7.6 Hz, 3H).

N-(3-ethylphenyl)-3-methyl-5-oxo-1-(4-(trifluoromethyl)phenyl)-4,5-dihydro-1H-pyrazole-4-carboxamide Compound ID: 127

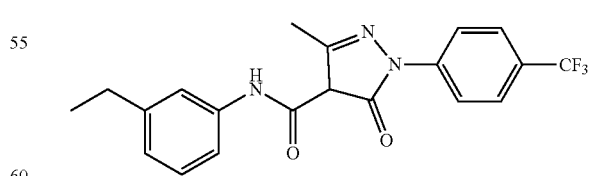

LCMS: m/z 390.2 [M+H]$^+$;
$^1$H NMR (400 MHz, CHLOROFORM-d) δ 7.83 (s, 2H), 7.65 (s, 2H), 7.39-7.29 (m, 2H), 7.22 (s, 1H), 6.98 (d, J=7.2 Hz, 1H), 2.62 (d, J=7.2 Hz, 2H), 2.54 (s, 3H), 1.22 (t, J=7.6 Hz, 3H).

231
N-(3-ethylphenyl)-3-isopropyl-5-oxo-1-phenyl-4,5-dihydro-1H-pyrazole-4-carboxamide Compound ID: 128

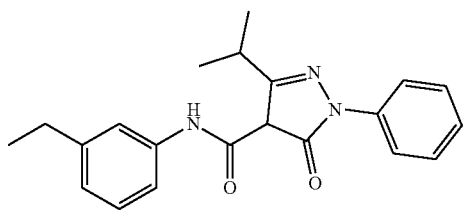 [SMILES: CCc1cccc(NC(=O)C2C(=O)N(c3ccccc3)N=C2C(C)C)c1]

LCMS: m/z 350.3 [M+H]⁺;
¹H NMR (400 MHz, DMSO-d₆) δ 10.90 (s, 1H), 7.67 (d, J=8.0 Hz, 2H), 7.53 (t, J=8.0 Hz, 2H), 7.47 (s, 1H), 7.42 (d, J=8.0 Hz, 1H), 7.34 (d, J=8.0 Hz, 1H), 7.20 (t, J=7.6 Hz, 1H), 6.88 (d, J=8.0 Hz, 1H), 3.95-3.91 (m, 1H), 2.59-2.51 (m, 2H), 1.32 (d, J=7.2 Hz, 6H), 1.18 (t, J=7.6 Hz, 3H).

3-benzyl-N-(3-ethylphenyl)-5-oxo-1-phenyl-4,5-dihydro-1H-pyrazole-4-carboxamide

Compound ID: 129

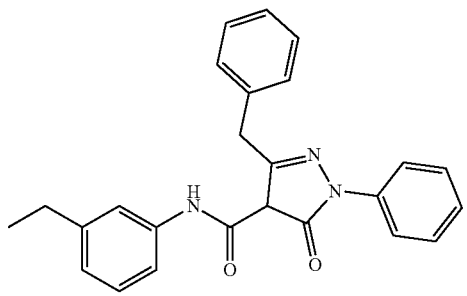 [SMILES: CCc1cccc(NC(=O)C2C(=O)N(c3ccccc3)N=C2Cc2ccccc2)c1]

LCMS: m/z 398.3 [M+H]⁺;
¹H NMR (400 MHz, DMSO-d₆) δ 10.74 (s, 1H), 7.72 (d, J=8.0 Hz, 2H), 7.54 (t, J=8.0 Hz, 2H), 7.45-7.43 (m, 4H), 7.43-7.41 (m, 3H), 7.34-7.32 (m, 2H), 6.88 (d, J=7.8 Hz, 1H), 4.36 (s, 2H), 2.59 (q, J=7.8 Hz, 2H), 1.17 (t, J=7.5 Hz, 3H).

N-(3-ethylphenyl)-5-oxo-1-phenyl-3-(trifluoromethyl)-4,5-dihydro-1H-pyrazole-4-carboxamide Compound ID: 130

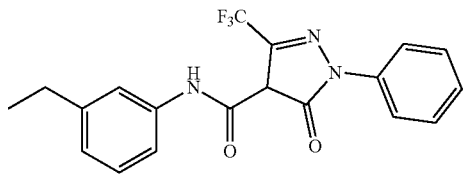 [SMILES: CCc1cccc(NC(=O)C2C(=O)N(c3ccccc3)N=C2C(F)(F)F)c1]

LCMS: m/z 376.2 [M+H]⁺;
¹H NMR (400 MHz, DMSO-d₆) δ 11.03 (s, 1H), 8.02 (d, J=8.0 Hz, 2H), 7.49 (s, 1H), 7.42-7.40 (m, 3H), 7.24-7.13 (m, 2H), 6.81-6.79 (d, J=8.0 Hz, 1H), 2.53-2.61 (m, 2H), 1.18 (t, J=7.6 Hz, 3H).

232
N-(3-((dimethylamino)methyl)phenyl)-3-methyl-5-oxo-1-phenyl-4,5-dihydro-1H-pyrazole-4-carboxamide Compound ID: 131

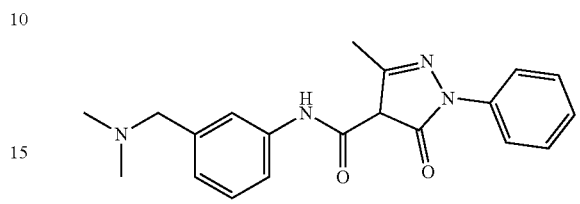

LCMS: m/z 351.2 [M+H]⁺;
¹H NMR (400 MHz, METHANOL-d₄) δ 7.80-7.77 (m, 3H), 7.65-7.58 (m, 1H), 7.44-7.36 (m, 3H), 7.23-7.20 (m, 1H), 7.07 (d, J=7.6 Hz, 1H), 4.21 (s, 2H), 2.80 (s, 6H), 2.45 (s, 3H)

3-methyl-5-oxo-1-phenyl-N-(3-(pyrimidin-5-yl)phenyl)-4,5-dihydro-1H-pyrazole-4-carboxamide Compound ID: 132

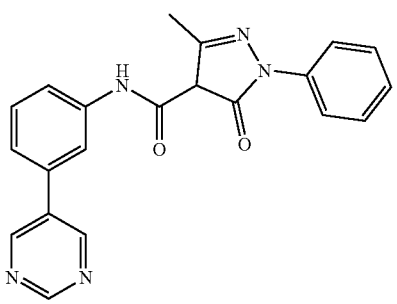 [SMILES: CC1=NN(c2ccccc2)C(=O)C1C(=O)Nc1cccc(-c2cncnc2)c1]

LCMS: m/z 372.2 [M+H]⁺;
¹H NMR (400 MHz, DMSO-d₆) δ 10.83 (s, 1H), 9.20 (s, 1H), 9.12 (s, 2H), 8.01 (s, 1H), 7.74 (d, J=7.6 Hz, 1H), 7.74-7.72 (m, 2H), 7.55-7.51 (t, J=8.0 Hz, 2H), 7.49-7.47 (m, 2H), 7.47-7.34 (m, 1H), 2.58 (s, 3H).

N-(3-ethylphenyl)-5-oxo-1-phenyl-4,5-dihydro-1H-pyrazole-4-carboxamide

Compound ID: 133

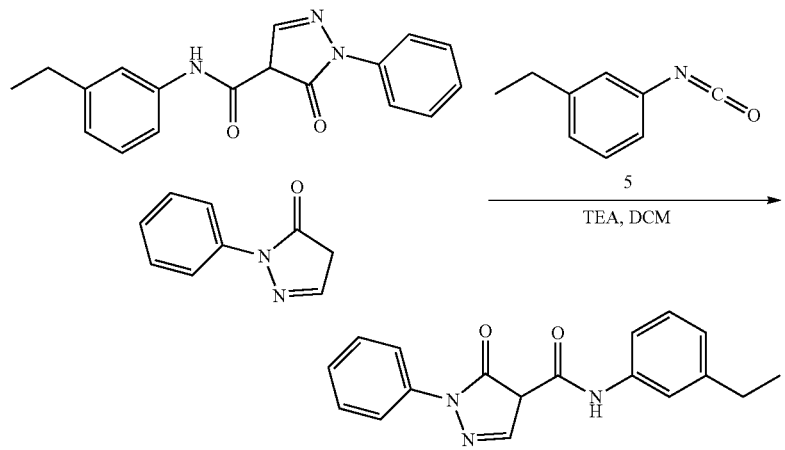

To a solution of 2-phenyl-4H-pyrazol-3-one (200 mg, 1.24 mmol, 1.00 eq) in DCM (5 mL) was added TEA (501.77 mg, 4.96 mmol, 690.19 uL, 4.00 eq) followed by 1-ethyl-3-isocyanato-benzene (0.4 M, 10 mL, 3.23 eq) at 0° C. The solution was allowed to warm to 20° C. for 1.5 hours. The solution was concentrated. The residue was suspended in MeOH (5 mL) and precipitate was filtered off. The filtrate was concentrated. The residue was purified by prep-HPLC to give the desired compound as a yellow solid.

LCMS: m/z 308.0 [M+H]$^+$;

$^1$H NMR (400 MHz, DMSO-d$_6$) δ 10.31 (s, 1H), 8.28 (s, 1H), 7.78 (d, J=8.4 Hz, 2H), 7.53-7.47 (m, 4H), 7.32-7.29 (m, 1H), 7.28-7.23 (m, 1H), 6.90 (d, J=7.6 Hz, 1H), 2.57 (q, J=7.6 Hz, 2H), 1.19 (t, J=7.6 Hz, 3H)

1-(4-ethoxyphenyl)-N-(3-ethylphenyl)-3-methyl-5-oxo-4,5-dihydro-1H-pyrazole-4-carboxamide Compound ID: 134

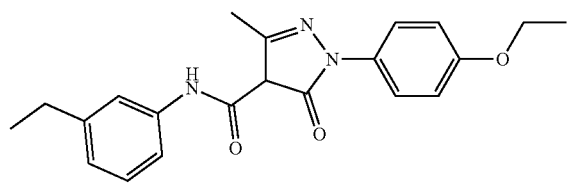 [SMILES: CCOc1ccc(N2N=C(C)C(C(=O)Nc3cccc(CC)c3)C2=O)cc1]

LCMS: m/z 285.1 [M−80];

$^1$H NMR (400 MHz, DMSO-d$_6$) δ 8.51 (s, 1H), 8.43 (s, 1H), 7.33 (d, J=8.8 Hz, 2H), 7.30 (s, 1H), 7.24-7.19 (m, 1H), 7.16 (t, J=7.6 Hz, 1H), 6.84 (d, J=7.2 Hz, 2H), 6.80 (d, J=7.6 Hz, 1H), 3.97 (q, J=6.8 Hz, 2H), 2.56 (q, J=7.6 Hz, 2H), 2.52 (s, 3H), 1.30 (t, J=6.8 Hz, 3H), 1.17 (t, J=7.6 Hz, 3H).

ethyl 4-(3-methyl-5-oxo-1-phenyl-4,5-dihydro-1H-pyrazole-4-carboxamido)picolinate Compound ID: 135

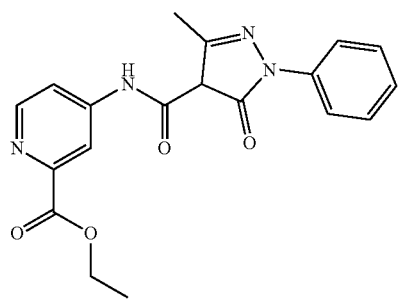 [SMILES: CCOC(=O)c1cc(NC(=O)C2C(=O)N(c3ccccc3)N=C2C)ccn1]

LCMS: m/z 367.0 [M+H]$^+$;

$^1$H NMR (400 MHz, DMSO-d$_6$) δ 11.81 (s, 1H), 8.51 (d, J=6.0 Hz, 1H), 8.44 (s, 1H), 7.87 (d, J=7.6 Hz, 3H), 7.44 (t, J=7.6 Hz, 2H), 7.20 (t, J=7.6 Hz, 1H), 4.39 (q, J=6.8 Hz, 2H), 2.43 (s, 3H), 1.36 (t, J=6.8 Hz, 3H)

3-ethyl-N-(3-ethylphenyl)-5-oxo-1-phenyl-4,5-dihydro-1H-pyrazole-4-carboxamide Compound ID: 136

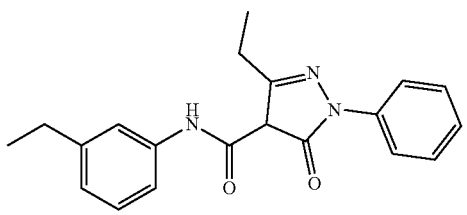 [SMILES: CCC1=NN(c2ccccc2)C(=O)C1C(=O)Nc1cccc(CC)c1]

LCMS: m/z 336.2 [M+H]$^+$;

$^1$H NMR (400 MHz, DMSO-d$_6$) δ 10.74 (s, 1H), 7.72 (d, J=8.0 Hz, 2H), 7.53 (t, J=7.6 Hz, 2H), 7.48 (s, 1H), 7.43 (d,

J=7.6 Hz, 1H), 7.38-7.30 (m, 1H), 7.21 (t, J=7.6 Hz, 1H), 6.89 (d, J=7.6 Hz, 1H), 2.97 (q, J=7.6 Hz, 2H), 2.59 (q, J=7.6 Hz, 2H), 1.28 (t, J=7.6 Hz, 3H), 1.18 (t, J=7.6 Hz, 3H).

N-(3-ethylphenyl)-5-oxo-1-phenyl-3-(pyridin-4-yl)-4,5-dihydro-1H-pyrazole-4-carboxamide Compound ID: 137

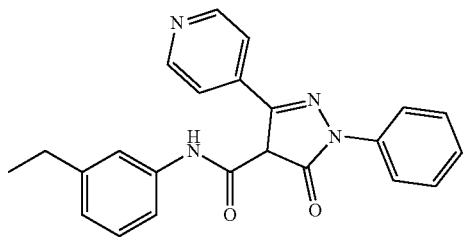 [SMILES: CCc1cccc(NC(=O)C2C(=O)N(c3ccccc3)N=C2c2ccncc2)c1]

LCMS: m/z 385.3 [M+H]+;
$^1$H NMR (400 MHz, DMSO-d$_6$) δ 11.79 (s, 1H), 8.81 (q, J=6.4 Hz, 4H), 8.21 (d, J=7.6 Hz, 2H), 7.49-7.40 (m, 4H), 7.18 (t, J=7.6 Hz, 2H), 6.81 (d, J=7.6 Hz, 1H), 2.58 (q, J=7.6 Hz, 2H), 1.19 (t, J=7.6 Hz, 3H).

N-(3-ethylphenyl)-1-(4-methoxyphenyl)-3-methyl-5-oxo-4,5-dihydro-1H-pyrazole-4-carboxamide Compound ID: 138

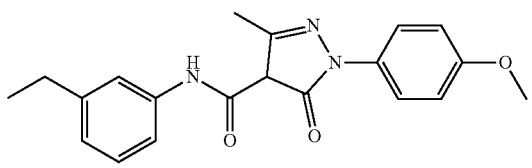 [SMILES: CCc1cccc(NC(=O)C2C(=O)N(c3ccc(OC)cc3)N=C2C)c1]

LCMS: m/z 352.0 [M+H]+;
$^1$H NMR (400 MHz, CHLOROFORM-d) δ 7.39 (s, 1H), 7.31 (d, J=7.6 Hz, 3H), 7.21 (t, J=7.6 Hz, 1H), 6.94 (d, J=7.2 Hz, 1H), 6.81 (d, J=7.2 Hz, 2H), 3.74 (s, 3H), 2.62 (q, J=7.2 Hz, 2H), 2.41 (s, 3H), 1.22 (t, J=7.6 Hz, 3H).

N-(3-(N,N-dimethylsulfamoyl)phenyl)-3-methyl-5-oxo-1-phenyl-4,5-dihydro-1H-pyrazole-4-carboxamide Compound ID: 139

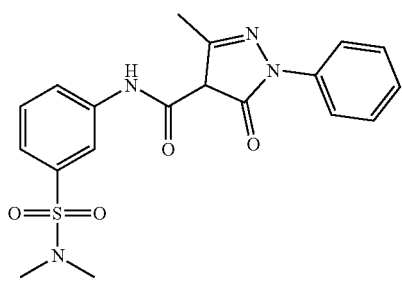 [SMILES: CC1=NN(c2ccccc2)C(=O)C1C(=O)Nc1cccc(S(=O)(=O)N(C)C)c1]

LCMS: m/z 401.0 [M+H]+;
$^1$H NMR (400 MHz, DMSO-d$_6$) δ 10.98 (s, 1H), 8.26 (t, J=1.6 Hz, 1H), 7.73 (d, J=8.0 Hz, 3H), 7.58 (t, J=7.6 Hz, 1H), 7.53 (t, J=8.0 Hz, 2H), 7.39 (d, J=8.0 Hz, 1H), 7.36-7.29 (m, 1H), 2.63 (s, 6H), 2.55 (s, 3H).

3-methyl-5-oxo-1-phenyl-N-(3-propylphenyl)-4,5-dihydro-1H-pyrazole-4-carboxamide Compound ID: 140

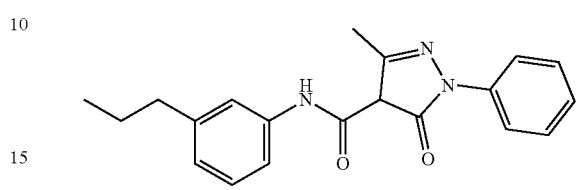

LCMS: m/z 336.1 [M+H]+;
$^1$H NMR (400 MHz, DMSO-d$_6$) δ 10.70 (s, 1H), 7.76 (d, J=7.6 Hz, 2H), 7.51 (t, J=8.0 Hz, 2H), 7.46 (s, 1H), 7.43 (d, J=8.0 Hz, 1H), 7.30 (t, J=7.6 Hz, 1H), 7.20 (t, J=7.6 Hz, 1H), 6.86 (d, J=7.6 Hz, 1H), 2.55 (s, 2H), 2.53 (s, 3H), 1.64-1.54 (m, 2H), 0.90 (t, J=7.6 Hz, 3H).

N-(3-(1,1-difluoroethyl)phenyl)-3-methyl-5-oxo-1-phenyl-4,5-dihydro-1H-pyrazole-4-carboxamide Compound ID: 141

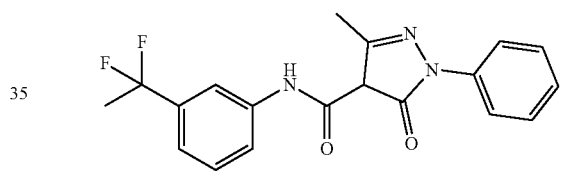

LCMS: m/z 358.1 [M+H]+;
$^1$H NMR (400 MHz, DMSO-d$_6$) δ 10.90 (s, 1H), 7.95 (s, 1H), 7.76 (d, J=7.6 Hz, 2H), 7.62 (d, J=8.0 Hz, 1H), 7.51 (t, J=7.6 Hz, 2H), 7.42 (t, J=8.0 Hz, 1H), 7.30 (t, J=7.6 Hz, 1H), 7.21 (d, J=8.0 Hz, 1H), 2.53 (s, 3H), 1.96 (t, J=18.8 Hz, 3H)

N-(3-ethylphenyl)-1-(4-isopropoxyphenyl)-3-methyl-5-oxo-4,5-dihydro-1H-pyrazole-4-carboxamide Compound ID: 142

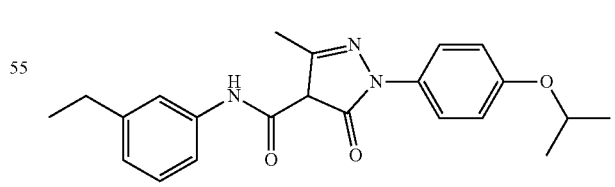

LCMS: m/z 380.3 [M+H]+;
$^1$H NMR (400 MHz, DMSO-d$_6$) δ 10.88 (s, 1H), 7.69 (s, 2H), 7.45 (s, 1H), 7.41 (d, J=8.0 Hz, 1H), 7.17 (t, J=7.6 Hz, 1H), 7.01-6.94 (m, 2H), 6.82 (d, J=7.2 Hz, 1H), 4.61 (td, J=5.6, 11.2 Hz, 1H), 2.62-2.53 (q, J=7.6 Hz, 2H), 2.42 (s, 3H), 1.27 (d, J=6.0 Hz, 6H), 1.18 (t, J=7.6 Hz, 3H)

237

1-(4-(cyclopropylmethoxy)phenyl)-N-(3-ethylphenyl)-3-methyl-5-oxo-4,5-dihydro-1H-pyrazole-4-carboxamide Compound ID: 143

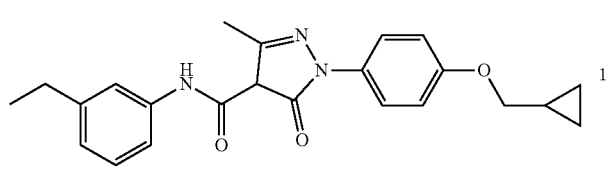

LCMS: m/z 392.2 [M+H]⁺;

¹H NMR (400 MHz, DMSO-d₆) δ 10.77 (s, 1H), 7.61 (d, J=9.2 Hz, 2H), 7.46 (s, 1H), 7.42 (d, J=8.0 Hz, 1H), 7.20 (t, J=8.0 Hz, 1H), 7.03 (d, J=9.2 Hz, 2H), 6.86 (d, J=7.6 Hz, 1H), 3.85 (d, J=6.8 Hz, 2H), 2.58 (q, J=7.6 Hz, 2H), 2.48 (s, 3H), 1.28-1.21 (m, 1H), 1.18 (t, J=7.6 Hz, 3H), 0.63-0.54 (m, 2H), 0.38-0.30 (m, 2H).

1-(4-acetamidophenyl)-N-(3-ethylphenyl)-3-methyl-5-oxo-4,5-dihydro-1H-pyrazole-4-carboxamide Compound ID: 144

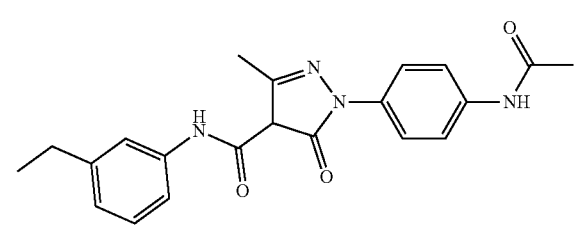 [SMILES: CCc1cccc(NC(=O)C2C(=O)N(c3ccc(NC(C)=O)cc3)N=C2C)c1]

LCMS: m/z 379.2 [M+H]⁺;

¹H NMR (400 MHz, DMSO-d₆) δ 10.70 (s, 1H), 10.07 (s, 1H), 7.69 (d, J=8.0 Hz, 2H), 7.62 (d, J=8.8 Hz, 2H), 7.46 (s, 1H), 7.42 (d, J=8.0 Hz, 1H), 7.20 (t, J=8.0 Hz, 1H), 6.87 (d, J=7.2 Hz, 1H), 2.58 (q, J=8.0 Hz, 2H), 2.51 (s, 3H), 2.06 (s, 3H), 1.17 (t, J=7.6 Hz, 3H)

3-methyl-5-oxo-N-(3-(2-oxopropyl)phenyl)-1-phenyl-4,5-dihydro-1H-pyrazole-4-carboxamide Compound ID: 145

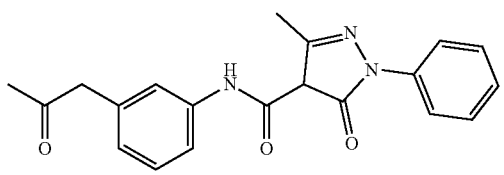 [SMILES: CC(=O)Cc1cccc(NC(=O)C2C(=O)N(c3ccccc3)N=C2C)c1]

LCMS: m/z 350.2 [M+H]⁺;

¹H NMR (400 MHz, DMSO-d₆) δ 10.71 (s, 1H), 7.74 (d, J=8.0 Hz, 2H), 7.54-7.49 (t, J=7.2 Hz, 3H), 7.47 (s, 1H), 7.31 (t, J=7.6 Hz, 1H), 7.25 (t, J=7.6 Hz, 1H), 6.86 (d, J=7.6 Hz, 1H), 3.74 (s, 2H), 2.54 (s, 3H), 2.13 (s, 3H).

238

N-(3-cyclopentylphenyl)-3-methyl-5-oxo-1-phenyl-4,5-dihydro-1H-pyrazole-4-carboxamide Compound ID: 146

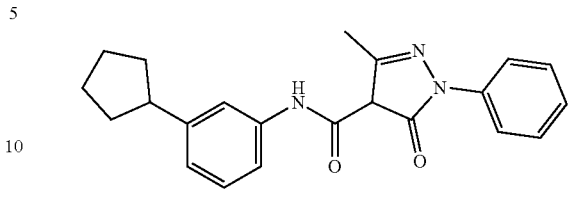

LCMS: m/z 362.2 [M+H]⁺;

¹H NMR (400 MHz, DMSO-d₆) δ 10.65 (s, 1H), 7.79-7.68 (d, J=7.8 Hz, 2H), 7.55-7.51 (m, 3H), 7.40 (d, J=8.0 Hz, 1H), 7.33 (d, J=7.6 Hz, 1H), 7.21 (t, J=8.0 Hz, 1H), 6.93 (d, J=7.6 Hz, 1H), 2.99-2.90 (m, 1H), 2.55 (s, 3H), 2.04-1.97 (m, 2H), 1.82-1.71 (m, 2H), 1.69-1.59 (m, 2H), 1.58-1.48 (m, 2H).

N-(3-isobutylphenyl)-3-methyl-5-oxo-1-phenyl-4,5-dihydro-1H-pyrazole-4-carboxamide Compound ID: 147

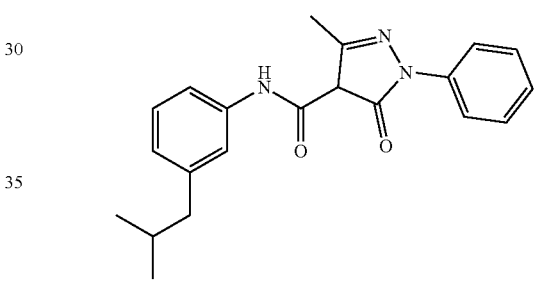

LCMS: m/z 350.1 [M+H]⁺;

¹H NMR (400 MHz, DMSO-d₆) δ 10.70 (s, 1H), 7.76 (d, J=8.0 Hz, 2H), 7.51 (d, J=7.6 Hz, 2H), 7.49-7.42 (m, 2H), 7.30-7.25 (m, 1H), 7.22-7.20 (m, 1H), 6.83-6.80 (m, 1H), 2.67 (s, 3H), 2.42 (d, J=7.2 Hz, 2H), 1.85-1.81 (m, 1H), 0.87 (d, J=6.8 Hz, 6H)

N-(3-(1H-imidazol-2-yl)phenyl)-3-methyl-5-oxo-1-(4-(trifluoromethyl)phenyl)-4,5-dihydro-1H-pyrazole-4-carboxamide Compound ID: 148

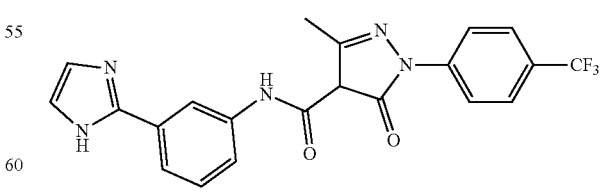

LCMS: m/z 428.2 [M+H]⁺;

¹H NMR (400 MHz, DMSO-d₆) δ 11.09 (s, 1H), 8.26 (s, 1H), 8.18 (d, J=8.4 Hz, 2H), 8.01 (d, J=8.0 Hz, 1H), 7.81 (s, 3H), 7.80 (s, 1H), 7.67 (d, J=7.6 Hz, 1H), 7.56 (t, J=8.0 Hz, 1H), 2.48 (s, 3H).

N-(3-(1H-imidazol-2-yl)phenyl)-3-methyl-5-oxo-1-(3-(trifluoromethyl)phenyl)-4,5-dihydro-1H-pyrazole-4-carboxamide

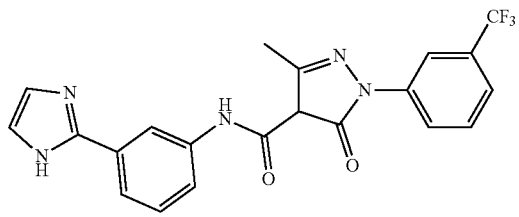 [SMILES: CC1=NN(c2cccc(C(F)(F)F)c2)C(=O)C1C(=O)Nc1cccc(-c2ncc[nH]2)c1]

Compound ID: 149

LCMS: m/z 428.0 [M+H]$^+$;

$^1$H NMR (400 MHz, DMSO-d$_6$) δ 10.98 (s, 1H), 8.37 (s, 1H), 8.23 (s, 1H), 8.13 (d, J=8.8 Hz, 1H), 8.07 (d, J=8.0 Hz, 1H), 7.82 (s, 2H), 7.74-7.71 (m, 2H), 7.60-7.56 (m, 2H), 2.54 (s, 3H).

3-methyl-5-oxo-N-(3-(pyrazin-2-yl)phenyl)-1-(4-(trifluoromethyl)phenyl)-4,5-dihydro-1H-pyrazole-4-carboxamide Compound ID: 150

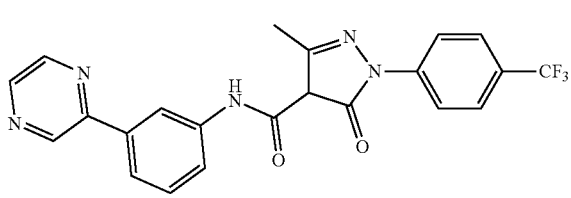 [SMILES: CC1=NN(c2ccc(C(F)(F)F)cc2)C(=O)C1C(=O)Nc1cccc(-c2cnccn2)c1]

LCMS: m/z 440.0 [M+H]$^+$;

$^1$H NMR (400 MHz, DMSO-d$_6$) δ 10.80 (s, 1H), 9.24 (d, J=1.6 Hz, 1H), 8.74 (dd, J=1.6, 2.4 Hz, 1H), 8.63 (d, J=2.4 Hz, 1H), 8.44 (s, 1H), 8.08 (d, J=8.8 Hz, 2H), 7.87 (d, J=8.8 Hz, 2H), 7.83-7.71 (m, 2H), 7.47 (t, J=7.6 Hz, 1H), 2.55 (s, 3H).

3-methyl-5-oxo-1-phenyl-N-(3-(2,2,2-trifluoroacetyl)phenyl)-4,5-dihydro-1H-pyrazole-4-carboxamide Compound ID: 152

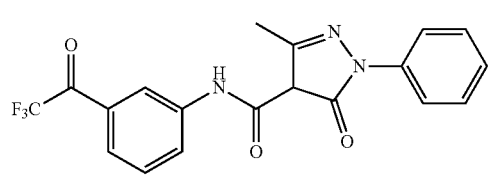 [SMILES: CC1=NN(c2ccccc2)C(=O)C1C(=O)Nc1cccc(C(=O)C(F)(F)F)c1]

LCMS: m/z 408.3 [M+H+H$_2$O]$^+$;

$^1$H NMR (400 MHz, DMSO-d$_6$) δ 10.77 (s, 1H), 7.82 (s, 1H), 7.74-7.71 (m, 2H), 7.55-7.51 (m, 3H), 7.36-7.32 (m, 3H), 2.56 (s, 3H)

$^{19}$F NMR (400 MHz, DMSO-d6) δ: −82.71 (s, 3F).

N-(3-ethylphenyl)-3-methyl-1-(4-nitrophenyl)-5-oxo-4,5-dihydro-1H-pyrazole-4-carboxamide Compound ID: 153

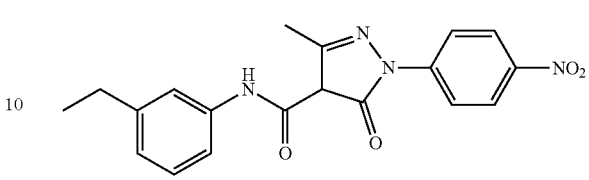

LCMS: m/z 367.2 [M+H]$^+$;

$^1$H NMR (400 MHz, DMSO-d$_6$) δ 10.48 (s, 1H), 8.37 (d, J=9.2 Hz, 2H), 8.12 (d, J=9.6 Hz, 2H), 7.47 (s, 1H), 7.44 (d, J=8.0 Hz, 1H), 7.21 (t, J=8.0 Hz, 1H), 6.87 (d, J=7.6 Hz, 1H), 2.58 (q, J=7.6 Hz, 2H), 2.54 (s, 3H), 1.18 (t, J=7.6 Hz, 3H).

1-(4-aminophenyl)-N-(3-ethylphenyl)-3-methyl-5-oxo-4,5-dihydro-1H-pyrazole-4-carboxamide Compound ID: 154

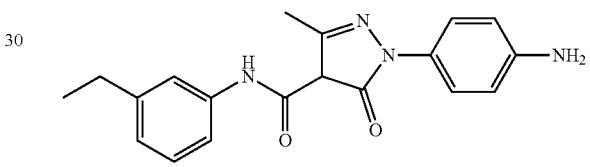

LCMS: m/z 337.2 [M+H]$^+$;

$^1$H NMR (400 MHz, DMSO-d$_6$) δ 10.80 (s, 1H), 7.45 (s, 1H), 7.41 (d, J=8.4 Hz, 1H), 7.28 (d, J=6.8 Hz, 2H), 7.20 (t, J=7.6 Hz, 1H), 6.86 (d, J=7.6 Hz, 1H), 6.69 (d, J=8.4 Hz, 2H), 2.57 (q, J=7.6 Hz, 2H), 2.47 (s, 3H), 1.17 (t, J=7.6 Hz, 3H)

1-(4-(3,3-dimethylureido)phenyl)-N-(3-ethylphenyl)-3-methyl-5-oxo-4,5-dihydro-1H-pyrazole-4-carboxamide Compound ID: 155

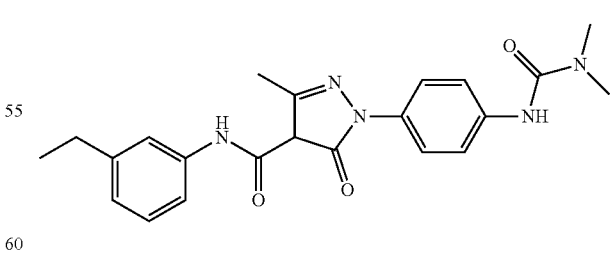

LCMS: m/z 408.3 [M+H]$^+$;

$^1$H NMR (400 MHz, DMSO-d$_6$) δ 10.90 (s, 1H), 8.32 (s, 1H), 7.67 (s, 2H), 7.50 (d, J=9.2 Hz, 2H), 7.45 (s, 1H), 7.41 (d, J=8.4 Hz, 1H), 7.16 (t, J=7.6 Hz, 1H), 6.81 (d, J=7.6 Hz, 1H), 2.93 (s, 6H), 2.56 (q, J=7.6 Hz, 2H), 2.41 (s, 3H), 1.17 (t, J=7.6 Hz, 3H).

N-(3-ethylphenyl)-5-oxo-1-phenyl-3-(pyridin-2-yl)-4,5-dihydro-1H-pyrazole-4-carboxamide Compound ID: 156

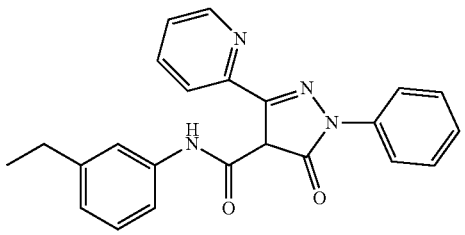 [SMILES: CCc1cccc(NC(=O)C2C(=O)N(c3ccccc3)N=C2c2ccccn2)c1]

LCMS: m/z 385.1 [M+H]⁺;
¹H NMR (400 MHz, DMSO-d₆) δ 12.03 (s, 1H), 9.00 (s, 1H), 8.65 (d, J=7.6 Hz, 1H), 8.49 (t, J=7.6 Hz, 1H), 8.21 (d, J=8.0 Hz, 2H), 7.90 (t, J=2.4 Hz, 1H), 7.53 (d, J=8.0 Hz, 1H), 7.50-7.46 (m, 3H), 7.30 (t, J=7.6 Hz, 1H), 7.25 (t, J=7.6 Hz, 1H), 6.98 (d, J=7.6 Hz, 1H), 2.66-2.60 (q, J=7.6 Hz, 2H), 1.21 (t, J=7.6 Hz, 3H).

N-(3-ethylphenyl)-5-oxo-1-phenyl-3-(pyridin-3-yl)-4,5-dihydro-1H-pyrazole-4-carboxamide Compound ID: 157

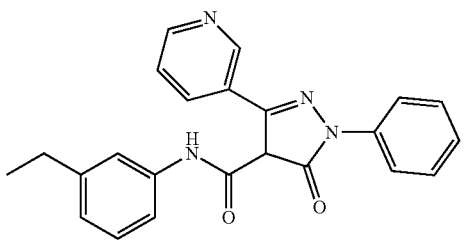 [SMILES: CCc1cccc(NC(=O)C2C(=O)N(c3ccccc3)N=C2c2cccnc2)c1]

LCMS: m/z 385.2 [M+H]⁺;
¹H NMR (400 MHz, DMSO-d₆) δ 11.66 (s, 1H), 9.68 (s, 1H), 9.11 (d, J=8.0 Hz, 1H), 8.81 (d, J=5.2 Hz, 1H), 8.20 (d, J=7.6 Hz, 2H), 8.04 (dd, J=5.6, 8.0 Hz, 1H), 7.49 (s, 1H), 7.47-7.37 (m, 3H), 7.16 (td, J=7.6, 10.0 Hz, 2H), 6.81 (d, J=7.6 Hz, 1H), 2.58 (q, J=7.6 Hz, 2H), 1.19 (t, J=7.6 Hz, 3H).

N-(3-ethylphenyl)-3-methyl-5-oxo-1-(4-propoxyphenyl)-4,5-dihydro-1H-pyrazole-4-carboxamide Compound ID: 158

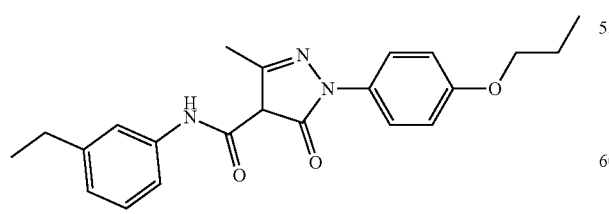

LCMS: m/z 380.1 [M+H]⁺;
¹H NMR (400 MHz, DMSO-d₆) δ 13.24 (s, 1H), 10.71 (s, 1H), 7.56 (d, J=9.2 Hz, 2H), 7.47-7.45 (m, 1H), 7.43-7.41 (m, 1H), 7.22-7.20 (m, 1H), 7.07 (d, J=8.8 Hz, 2H), 6.88 (d, J=7.6 Hz, 1H), 3.97 (t, J=6.4 Hz, 2H), 2.61-2.58 (m, 2H), 2.57 (s, 3H), 1.76 (t, J=6.8 Hz, 2H), 1.18 (t, J=7.6 Hz, 3H), 0.99 (t, J=7.6 Hz, 3H).

3-(4-((3-(furan-2-yl)phenyl)carbamoyl)-3-methyl-5-oxo-4,5-dihydro-1H-pyrazol-1-yl)benzoic acid Compound ID: 159

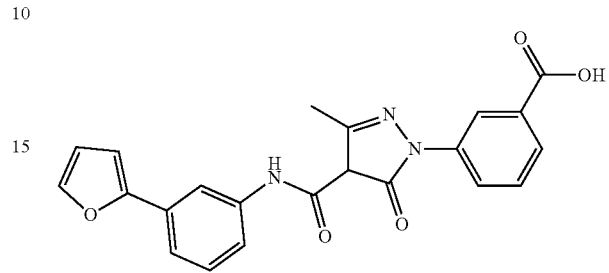

LCMS: m/z 404.0 [M+H]⁺;
¹H NMR (400 MHz, METHANOL-d₄) δ 8.33 (s, 1H), 7.89-8.10 (m, 3H), 7.66-7.63 (m, 1H), 7.55 (d, J=1.2 Hz, 1H), 7.48-7.40 (m, 2H), 7.36-7.34 (m, 1H), 6.78 (d, J=3.2 Hz, 1H), 6.52-6.50 (m, 1H), 2.63 (s, 3H).

1-(4-(N,N-dimethylsulfamoyl)phenyl)-N-(3-(furan-2-yl)phenyl)-3-methyl-5-oxo-4,5-dihydro-1H-pyrazole-4-carboxamide Compound ID: 160

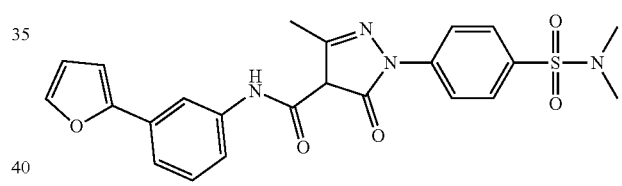

LCMS: m/z 467.1 [M+H]⁺;
¹H NMR (400 MHz, METHANOL-d₄) δ 8.19-8.05 (m, 3H), 7.88 (d, J=8.4 Hz, 2H), 7.57 (d, J=1.2 Hz, 1H), 7.50 (d, J=7.6 Hz, 1H), 7.45-7.39 (m, 1H), 7.38-7.31 (m, 1H), 6.80 (d, J=3.2 Hz, 1H), 6.54 (dd, J=1.6, 3.2 Hz, 1H), 2.73 (s, 6H), 2.58 (s, 3H).

3-methyl-5-oxo-1-phenyl-N-(3-(2,2,2-trifluoroethyl)phenyl)-4,5-dihydro-1H-pyrazole-4-carboxamide Compound ID: 161

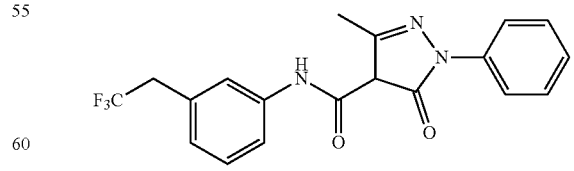

LCMS: m/z 376.0 [M+H]⁺;
¹H NMR (400 MHz, DMSO-d₆) δ 10.83 (s, 1H), 7.78 (d, J=7.6 Hz, 2H), 7.67 (s, 1H), 7.60 (d, J=8.0 Hz, 1H), 7.50 (t, J=8.0 Hz, 2H), 7.34-7.25 (m, 2H), 7.01 (d, J=7.6 Hz, 1H), 3.63 (q, J=11.6 Hz, 2H), 2.52 (s, 3H).

243

N-(3-(furan-2-yl)phenyl)-3-methyl-5-oxo-1-(4-(trifluoromethyl)phenyl)-4,5-dihydro-1H-pyrazole-4-carboxamide

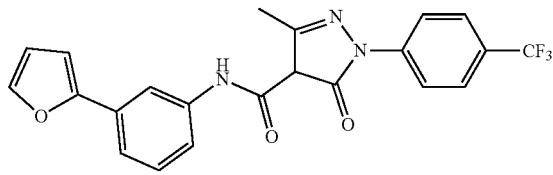 [SMILES: CC1=NN(c2ccc(C(F)(F)F)cc2)C(=O)C1C(=O)Nc1cccc(-c2ccco2)c1]

Compound ID: 162

LCMS: m/z 428.0 [M+H]$^+$;

$^1$H NMR (400 MHz, DMSO-d$_6$) δ 10.74 (s, 1H), 8.10 (d, J=8.0 Hz, 2H), 8.06 (s, 1H), 7.86 (s, 2H), 7.75 (s, 1H), 7.48 (s, 1H), 7.35 (s, 2H), 6.97-6.89 (m, 1H), 6.60 (s, 1H), 2.53 (s, 3H).

3-methyl-5-oxo-N-(3-(pyrazin-2-yl)phenyl)-1-(3-(trifluoromethyl)phenyl)-4,5-dihydro-1H-pyrazole-4-carboxamide Compound ID: 166

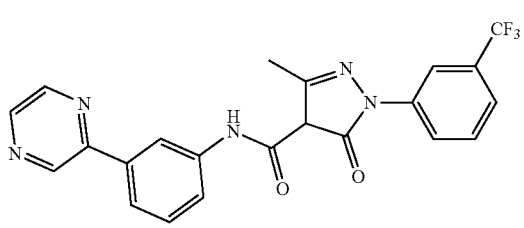 [SMILES: CC1=NN(c2cccc(C(F)(F)F)c2)C(=O)C1C(=O)Nc1cccc(-c2cnccn2)c1]

LCMS: m/z 440.2 [M+H]$^+$;

$^1$H NMR (400 MHz, DMSO-d$_6$) δ 10.81 (s, 1H), 9.25 (d, J=1.6 Hz, 1H), 8.77-8.71 (m, 1H), 8.63 (d, J=2.4 Hz, 1H), 8.44 (t, J=1.6 Hz, 1H), 8.28 (s, 1H), 8.12 (d, J=9.6 Hz, 1H), 7.80 (dd, J=2.0, 7.6 Hz, 2H), 7.74 (t, J=8.0 Hz, 1H), 7.62 (d, J=7.6 Hz, 1H), 7.48 (t, J=8.0 Hz, 1H), 2.55 (s, 3H).

3-methyl-5-oxo-N,1-diphenyl-4,5-dihydro-1H-pyrazole-4-carboxamide

Compound ID: 182

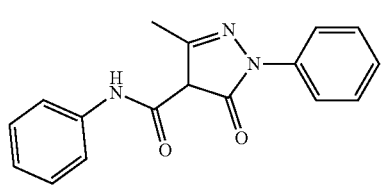 [SMILES: CC1=NN(c2ccccc2)C(=O)C1C(=O)Nc1ccccc1]

LCMS: m/z 294.2 [M+H]$^+$;

$^1$H NMR (400 MHz, DMSO-d$_6$) δ 13.39 (s, 1H), 10.68 (s, 1H), 7.75 (d, J=8.4 Hz, 2H), 7.62 (dd, J=7.6, 1.2 Hz, 2H), 7.52 (t, J=8.0 Hz, 2H), 7.34-7.29 (m, 3H), 7.03 (t, J=8.0 Hz, 1H), 2.57 (s, 3H).

244

N-(3-acetylphenyl)-3-methyl-5-oxo-1-phenyl-4,5-dihydro-1H-pyrazole-4-carboxamide Compound ID: 183 Batch 2

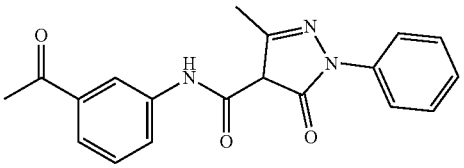 [SMILES: CC(=O)c1cccc(NC(=O)C2C(=O)N(c3ccccc3)N=C2C)c1]

LCMS: m/z 336.2 [M+H]$^+$;

$^1$H NMR (400 MHz, DMSO-d$_6$) δ 10.84 (s, 1H), 8.24 (s, 1H), 7.84 (d, J=8.0 Hz, 1H), 7.74 (d, J=7.6 Hz, 2H), 7.64 (d, J=8.0 Hz, 1H), 7.55 (t, J=8.0 Hz, 2H), 7.48 (t, J=8.0 Hz, 1H), 7.38-7.31 (m, 1H), 2.60 (s, 3H), 2.58 (s, 3H)

N-(3-ethylphenyl)-3-methyl-5-oxo-1-phenyl-4,5-dihydro-1H-pyrazole-4-carboxamide

Compound ID: 184

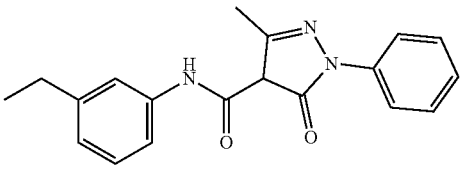 [SMILES: CCc1cccc(NC(=O)C2C(=O)N(c3ccccc3)N=C2C)c1]

LCMS: m/z 322.2 [M+H]$^+$;

$^1$H NMR (400 MHz, DMSO-d$_6$) δ 10.65 (s, 1H), 7.71 (dd, J=1.0, 8.4 Hz, 2H), 7.57-7.50 (m, 2H), 7.47 (s, 1H), 7.44 (d, J=8.0 Hz, 1H), 7.37-7.29 (m, 1H), 7.22 (t, J=7.6 Hz, 1H), 6.89 (d, J=7.6 Hz, 1H), 2.62-2.57 (m, 2H), 2.56 (s, 3H), 1.18 (t, J=7.6 Hz, 3H).

$^1$H NMR (400 MHz, CHLOROFORM-d) δ 8.02 (s, 1H), 7.95 (d, J=8.0 Hz, 1H), 7.86 (br s, 1H), 7.69 (d, J=7.6 Hz, 1H), 7.43 (t, J=8.0 Hz, 1H), 2.61 (s, 3H), 2.22 (s, 3H).

3-methyl-N-(naphthalen-1-yl)-5-oxo-1-phenyl-4,5-dihydro-1H-pyrazole-4-carboxamide Compound ID: 185

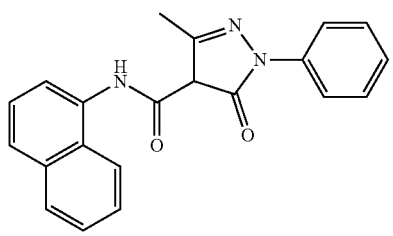 [SMILES: CC1=NN(c2ccccc2)C(=O)C1C(=O)Nc1cccc2ccccc12]

LCMS: m/z 344.2 [M+H]$^+$;

$^1$H NMR (400 MHz, MeOH) δ 8.28-8.30 (d, J=8.0 Hz, 2H), 7.86-7.88 (d, J=8.0 Hz, 1H), 7.72-7.74 (d, J=8.0 Hz, 2H), 7.63-7.65 (d, J=8.0 Hz, 1H), 7.45-7.57 (m, 5H), 7.36 (t, J=8.0 Hz, 1H), 3.31 (s, 1H).

245

N-benzyl-3-methyl-5-oxo-1-phenyl-4,5-dihydro-1H-pyrazole-4-carboxamide

Compound ID: 186

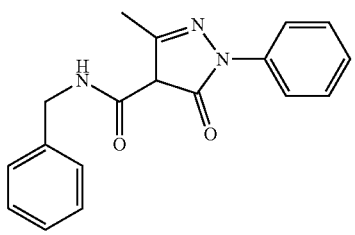 [SMILES: CC1=NN(c2ccccc2)C(=O)C1C(=O)NCc1ccccc1]

LCMS: m/z 308.0 [M+H]$^+$;

$^1$H NMR (400 MHz, DMSO-d$_6$) δ 8.8 (s, 1H), 7.68-7.71 (m, 2H), 7.49 (t, J=8.8, 2H), 7.23-7.32 (m, 6H), 4.54 (s, 2H), 2.54-2.56 (m, 3H).

1-isopropyl-3-methyl-5-oxo-N-phenyl-4,5-dihydro-1H-pyrazole-4-carboxamide

Compound ID: 187

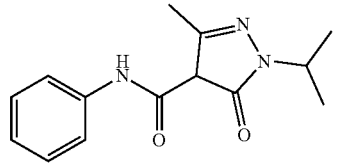 [SMILES: CC1=NN(C(C)C)C(=O)C1C(=O)Nc1ccccc1]

LCMS: m/z 260.1 [M+H]$^+$;

$^1$H NMR (400 MHz, DMSO-d$_6$) δ 10.84 (s, 1H), 7.56 (d, J=7.6, 2H), 7.29 (t, J=8.0, 2H), 7.00 (t, J=7.2, 1H), 4.50-4.57 (m, 1H), 2.45 (s, 3H), 1.28 (d, J=6.8 Hz, 6H).

N-(4-methoxyphenyl)-3-methyl-5-oxo-1-phenyl-4,5-dihydro-1H-pyrazole-4-carboxamide Compound ID: 188

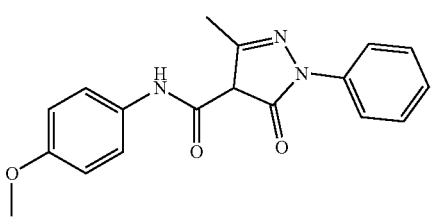

LCMS: m/z 324.1 [M+H]$^+$;

$^1$H NMR (400 MHz, DMSO-d$_6$) δ 13.24 (s, 1H), 10.52 (s, 1H), 7.72 (d, J=7.6 Hz, 2H), 7.55-7.50 (m, 4H), 7.35-7.32 (m, 1H), 6.90 (d, J=7.2 Hz, 2H), 3.73 (s, 3H), 2.55 (s, 3H)

246

N-(4-fluorophenyl)-3-methyl-5-oxo-1-phenyl-4,5-dihydro-1H-pyrazole-4-carboxamide Compound ID: 189

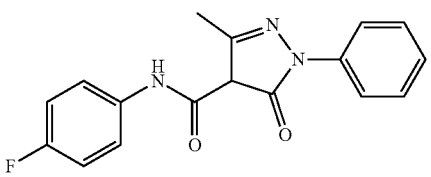

LCMS: m/z 312.0 [M+H]$^+$;

$^1$H NMR (400 MHz, DMSO-d$_6$) δ=13.18 (s, 1H), 10.68 (s, 1H), 7.73-7.72 (m, 2H), 7.71-7.64 (m, 2H), 7.64-7.52 (m, 2H), 7.40-7.30 (m, 1H), 7.18-7.15 (m, 2H), 2.55 (s, 3H)

1,5-dimethyl-3-oxo-N,2-diphenyl-2,3-dihydro-1H-pyrazole-4-carboxamide

Compound ID: 190

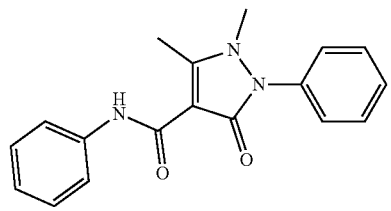 [SMILES: Cc1c(C(=O)Nc2ccccc2)c(=O)n(-c2ccccc2)n1C]

LCMS: m/z 308.3 [M+H]$^+$;

$^1$H NMR (400 MHz, DMSO-d$_6$) δ=10.60 (s, 1H), 7.59 (d, J=8.0 Hz, 2H), 7.48 (t, J=7.6 Hz, 2H), 7.38 (t, J=7.6 Hz, 1H), 7.29 (d, J=7.6 Hz, 2H), 7.23 (t, J=7.6 Hz, 2H), 6.98 (t, J=7.2 Hz, 1H), 3.27 (s, 3H), 2.72 (s, 3H).

3-methyl-5-oxo-1-phenyl-N-(pyridin-3-yl)-4,5-dihydro-1H-pyrazole-4-carboxamide

Compound ID: 191

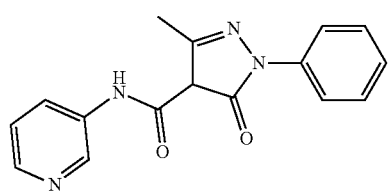 [SMILES: CC1=NN(c2ccccc2)C(=O)C1C(=O)Nc1cccnc1]

LCMS: m/z 295.2 [M+H]$^+$;

$^1$H NMR (400 MHz, DMSO-d$_6$) δ=11.32 (s, 1H), 8.83 (s, 1H), 8.13-8.09 (m, 2H), 8.01 (d, J=8.0 Hz, 2H), 7.35 (t, J=8.0 Hz, 3H), 7.07 (t, J=7.6 Hz, 1H), 2.34 (s, 3H).

5-hydroxy-3-methyl-N-phenyl-1-(pyridin-2-yl)-1H-pyrazole-4-carboxamide

Compound ID: 192

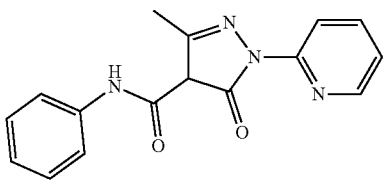 [SMILES: CC1=NN(c2ccccn2)C(=O)C1C(=O)Nc1ccccc1]

LCMS: m/z 295.0 [M+H]$^+$;

$^1$H NMR (400 MHz, DMSO-d$_6$) δ=10.53 (s, 1H), 8.49 (d, J=8.0 Hz, 1H), 8.40 (d, J=8.0 Hz, 1H), 8.02 (d, J=8.0 Hz, 1H), 7.61 (d, J=8.0 Hz, 2H), 7.29-7.35 (m, 3H), 7.03 (d, J=8.0 Hz, 1H), 2.52 (s, 3H).

3-methyl-5-oxo-N-phenyl-1-(pyridin-4-yl)-4,5-dihydro-1H-pyrazole-4-carboxamide Compound ID: 193

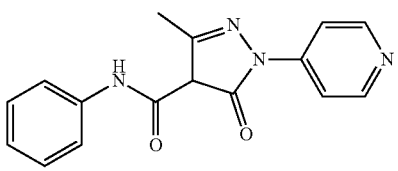

LCMS: m/z 295.2 [M+H]$^+$;

$^1$H NMR (400 MHz, DMSO-d$_6$) δ=10.51 (s, 1H), 8.65-8.41 (m, 4H), 7.57 (d, J=7.6 Hz, 2H), 7.25 (t, J=7.2 Hz, 2H), 6.93 (t, J=7.2 Hz, 1H), 2.32 (s, 3H).

1-benzyl-5-hydroxy-3-methyl-N-phenyl-1H-pyrazole-4-carboxamide

Compound ID: 194

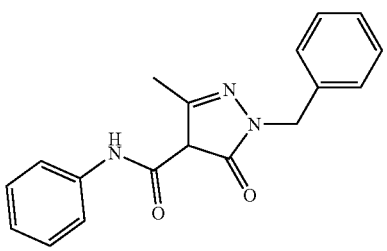 [SMILES: CC1=NN(Cc2ccccc2)C(=O)C1C(=O)Nc1ccccc1]

LCMS: m/z 308.1 [M+H]$^+$;

$^1$H NMR (400 MHz, DMSO-d$_6$) δ 10.80 (s, 1H), 7.59 (d, J=7.6 Hz, 2H), 7.37 (t, J=7.6 Hz, 2H), 7.30 (t, J=8.0 Hz, 3H), 7.23 (d, J=7.2 Hz, 2H), 7.01 (t, J=8.0 Hz, 1H), 4.98 (s, 2H), 2.41 (s, 3H).

3-methyl-5-oxo-N-phenyl-1-(pyridin-3-yl)-4,5-dihydro-1H-pyrazole-4-carboxamide Compound ID: 195

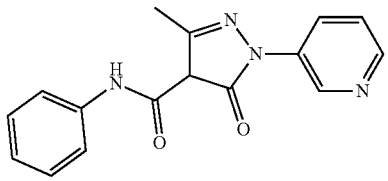 [SMILES: CC1=NN(c2cccnc2)C(=O)C1C(=O)Nc1ccccc1]

LCMS: m/z 295.1 [M+H]$^+$;

$^1$H NMR (400 MHz, DMSO-d$_6$) δ 10.60 (s, 1H), 9.38 (s, 1H), 8.71 (d, J=8.0 Hz, 1H), 8.52 (dd, J=1.2, 5.2 Hz, 1H), 7.86 (dd, J=5.2, 8.4 Hz, 1H), 7.60 (d, J=7.6 Hz, 2H), 7.28 (t, J=8.0 Hz, 2H), 7.06-6.88 (m, 1H), 2.42 (s, 3H).

1,3-dimethyl-5-oxo-N-phenyl-4,5-dihydro-1H-pyrazole-4-carboxamide

Compound ID: 196

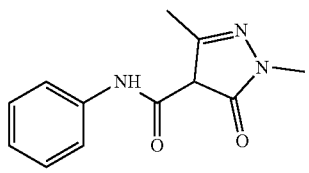 [SMILES: CC1=NN(C)C(=O)C1C(=O)Nc1ccccc1]

LCMS: m/z 232.2 [M+H]$^+$;

$^1$H NMR (400 MHz, DMSO-d$_6$) δ 10.80 (s, 1H), 7.59 (d, J=7.6 Hz, 2H), 7.28-7.32 (m, 2H), 6.99-7.03 (m, 1H), 3.35 (s, 3H), 2.43 (s, 3H).

1-(4-methoxyphenyl)-3-methyl-5-oxo-N-phenyl-4,5-dihydro-1H-pyrazole-4-carboxamide Compound ID: 197

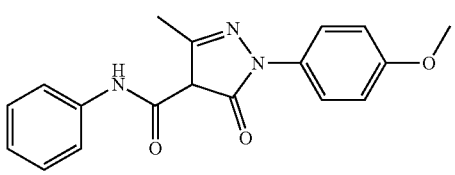 [SMILES: COc1ccc(N2N=C(C)C(C(=O)Nc3ccccc3)C2=O)cc1]

LCMS: m/z 324.1 [M+H]$^+$;

$^1$H NMR (400 MHz, DMSO-d$_6$) δ 10.76 (s, 1H), 7.59-7.61 (m, 4H), 7.29 (t, J=8.0 Hz, 2H), 7.06-7.07 (m, 2H), 7.00-7.05 (m, 1H), 3.79 (s, 3H), 2.48 (s, 3H).

$^1$H NMR (400 MHz, DMSO-d$_6$) δ 12.58 (s, 1H), 8.72 (d, J=7.2 Hz, 1H), 7.90 (dd, J=1.6, 8.0 Hz, 1H), 7.46-7.34 (m, 1H), 7.18 (t, J=7.2 Hz, 2H), 6.93-6.85 (m, 2H), 6.79 (s, 3H), 4.29 (m, 1H), 3.88-3.69 (m, 1H), 2.45-2.36 (m, 1H), 2.04-1.90 (m, 2H), 1.84-1.69 (m, 1H), 1.68-1.60 (m, 1H), 1.59-1.47 (m, 1H).

5-hydroxy-3-methyl-1-(naphthalen-2-yl)-N-phenyl-1H-pyrazole-4-carboxamide

Compound ID: 198

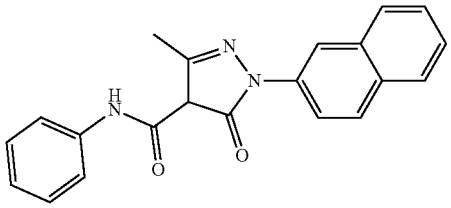 [SMILES: CC1=NN(c2ccc3ccccc3c2)C(=O)C1C(=O)Nc1ccccc1]

LCMS: m/z 366.0 [M+H]⁺;

¹H NMR (400 MHz, DMSO-d₆) δ 10.73 (s, 1H), 8.24 (s, 1H), 8.07 (d, J=8.8 Hz, 1H), 8.05-7.94 (m, 3H), 7.64 (d, J=7.6 Hz, 2H), 7.63-7.49 (m, 2H), 7.32 (t, J=8.0 Hz, 2H), 7.03 (t, J=7.2 Hz, 1H), 2.58 (s, 3H)

N,3-dimethyl-5-oxo-1-phenyl-4,5-dihydro-1H-pyrazole-4-carboxamide

Compound ID: 199

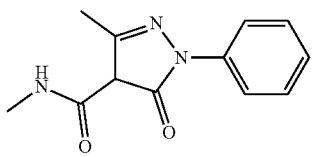 [SMILES: CNC(=O)C1C(=O)N(c2ccccc2)N=C1C]

LCMS: m/z 232.1 [M+H]⁺;

¹H NMR (400 MHz, CHLOROFORM-d) δ 11.10 (s, 1H), 7.96 (s, 1H), 7.45 (m, 2H), 7.37 (m, 2H), 7.29 (m, 1H), 2.78 (s, 3H), 2.40 (s, 3H).

N-isopropyl-3-methyl-5-oxo-1-phenyl-4,5-dihydro-1H-pyrazole-4-carboxamide

Compound ID: 200

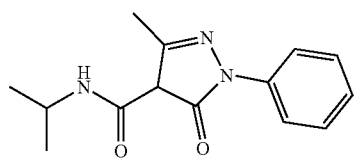 [SMILES: CC1=NN(c2ccccc2)C(=O)C1C(=O)NC(C)C]

LCMS: m/z 260.2 [M+H]⁺;

¹H NMR (400 MHz, DMSO-d₆) δ 12.83 (s, 1H), 8.30 (s, 1H), 7.70 (d, J=7.6 Hz, 2H), 7.47 (t, J=8.0 Hz, 2H), 7.27 (t, J=7.2 Hz, 1H), 4.00 (dt, J=12.8, 6.4 Hz, 1H), 2.46 (s, 3H), 1.12 (d, J=6.8 Hz, 6H)

3-methyl-5-oxo-N-phenyl-1-(4-(trifluoromethyl)phenyl)-4,5-dihydro-1H-pyrazole-4-carboxamide Compound ID: 201

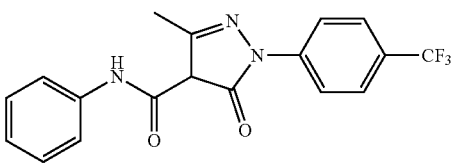 [SMILES: CC1=NN(c2ccc(C(F)(F)F)cc2)C(=O)C1C(=O)Nc1ccccc1]

LCMS: m/z 362.1 [M+H]⁺;

¹H NMR (400 MHz, DMSO-d₆) δ 10.56 (s, 1H), 8.03 (d, J=8.4 Hz, 2H), 7.89 (d, J=8.8 Hz, 2H), 7.62 (dd, J=8.8, 1.2 Hz, 2H), 7.32 (t, J=8.0 Hz, 2H), 7.04 (t, J=7.2 Hz, 1H), 2.57 (s, 3H)

1-(1,1-dioxidotetrahydrothiophen-3-yl)-3-methyl-5-oxo-N-phenyl-4,5-dihydro-1H-pyrazole-4-carboxamide Compound ID: 202

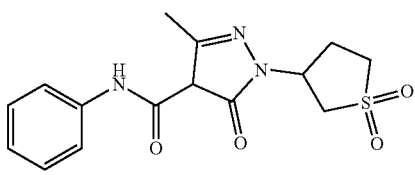 [SMILES: CC1=NN(C2CCS(=O)(=O)C2)C(=O)C1C(=O)Nc1ccccc1]

LCMS: m/z 336.0 [M+H]⁺;

¹H NMR (400 MHz, DMSO-d₆) δ 10.54 (s, 1H), 7.56 (d, J=8.0 Hz, 2H), 7.30 (t, J=7.6 Hz, 2H), 7.02 (t, J=7.6 Hz, 1H), 5.15-5.04 (m, 1H), 3.58-3.52 (m, 1H), 3.50-3.42 (m, 1H), 3.36-3.20 (m, 2H), 2.49-2.46 (m, 2H), 2.44 (s, 3H)

N-(4-acetylphenyl)-3-methyl-5-oxo-1-phenyl-4,5-dihydro-1H-pyrazole-4-carboxamide Compound ID: 203

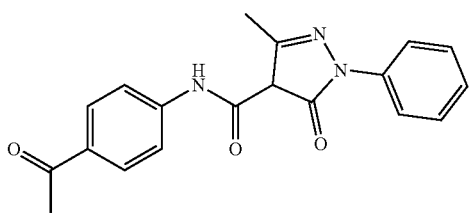 [SMILES: CC(=O)c1ccc(NC(=O)C2C(=O)N(c3ccccc3)N=C2C)cc1]

LCMS: m/z 336.2 [M+H]⁺;

¹H NMR (400 MHz, DMSO-d₆) δ 11.33 (s, 1H), 7.95-7.85 (m, 4H), 7.73 (d, J=8.4 Hz, 2H), 7.41 (t, J=8.0 Hz, 2H), 7.15 (t, J=7.6 Hz, 1H), 2.40 (s, 3H)

N,3-dimethyl-5-oxo-N,1-diphenyl-4,5-dihydro-1H-pyrazole-4-carboxamide

Compound ID: 204

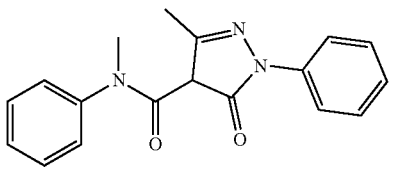 [SMILES: CC1=NN(c2ccccc2)C(=O)C1C(=O)N(C)c1ccccc1]

To a solution of N-methylaniline (6.26 g, 58.45 mmol, 6.35 mL, 1.10 eq) and TEA (10.75 g, 106.27 mmol, 14.79 mL, 2.00 eq) in DCM (100 mL) was added ethyl 3-chloro-3-oxo-propanoate (8.00 g, 53.13 mmol, 6.67 mL, 1.00 eq) dropwise at 0° C., then was allowed to warm to 15° C. and stirred for 1.5 hrs. The reaction mixture was diluted with DCM (100 mL), washed with water (50 mL×2) and brine (50 mL), then dried over Na$_2$SO$_4$, filtered and concentrated under vacuo. The residue was purified by column chromatography on silica gel (PE:EA=15:1 to 10:1) to give the desired product ethyl 3-(N-methylanilino)-3-oxo-propanoate (4.90 g, 20.30 mmol, 38.20% yield, 91.65% purity) as yellow oil.

LCMS: m/z 222.2 [M+H]$^+$;

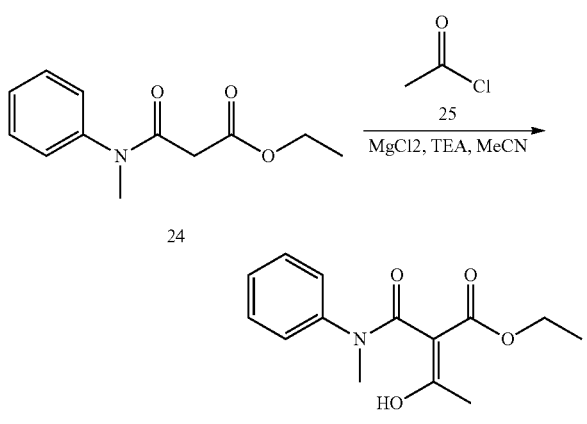

To a solution of MgCl$_2$ (372.97 mg, 3.92 mmol, 160.76 uL, 0.95 eq) in MeCN (30 mL) was added ethyl 3-(N-methylanilino)-3-oxo-propanoate (1.00 g, 4.14 mmol, 1.00 eq) at 0° C., then TEA (792.77 mg, 7.83 mmol, 1.09 mL, 1.89 eq) was added, the mixture was stirred at 0° C. for 15 min, then acetyl chloride (307.49 mg, 3.92 mmol, 279.54 uL, 0.95 eq) was added. The mixture was stirred at 0° C. for 1 hr and then heated to 20° C. and stirred for 12 hrs. The reaction mixture was quenched by HCl solution (6M, 20 mL), then extracted with EA (50 mL×3), the organic layers were combined and washed with water (50 mL) and brine (50 mL), then dried over Na$_2$SO$_4$, filtered and concentrated under vacuo to give the crude desired product ethyl (E)-3-hydroxy-2-[methyl(phenyl)carbamoyl]but-2-enoate (1.1 g, crude) as yellow oil.

LCMS: m/z 264.1 [M+H]$^+$;

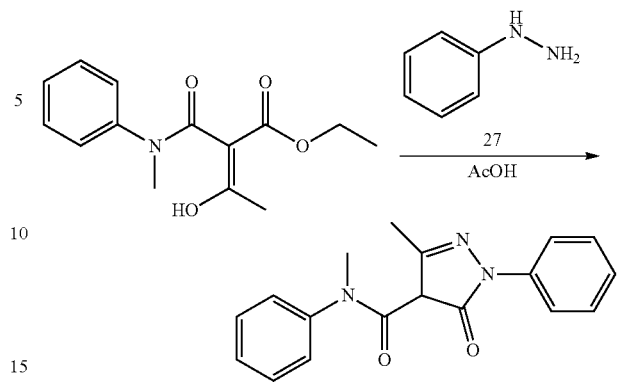

To a solution of ethyl (E)-3-hydroxy-2-[methyl(phenyl)carbamoyl]but-2-enoate (150.10 mg, 570.10 umol, 1.00 eq) in AcOH (5 mL) was added phenylhydrazine (184.95 mg, 1.71 mmol, 168.14 uL, 3.00 eq) at 25° C., the mixture was heated to 25° C. and stirred for 12 hrs. The reaction mixture was concentrated under vacuo. MeOH (5 mL) was added into the residue, then filtered. The filtrate was purified by Prep-HPLC to give the desired product N,3-dimethyl-5-oxo-N,1-diphenyl-4H-pyrazole-4-carboxamide (32 mg, 102.76 umol, 18.03% yield, 98.70% purity) as a white solid.

LCMS: m/z 308.1 [M+H]$^+$;

$^1$H NMR (400 MHz, DMSO-d$_6$+D$_2$O) δ 7.48 (d, J=7.6 Hz, 2H), 7.38 (t, J=7.2 Hz, 2H), 7.28 (t, J=8.0 Hz, 2H), 7.23-7.10 (m, 4H), 3.31 (s, 3H), 1.98 (s, 3H)

N-(4-hydroxyphenyl)-3-methyl-5-oxo-1-phenyl-4,5-dihydro-1H-pyrazole-4-carboxamide Compound ID: 205

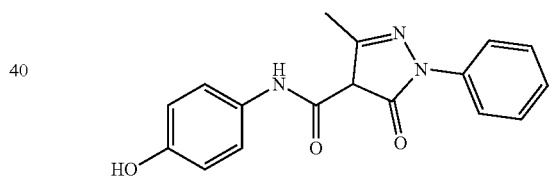

LCMS: m/z 310.2 [M+H]$^+$;

$^1$H NMR (400 MHz, DMSO-d$_6$) δ 13.07 (s, 1H), 10.42 (s, 1H), 9.17 (s, 1H), 7.72 (d, J=7.6 Hz, 2H), 7.52 (d, J=7.6 Hz, 2H), 7.41-7.38 (m, 2H), 7.38-7.31 (m, 1H), 6.72-6.69 (m, 2H), 2.53 (s, 3H)

3-(3-methyl-5-oxo-1-phenyl-4,5-dihydro-1H-pyrazole-4-carboxamido)benzoate

Compound ID: 206

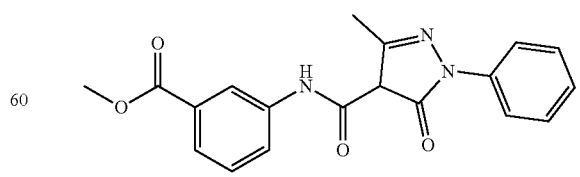

LCMS: m/z 352.2 [M+H]$^+$;

$^1$H NMR (400 MHz, DMSO-d$_6$) δ 11.03 (s, 1H), 8.36 (s, 1H), 7.83 (d, J=6.8 Hz, 2H), 7.76 (d, J=8.8 Hz, 1H), 7.59 (d,

J=7.2 Hz, 1H), 7.48-7.42 (m, 3H), 7.25-7.23 (m, 1H), 3.86 (s, 3H), 2.47 (s, 3H).

N-benzoyl-3-methyl-5-oxo-1-phenyl-4,5-dihydro-1H-pyrazole-4-carboxamide

Compound ID: 207

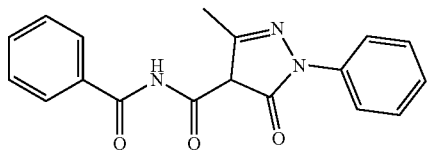 [SMILES: CC1=NN(c2ccccc2)C(=O)C1C(=O)NC(=O)c1ccccc1]

LCMS: m/z 322.1 [M+H]⁺;

¹H NMR (400 MHz, DMSO-d₆) δ 12.42 (s, 1H), 7.97 (d, J=7.6 Hz, 2H), 7.74 (d, J=7.6 Hz, 2H), 7.68-7.62 (m, 1H), 7.61-7.55 (m, 2H), 7.52 (t, J=8.0 Hz, 2H), 7.37-7.28 (m, 1H), 2.52 (s, 3H)

3-methyl-5-oxo-1-phenyl-N-(3-(trifluoromethyl)phenyl)-4,5-dihydro-1H-pyrazole-4-carboxamide Compound ID: 208

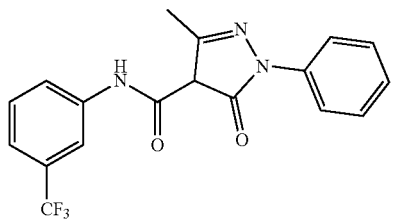 [SMILES: CC1=NN(c2ccccc2)C(=O)C1C(=O)Nc1cccc(C(F)(F)F)c1]

LCMS: m/z 362.0 [M+H]⁺;

¹H NMR (400 MHz, DMSO-d₆) δ 10.95 (s, 1H), 8.28 (s, 1H), 7.72 (d, J=8.0 Hz, 2H), 7.67 (d, J=8.4 Hz, 1H), 7.57-7.50 (m, 3H), 7.38 (d, J=7.6 Hz, 1H), 7.36-7.29 (m, 1H), 2.55 (s, 3H)

N-(2,3-dihydro-1H-inden-5-yl)-3-methyl-5-oxo-1-phenyl-4,5-dihydro-1H-pyrazole-4-carboxamide Compound ID: 209

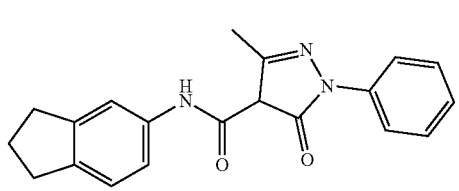 [SMILES: CC1=NN(c2ccccc2)C(=O)C1C(=O)Nc1ccc2c(c1)CCC2]

LCMS: m/z 334.1 [M+H]⁺;

¹H NMR (400 MHz, DMSO-d₆) δ 10.63 (s, 1H), 7.75 (d, J=7.6 Hz, 2H), 7.58 (s, 1H), 7.52 (t, J=7.6 Hz, 2H), 7.34-7.26 (m, 2H), 7.14 (d, J=8.0 Hz, 1H), 2.87-2.79 (m, 4H), 2.54 (s, 3H), 2.06-1.97 (m, 2H)

N-(3-chlorophenyl)-3-methyl-5-oxo-1-phenyl-4,5-dihydro-1H-pyrazole-4-carboxamide Compound ID: 210

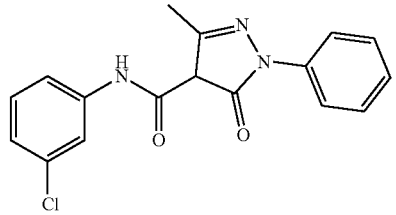

LCMS: m/z 350.2 [M+Na]*;

¹H NMR (400 MHz, DMSO-d₆) δ 10.84 (s, 1H), 8.05-7.91 (m, 1H), 7.79-7.65 (m, 2H), 7.56-7.47 (m, 2H), 7.36-7.26 (m, 3H), 7.14-7.00 (m, 1H), 2.54 (s, 3H).

N-(3-methoxyphenyl)-3-methyl-5-oxo-1-phenyl-4,5-dihydro-1H-pyrazole-4-carboxamide Compound ID: 211

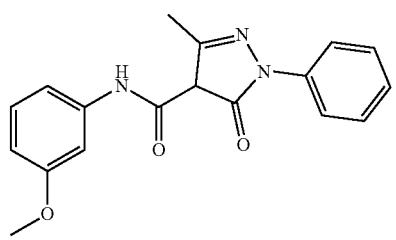 [SMILES: COc1cccc(NC(=O)C2C(=O)N(c3ccccc3)N=C2C)c1]

LCMS: m/z 324.2 [M+H]⁺;

¹H NMR (400 MHz, DMSO-d₆) δ 10.71 (s, 1H), 7.75-7.66 (m, 2H), 7.52 (t, J=7.6 Hz, 2H), 7.39 (t, J=2.4 Hz, 1H), 7.36-7.29 (m, 1H), 7.24-7.16 (m, 1H), 7.08-7.04 (m, 1H), 6.61 (dd, J=1.6, 8.0 Hz, 1H), 3.75 (s, 3H), 2.54 (s, 3H)

3-methyl-5-oxo-1-phenyl-N-(m-tolyl)-4,5-dihydro-1H-pyrazole-4-carboxamide

Compound ID: 212

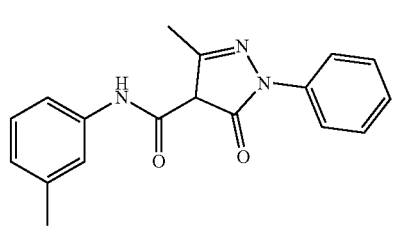 [SMILES: CC1=NN(c2ccccc2)C(=O)C1C(=O)Nc1cccc(C)c1]

LCMS: m/z 308.1 [M+H]⁺;

¹H NMR (400 MHz, DMSO-d₆) δ 10.72 (s, 1H), 7.78 (d, J=8.0 Hz, 2H), 7.53-7.44 (m, 3H), 7.40 (d, J=8.0 Hz, 1H), 7.27 (t, J=8.0 Hz, 1H), 7.17 (t, J=7.6 Hz, 1H), 6.83 (d, J=7.6 Hz, 1H), 2.53 (s, 3H), 2.28 (s, 3H)

3-methyl-5-oxo-1-phenyl-N-(3-(pyrazin-2-yl)phenyl)-4,5-dihydro-1H-pyrazole-4-carboxamide Compound ID: 213

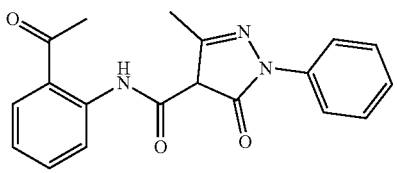 [SMILES: CC(=O)c1ccccc1NC(=O)C1C(=O)N(c2ccccc2)N=C1C]

LCMS: m/z 336.1 [M+H]⁺;

¹H NMR (400 MHz, DMSO-d₆) δ 11.81 (s, 1H), 8.42 (d, J=8.0 Hz, 1H), 7.89 (dd, J=1.2, 7.6 Hz, 1H), 7.77 (d, J=7.6 Hz, 2H), 7.56-7.45 (m, 3H), 7.27 (t, J=7.2 Hz, 1H), 7.19-7.10 (m, 1H), 2.57 (s, 3H), 2.51-2.55 (m, 3H)

3-methyl-5-oxo-1-phenyl-N-(pyridin-2-yl)-4,5-dihydro-1H-pyrazole-4-carboxamide Compound ID: 214

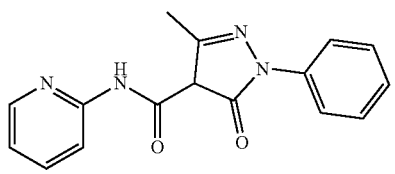 [SMILES: CC1=NN(c2ccccc2)C(=O)C1C(=O)Nc1ccccn1]

LCMS: m/z 295.0 [M+H]⁺;

¹H NMR (400 MHz, DMSO-d₆) δ 11.64 (s, 1H), 8.27 (d, J=4.4 Hz, 1H), 8.11-8.00 (m, 1H), 7.95-7.76 (m, 3H), 7.45 (t, J=7.6 Hz, 2H), 7.22 (t, J=7.6 Hz, 1H), 7.12 (t, J=6.8 Hz, 1H), 2.46 (s, 3H).

N-(3-bromophenyl)-3-methyl-5-oxo-1-phenyl-4,5-dihydro-1H-pyrazole-4-carboxamide Compound ID: 215

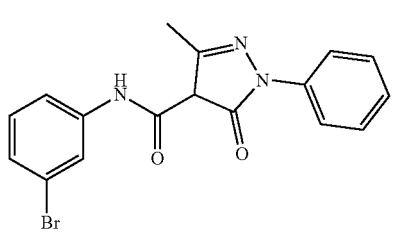

LCMS: m/z 371.9 [M+H]⁺;

¹H NMR (400 MHz, DMSO-d₆) δ=10.84 (s, 1H), 8.14 (s, 1H), 7.74 (d, J=8.0 Hz, 2H), 7.53 (t, J=7.6 Hz, 2H), 7.40 (d, J=7.6 Hz, 1H), 7.35-7.19 (m, 3H), 2.54 (s, 3H).

3-methyl-5-oxo-1-phenyl-N-(pyridin-4-yl)-4,5-dihydro-1H-pyrazole-4-carboxamide Compound ID: 216

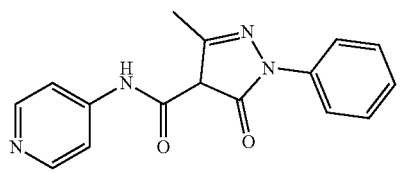 [SMILES: CC1=NN(c2ccccc2)C(=O)C1C(=O)Nc1ccncc1]

LCMS: m/z 295.0 [M+H]⁺;

¹H NMR (400 MHz, DMSO-d₆) δ 12.58 (s, 1H), 8.49 (d, J=6.8 Hz, 2H), 8.14-7.97 (m, 4H), 7.32 (t, J=7.6 Hz, 2H), 7.03 (t, J=7.6 Hz, 1H), 2.27 (s, 3H)

¹³C NMR (101 MHz, DMSO-d) δ 165.63, 163.57, 154.18, 149.06, 142.29, 141.04, 128.79, 122.97, 118.23, 113.47, 93.82, 15.84

3-methyl-5-oxo-1-phenyl-N-(thiazol-2-yl)-4,5-dihydro-1H-pyrazole-4-carboxamide Compound ID: 217

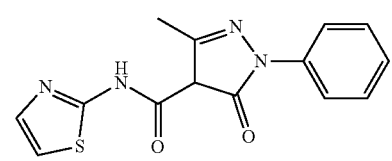 [SMILES: CC1=NN(c2ccccc2)C(=O)C1C(=O)Nc1nccs1]

LCMS: m/z 301.2 [M+H]⁺;

¹H NMR (400 MHz, METHANOL-d₄) δ 7.65 (d, J=7.6 Hz, 2H), 7.54 (t, J=8.0 Hz, 2H), 7.47 (d, J=3.6 Hz, 1H), 7.43-7.34 (m, 1H), 7.16 (d, J=3.6 Hz, 1H), 2.63 (s, 3H).

(2S)-2-(3-methyl-5-oxo-1-phenyl-4,5-dihydro-1H-pyrazole-4-carboxamido)propanoic acid Compound ID: 218

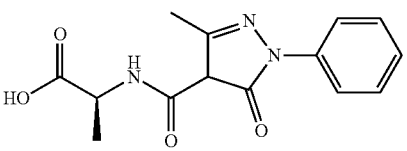 [SMILES: CC1=NN(c2ccccc2)C(=O)C1C(=O)N[C@@H](C)C(=O)O]

LCMS: m/z 290.4 [M+H]⁺;

¹H NMR (400 MHz, DMSO-d₆) δ 12.72 (s, 1H), 8.77 (d, J=6.4 Hz, 1H), 7.72 (d, J=8.0 Hz, 2H), 7.49 (t, J=8.0 Hz, 2H), 7.28 (t, J=8.0 Hz, 1H), 4.41 (m, 1H), 2.47 (s, 3H), 1.34 (d, J=7.2 Hz, 3H).

257

N-(1H-benzo[d]imidazol-5-yl)-3-methyl-5-oxo-1-phenyl-4,5-dihydro-1H-pyrazole-4-carboxamide Compound ID: 219

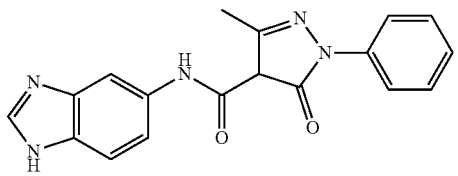 [SMILES: CC1=NN(c2ccccc2)C(=O)C1C(=O)Nc1ccc2[nH]cnc2c1]

LCMS: m/z 334.2 [M+H]⁺;

¹H NMR (400 MHz, DMSO-d₆) δ=11.05 (d, J=9.2 Hz, 1H), 9.49 (d, J=14.8 Hz, 1H), 8.51 (d, J=1.6 Hz, 1H), 7.86-7.70 (m, 3H), 7.59-7.44 (m, 3H), 7.33 (t, J=7.2 Hz, 1H), 2.59 (d, J=4.0 Hz, 3H).

N-(3-(dimethylcarbamoyl)phenyl)-3-methyl-5-oxo-1-phenyl-4,5-dihydro-1H-pyrazole-4-carboxamide Compound ID: 220

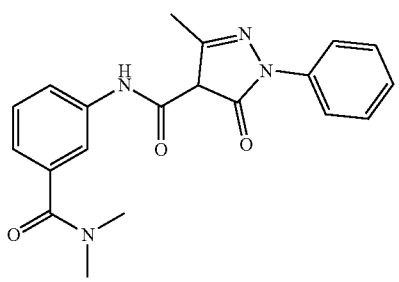

LCMS: m/z 365.3 [M+H]⁺;

¹H NMR (400 MHz, DMSO-d₆) δ 10.81 (s, 1H), 7.79 (t, J=1.6 Hz, 1H), 7.76-7.69 (m, 2H), 7.56-7.47 (m, 3H), 7.37 (t, J=8.0 Hz, 1H), 7.35-7.29 (m, 1H), 7.04 (d, J=7.6 Hz, 1H), 3.08-2.84 (m, 6H), 2.54 (s, 3H).

3-methyl-1-(1-methylpiperidin-4-yl)-5-oxo-N-phenyl-4,5-dihydro-1H-pyrazole-4-carboxamide Compound ID: 221

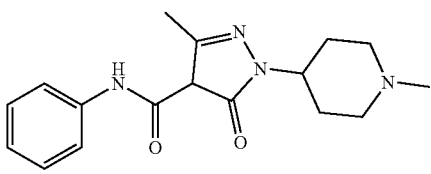 [SMILES: CC1=NN(C2CCN(C)CC2)C(=O)C1C(=O)Nc1ccccc1]

LCMS: m/z 315.2 [M+H]⁺;

¹H NMR (400 MHz, DMSO-d₆) δ 11.19 (s, 1H), 8.16 (s, 1H), 7.52 (d, J=7.6 Hz, 2H), 7.19 (t, J=7.6 Hz, 2H), 6.84 (t, J=7.6 Hz, 1H), 4.25-4.15 (m, 1H), 3.34-3.33 (m, 2H), 2.93 (t, J=12.0 Hz, 2H), 2.68 (s, 3H), 2.15 (s, 3H), 2.14-2.03 (m, 2H), 1.78 (d, J=11.7 Hz, 2H)

258

N-(3-hydroxyphenyl)-3-methyl-5-oxo-1-phenyl-4,5-dihydro-1H-pyrazole-4-carboxamide Compound ID: 222

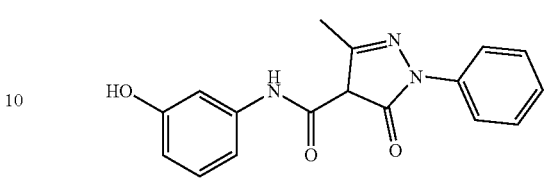

To a solution of N-(3-methoxyphenyl)-3-methyl-5-oxo-1-phenyl-4H-pyrazole-4-carboxamide (45 mg, 139.17 umol, 1.00 eq) in DCM (5 mL) was added BBr₃ (348 mg, 1.39 mmol, 10.00 eq) at 0° C. The mixture was stirred at 20° C. for 30 hours. It was quenched with MeOH (50 mL), and concentrated in vacuum. The residue was purified by prep-HPLC (column: Luna C18 150*25 5u; mobile phase: [water (0.225% FA)-ACN]; B %: 22%-49%, 10 min). N-(3-hydroxyphenyl)-3-methyl-5-oxo-1-phenyl-4H-pyrazole-4-carboxamide (15 mg, 48.13 umol, 34.59% yield, 99.26% purity) was obtained as a white solid.

LCMS: m/z 310.2 [M+H]⁺;

¹H NMR (400 MHz, DMSO-d₆) δ 10.76 (s, 1H), 9.28 (s, 1H), 7.86 (d, J=7.6 Hz, 2H), 7.44 (t, J=7.6 Hz, 2H), 7.25 (t, J=2.0 Hz, 1H), 7.23-7.17 (m, 1H), 7.08-7.02 (m, 1H), 6.92-6.87 (m, 1H), 6.39 (dd, J=1.6, 7.2 Hz, 1H), 2.45 (s, 3H).

3-(3-methyl-5-oxo-4-((3-(pyrazin-2-yl)phenyl)carbamoyl)-4,5-dihydro-1H-pyrazol-1-yl)benzoate Compound ID: 164

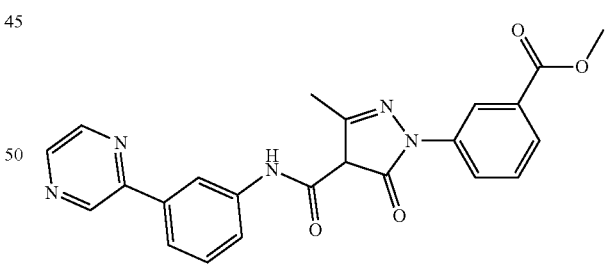

LCMS: (ESI) m/z 430.1 [M+H]⁺.

¹H NMR: (400 MHz, MeOD-d₄) δ: 9.11 (d, J=0.8 Hz, 1H), 8.67 (d, J=2.0 Hz, 1H), 8.52 (d, J=2.4 Hz, 1H), 8.41 (s, 1H), 8.32 (s, 1H), 7.99-7.97 (m, 2H), 7.79 (d, J=7.6 Hz, 1H), 7.75-7.70 (m, 1H), 7.66-7.63 (m, 1H), 7.51-7.48 (m, 1H), 3.95 (s, 3H), 2.63 (s, 3H).

N-(3-(furan-2-yl)phenyl)-3-methyl-5-oxo-1-(3-(trifluoromethyl)phenyl)-4,5-dihydro-1H-pyrazole-4-carboxamide Compound ID: 165

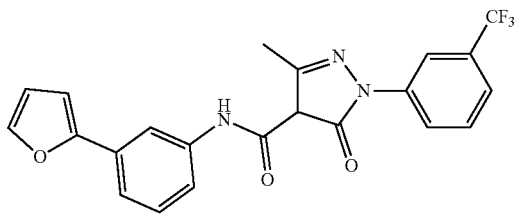 [SMILES: CC1=NN(c2cccc(C(F)(F)F)c2)C(=O)C1C(=O)Nc1cccc(-c2ccco2)c1]

Compound 165 was obtained via general procedure IV from 3-methyl-5-oxo-1-(3-(trifluoromethyl)phenyl)-4,5-dihydro-1H-pyrazole-4-carboxylate and 3-(furan-2-yl)aniline.
LCMS: (ESI) m/z 428.0 [M+H]$^+$.
$^1$H NMR: (400 MHz, DMSO-d$_6$) δ: 10.64 (s, 1H), 8.21 (s, 1H), 8.09-8.06 (m, 2H), 7.79-7.75 (m, 2H), 7.66 (d, J=7.6 Hz, 1H), 7.51 (dt, J=2.0 Hz, 7.6 Hz, 1H), 7.40-7.34 (m, 2H), 6.95 (d, J=2.8 Hz, 1H), 6.60 (dd, J=1.6 Hz, 3.2 Hz, 1H), 2.58 (s, 3H).

Methyl 3-(4-((3-(1H-imidazol-2-yl)phenyl)carbamoyl)-3-methyl-5-oxo-4,5-dihydro-1H-pyrazol-1-yl)benzoate Compound ID: 167

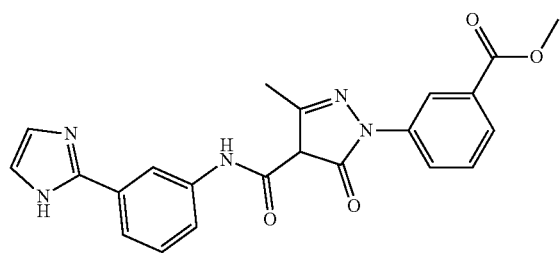 [SMILES: COC(=O)c1cccc(N2N=C(C)C(C(=O)Nc3cccc(-c4ncc[nH]4)c3)C2=O)c1]

Compound 167 was obtained via general procedure IV from 1-(3-(methoxycarbonyl)phenyl)-3-methyl-5-oxo-4,5-dihydro-1H-pyrazole-4-carboxylate and 3-(1H-imidazol-2-yl)aniline.
LCMS: (ESI) m/z 418.1 [M+H]$^+$.
$^1$H NMR: (400 MHz, MeOD-d$_4$) δ: 8.56 (d, J=2.0 Hz, 1H), 8.21 (d, J=2.0 Hz, 1H), 8.12-8.09 (m, 1H), 7.83-7.80 (m, 2H), 7.58 (s, 2H), 7.55-7.51 (m, 3H), 3.93 (s, 3H), 2.46 (s, 3H).

1-(benzo[d][1,3]dioxol-5-yl)-N-(3-ethylphenyl)-3-methyl-5-oxo-4,5-dihydro-1H-pyrazole-4-carboxamide Compound ID: 168

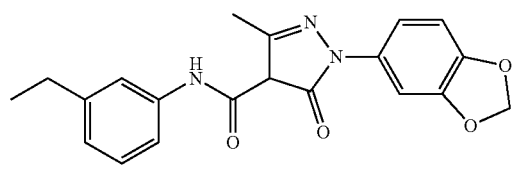 [SMILES: CCc1cccc(NC(=O)C2C(=O)N(c3ccc4c(c3)OCO4)N=C2C)c1]

Compound 168 was obtained via general procedure V.
LCMS: m/z: 366.0 [M+H]$^+$.
$^1$H NMR: (400 MHz, MeOD-d$_4$) δ: 7.46 (s, 1H), 7.42 (d, J=8.0 Hz, 1H), 7.22 (t, J=7.6 Hz, 1H), 7.17 (d, J=1.6 Hz, 1H), 7.07 (dd, J=1.6, 8.4 Hz, 1H), 6.97-6.89 (m, 2H), 6.04 (s, 2H), 2.64 (q, J=7.6 Hz, 2H), 2.56 (s, 3H), 1.24 (t, J=7.6 Hz, 3H).

3-(3-methyl-4-((3-(oxazol-2-yl)phenyl)carbamoyl)-5-oxo-4,5-dihydro-1H-pyrazol-1-yl)benzoic acid Compound ID: 170

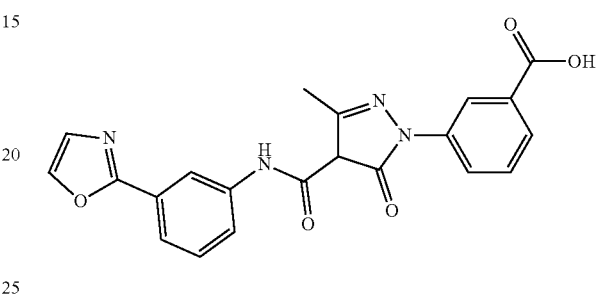

To a solution of methyl 3-[3-methyl-4-[(3-oxazol-2-ylphenyl)carbamoyl]-5-oxo-4H-pyrazol-1-yl]benzoate (20.0 mg, 47.8 umol, 1.0 eq) in methanol (1 mL) and water (0.5 mL) was added lithium hydroxide monohydrate (5.01 mg, 119 umol, 2.5 eq). The solution was stirred at 25° C. for 3 h. The solution was adjusted to pH=3 by addition of hydrochloric acid (6 N) and the mixture was concentrated. The residue was purified by prep-HPLC (column: Boston Green ODS 150*30 5u; mobile phase: [water(0.225% FA)-ACN]; B %: 37%-61%, 10 min) to give 10.0 mg (40% yield) of Compound 170 as a white solid.
LCMS: (ESI) m/z 405.1 [M+H]$^+$.
$^1$H NMR: (400 MHz, MeOD-d$_4$) δ: 8.43 (s, 1H), 8.35 (s, 1H), 8.08-7.99 (m, 3H), 7.76-7.73 (m, 2H), 7.71-7.70 (m, 1H), 7.47 (t, J=7.6 Hz, 1H), 7.30 (s, 1H), 2.63 (s, 3H).

N-(3-(1H-imidazol-2-yl)phenyl)-1-(3-(N,N-dimethylsulfamoyl)phenyl)-3-methyl-5-oxo-4,5-dihydro-1H-pyrazole-4-carboxamide Compound ID: 171

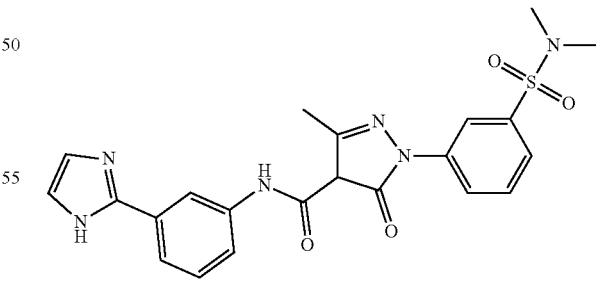

Compound 171 was obtained via general procedure IV from 4-nitrophenyl 1-(3-(N,N-dimethylsulfamoyl)phenyl)-3-methyl-5-oxo-4,5-dihydro-1H-pyrazole-4-carboxylate and 3-(1H-imidazol-2-yl)aniline.
LCMS: (ESI) m/z 467.0 [M+H]$^+$;
$^1$H NMR: (400 MHz, DMSO-d$_6$) δ: 11.32 (s, 1H), 8.66 (s, 1H), 8.39 (d, J=8.0 Hz, 1H), 8.20 (s, 1H), 8.01 (d, J=7.6 Hz, 1H), 7.71 (s, 2H), 7.58 (t, J=8.0 Hz, 1H), 7.54-7.45 (m, 2H), 7.34 (d, J=7.6 Hz, 1H), 2.63 (s, 6H), 2.30 (s, 3H).

3-(4-((3-(1H-imidazol-2-yl)phenyl)carbamoyl)-3-methyl-5-oxo-4,5-dihydro-1H-pyrazol-1-yl)benzoic acid Compound ID: 172

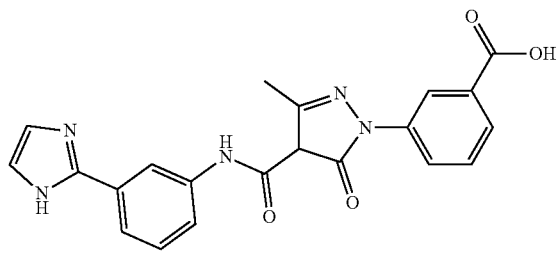 [SMILES: CC1=NN(c2cccc(C(=O)O)c2)C(=O)C1C(=O)Nc1cccc(-c2ncc[nH]2)c1]

Compound 172 was obtained via the similar synthetic method of Compound 170 from Compound 167.

LCMS: (ESI) m/z 404.0 [M+H]+.

$^1$H NMR: (400 MHz, MeOD-d$_4$) δ: 8.51 (s, 1H), 8.24 (s, 1H), 8.05-7.91 (m, 1H), 7.91-7.84 (m, 2H), 7.63 (s, 2H), 7.58-7.54 (m, 3H), 2.51 (s, 3H).

N-(3-(1H-imidazol-2-yl)phenyl)-1-(4-(N,N-dimethylsulfamoyl)phenyl)-3-methyl-5-oxo-4,5-dihydro-1H-pyrazole-4-carboxamide Compound ID: 173

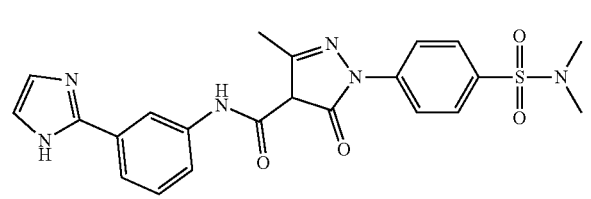 [SMILES: CC1=NN(c2ccc(S(=O)(=O)N(C)C)cc2)C(=O)C1C(=O)Nc1cccc(-c2ncc[nH]2)c1]

LCMS: m/z 467.1 [M+H]+;

$^1$H NMR (400 MHz, METHANOL-d$_4$) δ 8.35 (s, 1H), 7.99 (q, J=8.8 Hz, 4H), 7.90-7.86 (m, 1H), 7.69 (s, 2H), 7.66-7.61 (m, 2H), 2.75 (s, 6H), 2.72 (s, 3H)

N-(3-(4H-1,2,4-triazol-3-yl)phenyl)-3-methyl-5-oxo-1-phenyl-4,5-dihydro-1H-pyrazole-4-carboxamide Compound ID: 174

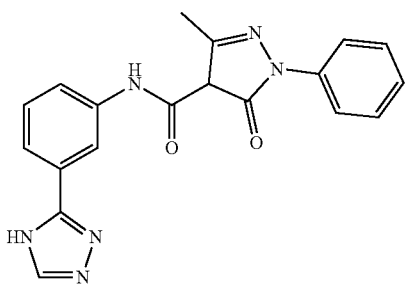 [SMILES: CC1=NN(c2ccccc2)C(=O)C1C(=O)Nc1cccc(-c2nnc[nH]2)c1]

Compound 174 was obtained via general procedure IV.

LCMS: (ESI) m/z 361.0 [M+H]+;

$^1$H NMR: (400 MHz, DMSO-d$_6$) δ: 10.84 (s, 1H), 8.44 (br s, 1H), 8.33 (s, 1H), 7.74 (d, J=7.6 Hz, 2H), 7.69 (d, J=7.6 Hz, 2H), 7.53 (t, J=8.0 Hz, 2H), 7.46-7.40 (m, 1H), 7.36-7.30 (m, 1H), 2.57 (s, 3H).

N-(3-(1-(ethylamino)-2,2,2-trifluoroethyl)phenyl)-3-methyl-5-oxo-1-phenyl-4,5-dihydro-1H-pyrazole-4-carboxamide Compound ID: 176

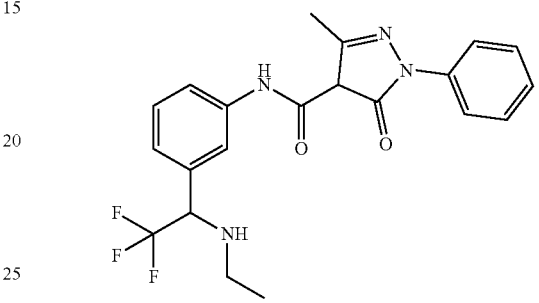

Compound 176 was obtained via general procedure IV.

LCMS: (ESI) m/z 419.2 [M+H]+.

$^1$H NMR: (400 MHz, DMSO-d$_6$) δ: 10.94 (s, 1H), 7.94 (s, 1H), 7.81-7.79 (m, 1H), 7.76-7.74 (m, 3H), 7.54-7.46 (m, 3H), 7.34-7.19 (m, 2H), 5.44-5.37 (m, 1H), 2.83-2.85 (m, 2H), 2.67 (s, 3H), 1.19-1.10 (m, 3H).

3-(3-methyl-5-oxo-4-((3-(pyrazin-2-yl)phenyl)carbamoyl)-4,5-dihydro-1H-pyrazol-1-yl)benzoic acid Compound ID: 169

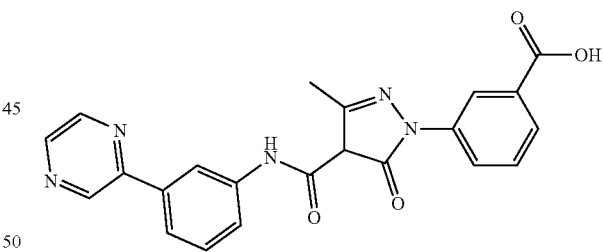

To a solution of methyl 3-[3-methyl-5-oxo-4-[(3-pyrazin-2-ylphenyl)carbamoyl]-4H-pyrazol-1-yl]benzoate (145 mg, 320 umol, 1.0 eq) in methanol (6 mL) and water (2 mL) was added lithium hydroxide monohydrate (33.6 mg, 801 umol, 2.5 eq). The solution was stirred at 25° C. for 16 h. The solution was adjusted to pH=2 by aqueous hydrochloric acid (6 N) and precipitate was formed. The suspension was filtered and filter cake was dried in vacuo to give 125 mg (87% yield) of Compound 169 as a yellow solid.

LCMS: (ESI) m/z 416.1 [M+H]+.

$^1$H NMR: (400 MHz, MeOD-d$_6$) δ: 9.14 (s, 1H), 8.70 (s, 1H), 8.55 (s, 1H), 8.45 (s, 1H), 8.33 (s, 1H), 8.04 (d, J=8.0 Hz, 1H), 7.97 (d, J=6.8 Hz, 1H), 7.82 (d, J=8.4 Hz, 1H), 7.75 (d, J=8.4 Hz, 1H), 7.70-7.60 (m, 1H), 7.55-7.51 (m, 1H), 2.67 (s, 3H).

4-((3-ethylphenyl)carbamoyl)-3-methyl-1-(4-(methylamino)phenyl)-1H-pyrazol-5-yl dimethylcarbamate Compound ID: 224

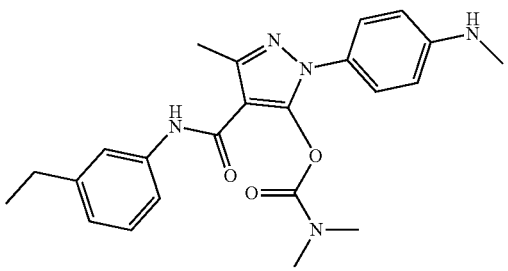 [SMILES: CCc1cccc(NC(=O)c2c(C)nn(-c3ccc(NC)cc3)c2OC(=O)N(C)C)c1]

LCMS: m/z 422.1 [M+H]+;
$^1$H NMR (400 MHz, DMSO-d$_6$) δ 9.50 (s, 1H), 7.51 (s, 1H), 7.41 (d, J=8.0 Hz, 1H), 7.26-7.16 (m, 3H), 6.92 (d, J=7.6 Hz, 1H), 6.62 (d, J=8.8 Hz, 2H), 6.04-5.97 (m, 1H), 3.02 (s, 3H), 2.79 (s, 3H), 2.71 (d, J=4.8 Hz, 3H), 2.59 (q, J=7.6 Hz, 2H), 2.37 (s, 3H), 1.18 (t, J=7.6 Hz, 3H).

N-(3-(1,1-difluoroethyl)phenyl)-3-methyl-5-oxo-1-(4-(trifluoromethoxy)phenyl)-4,5-dihydro-1H-pyrazole-4-carboxamide Compound ID: 226

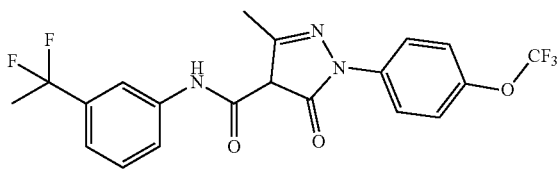 [SMILES: CC1=NN(c2ccc(OC(F)(F)F)cc2)C(=O)C1C(=O)Nc1cccc(C(C)(F)F)c1]

Compound 226 was obtained via general procedure IV from 3-methyl-5-oxo-1-(4-(trifluoromethoxy)phenyl)-4,5-dihydro-1H-pyrazole-4-carboxylate and 3-(1,1-difluoroethyl)aniline. LCMS: (ESI) m/z 442.1 [M+H]+.
$^1$H NMR (400 MHz, DMSO-d$_6$) δ: 10.77 (s, 1H), 7.94 (s, 1H), 7.91-7.84 (m, 2H), 7.65-7.58 (m, 1H), 7.53 (d, J=8.0 Hz, 2H), 7.42 (t, J=8.0 Hz, 1H), 7.24-7.18 (m, 1H), 2.54 (s, 3H), 1.96 (t, J=18.8 Hz, 3H).

3-methyl-1-(3-(oxazol-2-yl)phenyl)-5-oxo-N-(3-(pyrazin-2-yl)phenyl)-4,5-dihydro-1H-pyrazole-4-carboxamide Compound ID: 227

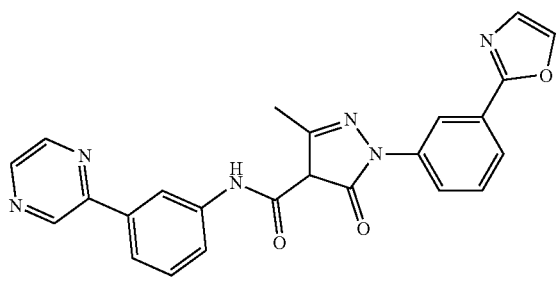 [SMILES: CC1=NN(c2cccc(-c3ncco3)c2)C(=O)C1C(=O)Nc1cccc(-c2cnccn2)c1]

Compound 227 was obtained via general procedure IV from 3-methyl-1-(3-(oxazol-2-yl)phenyl)-5-oxo-4,5-dihydro-1H-pyrazole-4-carboxylate and 3-(pyrazin-2-yl)aniline.
LCMS: (ESI) m/z 439.0 [M+H]+.
$^1$H NMR: (400 MHz, DMSO-d$_6$) δ: 10.92 (s, 1H), 9.24 (s, 1H), 8.74 (s, 1H), 8.63 (d, J=2.4 Hz, 1H), 8.55 (s, 1H), 8.44 (s, 1H), 8.28 (s, 1H), 8.00 (d, J=8.0 Hz, 1H), 7.85 (d, J=7.6 Hz, 1H), 7.82-7.75 (m, 2H), 7.64 (t, J=8.0 Hz, 1H), 7.47 (t, J=8.0 Hz, 1H), 7.44 (s, 1H), 2.54 (s, 3H).

N-(3-(furan-2-yl)phenyl)-3-methyl-1-(3-(oxazol-2-yl)phenyl)-5-oxo-4,5-dihydro-1H-pyrazole-4-carboxamide Compound ID: 228

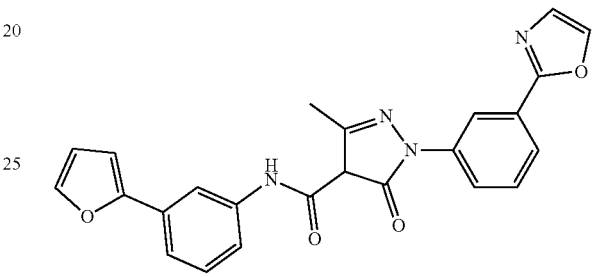

Compound 228 was obtained via general procedure IV from 3-methyl-1-(3-(oxazol-2-yl)phenyl)-5-oxo-4,5-dihydro-1H-pyrazole-4-carboxylate and 3-(furan-2-yl)aniline.
LCMS: (ESI) m/z 427.2 [M+H]+.
$^1$H NMR: (400 MHz, DMSO-d$_6$) δ: 10.7 (s, 1H), 8.45 (t, J=1.6 Hz, 1H), 8.28 (s, 1H), 8.09-8.04 (m, 1H), 7.91 (dd, J=1.6, 8.0 Hz, 2H), 7.75 (d, J=1.2 Hz, 1H), 7.71-7.65 (m, 1H), 7.51 (td, J=2.0, 7.2 Hz, 1H), 7.44 (s, 1H), 7.40-7.33 (m, 2H), 6.94 (d, J=3.2 Hz, 1H), 6.59 (dd, J=1.6, 3.2 Hz, 1H), 2.58 (s, 3H).

N-(3-(1,1-difluoroethyl)phenyl)-3-methyl-1-(3-(5-methyloxazol-2-yl)phenyl)-5-oxo-4,5-dihydro-1H-pyrazole-4-carboxamide Compound ID: 229

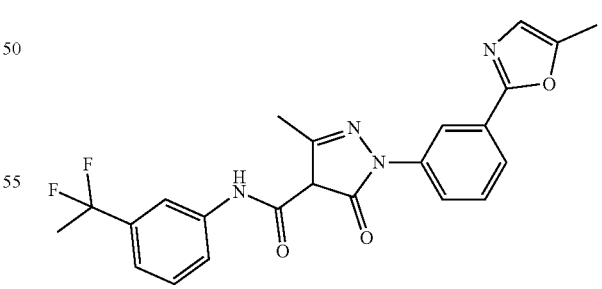

Compound 229 was obtained via general procedure IV from 3-methyl-1-(3-(5-methyloxazol-2-yl)phenyl)-5-oxo-4,5-dihydro-1H-pyrazole-4-carboxylate and 3-(1,1-difluoroethyl)aniline.
LCMS: (ESI) m/z 439.2 [M+H]+.
$^1$H NMR: (400 MHz, MeOD-d$_4$) δ: 8.40 (s, 1H), 7.93 (s, 1H), 7.88 (d, J=6.8 Hz, 2H), 7.64 (d, J=7.6 Hz, 1H), 7.59 (t, J=8.0 Hz, 1H), 7.39 (t, J=8.0 Hz, 1H), 7.21 (d, J=8.0 Hz, 1H), 6.94 (s, 1H), 2.56 (s, 3H), 2.44 (s, 3H), 1.86-1.99 (m, 3H).

N-(3-(1,1-difluoroethyl)phenyl)-3-methyl-1-(3-(oxazol-2-yl)phenyl)-5-oxo-4,5-dihydro-1H-pyrazole-4-carboxamide Compound ID: 230

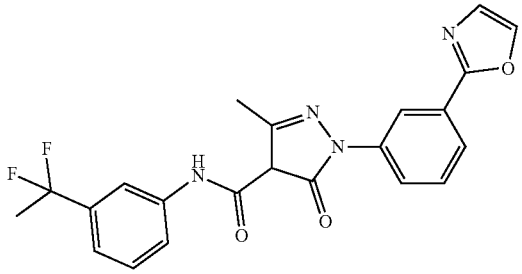 [SMILES: CC1=NN(c2cccc(-c3ncco3)c2)C(=O)C1C(=O)Nc1cccc(C(C)(F)F)c1]

Compound 230 was obtained via general procedure IV from 3-methyl-1-(3-(oxazol-2-yl)phenyl)-5-oxo-4,5-dihydro-1H-pyrazole-4-carboxylate and 3-(1,1-difluoroethyl)aniline.

LCMS: (ESI) m/z 425.1 [M+H]$^+$.

$^1$H NMR: (400 MHz, MeOD-d$_4$) δ: 8.42 (s, 1H), 8.03 (s, 1H), 7.98 (d, J=7.6 Hz, 1H), 7.93 (s, 1H), 7.88 (d, J=8.0 Hz, 1H), 7.70-7.60 (m, 2H), 7.41 (t, J=8.0 Hz, 1H), 7.34 (s, 1H), 7.23 (d, J=7.6 Hz, 1H), 2.61 (s, 3H), 1.93 (t, J=18.4 Hz, 3H).

N-(3-(1,1-difluoroethyl)phenyl)-3-methyl-5-oxo-1-(pyridin-4-yl)-4,5-dihydro-1H-pyrazole-4-carboxamide Compound ID: 231

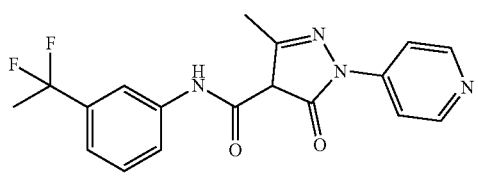 [SMILES: CC1=NN(c2ccncc2)C(=O)C1C(=O)Nc1cccc(C(C)(F)F)c1]

Compound 231 was obtained via general procedure IV from 3-methyl-5-oxo-1-(pyridin-4-yl)-4,5-dihydro-1H-pyrazole-4-carboxylate and 3-(1,1-difluoroethyl)aniline.

LCMS: (ESI) m/z 358.9 [M+H]$^+$.

$^1$H NMR: (400 MHz, DMSO-d$_6$) δ: 14.35 (br s, 1H), 10.65 (s, 1H), 8.63 (d, J=7.2 Hz, 4H), 7.94 (s, 1H), 7.58 (d, J=8.0 Hz, 1H), 7.38 (t, J=7.6 Hz, 1H), 7.13 (d, J=8.4 Hz, 1H), 2.34 (s, 3H), 1.96 (t, J=18.8 Hz, 3H).

3-methyl-5-oxo-N-(3-(pyrazin-2-yl)phenyl)-1-(pyridin-4-yl)-4,5-dihydro-1H-pyrazole-4-carboxamide Compound ID: 232

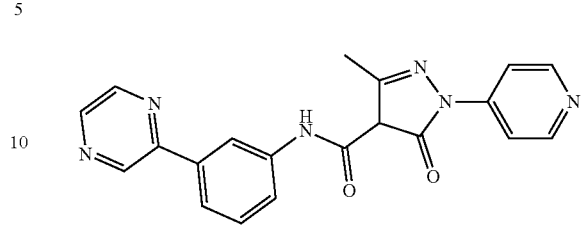

Compound 232 was obtained via general procedure IV from 3-methyl-5-oxo-1-(pyridin-4-yl)-4,5-dihydro-1H-pyrazole-4-carboxylate and 3-(pyrazin-2-yl)aniline.

LCMS: (ESI) m/z 372.9 [M+H]$^+$;

$^1$H NMR (400 MHz, DMSO-d$_6$) δ: 14.31 (br s, 1H), 10.69 (s, 1H), 9.22 (s, 1H), 8.74 (d, J=2.4 Hz, 1H), 8.69-8.45 (m, 5H), 8.41 (t, J=2.0 Hz, 1H), 7.72 (t, J=6.8 Hz, 2H), 7.43 (t, J=8.0 Hz, 1H), 2.34 (s, 3H).

N-(3-(1H-imidazol-2-yl)phenyl)-3-methyl-5-oxo-1-(pyridin-4-yl)-4,5-dihydro-1H-pyrazole-4-carboxamide Compound ID: 233

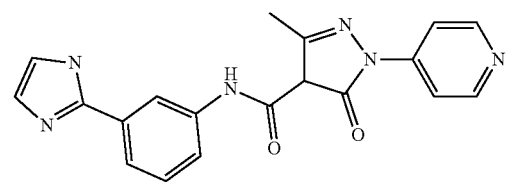 [SMILES: CC1=NN(c2ccncc2)C(=O)C1C(=O)Nc1cccc(-c2ncc[nH]2)c1]

Compound 233 was obtained via general procedure IV from 3-methyl-5-oxo-1-(pyridin-4-yl)-4,5-dihydro-1H-pyrazole-4-carboxylate and 3-(1H-imidazol-2-yl)aniline.

LCMS: (ESI) m/z 361.0 [M+H]$^+$.

$^1$H NMR: (400 MHz, MeOD-d$_4$) δ: 8.65 (d, J=6.4 Hz, 2H), 8.59-8.55 (m, 2H), 8.35 (t, J=1.6 Hz, 1H), 7.75 (d, J=7.6 Hz, 1H), 7.66 (s, 2H), 7.62-7.52 (m, 2H), 2.46 (s, 3H).

isopropyl 3-(3-methyl-5-oxo-4-((3-(pyrazin-2-yl)phenyl)carbamoyl)-4,5-dihydro-1H-pyrazol-1-yl)benzoate Compound ID: 234

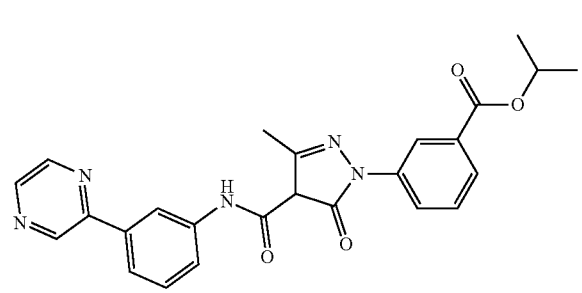 [SMILES: CC1=NN(c2cccc(C(=O)OC(C)C)c2)C(=O)C1C(=O)Nc1cccc(-c2cnccn2)c1]

234 was obtained via general procedure IV from 1-(3-(isopropoxycarbonyl)phenyl)-3-methyl-5-oxo-4,5-dihydro-1H-pyrazole-4-carboxylate and 3-(pyrazin-2-yl)aniline.

LCMS: (ESI) m/z 458.0 [M+H]+.

$^1$H NMR: (400 MHz, CDCl$_3$-d) δ: 10.61 (s, 1H), 8.99 (s, 1H), 8.59 (s, 1H), 8.51 (s, 1H), 8.31 (s, 1H), 8.06 (s, 1H), 7.83 (d, J=7.2 Hz, 2H), 7.57 (d, J=6.8 Hz, 2H), 7.42-7.37 (m, 2H), 5.20-5.14 (m, 1H), 2.60 (s, 3H), 1.33 (d, J=6.4 Hz, 6H).

isopropyl 3-(4-((3-(1H-imidazol-2-yl)phenyl)carbamoyl)-3-methyl-5-oxo-4,5-dihydro-1H-pyrazol-1-yl)benzoate Compound ID: 235

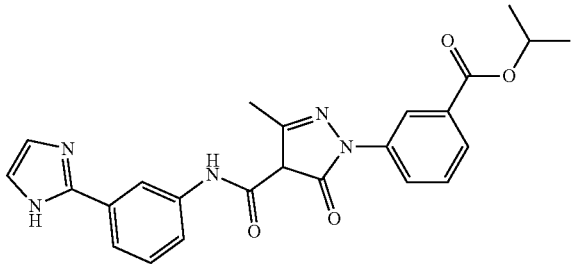 [SMILES: CC1=NN(c2cccc(C(=O)OC(C)C)c2)C(=O)C1C(=O)Nc1cccc(-c2ncc[nH]2)c1]

Compound 235 was obtained via general procedure IV from 1-(3-(isopropoxycarbonyl)phenyl)-3-methyl-5-oxo-4,5-dihydro-1H-pyrazole-4-carboxylate and 3-(1H-imidazol-2-yl)aniline.

LCMS: (ESI) m/z 446.1 [M+H]+.

$^1$H NMR: (400 MHz, MeOD-d$_4$) δ: 8.52 (s, 1H), 8.20 (s, 1H), 8.10-8.08 (m, 1H), 7.83 (t, J=6.4 Hz, 2H), 7.58-7.52 (m, 5H), 5.28-5.21 (m, 1H), 2.47 (s, 3H), 1.40 (d, J=6.4 Hz, 6H).

isopropyl 3-(4-((3-(1,1-difluoroethyl)phenyl)carbamoyl)-3-methyl-5-oxo-4,5-dihydro-1H-pyrazol-1-yl)benzoate Compound ID: 236

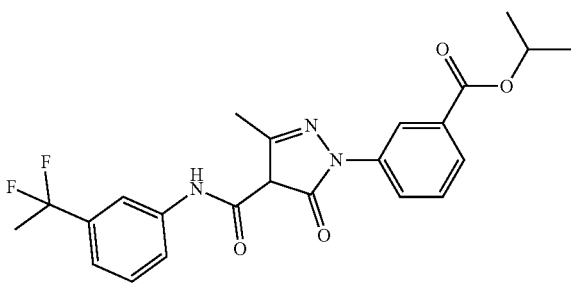 [SMILES: CC1=NN(c2cccc(C(=O)OC(C)C)c2)C(=O)C1C(=O)Nc1cccc(C(C)(F)F)c1]

Compound 236 was obtained via general procedure IV from 1-(3-(isopropoxycarbonyl)phenyl)-3-methyl-5-oxo-4,5-dihydro-1H-pyrazole-4-carboxylate and 3-(1,1-difluoroethyl)aniline.

LCMS: (ESI) m/z 444.2 [M+H]+.

$^1$H NMR: (400 MHz, MeOD-d$_4$) δ: 8.28 (s, 1H), 8.01-7.92 (m, 3H), 7.65 (t, J=8.0 Hz, 2H), 7.42-7.39 (m, 1H), 7.25 (d, J=7.6 Hz, 1H), 5.30-5.23 (m, 1H), 2.64 (s, 3H), 1.93 (t, J=18.4 Hz, 3H), 1.40 (d, J=6.4 Hz, 6H).

isopropyl 3-(4-((3-(furan-2-yl)phenyl)carbamoyl)-3-methyl-5-oxo-4,5-dihydro-1H-pyrazol-1-yl)benzoate Compound ID: 237

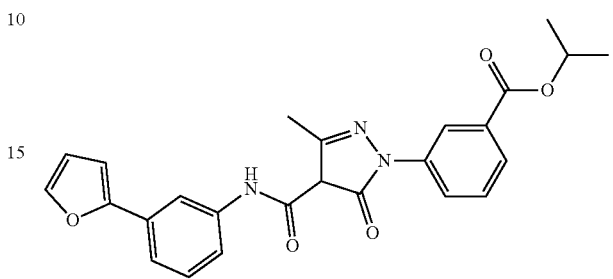

Compound 237 was obtained via general procedure IV from 1-(3-(isopropoxycarbonyl)phenyl)-3-methyl-5-oxo-4,5-dihydro-1H-pyrazole-4-carboxylate and 3-(furan-2-yl)aniline.

LCMS: (ESI) m/z 446.2 [M+H]+.

$^1$H NMR: (400 MHz, MeOD-d$_4$) δ: 8.34 (s, 1H), 8.08 (s, 1H), 8.06-7.94 (m, 2H), 7.62 (t, J=8.0 Hz, 1H), 7.55 (s, 1H), 7.47 (d, J=8.0 Hz, 1H), 7.40-7.34 (m, 2H), 6.78 (d, J=3.2 Hz, 1H), 6.53-6.51 (m, 1H), 5.28-5.24 (m, 1H), 2.61 (s, 3H), 1.40 (d, J=6.0 Hz, 6H).

isopropyl 3-(3-methyl-4-((3-(oxazol-2-yl)phenyl)carbamoyl)-5-oxo-4,5-dihydro-1H-pyrazol-1-yl)benzoate Compound ID: 238

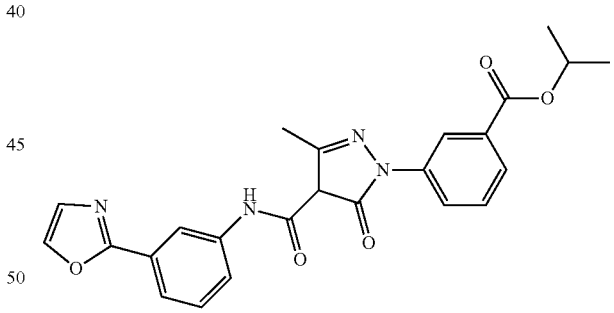

To a solution of 3-[3-methyl-4-[(3-oxazol-2-ylphenyl)carbamoyl]-5-oxo-4H-pyrazol-1-yl]benzoic acid (36.0 mg, 86.5 umol, 1.0 eq) in isopropanol (2 mL) was added thionyl chloride (1.64 g, 13.8 mmol, 159 eq). The solution was stirred at 70° C. for 12 h. The solution was concentrated. The residue was purified by prep-HPLC (column: Phenomenex Synergi C18 150*25*10 um; mobile phase: [water(0.225% FA)-ACN]; B %: 45%-75%, 10 min) to give 25.0 mg (64% yield) of Compound 238 as a white solid.

LCMS: (ESI) m/z 447.1 [M+H]+.

$^1$H NMR: (400 MHz, MeOD-d$_4$) δ: 8.34 (s, 1H), 8.24 (s, 1H), 8.08 (s, 1H), 7.91 (d, J=8.4 Hz, 3H), 7.68 (t, J=7.6 Hz, 2H), 7.58 (t, J=8.0 Hz, 1H), 7.42 (t, J=8.0 Hz, 1H), 7.27 (s, 1H), 5.25-5.21 (m, 1H), 2.58 (s, 3H), 1.38 (d, J=6.0 Hz, 6H).

N-(3-(isoxazol-3-yl)phenyl)-3-methyl-5-oxo-1-phenyl-4,5-dihydro-1H-pyrazole-4-carboxamide Compound ID: 239

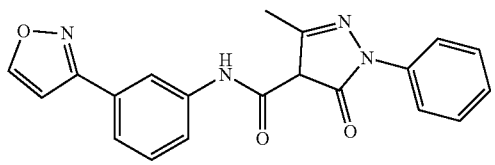 [SMILES: CC1=NN(c2ccccc2)C(=O)C1C(=O)Nc1cccc(-c2ccon2)c1]

Compound 239 was obtained via general procedure IV from 3-(isoxazol-3-yl)aniline and 3-methyl-5-oxo-1-phenyl-4,5-dihydro-1H-pyrazole-4-carboxylate.

LCMS: (ESI) m/z: 360.9 [M+H]$^+$.

$^1$H NMR (400 MHz, DMSO-d$_4$) δ: 10.92 (s, 1H), 8.21 (d, J=1.6 Hz, 1H), 7.95-7.93 (m, 1H), 7.75-7.73 (m, 3H), 7.60-7.58 (m, 1H), 7.53-7.50 (m, 4H), 7.33-7.30 (m, 1H), 2.54 (s, 3H).

N-(3-(furan-2-yl)phenyl)-3-methyl-5-oxo-1-(pyridin-4-yl)-4,5-dihydro-1H-pyrazole-4-carboxamide Compound ID: 240

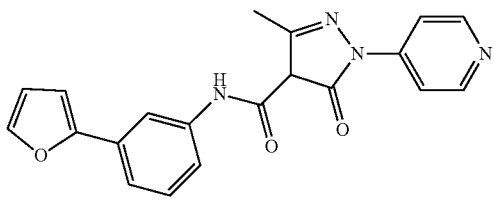 [SMILES: CC1=NN(c2ccncc2)C(=O)C1C(=O)Nc1cccc(-c2ccco2)c1]

Compound 240 was obtained via general procedure IV from 3-methyl-5-oxo-1-(pyridin-4-yl)-4,5-dihydro-1H-pyrazole-4-carboxylate and 3-(furan-2-yl)aniline.

LCMS: (ESI) m/z 361.0 [M+H]$^+$.

$^1$H NMR (400 MHz, MeOD-d$_4$) δ: 8.53 (q, J=6.4 Hz, 4H), 8.05 (s, 1H), 7.55 (d, J=1.2 Hz, 1H), 7.47 (d, J=8.0 Hz, 1H), 7.38-7.30 (m, 2H), 6.78 (d, J=2.8 Hz, 1H), 6.52 (dd, J=3.2, 1.6 Hz, 1H), 2.45 (s, 3H).

1-(4-methoxyphenyl)-3-methyl-5-oxo-N-(3-(pyrazin-2-yl)phenyl)-4,5-dihydro-1H-pyrazole-4-carboxamide Compound ID: 241

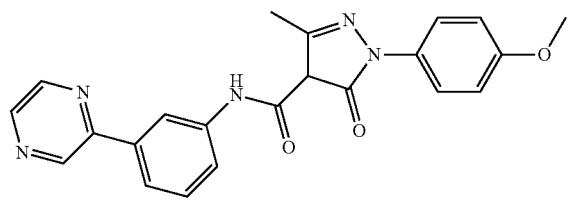 [SMILES: COc1ccc(N2N=C(C)C(C(=O)Nc3cccc(-c4cnccn4)c3)C2=O)cc1]

Compound 241 was obtained via general procedure IV from 1-(4-methoxyphenyl)-3-methyl-5-oxo-4,5-dihydro-1H-pyrazole-4-carboxylate and 3-(pyrazin-2-yl)aniline.

LCMS: (ESI) m/z 402.0 [M+H]$^+$.

$^1$H NMR: (400 MHz, DMSO-d) δ: 11.04 (s, 1H), 9.23 (d, J=1.2 Hz, 1H), 8.77-8.70 (m, 1H), 8.62 (d, J=2.4 Hz, 1H), 8.42 (s, 1H), 7.80-7.72 (m, 2H), 7.68 (d, J=8.8 Hz, 2H), 7.46 (t, J=8.0 Hz, 1H), 7.04 (d, J=8.8 Hz, 2H), 3.79 (s, 3H), 2.48 (s, 3H).

N-(3-(1,1-difluoroethyl)phenyl)-1-(6-methoxypyridin-3-yl)-3-methyl-5-oxo-4,5-dihydro-1H-pyrazole-4-carboxamide Compound ID: 242

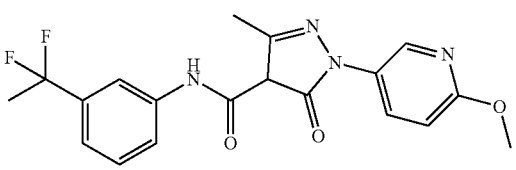 [SMILES: COc1ccc(N2N=C(C)C(C(=O)Nc3cccc(C(C)(F)F)c3)C2=O)cn1]

Compound 242 was obtained via general procedure IV from 1-(6-methoxypyridin-3-yl)-3-methyl-5-oxo-4,5-dihydro-1H-Pyrazole-4-carboxylate and 3-(1,1-difluoroethyl)aniline.

LCMS: (ESI) m/z 388.9 [M+H]$^+$.

$^1$H NMR (400 MHz, DMSO-d$_6$) δ: 10.79 (s, 1H), 8.47 (d, J=2.4 Hz, 1H), 8.02 (dd, J=2.8, 8.8 Hz, 1H), 7.94 (s, 1H), 7.61 (d, J=8.0 Hz, 1H), 7.42 (t, J=8.0 Hz, 1H), 7.21 (d, J=8.0 Hz, 1H), 6.99 (d, J=8.8 Hz, 1H), 3.90 (s, 3H), 2.53 (s, 3H), 1.96 (t, J=18.8 Hz, 3H).

1-(6-methoxypyridin-3-yl)-3-methyl-5-oxo-N-(3-(pyrazin-2-yl)phenyl)-4,5-dihydro-1H-pyrazole-4-carboxamide Compound ID: 243

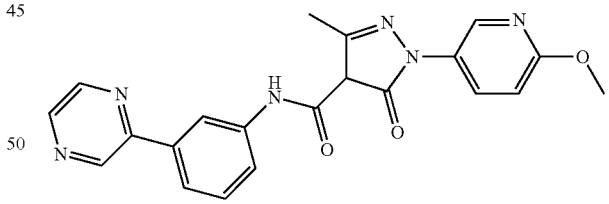

Compound 243 was obtained via general procedure IV from 1-(6-methoxypyridin-3-yl)-3-methyl-5-oxo-4,5-dihydro-1H-Pyrazole-4-carboxylate and 3-(pyrazin-2-yl)aniline.

LCMS: (ESI) m/z 403.2 [M+H]$^+$.

$^1$H NMR: (400 MHz, DMSO-d$_6$) δ: 10.85 (s, 1H), 9.23 (s, 1H), 8.76-8.70 (m, 1H), 8.62 (d, J=2.4 Hz, 1H), 8.50 (d, J=2.4 Hz, 1H), 8.43 (s, 1H), 8.06 (dd, J=2.8, 8.8 Hz, 1H), 7.79 (d, J=7.6 Hz, 1H), 7.75 (d, J=7.6 Hz, 1H), 7.47 (t, J=8.0 Hz, 1H), 6.98 (d, J=8.8 Hz, 1H), 3.89 (s, 3H), 2.52 (s, 3H).

N-(3-(1H-imidazol-2-yl)phenyl)-1-(6-methoxypyridin-3-yl)-3-methyl-5-oxo-4,5-dihydro-1H-pyrazole-4-carboxamide Compound ID: 244

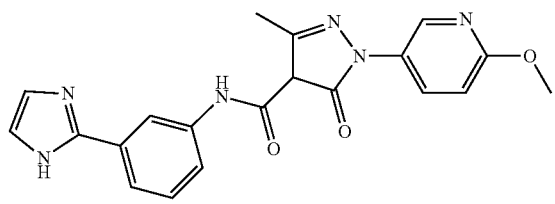 [SMILES: COc1ccc(N2N=C(C)C(C(=O)Nc3cccc(-c4ncco4)c3)C2=O)cn1]

Compound 244 was obtained via general procedure IV from 1-(6-methoxypyridin-3-yl)-3-methyl-5-oxo-4,5-dihydro-1H-Pyrazole-4-carboxylate and 3-(1H-imidazol-2-yl)aniline.

LCMS: (ESI) m/z 391.0 [M+H]$^+$.
$^1$H NMR: (400 MHz, DMSO-d$_6$) δ: 11.38 (s, 1H), 8.80 (d, J=2.4 Hz, 1H), 8.34 (dd, J=2.4, 8.8 Hz, 1H), 8.21 (s, 1H), 7.91 (d, J=7.6 Hz, 1H), 7.64 (s, 2H), 7.53-7.41 (m, 2H), 6.80 (d, J=8.8 Hz, 1H), 3.84 (s, 3H), 2.29 (s, 3H).

1-(6-methoxypyridin-3-yl)-3-methyl-N-(3-(oxazol-2-yl)phenyl)-5-oxo-4,5-dihydro-1H-pyrazole-4-carboxamide Compound ID: 245

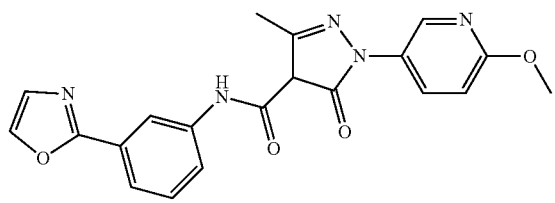

Compound 245 was obtained via general procedure IV from 1-(6-methoxypyridin-3-yl)-3-methyl-5-oxo-4,5-dihydro-1H-Pyrazole-4-carboxylate and 3-(oxazol-2-yl)aniline.

LCMS: (ESI) m/z 414.0 [M+Na]$^+$.
$^1$H NMR: (400 MHz, DMSO-d$_6$) δ: 10.94 (s, 1H), 8.56 (s, 1H), 8.44 (s, 1H), 8.22 (s, 1H), 8.11 (d, J=6.0 Hz, 1H), 7.66-7.55 (m, 2H), 7.47-7.41 (m, 1H), 7.38 (s, 1H), 6.94 (d, J=8.8 Hz, 1H), 3.88 (s, 3H), 2.47 (s, 3H).

N-(3-(furan-2-yl)phenyl)-1-(6-methoxypyridin-3-yl)-3-methyl-5-oxo-4,5-dihydro-1H-pyrazole-4-carboxamide Compound ID: 246

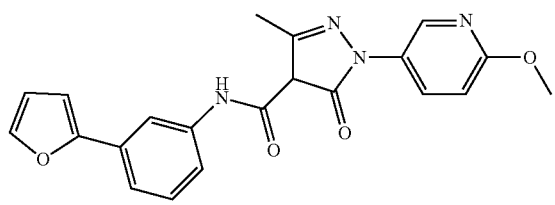 [SMILES: COc1ccc(N2N=C(C)C(C(=O)Nc3cccc(-c4ccco4)c3)C2=O)cn1]

Compound 246 was obtained via general procedure IV from 1-(6-methoxypyridin-3-yl)-3-methyl-5-oxo-4,5-dihydro-1H-Pyrazole-4-carboxylate and 3-(furan-2-yl)aniline.

LCMS: (ESI) m/z 391.0 [M+H]$^+$.
$^1$H NMR: (400 MHz, DMSO-d$_6$) δ: 10.73 (s, 1H), 8.47 (d, J=2.4 Hz, 1H), 8.07-8.00 (m, 2H), 7.75 (s, 1H), 7.49-7.43 (m, 1H), 7.40-7.30 (m, 2H), 7.00 (d, J=8.8 Hz, 1H), 6.93 (d, J=3.2 Hz, 1H), 6.60 (dd, J=1.6, 3.2 Hz, 1H), 3.90 (s, 3H), 2.54 (s, 3H).

N-(3-(furan-2-yl)phenyl)-1-(3-methoxyphenyl)-3-methyl-5-oxo-4,5-dihydro-1H-pyrazole-4-carboxamide Compound ID: 247

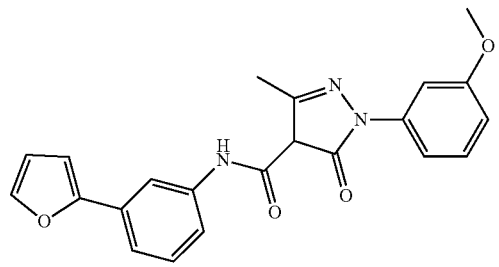 [SMILES: COc1cccc(N2N=C(C)C(C(=O)Nc3cccc(-c4ccco4)c3)C2=O)c1]

Compound 247 was obtained via general procedure IV from 1-(3-methoxyphenyl)-3-methyl-5-oxo-4,5-dihydro-1H-pyrazole-4-carboxylate and 3-(furan-2-yl)aniline.

LCMS: (ESI) m/z 390.0 [M+H]$^+$.
$^1$H NMR: (400 MHz, DMSO-d$_6$) δ: 10.86 (s, 1H), 8.05 (s, 1H), 7.75 (d, J=0.8 Hz, 1H), 7.48-7.47 (m, 2H), 7.40-7.33 (m, 4H), 6.93 (d, J=3.6 Hz, 1H), 6.83-6.75 (m, 1H), 6.59 (d, J=3.2 Hz, 1H), 3.81 (s, 3H), 2.50 (s, 3H).

N-(3-(1H-imidazol-2-yl)phenyl)-1-(3-methoxyphenyl)-3-methyl-5-oxo-4,5-dihydro-1H-pyrazole-4-carboxamide Compound ID: 248

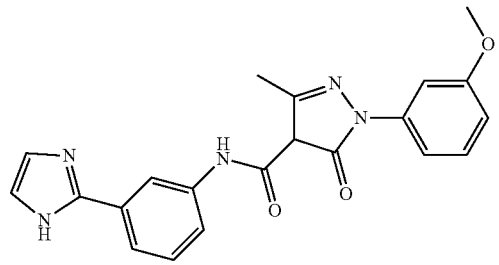 [SMILES: COc1cccc(N2N=C(C)C(C(=O)Nc3cccc(-c4ncc[nH]4)c3)C2=O)c1]

Compound 248 was obtained via general procedure IV from 1-(3-methoxyphenyl)-3-methyl-5-oxo-4,5-dihydro-1H-pyrazole-4-carboxylate and 3-(1H-imidazol-2-yl)aniline.

LCMS: (ESI) m/z 390.1 [M+H]$^+$.
$^1$H NMR: (400 MHz, DMSO-d$_6$) δ: 11.43 (s, 1H), 8.20 (s, 1H), 7.98-7.90 (m, 1H), 7.79 (d, J=2.0 Hz, 1H), 7.68 (d, J=8.0 Hz, 1H), 7.61 (s, 2H), 7.50-7.47 (m, 1H), 7.46-7.25 (m, 1H), 7.23-7.20 (m, 1H), 6.60-6.57 (m, 1H), 3.76 (s, 3H), 2.32 (s, 3H).

1-(3-methoxyphenyl)-3-methyl-5-oxo-N-(3-(pyrazin-2-yl)phenyl)-4,5-dihydro-1H-pyrazole-4-carboxamide Compound ID: 249

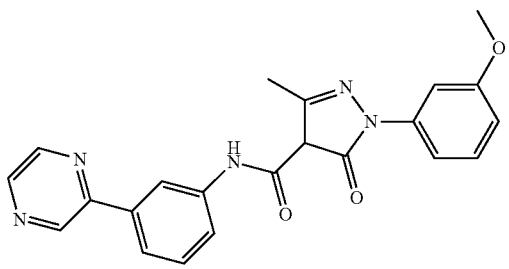 [SMILES: COc1cccc(N2N=C(C)C(C(=O)Nc3cccc(-c4cnccn4)c3)C2=O)c1]

Compound 249 was obtained via general procedure IV from 1-(3-methoxyphenyl)-3-methyl-5-oxo-4,5-dihydro-1H-pyrazole-4-carboxylate and 3-(pyrazin-2-yl)aniline.

LCMS: (ESI) m/z 402.2 [M+H]$^+$.

$^1$H NMR: (400 MHz, DMSO-d$_6$) δ: 10.88 (s, 1H), 9.24 (d, J=1.6 Hz, 1H), 8.74 (d, J=0.4 Hz, 1H), 8.62 (d, J=2.4 Hz, 1H), 8.43 (t, J=1.6 Hz, 1H), 7.90-7.78 (m, 2H), 7.50-7.36 (m, 4H), 6.90-6.86 (m, 1H), 3.82 (s, 3H), 2.55 (s, 3H).

N-(3-(1,1-difluoroethyl)phenyl)-1-(3-methoxyphenyl)-3-methyl-5-oxo-4,5-dihydro-1H-pyrazole-4-carboxamide Compound ID: 250

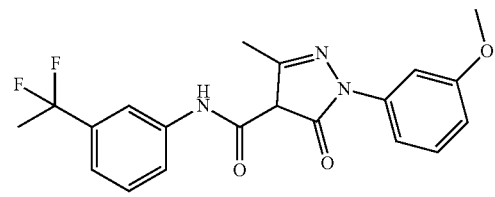 [SMILES: COc1cccc(N2N=C(C)C(C(=O)Nc3cccc(C(C)(F)F)c3)C2=O)c1]

Compound 250 was obtained via general procedure IV from 1-(3-methoxyphenyl)-3-methyl-5-oxo-4,5-dihydro-1H-pyrazole-4-carboxylate and 3-(1,1-difluoroethyl)aniline.

LCMS: (ESI) m/z 388.1 [M+H]$^+$.

$^1$H NMR: (400 MHz, MeOD-d$_4$) δ: 7.92 (s, 1H), 7.70-7.63 (m, 1H), 7.40 (t, J=8.0 Hz, 2H), 7.33 (d, J=2.0 Hz, 1H), 7.24 (t, J=8.0 Hz, 2H), 6.92 (d, J=2.0 Hz, 1H), 3.86 (s, 3H), 2.59 (s, 3H), 1.92 (t, J=22.4 Hz, 3H).

1-(3-methoxyphenyl)-3-methyl-N-(3-(oxazol-2-yl)phenyl)-5-oxo-4,5-dihydro-1H-pyrazole-4-carboxamide Compound ID: 251

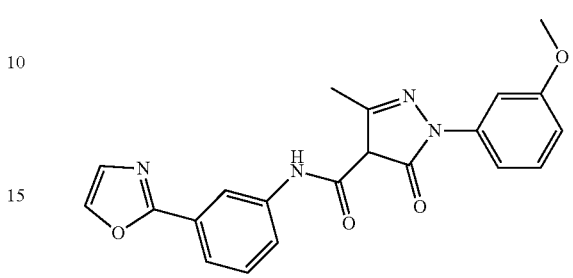

Compound 251 was obtained via general procedure IV from 1-(3-methoxyphenyl)-3-methyl-5-oxo-4,5-dihydro-1H-pyrazole-4-carboxylate and 3-(oxazol-2-yl)aniline.

LCMS: (ESI) m/z 391.0 [M+H]$^+$.

$^1$H NMR: (400 MHz, DMSO-d$_6$) δ: 10.87 (s, 1H), 8.46 (s, 1H), 8.23 (s, 1H), 7.67-7.64 (m, 2H), 7.50-7.35 (m, 5H), 6.90 (d, J=2.0 Hz, 1H), 3.82 (s, 3H), 2.56 (s, 3H).

N-(3-(1,1-difluoroethyl)phenyl)-1-(3-(N,N-dimethylsulfamoyl)phenyl)-3-methyl-5-oxo-4,5-dihydro-1H-pyrazole-4-carboxamide Compound ID: 252

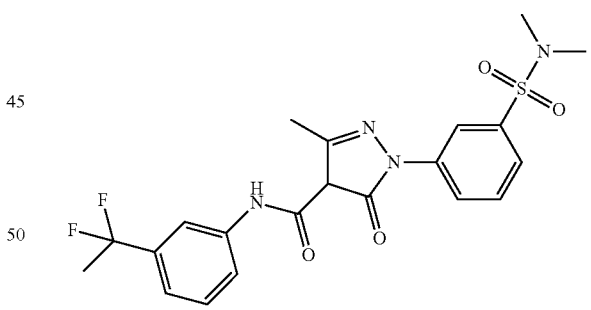

Compound 252 was obtained via general procedure IV from 3-(1,1-difluoroethyl)aniline and 4-nitrophenyl 1-(3-(N,N-dimethylsulfamoyl)phenyl)-3-methyl-5-oxo-4,5-dihydro-1H-pyrazole-4-carboxylate.

LCMS: (ESI) m/z 464.9 [M+H]$^+$.

$^1$H NMR: (400 MHz, MeOD-d$_4$) δ: 8.19 (s, 1H), 8.00 (d, J=7.2 Hz, 1H), 7.92 (s, 1H), 7.82-7.73 (m, 2H), 7.65 (d, J=8.4 Hz, 1H), 7.41 (t, J=7.6 Hz, 1H), 7.25 (d, J=7.6 Hz, 1H), 2.77 (s, 6H), 2.66 (s, 3H), 1.93 (t, J=18.0 Hz, 3H).

N-(3-(1,1-difluoroethyl)phenyl)-1-(4-(N,N-dimethylsulfamoyl)phenyl)-3-methyl-5-oxo-4,5-dihydro-1H-pyrazole-4-carboxamide Compound ID: 253

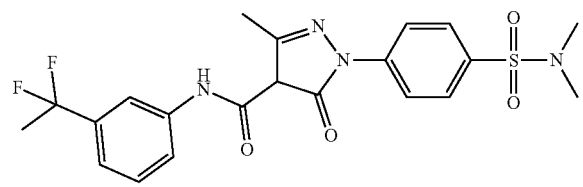 [SMILES: CC1=NN(c2ccc(S(=O)(=O)N(C)C)cc2)C(=O)C1C(=O)Nc1cccc(C(C)(F)F)c1]

Compound 253 was obtained via general procedure IV from 3-(1,1-difluoroethyl)aniline and 1-(4-(N,N-dimethylsulfamoyl)phenyl)-3-methyl-5-oxo-4,5-dihydro-1H-pyrazole-4-carboxylate.

LCMS: (ESI) m/z: 465.0 [M+H]$^+$.

$^1$H NMR: (400 MHz, MeOD-d$_4$) δ: 8.13 (d, J=8.8 Hz, 2H), 7.91 (s, 1H), 7.84 (d, J=8.8 Hz, 2H), 7.64 (d, J=8.0 Hz, 1H), 7.39 (t, J=7.6 Hz, 1H), 7.21 (d, J=7.6 Hz, 1H), 2.70 (s, 6H), 2.53 (s, 3H), 1.92 (t, J=18.0 Hz, 3H).

1-(4-(N,N-dimethylsulfamoyl)phenyl)-3-methyl-N-(3-(oxazol-2-yl)phenyl)-5-oxo-4,5-dihydro-1H-pyrazole-4-carboxamide Compound ID: 254

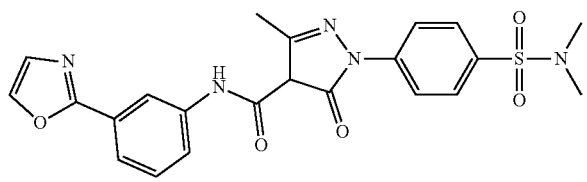 [SMILES: CC1=NN(c2ccc(S(=O)(=O)N(C)C)cc2)C(=O)C1C(=O)Nc1cccc(-c2ncco2)c1]

Compound 254 was obtained via general procedure IV from 3-(oxazol-2-yl)aniline and 1-(4-(N,N-dimethylsulfamoyl)phenyl)-3-methyl-5-oxo-4,5-dihydro-1H-pyrazole-4-carboxylate.

LCMS: (ESI) m/z 468.0 [M+H]$^+$.

$^1$H NMR: (400 MHz, DMSO-d$_6$) δ: 10.86 (s, 1H), 8.47 (s, 1H), 8.23 (s, 1H), 8.16 (d, J=8.8 Hz, 2H), 7.84 (d, J=8.8 Hz, 2H), 7.63 (d, J=8.0 Hz, 2H), 7.50-7.43 (m, 1H), 7.39 (s, 1H), 2.64-2.61 (s, 6H), 2.53 (s, 3H).

N-[3-(1H-imidazol-2-yl)phenyl]-1-(4-methoxyphenyl)-3-methyl-5-oxo-4H-pyrazole-4-carboxamide Compound ID: 255

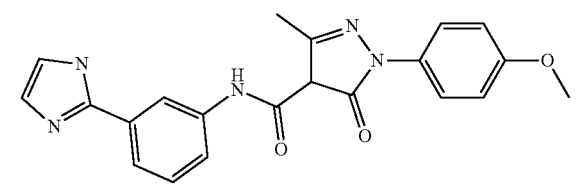 [SMILES: COc1ccc(N2N=C(C)C(C(=O)Nc3cccc(-c4ncc[nH]4)c3)C2=O)cc1]

Compound 255 was obtained via general procedure IV from 1-(4-methoxyphenyl)-3-methyl-5-oxo-4,5-dihydro-1H-pyrazole-4-carboxylate and 3-(1H-imidazol-2-yl)aniline.

LCMS: (ESI) m/z 390.0 [M+H]$^+$.

$^1$H NMR: (400 MHz, MeOD-d$_4$) δ: 8.27 (s, 1H), 7.85-7.82 (m, 1H), 7.66 (s, 2H), 7.62-7.60 (m, 2H), 7.51 (dd, J=9.2, 2.0 Hz, 2H), 7.10 (dd, J=9.2, 2.0 Hz, 2H), 3.86 (s, 3H), 2.63 (s, 3H).

1-(4-methoxyphenyl)-3-methyl-N-(3-(oxazol-2-yl)phenyl)-5-oxo-4,5-dihydro-1H-pyrazole-4-carboxamide Compound ID: 256

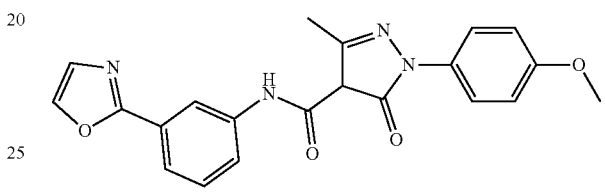

Compound 256 was obtained via general procedure IV from 1-(4-methoxyphenyl)-3-methyl-5-oxo-4,5-dihydro-1H-pyrazole-4-carboxylate and 3-(oxazol-2-yl)aniline.

LCMS: (ESI) m/z 391.0 [M+H]$^+$.

$^1$H NMR: (400 MHz, MeOD-d$_4$) δ: 8.41 (s, 1H), 8.00 (s, 1H), 7.74 (d, J=7.6 Hz, 1H), 7.70 (d, J=8.0 Hz, 1H), 7.53 (d, J=8.8 Hz, 2H), 7.47 (t, J=8.0 Hz, 1H), 7.30 (s, 1H), 7.07 (d, J=9.2 Hz, 2H), 3.85 (s, 3H), 2.59 (s, 3H).

3-methyl-N-(3-(oxazol-2-yl)phenyl)-5-oxo-1-(3-(trifluoromethyl)phenyl)-4,5-dihydro-1H-pyrazole-4-carboxamide Compound ID: 257

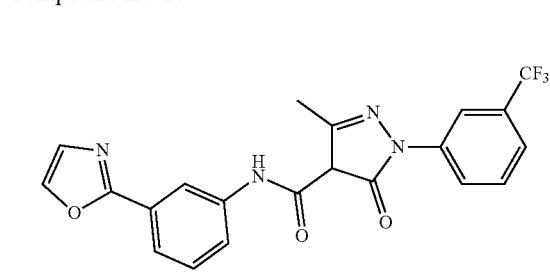

Compound 257 was obtained via general procedure IV from 3-methyl-5-oxo-1-(3-(trifluoromethyl)phenyl)-4,5-dihydro-1H-pyrazole-4-carboxylate and 3-(oxazol-2-yl)aniline.

LCMS: (ESI) m/z 429.3 [M+H]$^+$.

$^1$H NMR: (400 MHz, DMSO-d$_6$) δ: 10.74 (s, 1H), 8.48 (t, J=1.6 Hz, 1H), 8.22-8.21 (m, 2H), 8.08 (d, J=8.4 Hz, 1H), 7.76 (t, J=8.0 Hz, 1H), 7.66-7.60 (m, 3H), 7.47 (t, J=8.0 Hz, 1H), 7.39 (d, J=0.8 Hz, 1H), 2.57 (s, 3H).

3-(4-((3-(1,1-difluoroethyl)phenyl)carbamoyl)-3-methyl-5-oxo-4,5-dihydro-1H-pyrazol-1-yl)benzoic acid Compound ID: 258

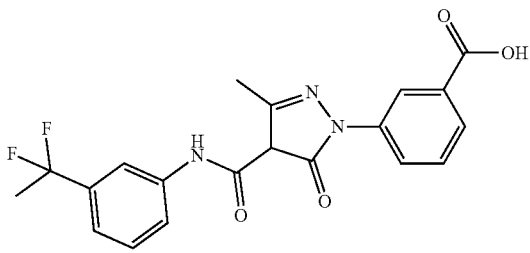 [SMILES: CC1=NN(c2cccc(C(=O)O)c2)C(=O)C1C(=O)Nc1cccc(C(C)(F)F)c1]

Compound 258 was obtained via similar synthetic method of Compound 170 from Compound 261.
LCMS: (ESI) m/z 402.2 [M+H]⁺.
¹H NMR: (400 MHz, MeOD-d₄) δ: 8.31 (s, 1H), 8.03 (d, J=7.6 Hz, 1H), 7.97-7.92 (m, 2H), 7.68-7.62 (m, 2H), 7.45-7.40 (m, 1H), 7.25 (d, J=8.0 Hz, 1H), 2.65 (s, 3H), 1.93 (t, J=18.4 Hz, 3H).

methyl 3-(3-methyl-4-((3-(oxazol-2-yl)phenyl)carbamoyl)-5-oxo-4,5-dihydro-1H-pyrazol-1-yl)benzoate Compound ID: 259

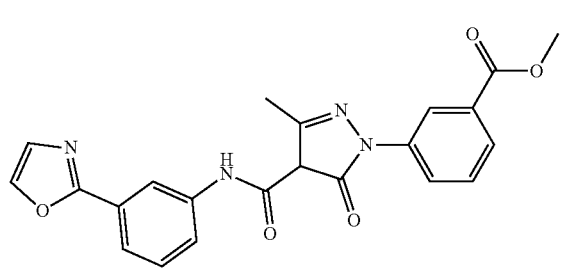 [SMILES: COC(=O)c1cccc(N2N=C(C)C(C(=O)Nc3cccc(-c4ncco4)c3)C2=O)c1]

Compound 259 was obtained via general procedure IV from 1-(3-(methoxycarbonyl)phenyl)-3-methyl-5-oxo-4,5-dihydro-1H-pyrazole-4-carboxylate and 3-(oxazol-2-yl)aniline.
LCMS: (ESI) m/z 419.2 [M+H]⁺.
¹H NMR: (400 MHz, DMSO-d₆) δ: 10.83 (s, 1H), 8.48 (d, J=2.0 Hz, 1H), 8.48-8.40 (m, 1H), 8.23 (s, 1H), 8.15-8.05 (m, 1H), 7.90-7.80 (m, 1H), 7.69-7.64 (m, 3H), 7.49-7.46 (m, 1H), 7.40-7.39 (m, 1H), 3.91 (s, 3H), 2.56 (s, 3H).

N-(5-ethylthiophen-2-yl)-3-methyl-5-oxo-1-phenyl-4,5-dihydro-1H-pyrazole-4-carboxamide Compound ID: 260

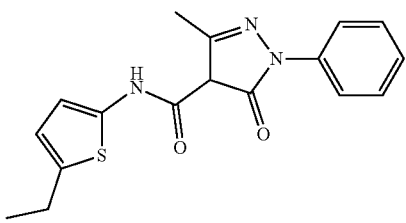 [SMILES: CCc1ccc(NC(=O)C2C(=O)N(c3ccccc3)N=C2C)s1]

Compound 260 was obtained via general procedure IV from 5-ethylthiophen-2-amine and 3-methyl-5-oxo-1-phenyl-4,5-dihydro-1H-pyrazole-4-carboxylate.
LCMS: (ESI) m/z 328.0 [M+H]⁺.
¹H NMR: (400 Hz, DMSO-d₆) δ: 11.22 (s, 1H), 7.73 (d, J=7.6 Hz, 2H), 7.53-7.48 (m, 2H), 7.33-7.28 (m, 1H), 6.54 (d, J=4.0 Hz, 1H), 6.50 (d, J=3.6 Hz, 1H), 2.68 (q, J=7.2 Hz, 2H), 2.52 (s, 3H), 1.22 (t, J=7.6 Hz, 3H).

methyl 3-(4-((3-(1,1-difluoroethyl)phenyl)carbamoyl)-3-methyl-5-oxo-4,5-dihydro-1H-pyrazol-1-yl)benzoate (261)

Compound ID: 261

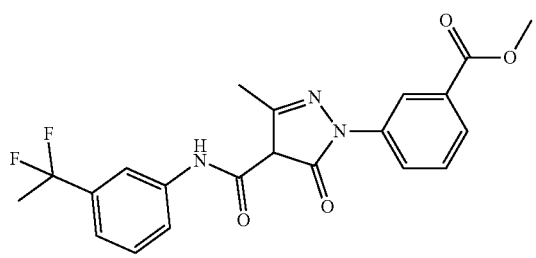 [SMILES: COC(=O)c1cccc(N2N=C(C)C(C(=O)Nc3cccc(C(C)(F)F)c3)C2=O)c1]

Compound 261 was obtained via general procedure IV from 1-(3-(methoxycarbonyl)phenyl)-3-methyl-5-oxo-4,5-dihydro-1H-pyrazole-4-carboxylate and 3-(1,1-difluoroethyl)aniline.
LCMS: (ESI) m/z 416.2 [M+H]⁺.
¹H NMR: (400 MHz, MeOD-d₄) δ: 8.32 (s, 1H), 8.02 (d, J=7.6 Hz, 1H), 7.95 (d, J=1.2 Hz, 1H), 7.92 (s, 1H), 7.69-7.62 (m, 2H), 7.42-7.40 (m, 1H), 7.25 (d, J=7.6 Hz, 1H), 3.95 (s, 3H), 2.65 (s, 3H), 1.93 (t, J=18.0 Hz, 3H).

1-(4-(N,N-dimethylsulfamoyl)phenyl)-3-methyl-5-oxo-N-(3-(pyrazin-2-yl)phenyl)-4,5-dihydro-1H-pyrazole-4-carboxamide (262)

Compound ID: 262

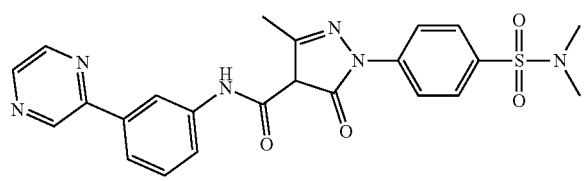 [SMILES: CC1=NN(c2ccc(S(=O)(=O)N(C)C)cc2)C(=O)C1C(=O)Nc1cccc(-c2cnccn2)c1]

Compound 262 was obtained via general procedure IV from 1-(4-(N,N-dimethylsulfamoyl)phenyl)-3-methyl-5-oxo-4,5-dihydro-1H-pyrazole-4-carboxylate and 3-(pyrazin-2-yl)aniline.
LCMS: (ESI) m/z: 479.0 [M+H]⁺.
¹H NMR: (400 MHz, DMSO-d₆) δ: 10.89 (s, 1H), 9.24 (s, 1H), 8.78-8.69 (m, 1H), 8.63 (d, J=2.4 Hz, 1H), 8.44 (s, 1H), 8.19 (d, J=8.8 Hz, 2H), 7.84 (d, J=8.8 Hz, 2H), 7.80-7.73 (m, 2H), 7.47 (t, J=8.0 Hz, 1H), 2.62 (s, 6H), 2.52 (s, 3H).

1-(3-(N,N-dimethylsulfamoyl)phenyl)-N-(3-(furan-2-yl)phenyl)-3-methyl-5-oxo-4,5-dihydro-1H-pyrazole-4-carboxamide (263)

Compound ID: 263

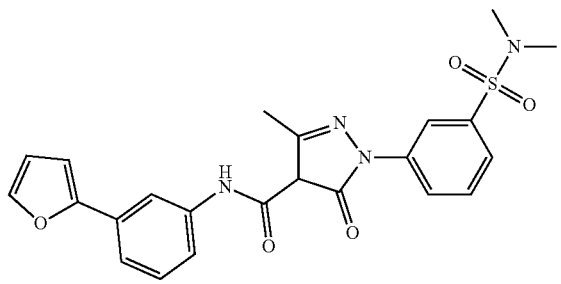 [SMILES: CC1=NN(c2cccc(S(=O)(=O)N(C)C)c2)C(=O)C1C(=O)Nc1cccc(-c2ccco2)c1]

Compound 263 was obtained via general procedure IV from 4-nitrophenyl 1-(3-(N,N-dimethylsulfamoyl)phenyl)-3-methyl-5-oxo-4,5-dihydro-1H-pyrazole-4-carboxylate and 3-(furan-2-yl)aniline.

LCMS: (ESI) m/z 467.0 [M+H]$^+$, $^1$H NMR: (400 MHz, DMSO-d$_6$) δ: 10.80 (s, 1H), 8.34 (s, 1H), 8.25 (d, J=8.0 Hz, 1H), 8.06 (s, 1H), 7.75 (d, J=1.2 Hz, 1H), 7.71 (t, J=8.0 Hz, 1H), 7.57-7.46 (m, 2H), 7.38-7.31 (m, 2H), 6.93 (d, J=3.2 Hz, 1H), 6.59 (m, 1H), 2.66 (s, 6H), 2.48 (s, 3H).

N-(3-(1,1-difluoroethyl)phenyl)-3-methyl-5-oxo-1-(4-(trifluoromethyl)phenyl)-4,5-dihydro-1H-pyrazole-4-carboxamide (264)

Compound ID: 264

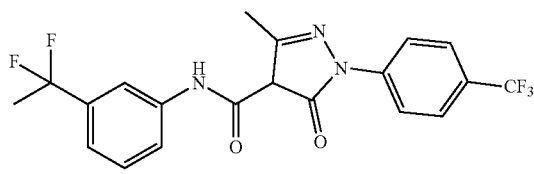 [SMILES: CC1=NN(c2ccc(C(F)(F)F)cc2)C(=O)C1C(=O)Nc1cccc(C(C)(F)F)c1]

Compound 264 was obtained via general procedure IV from 3-methyl-5-oxo-1-(4-(trifluoromethyl)phenyl)-4,5-dihydro-1H-pyrazole-4-carboxylate and 3-(1,1-difluoroethyl)aniline.

LCMS: (ESI) m/z 426.2 [M+H]$^+$.

$^1$H NMR: (400 MHz, MeOD-d$_4$) δ: 7.92 (d, J=8.4 Hz, 3H), 7.84 (d, J=8.8 Hz, 2H), 7.64 (d, J=7.6 Hz, 1H), 7.41 (t, J=8.0 Hz, 1H), 7.25 (d, J=8.0 Hz, 1H), 2.66 (s, 3H), 1.93 (t, J=18.0 Hz, 3H).

N-(3-(1,1-difluoroethyl)phenyl)-1-(4-methoxyphenyl)-3-methyl-5-oxo-4,5-dihydro-1H-pyrazole-4-carboxamide (265)

Compound ID: 265

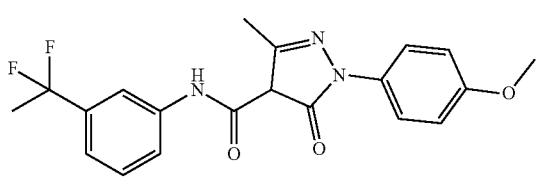 [SMILES: COc1ccc(N2N=C(C)C(C(=O)Nc3cccc(C(C)(F)F)c3)C2=O)cc1]

Step 1: Synthesis of 1-(4-methoxyphenyl)-3-methyl-1H-pyrazol-5(4H)-one (241-A)

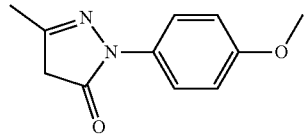

241-A was obtained via general procedure II from (4-methoxyphenyl)hydrazine.

LCMS: (ESI) m/z 205.1 [M+H]$^+$.

Step 2: Synthesis of 4-nitrophenyl 1-(4-methoxyphenyl)-3-methyl-5-oxo-4,5-dihydro-1H-pyrazole-4-carboxylate (241-B)

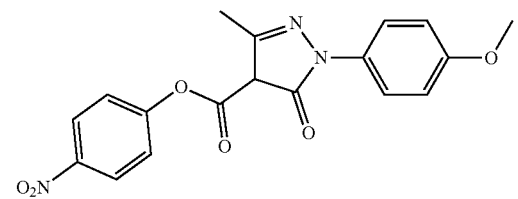 [SMILES: COc1ccc(N2N=C(C)C(C(=O)Oc3ccc([N+](=O)[O-])cc3)C2=O)cc1]

241-B was obtained via general procedure III from 241-A.

LCMS: (ESI) m/z 370.1 [M+H]$^+$.

Compound 265 was obtained via general procedure IV from 1-(4-methoxyphenyl)-3-methyl-5-oxo-4,5-dihydro-1H-pyrazole-4-carboxylate (241-B) and 3-(1,1-difluoroethyl)aniline.

LCMS: (ESI) m/z 388.2 [M+H]$^+$.

$^1$H NMR: (400 MHz, MeOD-d$_4$) δ: 7.90 (s, 1H), 7.62 (d, J=8.0 Hz, 1H), 7.52-7.48 (m, 2H), 7.40 (t, J=8.0 Hz, 1H), 7.24 (d, J=7.6 Hz, 1H), 7.10-7.06 (m, 2H), 3.85 (s, 3H), 2.60 (s, 3H), 1.92 (t, J=18.4 Hz, 3H).

N-(3-(furan-2-yl)phenyl)-1-(4-methoxyphenyl)-3-methyl-5-oxo-4,5-dihydro-1H-pyrazole-4-carboxamide (266)

Compound ID: 266

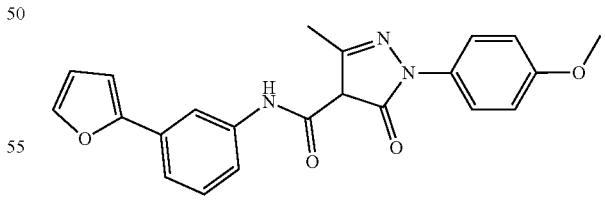

Compound 266 was obtained via general procedure IV from 1-(4-methoxyphenyl)-3-methyl-5-oxo-4,5-dihydro-1H-pyrazole-4-carboxylate and 3-(furan-2-yl)aniline.

LCMS: (ESI) m/z 390.0 [M+H]$^+$.

$^1$H NMR: (400 MHz, DMSO-d$_6$) δ: 10.83 (s, 1H), 8.05 (s, 1H), 7.76 (d, J=0.8 Hz, 1H), 7.59 (d, J=9.2 Hz, 2H), 7.46 (dt, J=7.2, 2.0 Hz, 1H), 7.39-7.35 (m, 2H), 7.09 (d, J=8.8 Hz, 2H), 6.94 (d, J=3.2 Hz, 1H), 6.60 (dd, J=3.2, 1.6 Hz, 1H), 3.81 (s, 3H), 2.54 (s, 3H).

N-(3-ethylphenyl)-3-methyl-5-oxo-1-(quinolin-7-yl)-4,5-dihydro-1H-pyrazole-4-carboxamide (267)

Compound ID: 267

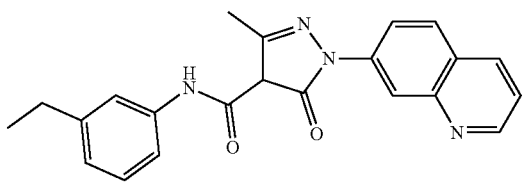 [SMILES: CCc1cccc(NC(=O)C2C(=O)N(c3ccc4cccnc4c3)N=C2C)c1]

Compound 267 was obtained via general procedure II from 3-methyl-1-(quinolin-7-yl)-1H-pyrazol-5(4H)-one and 1-ethyl-3-isocyanatobenzene.

LCMS: (ESI) m/z 373.0 [M+H]+.

$^1$H NMR (400 MHz, DMSO-$d_6$) δ: 10.83 (s, 1H), 9.02 (d, J=3.6 Hz, 1H), 8.85 (br s, 1H), 8.73 (br s, 1H), 8.60 (br s, 1H), 8.18 (d, J=9.2 Hz, 1H), 7.68 (dd, J=5.2, 8.0 Hz, 1H), 7.48 (s, 1H), 7.42 (d, J=8.2 Hz, 1H), 7.17 (t, J=7.6 Hz, 1H), 6.80 (d, J=7.6 Hz, 1H), 2.58 (q, J=7.6 Hz, 2H), 2.40 (s, 3H), 1.19 (t, J=7.6 Hz, 3H).

3-methyl-N-(1-methyl-1H-imidazol-2-yl)-5-oxo-1-phenyl-4,5-dihydro-1H-pyrazole-4-carboxamide (268)

Compound ID: 268

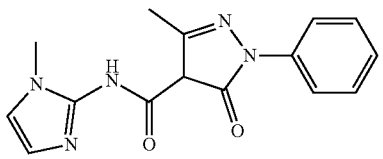 [SMILES: CC1=NN(c2ccccc2)C(=O)C1C(=O)Nc1nccn1C]

Compound 268 was obtained via general procedure IV from 1-methyl-H-imidazol-2-amine and 3-methyl-5-oxo-1-phenyl-4,5-dihydro-1H-pyrazole-4-carboxylate.

LCMS: (ESI) m/z 298.1.1 [M+H]+.

$^1$H NMR: (400 MHz, DMSO-$d_6$) δ: 13.38 (d, J=2.4 Hz, 1H), 12.99 (s, 1H), 8.04 (d, J=7.6 Hz, 2H), 7.40-7.29 (m, 3H), 7.07 (d, J=7.6 Hz, 2H), 3.82 (s, 3H), 2.32 (s, 3H).

methyl 3-(4-((3-(furan-2-yl)phenyl)carbamoyl)-3-methyl-5-oxo-4,5-dihydro-1H-pyrazol-1-yl)benzoate (269)

Compound ID: 269

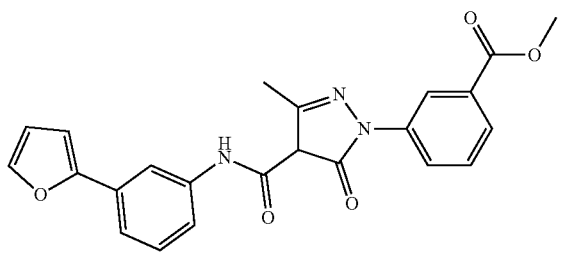 [SMILES: COC(=O)c1cccc(N2N=C(C)C(C(=O)Nc3cccc(-c4ccco4)c3)C2=O)c1]

Compound 269 was obtained via general procedure IV from 1-(3-(methoxycarbonyl)phenyl)-3-methyl-5-oxo-4,5-dihydro-1H-pyrazole-4-carboxylate and 3-(furan-2-yl)aniline.

LCMS: (ESI) m/z 418.1 [M+H]+.

$^1$H NMR: (400 MHz, MeOD-$d_4$) δ: 8.41 (s, 1H), 8.06 (s, 1H), 8.02 (d, J=8.0 Hz, 1H), 7.96 (d, J=8.0 Hz, 1H), 7.70-7.60 (m, 1H), 7.56 (s, 1H), 7.55-7.47 (m, 1H), 7.45-7.40 (m, 1H), 7.35 (d, J=8.0 Hz, 1H), 6.78 (d, J=3.2 Hz, 1H), 6.53-6.51 (m, 1H), 3.95 (s, 3H), 2.61 (s, 3H).

N-(3-(furan-2-yl)phenyl)-3-methyl-5-oxo-1-(4-(trifluoromethyl)phenyl)-4,5-dihydro-1H-pyrazole-4-carboxamide (270)

Compound ID: 270

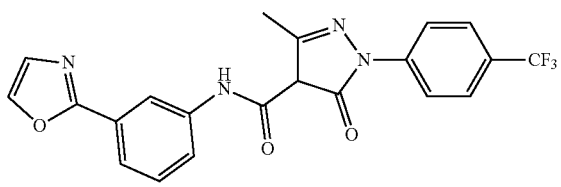

Compound 270 was obtained via general procedure IV from 3-methyl-5-oxo-1-(4-(trifluoromethyl)phenyl)-4,5-dihydro-1H-pyrazole-4-carboxylate and 3-(oxazol-2-yl)aniline.

LCMS: (ESI) m/z 428.9 [M+H]+.

$^1$H NMR: (400 MHz, MeOD-$d_4$) δ: 8.40 (s, 1H), 7.99 (s, 1H), 7.96 (d, J=7.6 Hz, 2H), 7.80 (d, J=7.6 Hz, 2H), 7.73 (t, J=8.0 Hz, 2H), 7.47 (t, J=7.2 Hz, 1H), 7.30 (s, 1H), 2.63 (s, 3H).

N-(3-(1,1-difluoroethyl)phenyl)-3-methyl-5-oxo-1-(3-(trifluoromethyl)phenyl)-4,5-dihydro-1H-pyrazole-4-carboxamide (271)

Compound ID: 271

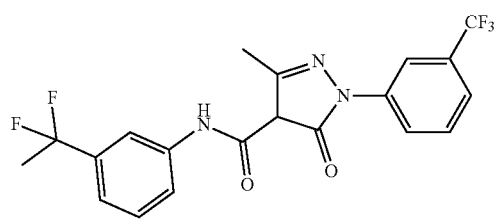 [SMILES: CC1=NN(c2cccc(C(F)(F)F)c2)C(=O)C1C(=O)Nc1cccc(C(C)(F)F)c1]

Compound 271 was obtained via general procedure IV from 3-methyl-5-oxo-1-(3-(trifluoromethyl)phenyl)-4,5-dihydro-1H-pyrazole-4-carboxylate and 3-(1,1-difluoroethyl)aniline.

LCMS: (ESI) m/z 426.3 [M+H]+.

$^1$H NMR: (400 MHz, DMSO-$d_6$) δ: 10.86 (br s, 1H), 8.33 (s, 1H), 8.15 (d, J=8.4 Hz, 1H), 7.92 (s, 1H), 7.37-7.61 (m, 2H), 7.51 (d, J=8.0 Hz, 1H), 7.37 (t, J=8.0 Hz, 1H), 7.14 (d, J=7.6 Hz, 1H), 2.44 (s, 3H), 1.94 (t, J=18.8 Hz, 3H).

283

1-(3-(N,N-dimethylsulfamoyl)phenyl)-3-methyl-5-oxo-N-(3-(pyrazin-2-yl)phenyl)-4,5-dihydro-1H-pyrazole-4-carboxamide (272)

Compound ID: 272

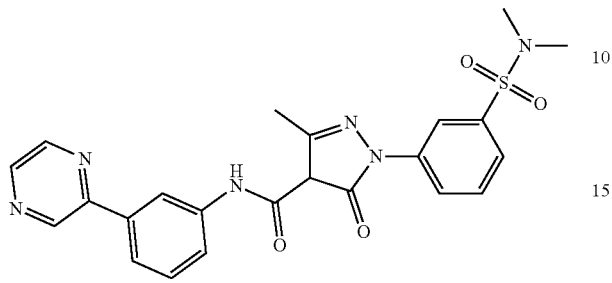

Compound 272 was obtained via general procedure IV from 4-nitrophenyl 1-(3-(N,N-dimethylsulfamoyl)phenyl)-3-methyl-5-oxo-4,5-dihydro-1H-pyrazole-4-carboxylate and 3-(pyrazin-2-yl)aniline.

LCMS: (ESI) m/z 479.0 [M+H]$^+$.

$^1$H NMR: (400 MHz, DMSO-d$_6$): δ: 10.75 (s, 1H), 9.25 (s, 1H), 8.78-8.72 (d, J=2.4 Hz, 1H), 8.63 (d, J=2.4 Hz, 1H), 8.45 (s, 1H), 8.24 (s, 1H), 8.20-8.10 (m, 1H), 7.85-7.75 (m, 3H), 7.63 (d, J=7.6 Hz, 1H), 7.49 (t, J=8.0 Hz, 1H), 2.67 (s, 6H), 2.57 (s, 3H).

N-(3-(1H-imidazol-2-yl)phenyl)-3-methyl-1-(3-(oxazol-2-yl)phenyl)-5-oxo-4,5-dihydro-1H-pyrazole-4-carboxamide (279)

Compound ID: 279

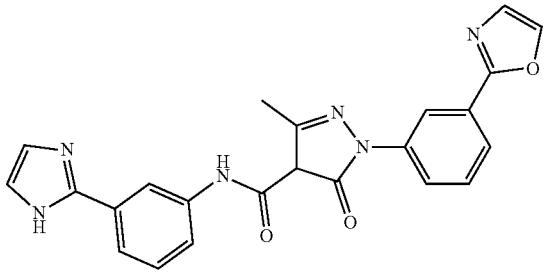 [SMILES: CC1=NN(c2cccc(-c3ncco3)c2)C(=O)C1C(=O)Nc1cccc(-c2ncc[nH]2)c1]

Compound 279 was obtained via general procedure IV from 3-methyl-1-(3-(oxazol-2-yl)phenyl)-5-oxo-4,5-dihydro-1H-pyrazole-4-carboxylate and 3-(1H-imidazol-2-yl)aniline.

LCMS: (ESI) m/z 427.0 [M+H]$^+$.

$^1$H NMR: (400 MHz, DMSO-d$_6$) δ: 11.05 (s, 1H), 8.60 (s, 1H), 8.30 (s, 1H), 8.25 (s, 1H), 8.12-8.06 (m, 1H), 7.99-7.93 (m, 1H), 7.88 (d, J=7.6 Hz, 1H), 7.82 (s, 2H), 7.74 (d, J=8.0 Hz, 1H), 7.69-7.64 (m, 1H), 7.62-7.56 (m, 1H), 7.45 (s, 1H), 2.57 (s, 3H).

284

N-(3-(1,1-difluoroethyl)phenyl)-3-methyl-1-(3-(5-methyl-1,3,4-oxadiazol-2-yl)phenyl)-5-oxo-4,5-dihydro-1H-pyrazole-4-carboxamide (280)

Compound ID: 280

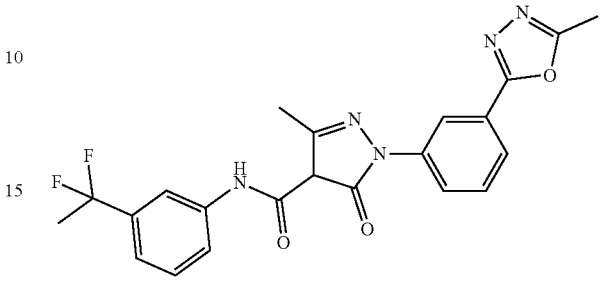

Compound 280 was obtained via general procedure IV from 3-methyl-1-(3-(5-methyl-1,3,4-oxadiazol-2-yl)phenyl)-5-oxo-4,5-dihydro-1H-pyrazole-4-carboxylate and 3-(1,1-difluoroethyl)aniline.

LCMS: (ESI) m/z 440.3 [M+H]$^+$.

$^1$H NMR: (400 MHz, DMSO-d$_6$) δ: 10.99 (br s, 1H), 8.61 (br s, 1H), 8.16 (d, J=8.4 Hz, 1H), 7.95 (s, 1H), 7.75 (d, J=7.6 Hz, 1H), 7.57-7.69 (m, 2H), 7.39 (t, J=7.6 Hz, 1H), 7.15 (d, J=7.6 Hz, 1H), 2.61 (s, 3H), 2.44 (s, 3H), 1.96 (t, J=18.4 Hz, 3H).

N-(3-(1,1-difluoroethyl)phenyl)-1-(3-hydroxy-4-methoxyphenyl)-3-methyl-5-oxo-4,5-dihydro-1H-pyrazole-4-carboxamide (281)

Compound ID: 281

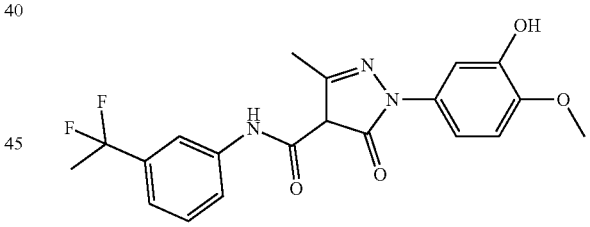

To a solution of 1-(3-(benzyloxy)-4-methoxyphenyl)-N-(3-(1,1-difluoroethyl)phenyl)-3-methyl-5-oxo-4,5-dihydro-1H-pyrazole-4-carboxamide (5.0 mg, 7.43 umol, 1.0 eq) in tetrahydrofuran (1 mL) was added palladium (5.00 mg, 10% purity on barium sulfate) under nitrogen. The mixture was stirred under hydrogen (15 Psi) at 25° C. for 12 h. The reaction mixture was filtered, and the filtrate was concentrated to give a yellow solid. The solid was purified by prep-HPLC (column: Boston Green ODS 150*30 5u; mobile phase: [water(0.225% formic acid)-ACN]; B %: 35%-65%, 10 min) to give 3.00 mg (92% yield) of Compound 281 as a white solid.

LCMS: (ESI) m/z 404.1 [M+H]$^+$.

$^1$H NMR: (400 MHz, MeOD-d$_4$) δ: 8.33 (br s, 1H), 7.93 (s, 1H), 7.64 (d, J=7.6 Hz, 1H), 7.39 (t, J=8.0 Hz, 1H), 7.14-7.22 (m, 2H), 6.99 (d, J=8.4 Hz, 1H), 3.89 (s, 3H), 2.46 (s, 3H), 1.94 (t, J=18.0 Hz, 3H).

N-benzyl-3-methyl-5-oxo-1-phenyl-4,5-dihydro-1H-pyrazole-4-carboxamide (282)

Compound ID: 282

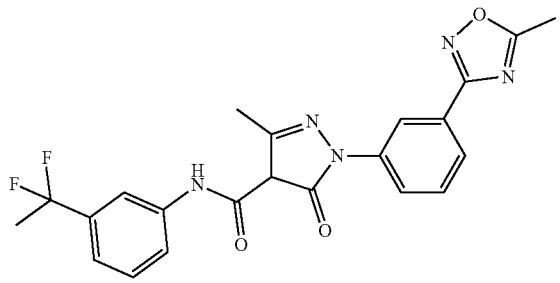 [SMILES: CC1=NN(c2cccc(-c3noc(C)n3)c2)C(=O)C1C(=O)Nc1cccc(C(C)(F)F)c1]

Compound 282 was obtained via general procedure IV from (4-nitrophenyl)3-methyl-1-[3-(5-methyl-1,2,4-oxadiazol-3-yl)phenyl]-5-oxo-4H-pyrazole-4-carboxylate and 3-(1,1-difluoroethyl)aniline.

LCMS: (ESI) m/z: 440.0 [M+H]$^+$;

$^1$H NMR (400 MHz, DMSO-d$_6$) δ: 10.87 (s, 1H), 8.53 (s, 1H), 8.04 (s, 1H), 7.96 (s, 1H), 7.89-7.86 (m, 1H), 7.68 (t, J=8.8 Hz, 2H), 7.43 (t, J=7.6 Hz, 1H), 7.19 (d, J=8.4 Hz, 1H), 2.71 (s, 3H), 1.97 (t, J=18.8 Hz, 3H).

3-methyl-N-(4-methylthiophen-3-yl)-5-oxo-1-phenyl-4,5-dihydro-1H-pyrazole-4-carboxamide (283)

Compound ID: 283

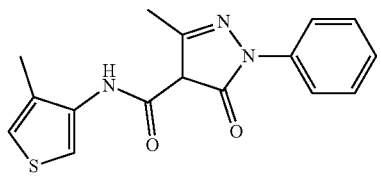 [SMILES: CC1=NN(c2ccccc2)C(=O)C1C(=O)Nc1cscc1C]

Compound 283 was obtained via general procedure IV from 4-methylthiophen-3-amine and 3-methyl-5-oxo-1-phenyl-4,5-dihydro-1H-pyrazole-4-carboxylate.

LCMS: (ESI) m/z 314.0 [M+H]$^+$.

$^1$H NMR: (400 MHz, MeOD-d$_4$) δ: 7.72 (d, J=8.0 Hz, 2H), 7.52 (t, J=8.0 Hz, 2H), 7.26 (t, J=7.6 Hz, 1H), 6.52 (s, 1H), 6.43 (s, 1H), 2.50 (s, 3H), 2.18 (s, 3H).

N-(5-ethylthiophen-3-yl)-3-methyl-5-oxo-1-phenyl-4,5-dihydro-1H-pyrazole-4-carboxamide (284)

Compound ID: 284

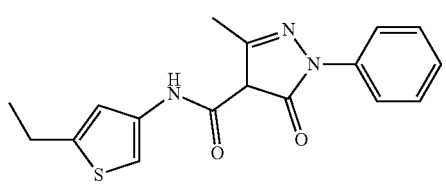 [SMILES: CCc1cc(NC(=O)C2C(=O)N(c3ccccc3)N=C2C)cs1]

Compound 284 was obtained via general procedure IV from 3-methyl-5-oxo-1-phenyl-4,5-dihydro-1H-pyrazole-4-carboxylate and 4-ethylthiophen-2-amine.

LCMS: (ESI) m/z 328.2 [M+H]$^+$.

$^1$H NMR: (400 MHz, MeOD-d$_4$) δ: 7.70 (d, J=7.6 Hz, 2H), 7.48 (t, J=7.6 Hz, 2H), 7.36-7.21 (m, 2H), 6.84 (s, 1H), 2.81 (q, J=7.6 Hz, 2H), 2.54 (s, 3H), 1.30 (t, J=7.6 Hz, 3H).

N-(4-ethylthiophen-2-yl)-3-methyl-5-oxo-1-phenyl-4,5-dihydro-1H-pyrazole-4-carboxamide (285)

Compound ID: 285

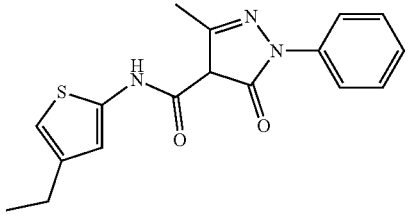

Compound 285 was obtained via general procedure IV from 4-ethylthiophen-2-amine and 3-methyl-5-oxo-1-phenyl-4,5-dihydro-1H-pyrazole-4-carboxylate.

LCMS: (ESI) m/z: 328.2 [M+H]$^+$.

$^1$H NMR (400 MHz, MeOD-d$_4$) δ: 7.66 (d, J=8.0 Hz, 2H), 7.51 (t, J=8.0 Hz, 2H), 7.36 (t, J=7.6 Hz, 1H), 6.61 (s, 1H), 6.50 (s, 1H), 2.54-2.59 (m, 5H), 1.21 (t, J=7.6 Hz, 3H).

3-(dimethylamino)-1-(3-nitrophenyl)prop-2-en-1-one (286)

Compound ID: 286

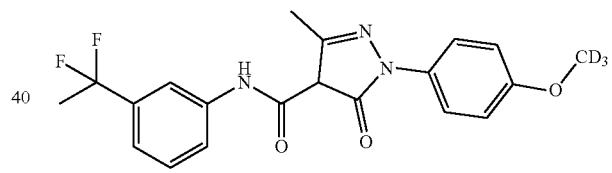

Compound 286 was obtained via general procedure IV from 3-(dimethylamino)-1-(3-nitrophenyl)prop-2-en-1-one and 3-(1,1-difluoroethyl)aniline.

LCMS: (ESI) m/z: 391.0 [M+H]$^+$.

$^1$H NMR (400 MHz, DMSO-d$_6$) δ: 11.02 (s, 1H), 7.93 (s, 1H), 7.67 (d, J=8.8 Hz, 2H), 7.60 (d, J=8.8 Hz, 1H), 7.40 (t, J=8.0 Hz, 1H), 7.16 (d, J=8.0 Hz, 1H), 7.02 (d, J=9.2 Hz, 2H), 2.46 (s, 3H), 1.95 (t, J=18.8 Hz, 3H).

N-(3-(1,1-difluoroethyl)phenyl)-1-(3,4-dimethoxyphenyl)-3-methyl-5-oxo-4,5-dihydro-1H-pyrazole-4-carboxamide (287)

Compound ID: 287

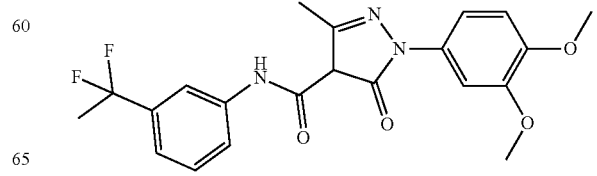

287

Compound 287 was obtained via general procedure IV from 1-(3,4-dimethoxyphenyl)-3-methyl-5-oxo-4,5-dihydro-1H-pyrazole-4-carboxylate and 3-(1,1-difluoroethyl)aniline.

LCMS: (ESI) m/z 418.0 [M+H]⁺.

$^1$H NMR: (400 MHz, MeOD-d$_4$) δ: 7.90 (s, 1H), 7.64 (d, J=8.0 Hz, 1H), 7.39 (t, J=8.0 Hz, 1H), 7.32 (d, J=2.0 Hz, 1H), 7.22-7.17 (m, 2H), 7.06 (d, J=8.4 Hz, 1H), 3.90 (s, 3H), 3.87 (s, 3H), 2.55 (s, 3H), 1.92 (t, J=18.0 Hz, 3H).

N-(3-ethylthiophen-2-yl)-3-methyl-5-oxo-1-phenyl-4,5-dihydro-1H-pyrazole-4-carboxamide (288)

Compound ID: 288

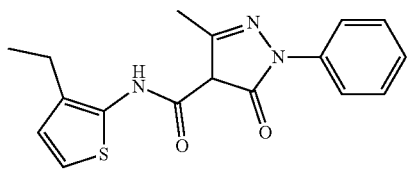 [SMILES: CCc1ccsc1NC(=O)C1C(=O)N(c2ccccc2)N=C1C]

Compound 288 was obtained via general procedure IV from 3-ethylthiophen-2-amine and 3-methyl-5-oxo-1-phenyl-4,5-dihydro-1H-pyrazole-4-carboxylate.

LCMS: (ESI) m/z: 328.1 [M+H]⁺

$^1$H NMR (400 MHz, DMSO-d$_6$) δ: 11.36 (s, 1H), 7.73 (d, J=7.6 Hz, 2H), 7.52 (t, J=7.6 Hz, 2H), 7.32 (t, J=7.2 Hz, 1H), 6.88 (d, J=5.6 Hz, 1H), 6.80 (d, J=5.6 Hz, 1H), 2.56-2.50 (m, 5H), 1.18 (t, J=7.2 Hz, 3H).

N-(3-(furan-2-yl)phenyl)-3-methyl-1-(3-(oxazol-2-yl)-4-(trifluoromethoxy)phenyl)-5-oxo-4,5-dihydro-1H-pyrazole-4-carboxamide (292)

Compound ID: 292

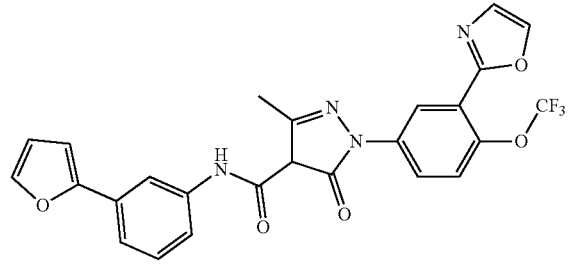 [SMILES: CC1=NN(c2ccc(OC(F)(F)F)c(-c3ncco3)c2)C(=O)C1C(=O)Nc1cccc(-c2ccco2)c1]

Compound 292 was obtained via general procedure IV from 3-methyl-1-(3-(oxazol-2-yl)-4-(trifluoromethoxy)phenyl)-5-oxo-4,5-dihydro-1H-pyrazole-4-carboxylate and 3-(furan-2-yl)aniline.

LCMS: (ESI) m/z 511.0 [M+H]⁺.

$^1$H NMR: (400 MHz, DMSO-d$_6$) δ: 10.79 (s, 1H), 8.71 (s, 1H), 8.40 (s, 1H), 8.17-8.14 (m, 1H), 8.07 (s, 1H), 7.76 (s, 1H), 7.70-7.60 (m, 1H), 7.54-7.50 (m, 2H), 7.36-7.34 (m, 2H), 6.95 (d, J=3.2 Hz, 1H), 6.61 (t, J=1.6 Hz, 1H), 2.54 (s, 3H).

288

3-methyl-5-oxo-1-phenyl-N-(thiazol-2-yl)-4,5-dihydro-1H-pyrazole-4-carboxamide (293)

Compound ID: 293

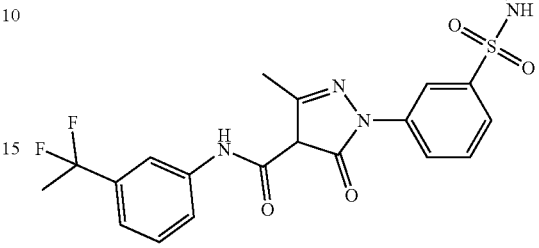

Compound 293 was obtained via general procedure IV from N-[3-(3-methyl-5-oxo-4H-pyrazol-1-yl)phenyl]sulfonylacetamide and 3-(1,1-difluoroethyl)aniline.

LCMS: (ESI) m/z: 479.0 [M+H]⁺;

$^1$H NMR (400 MHz, DMSO-d$_6$) δ: 12.08 (s, 1H), 11.09 (s, 1H), 8.64 (s, 1H), 8.37 (s, 1H), 7.95 (s, 1H), 7.61-7.59 (m, 3H), 7.37 (t, J=7.6 Hz, 1H), 7.11 (d, J=8.4 Hz, 1H), 2.36 (s, 3H), 1.96 (t, J=18.8 Hz, 3H), 1.95 (s, 3H).

1-(3-(N-acetylsulfamoyl)-4-(trifluoromethoxy)phenyl)-N-(3-(1,1-difluoroethyl)phenyl)-3-methyl-5-oxo-4,5-dihydro-1H-pyrazole-4-carboxamide (294)

Compound ID: 294

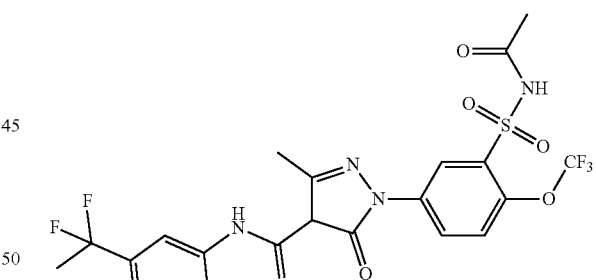

Compound 294 was obtained via general procedure IV from N-((5-(3-methyl-5-oxo-4,5-dihydro-1H-pyrazol-1-yl)-2-(trifluoromethoxy)phenyl)sulfonyl)acetamide and 3-(1,1-difluoroethyl)aniline.

LCMS: (ESI) m/z: 563.0 [M+H]⁺.

$^1$H NMR: (400 MHz, MeOD-d$_4$) δ: 8.44 (d, J=2.8 Hz, 1H), 8.21 (dd, J=2.8, 9.2 Hz, 1H), 7.92 (s, 1H), 7.71-7.63 (m, 2H), 7.41 (t, J=8.0 Hz, 1H), 7.25 (d, J=7.6 Hz, 1H), 2.66 (s, 3H), 2.03 (s, 3H), 1.93 (t, J=18.0 Hz, 3H).

N-(5-(1,1-difluoroethyl)thiophen-3-yl)-3-methyl-5-oxo-1-(4-(trifluoromethoxy)phenyl)-4,5-dihydro-1H-pyrazole-4-carboxamide (295)

Compound ID: 295

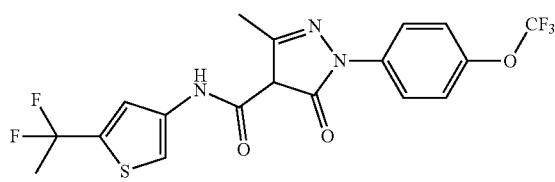 [SMILES: CC1=NN(c2ccc(OC(F)(F)F)cc2)C(=O)C1C(=O)Nc1csc(C(C)(F)F)c1]

Compound 295 was obtained via general procedure IV from 3-methyl-5-oxo-1-(4-(trifluoromethoxy)phenyl)-4,5-dihydro-1H-pyrazole-4-carboxylate and 5-(1,1-difluoroethyl)thiophen-3-amine.

LCMS: (ESI) m/z: 448.0 [M+H]$^+$.

$^1$H NMR (400 MHz, DMSO-d$_6$) δ: 10.99 (s, 1H), 8.02 (d, J=8.8 Hz, 2H), 7.63 (s, 1H), 7.54 (s, 1H), 7.42 (d, J=8.8 Hz, 2H), 2.42 (s, 3H), 2.08 (t, J=18.4 Hz, 3H).

N-(4-(1,1-difluoroethyl)thiophen-2-yl)-3-methyl-5-oxo-1-(4-(trifluoromethoxy)phenyl)-4,5-dihydro-1H-pyrazole-4-carboxamide (296)

Compound ID: 296

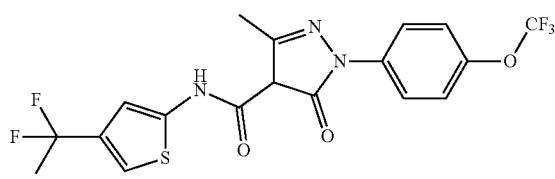 [SMILES: CC1=NN(c2ccc(OC(F)(F)F)cc2)C(=O)C1C(=O)Nc1cc(C(C)(F)F)cs1]

Compound 296 was obtained via general procedure IV from 3-methyl-5-oxo-1-(4-(trifluoromethoxy)phenyl)-4,5-dihydro-1H-pyrazole-4-carboxylate and 5-(1,1-difluoroethyl)thiophen-3-amine.

LCMS: (ESI) m/z: 448.0 [M+H]$^+$.

$^1$H NMR: (400 MHz, DMSO-d$_6$) δ: 11.41 (s, 1H), 7.90 (d, J=8.8 Hz, 2H), 7.53 (d, J=8.8 Hz, 2H), 7.21 (s, 1H), 6.88 (d, J=1.6 Hz, 1H), 2.52 (s, 3H), 1.94 (t, J=18.4 Hz, 3H).

1-(4-(1H-tetrazol-5-yl)phenyl)-N-(3-(1,1-difluoroethyl)phenyl)-3-methyl-5-oxo-4,5-dihydro-1H-pyrazole-4-carboxamide (297)

Compound ID: 297

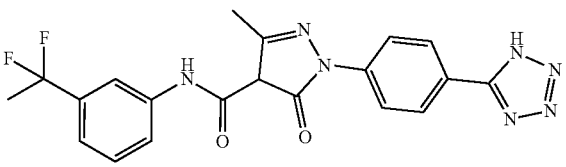 [SMILES: CC1=NN(c2ccc(-c3nnn[nH]3)cc2)C(=O)C1C(=O)Nc1cccc(C(C)(F)F)c1]

To a mixture of N-[3-(1,1-difluoroethyl)phenyl]-1-[4-[1-[(4-methoxyphenyl)methyl]tetrazol-5-yl]phenyl]-3-methyl-5-oxo-4H-pyrazole-4-carboxamide (15.0 mg, 25.9 umol, 1.0 eq) in methanol (10 mL) was added palladium hydroxide (15.0 mg, 10% on carbon). The mixture was stirred at 20° C. for 12 h under an atmosphere of hydrogen (15 psi). The solution was filtered through a celite pad and the filtrate was concentrated. The residue was purified by prep-HPLC (column: Kromasil 150*25 mm*10 um; mobile phase: [water (0.225% FA)-ACN]; B %: 40%-70%, 8 min) to give 2.30 mg (19% yield) of Compound 297 as a white solid.

LCMS: (ESI) m/z 426.1 [M+H]$^+$.

$^1$H NMR: (400 MHz, MeOD-d$_6$) δ: 8.18 (s, 2H), 8.12-8.05 (m, 2H), 7.92 (s, 1H), 7.64 (d, J=8.0 Hz, 1H), 7.38 (t, J=8.0 Hz, 1H), 7.18 (d, J=3.2 Hz, 1H), 2.48 (s, 3H), 1.93 (t, J=18.4 Hz, 3H).

N-(3-(1,1-difluoroethyl)phenyl)-1-(4-(difluoromethoxy)phenyl)-3-methyl-5-oxo-4,5-dihydro-1H-pyrazole-4-carboxamide (298)

Compound ID: 298

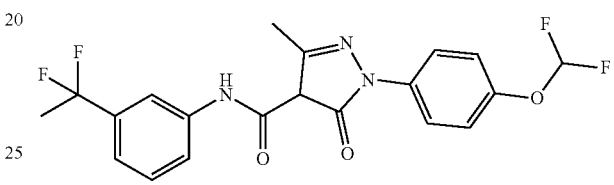

Compound 298 was obtained via general procedure IV from 1-(4-(difluoromethoxy)phenyl)-3-methyl-5-oxo-4,5-dihydro-1H-pyrazole-4-carboxylate and 3-(1,1-difluoroethyl)aniline.

LCMS: (ESI) m/z: 424.2 [M+H]$^+$.

$^1$H NMR: (400 MHz, MeOD-d$_4$) δ: 7.90 (s, 1H), 7.69-7.66 (m, 2H), 7.62 (d, J=8.0 Hz, 1H), 7.40 (t, J=8.0 Hz, 1H), 7.32-7.30 (m, 2H), 7.24 (d, J=7.6 Hz, 1H), 6.89 (t, J=72.0 Hz, 1H), 2.61 (d, J=3.6 Hz, 3H), 1.92 (t, J=18.0 Hz, 3H).

1-(3-(N-acetylsulfamoyl)-4-(trifluoromethoxy)phenyl)-N-(3-(furan-2-yl)phenyl)-3-methyl-5-oxo-4,5-dihydro-1H-pyrazole-4-carboxamide (299)

Compound ID: 299

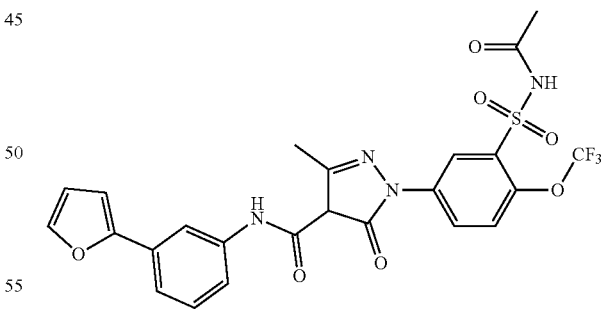

Compound 299 was obtained via general procedure IV from 1-(3-(N-acetylsulfamoyl)-4-(trifluoromethoxy)phenyl)-3-methyl-5-oxo-4,5-dihydro-1H-pyrazole-4-carboxylate and 3-(furan-2-yl)aniline.

LCMS: (ESI) m/z: 565.0 [M+H]$^+$.

$^1$H NMR: (400 MHz, DMSO-d$_6$) δ: 12.41 (br s, 1H), 11.05 (s, 1H), 8.83 (s, 1H), 8.53 (d, J=8.0 Hz, 1H), 8.04 (s, 1H), 7.73 (d, J=1.6 Hz, 1H), 7.49-7.45 (m, 2H), 7.28-7.25 (m, 2H), 6.89 (d, J=3.6 Hz, 1H), 6.59-6.56 (m, 1H), 2.29 (s, 3H), 1.95 (s, 3H).

N-(3-(1,1-difluoroethyl)phenyl)-1-(4-methoxy-3-(1-methyl-1H-imidazol-2-yl)phenyl)-3-methyl-5-oxo-4,5-dihydro-1H-pyrazole-4-carboxamide (300)

Compound ID: 300

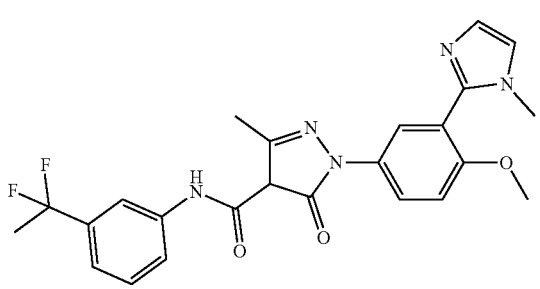

Compound 300 was obtained via general procedure IV from 1-(4-methoxy-3-(1-methyl-1H-imidazol-2-yl)phenyl)-3-methyl-5-oxo-4,5-dihydro-1H-pyrazole-4-carboxylate and 3-(1,1-difluoroethyl)aniline.

LCMS: (ESI) m/z 468.1 [M+H]+.

$^1$H NMR: (400 MHz, DMSO-d$_6$) δ: 11.39 (s, 1H), 8.13-8.15 (m, 2H), 7.92 (s, 1H), 7.57 (d, J=8.4 Hz, 1H), 7.30-7.32 (m, 1H), 7.26 (s, 1H), 7.10 (d, J=9.2 Hz, 1H), 7.04 (d, J=8.8 Hz, 2H), 3.78 (s, 3H), 3.48 (s, 3H), 2.24 (s, 3H), 1.94 (t, J=18.8 Hz, 3H).

N-(3-(1,1-difluoroethyl)phenyl)-1-(4-methoxy-3-(oxazol-2-yl)phenyl)-3-methyl-5-oxo-4,5-dihydro-1H-pyrazole-4-carboxamide (301)

Compound ID: 301

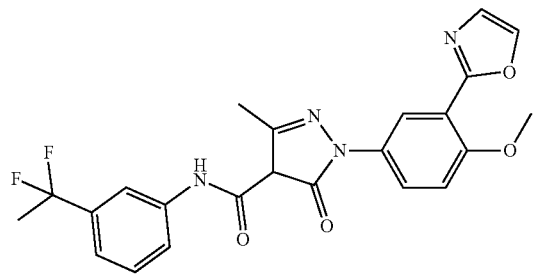 [SMILES: COc1ccc(N2N=C(C)C(C(=O)Nc3cccc(C(C)(F)F)c3)C2=O)cc1-c1ncco1]

Compound 301 was obtained via general procedure IV from 1-(4-methoxy-3-(oxazol-2-yl)phenyl)-3-methyl-5-oxo-4,5-dihydro-1H-pyrazole-4-carboxylate and 3-(1,1-difluoroethyl)aniline.

LCMS: (ESI) m/z 455.1 [M+H]+.

$^1$H NMR: (400 MHz, DMSO-d$_6$) δ: 10.83 (s, 1H), 8.23 (d, J=17.6 Hz, 2H), 7.95 (s, 1H), 7.83 (d, J=7.2 Hz, 1H), 7.64 (d, J=7.2 Hz, 1H), 7.39 (m, 3H), 7.21 (d, J=6.8 Hz, 1H), 3.93 (s, 3H), 2.54 (s, 3H), 1.96 (t, J=18.4 Hz, 3H).

N-(3-(1,1-difluoroethyl)phenyl)-1-(4-methoxy-2-methylphenyl)-3-methyl-5-oxo-4,5-dihydro-1H-pyrazole-4-carboxamide (302)

Compound ID: 302

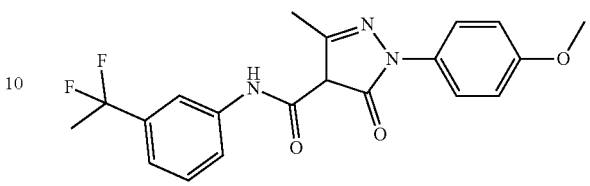

Compound 302 was obtained via general procedure IV from 1-(4-methoxy-2-methylphenyl)-3-methyl-5-oxo-4,5-dihydro-1H-pyrazole-4-carboxylate and 3-(1,1-difluoroethyl)aniline.

LCMS: (ESI) m/z 402.3 [M+H]+.

$^1$H NMR: (400 MHz, MeOD-d$_4$) δ: 7.90 (s, 1H), 7.62 (d, J=8.0 Hz, 1H), 7.40 (t, J=8.0 Hz, 1H), 7.29 (d, J=8.4 Hz, 1H), 7.24 (d, J=7.6 Hz, 1H), 6.98 (d, J=2.8 Hz, 1H), 6.92 (d, J=2.8 Hz, 1H), 3.84 (s, 3H), 2.58 (s, 3H), 2.21 (s, 3H), 1.92 (t, J=18.4 Hz, 3H).

N-(3-(1,1-difluoroethyl)phenyl)-1-(4-methoxy-3-methylphenyl)-3-methyl-5-oxo-4,5-dihydro-1H-pyrazole-4-carboxamide (303)

Compound ID: 303

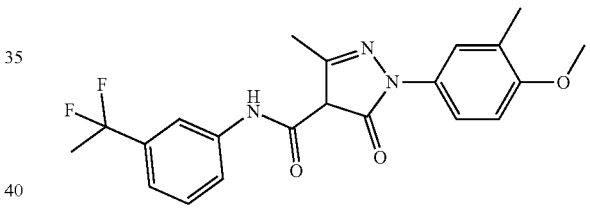

Compound 303 was obtained via general procedure IV from 1-(4-methoxy-3-methylphenyl)-3-methyl-5-oxo-4,5-dihydro-1H-pyrazole-4-carboxylate and 3-(1,1-difluoroethyl)aniline.

LCMS: (ESI) m/z 402.2 [M+H]+.

$^1$H NMR: (400 MHz, MeOD-d$_4$) δ: 7.90 (s, 1H), 7.62 (d, J=7.6 Hz, 1H), 7.33-7.48 (m, 3H), 7.21 (d, J=7.2 Hz, 1H), 7.00 (d, J=8.0 Hz, 1H), 3.86 (s, 3H), 2.53 (s, 3H), 2.24 (s, 3H), 1.92 (t, J=18.0 Hz, 3H).

N-(3-(1,1-difluoroethyl)phenyl)-1-(5-methoxypyridin-2-yl)-3-methyl-5-oxo-4,5-dihydro-1H-pyrazole-4-carboxamide (304)

Compound ID: 304

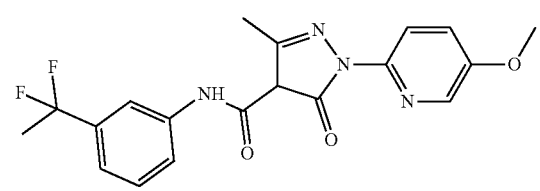 [SMILES: COc1ccc(N2N=C(C)C(C(=O)Nc3cccc(C(C)(F)F)c3)C2=O)nc1]

Compound 304 was obtained via general procedure IV from 1-(5-methoxypyridin-2-yl)-3-methyl-5-oxo-4,5-dihydro-1H-pyrazole-4-carboxylate and 3-(1,1-difluoroethyl)aniline.

LCMS: (ESI) m/z: 389.1 [M+H]⁺.

¹H NMR: (400 MHz, MeOD-d₄) δ: 8.12 (s, 1H), 8.06-8.04 (m, 1H), 7.88 (s, 1H), 7.60 (d, J=5.6 Hz, 1H), 7.53-7.50 (m, 1H), 7.37-7.35 (m, 1H), 7.18 (d, J=7.6 Hz, 1H), 3.58 (s, 3H), 2.52 (s, 3H), 1.90 (t, J=18.0 Hz, 3H).

N-[3-(1,1-difluoroethyl)phenyl]-1-[4-(difluoromethoxy)-3-(2-pyridyl)phenyl]-3-methyl-5-oxo-4H-pyrazole-4-carboxamide (327)

Compound ID: 327

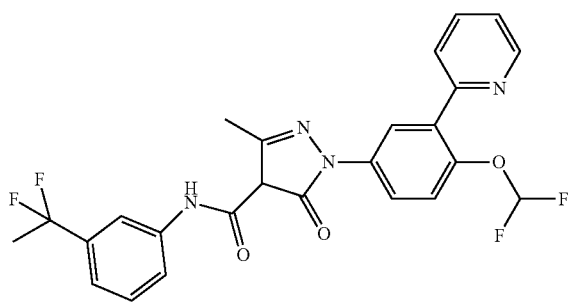 [SMILES: CC1=NN(c2ccc(OC(F)F)c(-c3ccccn3)c2)C(=O)C1C(=O)Nc1cccc(C(C)(F)F)c1]

Compound 320 was obtained via general procedure IV from 1-[4-(difluoromethoxy)-3-(2-pyridyl)phenyl]-3-methyl-5-oxo-4H-pyrazole-4-carboxylate and 3-(1,1-difluoroethyl)aniline.

LCMS: (ESI) m/z 500.9 [M+H]⁺.

¹H NMR: (400 MHz, DMSO-d₆): δ 10.78 (s, 1H), 8.76 (s, 1H), 8.17 (d, J=2.4 Hz, 1H), 8.05-7.95 (m, 3H), 7.83 (d, J=8.0 Hz, 1H), 7.68-7.60 (m, 1H), 7.51-7.27 (m, 3H), 7.23-7.08 (m, 2H), 2.56 (s, 3H), 1.96 (t, J=18.8 Hz, 3H).

N-[3-(1,1-difluoroethyl)phenyl]-1-[4-(difluoromethoxy)-3-pyrazin-2-yl-phenyl]-3-methyl-5-oxo-4H-pyrazole-4-carboxamide (328)

Compound ID: 328

Compound 328 was obtained via general procedure IV from (4-nitrophenyl) 1-[4-(difluoromethoxy)-3-pyrazin-2-yl-phenyl]-3-methyl-5-oxo-4H-pyrazole-4-carboxylate and 3-(1,1-difluoroethyl)aniline.

LCMS: (ESI) m/z: 502.0 [M+H]⁺;

¹H NMR: (400 MHz, MeOD-d₄): δ: 9.08 (s, 1H), 8.76 (d, J=1.6 Hz, 1H), 8.61 (d, J=2.4 Hz, 1H), 8.23 (d, J=2.8 Hz, 1H), 7.92-7.89 (m, 2H), 7.70-7.62 (m, 1H), 7.50 (d, J=8.8 Hz, 1H), 7.41-7.39 (m, 1H), 7.23 (d, J=7.6 Hz, 1H), 6.96 (t, J=73.6 Hz, 1H), 2.61 (s, 3H), 1.92 (t, J=18.4 Hz, 3H).

1-[4-(difluoromethoxy)phenyl]-3-methyl-N-[3-(oxetan-3-yl)phenyl]-5-oxo-4H-pyrazole-4-carboxamide (329)

Compound ID: 329

Compound 329 was obtained via general procedure IV from 3-(oxetan-3-yl)aniline and 4-nitrophenyl 1-(4-(difluoromethoxy)phenyl)-3-methyl-5-oxo-4,5-dihydro-1H-pyrazole-4-carboxylate.

LCMS: (ESI) m/z: 416.0 [M+H]⁺.

¹H NMR: (400 MHz, DMSO-d6) δ: 10.73 (s, 1H), 7.81 (d, J=9. Hz, 2H), 7.71 (s, 1H), 7.52-7.46 (m, 1H), 7.36-7.25 (m, 4H), 7.11-7.03 (m, 1H), 4.95 (dd, J=6.0, 8.4 Hz, 2H), 4.66-4.59 (m, 2H), 4.30-4.18 (m, 1H), 2.54 (s, 3H).

N-[3-(1,1-difluoropropyl)phenyl]-1-(4-methoxyphenyl)-3-methyl-5-oxo-4H-pyrazole-4-carboxamide (330)

Compound ID: 330

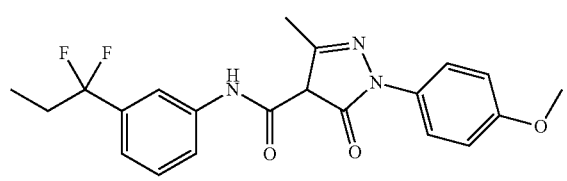 [SMILES: CCC(F)(F)c1cccc(NC(=O)C2C(=O)N(c3ccc(OC)cc3)N=C2C)c1]

Compound 330 was obtained via general procedure IV from 3-(1,1-difluoropropyl)aniline and 1-(4-methoxyphenyl)-3-methyl-5-oxo-4,5-dihydro-1H-pyrazole-4-carboxylate.

LCMS: (ESI) m/z: 401.9 [M+H]⁺.

¹H NMR (400 MHz, DMSO-d₆) δ: 10.94 (s, 1H), 7.90 (s, 1H), 7.66-7.56 (m, 3H), 7.41 (t, J=8.0 Hz, 1H), 7.14 (d, J=7.6 Hz, 1H), 7.06 (d, J=8.8 Hz, 2H), 3.80 (s, 3H), 2.27-2.11 (m, 2H), 0.92 (t, J=7.6 Hz, 3H).

N-(3-(1,1-difluoroethyl)phenyl)-1-(4-methoxy-3-(pyridin-2-yl)phenyl)-3-methyl-5-oxo-4,5-dihydro-1H-pyrazole-4-carboxamide (331)

Compound ID: 331

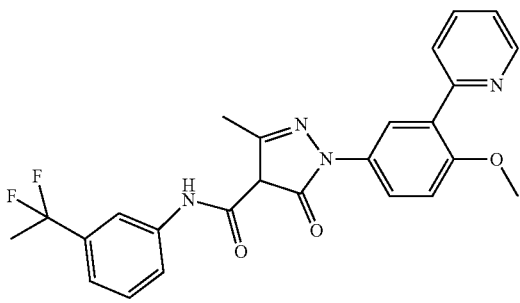 [SMILES: COc1ccc(N2N=C(C)C(C(=O)Nc3cccc(C(C)(F)F)c3)C2=O)cc1-c1ccccn1]

Compound 331 was obtained via general procedure IV from 4-nitrophenyl 1-(4-methoxy-3-(pyridin-2-yl)phenyl)-3-methyl-5-oxo-4,5-dihydro-1H-pyrazole-4-carboxylate and 3-(1,1-difluoroethyl)aniline.

LCMS: (ESI) m/z: 465.0 [M+H]$^+$.

$^1$H NMR (400 MHz, MeOD-d$_4$) δ: 8.63 (d, J=4.8 Hz, 1H), 7.96-7.90 (m, 4H), 7.76 (dd, J=2.4, 8.8 Hz), 7.62 (d, J=8.4 Hz, 1H), 7.46-7.43 (m, 1H), 7.38 (t, J=7.6 Hz, 1H), 7.26 (d, J=9.2 Hz, 1H), 7.20 (d, J=8.0 Hz, 1H), 3.91 (s, 3H), 2.53 (s, 3H), 1.92 (t, J=18.4 Hz, 3H).

N-(3-(1,1-difluoroethyl)phenyl)-1-(4-methoxy-3-(pyrazin-2-yl)phenyl)-3-methyl-5-oxo-4,5-dihydro-1H-pyrazole-4-carboxamide (332)

Compound ID: 332

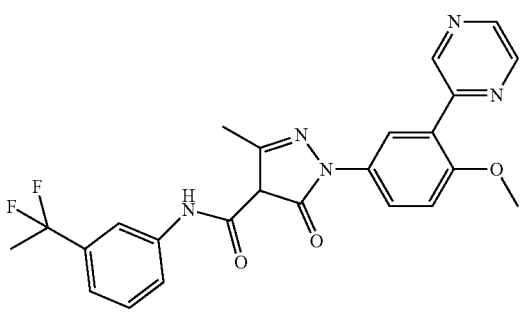 [SMILES: COc1ccc(N2N=C(C)C(C(=O)Nc3cccc(C(C)(F)F)c3)C2=O)cc1-c1cnccn1]

Compound 332 was obtained via general procedure IV from 4-nitrophenyl 1-(4-methoxy-3-(pyrazin-2-yl)phenyl)-3-methyl-5-oxo-4,5-dihydro-1H-pyrazole-4-carboxylate and 3-(1,1-difluoroethyl)aniline.

LCMS: (ESI) m/z: 466.0 [M+H]$^+$.

$^1$H NMR (400 MHz, DMSO-d$_6$) δ: 10.86 (s, 1H), 9.19 (d, J=1.6 Hz, 1H), 8.78 (d, J=2.0 Hz, 1H), 8.62 (d, J=2.4 Hz, 1H), 8.14 (d, J=2.8 Hz, 1H), 7.94 (s, 1H), 7.81 (dd, J=2.8, 8.8 Hz, 1H), 7.64 (d, J=7.6 Hz, 1H), 7.42 (t, J=8.0 Hz, 1H), 7.38 (d, J=8.8 Hz, 1H), 7.21 (d, J=7.6 Hz, 1H), 3.94 (s, 3H), 2.55 (s, 3H), 1.96 (t, J=18.8 Hz, 3H).

1-(3-(aminomethyl)phenyl)-N-(3-(1,1-difluoroethyl)phenyl)-3-methyl-5-oxo-4,5-dihydro-1H-pyrazole-4-carboxamide (335)

Compound ID: 335

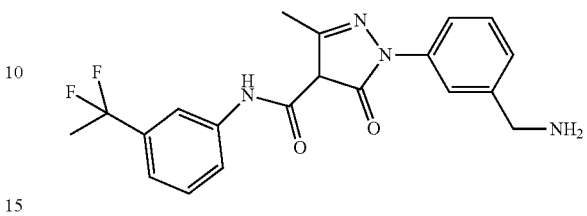

To a 50 mL flask equipped with a magnetic stir bar was added N-(3-(1,1-difluoroethyl)phenyl)-1-(3-((1,3-dioxoisoindolin-2-yl)methyl)phenyl)-3-methyl-5-oxo-4,5-dihydro-1H-pyrazole-4-carboxamide (60.0 mg, 72.3 umol, 1.0 eq) followed by the addition of acetonitrile (1 mL). The solution was cooled to 0° C. Next, hydrazine hydrate (11.6 mg, 232 umol, 3.2 eq) was added dropwise. The mixture was allowed to warm to 25° C. and stir for 0.5 h. The mixture was concentrated under reduced pressure affording the crude product. The crude product was purified by prep-HPLC: column: Xtimate C18 150*25 mm*5 um; mobile phase: [water (0.05% ammonia hydroxide v/v)-ACN]; B %: 15%-30%, 10 min to give 20.0 mg (72% yield) of Compound 335 as a white solid.

LCMS: (ESI) m/z: 387.3 [M+H]$^+$.

$^1$H NMR (400 MHz, DMSO-d$_6$) δ: 11.4 (s, 1H), 8.17-8.15 (m, 2H), 7.92 (s, 1H), 7.67-7.60 (m, 1H), 7.43-7.28 (m, 2H), 7.05 (d, J=8.0 Hz, 1H), 7.03 (s, 1H), 3.93 (s, 1H), 2.26 (s, 3H), 1.96 (t, J=18.4 Hz, 3H).

4-nitrophenyl 1-(4-(difluoromethoxy)-3-(5-methyloxazol-2-yl)phenyl)-3-methyl-5-oxo-4,5-dihydro-1H-pyrazole-4-carboxylate (336)

Compound ID: 336

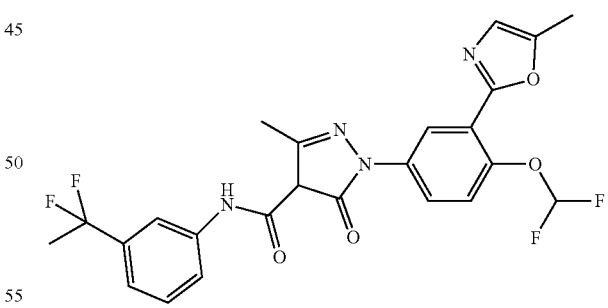

Compound 336 was obtained via general procedure IV from 4-nitrophenyl 1-(4-(difluoromethoxy)-3-(5-methyloxazol-2-yl)phenyl)-3-methyl-5-oxo-4,5-dihydro-1H-pyrazole-4-carboxylate.

LCMS: (ESI) m/z 505.0 [M+H]$^+$.

$^1$H NMR: (400 MHz, MeOD-d$_4$) δ: 8.30 (d, J=2.0 Hz, 1H), 7.92 (s, 1H), 7.85 (d, J=6.8 Hz, 1H), 7.63 (d, J=6.8 Hz, 1H), 7.50 (d, J=8.8 Hz, 1H), 7.41 (t, J=6.8 Hz, 1H), 7.24 (d, J=8.0 Hz, 1H), 7.13-6.75 (m, 2H), 2.64 (s, 3H), 2.44 (s, 3H), 1.93 (t, J=18.4 Hz, 3H).

1-(4-(difluoromethoxy)phenyl)-N-(3-(1-hydroxy-1-phenylethyl)phenyl)-3-methyl-5-oxo-4,5-dihydro-1H-pyrazole-4-carboxamide (337)

Compound ID: 337

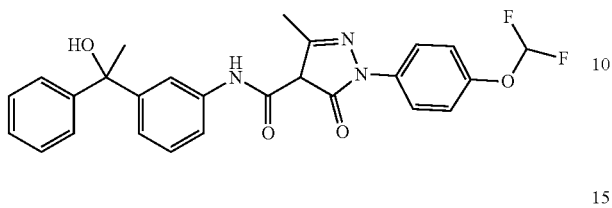

Compound 337 was obtained via the general procedure IV from 1-(3-aminophenyl)-1-phenylethanol and 4-nitrophenyl 1-(4-(difluoromethoxy)phenyl)-3-methyl-5-oxo-4,5-dihydro-1H-pyrazole-4-carboxylate.

LCMS: (ESI) m/z 502.0 [M+Na]$^+$.

$^1$H NMR: (400 MHz, MeOD-d$_4$) δ: 7.69-7.63 (m, 2H), 7.60 (s, 1H), 7.58 (d, J=8.0 Hz, 1H), 7.44 (d, J=1.6 Hz, 2H), 7.30-7.27 (m, 5H), 7.27-7.25 (m, 2H), 6.87 (t, J=74.0 Hz, 1H), 2.57 (s, 3H), 1.91 (s, 3H).

Synthesis of 3-(1,1-difluoroethyl)-N-(1-(4-(difluoromethoxy)phenyl)-3-methyl-5-oxo-4,5-dihydro-1H-pyrazol-4-yl)benzamide (341)

Compound ID: 341

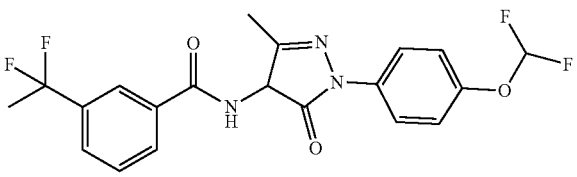 [SMILES: CC1=NN(c2ccc(OC(F)F)cc2)C(=O)C1NC(=O)c1cccc(C(C)(F)F)c1]

To a 50 mL round-bottom flask equipped with a magnetic stir bar was added 3-(1,1-difluoroethyl)benzoic acid (38.9 mg, 192 umol, 1.1 eq) followed by the addition of pyridine (4.0 mL). Then 1-(3-dimethylaminopropyl)-3-ethylcarbodimidehydrochloride (39.4 mg, 206 umol, 1.2 eq) was added at 25° C. The mixture was stirred at 25° C. for 5 min. Then 4-amino-1-(4-(difluoromethoxy)phenyl)-3-methyl-1H-pyrazol-5(4H)-one (50.0 mg, 171 umol, 1.0 eq) was added at 25° C. The reaction mixture was stirred at 25° C. for 30 min. The mixture was concentrated and the residue was purified by preparative HPLC: (column: Phenomenex Synergi C18 150*25*10 um; mobile phase: [water(0.225% FA)-ACN]; B %: 35%-65%, 10 min) to give 25.0 mg (34% yield) of Compound 341 as a white solid.

LCMS: (ESI) m/z 424.0 [M+H]$^+$ $^1$H NMR: (400 MHz, MeOD-d$_4$) δ: 8.18 (s, 1H), 8.09 (d, J=7.6 Hz, 1H), 7.77 (d, J=7.6 Hz, 1H), 7.72 (d, J=9.2 Hz, 2H), 7.67-7.58 (m, 1H), 7.27 (d, J=8.8 Hz, 2H), 7.08-6.66 (m, 1H), 2.24 (s, 3H), 1.98 (t, J=18.0 Hz, 3H).

Synthesis of N-(3-(1,1-difluoroethyl)phenyl)-1-(1H-indol-5-yl)-3-methyl-5-oxo-4,5-dihydro-1H-pyrazole-4-carboxamide (342)

Compound ID: 342

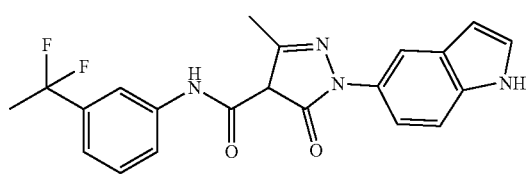 [SMILES: CC1=NN(c2ccc3[nH]ccc3c2)C(=O)C1C(=O)Nc1cccc(C(C)(F)F)c1]

To a solution of N-(3-(1,1-difluoroethyl)phenyl)-3-methyl-5-oxo-1-(1-tosyl-1H-indol-5-yl)-4,5-dihydro-1H-pyrazole-4-carboxamide (50.0 mg, 90.8 umol, 1.0 eq) in methanol (5.0 mL) was added potassium hydroxide (20.4 mg, 363 umol, 4.0 eq). The solution was stirred at 60° C. for 1 h. The solution was concentrated. The residue was purified by prep-HPLC (column: Shim-pack C18 150*25*10 um; mobile phase: [water(0.225% FA)-ACN]; B %: 35%-65%, 10 min) to give 19.0 mg (44% yield) of Compound 342 as a yellow solid.

LCMS: (ESI) m/z 397.0 [M+H]$^+$.

$^1$H NMR: (400 MHz, MeOD-d$_4$) δ: 7.92 (s, 1H), 7.75 (d, J=1.8 Hz, 1H), 7.63 (dd, J=1.2, 8.2 Hz, 1H), 7.54 (d, J=8.6 Hz, 1H), 7.41 (t, J=7.8 Hz, 1H), 7.37 (d, J=3.1 Hz, 1H), 7.29 (dd, J=1.8, 8.6 Hz, 1H), 7.23 (dd, J=0.6, 7.8 Hz, 1H), 6.57 (d, J=2.6 Hz, 1H), 2.61 (s, 3H), 1.92 (t, J=18.2 Hz, 3H).

Synthesis of 1-(4-bromophenyl)-N-[3-(1,1-difluoroethyl)phenyl]-3-methyl-5-oxo-4H-pyrazole-4-carboxamide (344)

Compound ID: 344

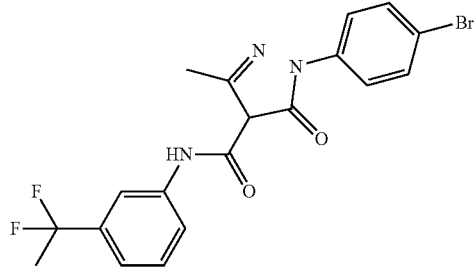 [SMILES: CC(=N)C(C(=O)Nc1ccc(Br)cc1)C(=O)Nc1cccc(C(C)(F)F)c1]

Compound 344 was obtained via general procedure IV from (4-nitrophenyl) 1-(4-bromophenyl)-3-methyl-5-oxo-4H-pyrazole-4-carboxylate and 3-(1,1-difluoroethyl)aniline.

LCMS: (ESI) m/z: 436.0 [M+H]$^+$.

$^1$H NMR (400 MHz, DMSO-d$_6$) δ: 11.27 (s, 1H), 8.10 (d, J=8.8 Hz, 2H), 7.92 (s, 1H), 7.56 (br d, J=8.4 Hz, 1H), 7.44 (d, J=8.8 Hz, 2H), 7.33 (t, J=8.0 Hz, 1H), 7.05 (br d, J=7.6 Hz, 1H), 2.25 (s, 3H), 1.94 (t, J=18.8 Hz, 3H).

N-[3-(1,1-difluoroethyl)phenyl]-1-[4-methoxy-3-(1-oxidopyridin-1-ium-4-yl)phenyl]-3-methyl-5-oxo-4H-pyrazole-4-carboxamide (345)

Compound ID: 345

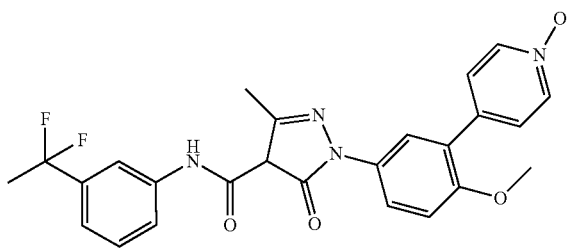

To a solution of Compound 353 (20.0 mg, 41.9 umol, 1.0 eq) in acetic acid (0.50 mL) was added hydrogen peroxide (1.18 g, 10.4 mmol, 249 eq). The reaction was purified by prep-HPLC (column: Phenomenex Synergi C18 150*25*10 um; mobile phase: [water(0.225% FA)-ACN]; B %: 17%-47%, 10 min) to give 5.00 mg (24% yield) of Compound 345 as a white solid.

LCMS: (ESI) m/z 481.2 [M+H]$^+$.

$^1$H NMR: (400 MHz, MeOD-d$_4$) δ: 8.56 (d, J=5.8 Hz, 2H), 7.94-7.86 (m, 3H), 7.74 (d, J=8.0 Hz, 1H), 7.67-7.58 (m, 2H), 7.45 (t, J=7.8 Hz, 1H), 7.34 (d, J=7.6 Hz, 1H), 7.22 (d, J=8.8 Hz, 1H), 2.17 (s, 3H), 1.91 (t, J=18.4 Hz, 3H).

1-[4-(difluoromethoxy)phenyl]-N-(1H-indol-7-yl)-3-methyl-5-oxo-4H-pyrazole-4-carboxamide (346)

Compound ID: 346

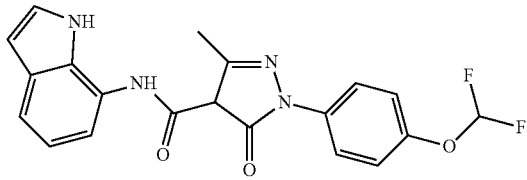 [SMILES: CC1=NN(c2ccc(OC(F)F)cc2)C(=O)C1C(=O)Nc1cccc2cc[nH]c12]

Compound 346 was obtained via general procedure IV from 4-nitrophenyl 1-(4-(difluoromethoxy)phenyl)-3-methyl-5-oxo-4,5-dihydro-1H-pyrazole-4-carboxylate and 1H-indol-7-amine.

LCMS: (ESI) m/z 399.0 [M+H]$^+$.

$^1$H NMR (400 MHz, DMSO-d$_6$) δ: 10.92 (br s, 2H), 7.94 (br d, J=8.8 Hz, 2H), 7.33 (t, J=2.8 Hz, 1H), 7.32-7.26 (m, 3H), 7.24 (t, J=72.8 Hz, 1H), 7.05 (d, J=8.0 Hz, 1H), 6.97-6.91 (m, 1H), 6.44 (dd, J=2.0, 2.8 Hz, 1H), 2.53 (s, 3H).

1-[4-(difluoromethoxy)phenyl]-N-(1H-indol-5-yl)-3-methyl-5-oxo-4H-pyrazole-4-carboxamide (347)

Compound ID: 347

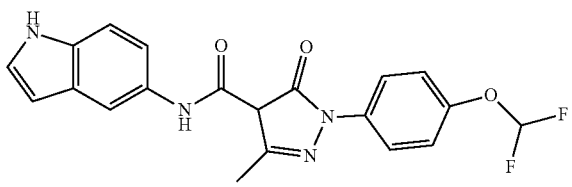 [SMILES: CC1=NN(c2ccc(OC(F)F)cc2)C(=O)C1C(=O)Nc1ccc2[nH]ccc2c1]

Compound 347 was obtained via general procedure IV from 4-nitrophenyl 1-(4-(difluoromethoxy)phenyl)-3-methyl-5-oxo-4,5-dihydro-1H-pyrazole-4-carboxylate and 1H-indol-5-amine.

LCMS: (ESI) m/z 399.0 [M+H]$^+$.

$^1$H NMR: (400 MHz, DMSO-d$_6$) δ: 10.97 (br s, 1H), 10.51 (s, 1H), 7.94 (d, J=2.0 Hz, 1H), 7.85-7.75 (m, 2H), 7.35-7.29 (m, 4H), 7.27 (t, J=73.0 Hz, 1H), 7.16 (dd, J=2.0, 8.8 Hz, 1H), 6.36 (t, J=2.0 Hz, 1H), 2.55 (s, 3H).

N-[3-(1,1-difluoroethyl)phenyl]-3-methyl-1-[4-(oxetan-3-yl)phenyl]-5-oxo-4H-pyrazole-4-carboxamide (348)

Compound ID: 348

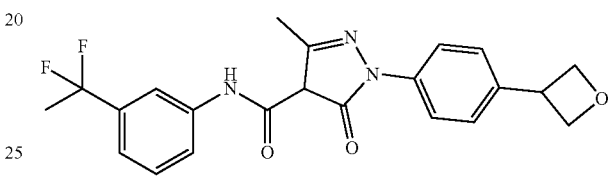

Compound 348 was obtained via general procedure IV from 4-nitrophenyl 3-methyl-1-(4-(oxetan-3-yl)phenyl)-5-oxo-4,5-dihydro-1H-pyrazole-4-carboxylate and 3-(1,1-difluoroethyl)aniline.

LCMS: (ESI) m/z: 414.2 [M+H]$^+$.

$^1$H NMR (400 MHz, MeOD-d$_4$) δ: 7.91 (s, 1H), 7.70 (d, J=8.4 Hz, 2H), 7.64 (br d, J=8.0 Hz, 1H), 7.58 (d, J=8.4 Hz, 2H), 7.40 (t, J=8.0 Hz, 1H), 7.23 (d, J=7.6 Hz, 1H), 5.12 (dd, J=6.0, 8.4 Hz, 2H), 4.78 (s, 2H), 4.40-4.30 (m, 1H), 2.59 (s, 3H), 1.92 (t, J=18.0 Hz, 3H).

1-[4-(difluoromethoxy)phenyl]-N-(1H-indol-6-yl)-3-methyl-5-oxo-4H-pyrazole-4-carboxamide (349)

Compound ID: 349

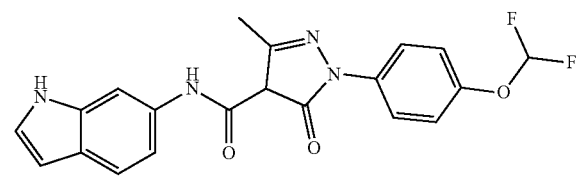 [SMILES: CC1=NN(c2ccc(OC(F)F)cc2)C(=O)C1C(=O)Nc1ccc2cc[nH]c2c1]

Compound 349 was obtained via general procedure IV from 4-nitrophenyl 1-(4-(difluoromethoxy)phenyl)-3-methyl-5-oxo-4,5-dihydro-1H-pyrazole-4-carboxylate and 1H-indol-6-amine.

LCMS: (ESI) m/z 399.1 [M+H]$^+$.

$^1$H NMR (400 MHz, DMSO-d$_6$) δ: 10.97 (br s, 1H), 10.60 (s, 1H), 8.06 (s, 1H), 7.81-7.76 (m, 2H), 7.44 (d, J=8.4 Hz, 1H), 7.35 (d, J=8.8 Hz, 2H), 7.28 (t, J=73.6 Hz, 1H), 7.27-7.24 (m, 1H), 6.93 (dd, J=1.6, 8.4 Hz, 1H), 6.38-6.33 (m, 1H), 2.57 (s, 3H).

301

Synthesis of 1-(4-(difluoromethoxy)phenyl)-N-(1H-indol-4-yl)-3-methyl-5-oxo-4,5-dihydro-1H-pyrazole-4-carboxamide (350)

Compound ID: 350

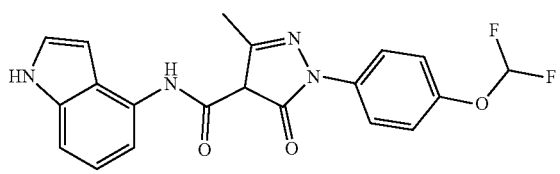 [SMILES: CC1=NN(c2ccc(OC(F)F)cc2)C(=O)C1C(=O)Nc1cccc2[nH]ccc12]

Compound 350 was obtained via general procedure IV from 4-nitrophenyl 1-(4-(difluoromethoxy)phenyl)-3-methyl-5-oxo-4,5-dihydro-1H-pyrazole-4-carboxylate and 1H-indol-4-amine.

LCMS: (ESI) m/z 399.0 [M+H]$^+$.

$^1$H NMR: (400 MHz, DMSO-d$_6$) δ: 11.15 (br s, 1H), 11.05 (s, 1H), 7.95 (dd, J=0.6, 7.6 Hz, 1H), 7.87-7.78 (m, 2H), 7.47 (s, 1H), 7.36 (d, J=8.8 Hz, 2H), 7.33-7.30 (m, 1H), 7.28 (s, 1H), 7.13-7.07 (m, 1H), 7.06-6.95 (m, 1H), 6.56 (s, 1H), 3.33 (s, 43H), 2.57 (s, 5H)

N-(3-(1,1-difluoroethyl)phenyl)-1-(4-(difluoromethoxy)-3-(5-methyl-1,3,4-oxadiazol-2-yl)phenyl)-3-methyl-5-oxo-4,5-dihydro-1H-pyrazole-4-carboxamide (351)

Compound ID: 351

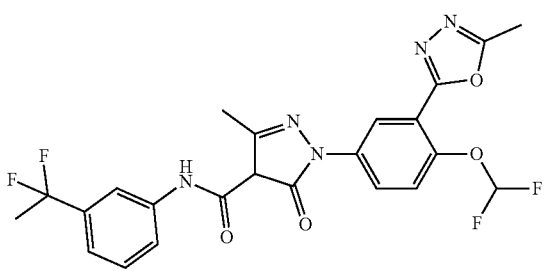

Compound 351 was obtained via general procedure IV from 4-nitrophenyl 1-(4-(difluoromethoxy)-3-(5-methyl-1,3,4-oxadiazol-2-yl)phenyl)-3-methyl-5-oxo-4,5-dihydro-1H-pyrazole-4-carboxylate and 3-(1,1-difluoroethyl)aniline.

LCMS: (ESI) m/z 506.0 [M+H]$^+$.

$^1$H NMR: (400 MHz, MeOD-d$_4$) δ: 8.40 (d, J=2.4 Hz, 1H), 8.00 (dd, J=2.6, 8.9 Hz, 1H), 7.91 (s, 1H), 7.64 (br d, J=8.0 Hz, 1H), 7.58 (d, J=8.8 Hz, 1H), 7.41 (t, J=8.0 Hz, 1H), 7.24 (br d, J=7.6 Hz, 1H), 7.00 (s, 1H), 2.65 (s, 3H), 1.93 (t, J=18.2 Hz, 6H), 1.93 (t, J=18.2 Hz, 3H)

302

N-(3-(1,1-difluoroethyl)phenyl)-1-(4-methoxy-3-(5-methyloxazol-2-yl)phenyl)-3-methyl-5-oxo-4,5-dihydro-1H-pyrazole-4-carboxamide (352)

Compound ID: 352

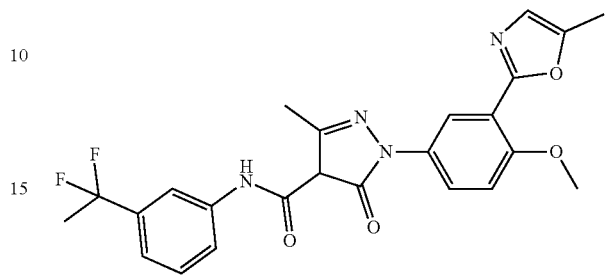

Compound 352 was obtained via general procedure IV from 4-nitrophenyl 1-(4-methoxy-3-(5-methyloxazol-2-yl)phenyl)-3-methyl-5-oxo-4,5-dihydro-1H-pyrazole-4-carboxylate and 3-(1,1-difluoroethyl)aniline.

LCMS: (ESI) m/z 469.0 [M+H]$^+$.

$^1$H NMR (400 MHz, MeOD-d$_4$) δ: 8.09 (s, 1H), 7.91 (s, 1H), 7.72 (dd, J=2.0, 8.8 Hz, 1H), 7.63 (d, J=8.0 Hz, 1H), 7.41 (t, J=8.0 Hz, 1H), 7.33 (d, J=9.2 Hz, 1H), 7.24 (d, J=7.6 Hz, 1H), 6.97 (s, 1H), 3.99 (s, 3H), 2.62 (s, 3H), 2.42 (s, 3H), 1.92 (t, J=18.4 Hz, 3H).

N-(3-(1,1-difluoroethyl)phenyl)-1-(4-methoxy-3-(pyridin-4-yl)phenyl)-3-methyl-5-oxo-4,5-dihydro-1H-pyrazole-4-carboxamide Compound ID: 353

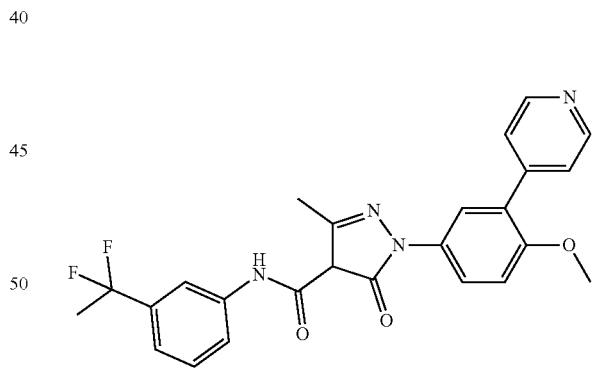

Compound 353 was obtained via general procedure IV from 4-nitrophenyl 1-(4-methoxy-3-(pyridin-4-yl)phenyl)-3-methyl-5-oxo-4,5-dihydro-1H-pyrazole-4-carboxylate.

LCMS: (ESI) m/z 465.1 [M+H]$^+$.

$^1$H NMR: (400 MHz, MeOD-d$_4$) δ: 8.83 (d, J=6.8 Hz, 2H), 8.29 (d, J=5.6 Hz, 2H), 7.94 (s, 1H), 7.90 (s, 1H), 7.81 (d, J=2.4 Hz, 1H), 7.79 (d, J=2.8 Hz, 1H), 7.45-7.42 (m, 2H), 7.29-7.27 (m, 1H), 4.00 (s, 3H), 2.65 (s, 3H), 1.94 (t, J=18.0 Hz, 3H).

303

1-(4-methoxyphenyl)-3-methyl-N-[3-(oxetan-3-yl)phenyl]-5-oxo-4H-pyrazole-4-carboxamide (354)

Compound ID: 354

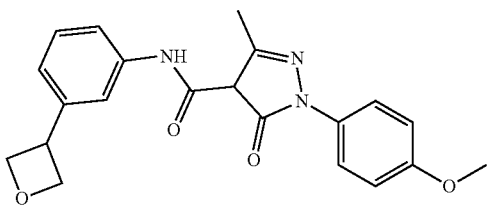 [SMILES: COc1ccc(N2N=C(C)C(C(=O)Nc3cccc(C4COC4)c3)C2=O)cc1]

Compound 354 was obtained via general procedure IV from 3-(oxetan-3-yl)aniline and 1-(4-methoxyphenyl)-3-methyl-5-oxo-4,5-dihydro-1H-pyrazole-4-carboxylate.

LCMS: (ESI) m/z: 380.2 [M+H]$^+$.

$^1$H NMR: (400 MHz, MeOD-d$_4$) δ: 7.75 (s, 1H), 7.54-7.46 (m, 3H), 7.34 (t, J=8.0 Hz, 1H), 7.14 (d, J=7.6 Hz, 1H), 7.09 (d, J=9.2 Hz, 2H), 5.09 (dd, J=6.0, 8.4 Hz, 2H), 4.79-4.70 (m, 2H), 4.34-4.23 (m, 1H), 3.86 (s, 3H), 2.61 (s, 3H).

1-(3-(3-aminoprop-1-yn-1-yl)phenyl)-N-(3-(1,1-difluoroethyl)phenyl)-3-methyl-5-oxo-4,5-dihydro-1H-pyrazole-4-carboxamide hydrochloride (356)

Compound ID: 356

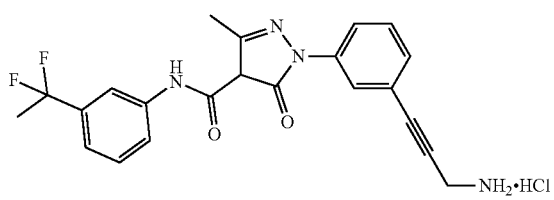

To a 4 mL round-cylinder flask equipped with a magnetic stir bar was added tert-butyl (3-(3-(4-((3-(1,1-difluoroethyl)phenyl)carbamoyl)-3-methyl-5-oxo-4,5-dihydro-1H-pyrazol-1-yl)phenyl)prop-2-yn-1-yl)carbamate (80 mg, crude) followed by the addition of dichloromethane (3 mL). The solution was cooled to 0° C. Then trifluoroacetic acid (0.5 mL) was added drop-wise. The mixture was stirred at 0° C. for 15 min. The mixture was quenched with 4 mL of water and the pH value was adjusted to 7 by saturated aqueous sodium bicarbonate. The resulting mixture was washed with dichloromethane (10 mL×3) and the aqueous phase was dried by lyophilization. The obtained yellow solid was purified by prep-HPLC (column: Phenomenex Synergi C18 150*25*10 um; mobile phase: [water(0.05% HC)-ACN]; B %: 19%-39%, 9 min) to give 2.3 mg (3% yield) of 356 as a yellow solid.

LCMS: (ESI) m/z 411.0 [M+H]$^+$.

$^1$H NMR: (400 MHz, MeOD-d$_4$) δ: 7.91 (br d, J=9.2 Hz, 2H), 7.65 (br t, J=8.4 Hz, 2H), 7.57 (t, J=8.0 Hz, 1H), 7.52-7.47 (m, 1H), 7.42 (t, J=8.0 Hz, 1H), 7.26 (d, J=8.0 Hz, 1H), 4.08 (s, 2H), 2.65 (s, 3H), 1.93 (t, J=18.0 Hz, 3H).

304

N-[3-(1,1-difluoroethyl)phenyl]-1-[4-methoxy-3-(1-oxidopyridin-1-ium-3-yl)phenyl]-3-methyl-5-oxo-4H-pyrazole-4-carboxamide (340)

Compound ID: 340

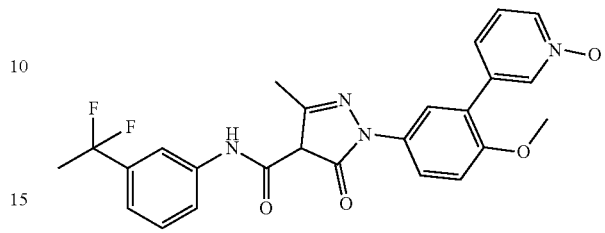

To a 10 mL round-bottom flask equipped with a magnetic stir bar and a reflux condenser was added Compound 320 (30.0 mg, 63.4 umol, 1.0 eq), followed by the addition of acetic acid (500 uL). Then hydrogen dioxide (590 mg, 5.20 mmol, 30% purity, 209 eq) was added into the mixture dropwise at 25° C. The mixture was heated to 80° C. and stirred for 2 h. The mixture was concentrated under reduced pressure affording the crude product. The crude product was purified by preparative HPLC: (column: Phenomenex Synergi C18 150*25*10 um; mobile phase: [water (0.225% FA)-ACN]; B %: 24%-54%, 10 min) to give 2.50 mg (8% yield) of Compound 340 as a white solid.

LCMS: (ESI) m/z: 481.1 [M+H]$^+$.

$^1$H NMR (400 MHz, MeOD-d$_4$) δ: 8.69 (s, 1H), 8.49 (s, 1H), 8.01 (d, J=8.0 Hz, 1H), 7.90-7.86 (m, 2H), 7.84 (d, J=2.8 Hz, 1H), 7.74 (d, J=8.8 Hz, 1H), 7.53-7.42 (m, 2H), 7.34 (d, J=8.0 Hz, 1H), 7.21 (d, J=8.8 Hz, 1H), 3.87 (s, 3H), 2.17 (s, 3H), 1.91 (t, J=18.4 Hz, 3H).

Synthesis of (4-(4-((3-(1,1-difluoroethyl)phenyl)carbamoyl)-3-methyl-5-oxo-4,5-dihydro-1H-pyrazol-1-yl)phenyl)boronic acid (357)

Compound ID: 357

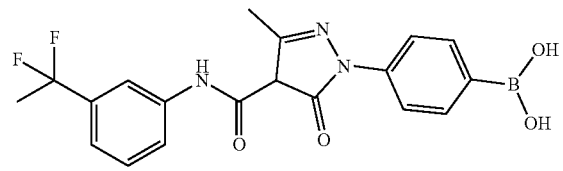 [SMILES: CC1=NN(c2ccc(B(O)O)cc2)C(=O)C1C(=O)Nc1cccc(C(C)(F)F)c1]

To a solution of N-(3-(1,1-difluoroethyl)phenyl)-3-methyl-5-oxo-1-(4-(4,4,5,5-tetramethyl-1,3,2-dioxaborolan-2-yl)phenyl)-4,5-dihydro-1H-pyrazole-4-carboxamide (270 mg, 559 umol, 1.0 eq) in acetonitrile (3.0 mL) was added hydrochloric acid (6 M, 3.0 mL). The solution was stirred at 50° C. for 0.5 h. The solution was concentrated. The residue was purified by prep-HPLC (column: Phenomenex Synergi C18 150*25*10 um; mobile phase: [water (0.225% FA)-ACN]; B %: 28%-58%, 10 min) to give 15.0 mg (7% yield) of Compound 357 as a pink solid.

LCMS: (ESI) m/z 401.9 [M+H]$^+$.

$^1$H NMR: (400 MHz, MeOD-d$_4$) δ: 7.97-7.75 (m, 3H), 7.73-7.53 (m, 3H), 7.47-7.35 (m, 1H), 7.24 (br d, J=7.6 Hz, 1H), 2.65-2.58 (m, 3H), 1.93 (t, J=18.2 Hz, 3H)

1-(4-(tert-butoxy)phenyl)-N-(3-(1,1-difluoroethyl)
phenyl)-3-methyl-5-oxo-4,5-dihydro-1H-pyrazole-4-
carboxamide (324)

Compound ID: 324

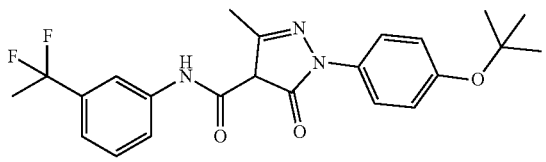 [SMILES: CC1=NN(c2ccc(OC(C)(C)C)cc2)C(=O)C1C(=O)Nc1cccc(C(C)(F)F)c1]

Compound 324 was obtained via general procedure IV from 4-nitrophenyl 1-(4-(tert-butoxy)phenyl)-3-methyl-5-oxo-4,5-dihydro-1H-pyrazole-4-carboxylate and 3-(1,1-difluoroethyl)aniline.

LCMS: (ESI) m/z: 430.0 [M+H]$^+$.

$^1$H NMR: (400 MHz, MeOD-d$_4$) δ: 7.91 (s, 1H), 7.63 (d, J=8.0 Hz, 1H), 7.58-7.53 (m, 2H), 7.40 (t, J=8.0 Hz, 1H), 7.24-7.21 (m, 1H), 7.16-7.13 (m, 2H), 2.58 (s, 3H), 1.92 (t, J=18.4 Hz, 3H), 1.38 (s, 9H).

N-(3-(1,1-difluoroethyl)phenyl)-1-(4-methoxy-3-
(pyrimidin-5-yl)phenyl)-3-methyl-5-oxo-4,5-di-
hydro-1H-pyrazole-4-carboxamide (323)

Compound ID: 323

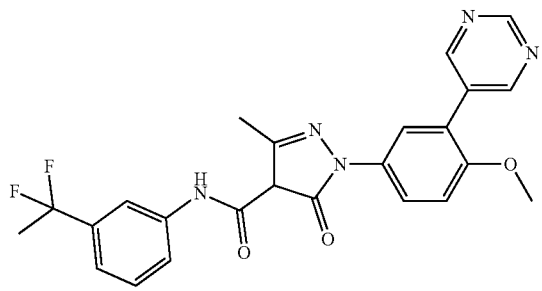 [SMILES: COc1ccc(N2N=C(C)C(C(=O)Nc3cccc(C(C)(F)F)c3)C2=O)cc1-c1cncnc1]

Compound 323 was obtained via general procedure IV from 4-nitrophenyl 1-(4-methoxy-3-(pyrimidin-5-yl)phenyl)-3-methyl-5-oxo-4,5-dihydro-1H-pyrazole-4-carboxylate and 3-(1,1-difluoroethyl)aniline.

LCMS: (ESI) m/z: 466.1 [M+H]$^+$.

$^1$H NMR: (400 MHz, MeOD-d$_4$) δ: 9.11 (s, 1H), 9.03 (s, 2H), 7.91 (s, 1H), 7.74-7.71 (m, 2H), 7.63 (d, J=8.0 Hz, 1H), 7.40 (t, J=8.0 Hz, 1H), 7.31 (d, J=8.8 Hz, 1H), 7.23 (d, J=8.0 Hz, 1H), 3.93 (s, 3H), 2.59 (s, 3H), 1.92 (t, J=18.4 Hz, 3H).

1-[4-(cyclohexoxy)phenyl]-N-[3-(1,1-difluoroethyl)
phenyl]-3-methyl-5-oxo-4H-pyrazole-4-carboxamide
(322)

Compound ID: 322

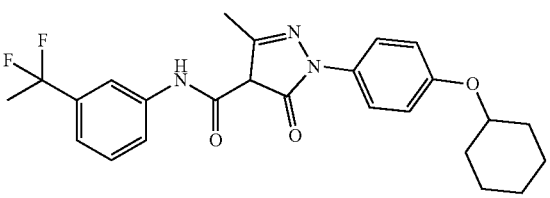 [SMILES: CC1=NN(c2ccc(OC3CCCCC3)cc2)C(=O)C1C(=O)Nc1cccc(C(C)(F)F)c1]

Compound 322 was obtained via general procedure IV from (4-nitrophenyl) 1-[4-(cyclohexoxy)phenyl]-3-methyl-5-oxo-4H-pyrazole-4-carboxylate and 3-(1,1-difluoroethyl)aniline.

LCMS: (ESI) m/z 456.2 [M+H]$^+$.

$^1$H NMR: (400 MHz, DMSO-d$_6$) δ: 10.98 (s, 1H), 7.93 (s, 1H), 7.60 (d, J=8.8 Hz, 3H), 7.41 (t, J=8.0 Hz, 1H), 7.18 (br d, J=8.0 Hz, 1H), 7.09-6.99 (m, 2H), 4.43-4.31 (m, 1H), 4.43-4.31 (m, 1H), 2.48 (s, 3H), 2.03-1.83 (m, 5H), 1.78-1.65 (m, 2H), 1.60-1.50 (m, 1H), 1.49-1.33 (m, 4H), 1.33-1.20 (m, 1H).

N-[3-(1,1-difluoroethyl)phenyl]-3-methyl-5-oxo-1-
(4-sec-butoxyphenyl)-4H-pyrazole-4-carboxamide
(321)

Compound ID: 321

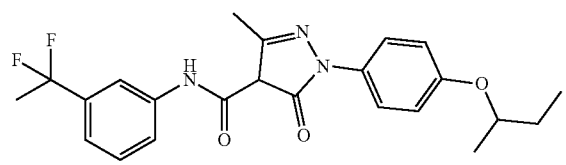 [SMILES: CCC(C)Oc1ccc(N2N=C(C)C(C(=O)Nc3cccc(C(C)(F)F)c3)C2=O)cc1]

Compound 321 was obtained via general procedure IV from (4-nitrophenyl) 3-methyl-5-oxo-1-(4-sec-butoxyphenyl)-4H-pyrazole-4-carboxylate and 3-(1,1-difluoroethyl)aniline.

LCMS: (ESI) m/z 430.2 [M+H]$^+$.

$^1$H NMR: (400 MHz, DMSO-d$_6$) δ: 7.90 (s, 1H), 7.62 (d, J=8.0 Hz, 1H), 7.51 (d, J=8.8 Hz, 2H), 7.39 (t, J=8.0 Hz, 1H), 7.22 (d, J=73.6 Hz, 1H), 7.02 (d, J=9.2 Hz, 1H), 4.45-4.34 (m, 1H), 2.55 (s, 3H), 1.92 (t, J=18.4 Hz, 3H), 1.75-1.64 (m, 2H), 1.29 (d, J=6.4 Hz, 3H), 1.00 (t, J=7.2 Hz, 3H).

N-(3-(1,1-difluoroethyl)phenyl)-1-(4-methoxy-3-
(pyridin-3-yl)phenyl)-3-methyl-5-oxo-4,5-dihydro-
1H-pyrazole-4-carboxamide (320)

Compound ID: 320

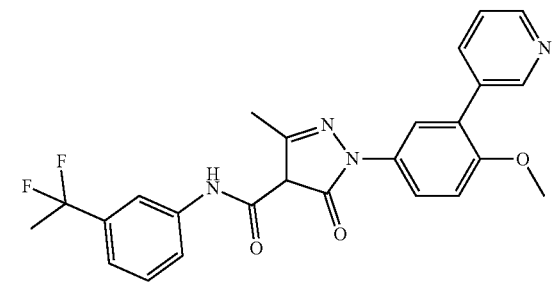 [SMILES: COc1ccc(N2N=C(C)C(C(=O)Nc3cccc(C(C)(F)F)c3)C2=O)cc1-c1cccnc1]

Compound 320 was obtained via general procedure IV from 4-nitrophenyl 1-(4-methoxy-3-(pyridin-3-yl)phenyl)-3-methyl-5-oxo-4,5-dihydro-1H-pyrazole-4-carboxylate and 3-(1,1-difluoroethyl)aniline.

LCMS: (ESI) m/z: 465.1 [M+H]$^+$.

$^1$H NMR: (400 MHz, MeOD-d$_4$) δ: 8.79 (d, J=2.0 Hz, 1H), 8.53 (dd, J=1.2, 4.8 Hz, 1H), 8.14 (td, J=2.0, 8.0 Hz, 1H), 7.91 (s, 1H), 7.72-7.69 (m, 2H), 7.64 (d, J=7.6 Hz, 1H), 7.57 (dd, J=5.2, 8.0 Hz), 7.40 (t, J=8.0 Hz, 1H), 7.29-7.27 (m, 1H), 7.22 (d, J=7.6 Hz, 1H), 3.90 (s, 3H), 2.57 (s, 3H), 1.93 (t, J=18.0 Hz, 3H).

1-[4-(cyclopentoxy)phenyl]-N-[3-(1,1-difluoroethyl)phenyl]-3-methyl-5-oxo-4H-pyrazole-4-carboxamide (319)

Compound ID: 319

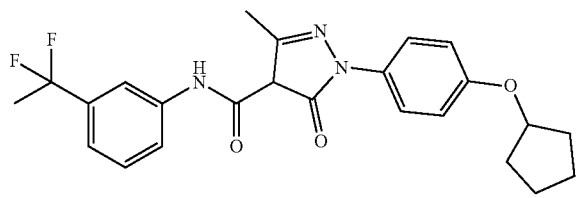

Compound 319 was obtained via general procedure IV from (4-nitrophenyl) 1-[4-(cyclopentoxy)phenyl]-3-methyl-5-oxo-4H-pyrazole-4-carboxylate and 3-(1,1-difluoroethyl)aniline.

LCMS: (ESI) m/z 442.2 [M+H]⁺.

$^1$H NMR: (400 MHz, DMSO-d$_6$) δ: 10.90 (s, 1H), 7.93 (s, 1H), 7.61 (d, J=8.4 Hz, 1H), 7.57-7.52 (m, 2H), 7.42 (t, J=8.0 Hz, 1H), 7.21 (d, J=8.0 Hz, 1H), 7.07-7.01 (m, 2H), 4.90-4.83 (m, 1H), 2.52 (s, 3H), 2.03-1.88 (m, 5H), 1.78-1.68 (m, 4H), 1.65-1.55 (m, 2H).

N-[3-(1,1-difluoroethyl)phenyl]-1-(4-isopropoxyphenyl)-3-methyl-5-oxo-4H-pyrazole-4-carboxamide (318)

Compound ID: 318

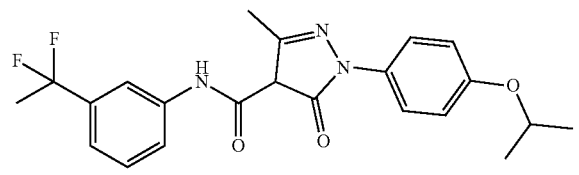 [SMILES: CC1=NN(c2ccc(OC(C)C)cc2)C(=O)C1C(=O)Nc1cccc(C(C)(F)F)c1]

Compound 318 was obtained via general procedure IV from (4-nitrophenyl) 1-(4-isopropoxyphenyl)-3-methyl-5-oxo-4H-pyrazole-4-carboxylate and 3-(1,1-difluoroethyl)aniline.

LCMS: (ESI) m/z 416.0 [M+H]⁺.

$^1$H NMR: (400 MHz, DMSO-d$_6$) δ: 11.32 (s, 1H), 8.66 (s, 1H), 8.39 (d, J=8.0 Hz, 1H), 8.20 (s, 1H), 8.01 (d, J=7.6 Hz, 1H), 7.71 (s, 2H), 7.58 (t, J=8.0 Hz, 1H), 7.54-7.45 (m, 2H), 7.34 (d, J=7.6 Hz, 1H), 2.63 (s, 6H), 2.30 (s, 3H).

N-[3-(1,1-difluoroethyl)phenyl]-3-methyl-5-oxo-1-(4-propoxyphenyl)-4H-pyrazole-4-carboxamide (317)

Compound ID: 317

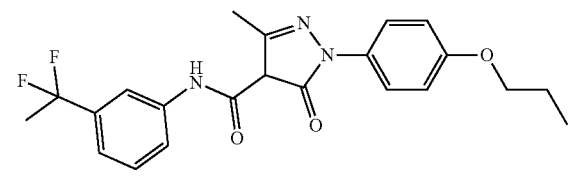 [SMILES: CCCOc1ccc(N2N=C(C)C(C(=O)Nc3cccc(C(C)(F)F)c3)C2=O)cc1]

Compound 317 was obtained via general procedure IV from (4-nitrophenyl) 3-methyl-5-oxo-1-(4-propoxyphenyl)-4H-pyrazole-4-carboxylate and 3-(1,1-difluoroethyl)aniline.

LCMS: (ESI) m/z 416.3 [M+H]⁺.

$^1$H NMR: (400 MHz, MeOD-d$_4$) δ: 7.90 (s, 1H), 7.62 (d, J=8.0 Hz, 1H), 7.49 (d, J=8.4 Hz, 2H), 7.40 (t, J=8.0 Hz, 1H), 7.23 (d, J=8.0 Hz, 1H), 7.08-7.05 (m, 2H), 4.01-3.97 (m, 2H), 2.59 (s, 3H), 1.92 (t, J=18.4 Hz, 3H), 1.85-1.79 (m, 2H), 1.06 (t, J=7.2 Hz, 3H).

N-(3-(1,1-difluoroethyl)phenyl)-1-(4-(difluoromethoxy)-3-(pyrimidin-5-yl)phenyl)-3-methyl-5-oxo-4,5-dihydro-1H-pyrazole-4-carboxamide (316)

Compound ID: 316

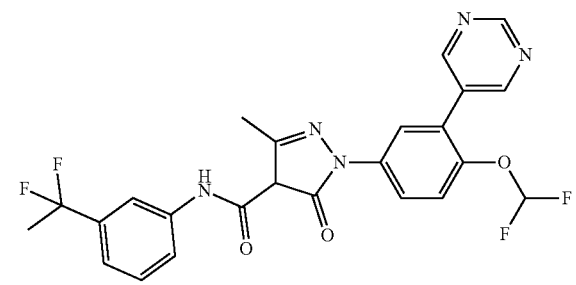

Compound 316 was obtained via general procedure IV from 4-nitrophenyl 1-(4-(difluoromethoxy)-3-(pyrimidin-5-yl)phenyl)-3-methyl-5-oxo-4,5-dihydro-1H-pyrazole-4-carboxylate and 3-(1,1-difluoroethyl)aniline.

LCMS: (ESI) m/z: 502.1 [M+H]⁺.

$^1$H NMR: (400 MHz, MeOD-d$_4$) δ: 9.18 (s, 1H), 9.03 (s, 2H), 7.98 (d, J=2.4 Hz, 1H), 7.90 (t, J=5.6 Hz, 2H), 7.63 (d, J=8.4 Hz, 1H), 7.48 (d, J=8.8 Hz, 1H), 7.39 (t, J=7.6 Hz, 1H), 7.21 (d, J=7.6 Hz, 1H), 6.89 (t, J=73.2 Hz, 1H), 2.56 (s, 3H), 1.92 (t, J=18.0 Hz, 3H).

N-(3-(1,1-difluoroethyl)phenyl)-1-(4-(difluoromethoxy)-3-(pyridin-4-yl)phenyl)-3-methyl-5-oxo-4,5-dihydro-1H-pyrazole-4-carboxamide (315)

Compound ID: 315

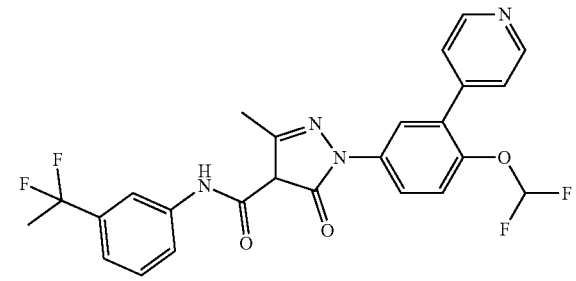

Compound 315 was obtained via general procedure IV from 4-nitrophenyl 1-(4-(difluoromethoxy)-3-(pyridin-4-yl)phenyl)-3-methyl-5-oxo-4,5-dihydro-1H-pyrazole-4-carboxylate and 3-(1,1-difluoroethyl)aniline.

LCMS: (ESI) m/z: 501.1 [M+H]⁺.

$^1$H NMR: (400 MHz, MeOD-d$_4$) δ: 8.67 (d, J=5.6 Hz, 2H), 8.01 (d, J=2.4 Hz, 1H), 7.93-7.90 (m, 2H), 7.78 (d, J=5.6 Hz, 2H), 7.63 (d, J=8.0 Hz, 1H), 7.45 (d, J=9.2 Hz,

1H), 7.39 (t, J=7.6 Hz, 1H), 7.20 (d, J=7.6 Hz, 1H), 6.85 (t, J=73.2 Hz, 1H), 2.53 (s, 3H), 1.92 (t, J=18.0 Hz, 3H).

N-(3-(1,1-difluoroethyl)phenyl)-1-(2-fluoro-4-methoxyphenyl)-3-methyl-5-oxo-4,5-dihydro-1H-pyrazole-4-carboxamide (314)

Compound ID: 314

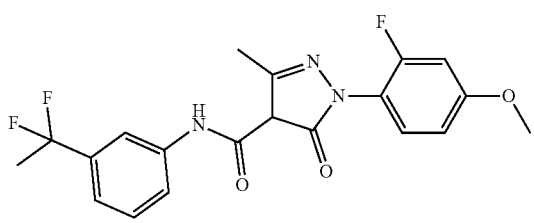 [SMILES: COc1ccc(N2N=C(C)C(C(=O)Nc3cccc(C(C)(F)F)c3)C2=O)c(F)c1]

Compound 314 was obtained via general procedure IV from 4-nitrophenyl 1-(2-fluoro-4-methoxyphenyl)-3-methyl-5-oxo-4,5-dihydro-1H-pyrazole-4-carboxylate and 3-(1,1-difluoroethyl)aniline.

LCMS: (ESI) m/z: 406.1 [M+H]$^+$.

$^1$H NMR: (400 MHz, MeOD-d$_4$) δ: 7.90 (s, 1H), 7.62-7.60 (m, 1H), 7.45 (t, J=8.8 Hz, 1H), 7.40 (t, J=8.0 Hz, 1H), 7.23 (d, J=8.0 Hz, 1H), 6.97-6.91 (m, 2H), 3.87 (s, 3H), 2.57 (s, 3H), 1.92 (t, J=18.4 Hz, 3H).

N-[3-(1,1-difluoroethyl)phenyl]-1-(4-methoxy-3-phenyl-phenyl)-3-methyl-5-oxo-4H-pyrazole-4-carboxamide (313)

Compound ID: 313

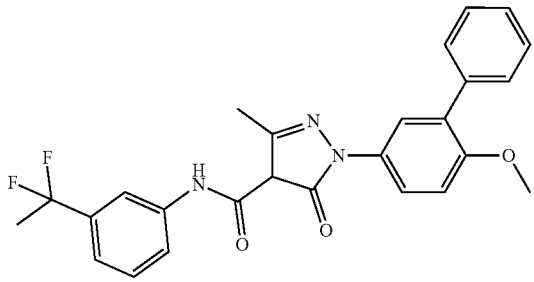 [SMILES: COc1ccc(N2N=C(C)C(C(=O)Nc3cccc(C(C)(F)F)c3)C2=O)cc1-c1ccccc1]

Compound 313 was obtained via general procedure IV from (4-nitrophenyl) 1-(4-methoxy-3-phenyl-phenyl)-3-methyl-5-oxo-4H-pyrazole-4-carboxylate and 3-(1,1-difluoroethyl)aniline.

LCMS: (ESI) m/z 464.0 [M+H]$^+$.

$^1$H NMR: (400 MHz, MeOD-d$_4$) δ: 7.91 (s, 1H), 7.62-7.53 (m, 5H), 7.43-7.40 (m, 3H), 7.38-7.33 (m, 1H), 7.24 (d, J=7.6 Hz, 2H), 3.86 (s, 3H), 2.61 (s, 3H), 1.92 (t, J=18.4 Hz, 3H).

N-(3-(1,1-difluoroethyl)phenyl)-1-(6-(difluoromethoxy)-[1,1'-biphenyl]-3-yl)-3-methyl-5-oxo-4,5-dihydro-1H-pyrazole-4-carboxamide (312)

Compound ID: 312

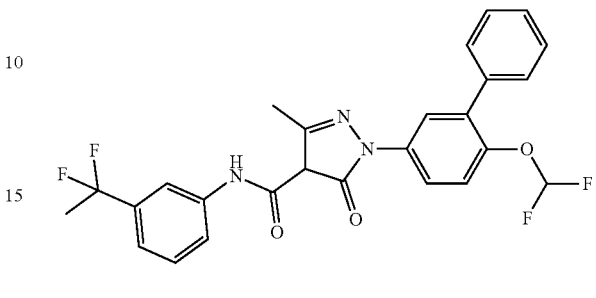

Compound 312 was obtained via general procedure IV from 4-nitrophenyl 1-(4-(difluoromethoxy)phenyl)-3-methyl-5-oxo-4,5-dihydro-1H-pyrazole-4-carboxylate and 3-(1,1-difluoroethyl)aniline.

LCMS: (ESI) m/z: 500.1 [M+H]$^+$.

$^1$H NMR: (400 MHz, MeOD-d$_4$) δ: 7.92 (s, 1H), 7.80 (d, J=2.4 Hz, 1H), 7.72 (dd, J=2.8, 8.8 Hz, 1H), 7.63 (d, J=8.4 Hz, 1H), 7.56 (d, J=8.0 Hz, 2H), 7.46 (t, J=7.2 Hz, 2H), 7.42-7.38 (m, 3H), 7.22 (d, J=8.0 Hz, 1H), 6.71 (t, J=74.0 Hz, 1H), 2.59 (s, 3H), 1.92 (t, J=18.4 Hz, 3H).

1-difluoroethyl)phenyl]-1-[4-(difluoromethoxy)-3-methoxy-phenyl]-3-methyl-5-oxo-4H-pyrazole-4-carboxamide (311)

Compound ID: 311

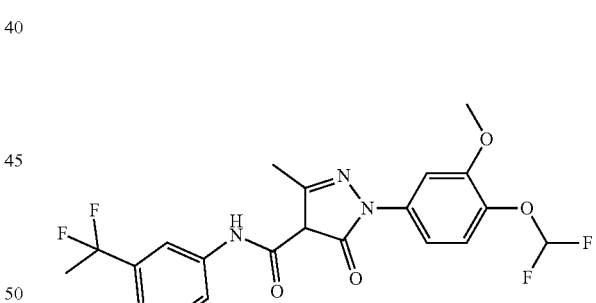

Compound 311 was obtained via general procedure IV from (4-nitrophenyl) 1-[4-(difluoromethoxy)-3-methoxy-phenyl]-3-methyl-5-oxo-4H-pyrazole-4-carboxylate and 3-(1,1-difluoroethyl)aniline.

LCMS: (ESI) m/z 454.1 [M+H]$^+$.

$^1$H NMR: (400 MHz, MeOD-d$_4$) δ: 7.92 (s, 1H), 7.65 (d, J=8.0 Hz, 1H), 7.55 (s, 1H), 7.43-7.31 (m, 1H), 7.30-7.22 (m, 3H), 6.79 (t, J=75.2 Hz, 1H), 3.98 (s, 3H), 2.64 (s, 3H), 1.94 (t, J=18.4 Hz, 3H).

N-(3-(1,1-difluoroethyl)phenyl)-1-(4-(difluoromethoxy)-3-(pyridin-3-yl)phenyl)-3-methyl-5-oxo-4,5-dihydro-1H-pyrazole-4-carboxamide (310)

Compound ID: 310

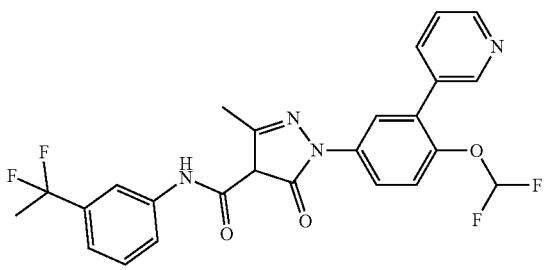 [SMILES: CC1=NN(c2ccc(OC(F)F)c(-c3ccccc3)c2)C(=O)C1C(=O)Nc1cccc(C(C)(F)F)c1]

Compound 310 was obtained via general procedure IV from 4-nitrophenyl 1-(4-(difluoromethoxy)-3-(pyridin-3-yl)phenyl)-3-methyl-5-oxo-4,5-dihydro-1H-pyrazole-4-carboxylate and 3-(1,1-difluoroethyl)aniline.
LCMS: (ESI) m/z 501.1 [M+H]$^+$.
$^1$H NMR: (400 MHz, MeOD-d$_4$) δ: 8.80 (s, 1H), 8.63-8.61 (m, 1H), 8.19-8.15 (m, 1H), 7.90 (d, J=2.4 Hz, 2H), 7.82 (d, J=2.4 Hz, 1H), 7.65-7.62 (m, 2H), 7.49 (d, J=8.8 Hz, 1H), 7.41-7.35 (m, 1H), 7.25-7.20 (m, 1H), 6.87 (t, J=73.2 Hz, 1H), 2.60 (s, 3H), 1.92 (t, J=13.2 Hz, 3H).

N-(3-(1,1-difluoroethyl)phenyl)-1-(4-(difluoromethoxy)-2-fluorophenyl)-3-methyl-5-oxo-4,5-dihydro-1H-pyrazole-4-carboxamide (309)

Compound ID: 309

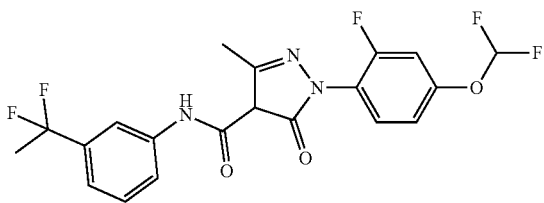 [SMILES: CC1=NN(c2ccc(OC(F)F)cc2F)C(=O)C1C(=O)Nc1cccc(C(C)(F)F)c1]

Compound 309 was obtained via general procedure IV from 4-nitrophenyl 1-(4-(difluoromethoxy)-2-fluorophenyl)-3-methyl-5-oxo-4,5-dihydro-1H-pyrazole-4-carboxylate and 3-(1,1-difluoroethyl)aniline.
LCMS: (ESI) m/z: 442.1 [M+H]$^+$.
$^1$H NMR: (400 MHz, MeOD-d$_4$) δ: 7.90 (s, 1H), 7.67-7.60 (m, 2H), 7.41 (t, J=8.0 Hz, 1H), 7.28-7.23 (m, 2H), 7.19-6.82 (m, 2H), 2.61 (s, 3H), 1.92 (t, J=18.4 Hz, 3H).

1-(4-cyclopropylphenyl)-N-(3-(1,1-difluoroethyl)phenyl)-3-methyl-5-oxo-4,5-dihydro-1H-pyrazole-4-carboxamide (308)

Compound ID: 308

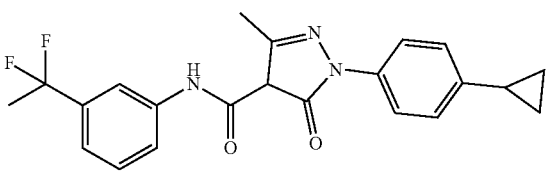

Compound 308 was obtained via general procedure IV from 4-nitrophenyl 1-(4-cyclopropylphenyl)-3-methyl-5-oxo-4,5-dihydro-1H-pyrazole-4-carboxylate and 3-(1,1-difluoroethyl)aniline.
LCMS: (ESI) m/z: 398.1 [M+H]$^+$.
$^1$H NMR: (400 MHz, MeOD-d$_4$) δ: 7.91 (s, 1H), 7.63 (d, J=8.4 Hz, 1H), 7.48 (d, J=8.4 Hz, 2H), 7.41 (t, J=7.6 Hz, 1H), 7.24 (d, J=8.4 Hz, 3H), 2.61 (s, 3H), 2.00-1.98 (m, 1H), 1.92 (t, J=18.4 Hz, 2H), 1.04-1.00 (m, 2H), 0.74-0.72 (m, 2H).

1-(4-(difluoromethoxy)phenyl)-N-((1S,3S,4R)-3,4-dihydroxycyclohexyl)-3-methyl-5-oxo-4,5-dihydro-1H-pyrazole-4-carboxamide (307)

Compound ID: 307

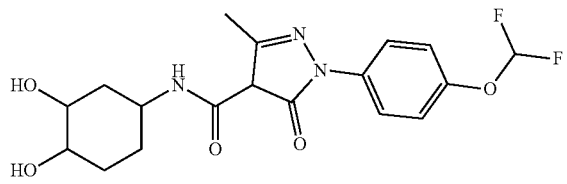 [SMILES: CC1=NN(c2ccc(OC(F)F)cc2)C(=O)C1C(=O)NC1CCC(O)C(O)C1]

To a solution of N-(3,4-bis((tert-butyldimethylsilyl)oxy)cyclohexyl)-1-(4-(difluoromethoxy)phenyl)-3-methyl-5-oxo-4,5-dihydro-1H-pyrazole-4-carboxamide (40.0 mg, 59.6 umol, 1.0 eq) in dichloromethane (1 mL) was added dropwise hydrogen chloride/methanol (4 M, 59 uL, 4.0 eq) at 0° C., then the mixture was stirred at 15° C. for 1 h. The mixture was concentrated in vacuo to give brown solid. The solid was purified by prep-HPLC (column: Phenomenex Synergi C18 150*25*10 um; mobile phase: [water(0.1% trifluoroacetic acid)-ACN]; B %: 10%-40%, 9 min) to give 19.0 mg (80% yield) of Compound 307 as a white solid.
LCMS: (ESI) m/z 398.2 [M+H]$^+$.
$^1$H NMR: (400 MHz, MeOD-d$_4$) δ: 7.63 (d, J=8.8 Hz, 2H), 7.29 (d, J=8.8 Hz, 2H), 6.89 (t, J=73.2 Hz, 1H), 3.95 (dt, J=4.4 Hz, 8.8 Hz, 1H), 3.78-3.86 (m, 1H), 3.71 (dt, J=3.2 Hz, 9.6 Hz, 1H), 2.56 (s, 3H), 1.84-1.94 (m, 2H), 1.70-1.79 (m, 1H), 1.61-1.70 (m, 2H), 1.52-1.61 (m, 1H).

N-(5-(1,1-difluoroethyl)-2-(hydroxymethyl)phenyl)-1-(4-(difluoromethoxy)phenyl)-3-methyl-5-oxo-4,5-dihydro-1H-pyrazole-4-carboxamide (306)

Compound ID: 306

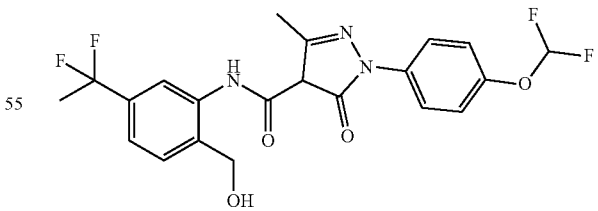

A solution of N-[2-[[tert-butyl(dimethyl)silyl]oxymethyl]-5-(1,1-difluoroethyl)phenyl]-1-[4-(difluoromethoxy)phenyl]-3-methyl-5-oxo-4H-pyrazole-4-carboxamide (80.0 mg, 141 umol, 1.0 eq) in hydrochloric acid/methanol (4 M, 5 mL) was stirred at 15° C. for 5 min. The solution was concentrated. The residue was purified by prep-HPLC (column: Luna C18 150*25 5u; mobile phase: [water(0.225%

FA)-ACN]; B %: 46%-66%, 7.8 min) to give 30 mg (45% yield) of Compound 306 as a white solid.

LCMS: (ESI) m/z 454.1 [M+H]⁺.

¹H NMR: (400 MHz, MeOD-d₄) δ: 8.36 (s, 1H), 7.70-7.67 (m, 2H), 7.50 (s, J=8.0 Hz, 1H), 7.32-7.27 (m, 3H), 6.89 (t, J=73.6 Hz, 1H), 4.73 (s, 2H), 2.61 (s, 3H), 1.93 (t, J=18.4 Hz, 3H).

1-(2-(tert-butyl)-4-methoxyphenyl)-N-(3-(1,1-difluoroethyl)phenyl)-3-methyl-5-oxo-4,5-dihydro-1H-pyrazole-4-carboxamide (305)

Compound ID: 305

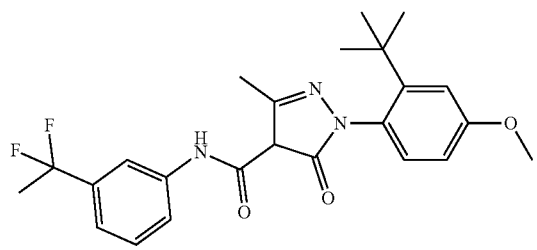 [SMILES: COc1ccc(N2N=C(C)C(C(=O)Nc3cccc(C(C)(F)F)c3)C2=O)c(C(C)(C)C)c1]

Compound 305 was obtained via general procedure IV from 4-nitrophenyl 1-(2-(tert-butyl)-4-methoxyphenyl)-3-methyl-5-oxo-4,5-dihydro-1H-pyrazole-4-carboxylate and 3-(1,1-difluoroethyl)aniline.

LCMS: (ESI) m/z 444.2 [M+H]⁺.

¹H NMR: (400 MHz, MeOD-d₄) δ: 7.91 (s, 1H), 7.65-7.61 (m, 1H), 7.40 (t, J=8.0 Hz, 1H), 7.23 (d, J=7.6 Hz, 1H), 7.16 (d, J=2.8 Hz, 1H), 7.10 (d, J=8.8 Hz, 1H), 6.95-6.92 (m, 1H), 3.85 (s, 3H), 2.58 (s, 3H), 1.92 (t, J=18.0 Hz, 3H), 1.34 (s, 9H).

Synthesis of 298

Step 1: Synthesis of (4-(difluoromethoxy)phenyl)hydrazine (298-A)

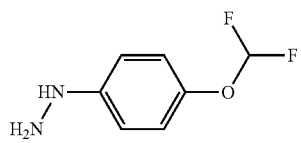

298-A was obtained via general procedure I from 4-(difluoromethoxy)aniline.

LCMS: (ESI) m/z: 175.1 [M+H]⁺.

Step 2: Synthesis of 1-(4-(difluoromethoxy)phenyl)-3-methyl-1H-pyrazol-5(4H)-one (298-B)

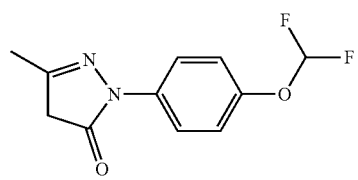 [SMILES: CC1=NN(c2ccc(OC(F)F)cc2)C(=O)C1]

298-B was obtained via general procedure II from 298-A.
LCMS: (ESI) m/z: 241.2 [M+H]⁺.

Step 3: Synthesis of 4-nitrophenyl 1-(4-(difluoromethoxy)phenyl)-3-methyl-5-oxo-4,5-dihydro-1H-pyrazole-4-carboxylate (298-C)

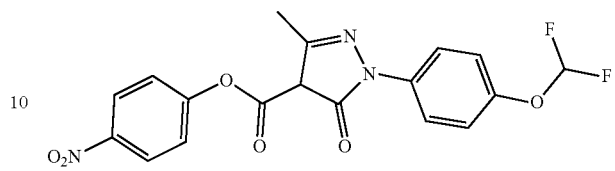

298-C was obtained via general procedure III from 298-B.
LCMS: (ESI) m/z: 406.0 [M+H]⁺.

Step 4: Synthesis of N-(3-(1,1-difluoroethyl)phenyl)-1-(4-(difluoromethoxy)phenyl)-3-methyl-5-oxo-4,5-dihydro-1H-pyrazole-4-carboxamide (298)

Compound ID: 298

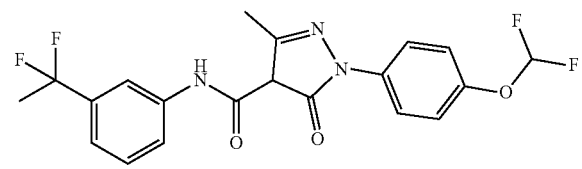

298 was obtained via general procedure IV from 298-C and 3-(1,1-difluoroethyl)aniline.

LCMS: (ESI) m/z: 424.2 [M+H]⁺.

¹H NMR: (400 MHz, MeOD-d₄) δ: 7.90 (s, 1H), 7.69-7.66 (m, 2H), 7.62 (d, J=8.0 Hz, 1H), 7.40 (t, J=8.0 Hz, 1H), 7.32-7.30 (m, 2H), 7.24 (d, J=7.6 Hz, 1H), 6.89 (t, J=72.0 Hz, 1H), 2.61 (d, J=3.6 Hz, 3H), 1.92 (t, J=18.0 Hz, 3H).

Synthesis of 409

Step 1: Synthesis of 1-(3-(dibenzylamino)phenyl)ethanone (409-A)

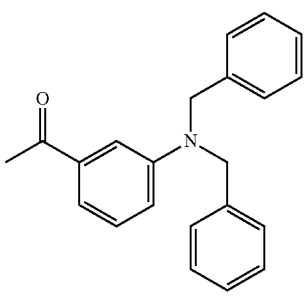 [SMILES: CC(=O)c1cccc(N(Cc2ccccc2)Cc2ccccc2)c1]

A mixture of 1-(3-aminophenyl)ethanone (10.0 g, 74.0 mmol, 1.0 eq), bromomethylbenzene (31.6 g, 185 mmol, 2.5 eq) and potassium carbonate (30.7 g, 222 mmol, 3.0 eq) in acetonitrile (150 mL) was heated to 70° C. and stirred for 5 h. The mixture was diluted with water (250 mL) and extracted with ethyl acetate (150 mL×3). The combined organic layer was washed with brine (200 mL), dried over anhydrous sodium sulfate, filtered, and concentrated. The crude product was purified by silica gel column chromatography (petroleum ether/ethyl acetate=10/1) to give 16.0 g (69% yield) of 409-A as a yellow solid.

LCMS: (ESI) m/z: 316.1 [M+H]$^+$.

$^1$H NMR (400 MHz, CDCl$_3$-d) δ: 7.25-7.15 (m, 13H), 6.83 (d, J=8.0 Hz, 1H), 4.62 (s, 4H), 2.41 (s, 3H).

Step 2: Synthesis of 2-(3-(dibenzylamino)phenyl)-3-methylbutan-2-ol (409-B)

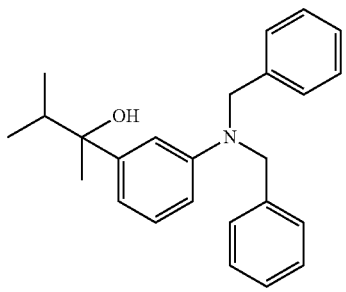 [SMILES: CC(C)C(C)(O)c1cccc(N(Cc2ccccc2)Cc2ccccc2)c1]

To a solution of 409-A (7.00 g, 22.2 mmol, 1.0 eq) in tetrahydrofuran (100 mL) was added dropwise isopropylmagnesium bromide (3 M, 22.2 mL, 3.0 eq) at 0° C. under nitrogen atmosphere. The mixture was slowly warmed to 25° C. and stirred for 12 h. The reaction mixture was quenched by addition saturated ammonia chloride aqueous (200 mL) and extracted with ethyl acetate (200 mL×2). The combined organic layer was washed with brine (300 mL), dried over anhydrous sodium sulfate, filtered and concentrated. The residue was purified by column chromatography (petroleum ether/ethyl acetate=80/1) to give 3.70 g (38% yield) of 409-B as a yellow oil.

LCMS: (ESI) m/z: 360.3 [M+H]$^+$.

Step 3: Synthesis of 2-(3-aminophenyl)-3-methylbutan-2-ol (409-C)

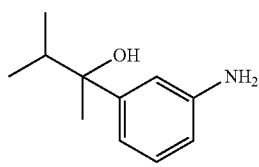

To a solution of 409-B (3.70 g, 8.44 mmol, 1.0 eq) in methanol (50 mL) was added palladium (200 mg, 10% purity in carbon). The mixture was stirred at 25° C. for 12 h under hydrogen (50 psi). The mixture was filtered through a celite pad and the filtrate was concentrated. The residue was purified by column chromatography (petroleum ether/ethyl acetate=3/1) to give 650 mg (42% yield) of 409-C as a light yellow solid.

LCMS: (ESI) m/z: 180.1 [M+H]$^+$.

$^1$H NMR (400 MHz, CDCl$_3$-d) δ: 7.15-7.09 (m, 1H), 6.82-6.76 (m, 2H), 6.60-6.54 (m, 1H), 3.68 (br s, 2H), 2.04-1.98 (m, 1H), 1.49 (s, 3H), 0.91 (d, J=6.8 Hz, 3H), 0.82 (d, J=6.8 Hz, 3H).

Step 4: Synthesis of 1-(4-(difluoromethoxy)phenyl)-N-(3-(2-hydroxy-3-methylbutan-2-yl)phenyl)-3-methyl-5-oxo-4,5-dihydro-1H-pyrazole-4-carboxamide (409-D)

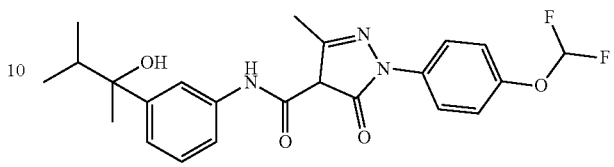

409-D was obtained via general procedure IV from 409-C and 298-C.

LCMS: (ESI) m/z: 446.1 [M+H]$^+$.

Step 5: Synthesis of 1-(4-(difluoromethoxy)phenyl)-N-(3-(2-fluoro-3-methylbutan-2-yl)phenyl)-3-methyl-5-oxo-4,5-dihydro-1H-pyrazole-4-carboxamide (409)

Compound ID: 409

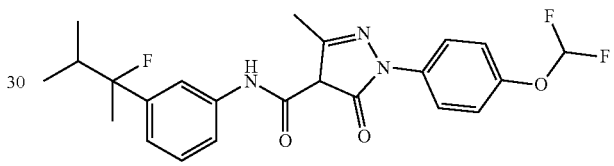

To a solution of 409-D (0.160 g, 320 umol, 1.0 eq) in dichloromethane (5 mL) was added diethylaminosulfur trifluoride (103 mg, 639 umol, 2.0 eq). The mixture was stirred at 25° C. for 0.5 h. The mixture was concentrated. The residue was purified by prep-HPLC (column: Phenomenex Synergi C18 150*30 mm*4 um; mobile phase: [water (0.225% formic acid)-acetonitrile]; B %: 55%-85%, 10 min) to give 21.0 mg (14% yield) of 409 as a yellow solid.

LCMS: (ESI) m/z: 448.0 [M+H]$^+$.

$^1$H NMR (400 MHz, MeOD-d$_4$) δ: 7.69 (d, J=8.0 Hz, 2H), 7.62 (s, 1H), 7.54 (d, J=8.4 Hz, 1H), 7.36-7.28 (m, 3H), 7.06 (d, J=8.0 Hz, 1H), 6.90 (t, J=73.6 Hz, 1H), 2.62 (s, 3H), 2.15-2.09 (m, 1H), 1.62 (d, J=22.8 Hz, 3H), 0.97 (d, J=6.8 Hz, 3H), 0.85 (d, J=6.8 Hz, 3H).

Synthesis of 408

Step 1: Synthesis of 4-bromo-2-iodo-6-nitro-aniline (408-A)

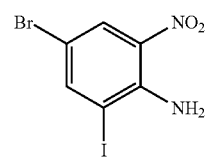 [SMILES: Nc1c(I)cc(Br)cc1[N+](=O)[O-]]

A solution of 4-bromo-2-nitro-aniline (8.00 g, 36.9 mmol, 1.0 eq) in acetic acid (48 mL) was heated to 80° C. Then N-iodosuccinimide (12.4 g, 55.3 mmol, 1.5 eq) was added into the mixture. It was stirred at 80° C. for 2 h. The reaction mixture was quenched with ice-cooled water (100 mL) and neutralized with saturated sodium carbonate (60 mL) solution. The mixture was extracted with ethyl acetate (60 mL×3) and the organic layer was washed with saturated sodium carbonate (100 mL) solution, water (3×100 mL) and brine (100 mL). The organic layer was dried over sodium sulfate, filtered and concentrated to give 14.0 g (crude) of 408-A as a brown solid.

$^1$H NMR: (400 MHz, CDCl$_3$-d) δ: 8.32 (d, J=2.4 Hz, 1H), 8.02 (d, J=2.4 Hz, 1H), 6.68 (br s, 2H).

Step 2: Synthesis of 4-bromo-2-nitro-6-(2-trimethylsilylethynyl)aniline (408-B)

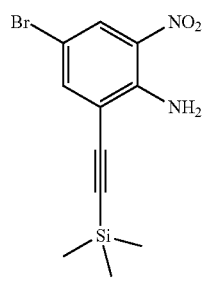 [SMILES: C[Si](C)(C)C#Cc1cc(Br)cc([N+](=O)[O-])c1N]

[1,1-Bis(diphenylphosphino)ferrocene]dichloropalladium (II) (819 mg, 1.17 mmol, 0.050 eq), Copper (I) iodide (222 mg, 1.17 mmol, 0.05 eq) and triethylamine (11.80 g, 117 mmol, 5.0 eq) was added into the solution of 408-A (8.00 g, 23.3 mmol, 1.0 eq) in tetrahydrofuran (80 mL). Then ethynyl(trimethyl)silane (2.75 g, 28.0 mmol, 1.2 eq) was added into the mixture dropwise. It was stirred at 25° C. for 3 h under nitrogen. The two batches were combined, and the reaction mixture was concentrated to give a residue. The residue was purified by column chromatography on silica gel (petroleum ether/ethyl acetate=1/0) to give 8.76 g (crude) of 408-B as a yellow solid.

$^1$H NMR: (400 MHz, CDCl$_3$-d) δ: 8.26 (d, J=2.4 Hz, 1H), 7.65 (d, J=2.4 Hz, 1H), 6.73 (br s, 2H), 0.30 (s, 9H).

Step 3: 5-bromo-7-nitro-1H-indole (408-C)

Potassium tert-butoxide (3.12 g, 27.8 mmol, 2.0 eq) was added into the solution of 408-B (4.35 g, 13.9 mmol, 1.0 eq) in 1-methyl-2-pyrrolidinone (40 mL). It was stirred at 25° C. for 12 h. The reaction was diluted with water (100 mL) and adjusted pH to 7 with hydrochloric acid (1 M). Then the mixture was extracted with ethyl acetic (100 mL×3) and the organic layer was washed with water (300 mL×3) and brine (300 mL). The organic layer was dried over sodium sulfate, filtered and concentrated to obtain 4.36 g (crude) of 408-C as a brown solid.

$^1$H NMR: (400 MHz, DMSO-d$_6$) δ: 12.09 (br s, 1H), 8.29 (d, J=1.2 Hz, 1H), 8.16 (d, J=2.0 Hz, 1H), 7.59 (t, J=2.8 Hz, 1H), 6.73 (dd, J=2.0, 1.2 Hz, 1H).

Step 4: Synthesis of 1-(7-nitro-1H-indol-5-yl)ethanone (408-D)

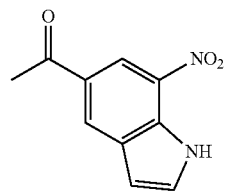

A mixture of 408-C (2.00 g, 8.30 mmol, 1.0 eq), tributyl(1-ethoxyvinyl)stannane (8.99 g, 24.9 mmol, 3.0 eq), tetrakis(triphenylphosphine)palladium(0) (959 mg, 830 umol, 0.10 eq), lithium chloride anhydrous (1.06 g, 24.9 mmol, 3.0 eq) in dioxane (60 mL) was degassed and purged with nitrogen for 3 times, and then the mixture was stirred at 100° C. for 12 h under nitrogen. The reaction mixture was cooled to room temperature. Hydrochloric acid (60 mL, 1 M) was added into the mixture, and stirred for 30 min at 25° C. The mixture was extracted with ethyl acetic (60 mL×3) and the organic layer was washed with water (200 mL×3) and brine (200 mL). The organic layer was dried over sodium sulfate, filtered and concentrated to obtain the residue. The residue was purified by column chromatography on silica gel (petroleum ether/ethyl acetate, from 1/0 to 3/1) to give 1.70 g (85% yield) of 408-D as a brown solid.

$^1$H NMR: (400 MHz, CDCl$_3$-d) δ: 10.15 (br s, 1H), 8.79 (d, J=1.6 Hz, 1H), 8.64 (s, 1H), 7.67-7.65 (m, 1H), 6.86 (dd, J=2.0, 1.2 Hz, 1H), 2.74 (s, 3H).

Step 5: Synthesis of 1-(7-amino-1H-indol-5-yl)ethanone (408-E)

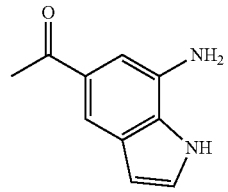

Palladium (20.0 mg, 10% purity on carbon) was added into the solution of 408-D (200 mg, 980 umol, 1.0 eq) in methanol (3 mL). It was stirred at 25° C. for 10 min under hydrogen (15 psi). The slurry was filtered and the filtrate was concentrated under reduced pressure to give 130 mg (65% yield) of 408-E as brown oil.

LCMS: (ESI) m/z: 175.1 [M+H]$^+$.

Step 6: Synthesis of N-(5-acetyl-H-indol-7-yl)-1-[4-(difluoromethoxy)phenyl]-3-methyl-5-oxo-4H-pyrazole-4-carboxamide (408)

Compound ID: 408

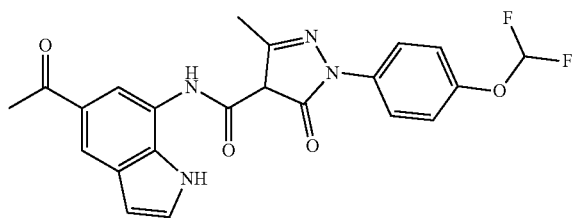 [SMILES: CC(=O)c1cc(NC(=O)C2C(=O)N(c3ccc(OC(F)F)cc3)N=C2C)c2[nH]ccc2c1]

408 was obtained via general procedure IV from 408-E and 298-C.
LCMS: (ESI) m/z: 441.0 [M+H]$^+$.
$^1$H NMR: (400 MHz, MeOD-d$_4$) δ: 8.17 (d, J=1.2 Hz, 1H), 7.92 (d, J=1.2 Hz, 1H), 7.82 (d, J=9.2 Hz, 2H), 7.37 (d, J=2.8 Hz, 1H), 7.26 (d, J=8.8 Hz, 2H), 6.85 (m, 2H), 2.66 (s, 3H), 2.57 (s, 3H).

Synthesis of 407

Step 1: Synthesis of (E)-2-hydroxy-5-nitrobenzaldehyde oxime (407-A)

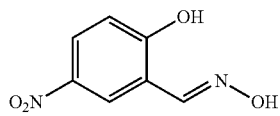 [SMILES: O=[N+]([O-])c1ccc(O)c(/C=N/O)c1]

To a 500 mL round-bottom flask equipped with a magnetic stir bar and a reflux condenser was added 2-hydroxy-5-nitro-benzaldehyde (25.0 g, 150 mmol, 1.0 eq) followed by the addition of ethanol (300 mL). Then hydroxylamine hydrochloride (52.0 g, 748 mmol, 5.0 eq), pyridine (23.7 g, 299 mmol, 2.0 eq) was added into the mixture dropwise at 25° C. The mixture was heated to 60° C. and stirred for 3 hr. The mixture was concentrated under reduced pressure to give a residue. The residue was partitioned between ethyl acetate (1 L) and hydrochloric acid (800 mL, 1 M). The ethyl acetate layer was washed again with hydrochloric acid (400 mL, 1 M), water (2×300 mL), and brine (400 mL), dried over anhydrous sodium sulfate, filtered and concentrated to give 54.9 g (94% yield) of 188-A as a yellow solid.
LCMS: (ESI) m/z: 183.1 [M+H]$^+$.

Step 2: Synthesis of 2-hydroxy-5-nitrobenzonitrile (407-B)

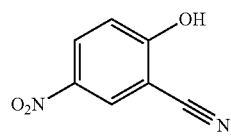 [SMILES: N#Cc1cc([N+](=O)[O-])ccc1O]

To a 1 L round-bottom flask equipped with a magnetic stir bar was added 407-A, triphenylphosphine (83.8 g, 319 mmol, 2.5 eq) followed by the addition of dichloromethane (600 mL). The solution was cooled to 0° C. Next, diisopropyl azodicarboxylate (64.6 g, 319 mmol, 2.5 eq) was added dropwise. The mixture was allowed to warm to 25° C. and stirred for 12 hr. To the mixture was added sodium hydroxide solution (1 M, 2 L). The resulting mixture was transferred to a separatory funnel, the organic layer was washed again with sodium hydroxide (1 M, 500 mL). The pH of combined aqueous layer was adjusted to 3 by hydrochloric acid (6 M). The resulting mixture was extracted with ethyl acetate (700 mL×3). The combined organic layer was washed with brine (600 mL), dried over anhydrous sodium sulfate, filtered, and concentrated under reduced pressure affording 22.0 g (94% yield) of 407-B as a yellow solid.
LCMS: (ESI) m/z: 164.9 [M+H]$^+$.

Step 3: Synthesis of N',2-dihydroxy-5-nitrobenzimidamide (407-C)

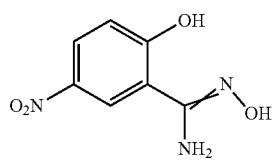 [SMILES: NC(=NO)c1cc([N+](=O)[O-])ccc1O]

To a 50 mL round-bottom flask equipped with a magnetic stir bar and a reflux condenser was added 407-B (15.0 g, 81.9 mmol, 1.0 eq), Hydroxylamine hydrochloride (28.5 g, 410 mmol, 5.0 eq) followed by the addition of ethanol (150 mL). Then a solution of sodium carbonate (43.4 g, 409.55 mmol, 5.0 eq) in water (150 mL) was added into the mixture dropwise at 25° C. The mixture was heated to 75° C. and stirred for 12 hr. The mixture was concentrated under reduced pressure to give a residue. The residue was dissolved in water (1 L) and the pH of the mixture was adjusted to 2 by hydrochloric acid solution (6 M). The mixture was transferred to a separatory funnel, and the aqueous layer mixture was extracted with ethyl acetate (200 mL×2). The combined organic layer was washed with hydrochloric acid solution (2 M, 200 mL), the combined aqueous layer was concentrated under reduced pressure affording a residue. The residue was added to methanol (100 mL), the mixture was filtered, the filtrate was concentrated under reduced pressure to give 28.0 g (crude) of 407-C as a yellow solid.
LCMS: (ESI) m/z: 198.0 [M+H]$^+$.

Step 4: Synthesis of 2-(5-methyl-1,2,4-oxadiazol-3-yl)-4-nitrophenol (407-D)

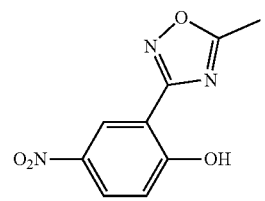 [SMILES: Cc1nc(-c2cc([N+](=O)[O-])ccc2O)no1]

To a 250 mL round-bottom flask equipped with a magnetic stir bar and a reflux condenser was added 407-C (14.0 g, 71.01 mmol, 1.0 eq) followed by the addition of acetic oxide (100 mL). The mixture was heated to 80° C. and stirred for 2 hr. The mixture was concentrated under reduced pressure to give a residue. The residue was dissolved in water (150 mL) and ethyl acetate (50 mL). The mixture was transferred to a separatory funnel, and the aqueous layer mixture was extracted with ethyl acetate (30 mL×2). The combined organic layer was washed with brine, dried over anhydrous sodium sulfate, filtered, and concentrated under reduced pressure affording a residue. The residue was purified by silica gel column chromatography (petroleum ether/ethyl acetate, from 2/1 to 1/2) to give 4.70 g (22% yield) of 407-D as a yellow solid.

LCMS: (ESI) m/z: 222.0 [M+H]$^+$.

Step 5: Synthesis of 3-(2-(difluoromethoxy)-5-nitrophenyl)-5-methyl-1,2,4-oxadiazole (407-E)

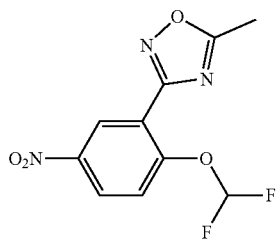 [SMILES: Cc1nc(-c2cc([N+](=O)[O-])ccc2OC(F)F)no1]

To a 250 mL round-bottom flask equipped with a magnetic stir bar was added 407-D (4.50 g, 14.7 mmol, 1.0 eq), sodium carbonate (3.11 g, 29.3 mmol, 2.0 eq) followed by the addition of dimethylformamide (100 mL). Next (2-chloro-2,2-difluoro-acetyl)oxysodium (4.47 g, 29.3 mmol, 2.0 eq) was added into the mixture dropwise at 25° C. The mixture was heated to 100° C. and stirred for 2 hr. The mixture was concentrated under reduced pressure to give a residue. The residue was dissolved in water (100 mL). The mixture was extracted with ethyl acetate (40 mL×3). The combined organic layer was washed with brine (50 mL), dried over anhydrous sodium sulfate, filtered and concentrated to give a residue. The residue was purified by column chromatography on silica gel (petroleum ether/ethyl acetate, 10/1) to give a yellow solid. The solid was dissolved in ethyl acetate (30 mL) and water (30 mL) and the pH of the mixture was adjusted to 9 by sodium hydroxide solution (2 M). The mixture was transferred to a separatory funnel, and the aqueous layer mixture was extracted with ethyl acetate (20 mL×2). The combined organic layer was washed with brine (40 mL), dried over anhydrous sodium sulfate, filtered, and concentrated under reduced pressure affording 1.00 g (24% yield) of 407-E as a yellow solid.

LCMS: (ESI) m/z: 272.0 [M+H]$^+$.

Step 6: Synthesis of 4-(difluoromethoxy)-3-(5-methyl-1,2,4-oxadiazol-3-yl)aniline (407-F)

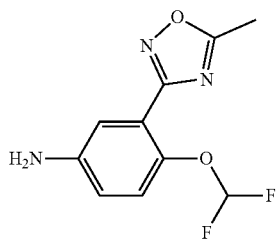 [SMILES: Cc1nc(-c2cc(N)ccc2OC(F)F)no1]

To a 100 ml round-bottom flask equipped with a magnetic stir bar and a reflux condenser was added 407-E (700 mg, 2.49 mmol, 1.0 eq), iron (696 mg, 12.5 mmol, 5.0 eq), ammonium chloride (666 mg, 12.5 mmol, 5.0 eq) followed by the addition of ethanol (20 mL), water (20 mL). The mixture was heated to 50° C. and stirred for 1 hr. The mixture was filtered, the filter cake was washed by ethanol. The filtrate was concentrated under reduced pressure to give a residue. The residue was partitioned between water (30 mL) and ethyl acetate (20 mL). The resulting mixture was transferred to a separatory funnel, and the aqueous layer mixture was extracted with ethyl acetate (20 mL×2). The combined organic layer was washed with brine (3 mL), dried over anhydrous sodium sulfate, filtered, and concentrated under reduced pressure to give 540 mg (87.36% yield) of 407-F as a brown solid.

LCMS: (ESI) m/z: 222.3 [M−F]$^+$.

Step 7: Synthesis of 3-(2-(difluoromethoxy)-5-hydrazinylphenyl)-5-methyl-1,2,4-oxadiazole (407-G)

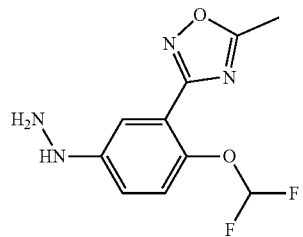 [SMILES: Cc1nc(-c2cc(NN)ccc2OC(F)F)no1]

407-G was obtained via general procedure I from 407-F
LCMS: (ESI) m/z: 257.1 [M+H]$^+$.

Step 8: Synthesis of 1-(4-(difluoromethoxy)-3-(5-methyl-1,2,4-oxadiazol-3-yl)phenyl)-3-methyl-1H-pyrazol-5(4H)-one (407-H)

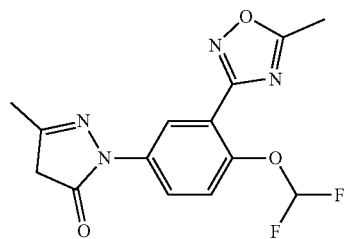 [SMILES: CC1=NN(c2ccc(OC(F)F)c(-c3noc(C)n3)c2)C(=O)C1]

407-H was obtained via general procedure II from 407-G
LCMS: (ESI) m/z: 323.0 [M+H]$^+$.

Step 9: Synthesis of 4-nitrophenyl 1-(4-(difluoromethoxy)-3-(5-methyl-1,2,4-oxadiazol-3-yl)phenyl)-3-methyl-5-oxo-4,5-dihydro-1H-pyrazole-4-carboxylate (407-I)

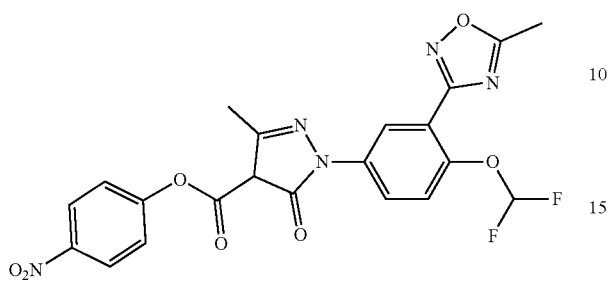

407-I was obtained via general procedure III from 407-H.
LCMS: (ESI) m/z: 488.0 [M+H]+.

Step 10: Synthesis of N-(3-(1,1-difluoroethyl)phenyl)-1-(4-(difluoromethoxy)-3-(5-methyl-1,2,4-oxadiazol-3-yl)phenyl)-3-methyl-5-oxo-4,5-dihydro-1H-pyrazole-4-carboxamide (407)

Compound ID: 407

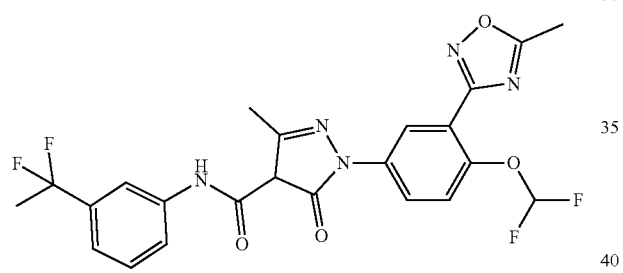

407 was obtained via general procedure IV from 407 and 3-(1,1-difluoroethyl)aniline
LCMS: (ESI) m/z: 506.0 [M+H]+.
$^1$H NMR (400 MHz, MeOD-$d_4$) δ: 8.38 (d, J=2.4 Hz, 1H), 7.92-7.94 (m, 2H), 7.64 (d, J=8.4 Hz, 1H), 7.55 (d, J=8.8 Hz, 1H), 7.41 (t, J=7.6 Hz, 1H), 7.24-7.26 (m, 1H), 6.93 (t, J=74.0 Hz, 1H), 2.67 (d, J=17.6 Hz, 6H), 1.93 (t, J=18.4 Hz, 3H).

Synthesis of 405

Step 1: Synthesis of 1H-benzo[d]imidazol-5-amine (405-A)

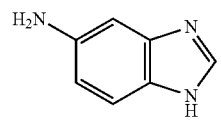

To a 100 mL round-bottom flask equipped with a magnetic stir bar was added 5-nitro-1H-benzimidazole (10.0 g, 61.3 mmol, 1.0 eq) followed by the addition of ethanol (100 mL) and water (20 mL). Then ammonium chloride (16.4 g, 307 mmol, 5.0 eq) and iron powder (17.1 g, 307 mmol, 5.0 eq) were added into the mixture at 25° C. The mixture was stirred at 70° C. for 12 hr. The mixture was filtered and concentrated under reduced pressure to give a yellow solid. The yellow solid was purified by C-18 reversed phase column (ammonium hydroxide) to give 6.20 g (74% yield) of 405-A as a red solid.
LCMS: (ESI) m/z: 134.3 [M+H]+.
$^1$H NMR (400 MHz, DMSO-$d_6$) δ: 8.13 (s, 1H), 7.29 (d, J=8.4 Hz, 1H), 6.71 (d, J=1.6 Hz, 1H), 6.58 (dd, $J_1$, $J_2$=2.0, 8.4 Hz, 1H).

Step 2: Synthesis of 5-hydrazinyl-1H-benzo[d]imidazole (405-B)

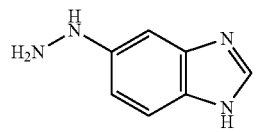 [SMILES: NNc1ccc2[nH]cnc2c1]

405-B was obtained via general procedure I from 405-A
LCMS: (ESI) m/z: 149.1 [M+H]+.

Step 3: Synthesis of 1-(H-benzo[d]imidazol-5-yl)-3-methyl-1H-pyrazol-5(4H)-one (405-C)

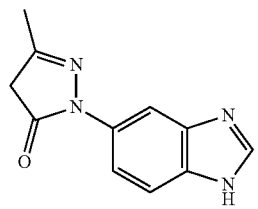 [SMILES: CC1=NN(c2ccc3[nH]cnc3c2)C(=O)C1]

405-C was obtained via general procedure II from 405-B
LCMS: (ESI) m/z: 215.1 [M+H]+.

Step 4: Synthesis of 1-(1,1-difluoroethyl)-3-isocyanatobenzene (405-D)

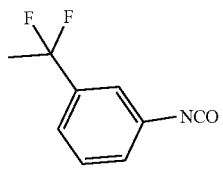

To a suspension of triphosgene (755 mg, 2.55 mmol, 0.40 eq) in dichloromethane (15 mL) was added a solution of 3-(1,1-difluoroethyl)aniline (1.00 g, 6.36 mmol, 1.0 eq) and triethylamine (400 mg, 3.95 mmol, 6.2e-1 eq) in dichloromethane (5 mL) dropwise at 0° C. The mixture was stirred at 0° C. for 1 h to give 1.17 g (92% yield) of 405-D as a brown liquid in dichloromethane (20 mL).

Step 5: Synthesis of 1-(1H-benzo[d]imidazol-5-yl)-N-(3-(1,1-difluoroethyl)phenyl)-3-methyl-5-oxo-4,5-dihydro-1H-pyrazole-4-carboxamide (405)

Compound ID: 405

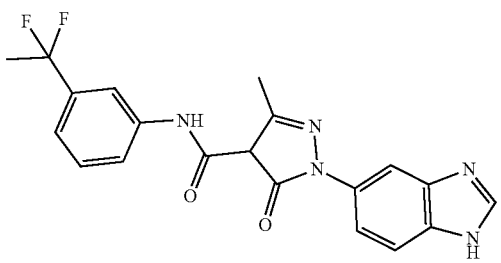 [SMILES: CC1=NN(c2ccc3[nH]cnc3c2)C(=O)C1C(=O)Nc1cccc(C(C)(F)F)c1]

To a 50 mL round-bottom flask equipped with a magnetic stir bar was added 405-C (50.0 mg, 214 umol, 1.0 eq) followed by the addition of dichloromethane (2 mL). Next, 405-D (92.9 mg, 467 umol, 2.2 eq) and N-ethyl-N-isopropylpropan-2-amine (121 mg, 934 umol, 4.4 eq) were added dropwise. The mixture was stirred at 25° C. for 1 hr. The mixture was concentrated under reduced pressure to give a yellow oil. The yellow oil was purified by prep-HPLC (column: Waters Xbridge 150*25 5u; mobile phase: [water (0.05% ammonia hydroxide v/v)-acetonitrile]; B %: 2%-32%, 10 min) to give 1.50 mg (2% yield) of 405 as a yellow oil.

LCMS: (ESI) m/z: 398.3 [M+H]$^+$.

$^1$H NMR (400 MHz, DMSO-d$_6$) δ: 12.23 (br s, 1H), 11.52 (s, 1H), 8.34 (d, J=1.6 Hz, 1H), 8.09 (s, 1H), 8.00-7.91 (m, 2H), 7.58 (br d, J=8.0 Hz, 1H), 7.48 (br d, J=8.8 Hz, 1H), 7.33 (t, J=8.0 Hz, 1H), 7.04 (d, J=7.6 Hz, 1H), 2.27 (s, 3H), 1.95 (t, J=18.8 Hz, 3H).

Synthesis of 404

Step 1: Synthesis of 1-(3-bromophenyl)-3-methyl-1H-pyrazol-5(4H)-one (404-A)

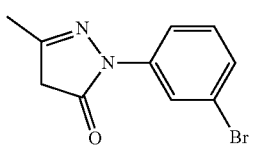

404-A was obtained via general procedure II from (3-bromophenyl)hydrazine
LCMS: (ESI) m/z: 254.0 [M+H]$^+$.

Step 2: Synthesis of 4-nitrophenyl 1-(3-bromophenyl)-3-methyl-5-oxo-4,5-dihydro-1H-pyrazole-4-carboxylate (404-B)

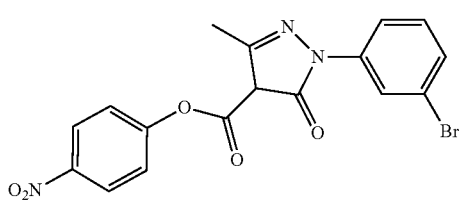 [SMILES: CC1=NN(c2cccc(Br)c2)C(=O)C1C(=O)Oc1ccc([N+](=O)[O-])cc1]

404-B was obtained via general procedure III from 404-A
LCMS: (ESI) m/z: 254.0 [M+H]$^+$.

Step 3: Synthesis of 1-(3-bromophenyl)-N-(3-(1,1-difluoroethyl)phenyl)-3-methyl-5-oxo-4,5-dihydro-1H-pyrazole-4-carboxamide (404)

Compound ID: 404

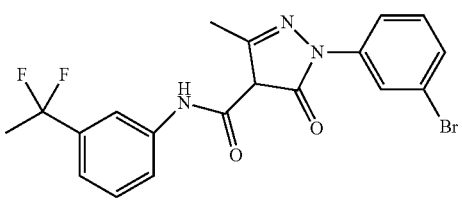 [SMILES: CC1=NN(c2cccc(Br)c2)C(=O)C1C(=O)Nc1cccc(C(C)(F)F)c1]

404 was obtained via general procedure IV from 404-B
LCMS: (ESI) m/z: 438.1 [M+H]$^+$.

$^1$H NMR (400 MHz, MeOD-d$_4$) δ: 7.97 (s, 1H), 7.91 (s, 1H), 7.69 (d, J=7.6 Hz, 1H), 7.62 (d, J=7.6 Hz, 1H), 7.46-7.49 (m, 1H), 7.37-7.43 (m, 2H), 7.23 (d, J=8.0 Hz, 1H), 2.58 (s, 3H), 1.92 (t, J=18.0 Hz, 3H).

Synthesis of 403

Step 1: Synthesis of 5-bromo-2-hydroxy-3-nitro-benzaldehyde (403-A)

To a solution of 5-bromo-2-hydroxy-benzaldehyde (10.0 g, 49.8 mmol, 1.0 eq) in acetic acid (50 mL) was added dropwise nitric acid (4.10 g, 65.1 mmol, 1.3 eq) at 10° C. The mixture was slowly warmed to 25° C. and stirred for 1 h. The mixture was poured into ice water (300 mL) and extracted with ethyl acetate (200 mL×2). The combined organic layer was washed with brine (300 mL), dried over anhydrous sodium sulfate, filtered and concentrated under reduced pressure to give a residue. The residue was triturated with methyl tert-butyl ether (30 mL), the solid was collected and dried in vacuo to give 7.20 g (crude) of 403-A as a yellow solid.

$^1$H NMR: (400 MHz, CDCl$_3$-d) δ: 11.25 (s, 1H), 10.38 (s, 1H), 8.47 (d, J=2.4 Hz, 1H), 8.20 (d, J=2.4 Hz, 1H).

Step 2: Synthesis of ethyl 5-bromo-7-nitro-benzofuran-2-carboxylate (403-B)

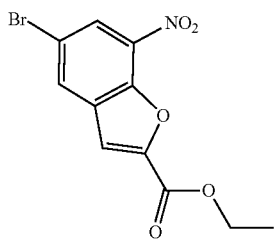 [SMILES: CCOC(=O)c1cc2cc(Br)cc([N+](=O)[O-])c2o1]

To a solution of 403-A (6.80 g, 27.6 mmol, 1.0 eq) in toluene (100 mL) was added diethyl bromomalonate (7.27 g, 30.4 mmol, 5 mL, 1.1 eq), potassium carbonate (5.73 g, 41.5 mmol, 1.5 eq) and tetrabutylammonium bromide (891 mg, 2.76 mmol, 0.10 eq). The mixture was heated 110° C. and stirred for 20 h. The mixture was diluted with water (100 mL) and the pH of mixture was adjusted to 6 by using hydrochloric acid (1 M), then extracted with ethyl acetate (100 mL×3). The combined organic layer was washed with brine (200 mL), dried over anhydrous sodium sulfate, filtered and concentrated under reduced pressure to give a residue. The crude product was purified by silica gel column chromatography (petroleum ether/ethyl acetate, from 100/1 to 5/1) to give 2.00 g (22% yield) of 403-B as a yellow solid.

LCMS: (ESI) m/z: 313.9 [M+H]$^+$.

$^1$H NMR: (400 MHz, CDCl$_3$-d) δ: 8.42 (d, J=1.6 Hz, 1H), 8.15 (d, J=2.0 Hz, 1H), 7.59 (s, 1H), 4.50 (q, J=7.2 Hz, 2H), 1.46 (t, J=7.2 Hz, 3H).

Step 3: Synthesis of 5-bromo-7-nitro-benzofuran-2-carboxylic acid (403-C)

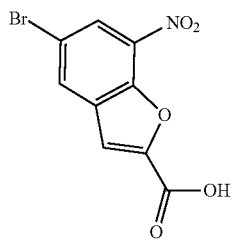 [SMILES: O=C(O)c1cc2cc(Br)cc([N+](=O)[O-])c2o1]

To a solution of 403-B (2.00 g, 5.99 mmol, 1.0 eq) in methyl alcohol (20 mL) was added lithium hydroxide hydrate (802 mg, 19.1 mmol, 3.2 eq), water (20 mL) and tetrahydrofuran (20 mL). The mixture was stirred at 20° C. for 1 h. The mixture was concentrated under reduced pressure dried over, then diluted with water (50 mL) and the pH of mixture was adjusted to 2 by using hydrochloric acid (1 M), next extracted with ethyl acetate (40 mL×3), The combined organic layer was washed with brine (50 mL), dried over anhydrous sodium sulfate, and concentrated under reduced pressure affording 1.60 g (crude) of 403-C as a yellow solid.

LCMS: (ESI) m/z: 286.0 [M+H]$^+$.

Step 4: Synthesis of 5-bromo-7-nitro-benzofuran (403-D)

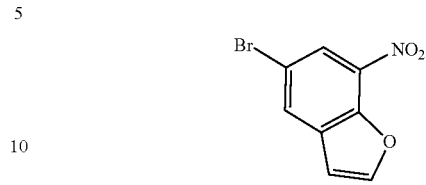

To 403-C (1.60 g, 5.59 mmol, 1.0 eq) were added quinoline (10 mL) and copper powder (389 mg, 6.13 mmol, 1.1 eq). The mixture was stirred at 200° C. for 0.5 hr. The mixture was adjusted with hydrochloric acid (1 M) aqueous to pH=2 and extracted with ethyl acetate (100 mL×2). The combined organic layer was washed with brine (100 mL), dried over anhydrous sodium sulfate, filtered and concentrated under reduced pressure to give a residue. The residue was purified by silica gel column chromatography (petroleum ether/ethyl acetate, from 50/1 to 20/1) to give 1.00 g (74% yield) of 403-D as a brown solid.

$^1$H NMR: (400 MHz, CDCl$_3$-d) δ: 8.30 (d, J=1.6 Hz, 1H), 8.07 (d, J=1.6 Hz, 1H), 7.87 (d, J=2.4 Hz, 1H), 6.91 (d, J=2.0 Hz, 1H).

Step 5: Synthesis of 1-(7-nitrobenzofuran-5-yl)ethanone (403-E)

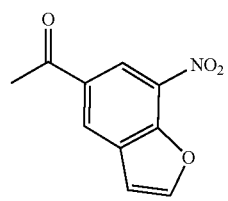

A mixture of 403-D (0.900 g, 3.72 mmol, 1.0 eq), tributyl(1-ethoxyvinyl)stannane (4.03 g, 11.2 mmol, 3.0 eq), tetrakis(triphenylphosphine)platinum (430 mg, 372 umol, 0.10 eq), lithium chloride (473 mg, 11.2 mmol, 3.0 eq) in dioxane (15 mL) was degassed and purged with nitrogen for 3 times, and then the mixture was stirred at 100° C. for 12 hr under nitrogen atmosphere. The reaction mixture was cooled to room temperature. hydrochloric acid (15 ml, 1 M) was added into the mixture, and stirred for 30 min at 20° C. The mixture was extracted with ethyl acetate (15×3 mL) and the combined organic layer were washed with brine (20 mL), then dried over anhydrous sodium sulfate, filtered and concentrated to obtain the residue. The residue was purified by silica gel column chromatography (petroleum ether/ethyl acetate, from 30/1 to 10/1) to give 300 mg (39% yield) of 403-E as a black brown solid.

LCMS: (ESI) m/z: 205.0 [M+H]$^+$.

$^1$H NMR: (400 MHz, CDCl$_3$-d) δ: 8.73 (d, J=1.2 Hz, 1H), 8.53 (d, J=1.6 Hz, 1H), 7.89 (d, J=2.0 Hz, 1H), 7.01 (d, J=2.0 Hz, 1H), 2.70 (s, 3H).

Step 6: Synthesis of 5-(2-methyl-1,3-dithiolan-2-yl)-7-nitro-benzofuran (403-F)

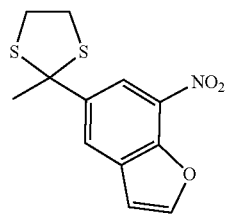 [SMILES: CC1(c2cc([N+](=O)[O-])c3occc3c2)SCCS1]

To a solution of 403-E (200 mg, 975 umol, 1.0 eq) in dichloromethane (10 mL) was added ethane-1,2-dithiol (275 mg, 2.92 mmol, 3.0 eq) and boron trifluoride diethyl etherate (415 mg, 2.92 mmol, 3.0 eq). The mixture was stirred at 20° C. for 12 h. The mixture was concentrated under reduced pressure to give a residue. The residue was purified by silica gel column chromatography (petroleum ether/ethyl acetate, from 30/1 to 10/1) to give 0.100 g (36% yield) of 403-F as a yellow oil.

$^1$H NMR: (400 MHz, CDCl$_3$-d) δ: 8.64 (d, J=1.6 Hz, 1H), 8.37 (d, J=2.0 Hz, 1H), 7.85 (d, J=2.0 Hz, 1H), 6.92 (d, J=2.0 Hz, 1H), 3.57-3.51 (m, 2H), 3.45-3.38 (m, 2H), 2.24 (s, 3H).

Step 7: Synthesis of 5-(1,1-difluoroethyl)-7-nitro-benzofuran (403-G)

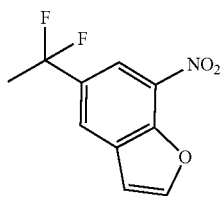 [SMILES: CC(F)(F)c1cc([N+](=O)[O-])c2occc2c1]

To a solution of 1-iodopyrrolidine-2,5-dione (320 mg, 1.42 mmol, 4.0 eq) in dichloromethane (5 mL) was added dropwise pyridine hydrogenfluoride (151 mg, 1.07 mmol, 3.0 eq) at −78° C. under nitrogen atmosphere. After the addition, a solution of 403-F (100 mg, 355 umol, 1.0 eq) in dichloromethane (2 mL) was added dropwise at −78° C. The mixture was stirred at −78° C. for 0.5 hr. The mixture was poured in cool saturated sodium bicarbonate until the pH=7, then extracted with dichloromethane (30 mL×3). The combined organic layer was washed with saturated natrium sulfurosum aqueous (30 mL), dried over anhydrous sodium sulfate, filtered and concentrated under reduced pressure to give 50.0 mg (crude) of 403-G as a yellow solid.

$^1$H NMR: (400 MHz, CDCl$_3$-d) δ: 8.33 (s, 1H), 8.11 (s, 1H), 7.93 (d, J=2.0 Hz, 1H), 7.00 (d, J=2.4 Hz, 1H), 2.03 (t, J=18.0 Hz, 3H).

Step 8: Synthesis of 5-(1,1-difluoroethyl)benzofuran-7-amine (403-H)

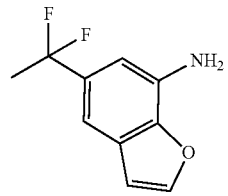

To a solution of 403-G (40.0 mg, 176 umol, 1.0 eq) in ethyl alcohol (2.5 mL) was added a solution of ammonium chloride (47.1 mg, 880 umol, 5.0 eq) in water (0.5 mL), following added iron powder (49.2 mg, 880 umol, 5.0 eq). The mixture was stirred at 80° C. for 1 hr. The mixture was diluted with water (20 mL), and then extracted with ethyl acetate (20 mL×3). The combined organic layer was washed with brine (20 mL), dried over anhydrous sodium sulfate, filtered and concentrated under reduced pressure to give 35.0 mg (crude) of 403-H as a yellow oil.

LCMS: (ESI) m/z: 198.1 [M+H]$^+$.

Step 9: Synthesis of N-[5-(1,1-difluoroethyl)benzofuran-7-yl]-1-[4-(difluoromethoxy)phenyl]-3-methyl-5-oxo-4H-pyrazole-4-carboxamide (403)

Compound ID: 403

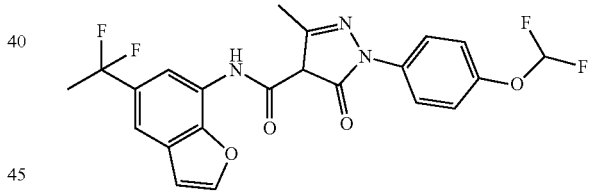

A mixture of 403-H (35 mg, 178 umol, 1.0 eq), 298-C (144 mg, 355 umol, 2.0 eq), hydroxybenzotriazole (28.8 mg, 213 umol, 1.2 eq), triethylamine (53.9 mg, 533 umol, 3.0 eq) in acetonitrile (5 mL) was stirred at 70° C. for 12 hr. The residue was purified by prep-TLC (dichloromethane:methyl alcohol=10:1) to afford 50.0 mg crude product, then purified by prep-HPLC (column: Phenomenex Synergi C 18150*30 mm*4 um; mobile phase: [water (0.225% formic acid)-acetonitrile]; B %: 45%-75%, 10 min), and then freeze-dried to give 13.1 mg (14% yield) of 403 as a pink solid.

LCMS: (ESI) m/z: 464.0 [M+H]$^+$.

$^1$H NMR: (400 MHz, MeOD-d$_4$) δ: 8.49 (s, 1H), 7.86 (J=2.0 Hz, 1H), 7.75 (d, J=8.8 Hz, 2H), 7.51 (s, 1H), 7.29 (d, J=8.8 Hz, 2H), 7.07-6.69 (m, 2H), 2.60 (s, 3H), 1.99 (t, J=18.0 Hz, 3H).

Synthesis of 402

Step 1: Synthesis of 1,3-dibromo-2-methoxy-5-nitrobenzene (402-A)

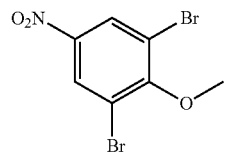

To a 50 mL round-bottom flask equipped with a magnetic stir bar was added 2,6-dibromo-4-nitro-phenol (4.00 g, 13.5 mmol, 1.0 eq) followed by the addition of potassium carbonate (5.59 g, 40.4 mmol, 3.0 eq) and N,N-dimethylformamide (15 mL). Then iodomethane (9.56 g, 67.7 mmol, 5.0 eq) was added into the mixture at 25° C. The mixture was stirred at 25° C. for 10 h. It was quenched with 100 mL of water and stirred for 10 min. The resulting solid was collected with filtration and washed with sodium hydroxide (20 mL, 1 M). The solid was dried in vacuo to afford 2.90 g (69% yield) of 402-A as a yellow solid.

Step 2: Synthesis of 3,5-dibromo-4-methoxyaniline (402-B)

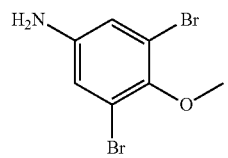

To a solution of 402-A (1.20 g, 3.86 mmol, 1.0 eq) in ethanol (20 mL) and water (1 mL) was added iron powder (2.16 g, 38.6 mmol, 10 eq) and ammonium chloride (2.06 g, 38.6 mmol, 10 eq). The reaction mixture was stirred at 80° C. for 5 h. It was filtered and the filter cake was washed with ethyl acetate (20 mL×2). The combined filtrate was concentrated in vacuo. It was purified by silica gel column chromatography (ethyl acetate/petroleum ether, from 0/1 to 1/1) to afford 0.900 g (82% yield) of 402-B as off-white solid.

LCMS: (ESI) m/z: 281.9 [M+H]$^+$.
$^1$H NMR (400 MHz, CDCl$_3$-d) δ: 6.82 (s, 2H), 3.87 (s, 3H), 3.60 (s, 2H).

Step 3: Synthesis of (3,5-dibromo-4-methoxyphenyl)hydrazine (402-C)

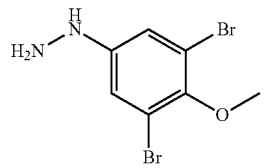

402-C was obtained via general procedure I from 402-B
LCMS: (ESI) m/z: 296.8 [M+H]$^+$.

Step 4: Synthesis of 1-(3,5-dibromo-4-methoxyphenyl)-3-methyl-1H-pyrazol-5(4H)-one (402-D)

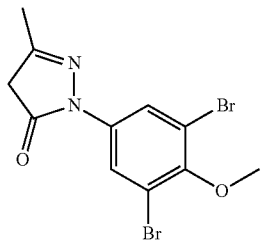 [SMILES: COc1c(Br)cc(N2N=C(C)CC2=O)cc1Br]

402-D was obtained via general procedure II from 402-C
$^1$H NMR (400 MHz, DMSO-d$_6$) δ: 8.00 (s, 2H), 5.37 (s, 1H), 3.80 (s, 3H), 2.11 (s, 3H).

Step 5: Synthesis of 4-nitrophenyl 1-(3,5-dibromo-4-methoxyphenyl)-3-methyl-5-oxo-4,5-dihydro-1H-pyrazole-4-carboxylate (402-E)

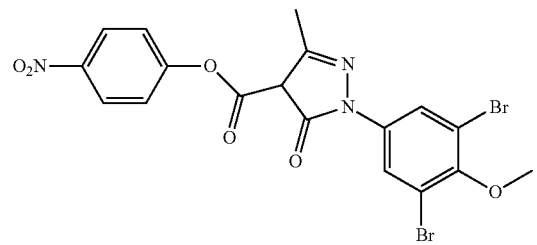 [SMILES: COc1c(Br)cc(N2N=C(C)C(C(=O)Oc3ccc([N+](=O)[O-])cc3)C2=O)cc1Br]

402-E was obtained via general procedure III from 402-D
LCMS: (ESI) m/z: 527.8 [M+H]$^+$.

Step 6: Synthesis of 1-(3,5-dibromo-4-methoxyphenyl)-N-(3-(1,1-difluoroethyl)phenyl)-3-methyl-5-oxo-4,5-dihydro-1H-pyrazole-4-carboxamide (402-F)

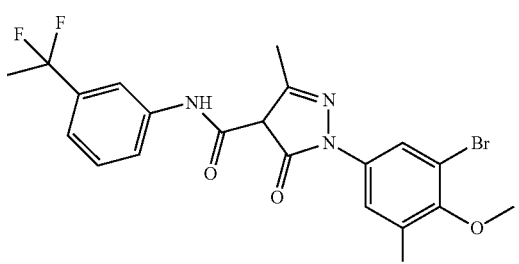

402-F was obtained via general procedure IV from 402-E and 3-(1,1-difluoroethyl)aniline
LCMS: (ESI) m/z: 546.1 [M+H]$^+$.

Step 7: Synthesis of N-(3-(1,1-difluoroethyl)phenyl)-1-(2'-methoxy-[1,1':3',1''-terphenyl]-5'-yl)-3-methyl-5-oxo-4,5-dihydro-1H-pyrazole-4-carboxamide (402)

Compound ID: 402

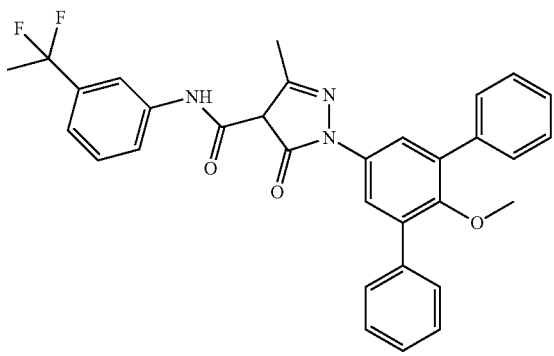 [SMILES: COc1c(-c2ccccc2)cc(N2N=C(C)C(C(=O)Nc3cccc(C(C)(F)F)c3)C2=O)cc1-c1ccccc1]

To a solution of phenylboronic acid (19.1 mg, 156 umol, 2.5 eq), 402-F (0.0350 g, 62.6 umol, 1.0 eq) and sodium bicarbonate (26.3 mg, 313 umol, 5.0 eq) in water (1 mL) and dioxane (4 mL) was added cyclopentyl(diphenyl)phosphane; dichloropalladium; iron (4.58 mg, 6.26 umol, 0.10 eq) under nitrogen. The reaction mixture was stirred at 80° C. for 10 h. The reaction was diluted with 5 mL of water, extracted with ethyl acetate (10 mL×3). The combined organic layer was concentrated in vacuo. The residue was purified by prep-TLC (ethyl acetate) to afford an impure product, and further purified by prep-HPLC column: Phenomenex Synergi C18 150*25*10 um; mobile phase: [water (0.1% trifluoroacetic acid)-acetonitrile]; B %: 70%-90%, 10 min to afford 8.10 mg (11% yield) of 402 as pink solid.

LCMS: (ESI) m/z: 540.3 [M+H]$^+$.

$^1$H NMR (400 MHz, MeOD-d$_4$) δ: 7.94 (s, 1H), 7.73-7.65 (m, 7H), 7.52-7.47 (m, 4H), 7.45-7.40 (m, 3H), 7.27 (br d, J=7.6 Hz, 1H), 3.18 (s, 3H), 2.65 (s, 3H), 1.97 (t, J=7.6 Hz, 3H).

Synthesis of 398

Step 1: Synthesis of N-(3-(1,1-difluoroethyl)phenyl)-1-(4-(difluoromethoxy)phenyl)-N,3-dimethyl-5-oxo-4,5-dihydro-1H-pyrazole-4-carboxamide (398)

Compound ID: 398

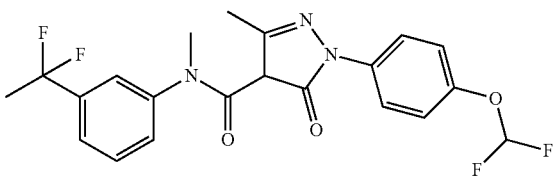 [SMILES: CC1=NN(c2ccc(OC(F)F)cc2)C(=O)C1C(=O)N(C)c1cccc(C(C)(F)F)c1]

To a solution of 298 (200 mg, 472 umol, 1.0 eq) in tetrahydrofuran (5 mL) was added tetra-butyl ammonium fluoride (1 M in tetrahydrofuran, 567 uL, 1.2 eq) and iodomethane (100 mg, 708 umol, 1.5 eq). The mixture was stirred at 25° C. for 12 h. The mixture was concentrated. The residue was purified by prep-TLC (petroleum ether/ethyl acetate, 3/1) to give 14.3 mg (7% yield) of 398 as white solid.

LCMS: (ESI) m/z: 438.2 [M+H]$^+$.

$^1$H NMR: (400 MHz, MeOD-d$_4$) δ: 7.88 (s, 1H), 7.59 (d, J=8.0 Hz, 1H), 7.50 (d, J=8.8 Hz, 2H), 7.42-7.36 (m, 3H), 7.24 (d, J=8.0 Hz, 1H), 6.98 (t, J=73.6 Hz, 1H), 3.41 (s, 3H), 2.76 (s, 3H), 1.91 (t, J=18.4 Hz, 3H).

Synthesis of 397

Step 1: Synthesis of methyl 5-acetyl-2-methyl-3-nitrobenzoate (397-A)

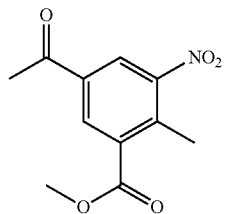 [SMILES: COC(=O)c1cc(C(C)=O)cc([N+](=O)[O-])c1C]

A mixture of methyl methyl 5-bromo-2-methyl-3-nitrobenzoate (5.74 g, 20.9 mmol, 1.0 eq), tributyl(1-ethoxyvinyl)stannane (15.1 g, 41.89 mmol, 2.0 eq), tetrakis(triphenylphosphine)platinum (1.21 g, 1.05 mmol, 0.050 eq), and lithium chloride (2.66 g, 62.8 mmol, 3.0 eq) in dioxane (70 mL) was degassed and purged with nitrogen for 3 times, and then the mixture was stirred at 100° C. for 12 hr under nitrogen atmosphere. The reaction mixture was cooled to room temperature. Hydrochloric acid (70 ml, 1 M) was added into the mixture, and stirred for 30 min at 25° C. The mixture was extracted with ethyl acetate (60 ml×2). The organic layer was washed with the saturation of potassium fluoride (100 mL) and brine (100 mL). The organic layer was dried over anhydrous sodium sulfate, filtered and concentrated to give 7.70 g (crude) of 397-A as a brown solid.

$^1$H NMR (400 MHz, CDCl$_3$-d) δ: 8.55 (d, J=1.6 Hz, 1H), 8.39 (d, J=1.6 Hz, 1H), 3.99 (s, 3H), 2.70 (s, 3H), 2.67 (s, 3H).

Step 2: Synthesis of methyl 2-methyl-5-(2-methyl-1,3-dithiolan-2-yl)-3-nitrobenzoate (397-B)

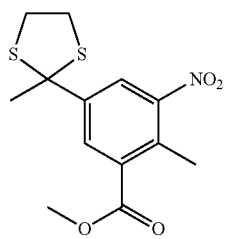 [SMILES: COC(=O)c1cc(C2(C)SCCS2)cc([N+](=O)[O-])c1C]

397-A (7.70 g, 32.5 mmol, 1.0 eq) and ethane-1,2-dithiol (9.17 g, 97.4 mmol, 3.0 eq) was dissolved in dichloromethane (70 mL). Boron trifluoride etherate (13.8 g, 97.4 mmol, 3.0 eq) was added into the mixture. It was stirred at 25° C. for 5 hr. The reaction was quenched with water (70 mL) and extracted with dichloromethane (50 mL×2). The organic layer was washed with water (100 mL×3) and brine (100 mL). The organic layer was dried over anhydrous sodium sulfate, filtered and concentrated to obtain the crude product. The residue was purified by silica gel column chromatography (petroleum ether/ethyl acetate, from 1/0 to 10/1) to give 9.00 g (crude) of 397-B as a white solid.

$^1$H NMR (400 MHz, CDCl$_3$-d) δ: 8.36 (d, J=2.0 Hz, 1H), 8.28 (d, J=2.0 Hz, 1H), 3.96 (s, 3H), 3.54-3.48 (m, 2H), 3.38-3.34 (m, 2H), 2.60 (s, 3H), 2.15 (s, 3H).

Step 3: Synthesis of methyl 5-(1,1-difluoroethyl)-2-methyl-3-nitrobenzoate (397-C)

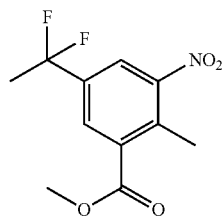 [SMILES: COC(=O)c1cc(C(C)(F)F)cc([N+](=O)[O-])c1C]

1-iodopyrrolidine-2,5-dione (20.1 g, 89.4 mmol, 4.0 eq) was dissolved in dichloromethane (50 mL) at −78° C. Hydrogen fluoride-pyridine (9.49 g, 67.01 mmol, 8.62 mL, 3.0 eq) was added into the solution of 397-B (7.00 g, 22.3 mmol, 1.0 eq) in dichloromethane (30 mL) was added into the mixture. It was stirred at −78° C. for 1 hr. The reaction was quenched with the saturation of sodium sulfite (100 mL). The mixture was extracted with ethyl acetate (50 mL×2) and the organic layer was washed with water (100 mL×3) and brine (100 mL). The organic layer was dried over anhydrous sodium sulfate, filtered and concentrated to obtain a residue. The residue was purified by silica gel column chromatography (petroleum ether/ethyl acetate, from 1/0 to 10/1) to give 2.30 g (crude) of 397-C as a colorless oil.

$^1$H NMR (400 MHz, CDCl$_3$-d) δ: 8.13 (s, 1H), 7.99 (d, J=1.2 Hz, 1H), 3.98 (s, 3H), 2.67 (s, 3H), 1.97 (t, J=18.4 Hz, 3H).

Step 4: Synthesis of methyl 2-(bromomethyl)-5-(1,1-difluoroethyl)-3-nitrobenzoate (397-D)

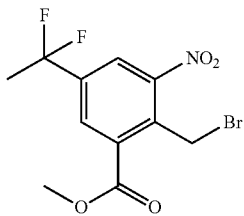 [SMILES: COC(=O)c1cc(C(C)(F)F)cc([N+](=O)[O-])c1CBr]

1-bromopyrrolidine-2,5-dione (1.81 g, 10.2 mmol, 1.2 eq) was added into the solution of 397-C (2.20 g, 8.49 mmol, 1.0 eq) in carbon tetrachloride (20 mL). benzoyl peroxide (206 mg, 849 umol, 0.10 eq) was added into the mixture. It was stirred at 80° C. for 12 hr under nitrogen atmosphere. 1-bromopyrrolidine-2,5-dione (906 mg, 5.09 mmol, 0.60 eq) and benzoyl peroxide (103 mg, 424 umol, 0.050 eq) was added into the mixture. It was stirred at 80° C. for 5 hr under nitrogen atmosphere. The reaction mixture was filtered to give the filtrate. Then it was concentrated to give 3.40 g (crude) of 397-D as a yellow oil.

$^1$H NMR (400 MHz, CDCl$_3$-d) δ: 8.22 (d, J=1.2 Hz, 1H), 8.10 (s, 1H), 5.17 (s, 2H), 4.03 (s, 3H), 1.98 (t, J=18.4 Hz, 3H).

Step 5: Synthesis of 6-(1,1-difluoroethyl)-4-nitroisobenzofuran-1(3H)-one (397-E)

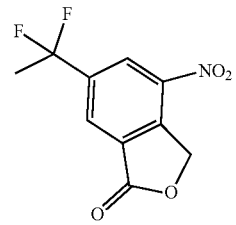 [SMILES: CC(F)(F)c1cc2c(c([N+](=O)[O-])c1)COC2=O]

397-D (3.40 g, 10.1 mmol, 1.0 eq) was dissolved in dioxane (150 mL) and water (150 mL). It was stirred at 100° C. for 5 hr. The reaction mixture was concentrated to remove dioxane. Then the residue aqueous was extracted with ethyl acetate (50 mL×2) and the organic layer washed with water (100 mL×2) and brine (100 mL). The organic layer was dried over anhydrous sodium sulfate, filtered and concentrated to obtain the residue. The residue was purified by silica gel column chromatography (petroleum ether/ethyl acetate=1/0 to 5/1) to give 1.50 g (crude) of 397-E as a white solid.

$^1$H NMR (400 MHz, CDCl$_3$-d) δ: 8.67 (s, 1H), 8.41 (s, 1H), 5.80 (s, 2H), 2.05 (t, J=18.0 Hz, 3H).

Step 6: Synthesis of 6-(1,1-difluoroethyl)-4-nitro-1,3-dihydroisobenzofuran-1-ol (397-F)

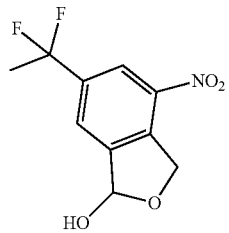 [SMILES: CC(F)(F)c1cc2c(c([N+](=O)[O-])c1)COC2O]

Diisobutylaluminum hydride (1 M, 8.22 mL, 2.0 eq) was added into the solution of 397-E (1.00 g, 4.11 mmol, 1.0 eq) in dichloromethane (10 mL) at −78° C. under nitrogen. It was stirred at −78° C. for 2 h. The reaction mixture was added into the ice saturation of ammonium chloride (10 mL). It was extracted with dichloromethane (10 mL) and the organic layer was washed with water (20 mL×3) and brine (20 mL). The organic layer was dried over anhydrous sodium sulfate, filtered and concentrated to give 750 mg (crude) of 397-F as a yellow solid.

$^1$H NMR (400 MHz, CDCl$_3$-d) δ: 8.41 (s, 1H), 7.93 (s, 1H), 6.63 (br s, 1H), 5.68 (d, J=16.0 Hz, 1H), 5.51 (d, J=16.0 Hz, 1H), 3.25 (br s, 1H), 2.01 (t, J=18.0 Hz, 3H).

Step 7: Synthesis of 6-(1,1-difluoroethyl)-4-nitro-1, 3-dihydroisobenzofuran-1-yl 2,2,2-trifluoroacetate (397-G)

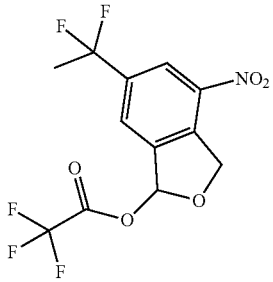 [SMILES: CC(F)(F)c1cc2c(c([N+](=O)[O-])c1)COC2OC(=O)C(F)(F)F]

To a solution of 397-F (750 mg, 3.06 mmol, 1.0 eq) in dichloromethane (7 mL) was added triethylsilane (925 mg, 7.95 mmol, 2.6 eq) and trifluoroacetic acid (384 mg, 3.36 mmol, 1.1 eq) at 0° C. The reaction was stirred at 25° C. for 2 h. The reaction was quenched with the saturation of sodium bicarbonate (30 mL). The mixture was extracted with dichloromethane (30 mL×2) and the organic layer was washed with water (100 mL×3) and brine (100 mL). The organic layer was dried over anhydrous sodium sulfate, filtered and concentrated to obtain the crude product. The residue was purified by silica gel column chromatography (petroleum ether/ethyl acetate=1/0 to 10/1) to give 170 mg (crude) of 397-G as a yellow solid.

$^1$H NMR (400 MHz, CDCl$_3$-d) δ: 8.39 (s, 1H), 7.88 (s, 1H), 6.79 (d, J=1.6 Hz, 1H), 5.73-5.58 (m, 2H), 1.97 (t, J=18.4 Hz, 3H).

Step 8: Synthesis of 6-(1,1-difluoroethyl)-4-nitro-1, 3-dihydroisobenzofuran-1-ol (397-H)

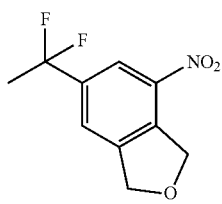 [SMILES: CC(F)(F)c1cc2c(c([N+](=O)[O-])c1)COC2]

To a solution of 397-G (140 mg, 410 umol, 1.0 eq) in dichloromethane (5 mL) was added triethylsilane (124 mg, 1.07 mmol, 2.6 eq) and trifluoroacetic acid (51.5 mg, 451 umol, 1.1 eq) at 0° C. The reaction was stirred at 25° C. for 12 h. The reaction was quenched with the saturation of sodium bicarbonate (20 mL). The mixture was extracted with dichloromethane (20 mL×2) and the organic layer was washed with water (50 mL×3) and brine (50 mL). The organic layer was dried over anhydrous sodium sulfate, filtered and concentrated to give 110 mg (crude) of 397-H as a yellow solid.

$^1$H NMR (400 MHz, CDCl$_3$-d) δ: 8.29 (s, 1H), 7.71 (s, 1H), 5.56 (s, 2H), 5.23 (s, 2H), 1.99 (t, J=18.0 Hz, 3H).

Step 9: Synthesis of 6-(1,1-difluoroethyl)-1,3-dihydroisobenzofuran-4-amine (397-I)

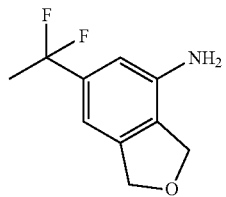

Pd/C (8 mg, 10% purity) was added into the solution of 397-H (80.0 mg, 349 umol, 1.0 eq) in methanol (8 mL). It was stirred at 25° C. for 1 h under hydrogen (15 psi). The slurry was filtered and the filtrate was concentrated under reduced pressure to give 70.0 mg (crude) of 397-I as a white solid.

LCMS: (ESI) m/z: 200.0 [M+H]$^+$.

Step 10: Synthesis of N-(6-(1,1-difluoroethyl)-1,3-dihydroisobenzofuran-4-yl)-1-(4-(difluoromethoxy)phenyl)-3-methyl-5-oxo-4,5-dihydro-1H-pyrazole-4-carboxamide (397)

Compound ID: 397

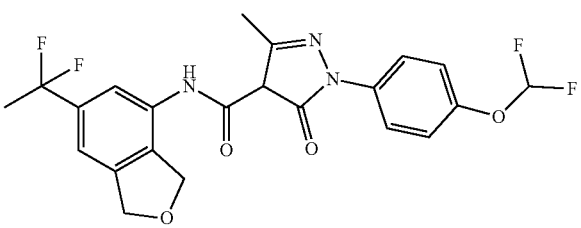 [SMILES: CC1=NN(c2ccc(OC(F)F)cc2)C(=O)C1C(=O)Nc1cc(C(C)(F)F)cc2c1COC2]

397 was obtained via general procedure IV from 298-C and 397-G

LCMS: (ESI) m/z: 466.2 [M+H]$^+$.

$^1$H NMR (400 MHz, MeOD-d$_4$) δ: 8.28 (s, 1H), 7.71 (d, J=8.0 Hz, 2H), 7.30 (d, J=8.0 Hz, 2H), 7.18 (s, 1H), 6.88 (t, J=76 Hz, 1H), 5.16 (s, 2H), 5.13 (s, 2H), 2.59 (s, 3H), 1.94 (t, J=18.4 Hz, 3H).

Synthesis of 396

Step 1: Synthesis of 3-bromo-4-methoxyaniline (396-A)

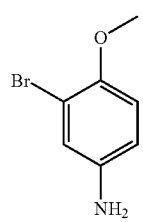

To a solution of 2-bromo-1-methoxy-4-nitro-benzene (1.00 g, 4.31 mmol, 1.0 eq) in ethanol (10 mL)/water (2 mL) was added iron powder (2.41 g, 43.1 mmol, 10 eq) and ammonium chloride (2.31 g, 43.1 mmol, 10 eq), the mixture was stirred at 80° C. for 2 h. The suspension was filtered and the filtrated was concentrated. The residue was purified by silica gel column chromatography (petroleum ether/ethyl acetate, from 5/1 to 2/1) to give 700 mg (78% yield) of 396-A as a brown solid.

LCMS: (ESI) m/z: 204.2 [M+H]⁺.

Step 2: Synthesis of (3-bromo-4-methoxyphenyl)hydrazine (396-B)

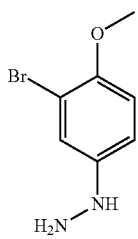

396-B was obtained via general procedure I from 396-A.
LCMS: (ESI) m/z: 201.9 [M-NH]⁺.
¹H NMR: (400 MHz, DMSO-d₆) δ: 10.20 (brs, 2H), 7.31 (s, 1H), 7.07-7.02 (m, 2H), 3.77 (s, 3H).

Step 3: Synthesis of 1-(3-bromo-4-methoxyphenyl)-3-methyl-1H-pyrazol-5(4H)-one (396-C)

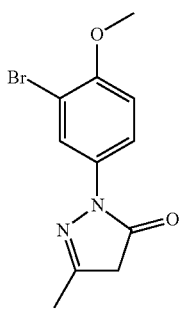

396-C was obtained via general procedure II from 396-B.
LCMS: (ESI) m/z: 282.9 [M+H]⁺.

Step 4: Synthesis of 4-nitrophenyl 1-(3-bromo-4-methoxyphenyl)-3-methyl-5-oxo-4,5-dihydro-1H-pyrazole-4-carboxylate (396-D)

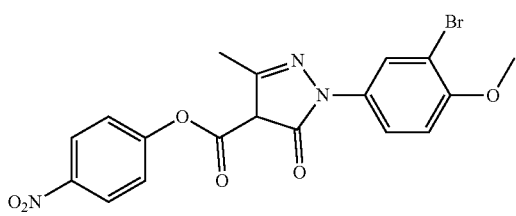 [SMILES: COc1ccc(N2N=C(C)C(C(=O)Oc3ccc([N+](=O)[O-])cc3)C2=O)cc1Br]

396-D was obtained via general procedure III from 396-C.
LCMS: (ESI) m/z: 448.0 [M+H]⁺.

Step 5: Synthesis of 1-(3-bromo-4-methoxyphenyl)-N-(3-(1,1-difluoroethyl)phenyl)-3-methyl-5-oxo-4,5-dihydro-1H-pyrazole-4-carboxamide (396-E)

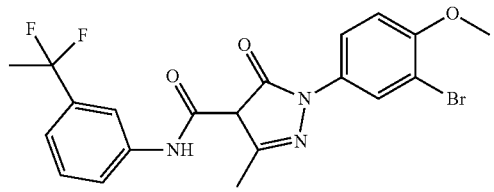 [SMILES: COc1ccc(N2N=C(C)C(C(=O)Nc3cccc(C(C)(F)F)c3)C2=O)cc1Br]

396-E was obtained via general procedure IV from 396-D and 3-(1,1-difluoroethyl)aniline.
LCMS: (ESI) m/z: 466.2 [M+H]⁺.

Step 6: Synthesis of N-[3-(1,1-difluoroethyl)phenyl]-1-(4-methoxy-3-methyl-5-phenyl-phenyl)-3-methyl-5-oxo-4H-pyrazole-4-carboxamide (396)

Compound ID: 396

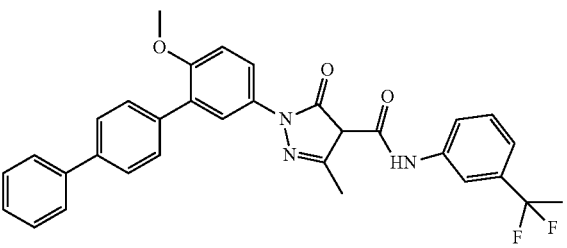 [SMILES: COc1ccc(N2N=C(C)C(C(=O)Nc3cccc(C(C)(F)F)c3)C2=O)cc1-c1ccc(-c2ccccc2)cc1]

To a solution of 396-E (100 mg, 214 umol, 1.0 eq) and (4-phenylphenyl)boronic acid (84.9 mg, 429 umol, 2.0 eq) in dioxane (5 mL)/water (2 mL) was added 1,1-bis(diphenylphosphino)ferrocene-palladium(II)dichloride dichloromethane complex (17.5 mg, 21.5 umol, 0.10 eq) and sodium bicarbonate (36.0 mg, 429 umol, 2.0 eq). The suspension was degassed under vacuum and purged with nitrogen several times. The mixture was stirred under nitrogen at 80° C. for 2 h. The solution was poured into water (10 mL), extracted with ethyl acetate (10 mL×3). The combined organic phase was washed with brine (20 mL), dried with anhydrous sodium sulfate, filtered and concentrated. The residue was purified by silica column (petroleum ether/ethyl acetate, from 2/1 to 1/1) to afford the crude product. The crude product was purified by preparative HPLC (column: Phenomenex Synergi C18 150*30 mm*4 um; mobile phase: [water (0.225% formic acid)-acetonitrile]; B %: 60%-90%, 12 min) to give 44.7 mg (38% yield) of 396 as a white solid.

LCMS: (ESI) m/z: 540.3 [M+H]⁺.
¹H NMR: (400 MHz, DMSO-d₆) δ: 10.91 (s, 1H), 7.94 (s, 1H), 7.77-7.71 (m, 6H), 7.66-7.63 (m, 3H), 7.50 (t, J=7.6 Hz, 2H), 7.44-7.39 (m, 2H), 7.28 (d, J=9.6 Hz, 1H), 7.20 (d, J=7.6 Hz, 1H), 3.85 (s, 3H), 2.54 (s, 3H), 1.96 (t, J=18.8 Hz, 3H).

Synthesis of 393

Step 1: Synthesis of N-(3-chloro-5-methyl-phenyl)-1-[4-(difluoromethoxy)phenyl]-3-methyl-5-oxo-4H-pyrazole-4-carboxamide (393-A)

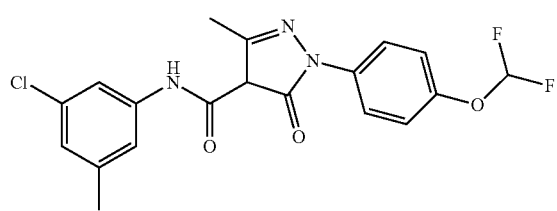 [SMILES: CC1=NN(c2ccc(OC(F)F)cc2)C(=O)C1C(=O)Nc1cc(C)cc(Cl)c1]

393-A was obtained via general procedure IV from 298-C and 3-chloro-5-methylaniline.
LCMS: (ESI) m/z: 408.1 [M+H]$^+$.

Step 2: Synthesis of N-(3-chloro-5-methyl-phenyl)-1-[4-(difluoromethoxy)phenyl]-N,3-dimethyl-5-oxo-4H-pyrazole-4-carboxamide (393)

Compound ID: 393

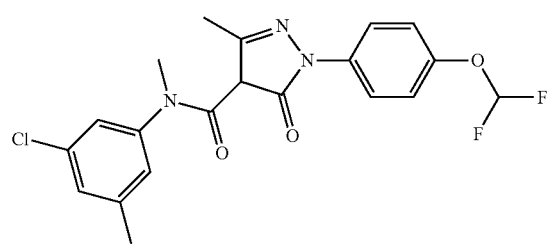 [SMILES: CC1=NN(c2ccc(OC(F)F)cc2)C(=O)C1C(=O)N(C)c1cc(C)cc(Cl)c1]

393 was obtained via similar procedure of 395 from 393-A and iodomethane
LCMS: (ESI) m/z: 422.2 [M+H]$^+$.
$^1$H NMR (400 MHz, MeOD-d$_4$) δ: 7.65 (s, 1H), 7.50 (d, J=8.8 Hz, 2H), 7.38 (d, J=8.8 Hz, 2H), 7.19 (s, 1H), 6.97 (t, J=73.2 Hz, 1H), 6.92 (s, 1H), 3.41 (s, 3H), 2.74 (s, 3H), 2.31 (s, 3H)

Synthesis of 392

Step 1: Synthesis of N-(3-chloro-5-methoxy-phenyl)-1-[4-(difluoromethoxy)phenyl]-3-methyl-5-oxo-4H-pyrazole-4-carboxamide (392-A)

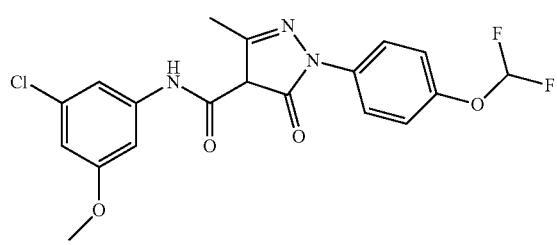 [SMILES: COc1cc(Cl)cc(NC(=O)C2C(=O)N(c3ccc(OC(F)F)cc3)N=C2C)c1]

392-A was obtained via general procedure IV from 298-C and 3-chloro-5-methoxyaniline.
LCMS: (ESI) m/z: 424.1 [M+H]$^+$.

Step 2: Synthesis of N-(3-chloro-5-methoxy-phenyl)-1-[4-(difluoromethoxy)phenyl]-N,3-dimethyl-5-oxo-4H-pyrazole-4-carboxamide (392)

Compound ID: 392

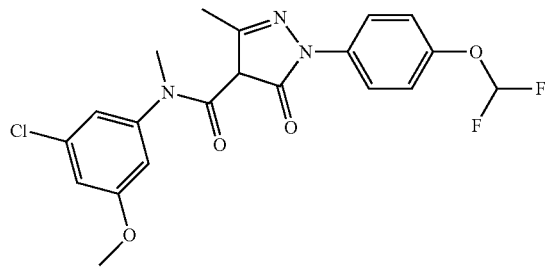 [SMILES: COc1cc(Cl)cc(N(C)C(=O)C2C(=O)N(c3ccc(OC(F)F)cc3)N=C2C)c1]

392 was obtained via similar procedure of 395 from 392-A and iodomethane
LCMS: (ESI) m/z: 438.2 [M+H]$^+$.
$^1$H NMR (400 MHz, MeOD-d$_4$) δ: 7.49 (d, J=8.8 Hz, 2H), 7.38 (d, J=8.8 Hz, 2H), 7.28 (t, J=2.0 Hz, 1H), 7.16 (s, 1H), 6.97 (t, J=73.2 Hz, 1H), 6.67 (t, J=2.0 Hz, 1H), 3.79 (s, 3H), 3.41 (s, 3H), 2.74 (s, 3H).

Synthesis of 391

Step 1: Synthesis of N-(3,5-dichloro-4-fluoro-phenyl)-1-[4-(difluoromethoxy)phenyl]-N,3-dimethyl-5-oxo-4H-pyrazole-4-carboxamide (391)

Compound ID: 391

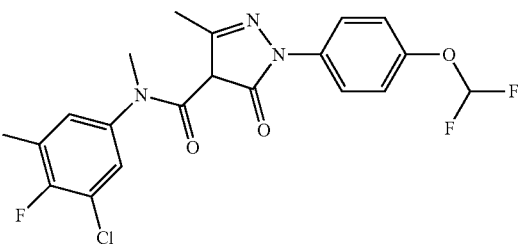

391 was obtained via similar procedure of 395.
LCMS: (ESI) m/z: 460.1 [M+H]$^+$.
$^1$H NMR (400 MHz, MeOD-d$_4$) δ: 7.77 (s, 1H), 7.76 (s, 1H), 7.49 (d, J=8.8 Hz, 2H), 7.38 (d, J=9.2 Hz, 2H), 6.97 (t, J=73.6 Hz, 1H), 3.41 (s, 3H), 2.74 (s, 3H).

Synthesis of 385

Step 1: Synthesis of methyl 2-methoxy-5-nitrobenzoate (385-A)

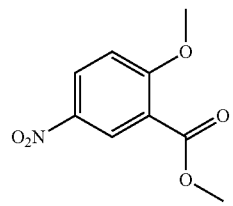

To a solution of 2-hydroxy-5-nitro-benzoic acid (25.5 g, 139 mmol, 1.0 eq) in N,N-dimethylformide (150 mL) was added potassium carbonate (48.1 g, 348 mmol, 2.5 eq) followed by iodomethane (79.1 g, 557 mmol, 4.0 eq). The solution was stirred at 60° C. for 2 h. The solution was filtered and the filtrate was concentrated. The residue was partitioned between ethyl acetate (500 mL) and water (300 mL). The aqueous layer was extracted with ethyl acetate (100 mL×2). The combined organic layer was washed with brine (300 mL), dried over sodium sulfate, filtered and concentrated to give 30.0 g (crude) of 385-A as a yellow solid.

$^1$H NMR: (400 MHz, MeOD-$d_4$) δ: 8.70 (d, J=2.8 Hz, 1H), 8.37 (dd, J=2.8, 9.2 Hz, 1H), 7.07 (d, J=9.2 Hz, 1H), 4.03 (s, 3H), 3.94 (s, 3H).

Step 2: Synthesis of 2-methoxy-5-nitrobenzohydrazide (385-B)

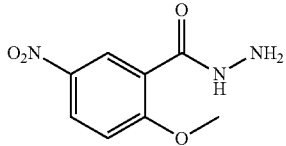

To a solution of 385-A (15.0 g, 71.0 mmol, 1.0 eq) in methanol (100 mL) was added hydrazine (5.81 g, 177 mmol, 2.5 eq). The solution was stirred at 70° C. for 1 h. The solution was concentrated. The residue was triturated with methanol (20 mL) to give 11.5 g (72% yield) of 385-B as a brown solid.

LCMS: (ESI) m/z: 212.2 [M+H]$^+$.
$^1$H NMR: (400 MHz, DMSO-$d_6$) δ: 9.47 (br s, 1H), 8.43 (d, J=2.8 Hz, 1H), 8.34 (dd, J=2.8, 9.2 Hz, 1H), 7.35 (d, J=9.2 Hz, 1H), 4.62 (br s, 2H), 3.99 (s, 3H).

Step 3: Synthesis of 3-(2-methoxy-5-nitrophenyl)-5-methyl-4H-1,2,4-triazole (385-C)

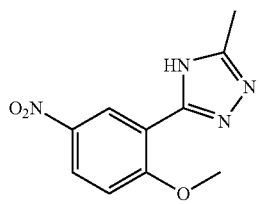 [SMILES: COc1ccc([N+](=O)[O-])cc1-c1nnc(C)[nH]1]

To a solution of acetamidine; hydrochloride (5.37 g, 56.8 mmol, 1.5 eq) in methanol (70 mL) was added sodium methanolate (5 M, 12 mL, 1.6 eq). The solution was stirred at 20° C. for 30 min, and then a solution of 385-B (8.5 g, 37.9 mmol, 1.0 eq) in methanol (70 mL) was added. The resulting solution was stirred at 20° C. for 12 h. Then the solution was heated to 75° C. for 12 h. The solution was poured into water (200 mL) and the mixture was adjusted to pH=5 by addition of aqueous concentrated hydrogen chloride (12 M). The mixture was then partitioned between saturated sodium bicarbonate (300 mL) and ethyl acetate (200 mL). The aqueous layer was extracted with ethyl acetate (100 mL×2). The combined organic layer was washed with brine (200 mL), dried over sodium sulfate, filtered and concentrated to give a yellow solid. The yellow solid was triturated with ethyl acetate (20 mL) to give 7.40 g (82% yield) of 385-C as a yellow solid.

LCMS: (ESI) m/z: 235.2 [M+H]$^+$.
$^1$H NMR: (400 MHz, DMSO-$d_6$) δ: 13.76-13.67 (m, 1H), 8.85-8.55 (m, 1H), 8.40-8.31 (m, 1H), 7.47-7.34 (m, 1H), 4.10-3.84 (m, 3H), 2.42-2.34 (m, 3H).

Step 4: Synthesis of 3-(2-methoxy-5-nitrophenyl)-4-(4-methoxybenzyl)-5-methyl-4H-1,2,4-triazole (385-D)

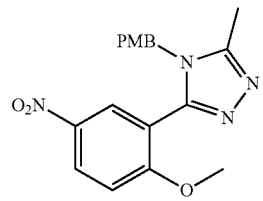

To a solution of 385-C (3.00 g, 12.6 mmol, 1.0 eq) in N,N-dimethylformide (30 mL) was added cesium carbonate (6.15 g, 18.9 mmol, 1.5 eq) followed by 1-(chloromethyl)-4-methoxybenzene (2.37 g, 15.1 mmol, 1.2 eq). The solution was stirred at 60° C. for 2 h. The solution was filtered and the filtrate was partitioned between ethyl acetate (200 mL) and water (300 mL). The aqueous layer was extracted with ethyl acetate (100 mL×2). The combined organic layer was washed with brine (150 mL), dried over sodium sulfate, filtered and concentrated to give 7.00 g (crude) of 385-D as a yellow oil.

LCMS: (ESI) m/z: 355.3 [M+H]$^+$.

Step 5: Synthesis of 4-methoxy-3-(4-(4-methoxybenzyl)-5-methyl-4H-1,2,4-triazol-3-yl)aniline (385-E)

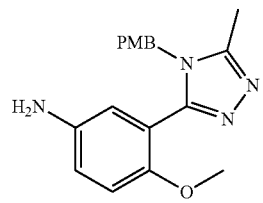

To a solution of 385-D (7.00 g, 19.8 mmol, 1.0 eq) in ethanol (40 mL) and water (8 mL) was added iron powder (11.0 g, 197 mmol, 10 eq) followed by ammonium chloride (10.5 g, 197 mmol, 10 eq). The solution was stirred at 80° C. for 1 h. The solution was filtered through a celite pad and the filtrate was concentrated. The residue was dissolved in ethyl acetate (200 mL) and the mixture was washed with saturated sodium bicarbonate (200 mL), brine (150 mL), dried over sodium sulfate, filtered and concentrated to give 4.70 g (crude) of 385-E as a brown oil.

LCMS: (ESI) m/z: 325.4 [M+H]$^+$.

Step 6: Synthesis of 3-(5-hydrazinyl-2-methoxyphenyl)-4-(4-methoxybenzyl)-5-methyl-4H-1,2,4-triazole (385-F)

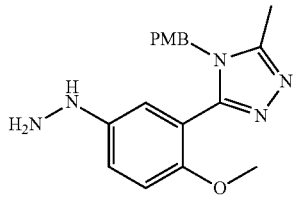

385-F was obtained via general procedure I from 385-E.
LCMS: (ESI) m/z: 340.3 [M+H]⁺.

Step 7: Synthesis of 1-(4-methoxy-3-(4-(4-methoxybenzyl)-5-methyl-4H-1,2,4-triazol-3-yl)phenyl)-3-methyl-1H-pyrazol-5(4H)-one (385-G)

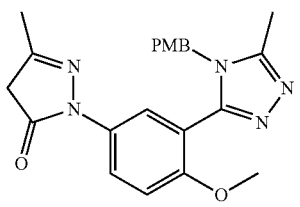

385-G was obtained via general procedure II from 385-F.
LCMS: (ESI) m/z: 406.1 [M+H]⁺.

Step 8: Synthesis of 4-nitrophenyl 1-(4-methoxy-3-(4-(4-methoxybenzyl)-5-methyl-4H-1,2,4-triazol-3-yl)phenyl)-3-methyl-5-oxo-4,5-dihydro-1H-pyrazole-4-carboxylate (385-H)

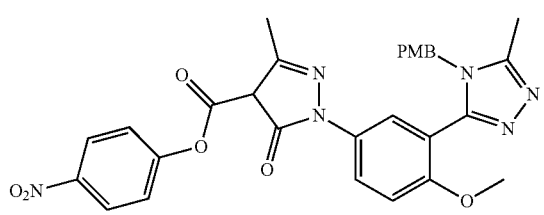

385-H was obtained via general procedure III from 385-G.
LCMS: (ESI) m/z: 571.2 [M+H]⁺.

Step 9: Synthesis of N-(3-(1,1-difluoroethyl)phenyl)-1-(4-methoxy-3-(4-(4-methoxybenzyl)-5-methyl-4H-1,2,4-triazol-3-yl)phenyl)-3-methyl-5-oxo-4,5-dihydro-1H-pyrazole-4-carboxamide (385-I)

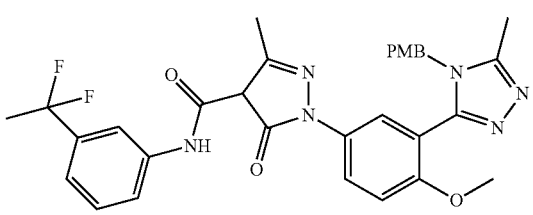

385-I was obtained via general procedure IV from 385-H.
LCMS: (ESI) m/z: 589.2 [M+H]⁺.

Step 10: Synthesis of N-(3-(1,1-difluoroethyl)phenyl)-1-(4-methoxy-3-(5-methyl-4H-1,2,4-triazol-3-yl)phenyl)-3-methyl-5-oxo-4,5-dihydro-1H-pyrazole-4-carboxamide (385)

Compound ID: 385

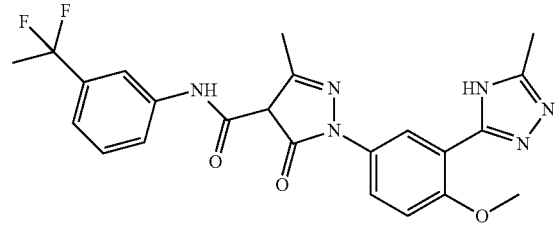 [SMILES: COc1ccc(N2N=C(C)C(C(=O)Nc3cccc(C(C)(F)F)c3)C2=O)cc1-c1nnc(C)[nH]1]

To a solution of 385-I (50.0 mg, 84.9 umol, 1.0 eq) in methanol (8 mL) was added palladium (20.0 mg, 10% on carbon). The solution was stirred at 15° C. for 12 h under hydrogen (15 psi). The solution was filtered through a celite pad and the filtrate was concentrated. The residue was purified by prep-HPLC (column: Xtimate C18 150*25 mm*5 um; mobile phase: [water (0.05% ammonia hydroxide v/v)-acetonitrile]; B %: 1%-31%, 10 min) to give 9.10 mg (22% yield) of 385 as a white solid.
LCMS: (ESI) m/z: 469.4 [M+H]⁺.
¹H NMR: (400 MHz, MeOD-d₄) δ: 8.39 (d, J=2.8 Hz, 1H), 7.92 (s, 1H), 7.85 (dd, J=2.8, 9.2 Hz, 1H), 7.63 (dd, J=1.2, 8.0 Hz, 1H), 7.36 (t, J=8.0 Hz, 1H), 7.24 (d, J=9.2 Hz, 1H), 7.16 (d, J=7.6 Hz, 1H), 4.02 (s, 3H), 2.45 (s, 3H), 2.42 (s, 3H), 1.92 (t, J=18.4 Hz, 3H).

Synthesis of 383

Step 1: Synthesis of 2-chloro-5-(difluoromethoxy)pyridine (383-A)

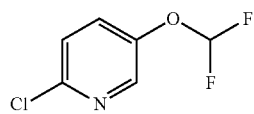 [SMILES: FC(F)Oc1ccc(Cl)nc1]

To a solution of 6-chloropyridin-3-ol (5.80 g, 44.8 mmol, 1.0 eq) and (2-chloro-2,2-difluoro-acetyl)oxysodium (10.2 g, 67.2 mmol, 1.5 eq) in N,N-dimethyl-formamide (60 mL) was added sodium carbonate (7.12 g, 67.2 mmol, 1.5 eq), the solution was stirred at 100° C. for 12 h. The solution was poured into water (200 mL), extracted with ethyl acetate (200 mL×3). The combined organic phase was washed with brine (200 mL), dried with anhydrous sodium sulfate, filtered and concentrated. The residue was purified by silica column (petroleum ether/ethyl acetate, from 1/0 to 20/1) to give 6.20 g (77% yield) of 383-A as a colorless oil.

LCMS: (ESI) m/z: 180.0 [M+H]$^+$.

$^1$H NMR: (400 MHZ, CDCl$_3$-d) δ: 8.26 (d, J=2.8 Hz, 1H), 7.49-7.46 (m, 1H), 7.34 (d, J=8.4 Hz, 1H), 6.55 (t, J=72.0 Hz, 1H).

Step 2: Synthesis of [5-(difluoromethoxy)-2-pyridyl]hydrazine (383-B)

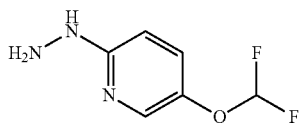 [SMILES: NNc1ccc(OC(F)F)cn1]

The solution of 383-A (2.00 g, 11.1 mmol, 1.0 eq) in hydrazine hydrate (10.3 g, 174 mmol, 16 eq) was stirred at 160° C. for 1 h under microwave (2 bar). The suspension was filtered. The filter cake was dried under vacuum to give 1.90 g (97% yield) of 383-B as a white solid.

LCMS: (ESI) m/z: 176.1 [M+H]$^+$.

Step 3: Synthesis of 2-[5-(difluoromethoxy)-2-pyridyl]-5-methyl-4H-pyrazol-3-one (383-C)

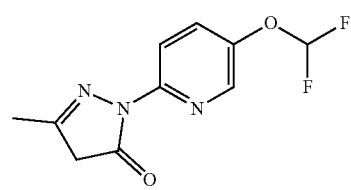 [SMILES: CC1=NN(c2ccc(OC(F)F)cn2)C(=O)C1]

383-C was obtained via general procedure II from 383-B.
LCMS: (ESI) m/z: 242.1 [M+H]$^+$.

Step 4: Synthesis of 4-nitrophenyl 1-(5-(difluoromethoxy)pyridin-2-yl)-3-methyl-5-oxo-4,5-dihydro-1H-pyrazole-4-carboxylate (383-D)

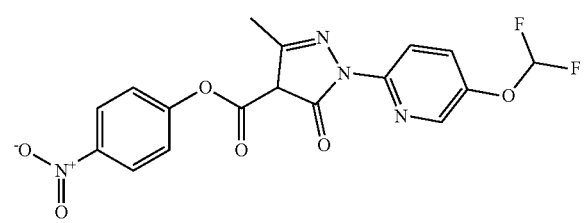

383-D was obtained via general procedure III from 383-C.
LCMS: (ESI) m/z: 429.2 [M+Na]$^+$.

Step 5: Synthesis of 1-[5-(difluoromethoxy)-2-pyridyl]-N-[3-(1,1-difluoropropyl)phenyl]-3-methyl-5-oxo-4H-pyrazole-4-carboxamide (383)

Compound ID: 383

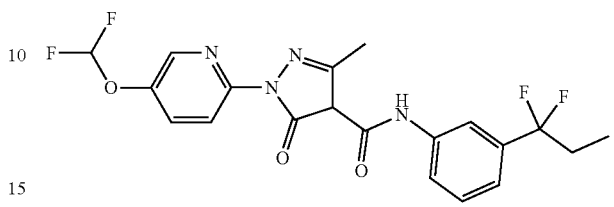

383 was obtained via general procedure IV from 383-D.
LCMS: (ESI) m/z: 439.1 [M+H]$^+$.

$^1$H NMR: (400 MHZ, MeOD-d$_4$) δ: 8.46 (d, J=8.8 Hz, 1H), 8.35 (s, 1H), 7.87 (s, 1H), 7.81 (dd, J=8.8 Hz, 2.0 Hz, 1H), 7.66 (d, J=8.0 Hz, 1H, 7.42 (t, J=7.6 Hz, 1H), 7.20 (d, J=7.6 Hz, 1H), 6.93 (t, J=72.8 Hz, 1H), 2.64 (s, 3H), 2.24-2.12 (m, 2H), 0.99 (t, J=7.6 Hz, 3H).

Synthesis of 377

Step 1: Synthesis of 2-[2-(difluoromethoxy)-5-nitrophenyl]-4,4,5,5-tetramethyl-1,3,2-dioxaborolane (377-A)

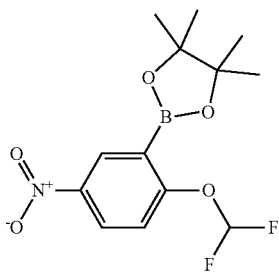

To a mixture of 312-A (7.00 g, 21.2 mmol, 1.0 eq), 4,4,5,5-tetramethyl-2-(4,4,5,5-tetramethyl-1,3,2-dioxaborolan-2-yl)-1,3,2-dioxaborolane (10.7 g, 42.3 mmol, 2.0 eq), potassium acetate (6.23 g, 63.5 mmol, 3.0 eq) in dioxane (80 mL) was added 1,1-bis(diphenylphosphino)ferrocene]dichloropalladium(II) (774 mg, 1.06 mmol, 0.050 eq). The solution was degassed under vacuum and purged with nitrogen several times. The mixture was stirred under nitrogen at 85° C. for 12 hr. The reaction mixture was filtered, and the filter cake was washed with ethyl acetate. The filtrate was concentrated under reduced pressure to give a residue. The crude product was purified by silica gel column chromatography (petroleum ether/ethyl acetate, from 1/0 to 10/1) to give 9.00 g (crude) of 377-A as an off-white solid.

$^1$H NMR: (400 MHz, CDCl$_3$-d) δ: 8.60 (d, J=2.8 Hz, 1H), 8.32-8.25 (m, 1H), 7.24 (d, J=2.2 Hz, 1H), 6.79-6.39 (m, 1H), 1.50-1.50 (m, 1H), 1.35 (s, 12H).

Step 2: Synthesis of 2-[2-(difluoromethoxy)-5-nitro-phenyl]pyridine (377-B)

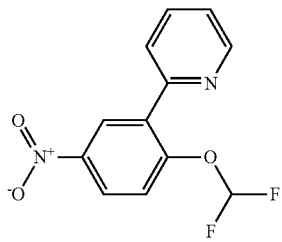

To a solution of 377-A (6.00 g, 19.0 mmol, 1.0 eq) and 2-bromopyridine (3.26 g, 20.6 mmol, 1.1 eq) in dioxane (60 mL) was added a solution of cesium carbonate (13.4 g, 41.2 mmol, 2.2 eq) in water (15 mL) and 1,1-bis(diphenylphosphino)ferrocene]dichloropalladium(II) (503 mg, 687 umol, 3.6e-2 eq). The suspension was degassed under vacuum and purged with nitrogen several times. The mixture was stirred under nitrogen at 80° C. for 2 hr. To the reaction mixture was added water (100 mL), and the reaction mixture was extracted with ethyl acetate (100 mL×3). The combined organic layer was dried over with sodium sulfate, filtered, concentrated under reduced pressure to give a residue. The crude product was purified by silica gel column chromatography (petroleum ether/ethyl acetate, from 1/0 to 5/1) to give 1.90 g (37% yield) of 377-B as a light yellow solid.

LCMS: (ESI) m/z: 267.1 [M+H]$^+$.

Step 3: Synthesis of 4-(difluoromethoxy)-3-(2-pyridyl)aniline (377-C)

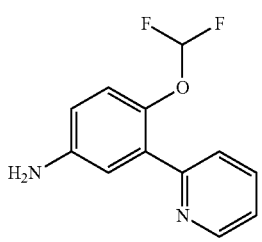 [SMILES: Nc1ccc(OC(F)F)c(-c2ccccn2)c1]

To a solution of 377-B (1.90 g, 6.96 mmol, 1.0 eq) in ethanol (3 mL) was added Pd/C (200 mg, 10% purity) under nitrogen. The suspension was degassed under vacuum and purged with hydrogen several times. The mixture was stirred under hydrogen (15 psi) at 25° C. for 2 hr. The reaction mixture was filtered, concentrated under reduced pressure to give 1.65 g (99% yield) of 377-C as a off-white gum.

LCMS: (ESI) m/z: 237.0 [M+H]$^+$.

Step 4: Synthesis of [4-(difluoromethoxy)-3-(2-pyridyl)phenyl]hydrazine (377-D)

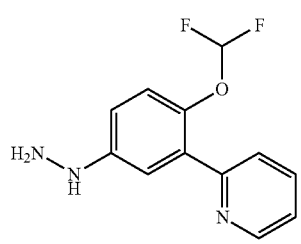 [SMILES: NNc1ccc(OC(F)F)c(-c2ccccn2)c1]

377-D was obtained via general procedure I from 377-C.
LCMS: (ESI) m/z: 252.1 [M+H]$^+$.

Step 5: Synthesis of 2-[4-(difluoromethoxy)-3-(2-pyridyl)phenyl]-5-methyl-4H-pyrazol-3-one (377-E)

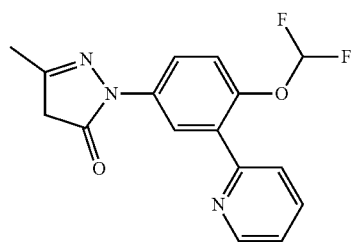 [SMILES: CC1=NN(c2ccc(OC(F)F)c(-c3ccccn3)c2)C(=O)C1]

377-E was obtained via general procedure II from 377-D.
LCMS: (ESI) m/z: 318.1 [M+H]$^+$.

Step 6: Synthesis of (4-nitrophenyl) 1-[4-(difluoromethoxy)-3-(2-pyridyl)phenyl]-3-methyl-5-oxo-4H-pyrazole-4-carboxylate (377-F)

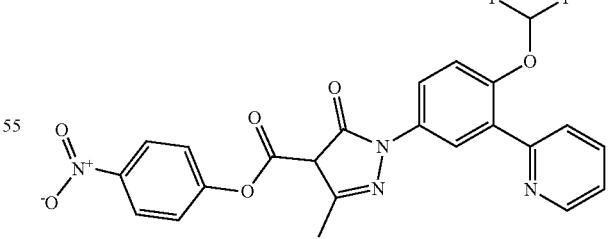

377-F was obtained via general procedure III from 377-E.
LCMS: (ESI) m/z: 483.1 [M+H]$^+$.

Step 7: Synthesis of 1-[4-(difluoromethoxy)-3-(2-pyridyl)phenyl]-N-[3-(1,1-difluoropropyl)phenyl]-3-methyl-5-oxo-4H-pyrazole-4-carboxamide (377)

Compound ID: 377

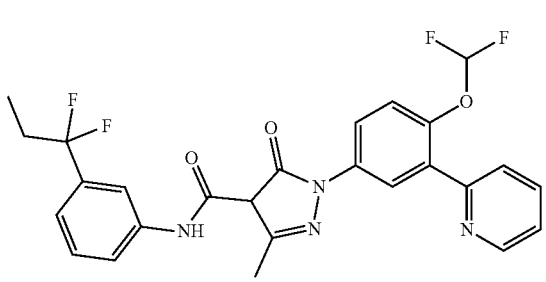 [SMILES: CCC(F)(F)c1cccc(NC(=O)C2C(=O)N(c3ccc(OC(F)F)c(-c4ccccn4)c3)N=C2C)c1]

377 was obtained via general procedure IV from 377-F and 3-(1,1-difluoropropyl)aniline.

LCMS: (ESI) m/z: 515.1 [M+H]$^+$.

$^1$H NMR: (400 MHz, DMSO-d$_6$) δ: 10.79 (s, 1H), 8.89-8.64 (m, 1H), 8.18 (d, J=2.8 Hz, 1H), 7.97 (dt, J=1.8, 7.8 Hz, 1H), 7.94-7.88 (m, 2H), 7.82 (d, J=7.8 Hz, 1H), 7.67-7.60 (m, 1H), 7.51-7.45 (m, 2H), 7.42 (t, J=7.8 Hz, 1H), 7.28 (s, 1H), 7.16 (d, J=7.8 Hz, 1H), 7.09 (s, 1H), 2.55 (s, 3H), 2.29-2.10 (m, 2H), 0.92 (t, J=7.4 Hz, 3H).

Synthesis of 371

Step 1: Synthesis of 2-(4-(4-methoxybenzyl)-5-methyl-4H-1,2,4-triazol-3-yl)-4-nitrophenol (371-A)

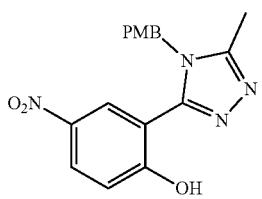

To a solution of 385-D (3.30 g, 8.95 mmol, 1.0 eq) in N,N-dimethylformamide (30 mL) was added lithium chloride (7.90 g, 186 mmol, 20.8 eq) followed by 4-methylbenzenesulfonic acid hydrate (35.4 g, 186 mmol, 20.8 eq). The solution was heated to 130° C. and stirred for 36 h. The solution was partitioned between ethyl acetate (150 mL) and water (200 mL). The aqueous layer was extracted with ethyl acetate (100 mL). The combined organic layer was washed with brine (100 mL), dried over anhydrous sodium sulfate, filtered and concentrated. The residue was triturated with methanol (10 mL) to give 1.30 g (42% yield) of 371-A as a white solid.

LCMS: (ESI) m/z: 341.1 [M+H]$^+$.

Step 2: Synthesis of 3-(2-(difluoromethoxy)-5-nitrophenyl)-4-(4-methoxybenzyl)-5-methyl-4H-1,2,4-triazole (371-B)

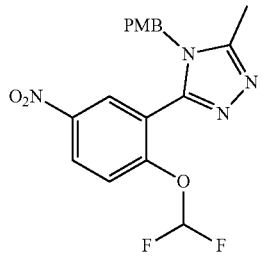

To a solution of 371-A (1.30 g, 3.82 mmol, 1.0 eq) in N,N-dimethylformamide (15 mL) was added sodium carbonate (809 mg, 7.64 mmol, 2.0 eq) followed by (2-chloro-2,2-difluoro-acetyl)oxysodium (874 mg, 5.73 mmol, 1.5 eq). The solution was stirred at 100° C. for 1 h. The solution was partitioned between ethyl acetate (100 mL) and water (200 mL). The aqueous layer was extracted with ethyl acetate (100 mL×3). The combined organic layer was washed with brine (200 mL), dried over anhydrous sodium sulfate, filtered and concentrated. The residue was purified by column chromatography on silica gel (petroleum ether/ethyl acetate, 3/1) to give 1.40 g (94% yield) of 371-B as a yellow solid.

LCMS: (ESI) m/z: 390.8 [M+H]$^+$.

$^1$H NMR: (400 MHz, MeOD-d$_4$) δ: 8.73 (d, J=3.2 Hz, 1H), 8.34 (dd, J=3.2, 9.2 Hz, 1H), 7.55 (d, J=9.2 Hz, 1H), 7.39 (t, J=73.6 Hz, 1H), 7.28 (d, J=8.8 Hz, 2H), 6.92 (d, J=8.8 Hz, 2H), 5.37 (s, 2H), 3.73 (s, 3H), 2.49 (s, 3H).

Step 3: Synthesis of 4-(difluoromethoxy)-3-(4-(4-methoxybenzyl)-5-methyl-4H-1,2,4-triazol-3-yl)aniline (371-C)

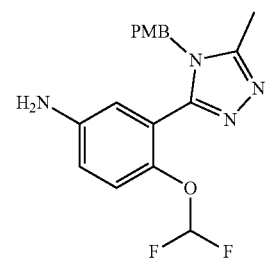

371-C was obtained via the similar synthetic method of 385-D from 371-B and iron powder.

LCMS: (ESI) m/z: 361.0 [M+H]$^+$.

Step 4: Synthesis of 3-(2-(difluoromethoxy)-5-hydrazinylphenyl)-4-(4-methoxybenzyl)-5-methyl-4H-1,2,4-triazole (371-D)

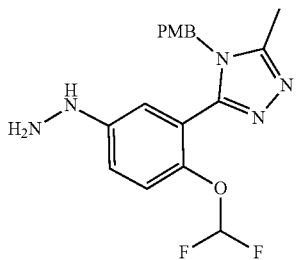

371-D was obtained via general procedure I from 371-C.
LCMS: (ESI) m/z: 376.1 [M+H]$^+$.

Step 5: Synthesis of 1-(4-(difluoromethoxy)-3-(4-(4-methoxybenzyl)-5-methyl-4H-1,2,4-triazol-3-yl)phenyl)-3-methyl-1H-pyrazol-5(4H)-one (371-E)

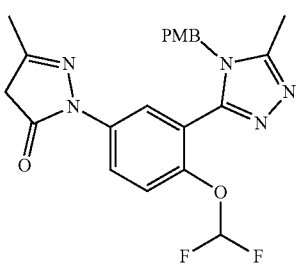

371-E was obtained via general procedure II from 371-D.
LCMS: (ESI) m/z: 442.0 [M+H]$^+$.

Step 6: Synthesis of 4-nitrophenyl 1-(4-(difluoromethoxy)-3-(4-(4-methoxybenzyl)-5-methyl-4H-1,2,4-triazol-3-yl)phenyl)-3-methyl-5-oxo-4,5-dihydro-1H-pyrazole-4-carboxylate (371-F)

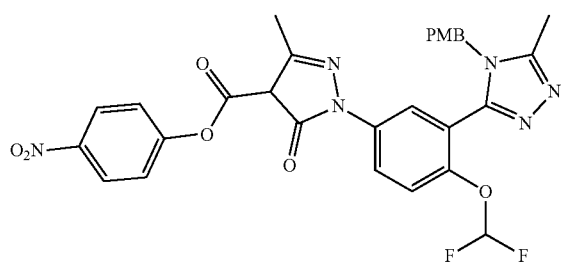

371-F was obtained via general procedure III from 371-E.
LCMS: (ESI) m/z: 606.8 [M+H]$^+$.

Step 7: Synthesis of N-(3-(1,1-difluoroethyl)phenyl)-1-(4-(difluoromethoxy)-3-(4-(4-methoxybenzyl)-5-methyl-4H-1,2,4-triazol-3-yl)phenyl)-3-methyl-5-oxo-4,5-dihydro-1H-pyrazole-4-carboxamide (371-G)

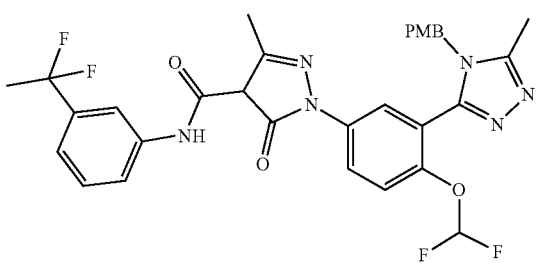

371-G was obtained via general procedure IV from 371-F.
LCMS: (ESI) m/z: 624.9 [M+H]$^+$.

Step 8: Synthesis of N-(3-(1,1-difluoroethyl)phenyl)-1-(4-(difluoromethoxy)-3-(5-methyl-4H-1,2,4-triazol-3-yl)phenyl)-3-methyl-5-oxo-4,5-dihydro-1H-pyrazole-4-carboxamide (371)

Compound ID: 371

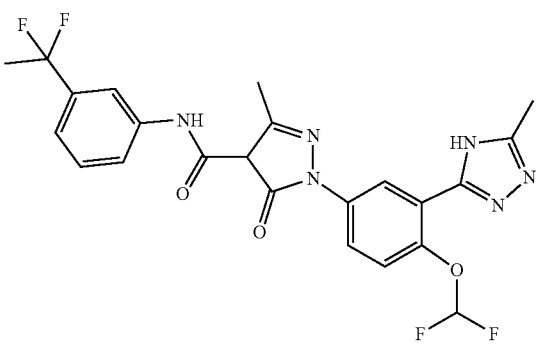 [SMILES: CC1=NN(c2ccc(OC(F)F)c(-c3nnc(C)[nH]3)c2)C(=O)C1C(=O)Nc1cccc(C(C)(F)F)c1]

371 was obtained via the similar synthetic method of 385 from 371-G and hydrogen.
LCMS: (ESI) m/z: 505.3 [M+H]$^+$.
$^1$H NMR: (400 MHz, MeOD-d$_4$) δ: 8.32 (d, J=2.0 Hz, 1H), 8.00-7.85 (m, 2H), 7.65 (d, J=8.4 Hz, 1H), 7.46 (d, J=8.8 Hz, 1H), 7.41 (t, J=8.0 Hz, 1H), 7.22 (d, J=7.6 Hz, 1H), 6.90 (t, J=73.6 Hz, 1H), 2.56 (s, 3H), 2.51 (s, 3H), 1.94 (t, J=18.4 Hz, 3H).

Synthesis of 370

Step 1: Synthesis of 1-(4-(difluoromethoxy)-3-(4-(4-methoxybenzyl)-5-methyl-4H-1,2,4-triazol-3-yl)phenyl)-N-(3-(1,1-difluoropropyl)phenyl)-3-methyl-5-oxo-4,5-dihydro-1H-pyrazole-4-carboxamide (370-A)

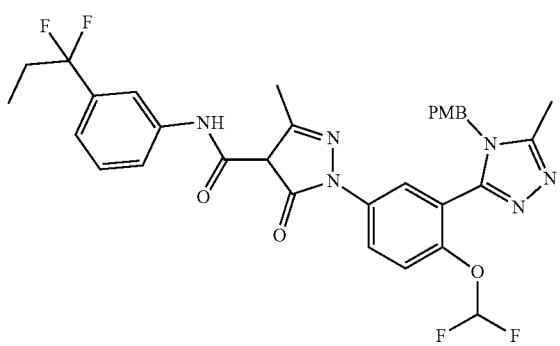

370-A was obtained via general procedure IV from 371-F and 3-(1,1-difluoropropyl)aniline.
LCMS: (ESI) m/z: 639.1 [M+H]⁺.

Step 2: Synthesis of 1-(4-(difluoromethoxy)-3-(5-methyl-4H-1,2,4-triazol-3-yl)phenyl)-N-(3-(1,1-difluoropropyl)phenyl)-3-methyl-5-oxo-4,5-dihydro-1H-pyrazole-4-carboxamide (370)

Compound ID: 370

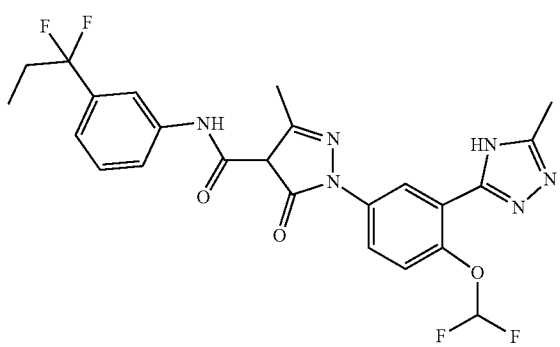 [SMILES: CCC(F)(F)c1cccc(NC(=O)C2C(=O)N(c3ccc(OC(F)F)c(-c4nnc(C)[nH]4)c3)N=C2C)c1]

370 was obtained via the similar synthetic method of 371 from 370-A and hydrogen.
LCMS: (ESI) m/z: 519.1 [M+H]⁺.
$^1$H NMR: (400 MHz, MeOD-d$_4$) δ: 8.32 (d, J=2.8 Hz, 1H), 7.93 (dd, J=2.4, 8.8 Hz, 1H), 7.87 (s, 1H), 7.64 (d, J=8.8 Hz, 1H), 7.44 (d, J=8.8 Hz, 1H), 7.39 (t, J=8.0 Hz, 1H), 7.16 (d, J=7.6 Hz, 1H), 6.88 (t, J=74.0 Hz, 1H), 2.53 (s, 3H), 2.49 (s, 3H), 2.28-2.08 (m, 2H), 0.98 (t, J=7.6 Hz, 3H).

Synthesis of 369

Step 1: Synthesis of N-[3-(1,1-difluoropropyl)phenyl]-3-methyl-5-oxo-1-[1-(p-tolylsulfonyl)indol-6-yl]-4H-pyrazole-4-carboxamide (369-A)

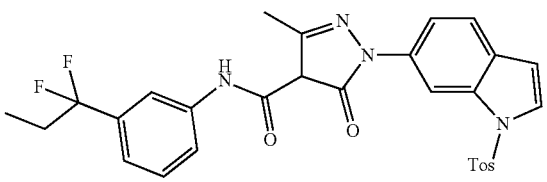

369-A was obtained via general procedure IV from 410-E and 3-(1,1-difluoropropyl)aniline
LCMS: (ESI) m/z: 565.1 [M+H]⁺.

Step 2: Synthesis of N-[3-(1,1-difluoropropyl)phenyl]-1-(1H-indol-6-yl)-3-methyl-5-oxo-4H-pyrazole-4-carboxamide (369)

Compound ID: 369

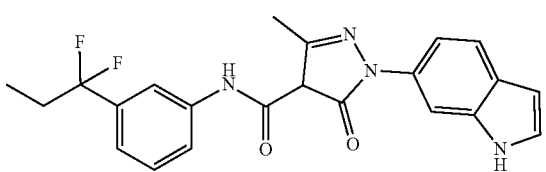 [SMILES: CCC(F)(F)c1cccc(NC(=O)C2C(=O)N(c3ccc4cc[nH]c4c3)N=C2C)c1]

369 was obtained via similar procedure of 410 from 369-A and potassium hydroxide
LCMS: (ESI) m/z: 411.2 [M+H]⁺.
$^1$H NMR: (400 MHz, MeOD-d$_4$) δ: 7.87 (s, 1H), 7.70 (d, J=8.4 Hz, 1H), 7.65 (s, 2H), 7.44-7.36 (m, 2H), 7.20 (d, J=8.4 Hz, 2H), 6.54 (d, J=2.8 Hz, 1H), 2.62 (s, 3H), 2.18 (m, 2H), 0.98 (t, J=7.4 Hz, 3H).

Synthesis of 368

Step 1: Synthesis of N-[3-(1,1-difluoropropyl)phenyl]-1-(4-methoxy-3-phenyl-phenyl)-3-methyl-5-oxo-4H-pyrazole-4-carboxamide (368)

Compound ID: 368

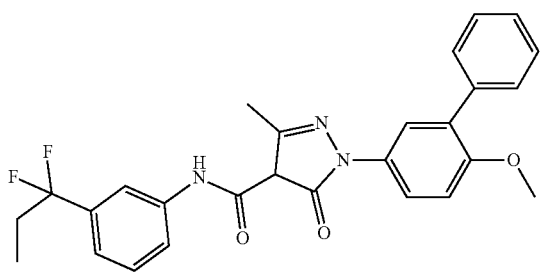 [SMILES: CCC(F)(F)c1cccc(NC(=O)C2C(=O)N(c3ccc(OC)c(-c4ccccc4)c3)N=C2C)c1]

368 was obtained via general procedure IV from 313-E and 3-(1,1-difluoropropyl)aniline
LCMS: (ESI) m/z: 478.3 [M+H]⁺.
$^1$H NMR: (400 MHz, MeOD-d$_4$) δ: 7.87 (s, 1H), 7.66-7.62 (m, 1H), 7.59-7.54 (m, 4H), 7.44-7.38 (m, 3H), 7.36-7.33 (m, 1H), 7.25 (d, J=8.4 Hz, 1H), 7.20 (d, J=8.4 Hz, 1H), 3.87 (s, 3H), 2.61 (s, 3H), 2.26-2.11 (m, 2H), 0.98 (t, J=7.2 Hz, 3H).

Synthesis of 367

Step 1: Synthesis of 1-(1-benzylindol-6-yl)-N-[3-(1,1-difluoroethyl)phenyl]-3-methyl-5-oxo-4H-pyrazole-4-carboxamide (367)

Compound ID: 367

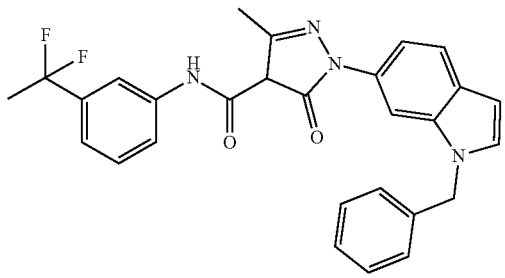 [SMILES: CC1=NN(c2ccc3ccn(Cc4ccccc4)c3c2)C(=O)C1C(=O)Nc1cccc(C(C)(F)F)c1]

To a solution of 410 (100 mg, 227 umol, 1.0 eq) in N,N-dimethyl formamide (5 mL) was added sodium hydride (12.9 mg, 322 umol, 60% purity, 1.4 eq) at 0° C. slowly under nitrogen, the mixture was stirred 0.5 h, then the (bromomethyl)benzene (36.7 mg, 214 umol, 9.5e-1.0 eq) was injected and the mixture was stirred at 20° C. for 0.5 h. The mixture was quenched with water (30 mL), then extracted with ethyl acetate (20 mL×3), the combined organic layer was washed with brine (30 mL×1), dried over anhydrous sodium sulfate, filtered and concentrated under reduced pressure to give a residue. The residue was purified by prep-TLC (dichloromethane/methanol=10/1) to give a crude product, then the crude product was purified by column: (Boston Green ODS 150*30 mm*5 um; mobile phase: [water (0.225% formic acid)-acetonitrile]; B %: 55%-85%, 10 min) to give 23.1 mg (21% yield) of 367 as a white solid.

LCMS: (ESI) m/z: 487.2[M+H]$^+$.
$^1$H NMR: (400 MHz, DMSO-d$_6$) δ: 10.95 (s, 1H), 7.95 (s, 1H), 7.81 (s, 1H), 7.69 (d, J=8.4 Hz, 1H), 7.60 (s, 1H), 7.58 (d, J=3.2 Hz, 1H), 7.42 (s, 1H), 7.36-7.29 (m, 3H), 7.28-7.23 (m, 1H), 7.22-7.16 (m, 3H), 6.58 (d, J=3.2 Hz, 1H), 5.46 (s, 2H), 2.53 (s, 3H), 1.96 (t, J=18.8 Hz, 3H).

Synthesis of 366

Step 1: Synthesis of N-[3-(1,1-difluoroethyl)phenyl]-3-methyl-1-(1-methylindol-6-yl)-5-oxo-4H-pyrazole-4-carboxamide (366)

Compound ID: 366

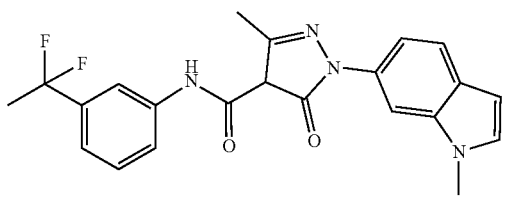 [SMILES: CC1=NN(c2ccc3ccn(C)c3c2)C(=O)C1C(=O)Nc1cccc(C(C)(F)F)c1]

366 was obtained via similar procedure of 367 from 410 and iodomethane

LCMS: (ESI) m/z: 411.1 [M+H]$^+$.
$^1$H NMR: (400 MHz, DMSO-d$_6$) δ: 10.99 (s, 1H), 7.95 (s, 1H), 7.81-7.76 (m, 1H), 7.68-7.62 (m, 2H), 7.44-7.40 (m, 2H), 7.34 (dd, J=8.8, 2.0 Hz, 1H), 7.21 (d, J=7.6 Hz, 1H), 6.49 (dd, J=2.8, 0.8 Hz, 1H), 3.83 (s, 3H), 2.56 (s, 3H), 1.96 (t, J=18.8 Hz, 3H).

Synthesis of 364

Step 1: Synthesis of N-[3-(1,1-difluoroethyl)phenyl]-1-(1-isopropylindol-6-yl)-3-methyl-5-oxo-4H-pyrazole-4-carboxamide (364)

Compound ID: 364

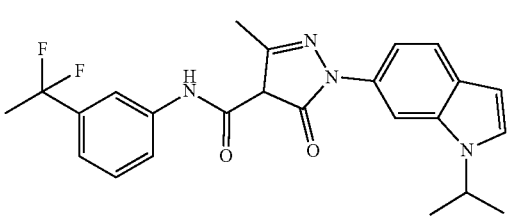 [SMILES: CC1=NN(c2ccc3ccn(C(C)C)c3c2)C(=O)C1C(=O)Nc1cccc(C(C)(F)F)c1]

364 was obtained via similar procedure of 367 from 410 and 2-iodopropane

LCMS: (ESI) m/z: 439.3[M+H]$^+$.
$^1$H NMR: (400 MHz, DMSO-d$_6$) δ: 10.99 (s, 1H), 7.95 (s, 1H), 7.84 (s, 1H), 7.65 (d, J=8.4 Hz, 2H), 7.59 (d, J=3.2 Hz, 1H), 7.42 (t, J=7.6 Hz, 1H), 7.34 (dd, J=8.4, 1.6 Hz, 1H), 7.21 (d, J=7.6 Hz, 1H), 6.53 (d, J=3.2 Hz, 1H), 4.82-4.70 (m, 1H), 2.56 (s, 3H), 1.96 (t, J=18.8 Hz, 3H), 1.49 (d, J=6.8 Hz, 6H).

Synthesis of 363

Step 1: Synthesis of N-[3-(1,1-difluoroethyl)phenyl]-3-methyl-5-oxo-1-(1-propylindol-6-yl)-4H-pyrazole-4-carboxamide (363)

Compound ID: 363

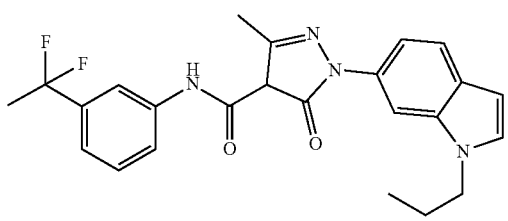 [SMILES: CCCn1ccc2ccc(N3N=C(C)C(C(=O)Nc4cccc(C(C)(F)F)c4)C3=O)cc21]

363 was obtained via similar procedure of 367 from 410 and 1-iodopropane

LCMS: (ESI) m/z: 439.2[M+H]$^+$.
$^1$H NMR: (400 MHz, DMSO-d$_6$) δ: 10.97 (s, 1H), 7.96 (s, 1H), 7.78 (s, 1H), 7.68-7.62 (m, 2H), 7.48 (d, J=3.2 Hz, 1H), 7.43 (t, J=8.0 Hz, 1H), 7.31 (dd, J=8.4, 2.0 Hz, 1H), 7.21 (d, J=8.0 Hz, 1H), 6.50 (d, J=2.8 Hz, 1H), 4.16 (t, J=7.0 Hz, 2H), 2.57 (s, 3H), 1.96 (t, J=18.8 Hz, 3H), 1.81 (d, J=7.2 Hz, 2H), 0.86 (t, J=7.4 Hz, 3H).

Synthesis of 362

Step 1: Synthesis of 2-methyl-1-(3-nitrophenyl)propan-1-one (362-A)

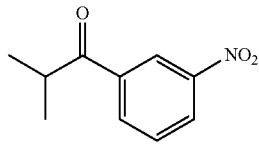

Nitric acid (2.53 g, 38.1 mmol, 2.8 eq) was added to sulfuric acid (8.33 g, 84.9 mmol, 6.3 eq) with stirring at −5° C., the resulting solution was added drop-wise to another solution of 2-methyl-1-phenyl-propan-1-one (2.00 g, 13.5 mmol, 1.0 eq) in sulfuric acid (5 mL) at −10° C. The reaction was stirred at −10° C. for 30 mins. The reaction mixture was poured into ice-water (100 mL), and the resulting mixture was extracted with ethyl acetate (20 mL×3). The combined organic layer was washed with saturated sodium bicarbonater solution (30 mL) and concentrated in vacuo. The residue was purified by silica gel column chromatography (petroleum ether/ethyl acetate, 20/1) to afford 1.50 g (58% yield) of 362-A as yellow oil.

$^1$H NMR (400 MHz, CDCl$_3$-d) δ: 8.78 (t, J=2.0 Hz, 1H), 8.47-8.38 (m, 1H), 8.32-8.23 (m, 1H), 7.70 (t, J=8.0 Hz, 1H), 3.64-3.53 (m, J=6.8 Hz, 1H), 1.27 (d, J=6.8 Hz, 6H).

Step 2: Synthesis of 1-(1,1-difluoro-2-methylpropyl)-3-nitrobenzene (362-B)

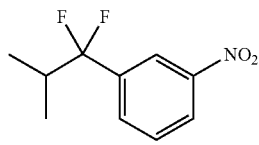

To a solution of 362-A (1.00 g, 5.18 mmol, 1.0 eq) in chloroform (5 mL) was added diethylaminosulfur trifluoride (2.70 g, 16.8 mmol, 3.2 eq). The reaction was stirred at 70° C. for 10 h. It was quenched with 50 mL of saturated sodium bicarbonate and extracted with dichloromethane (20 mL×3). The combined organic layer was concentrated in vacuo. The residue was purified by silica gel column chromatography (ethyl acetate/petroleum ether, 1/20) to afford 0.650 g (58% yield) of 362-B as yellow oil.

$^1$H NMR (400 MHz, CDCl$_3$-d) δ: 7.63-7.56 (m, 1H), 7.52-7.46 (m, 0.5H), 7.45-7.38 (m, 1H), 7.36-7.29 (m, 0.5H), 7.25 (d, J=1.6 Hz, 0.5H), 7.17 (dd, J=2.4, 3.2 Hz, 0.5H), 3.66 (q, J=7.2 Hz, 1H), 1.50 (s, 6H).

Step 3: Synthesis of 3-(1,1-difluoro-2-methylpropyl)aniline (362-C)

A suspension of 362-B (300 mg, 1.39 mmol, 1.0 eq), iron powder (779 mg, 13.9 mmol, 10 eq) and ammonium chloride (746 mg, 13.9 mmol, 10 eq) in ethanol (8 mL) and water (2 mL) was stirred at 70° C. for 1 h. It was concentrated to remove ethanol. The result solution was diluted with 10 mL of water and extracted with ethyl acetate (10 mL×3). The combined organic layer was concentrated in vacuo to afford 0.150 g (crude) of 362-C as light-yellow oil.

$^1$H NMR (400 MHz, CDCl$_3$-d) δ: 7.19 (t, J=7.8 Hz, 1H), 6.82 (d, J=7.8 Hz, 1H), 6.75 (s, 1H), 6.72 (dd, J=2.0, 8.0 Hz, 1H), 3.53 (br s, 2H), 2.39-2.24 (m, 1H), 1.00 (d, J=6.8 Hz, 6H).

Step 4: Synthesis of N-(3-(1,1-difluoro-2-methylpropyl)phenyl)-1-(4-(difluoromethoxy)phenyl)-3-methyl-5-oxo-4,5-dihydro-1H-pyrazole-4-carboxamide (362)

Compound ID: 362

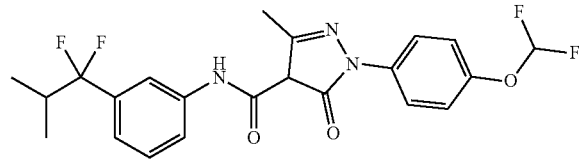 [SMILES: CC1=NN(c2ccc(OC(F)F)cc2)C(=O)C1C(=O)Nc1cccc(C(F)(F)C(C)C)c1]

362 was obtained via general procedure IV from 298-C and 362-C

LCMS: (ESI) m/z: 452.2 [M+H]$^+$.

$^1$H NMR (400 MHz, MeOD-d$_4$) δ: 7.83 (s, 1H), 7.72-7.63 (m, 3H), 7.43-7.28 (m, 3H), 7.17 (d, J=8.0 Hz, 1H), 6.91 (t, J=73.6 Hz, 1H), 2.62 (s, 3H), 2.37 (qd, J=6.8, 14.0 Hz, 1H), 1.00 (d, J=6.8 Hz, 6H).

Synthesis of 361

Step 1: Synthesis of N-[3-(1,1-difluoroethyl)phenyl]-3-methyl-5-oxo-1-(1-phenylindol-6-yl)-4H-pyrazole-4-carboxamide (361)

Compound ID: 361

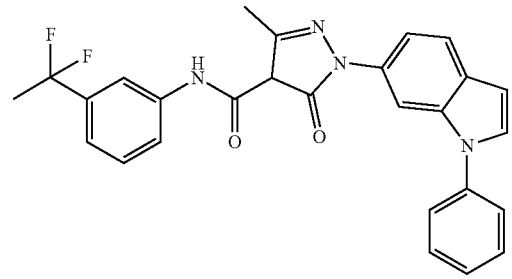 [SMILES: CC1=NN(c2ccc3ccn(-c4ccccc4)c3c2)C(=O)C1C(=O)Nc1cccc(C(C)(F)F)c1]

A mixture of 410 (100 mg, 242 umol, 1.0 eq), iodobenzene (69.5 mg, 341 umol, 1.4 eq), N,N'-dimethylethane-1,2-diamine (6.00 mg, 68.1 umol, 2.8e-1 eq), cesium carbonate (222 mg, 681 umol, 2.81 eq) and copper iodide (8.65 mg, 45.4 umol, 1.8e-1 eq) in N,N-dimethylformamide (3 mL) was degassed and purged with nitrogen for 3 times, and then the mixture was stirred at 80° C. for 12 hr under nitrogen atmosphere. The mixture was quenched with water (30 ml), then extracted with ethyl acetate (20 mL×3). The combined organic phase was washed with brine (30 mL) and dried over with anhydrous sodium sulfate, filtered and concentrated under reduced pressure to give a residue. The residue was purified by pre-HPLC (column: Boston Green ODS 150*30 mm*5 um; mobile phase: [water (0.225% formic acid)-acetonitrile]; B %: 53%-83%, 10 min) to give 8.30 mg (7% yield) of 361 as a yellow solid.

LCMS: (ESI) m/z: 473.3[M+H]$^+$.

$^1$H NMR: (400 MHz, MeOD-d$_4$) δ: 7.91 (s, 1H), 7.82-7.76 (m, 2H), 7.64-7.56 (m, 6H), 7.45-7.34 (m, 3H), 7.23 (d, J=8.0 Hz, 1H), 6.76 (d, J=3.2 Hz, 1H), 2.60 (s, 3H), 1.92 (t, J=18.2 Hz, 3H).

Synthesis of 360

Step 1: Synthesis of N-[3-(1,1-difluoropropyl)phenyl]-1-(1-isopropylindol-6-yl)-3-methyl-5-oxo-4H-pyrazole-4-carboxamide (360)

Compound ID: 360

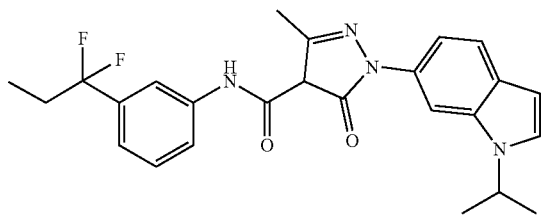 [SMILES: CCC(F)(F)c1cccc(NC(=O)C2C(=O)N(c3ccc4ccn(C(C)C)c4c3)N=C2C)c1]

360 was obtained via similar procedure of 364 from 369 and 2-iodopropane.

LCMS: (ESI) m/z: 453.3[M+H]$^+$.

$^1$H NMR: (400 MHz, DMSO-d$_6$) δ: 10.98 (s, 1H), 7.92 (s, 1H), 7.83 (s, 1H), 7.67-7.60 (m, 3H), 7.43 (t, J=7.6 Hz, 1H), 7.32 (dd, J=8.4, 1.6 Hz, 1H), 7.16 (d, J=7.6 Hz, 1H), 6.53 (d, J=3.2 Hz, 1H), 4.80-4.72 (m, 1H), 2.56 (s, 3H), 2.26-2.15 (m, 2H), 1.48 (d, J=6.4 Hz, 6H), 0.92 (t, J=7.6 Hz, 3H).

Synthesis of 359

Step 1: Synthesis of N-[3-(1,1-difluoropropyl)phenyl]-3-methyl-5-oxo-1-(1-propylindol-6-yl)-4H-pyrazole-4-carboxamide (359)

Compound ID: 359

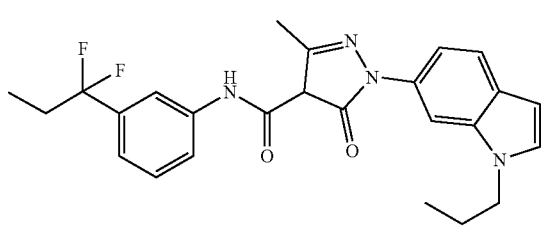 [SMILES: CCCn1ccc2ccc(N3N=C(C)C(C(=O)Nc4cccc(C(F)(F)CC)c4)C3=O)cc21]

359 was obtained via similar procedure of 363 from 369 and 1-iodopropane.

LCMS: (ESI) m/z: 453.3[M+H]$^+$.

$^1$H NMR: (400 MHz, DMSO-d$_6$) δ: 10.98 (s, 1H), 7.92 (s, 1H), 7.79 (s, 1H), 7.70-7.60 (m, 2H), 7.48 (d, J=3.2 Hz, 1H), 7.42 (t, J=8.0 Hz, 1H), 7.32 (dd, J=8.4, 2.0 Hz, 1H), 7.16 (d, J=7.6 Hz, 1H), 6.50 (d, J=2.8 Hz, 1H), 4.16 (t, J=7.2 Hz, 2H), 2.56 (s, 3H), 2.26-2.13 (m, 2H), 1.86-1.76 (m, 2H), 0.92 (t, J=7.6 Hz, 3H), 0.85 (t, J=7.2 Hz, 3H).

Synthesis of 462

Step 1: Synthesis of N-[3-(1,1-difluoropropyl)phenyl]-3-methyl-1-(1-methylindol-6-yl)-5-oxo-4H-pyrazole-4-carboxamide (462)

Compound ID: 462

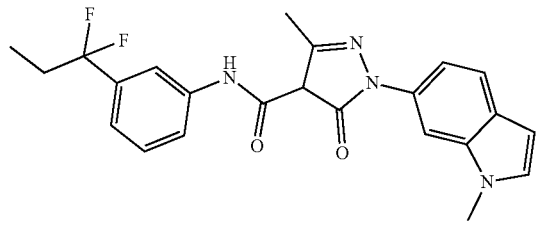 [SMILES: CCC(F)(F)c1cccc(NC(=O)C2C(=O)N(c3ccc4ccn(C)c4c3)N=C2C)c1]

462 was obtained via similar procedure of 366 from 369 and iodomethane.

LCMS: (ESI) m/z: 425.2[M+H]$^+$.

$^1$H NMR: (400 MHz, DMSO-d$_6$) δ: 11.02 (s, 1H), 7.92 (s, 1H), 7.80 (s, 1H), 7.71-7.57 (m, 2H), 7.50-7.32 (m, 3H), 7.15 (d, J=7.6 Hz, 1H), 6.56-6.43 (m, 1H), 3.82 (s, 3H), 2.54 (s, 3H), 2.25-2.15 (m, 2H), 0.92 (t, J=7.2 Hz, 3H).

Synthesis of 463

Step 1: Synthesis of 1-(1-benzylindol-6-yl)-N-[3-(1,1-difluoropropyl)phenyl]-3-methyl-5-oxo-4H-pyrazole-4-carboxamide (463)

Compound ID: 463

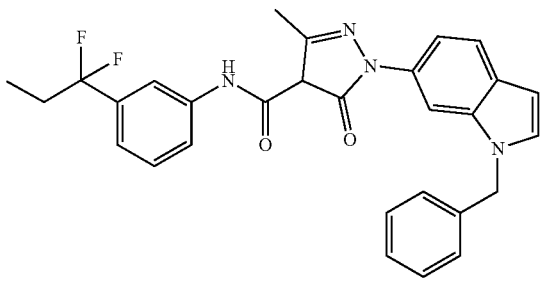 [SMILES: CCC(F)(F)c1cccc(NC(=O)C2C(=O)N(c3ccc4ccn(Cc5ccccc5)c4c3)N=C2C)c1]

463 was obtained via similar procedure of 367 from 369 and (bromomethyl)benzene.

LCMS: (ESI) m/z: 501.3 [M+H]$^+$.

$^1$H NMR: (400 MHz, DMSO-d$_6$) δ: 10.95 (s, 1H), 7.91 (s, 1H), 7.81 (s, 1H), 7.69 (d, J=8.4 Hz, 1H), 7.63-7.56 (m, 2H), 7.42 (s, 1H), 7.35-7.30 (m, 3H), 7.26 (d, J=7.2 Hz, 1H), 7.20-7.14 (m, 3H), 6.58 (d, J=3.2 Hz, 1H), 5.46 (s, 2H), 2.53 (s, 3H), 2.20 (br d, J=7.5 Hz, 2H), 0.92 (t, J=7.6 Hz, 3H).

Synthesis of 464

Step 1: Synthesis of cyclopropyl(3-nitrophenyl)methanone (464-A)

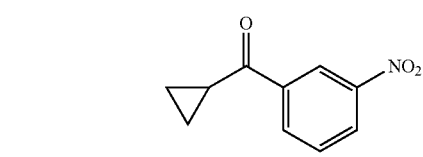 [SMILES: O=C(c1cccc([N+](=O)[O-])c1)C1CC1]

Nitric acid (4.20 g, 63.3 mmol, 4.6 eq) was added to sulfuric acid (11.0 g, 113 mmol, 8.2 eq) with stirring at −5° C., the resulting solution was added drop-wise to another solution of cyclopropyl(phenyl)methanone (2.00 g, 13.7 mmol, 1.0 eq) in sulfuric acid (5 mL) at −10° C. The reaction was stirred at −10° C. for 30 mins. The reaction mixture was poured into ice-water (100 mL), and the resulting mixture was extracted with ethyl acetate (20 mL×3). The combined organic layer was washed with saturated sodium bicarbonate solution (30 mL) and concentrated in vacuo. The residue was purified by silica gel column chromatography (petroleum ether/ethyl acetate, 20/1) to give 2.00 g (76% yield) of 464-A as light-yellow oil.

$^1$H NMR (400 MHz, CDCl$_3$-d) δ: 8.78 (t, J=1.9 Hz, 1H), 8.36-8.34 (m, 1H), 8.28-8.25 (m, 1H), 7.61 (t, J=8.0 Hz, 1H), 2.65-2.63 (m, 1H), 1.28-1.22 (m, 2H), 1.14-1.06 (m, 2H).

Step 2: Synthesis of 1-(cyclopropyldifluoromethyl)-3-nitrobenzene (464-B)

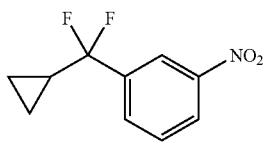 [SMILES: O=[N+]([O-])c1cccc(C(F)(F)C2CC2)c1]

To a solution of 464-A (2.00 g, 10.5 mmol, 1.0 eq) in chloroform (8 mL) was added bis(2-methoxyethyl)aminosulfur trifluoride (4.63 g, 20.9 mmol, 2.0 eq) under nitrogen, the mixture was stirred at 70° C. for 12 hr. The mixture was quenched by water (100 ml) and extracted with ethyl acetate (50 mL×3), the combined organic layer was washed with brine (150 mL), dried over anhydrous sodium sulfate, filtered and concentrated in vacuo. The residue was purified by silica gel column chromatography (petroleum ether/ethyl acetate, from 30/1 to 20/1) to give 250 mg (11% yield) of 464-B as a yellow oil $^1$H NMR (400 MHz, CDCl$_3$-d) δ: 0.69-0.91 (m, 5H) 7.62-7.67 (m, 1H) 7.88-7.91 (m, 1H) 8.30-8.34 (m, 1H) 8.41-8.44 (m, 1H).

Step 3: Synthesis of 3-(cyclopropyldifluoromethyl)aniline (464-C)

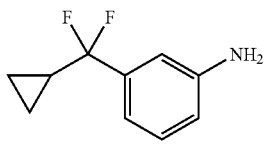

To a solution of 464-B (250 mg, 1.17 mmol, 1.0 eq) in ethanol (10 mL) and water (1 mL) was added iron powder (655 mg, 11.7 mmol, 10 eq) and ammonium chloride (627 mg, 11.7 mmol, 10 eq), the mixture was stirred at 70° C. for 12 hr. The reaction was diluted by water (100 mL) and extracted with ethyl acetate (100 mL×3), the combined organic layer was washed with brine (300 mL), dried over anhydrous sodium sulfate, filtered and concentrated in vacuo to give 200 mg (crude) of 464-C as a yellow oil.

LCMS: (ESI) m/z: 184.1 [M+H]$^+$.

Step 4: Synthesis of N-(3-(cyclopropyldifluoromethyl)phenyl)-1-(5-(difluoromethoxy)pyridin-2-yl)-3-methyl-5-oxo-4,5-dihydro-1H-pyrazole-4-carboxamide (464)

Compound ID: 464

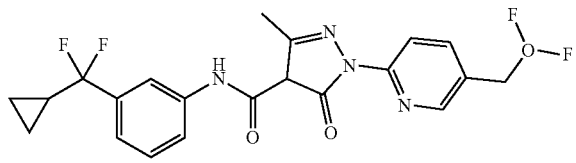

464 was obtained via general procedure IV from 383-D and 464-C.

LCMS: (ESI) m/z: 451.2 [M+H]$^+$.

$^1$H NMR (400 MHz, DMSO-d$_6$) δ: 10.69 (s, 1H), 8.45 (d, J=9.2 Hz, 1H), 8.40 (d, J=2.4 Hz, 1H), 7.96 (s, 1H), 7.91 (dd, J=8.8 Hz, 2.4 Hz, 1H), 7.61 (d, J=8.4 Hz, 1H), 7.42 (t, J=8.0 Hz, 1H), 7.33 (t, J=73.2 Hz, 1H), 7.21 (d, J=7.6 Hz, 1H), 2.55 (s, 3H), 1.75-1.64 (m, 1H), 0.72-0.62 (m, 4H).

Synthesis of 470

Step 1: Synthesis of cyclopentyl(3-nitrophenyl)methanone (470-A)

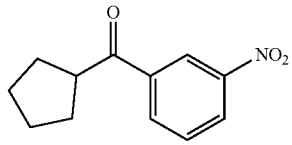 [SMILES: O=C(c1cccc([N+](=O)[O-])c1)C1CCCC1]

Nitric acid (2.12 g, 31.9 mmol, 4.6 eq) was added to sulfuric acid (5.56 g, 56.7 mmol, 8.2 eq) with stirring at −5° C., the resulting solution was added drop-wise to another solution of cyclopentyl(phenyl)methanone (1.20 g, 6.89 mmol, 1.0 eq) in sulfuric acid (5 mL) at −10° C. The reaction was stirred at −10° C. for 30 mins. The reaction mixture was poured into ice-water (100 mL), and the resulting mixture was extracted with ethyl acetate (20 mL×3). The combined organic layer was washed with saturated sodium bicarbonater solution (30 mL) and concentered in vacuo. The residue was purified by silica gel column chromatography (petroleum ether/ethyl acetate, 20/1) to afford 0.600 g (40% yield) of 470-A as light-yellow oil.

$^1$H NMR (400 MHz, DMSO-d$_6$) δ: 8.65 (t, J=2.0 Hz, 1H), 8.49-8.41 (m, 2H), 7.84 (t, J=8.0 Hz, 1H), 3.96-3.92 (m, 1H), 1.97-1.86 (m, 2H), 1.83-1.70 (m, 2H), 1.70-1.58 (m, 4H).

Step 2: Synthesis of 1-(cyclopentyldifluoromethyl)-3-nitrobenzene (470-B)

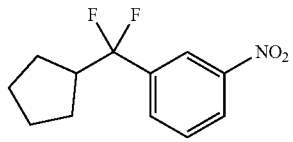 [SMILES: O=[N+]([O-])c1cccc(C(F)(F)C2CCCC2)c1]

Diethylaminosulfur trifluoride (582 mg, 3.61 mmol, 5.3 eq) was added to a solution of 470-A (0.150 g, 684 umol, 1.0 eq) in chloroform (2 mL). The reaction was stirred at 70° C. for 12 hr. The reaction mixture was poured into ice-water (100 mL), and the resulting mixture was extracted with ethyl acetate (20 mL×3). The combined organic layer was washed with saturated sodium bicarbonater solution (30 mL) and concentrated in vacuo. The residue was purified by silica gel column chromatography (petroleum ether/ethyl acetate=20/1) to afford 0.150 g (91% yield) of 470-B as light-yellow oil.

$^1$H NMR (400 MHz, CDCl$_3$-d) δ: 8.27 (s, 1H), 8.22 (br d, J=8.2 Hz, 1H), 7.74 (d, J=7.8 Hz, 1H), 7.60-7.48 (m, 1H), 2.63-2.48 (m, 1H), 1.69-1.52 (m, 6H), 1.52-1.48 (m, 2H).

Step 3: Synthesis of 3-(cyclopentyldifluoromethyl)aniline (470-C)

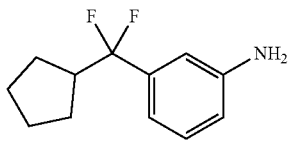 [SMILES: Nc1cccc(C(F)(F)C2CCCC2)c1]

A suspension of 470-B (0.100 g, 415 umol, 1.0 eq), iron powder (232 mg, 4.15 mmol, 10 eq) and ammonium chloride (222 mg, 4.15 mmol, 10 eq) in ethanol (8 mL) and water (2 mL) was stirred at 70° C. for 1 h. It was concentrated to remove ethanol. The result solution was diluted with water (10 mL) and extracted with ethyl acetate (10 mL×3). The combined organic layer was concentrated in vacuo to afford 0.100 g (crude) of 470-C as light-yellow oil.

LCMS: (ESI) m/z: 212.1 [M+H]$^+$.

Step 4: Synthesis of N-(3-(cyclopentyldifluoromethyl)phenyl)-1-(4-(difluoromethoxy)phenyl)-3-methyl-5-oxo-4,5-dihydro-1H-pyrazole-4-carboxamide (470)

Compound ID: 470

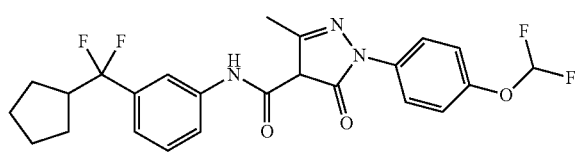 [SMILES: CC1=NN(c2ccc(OC(F)F)cc2)C(=O)C1C(=O)Nc1cccc(C(F)(F)C2CCCC2)c1]

470 was obtained via general procedure IV from 298-C and 470-C.

LCMS: (ESI) m/z: 478.2 [M+H]$^+$.

$^1$H NMR (400 MHz, MeOD-d$_4$) δ: 7.86 (s, 1H), 7.73 (d, J=8.8 Hz, 2H), 7.63 (br d, J=8.2 Hz, 1H), 7.39 (t, J=7.8 Hz, 1H), 7.28 (d, J=8.8 Hz, 2H), 7.18 (d, J=7.8 Hz, 1H), 7.07-6.68 (m, 1H), 2.76-2.66 (m, 1H), 2.57 (s, 3H), 1.71-1.55 (m, 8H)

Synthesis of 471

Step 1: Synthesis of ethyl 2,2-difluoro-2-(3-nitrophenyl)acetate (471-A)

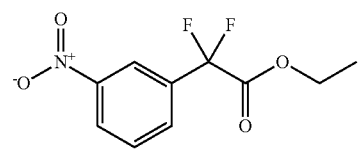

To a solution of 1-iodo-3-nitro-benzene (10.0 g, 40.2 mmol, 1.0 eq) and ethyl 2-bromo-2,2-difluoro-acetate (10.6 g, 52.2 mmol, 1.3 eq) in dimethyl sulfoxide (100 mL) was added copper powder (7.66 g, 120 mmol, 3.0 eq). The solution was stirred at 70° C. for 16 h under nitrogen atmosphere. The solution was diluted with ethyl acetate (200 mL) and the mixture was stirred for 15 min. The mixture was filtered through a celite pad and the filtrate was washed with aqueous hydrochloric acid (1 M, 350 mL). The aqueous layer was extracted with ethyl acetate (100 mL×2). The combined organic layer was washed with brine (250 mL), dried over anhydrous sodium sulfate, filtered and concentrated. The residue was purified by column chromatography on silica gel (petroleum ether/ethyl acetate, from 30/1 to 20/1) to give 4.50 g (46% yield) of 471-A as a yellow oil.

$^1$H NMR (400 MHz, CDCl$_3$-d) δ: 8.51 (s, 1H), 8.39 (dd, J=1.2, 8.4 Hz, 1H), 7.97 (d, J=8.0 Hz, 1H), 7.70 (t, J=8.0 Hz, 1H), 4.35 (q, J=7.2 Hz, 2H), 1.34 (t, J=7.2 Hz, 3H).

Step 2: Synthesis of ethyl 2-(3-aminophenyl)-2,2-difluoroacetate (471-B)

To a solution of 471-A (4.50 g, 18.4 mmol, 1.0 eq) in ethanol (50 mL) and water (10 mL) was added iron powder (5.12 g, 91.8 mmol, 5.0 eq) and ammonium chloride (4.91 g, 91.8 mmol, 5.0 eq). The solution was stirred at 60° C. for 2 h. The solution was filtered through a celite pad and the filtrate was concentrated. The residue was partitioned between ethyl acetate (100 mL) and water (300 mL). The aqueous layer was extracted with ethyl acetate (70 mL×2). The combined organic layer was washed with brine (150 mL), dried over anhydrous sodium sulfate, filtered and concentrated. The residue was purified by column chromatography on silica gel (petroleum ether/ethyl acetate, from 10/1 to 5/1) to give 3.87 g (74% yield) of 471-B as a yellow oil.

$^1$H NMR (400 MHz, CDCl$_3$-d) δ: 7.22 (t, J=8.0 Hz, 1H), 6.98 (dd, J=0.4, 7.6 Hz, 1H), 6.90 (s, 1H), 6. (dd, J=1.2, 7.6 Hz, 1H), 4.30 (q, J=7.2 Hz, 2H), 3.81 (br s, 2H), 1.31 (t, J=7.2 Hz, 3H).

Step 3: Synthesis of ethyl 2-(3-((tert-butoxycarbonyl)amino)phenyl)-2,2-difluoroacetate (471-C)

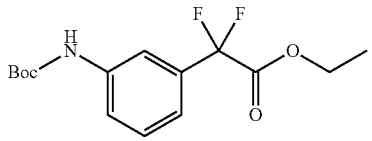 [SMILES: CCOC(=O)C(F)(F)c1cccc(NC(=O)OC(C)(C)C)c1]

To a solution of 471-B (3.87 g, 18.0 mmol, 1.0 eq) in toluene (25 mL) was added di-tert-butyl dicarbonate (5.89 g, 27.0 mmol, 1.5 eq). The solution was stirred at 80° C. for 12 h. The solution was concentrated. The residue was purified by column chromatography on silica gel (petroleum ether/ethyl acetate, 10/1) to give 2.68 g (47% yield) of 471-C a yellow oil.

$^1$H NMR (400 MHz, CDCl$_3$-d) δ: 7.62-7.53 (m, 2H), 7.37 (t, J=8.4 Hz, 1H), 7.31-7.24 (m, 1H), 6.63 (br s, 1H), 4.31 (q, J=7.2 Hz, 2H), 1.53 (s, 9H), 1.32 (t, J=7.2 Hz, 3H).

Step 4: Synthesis of 2-(3-((tert-butoxycarbonyl)amino)phenyl)-2,2-difluoroacetic acid (471-D)

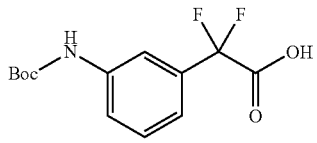 [SMILES: CC(C)(C)OC(=O)Nc1cccc(C(F)(F)C(=O)O)c1]

To a solution of 471-C (2.68 g, 8.48 mmol, 1.0 eq) in ethanol (20 mL) and water (5 mL) was added sodium hydroxide (850 mg, 21.3 mmol, 2.5 eq). The solution was stirred at 15° C. for 12 h. The organic solvent was removed under reduced pressure and the residue was diluted with water (50 mL). The mixture was adjusted to pH=2 by addition of aqueous hydrochloric acid (1 M). The mixture was extracted with ethyl acetate (100 mL×2). The combined organic layer was washed with brine (150 mL), dried over anhydrous sodium sulfate, filtered and concentrated to give 2.25 g (90% yield) of 471-D a yellow gum.

$^1$H NMR (400 MHz, CDCl$_3$-d) δ: 7.54 (br s, 1H), 7.43 (d, J=7.6 Hz, 1H), 7.31 (t, J=7.6 Hz, 1H), 7.25 (d, J=0.8 Hz, 1H), 5.72 (br s, 2H), 1.50 (s, 9H).

Step 5: Synthesis of tert-butyl (3-(1,1-difluoro-2-(methoxy(methyl)amino)-2-oxoethyl)phenyl)carbamate (471-E)

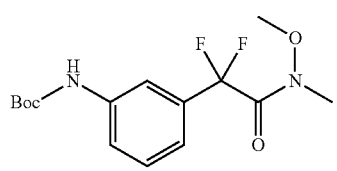 [SMILES: CON(C)C(=O)C(F)(F)c1cccc(NC(=O)OC(C)(C)C)c1]

To a solution of 471-D (2.25 g, 7.82 mmol, 1.0 eq) in ethyl acetate (30 mL) was added propylphosphonic anhydride (9.95 g, 15.6 mmol, 50% purity, 2.0 eq) and N,N-diisopropylethylamine (4.04 g, 31.3 mmol, 4.0 eq). Then N-methoxymethanamine (1.07 g, 10.9 mmol, 1.4 eq, hydrochloride) was added. The solution was stirred at 15° C. for 12 h. The solution was diluted with ethyl acetate (50 ml) and washed with water (100 mL). The aqueous layer was extracted with ethyl acetate (50×2 mL). The combined organic layer was dried over anhydrous sodium sulfate, filtered and concentrated. The residue was purified by column chromatography on silica gel (petroleum ether/ethyl acetate, 5/1) to give 1.98 g (75% yield) of 471-E as a light yellow gum.

$^1$H NMR (400 MHz, CDCl$_3$-d) δ: 7.57 (d, J=7.2 Hz, 1H), 7.49 (s, 1H), 7.36 (t, J=8.0 Hz, 1H), 7.20 (d, J=7.6 Hz, 1H), 6.62 (br s, 1H), 4.13 (q, J=7.2 Hz, 1H), 3.54 (br s, 3H), 3.22 (s, 3H), 1.55 (s, 9H).

Step 6: Synthesis of 2-(3-aminophenyl)-2,2-difluoro-N-methoxy-N-methylacetamide (471-F)

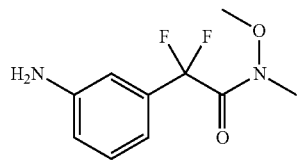 [SMILES: CON(C)C(=O)C(F)(F)c1cccc(N)c1]

To a solution of 471-E (600 mg, 1.77 mmol, 1.0 eq) in dichloromethane (10 mL) was added hydrochloric acid/ethyl acetate (4 M, 4 mL, 9.0 eq). The solution was stirred at 20° C. for 1 h. The solution was added to saturated sodium bicarbonate solution (50 mL) and extracted with dichloromethane (50 mL×2). The combined organic layer was washed with brine (50 mL), dried over anhydrous sodium sulfate, filtered and concentrated. The residue was purified by prep-TLC (petroleum ether/ethyl acetate, 2/1) to give 330 mg (79% yield) of 471-F a yellow gum.

LCMS: (ESI) m/z: 231.2 [M+H]$^+$.

$^1$H NMR (400 MHz, CDCl$_3$-d) δ: 7.22 (t, J=8.0 Hz, 1H), 6.94 (dd, J=0.8, 8.0 Hz, 1H), 6.85 (s, 1H), 6.78-6.75 (m, 1H), 3.52 (br s, 3H), 3.23 (s, 3H).

Step 7: Synthesis of N-(3-(1,1-difluoro-2-(methoxy(methyl)amino)-2-oxoethyl)phenyl)-1-(4-(difluoromethoxy)-3-(pyridin-2-yl)phenyl)-3-methyl-5-oxo-4,5-dihydro-1H-pyrazole-4-carboxamide (471)

Compound ID: 471

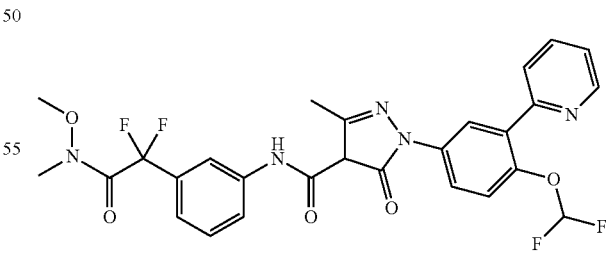

471 was obtained via general procedure IV from 377-F and 471-F.

LCMS: (ESI) m/z: 574.3 [M+H]$^+$.

$^1$H NMR (400 MHz, MeOD-d$_4$) δ: 8.70 (d, J=4.4 Hz, 1H), 8.07-7.98 (m, 3H), 7.88-7.84 (m, 2H), 7.67 (d, J=8.0 Hz, 1H), 7.53-7.42 (m, 3H), 7.21 (d, J=8.0 Hz, 1H), 6.89 (t, J=73.6 Hz, 1H), 3.51 (s, 3H), 3.24 (s, 3H), 2.60 (s, 3H).

Synthesis of 472

Step 1: Synthesis of N-[3-(1,1-difluoropropyl)phenyl]-3-methyl-5-oxo-1-(1-phenylindol-6-yl)-4H-pyrazole-4-carboxamide (472)

Compound ID: 472

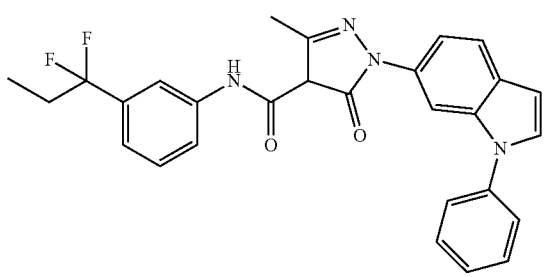 [SMILES: CCC(F)(F)c1cccc(NC(=O)C2C(=O)N(c3ccc4ccn(-c5ccccc5)c4c3)N=C2C)c1]

472 was obtained via similar procedure of 361 from 369 and iodobenzene.

LCMS: (ESI) m/z: 487.2[M+H]⁺.

¹H NMR: (400 MHz, DMSO-d₆) δ: 11.05 (br s, 1H), 8.04 (br s, 1H), 7.90 (s, 1H), 7.56-7.73 (m, 8H), 7.41-7.47 (m, 1H), 7.38 (t, J=7.6 Hz, 1H), 7.10 (d, J=7.6 Hz, 1H), 6.72 (d, J=3.2 Hz, 1H), 2.44 (br s, 3H), 2.14-2.24 (m, 2H), 0.92 (t, J=7.2 Hz, 3H).

Synthesis of 474

Step 1: Synthesis of di-tert-butyl 1-(quinolin-7-yl)hydrazine-1,2-dicarboxylate (474-A)

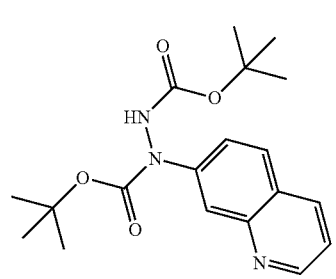 [SMILES: CC(C)(C)OC(=O)NN(C(=O)OC(C)(C)C)c1ccc2cccnc2c1]

To a 100 mL round-bottom flask equipped with a magnetic stir bar was added 7-bromoquinoline (2.00 g, 9.61 mmol, 1.0 eq), tert-butyl N-(tert-butoxycarbonylamino)carbamate (3.35 g, 14.4 mmol, 1.5 eq), 1,10-phenanthroline (866 mg, 4.81 mmol, 0.50 eq), cesium carbonate (6.26 g, 19.2 mmol, 2.0 eq) followed by the addition of N,N-dimethylformamide (50 mL). Then copper (I) iodide (1.83 g, 9.61 mmol, 1.0 eq) was added into the mixture. The flask was then evacuated and backfilled with nitrogen for three times. The mixture was stirred at 80° C. under an atmosphere of nitrogen for 12 hr. The mixture was concentrated in vacuum directly to give a residue. Then the residue was diluted with saturated ammonium chloride solution (200 mL) and ethyl acetate 80 (mL) and filtered, the filtrate was extracted with ethyl acetate (50 mL×2). The combined organic layer was washed with water (50 mL) and brine (50 mL), dried over anhydrous sodium sulfate, filtered, and concentrated under reduced pressure affording a residue. The residue was purified by silica gel column chromatography (petroleum ether/ethyl acetate, from 5/1 to 3/1) to give 1.43 g (38% yield) of 474-A as a light yellow oil.

LCMS: (ESI) m/z: 360.1 [M+H]⁺.

Step 2: Synthesis of 7-hydrazinylquinoline (474-B)

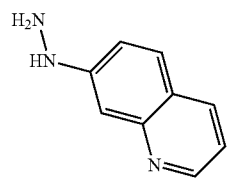 [SMILES: NNc1ccc2cccnc2c1]

To a 50 mL round-bottom flask equipped with a magnetic stir bar was added 474-A (0.700 g, 1.95 mmol, 1.0 eq) followed by the addition of ethyl acetate (5 mL). Then hydrogen chloride/ethyl acetate (4 M, 5 mL, 10 eq) was added into the mixture. The mixture was stirred at 30° C. for 3 h. The mixture was concentrated under reduced pressure to give 540 mg (crude, hydrochloride) of 474-B as a light yellow solid.

LCMS: (ESI) m/z: 160.3 [M+H]⁺.

Step 3: Synthesis of 3-methyl-1-(quinolin-7-yl)-1H-pyrazol-5(4H)-one (474-C)

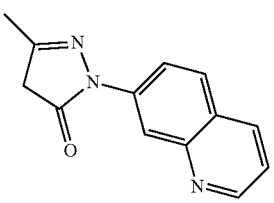 [SMILES: CC1=NN(c2ccc3cccnc3c2)C(=O)C1]

474-C was obtained via general procedure II from 474-B

LCMS: (ESI) m/z: 226.1 [M+H]⁺.

Step 4: Synthesis of 4-nitrophenyl 3-methyl-5-oxo-1-(quinolin-7-yl)-4,5-dihydro-1H-pyrazole-4-carboxylate (474-D)

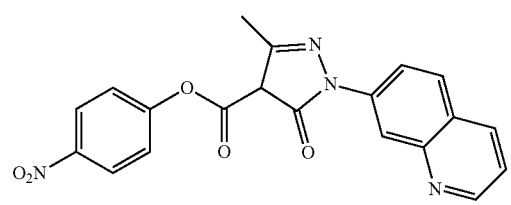 [SMILES: CC1=NN(c2ccc3cccnc3c2)C(=O)C1C(=O)Oc1ccc([N+](=O)[O-])cc1]

474-D was obtained via general procedure III from 474-C

LCMS: (ESI) m/z: 391.1 [M+H]⁺.

Step 5: Synthesis of N-(3-(1,1-difluoropropyl)phenyl)-3-methyl-5-oxo-1-(quinolin-7-yl)-4,5-dihydro-1H-pyrazole-4-carboxamide (474)

Compound ID: 474

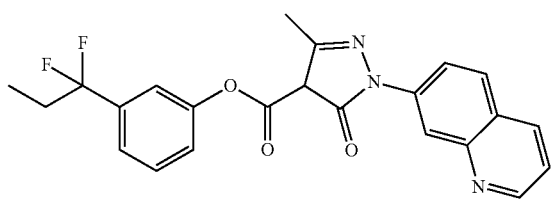 [SMILES: CCC(F)(F)c1cccc(OC(=O)C2C(=O)N(c3ccc4cccnc4c3)N=C2C)c1]

474 was obtained via general procedure IV from 474-D
LCMS: (ESI) m/z: 423.1 [M+H]+.
1H NMR (MeOD-d4, 400 MHz) δ: 8.91 (d, J=4.4 Hz, 1H), 8.65-8.68 (m, 2H), 8.46 (d, J=7.6 Hz, 1H), 8.14 (d, J=9.2 Hz, 1H), 7.86 (s, 1H), 7.65 (d, J=8.0 Hz, 2H), 7.39 (t, J=8.0 Hz, 1H), 7.16 (d, J=8.0 Hz, 1H), 2.53 (s, 3H), 2.12-2.26 (m, 2H), 0.99 (t, J=7.6 Hz, 3H).

Synthesis of 475

Step 1: Synthesis of (1H-benzo[d][1,2,3]triazol-1-yl)(phenyl)methanone (475-A)

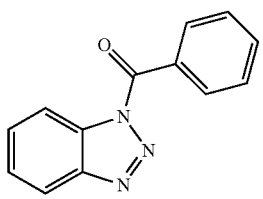 [SMILES: O=C(c1ccccc1)n1nnc2ccccc21]

475-A was obtained via similar procedure of 478-A from 1H-benzotriazole and benzoyl chloride Step 2: Synthesis of 1-(1-benzoylindol-6-yl)-N-[3-(1,1-difluoropropyl)phenyl]-3-methyl-5-oxo-4H-pyrazole-4-carboxamide (475)

Compound ID: 475

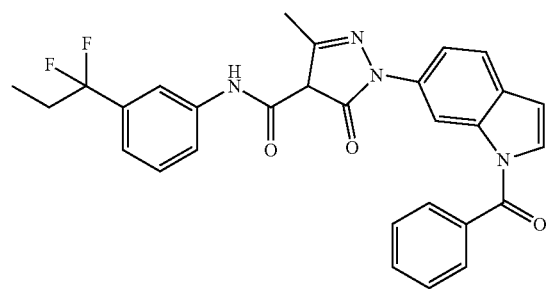 [SMILES: CCC(F)(F)c1cccc(NC(=O)C2C(=O)N(c3ccc4ccn(C(=O)c5ccccc5)c4c3)N=C2C)c1]

475 was obtained via similar procedure of 478 from 369 and 475-A.
LCMS: (ESI) m/z: 515.2 [M+H]+.
1H NMR: (400 MHz, DMSO-d6) δ: 10.90 (s, 1H), 8.75 (d, J=1.6 Hz, 1H), 7.93 (s, 1H), 7.83-7.79 (m, 3H), 7.74-7.69 (m, 2H), 7.64 (d, J=7.6 Hz, 2H), 7.46 (d, J=3.6 Hz, 1H), 7.43 (t, J=8.0 Hz, 1H), 7.16 (d, J=8.0 Hz, 1H), 6.82 (d, J=3.6 Hz, 1H), 2.58 (s, 3H), 2.25-2.15 (m, 2H), 0.92 (t, J=7.6 Hz, 3H).

Synthesis of 476

Step 1: Synthesis of N-(3-(1,1-difluoropropyl)phenyl)-3-methyl-5-oxo-1-(1-(phenylsulfonyl)-1H-indol-6-yl)-4,5-dihydro-1H-pyrazole-4-carboxamide (476)

Compound ID: 476

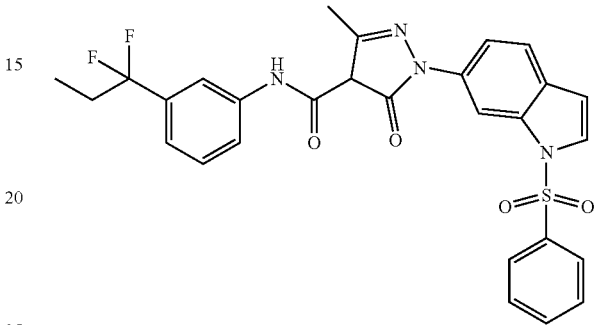

476 was obtained via similar procedure of 367 from 369 and benzenesulfonyl chloride.
LCMS: (ESI) m/z: 551.1 [M+H]+.
1H NMR (400 MHz, DMSO-d6) δ: 10.88 (s, 1H), 8.46 (s, 1H), 8.04-8.00 (m, 2H), 7.96 (s, 1H), 7.85 (d, J=3.6 Hz, 1H), 7.70 (t, J=8.8 Hz, 2H), 7.64-7.58 (m, 4H), 7.43 (t, J=8.0 Hz, 1H), 7.16 (d, J=7.6 Hz, 1H), 6.89 (d, J=4.0 Hz, 1H), 2.56 (s, 3H), 2.25-2.16 (m, 2H), 0.93 (t, J=7.2 Hz, 3H).

Synthesis of 477

Step 1: Synthesis of N-[3-(1,1-difluoropropyl)phenyl]-3-methyl-5-oxo-1-[1-(2-phenylethyl)indol-6-yl]-4H-pyrazole-4-carboxamide (477)

Compound ID: 477

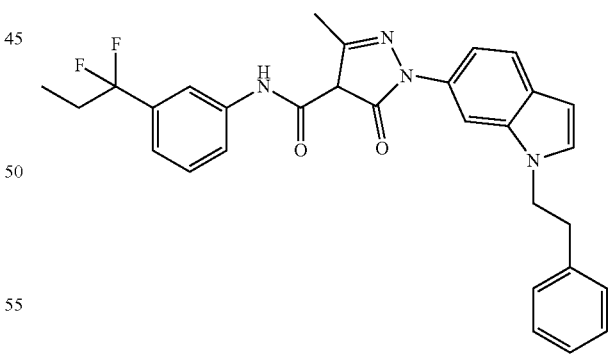

477 was obtained via similar procedure of 367 from 369 and 2-iodoethylbenzene.
LCMS: (ESI) m/z: 515.2[M+H]+.
1H NMR: (400 MHz, DMSO-d6) δ: 10.99 (s, 1H), 7.93 (s, 1H), 7.84 (s, 1H), 7.67-7.61 (m, 2H), 7.43 (t, J=8.0 Hz, 1H), 7.36-7.31 (m, 2H), 7.29-7.25 (m, 2H), 7.24-7.19 (m, 3H), 7.16 (d, J=8.0 Hz, 1H), 6.44 (d, J=3.2 Hz, 1H), 4.44 (t, J=7.6 Hz, 2H), 3.11 (t, J=7.2 Hz, 2H), 2.58 (s, 3H), 2.26-2.15 (m, 2H), 0.92 (t, J=7.6 Hz, 3H).

Synthesis of 478

Step 1: Synthesis of 1-(benzotriazol-1-yl)butan-1-one (478-A)

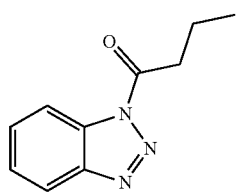

To a solution of 1H-benzotriazole (0.500 g, 4.20 mmol, 1.0 eq) in dichloromethane (5 mL) was added triethylamine (1.30 g, 12.6 mmol, 3.0 eq) under 25° C., it was stirred 15 min, Then the butanoyl chloride (0.540 g, 5.04 mmol, 1.2 eq) was added into the solution. The mixture was stirred at 25° C. for 15 min. The mixture was concentrated in vacuum directly to give 0.750 g (crude) of 478-A as a yellow solid.

Step 2: Synthesis of 1-(1-butanoylindol-6-yl)-N-[3-(1,1-difluoropropyl)phenyl]-3-methyl-5-oxo-4H-pyrazole-4-carboxamide (478)

Compound ID: 478

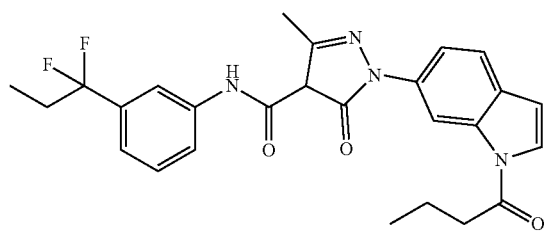 [SMILES: CCCC(=O)n1ccc2ccc(N3N=C(C)C(C(=O)Nc4cccc(C(F)(F)CC)c4)C3=O)cc21]

To a solution of 367 (80.0 mg, 195 umol, 1.0 eq) in N,N-dimethyl formamide (1 mL) was added sodium hydride (16.0 mg, 404 umol, 60% purity, 2.1 eq) under 0° C., it was stirred at 5 min. Then the 478-A (46.0 mg, 242 umol, 1.2 eq) was added into the solution. The mixture was stirred at 0° C. for 10 min. The mixture was quenched with hydrochloric acid (20 mL, 0.5 M), then extracted with ethyl acetate (10 mL×3), the combined organic layer was washed with brine (20 mL×1), dried over anhydrous sodium sulfate, filtered and concentrated under reduced pressure to give a residue. The residue was purified by pre-HPLC (column: Phenomenex Synergi C18 150*25*10 um; mobile phase: [water (0.225% formic acid)-acetonitrile]; B %: 52%-82%, 10 min) to give 13.0 mg (14% yield) of 478 as a yellow solid.

LCMS: (ESI) m/z: 481.2 [M+H]$^+$.

$^1$H NMR: (400 MHz, DMSO-$d_6$) δ: 10.89 (s, 1H), 8.75 (s, 1H), 8.00 (d, J=3.6 Hz, 1H), 7.92 (s, 1H), 7.75 (d, J=8.8 Hz, 1H), 7.66-7.60 (m, 2H), 7.43 (t, J=8.0 Hz, 1H), 7.17 (d, J=7.6 Hz, 1H), 6.80 (d, J=3.6 Hz, 1H), 3.06 (t, J=7.2 Hz, 2H), 2.57 (s, 3H), 2.26-2.15 (m, 2H), 1.78-1.71 (m, 2H), 1.01 (t, J=7.6 Hz, 3H), 0.92 (t, J=7.6 Hz, 3H).

Synthesis of 479

Step 1: Synthesis of (1H-benzo[d][1,2,3]triazol-1-yl)(o-tolyl)methanone (479-A)

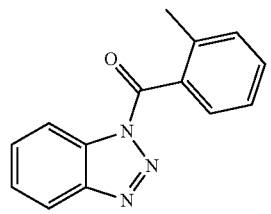 [SMILES: Cc1ccccc1C(=O)n1nnc2ccccc21]

479-A was obtained via similar procedure of 478-A from 1H-benzotriazole and 2-methylbenzoyl chloride.

Step 2: Synthesis of N-[3-(1,1-difluoropropyl)phenyl]-3-methyl-1-[1-(2-methylbenzoyl)indol-6-yl]-5-oxo-4H-pyrazole-4-carboxamide (479)

Compound ID: 479

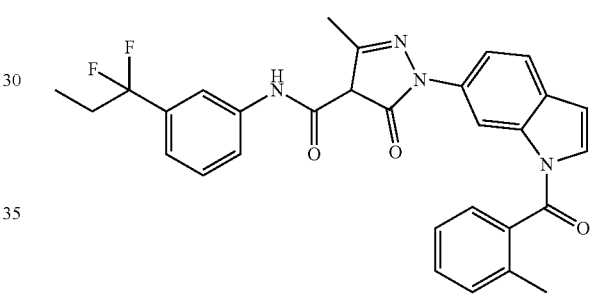

479 was obtained via similar procedure of 478 from 369 and 479-A.

LCMS: (ESI) m/z: 529.2[M+H]$^+$.

$^1$H NMR: (400 MHz, DMSO-$d_6$) δ: 10.88 (s, 1H), 8.78 (d, J=1.6 Hz, 1H), 7.93 (s, 1H), 7.81 (d, J=8.4 Hz, 1H), 7.71 (dd, J=8.4, 2.0 Hz, 1H), 7.67-7.63 (m, 1H), 7.53 (d, J=7.6 Hz, 2H), 7.46-7.38 (m, 3H), 7.17 (d, J=7.6 Hz, 1H), 7.11 (d, J=3.6 Hz, 1H), 6.79 (d, J=3.6 Hz, 1H), 2.59 (s, 3H), 2.28 (s, 3H), 2.25-2.15 (m, 2H), 0.92 (t, J=7.6 Hz, 3H).

Synthesis of 480

Step 1: Synthesis of (1H-benzo[d][1,2,3]triazol-1-yl)(p-tolyl)methanone (480-A)

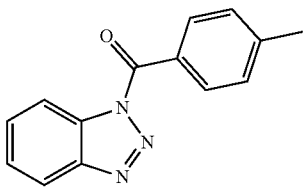 [SMILES: Cc1ccc(C(=O)n2nnc3ccccc32)cc1]

480-A was obtained via similar procedure of 478-A from 1H-benzotriazole and 4-methylbenzoyl chloride Step 2: Synthesis of N-[3-(1,1-difluoropropyl)phenyl]-3-methyl-1-[1-(4-methylbenzoyl)indol-6-yl]-5-oxo-4H-pyrazole-4-carboxamide (480)

Compound ID: 480

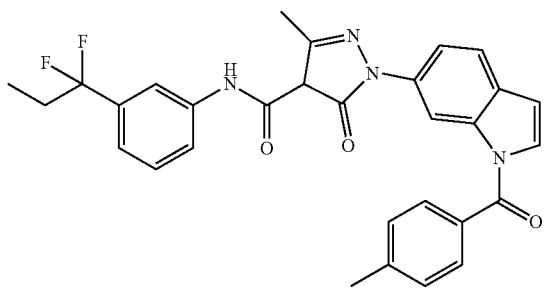 [SMILES: CCC(F)(F)c1cccc(NC(=O)C2C(=O)N(c3ccc4ccn(C(=O)c5ccc(C)cc5)c4c3)N=C2C)c1]

480 was obtained via similar procedure of 478 from 369 and 480-A.
LCMS: (ESI) m/z: 529.2[M+H]+.
1H NMR: (400 MHz, DMSO-d6) δ: 10.91 (s, 1H), 8.72 (d, J=1.6 Hz, 1H), 7.92 (s, 1H), 7.80 (d, J=8.4 Hz, 1H), 7.70 (d, J=8.0 Hz, 3H), 7.64 (d, J=8.0 Hz, 1H), 7.49 (d, J=3.6 Hz, 1H), 7.46-7.40 (m, 3H), 7.16 (d, J=7.6 Hz, 1H), 6.81 (d, J=3.6 Hz, 1H), 2.57 (s, 3H), 2.44 (s, 3H), 2.26-2.15 (m, 2H), 0.92 (t, J=7.6 Hz, 3H).

Synthesis of 481

Step 1: Synthesis of N-(3-(cyclopropyldifluoromethyl)phenyl)-1-(4-(difluoromethoxy)phenyl)-3-methyl-5-oxo-4,5-dihydro-1H-pyrazole-4-carboxamide (481)

Compound ID: 481

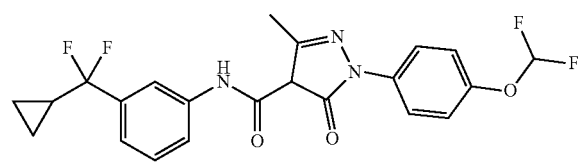 [SMILES: CC1=NN(c2ccc(OC(F)F)cc2)C(=O)C1C(=O)Nc1cccc(C(F)(F)C2CC2)c1]

481 was obtained via general procedure IV from 298-C and 464-C.
LCMS: (ESI) m/z: 450.0 [M+H]+.
1HNMR (400 MHz, MeOD-d4) δ: 7.92 (s, 1H), 7.69 (d, J=2.0 Hz, 2H), 7.63 (d, J=8.0 Hz, 1H), 7.41 (t, J=8.0 Hz, 1H), 7.32 (d, J=8.0 Hz, 2H), 7.26 (d, J=7.6 Hz, 1H), 6.91 (t, J=73.6 Hz, 1H), 2.63 (s, 3H), 1.66-1.54 (m, 1H), 0.72-0.69 (m, 4H).

Synthesis of 482

Step 1: Synthesis of 4-((tert-butyldimethylsilyl)oxy)benzoic acid (482-A)

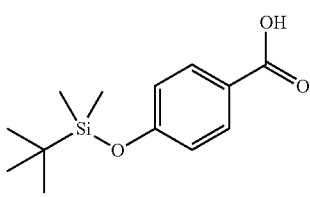 [SMILES: CC(C)(C)[Si](C)(C)Oc1ccc(C(=O)O)cc1]

482-A was obtained via similar procedure of 493-A from 4-hydroxybenzoic acid and tert-butylchlorodimethylsilane
LCMS: (ESI) m/z: 253.1 [M+H]+.

Step 2: Synthesis of 4-((tert-butyldimethylsilyl)oxy)benzoyl chloride (482-B)

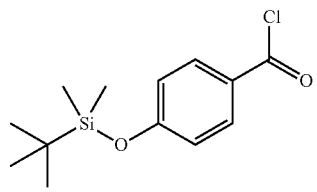 [SMILES: CC(C)(C)[Si](C)(C)Oc1ccc(C(=O)Cl)cc1]

482-B was obtained via similar procedure of 493-B from 482-A and oxalyl chloride Step 3: Synthesis of (1H-benzo[d][1,2,3]triazol-1-yl)(4-((tert-butyldimethylsilyl)oxy)phenyl)methanone (482-C)

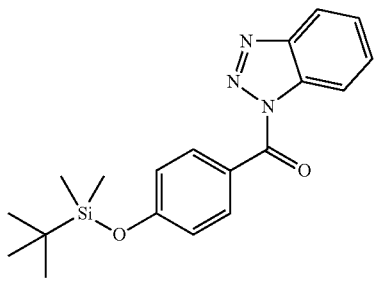 [SMILES: CC(C)(C)[Si](C)(C)Oc1ccc(C(=O)n2nnc3ccccc32)cc1]

482-C was obtained via similar procedure of 493-C from 482-B and 1H-benzo[d][1,2,3]triazole Step 4: Synthesis of N-(3-(1,1-difluoropropyl)phenyl)-1-(1-(4-hydroxybenzoyl)-1H-indol-6-yl)-3-methyl-5-oxo-4,5-dihydro-1H-pyrazole-4-carboxamide (482)

Compound ID: 482

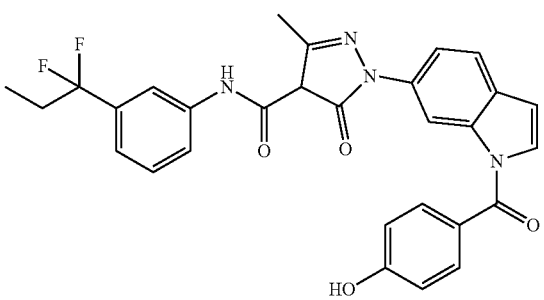 [SMILES: CCC(F)(F)c1cccc(NC(=O)C2C(=O)N(c3ccc4ccn(C(=O)c5ccc(O)cc5)c4c3)N=C2C)c1]

482 was obtained via similar procedure of 493 from 482-C and 369
LCMS: (ESI) m/z: 531.1 [M+H]+
1H NMR (400 MHz, DMSO-d6) δ: 10.92 (s, 1H), 10.45 (s, 1H), 8.66 (s, 1H), 7.92 (s, 1H), 7.79 (d, J=8.6 Hz, 1H), 7.74-7.66 (m, 3H), 7.63 (br d, J=8.6 Hz, 1H), 7.60-7.55 (m, 1H), 7.42 (t, J=8.0 Hz, 1H), 7.16 (br d, J=7.6 Hz, 1H), 7.06-6.92 (m, 2H), 6.79 (d, J=3.6 Hz, 1H), 2.56 (s, 3H), 2.20 (dt, J=7.6, 16.4 Hz, 2H), 0.92 (t, J=7.2, 3H).
Synthesis of 483

Step 1: Synthesis of (1H-benzo[d][1,2,3]triazol-1-yl)(m-tolyl)methanone (483-A)

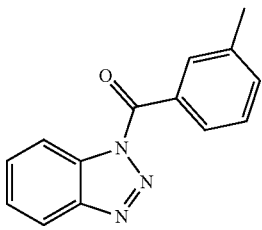 [SMILES: Cc1cccc(C(=O)n2nnc3ccccc32)c1]

483-A was obtained via similar procedure of 478-A from 1H-benzotriazole and 3-methylbenzoyl chloride Step 2: Synthesis of N-[3-(1,1-difluoropropyl)phenyl]-3-methyl-1-[1-(3-methylbenzoyl)indol-6-yl]-5-oxo-4H-pyrazole-4-carboxamide (483)

Compound ID: 483

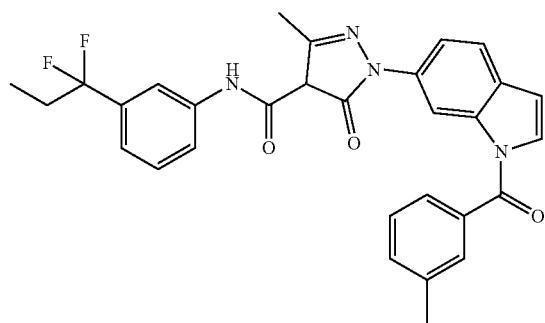 [SMILES: CCC(F)(F)c1cccc(NC(=O)C2C(=O)N(c3ccc4ccn(C(=O)c5cccc(C)c5)c4c3)N=C2C)c1]

483 was obtained via similar procedure of 478 from 369 and 483-A.
LCMS: (ESI) m/z: 529.2[M+H]$^+$.
$^1$H NMR: (400 MHz, DMSO-d$_6$) δ: 10.88 (s, 1H), 8.72 (d, J=1.6 Hz, 1H), 7.93 (s, 1H), 7.82 (d, J=8.4 Hz, 1H), 7.68 (dd, J=8.4, 2.0 Hz, 1H), 7.64 (d, J=9.2 Hz, 1H), 7.61 (s, 1H), 7.59-7.56 (m, 1H), 7.54-7.49 (m, 2H), 7.47 (d, J=3.6 Hz, 1H), 7.43 (t, J=8.0 Hz, 1H), 7.17 (d, J=7.6 Hz, 1H), 6.82 (d, J=3.6 Hz, 1H), 2.59 (s, 3H), 2.43 (s, 3H), 2.26-2.15 (m, 2H), 0.92 (t, J=7.6 Hz, 3H).
Synthesis of 484

Step 1: Synthesis of N-methoxy-N-methylisonicotinamide (484-A)

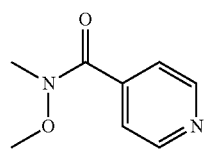

To a suspension of isonicotinic acid (3.00 g, 24.4 mmol, 1.0 eq) in dichloromethane (30 mL) was added N,N-carbonyldiimidazole (4.74 g, 29.2 mmol, 1.2 eq). The mixture was stirred at 25° C. for 0.5 h. Then N-methoxymethanamine (2.85 g, 29.2 mmol, 1.2 eq, hydrochloride) was added. The mixture was stirred at 25° C. for 12 h. The mixture was concentrated in vacuo. The residue was adjusted with saturated sodium bicarbonate aqueous to pH=8 and extracted with ethyl acetate (30 mL×5). The combined organic layer was dried over anhydrous sodium sulfate, filtered and concentrated to give 4.50 g (crude) of 484-A as a light yellow oil.
$^1$H NMR (400 MHz, CDCl$_3$-d) δ: 8.71 (d, J=6.0 Hz, 2H), 7.53 (d, J=6.0 Hz, 2H), 3.55 (s, 3H), 3.38 (s, 3H).

Step 2: Synthesis of 1-(pyridin-4-yl)propan-1-one (484-B)

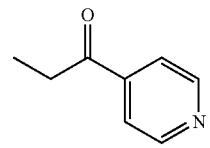

To a solution of 484-A (1.00 g, 6.02 mmol, 1.0 eq) in tetrahydrofuran (10 mL) was added dropwise ethylmagnesium bromide (3 M, 4.0 mL, 2.0 eq) at −78° C. The mixture was stirred at −78° C. for 1 h. The reaction mixture was quenched by addition saturated ammonium chloride aqueous (30 mL), and then extracted with ethyl acetate (30 mL×2). The combined organic layer was washed with brine (30 mL×1), dried over anhydrous sodium sulfate, filtered and concentrated under reduced pressure to give a residue. The residue was purified by silica gel column chromatography (petroleum ether/ethyl acetate, from 5/1 to 3/1) to give 0.450 g (55% yield) of 484-B as a colorless oil.
$^1$H NMR (400 MHz, CDCl$_3$-d) δ: 8.81 (d, J=6.0 Hz, 2H), 7.74 (d, J=6.0 Hz, 2H), 3.02 (q, J=7.2 Hz, 2H), 1.25 (t, J=7.2 Hz, 3H).

Step 3: Synthesis of 4-propionylpyridine 1-oxide (484-C)

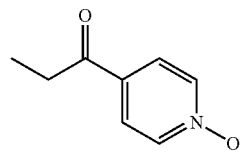

To a solution of 484-B (0.450 g, 3.33 mmol, 1.0 eq) in dichloromethane (10 mL) was added 3-chlorobenzenecarboperoxoic acid (676 mg, 3.33 mmol, 85% purity, 1.0 eq). The mixture was stirred at 25° C. for 12 hr. The mixture was concentrated directly. The residue was purified by silica gel column chromatography (petroleum ether/ethyl acetate=3/1 to ethyl acetate/methanol=10/1) to give 0.480 g (95% yield) of 484-C as a white solid.
$^1$H NMR (400 MHz, CDCl$_3$-d) δ: 8.26 (d, J=7.2 Hz, 2H), 7.83 (d, J=7.2 Hz, 2H), 2.97 (q, J=7.2 Hz, 2H), 1.25 (t, J=7.2 Hz, 3H).

Step 4: Synthesis of 2-(4-propionylpyridin-2-yl)isoindoline-1,3-dione (484-D)

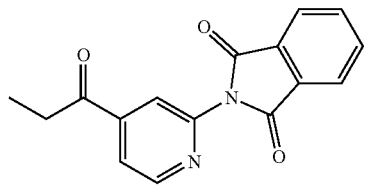 [SMILES: CCC(=O)c1ccnc(N2C(=O)c3ccccc3C2=O)c1]

To a solution of 484-C (0.380 g, 2.51 mmol, 1.0 eq) in dichloromethane (10 mL) were added isoindoline-1,3-dione (370 mg, 2.51 mmol, 1.0 eq), 4-methylbenzene-1-sulfonyl chloride (719 mg, 3.77 mmol, 1.5 eq) and N,N-diisopropylethylamine (650 mg, 5.03 mmol, 2.0 eq). The mixture was stirred at 25° C. for 1 hr. The mixture was concentrated in vacuo. The residue was purified by silica gel column chromatography (petroleum ether/ethyl acetate, from 5/1 to 2/1) to give 0.740 g (73% yield) of 484-D as a light yellow solid.

LCMS: (ESI) m/z: 281.0 [M+H]$^+$.

$^1$H NMR (400 MHz, CDCl$_3$-d) δ: 8.86 (d, J=5.2 Hz, 1H), 8.01 (dd, J=3.2, 5.2 Hz, 2H), 7.92-7.89 (m, 1H), 7.87-7.79 (m, 3H), 3.06 (q, J=7.2 Hz, 2H), 1.27 (t, J=7.2 Hz, 3H).

Step 5: Synthesis of 2-(4-(1,1-difluoropropyl)pyridin-2-yl)isoindoline-1,3-dione (484-E)

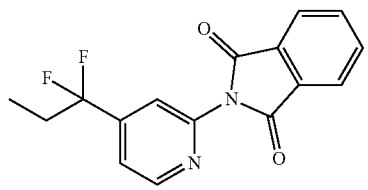 [SMILES: CCC(F)(F)c1ccnc(N2C(=O)c3ccccc3C2=O)c1]

To a solution of 484-D (0.640 g, 2.01 mmol, 1.0 eq) in chloroform (10 mL) was added diethylaminosulfur trifluoride (1.62 g, 10.1 mmol, 5.0 eq). The mixture was stirred at 50° C. for 2 hr. The reaction mixture was poured into saturated sodium bicarbonate aqueous (20 mL) and extracted with ethyl acetate (20 mL×2). The combined organic layer was washed with brine (20 mL×1), dried over anhydrous sodium sulfate, filtered and concentrated under reduced pressure to give a residue. The residue was purified by silica gel column (petroleum ether/ethyl acetate, from 10/1 to 5/1) to give 0.450 g (73% yield) of 484-E as a yellow gum.

LCMS: (ESI) m/z: 303.1 [M+H]$^+$.

$^1$H NMR (400 MHz, CDCl$_3$-d) δ: 8.70 (d, J=5.2 Hz, 1H), 7.93 (dd, J=3.2, 5.2 Hz, 2H), 7.76 (dd, J=3.2, 5.2 Hz, 2H), 7.48 (s, 1H), 7.37 (d, J=5.2 Hz, 1H), 2.17-2.06 (m, 2H), 0.99 (t, J=7.6 Hz, 3H).

Step 6: Synthesis of 4-(1,1-difluoropropyl)pyridin-2-amine (484-F)

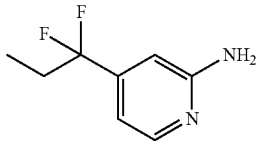

To a solution of 484-E (0.450 g, 1.47 mmol, 1.0 eq) in ethanol (5 mL) was added hydrazine hydrate (174 mg, 2.95 mmol, 85% purity, 2.0 eq). The mixture was stirred at 25° C. for 1 hr. The mixture was diluted with dichloromethane (10 ml) and filtered. The organic layer was washed with water (10 mL), dried over anhydrous sodium sulfate, filtered and concentrated to give 0.220 g (87% yield) of 484-F as a light yellow solid.

$^1$H NMR (400 MHz, CDCl$_3$-d) δ: 8.13 (d, J=5.2 Hz, 1H), 6.69 (dd, J=5.2, 1.2 Hz, 1H), 6.57 (s, 1H), 4.59 (br s, 2H), 2.14-2.03 (m, 2H), 0.99 (t, J=7.6 Hz, 3H).

Step 7: Synthesis of 1-(4-(difluoromethoxy)phenyl)-N-(4-(1,1-difluoropropyl)pyridin-2-yl)-3-methyl-5-oxo-4,5-dihydro-1H-pyrazole-4-carboxamide (484)

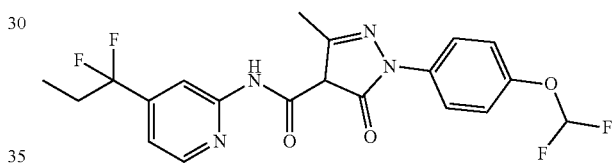

484 was obtained via general procedure IV from 402-C and 484-E.

LCMS: (ESI) m/z: 439.1 [M+H]$^+$.

$^1$H NMR (400 MHz, MeOD-d$_4$) δ: 8.38-8.33 (m, 2H), 7.70 (d, J=8.8 Hz, 2H), 7.30 (d, J=8.8 Hz, 2H), 7.20 (dd, J=1.6, 5.2 Hz, 1H), 6.89 (t, J=73.2 Hz, 1H), 2.61 (s, 3H), 2.26-2.16 (m, 2H), 1.02 (t, J=7.6 Hz, 3H).

Synthesis of 485

Step 1: Synthesis of di-tert-butyl 1-(benzo[b]thiophen-6-yl)hydrazine-1,2-dicarboxylate (485-A)

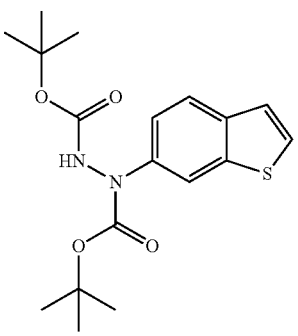 [SMILES: CC(C)(C)OC(=O)NN(C(=O)OC(C)(C)C)c1ccc2ccsc2c1]

485-A was obtained via similar procedure of 410-B from 6-bromobenzo[b]thiophene and di-tert-butyl hydrazine-1,2-dicarboxylate.

¹H NMR (400 MHz, DMSO-d₆) δ: 8.29 (br s, 1H), 7.83 (d, J=8.8 Hz, 1H), 7.79-7.78 (m, 1H), 7.53-7.51 (m, 1H), 7.46 (d, J=5.6 Hz, 1H).

Step 2: Synthesis of benzo[b]thiophen-6-ylhydrazine (485-B)

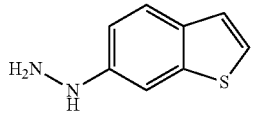 [SMILES: NNc1ccc2ccsc2c1]

485-B was obtained via similar procedure of 410-C from 485-A and ethyl acetate/hydrochloride LCMS: (ESI) m/z: 149.2 [M-NH₂+H]⁺.

Step 3: Synthesis of 1-(benzo[b]thiophen-6-yl)-3-methyl-1H-pyrazol-5(4H)-one (485-C)

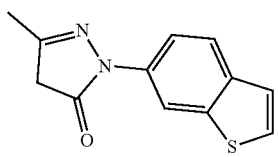 [SMILES: CC1=NN(c2ccc3ccsc3c2)C(=O)C1]

485-C was obtained via general procedure II from 485-B

LCMS: (ESI) m/z: 231.1 [M+H]⁺

Step 4: Synthesis of 4-nitrophenyl 1-(benzo[b]thiophen-6-yl)-3-methyl-5-oxo-4,5-dihydro-1H-pyrazole-4-carboxylate (485-D)

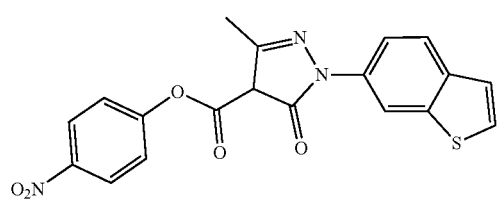 [SMILES: CC1=NN(c2ccc3ccsc3c2)C(=O)C1C(=O)Oc1ccc([N+](=O)[O-])cc1]

485-D was obtained via general procedure III from 485-C

LCMS: (ESI) m/z: 396.0 [M+H]⁺.

Step 5: Synthesis of 1-(benzo[b]thiophen-6-yl)-N-(3-(1,1-difluoropropyl)phenyl)-3-methyl-5-oxo-4,5-dihydro-1H-pyrazole-4-carboxamide (485)

Compound ID: 485

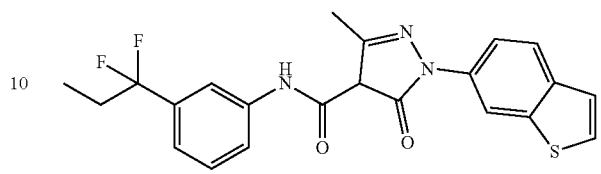

485 was obtained via general procedure IV from 485-D

LCMS: (ESI) m/z: 428.0 [M+H]⁺.

¹H NMR (400 MHz, MeOD-d₄) δ: 8.22 (s, 1H), 8.01 (d, J=8.4 Hz, 1H), 7.88 (s, 1H), 7.70 (d, J=5.6 Hz, 1H), 7.65-7.62 (m, 2H), 7.46 (d, J=5.2 Hz, 1H), 7.42 (t, J=8.0 Hz, 1H), 7.21 (d, J=7.6 Hz, 1H), 2.65 (s, 3H), 2.25-2.14 (m, 2H), 0.98 (t, J=7.6 Hz, 3H).

Synthesis of 486

Step 1: Synthesis of 1-(pyridin-2-yl)propan-1-one (486-A)

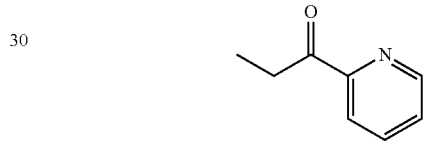

To solution of pyridine-2-carbonitrile (10.0 g, 96.1 mmol, 1.0 eq) in tetrahydrofuran (80 mL) was added dropwise ethylmagnesium bromide (3 M, 38.4 mL, 1.2 eq) at −75° C., the reaction mixture was stirred at −75° C. for hr. Then the reaction was warmed to 25° C., stirred at 25° C. for 3 hr. The mixture was quenched by slow addition of hydrochloric acid solution (2 M, 50 mL). The pH of mixture was adjusted to 8-9 by using sodium hydroxide (2 M). The resulting mixture was transferred to a separatory funnel, and the aqueous layer mixture was extracted with ethyl acetate (50 mL×3). The combined organic layer was washed with brine (100 mL), dried over anhydrous sodium sulfate, filtered, and concentrated under reduced pressure. The crude product was purified by silica gel column chromatography (petroleum ether/ethyl acetate, from 1/0 to 10/1) to give 9.50 g (73% yield) of 486-A as a yellow oil.

¹H NMR (400 MHz, CDCl₃-d) δ: 8.66-8.65 (m, 1H), 8.03-8.01 (m, 1H), 7.81 (td, J=1.6, 7.6 Hz, 1H), 7.46-7.44 (m, 1H), 3.23 (q, J=7.2 Hz, 2H), 1.20 (t, J=7.2 Hz, 3H).

Step 2: Synthesis of 2-propionylpyridine 1-oxide (486-B)

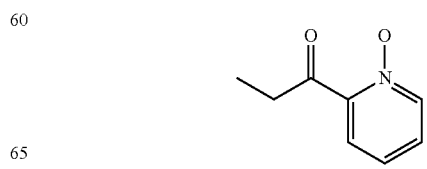

To a solution of 486-A (2.00 g, 14.8 mmol, 1 eq) in dichloromethane (30 mL) was added 3-chlorobenzoperoxoic acid (3.60 g, 17.8 mmol, 85% purity, 1.2 eq). The mixture was stirred at 25° C. for 4 hr. The mixture was concentrated under reduced pressure. The crude product was purified by silica gel column chromatography (from petroleum ether/ethyl acetate, from 5/1 to dichloromethane/methanol, 10/1) to give 1.00 g (45% yield) of 486-B as a brown oil.

$^1$H NMR (400 MHz, CDCl$_3$-d) δ: 8.20 (dd, J=0.8, 6.4 Hz, 1H), 7.65 (dd, J=2.4, 7.8 Hz, 1H), 7.37-7.29 (m, 2H), 3.23 (q, J=7.2 Hz, 2H), 1.20 (t, J=7.2 Hz, 3H).

Step 3: Synthesis of 2-(6-propionylpyridin-2-yl)isoindoline-1,3-dione (486-C)

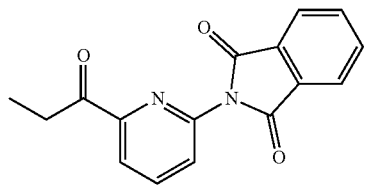 [SMILES: CCC(=O)c1cccc(N2C(=O)c3ccccc3C2=O)n1]

To a solution of 486-B (1.00 g, 6.62 mmol, 1.0 eq) in dichloromethane (10 mL) were added isoindoline-1,3-dione (974 mg, 6.62 mmol, 1.0 eq), 4-methylbenzene-1-sulfonyl chloride (1.89 g, 9.93 mmol, 1.5 eq) and N,N-diisopropylethylamine (1.71 g, 13.2 mmol, 2.0 eq). The mixture was stirred at 25° C. for 2 hr. The reaction mixture was concentrated under reduced pressure. The crude product was purified by silica gel column chromatography (petroleum ether/ethyl acetate, from 10/1 to 3/1) to give 1.60 g (81% yield) of 486-C as a light brown solid.

$^1$H NMR (400 MHz, DMSO-d$_6$) δ: 8.25 (t, J=8.0 Hz, 1H), 8.07-8.01 (m, 3H), 7.99-7.95 (m, 2H), 7.86-7.83 (m, 1H), 3.13 (q, J=7.2 Hz, 2H), 1.10 (t, J=7.2 Hz, 3H).

Step 4: Synthesis of 2-(6-(1,1-difluoropropyl)pyridin-2-yl)isoindoline-1,3-dione (486-D)

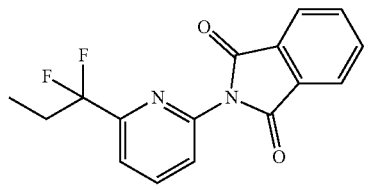 [SMILES: CCC(F)(F)c1cccc(N2C(=O)c3ccccc3C2=O)n1]

To a solution of 486-C (1.00 g, 3.34 mmol, 1.0 eq) in chloroform (20 mL) was added diethylaminosulfur trifluoride (5.39 g, 33.4 mmol, 10 eq). The suspension was degassed under vacuum and purged with nitrogen several times. The solution was then stirred at 70° C. for 4 hours. The mixture was quenched by slow addition of water (50 mL). The resulting mixture was transferred to a separatory funnel, and the aqueous layer mixture was extracted with ethyl acetate (30 mL×3). The combined organic layer was washed with brine (50 mL), dried over anhydrous sodium sulfate, filtered, and concentrated under reduced pressure. The crude product was purified by silica gel column chromatography (petroleum ether/ethyl acetate, from 1/0 to 10/1) to give 800 mg (63% yield) of 486-D as a light yellow solid.

$^1$H NMR (400 MHz, DMSO-d$_6$) δ: 8.24 (t, J=8.0 Hz, 1H), 8.03-7.94 (m, 4H), 7.83-7.81 (m, 1H), 7.73 (d, J=8.0 Hz, 1H), 2.36-2.24 (m, 2H), 0.95 (t, J=7.6 Hz, 3H).

Step 5: Synthesis of 6-(1,1-difluoropropyl)pyridin-2-amine (486-E)

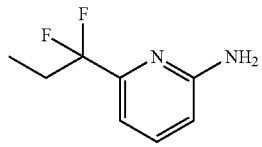

To a solution of 486-D (800 mg, 2.12 mmol, 1.00 eq) in ethanol (30 mL) was added hydrazine hydrate (212 mg, 4.24 mmol, 100% purity, 2.0 eq), the reaction mixture was stirred at 25° C. for 1 hr. To the reaction mixture was added dichloromethane (50 mL). The suspension was filtered through a pad of celite. The celite pad was eluted with dichloromethane (50 mL). The filtrate was washed with water (50 mL×2), the organic layer was washed with brine (50 mL), dried over anhydrous sodium sulfate, filtered, and concentrated under reduced pressure. The crude product was purified by silica gel column chromatography (petroleum ether/ethyl acetate, from 1/0 to 10/1) to give 350 mg (87% yield) of 486-E as a light yellow oil.

LCMS: (ESI) m/z: 173.1 [M+H]$^+$.

Step 6: Synthesis of 1-(4-(difluoromethoxy)phenyl)-N-(6-(1,1-difluoropropyl)pyridin-2-yl)-3-methyl-5-oxo-4,5-dihydro-1H-pyrazole-4-carboxamide (486)

Compound ID: 486

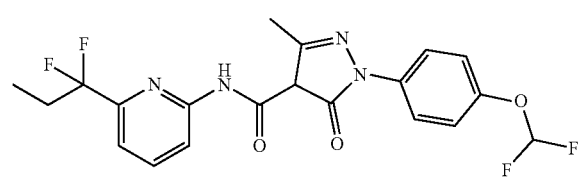 [SMILES: CCC(F)(F)c1cccc(NC(=O)C2C(=O)N(c3ccc(OC(F)F)cc3)N=C2C)n1]

486 was obtained via general procedure IV from 298-C and 486-E

LCMS: (ESI) m/z: 439.0[M+H]$^+$.

$^1$H NMR (400 MHz, MeOD-d$_4$) δ: 8.33 (d, J=8.4 Hz, 1H), 7.88 (t, J=8.0 Hz, 1H), 7.68-7.66 (m, 2H), 7.36-7.31 (m, 3H), 6.91 (t, J=73.6 Hz, 1H), 2.64 (s, 3H), 2.37-2.25 (m, 2H), 0.96 (t, J=7.6 Hz, 3H)

Synthesis of 487

Step 1: Synthesis of 6-bromo-1-tosyl-1H-indazole (487-A)

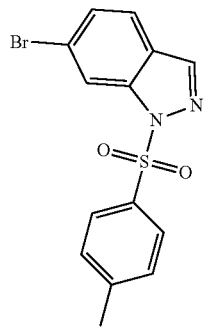 [SMILES: Cc1ccc(S(=O)(=O)n2ncc3ccc(Br)cc32)cc1]

487-A was obtained via similar procedure of 410-A from 6-bromo-1H-indazole and 4-methylbenzene-1-sulfonyl chloride.

$^1$H NMR (DMSO-d$_6$, 400 MHz) δ: 8.55 (d, J=0.4 Hz, 1H), 8.28 (s, 1H), 7.84-7.86 (m, 2H), 7.59 (dd, J=8.4, 1.6 Hz, 1H), 7.41 (d, J=8.8 Hz, 3H), 2.33 (s, 3H).

Step 2: Synthesis of di-tert-butyl 1-(1-tosyl-1H-indazol-6-yl)hydrazine-1,2-dicarboxylate (487-B)

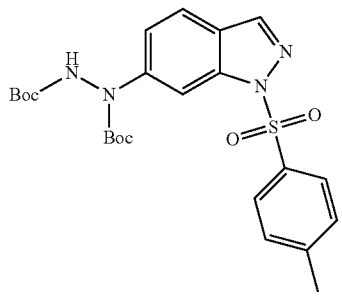 [SMILES: Cc1ccc(S(=O)(=O)n2ncc3ccc(N(NC(=O)OC(C)(C)C)C(=O)OC(C)(C)C)cc32)cc1]

487-B was obtained via similar procedure of 410-B from 487-A and di-tert-butyl hydrazine-1,2-dicarboxylate.

$^1$H NMR (CDCl$_3$-d, 400 MHz) δ: 8.27 (s, 1H), 8.11 (s, 1H), 7.87 (d, J=8.4 Hz, 2H), 7.74 (d, J=8.4 Hz, 1H), 7.58 (s, 1H), 7.25 (d, J=8.0 Hz, 2H), 6.90-7.15 (m, 1H), 2.37 (s, 3H), 1.55 (s, 18H).

Step 3: Synthesis of 6-hydrazinyl-1-tosyl-1H-indazole (487-C)

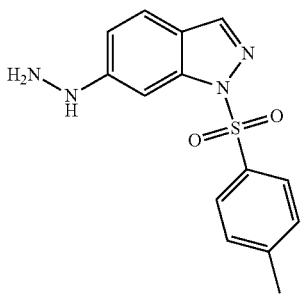 [SMILES: Cc1ccc(S(=O)(=O)n2ncc3ccc(NN)cc32)cc1]

487-C was obtained via similar procedure of 410-C from 487-B and ethyl acetate/hydrochloride LCMS: (ESI) m/z: 303.1 [M+H]$^+$.

Step 4: Synthesis of 3-methyl-1-(1-tosyl-H-indazol-6-yl)-1H-pyrazol-5(4H)-one (487-D)

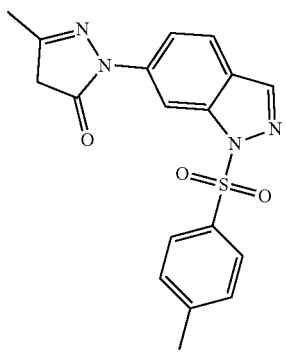 [SMILES: CC1=NN(c2ccc3cnn(S(=O)(=O)c4ccc(C)cc4)c3c2)C(=O)C1]

487-D was obtained via general procedure II from 487-C

LCMS: (ESI) m/z: 369.1 [M+H]$^+$.

Step 5: Synthesis of 4-nitrophenyl 3-methyl-5-oxo-1-(1-tosyl-1H-indazol-6-yl)-4,5-dihydro-1H-pyrazole-4-carboxylate (487-E)

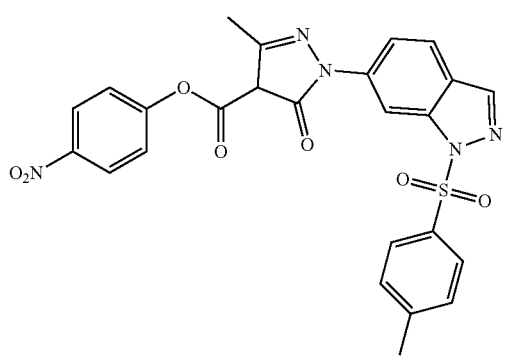 [SMILES: CC1=NN(c2ccc3cnn(S(=O)(=O)c4ccc(C)cc4)c3c2)C(=O)C1C(=O)Oc1ccc([N+](=O)[O-])cc1]

487-E was obtained via general procedure III from 487-D

LCMS: (ESI) m/z: 534.0 [M+H]$^+$.

Step 6: Synthesis of N-[3-(1,1-difluoropropyl)phenyl]-3-methyl-5-oxo-1-[1-(p-tolylsulfonyl)indazol-6-yl]-4H-pyrazole-4-carboxamide (487)

Compound ID: 487

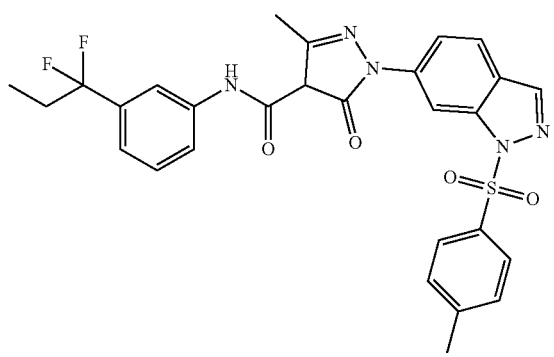 [SMILES: CCC(F)(F)c1cccc(NC(=O)C2C(=O)N(c3ccc4cnn(S(=O)(=O)c5ccc(C)cc5)c4c3)N=C2C)c1]

487 was obtained via general procedure IV from 487-E
LCMS: (ESI) m/z: 566.2[M+H]⁺.
¹H NMR: (400 MHz, MeOD-$d_4$) δ: 8.70 (s, 1H), 8.32 (s, 1H), 7.94-7.90 (m, 3H), 7.87 (d, J=12.8 Hz, 2H), 7.69 (d, J=7.2 Hz, 1H), 7.41 (s, 1H), 7.34 (d, J=8.0 Hz, 2H), 7.18 (d, J=7.6 Hz, 1H), 2.59 (s, 3H), 2.36 (s, 3H), 2.24-2.15 (m, 2H), 0.99 (t, J=7.6 Hz, 3H).

Synthesis of 488

Step 1: Synthesis of di-tert-butyl 1-(quinoxalin-6-yl)hydrazine-1,2-dicarboxylate (488-A)

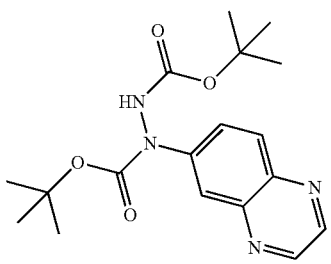 [SMILES: CC(C)(C)OC(=O)NN(C(=O)OC(C)(C)C)c1ccc2nccnc2c1]

488-A was obtained via similar procedure of 474-A from 6-bromoquinoxaline and tert-butyl N-(tert-butoxycarbonylamino)carbamate.
LCMS: (ESI) m/z: 361.1 [M+H]⁺.

Step 2: Synthesis of 6-hydrazinylquinoxaline (488-B)

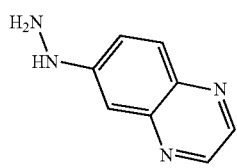 [SMILES: NNc1ccc2nccnc2c1]

To a 100 mL round-bottom flask equipped with a magnetic stir bar was added 474-A (4.00 g, 10.8 mmol, 1.0 eq) followed by the addition of ethyl acetate (25 mL). Then hydrogen chloride/ethyl acetate (4 M, 25 mL, 9.2 eq) was added into the mixture. The mixture was stirred at 35° C. for 12 h. The mixture was concentrated under reduced pressure to give a residue. The residue was dissolved in water (4 mL). The pH of the solution was adjusted by sodium hydroxide solution (2 M) to 11. The mixture was filtered to give 0.600 g (32% yield) of 488-B as a yellow solid.
LCMS: (ESI) m/z: 161.1 [M+H]⁺.

Step 3: Synthesis of 3-methyl-1-(quinoxalin-6-yl)-1H-pyrazol-5(4H)-one (488-C)

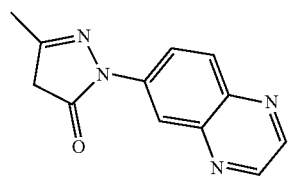 [SMILES: CC1=NN(c2ccc3nccnc3c2)C(=O)C1]

488-C was obtained via general procedure II from 488-B
LCMS: (ESI) m/z: 227.1 [M+H]⁺.

Step 4: Synthesis of 4-nitrophenyl 3-methyl-5-oxo-1-(quinoxalin-6-yl)-4,5-dihydro-1H-pyrazole-4-carboxylate (488-D)

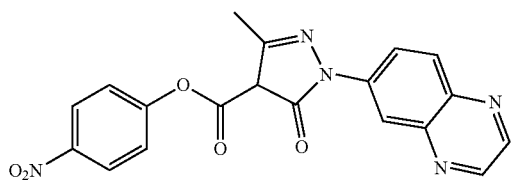 [SMILES: CC1=NN(c2ccc3nccnc3c2)C(=O)C1C(=O)Oc1ccc([N+](=O)[O-])cc1]

488-D was obtained via general procedure III from 488-C
LCMS: (ESI) m/z: 253.1 [M-(p-NO₂-PhO)]⁺.

Step 5: Synthesis of N-(3-(1,1-difluoropropyl)phenyl)-3-methyl-5-oxo-1-(quinoxalin-6-yl)-4,5-dihydro-1H-pyrazole-4-carboxamide (488)

Compound ID: 488

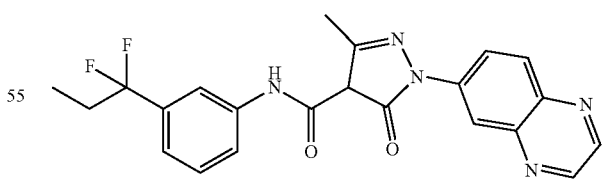

488 was obtained via general procedure IV from 488-D
LCMS: (ESI) m/z: 424.1 [M+H]⁺.
¹H NMR (MeOD-$d_4$, 400 MHz) δ: 8.84 (s, 1H), 8.78 (s, 1H), 8.72 (s, 1H), 8.60 (dd, J=2.4, 9.2 Hz, 1H), 8.10 (d, J=9.6 Hz, 1H), 7.89 (s, 1H), 7.67 (d, J=8.0 Hz, 1H), 7.40 (t, J=7.6 Hz, 1H), 7.17 (s, 1H), 2.51 (s, 3H), 2.10-2.30 (m, 2H), 1.00 (t, J=7.2 Hz, 3H).

Synthesis of 489

Step 1: Synthesis of 2-chloro-5-hydrazinylpyrazine (489-A)

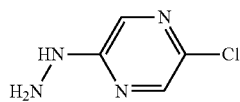

The solution of 2,5-dichloropyrazine (1.00 g, 6.71 mmol, 1.0 eq) in 2-propanol (5 mL) was added hydrazine hydrate (791 mg, 13.4 mmol, 85% purity, 2.0 eq), the solution was stirred at 50° C. for 12 h. The suspension was filtered and the filter cake was washed with water (1 mL×3). The filter cake was dried under vacuum to give 450 mg (46% yield) of 489-A as a white solid.

$^1$H NMR (400 MHz, DMSO-d$_6$) δ: 8.16 (s, 1H), 8.03 (d, J=1.2 Hz, 1H), 7.92 (d, J=1.6 Hz, 1H), 4.33 (s, 2H).

Step 2: Synthesis of 1-(5-chloropyrazin-2-yl)-3-methyl-1H-pyrazol-5(4H)-one (489-B)

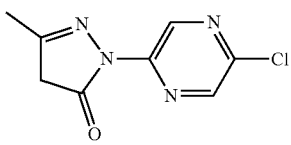

489-B was obtained via general procedure II from 489-A
LCMS: (ESI) m/z: 211.0 [M+H]$^+$.
$^1$H NMR (400 MHz, MeOD-d$_4$) δ: 9.42 (s, 1H), 8.49 (s, 1H), 2.28 (s, 3H).

Step 3: Synthesis of 4-nitrophenyl 1-(5-chloropyrazin-2-yl)-3-methyl-5-oxo-4,5-dihydro-1H-pyrazole-4-carboxylate (489-C)

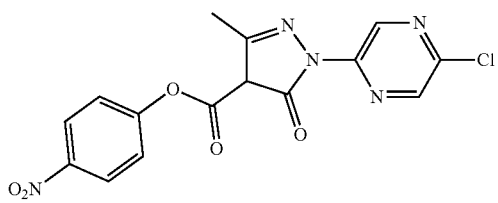 [SMILES: CC1=NN(c2cnc(Cl)cn2)C(=O)C1C(=O)Oc1ccc([N+](=O)[O-])cc1]

489-C was obtained via general procedure III from 489-B
LCMS: (ESI) m/z: 376.0 [M+H]$^+$.

Step 4: Synthesis of 1-(5-chloropyrazin-2-yl)-N-(3-(1,1-difluoropropyl)phenyl)-3-methyl-5-oxo-4,5-dihydro-1H-pyrazole-4-carboxamide (489)

Compound ID: 489

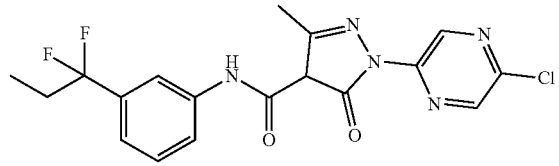 [SMILES: CCC(F)(F)c1cccc(NC(=O)C2C(=O)N(c3cnc(Cl)cn3)N=C2C)c1]

489 was obtained via general procedure IV from 489-C
LCMS: (ESI) m/z: 407.9 [M+H]$^+$.
$^1$H NMR (400 MHz, MeOD-d$_4$) δ: 9.50 (s, 1H), 8.52 (s, 1H), 7.87 (s, 1H), 7.63 (s, J=8.0 Hz, 1H), 7.41 (t, J=7.6 Hz, 1H), 7.20 (d, J=7.6 Hz, 1H), 2.65 (s, 3H), 2.26-2.14 (m, 2H), 0.99 (t, J=7.6 Hz, 3H).

Synthesis of 490

Step 1: Synthesis of 3-chloro-6-hydrazinylpyridazine (490-A)

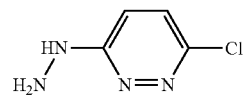

490-A was obtained via similar procedure of 489-A from 3,6-dichloropyridazine and hydrazine hydrate.
LCMS: (ESI) m/z: 145.0 [M+H]$^+$.

Step 2: Synthesis of 1-(6-chloropyridazin-3-yl)-3-methyl-1H-pyrazol-5(4H)-one (490-B)

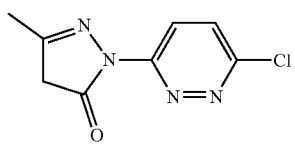

490-B was obtained via general procedure II from 490-A
LCMS: (ESI) m/z: 211.0 [M+H]$^+$.

Step 3: Synthesis of 4-nitrophenyl 1-(6-methoxypyridazin-3-yl)-3-methyl-5-oxo-4,5-dihydro-1H-pyrazole-4-carboxylate (490-C)

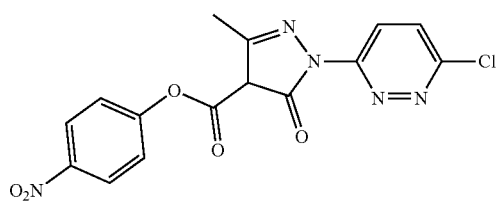 [SMILES: CC1=NN(c2ccc(Cl)nn2)C(=O)C1C(=O)Oc1ccc([N+](=O)[O-])cc1]

490-C was obtained via general procedure III from 490-B
LCMS: (ESI) m/z: 237.0 [M-(p-NO$_2$-PhO)]$^+$.

Step 4: Synthesis of 1-(6-chloropyridazin-3-yl)-N-(3-(1,1-difluoropropyl)phenyl)-3-methyl-5-oxo-4,5-dihydro-1H-pyrazole-4-carboxamide (490)

Compound ID: 490

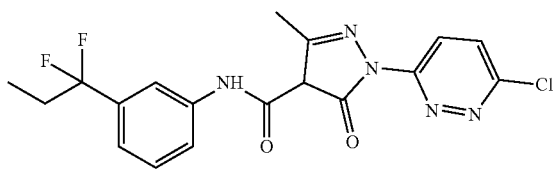 [SMILES: CCC(F)(F)c1cccc(NC(=O)C2C(=O)N(c3ccc(Cl)nn3)N=C2C)c1]

490 was obtained via general procedure IV from 490-C
LCMS: (ESI) m/z: 407.9 [M+H]$^+$.

$^1$H NMR (400 MHz, MeOD-d$_4$) δ: 8.77 (d, J=9.2 Hz, 1H), 7.92 (d, J=9.6 Hz, 1H), 7.87 (s, 1H), 7.65 (d, J=8.0 Hz, 1H), 7.43 (t, J=8.0 Hz, 1H), 7.21 (d, J=7.2 Hz, 1H), 2.65 (s, 3H), 2.27-2.14 (m, 2H), 1.00 (t, J=7.2 Hz, 3H).

Synthesis of 491

Step 1: Synthesis of 1-bromo-3-(2,2-diethoxyethoxy)benzene (491-A)

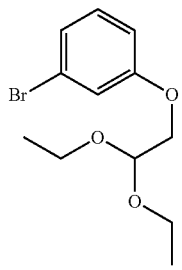 [SMILES: CCOC(COc1cccc(Br)c1)OCC]

To a suspension of sodium hydride (1.27 g, 31.8 mmol, 60% purity, 1.1 eq) in N,N-dimethylformamide (10 mL) was added dropwise a solution of 3-bromophenol (5.00 g, 28.9 mmol, 1.0 eq) in N,N-dimethylformamide (30 mL) at 0° C. The reaction was degassed under vacuum and purged with nitrogen several times. The reaction mixture was stirred at 0° C. for 1 hr, then to the reaction mixture was added 2-bromo-1,1-diethoxy-ethane (6.83 g, 34.7 mmol, 1.2 eq) at 0° C. under nitrogen. The reaction was stirred at 25° C. for 12 hr under nitrogen. The mixture was quenched by slow addition of ice water (200 mL). The resulting mixture was transferred to a separatory funnel, and the aqueous layer mixture was extracted with ethyl acetate (50 mL×3). The combined organic layer was washed with brine (100 mL), dried over anhydrous sodium sulfate, filtered, and concentrated under reduced pressure. The crude product was purified by silica gel column chromatography (petroleum ether/ethyl acetate, from 1/0 to 10/1) to give 15.5 g (93% yield) of 491-A as a light yellow oil.

$^1$H NMR (400 MHz, CDCl$_3$-d) δ: 7.14-7.09 (m, 3H), 6.88-6.85 (m, 1H), 4.82 (t, J=5.2 Hz, 1H), 3.99 (d, J=5.2 Hz, 2H), 3.81-3.71 (m, 2H), 3.60-3.59 (m, 2H), 1.27-1.24 (m, 6H).

Step 2: Synthesis of 6-bromobenzofuran (491-B)

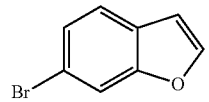

To a solution of polyphosphoric acid (30.0 g) in chlorobenzene (30 mL) was added dropwise a solution of 491-A (14.0 g, 48.4 mmol, 1.0 eq) in chlorobenzene (30 mL), the reaction mixture was stirred at 130° C. for 12 hr. The pH of mixture was adjusted to 7-8 by using saturated aqueous sodium hydroxide (2 M). The resulting mixture was transferred to a separatory funnel, and the aqueous layer mixture was extracted with ethyl acetate (200 mL×3). The combined organic layers were washed with brine (300 mL), dried over anhydrous sodium sulfate, filtered, and concentrated under reduced pressure. The crude product was purified by silica gel column chromatography (petroleum ether/ethyl acetate, from 1/0 to 10/1) to give 5.50 g (crude) of the mixture of 491-B and 492-A.

$^1$H NMR (400 MHz, CDCl$_3$-d) δ: 7.72 (s, 1H), 7.69 (d, J=2.0 Hz, 1H), 7.62 (d, J=2.0 Hz, 1H), 7.49 (d, J=8.4 Hz, 2H), 7.43 (d, J=8.0 Hz, 1H), 7.41-7.38 (m, 1H), 7.20 (t, J=8.0 Hz, 1H), 6.87-6.82 (m, 1H), 6.80-6.74 (m, 1H).

Step 3: Synthesis of di-tert-butyl 1-(benzofuran-6-yl)hydrazine-1,2-dicarboxylate (491-C)

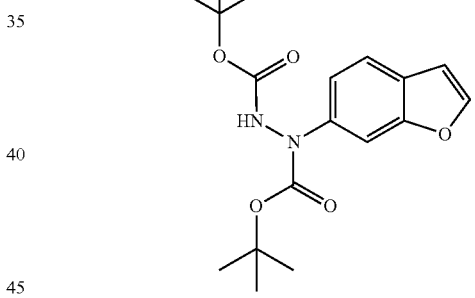

491-C was obtained via similar procedure of 410-B from 491-B and di-tert-butyl hydrazine-1,2-dicarboxylate.

$^1$H NMR (400 MHz, DMSO-d$_6$) δ: 9.78-9.70 (m, 1H), 8.62-8.59 (m, 2H), 8.27-7.93 (m, 2H), 7.62-7.42 (m, 2H), 7.33-7.17 (m, 2H), 6.94-6.90 (m, 1H), 1.40 (s, 36H).

Step 4: Synthesis of benzofuran-6-ylhydrazine (491-D)

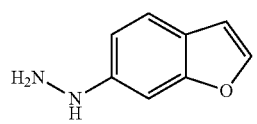 [SMILES: NNc1ccc2ccoc2c1]

491-D was obtained via similar procedure of 410-C from 491-C and ethyl acetate/hydrochloride
LCMS: (ESI) m/z: 149.1 [M+H]$^+$.

Step 5: Synthesis of 1-(benzofuran-6-yl)-3-methyl-1H-pyrazol-5(4H)-one (491-E)

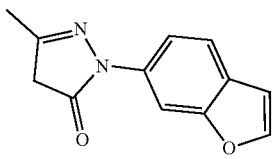 [SMILES: CC1=NN(c2ccc3ccoc3c2)C(=O)C1]

491-E was obtained via general procedure II from 491-D

¹H NMR (400 MHz, CDCl₃-d) δ: 7.98 (s, 1H), 7.71 (dd, J=2.0, 8.4 Hz, 1H), 7.56 (d, J=2.0 Hz, 1H), 7.52 (d, J=8.8 Hz, 1H), 6.69 (dd, J=0.8, 2.0 Hz, 1H), 3.44 (s, 2H), 2.16 (s, 3H).

Step 6: Synthesis of 4-nitrophenyl 1-(benzofuran-6-yl)-3-methyl-5-oxo-4,5-dihydro-1H-pyrazole-4-carboxylate (491-F)

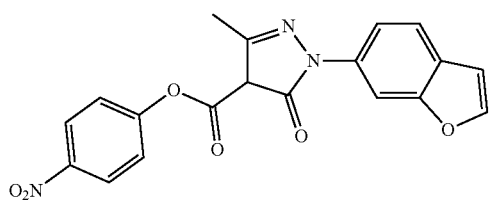 [SMILES: CC1=NN(c2ccc3ccoc3c2)C(=O)C1C(=O)Oc1ccc([N+](=O)[O-])cc1]

491-F was obtained via general procedure III from 491-E

LCMS: (ESI) m/z: 380.1 [M+H]⁺.

Step 7: Synthesis of 1-(benzofuran-6-yl)-N-(3-(1,1-difluoropropyl)phenyl)-3-methyl-5-oxo-4,5-dihydro-1H-pyrazole-4-carboxamide (491)

Compound ID: 491

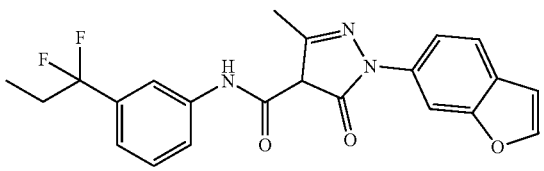 [SMILES: CCC(F)(F)c1cccc(NC(=O)C2C(=O)N(c3ccc4ccoc4c3)N=C2C)c1]

491 was obtained via general procedure IV from 491-F

LCMS: (ESI) m/z: 412.1 [M+H]⁺.

¹H NMR (400 MHz, MeOD-d₄) δ: 7.88-7.86 (m, 3H), 7.76 (d, J=8.4 Hz, 1H), 7.65 (d, J=8.4 Hz, 1H), 7.54 (dd, J=1.6, 8.4 Hz, 1H), 7.41 (t, J=8.0 Hz, 1H), 7.19 (d, J=7.6 Hz, 1H), 6.93 (d, J=1.6 Hz, 1H), 2.62 (s, 3H), 2.25-2.12 (m, 2H), 0.98 (t, J=7.2 Hz, 3H).

Synthesis of 492

Step 1: Synthesis of 4-bromobenzofuran (492-A)

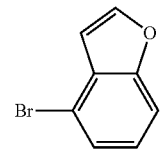

492-A was obtained via similar procedure of 491-B from 491-A and polyphosphoric acid.

¹H NMR (400 MHz, CDCl₃-d) δ: 7.72 (s, 1H), 7.69 (d, J=2.0 Hz, 1H), 7.62 (d, J=2.0 Hz, 1H), 7.49 (d, J=8.4 Hz, 2H), 7.43 (d, J=8.0 Hz, 1H), 7.41-7.38 (m, 1H), 7.20 (t, J=8.0 Hz, 1H), 6.87-6.82 (m, 1H), 6.80-6.74 (m, 1H).

Step 2: Synthesis of di-tert-butyl 1-(benzofuran-4-yl)hydrazine-1,2-dicarboxylate (492-B)

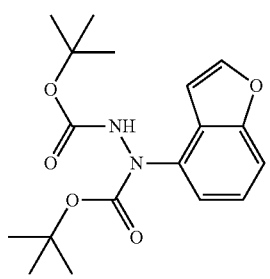 [SMILES: CC(C)(C)OC(=O)NN(C(=O)OC(C)(C)C)c1cccc2occc12]

492-B was obtained via similar procedure of 491-C from 492-A and di-tert-butyl hydrazine-1,2-dicarboxylate.

¹H NMR (400 MHz, DMSO-d₆) δ: 9.78-9.70 (m, 1H), 8.62-8.59 (m, 2H), 8.27-7.93 (m, 2H), 7.62-7.42 (m, 2H), 7.33-7.17 (m, 2H), 6.94-6.90 (m, 1H), 1.40 (s, 36H).

Step 3: Synthesis of benzofuran-4-ylhydrazine (492-C)

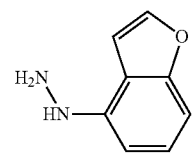 [SMILES: NNc1cccc2occc12]

492-C was obtained via similar procedure of 491-D from 492-B and ethyl acetate/hydrochloride LCMS: (ESI) m/z: 149.1 [M+H]⁺.

Step 4: Synthesis of 1-(benzofuran-4-yl)-3-methyl-1H-pyrazol-5(4H)-one (492-D)

492-D was obtained via general procedure II from 492-C $^1$H NMR (400 MHz, CDCl$_3$-d) δ: 7.64-7.62 (m, 2H), 7.43 (d, J=8.4 Hz, 1H), 7.33 (t, J=8.0 Hz, 1H), 7.03 (dd, J=0.8, 2.0 Hz, 1H), 3.52 (s, 2H), 2.26 (s, 3H).

Step 5: Synthesis of 4-nitrophenyl 1-(benzofuran-4-yl)-3-methyl-5-oxo-4,5-dihydro-1H-pyrazole-4-carboxylate (492-E)

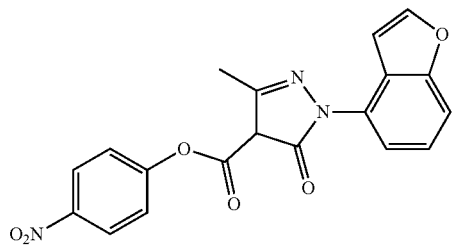 [SMILES: CC1=NN(c2cccc3occc23)C(=O)C1C(=O)Oc1ccc([N+](=O)[O-])cc1]

492-E was obtained via general procedure III from 492-D
LCMS: (ESI) m/z: 380.1 [M+H]$^+$.

Step 6: Synthesis of 1-(benzofuran-4-yl)-N-(3-(1,1-difluoropropyl)phenyl)-3-methyl-5-oxo-4,5-dihydro-1H-pyrazole-4-carboxamide (492)

Compound ID: 492

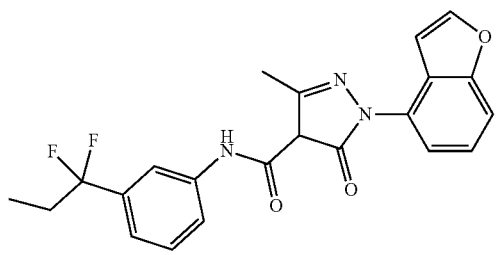 [SMILES: CCC(F)(F)c1cccc(NC(=O)C2C(=O)N(c3cccc4occc34)N=C2C)c1]

492 was obtained via general procedure IV from 492-E
LCMS: (ESI) m/z: 412.1 [M+H]$^+$.

$^1$H NMR (400 MHz, MeOD-d$_4$) δ: 7.88-7.87 (m, 2H), 7.66-7.63 (m, 2H), 7.48 (t, J=8.0 Hz, 1H), 7.41 (t, J=7.2 Hz, 2H), 7.20 (d, J=8.0 Hz, 1H), 6.96 (dd, J=0.8, 2.0 Hz, 1H), 2.65 (s, 3H), 2.23-2.13 (m, 2H), 0.98 (t, J=7.2 Hz, 3H).

Synthesis of 493

Step 1: Synthesis of 3-((tert-butyldimethylsilyl)oxy)benzoic acid (493-A)

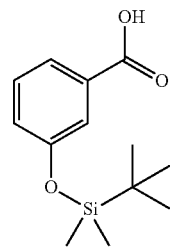 [SMILES: CC(C)(C)[Si](C)(C)Oc1cccc(C(=O)O)c1]

To a 50 mL round-bottom flask equipped with a magnetic stir bar was added 3-hydroxybenzoic acid (1.00 g, 7.24 mmol, 1.0 eq) followed by the addition of dichloromethane (10 mL) and triethylamine (2.20 g, 21.7 mmol, 3.0 eq). Then a solution of tert-butylchlorodimethylsilane (2.18 g, 14.5 mmol, 2.0 eq) in dichloromethane (5 mL) was added into the mixture. The mixture was stirred at 25° C. for 2 hr. The mixture was concentrated under reduced pressure to give a residue. The residue was dissolved in tetrahydrofuran (10 mL). To the mixture was added sodium hydroxide solution (2 M, 4 mL). The result solution was stirred at 25° C. for 0.5 h. The solution was diluted with water (10 mL), then the pH of the mixture was adjusted to 6 by hydrochloric acid solution (1 M). The mixture was extracted with ethyl acetate (10 mL×3). The combined organic layer was washed with brine (10 mL), dried over anhydrous sodium sulfate, filtered, and concentrated under reduced pressure affording a residue. The residue was purified by silica gel column chromatography (petroleum ether/ethyl acetate, from 100/1 to 50/1) to give 1.80 g (96% yield) of 493-A as a light yellow solid.

LCMS: (ESI) m/z: 253.1 [M+H]$^+$.

Step 2: Synthesis of 3-((tert-butyldimethylsilyl)oxy)benzoyl chloride (493-B)

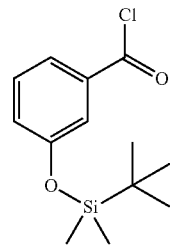 [SMILES: CC(C)(C)[Si](C)(C)Oc1cccc(C(=O)Cl)c1]

To a 50 mL round-bottom flask equipped with a magnetic stir bar was added 493-A (1.00 g, 3.85 mmol, 1.0 eq) followed by the addition of dichloromethane (10 mL) and N,N-dimethylformamide (28.2 mg, 385 umol, 0.10 eq). The solution was cooled to 0° C. Next, a solution of oxalyl chloride (733 mg, 5.78 mmol, 1.5 eq) in dichloromethane (5 mL) was added dropwise. The mixture was allowed to warm to 25° C. and stir for 1 hr. The mixture was concentrated under reduced pressure to give 1.00 g (crude) of 493-B as a yellow oil.

Step 3: Synthesis of (1H-benzo[d][1,2,3]triazol-1-yl)(3-((tert-butyldimethylsilyl)oxy)phenyl)methanone (493-C)

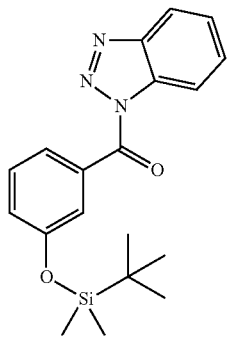 [SMILES: CC(C)(C)[Si](C)(C)Oc1cccc(C(=O)n2nnc3ccccc32)c1]

To a 50 mL round-bottom flask equipped with a magnetic stir bar was added 1H-benzotriazole (330 mg, 2.77 mmol, 1.5 eq), triethylamine (187 mg, 1.85 mmol, 1.0 eq) followed by the addition of dichloromethane (10 mL). Then a solution of 493-B (500 mg, 1.85 mmol, 1.0 eq) in dichloromethane (5 mL) was added into the mixture. The mixture was stirred at 25° C. for 2 hr. The mixture was concentrated under reduced pressure to give 700 mg (crude) of 493-C as a yellow solid.

Step 4: Synthesis of N-(3-(1,1-difluoropropyl)phenyl)-1-(1-(3-hydroxybenzoyl)-1H-indol-6-yl)-3-methyl-5-oxo-4,5-dihydro-1H-pyrazole-4-carboxamide (493)

Compound ID: 493

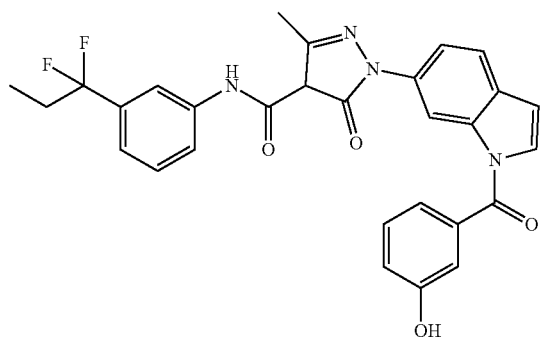 [SMILES: CCC(F)(F)c1cccc(NC(=O)C2C(=O)N(c3ccc4ccn(C(=O)c5cccc(O)c5)c4c3)N=C2C)c1]

To a 10 mL round-bottom flask equipped with a magnetic stir bar was added 369 (100 mg, 244 umol, 1.0 eq) followed by the addition of N,N-dimethylformamide (2 mL). Then sodium hydride (19.5 mg, 487 umol, 60% purity, 2.0 eq) was added into the mixture at 0° C. The mixture was stirred at 0° C. for 10 min. To the mixture was added a solution of 493-C (129 mg, 365 umol, 1.5 eq) in N,N-dimethylformamide (2 mL) dropwise. The mixture was stirred at 0° C. for 10 min. The mixture was quenched with hydrochloric acid solution (2 mL, 1M). The mixture was extracted with ethyl acetate (2 mL×3). The combined organic layer was washed with brine (5 mL), dried over anhydrous sodium sulfate, filtered, and concentrated under reduced pressure affording a residue. The residue was purified by prep-HPLC (column: UniSil 3-100 C18 Ultra (150*25 mm*3 um); mobile phase: [water (0.225% formic acid)-acetonitrile]; B %: 50%-80%, 10 min) to give 24.5 mg (19% yield) of 493 as a yellow solid.

LCMS: (ESI) m/z: 531.0 [M+H]$^+$.

$^1$H NMR (MeOD-d$_4$, 400 MHz) δ: 8.80 (s, 1H), 7.87 (s, 1H), 7.73 (d, J=7.6 Hz, 1H), 7.63-7.66 (m, 2H), 7.37-7.41 (m, 3H), 7.14-7.18 (m, 3H), 7.07 (J=2.0, 8.4 Hz, 1H), 6.68 (d, J=3.6 Hz, 1H), 2.51 (s, 3H), 2.11-2.27 (m, 2H), 0.98 (t, J=7.2 Hz, 3H).

Synthesis of 494

Step 1: Synthesis of 1-nitro-3-(prop-1-yn-1-yl)benzene (494-A)

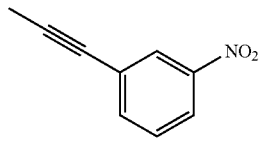

To a solution of 1-ethynyl-3-nitro-benzene (1.00 g, 6.80 mmol, 1.0 eq) in tetrahydrofuran (10 mL) was added sodium bis(trimethylsilyl)amide (1 M, 20.4 mL, 3.0 eq) at −78° C. under nitrogen atmosphere. The mixture was stirred at −78° C. for 30 min. Then iodomethane (2.89 g, 20.4 mmol, 3.0 eq) was added. The mixture was slowly warmed to 25° C. and stirred for 12 h. The reaction mixture was quenched by addition hydrochloric acid aqueous (1 M, 50 mL), and then extracted with ethyl acetate (30 mL×2). The combined organic layer was washed with brine (30 mL×1), dried over anhydrous sodium sulfate, filtered and concentrated under reduced pressure to give a residue. The residue was purified by silica gel column chromatography (pure petroleum ether) to give 0.900 g (82% yield) of 494-A was obtained as a colorless oil.

$^1$H NMR (400 MHz, CDCl$_3$-d) δ: 8.24 (t, J=2.0 Hz, 1H), 8.15-8.09 (m, 1H), 7.68 (d, J=8.0 Hz, 1H), 7.46 (t, J=8.0 Hz, 1H), 2.09 (s, 3H).

Step 2: Synthesis of 3-(prop-1-yn-1-yl)aniline (494-B)

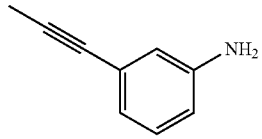

To a solution of 494-A (0.900 g, 5.58 mmol, 1.0 eq) in ethanol (10 mL) and water (3 mL) were added iron powder (1.56 g, 27.9 mmol, 5.0 eq) and ammonium chloride (1.49 g, 27.9 mmol, 5.0 eq). The mixture was stirred at 80° C. for 2 hr. The mixture was diluted with ethyl acetate (50 mL), then filtered through diatomite. The filtrate was collected and washed with brine (50 mL), the organic layer was dried over anhydrous sodium sulfate, filtered and concentrated to give 0.750 g (crude) of 494-B as a yellow oil.

LCMS: (ESI) m/z: 132.3 [M+H]$^+$.

Step 3: Synthesis of tert-butyl (3-(prop-1-yn-1-yl)phenyl)carbamate (494-C)

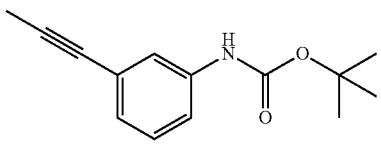 [SMILES: CC#Cc1cccc(NC(=O)OC(C)(C)C)c1]

A solution of 494-B (0.750 g, 5.72 mmol, 1.0 eq) and di-tert-butyl dicarbonate (1.50 g, 6.86 mmol, 1.2 eq) of tetrahydrofuran (10 mL) was stirred at 70° C. for 12 hr. mixture was concentrated. The residue was purified by silica gel column chromatography (petroleum ether/ethyl acetate, from 30/1 to 10/1) to give 1.20 g (88% yield) of 494-C as a yellow oil.

LCMS: (ESI) m/z: 254.1 [M+Na]$^+$.

$^1$H NMR (400 MHz, CDCl$_3$-d) δ: 7.41 (s, 1H), 7.30-7.27 (m, 1H), 7.20 (t, J=7.6 Hz, 1H), 7.06 (d, J=7.6 Hz, 1H), 6.42 (br s, 1H), 2.03 (s, 3H), 1.52 (s, 9H).

Step 4: Synthesis of tert-butyl N-tert-butoxycarbonyl-N-(3-prop-1-ynylphenyl)carbamate (494-D)

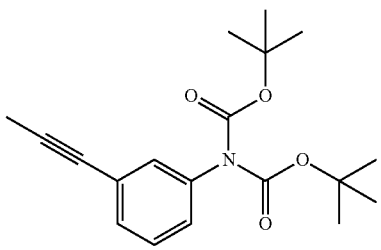 [SMILES: CC#Cc1cccc(N(C(=O)OC(C)(C)C)C(=O)OC(C)(C)C)c1]

To a solution of 494-C (0.960 g, 4.03 mmol, 1.0 eq) and di-tert-butyl dicarbonate (1.05 g, 4.83 mmol, 1.2 eq) in tetrahydrofuran (10 mL) was added triethylamine (611 mg, 6.04 mmol, 1.5 eq) and N,N-dimethylpyridin-4-amine (98.4 mg, 805 umol, 0.20 eq). The mixture was stirred at 50° C. for 12 hr. The mixture was concentrated to give a residue. The residue was purified by silica gel column chromatography (petroleum ether/ethyl acetate, 10/1) to give 1.20 g (90% yield) of 494-D as a yellow solid.

LCMS: (ESI) m/z: 685.3 [2M+Na]$^+$.

Step 5: Synthesis of tert-butyl N-tert-butoxycarbonyl-N-(3-prop-1-enylphenyl)carbamate (494-E)

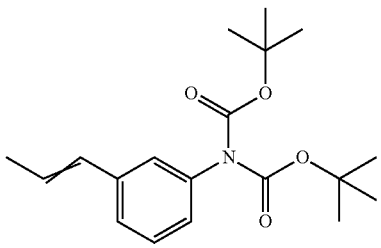 [SMILES: CC=Cc1cccc(N(C(=O)OC(C)(C)C)C(=O)OC(C)(C)C)c1]

To a solution of 494-D (0.530 g, 1.60 mmol, 1.0 eq) in tetrahydrofuran (10 mL) were added bis(triphenylphosphine)palladium(II)dichloride (56.1 mg, 80.0 umol, 0.050 eq), zinc powder (627 mg, 9.60 mmol, 6.0 eq) and diiodozinc (1 M, 1.60 mL, 1.0 eq). The suspension was degassed and purged with hydrogen for 3 times. The mixture was stirred under hydrogen (50 psi) at 25° C. for 12 hr. The mixture was poured into saturated sodium bicarbonate aqueous (30 mL) and extracted with ethyl acetate (30 mL×2). The combined organic layers were washed with brine (30 mL×2), dried over anhydrous sodium sulfate, filtered and concentrated under reduced pressure to give a residue. The residue was purified by silica gel column chromatography (petroleum ether/ethyl acetate, from 20/1 to 10/1) to give 0.500 g (87% yield) of 494-E as a yellow oil.

LCMS: (ESI) m/z: 689.3 [2M+Na]$^+$.

Step 5: Synthesis of tert-butyl N-tert-butoxycarbonyl-N-[3-(1-fluoro-2-iodo-propyl)phenyl]carbamate (494-F)

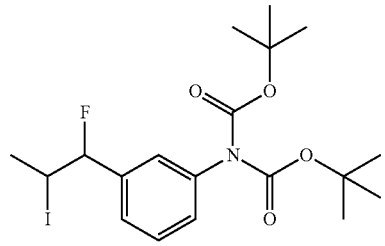 [SMILES: CC(I)C(F)c1cccc(N(C(=O)OC(C)(C)C)C(=O)OC(C)(C)C)c1]

To a solution of 494-E (0.300 g, 837 umol, 1.0 eq) in dichloromethane (6 mL) was added 1-iodopyrrolidine-2,5-dione (297 mg, 1.32 mmol, 1.6 eq) and dihydrogen tetrabutylammonium fluoride (398 mg, 1.32 mmol, 1.6 eq) at 0° C. The mixture was warmed to 25° C. and stirred for 4 h. The mixture was concentrated. The residue was diluted with ethyl acetate (20 mL) and washed with hydrochloric acid aqueous (0.1M, 20 mL×2). The organic layer was dried over anhydrous sodium sulfate, filtered and concentrated under reduced pressure to give a residue. The residue was purified by silica gel column chromatography (petroleum ether/ethyl acetate, 50/1) to give 0.350 g (87% yield) of 494-F as a yellow oil.

LCMS: (ESI) m/z: 368.1 [M+H-2tBu]$^+$.

Step 6: Synthesis of tert-butyl N-tert-butoxycarbonyl-N-[3-(1-fluoroprop-1-enyl)phenyl]carbamate (494-G)

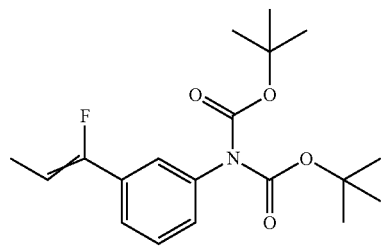 [SMILES: CC=C(F)c1cccc(N(C(=O)OC(C)(C)C)C(=O)OC(C)(C)C)c1]

To a solution of 494-F (0.300 g, 626 umol, 1.0 eq) in dichloromethane (5 mL) was added 1,8-diazabicyclo[5.4.0]

undec-7-ene (143 mg, 939 umol, 1.5 eq). The mixture was stirred at 25° C. for 12 hr. The mixture was concentrated in vacuo. The residue was purified by silica gel column chromatography (petroleum ether/ethyl acetate, 50/1) to give 140 mg (51% yield) of 494-G as a yellow oil.

LCMS: (ESI) m/z: 725.1 [2M+Na]$^+$.

Step 7: Synthesis of (Z)-3-(1-fluoroprop-1-en-1-yl)aniline (494-H)

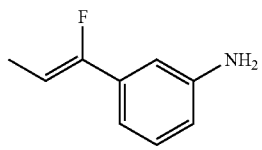

To a solution of 494-G (140 mg, 319 umol, 1.0 eq) in dichloromethane (1.5 mL) was added hydrochloride/dioxane (4 M, 0.5 mL, 6.3 eq) at 0° C. The mixture was stirred at 0° C. for 0.5 hr. The mixture was concentrated in vacuo. The residue was adjusted with saturated sodium bicarbonate aqueous to pH=8 and extracted with ethyl acetate (10 mL×2). The combined organic layer was dried over anhydrous sodium sulfate, filtered and concentrated under reduced pressure to give a residue. The residue was purified by prep-HPLC (column: Waters Xbridge 150*25 mm*5 um; mobile phase: [water (10 mM ammonium bicarbonate)-acetonitrile]; B %: 36%-56%, 10 min), then freeze-dried to give 18.0 mg (37% yield) of 494-H as a yellow oil.

$^1$H NMR (400 MHz, CDCl$_3$-d) δ: 7.13 (t, J=7.6 Hz, 1H), 6.90 (d, J=7.6 Hz, 1H), 6.82 (t, J=2.0 Hz, 1H), 6.63 (dd, J=8.0, 2.0 Hz, 1H), 5.43 (dq, J=37.2, 7.2 Hz, 1H), 3.88-3.51 (m, 2H), 1.80 (dd, J=7.2, 2.4 Hz, 3H).

Step 8: Synthesis of (Z)-1-(4-(difluoromethoxy)phenyl)-N-(3-(1-fluoroprop-1-en-1-yl)phenyl)-3-methyl-5-oxo-4,5-dihydro-1H-pyrazole-4-carboxamide (494)

Compound ID: 494

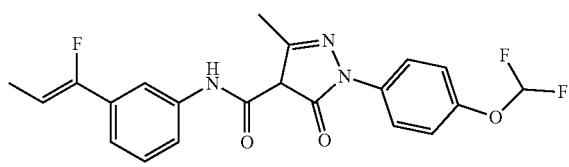 [SMILES: C/C=C(\F)c1cccc(NC(=O)C2C(=O)N(c3ccc(OC(F)F)cc3)N=C2C)c1]

494 was obtained via general procedure IV from 298-C and 494-H.

LCMS: (ESI) m/z: 418.1 [M+H]$^+$.

$^1$H NMR (400 MHz, MeOD-d$_4$) δ: 7.85 (s, 1H), 7.74 (d, J=8.8 Hz, 2H), 7.53 (d, J=8.0 Hz, 1H), 7.31 (t, J=8.0 Hz, 1H), 7.27 (d, J=8.8 Hz, 2H), 7.21 (d, J=8.0 Hz, 1H), 7.05 (t, J=74.0 Hz, 1H), 5.58 (dq, J=37.2, 7.2 Hz, 1H), 2.55 (s, 3H), 1.80 (dd, J=7.2, 2.4 Hz, 3H).

Synthesis of 495

Step 1: Synthesis of (E)-3-(1-fluoroprop-1-en-1-yl)aniline (495-A)

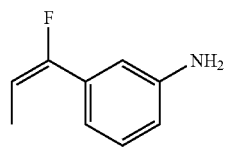

495-A was obtained via similar procedure of 494-H from 494-G and hydrochloride/dioxane.

$^1$H NMR (400 MHz, CDCl$_3$-d) δ: 7.19 (t, J=7.6 Hz, 1H), 6.89 (d, J=7.6 Hz, 1H), 6.80 (t, J=2.0 Hz, 1H), 6.69 (dd, J=8.0, 2.0 Hz, 1H), 5.43 (dq, J=22.4, 7.6 Hz, 1H), 3.73 (br s, 2H), 1.79 (dd, J=7.6, 2.4 Hz, 3H).

Step 2: Synthesis of (E)-1-(4-(difluoromethoxy)phenyl)-N-(3-(1-fluoroprop-1-en-1-yl)phenyl)-3-methyl-5-oxo-4,5-dihydro-1H-pyrazole-4-carboxamide (495)

Compound ID: 495

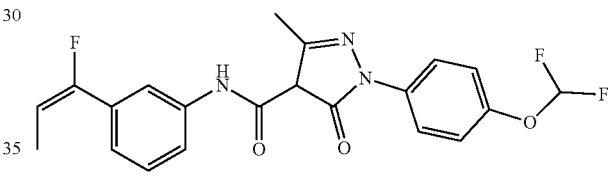

495 was obtained via general procedure IV from 298-C and 495-A.

LCMS: (ESI) m/z: 418.1 [M+H]$^+$.

$^1$H NMR (400 MHz, MeOD-d$_4$) δ: 7.86 (s, 1H), 7.73 (d, J=8.8 Hz, 2H), 7.57 (d, J=8.4 Hz, 1H), 7.38 (t, J=8.0 Hz, 1H), 7.28 (d, J=8.8 Hz, 2H), 7.19 (d, J=7.6 Hz, 1H), 7.06 (br t, J=74.0 Hz, 1H), 5.45 (dq, J=22.4, 7.6 Hz, 1H), 2.57 (s, 3H), 1.82 (dd, J=7.6, 2.4 Hz, 3H).

Synthesis of 496

Step 1: Synthesis of diethoxyphosphoryl-(3-nitrophenyl)methanol (496-A)

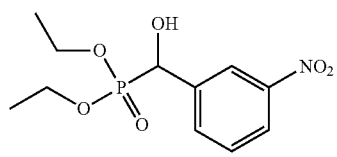 [SMILES: CCOP(=O)(OCC)C(O)c1cccc([N+](=O)[O-])c1]

3-nitrobenzaldehyde (5.00 g, 33.1 mmol, 1.0 eq) was dissolved in 1-ethoxyphosphonoyloxyethane (4.60 g, 33.1 mmol, 1.0 eq) at 40° C. The solution was brought to 25° C. and potassium fluoride (9.60 g, 165 mmol, 5.0 eq) was added. The mixture was stirred vigorously for 15 min. The reaction mixture was partitioned between ethyl acetate (100 mL) and water (100 mL). The organic phase was separated, washed with brine (100 mL×1), dried over anhydrous sodium sulfate, filtered and concentrated under reduced pressure to give a residue. The residue was triturated with methyl tertiary-butyl ether (30 mL) to give 8.50 g (89% yield) of 496-A as a light yellow solid.

LCMS: (ESI) m/z: 290.1 [M+H]$^+$.

$^1$H NMR (400 MHz, CDCl$_3$-d) δ: 8.41 (d, J=2.0 Hz, 1H), 8.18 (d, J=8.0 Hz, 1H), 7.83 (d, J=7.6 Hz, 1H), 7.55 (t, J=8.0 Hz, 1H), 5.17 (dd, J=5.2, 11.2 Hz, 1H), 4.75 (t, J=6.0 Hz, 1H), 4.19-4.08 (m, 4H), 1.33-1.25 (m, 6H).

Step 2: Synthesis of 1-[diethoxyphosphoryl(fluoro) methyl]-3-nitro-benzene (496-B)

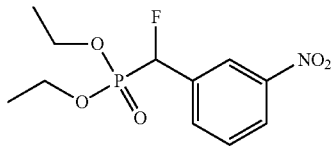 [SMILES: CCOP(=O)(OCC)C(F)c1cccc([N+](=O)[O-])c1]

To a solution of 496-A (5.00 g, 17.3 mmol, 1.0 eq) in dichloromethane (50 mL) was added dropwise a solution of diethylamine group sulfur trifluoride (4.20 g, 26 mmol, 1.5 eq) in dichloromethane (10 mL) at −78° C. The mixture was slowly warmed to 25° C. and stirred for 12 h. The reaction mixture was poured into saturated sodium bicarbonate aqueous (100 mL) and extracted with dichloromethane (100 mL×2). The combined organic layer was washed with brine (100 mL×1), dried over anhydrous sodium sulfate, filtered and concentrated under reduced pressure to give a residue. The residue was purified by silica gel column chromatography (petroleum ether/ethyl acetate, from 10/1 to 3/1) to give 3.50 g (70% yield) of 496-B as a yellow oil.

$^1$H NMR (400 MHz, CDCl$_3$-d) δ: 8.34 (d, J=1.2 Hz, 1H), 8.24 (d, J=8.4 Hz, 1H), 7.82 (d, J=8.0 Hz, 1H), 7.61 (t, J=8.0 Hz, 1H), 5.79 (dd, J=44.4, 8.8 Hz, 1H), 4.23-4.08 (m, 4H), 1.37-1.26 (m, 6H).

Step 3: Synthesis of 1-(1-fluoro-2-methyl-prop-1-enyl)-3-nitro-benzene (496-C)

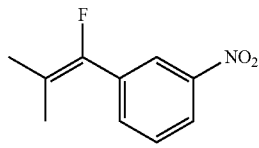

To a solution of 496-B (200 mg, 687 umol, 1.0 eq) in tetrahydrofuran (5 mL) was added lithium diisopropylamide (2 M, 687 uL, 2.0 eq) under −78° C., it was stirred at −78° C. for 30 min, then the acetone (120 mg, 2.06 mmol, 3.0 eq) was added into the solution. The mixture was stirred at 25° C. for 30 min. The mixture was quenched with saturated ammonium chloride (30 mL), then extracted with ethyl acetate (20 mL×2). The combined organic layer was washed with brine (40 mL), dried over anhydrous sodium sulfate, filtered and concentrated under reduced pressure to give 130 mg (crude) of 496-C as a black brown oil.

$^1$H NMR (400 MHz, CDCl$_3$-d) δ: 8.29 (s, 1H), 8.20-8.16 (m, 1H), 7.75 (d, J=7.6 Hz, 1H), 7.57 (t, J=8.0 Hz, 1H), 1.90 (d, J=3.6 Hz, 3H), 1.85 (d, J=2.8 Hz, 3H).

Step 4: Synthesis of 3-(1-fluoro-2-methyl-prop-1-enyl)aniline (496-D)

To a solution of 496-C (130 mg, 666 umol, 1.0 eq) in ethanol (2.5 mL) was added water (0.5 mL), ammonium chloride (178 mg, 3.33 mmol, 5.0 eq) and iron powder (186 mg, 3.33 mmol, 5.0 eq). The mixture was stirred at 70° C. for 12 h. The suspension was filtered and the filtrate was concentrated under reduced pressure to give a residue. The residue was purified by silica gel column chromatography (petroleum ether/ethyl acetate, from 50/1 to 5/1) to give 80.0 mg (61% yield) of 496-D as a yellow liquid.

LCMS: (ESI) m/z: 166.1 [M+H]$^+$.

Step 5: Synthesis of 1-[4-(difluoromethoxy)phenyl]-N-[3-(1-fluoro-2-methyl-prop-1-enyl)phenyl]-3-methyl-5-oxo-4H-pyrazole-4-carboxamide (496)

Compound ID: 496

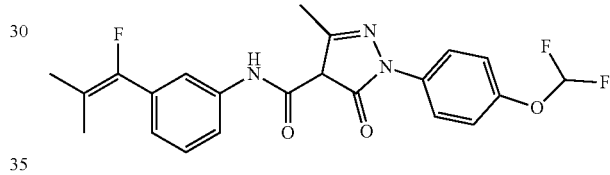

To a solution of 496-D (80.0 mg, 407 umol, 1.0 eq) in acetonitrile (3 mL) was added triethylamine (123 mg, 1.22 mmol, 3.0 eq) and 298-C (330 mg, 814 umol, 2.0 eq). The mixture was stirred at 70° C. for 12 h. The mixture was concentrated in vacuum directly, then diluted with ethyl acetate (20 mL), the organic layer was washed with hydrochloric acid (15 mL, 0.5 M), the organic layer was dried over anhydrous sodium sulfate, filtered and concentrated to obtain the residue. The residue was purified by pre-TLC (petroleum ether/ethyl acetate, 0/1) to give the crude product. The crude product was purified by prep-HPLC (column: UniSil 3-100 C18 Ultra (150*25 mm*3 um); mobile phase: [water (0.225% formic acid)-acetonitrile]; B %: 50%-80%, 10 min) to give 15.6 mg (9% yield) of 496 as a yellow solid.

LCMS: (ESI) m/z: 432.2 [M+H]$^+$.

$^1$H NMR: (400 MHz, MeOD-d$_4$) δ: 7.76 (s, 1H), 7.70 (d, J=8.8 Hz, 2H), 7.54 (d, J=8.0 Hz, 1H), 7.34 (t, J=8.0 Hz, 1H), 7.30 (d, J=8.4 Hz, 2H), 7.12 (d, J=7.6 Hz, 1H), 6.90 (t, J=74.0 Hz, 1H), 2.59 (s, 3H), 1.83 (dd, J=10.8, 3.2 Hz, 6H).

Synthesis of 497

Step 1: Synthesis of 6-bromo-1H-indole-3-carbaldehyde (497-A)

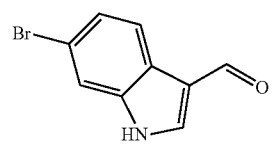 [SMILES: O=Cc1c[nH]c2cc(Br)ccc12]

Phosphoryl trichloride (4.89 g, 31.9 mmol, 1.3 eq) was added into N,N-dimethylformamide (14.3 g, 195 mmol, 7.6 eq) dropwise at 0° C. It was stirred at 0° C. for 30 min. 6-bromo-1H-indole (5.00 g, 25.5 mmol, 1.0 eq) in N,N-dimethylformamide (30 mL) was added into the mixture. It was stirred at 25° C. for 3 h. The reaction was quenched with water (100 mL). The slurry was filtered to give 4.80 g (83% yield) of 497-A as a red solid.

LCMS: (ESI) m/z: 224.3 [M+H]$^+$.

$^1$H NMR (400 MHz, DMSO-d$_6$) δ: 12.22 (s, 1H), 9.93 (s, 1H), 8.32 (d, J=3.2 Hz, 1H), 8.02 (d, J=8.4 Hz, 1H), 7.71 (d, J=1.6 Hz, 1H), 7.36 (dd, J=8.8, 2.0 Hz, 1H).

Step 2: Synthesis of 6-bromo-3-methyl-1H-indole (497-B)

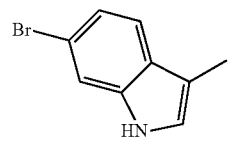

To a solution of 497-A (3.80 g, 16.8 mmol, 1.0 eq) in tetrahydrofuran (40 mL) was added aluminum(III) lithium hydride (1.27 g, 33.6 mmol, 2.0 eq) at 0° C. It was stirred at 70° C. for 4 h under nitrogen. The reaction was quenched with hydrochloric acid solution (1 M, 100 mL) and then extracted with ethyl acetate (50 mL×2). The organic layer was washed with brine (100 mL). The organic layer was dried over anhydrous sodium sulfate, filtered and concentrated to give 3.60 g (crude) of 497-B as a yellow solid.

LCMS: (ESI) m/z: 210.1 [M+H]$^+$.

Step 3: Synthesis of 6-bromo-3-methyl-1-tosyl-1H-indole (497-C)

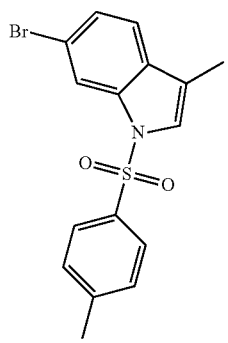 [SMILES: Cc1ccc(S(=O)(=O)n2cc(C)c3ccc(Br)cc32)cc1]

497-C was obtained via similar procedure of 410-A from 497-B and 4-methylbenzene-1-sulfonyl chloride.

$^1$H NMR (400 MHz, DMSO-d$_6$) δ: 8.03 (d, J=1.6 Hz, 1H), 7.84 (d, J=8.4 Hz, 2H), 7.62 (d, J=0.8 Hz, 1H), 7.53-7.50 (m, 1H), 7.45-7.42 (m, 1H), 7.40 (d, J=8.0 Hz, 2H), 2.32 (s, 3H), 2.19 (d, J=1.2 Hz, 3H).

Step 4: Synthesis of di-tert-butyl 1-(3-methyl-1-tosyl-1H-indol-6-yl)hydrazine-1,2-dicarboxylate (497-D)

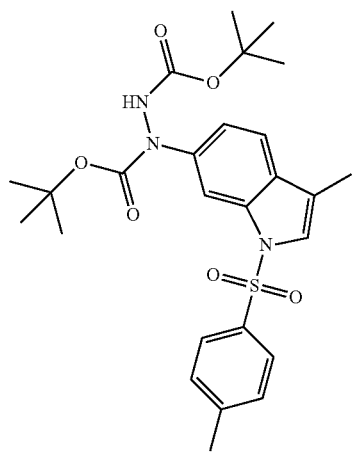 [SMILES: Cc1ccc(S(=O)(=O)n2cc(C)c3ccc(N(NC(=O)OC(C)(C)C)C(=O)OC(C)(C)C)cc32)cc1]

497-D was obtained via similar procedure of 410-B from 497-C and di-tert-butyl hydrazine-1,2-dicarboxylate.

LCMS: (ESI) m/z: 538.1 [M+H]$^+$.

Step 5: Synthesis of 6-hydrazinyl-3-methyl-1-tosyl-1H-indole (497-E)

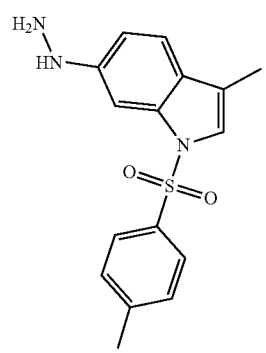 [SMILES: Cc1ccc(S(=O)(=O)n2cc(C)c3ccc(NN)cc32)cc1]

497-E was obtained via similar procedure of 410-C from 497-D and ethyl acetate/hydrochloride LCMS: (ESI) m/z: 316.1 [M+H]$^+$.

Step 6: Synthesis of 3-methyl-1-(3-methyl-1-tosyl-1H-indol-6-yl)-1H-pyrazol-5(4H)-one (497-F)

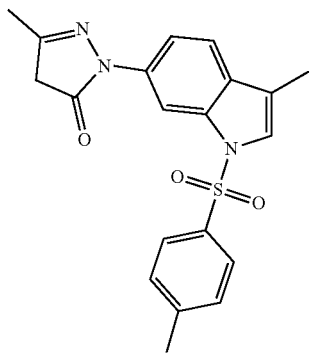

497-F was obtained via general procedure II from 497-E $^1$H NMR (400 MHz, DMSO-$d_6$) δ: 8.28 (d, J=1.2 Hz, 1H), 7.84 (d, J=8.4 Hz, 2H), 7.63-7.58 (m, 3H), 7.36 (d, J=8.0 Hz, 2H), 5.67 (s, 1H), 2.30 (s, 3H), 2.25 (s, 3H), 2.21 (d, J=0.8 Hz, 3H).

Step 7: Synthesis of 4-nitrophenyl 3-methyl-1-(3-methyl-1-tosyl-1H-indol-6-yl)-5-oxo-4,5-dihydro-1H-pyrazole-4-carboxylate (497-G)

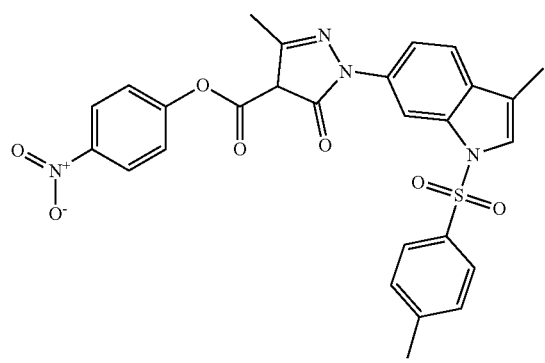 [SMILES: CC1=NN(c2ccc3c(C)cn(S(=O)(=O)c4ccc(C)cc4)c3c2)C(=O)C1C(=O)Oc1ccc([N+](=O)[O-])cc1]

497-G was obtained via general procedure III from 497-F
LCMS: (ESI) m/z: 546.9 [M+H]$^+$.

Step 8: Synthesis of N-(3-(1,1-difluoropropyl)phenyl)-3-methyl-1-(3-methyl-1-tosyl-1H-indol-6-yl)-5-oxo-4,5-dihydro-1H-pyrazole-4-carboxamide (497-H)

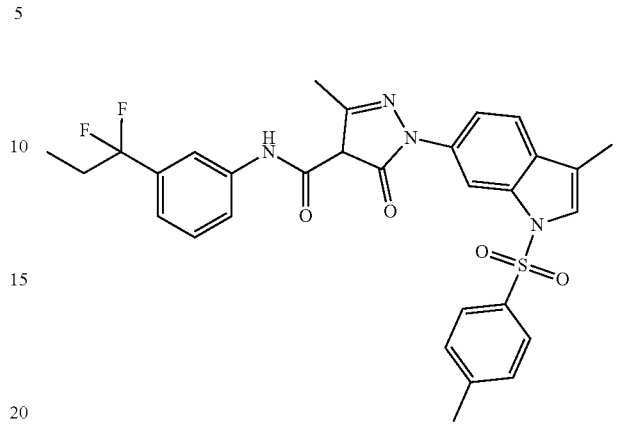

497-H was obtained via general procedure IV from 502-G
LCMS: (ESI) m/z: 579.0 [M+H]$^+$.

Step 9: Synthesis of N-(3-(1,1-difluoropropyl)phenyl)-3-methyl-1-(3-methyl-1H-indol-6-yl)-5-oxo-4,5-dihydro-1H-pyrazole-4-carboxamide (497-I)

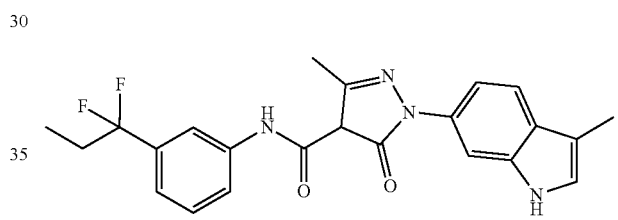

497-I was obtained via similar procedure of 410 from 497-H and potassium hydroxide.
LCMS: (ESI) m/z: 425.0 [M+H]$^+$.

Step 10: Synthesis of N-(3-(1,1-difluoropropyl)phenyl)-1-(1,3-dimethyl-1H-indol-6-yl)-3-methyl-5-oxo-4,5-dihydro-1H-pyrazole-4-carboxamide (497)

Compound ID: 497

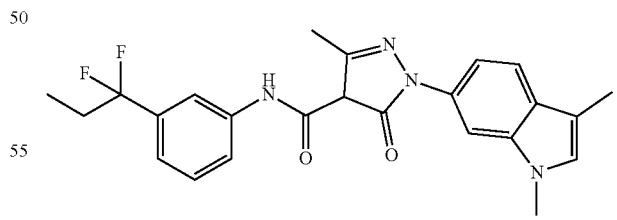

497 was obtained via similar procedure of 366 from 497-I and iodomethane.
LCMS: (ESI) m/z: 439.1 [M+H]$^+$.

$^1$H NMR (400 MHz, DMSO-$d_6$) δ: 11.04 (br s, 1H), 7.91 (s, 1H), 7.75 (s, 1H), 7.63 (d, J=9.2 Hz, 1H), 7.58 (d, J=8.4 Hz, 1H), 7.42 (t, J=8.0 Hz, 1H), 7.37 (d, J=8.4 Hz, 1H), 7.13-7.17 (m, 2H), 3.75 (s, 3H), 2.53 (br s, 3H), 2.27 (d, J=0.4 Hz, 3H), 2.17-2.24 (m, 2H), 0.92 (t, J=7.6 Hz, 3H).

Synthesis of 498

Step 1: Synthesis of
6-chloro-2-iodo-3-methoxypyridine (498-A)

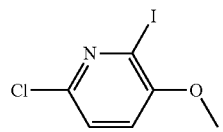

To a solution of 223-A (3.00 g, 11.7 mmol, 1.0 eq) in acetonitrile (30 mL) was added potassium carbonate (3.25 g, 23.5 mmol, 2.0 eq). Iodomethane (2.50 g, 17.6 mmol, 1.5 eq) was added into the mixture. It was stirred at 50° C. for 1 h. The reaction mixture was quenched with water (100 mL) and then extracted with ethyl acetate (100 mL). The organic layer was washed with brine (100 mL). The organic layer was dried over anhydrous sodium sulfate, filtered and concentrated to give 2.80 g (88% yield) of 498-A as a yellow solid.

$^1$H NMR (400 MHz, DMSO-$d_6$) δ: 7.50-7.47 (m, 1H), 7.44-7.41 (m, 1H), 3.88 (s, 3H).

Step 2: Synthesis of
6-chloro-3-methoxy-2-phenylpyridine (498-B)

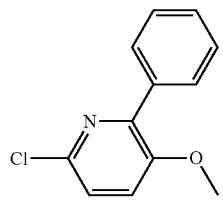

498-B was obtained via similar procedure of 223-C from 498-A and phenylboronic acid.
LCMS: (ESI) m/z: 220.1 [M+H]$^+$.

Step 3: Synthesis of di-tert-butyl 1-(5-methoxy-6-phenylpyridin-2-yl)hydrazine-1,2-dicarboxylate (498-C)

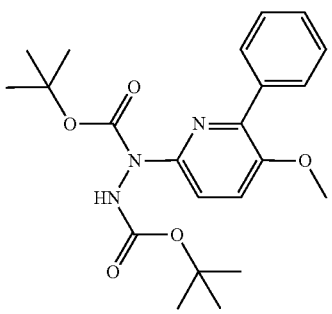 [SMILES: COc1ccc(N(NC(=O)OC(C)(C)C)C(=O)OC(C)(C)C)nc1-c1ccccc1]

498-C was obtained via similar procedure of 410-B from 498-B and di-tert-butyl hydrazine-1,2-dicarboxylate.
LCMS: (ESI) m/z: 416.2 [M+H]$^+$.

Step 4: Synthesis of
6-hydrazinyl-3-methoxy-2-phenylpyridine (498-D)

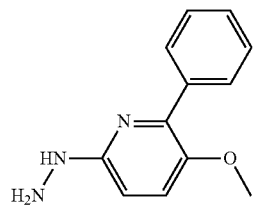 [SMILES: COc1ccc(NN)nc1-c1ccccc1]

498-D was obtained via similar procedure of 410-C from 498-C and ethyl acetate/hydrochloride.
LCMS: (ESI) m/z: 216.1 [M+H]$^+$.

Step 5: Synthesis of 1-(5-methoxy-6-phenylpyridin-2-yl)-3-methyl-1H-pyrazol-5(4H)-one (498-E)

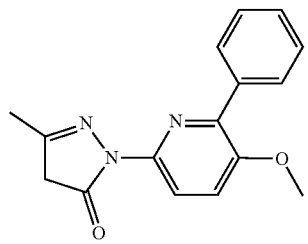 [SMILES: COc1ccc(N2N=C(C)CC2=O)nc1-c1ccccc1]

498-E was obtained via general procedure II from 498-D
$^1$H NMR (400 MHz, DMSO-$d_6$) δ: 12.00-11.53 (m, 1H), 8.32 (d, J=8.8 Hz, 1H), 8.02 (d, J=6.8 Hz, 1H), 7.84 (br d, J=8.4 Hz, 1H), 7.76-7.65 (m, 1H), 7.53-7.39 (m, 3H), 5.45-5.11 (m, 1H), 3.90-3.86 (m, 3H), 2.20-2.14 (m, 3H).

Step 6: Synthesis of 4-nitrophenyl 1-(5-methoxy-6-phenylpyridin-2-yl)-3-methyl-5-oxo-4,5-dihydro-1H-pyrazole-4-carboxylate (498-F)

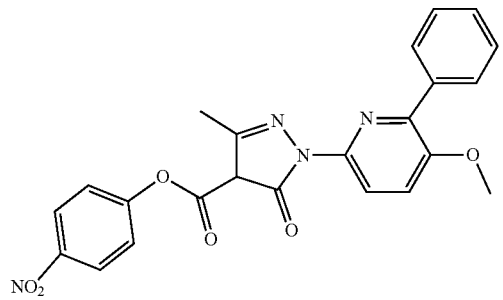 [SMILES: COc1ccc(N2N=C(C)C(C(=O)Oc3ccc([N+](=O)[O-])cc3)C2=O)nc1-c1ccccc1]

498-F was obtained via general procedure III from 498-E
LCMS: (ESI) m/z: 447.3 [M+H]$^+$.

Step 7: Synthesis of N-(3-(1,1-difluoropropyl)phenyl)-1-(5-methoxy-6-phenylpyridin-2-yl)-3-methyl-5-oxo-4,5-dihydro-1H-pyrazole-4-carboxamide (498)

Compound ID: 498

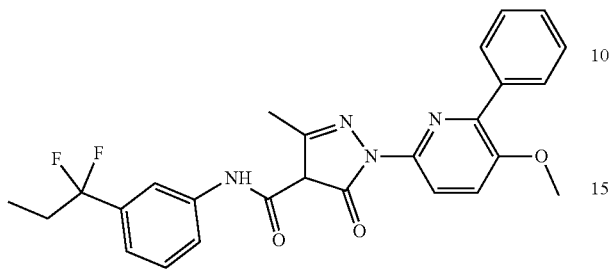

498 was obtained via general procedure IV from 498-F.
LCMS: (ESI) m/z: 479.1 [M+H]⁺.
¹H NMR (400 MHz, DMSO-d₆) δ: 10.80 (s, 1H), 8.27 (d, J=9.2 Hz, 1H), 8.02-7.99 (m, 2H), 7.92 (s, 1H), 7.83 (d, J=9.2 Hz, 1H), 7.65 (d, J=8.0 Hz, 1H), 7.51-7.42 (m, 4H), 7.18 (d, J=7.6 Hz, 1H), 3.90 (s, 3H), 2.59 (s, 3H), 2.27-2.17 (m, 2H), 0.93 (t, J=7.6 Hz, 3H).

Synthesis of 499

Step 1: Synthesis of 6-bromo-1-(4-methoxybenzyl)-1H-indazole (499-A)

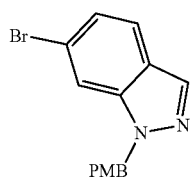

To a solution of 6-bromo-1H-indazole (1.60 g, 8.12 mmol, 1.0 eq) in N,N-dimethylformamide (15 mL) was added potassium carbonate (2.24 g, 16.2 mmol, 2.0 eq), it was stirred at 25° C. for 30 min, then the 1-(chloromethyl)-4-methoxy-benzene (1.53 g, 9.74 mmol, 1.2 eq) in N,N-dimethylformamide (3 mL) was added into the solution. The mixture was stirred at 50° C. for 2.5 h. The reaction mixture was quenched by addition water (150 mL), and extracted with ethyl acetate (50 mL×3). The combined organic layer was washed with brine (100 mL), dried over anhydrous sodium sulfate, filtered and concentrated under reduced pressure to give 2.50 g (97% yield) of 499-A as a brown liquid.
LCMS: (ESI) m/z: 319.0 [M+H]⁺.

Step 2: Synthesis of di-tert-butyl 1-(1-(4-methoxybenzyl)-1H-indazol-6-yl)hydrazine-1,2-dicarboxylate (499-B)

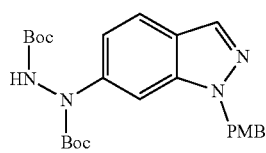

499-B was obtained via similar procedure of 410-B from 499-A and di-tert-butyl hydrazine-1,2-dicarboxylate.
LCMS: (ESI) m/z: 469.2 [M+H]⁺.

Step 3: Synthesis of 6-hydrazinyl-1-(4-methoxybenzyl)-1H-indazole (499-C)

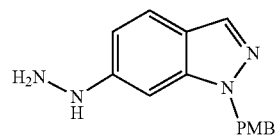

499-C was obtained via similar procedure of 410-C from 499-B and ethyl acetate/hydrochloride
LCMS: (ESI) m/z: 269.1 [M+H]⁺.

Step 4: Synthesis of 1-(1-(4-methoxybenzyl)-1H-indazol-6-yl)-3-methyl-1H-pyrazol-5(4H)-one (499-D)

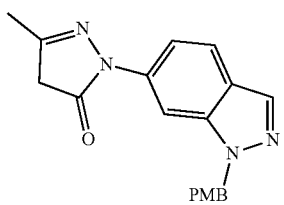

499-D was obtained via general procedure II from 499-C
LCMS: (ESI) m/z: 335.1 [M+H]⁺.

Step 5: Synthesis of 4-nitrophenyl 1-(1-(4-methoxybenzyl)-1H-indazol-6-yl)-3-methyl-5-oxo-4,5-dihydro-1H-pyrazole-4-carboxylate (499-E)

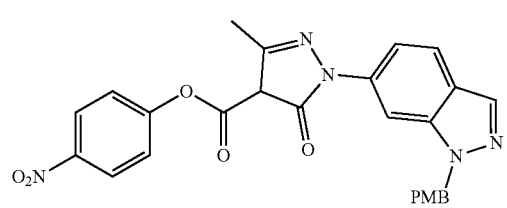

499-E was obtained via general procedure III from 499-D
LCMS: (ESI) m/z: 500.1 [M+H]⁺.

Step 6: Synthesis of N-(3-(1,1-difluoropropyl)phe-
nyl)-1-(1-(4-methoxybenzyl)-1H-indazol-6-yl)-3-
methyl-5-oxo-4,5-dihydro-1H-pyrazole-4-carboxam-
ide (499-F)

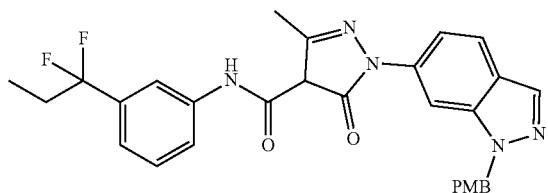

499-F was obtained via general procedure IV from 499-E.
LCMS: (ESI) m/z: 532.2 [M+H]$^+$.

Step 7: Synthesis of N-[3-(1,1-difluoropropyl)phe-
nyl]-1-(1H-indazol-6-yl)-3-methyl-5-oxo-4H-pyra-
zole-4-carboxamide (499)

Compound ID: 499

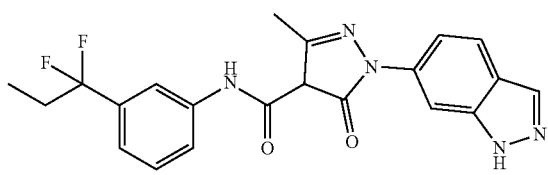 [SMILES: CCC(F)(F)c1cccc(NC(=O)C2C(=O)N(c3ccc4cn[nH]c4c3)N=C2C)c1]

To a solution of 499-F (800 mg, 1.51 mmol, 1.0 eq) in methanol (5 mL) was added Pd/C (200 mg, 10% purity). It was stirred at 25° C. for 12 h under hydrogen (15 psi). The suspension was filtered and the filtrate concentrated under reduced pressure to give the residue. The residue was purified by silica gel column chromatography (petroleum ether/ethyl acetate=10/1 to 0/1) twice time to give the crude product. The crude product was purified by prep-TLC (ethyl acetate/methanol, 10/1) to give the impure product. The impure product was purified by prep-HPLC (column: Phenomenex Gemini-NX C18 75*30 mm*3 um; mobile phase: [water (0.225% formic acid)-acetonitrile]; B %: 35%-65%, 7 min) to give 7.40 mg (1% yield) of 499 as a yellow solid.
LCMS: (ESI) m/z: 412.1 [M+H]$^+$.
$^1$H NMR (400 MHz, MeOD-d$_4$) δ: 8.09 (d, J=5.2 Hz, 1H), 7.94-7.84 (m, 3H), 7.65 (d, J=7.6 Hz, 1H), 7.52 (d, J=8.8 Hz, 1H), 7.40 (t, J=8.0 Hz, 1H), 7.18 (d, J=7.6 Hz, 1H), 2.58 (s, 3H), 2.23-2.13 (m, 2H), 0.98 (t, J=7.6 Hz, 3H).
Synthesis of 500

Step 1: Synthesis of 6-bromo-1-(4-methoxybenzyl)-
1H-benzo[d]imidazole (500-A)

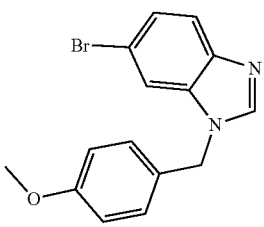 [SMILES: COc1ccc(Cn2cnc3ccc(Br)cc32)cc1]

500-A was obtained via similar procedure of 499 from 6-bromo-1H-benzimidazole and 1-(chloromethyl)-4-methoxy-benzene.
$^1$H NMR (400 MHz, DMSO-d$_6$) δ: 8.44 (d, J=8.4 Hz, 1H), 7.83 (dd, J=5.6, 1.6 Hz, 1H), 7.56 (dd, J=30.8, 8.4 Hz, 1H), 7.37-7.32 (m, 1H), 7.32-7.27 (m, 2H), 6.92-6.87 (m, 2H), 5.41 (s, 2H), 3.71 (d, J=2.8 Hz, 3H).

Step 2: Synthesis of di-tert-butyl 1-(1-(4-methoxy-
benzyl)-1H-benzo[d]imidazol-6-yl)hydrazine-1,2-
dicarboxylate (500-B)

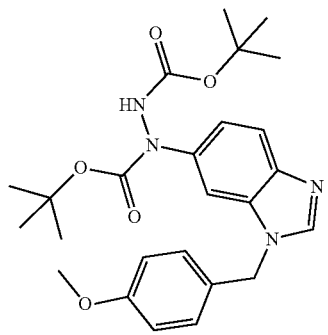 [SMILES: COc1ccc(Cn2cnc3ccc(N(NC(=O)OC(C)(C)C)C(=O)OC(C)(C)C)cc32)cc1]

500-B was obtained via similar procedure of 499-B from 500-A and di-tert-butyl hydrazine-1,2-dicarboxylate.
LCMS: (ESI) m/z: 469.2 [M+H]$^+$.

Step 3: Synthesis of 6-hydrazinyl-1-(4-methoxyben-
zyl)-1H-benzo[d]imidazole (500-C)

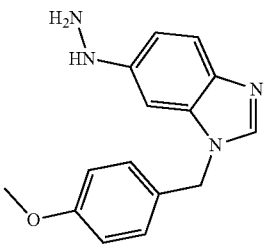 [SMILES: COc1ccc(Cn2cnc3ccc(NN)cc32)cc1]

500-C was obtained via similar procedure of 499-C from 500-B and ethyl acetate/hydrochloride
LCMS: (ESI) m/z: 269.1 [M+H]$^+$.

Step 4: Synthesis of 1-(1-(4-methoxybenzyl)-1H-
benzo[d]imidazol-6-yl)-3-methyl-1H-pyrazol-5(4H)-
one (500-D)

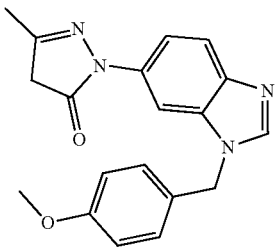 [SMILES: COc1ccc(Cn2cnc3ccc(N4N=C(C)CC4=O)cc32)cc1]

500-D was obtained via general procedure II from 500-C
$^1$H NMR (400 MHz, DMSO-d$_6$) δ: 8.42 (br d, J=12.8 Hz, 1H), 7.86-7.72 (m, 1H), 7.70-7.63 (m, 1H), 7.57-7.51 (m, 1H), 7.27 (dd, J=22.0, 8.8 Hz, 2H), 6.90 (dd, J=8.8, 2.8 Hz, 2H), 5.44 (br d, J=2.8 Hz, 2H), 3.72-3.70 (m, 3H), 2.14-2.08 (m, 3H).

Step 5: Synthesis of 1-(1,1-difluoropropyl)-3-isocyanatobenzene (500-E)

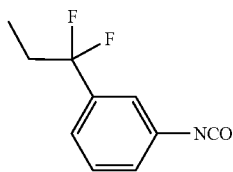

500-E was obtained via similar procedure of 405-D from 3-(1,1-difluoropropyl)aniline and triphosgene.

Step 6: Synthesis of N-(3-(1,1-difluoropropyl)phenyl)-1-(1-(4-methoxybenzyl)-1H-benzo[d]imidazol-6-yl)-3-methyl-5-oxo-4,5-dihydro-1H-pyrazole-4-carboxamide (500-F)

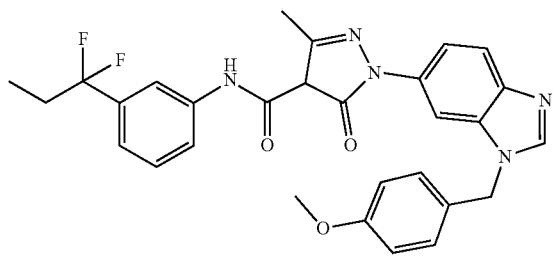 [SMILES: CCC(F)(F)c1cccc(NC(=O)C2C(=O)N(c3ccc4ncn(Cc5ccc(OC)cc5)c4c3)N=C2C)c1]

500-F was obtained via similar procedure of 405 from 500-D and 500-E.

LCMS: (ESI) m/z: 532.3 [M+H]+.

Step 6: Synthesis of 1-(1H-benzo[d]imidazol-6-yl)-N-(3-(1,1-difluoropropyl)phenyl)-3-methyl-5-oxo-4,5-dihydro-1H-pyrazole-4-carboxamide (500)

Compound ID: 500

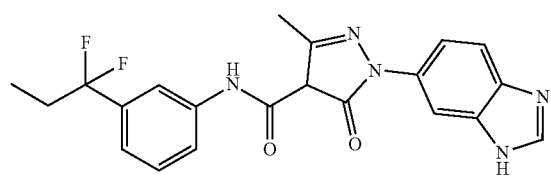 [SMILES: CCC(F)(F)c1cccc(NC(=O)C2C(=O)N(c3ccc4nc[nH]c4c3)N=C2C)c1]

500 was obtained via similar procedure of 499 from 500-F and hydrogen.

LCMS: (ESI) m/z: 412.1 [M+H]+.

¹H NMR (400 MHz, MeOD-d₄) δ: 8.38 (s, 1H), 8.22 (s, 1H), 8.02 (s, 1H), 7.87 (s, 1H), 7.77-7.69 (m, 2H), 7.65 (d, J=8.4 Hz, 1H), 7.38 (t, J=8.0 Hz, 1H), 7.14 (br d, J=7.2 Hz, 1H), 2.50 (s, 3H), 2.23-2.14 (m, 2H), 0.98 (t, J=7.6 Hz, 3H).

Synthesis of 501

Step 1: Synthesis of 4-(3-methyl-5-oxo-4,5-dihydro-1H-pyrazol-1-yl)benzonitrile (501-A)

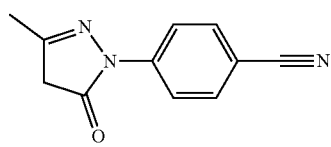

501-A was obtained via general procedure II from 4-hydrazinobenzonitrile

¹H NMR (400 MHz, CDCl₃-d) δ: 2.24 (s, 3H) 3.47-3.52 (m, 1H) 3.49 (s, 1H) 7.68 (d, J=8.88 Hz, 2H) 8.08 (d, J=8.88 Hz, 2H).

Step 2: Synthesis of 4-nitrophenyl 1-(4-cyanophenyl)-3-methyl-5-oxo-4,5-dihydro-1H-pyrazole-4-carboxylate (501-B)

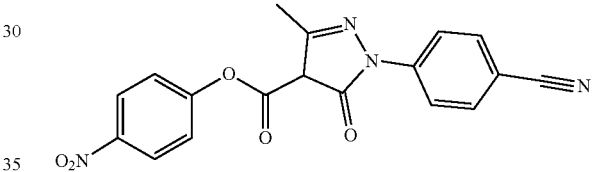

501-B was obtained via general procedure III from 501-A

LCMS: (ESI) m/z: 365.2 [M+H]+.

Step 3: Synthesis of 1-(4-cyanophenyl)-N-(3-(1,1-difluoropropyl)phenyl)-3-methyl-5-oxo-4,5-dihydro-1H-pyrazole-4-carboxamide (501)

Compound ID: 501

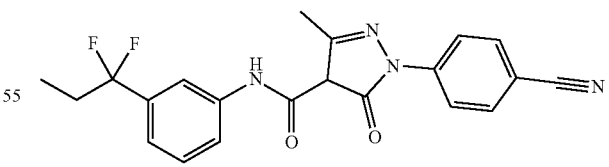

501 was obtained via general procedure IV from 501-B and 3-(1,1-difluoropropyl)aniline LCMS: (ESI) m/z: 397.2 [M+H]+.

1H NMR (400 MHz, DMSO-d₆) δ: 0.92 (t, J=7.4 Hz, 3H) 2.20 (m, 2H) 2.54 (s, 3H) 7.16 (d, J=8.0 Hz, 1H) 7.42 (t, J=8.0 Hz, 1H) 7.61 (d, J=8.0 Hz, 1H) 7.91 (s, 1H) 7.94-8.00 (m, 2H) 8.00-8.04 (m, 2H) 10.66 (s, 1H).

Synthesis of 502

Step 1: Synthesis of (E)-2-(4-bromo-2-nitro-phenyl)-N,N-dimethyl-ethenamine (502-A)

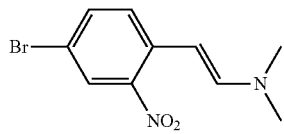

To a solution of 4-bromo-1-methyl-2-nitro-benzene (10.0 g, 46.3 mmol, 1.0 eq) in N,N-dimethyl formamide (20 mL) was added N,N-dimethyl formamide dimethyl acetal (36.0 g, 301 mmol, 6.5 eq). The mixture was stirred at 110° C. for 12 h. The mixture was quenched with water (500 mL), then extracted with ethyl acetate (300 mL×2). The combined organic layer was washed with brine (400 mL), dried over anhydrous sodium sulfate, filtered and concentrated under reduced pressure to give 12.0 g (96% yield) of 502-A as a red liquid.

$^1$H NMR (400 MHz, CDCl$_3$-d) δ: 7.99 (d, J=2.0 Hz, 1H), 7.39 (d, J=2.0 Hz, 1H), 7.34-7.30 (m, 1H), 6.96 (d, J=13.2 Hz, 1H), 5.82 (d, J=13.2 Hz, 1H), 2.92 (s, 6H).

Step 2: Synthesis of (Z)-3-(4-bromo-2-nitro-phenyl)-4-(dimethylamino)but-3-en-2-one (502-B)

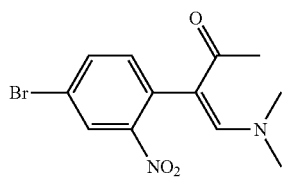

To a solution of 502-A (12.0 g, 42.4 mmol, 1.0 eq) in tetrahydrofuran (60 mL) was added pyridine (5.40 g, 67.9 mmol, 1.6 eq) and acetyl chloride (4.70 g, 59.4 mmol, 1.4 eq). The mixture was stirred at 50° C. for 12 h. The mixture was concentrated in vacuum and diluted with water (150 mL), then extracted with ethyl acetate (80 mL×3). The combined organic layer was washed with brine (150 mL), dried over anhydrous sodium sulfate, filtered and concentrated under reduced pressure to give 12.4 g (crude) of 502-B as a red liquid.

LCMS: (ESI) m/z: 313.0, 315.0 [M+H]$^+$.

Step 3: Synthesis of 1-(4-bromo-2-nitro-phenyl)propan-2-one (502-C)

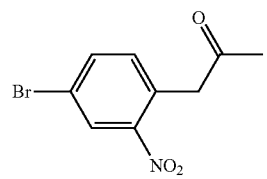

To a solution of 502-B (12.4 g, 39.6 mmol, 1.0 eq) in dioxane (150 mL) was added water (30 mL) The mixture was stirred at 110° C. for 16 h. The mixture was concentrated in vacuum to give a residue and diluted with water (150 mL), then extracted with ethyl acetate (80 mL×3), the combined organic layer was washed with brine (100 mL), dried over anhydrous sodium sulfate, filtered and concentrated under reduced pressure to give the crude product. The crude product was purified by silica gel column chromatography (petroleum ether/ethyl acetate, from 30/1 to 1/1) to give 7.00 g (63% yield) of 502-C as a yellow solid.

LCMS: (ESI) m/z: 258.0, 260.0 [M+H]$^+$.

Step 4: Synthesis of 1-(4-bromo-2-nitro-phenyl)propan-2-one (502-D)

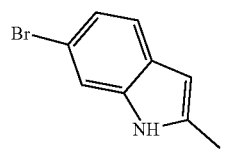

To a solution of 502-C (3.00 g, 10.7 mmol, 1.0 eq) in acetic acid (30 mL) was added iron powder (3.60 g, 64.2 mmol, 6.0 eq) slowly. The mixture was stirred at 110° C. for 12 h. The mixture was diluted with water (200 mL), then filtered and the aqueous phase was extracted with ethyl acetate (80 mL×3). The combined organic layer was washed was brine (150 mL), dried over anhydrous sodium sulfate, filtered and concentrated under reduced pressure to give 4.50 g (crude) of 502-D as a brown red solid.

LCMS: (ESI) m/z: 209.9, 212.0 [M+H]$^+$.

Step 5: Synthesis of 6-bromo-2-methyl-1-tosyl-1H-indole (502-E)

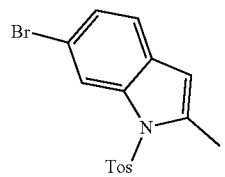

502-E was obtained via similar procedure of 410-A from 502-D and 4-methylbenzene-1-sulfonyl chloride.

$^1$H NMR (400 MHz, CDCl$_3$-d) δ: 8.37 (br s, 1H), 7.67 (d, J=8.4 Hz, 2H), 7.32 (dd, J=8.4, 1.6 Hz, 1H), 7.25 (t, J=7.2 Hz, 3H), 6.30 (s, 1H), 2.57 (d, J=1.2 Hz, 3H), 2.37 (s, 3H).

Step 6: Synthesis of di-tert-butyl 1-(2-methyl-1-tosyl-1H-indol-6-yl)hydrazine-1,2-dicarboxylate (502-F)

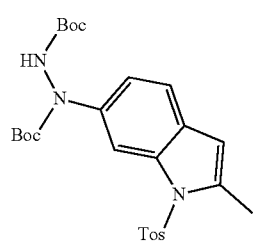

502-F was obtained via similar procedure of 410-B from 502-E and di-tert-butyl hydrazine-1,2-dicarboxylate.

$^1$H NMR (400 MHz, CDCl$_3$-d) δ: 8.22 (br s, 1H), 7.67 (d, J=7.2 Hz, 2H), 7.31 (d, J=7.6 Hz, 2H), 7.21 (d, J=8.0 Hz, 2H), 6.29 (s, 1H), 2.56 (d, J=0.8 Hz, 3H), 2.35 (s, 3H), 1.53-1.48 (m, 18H).

Step 7: Synthesis of 6-hydrazinyl-2-methyl-1-tosyl-1H-indole (502-G)

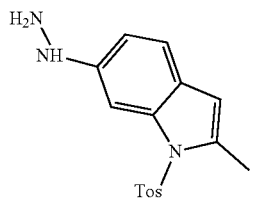

502-G was obtained via similar procedure of 410-C from 502-F and ethyl acetate/hydrochloride LCMS: (ESI) m/z: 299.1 [M-NH$_2$]$^+$.

Step 8: Synthesis of 3-methyl-1-(2-methyl-1-tosyl-1H-indol-6-yl)-1H-pyrazol-5(4H)-one (502-H)

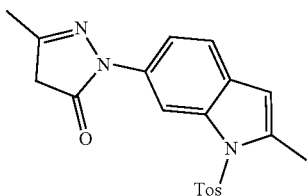

502-H was obtained via general procedure II from 502-G
LCMS: (ESI) m/z: 382.0 [M+H]$^+$.

Step 9: Synthesis of 4-nitrophenyl 3-methyl-1-(2-methyl-1-tosyl-1H-indol-6-yl)-5-oxo-4,5-dihydro-1H-pyrazole-4-carboxylate (502-I)

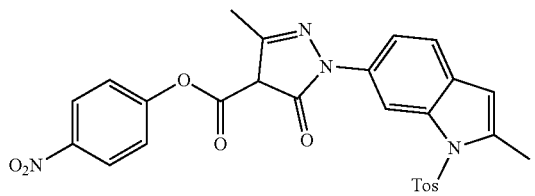

502-I was obtained via general procedure III from 502-H
LCMS: (ESI) m/z: 547.1 [M+H]$^+$.

Step 10: Synthesis of N-(3-(1,1-difluoropropyl)phenyl)-3-methyl-1-(2-methyl-1-tosyl-1H-indol-6-yl)-5-oxo-4,5-dihydro-1H-pyrazole-4-carboxamide (502-J)

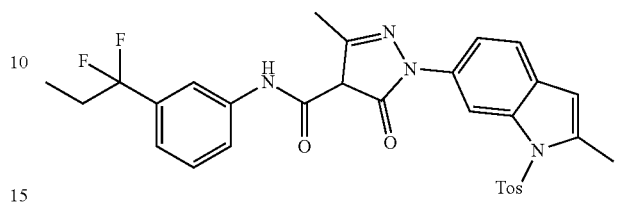

502-J was obtained via general procedure IV from 502-I.
LCMS: (ESI) m/z: 579.1 [M+H]$^+$.

Step 11: Synthesis of N-[3-(1,1-difluoropropyl)phenyl]-3-methyl-1-(2-methyl-1H-indol-6-yl)-5-oxo-4H-pyrazole-4-carboxamide (502-K)

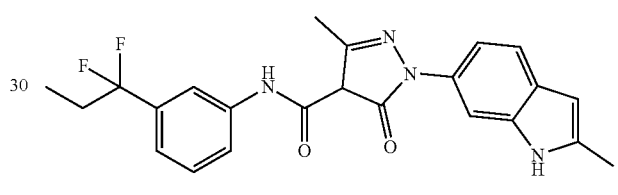

502-K was obtained via similar procedure of 410 from 502-J and potassium hydroxide.
LCMS: (ESI) m/z: 425.1 [M+H]$^+$.

Step 12: Synthesis of N-[3-(1,1-difluoropropyl)phenyl]-1-(1,2-dimethylindol-6-yl)-3-methyl-5-oxo-4H-pyrazole-4-carboxamide (502)

Compound ID: 502

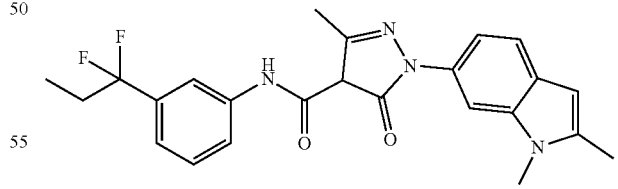

502 was obtained via similar procedure of 366 from 502-K and iodomethane.
LCMS: (ESI) m/z: 439.2 [M+H]$^+$.

$^1$H NMR: (400 MHz, DMSO-d$_6$) δ: 11.04 (s, 1H), 7.91 (s, 1H), 7.73 (s, 1H), 7.63 (d, J=8.0 Hz, 1H), 7.52 (d, J=8.4 Hz, 1H), 7.42 (t, J=7.6 Hz, 1H), 7.29 (d, J=8.0 Hz, 1H), 7.15 (d, J=7.6 Hz, 1H), 6.27 (s, 1H), 3.69 (s, 3H), 2.54 (s, 3H), 2.43 (s, 3H), 2.25-2.15 (m, 2H), 0.92 (t, J=7.2 Hz, 3H).

Synthesis of 503

Step 1: Synthesis of tert-butyl (5-cyanopyridin-3-yl)carbamate (503-A)

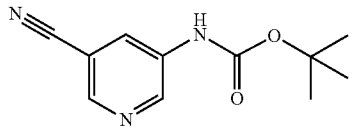 [SMILES: CC(C)(C)OC(=O)Nc1cncc(C#N)c1]

To a solution of 5-bromopyridine-3-carbonitrile (3.00 g, 16.4 mmol, 1.0 eq) and tert-butyl carbamate (3.84 g, 32.8 mmol, 2.0 eq) in dioxane (10 mL) was added cesium carbonate (10.7 g, 32.8 mmol, 2.0 eq), palladium acetate (368 mg, 1.64 mmol, 0.10 eq) and dicyclohexyl-[2-[2,4,6-tri(propan-2-yl)phenyl]phenyl]phosphane (3.13 g, 6.56 mmol, 0.40 eq). The reaction mixture was degassed and purged with nitrogen for 3 times, and then the mixture was stirred at 100° C. for 12 hr under nitrogen atmosphere. To the reaction mixture was added water (100 mL), and the aqueous layer mixture was extracted with ethyl acetate (30 mL×3). The combined organic layer was washed with brine (50 mL), dried over anhydrous sodium sulfate, filtered, and concentrated under reduced pressure. The crude product was purified by silica gel column chromatography (petroleum ether/ethyl acetate, from 10/1 to 5/1) to give 3.60 g (100% yield) of 503-A as a yellow solid.

LCMS: (ESI) m/z: 220.1 [M+H]$^+$.

Step 2: Synthesis of 5-aminonicotinonitrile (503-B)

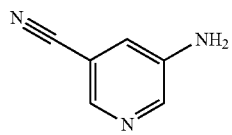

The solution of 503-A (200 mg, 910 umol, 1.0 eq) in dichloromethane (2 mL) and trifluoroacetic acid (2 mL) was stirred at 25° C. for hr. The reaction mixture was concentrated under reduced pressure to give 200 mg (crude, trifluoroacetic acid salt) of 503-B as a light yellow solid.

LCMS: (ESI) m/z: 120.1 [M+H]$^+$.

Step 3: Synthesis of N-(5-cyanopyridin-3-yl)-1-(4-(difluoromethoxy)phenyl)-3-methyl-5-oxo-4,5-dihydro-1H-pyrazole-4-carboxamide (503)

Compound ID: 503

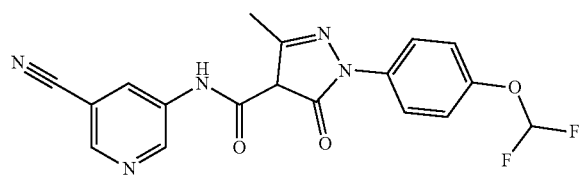 [SMILES: CC1=NN(c2ccc(OC(F)F)cc2)C(=O)C1C(=O)Nc1cncc(C#N)c1]

503 was obtained via general procedure IV from 298-C and 503-B.

LCMS: (ESI) m/z: 386.2 [M+H]$^+$.

$^1$H NMR (400 MHz, MeOD-d$_4$) δ: 8.97 (d, J=2.4 Hz, 1H), 8.66 (t, J=2.0 Hz, 1H), 8.57 (d, J=1.6 Hz, 1H), 7.70 (d, J=8.8 Hz, 2H), 7.33 (d, J=9.2 Hz, 2H), 6.90 (d, J=74.0 Hz, 1H), 2.62 (s, 3H).

Synthesis of 504

Step 1: Synthesis of tert-butyl (2-cyanopyridin-4-yl)carbamate (504-A)

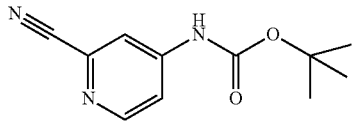 [SMILES: CC(C)(C)OC(=O)Nc1ccnc(C#N)c1]

504-A was obtained via similar procedure of 503-A from 4-chloropyridine-2-carbonitrile and tert-butyl carbamate.

LCMS: (ESI) m/z: 220.1 [M+H]$^+$.

Step 2: Synthesis of 4-aminopicolinonitrile (504-B)

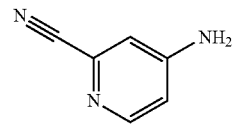

504-B was obtained via similar procedure of 503-B from 504-A and trifluoroacetic acid.

LCMS: (ESI) m/z: 120.1 [M+H]$^+$.

Step 3: Synthesis of N-(2-cyanopyridin-4-yl)-1-(4-(difluoromethoxy)phenyl)-3-methyl-5-oxo-4,5-dihydro-1H-pyrazole-4-carboxamide (504)

Compound ID: 504

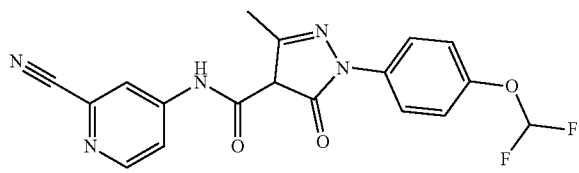 [SMILES: CC1=NN(c2ccc(OC(F)F)cc2)C(=O)C1C(=O)Nc1ccnc(C#N)c1]

504 was obtained via general procedure IV from 298-C and 504-B

LCMS: (ESI) m/z: 386.2 [M+H]$^+$.

$^1$H NMR (400 MHz, MeOD-d$_4$) δ: 8.50 (d, J=5.6 Hz, 1H), 8.31 (d, J=2.0 Hz, 1H), 7.79 (dd, J=6.0, 2.4 Hz, 1H), 7.71 (d, J=9.2 Hz, 2H), 7.31 (d, J=8.8 Hz, 2H), 6.89 (t, J=73.6 Hz, 1H), 2.59 (s, 3H).

Synthesis of 505

Step 1: Synthesis of (2-fluoro-4-methoxyphenyl)hydrazine (505-A)

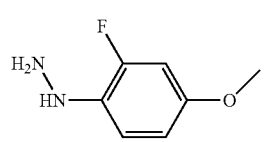

505-A was obtained via general procedure I from 2-fluoro-4-methoxyaniline.

LCMS: (ESI) m/z: 157.1 [M+H]⁺.

Step 2: Synthesis of 1-(2-fluoro-4-methoxyphenyl)-3-methyl-1H-pyrazol-5(4H)-one (505-B)

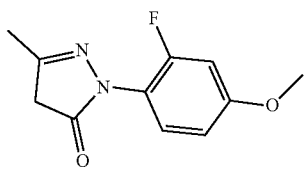

505-B was obtained via general procedure II from 505-A

LCMS: (ESI) m/z: 223.2 [M+H]⁺.

Step 3: Synthesis of 4-nitrophenyl 1-(2-fluoro-4-methoxyphenyl)-3-methyl-5-oxo-4,5-dihydro-1H-pyrazole-4-carboxylate (505-C)

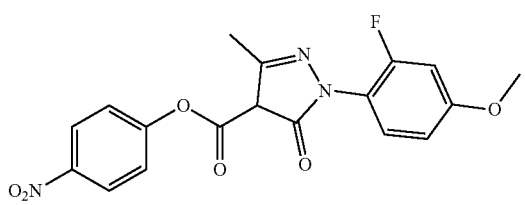 [SMILES: COc1ccc(N2N=C(C)C(C(=O)Oc3ccc([N+](=O)[O-])cc3)C2=O)c(F)c1]

505-C was obtained via general procedure III from 505-B

LCMS: (ESI) m/z: 388.0 [M+H]⁺.

Step 4: Synthesis of N-(3-(1,1-difluoropropyl)phenyl)-1-(2-fluoro-4-methoxyphenyl)-3-methyl-5-oxo-4,5-dihydro-1H-pyrazole-4-carboxamide (505)

Compound ID: 505

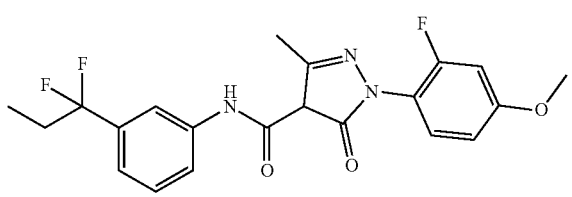 [SMILES: CCC(F)(F)c1cccc(NC(=O)C2C(=O)N(c3ccc(OC)cc3F)N=C2C)c1]

505 was obtained via general procedure IV from 505-C and 3-(1,1-difluoropropyl)aniline LCMS: (ESI) m/z: 420.1 [M+H]⁺.

¹H NMR (MeOD-d₄, 400 MHz) δ: 7.85 (s, 1H), 7.1 (d, J=8.0 Hz, 1H), 7.46 (t, J=8.4 Hz, 1H), 7.40 (t, J=8.0 Hz, 1H), 7.19 (d, J=7.6 Hz, 1H), 6.90-6.98 (m, 2H), 3.86 (s, 3H), 2.58 (s, 3H), 2.12-2.22 (m, 2H), 0.97 (t, J=7.6 Hz, 3H).

Synthesis of 506

Step 1: Synthesis of tert-butyl (2-propionylpyridin-4-yl)carbamate (506-A)

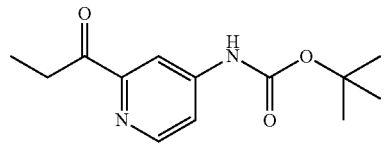 [SMILES: CCC(=O)c1cc(NC(=O)OC(C)(C)C)ccn1]

506-A was obtained via similar procedure of 486-A from 504-A and ethylmagnesium bromide.

LCMS: (ESI) m/z: 251.1 [M+H]⁺.

Step 2: Synthesis of 1-(4-aminopyridin-2-y)propan-1-one (506-B)

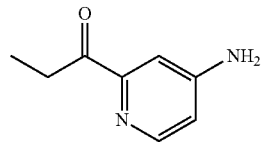

506-B was obtained via similar procedure of 503-B from 506-A and trifluoroacetic acid.

LCMS: (ESI) m/z: 151.3 [M+H]⁺.

Step 3: Synthesis of 2-(2-propionylpyridin-4-yl)isoindoline-1,3-dione (506-C)

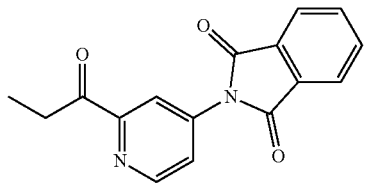 [SMILES: CCC(=O)c1cc(N2C(=O)c3ccccc3C2=O)ccn1]

To a solution of 506-B (1.25 g, 4.73 mmol, 1.0 eq, trifluoroacetic acid salt) and isobenzofuran-1,3-dione (2.10 g, 14.2 mmol, 3.0 eq) in toluene (20 mL) was added triethylamine (1.44 g, 14.2 mmol, 3.0 eq), the reaction mixture was degassed and purged with nitrogen for 3 times, and then the mixture was stirred at 110° C. for 4 hr under nitrogen atmosphere. To the reaction mixture was added water (20 mL), and the water phase was extracted by ethyl acetate (10 mL×3) and the combined organic phase was washed with brine (20 mL), dried over anhydrous sodium sulfate, filtered, and concentrated under reduced pressure. The crude product was purified by silica gel column chromatography (petroleum ether/ethyl acetate, from 10/1 to 5/1) to give 650 mg (49% yield) of 506-C as a white solid.

¹H NMR (400 MHz, CDCl₃-d) δ: 8.81 (d, J=5.2 Hz, 1H), 8.33 (d, J=2.4 Hz, 1H), 8.03-8.01 (m, 2H), 7.87-7.85 (m, 2H), 7.77 (dd, J=5.2, 2.0 Hz, 1H), 3.29 (q, J=7.2 Hz, 2H), 1.26 (t, J=7.2 Hz, 3H).

Step 4: Synthesis of 2-(2-(1,1-difluoropropyl)pyridin-4-yl)isoindoline-1,3-dione (506-D)

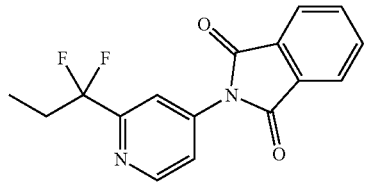 [SMILES: CCC(F)(F)c1cc(N2C(=O)c3ccccc3C2=O)ccn1]

506-D was obtained via similar procedure of 486-D from 506-C and diethylaminosulfur trifluoride.

LCMS: (ESI) m/z: 303.0 [M+H]$^+$.

$^1$H NMR (400 MHz, CDCl$_3$-d) δ: 8.80 (d, J=5.2 Hz, 1H), 8.00-8.01 (m, 2H), 7.96 (d, J=1.6 Hz, 1H), 7.82-7.85 (m, 2H), 7.69 (dd, J=5.2, 1.6 Hz, 1H), 2.31-2.45 (m, 2H), 1.05 (t, J=7.6 Hz, 3H).

Step 5: Synthesis of 2-(1,1-difluoropropyl)pyridin-4-amine (506-E)

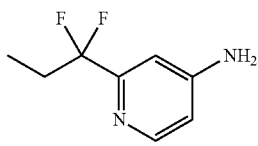

506-E was obtained via similar procedure of 486-E from 506-D and hydrazine hydrate.

LCMS: (ESI) m/z: 173.1 [M+H]$^+$.

Step 6: Synthesis of 1-(4-(difluoromethoxy)phenyl)-N-(2-(1,1-difluoropropyl)pyridin-4-yl)-3-methyl-5-oxo-4,5-dihydro-1H-pyrazole-4-carboxamide (506)

Compound ID: 506

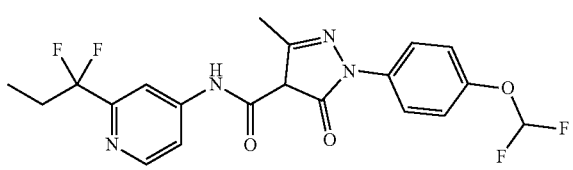 [SMILES: CCC(F)(F)c1cc(NC(=O)C2C(=O)N(c3ccc(OC(F)F)cc3)N=C2C)ccn1]

506 was obtained via general procedure IV from 298-C and 506-E

LCMS: (ESI) m/z: 439.2 [M+H]$^+$.

$^1$H NMR (400 MHz, MeOD-d$_4$) δ: 8.51 (d, J=6.0 Hz, 1H), 8.17 (d, J=2.0 Hz, 1H), 7.93 (dd, J=6.0, 2.0 Hz, 1H), 7.69 (dd, J=6.8, 2.0 Hz, 2H), 7.33 (d, J=9.2 Hz, 2H), 6.91 (t, J=73.6, 1H), 2.62 (s, 3H), 2.28-2.38 (m, 2H), 1.03 (t, J=7.6 Hz, 3H).

Synthesis of 507

Step 1: Synthesis of 6-chloro-1-(phenylsulfonyl)-1H-pyrrolo[3,2-c]pyridine (507-A)

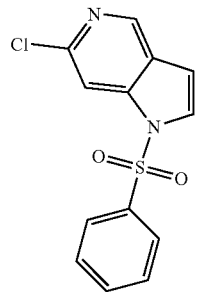 [SMILES: O=S(=O)(c1ccccc1)n1ccc2cnc(Cl)cc21]

507-A was obtained via similar procedure of 410-A from 6-chloro-1H-pyrrolo[3,2-c]pyridine and benzenesulfonyl chloride.

$^1$H NMR (400 MHz, CDCl$_3$-d) δ: 8.63 (s, 1H), 7.91-7.94 (m, 3H), 7.64 (t, J=7.6 Hz, 1H), 7.58 (d, J=3.6 Hz, 1H), 7.53 (t, J=8.0 Hz, 1H), 6.73 (d, J=3.6 Hz, 1H).

Step 2: Synthesis of tert-butyl (1-(phenylsulfonyl)-1H-pyrrolo[3,2-c]pyridin-6-yl)carbamate (507-B)

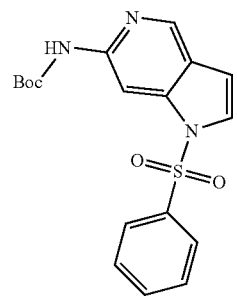 [SMILES: CC(C)(C)OC(=O)Nc1cc2c(ccn2S(=O)(=O)c2ccccc2)cn1]

A mixture of 507-A (3.00 g, 10.3 mmol, 1.0 eq), tert-butyl carbamate (2.40 g, 20.5 mmol, 2.0 eq), palladium acetate (230 mg, 1.02 mmol, 0.10 eq), dicyclohexyl-[2-[2,4,6-tri(propan-2-yl)phenyl]phenyl]phosphane (489 mg, 1.02 mmol, 0.10 eq) and cesium carbonate (5.01 g, 15.4 mmol, 1.5 eq) in dioxane (50 mL) was degassed and purged with nitrogen for 3 times, and then the mixture was stirred at 100° C. for 2 hr under nitrogen atmosphere. The reaction mixture was partitioned between ethyl acetate (150 mL) and water (150 mL). The organic phase was separated, washed with brine (150 mL), dried over anhydrous sodium sulfate, filtered and concentrated under reduced pressure to give a residue. The residue was purified by silica gel column chromatography (petroleum ether/ethyl acetate, from 10/1 to 3/1) to give 4.00 g (64% yield) of 507-B as a light yellow solid.

LCMS: (ESI) m/z: 374.1 [M+H]$^+$.

Step 3: Synthesis of tert-butyl 1-(1-(phenylsulfo-nyl)-1H-pyrrolo[3,2-c]pyridin-6-yl)hydrazinecarboxylate (507-C)

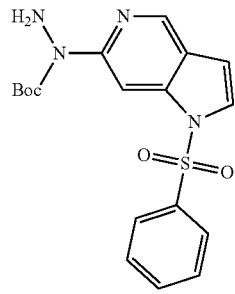 [SMILES: CC(C)(C)OC(=O)N(N)c1cc2c(ccn2S(=O)(=O)c2ccccc2)cn1]

To a suspension of sodium hydride (49.0 mg, 1.23 mmol, 60% purity, 1.5 eq) in N,N-dimethylformamide (5 mL) was added a solution of 507-B (0.500 g, 817 umol, 1.0 eq) in N,N-dimethylformamide (5 mL) at 0° C. under nitrogen atmosphere. The mixture was stirred at 25° C. for 15 min. Then a solution of amino 4-nitrobenzoate (223 mg, 1.23 mmol, 1.5 eq) in N,N-dimethylformamide (5 mL) was added at 0° C. The mixture was stirred at 25° C. for another 15 min. The reaction mixture was quenched by addition saturated ammonium chloride aqueous (50 mL), and then extracted with ethyl acetate (50 mL×1). The combined organic layer was washed with brine (50 mL×1), dried over anhydrous sodium sulfate, filtered and concentrated under reduced pressure to give a residue. The residue was purified by silica gel column chromatography (petroleum ether/ethyl acetate, from 5/1 to 0/1) to give 0.150 g (40% yield) of 507-C as a yellow oil.

LCMS: (ESI) m/z: 389.0 [M+H]$^+$.

$^1$H NMR (400 MHz, CDCl$_3$-d) δ: 8.66 (s, 1H), 8.12 (s, 1H), 7.92 (d, J=7.6 Hz, 2H), 7.63-7.58 (m, 1H), 7.55 (d, J=3.6 Hz, 1H), 7.52-7.48 (m, 2H), 6.70 (d, J=4.0 Hz, 1H), 4.82 (br s, 2H), 1.56 (s, 9H).

Step 4: Synthesis of 6-hydrazinyl-1-(phenylsulfo-nyl)-1H-pyrrolo[3,2-c]pyridine (507-D)

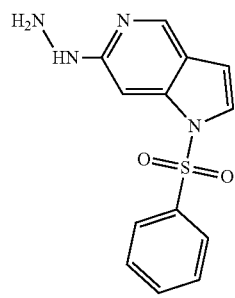 [SMILES: NNc1cc2c(ccn2S(=O)(=O)c2ccccc2)cn1]

507-D was obtained via similar procedure of 410-C from 507-C and ethyl acetate/hydrochloride LCMS: (ESI) m/z: 289.1 [M+H]$^+$.

Step 5: Synthesis of 3-methyl-1-(1-(phenylsulfo-nyl)-1H-pyrrolo[3,2-c]pyridin-6-yl)-1H-pyrazol-5(4H)-one (507-E)

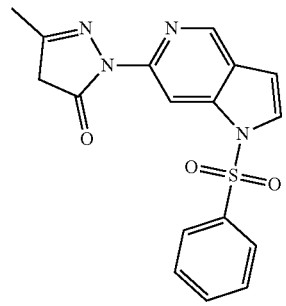 [SMILES: CC1=NN(c2cc3c(ccn3S(=O)(=O)c3ccccc3)cn2)C(=O)C1]

507-E was obtained via general procedure II from 507-D
LCMS: (ESI) m/z: 355.2 [M+H]$^+$.

$^1$H NMR (400 MHz, CDCl$_3$-d) δ: 8.50-8.47 (m, 2H), 8.02 (d, J=7.6 Hz, 2H), 7.60 (d, J=3.6 Hz, 2H), 7.54 (d, J=7.6 Hz, 2H), 6.73 (d, J=3.6 Hz, 1H), 5.45 (s, 1H), 2.31 (s, 3H).

Step 6: Synthesis of 4-nitrophenyl 3-methyl-5-oxo-1-(1-(phenylsulfonyl)-1H-pyrrolo[3,2-c]pyridin-6-yl)-4,5-dihydro-1H-pyrazole-4-carboxylate (507-F)

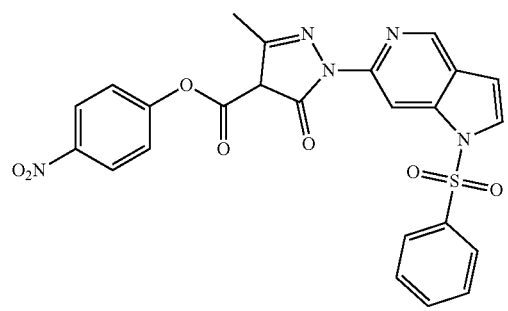 [SMILES: CC1=NN(c2cc3c(ccn3S(=O)(=O)c3ccccc3)cn2)C(=O)C1C(=O)Oc1ccc([N+](=O)[O-])cc1]

507-F was obtained via general procedure III from 507-E
LCMS: (ESI) m/z: 381.0 [M-(p-NO$_2$-PhO)]$^+$.

Step 7: Synthesis of N-(3-(1,1-difluoropropyl)phenyl)-3-methyl-5-oxo-1-(1-(phenylsulfonyl)-1H-pyrrolo[3,2-c]pyridin-6-yl)-4,5-dihydro-1H-pyrazole-4-carboxamide (507-G)

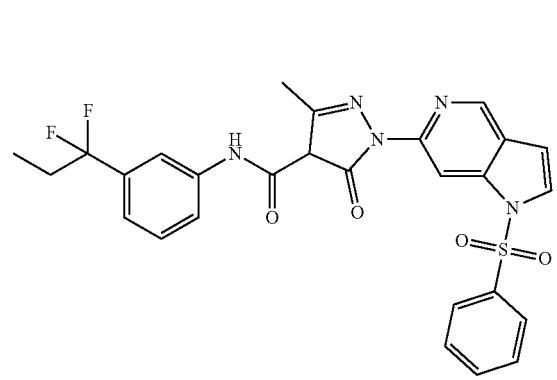 [SMILES: CCC(F)(F)c1cccc(NC(=O)C2C(=O)N(c3cc4c(ccn4S(=O)(=O)c4ccccc4)cn3)N=C2C)c1]

507-G was obtained via general procedure IV from 507-F
LCMS: (ESI) m/z: 552.1 [M+H]$^+$.

Step 8: Synthesis of N-(3-(1,1-difluoropropyl)phenyl)-3-methyl-5-oxo-1-(1H-pyrrolo[3,2-c]pyridin-6-yl)-4,5-dihydro-1H-pyrazole-4-carboxamide (507)

Compound ID: 507

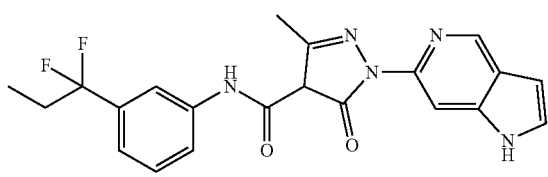 [SMILES: CCC(F)(F)c1cccc(NC(=O)C2C(=O)N(c3cc4[nH]ccc4cn3)N=C2C)c1]

507 was obtained via similar procedure of 410 from 507-G and potassium hydroxide.

LCMS: (ESI) m/z: 412.2 [M+H]$^+$.

$^1$H NMR (400 MHz, MeOD-d$_4$) δ: 8.77 (s, 1H), 8.35 (s, 1H), 8.11 (s, 1H), 7.86 (s, 1H), 7.70-7.56 (m, 2H), 7.43-7.35 (m, 1H), 7.15 (d, J=7.6 Hz, 1H), 6.84 (s, 1H), 2.48 (s, 3H), 2.21-2.15 (m 2H), 0.99 (t, J=7.6 Hz, 3H)

Synthesis of 508

Step 1: Synthesis of 3-methyl-1-(4-(methylsulfonyl)phenyl)-1H-pyrazol-5(4H)-one (508-A)

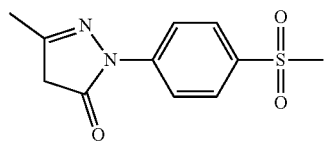

508-A was obtained via general procedure II from (4-methylsulfonylphenyl)hydrazine.

LCMS: (ESI) m/z: 253.0 [M+H]$^+$.

Step 2: Synthesis of 4-nitrophenyl 3-methyl-1-(4-(methylsulfonyl)phenyl)-5-oxo-4,5-dihydro-1H-pyrazole-4-carboxylate (508-B)

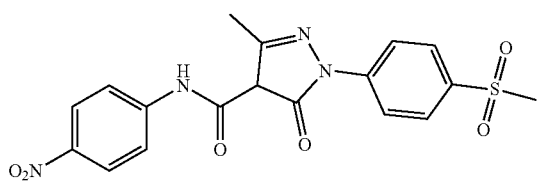 [SMILES: CC1=NN(c2ccc(S(C)(=O)=O)cc2)C(=O)C1C(=O)Nc1ccc([N+](=O)[O-])cc1]

508-B was obtained via general procedure III from 508-A

LCMS: (ESI) m/z: 418.1 [M+H]$^+$.

Step 3: Synthesis of N-(3-(1,1-difluoropropyl)phenyl)-3-methyl-1-(4-(methylsulfonyl)phenyl)-5-oxo-4,5-dihydro-1H-pyrazole-4-carboxamide (508)

Compound ID: 508

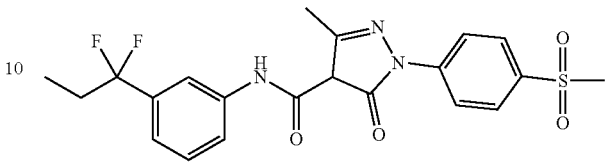

508 was obtained via general procedure IV from 508-B and 3-(1,1-difluoropropyl)aniline LCMS: (ESI) m/z: 450.2 [M+H]$^+$.

$^1$H NMR (400 MHz, DMSO-d$_6$) δ: 0.93 (t, J=7.2 Hz, 3H) 2.21 (m, 2H) 2.53 (s, 3H) 3.24 (s, 3H) 7.14 (d, J=8.0 Hz, 1H) 7.42 (t, J=8.0 Hz, 1H) 7.62 (d, J=8.0 Hz, 1H) 7.93 (s, 1H) 8.01 (d, J=8.2 Hz, 2H) 8.17 (d, J=8.2 Hz, 2H) 10.83 (s, 1H).

Synthesis of 509

Step 1: Synthesis of methyl 2-(benzyloxy)benzoate (509-A)

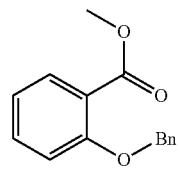 [SMILES: COC(=O)c1ccccc1OCc1ccccc1]

To a 100 mL round-bottom flask equipped with a magnetic stir bar was added methyl 2-hydroxybenzoate (1.00 g, 6.57 mmol, 1.0 eq) followed by the addition of propan-2-one (20 mL). Then potassium carbonate (1.36 g, 9.86 mmol, 1.5 eq) and (bromomethyl)benzene (1.24 g, 7.23 mmol, 1.1 eq) was added into the mixture. The mixture was stirred at 60° C. for 3 hr. The mixture was filtrated and the filter cake was washed with propan-2-one (10 mL). The filtrate was concentrated under reduced pressure affording the residue as colorless oil. The residue was purified by silica gel column chromatography (petroleum ether/ethyl acetate, from 1/0 to 50/1) to give 1.60 g (98% yield) of (509-A) as a colorless oil.

LCMS: (ESI) m/z: 243.1 [M+H]$^+$.

$^1$H NMR (DMSO-d$_6$, 400 MHz) δ: 7.68 (d, 1H, J=8.0, 7.6 Hz), 7.48-7.54 (m, 3H), 7.38-7.41 (m, 2H), 7.29-7.33 (m, 1H), 7.22 (d, 1H, J=8.4 Hz), 7.00-7.04 (m, 1H), 5.21 (s, 2H), 3.80 (s, 3H).

Step 2: Synthesis of 2-(benzyloxy)benzoic acid (509-B)

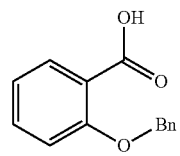 [SMILES: O=C(O)c1ccccc1OCc1ccccc1]

To a 100 mL round-bottom flask equipped with a magnetic stir bar was added 509-A (800 mg, 3.30 mmol, 1.0 eq) followed by the addition of methanol (6 mL) and water (2 mL). Then sodium hydroxide (396 mg, 9.91 mmol, 3.0 eq) was added into the mixture. The mixture was stirred at 50° C. for 2 hr. The mixture was concentrated under reduced pressure affording the residue as white solid. The residue was dissolved in water (10 mL), the pH of the mixture was adjusted to 4 by using hydrochloric acid (2 M). The resulting mixture was transferred to a separatory funnel, and the aqueous layer mixture was extracted with ethyl acetate (10 mL×3). The combined organic layer was washed with brine (25 mL), dried over anhydrous sodium sulfate, filtered, and concentrated under reduced pressure affording 660 mg (88% yield) of 509-B as a yellow oil.

LCMS: (ESI) m/z: 229.4 [M+H]$^+$.

Step 3: Synthesis of 2-(benzyloxy)benzoyl chloride (509-C)

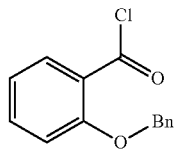 [SMILES: O=C(Cl)c1ccccc1OCc1ccccc1]

509-C was obtained via similar procedure of 493-B from 509-B and oxalyl chloride.

Step 4: Synthesis of (1H-benzo[d][1,2,3]triazol-1-yl)(2-(benzyloxy)phenyl)methanone (509-D)

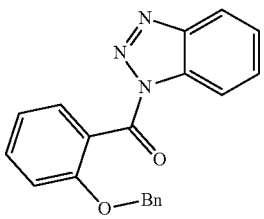 [SMILES: O=C(c1ccccc1OCc1ccccc1)n1nnc2ccccc21]

509-D was obtained via similar procedure of 493-C from 509-C and 1H-benzotriazole.

Step 5: Synthesis of 1-(1-(2-(benzyloxy)benzoyl)-1H-indol-6-yl)-N-(3-(1,1-difluoropropyl)phenyl)-3-methyl-5-oxo-4,5-dihydro-1H-pyrazole-4-carboxamide (509-E)

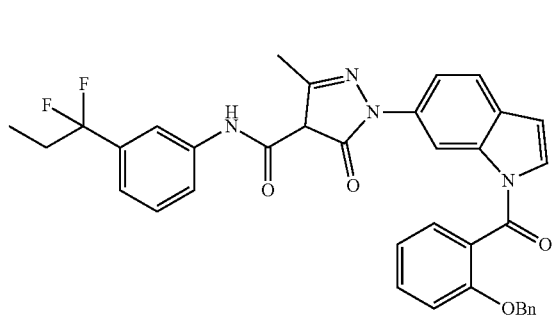

509-E was obtained via similar procedure of 493 from 509-D and 369.

LCMS: (ESI) m/z: 621.1 [M+H]$^+$.

Step 6: Synthesis of N-(3-(1,1-difluoropropyl)phenyl)-1-(1-(2-hydroxybenzoyl)-1H-indol-6-yl)-3-methyl-5-oxo-4,5-dihydro-1H-pyrazole-4-carboxamid (509)

Compound ID: 509

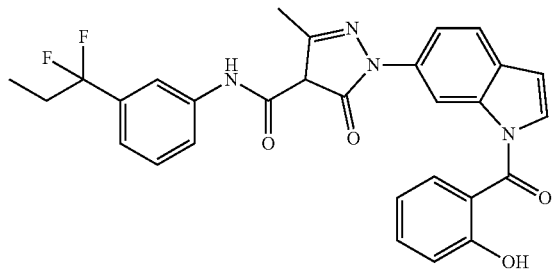 [SMILES: CCC(F)(F)c1cccc(NC(=O)C2C(=O)N(c3ccc4ccn(C(=O)c5ccccc5O)c4c3)N=C2C)c1]

To a 10 mL round-bottom flask equipped with a magnetic stir bar was added 509-E (30.0 mg, 48.3 umol, 1.0 eq), triethylsilane (11.2 mg, 96.7 umol, 2.0 eq) followed by the addition of tetrahydrofuran (2 mL). Then Pd/C (10.0 mg, 10% purity) was added into the mixture. The mixture was stirred at 25° C. for 0.5 h. The mixture was filtered, the filtrate was concentrated under reduced pressure to give a residue. The residue was purified by prep-HPLC (column: Phenomenex Gemini-NX C18 75*30 mm*3 um; mobile phase: [water (0.225% formic acid)-acetonitrile]; B %: 45%-75%, 7 min) to give 3.30 mg (13% yield) of 509 as a white solid.

LCMS: (ESI) m/z: 531.3 [M+H]$^+$.

$^1$H NMR (MeOD-d$_4$, 400 MHz) δ: 8.76 (s, 1H), 8.16 (s, 1H), 7.88 (s, 1H), 7.61-7.71 (m, 3H), 7.36-7.48 (m, 3H), 7.24 (d, J=3.6 Hz, 1H), 7.17 (d, J=8.0 Hz, 1H), 6.95-7.04 (m, 2H), 6.66 (d, J=3.6 Hz, 1H), 2.57 (s, 3H), 2.09-2.27 (m, 2H), 0.98 (t, J=7.2 Hz, 3H).

Synthesis of 510

Step 1: Synthesis of N-(3-(1,1-difluoropropyl)phenyl)-1-(6-hydroxypyridazin-3-yl)-3-methyl-5-oxo-4,5-dihydro-1H-pyrazole-4-carboxamide (510-A)

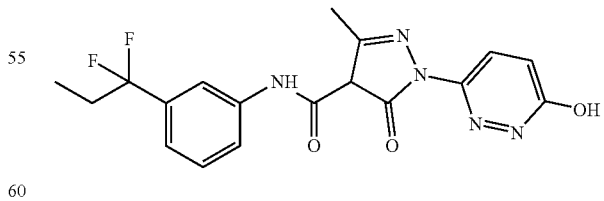

To a solution of 490 (100 mg, 201.08 umol, 1 eq) in dimethyl sulfoxide (5 mL) was added sodium hydroxide (1 M, 5 mL, 25 eq), the solution was stirred at 50° C. for 12 h to give 100 mg (crude) of 510-A in the reaction solution, which was used to next step directly.

LCMS: (ESI) m/z: 390.1 [M+H]$^+$.

Step 2: Synthesis of N-(3-(1,1-difluoropropyl)phenyl)-1-(6-methoxypyridazin-3-yl)-3-methyl-5-oxo-4,5-dihydro-1H-pyrazole-4-carboxamide (510)

Compound ID: 510

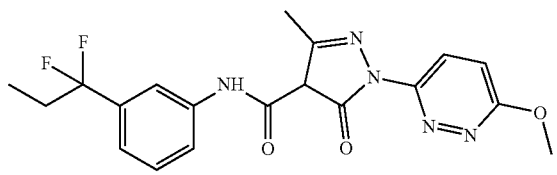 [SMILES: CCC(F)(F)c1cccc(NC(=O)C2C(=O)N(c3ccc(OC)nn3)N=C2C)c1]

To a solution of 510-A (100 mg, 256 umol, 1.0 eq) in dimethyl sulfoxide (1 mL)/water (1 mL) was added iodomethane (40.1 mg, 283 umol 1.1 eq), the solution was stirred at 25° C. for 12 h. The solution was concentrated to give a residue. The residue was purified by prep-HPLC (column: Phenomenex Gemini-NX C18 75*30 mm*3 um; mobile phase: [water (0.1% trifluoroacetic acid)-acetonitrile]; B %: 35%-45%, 7 min) and prep-HPLC (column: Phenomenex Gemini-NX C18 75*30 mm*3 um; mobile phase: [water (0.1% trifluoroacetic acid)-acetonitrile]; B %: 40%-50%, 7 min) to give 5.80 mg (6% yield) of 510 as a yellow solid.

LCMS: (ESI) m/z: 404.2 [M+H]$^+$.

$^1$HNMR (400 MHz, MeOD-d$_4$) δ: 8.54 (d, J=10.0 Hz, 1H), 7.85 (s, 1H), 7.63 (d, J=8.4 Hz, 1H), 7.41 (d, J=8.0 Hz, 1H), 7.19 (t, J=7.6 Hz, 1H), 7.15 (d, J=10.0 Hz, 1H), 3.79 (s, 3H), 2.63 (s, 3H), 2.15-2.23 (m, 2H), 0.98 (t, J=7.2 Hz, 3H).

Synthesis of 511

Step 1: Synthesis of 1-(5-bromopyridin-3-yl)propan-1-one (511-A)

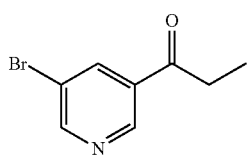

To a solution of 5-bromopyridine-3-carboxylic acid (5.00 g, 24.8 mmol, 1.0 eq) in N,N-dimethylformamide (1 mL)/dichloromethane (80 mL) was added oxalyl dichloride (4.71 g, 37.1 mmol, 1.5 eq) at 0° C. under nitrogen atmosphere. The reaction was stirred at 25° C. for 1 h. The reaction mixture was concentrated under reduced pressure to give a residue A.

To a solution of 2,2'-oxybis(N,N-dimethylethanamine) (4.76 g, 29.7 mmol, 1.2 eq) in tetrahydrofuran (40 mL) was added ethylmagnesium bromide (3 M, 9.90 mL, 1.2 eq) at 0° C. The mixture was stirred at 0-5° C. for 15 min to give a solution B To a solution of the residue A in tetrahydrofuran (40 mL) was added solution B at −75° C., the reaction was degassed and purged with nitrogen for 3 times, and then the mixture was stirred at −75° C. for 1 hr under nitrogen atmosphere. Then the reaction was warmed to 25° C., stirred at 25° C. for 3 hr. The mixture was quenched by slow addition of hydrochloric acid solution (1 M, 100 mL). The pH of mixture was adjusted to 9-10 by using sodium hydroxide solution (2 M). The resulting mixture was transferred to a separatory funnel, and the aqueous layer mixture was extracted with ethyl acetate (30 mL×3). The combined organic layer was washed with brine (50 mL), dried over anhydrous sodium sulfate, filtered, and concentrated under reduced pressure. The crude product was purified by silica gel column chromatography (petroleum ether/ethyl acetate, from 10/1 to 5/1) to give 2.40 g (42% yield) of 511-A as a white solid.

LCMS: (ESI) m/z: 213.9, 215.9 [M+H]$^+$.

Step 2: Synthesis of tert-butyl (5-propionylpyridin-3-yl)carbamate (511-B)

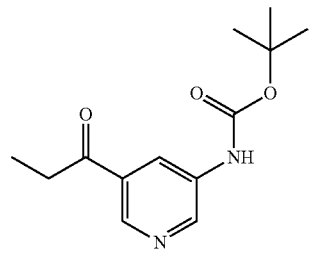 [SMILES: CCC(=O)c1cncc(NC(=O)OC(C)(C)C)c1]

511-B was obtained via similar procedure of 503-A from 511-A and tert-butyl carbamate.

LCMS: (ESI) m/z: 251.1 [M+H]$^+$.

Step 3: Synthesis of 1-(5-aminopyridin-3-yl)propan-1-one (511-C)

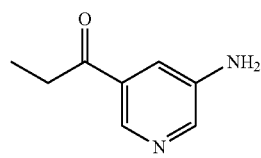

511-C was obtained via similar procedure of 503-B from 511-B and trifluoroacetic acid.

LCMS: (ESI) m/z: 151.1 [M+H]$^+$.

Step 4: Synthesis of 2-(5-propionylpyridin-3-yl)isoindoline-1,3-dione (511-D)

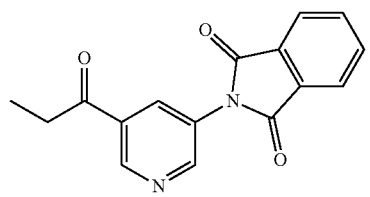 [SMILES: CCC(=O)c1cncc(N2C(=O)c3ccccc3C2=O)c1]

511-D was obtained via similar procedure of 506-C from 511-C and isobenzofuran-1,3-dione.

LCMS: (ESI) m/z: 281.1 [M+H]$^+$.

Step 5: Synthesis of 2-(5-(1,1-difluoropropyl)pyridin-3-yl)isoindoline-1,3-dione (511-E)

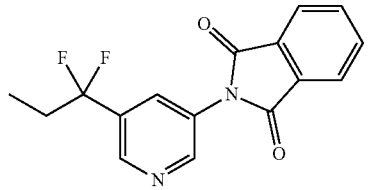 [SMILES: CCC(F)(F)c1cncc(N2C(=O)c3ccccc3C2=O)c1]

511-E was obtained via similar procedure of 486-D from 511-D and diethylaminosulfur trifluoride.

LCMS: (ESI) m/z: 303.1 [M+H]+.

1H NMR (400 MHz, CDCl3-d) δ: 8.89 (d, J=2.4 Hz, 1H), 8.75 (d, J=1.2 Hz, 1H), 8.00-8.03 (m, 2H), 7.98 (t, J=2.4 Hz, 1H), 7.85-7.87 (m, 2H), 2.18-2.28 (m, 2H), 1.08 (t, J=7.6 Hz, 3H).

Step 6: Synthesis of 5-(1,1-difluoropropyl)pyridin-3-amine (511-F)

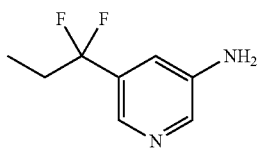

511-F was obtained via similar procedure of 486-E from 511-E and hydrazine hydrate.

LCMS: (ESI) m/z: 173.1 [M+H]+.

Step 7: Synthesis of 1-(4-(difluoromethoxy)phenyl)-N-(5-(1,1-difluoropropyl)pyridin-3-yl)-3-methyl-5-oxo-4,5-dihydro-1H-pyrazole-4-carboxamide (511)

Compound ID: 511

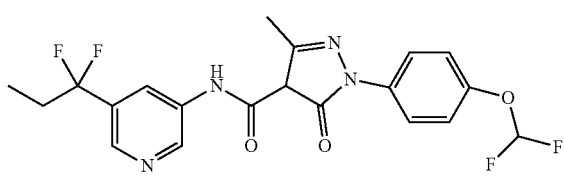 [SMILES: CCC(F)(F)c1cncc(NC(=O)C2C(=O)N(c3ccc(OC(F)F)cc3)N=C2C)c1]

511 was obtained via general procedure IV from 298-C and 511-F

LCMS: (ESI) m/z: 439.2 [M+H]+.

1H NMR (400 MHz, MeOD-d4) δ: 8.91 (s, 1H), 8.39 (s, 2H), 7.70 (d, J=2.0 Hz, 2H), 7.32 (d, J=9.2 Hz, 2H), 6.90 (t, J=73.6 Hz, 1H), 2.61 (s, 3H), 2.20-2.30 (m, 2H), 1.03 (t, J=7.2 Hz, 3H).

Synthesis of 512

Step 1: Synthesis of N-(3-(1,1-difluoropropyl)phenyl)-1-(5-hydroxypyrazin-2-yl)-3-methyl-5-oxo-4,5-dihydro-1H-pyrazole-4-carboxamide (512-A)

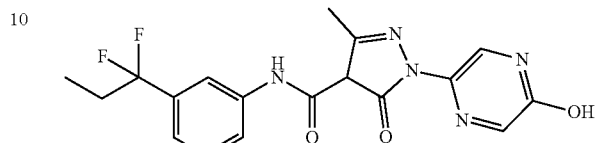

To a solution of 489 (350 mg, 730 umol, 1.0 eq) in dimethyl sulfoxide (15 mL) was added sodium hydroxide (1 M, 15 mL, 21 eq), the solution was stirred at 50° C. for 12 h. The pH of mixture was adjusted to 7 by using hydrochloric acid (1 M), and concentrated under reduced pressure affording a residue. The crude product was purified by C-18 reversed phase column (0.1% trifluoroacetic acid) to give 105 mg (23% yield) of 512-A as a white solid.

LCMS: (ESI) m/z: 390.1 [M+H]+.

Step 2: Synthesis of N-(3-(1,1-difluoropropyl)phenyl)-1-(5-methoxypyrazin-2-yl)-3-methyl-5-oxo-4,5-dihydro-1H-pyrazole-4-carboxamide (512)

Compound ID: 512

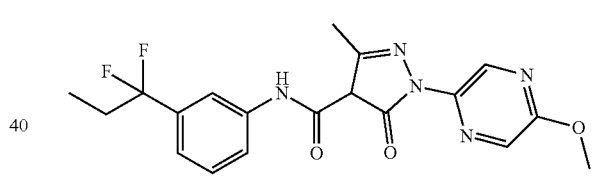

To a solution of 512-A (50 mg, 84.8 umol, 1.0 eq) in dichloromethane (4 mL) was added diazomethyl(trimethyl)silane (2 M, 42.4 uL, 1.0 eq) at 0° C. under nitrogen, the solution was stirred at 25° C. for 2 h. The mixture was quenched by slow addition of water. The solution mixture was transferred to a separatory funnel, and the aqueous layer mixture was extracted with dichloromethane (5 mL×3). The combined organic layer was washed with brine (10 mL), dried over anhydrous sodium sulfate, filtered, and concentrated under reduced pressure affording a residue. The mixture was further purification by pre-HPLC (column: Xtimate C18 150*40 mm*10 um; mobile phase: [water (0.05% ammonia hydroxide v/v)-acetonitrile]; B %: 13%-43%, 10 min) to give 7.10 mg (21% yield) of 512 as a white solid.

LCMS: (ESI) m/z: 404.2 [M+H]+.

1H NMR (400 MHz, MeOD-d4) δ: 8.03 (s, 1H), 7.90 (s, 1H), 7.83 (s, 1H), 7.60 (d, J=8.4 Hz, 1H), 7.40 (t, J=8.0 Hz, 1H), 7.19 (d, J=8.0 Hz, 1H), 3.51 (s, 3H), 2.74 (s, 3H), 2.17 (m, 2H), 0.97 (t, J=7.2 Hz, 3H).

Synthesis of 516

Step 1: Synthesis of (2-bromo-4-methoxyphenyl)hydrazine (516-A)

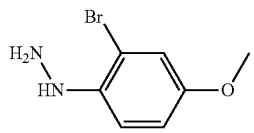

516-A was obtained via general procedure I from 2-bromo-4-methoxyaniline
LCMS: (ESI) m/z: 202.2 [M-NH$_2$]$^+$.

Step 2: Synthesis of 1-(2-bromo-4-methoxyphenyl)-3-methyl-1H-pyrazol-5(4H)-one (516-B)

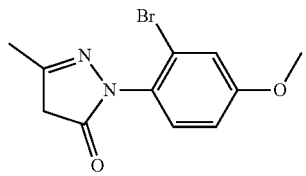

516-B was obtained via general procedure II from 516-A
LCMS: (ESI) m/z: 282.9 [M+H]$^+$.

Step 3: Synthesis of 1-(2-acetyl-4-methoxyphenyl)-3-methyl-1H-pyrazol-5(4H)-one (516-C)

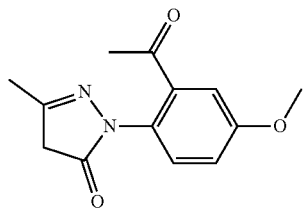

A mixture of 516-B (600 mg, 2.12 mmol, 1.0 eq), tributyl (1-ethoxyvinyl)stannane (1.53 g, 4.24 mmol, 2.0 eq), bis(triphenylphosphine)palladium(II)dichloride (149 mg, 213 umol, 0.10 eq) and copper iodide (40.4 mg, 212 umol, 0.10 eq) in dioxane (10 mL) was degassed and purged with nitrogen for 3 times, and then the mixture was stirred at 90° C. for 12 h under nitrogen. The reaction mixture was added into hydrochloric acid (1 M, 30 mL). Then it was added into the saturation of potassium fluoride (30 mL). The mixture was concentrated under reduced pressure to give a residue. The crude product was purified by C-18 reversed-phase column (0.1% formic acid condition, 35%-55% acetonitrile) to give 70.0 mg (13% yield) of 516-C as a yellow solid.
LCMS: (ESI) m/z: 247.2 [M+H]$^+$.

Step 4: Synthesis of 1-(2-acetyl-4-methoxyphenyl)-N-(3-(1,1-difluoropropyl)phenyl)-3-methyl-5-oxo-4,5-dihydro-1H-pyrazole-4-carboxamide (516)

Compound ID: 516

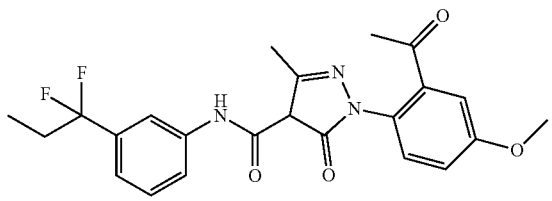 [SMILES: CCC(F)(F)c1cccc(NC(=O)C2C(=O)N(c3ccc(OC)cc3C(C)=O)N=C2C)c1]

516 was obtained via similar procedure of 405 from 516-C and 500-E.
LCMS: (ESI) m/z: 444.2 [M+H]$^+$.
$^1$H NMR (400 MHz, DMSO-d$_6$) δ: 7.86 (s, 1H), 7.60-7.34 (m, 3H), 7.28-7.16 (m, 2H), 7.15-7.08 (m, 1H), 3.84 (s, 3H), 2.78 (s, 1H), 2.43 (s, 2H), 2.32 (s, 2H), 2.24-2.14 (m, 2H), 2.02 (s, 1H), 0.91 (t, J=7.2 Hz, 3H).

Synthesis of 524

Step 1: Synthesis of (Z)-2,4-dibromo-1-(2-bromovinyl)benzene (524-A)

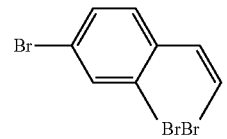

To a solution of bromomethyl(triphenyl)phosphonium; bromide (5.45 g, 12.5 mmol, 1.1 eq) in tetrahydrofuran (80 mL) was added potassium tert-butoxide (1 M, 12.5 mL, 1.1 eq) at −78° C., when the color of the solution changed to light yellow, 2,4-dibromobenzaldehyde (3.00 g, 11.4 mmol, 1.0 eq) was added into the mixture. The mixture was stirred at −78° C. for 2 hr. The reaction mixture was quenched by saturated ammonium chloride solution (150 mL) at 0° C., and extracted with ethyl acetate (70 mL×3). The combined organic layer was washed with brine (200 mL), dried over anhydrous sodium sulfate, filtered and concentrated under reduced pressure to give a residue. The residue was purified by silica gel column chromatography (pure petroleum ether) to give 2.35 g (61% yield) of 524-A as a white solid.
$^1$H NMR (400 MHz, CDCl$_3$-d) δ: 7.78 (d, J=2.0 Hz, 1H), 7.70-7.64 (m, 1H), 7.48 (dd, J=2.0, 8.0 Hz, 1H), 7.13 (d, J=8.0 Hz, 1H), 6.62 (d, J=8.0 Hz, 1H).

Step 2: Synthesis of di-tert-butyl 7-bromocinnoline-1,2-dicarboxylate (524-B)

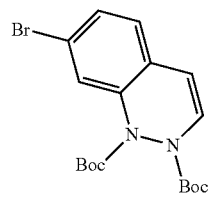

To a solution of 524-A (2.35 g, 6.89 mmol, 1.0 eq) and tert-butyl N-(tert-butoxycarbonylamino)carbamate (6.41 g, 27.6 mmol, 4.0 eq) in dioxane (80 mL) was added copper iodide (657 mg, 3.45 mmol, 0.50 eq), potassium carbonate (3.81 g, 27.6 mmol, 4.0 eq), $N^1,N^2$-dimethylethane-1,2-diamine (304 mg, 3.45 mmol, 0.50 eq). The mixture was stirred at 90° C. for 12 hr under nitrogen atmosphere. The reaction mixture was diluted with water (100 mL) and extracted with ethyl acetate (30 mL×3). The combined organic layer was washed with brine (100 mL), dried over anhydrous sodium sulfate, filtered and concentrated under reduced pressure to give a residue. The residue was purified by silica gel column chromatography (petroleum ether/ethyl acetate, from 15/1 to 10/1) to give 2.50 g (87% yield) of 524-B as a yellow oil.

LCMS: (ESI) m/z: 433.0 [M+Na]$^+$.

Step 3: Synthesis of di-tert-butyl 7-(1,2-bis(tert-butoxycarbonyl)hydrazinyl)cinnoline-1,2-dicarboxylate (524-C)

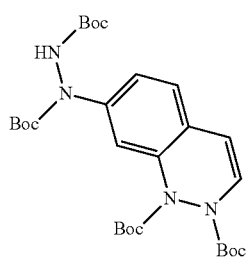 [SMILES: CC(C)(C)OC(=O)NN(C(=O)OC(C)(C)C)c1ccc2c(c1)N(C(=O)OC(C)(C)C)N(C(=O)OC(C)(C)C)C=C2]

524-C was obtained via similar procedure of 524-B from 524-B and tert-butyl N-(tert-butoxycarbonylamino)carbamate LCMS: (ESI) m/z: 580.4 [M+H$_2$O]$^+$.

Step 4: Synthesis of 7-hydrazinylcinnoline (524-D)

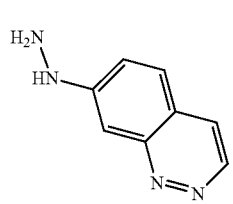 [SMILES: NNc1ccc2ccnnc2c1]

To a solution of 524-C (10.0 g, 17.8 mmol, 1.0 eq) in ethyl acetate (50 mL) was added hydrogen chloride/ethyl acetate (4 M, 50.0 mL, 11 eq) at 0° C. The mixture was stirred at 25° C. for 2 hr. The reaction mixture was concentrated under reduced pressure to give 3.49 g (crude, hydrochloride) of 524-D as a yellow solid.

LCMS: (ESI) m/z: 161.2 [M+H]$^+$.

Step 5: Synthesis of 1-(cinnolin-7-yl)-3-methyl-1H-pyrazol-5(4H)-one (524-E)

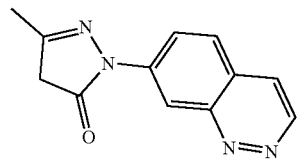 [SMILES: CC1=NN(c2ccc3ccnnc3c2)C(=O)C1]

524-E was obtained via general procedure II from 524-D

LCMS: (ESI) m/z: 227.2 [M+H]$^+$.

Step 6: Synthesis of 4-nitrophenyl 1-(cinnolin-7-yl)-3-methyl-5-oxo-4,5-dihydro-1H-pyrazole-4-carboxylate (524-F)

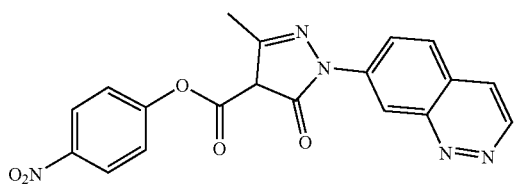 [SMILES: CC1=NN(c2ccc3ccnnc3c2)C(=O)C1C(=O)Oc1ccc([N+](=O)[O-])cc1]

524-F was obtained via general procedure III from 524-E

LCMS: (ESI) m/z: 253.2 [M-(p-NO$_2$-PhO)]$^+$.

Step 7: Synthesis of 1-(cinnolin-7-yl)-N-(3-(1,1-difluoropropyl)phenyl)-3-methyl-5-oxo-4,5-dihydro-1H-pyrazole-4-carboxamide (524)

Compound ID: 524

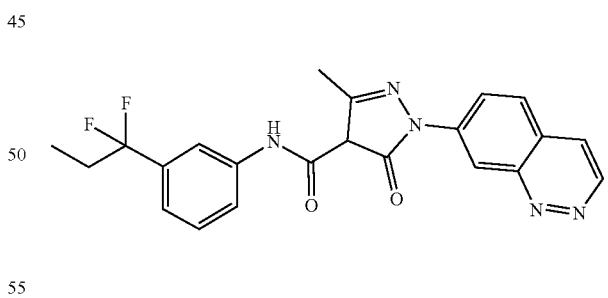

524 was obtained via general procedure IV from 524-F

LCMS: (ESI) m/z: 424.1 [M+H]$^+$.

$^1$H NMR (400 MHz, DMSO-d$_6$) δ: 11.15 (s, 1H), 9.25 (d, J=7.6 Hz, 1H), 9.07 (s, 1H), 8.78 (d, J=8.8 Hz, 1H), 8.14-8.04 (m, 2H), 7.93 (s, 1H), 7.61 (d, J=7.6 Hz, 1H), 7.47-7.43 (m, 1H), 7.37 (t, J=8.4 Hz, 1H), 7.10-7.02 (m, 1H), 2.38 (s, 3H), 2.25-2.15 (m, 2H), 0.93 (t, J=7.6 Hz, 3H).

Synthesis of 529

Step 1: Synthesis of methyl 1-(4-methoxyphenyl)-5-oxo-4,5-dihydro-1H-pyrazole-3-carboxylate (529-A)

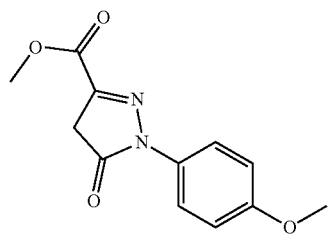

To a solution of (4-methoxyphenyl)hydrazine (10.0 g, 57.3 mmol, 1.0 eq, hydrochloride) in methanol (100 mL) was added dimethyl but-2-ynedioate (10.0 g, 70.4 mmol, 1.2 eq) at 0° C. Then triethylamine (11.6 g, 115 mmol, 2.0 eq) was added slowly over 1 hr. The solution was stirred at 25° C. for 16 hr. The solvent was removed under reduced pressure and the residue was dissolved in ethyl acetate (50 mL). After washing with aqueous hydrochloric acid (1 M, 50 mL), the solvent was removed under reduced pressure. The precipitate was slurried in ethyl acetate and collected by filtration to give 7.00 g (crude) of 529-A as a black brown solid.

LCMS: (ESI) m/z: 249.1 [M+H]$^+$.

Step 2: Synthesis of 1-(4-methoxyphenyl)-5-oxo-4,5-dihydro-1H-pyrazole-3-carboxylic acid (529-B)

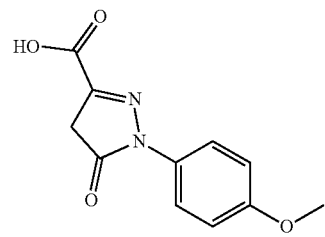 [SMILES: COc1ccc(N2N=C(C(=O)O)CC2=O)cc1]

To a solution of 529-A (1.00 g, 4.03 mmol, 1.0 eq) in methanol (10 mL) and water (10 mL) was added sodium hydroxide (1.61 g, 40.3 mmol, 10 eq), the mixture was stirred at 25° C. for 1 hr. The pH of the mixture was adjusted to 3 with diluted hydrochloric acid (1 M). Then the mixture was extracted with ethyl acetate (20 mL×2). The combined organic phase was washed with brine (20 mL) and dried over anhydrous sodium sulfate. The mixture was filtered and evaporated under reduced pressure to give 1.00 g (crude) of 529-B as a black brown solid.

LCMS: (ESI) m/z: 235.1 [M+H]$^+$.

Step 3: Synthesis of N-methoxy-1-(4-methoxyphenyl)-N-methyl-5-oxo-4,5-dihydro-1H-pyrazole-3-carboxamide (529-C)

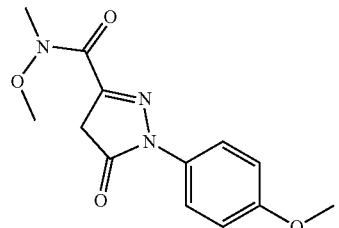

To a solution of 529-B (1.00 g, 4.27 mmol, 1.0 eq), N-methoxymethanamine (1.25 g, 12.8 mmol, 3.0 eq, hydrochloride), 1H-benzo[d][1,2,3]triazol-1-ol (1.15 g, 8.54 mmol, 2.0 eq), triethylamine (864 mg, 8.54 mmol, 2.0 eq) in dichloromethane (20 mL) was added N-[3-(dimethylamino)propyl]-N-ethylcarbodiimide hydrochloride (1.64 g, 8.54 mmol, 2.0 eq). The reaction mixture was stirred at 25° C. for 12 hr. The solution was concentrated under reduced pressure, and dissolved in ethyl acetate (20 mL). The mixture was then washed with water (20 mL×2) and brine (20 mL), dried over anhydrous sodium sulfate. The organic layer was filtered and concentrated under reduced pressure to provide a residue. The residue was purified by column chromatography (SiO2, petroleum/ethyl acetate=2/1 to 1/2) to give 350 mg (30% yield) of 529-C as a light yellow solid.

LCMS: (ESI) m/z: 278.0 [M+H]$^+$.

Step 4: Synthesis of 3-acetyl-1-(4-methoxyphenyl)-1H-pyrazol-5(4H)-one (529-D)

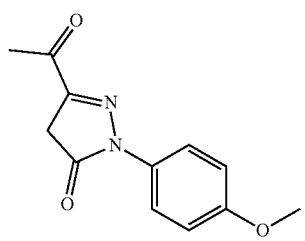 [SMILES: COc1ccc(N2N=C(C(C)=O)CC2=O)cc1]

A solution of methylmagnesium bromide (3 M, 1.26 mL, 3.0 eq) was added into a solution of 529-C (350 mg, 1.26 mmol, 1.0 eq) in tetrahydrofuran (10 mL) via string over a period of 10 min at −75° C. under nitrogen atmosphere. The reaction mixture was stirred at −75° C. for 4 hr under nitrogen atmosphere. The reaction was quenched by addition of methanol (1 mL). Then the pH of the mixture was adjusted to 3 with diluted hydrochloride acid (1 M). Ethyl acetate (20 mL) and water (20 mL) was added and organic layer was separated. The aqueous phase was extracted with ethyl acetate (20 mL×2). The combined organic layer was washed with brine (20 mL) and dried over anhydrous sodium sulfate, filtered, and concentrated under reduced pressure to give 320 mg (crude) of 529-D as a green solid.

LCMS: (ESI) m/z: 233.1 [M+H]$^+$.

Step 5: Synthesis of 4-nitrophenyl 3-acetyl-1-(4-methoxyphenyl)-5-oxo-4,5-dihydro-1H-pyrazole-4-carboxylate (529-E)

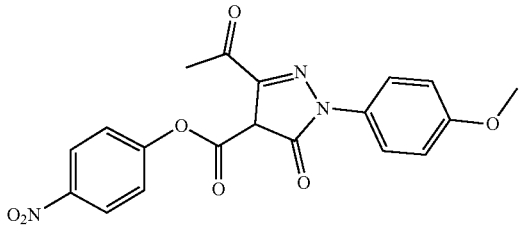 [SMILES: COc1ccc(N2N=C(C(C)=O)C(C(=O)Oc3ccc([N+](=O)[O-])cc3)C2=O)cc1]

529-E was obtained via general procedure III from 529-D
LCMS: (ESI) m/z: 398.2 [M+H]⁺.

Step 6: Synthesis of 3-acetyl-N-(3-(1,1-difluoropropyl)phenyl)-1-(4-methoxyphenyl)-5-oxo-4,5-dihydro-1H-pyrazole-4-carboxamide (529)

Compound ID: 529

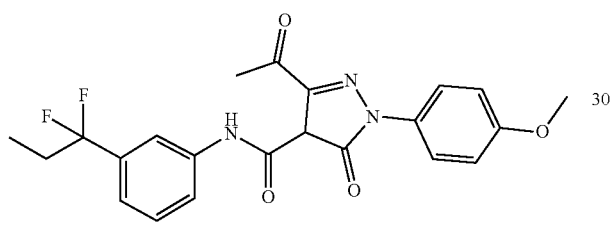

529 was obtained via general procedure IV from 529-E
LCMS: (ESI) m/z: 430.1 [M+H]⁺.
$^1$H NMR (400 MHz, MeOD-d$_4$) δ: 7.92 (s, 1H), 7.85-7.71 (m, 3H), 7.50-7.41 (m, 1H), 7.29-7.23 (m, 1H), 7.07 (d, J=8.8 Hz, 2H), 3.86 (s, 3H), 2.73 (s, 3H), 2.26-2.11 (m, 2H), 1.00 (t, J=7.6 Hz, 3H).
Synthesis of 530

Step 1: Synthesis of 3-bromo-4-methoxyaniline (530-A)

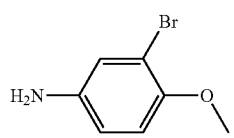

A suspension of 2-bromo-1-methoxy-4-nitro-benzene (25.0 g, 108 mmol, 1.0 eq), iron powder (30.1 g, 539 mmol, 5.0 eq), ammonium chloride (28.8 g, 539 mmol, 5.0 eq) in ethanol (250 mL)/water (80 mL) was stirred at 80° C. for 8 hr. The reaction mixture was filtered, and the filtrate was diluted with water (500 mL). The aqueous layer was extracted with ethyl acetate (150 mL×3), the combined organic layer was washed with water (200 mL×3), washed with brine (200 mL), dried over anhydrous sodium sulfate, filtered, and concentrated under reduced pressure to give 22.5 g (crude) of 530-A as a red solid.
LCMS: (ESI) m/z: 202.0 [M+H]⁺.

Step 2: Synthesis of (3-bromo-4-methoxyphenyl)hydrazine (530-B)

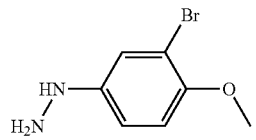

530-B was obtained via general procedure I from 530-A
LCMS: (ESI) m/z: 217.0 [M+H]⁺.

Step 3: Synthesis of 1-(3-bromo-4-methoxyphenyl)-3-methyl-1H-pyrazol-5(4H)-one (530-C)

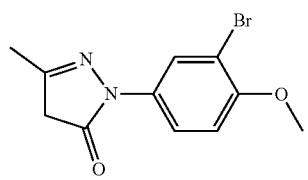

530-C was obtained via general procedure II from 530-B
LCMS: (ESI) m/z: 284.9 [M+H]⁺.

Step 4: Synthesis of 4-nitrophenyl 1-(3-bromo-4-methoxyphenyl)-3-methyl-5-oxo-4,5-dihydro-1H-pyrazole-4-carboxylate (530-D)

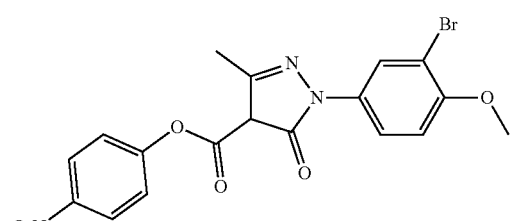

530-D was obtained via general procedure III from 530-C
LCMS: (ESI) m/z: 447.9 [M+H]⁺.

Step 5: Synthesis of 1-(3-bromo-4-methoxyphenyl)-N-(3-(1,1-difluoropropyl)phenyl)-3-methyl-5-oxo-4,5-dihydro-1H-pyrazole-4-carboxamide (530-E)

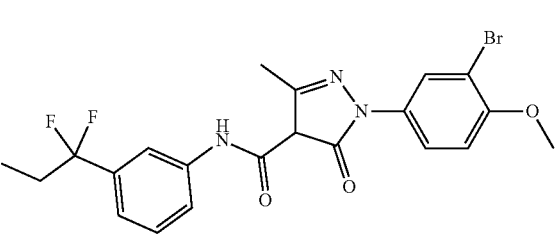 [SMILES: CCC(F)(F)c1cccc(NC(=O)C2C(=O)N(c3ccc(OC)c(Br)c3)N=C2C)c1]

530-E was obtained via general procedure IV from 530-D
LCMS: (ESI) m/z: 480.9 [M+H]⁺.

¹H NMR (400 MHz, MeOD-d₄) δ: 7.86 (s, 2H), 7.62 (d, J=7.2 Hz, 1H), 7.57 (d, J=6.4 Hz, 1H), 7.39 (t, J=7.6 Hz, 1H), 7.18 (d, J=7.2 Hz, 1H), 7.14 (d, J=7.6 Hz, 1H), 3.91 (s, 3H), 2.56 (s, 3H), 2.13-2.22 (m, 2H), 0.98 (t, J=7.2 Hz, 3H).

Step 6: Synthesis of N-(3-(1,1-difluoropropyl)phenyl)-1-(4-methoxy-3-(2-methylpyridin-4-yl)phenyl)-3-methyl-5-oxo-4,5-dihydro-1H-pyrazole-4-carboxamide (530)

Compound ID: 530

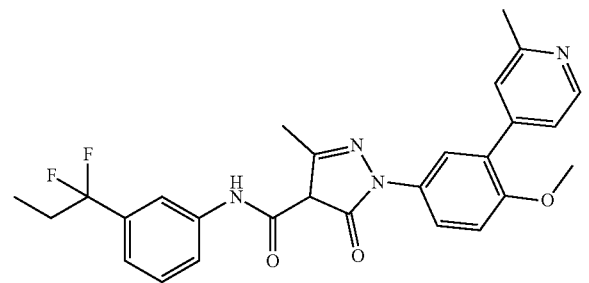 [SMILES: CCC(F)(F)c1cccc(NC(=O)C2C(=O)N(c3ccc(OC)c(-c4ccnc(C)c4)c3)N=C2C)c1]

A suspension of 530-E (200 mg, 371 umol, 1.0 eq), (2-methyl-4-pyridyl)boronic acid (76.1 mg, 556 umol, 1.5 eq), 1,1-bis(diphenylphosphino)ferrocene]dichloropalladium(II) (27.1 mg, 37.1 umol, 0.10 eq) and cesium carbonate (242 mg, 741 umol, 2.0 eq) in dioxane (5 mL) and water (0.5 mL) was degassed under vacuum and purged with nitrogen several times, then the reaction was stirred at 80° C. for 12 hr. The reaction mixture was filtered, and the filtrate was concentrated under reduced pressure. The crude product was purified by preparative HPLC: (Phenomenex Gemini C18 column: Phenomenex Luna C18 150*25 mm*10 um; mobile phase: [water (0.225% formic acid)-acetonitrile]; B %: 20%-50%, 10 min) to give 54.0 mg (30% yield) of 530 as a light yellow solid.

LCMS: (ESI) m/z: 493.3 [M+H]⁺.
¹H NMR (400 MHz, MeOD-d₄) δ: 8.53 (d, J=6.0 Hz, 1H), 7.81-7.90 (m, 5H), 7.65 (d, J=9.2 Hz, 1H), 7.38 (t, J=8.0 Hz, 1H), 7.28 (d, J=8.8 Hz, 1H), 7.15 (d, J=8.0 Hz, 1H), 3.92 (s, 3H), 2.71 (s, 3H), 2.50 (s, 3H), 2.13-2.23 (m, 2H), 0.98 (t, J=7.6 Hz, 3H).

Synthesis of 531

Step 1: Synthesis of N-(3-(1,1-difluoropropyl)phenyl)-1-(3-(2,6-dimethylpyridin-4-yl)-4-methoxyphenyl)-3-methyl-5-oxo-4,5-dihydro-1H-pyrazole-4-carboxamide (531)

Compound ID: 531

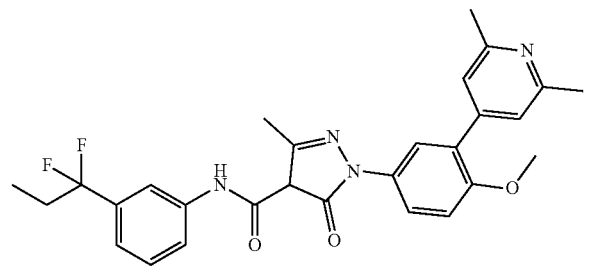 [SMILES: CCC(F)(F)c1cccc(NC(=O)C2C(=O)N(c3ccc(OC)c(-c4cc(C)nc(C)c4)c3)N=C2C)c1]

531 was obtained via similar procedure of 530 from 530-E and (2,6-dimethyl-4-pyridyl)boronic acid.

LCMS: (ESI) m/z: 507.3 [M+H]⁺.
¹H NMR (400 MHz, MeOD-d₄) δ: 7.83-7.91 (m, 5H), 7.66 (d, J=8.0 Hz, 1H), 7.37 (t, J=8.0 Hz, 1H), 7.26 (d, J=8.8 Hz, 1H), 7.13 (d, J=7.6 Hz, 1H), 3.92 (s, 3H), 2.71 (s, 6H), 2.46 (s, 3H), 2.11-2.25 (m, 2H), 0.98 (t, J=7.6 Hz, 3H).

Synthesis of 532

Step 1: Synthesis of N-(3-(1,1-difluoropropyl)phenyl)-1-(4-methoxy-3-(3-methylpyridin-4-yl)phenyl)-3-methyl-5-oxo-4,5-dihydro-1H-pyrazole-4-carboxamide (532)

Compound ID: 532

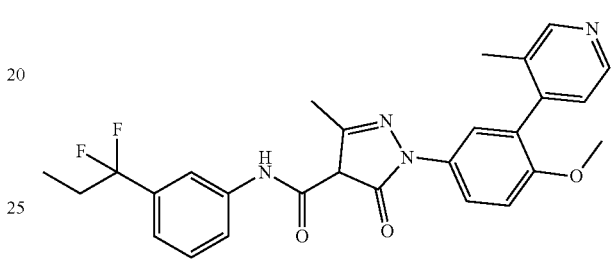

532 was obtained via similar procedure of 530 from 530-E and (3-methyl-4-pyridyl)boronic acid.

LCMS: (ESI) m/z: 493.3 [M+H]⁺.
¹H NMR (400 MHz, MeOD-d₄) δ: 8.50 (s, 1H), 8.46 (d, J=4.8 Hz, 1H), 7.85 (s, 1H), 7.76 (dd, J=8.8, 2.8 Hz, 1H), 7.63 (d, J=8.4 Hz, 1H), 7.53 (d, J=2.8 Hz, 1H), 7.44 (d, J=5.2 Hz, 1H), 7.39 (t, J=8.0 Hz, 1H), 7.26 (d, J=8.8 Hz, 1H), 7.16 (d, J=7.6 Hz, 1H), 3.84 (s, 3H), 2.53 (s, 3H), 2.24 (s, 3H), 2.13-2.21 (m, 2H), 0.97 (t, J=7.6 Hz, 3H).

Synthesis of 534

Step 1: Synthesis of N-(3-(1,1-difluoropropyl)phenyl)-1-(4-methoxy-3-(4,4,5,5-tetramethyl-1,3,2-dioxaborolan-2-yl)phenyl)-3-methyl-5-oxo-4,5-dihydro-1H-pyrazole-4-carboxamide (534-A)

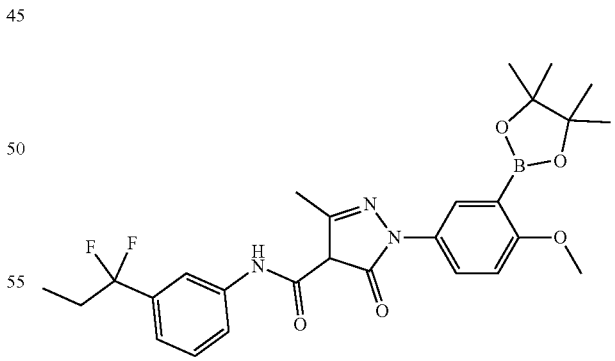

A solution of 530-E (500 mg, 927 umol, 1.0 eq), 4,4,5,5-tetramethyl-2-(4,4,5,5-tetramethyl-1,3,2-dioxaborolan-2-yl)-1,3,2-dioxaborolane (471 mg, 1.85 mmol, 2.0 eq), potassium acetate (273 mg, 2.78 mmol, 3.0 eq) and 1,1-bis(diphenylphosphino)ferrocene]dichloropalladium(II) (67.8 mg, 92.7 umol, 0.10 eq) in N,N-dimethylformamide (15 mL) was degassed under vacuum and purged with nitrogen several times, then the reaction was stirred under nitrogen at 110° C. for 2 hr in 2 batches. The reaction mixture was diluted with water (30 mL), the aqueous layer was extracted with ethyl acetate (5 mL×3). The combined organic layer was washed with brine, dried over anhydrous sodium sulfate, filtered and concentrated under reduced pressure to give 1.60 g (crude) of 534-A as black brown oil.

LCMS: (ESI) m/z: 258.1 [M+H]+.

Step 2: Synthesis of N-(3-(1,1-difluoropropyl)phenyl)-1-(4-methoxy-3-(5-methylpyridin-2-yl)phenyl)-3-methyl-5-oxo-4,5-dihydro-1H-pyrazole-4-carboxamide (534)

Compound ID: 534

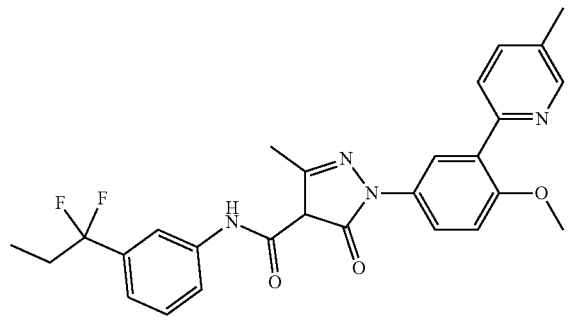 [SMILES: CCC(F)(F)c1cccc(NC(=O)C2C(=O)N(c3ccc(OC)c(-c4ccc(C)cn4)c3)N=C2C)c1]

534 was obtained via similar procedure of 530 from 2-bromo-5-methylpyridine and 534-A.

LCMS: (ESI) m/z: 493.2 [M+H]+.

$^1$H NMR (400 MHz, CDCl$_3$-d) δ: 10.58 (s, 1H), 8.49 (s, 1H), 7.78-7.66 (m, 3H), 7.63-7.53 (m, 2H), 7.40-7.30 (m, 2H), 7.14 (d, J=7.6 Hz, 1H), 6.71 (d, J=8.8 Hz, 1H), 3.62 (s, 3H), 2.61 (s, 3H), 2.43 (s, 3H), 2.10-2.20 (m, 2H), 0.99 (t, J=7.4 Hz, 3H).

Synthesis of 535

Step 1: Synthesis of N-(3-(1,1-difluoropropyl)phenyl)-1-(4-methoxy-3-(3-methylpyridin-2-yl)phenyl)-3-methyl-5-oxo-4,5-dihydro-1H-pyrazole-4-carboxamide (535)

Compound ID: 535

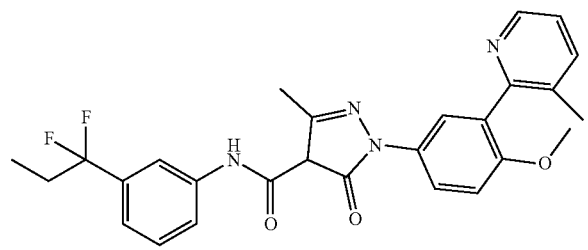 [SMILES: CCC(F)(F)c1cccc(NC(=O)C2C(=O)N(c3ccc(OC)c(-c4ncccc4C)c3)N=C2C)c1]

535 was obtained via similar procedure of 530 from 2-bromo-3-methylpyridine and 534-A.

LCMS: (ESI) m/z: 493.2 [M+H]+

$^1$H NMR (400 MHz, MeOD-d$_4$) δ: 8.75-8.65 (m, 1H), 8.48 (d, J=8.0 Hz, 1H), 7.93 (dd, J=5.6, 8.0 Hz, 1H), 7.87-7.81 (m, 2H), 7.78 (d, J=2.6 Hz, 1H), 7.63 (d, J=8.2 Hz, 1H), 7.47-7.38 (m, 2H), 7.20 (d, J=7.8 Hz, 1H), 3.92 (s, 3H), 2.62 (s, 3H), 2.42 (s, 3H), 2.24-2.09 (m, 2H), 0.97 (t, J=7.4 Hz, 3H).

Synthesis of 536

Step 1: Synthesis of N-(3-(1,1-difluoropropyl)phenyl)-1-(4-methoxy-3-(6-methylpyridin-2-yl)phenyl)-3-methyl-5-oxo-4,5-dihydro-1H-pyrazole-4-carboxamide (536)

Compound ID: 536

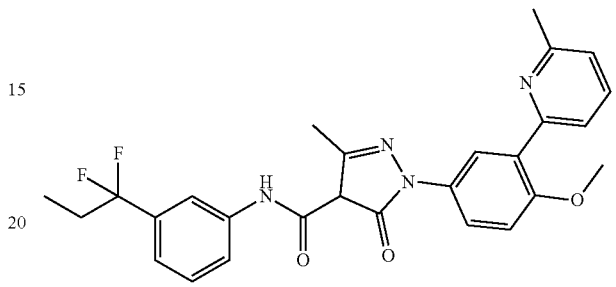

536 was obtained via similar procedure of 530 from 2-bromo-6-methylpyridine and 534-A.

LCMS: (ESI) m/z: 493.4 [M+H]+.

$^1$H NMR (400 MHz, MeOD-d$_4$) δ: 8.07 (t, J=7.6 Hz, 1H), 7.93 (d, J=2.4 Hz, 1H), 7.82-7.85 (m, 3H), 7.64 (d, J=7.6 Hz, 1H), 7.50 (d, J=8.0 Hz, 1H), 7.38 (t, J=8.0 Hz, 1H), 7.30 (d, J=8.8 Hz, 1H), 7.15 (d, J=7.6 Hz, 1H), 3.92 (s, 3H), 2.70 (s, 3H), 2.51 (s, 3H), 2.13-2.23 (m, 2H), 0.98 (t, J=7.6 Hz, 3H).

Synthesis of 537

Step 1: Synthesis of N-(3-(1,1-difluoropropyl)phenyl)-1-(4-methoxy-3-(4-methylpyridin-2-yl)phenyl)-3-methyl-5-oxo-4,5-dihydro-1H-pyrazole-4-carboxamide (537)

Compound ID: 537

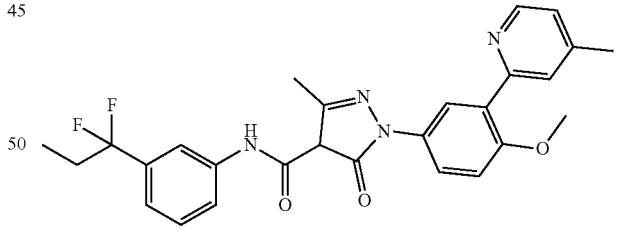

537 was obtained via similar procedure of 530 from 2-bromo-4-methylpyridine and 534-A.

LCMS: (ESI) m/z: 493.3 [M+H]+.

$^1$H NMR (400 MHz, MeOD-d$_4$) δ: 8.54 (d, J=5.2 Hz, 1H), 7.97 (d, J=2.4 Hz, 1H), 7.94 (s, 1H), 7.85-7.87 (m, 2H), 7.64 (d, J=8.4 Hz, 1H), 7.52 (d, J=4.8 Hz, 1H), 7.38 (t, J=7.6 Hz, 1H), 7.30 (d, J=8.8 Hz, 1H), 7.15 (d, J=7.6 Hz, 1H), 3.94 (s, 3H), 2.59 (s, 3H), 2.50 (s, 3H), 2.13-2.23 (m, 2H), 0.98 (t, J=7.6 Hz, 3H).

Analytical Data for Compound of the Invention:

| Compound Number | IUPAC name, Mass Spectra and H-NMR data |
|---|---|
| 359 | N-[3-(1,1-difluoropropyl)phenyl]-3-methyl-5-oxo-1-(1-propylindol-6-yl)-4H-pyrazole-4-carboxamide<br>LCMS: (ESI) m/z: 453.3[M + H]+;<br>1H NMR: (400 MHz, DMSO-d6) δ: 10.98 (s, 1H), 7.92 (s, 1H), 7.79 (s, 1H), 7.70-7.60 (m, 2H), 7.48 (d, J = 3.2 Hz, 1H), 7.42 (t, J = 8.0 Hz, 1H), 7.32 (dd, J = 8.4, 2.0 Hz, 1H), 7.16 (d, J = 7.6 Hz, 1H), 6.50 (d, J = 2.8 Hz, 1H), 4.16 (t, J = 7.2 Hz, 2H), 2.56 (s, 3H), 2.26-2.13 (m, 2H), 1.86-1.76 (m, 2H), 0.92 (t, J = 7.6 Hz, 3H), 0.85 (t, J = 7.2 Hz, 3H). |
| 360 | N-[3-(1,1-difluoropropyl)phenyl]-1-(1-isopropylindol-6-yl)-3-methyl-5-oxo-4H-pyrazole-4-carboxamide<br>LCMS: (ESI) m/z: 453.3[M + H]+;<br>1H NMR: (400 MHz, DMSO-d6) δ: 10.98 (s, 1H), 7.92 (s, 1H), 7.83 (s, 1H), 7.67-7.60 (m, 3H), 7.43 (t, J = 7.6 Hz, 1H), 7.32 (dd, J = 8.4, 1.6 Hz, 1H), 7.16 (d, J = 7.6 Hz, 1H), 6.53 (d, J = 3.2 Hz, 1H), 4.80-4.72 (m, 1H), 2.56 (s, 3H), 2.26-2.15 (m, 2H), 1.48 (d, J = 6.4 Hz, 6H), 0.92 (t, J = 7.6 Hz, 3H). |
| 361 | N-[3-(1,1-difluoroethyl)phenyl]-3-methyl-5-oxo-1-(1-phenylindol-6-yl)-4H-pyrazole-4-carboxamide<br>LCMS: (ESI) m/z: 473.3[M + H]+;<br>1H NMR: (400 MHz, MeOD-d4) δ: 7.91 (s, 1H), 7.82-7.76 (m, 2H), 7.64-7.56 (m, 6H), 7.45-7.34 (m, 3H), 7.23 (d, J = 8.0 Hz, 1H), 6.76 (d, J = 3.2 Hz, 1H), 2.60 (s, 3H), 1.92 (t, J = 18.2 Hz, 3H). |
| 362 | N-(3-(1,1-difluoro-2-methylpropyl)phenyl)-1-(4-(difluoromethoxy)phenyl)-3-methyl-5-oxo-4,5-dihydro-1H-pyrazole-4-carboxamide<br>LCMS: (ESI) m/z: 452.2 [M + H]+;<br>1H NMR (400 MHz, MeOD-d4) δ: 7.83 (s, 1H), 7.72-7.63 (m, 3H), 7.43-7.28 (m, 3H), 7.17 (d, J = 8.0 Hz, 1H), 6.91 (t, J = 73.6 Hz, 1H), 2.62 (s, 3H), 2.37 (qd, J = 6.8, 14.0 Hz, 1H), 1.00 (d, J = 6.8 Hz, 6H). |
| 363 | N-[3-(1,1-difluoroethyl)phenyl]-3-methyl-5-oxo-1-(1-propylindol-6-yl)-4H-pyrazole-4-carboxamide<br>LCMS: (ESI) m/z: 439.2[M + H]+;<br>1H NMR: (400 MHz, DMSO-d6) δ: 10.97 (s, 1H), 7.96 (s, 1H), 7.78 (s, 1H), 7.68-7.62 (m, 2H), 7.48 (d, J = 3.2 Hz, 1H), 7.43 (t, J = 8.0 Hz, 1H), 7.31 (dd, J = 8.4, 2.0 Hz, 1H), 7.21 (d, J = 8.0 Hz, 1H), 6.50 (d, J = 2.8 Hz, 1H), 4.16 (t, J = 7.0 Hz, 2H), 2.57 (s, 3H), 1.96 (t, J = 18.8 Hz, 3H), 1.81 (d, J = 7.2 Hz, 2H), 0.86 (t, J = 7.4 Hz, 3H). |
| 364 | N-[3-(1,1-difluoroethyl)phenyl]-1-(1-isopropylindol-6-yl)-3-methyl-5-oxo-4H-pyrazole-4-carboxamide<br>LCMS: (ESI) m/z: 439.3[M + H]+;<br>1H NMR: (400 MHz, DMSO-d6) δ: 10.99 (s, 1H), 7.95 (s, 1H), 7.84 (s, 1H), 7.65 (d, J = 8.4 Hz, 2H), 7.59 (d, J = 3.2 Hz, 1H), 7.42 (t, J = 7.6 Hz, 1H), 7.34 (dd, J = 8.4, 1.6 Hz, 1H), 7.21 (d, J = 7.6 Hz, 1H), 6.53 (d, J = 3.2 Hz, 1H), 4.82-4.70 (m, 1H), 2.56 (s, 3H), 1.96 (t, J = 18.8 Hz, 3H), 1.49 (d, J = 6.8 Hz, 6H). |
| 366 | N-[3-(1,1-difluoroethyl)phenyl]-3-methyl-1-(1-methylindol-6-yl)-5-oxo-4H-pyrazole-4-carboxamide<br>LCMS: (ESI) m/z: 411.1[M + H]+;<br>1H NMR: (400 MHz, DMSO-d6) δ: 10.99 (s, 1H), 7.95 (s, 1H), 7.81-7.76 (m, 1H), 7.68-7.62 (m, 2H), 7.44-7.40 (m, 2H), 7.34 (dd, J = 8.8, 2.0 Hz, 1H), 7.21 (d, J = 7.6 Hz, 1H), 6.49 (dd, J = 2.8, 0.8 Hz, 1H), 3.83 (s, 3H), 2.56 (s, 3H), 1.96 (t, J = 18.8 Hz, 3H). |
| 367 | 1-(1-benzylindol-6-yl)-N-[3-(1,1-difluoroethyl)phenyl]-3-methyl-5-oxo-4H-pyrazole-4-carboxamide<br>LCMS: (ESI) m/z: 487.2[M + H]+;<br>1H NMR: (400 MHz, DMSO-d6) δ: 10.95 (s, 1H), 7.95 (s, 1H), 7.81 (s, 1H), 7.69 (d, J = 8.4 Hz, 1H), 7.60 (s, 1H), 7.58 (d, J = 3.2 Hz, 1H), 7.42 (s, 1H), 7.36-7.29 (m, 3H), 7.28-7.23 (m, 1H), 7.22-7.16 (m, 3H), 6.58 (d, J = 3.2 Hz, 1H), 5.46 (s, 2H), 2.53 (s, 3H), 1.96 (t, J = 18.8 Hz, 3H). |
| 368 | N-[3-(1,1-difluoropropyl)phenyl]-1-(4-methoxy-3-phenyl-phenyl)-3-methyl-5-oxo-4H-pyrazole-4-carboxamide<br>LCMS: (ESI) m/z: 478.3 [M + H]+;<br>1H NMR: (400 MHz, MeOD-d4) δ: 7.87 (s, 1H), 7.66-7.62 (m, 1H), 7.59-7.54 (m, 4H), 7.44-7.38 (m, 3H), 7.36-7.33 (m, 1H), 7.25 (d, J = 8.4 Hz, 1H), 7.20 (d, J = 8.4 Hz, 1H), 3.87 (s, 3H), 2.61 (s, 3H), 2.26-2.11 (m, 2H), 0.98 (t, J = 7.2 Hz, 3H). |
| 369 | N-[3-(1,1-difluoropropyl)phenyl]-1-(1H-indol-6-yl)-3-methyl-5-oxo-4H-pyrazole-4-carboxamide<br>LCMS: (ESI) m/z: 411.2 [M + H]+;<br>1H NMR: (400 MHz, MeOD-d4) δ: 7.87 (s, 1H), 7.70 (d, J = 8.4 Hz, 1H), 7.65 (s, 2H), 7.44-7.36 (m, 2H), 7.20 (d, J = 8.4 Hz, 2H), 6.54 (d, J = 2.8 Hz, 1H), 2.62 (s, 3H), 2.18 (m, 2H), 0.98 (t, J = 7.4 Hz, 3H). |
| 370 | 1-(4-(difluoromethoxy)-3-(5-methyl-4H-1,2,4-triazol-3-yl)phenyl)-N-(3-(1,1-difluoropropyl)phenyl)-3-methyl-5-oxo-4,5-dihydro-1H-pyrazole-4-carboxamide<br>LCMS: (ESI) m/z: 519.1 [M + H]+;<br>1H NMR: (400 MHz, MeOD-d4) δ: 8.32 (d, J = 2.8 Hz, 1H), 7.93 (dd, J = 2.4, 8.8 Hz, 1H), 7.87 (s, 1H), 7.64 (d, J = 8.8 Hz, 1H), 7.44 (d, J = 8.8 Hz, 1H), 7.39 (t, J = 8.0 Hz, 1H), 7.16 (d, J = 7.6 Hz, 1H), 6.88(t, J = 74.0, 1H), 2.53 (s, 3H), 2.49 (s, 3H), 2.28-2.08 (m, 2H), 0.98 (t, J = 7.6 Hz, 3H). |

| Compound Number | IUPAC name, Mass Spectra and H-NMR data |
|---|---|
| 371 | N-(3-(1,1-difluoroethyl)phenyl)-1-(4-(difluoromethoxy)-3-(5-methyl-4H-1,2,4-triazol-3-yl)phenyl)-3-methyl-5-oxo-4,5-dihydro-1H-pyrazole-4-carboxamide<br>LCMS: (ESI) m/z: 505.3 [M + H]+;<br>1H NMR: (400 MHz, MeOD-d4) δ: 8.32 (d, J = 2.0 Hz, 1H), 8.00-7.85 (m, 2H), 7.65 (d, J = 8.4 Hz, 1H), 7.46 (d, J = 8.8 Hz, 1H), 7.41 (t, J = 8.0 Hz, 1H), 7.22 (d, J = 7.6 Hz, 1H), 6.90 (t, J = 73.6 Hz, 1H), 2.56 (s, 3H), 2.51 (s, 3H), 1.94 (t, J = 18.4 Hz, 3H). |
| 377 | 1-[4-(difluoromethoxy)-3-(2-pyridyl)phenyl]-N-[3-(1,1-difluoropropyl)phenyl]-3-methyl-5-oxo-4H-pyrazole-4-carboxamide<br>LCMS: (ESI) m/z: 515.1 [M + H]+;<br>1H NMR: (400 MHz, DMSO-d6) δ: 10.79 (s, 1H), 8.89-8.64 (m, 1H), 8.18 (d, J = 2.8 Hz, 1H), 7.97 (dt, J = 1.8, 7.8 Hz, 1H), 7.94-7.88 (m, 2H), 7.82 (d, J = 7.8 Hz, 1H), 7.67-7.60 (m, 1H), 7.51-7.45 (m, 2H), 7.42 (t, J = 7.8 Hz, 1H), 7.28 (s, 1H), 7.16 (d, J = 7.8 Hz, 1H), 7.09 (s, 1H), 2.55 (s, 3H), 2.29-2.10 (m, 2H), 0.92 (t, J = 7.4 Hz, 3H). |
| 383 | 1-[5-(difluoromethoxy)-2-pyridyl]-N-[3-(1,1-difluoropropyl)phenyl]-3-methyl-5-oxo-4H-pyrazole-4-carboxamide<br>LCMS: (ESI) m/z: 439.1 [M + H]+;<br>1H NMR: (400 MHZ, MeOD-d4) δ: 8.46(d, J = 8.8 Hz, 1H), 8.35(s, 1H), 7.87(s, 1H), 7.81(dd, J = 8.8 Hz, 2.0Hz, 1H), 7.66(d, J = 8.0 Hz, 1H, 7.42(t, J = 7.6 Hz, 1H), 7.20(d, J = 7.6 Hz, 1H), 6.93 (t, J = 72.8 Hz, 1H), 2.64(s, 3H), 2.24-2.12(m, 2H), 0.99(t, J = 7.6 Hz, 3H). |
| 385 | N-(3-(1,1-difluoroethyl)phenyl)-1-(4-methoxy-3-(5-methyl-4H-1,2,4-triazol-3-yl)phenyl)-3-methyl-5-oxo-4,5-dihydro-1H-pyrazole-4-carboxamide<br>LCMS: (ESI) m/z: 469.4 [M + H]+;<br>1H NMR: (400 MHz, MeOD-d4) δ: 8.39 (d, J = 2.8 Hz, 1H), 7.92 (s, 1H), 7.85 (dd, J = 2.8, 9.2 Hz, 1H), 7.63 (dd, J = 1.2, 8.0 Hz, 1H), 7.36 (t, J = 8.0 Hz, 1H), 7.24 (d, J = 9.2 Hz, 1H), 7.16 (d, J = 7.6 Hz, 1H), 4.02 (s, 3H), 2.45 (s, 3H), 2.42 (s, 3H), 1.92 (t, J = 18.4 Hz, 3H). |
| 391 | N-(3,5-dichloro-4-fluoro-phenyl)-1-[4-(difluoromethoxy)phenyl]-N,3-dimethyl-5-oxo-4H-pyrazole-4-carboxamide<br>LCMS: (ESI) m/z: 460.1 [M + H]+;<br>1H NMR (400 MHz, MeOD-d4) δ: 7.77 (s, 1H), 7.76 (s, 1H), 7.49 (d, J = 8.8 Hz, 2H), 7.38 (d, J = 9.2 Hz, 2H), 6.97 (t, J = 73.6 Hz, 1H), 3.41 (s, 3H), 2.74 (s, 3H). |
| 392 | N-(3-chloro-5-methoxy-phenyl)-1-[4-(difluoromethoxy)phenyl]-N,3-dimethyl-5-oxo-4H-pyrazole-4-carboxamide<br>LCMS: (ESI) m/z: 438.2 [M + H]+;<br>1H NMR (400 MHz, MeOD-d4) δ: 7.49 (d, J = 8.8 Hz, 2H), 7.38 (d, J = 8.8 Hz, 2H), 7.28 (t, J = 2.0 Hz, 1H), 7.16 (s, 1H), 6.97 (t, J = 73.2 Hz, 1H), 6.67 (t, J = 2.0 Hz, 1H), 3.79 (s, 3H), 3.41 (s, 3H), 2.74 (s, 3H). |
| 393 | N-(3-chloro-5-methyl-phenyl)-1-[4-(difluoromethoxy)phenyl]-N,3-dimethyl-5-oxo-4H-pyrazole-4-carboxamide<br>LCMS: (ESI) m/z: 422.2 [M + H]+;<br>1H NMR (400 MHz, MeOD-d4) δ: 7.65 (s, 1H), 7.50 (d, J = 8.8 Hz, 2H), 7.38 (d, J = 8.8 Hz, 2H), 7.19 (s, 1H), 6.97 (t, J = 73.2 Hz, 1H), 6.92 (s, 1H), 3.41 (s, 3H), 2.74 (s, 3H), 2.31 (s, 3H). |
| 394 | N-(3-chloro-5-fluoro-phenyl)-1-[4-(difluoromethoxy)phenyl]-N,3-dimethyl-5-oxo-4H-pyrazole-4-carboxamide<br>LCMS: (ESI) m/z: 426.2 [M + H]+.<br>1H NMR (400 MHz, MeOD-d4) δ: 7.51-7.46 (m, 4H), 7.38 (d, J = 9.2 Hz, 2H), 6.97 (t, J = 73.2 Hz, 1H), 6.89-6.87 (m, 1H), 3.41 (s, 3H), 2.74 (s, 3H). |
| 395 | N-(3-chlorophenyl)-1-[4-(difluoromethoxy)phenyl]-N,3-dimethyl-5-oxo-4H-pyrazole-4-carboxamide<br>LCMS: (ESI) m/z: 408.0 [M + H]+;<br>1H NMR (400 MHz, MeOD-d4) δ: 7.86 (t, J = 2.4 Hz, 1H), 7.49 (d, J = 9.2 Hz, 2H), 7.38 (d, J = 8.8 Hz, 2H), 7.36-7.35 (m, 1H), 7.28 (t, J = 8.0 Hz, 1H), 7.08-7.05 (m, 1H), 6.97 (t, J = 73.2 Hz, 1H), 3.40 (s, 3H), 2.74 (s, 3H). |
| 396 | N-[3-(1,1-difluoroethyl)phenyl]-1-(4-methoxy-3-methyl-5-phenyl-phenyl)-3-methyl-5-oxo-4H-pyrazole-4-carboxamide<br>LCMS: (ESI) m/z: 540.3 [M + H]+;<br>1H NMR: (400 MHz, DMSO-d6) δ: 10.91(s, 1H), 7.94(s, 1H), 7.77-7.71(m, 6H), 7.66-7.63(m, 3H), 7.50(t, J = 7.6 Hz, 2H), 7.44-7.39(m, 2H), 7.28(d, J = 9.6 Hz, 1H), 7.20(d, J = 7.6 Hz, 1H), 3.85(s, 3H), 2.54(s, 3H), 1.96(t, J = 18.8 Hz, 3H). |
| 397 | N-(6-(1,1-difluoroethyl)-1,3-dihydroisobenzofuran-4-yl)-1-(4-(difluoromethoxy)phenyl)-3-methyl-5-oxo-4,5-dihydro-1H-pyrazole-4-carboxamide<br>LCMS: (ESI) m/z: 466.2 [M + H]+;<br>1H NMR: (400 MHz, MeOD-d4) δ: 8.28 (s, 1H), 7.71 (d, J = 8.0 Hz, 2H), 7.30 (d, J = 8.0 Hz, 2H), 7.18 (s, 1H), 6.88 (t, J = 76 Hz, 1H), 5.16 (s, 2H), 5.13 (s, 2H), 2.59 (s, 3H), 1.94 (t, J = 18.4 Hz, 3H). |
| 398 | N-(3-(1,1-difluoroethyl)phenyl)-1-(4-(difluoromethoxy)phenyl)-N,3-dimethyl-5-oxo-4,5-dihydro-1H-pyrazole-4-carboxamide<br>LCMS: (ESI) m/z: 438.2 [M + H]+;<br>1H NMR: (400 MHz, MeOD-d4) δ: 7.88 (s, 1H), 7.59 (d, J = 8.0 Hz, 1H), 7.50 (d, J = 8.8 Hz, 2H), 7.42-7.36 (m, 3H), 7.24 (d, J = 8.0 Hz, 1H), 6.98 (t, J = 73.6 Hz, 1H), 3.41 (s, 3H), 2.76 (s, 3H), 1.91 (t, J = 18.4 Hz, 3H). |

-continued

| Compound Number | IUPAC name, Mass Spectra and H-NMR data |
|---|---|
| 402 | N-(3-(1,1-difluoroethyl)phenyl)-1-(2'-methoxy-[1,1':3',1''-terphenyl]-5'-yl)-3-methyl-5-oxo-4,5-dihydro-1H-pyrazole-4-carboxamide<br>LCMS: (ESI) m/z: 540.3 [M + H]+;<br>1H NMR (400 MHz, MeOD-d4) δ: 7.94 (s, 1H), 7.73-7.65 (m, 7H), 7.52-7.47 (m, 4H), 7.45-7.40 (m, 3H), 7.27 (br d, J = 7.6 Hz, 1H), 3.18 (s, 3H), 2.65 (s, 3H), 1.97 (t, J = 7.6 Hz, 3H). |
| 403 | N-[5-(1,1-difluoroethyl)benzofuran-7-yl]-1-[4-(difluoromethoxy)phenyl]-3-methyl-5-oxo-4H-pyrazole-4-carboxamide<br>LCMS: (ESI) m/z: 464.2 [M + H]+;<br>1H NMR: (400 MHz, MeOD-d4) δ: 8.49 (s, 1H), 8.08 (s, 1H) 7.86 (J = 2.0 Hz, 1H), 7.75 (d, J = 8.8 Hz, 2H), 7.51 (s, 1H), 7.29 (d, J = 8.8 Hz, 2H), 7.07-6.69 (m, 2H), 2.60 (s, 3H), 1.99 (t, J = 18.0 Hz, 3H). |
| 404 | 1-(3-bromophenyl)-N-(3-(1,1-difluoroethyl)phenyl)-3-methyl-5-oxo-4,5-dihydro-1H-pyrazole-4-carboxamide<br>LCMS: (ESI) m/z: 438.1 [M + H]+;<br>1H NMR (400 MHz, MeOD-d4) δ: 7.97 (s, 1H), 7.91 (s, 1H), 7.69 (d, J = 7.6 Hz, 1H), 7.62 (d, J = 7.6 Hz, 1H), 7.46-7.49 (m, 1H), 7.37-7.43 (m, 2H), 7.23 (d, J = 8.0 Hz, 1H), 2.58 (s, 3H), 1.92 (t, J = 18.0 Hz, 3H). |
| 405 | 1-(1H-benzo[d]imidazol-5-yl)-N-(3-(1,1-difluoroethyl)phenyl)-3-methyl-5-oxo-4,5-dihydro-1H-pyrazole-4-carboxamide<br>LCMS: (ESI) m/z: 398.3 [M + H]+;<br>1H NMR (400 MHz, DMSO-d6) δ: 12.23 (br s, 1H), 11.52 (s, 1H), 8.34 (d, J = 1.6 Hz, 1H), 8.09 (s, 1H), 8.00-7.91 (m, 2H), 7.58 (br d, J = 8.0 Hz, 1H), 7.48 (br d, J = 8.8 Hz, 1H), 7.33 (t, J = 8.0 Hz, 1H), 7.04 (d, J = 7.6 Hz, 1H), 2.27 (s, 3H), 1.95 (t, J = 18.8 Hz, 3H). |
| 407 | N-(3-(1,1-difluoroethyl)phenyl)-1-(4-(difluoromethoxy)-3-(5-methyl-1,2,4-oxadiazol-3-yl)phenyl)-3-methyl-5-oxo-4,5-dihydro-1H-pyrazole-4-carboxamide<br>LCMS: (ESI) m/z: 506.0 [M + H]+;<br>1H NMR (400 MHz, MeOD-d4) δ: 8.38 (d, J = 2.4 Hz, 1 H), 7.92-7.94 (m, 2 H), 7.64 (d, J = 8.4 Hz, 1 H), 7.55 (d, J = 8.8 Hz, 1 H), 7.41 (t, J = 7.6 Hz, 1 H), 7.24-7.26 (m, 1 H), 6.93 (t, J = 74.0 Hz, 1 H), 2.67 (d, J = 17.6 Hz, 6 H), 1.93 (t, J = 18.4 Hz, 3 H). |
| 408 | N-(5-acetyl-1H-indol-7-yl)-1-[4-(difluoromethoxy)phenyl]-3-methyl-5-oxo-4H-pyrazole-4-carboxamide<br>LCMS: (ESI) m/z: 441.0 [M + H]+;<br>1H NMR: (400 MHz, MeOD-d4) δ: 8.17 (d, J = 1.2 Hz, 1H), 7.92 (d, J = 1.2 Hz, 1H), 7.82 (d, J = 9.2 Hz, 2H), 7.37 (d, J = 2.8 Hz, 1H), 7.26 (d, J = 8.8 Hz, 2H), 6.85 (m, 2H), 2.66 (s, 3H), 2.57 (s, 3H). |
| 409 | 1-(4-(difluoromethoxy)phenyl)-N-(3-(2-fluoro-3-methylbutan-2-yl)phenyl)-3-methyl-5-oxo-4,5-dihydro-1H-pyrazole-4-carboxamide<br>LCMS: (ESI) m/z: 448.0 [M + H]+;<br>1HNMR (400 MHz, MeOD-d4) δ: 7.69 (d, J = 8.0 Hz, 2H), 7.62 (s, 1H), 7.54 (d, J = 8.4 Hz, 1H), 7.36-7.28 (m, 3H), 7.06 (d, J = 8.0 Hz, 1H), 6.90 (t, J = 73.6 Hz, 1H), 2.62 (s, 3H), 2.15-2.09 (m, 1H), 1.62 (d, J = 22.8 Hz, 3H), 0.97 (d, J = 6.8 Hz, 3H), 0.85 (d, J = 6.8 Hz, 3H). |
| 410 | N-[3-(1,1-difluoroethyl)phenyl]-1-(1H-indol-6-yl)-3-methyl-5-oxo-4H-pyrazole-4-carboxamide<br>LCMS: (ESI) m/z: 397.4 [M + H]+;<br>1H NMR: (400 MHz, MeOD-d4) δ: 7.92 (s, 1H), 7.71 (d, J = 8.4 Hz, 1H), 7.65 (s, 2H), 7.44-7.36 (m, 2H), 7.25 (d, J = 0.4 Hz, 1H), 7.18 (dd, J = 8.4, 2.0 Hz, 1H), 6.54 (dd, J = 3.2, 0.8 Hz, 1H), 2.63 (s, 3H), 1.92 (t, J = 18.0 Hz, 3H). |
| 462 | N-[3-(1,1-difluoropropyl)phenyl]-3-methyl-1-(1-methylindol-6-yl)-5-oxo-4H-pyrazole-4-carboxamide<br>LCMS: (ESI) m/z: 425.2[M + H]+;<br>1H NMR: (400 MHz, DMSO-d6) δ: 11.02 (s, 1H), 7.92 (s, 1H), 7.80 (s, 1H), 7.71-7.57 (m, 2H), 7.50-7.32 (m, 3H), 7.15 (d, J = 7.6 Hz, 1H), 6.56-6.43 (m, 1H), 3.82 (s, 3H), 2.54 (s, 3H), 2.25-2.15 (m, 2H), 0.92 (t, J = 7.2 Hz, 3H). |
| 463 | 1-(1-benzylindol-6-yl)-N-[3-(1,1-difluoropropyl)phenyl]-3-methyl-5-oxo-4H-pyrazole-4-carboxamide<br>LCMS: (ESI) m/z: 501.3 [M + H]+;<br>1H NMR: (400 MHz, DMSO-d6) δ: 10.95 (s, 1H), 7.91 (s, 1H), 7.81 (s, 1H), 7.69 (d, J = 8.4 Hz, 1H), 7.63-7.56 (m, 2H), 7.42 (s, 1H), 7.35-7.30 (m, 3H), 7.26 (d, J = 7.2 Hz, 1H), 7.20-7.14 (m, 3H), 6.58 (d, J = 3.2 Hz, 1H), 5.46 (s, 2H), 2.53 (s, 3H), 2.20 (br d, J = 7.5 Hz, 2H), 0.92 (t, J = 7.6 Hz, 3H). |
| 464 | N-(3-(cyclopropyldifluoromethyl)phenyl)-1-(5-(difluoromethoxy)pyridin-2-yl)-3-methyl-5-oxo-4,5-dihydro-1H-pyrazole-4-carboxamide<br>LCMS: (ESI) m/z: 451.2 [M + H]+;<br>1H NMR(400 MHz, DMSO-d6) δ: 10.69(s, 1H), 8.45(d, J = 9.2 Hz, 1H), 8.40(d, J = 2.4 Hz, 1H), 7.96(s, 1H), 7.91(dd, J = 8.8, 2.4 Hz, 1H), 7.61(d, J = 8.4 Hz, 1H), 7.42(t, J = 8.0 Hz, 1H), 7.33(t, J = 73.2 Hz, 1H), 7.21(d, J = 7.6 Hz, 1H), 2.55(s, 3H), 1.75-1.64(m, 1H), 0.72-0.62(m, 4H). |
| 470 | N-(3-(cyclopentyldifluoromethyl)phenyl)-1-(4-(difluoromethoxy)phenyl)-3-methyl-5-oxo-4,5-dihydro-1H-pyrazole-4-carboxamide<br>LCMS: (ESI) m/z: 478.2 [M + H]+;<br>1H NMR (400 MHz, MeOD-d4) δ: 7.86 (s, 1H), 7.73 (d, J = 8.8 Hz, 2H), 7.63 (br d, J = 8.2 Hz, 1H), 7.39 (t, J = 7.8 Hz, 1H), 7.28 (d, J = 8.8 Hz, 2H), 7.18 (d, J = 7.8 Hz, 1H), 7.07-6.68 (m, 1H), 2.76-2.66 (m, 1H), 2.57 (s, 3H), 1.71-1.55 (m, 8H). |

| Compound Number | IUPAC name, Mass Spectra and H-NMR data |
|---|---|
| 471 | N-(3-(1,1-difluoro-2-(methoxy(methyl)amino)-2-oxoethyl)phenyl)-1-(4-(difluoromethoxy)-3-(pyridin-2-yl)phenyl)-3-methyl-5-oxo-4,5-dihydro-1H-pyrazole-4-carboxamide<br>LCMS: (ESI) m/z: 574.3 [M + H]+;<br>1H NMR (400 MHz, MeOD-d4) δ: 8.70 (d, J = 4.4 Hz, 1H), 8.07-7.98 (m, 3H), 7.88-7.84 (m, 2H), 7.67 (d, J = 8.0 Hz, 1H), 7.53-7.42 (m, 3H), 7.21 (d, J = 8.0 Hz, 1H), 6.89 (t, J = 73.6 Hz, 1H), 3.51 (s, 3H), 3.24 (s, 3H), 2.60 (s, 3H). |
| 472 | N-[3-(1,1-difluoropropyl)phenyl]-3-methyl-5-oxo-1-(1-phenylindol-6-yl)-4H-pyrazole-4-carboxamide<br>LCMS: (ESI) m/z: 487.2[M + H]+;<br>1H NMR: (400 MHz, DMSO-d6) δ: 11.05 (br s, 1H), 8.04 (br s, 1H), 7.90 (s, 1H), 7.56-7.73 (m, 8H), 7.41-7.47 (m, 1H), 7.38 (t, J = 7.6 Hz, 1H), 7.10 (d, J = 7.6 Hz, 1H), 6.72 (d, J = 3.2 Hz, 1H), 2.44 (br s, 3H), 2.14-2.24 (m, 2H), 0.92 (t, J = 7.2 Hz, 3H). |
| 474 | N-(3-(1,1-difluoropropyl)phenyl)-3-methyl-5-oxo-1-(quinolin-7-yl)-4,5-dihydro-1H-pyrazole-4-carboxamide<br>LCMS: (ESI) m/z: 423.1 [M + H]+;<br>1H NMR (MeOD-d4, 400 MHz) δ: 8.91 (d, J = 4.4 Hz, 1H), 8.65-8.68 (m, 2H), 8.46 (d, J = 7.6 Hz, 1H), 8.14 (d, J = 9.2 Hz, 1H), 7.86 (s, 1H), 7.65 (d, J = 8.0 Hz, 2H), 7.39 (t, J = 8.0 Hz, 1H), 7.16 (d, J = 8.0 Hz, 1H), 2.53 (s, 3H), 2.12-2.26 (m, 2H), 0.99 (t, J = 7.6 Hz, 3H). |
| 475 | 1-(1-benzoylindol-6-yl)-N-[3-(1,1-difluoropropyl)phenyl]-3-methyl-5-oxo-4H-pyrazole-4-carboxamide<br>LCMS: (ESI) m/z: 515.2 [M + H]+;<br>1H NMR: (400 MHz, DMSO-d6) δ: 10.90 (s, 1H), 8.75 (d, J = 1.6 Hz, 1H), 7.93 (s, 1H), 7.83-7.79 (m, 3H), 7.74-7.69 (m, 2H), 7.64 (d, J = 7.6 Hz, 3H), 7.46 (d, J = 3.6 Hz, 1H), 7.43 (t, J = 8.0 Hz, 1H), 7.16 (d, J = 8.0 Hz, 1H), 6.82 (d, J = 3.6 Hz, 1H), 2.58 (s, 3H), 2.25-2.15 (m, 2H), 0.92 (t, J = 7.6 Hz, 3H). |
| 476 | N-(3-(1,1-difluoropropyl)phenyl)-3-methyl-5-oxo-1-(1-(phenylsulfonyl)-1H-indol-6-yl)-4,5-dihydro-1H-pyrazole-4-carboxamide<br>LCMS: (ESI) m/z: 551.1 [M + H]+;<br>1H NMR (400 MHz, DMSO-d6) δ: 10.88 (s, 1H), 8.46 (s, 1H), 8.04-8.00 (m, 2H), 7.96 (s, 1H), 7.85 (d, J = 3.6 Hz, 1H), 7.70 (t, J = 8.8 Hz, 2H), 7.64-7.58 (m, 4H), 7.43 (t, J = 8.0 Hz, 1H), 7.16 (d, J = 7.6 Hz, 1H), 6.89 (d, J = 4.0 Hz, 1H), 2.56 (s, 3H), 2.25-2.16 (m, 2H), 0.93 (t, J = 7.2 Hz, 3H). |
| 477 | N-[3-(1,1-difluoropropyl)phenyl]-3-methyl-5-oxo-1-[1-(2-phenylethyl)indol-6-yl]-4H-pyrazole-4-carboxamide<br>LCMS: (ESI) m/z: 515.2[M + H]+;<br>1H NMR: (400 MHz, DMSO-d6) δ: 10.99 (s, 1H), 7.93 (s, 1H), 7.84 (s, 1H), 7.67-7.61 (m, 2H), 7.43 (t, J = 8.0 Hz, 1H), 7.36-7.31 (m, 2H), 7.29-7.25 (m, 2H), 7.24-7.19 (m, 3H), 7.16 (d, J = 8.0 Hz, 1H), 6.44 (d, J = 3.2 Hz, 1H), 4.44 (t, J = 7.6 Hz, 2H), 3.11 (t, J = 7.2 Hz, 2H), 2.58 (s, 3H), 2.26-2.15 (m, 2H), 0.92 (t, J = 7.6 Hz, 3H). |
| 478 | 1-(1-butanoylindol-6-yl)-N-[3-(1,1-difluoropropyl)phenyl]-3-methyl-5-oxo-4H-pyrazole-4-carboxamide<br>LCMS: (ESI) m/z: 481.2 [M + H]+;<br>1H NMR: (400 MHz, DMSO-d6) δ: 10.89 (s, 1H), 8.75 (s, 1H), 8.00 (d, J = 3.6 Hz, 1H), 7.92 (s, 1H), 7.75 (d, J = 8.8 Hz, 1H), 7.66-7.60 (m, 2H), 7.43 (t, J = 8.0 Hz, 1H), 7.17 (d, J = 7.6 Hz, 1H), 6.80 (d, J = 3.6 Hz, 1H), 3.06 (t, J = 7.2 Hz, 2H), 2.57 (s, 3H), 2.26-2.15 (m, 2H), 1.78-1.71 (m, 2H), 1.01 (t, J = 7.6 Hz, 3H), 0.92 (t, J = 7.6 Hz, 3H). |
| 479 | N-[3-(1,1-difluoropropyl)phenyl]-3-methyl-1-[1-(2-methylbenzoyl)indol-6-yl]-5-oxo-4H-pyrazole-4-carboxamide<br>LCMS: (ESI) m/z: 529.2[M + H]+;<br>1H NMR: (400 MHz, DMSO-d6) δ: 10.88 (s, 1H), 8.78 (d, J = 1.6 Hz, 1H), 7.93 (s, 1H), 7.81 (d, J = 8.4 Hz, 1H), 7.71 (dd, J = 8.4, 2.0 Hz, 1H), 7.67-7.63 (m, 1H), 7.53 (d, J = 7.6 Hz, 2H), 7.46-7.38 (m, 3H), 7.17 (d, J = 7.6 Hz, 1H), 7.11 (d, J = 3.6 Hz, 1H), 6.79 (d, J = 3.6 Hz, 1H), 2.59 (s, 3H), 2.28 (s, 3H), 2.25-2.15 (m, 2H), 0.92 (t, J = 7.6 Hz, 3H). |
| 480 | N-[3-(1,1-difluoropropyl)phenyl]-3-methyl-1-[1-(4-methylbenzoyl)indol-6-yl]-5-oxo-4H-pyrazole-4-carboxamide<br>LCMS: (ESI) m/z: 529.2[M + H]+;<br>1H NMR: (400 MHz, DMSO-d6) δ: 10.91 (s, 1H), 8.72 (d, J = 1.6 Hz, 1H), 7.92 (s, 1H), 7.80 (d, J = 8.4 Hz, 1H), 7.70 (d, J = 8.0 Hz, 3H), 7.64 (d, J = 8.0 Hz, 1H), 7.49 (d, J = 3.6 Hz, 1H), 7.46-7.40 (m, 3H), 7.16 (d, J = 7.6 Hz, 1H), 6.81 (d, J = 3.6 Hz, 1H), 2.57 (s, 3H), 2.44 (s, 3H), 2.26-2.15 (m, 2H), 0.92 (t, J = 7.6 Hz, 3H). |
| 481 | N-(3-(cyclopropyldifluoromethyl)phenyl)-1-(4-(difluoromethoxy)phenyl)-3-methyl-5-oxo-4,5-dihydro-1H-pyrazole-4-carboxamide<br>LCMS: (ESI) m/z: 450.0 [M + H]+;<br>1HNMR(400 MHz, MeOD-d4) δ: 7.92(s, 1H), 7.69(d, J = 2.0 Hz, 2H), 7.63(d, J = 8.0 Hz, 1H), 7.41(t, J = 8.0 Hz, 1H), 7.32(d, J = 8.0 Hz, 2H), 7.26(d, J = 7.6 Hz, 1H), 6.91(t, J = 73.6 Hz, 1H), 2.63(s, 3H), 1.66-1.54(m, 1H), 0.72-0.69(m, 4H). |

| Compound Number | IUPAC name, Mass Spectra and H-NMR data |
|---|---|
| 482 | N-(3-(1,1-difluoropropyl)phenyl)-1-(1-(4-hydroxybenzoyl)-1H-indol-6-yl)-3-methyl-5-oxo-4,5-dihydro-1H-pyrazole-4-carboxamide<br>LCMS: (ESI) m/z: 531.1 [M + H]+;<br>1H NMR (400 MHz, DMSO-d6) δ: 10.92 (s, 1H), 10.45 (s, 1H), 8.66 (s, 1H), 7.92 (s, 1H), 7.79 (d, J = 8.6 Hz, 1H), 7.74-7.66 (m, 3H), 7.63 (br d, J = 8.6 Hz, 1H), 7.60-7.55 (m, 1H), 7.42 (t, J = 8.0 Hz, 1H), 7.16 (br d, J = 7.6 Hz, 1H), 7.06-6.92 (m, 2H), 6.79 (d, J = 3.6 Hz, 1H), 2.56 (s, 3H), 2.20 (dt, J = 7.6, 16.4 Hz, 2H), 0.92 (t, J = 7.2, 3H). |
| 483 | N-[3-(1,1-difluoropropyl)phenyl]-3-methyl-1-[1-(3-methylbenzoyl)indol-6-yl]-5-oxo-4H-pyrazole-4-carboxamide<br>LCMS: (ESI) m/z: 529.2[M + H]+;<br>1H NMR: (400 MHz, DMSO-d6) δ: 10.88 (s, 1H), 8.72 (d, J = 1.6 Hz, 1H), 7.93 (s, 1H), 7.82 (d, J = 8.4 Hz, 1H), 7.68 (dd, J = 8.4, 2.0 Hz, 1H), 7.64 (d, J = 9.2 Hz, 1H), 7.61 (s, 1H), 7.59-7.56 (m, 1H), 7.54-7.49 (m, 2H), 7.47 (d, J = 3.6 Hz, 1H), 7.43 (t, J = 8.0 Hz, 1H), 7.17 (d, J = 7.6 Hz, 1H), 6.82 (d, J = 3.6 Hz, 1H), 2.59 (s, 3H), 2.43 (s, 3H), 2.26-2.15 (m, 2H), 0.92 (t, J = 7.6 Hz, 3H). |
| 484 | 1-(4-(difluoromethoxy)phenyl)-N-(4-(1,1-difluoropropyl)pyridin-2-yl)-3-methyl-5-oxo-4,5-dihydro-1H-pyrazole-4-carboxamide<br>LCMS: (ESI) m/z: 439.1 [M + H]+;<br>1H NMR (400 MHz, MeOD-d4) δ: 8.38-8.33 (m, 2H), 7.70 (d, J = 8.8 Hz, 2H), 7.30 (d, J = 8.8 Hz, 2H), 7.20 (dd, J = 1.6, 5.2 Hz, 1H), 6.89 (t, J = 73.2 Hz, 1H), 2.61 (s, 3H), 2.26-2.16 (m, 2H), 1.02 (t, J = 7.6 Hz, 3H). |
| 485 | 1-(benzo[b]thiophen-6-yl)-N-(3-(1,1-difluoropropyl)phenyl)-3-methyl-5-oxo-4,5-dihydro-1H-pyrazole-4-carboxamide<br>LCMS: (ESI) m/z: 428.0 [M + H]+;<br>1H NMR (400 MHz, MeOD-d4) δ: 8.22 (s, 1H), 8.01 (d, J = 8.4 Hz, 1H), 7.88 (s, 1H), 7.70 (d, J = 5.6 Hz, 1H), 7.65-7.62 (m, 2H), 7.46 (d, J = 5.2 Hz, 1H), 7.42 (t, J = 8.0 Hz, 1H), 7.21 (d, J = 7.6 Hz, 1H), 2.65 (s, 3H), 2.25-2.14 (m, 2H), 0.98 (t, J = 7.6 Hz, 3H). |
| 486 | 1-(4-(difluoromethoxy)phenyl)-N-(6-(1,1-difluoropropyl)pyridin-2-yl)-3-methyl-5-oxo-4,5-dihydro-1H-pyrazole-4-carboxamide<br>LCMS: (ESI) m/z: 439.0[M + H]+;<br>1H NMR (400 MHz, MeOD-d4) δ: 8.33 (d, J = 8.4 Hz, 1H), 7.88 (t, J = 8.0 Hz, 1H), 7.68-7.66 (m, 2H), 7.36-7.31 (m, 3H), 6.91 (t, J = 73.6 Hz, 1H), 2.64 (s, 3H), 2.37-2.25 (m, 2H), 0.96 (t, J = 7.6 Hz, 3H) |
| 487 | N-[3-(1,1-difluoropropyl)phenyl]-3-methyl-5-oxo-1-[1-(p-tolylsulfonyl)indazol-6-yl]-4H-pyrazole-4-carboxamide<br>LCMS: (ESI) m/z: 566.2[M + H]+;<br>1H NMR: (400 MHz, MeOD-d4) δ: 8.70 (s, 1H), 8.32 (s, 1H), 7.94-7.90 (m, 3H), 7.87 (d, J = 12.8 Hz, 2H), 7.69 (d, J = 7.2 Hz, 1H), 7.41 (s, 1H), 7.34 (d, J = 8.0 Hz, 2H), 7.18 (d, J = 7.6 Hz, 1H), 2.59 (s, 3H), 2.36 (s, 3H), 2.24-2.15 (m, 2H), 0.99 (t, J = 7.6 Hz, 3H). |
| 488 | N-(3-(1,1-difluoropropyl)phenyl)-3-methyl-5-oxo-1-(quinoxalin-6-yl)-4,5-dihydro-1H-pyrazole-4-carboxamide<br>LCMS: (ESI) m/z: 424.1 [M + H]+;<br>1H NMR (MeOD-d4, 400 MHz) δ: 8.84 (s, 1H), 8.78 (s, 1H), 8.72 (s, 1H), 8.60 (dd, J = 2.4, 9.2 Hz, 1H), 8.10 (d, J = 9.6 Hz, 1H), 7.89 (s, 1H), 7.67 (d, J = 8.0 Hz, 1H), 7.40 (t, J = 7.6 Hz, 1H), 7.17 (s, 1H), 2.51 (s, 3H), 2.10-2.30 (m, 2H), 1.00 (t, J = 7.2 Hz, 3H). |
| 489 | 1-(5-chloropyrazin-2-yl)-N-(3-(1,1-difluoropropyl)phenyl)-3-methyl-5-oxo-4,5-dihydro-1H-pyrazole-4-carboxamide<br>LCMS: (ESI) m/z: 407.9 [M + H]+;<br>1H NMR(400 MHz, MeOD-d4) δ: 9.50(s, 1H), 8.52(s, 1H), 7.87(s, 1H), 7.63(s, J = 8.0 Hz, 1H), 7.41(t, J = 7.6 Hz, 1H), 7.20(d, J = 7.6 Hz, 1H), 2.65(s, 3H), 2.26-2.14(m, 2H), 0.99(t, J = 7.6 Hz, 3H). |
| 490 | 1-(6-chloropyridazin-3-yl)-N-(3-(1,1-difluoropropyl)phenyl)-3-methyl-5-oxo-4,5-dihydro-1H-pyrazole-4-carboxamide<br>LCMS: (ESI) m/z: 407.9 [M + H]+;<br>1H NMR (400 MHz, MeOD-d4) δ: 8.77(d, J = 9.2 Hz, 1H), 7.92(d, J = 9.6 Hz, 1H), 7.87(s, 1H), 7.65(d, J = 8.0 Hz, 1H), 7.43(t, J = 8.0 Hz, 1H), 7.21(d, J = 7.2 Hz, 1H), 2.65(s, 3H), 2.27-2.14(m, 2H), 1.00(t, J = 7.2 Hz, 3H). |
| 491 | 1-(benzofuran-6-yl)-N-(3-(1,1-difluoropropyl)phenyl)-3-methyl-5-oxo-4,5-dihydro-1H-pyrazole-4-carboxamide<br>LCMS: (ESI) m/z: 412.1[M + H]+;<br>1H NMR (400 MHz, MeOD-d4) δ: 7.88-7.86 (m, 3H), 7.76 (d, J = 8.4 Hz, 1H), 7.65(d, J = 8.4 Hz, 1H), 7.54 (dd, J = 1.6, 8.4 Hz, 1H), 7.41 (t, J = 8.0 Hz, 1H), 7.19 (d, J = 7.6 Hz, 1H), 6.93(d, J = 1.6 Hz, 1H), 2.62 (s, 3H), 2.25-2.12 (m, 2H), 0.98 (t, J = 7.2 Hz, 3H). |
| 492 | 1-(benzofuran-4-yl)-N-(3-(1,1-difluoropropyl)phenyl)-3-methyl-5-oxo-4,5-dihydro-1H-pyrazole-4-carboxamide<br>LCMS: (ESI) m/z: 412.1 [M + H]+;<br>1H NMR (400 MHz, MeOD-d4) δ: 7.88-7.87 (m, 2H), 7.66-7.63 (m, 2H), 7.48 (t, J = 8.0 Hz, 1H), 7.41 (t, J = 7.2 Hz, 2H), 7.20 (d, J = 8.0 Hz, 1H), 6.96 (dd, J = 0.8, 2.0 Hz, 1H), 2.65 (s, 3H), 2.23-2.13 (m, 2H), 0.98 (t, J = 7.2 Hz, 3H). |

| Compound Number | IUPAC name, Mass Spectra and H-NMR data |
|---|---|
| 493 | N-(3-(1,1-difluoropropyl)phenyl)-1-(1-(3-hydroxybenzoyl)-1H-indol-6-yl)-3-methyl-5-oxo-4,5-dihydro-1H-pyrazole-4-carboxamide<br>LCMS: (ESI) m/z: 531.0 [M + H]+;<br>1H NMR (MeOD-d4, 400 MHz) δ: 8.80 (s, 1H), 7.87 (s, 1H), 7.73 (d, J = 7.6 Hz, 1H), 7.63-7.66 (m, 2H), 7.37-7.41 (m, 3H), 7.14-7.18 (m, 3H), 7.07 (J = 2.0, 8.4 Hz, 1H), 6.68 (d, J = 3.6 Hz, 1H), 2.51 (s, 3H), 2.11-2.27 (m, 2H), 0.98 (t, J = 7.2 Hz, 3H). |
| 494 | (Z)-1-(4-(difluoromethoxy)phenyl)-N-(3-(1-fluoroprop-1-en-1-yl)phenyl)-3-methyl-5-oxo-4,5-dihydro-1H-pyrazole-4-carboxamide<br>LCMS: (ESI) m/z: 418.1 [M + H]+;<br>1H NMR (400 MHz, MeOD-d4) δ: 7.85 (s, 1H), 7.74 (d, J = 8.8 Hz, 2H), 7.53 (d, J = 8.0 Hz, 1H), 7.31 (t, J = 8.0 Hz, 1H), 7.27 (d, J = 8.8 Hz, 2H), 7.21 (d, J = 8.0 Hz, 1H), 7.05 (t, J = 74.0 Hz, 1H), 5.58 (dq, J = 37.2, 7.2 Hz, 1H), 2.55 (s, 3H), 1.80 (dd, J = 7.2, 2.4 Hz, 3H). |
| 495 | (E)-1-(4-(difluoromethoxy)phenyl)-N-(3-(1-fluoroprop-1-en-1-yl)phenyl)-3-methyl-5-oxo-4,5-dihydro-1H-pyrazole-4-carboxamide<br>LCMS: (ESI) m/z: 418.1 [M + H]+;<br>1H NMR (400 MHz, MeOD-d4) δ: 7.86 (s, 1H), 7.73 (d, J = 8.8 Hz, 2H), 7.57 (d, J = 8.4 Hz, 1H), 7.38 (t, J = 8.0 Hz, 1H), 7.28 (d, J = 8.8 Hz, 2H), 7.19 (d, J = 7.6 Hz, 1H), 7.06 (br t, J = 74.0 Hz, 1H), 5.45 (dq, J = 22.4, 7.6 Hz, 1H), 2.57 (s, 3H), 1.82 (dd, J = 7.6, 2.4 Hz, 3H). |
| 496 | 1-[4-(difluoromethoxy)phenyl]-N-[3-(1-fluoro-2-methyl-prop-1-enyl)phenyl]-3-methyl-5-oxo-4H-pyrazole-4-carboxamide<br>LCMS: (ESI) m/z: 432.2 [M + H]+;<br>1H NMR: (400 MHz, MeOD-d4) δ: 7.76 (s, 1H), 7.70 (d, J = 8.8 Hz, 2H), 7.54 (d, J = 8.0 Hz, 1H), 7.34 (t, J = 8.0 Hz, 1H), 7.30 (d, J = 8.4 Hz, 2H), 7.12 (d, J = 7.6 Hz, 1H), 6.90 (t, J = 74.0 Hz, 1H), 2.59 (s, 3H), 1.83 (dd, J = 10.8, 3.2 Hz, 6H). |
| 497 | N-(3-(1,1-difluoropropyl)phenyl)-1-(1,3-dimethyl-1H-indol-6-yl)-3-methyl-5-oxo-4,5-dihydro-1H-pyrazole-4-carboxamide<br>LCMS: (ESI) m/z: 439.1 [M + H]+;<br>1H NMR (400 MHz, DMSO-d6) δ: 11.04 (br s, 1H), 7.91 (s, 1H), 7.75 (s, 1H), 7.63 (d, J = 9.2 Hz, 1H), 7.58 (d, J = 8.4 Hz, 1H), 7.42 (t, J = 8.0 Hz, 1H), 7.37 (d, J = 8.4 Hz, 1H), 7.13-7.17 (m, 2H), 3.75 (s, 3H), 2.53 (br s, 3H), 2.27 (d, J = 0.4 Hz, 3H), 2.17-2.24 (m, 2H), 0.92 (t, J = 7.6 Hz, 3H). |
| 498 | N-(3-(1,1-difluoropropyl)phenyl)-1-(5-methoxy-6-phenylpyridin-2-yl)-3-methyl-5-oxo-4,5-dihydro-1H-pyrazole-4-carboxamide<br>LCMS: (ESI) m/z: 479.1 [M + H]+;<br>1H NMR (400 MHz, DMSO-d6) δ: 10.80 (s, 1H), 8.27 (d, J = 9.2 Hz, 1H), 8.02-7.99 (m, 2H), 7.92 (s, 1H), 7.83 (d, J = 9.2 Hz, 1H), 7.65 (d, J = 8.0 Hz, 1H), 7.51-7.42 (m, 4H), 7.18 (d, J = 7.6 Hz, 1H), 3.90 (s, 3H), 2.59 (s, 3H), 2.27-2.17 (m, 2H), 0.93 (t, J = 7.6 Hz, 3H). |
| 499 | N-[3-(1,1-difluoropropyl)phenyl]-1-(1H-indazol-6-yl)-3-methyl-5-oxo-4H-pyrazole-4-carboxamide<br>LCMS: (ESI) m/z: 412.1 [M + H]+;<br>1H NMR (400 MHz, MeOD-d4) δ: 8.09 (d, J = 5.2 Hz, 1H), 7.94-7.84 (m, 3H), 7.65 (d, J = 7.6 Hz, 1H), 7.52 (d, J = 8.8 Hz, 1H), 7.40 (t, J = 8.0 Hz, 1H), 7.18 (d, J = 7.6 Hz, 1H), 2.58 (s, 3H), 2.23-2.13 (m, 2H), 0.98 (t, J = 7.6 Hz, 3H). |
| 500 | 1-(1H-benzo[d]imidazol-6-yl)-N-(3-(1,1-difluoropropyl)phenyl)-3-methyl-5-oxo-4,5-dihydro-1H-pyrazole-4-carboxamide<br>LCMS: (ESI) m/z: 412.1 [M + H]+;<br>1H NMR (400 MHz, MeOD-d4) δ: 8.38 (s, 1H), 8.22 (s, 1H), 8.02 (s, 1H), 7.87 (s, 1H), 7.77-7.69 (m, 2H), 7.65 (d, J = 8.4 Hz, 1H), 7.38 (t, J = 8.0 Hz, 1H), 7.14 (br d, J = 7.2 Hz, 1H), 2.50 (s, 3H), 2.23-2.14 (m, 2H), 0.98 (t, J = 7.6 Hz, 3H). |
| 501 | 1-(4-cyanophenyl)-N-(3-(1,1-difluoropropyl)phenyl)-3-methyl-5-oxo-4,5-dihydro-1H-pyrazole-4-carboxamide<br>LCMS: (ESI) m/z: 397.2 [M + H]+;<br>1H NMR (400 MHz, DMSO-d6) δ: 0.92 (t, J = 7.4 Hz, 3 H) 2.20 (m, 2 H) 2.54 (s, 3 H) 7.16 (d, J = 8.0 Hz, 1 H) 7.42 (t, J = 8.0 Hz, 1 H) 7.61 (d, J = 8.0 Hz, 1 H) 7.91 (s, 1 H) 7.94-8.00 (m, 2 H) 8.00-8.04 (m, 2 H) 10.66 (s, 1 H). |
| 502 | N-[3-(1,1-difluoropropyl)phenyl]-1-(1,2-dimethylindol-6-yl)-3-methyl-5-oxo-4H-pyrazole-4-carboxamide<br>LCMS: (ESI) m/z: 439.2 [M + H]+;<br>1H NMR: (400 MHz, DMSO-d6) δ: 11.04 (s, 1H), 7.91 (s, 1H), 7.73 (s, 1H), 7.63 (d, J = 8.0 Hz, 1H), 7.52 (d, J = 8.4 Hz, 1H), 7.42 (t, J = 7.6 Hz, 1H), 7.29 (d, J = 8.0 Hz, 1H), 7.15 (d, J = 7.6 Hz, 1H), 6.27 (s, 1H), 3.69 (s, 3H), 2.54 (s, 3H), 2.43 (s, 3H), 2.25-2.15 (m, 2H), 0.92 (t, J = 7.2 Hz, 3H). |
| 503 | N-(5-cyanopyridin-3-yl)-1-(4-(difluoromethoxy)phenyl)-3-methyl-5-oxo-4,5-dihydro-1H-pyrazole-4-carboxamide<br>LCMS: (ESI) m/z: 386.2 [M + H]+;<br>1H NMR (400 MHz, MeOD-d4) δ: 8.97 (d, J = 2.4 Hz, 1H), 8.66 (t, J = 2.0 Hz, 1H), 8.57 (d, J = 1.6 Hz, 1H), 7.70 (d, J = 8.8 Hz, 2H), 7.33 (d, J = 9.2 Hz, 2H), 6.90 (d, J = 74.0 Hz, 1H), 2.62 (s, 3H). |

| Compound Number | IUPAC name, Mass Spectra and H-NMR data |
|---|---|
| 504 | N-(2-cyanopyridin-4-yl)-1-(4-(difluoromethoxy)phenyl)-3-methyl-5-oxo-4,5-dihydro-1H-pyrazole-4-carboxamide<br>LCMS: (ESI) m/z: 386.2 [M + H]+;<br>1H NMR (400 MHz, MeOD-d4) δ: 8.50 (d, J = 5.6 Hz, 1H), 8.31 (d, J = 2.0 Hz, 1H), 7.79 (dd, J = 6.0, 2.4 Hz, 1H), 7.71 (d, J = 9.2 Hz, 2H), 7.31 (d, J = 8.8 Hz, 2H), 6.89 (t, J = 73.6 Hz, 1H), 2.59 (s, 3H). |
| 505 | N-(3-(1,1-difluoropropyl)phenyl)-1-(2-fluoro-4-methoxyphenyl)-3-methyl-5-oxo-4,5-dihydro-1H-pyrazole-4-carboxamide<br>LCMS: (ESI) m/z: 420.1 [M + H]+;<br>1H NMR (MeOD-d4, 400 MHz) δ: 7.85 (s, 1H), 7.1 (d, 1H, J = 8.0 Hz), 7.46 (t, 1H, J = 8.4 Hz), 7.40 (t, 1H, J = 8.0 Hz), 7.19 (d, 1H, J = 7.6 Hz), 6.90-6.98 (m, 2H), 3.86 (s, 3H), 2.58 (s, 3H), 2.12-2.22(m, 2H), 0.97 (t, J = 7.6 Hz, 3H). |
| 506 | 1-(4-(difluoromethoxy)phenyl)-N-(2-(1,1-difluoropropyl)pyridin-4-yl)-3-methyl-5-oxo-4,5-dihydro-1H-pyrazole-4-carboxamide<br>LCMS: (ESI) m/z: 439.2 [M + H]+;<br>1H NMR (400 MHz, MeOD-d4) δ: 8.51 (d, J = 6.0z, 1H), 8.17 (d, J = 2.0 Hz, 1H), 7.93 (dd, J = 6.0, 2.0 Hz, 1H), 7.69 (dd, J = 6.8, 2.0 Hz, 2H), 7.33 (d, J = 9.2 Hz, 2H), 6.91 (t, J = 73.6, 1H), 2.62 (s, 3H), 2.28-2.38 (m, 2H), 1.03 (t, J = 7.6 Hz, 3H). |
| 507 | N-(3-(1,1-difluoropropyl)phenyl)-3-methyl-5-oxo-1-(1H-pyrrolo[3,2-c]pyridin-6-yl)-4,5-dihydro-1H-pyrazole-4-carboxamide<br>LCMS: (ESI) m/z: 412.2 [M + H]+;<br>1H NMR (400 MHz, MeOD-d4) δ: 8.77 (s, 1H), 8.35 (s, 1H), 8.11 (s, 1H), 7.86 (s, 1H), 7.70-7.56 (m, 2H), 7.43-7.35 (m, 1H), 7.15 (d, J = 7.6 Hz, 1H), 6.84 (s, 1H), 2.48 (s, 3H), 2.21-2.15 (m 2H), 0.99 (t, J = 7.6 Hz, 3H) |
| 508 | N-(3-(1,1-difluoropropyl)phenyl)-3-methyl-1-(4-(methylsulfonyl)phenyl)-5-oxo-4,5-dihydro-1H-pyrazole-4-carboxamide<br>LCMS: (ESI) m/z: 450.2 [M + H]+;<br>1H NMR (400 MHz, DMSO-d6) δ: 0.93 (t, J = 7.2 Hz, 3 H) 2.21 (m, 2 H) 2.53 (s, 3 H) 3.24 (s, 3 H) 7.14 (d, J = 8.0 Hz, 1 H) 7.42 (t, J = 8.0 Hz, 1 H) 7.62 (d, J = 8.0 Hz, 1 H) 7.93 (s, 1 H) 8.01 (d, J = 8.2 Hz, 2 H) 8.17 (d, J = 8.2 Hz, 2 H) 10.83 (s, 1 H). |
| 509 | N-(3-(1,1-difluoropropyl)phenyl)-1-(1-(2-hydroxybenzoyl)-1H-indol-6-yl)-3-methyl-5-oxo-4,5-dihydro-1H-pyrazole-4-carboxamid<br>LCMS: (ESI) m/z: 531.3 [M + H]+;<br>1H NMR (MeOD-d4, 400 MHz) δ: 8.76 (s, 1H), 8.16 (s, 1H), 7.88 (s, 1H), 7.61-7.71 (m, 3H), 7.36-7.48 (m, 3H), 7.24 (d, J = 3.6 Hz, 1H), 7.17 (d, J = 8.0 Hz, 1H), 6.95-7.04 (m, 2H), 6.66 (d, J = 3.6 Hz, 1H), 2.57 (s, 3H), 2.09-2.27 (m, 2H), 0.98 (t, J = 7.2 Hz, 3H). |
| 510 | N-(3-(1,1-difluoropropyl)phenyl)-1-(6-methoxypyridazin-3-yl)-3-methyl-5-oxo-4,5-dihydro-1H-pyrazole-4-carboxamide<br>LCMS: (ESI) m/z: 404.2 [M + H]+;<br>1HNMR (400 MHz, MeOD-d4) δ: 8.54(d, J = 10.0 Hz, 1H), 7.85(s, 1H), 7.63(d, J = 8.4 Hz, 1H), 7.41(d, J = 8.0 Hz, 1H), 7.19(t, J = 7.6 Hz, 1H), 7.15(d, J = 10.0 Hz, 1H), 3.79 (s, 3 H), 2.63 (s, 3 H), 2.15-2.23(m, 2H), 0.98(t, J = 7.2 Hz, 3H). |
| 511 | 1-(4-(difluoromethoxy)phenyl)-N-(5-(1,1-difluoropropyl)pyridin-3-yl)-3-methyl-5-oxo-4,5-dihydro-1H-pyrazole-4-carboxamide<br>LCMS: (ESI) m/z: 439.2 [M + H]+;<br>1H NMR (400 MHz, MeOD-d4) δ: 8.91 (s, 1H), 8.39 (s, 2H), 7.70 (d, J = 2.0 Hz, 2H), 7.32 (d, J = 9.2 Hz, 2H), 6.90 (t, J = 73.6 Hz, 1H), 2.61 (s, 3H), 2.20-2.30 (m, 2H), 1.03 (t, J = 7.2 Hz, 3H). |
| 512 | N-(3-(1,1-difluoropropyl)phenyl)-1-(5-methoxypyrazin-2-yl)-3-methyl-5-oxo-4,5-dihydro-1H-pyrazole-4-carboxamide<br>LCMS: (ESI) m/z: 404.2 [M + H]+;<br>1H NMR (400 MHz, MeOD-d4) δ: 8.03 (s, 1H), 7.90 (s, 1H), 7.83 (s, 1H), 7.60 (br d, J = 8.4 Hz, 1H), 7.40 (t, J = 8.0 Hz, 1H), 7.19 (d, J = 8.0 Hz, 1H), 3.51 (s, 3H), 2.74 (s, 3H), 2.17 (m, 2H), 0.97 (t, J = 7.2 Hz, 3H). |
| 513 | 7-(3-(1,1-difluoropropyl)phenyl)-3-(4-methoxyphenyl)-6,7-dihydropyrazolo[3,4-c]azepine-4,8(2H,5H)-dione<br>LCMS: (ESI) m/z: 426.2 [M + H]+;<br>1H NMR (400 MHz, DMSO-d6) δ: 7.65-7.68 (m, 2 H), 7.62 (s, 1 H), 7.57-7.60 (m, 2 H), 7.46-7.48 (m, 1 H), 6.98-7.01 (m, 2 H), 4.10-4.12 (m, 2 H), 3.81 (s, 3 H), 3.00-3.02 (m, 2 H), 2.19-2.32 (m, 2 H), 0.95 (t, J = 7.4 Hz, 3 H). |
| 514 | 2-benzyl-6-(3-(1,1-difluoropropyl)phenyl)-3-(4-methoxyphenyl)isoindolin-1-one<br>LCMS: (ESI) m/z: 484.2 [M + H]+;<br>1H NMR (400 MHz, CDCl3-d) δ: 8.17 (s, 1H), 7.74-7.66 (m, 3H), 7.55-7.47 (m, 2H), 7.35-7.28 (m, 3H), 7.24-7.18 (m, 3H), 7.02 (d, J = 8.8 Hz, 2H), 6.91 (d, J = 8.8 Hz, 2H), 5.42 (d, J = 14.8 Hz, 1H), 5.26 (s, 1H), 3.84 (s, 3H), 3.75 (d, J = 14.8 Hz, 1H), 2.28-2.14 (m, 2H), 1.03 (t, J = 7.6 Hz, 3H). |
| 515 | 6-(3-(1,1-difluoropropyl)phenyl)-3-(4-methoxyphenyl)isoindolin-1-one<br>LCMS: (ESI) m/z: 394.2 [M + H]+;<br>1H NMR (400 MHz, CDCl3-d) δ: 8.13 (d, J = 1.6 Hz, 1H), 7.72 (m, 3H), 7.50(d, J = 7.6 Hz, 2H), 7.31(d, J = 8.0 Hz, 1H), 7.21 (d, J = 8.8 Hz, 2H), 6.91(d, J = 8.8 Hz, 2H), 6.48(s, 1H), 5.65(s, 1H), 3.82 (s, 3H), 2.21 (q, J = 8.4 Hz, 2H), 1.03(t, J = 7.2 Hz, 3H). |

| Compound Number | IUPAC name, Mass Spectra and H-NMR data |
|---|---|
| 516 | 1-(2-acetyl-4-methoxyphenyl)-N-(3-(1,1-difluoropropyl)phenyl)-3-methyl-5-oxo-4,5-dihydro-1H-pyrazole-4-carboxamide<br>LCMS: (ESI) m/z: 444.2 [M + H]+;<br>1H NMR (400 MHz, DMSO-d6) δ: 7.86 (s, 1H), 7.60-7.34 (m, 3H), 7.28-7.16 (m, 2H), 7.15-7.08 (m, 1H), 3.84 (s, 3H), 2.78 (s, 1H), 2.43 (s, 2H), 2.32 (s, 2H), 2.24-2.14 (m, 2H), 2.02 (s, 1H), 0.91 (t, J = 7.2 Hz, 3H). |
| 517 | methyl 4-(2-((3-(1,1-difluoropropyl)phenyl)amino)-1-hydroxyethyl)-5-(4-methoxyphenyl)-1H-pyrazole-3-carboxylate (517)<br>LCMS: (ESI) m/z: 446.3 [M + H]+.<br>1H NMR (400 MHz, CDCl3-d) δ: 7.35 (d, J = 8.60 Hz, 2 H), 7.15 (t, J = 7.88 Hz, 1 H), 6.97 (d, J = 8.60 Hz, 2 H), 6.77 (d, J = 7.60 Hz, 1 H), 6.63 (s, 1 H), 6.57 (d, J = 8.00 Hz, 1 H), 4.99 (s, 1 H), 4.02 (s, 3 H), 3.85 (s, 3 H), 3.34-3.50 (m, 2 H), 2.04-2.14 (m, 2 H), 0.97 (t, J = 7.44 Hz, 3 H). |
| 518 | 6-(3-(1,1-difluoropropyl)phenyl)-3-(4-methoxyphenyl)-5,6-dihydropyrazolo[3,4-e][1,3]oxazin-7(2H)-one<br>LCMS: (ESI) m/z: 400.2 [M + H]+;<br>1H NMR (400 MHz, MeOD-d4) δ: 7.69-7.88 (m, 2H), 7.55-7.59 (m, 2H), 7.46-7.51 (m, 2H), 7.01-7.03 (m, 2H), 5.75 (s, 2H), 3.84 (s, 3H), 2.16-2.26 (m, 2H), 1.01 (t, J = 7.6 Hz, 3H). |
| 519 | 6-(3-(1,1-difluoropropyl)phenyl)-3-(4-methoxyphenyl)-2H-pyrazolo[4,3-d]pyrimidin-7(6H)-one<br>LCMS: (ESI) m/z: 397.1 [M + H]+;<br>1H NMR (400 MHz, MeOD-d4) δ: 8.33-8.03 (m, 3H), 7.74-7.64 (m, 3H), 7.64-7.58 (m, 1H), 7.04 (d, J = 8.0 Hz, 2H), 3.86 (s, 3H), 2.32-2.16 (m, 2H), 1.02 (t, J = 7.2 Hz, 3H). |
| 520 | 7-(3-(1,1-difluoropropyl)phenyl)-3-(4-methoxyphenyl)-6,7-dihydro-2H-pyrazolo[3,4-f][1,4]oxazepin-8(5H)-one<br>LCMS: (ESI) m/z: 414.1 [M + H]+;<br>1H NMR (400 MHz, MeOD-d4) δ: 7.88 (d, J = 8.4 Hz, 2H), 7.56 (t, J = 8.0, 1H), 7.51 (s, 1H), 7.45-7.47 (m, 2H), 6.97 (d, J = 8.8 Hz, 2H), 4.63-4.65 (m, 2H), 4.17-4.19 (m, 2H), 3.83 (s, 3H), 2.16-2.26 (m, 2H), 1.01 (t, J = 7.6 Hz, 3H). |
| 521 | N-(3-(1,1-difluoropropyl)phenyl)-1-(4-methoxyphenyl)-3,3-dimethyl-5-oxopyrazolidine-4-carboxamide<br>LCMS: (ESI) m/z: 418.1 [M + H]+;<br>1H NMR (400 MHz, CDCl3-d) δ: 10.29 (br s, 1H), 7.74-7.67 (m, 4H), 7.40-7.34 (m, 1H), 7.22 (d, J = 7.6 Hz, 1H), 6.96-6.89 (m, 2H), 4.54 (br s, 1H), 3.82 (s, 3H), 3.49 (s, 1H), 2.18-2.09 (m, 2H), 1.70 (s, 3H), 1.31 (s, 3H), 0.98 (t, J = 7.6 Hz, 3H). |
| 522 | 6-(3-(1,1-difluoropropyl)phenyl)-4-hydroxy-3-(4-methoxyphenyl)-5,6-dihydro-2H-pyrazolo[3,4-c]pyridin-7(4H)-one<br>LCMS: (ESI) m/z: 414.1 [M + H]+;<br>1H NMR (400 MHz, MeOD-d4) δ: 7.79-7.82 (m, 2 H), 7.61 (s, 1 H), 7.54-7.60 (m, 2 H), 7.46-7.49 (m, 1 H), 7.08-7.10 (m, 2 H), 4.99 (dd, J = 2.80, 2.00 Hz, 1 H), 4.98-4.99 (m, 1 H), 4.40-4.45 (m, 1 H), 3.97-4.00 (m, 1 H), 3.88 (s, 3 H), 2.18-2.28(m, 2 H), ), 1.02 (t, J = 7.40 Hz, 3 H). |
| 523 | 6-(3-(1,1-difluoropropyl)phenyl)-3-(4-methoxyphenyl)-2H-pyrazolo[3,4-c]pyridin-7(6H)-one<br>LCMS: (ESI) m/z: 396.0 [M + H]+;<br>1H NMR (400 MHz, MeOD-d4) δ: 7.83 (d, J = 8.8 Hz, 2H), 7.64 (d, J = 2.0 Hz, 4H), 7.24 (d, J = 7.4 Hz, 1H), 7.11 (d, J = 8.8 Hz, 2H), 7.02 (d, J = 7.4 Hz, 1H), 3.89 (s, 3H), 2.34-2.18 (m, 2H), 1.05 (d, J = 7.6 Hz, 3H). |
| 524 | 1-(cinnolin-7-yl)-N-(3-(1,1-difluoropropyl)phenyl)-3-methyl-5-oxo-4,5-dihydro-1H-pyrazole-4-carboxamide<br>LCMS: (ESI) m/z: 424.1 [M + H]+;<br>1H NMR (400 MHz, DMSO-d6) δ: 11.15 (s, 1H), 9.25 (d, J = 7.6 Hz, 1H), 9.07 (s, 1H), 8.78 (d, J = 8.8 Hz, 1H), 8.14-8.04(m, 2H), 7.93(s, 1H), 7.61(d, J = 7.6 Hz, 1 H), 7.47-7.43(m, 1H), 7.37(t, J = 8.4 Hz, 1 H), 7.10-7.02(m, 1 H), 2.38 (s, 3H), 2.25-2.15 (m, 2H), 0.93 (t, J = 7.6 Hz, 3H). |
| 525 | 6-(3-(1,1-difluoropropyl)phenyl)-3-(4-methoxyphenyl)-7,7-dimethyl-6,7-dihydro-2H-pyrazolo[4,3-d]pyrimidine<br>LCMS: (ESI) m/z: 411.3 [M + H]+;<br>1H NMR (400 MHz, MeOD-d4) δ: 7.57 (d, J = 8.8 Hz, 2H), 7.49 (d, J = 8.4 Hz, 1H), 7.05 (dd, J = 1.6, 8.4 Hz, 1H), 7.02-6.98 (m, 2H), 6.96 (d, J = 8.8 Hz, 2H), 3.81 (s, 3H), 2.20-1.98 (m, 8H), 0.94 (t, J = 7.4 Hz, 3H). |
| 526 | N-(3-(1,1-difluoropropyl)phenyl)-2-(4-methoxyphenyl)-5,5-dimethyl-3-oxo-1,2-diazabicyclo[2.1.1]hexane-4-carboxamide<br>LCMS: (ESI) m/z: 430.3 [M + H]+;<br>1H NMR (400 MHz, MeOD-d4) δ: 7.74-7.70 (m, 2H), 7.57 (s, 1H), 7.51-7.45 (m, 2H), 7.28-7.27 (m, 1H), 6.96-6.91 (m, 2H), 3.97-3.90 (m, 2H), 3.79 (s, 3H), 2.24-2.11 (m, 2H), 1.50 (s, 3H), 1.30 (s, 3H), 0.97 (t, J = 7.6 Hz, 3H). |
| 527 | N-(3-(1,1-difluoropropyl)phenyl)-5-hydroxy-5-(4-methoxyphenyl)-2-methyl-4-oxo-4,5-dihydro-1H-pyrrole-3-carboxamide<br>LCMS: (ESI) m/z: 417.3 [M + H]+;<br>1H NMR (400 MHz, CDCl3-d) δ: 10.01 (s, 1H), 7.69 (s, 1H), 7.63 (d, J = 8.4 Hz, 1H), 7.38-7.33 (m, 3H), 7.16 (d, J = 8.0 Hz, 1H), 6.92-6.88 (m, 2H), 6.64 (s, 1H), 3.80 (s, 3H), 2.74 (s, 3H), 2.20-2.11 (m, 2H), 0.97 (t, J = 7.2 Hz, 3H). |

| Compound Number | IUPAC name, Mass Spectra and H-NMR data |
|---|---|
| 528 | 1-(4-methoxyphenyl)-3-methyl-6-phenyl-6,7-dihydro-1H-pyrrolo[3,4-c]pyridazin-5(4H)-one<br>LCMS: (ESI) m/z: 334.1 [M + H]+;<br>1H NMR (400 MHz, CDCl3-d) δ: 7.59 (d, J = 8.0 Hz, 2H), 7.32-7.25 (m, 4H), 7.03 (t, J = 7.2 Hz, 1H), 6.97-6.95 (m, 2H), 4.24 (s, 2H), 3.84 (s, 3H), 3.20 (s, 2H), 2.04 (s, 3H). |
| 529 | 3-acetyl-N-(3-(1,1-difluoropropyl)phenyl)-1-(4-methoxyphenyl)-5-oxo-4,5-dihydro-1H-pyrazole-4-carboxamide<br>LCMS: (ESI) m/z: 430.1 [M + H]+;<br>1H NMR (400 MHz, MeOD-d4) δ: 7.92 (s, 1H), 7.85-7.71 (m, 3H), 7.50-7.41 (m, 1H), 7.29-7.23 (m, 1H), 7.07 (d, J = 8.8 Hz, 2H), 3.86 (s, 3H), 2.73 (s, 3H), 2.26-2.11 (m, 2H), 1.00 (t, J = 7.6 Hz, 3H). |
| 530 | N-(3-(1,1-difluoropropyl)phenyl)-1-(4-methoxy-3-(2-methylpyridin-4-yl)phenyl)-3-methyl-5-oxo-4,5-dihydro-1H-pyrazole-4-carboxamide<br>LCMS: (ESI) m/z: 493.3 [M + H]+;<br>1H NMR (400 MHz, MeOD-d4) δ: 8.53 (d, J = 6.0 Hz, 1H), 7.81-7.90 (m, 5H), 7.65 (d, J = 9.2 Hz, 1H), 7.38 (t, J = 8.0 Hz, 1H), 7.28 (d, J = 8.8 Hz, 1H), 7.15 (d, J = 8.0 Hz, 1H), 3.92 (s, 3H), 2.71 (s, 3H), 2.50 (s, 3H), 2.13-2.23 (m, 2H), 0.98 (t, J = 7.6 Hz, 3H). |
| 531 | N-(3-(1,1-difluoropropyl)phenyl)-1-(3-(2,6-dimethylpyridin-4-yl)-4-methoxyphenyl)-3-methyl-5-oxo-4,5-dihydro-1H-pyrazole-4-carboxamide<br>LCMS: (ESI) m/z: 507.3 [M + H]+;<br>1H NMR (400 MHz, MeOD-d4) δ: 7.83-7.91 (m, 5H), 7.66 (d, J = 8.0 Hz, 1H), 7.37 (t, J = 8.0 Hz, 1H), 7.26 (d, J = 8.8 Hz, 1H), 7.13 (d, J = 7.6 Hz, 1H), 3.92 (s, 3H), 2.71 (s, 6H), 2.46 (s, 3H), 2.11-2.25 (m, 2H), 0.98 (t, J = 7.6 Hz, 3H). |
| 532 | N-(3-(1,1-difluoropropyl)phenyl)-1-(4-methoxy-3-(3-methylpyridin-4-yl)phenyl)-3-methyl-5-oxo-4,5-dihydro-1H-pyrazole-4-carboxamide<br>LCMS: (ESI) m/z: 493.3 [M + H]+;<br>1H NMR (400 MHz, MeOD-d4) δ: 8.50 (s, 1H), 8.46 (d, J = 4.8 Hz, 1H), 7.85 (s, 1H), 7.76 (dd, J = 8.8, 2.8 Hz, 1H), 7.63 (d, J = 8.4 Hz, 1H), 7.53 (d, J = 2.8 Hz, 1H), 7.44 (d, J = 5.2 Hz, 1H), 7.39 (t, J = 8.0 Hz, 1H), 7.26 (d, J = 8.8 Hz, 1H), 7.16 (d, J = 7.6 Hz, 1H), 3.84 (s, 3H), 2.53 (s, 3H), 2.24 (s, 3H), 2.13-2.21 (m, 2H), 0.97 (t, J = 7.6 Hz, 3H). |
| 534 | N-(3-(1,1-difluoropropyl)phenyl)-1-(4-methoxy-3-(5-methylpyridin-2-yl)phenyl)-3-methyl-5-oxo-4,5-dihydro-1H-pyrazole-4-carboxamide<br>LCMS: (ESI) m/z: 493.2 [M + H]+;<br>1H NMR (400 MHz, CDCl3-d) δ: 10.58 (s, 1H), 8.49 (s, 1H), 7.78-7.66 (m, 3H), 7.63-7.53 (m, 2H), 7.40-7.30 (m, 2H), 7.14 (d, J = 7.6 Hz, 1H), 6.71 (d, J = 8.8 Hz, 1H), 3.62 (s, 3H), 2.61 (s, 3H), 2.43 (s, 3H), 2.10-2.20 (m, 2H), 0.99 (t, J = 7.4 Hz, 3H). |
| 535 | N-(3-(1,1-difluoropropyl)phenyl)-1-(4-methoxy-3-(3-methylpyridin-2-yl)phenyl)-3-methyl-5-oxo-4,5-dihydro-1H-pyrazole-4-carboxamide<br>LCMS: (ESI) m/z: 493.2 [M + H]+;<br>1H NMR (400 MHz, MeOD-d4) δ: 8.75-8.65 (m, 1H), 8.48 (d, J = 8.0 Hz, 1H), 7.93 (dd, J = 5.6, 8.0 Hz, 1H), 7.87-7.81 (m, 2H), 7.78 (d, J = 2.6 Hz, 1H), 7.63 (d, J = 8.2 Hz, 1H), 7.47-7.38 (m, 2H), 7.20 (d, J = 7.8 Hz, 1H), 3.92 (s, 3H), 2.62 (s, 3H), 2.42 (s, 3H), 2.24-2.09 (m, 2H), 0.97 (t, J = 7.4 Hz, 3H). |
| 536 | N-(3-(1,1-difluoropropyl)phenyl)-1-(4-methoxy-3-(6-methylpyridin-2-yl)phenyl)-3-methyl-5-oxo-4,5-dihydro-1H-pyrazole-4-carboxamide<br>LCMS: (ESI) m/z: 493.4 [M + H]+;<br>1H NMR (400 MHz, MeOD-d4) δ: 8.07 (t, J = 7.6 Hz, 1H), 7.93 (d, J = 2.4 Hz, 1H), 7.82-7.85 (m, 3H), 7.64 (d, J = 7.6 Hz, 1H), 7.50 (d, J = 8.0 Hz, 1H), 7.38 (t, J = 8.0 Hz, 1H), 7.30 (d, J = 8.8 Hz, 1H), 7.15 (d, J = 7.6 Hz, 1H), 3.92 (s, 3H), 2.70 (s, 3H), 2.51 (s, 3H), 2.13-2.23 (m, 2H), 0.98 (t, J = 7.6 Hz, 3H). |
| 537 | N-(3-(1,1-difluoropropyl)phenyl)-1-(4-methoxy-3-(4-methylpyridin-2-yl)phenyl)-3-methyl-5-oxo-4,5-dihydro-1H-pyrazole-4-carboxamide<br>LCMS: (ESI) m/z: 493.3 [M + H]+;<br>1H NMR (400 MHz, MeOD-d4) δ: 8.54 (d, J = 5.2 Hz, 1H), 7.97 (d, J = 2.4 Hz, 1H), 7.94 (s, 1H), 7.85-7.87 (m, 2H), 7.64 (d, J = 8.4 Hz, 1H), 7.52 (d, J = 4.8 Hz, 1H), 7.38 (t, J = 7.6 Hz, 1H), 7.30 (d, J = 8.8 Hz, 1H), 7.15 (d, J = 7.6 Hz, 1H), 3.94 (s, 3H), 2.59 (s, 3H), 2.50 (s, 3H), 2.13-2.23 (m, 2H), 0.98 (t, J = 7.6 Hz, 3H). |

Example 2

Biological Activity of Compounds of the Invention

ACSS2 Cell-Free Activity Assay (Cell-Free $IC_{50}$)

The assay is based on a coupling reaction with Pyrophosphatase: ACSS2 is converting ATP+CoA+Acetate=>AMP+pyrophosphate+Acetyl-CoA (Ac-CoA). Pyrophosphatase converts pyrophosphate, a product of the ACSS2 reaction, to phosphate which can be detected by measuring the absorbance at 620 nm after incubation with the Biomol green reagent (Enzo life Science, BML-AK111).

Cell-Free $IC_{50}$ Determination:

10 nM of human ACSS2 protein (OriGene Technologies, Inc) was incubated for 90 minutes at 37 C with various compounds' concentrations in a reaction containing 50 mM Hepes pH 7.5, 10 mM DTT, 90 mM KCl, 0.006% Tween-20, 0.1 mg/ml BSA, 2 mM $MgCl_2$, 10 M CoA, 5 mM NaAc, 300 μM ATP and 0.5 U/ml Pyrophosphatase (Sigma). At the end of the reaction, Biomol Green was added for 30 minutes at RT and the activity was measured by reading the absorbance at 620 nm. IC$_{50}$ values were calculated using non-linear regression curve fit with 0% and 100% constrains (CDD Vault, Collaborative Drug Discovery, Inc.).

Results:

The results are presented in Table 2 below:

TABLE 2

ACSS2 cell-free activity assay results (Cell-free IC$_{50}$).

| ACSS2 PPase IC$_{50}$ assay: IC$_{50}$ (uM) | From 1E−5 μM to 6E−3 μM | From 6E−3 μM to 0.1 μM | From 0.1 μM to 1 μM | From 1 μM to 100 uM | Above 100 uM |
|---|---|---|---|---|---|
| Compounds number | 226 | 159 | 233 | 111 | 186 |
| | 261 | 168 | 123 | 118 | 187 |
| | 271 | 237 | 146 | 131 | 190 |
| | 242 | 142 | 125 | 122 | 192 |
| | 228 | 259 | 173 | 105 | 193 |
| | 265 | 244 | 132 | 116 | 194 |
| | 269 | 255 | 100 | 126 | 195 |
| | 250 | 263 | 135 | 121 | 196 |
| | 247 | 149 | 174 | 112 | 199 |
| | 246 | 231 | 153 | 104 | 200 |
| | 141 | 251 | 144 | 128 | 202 |
| | 230 | 257 | 155 | 129 | 204 |
| | 236 | 107 | 154 | 130 | 213 |
| | 266 | 169 | 254 | 134 | 214 |
| | 253 | 138 | 147 | 136 | 217 |
| | 229 | 240 | 110 | 137 | 221 |
| | 264 | 124 | 270 | 152 | 106 |
| | 164 | 170 | 103 | 156 | |
| | 275 | 274 | 260 | 157 | |
| | 165 | 235 | 133 | 176 | |
| | 252 | 184 | 139 | 239 | |
| | 166 | 171 | 120 | 268 | |
| | 108 | 277 | 115 | 182 | |
| | 227 | 245 | 209 | 185 | |
| | 258 | 158 | 102 | 188 | |
| | 241 | 272 | 283 | 189 | |
| | 249 | 143 | 284 | 191 | |
| | 220 | 215 | 285 | 197 | |
| | 117 | 114 | 288 | 198 | |
| | 243 | 238 | 290 | 201 | |
| | 248 | 162 | 302 | 203 | |
| | 145 | 127 | 329 | 205 | |
| | 119 | 232 | 339 | 207 | |
| | 234 | 113 | 340 | 212 | |
| | 167 | 256 | 341 | 216 | |
| | 276 | 150 | 345 | 218 | |
| | 109 | 267 | 346 | 222 | |
| | 206 | 172 | 347 | 223 | |
| | 280 | 273 | 349 | 224 | |
| | 281 | 262 | 350 | 278 | |
| | 282 | 148 | 358 | | |
| | 286 | 101 | 373 | | |
| | 287 | 160 | 391 | | |
| | 289 | 103 | 392 | | |
| | 291 | 161 | 393 | | |
| | 292 | 183 | 394 | | |
| | 297 | 208 | 395 | | |
| | 298 | 210 | 397 | | |
| | 300 | 211 | 408 | | |
| | 301 | 215 | 409 | | |
| | 303 | 140 | 470 | | |
| | 304 | 279 | 471 | | |
| | 305 | 293 | 503 | | |
| | 306 | 294 | 504 | | |
| | 307 | 295 | 512 | | |
| | 308 | 296 | 529 | | |
| | 309 | 299 | | | |
| | 310 | 333 | | | |
| | 311 | 335 | | | |
| | 312 | 337 | | | |
| | 313 | 348 | | | |
| | 314 | 354 | | | |
| | 315 | 356 | | | |
| | 316 | 362 | | | |
| | 317 | 365 | | | |
| | 318 | 376 | | | |
| | 319 | 384 | | | |
| | 320 | 385 | | | |
| | 321 | 396 | | | |
| | 322 | 397 | | | |
| | 323 | 400 | | | |
| | 324 | 401 | | | |
| | 325 | 402 | | | |
| | 326 | 403 | | | |
| | 327 | 405 | | | |
| | 328 | 461 | | | |
| | 330 | 465 | | | |
| | 331 | 466 | | | |
| | 332 | 467 | | | |
| | 334 | 473 | | | |
| | 336 | 477 | | | |
| | 342 | 480 | | | |
| | 343 | 483 | | | |
| | 344 | 484 | | | |
| | 351 | 487 | | | |
| | 352 | 490 | | | |
| | 353 | 496 | | | |
| | 355 | 506 | | | |
| | 357 | 516 | | | |
| | 359 | 524 | | | |
| | 360 | | | | |
| | 361 | | | | |
| | 363 | | | | |
| | 364 | | | | |
| | 366 | | | | |
| | 367 | | | | |
| | 368 | | | | |
| | 369 | | | | |
| | 370 | | | | |
| | 371 | | | | |
| | 372 | | | | |
| | 374 | | | | |
| | 375 | | | | |
| | 377 | | | | |
| | 378 | | | | |
| | 379 | | | | |
| | 380 | | | | |
| | 381 | | | | |
| | 382 | | | | |
| | 383 | | | | |
| | 386 | | | | |
| | 387 | | | | |
| | 388 | | | | |
| | 389 | | | | |
| | 390 | | | | |
| | 399 | | | | |
| | 404 | | | | |
| | 406 | | | | |
| | 407 | | | | |
| | 410 | | | | |
| | 462 | | | | |
| | 463 | | | | |
| | 464 | | | | |
| | 468 | | | | |
| | 472 | | | | |
| | 474 | | | | |
| | 475 | | | | |
| | 476 | | | | |
| | 478 | | | | |
| | 479 | | | | |
| | 481 | | | | |
| | 482 | | | | |
| | 485 | | | | |

TABLE 2-continued

ACSS2 cell-free activity assay results (Cell-free $IC_{50}$).

| ACSS2 PPase $IC_{50}$ assay: $IC_{50}$ (uM) | From 1E−5 µM to 6E−3 µM | From 6E−3 µM to 0.1 µM | From 0.1 µM to 1 µM | From 1 µM to 100 uM | Above 100 uM |
|---|---|---|---|---|---|
| | 486 | | | | |
| | 488 | | | | |
| | 489 | | | | |
| | 491 | | | | |
| | 492 | | | | |
| | 493 | | | | |
| | 494 | | | | |
| | 495 | | | | |
| | 497 | | | | |
| | 498 | | | | |
| | 499 | | | | |
| | 500 | | | | |
| | 501 | | | | |
| | 502 | | | | |
| | 505 | | | | |
| | 507 | | | | |
| | 508 | | | | |
| | 509 | | | | |
| | 510 | | | | |
| | 511 | | | | |
| | 530 | | | | |
| | 531 | | | | |
| | 532 | | | | |
| | 534 | | | | |
| | 535 | | | | |
| | 536 | | | | |
| | 537 | | | | |

ACSS2 cellular activity assay (Cellular IC50)

The cellular activity of ACSS2 was based on tracing the incorporation of carbons from $^{13}$C-Acetate into fatty-acids.

Cell Treatment:

BT474/MDA-MB-468 cells growing in DMEM+25 mM D-glucose+1 mM sodium pyruvate+10% FBS+2 mM glutamine were plated in 12-well plates at $0.4 \times 10^6$ cells/well. The cells were then incubated at $CO_2$ incubator for 24 hrs at hypoxic conditions (1% $O_2$) before treated with compounds. At day 2, the medium was replaced to DMEM medium containing 15 mM Glucose, 1 mM Pyruvate, 0.65 mM Glutamine, 1% Dialyzed serum, 3.5 ug/ml Biotin, 0.2 mM $^{13}$C-Acetate and various concentrations of the compounds. The cells were incubated for 5 hours at $CO_2$ incubator in hypoxic conditions (1% $O_2$). At the end of the 5 hours' incubation, the cells were washed twice with cold PBS, harvested in 1 ml PBS and transfer into V-shaped HPLC glass vials and centrifuge for 10 min at 600 g at 4 C. The supernatant was removed, and the cells' pellets were stored at −80° C. until taken for saponification.

Saponification Assay

The cells pellets were resuspended with 0.5 ml of the 90% Methanol, 10% $H_2O$, 0.3M NaOH mixture and incubated at 80° C. for 60 min. Following the incubation, 50 µl formic acid and 0.4 ml hexane were added and the mixture was vortexed for 2 minutes. The vials were left few minutes for phases separation and then 200 µl of the top hexane phase extracted to a new glass vial. The hexane was dried under nitrogen and reconstituted in 100 µl of Methanol:Acetonitrile 5:3 mixture. The solution transferred to Eppendorf tubes, spun down at 17000 G for 20 min and transferred to LC-MS vials.

LCMS Method

The analysis was performed with Thermo Q Exactive mass spectrometer with HESI probe and Dionex Ultimate 3000 UHPLC system. The separations were performed on Phenomenex Kintex 2.6u XB-C18 100A 150×2.10 mm column by injecting 5 ul of each sample. The chromatography started with a linear gradient from 85% to 100% of organic solvent (Methanol:Acetonitrile 1:1) versus 10 mM Ammonium Acetate buffer pH 4.7 for 3.5 minutes, followed by 4.5 minutes of isocratic 100% organic solvent and then 3 minutes of isocratic initial conditions, at a flow rate of 0.3 ul/min. The MS source conditions that were used: capillary temperature 325° C., sheath flow 25, aux flow 15, spray voltage 3.8 kV, aux temperature 300° C. The data collected from Negative ion mode at resolution of 70000 at Full-MS mode in 75-1000 m/z range.

LCMS Results Analysis

The analysis of $^{13}$C acetate incorporation into fatty acids (palmitate, myristate and stearate) performed on TraceFinder 3.2.512.0. The negative control areas and $^{13}$C isotopic theoretical natural abundance were subtracted from the samples areas. Total $^{13}$C incorporation for each fatty-acid (palmitate, myristate and stearate) was calculated and presented as percentage of the total amount. Cellular $EC_{50}$ values were calculated using a non-linear regression curve fit with 0% and 100% constrains (CDD Vault, Collaborative Drug Discovery, Inc.)

Results:

The results are presented in Tables 3 and 4 below:

TABLE 3

$^{13}$C acetate incorporation into fatty acids (BT474 cells).
$IC_{50}$ (nM) BT474

| | Myristate | Palmitate | Stearate |
|---|---|---|---|
| <100 nM | 141, 108 | 141, 108, 117 | 141, 117, 108 |
| 100 nM < $IC_{50}$ < 1000 nM | 117, 138, 140, 142, | 138, 140, 142, 119, 109, 220, 206, 124 | 138, 140, 142, 119, 109, 220, 206, 124, 107, 114, 208, 215, 184 |
| >1000 nM | | 107, 114, 208, 215, 184, 183 | 183 |

TABLE 4

$^{13}$C acetate incorporation into fatty acids (BT474 cells).
$IC_{50}$ (nM) MDA-MB-468

| | Myristate | Palmitate | Stearate |
|---|---|---|---|
| <100 nM | 141, 108, 165, 119, 117, 138, 145, 164, 109, 167 | 141, 108, 165, 119, 117, 138, 145, 164, 109, 220, 167, 166 | 141, 108, 165, 119, 117, 138, 145, 164, 109, 220, 167, 166, 140 |

TABLE 4-continued $^{13}$C acetate incorporation into fatty acids (BT474 cells).
IC$_{50}$ (nM) MDA-MB-468

| | Myristate | Palmitate | Stearate |
|---|---|---|---|
| 100 nM < IC$_{50}$ < 1000 nM | 220, 166, 140, 107, 142, 124, 168, 208 | 140, 107, 142, 124, 168, 208 | 107, 142, 124, 168, 208 |
| >1000 nM | 159, 169 | 159, 169 | 159, 169 |

Fatty-Acid Assay

Testing the inhibitory effect of compounds on the cellular activity of ACSS2 was done by tracing the incorporation of $^{13}$C from $^{13}$C-acetate into fatty-acids in MDA-MB-468 cells under hypoxic conditions of 1% O2. The assay was done for 5 hours in DMEM with 5.5 mM glucose, 1 mM sodium Pyruvate, 0.65 mM Glutamine, 3.5 ug/ml Biotin, 1% dialyzed serum, 0.5 mM 13C-acetate and with different concentrations of the inhibitors. At the end of the incubation, the cells were washed with cold PBS, harvested into glass tubes and undergo saponification. The level of $^{13}$C incorporation into Palmitate was done by LC-MS analysis and the level of inhibition was calculated with PRISM software.

TABLE 5

Fatty-acid assay: Incorporation of $^{13}$C-Acetate for compounds of the invention.

| Compound | FA IC50 MDA468 (nM) |
|---|---|
| 107 | +++ |
| 108 | +++ |
| 109 | ++ |
| 117 | +++ |
| 119 | +++ |
| 124 | + |
| 138 | +++ |
| 140 | + |
| 141 | +++ |
| 142 | + |
| 145 | + |
| 149 | + |
| 159 | + |
| 164 | + |
| 165 | +++ |
| 166 | + |
| 167 | + |
| 168 | +++ |
| 169 | + |
| 206 | ++ |
| 208 | + |
| 220 | + |
| 226 | ++ |
| 227 | ++ |
| 228 | +++ |
| 229 | + |
| 230 | +++ |
| 231 | + |
| 234 | + |
| 235 | + |
| 236 | +++ |
| 237 | + |
| 241 | ++ |
| 242 | +++ |
| 243 | + |
| 244 | + |
| 246 | +++ |
| 247 | +++ |
| 248 | + |
| 249 | +++ |
| 250 | +++ |
| 251 | ++ |
| 252 | ++ |

TABLE 5-continued

Fatty-acid assay: Incorporation of $^{13}$C-Acetate for compounds of the invention.

| Compound | FA IC50 MDA468 (nM) |
|---|---|
| 253 | +++ |
| 255 | + |
| 257 | + |
| 258 | + |
| 259 | + |
| 261 | +++ |
| 263 | +++ |
| 264 | +++ |
| 265 | +++ |
| 266 | +++ |
| 269 | +++ |
| 271 | +++ |
| 279 | + |
| 280 | +++ |
| 282 | +++ |
| 286 | +++ |
| 287 | +++ |
| 289 | +++ |
| 291 | +++ |
| 292 | +++ |
| 297 | + |
| 298 | +++ |
| 300 | +++ |
| 301 | +++ |
| 303 | +++ |
| 304 | +++ |
| 305 | + |
| 306 | +++ |
| 307 | + |
| 308 | +++ |
| 309 | +++ |
| 310 | +++ |
| 311 | +++ |
| 312 | ++ |
| 313 | +++ |
| 314 | +++ |
| 315 | +++ |
| 316 | +++ |
| 317 | +++ |
| 318 | +++ |
| 319 | +++ |
| 320 | +++ |
| 321 | +++ |
| 322 | +++ |
| 323 | +++ |
| 324 | +++ |
| 325 | +++ |
| 326 | +++ |
| 327 | +++ |
| 328 | +++ |
| 330 | +++ |
| 331 | +++ |
| 332 | +++ |

+++ 0.5 nM to 50 nM
++ 50 nM to 100 nm
+ >100 nM

Example 3

Pharmacokinetic Profile of Compound 265 in Mice

Figure 4:
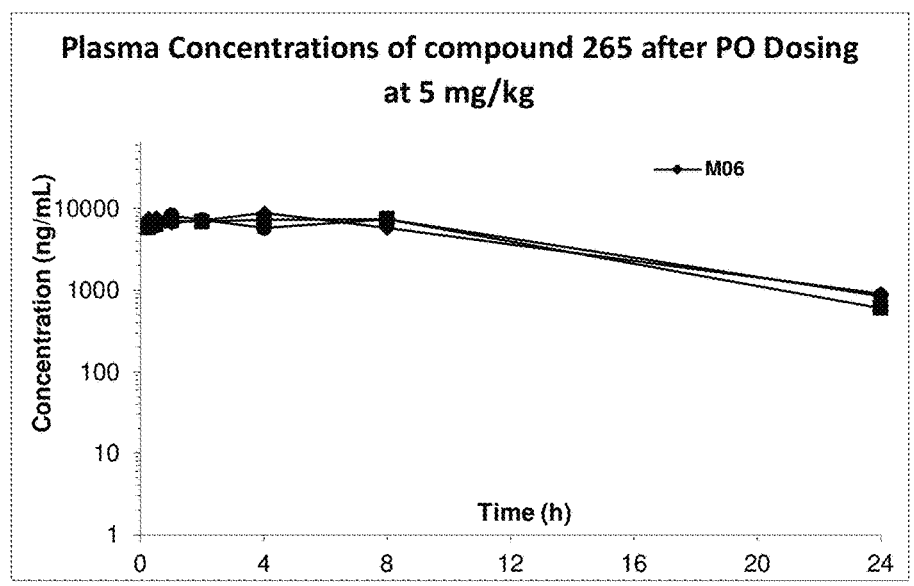
FIG. 4 depicts the oral pharmacokinetic profile of compound 265 in mice after administration of a single 5 mg/kg dose.

Compound 265 was dosed by the oral (5 mg/kg) and iv (1 mg/kg) routes in mice and compound levels in plasma were determined by LC/MS, at various timepoints within 24 hours. The oral pharmacokinetic profile of compound 265 after oral administration of a single 5 mg/kg dose is shown in FIG. 4. It demonstrates good bioavailability (74%), t1/2 of 6.51 hr (po) and low clearance (0.59 ml/min/kg).

Example 4

Thermal Stabilization of Recombinant ACSS2 Protein by ACSS2 Inhibitors

Thermal stabilization of recombinant ACSS2 protein by ACSS2 inhibitors. Interaction between the compound and recombinant ACSS2 protein was done by non-labeled Nano-DSF technic using the parameters described below. NanoDSF is a modified differential scanning fluorimetry method to determine protein stability that uses tryptophan or tyrosine fluorescence to monitor protein unfolding. The binding of compound to the protein leads to thermal stabilization that is quantified as the delta in the thermal melting points.

Figure 5:
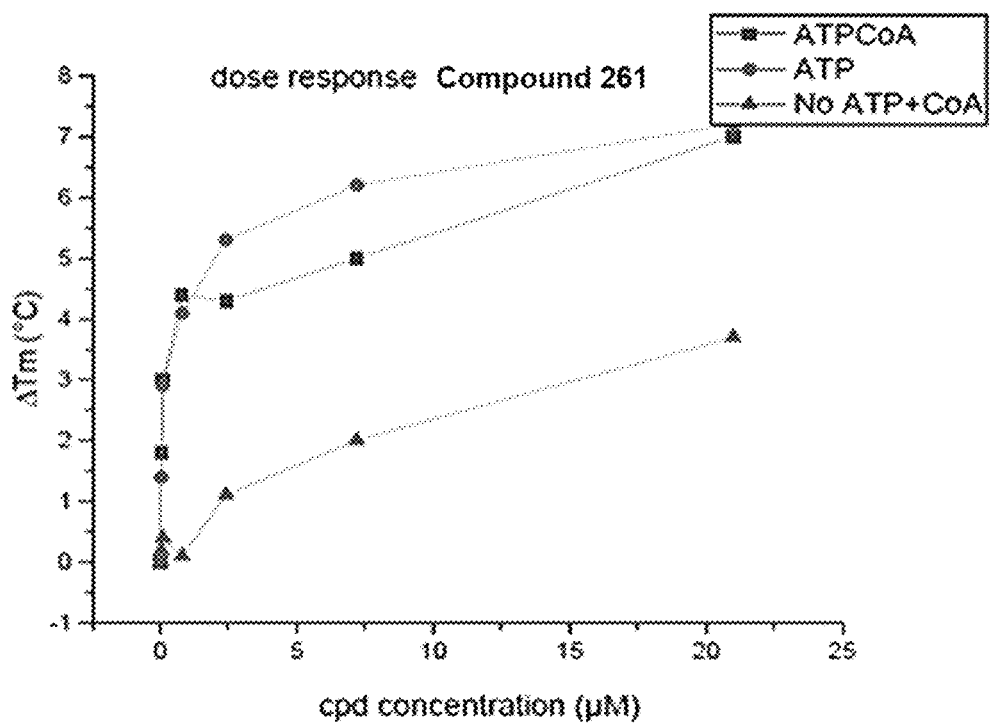
FIG. 5 depicts the thermal stabilization of recombinant ACSS2 protein by compound 261 in Nano-DSF assay in the presence of different substrates (ATP and CoA) combinations.

Assay conditions were as follows:
ACSS2 protein: 0.03 mg/ml
instrument Prometheus NT.48
capillary type: nanoDSF High Sensitivity Capillaries
Compound: 261 at different concentrations
Assay Buffer:
  a) Buffer A: 50 mM HEPES pH 7.5, 150 mM NaCl, 5 mM MgCl2, 0.005% Tween
  b) Buffer B: Buffer A+0.3 mM ATP
  c) Buffer C: Buffer A+0.3 mM ATP+0.01 mM CoA
Results:
The results are presented in FIG. 5.

The Nano-DSF assay shows that Compound 261 induced dose-dependent thermal shift in the melting temperature of ACSS2 as expected from a direct binder. The shift was higher in the presence of ATP or ATP and CoA implying that the binding of the compound to ACSS2 was facilitated by the presence of ATP. These results demonstrate an ATP cooperative mode of binding of Compound 261 to ACSS2.

Example 5

Binding of ACSS2 Inhibitor to Recombinant ACSS2 Protein by Label Free MST

Binding of ACSS2 inhibitor to recombinant ACSS2 protein by Label Free MST. MicroScale Thermophoresis (MST) is an optical fluorescent method that records the changes in fluorescence of a target molecule as a function of temperature and the concentration of the cognate ligand molecule. The binding of small-molecules to the target proteins lead to changes in the fluorescence that can be measured and translated into binding Kd.

Assay conditions were as follows:
Protein: 200 nM ACSS2
Instrument: Monolith NT.LF
capillary type Monolith NT.LF standard capillaries
compound 261 100 µM-3 nM
Assay Buffers:
Buffer A: 50 mM Hepes pH 7.5, 150 mM NaCl, 5 mM MgCl2, 0.005% Tween20
Buffer B: 50 mM Hepes pH 7.5, 150 mM NaCl, 5 mM MgCl2, 0.005% Tween-20, 0.3 mM ATP
Buffer C: 50 mM Hepes pH 7.5, 150 mM NaCl, 5 mM MgCl2, 0.005% Tween-20, 0.3 mM ATP, 0.01 mM CoA
Buffer D: 50 mM Hepes pH 7.5, 150 mM NaCl, 5 mM MgCl2, 0.005% Tween-20, 0.01 mM CoA
Results:
The results are presented in Table 6 below.

TABLE 6

The effects of ATP and CoA on the binding affinity of Compound 261 to ACSS2.

| Compound | Buffer | Kd [uM] Fluorescence |
|---|---|---|
| 261 | A | 0.46 ± 0.21 |
|  | B (+ATP) | 0.03 ± 0.01 |
|  | C (+ATP, +CoA) | 0.04 ± 0.02 |
|  | D (+CoA) | 0.61 ± 0.17 |

The binding Kds of Compound 261 to ACSS2 showed 10 fold reduction when ATP was added to the buffer, from 0.46 and 0.61 nM without ATP to 0.03 and 0.04 nM with ATP. These results demonstrate that the binding mode of the compound to ACSS2 protein is cooperative with ATP.

Example 6

Figure 6:
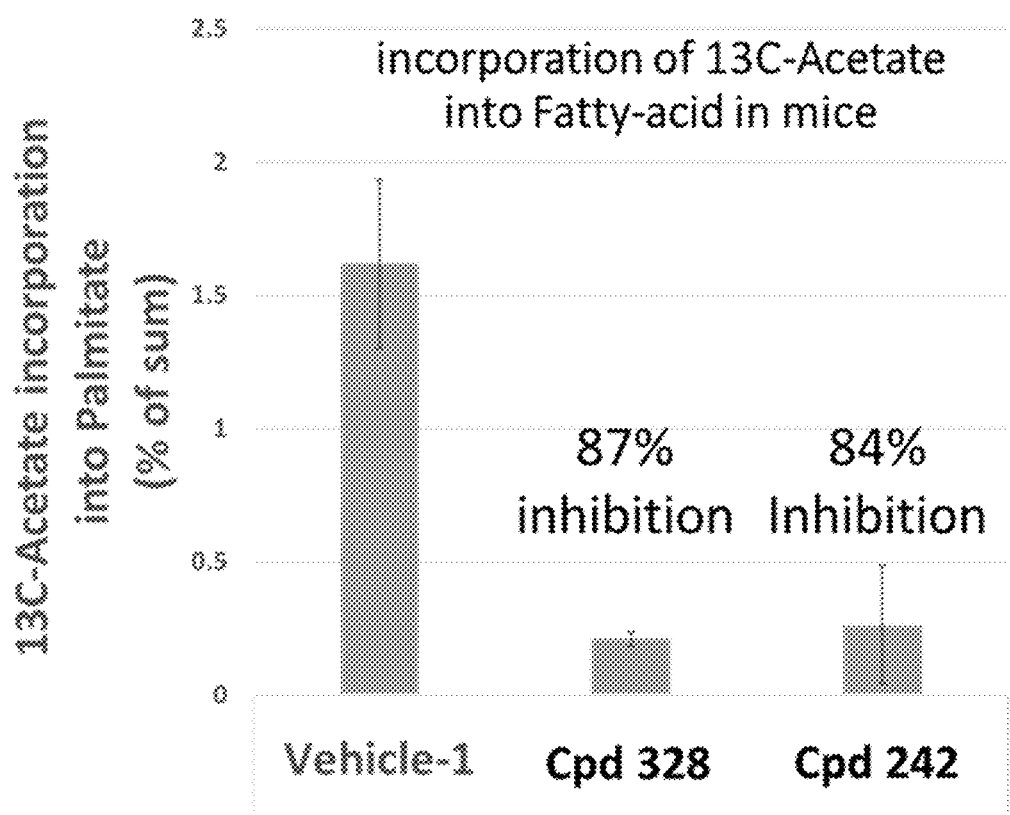
FIG. 6 depicts a PK/PD study. Inhibition of 13C-acetate incorporation into fatty-acid (palmitate) in-vivo by compounds 242 and 328.

PK-PD Study to Test the Inhibition of $^{13}$C-Acetyl-CoA Incorporation into Fatty-Acid Overnight fasted Female C57BL/6J mice (3n/group) were dosed at time=0 h with the indicated compound at 50 mg/kg IP (vehicle: 20% Solutol, 80% 0.2M Phosphate buffer pH 7.0). At time 1 h, 13C-ETOH (2.25 gr/kg 13C-ETOH dissolved in saline to a total volume of 10 ml/kg) were administrated by PO. At time 3 h plasma samples were taken for Fatty-acid analysis by Mass-spectrometry. The incorporation of $^{13}$C into palmitate was done by Mass-spectrometry after saponification of the samples and the percent incorporation of $^{13}$C was calculated.
Results:
The results are shown at FIG. 6. The results demonstrate the inhibition of ACSS2 by the two compounds in-vivo. $^{13}$C-ETOH is converted in the body to $^{13}$C-Acetate, the substrate of ACSS2 to form Ac-CoA which is the building block for de-novo fatty-acid synthesis. Compounds 328 and 242, both given at 50 mg/kg iv, inhibit $^{13}$C-Acetate incorporation into fatty-acids (palmitate) at 87% and 84% respectively.

Example 7

Acyl-CoA Synthetases Selectivity Panel

The biochemical assays for testing the selectivity of the compounds according to this invention, were done using human recombinant proteins (Cusabio, China). The readout of the assays was AMP levels, the substrate of the reactions, by HPLC method. The acyl substrates (Sigma-Aldrich) of the assays were as followed: ACSS1/ACSS2—Acetate, AACS—Acetoacetyl, ACSF2—Octanoate and ACSL5—Palmitate. The protein in this panel include ACSS1, the closest homolog of ACSS2, in addition to representative short/medium/long chain acyl-CoA syntatases.

Results:

The results are summarized in Table 7 below.

TABLE 7

Selectivity of compounds according to the invention against several Acyl-CoA synthetases in biochemical assays.

| COMPOUND | HPLC BASED ACTIVITY ASSAYS IC50 (UM) | | | | |
|---|---|---|---|---|---|
| (SC5090) | ACSS2 | ACSS1 | AACS | ACSF2 | ACSL5 |
| 261 | <0.001 | 1-10 | 24 | 46 | >100 |
| 108 | <0.001 | 10-100 | 84 | 36 | 76 |
| 269 | <0.001 | 10-100 | 19 | 28 | 45 |
| 265 | <0.001 | 1-10 | 171 | 152 | >100 |
| 266 | <0.001 | 10-100 | 64 | 51 | 35 |
| 141 | 0.001-0.01 | 10-100 | 149 | 160 | >100 |
| 264 | 0.001-0.01 | 1-10 | 52 | 43 | 115 |

The results demonstrate that the compounds are highly selective to ACSS2 with 1000-100000 fold selectivity to ACSS2 compared to its closest homolog ACSS1.

Example 8

In-Vivo Efficacy Study of Compound 265 and 298 in MDA-MB-468 Breast Cancer Cells Xenograft An in-vivo efficacy study was carried out by Charles-River Laboratories at the Freiburg, Germany site.

Tumor fragments from Breast cancer cell line MDA-MB-468 passaged as subcutaneous xenograft were subcutaneously implanted into female NMRI nude mice (Crl:NMRI-Foxn1nu). The animals were randomized into groups (n=10) when tumors volume reached 50 to 250 mm3. Vehicle control or compound 265 or compound 298 at 100 mg/kg were dosed orally once daily. Body weights and tumor volume [mm3] by caliper were measured twice weekly.

Figure 7:
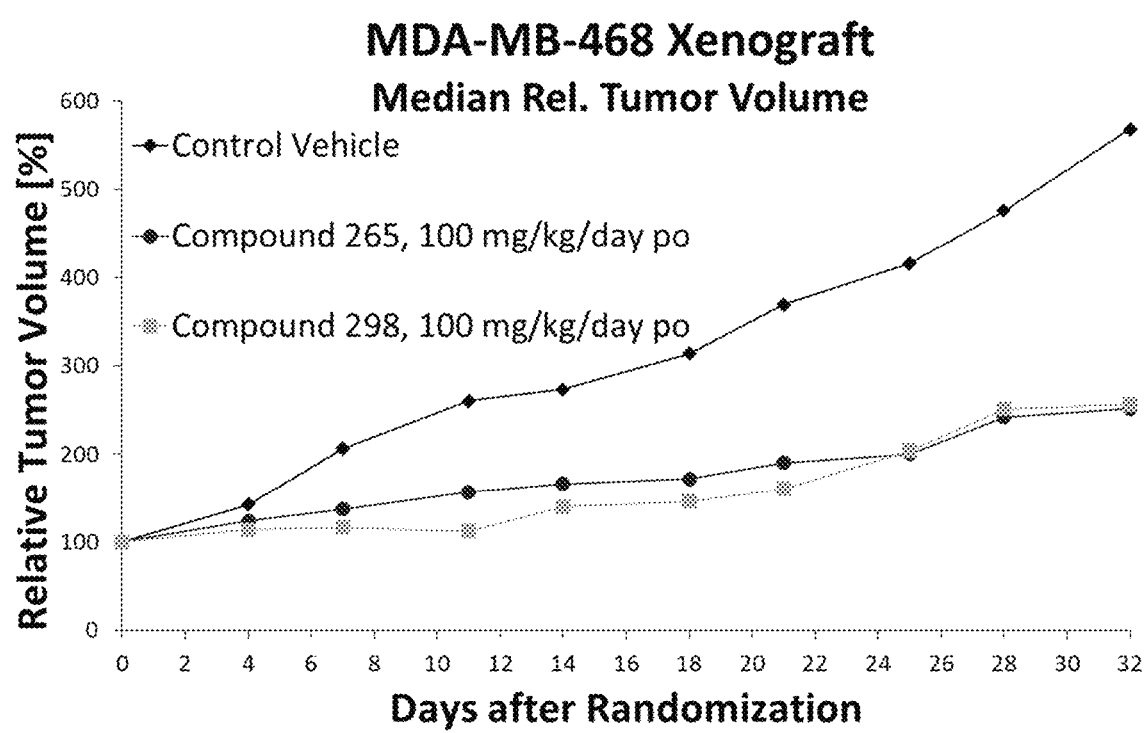
FIG. 7 depicts that Compounds 265 and 296 inhibits tumor growth in-vivo in MDA-MB-468 xenograft model.

The results are shown in FIG. 7.

The results show a significant tumor growth delay in the groups that were treated with 100 mg/kg of either compound 265, or its close analog Compound 298 (FIG. 7). The two compounds showed antitumor effect upon daily oral dosing in an acetate avid xenograft model (MDA-MB-468) whereas showed, as expected, no efficacy in a model that does not utilize acetate (HCT116).

In summary—the compounds of the invention show excellent rodent PK and stand-alone anti tumor efficacy in tumor xenografts characterized by high avidity for acetate and high expression of ACSS2.

What is claimed:

1. A method of suppressing, reducing or inhibiting tumor growth in a subject comprising administering a compound represented by the structure of formula (I):

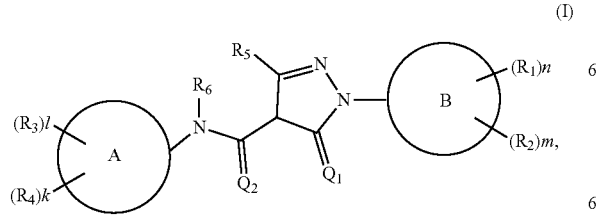

(I)

wherein

A and B rings are each independently a single or fused aromatic or heteroaromatic ring system, or a single or fused $C_3$-$C_{10}$ cycloalkyl or a single or fused $C_3$-$C_{10}$ heterocyclic ring;

$R_1$ and $R_2$ are each independently H, D, F, Cl, Br, I, OH, SH, $R_8$—OH, $CH_2$—OH, $R_8$—SH, —$R_8$—O—$R_{10}$, —$CH_2$—O—$CH_3$, $R_8$-aryl, $CH_2$-3-methoxy-phenyl, benzyl, $CH_2$-1-methoxy-phenyl, $CH_2$-4-chloro-phenyl, $CH_2CH_2$-phenyl, $CF_3$, $CD_3$, $OCD_3$, CN, $NO_2$, —$CH_2CN$, —$R_8CN$, $NH_2$, NHR, $N(R)_2$, $R_8$—$N(R_{10})$($R_{11}$), $CH_2$—$NH_2$, $CH_2$—$N(CH_3)_2$, $R_9$—$R_8$—$N(R_{10})$($R_{11}$), C≡C—$CH_2$—$NH_2$, $B(OH)_2$, —$OC(O)CF_3$, —$OCH_2Ph$, NHC(O)—$R_{10}$, $NHC(O)CH_3$, NHCO—N($R_{10}$)($R_{11}$), $NHC(O)N(CH_3)_2$, COOH, —C(O)Ph, —C(O)-aryl, C(O)-1-methyl-phenyl, C(O)-4-methyl-phenyl, C(O)-3-methyl-phenyl, C(O)-phenol, C(O)-4-hydroxy-phenyl, C(O)-3-hydroxy-phenyl, C(O)-2-hydroxy-phenyl, C(O)O—$R_{10}$, C(O)O—$CH_3$, C(O)O—$CH(CH_3)_2$, C(O)O—$CH_2CH_3$, $R_8$—C(O)—$R_{10}$, $CH_2C(O)CH_3$, C(O)H, C(O)—$R_{10}$, C(O)—$CH_3$, C(O)—$CH_2CH_3$, C(O)—$CH_2CH_2CH_3$, $C_1$-$C_5$ linear or branched C(O)-haloalkyl, C(O)—$CF_3$, —$C(O)NH_2$, C(O)NHR, $C(O)N(R_{10})(R_{11})$, $C(O)N(CH_3)_2$, $SO_2R$, $SO_2$-Ph, $SO_2$-toluene, $SO_2$—$CH_3$, $SO_2N(R_{10})(R_{11})$, $SO_2N(CH_3)_2$, $SO_2NHC(O)CH_3$, substituted or unsubstituted $C_1$-$C_5$ linear or branched or $C_3$-$C_8$ cyclic alkyl, methyl, 2, 3, or 4-$CH_2$—$C_6H_4$—Cl, ethyl, propyl, iso-propyl, cyclopropyl, t-Bu, iso-butyl, pentyl, benzyl, $C(CH_3)(OH)Ph$, $CH_2$-3-methoxy-phenyl, $CH_2$-1-methoxy-phenyl, $CH_2$-4-chloro-phenyl, $CH_2CH_2$-phenyl, $C_1$-$C_5$ linear or branched haloalkyl, $CF_3$, $CF_2CH_3$, $CH_2CF_3$, $CF_2CH_2CH_3$, $CH_2CH_2CF_3$, $CF_2CH(CH_3)_2$, $CF(CH_3)$—$CH(CH_3)_2$, $CF_2CH$-cyclopropyl, substituted or unsubstituted $C_1$-$C_5$ linear or branched or $C_3$-$C_8$ cyclic alkoxy, methoxy, ethoxy, propoxy, iso-propoxy, O—$CH_2$-cyclopropyl, O-cyclobutyl, O-cyclopentyl, O-cyclohexyl, 1-butoxy, 2-butoxy, O-tBu, substituted or unsubstituted $C_1$-$C_5$ linear or branched or $C_3$-$C_8$ cyclic alkoxy wherein at least one methylene group ($CH_2$) in the alkoxy is replaced with an oxygen atom, O-1-oxacyclobutyl, O-2-oxacyclobutyl, $C_1$-$C_5$ linear or branched thioalkoxy, S—$CH_3$, $C_1$-$C_5$ linear or branched haloalkoxy, $OCF_3$, $OCHF_2$, $C_1$-$C_5$ linear or branched alkoxyalkyl, substituted or unsubstituted $C_3$-$C_8$ cycloalkyl, cyclopropyl, cyclopentyl, substituted or unsubstituted $C_3$-$C_8$ heterocyclic ring, 3-methyl-4H-1,2,4-triazole, 5-methyl-1,2,4-oxadiazole, thiophene, oxazole, oxadiazole, imidazole, furan, triazole, tetrazole, pyridine (2, 3, or 4-pyridine), 2-methyl-4-pyridine, 2,6-dimethyl-4-pyridine, 3,5-dimethyl-4-pyridine, 2,5-dimethyl-4-pyridine, 3-methyl-4-pyridine, 5-methyl-2-pyridine, 3-methyl-2-pyridine, 3-ethyl-2-pyridine, 3-isopropyl-2-pyridine, 3-propyl-2-pyridine, 3-phenyl-2-pyridine, 4-methyl-2-pyridine, 6-methyl-2-pyridine, 5-methyl-2-pyridine, pyrimidine, 5-methyl-pyrimidine, pyrazine, oxacyclobutane (1 or 2-oxacyclobutane), indole, protonated or deprotonated pyridine oxide, substituted or unsubstituted aryl, phenyl, (wherein substitutions include: F, Cl, Br, I, $C_1$-$C_5$ linear or branched alkyl, methyl, ethyl, propyl, isopropyl, OH, alkoxy, N(R)$_2$, CF$_3$, aryl, phenyl, halophenyl, (benzyloxy)phenyl, CN, NO$_2$ or any combination thereof;

or R$_2$ and R$_1$ are joined to form a 5 or 6 membered substituted or unsubstituted, aliphatic or aromatic, carbocyclic or heterocyclic single or fused ring;

R$_3$ and R$_4$ are each independently H, F, Cl, Br, I, OH, SH, R$_8$—OH, CH$_2$—OH, R$_8$—SH, —R$_8$—O—R$_{10}$, CH$_2$—O—CH$_3$, CF$_3$, CD$_3$, OCD$_3$, CN, NO$_2$, —CH$_2$CN, —R$_8$CN, NH$_2$, NHR, N(R)$_2$, R$_8$—N(R$_{10}$)(R$_{11}$), CH$_2$—NH$_2$, CH$_2$—N(CH$_3$)$_2$, R$_8$—C(O)N(R$_{10}$)(R$_{11}$), CF$_2$C(O)N[(CH$_3$)(OCH$_3$)], R$_9$—R$_8$—N(R$_{10}$)(R$_{11}$), B(OH)$_2$, —OC(O)CF$_3$, —OCH$_2$Ph, —NHCO—R$_{10}$, NHC(O)CH$_3$, NHCO—N(R$_{10}$)(R$_{11}$), NHC(O)N(CH$_3$)$_2$, COOH, —C(O)Ph, C(O)O—R$_{10}$, C(O)O—CH$_3$, C(O)O—CH$_2$CH$_3$, R$_8$—C(O)—R$_{10}$, CH$_2$C(O)CH$_3$, C(O)H, C(O)—R$_{10}$, C(O)—CH$_3$, C(O)—CH$_2$CH$_3$, C(O)—CH$_2$CH$_2$CH$_3$, C$_1$-C$_5$ linear or branched C(O)-haloalkyl, C(O)—CF$_3$, —C(O)NH$_2$, C(O)NHR, C(O)N(R$_{10}$)(R$_{11}$), C(O)N(CH$_3$)$_2$, SO$_2$R, SO$_2$N(R$_{10}$)(R$_{11}$), SO$_2$N(CH$_3$)$_2$, C$_1$-C$_5$ linear or branched or C$_3$-C$_8$ cyclic, substituted or unsubstituted alkyl, methyl, C(OH)(CH$_3$)(Ph), ethyl, propyl, iso-propyl, t-Bu, iso-butyl, 2-butyl, pentyl, tert-pentyl, 1-ethylcyclopropyl, C(CH$_3$)(OH)Ph, C$_1$-C$_5$ linear or branched or C$_3$-C$_8$ cyclic haloalkyl, CF$_3$, CF$_2$CH$_3$, CH$_2$CF$_3$, CF$_2$CH$_2$CH$_3$, CF$_2$CHFCH$_3$, CHFCHFCH$_3$, CH$_2$CH$_2$CF$_3$, CF$_2$CH(CH$_3$)$_2$, CF(CH$_3$)—CH(CH$_3$)$_2$, CF$_2$-cyclopropyl, CF$_2$-cyclopentyl, C$_1$-C$_5$ linear or branched or C$_3$-C$_8$ cyclic haloalkenyl, CF=CH—CH$_3$ E, Z, CF=C—(CH$_3$)$_2$, C$_1$-C$_5$ linear or branched or C$_3$-C$_8$ cyclic alkoxy, methoxy, ethoxy, propoxy, isopropoxy, O—CH$_2$-cyclopropyl, C$_1$-C$_5$ linear or branched thioalkoxy, C$_1$-C$_5$ linear or branched haloalkoxy, C$_1$-C$_5$ linear or branched alkoxyalkyl, substituted or unsubstituted C$_3$-C$_8$ cycloalkyl, cyclopropyl, cyclopentyl, substituted or unsubstituted C$_3$-C$_8$ heterocyclic ring, 3-methyl-4H-1,2,4-triazole, 5-methyl-1,2,4-oxadiazole, thiophene, oxazole, isoxazole, imidazole, furan, pyrrole, 1-methyl-pyrrole, imidazole, 1-methyl-imidazole, triazole, pyridine (2, 3, or 4-pyridine), pyrimidine, pyrazine, oxacyclobutane (1 or 2-oxacyclobutane), indole, substituted or unsubstituted aryl or phenyl; wherein substitutions include: F, Cl, Br, I, C$_1$-C$_5$ linear or branched alkyl, OH, alkoxy, N(R)$_2$, CF$_3$, aryl, phenyl, halophenyl, (benzyloxy)phenyl, CN, NO$_2$ or any combination thereof;

or R$_3$ and R$_4$ are joined to form a 5 or 6 membered substituted or unsubstituted, aliphatic or aromatic, carbocyclic or heterocyclic ring;

R$_5$ is H, C$_1$-C$_5$ linear or branched, substituted or unsubstituted alkyl, methyl, CH$_2$SH, ethyl, iso-propyl, C$_1$-C$_5$ linear or branched haloalkyl, CF$_3$, CF$_2$CH$_3$, CH$_2$CF$_3$, CF$_2$CH$_2$CH$_3$, CH$_2$CH$_2$CF$_3$, CF$_2$CH(CH$_3$)$_2$, CF(CH$_3$)—CH(CH$_3$)$_2$, R$_8$-aryl, CH$_2$-Ph, C(O)—R$_{10}$, C(O)—CH$_3$, substituted or unsubstituted aryl, phenyl, substituted or unsubstituted heteroaryl, pyridine (2, 3, and 4-pyridine); wherein substitutions include: F, Cl, Br, I, C$_1$-C$_5$ linear or branched alkyl, OH, alkoxy, N(R)$_2$, CF$_3$, phenyl, halophenyl, (benzyloxy)phenyl, CN, NO$_2$ or any combination thereof;

R$_6$ is H, C$_1$-C$_5$ linear or branched alkyl, methyl, C(O)R, or S(O)$_2$R;

R$_8$ is [CH$_2$]$_p$ or [CF$_2$]$_p$
wherein p is between 1 and 10;

R$_9$ is [CH]$_q$, [C]$_q$
wherein q is between 2 and 10;

R$_{10}$ and R$_{11}$ are each independently H, C$_1$-C$_5$ linear or branched alkyl, methyl, ethyl, C(O)R, or S(O)$_2$R;

R is H, C$_1$-C$_5$ linear or branched alkyl, methyl, ethyl, C$_1$-C$_5$ linear or branched alkoxy, phenyl, aryl, toluene or heteroaryl, or two gem R substituents are joined to form a 5 or 6 membered heterocyclic ring;

m, n, l and k are each independently an integer between 0 and 4;

Q$_1$ and Q$_2$ are each independently S, O, N—OH, CH$_2$, C(R)$_2$ or N—OMe;

or its pharmaceutically acceptable salt thereof, to a subject, under conditions effective to suppress, reduce or inhibit said tumor growth in said subject.

2. The method of claim 1, wherein the tumor is cancerous; or wherein the subject is suffering from cancer; or wherein the tumor growth is enhanced by increased acetate uptake by cancer cells of said tumor; or wherein the tumor growth is suppressed due to suppression of lipid synthesis and/or regulating histones acetylation and function induced by ACSS2 mediated acetate metabolism to acetyl-CoA.

3. The method of claim 2, wherein the cancer cells are under hypoxic stress; or wherein the increased acetate uptake is mediated by ACSS2; or wherein the lipid is a fatty acid.

4. The method of claim 1, wherein the compound is characterized by R$_3$ being C$_2$-C$_5$ linear, branched or cyclic haloalkyl, CF$_2$CH$_3$, CH$_2$CF$_3$, CF$_2$CH$_2$CH$_3$, CF$_2$CHFCH$_3$, CHFCHFCH$_3$, CH$_2$CH$_2$CF$_3$, CF$_2$CH (CH$_3$)$_2$, CF (CH$_3$)—CH (CH$_3$)$_2$, CF$_2$-cyclopropyl, CF$_2$-cyclopentyl, substituted or unsubstituted C$_1$-C$_5$ linear or branched or C$_3$-C$_8$ cyclic haloalkenyl, CF=CH—CH$_3$ or CF=C—(CH$_3$)$_2$, or a pharmaceutically acceptable salt thereof.

5. The method of claim 4, wherein the compound is represented by the structure of formula (II):

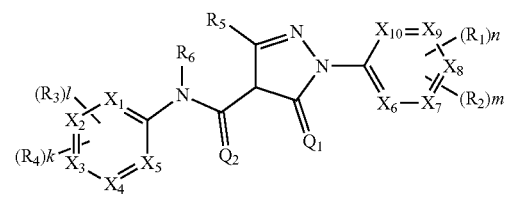

wherein
X$_1$, X$_2$, X$_3$, X$_4$, X$_5$, X$_6$, X$_7$, X$_8$, X$_9$ or X$_{10}$ are each independently C or N, or a pharmaceutically acceptable salt thereof.

6. The method of claim 5, wherein the compound is represented by the structure of formula (IV):

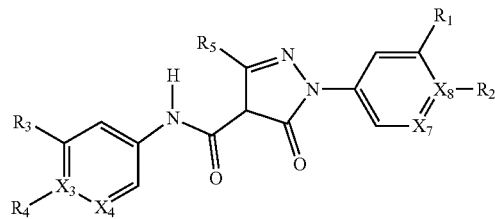

or a pharmaceutically acceptable salt thereof, wherein if $X_3$ is N, then $R_4$ is absent; and
if $X_8$ is N, then $R_2$ is absent.

7. The method of claim 5, wherein the compound is represented by the structure of formula (V):

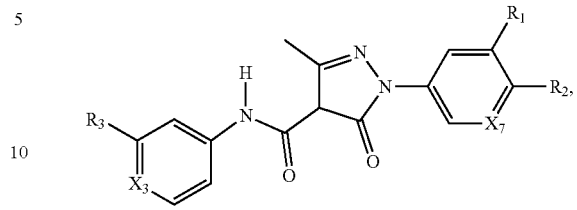

or a pharmaceutically acceptable salt thereof.

8. The method of claim 7, wherein $R_3$ is $CF_2CH_3$, $R_1$ is H or pyridine, and $R_2$ is $OCH_3$, $C(O)OCH_3$, $CF_3$ or $OCHF_2$, or a pharmaceutically acceptable salt thereof.

9. The method of claim 1, wherein the compound is represented by one of the following structures:

100

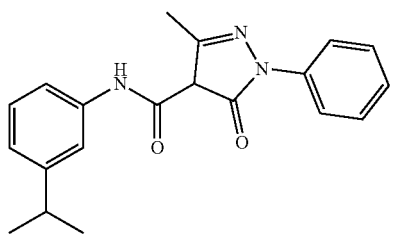 [SMILES: CC1=NN(c2ccccc2)C(=O)C1C(=O)Nc1cccc(C(C)C)c1]

101

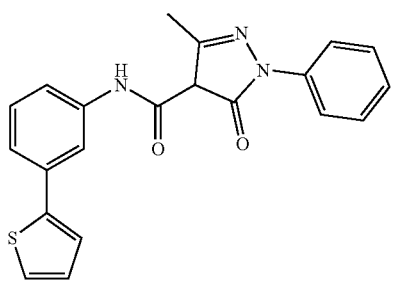 [SMILES: CC1=NN(c2ccccc2)C(=O)C1C(=O)Nc1cccc(-c2cccs2)c1]

102

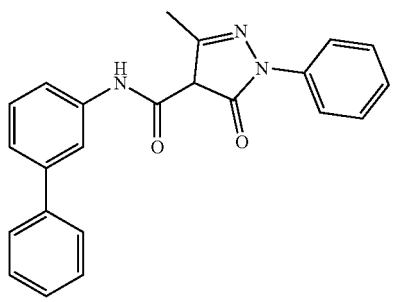 [SMILES: CC1=NN(c2ccccc2)C(=O)C1C(=O)Nc1cccc(-c2ccccc2)c1]

103

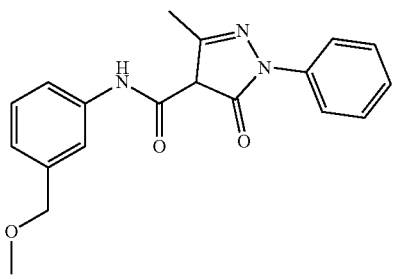 [SMILES: COCc1cccc(NC(=O)C2C(=O)N(c3ccccc3)N=C2C)c1]

| | |
|---|---|
| 104 | 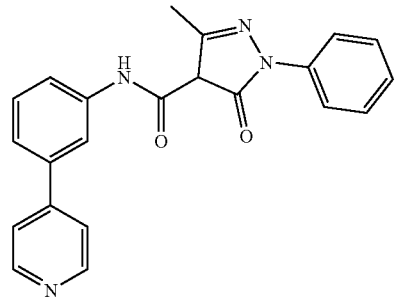 [SMILES: CC1=NN(c2ccccc2)C(=O)C1C(=O)Nc1cccc(-c2ccncc2)c1] |
| 105 | 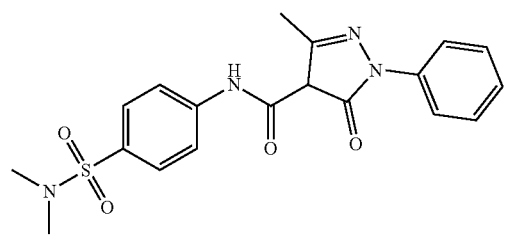 [SMILES: CC1=NN(c2ccccc2)C(=O)C1C(=O)Nc1ccc(S(=O)(=O)N(C)C)cc1] |
| 106 | 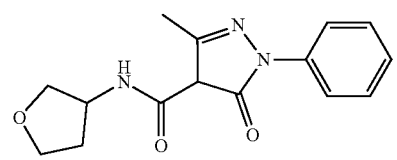 [SMILES: CC1=NN(c2ccccc2)C(=O)C1C(=O)NC1CCOC1] |
| 107 | 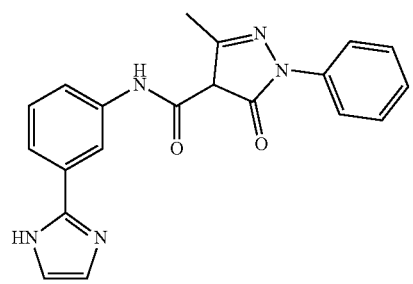 [SMILES: CC1=NN(c2ccccc2)C(=O)C1C(=O)Nc1cccc(-c2ncc[nH]2)c1] |
| 108 | 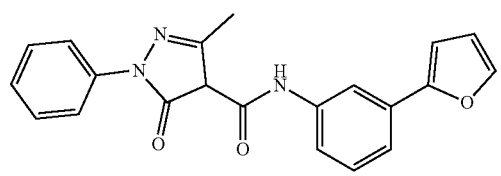 [SMILES: CC1=NN(c2ccccc2)C(=O)C1C(=O)Nc1cccc(-c2ccco2)c1] |
| 109 | 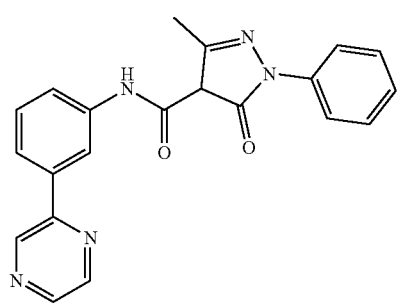 [SMILES: CC1=NN(c2ccccc2)C(=O)C1C(=O)Nc1cccc(-c2cnccn2)c1] |
| 110 | 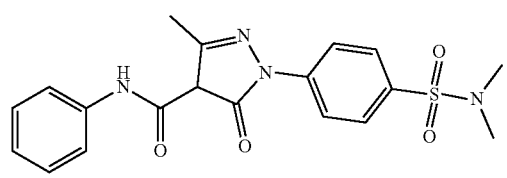 [SMILES: CC1=NN(c2ccc(S(=O)(=O)N(C)C)cc2)C(=O)C1C(=O)Nc1ccccc1] |

| 111 | 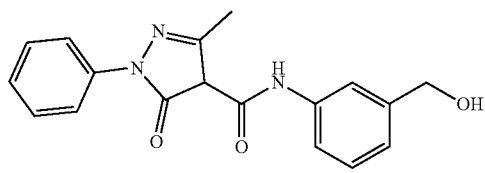 [SMILES: CC1=NN(c2ccccc2)C(=O)C1C(=O)Nc1cccc(CO)c1] |
| 112 | 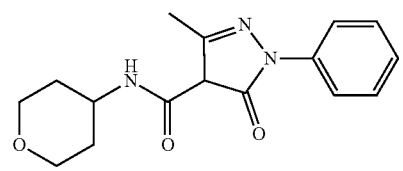 [SMILES: CC1=NN(c2ccccc2)C(=O)C1C(=O)NC1CCOCC1] |
| 113 | 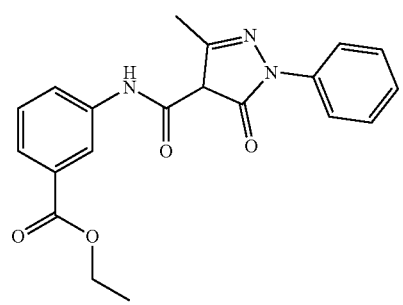 |
| 114 | 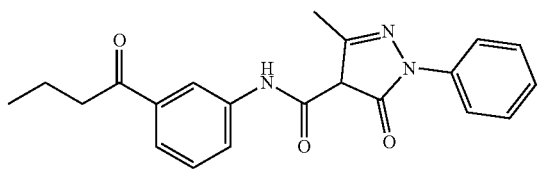 [SMILES: CCCC(=O)c1cccc(NC(=O)C2C(=O)N(c3ccccc3)N=C2C)c1] |
| 115 | 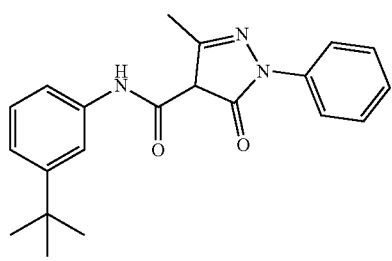 [SMILES: CC1=NN(c2ccccc2)C(=O)C1C(=O)Nc1cccc(C(C)(C)C)c1] |
| 116 | 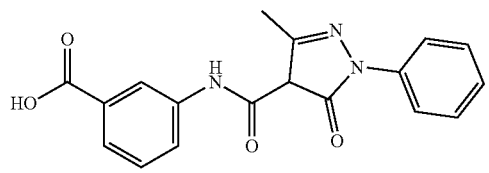 [SMILES: CC1=NN(c2ccccc2)C(=O)C1C(=O)Nc1cccc(C(=O)O)c1] |
| 117 | 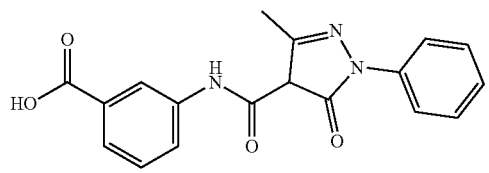 [SMILES: CC1=NN(c2ccccc2)C(=O)C1C(=O)Nc1cccc(C(=O)O)c1] |
| 118 | 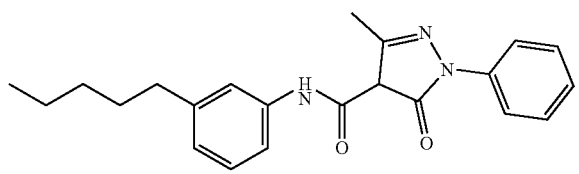 [SMILES: CCCCCc1cccc(NC(=O)C2C(=O)N(c3ccccc3)N=C2C)c1] |

| 119 | 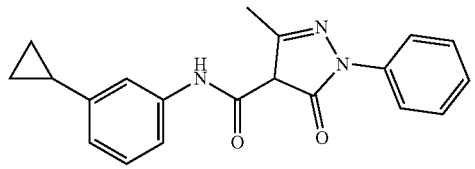 [SMILES: CC1=NN(c2ccccc2)C(=O)C1C(=O)Nc1cccc(C2CC2)c1] |
| --- | --- |
| 120 | 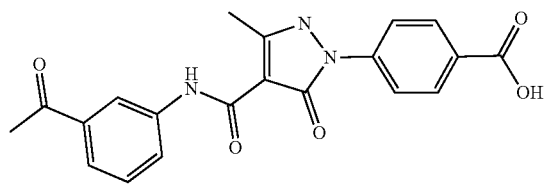 [SMILES: CC(=O)c1cccc(NC(=O)c2c(C)[nH]n(-c3ccc(C(=O)O)cc3)c2=O)c1] |
| 121 | 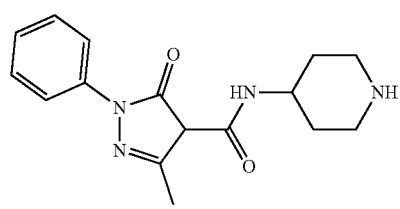 [SMILES: CC1=NN(c2ccccc2)C(=O)C1C(=O)NC1CCNCC1] |
| 122 | 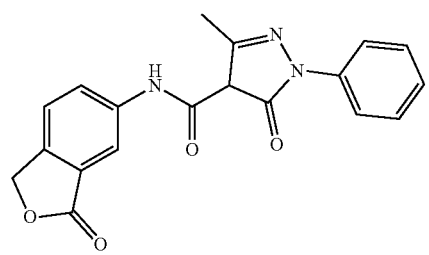 [SMILES: CC1=NN(c2ccccc2)C(=O)C1C(=O)Nc1ccc2c(c1)C(=O)OC2] |
| 123 | 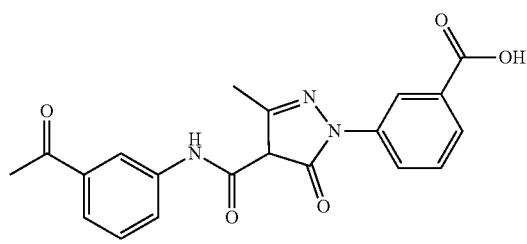 [SMILES: CC(=O)c1cccc(NC(=O)C2C(=O)N(c3cccc(C(=O)O)c3)N=C2C)c1] |
| 124 | 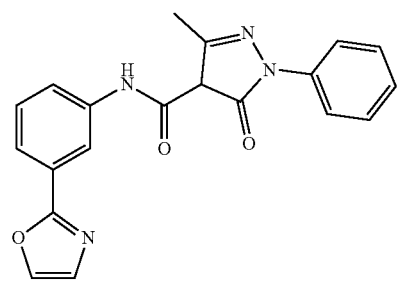 [SMILES: CC1=NN(c2ccccc2)C(=O)C1C(=O)Nc1cccc(-c2ncco2)c1] |
| 125 | 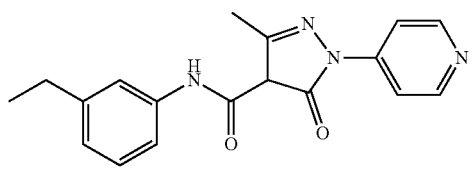 [SMILES: CCc1cccc(NC(=O)C2C(=O)N(c3ccncc3)N=C2C)c1] |

126 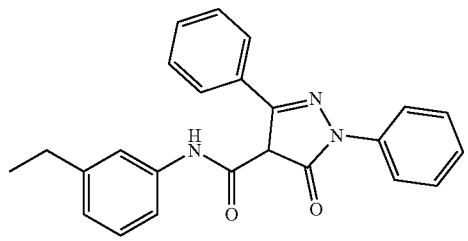
127 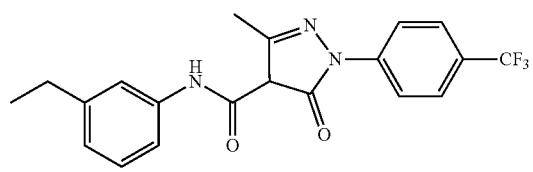 [SMILES: CCc1cccc(NC(=O)C2C(=O)N(c3ccc(C(F)(F)F)cc3)N=C2C)c1]
128 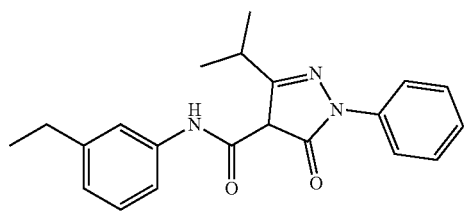 [SMILES: CCc1cccc(NC(=O)C2C(=O)N(c3ccccc3)N=C2C(C)C)c1]
129 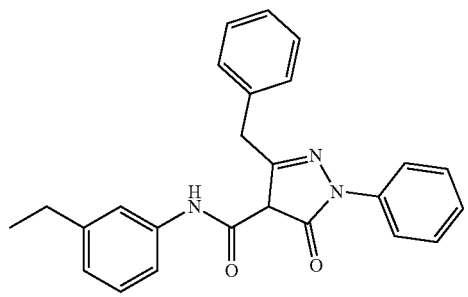 [SMILES: CCc1cccc(NC(=O)C2C(=O)N(c3ccccc3)N=C2Cc2ccccc2)c1]
130 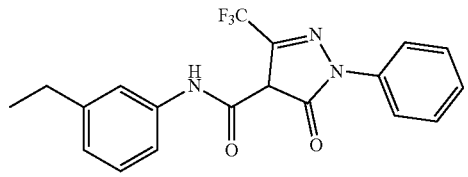 [SMILES: CCc1cccc(NC(=O)C2C(=O)N(c3ccccc3)N=C2C(F)(F)F)c1]
131 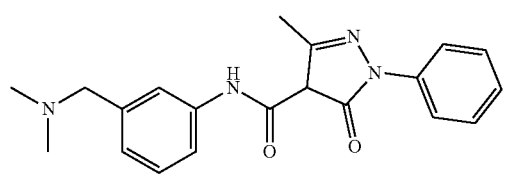 [SMILES: CC1=NN(c2ccccc2)C(=O)C1C(=O)Nc1cccc(CN(C)C)c1]
132 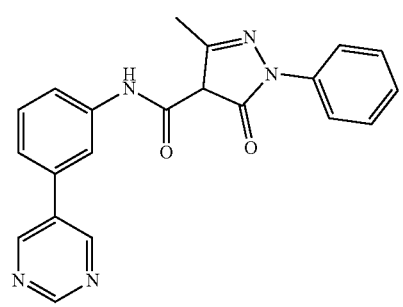

| | |
|---|---|
| 133 | 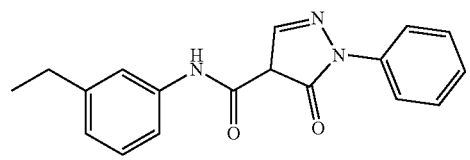 [SMILES: CCc1cccc(NC(=O)C2C=NN(c3ccccc3)C2=O)c1] |
| 134 | 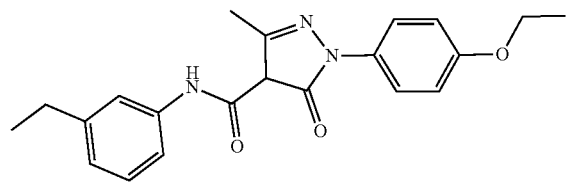 [SMILES: CCOc1ccc(N2N=C(C)C(C(=O)Nc3cccc(CC)c3)C2=O)cc1] |
| 135 | 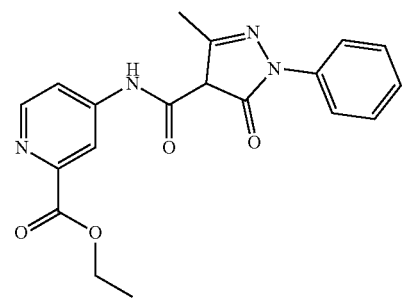 |
| 136 | 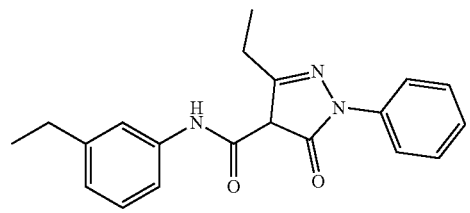 [SMILES: CCC1=NN(c2ccccc2)C(=O)C1C(=O)Nc1cccc(CC)c1] |
| 137 | 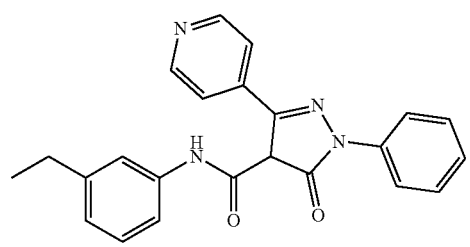 [SMILES: CCc1cccc(NC(=O)C2C(=O)N(c3ccccc3)N=C2c2ccncc2)c1] |
| 138 | 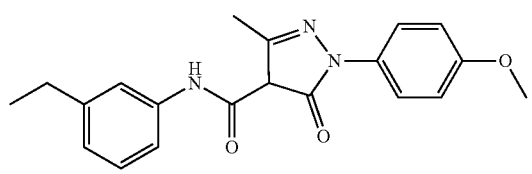 [SMILES: CCc1cccc(NC(=O)C2C(=O)N(c3ccc(OC)cc3)N=C2C)c1] |
| 139 | 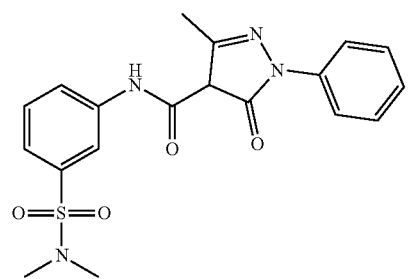 [SMILES: CC1=NN(c2ccccc2)C(=O)C1C(=O)Nc1cccc(S(=O)(=O)N(C)C)c1] |

-continued
140
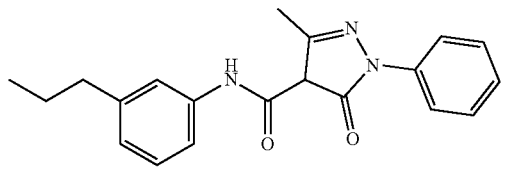 [SMILES: CCCc1cccc(NC(=O)C2C(=O)N(c3ccccc3)N=C2C)c1]
141
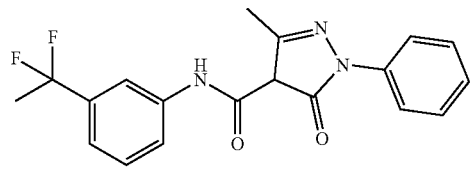 [SMILES: CC1=NN(c2ccccc2)C(=O)C1C(=O)Nc1cccc(C(C)(F)F)c1]
142
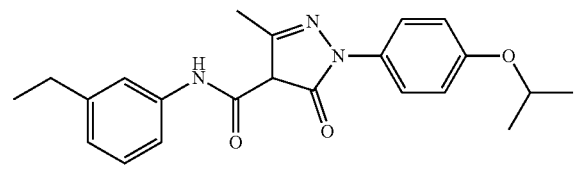 [SMILES: CCc1cccc(NC(=O)C2C(=O)N(c3ccc(OC(C)C)cc3)N=C2C)c1]
143
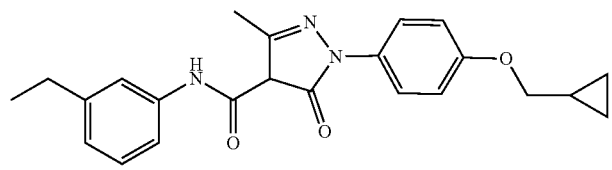 [SMILES: CCc1cccc(NC(=O)C2C(=O)N(c3ccc(OCC4CC4)cc3)N=C2C)c1]
144
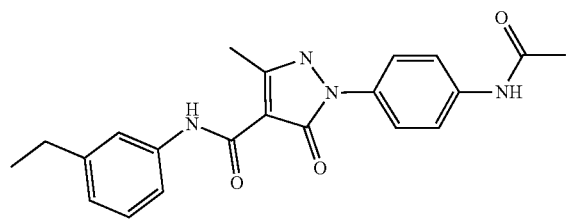 [SMILES: CCc1cccc(NC(=O)c2c(C)[nH]n(-c3ccc(NC(C)=O)cc3)c2=O)c1]
145
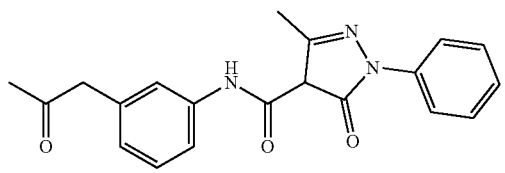 [SMILES: CC(=O)Cc1cccc(NC(=O)C2C(=O)N(c3ccccc3)N=C2C)c1]
146
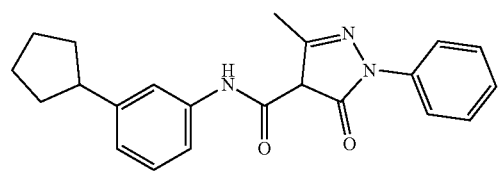 [SMILES: CC1=NN(c2ccccc2)C(=O)C1C(=O)Nc1cccc(C2CCCC2)c1]
147
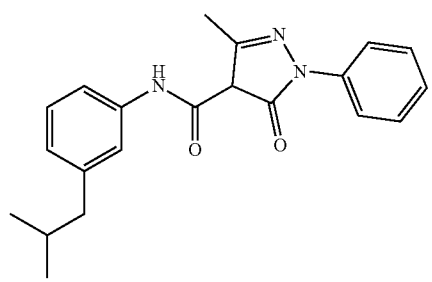 [SMILES: CC1=NN(c2ccccc2)C(=O)C1C(=O)Nc1cccc(CC(C)C)c1]

148 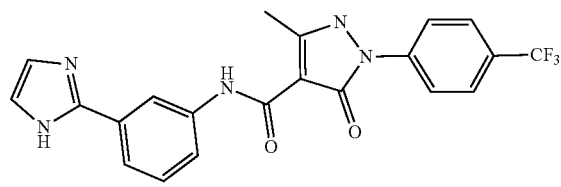 [SMILES: Cc1[nH]n(-c2ccc(C(F)(F)F)cc2)c(=O)c1C(=O)Nc1cccc(-c2ncc[nH]2)c1]
149 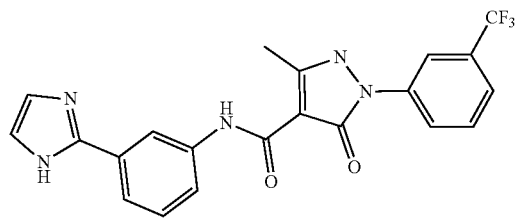 [SMILES: Cc1[nH]n(-c2cccc(C(F)(F)F)c2)c(=O)c1C(=O)Nc1cccc(-c2ncc[nH]2)c1]
150 
152 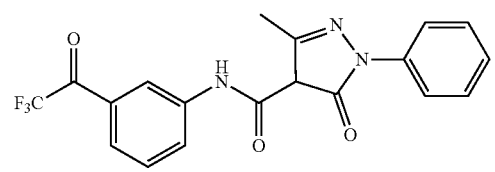 [SMILES: CC1=NN(c2ccccc2)C(=O)C1C(=O)Nc1cccc(C(=O)C(F)(F)F)c1]
153 
154 
155 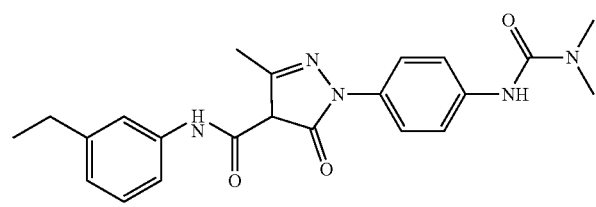 [SMILES: CCc1cccc(NC(=O)C2C(=O)N(c3ccc(NC(=O)N(C)C)cc3)N=C2C)c1]
156 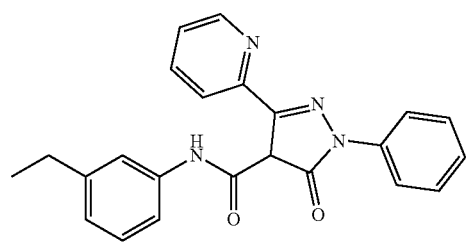 [SMILES: CCc1cccc(NC(=O)C2C(=O)N(c3ccccc3)N=C2c2ccccn2)c1]

157 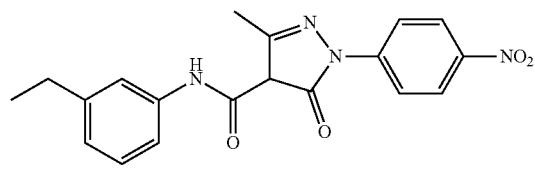
158 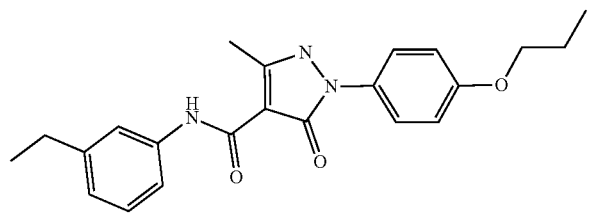 [SMILES: CCCOc1ccc(-n2[nH]c(C)c(C(=O)Nc3cccc(CC)c3)c2=O)cc1]
159 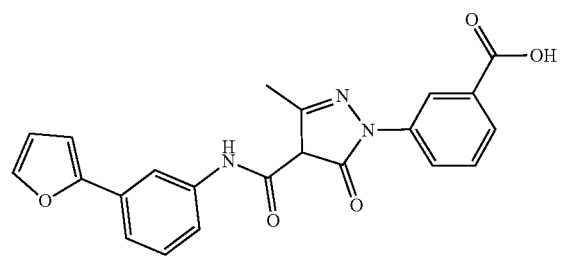 [SMILES: CC1=NN(c2cccc(C(=O)O)c2)C(=O)C1C(=O)Nc1cccc(-c2ccco2)c1]
160 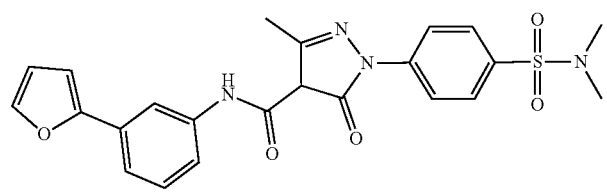 [SMILES: CC1=NN(c2ccc(S(=O)(=O)N(C)C)cc2)C(=O)C1C(=O)Nc1cccc(-c2ccco2)c1]
161 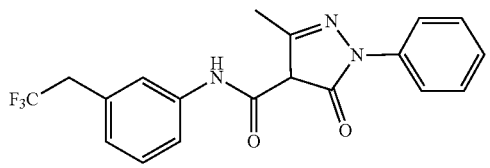 [SMILES: CC1=NN(c2ccccc2)C(=O)C1C(=O)Nc1cccc(CC(F)(F)F)c1]
162 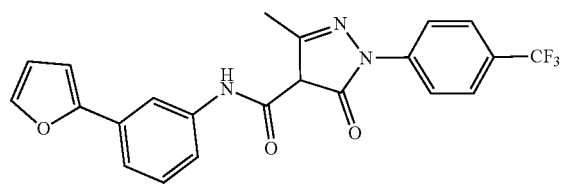 [SMILES: CC1=NN(c2ccc(C(F)(F)F)cc2)C(=O)C1C(=O)Nc1cccc(-c2ccco2)c1]
164 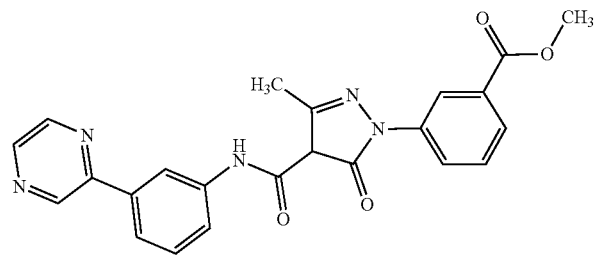 [SMILES: COC(=O)c1cccc(N2N=C(C)C(C(=O)Nc3cccc(-c4cnccn4)c3)C2=O)c1]

165 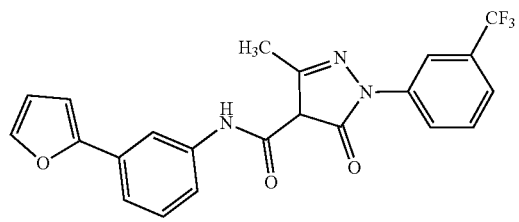 [SMILES: CC1=NN(c2cccc(C(F)(F)F)c2)C(=O)C1C(=O)Nc1cccc(-c2ccco2)c1]
166 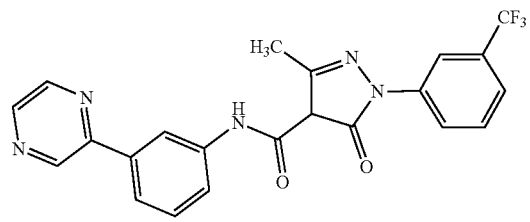 [SMILES: CC1=NN(c2cccc(C(F)(F)F)c2)C(=O)C1C(=O)Nc1cccc(-c2cnccn2)c1]
167 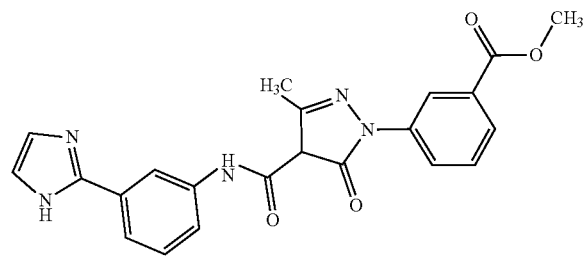 [SMILES: COC(=O)c1cccc(N2N=C(C)C(C(=O)Nc3cccc(-c4ncc[nH]4)c3)C2=O)c1]
168 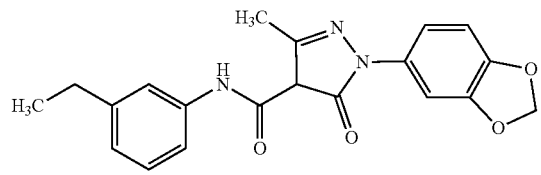 [SMILES: CCc1cccc(NC(=O)C2C(=O)N(c3ccc4c(c3)OCO4)N=C2C)c1]
169 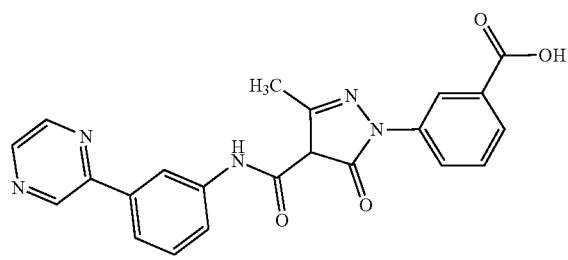 [SMILES: CC1=NN(c2cccc(C(=O)O)c2)C(=O)C1C(=O)Nc1cccc(-c2cnccn2)c1]
170 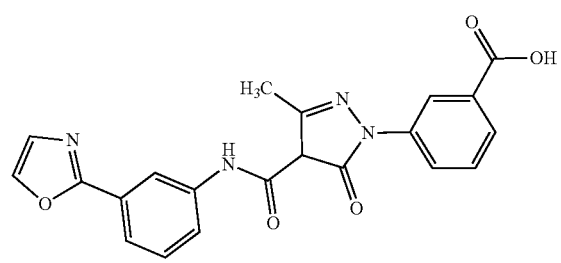 [SMILES: CC1=NN(c2cccc(C(=O)O)c2)C(=O)C1C(=O)Nc1cccc(-c2ncco2)c1]

| | |
|---|---|
| 171 | 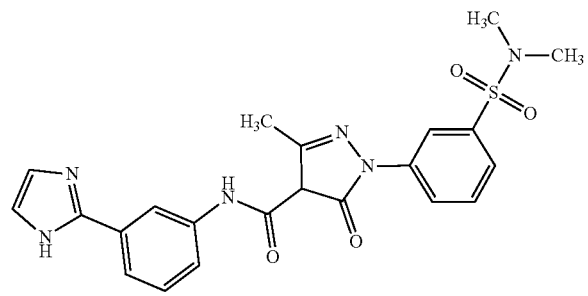 [SMILES: CC1=NN(c2cccc(S(=O)(=O)N(C)C)c2)C(=O)C1C(=O)Nc1cccc(-c2ncc[nH]2)c1] |
| 172 | 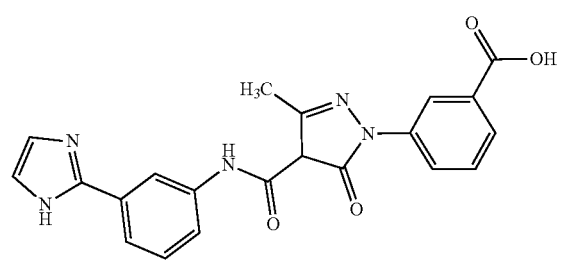 |
| 173 | 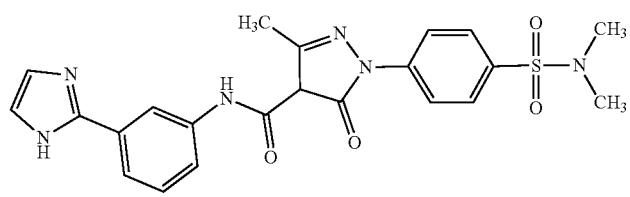 [SMILES: CC1=NN(c2ccc(S(=O)(=O)N(C)C)cc2)C(=O)C1C(=O)Nc1cccc(-c2ncc[nH]2)c1] |
| 174 | 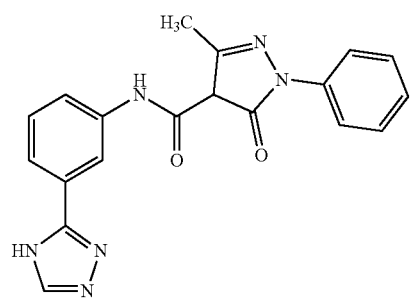 [SMILES: CC1=NN(c2ccccc2)C(=O)C1C(=O)Nc1cccc(-c2nnc[nH]2)c1] |
| 176 | 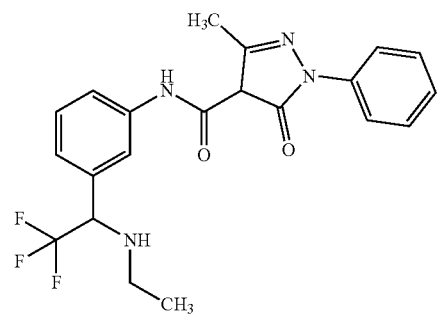 [SMILES: CCNC(c1cccc(NC(=O)C2C(=O)N(c3ccccc3)N=C2C)c1)C(F)(F)F] |
| 182 | 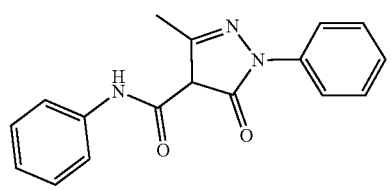 [SMILES: CC1=NN(c2ccccc2)C(=O)C1C(=O)Nc1ccccc1] |

-continued
183
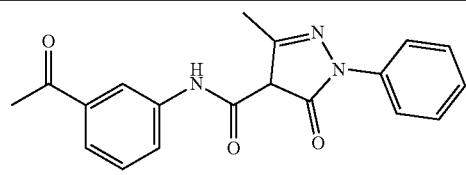
184
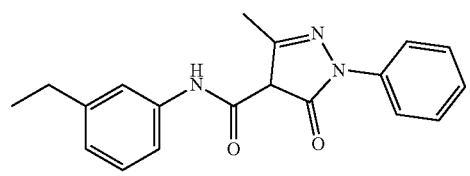 [SMILES: CCc1cccc(NC(=O)C2C(=O)N(c3ccccc3)N=C2C)c1]
185
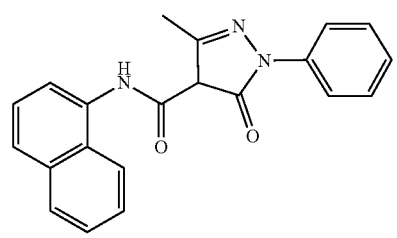 [SMILES: CC1=NN(c2ccccc2)C(=O)C1C(=O)Nc1cccc2ccccc12]
186
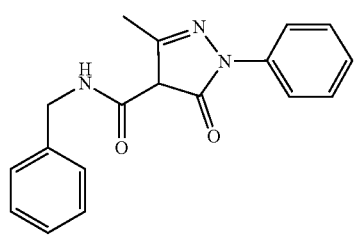 [SMILES: CC1=NN(c2ccccc2)C(=O)C1C(=O)NCc1ccccc1]
187
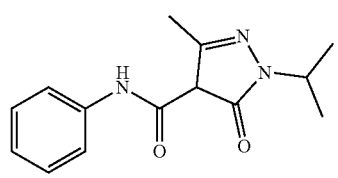 [SMILES: CC1=NN(C(C)C)C(=O)C1C(=O)Nc1ccccc1]
188
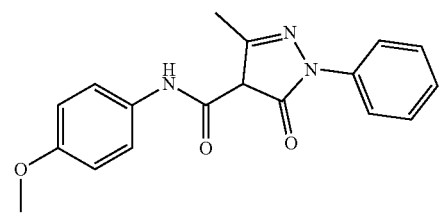
189
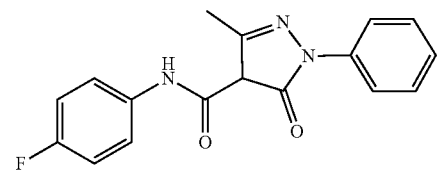 [SMILES: CC1=NN(c2ccccc2)C(=O)C1C(=O)Nc1ccc(F)cc1]
190
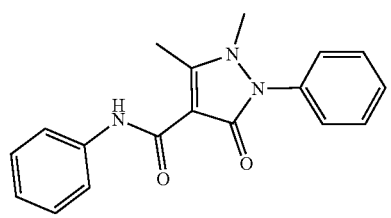 [SMILES: Cc1c(C(=O)Nc2ccccc2)c(=O)n(-c2ccccc2)n1C]

| | |
|---|---|
| 191 | 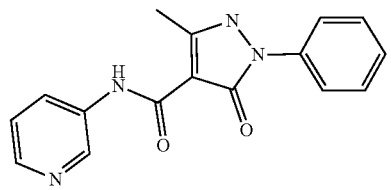 [SMILES: Cc1[nH]n(-c2ccccc2)c(=O)c1C(=O)Nc1cccnc1] |
| 192 | 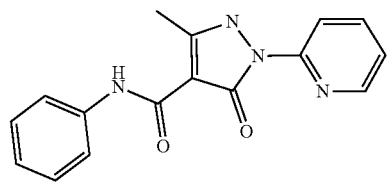 [SMILES: Cc1[nH]n(-c2ccccn2)c(=O)c1C(=O)Nc1ccccc1] |
| 193 | 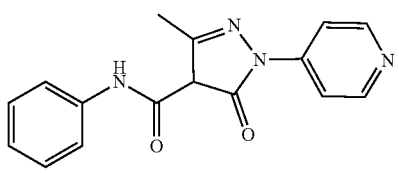 [SMILES: CC1=NN(c2ccncc2)C(=O)C1C(=O)Nc1ccccc1] |
| 194 | 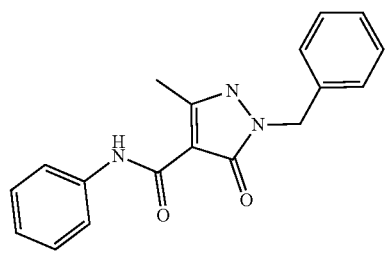 [SMILES: Cc1[nH]n(Cc2ccccc2)c(=O)c1C(=O)Nc1ccccc1] |
| 195 | 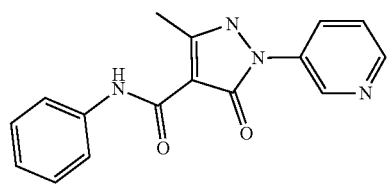 [SMILES: Cc1[nH]n(-c2cccnc2)c(=O)c1C(=O)Nc1ccccc1] |
| 196 | 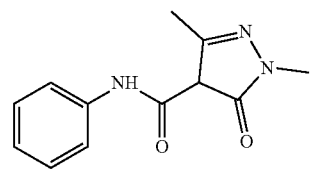 [SMILES: CC1=NN(C)C(=O)C1C(=O)Nc1ccccc1] |
| 197 | 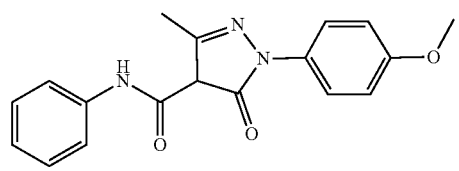 [SMILES: COc1ccc(N2N=C(C)C(C(=O)Nc3ccccc3)C2=O)cc1] |
| 198 | 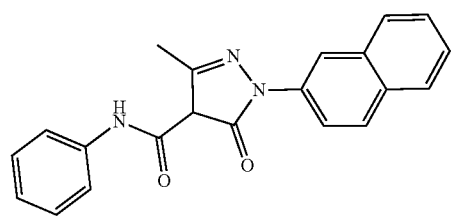 [SMILES: CC1=NN(c2ccc3ccccc3c2)C(=O)C1C(=O)Nc1ccccc1] |

-continued
| | |
|---|---|
| 199 | 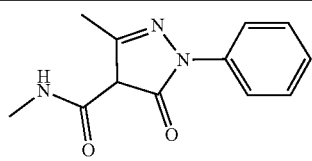 |
| 200 | 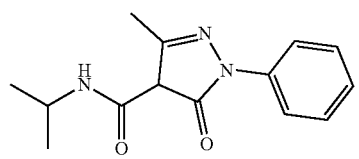 [SMILES: CC1=NN(c2ccccc2)C(=O)C1C(=O)NC(C)C] |
| 201 | 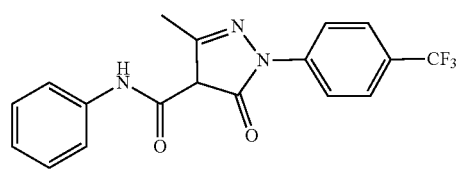 [SMILES: CC1=NN(c2ccc(C(F)(F)F)cc2)C(=O)C1C(=O)Nc1ccccc1] |
| 202 | 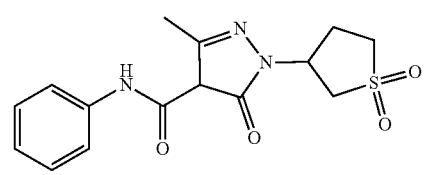 [SMILES: CC1=NN(C2CCS(=O)(=O)C2)C(=O)C1C(=O)Nc1ccccc1] |
| 203 | 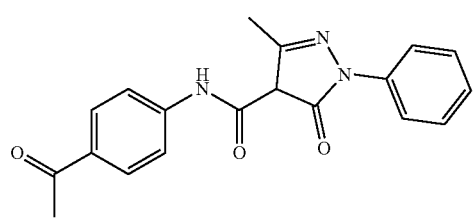 [SMILES: CC(=O)c1ccc(NC(=O)C2C(=O)N(c3ccccc3)N=C2C)cc1] |
| 204 | 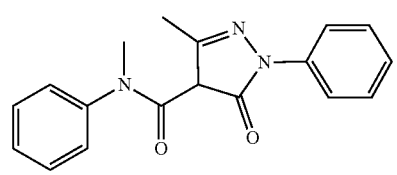 [SMILES: CC1=NN(c2ccccc2)C(=O)C1C(=O)N(C)c1ccccc1] |
| 205 | 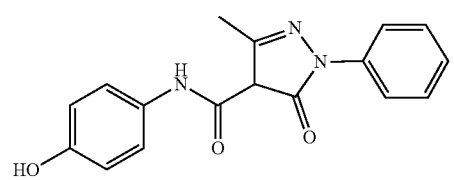 [SMILES: CC1=NN(c2ccccc2)C(=O)C1C(=O)Nc1ccc(O)cc1] |
| 206 | 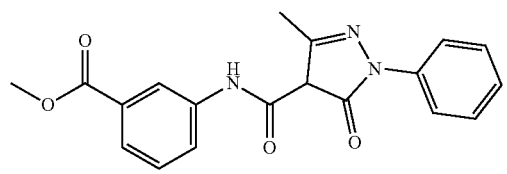 [SMILES: COC(=O)c1cccc(NC(=O)C2C(=O)N(c3ccccc3)N=C2C)c1] |
| 207 | 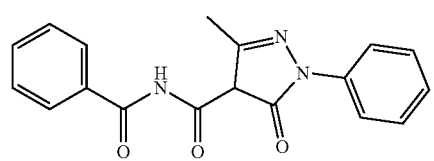 [SMILES: CC1=NN(c2ccccc2)C(=O)C1C(=O)NC(=O)c1ccccc1] |

| | |
|---|---|
| 208 | 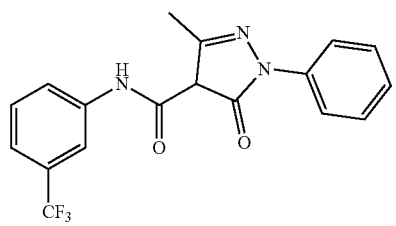 [SMILES: CC1=NN(c2ccccc2)C(=O)C1C(=O)Nc1cccc(C(F)(F)F)c1] |
| 209 | 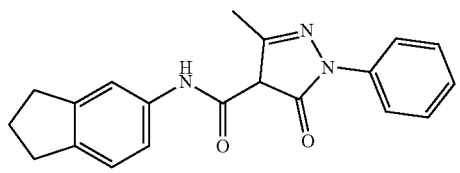 [SMILES: CC1=NN(c2ccccc2)C(=O)C1C(=O)Nc1ccc2c(c1)CCC2] |
| 210 | 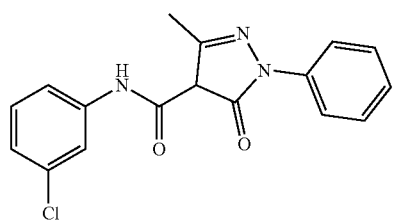 [SMILES: CC1=NN(c2ccccc2)C(=O)C1C(=O)Nc1cccc(Cl)c1] |
| 211 | 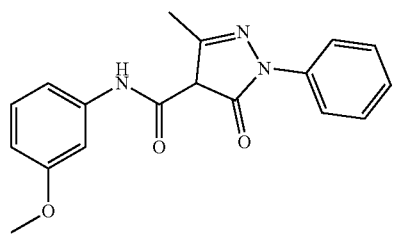 [SMILES: COc1cccc(NC(=O)C2C(=O)N(c3ccccc3)N=C2C)c1] |
| 212 | 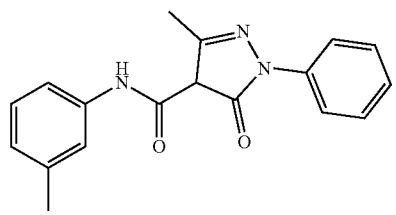 [SMILES: CC1=NN(c2ccccc2)C(=O)C1C(=O)Nc1cccc(C)c1] |
| 213 | 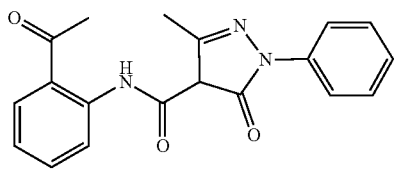 [SMILES: CC(=O)c1ccccc1NC(=O)C1C(=O)N(c2ccccc2)N=C1C] |
| 214 | 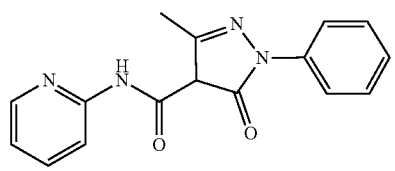 [SMILES: CC1=NN(c2ccccc2)C(=O)C1C(=O)Nc1ccccn1] |

215 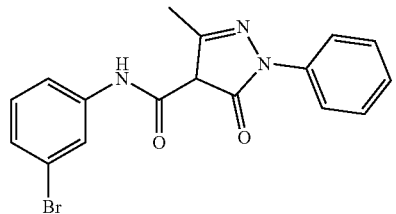
216 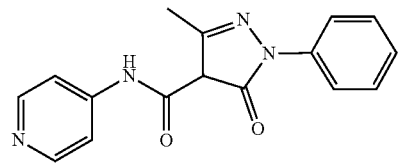 [SMILES: CC1=NN(c2ccccc2)C(=O)C1C(=O)Nc1ccncc1]
217 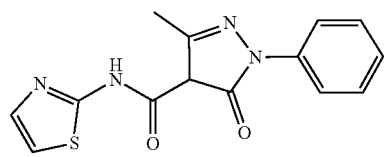 [SMILES: CC1=NN(c2ccccc2)C(=O)C1C(=O)Nc1nccs1]
218 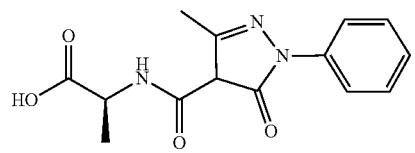 [SMILES: CC1=NN(c2ccccc2)C(=O)C1C(=O)N[C@@H](C)C(=O)O]
219 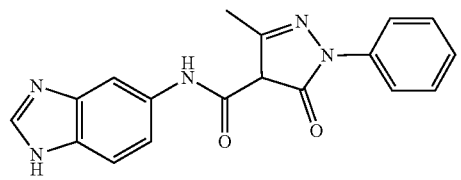 [SMILES: CC1=NN(c2ccccc2)C(=O)C1C(=O)Nc1ccc2[nH]cnc2c1]
220 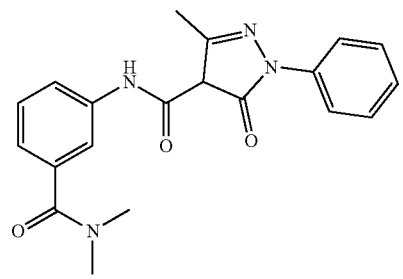 [SMILES: CC1=NN(c2ccccc2)C(=O)C1C(=O)Nc1cccc(C(=O)N(C)C)c1]
221 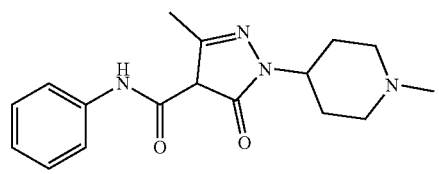 [SMILES: CC1=NN(C2CCN(C)CC2)C(=O)C1C(=O)Nc1ccccc1]
222 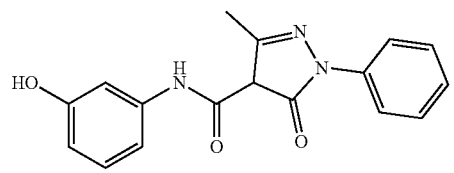 [SMILES: CC1=NN(c2ccccc2)C(=O)C1C(=O)Nc1cccc(O)c1]

223 
224 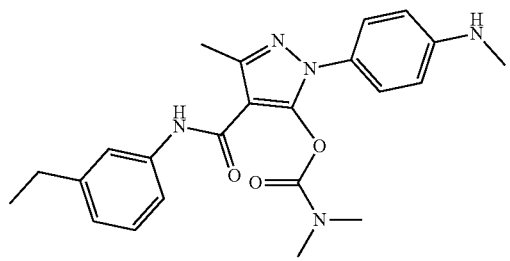 [SMILES: CCc1cccc(NC(=O)c2c(C)nn(-c3ccc(NC)cc3)c2OC(=O)N(C)C)c1]
226 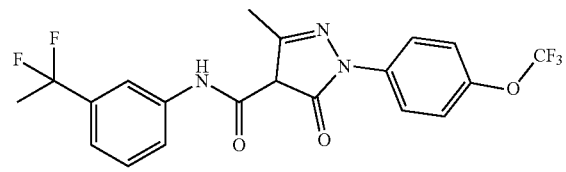
227 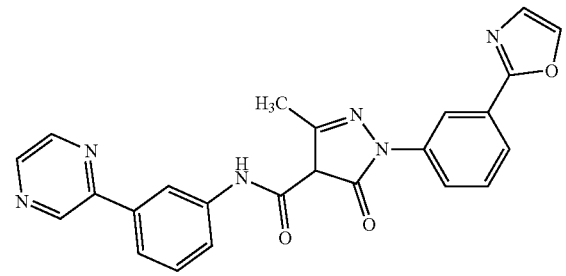 [SMILES: CC1=NN(c2cccc(-c3ncco3)c2)C(=O)C1C(=O)Nc1cccc(-c2cnccn2)c1]
228 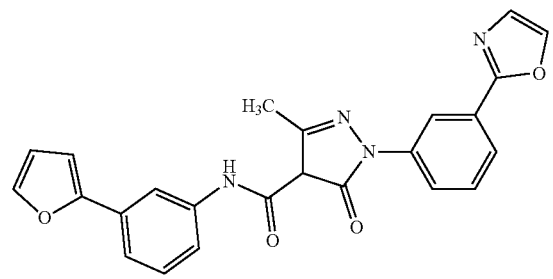 [SMILES: CC1=NN(c2cccc(-c3ncco3)c2)C(=O)C1C(=O)Nc1cccc(-c2ccco2)c1]
229 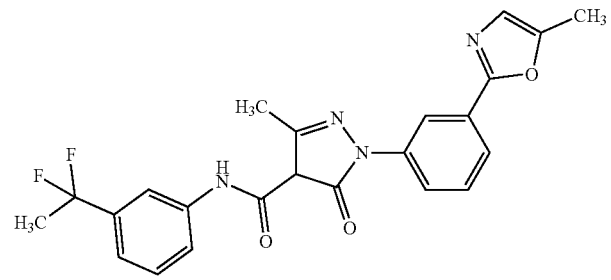 [SMILES: CC1=NN(c2cccc(-c3ncc(C)o3)c2)C(=O)C1C(=O)Nc1cccc(C(C)(F)F)c1]

230 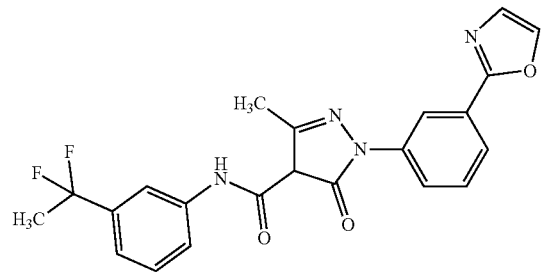 [SMILES: CC1=NN(c2cccc(-c3ncco3)c2)C(=O)C1C(=O)Nc1cccc(C(C)(F)F)c1]
231 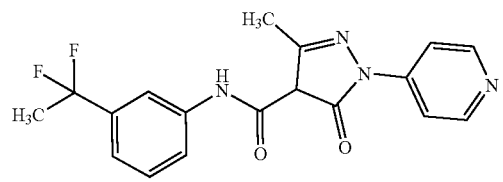 [SMILES: CC1=NN(c2ccncc2)C(=O)C1C(=O)Nc1cccc(C(C)(F)F)c1]
232 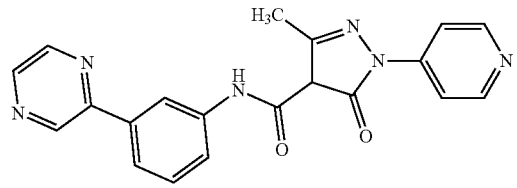 [SMILES: CC1=NN(c2ccncc2)C(=O)C1C(=O)Nc1cccc(-c2cnccn2)c1]
233 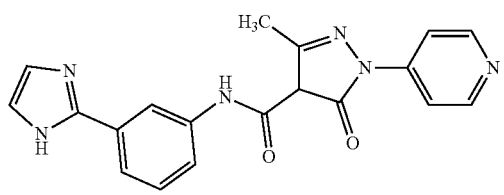 [SMILES: CC1=NN(c2ccncc2)C(=O)C1C(=O)Nc1cccc(-c2ncc[nH]2)c1]
234 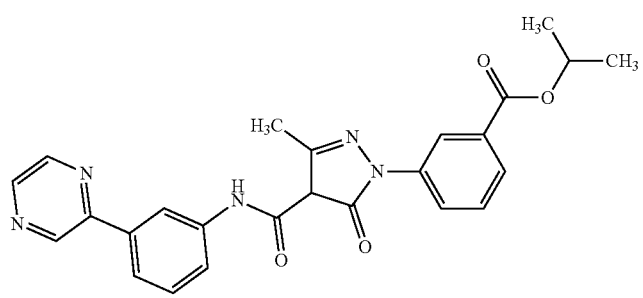 [SMILES: CC1=NN(c2cccc(C(=O)OC(C)C)c2)C(=O)C1C(=O)Nc1cccc(-c2cnccn2)c1]
235 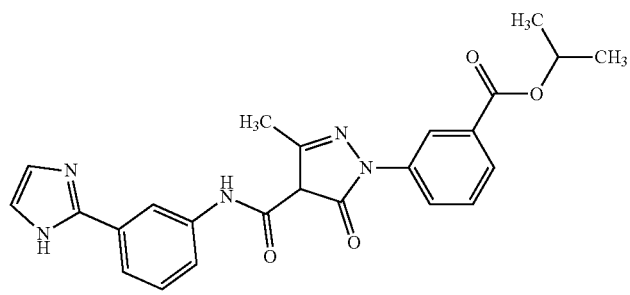 [SMILES: CC1=NN(c2cccc(C(=O)OC(C)C)c2)C(=O)C1C(=O)Nc1cccc(-c2ncc[nH]2)c1]

236 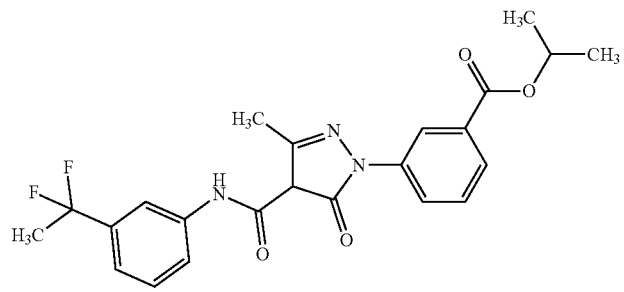 [SMILES: CC1=NN(c2cccc(C(=O)OC(C)C)c2)C(=O)C1C(=O)Nc1cccc(C(C)(F)F)c1]
237 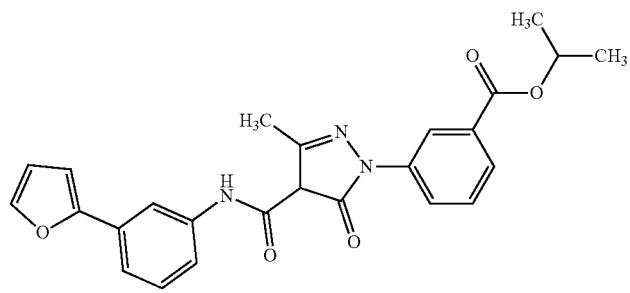 [SMILES: CC1=NN(c2cccc(C(=O)OC(C)C)c2)C(=O)C1C(=O)Nc1cccc(-c2ccco2)c1]
238 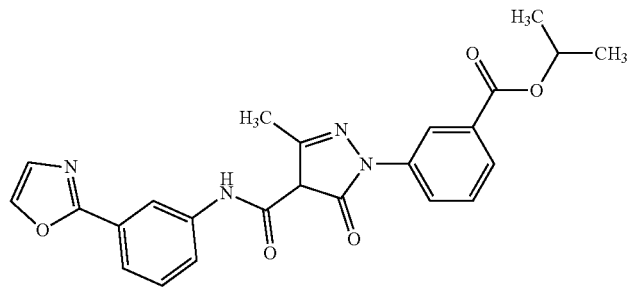 [SMILES: CC1=NN(c2cccc(C(=O)OC(C)C)c2)C(=O)C1C(=O)Nc1cccc(-c2ncco2)c1]
239 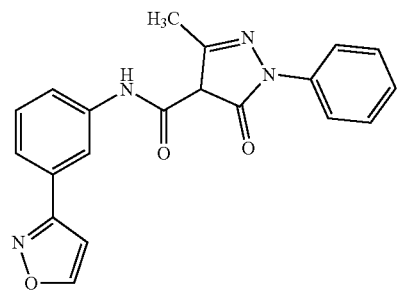 [SMILES: CC1=NN(c2ccccc2)C(=O)C1C(=O)Nc1cccc(-c2ccon2)c1]
240 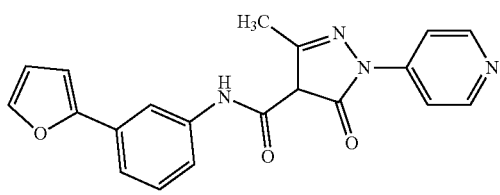 [SMILES: CC1=NN(c2ccncc2)C(=O)C1C(=O)Nc1cccc(-c2ccco2)c1]
241 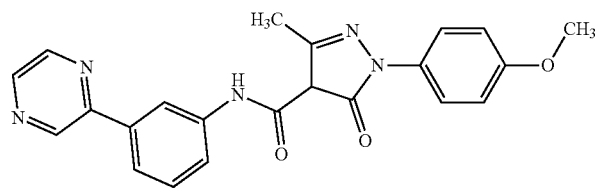 [SMILES: COc1ccc(N2N=C(C)C(C(=O)Nc3cccc(-c4cnccn4)c3)C2=O)cc1]

242 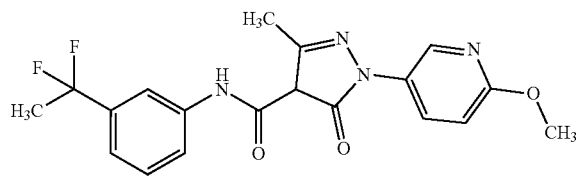 [SMILES: COc1ccc(N2N=C(C)C(C(=O)Nc3cccc(C(C)(F)F)c3)C2=O)cn1]
243 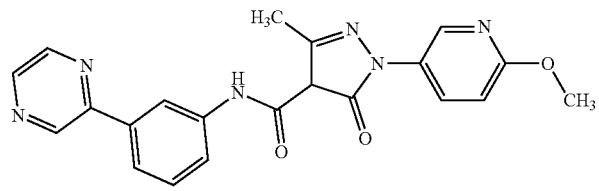
244 
245 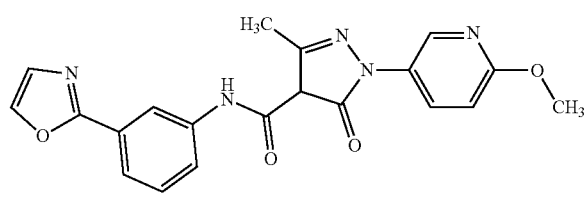 [SMILES: COc1ccc(N2N=C(C)C(C(=O)Nc3cccc(-c4ncco4)c3)C2=O)cn1]
246 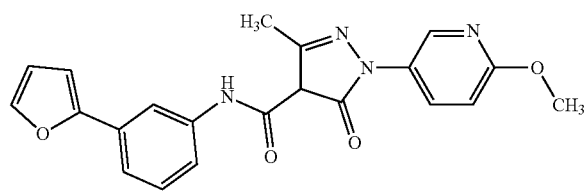 [SMILES: COc1ccc(N2N=C(C)C(C(=O)Nc3cccc(-c4ccco4)c3)C2=O)cn1]
247 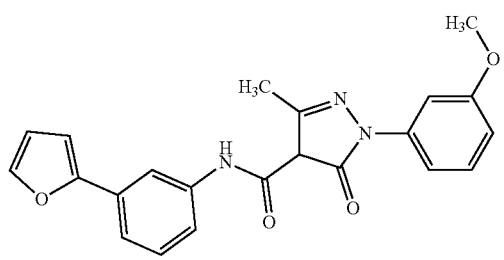 [SMILES: COc1cccc(N2N=C(C)C(C(=O)Nc3cccc(-c4ccco4)c3)C2=O)c1]
248 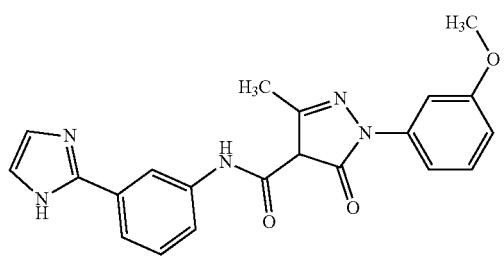 [SMILES: COc1cccc(N2N=C(C)C(C(=O)Nc3cccc(-c4ncc[nH]4)c3)C2=O)c1]

-continued
249
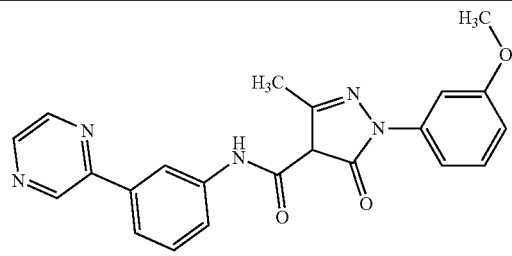
250
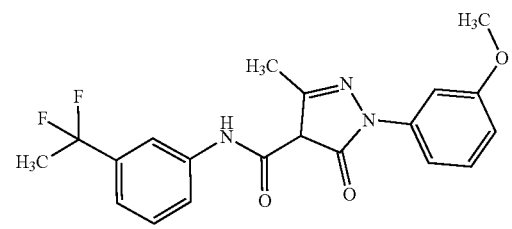 [SMILES: COc1cccc(N2N=C(C)C(C(=O)Nc3cccc(C(C)(F)F)c3)C2=O)c1]
251
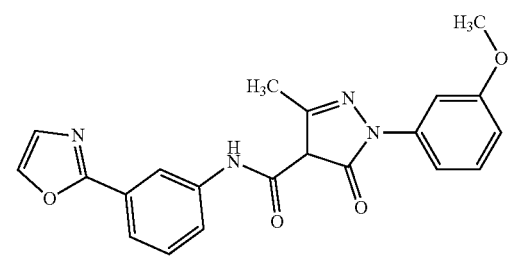 [SMILES: COc1cccc(N2N=C(C)C(C(=O)Nc3cccc(-c4ncco4)c3)C2=O)c1]
252
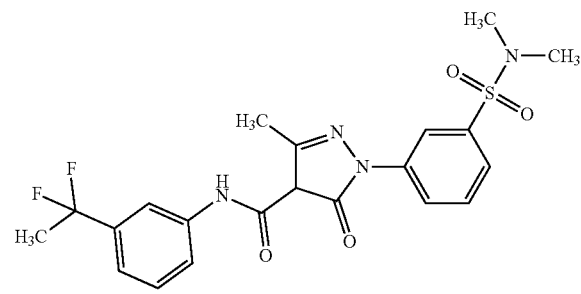 [SMILES: CC1=NN(c2cccc(S(=O)(=O)N(C)C)c2)C(=O)C1C(=O)Nc1cccc(C(C)(F)F)c1]
253
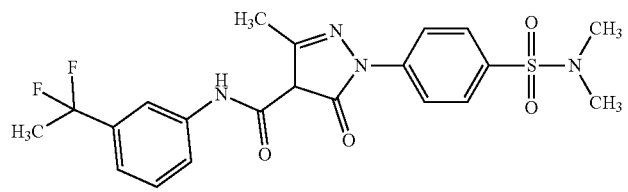 [SMILES: CC1=NN(c2ccc(S(=O)(=O)N(C)C)cc2)C(=O)C1C(=O)Nc1cccc(C(C)(F)F)c1]
254
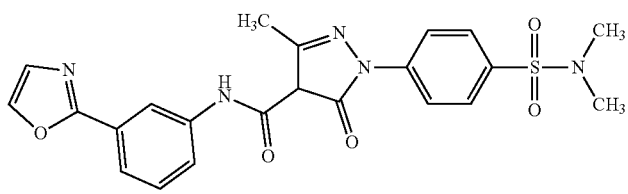 [SMILES: CC1=NN(c2ccc(S(=O)(=O)N(C)C)cc2)C(=O)C1C(=O)Nc1cccc(-c2ncco2)c1]
255
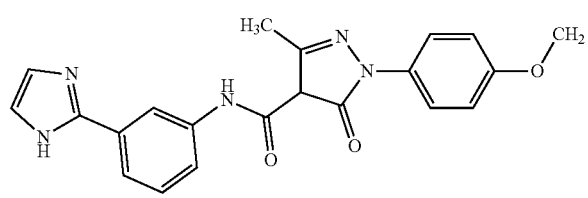 [SMILES: COc1ccc(N2N=C(C)C(C(=O)Nc3cccc(-c4ncc[nH]4)c3)C2=O)cc1]

-continued
| | |
|---|---|
| 256 | 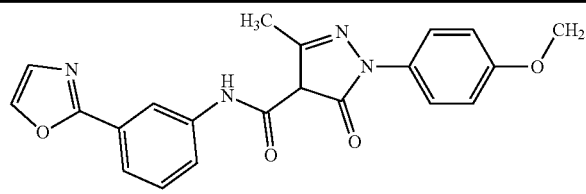 |
| 257 | 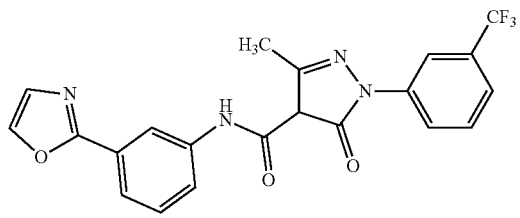 [SMILES: CC1=NN(c2cccc(C(F)(F)F)c2)C(=O)C1C(=O)Nc1cccc(-c2ncco2)c1] |
| 258 | 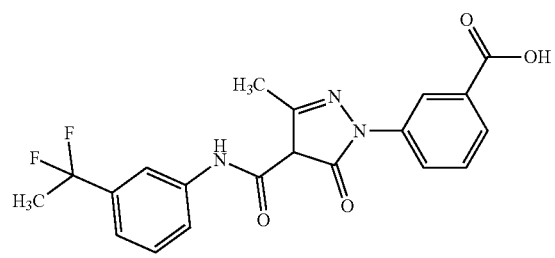 [SMILES: CC1=NN(c2cccc(C(=O)O)c2)C(=O)C1C(=O)Nc1cccc(C(C)(F)F)c1] |
| 259 | 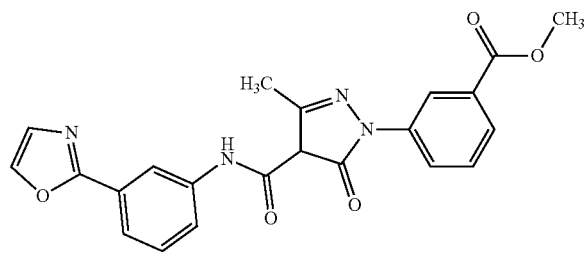 [SMILES: COC(=O)c1cccc(N2N=C(C)C(C(=O)Nc3cccc(-c4ncco4)c3)C2=O)c1] |
| 260 | 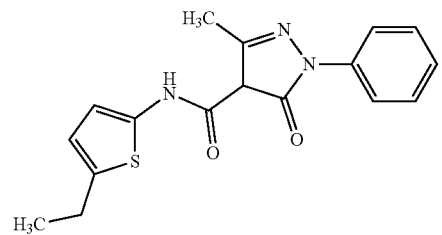 [SMILES: CCc1ccc(NC(=O)C2C(=O)N(c3ccccc3)N=C2C)s1] |
| 261 | 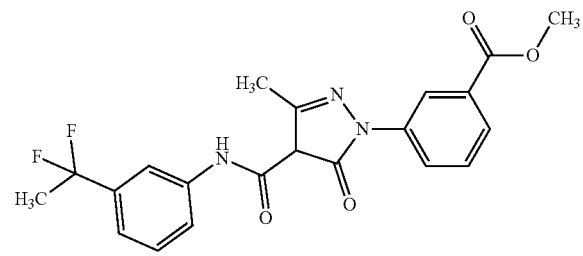 [SMILES: COC(=O)c1cccc(N2N=C(C)C(C(=O)Nc3cccc(C(C)(F)F)c3)C2=O)c1] |
| 262 | 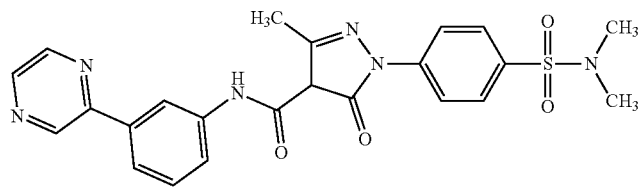 [SMILES: CC1=NN(c2ccc(S(=O)(=O)N(C)C)cc2)C(=O)C1C(=O)Nc1cccc(-c2cnccn2)c1] |

263 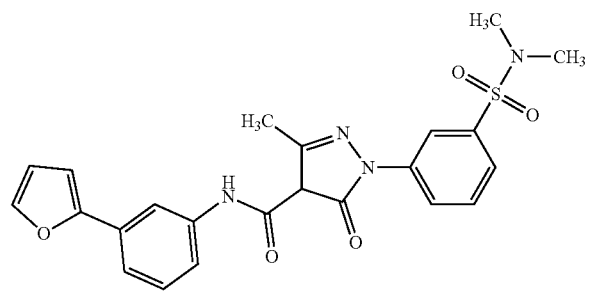 [SMILES: CC1=NN(c2cccc(S(=O)(=O)N(C)C)c2)C(=O)C1C(=O)Nc1cccc(-c2ccco2)c1]
264 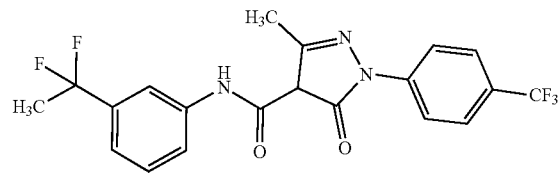 [SMILES: CC1=NN(c2ccc(C(F)(F)F)cc2)C(=O)C1C(=O)Nc1cccc(C(C)(F)F)c1]
265 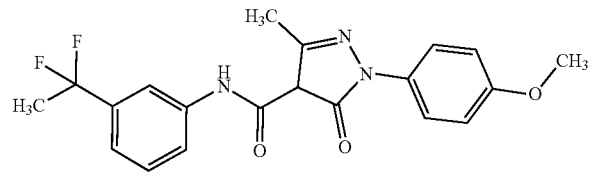 [SMILES: COc1ccc(N2N=C(C)C(C(=O)Nc3cccc(C(C)(F)F)c3)C2=O)cc1]
266 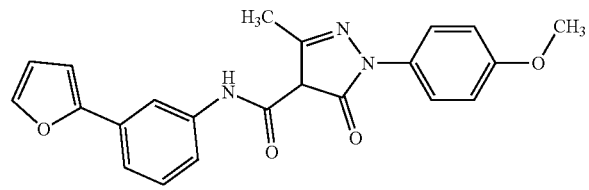
267 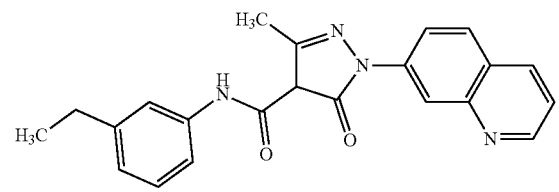 [SMILES: CCc1cccc(NC(=O)C2C(=O)N(c3ccc4cccnc4c3)N=C2C)c1]
268 
269 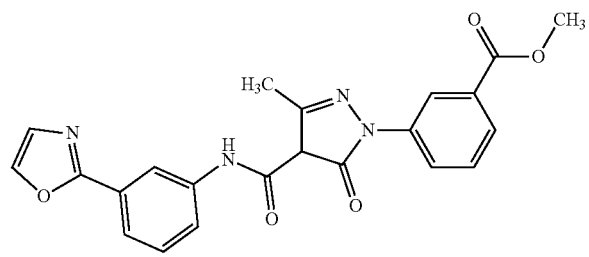 [SMILES: COC(=O)c1cccc(N2N=C(C)C(C(=O)Nc3cccc(-c4ncco4)c3)C2=O)c1]

| | |
|---|---|
| 270 | 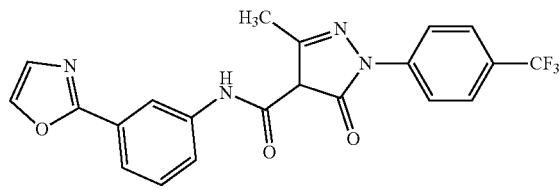 [SMILES: CC1=NN(c2ccc(C(F)(F)F)cc2)C(=O)C1C(=O)Nc1cccc(-c2ncco2)c1] |
| 271 | 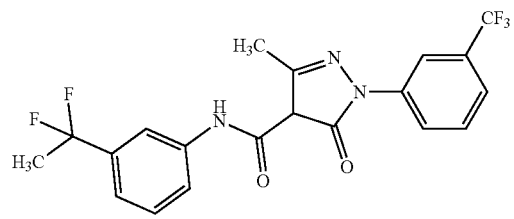 [SMILES: CC1=NN(c2cccc(C(F)(F)F)c2)C(=O)C1C(=O)Nc1cccc(C(C)(F)F)c1] |
| 272 | 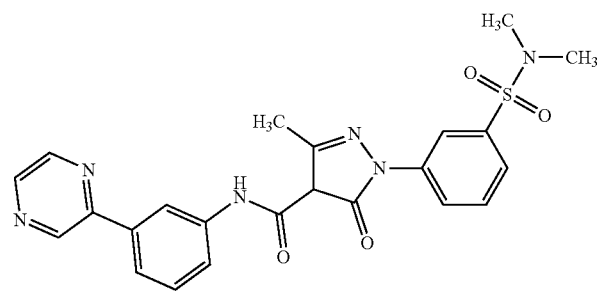 [SMILES: CC1=NN(c2cccc(S(=O)(=O)N(C)C)c2)C(=O)C1C(=O)Nc1cccc(-c2cnccn2)c1] |
| 273 | 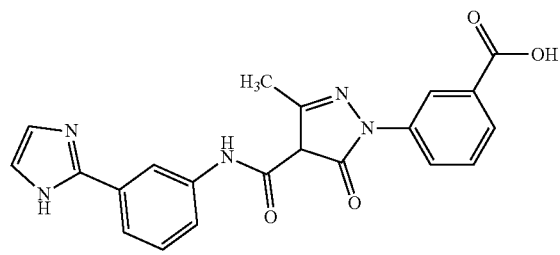 [SMILES: CC1=NN(c2cccc(C(=O)O)c2)C(=O)C1C(=O)Nc1cccc(-c2ncc[nH]2)c1] |
| 274 | 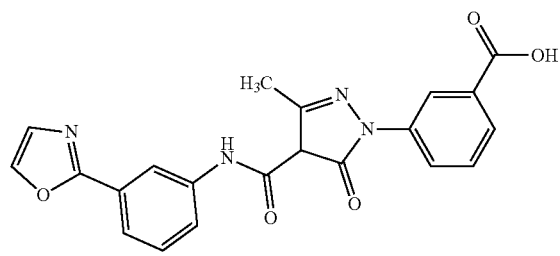 [SMILES: CC1=NN(c2cccc(C(=O)O)c2)C(=O)C1C(=O)Nc1cccc(-c2ncco2)c1] |
| 275 | 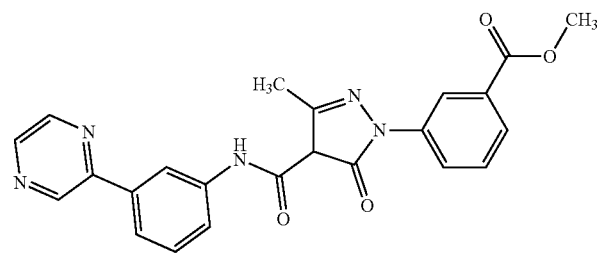 [SMILES: COC(=O)c1cccc(N2N=C(C)C(C(=O)Nc3cccc(-c4cnccn4)c3)C2=O)c1] |

276 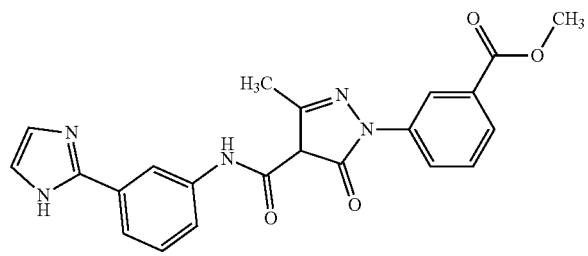 [SMILES: COC(=O)c1cccc(N2N=C(C)C(C(=O)Nc3cccc(-c4ncc[nH]4)c3)C2=O)c1]
277 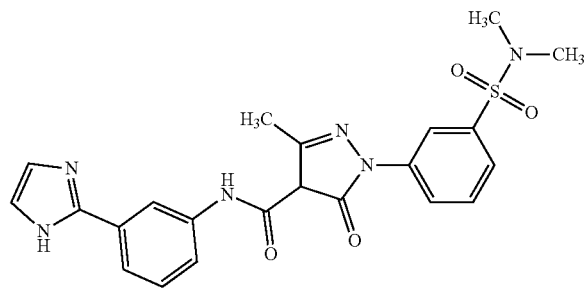 [SMILES: CC1=NN(c2cccc(S(=O)(=O)N(C)C)c2)C(=O)C1C(=O)Nc1cccc(-c2ncc[nH]2)c1]
278 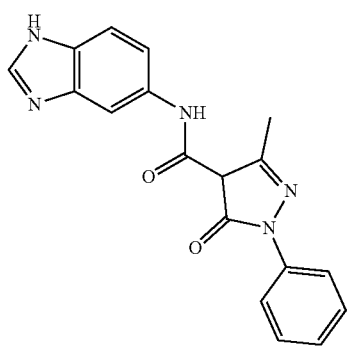 [SMILES: CC1=NN(c2ccccc2)C(=O)C1C(=O)Nc1ccc2[nH]cnc2c1]
279 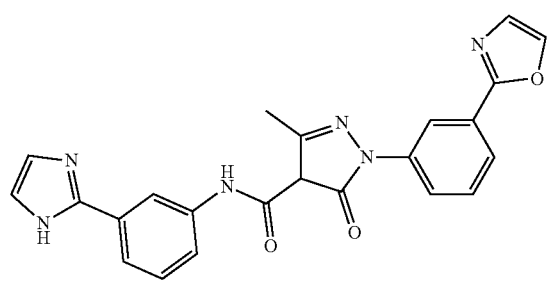 [SMILES: CC1=NN(c2cccc(-c3ncco3)c2)C(=O)C1C(=O)Nc1cccc(-c2ncc[nH]2)c1]
280 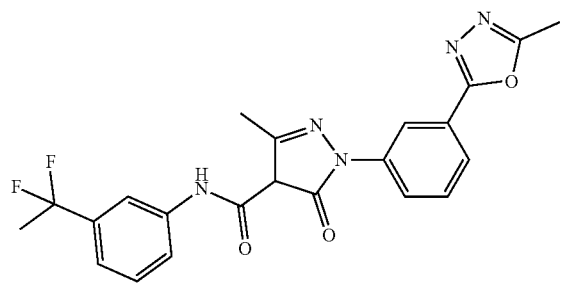

281 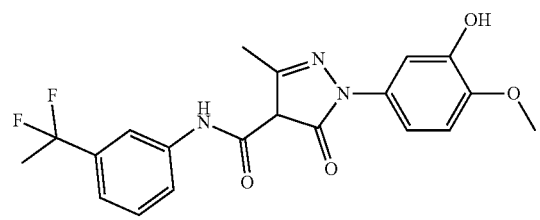 [SMILES: COc1ccc(N2N=C(C)C(C(=O)Nc3cccc(C(C)(F)F)c3)C2=O)cc1O]
282 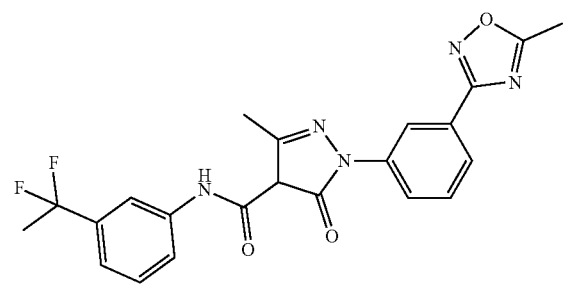 [SMILES: CC1=NN(c2cccc(-c3noc(C)n3)c2)C(=O)C1C(=O)Nc1cccc(C(C)(F)F)c1]
283 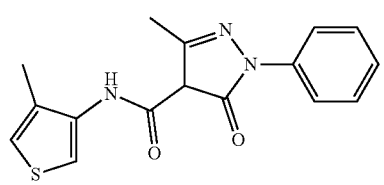 [SMILES: CC1=NN(c2ccccc2)C(=O)C1C(=O)Nc1cscc1C]
284 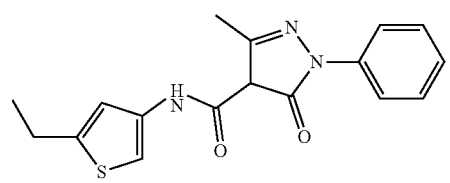
285 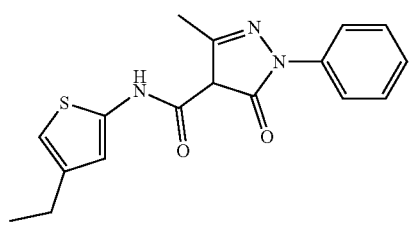 [SMILES: CCc1csc(NC(=O)C2C(=O)N(c3ccccc3)N=C2C)c1]
286 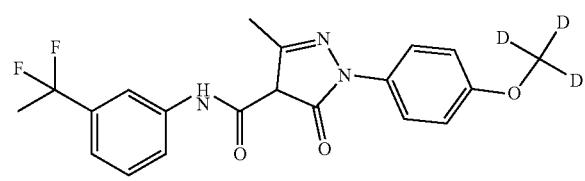 [SMILES: [2H]C([2H])([2H])Oc1ccc(N2N=C(C)C(C(=O)Nc3cccc(C(C)(F)F)c3)C2=O)cc1]
287 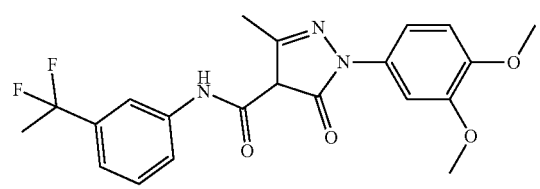 [SMILES: COc1ccc(N2N=C(C)C(C(=O)Nc3cccc(C(C)(F)F)c3)C2=O)cc1OC]

288 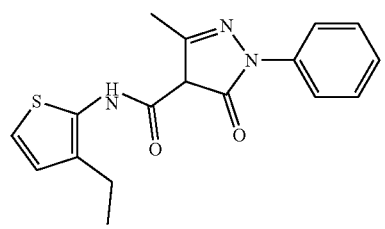 [SMILES: CCc1ccsc1NC(=O)C1C(=O)N(c2ccccc2)N=C1C]
289 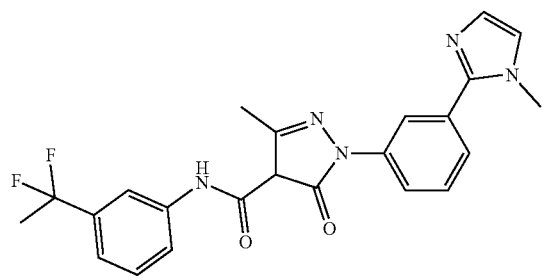 [SMILES: CC1=NN(c2cccc(-c3nccn3C)c2)C(=O)C1C(=O)Nc1cccc(C(C)(F)F)c1]
290 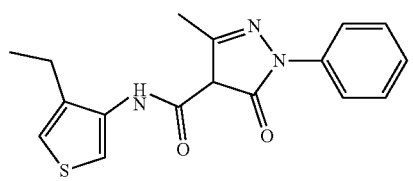 [SMILES: CCc1cscc1NC(=O)C1C(=O)N(c2ccccc2)N=C1C]
291 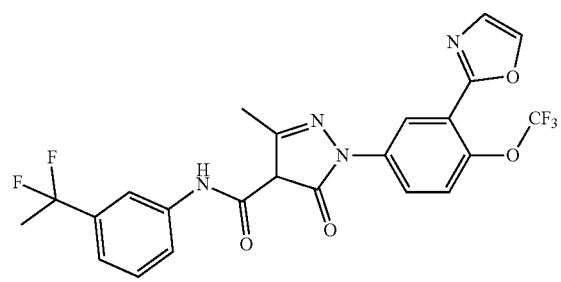 [SMILES: CC1=NN(c2ccc(OC(F)(F)F)c(-c3ncco3)c2)C(=O)C1C(=O)Nc1cccc(C(C)(F)F)c1]
292 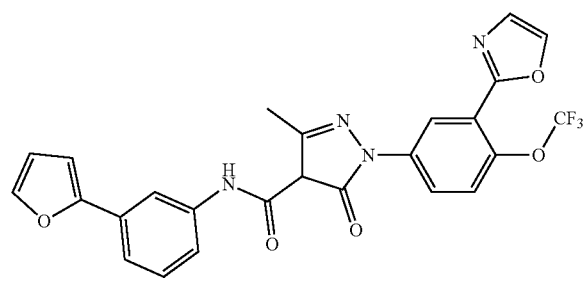 [SMILES: CC1=NN(c2ccc(OC(F)(F)F)c(-c3ncco3)c2)C(=O)C1C(=O)Nc1cccc(-c2ccco2)c1]
293 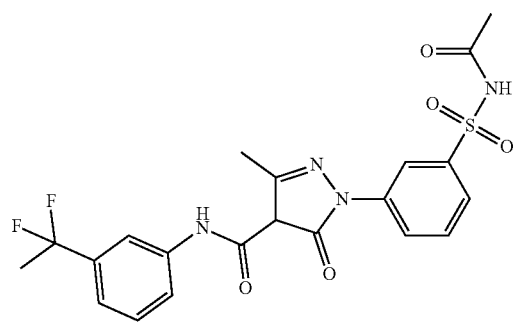 [SMILES: CC(=O)NS(=O)(=O)c1cccc(N2N=C(C)C(C(=O)Nc3cccc(C(C)(F)F)c3)C2=O)c1]

-continued
294
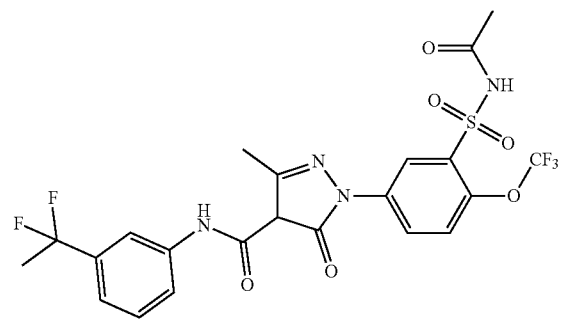 [SMILES: CC(=O)NS(=O)(=O)c1cc(N2N=C(C)C(C(=O)Nc3cccc(C(C)(F)F)c3)C2=O)ccc1OC(F)(F)F]
295
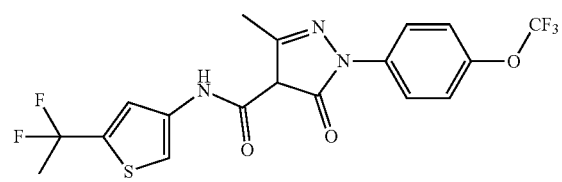 [SMILES: CC1=NN(c2ccc(OC(F)(F)F)cc2)C(=O)C1C(=O)Nc1csc(C(C)(F)F)c1]
296
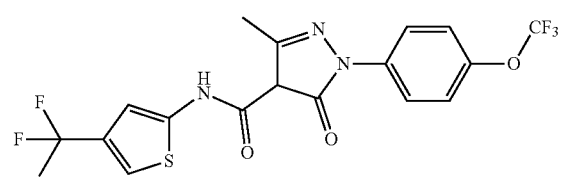 [SMILES: CC1=NN(c2ccc(OC(F)(F)F)cc2)C(=O)C1C(=O)Nc1cc(C(C)(F)F)cs1]
297
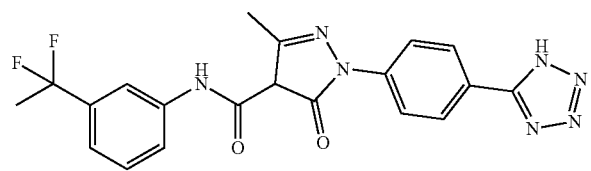 [SMILES: CC1=NN(c2ccc(-c3nnn[nH]3)cc2)C(=O)C1C(=O)Nc1cccc(C(C)(F)F)c1]
298
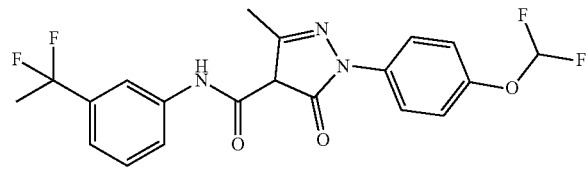 [SMILES: CC1=NN(c2ccc(OC(F)F)cc2)C(=O)C1C(=O)Nc1cccc(C(C)(F)F)c1]
299
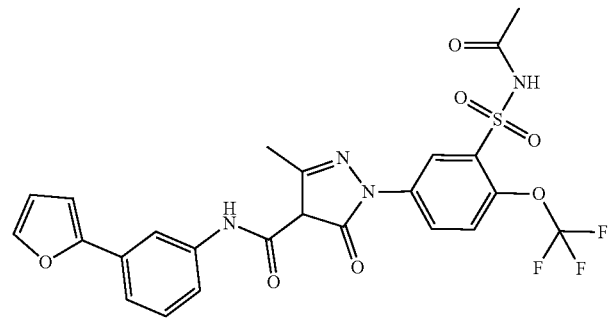 [SMILES: CC(=O)NS(=O)(=O)c1cc(N2N=C(C)C(C(=O)Nc3cccc(-c4ccco4)c3)C2=O)ccc1OC(F)(F)F]

300 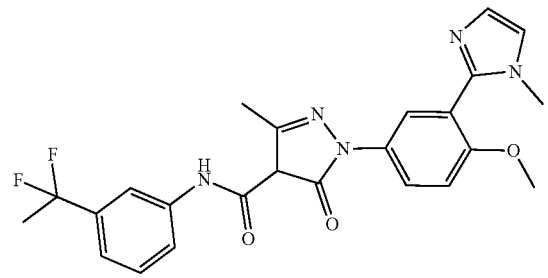 [SMILES: COc1ccc(N2N=C(C)C(C(=O)Nc3cccc(C(C)(F)F)c3)C2=O)cc1-c1nccn1C]
301 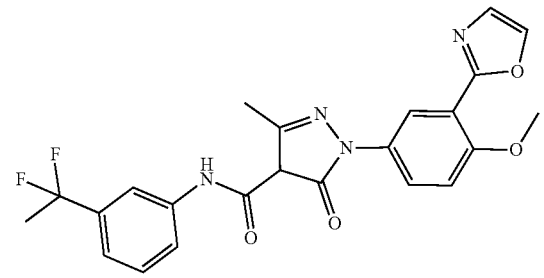 [SMILES: COc1ccc(N2N=C(C)C(C(=O)Nc3cccc(C(C)(F)F)c3)C2=O)cc1-c1ncco1]
302 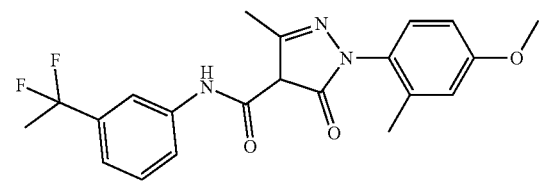
303 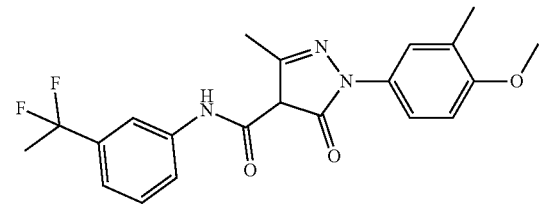 [SMILES: COc1ccc(N2N=C(C)C(C(=O)Nc3cccc(C(C)(F)F)c3)C2=O)cc1C]
304 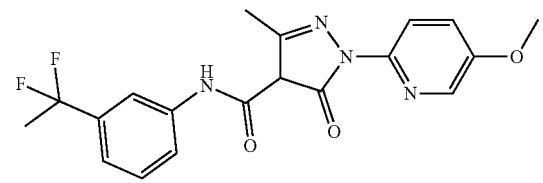
305 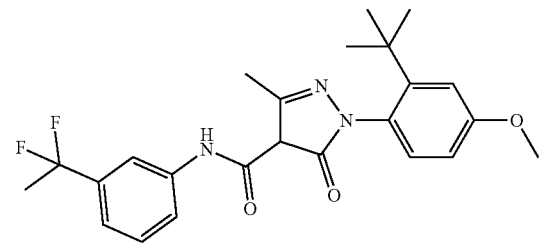 [SMILES: COc1ccc(N2N=C(C)C(C(=O)Nc3cccc(C(C)(F)F)c3)C2=O)c(C(C)(C)C)c1]
306 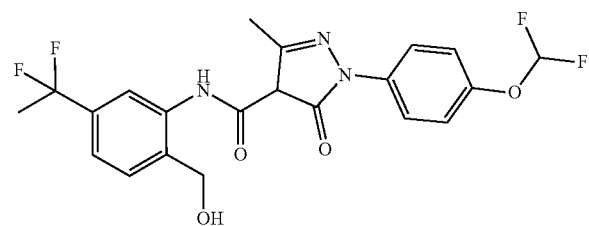 [SMILES: CC1=NN(c2ccc(OC(F)F)cc2)C(=O)C1C(=O)Nc1cc(C(C)(F)F)ccc1CO]

307 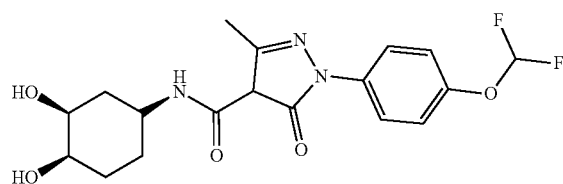
308 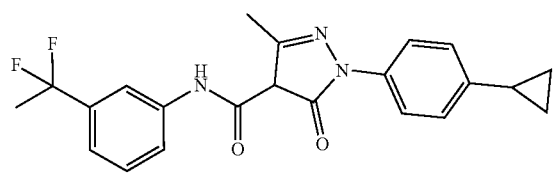 [SMILES: CC1=NN(c2ccc(C3CC3)cc2)C(=O)C1C(=O)Nc1cccc(C(C)(F)F)c1]
309 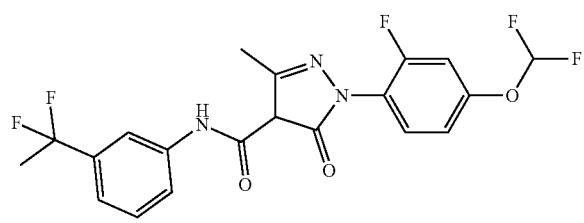 [SMILES: CC1=NN(c2ccc(OC(F)F)cc2F)C(=O)C1C(=O)Nc1cccc(C(C)(F)F)c1]
310 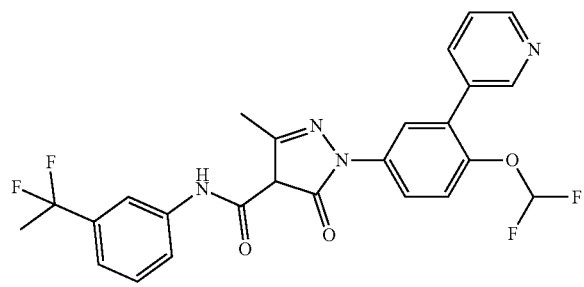 [SMILES: CC1=NN(c2ccc(OC(F)F)c(-c3cccnc3)c2)C(=O)C1C(=O)Nc1cccc(C(C)(F)F)c1]
311 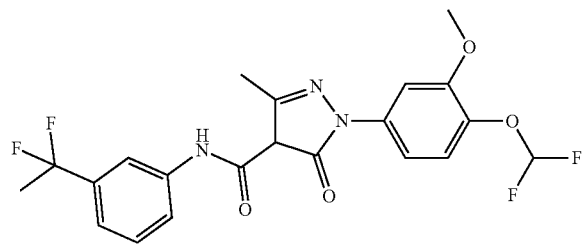 [SMILES: COc1cc(N2N=C(C)C(C(=O)Nc3cccc(C(C)(F)F)c3)C2=O)ccc1OC(F)F]
312 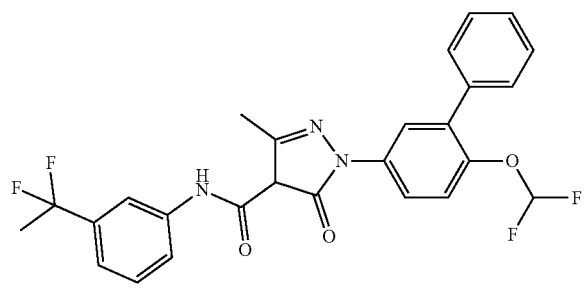

313 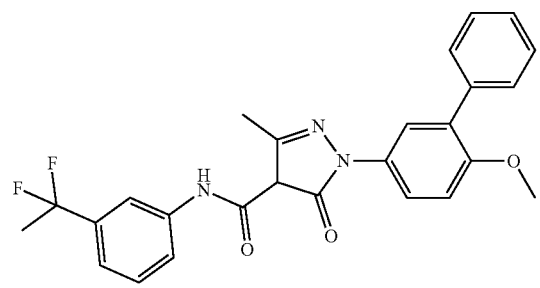 [SMILES: COc1ccc(N2N=C(C)C(C(=O)Nc3cccc(C(C)(F)F)c3)C2=O)cc1-c1ccccc1]
314 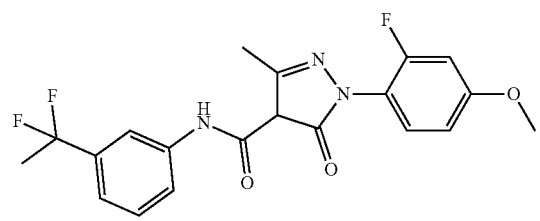 [SMILES: COc1ccc(N2N=C(C)C(C(=O)Nc3cccc(C(C)(F)F)c3)C2=O)c(F)c1]
315 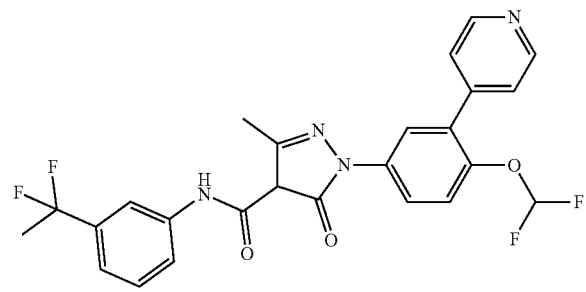
316 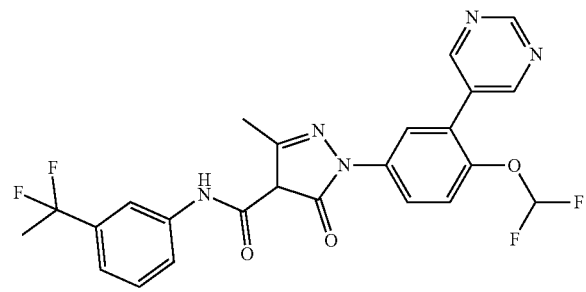
317 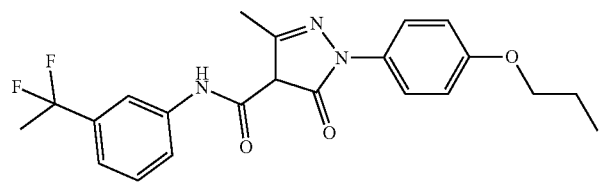 [SMILES: CCCOc1ccc(N2N=C(C)C(C(=O)Nc3cccc(C(C)(F)F)c3)C2=O)cc1]
318 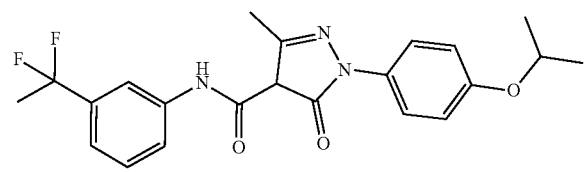 [SMILES: CC1=NN(c2ccc(OC(C)C)cc2)C(=O)C1C(=O)Nc1cccc(C(C)(F)F)c1]

| | |
|---|---|
| 319 | 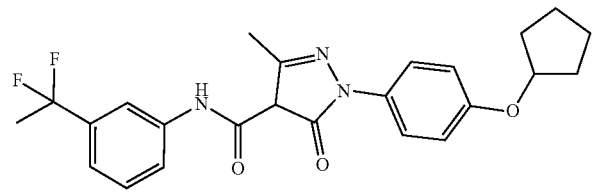 [SMILES: CC1=NN(c2ccc(OC3CCCC3)cc2)C(=O)C1C(=O)Nc1cccc(C(C)(F)F)c1] |
| 320 | 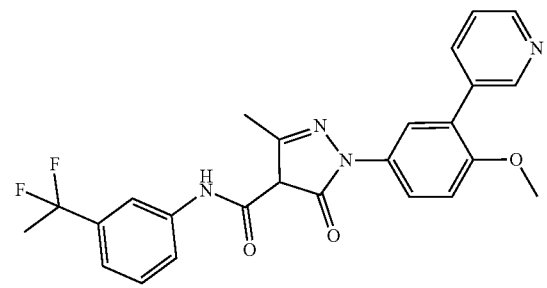 [SMILES: COc1ccc(N2N=C(C)C(C(=O)Nc3cccc(C(C)(F)F)c3)C2=O)cc1-c1cccnc1] |
| 321 | 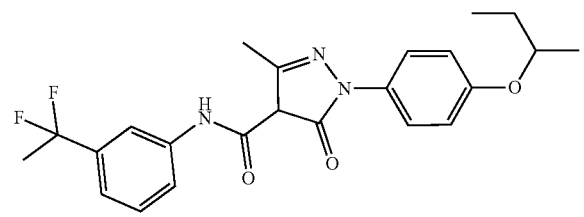 [SMILES: CCC(C)Oc1ccc(N2N=C(C)C(C(=O)Nc3cccc(C(C)(F)F)c3)C2=O)cc1] |
| 322 | 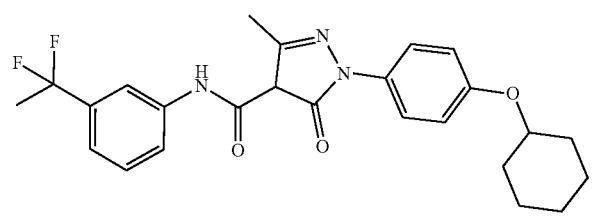 [SMILES: CC1=NN(c2ccc(OC3CCCCC3)cc2)C(=O)C1C(=O)Nc1cccc(C(C)(F)F)c1] |
| 323 | 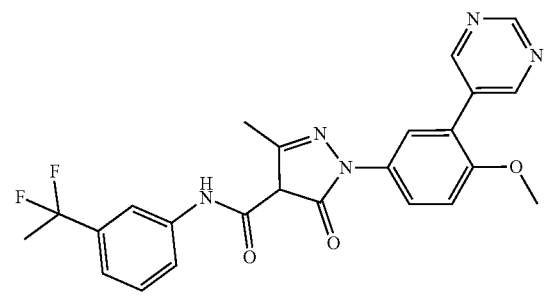 [SMILES: COc1ccc(N2N=C(C)C(C(=O)Nc3cccc(C(C)(F)F)c3)C2=O)cc1-c1cncnc1] |
| 324 | 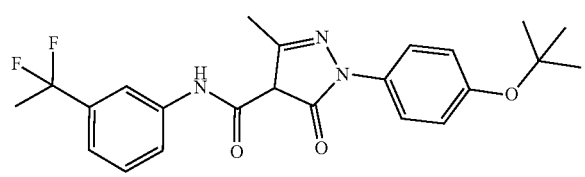 [SMILES: CC1=NN(c2ccc(OC(C)(C)C)cc2)C(=O)C1C(=O)Nc1cccc(C(C)(F)F)c1] |
| 325 | 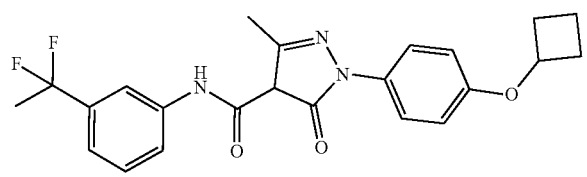 [SMILES: CC1=NN(c2ccc(OC3CCC3)cc2)C(=O)C1C(=O)Nc1cccc(C(C)(F)F)c1] |

| | |
|---|---|
| 326 | 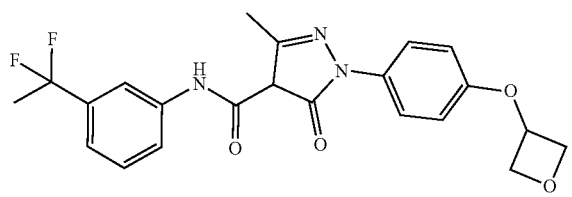 [SMILES: CC1=NN(c2ccc(OC3COC3)cc2)C(=O)C1C(=O)Nc1cccc(C(C)(F)F)c1] |
| 327 | 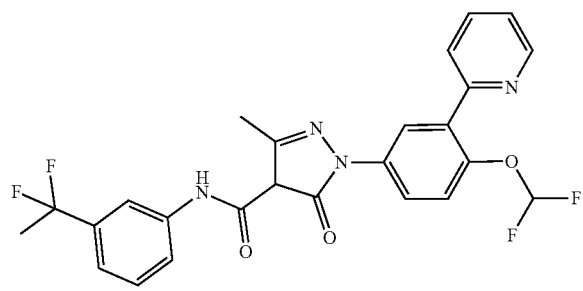 [SMILES: CC1=NN(c2ccc(OC(F)F)c(-c3ccccn3)c2)C(=O)C1C(=O)Nc1cccc(C(C)(F)F)c1] |
| 328 | 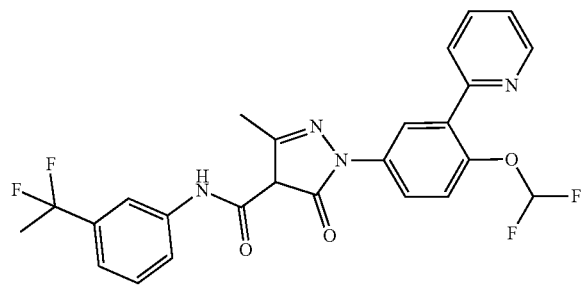 [SMILES: CC1=NN(c2ccc(OC(F)F)c(-c3ccccn3)c2)C(=O)C1C(=O)Nc1cccc(C(C)(F)F)c1] |
| 329 | 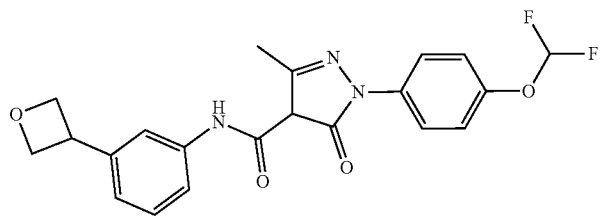 [SMILES: CC1=NN(c2ccc(OC(F)F)cc2)C(=O)C1C(=O)Nc1cccc(C2COC2)c1] |
| 330 | 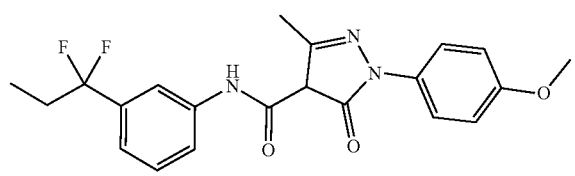 [SMILES: CCC(F)(F)c1cccc(NC(=O)C2C(=O)N(c3ccc(OC)cc3)N=C2C)c1] |
| 331 | 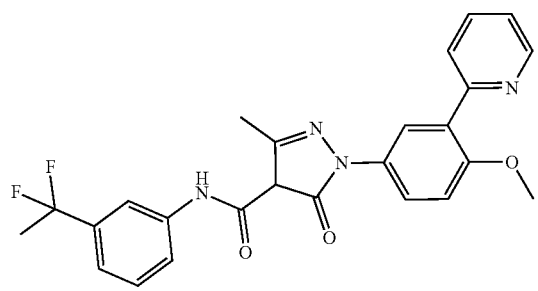 [SMILES: COc1ccc(N2N=C(C)C(C(=O)Nc3cccc(C(C)(F)F)c3)C2=O)cc1-c1ccccn1] |

332 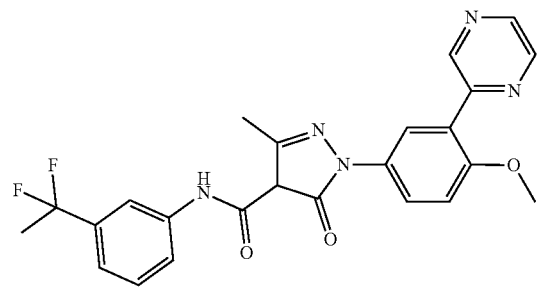 [SMILES: COc1ccc(N2N=C(C)C(C(=O)Nc3cccc(C(C)(F)F)c3)C2=O)cc1-c1cnccn1]
333 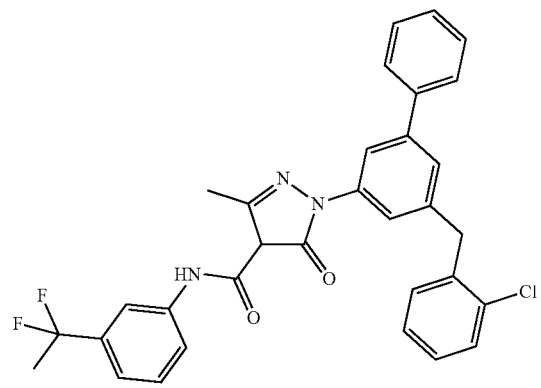 [SMILES: CC1=NN(c2cc(Cc3ccccc3Cl)cc(-c3ccccc3)c2)C(=O)C1C(=O)Nc1cccc(C(C)(F)F)c1]
334 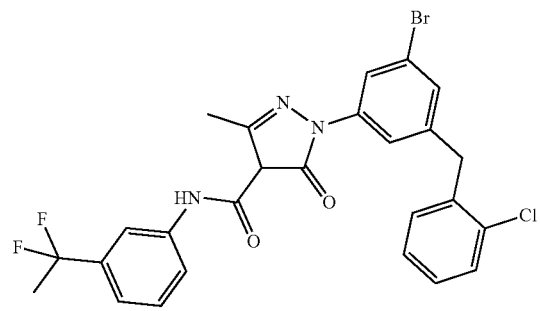 [SMILES: CC1=NN(c2cc(Br)cc(Cc3ccccc3Cl)c2)C(=O)C1C(=O)Nc1cccc(C(C)(F)F)c1]
335 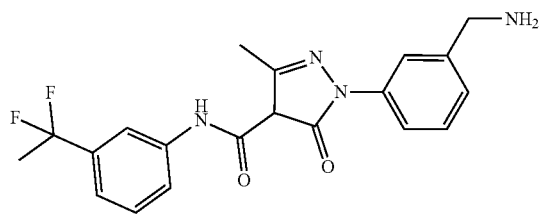 [SMILES: CC1=NN(c2cccc(CN)c2)C(=O)C1C(=O)Nc1cccc(C(C)(F)F)c1]
336 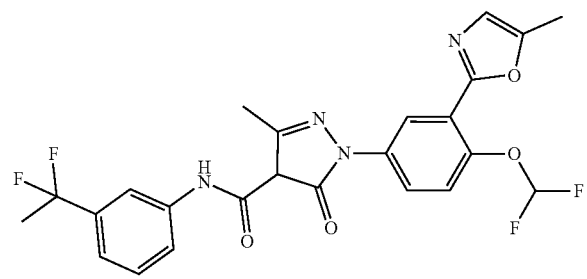 [SMILES: CC1=NN(c2ccc(OC(F)F)c(-c3ncc(C)o3)c2)C(=O)C1C(=O)Nc1cccc(C(C)(F)F)c1]

-continued
337 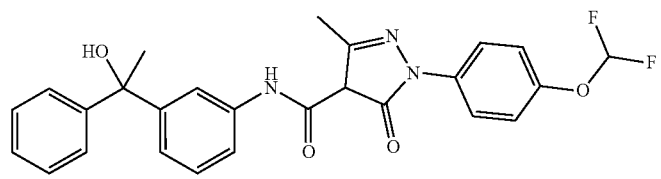 [SMILES: CC1=NN(c2ccc(OC(F)F)cc2)C(=O)C1C(=O)Nc1cccc(C(C)(O)c2ccccc2)c1]
339 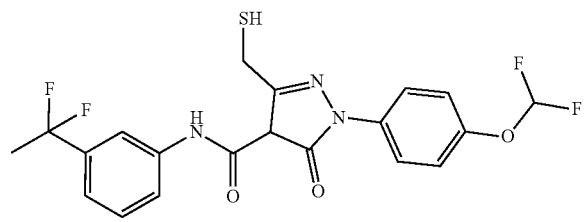 [SMILES: CC(F)(F)c1cccc(NC(=O)C2C(=O)N(c3ccc(OC(F)F)cc3)N=C2CS)c1]
340 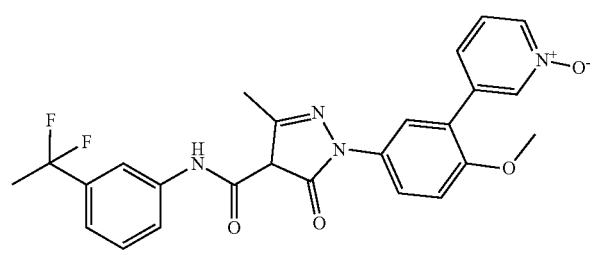 [SMILES: COc1ccc(N2N=C(C)C(C(=O)Nc3cccc(C(C)(F)F)c3)C2=O)cc1-c1ccc[n+]([O-])c1]
341 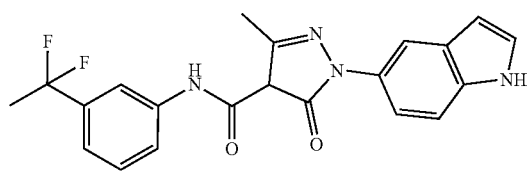 [SMILES: CC1=NN(c2ccc3[nH]ccc3c2)C(=O)C1C(=O)Nc1cccc(C(C)(F)F)c1]
342 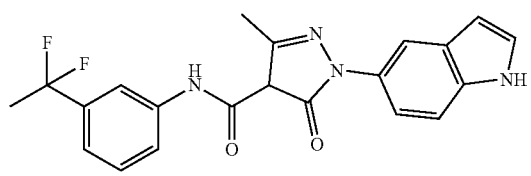 [SMILES: CC1=NN(c2ccc3[nH]ccc3c2)C(=O)C1C(=O)Nc1cccc(C(C)(F)F)c1]
343 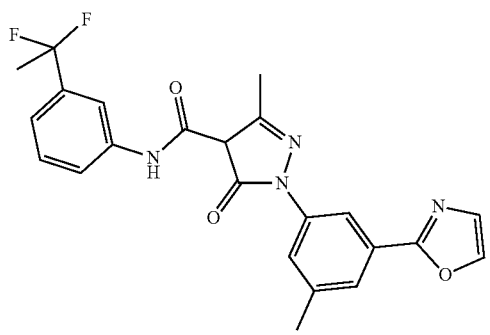 [SMILES: CC1=NN(c2cc(C)cc(-c3ncco3)c2)C(=O)C1C(=O)Nc1cccc(C(C)(F)F)c1]
344 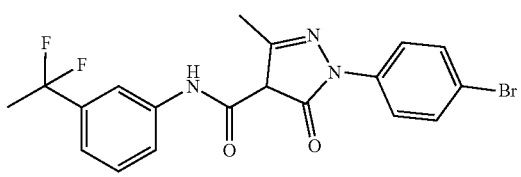 [SMILES: CC1=NN(c2ccc(Br)cc2)C(=O)C1C(=O)Nc1cccc(C(C)(F)F)c1]

345 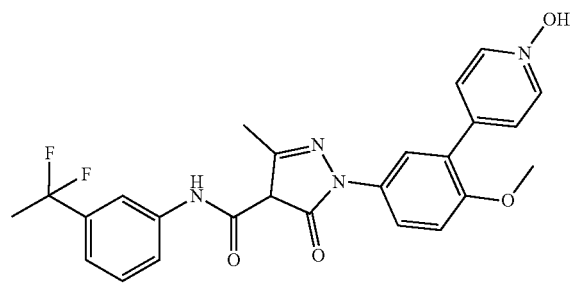
346 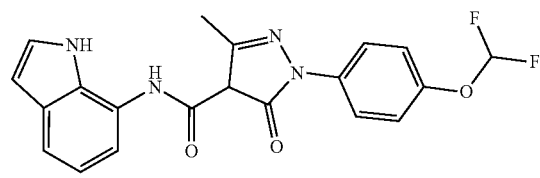 [SMILES: CC1=NN(c2ccc(OC(F)F)cc2)C(=O)C1C(=O)Nc1cccc2cc[nH]c12]
347 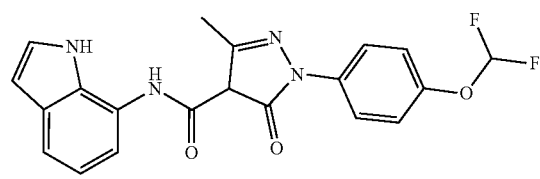 [SMILES: CC1=NN(c2ccc(OC(F)F)cc2)C(=O)C1C(=O)Nc1cccc2cc[nH]c12]
348 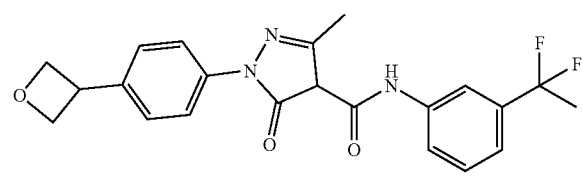 [SMILES: CC1=NN(c2ccc(C3COC3)cc2)C(=O)C1C(=O)Nc1cccc(C(C)(F)F)c1]
349 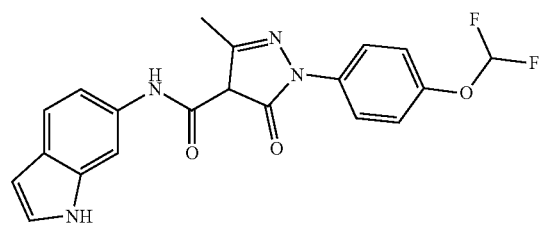 [SMILES: CC1=NN(c2ccc(OC(F)F)cc2)C(=O)C1C(=O)Nc1ccc2cc[nH]c2c1]
350 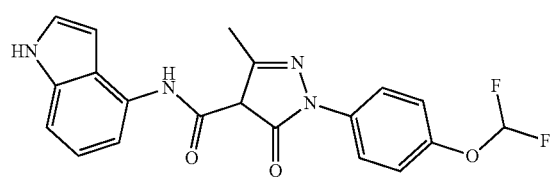 [SMILES: CC1=NN(c2ccc(OC(F)F)cc2)C(=O)C1C(=O)Nc1cccc2[nH]ccc12]
351 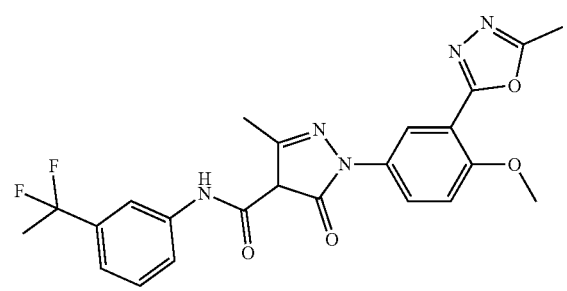 [SMILES: COc1ccc(N2N=C(C)C(C(=O)Nc3cccc(C(C)(F)F)c3)C2=O)cc1-c1nnc(C)o1]

| | |
|---|---|
| 352 | 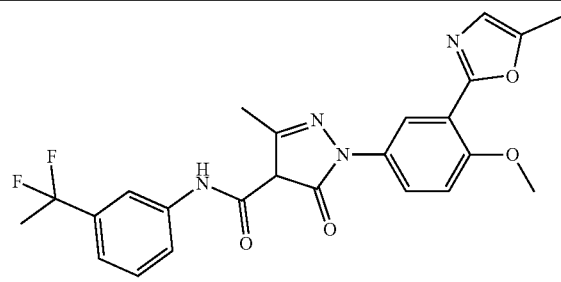 |
| 353 | 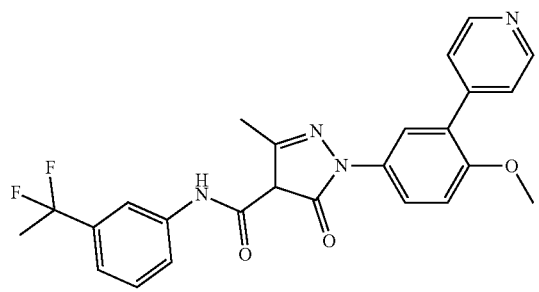 [SMILES: COc1ccc(N2N=C(C)C(C(=O)Nc3cccc(C(C)(F)F)c3)C2=O)cc1-c1ccncc1] |
| 354 | 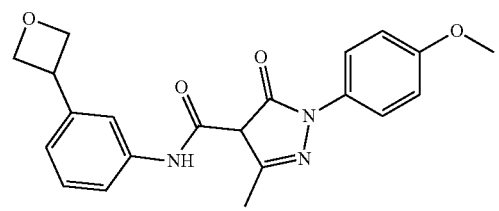 [SMILES: COc1ccc(N2N=C(C)C(C(=O)Nc3cccc(C4COC4)c3)C2=O)cc1] |
| 355 | 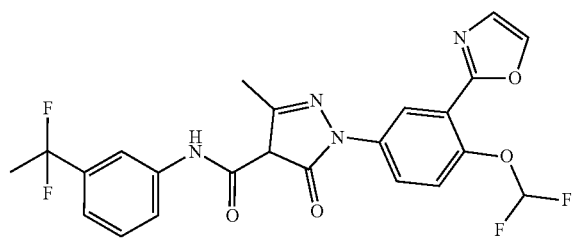 [SMILES: CC1=NN(c2ccc(OC(F)F)c(-c3ncco3)c2)C(=O)C1C(=O)Nc1cccc(C(C)(F)F)c1] |
| 356 | 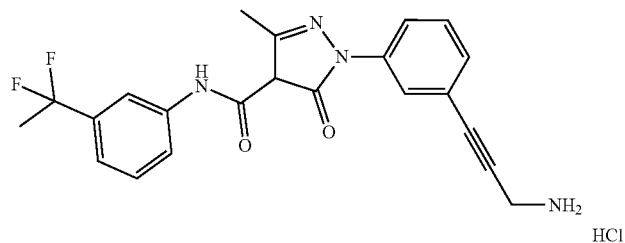 [SMILES: CC1=NN(c2cccc(C#CCN)c2)C(=O)C1C(=O)Nc1cccc(C(C)(F)F)c1 ; Cl] |
| 357 | 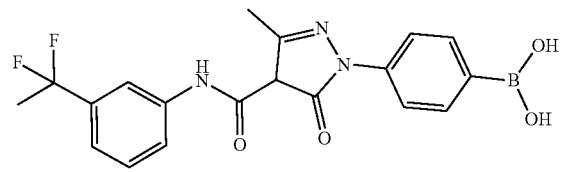 [SMILES: CC1=NN(c2ccc(B(O)O)cc2)C(=O)C1C(=O)Nc1cccc(C(C)(F)F)c1] |
| 358 | 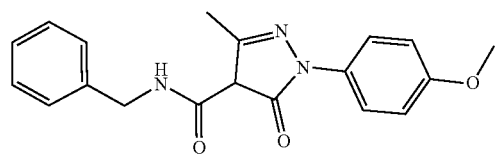 [SMILES: COc1ccc(N2N=C(C)C(C(=O)NCc3ccccc3)C2=O)cc1] |

| | |
|---|---|
| 359 | 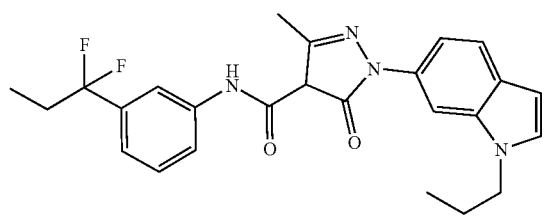 [SMILES: CCCn1ccc2ccc(N3N=C(C)C(C(=O)Nc4cccc(C(F)(F)CC)c4)C3=O)cc21] |
| 360 | 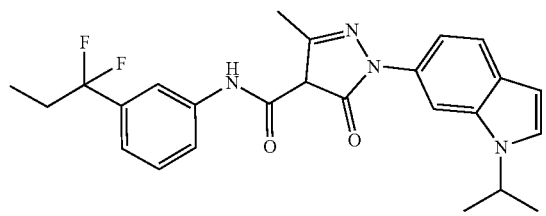 [SMILES: CCC(F)(F)c1cccc(NC(=O)C2C(=O)N(c3ccc4ccn(C(C)C)c4c3)N=C2C)c1] |
| 361 | 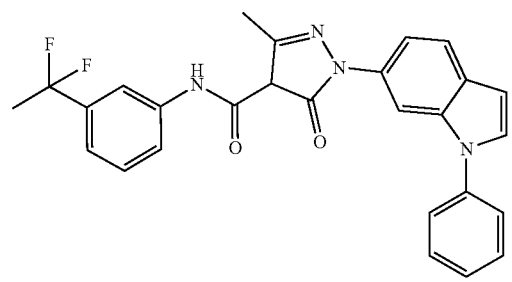 [SMILES: CC1=NN(c2ccc3ccn(-c4ccccc4)c3c2)C(=O)C1C(=O)Nc1cccc(C(C)(F)F)c1] |
| 362 | 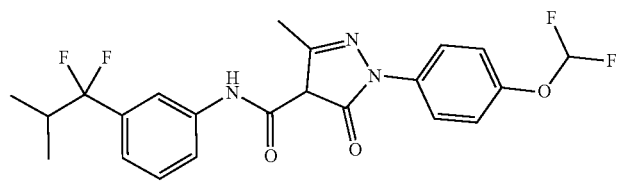 [SMILES: CC1=NN(c2ccc(OC(F)F)cc2)C(=O)C1C(=O)Nc1cccc(C(F)(F)C(C)C)c1] |
| 363 | 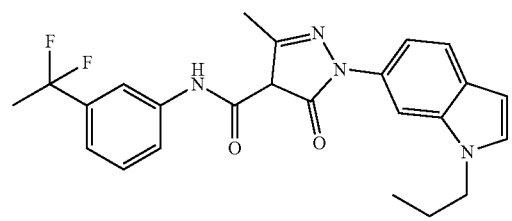 [SMILES: CCCn1ccc2ccc(N3N=C(C)C(C(=O)Nc4cccc(C(C)(F)F)c4)C3=O)cc21] |
| 364 | 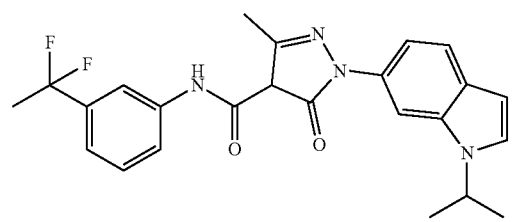 [SMILES: CC1=NN(c2ccc3ccn(C(C)C)c3c2)C(=O)C1C(=O)Nc1cccc(C(C)(F)F)c1] |

| | |
|---|---|
| 365 | 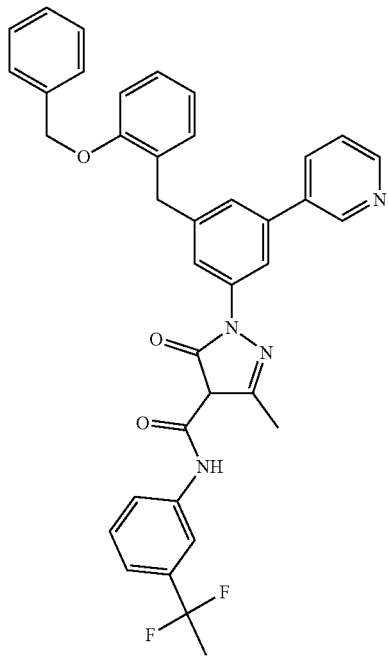 [SMILES: CC1=NN(c2cc(Cc3ccccc3OCc3ccccc3)cc(-c3cccnc3)c2)C(=O)C1C(=O)Nc1cccc(C(C)(F)F)c1] |
| 366 | 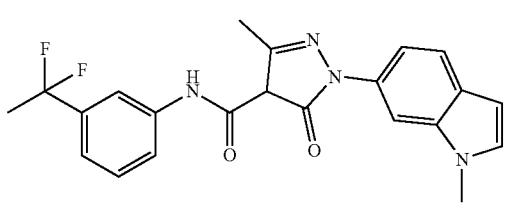 [SMILES: CC1=NN(c2ccc3ccn(C)c3c2)C(=O)C1C(=O)Nc1cccc(C(C)(F)F)c1] |
| 367 | 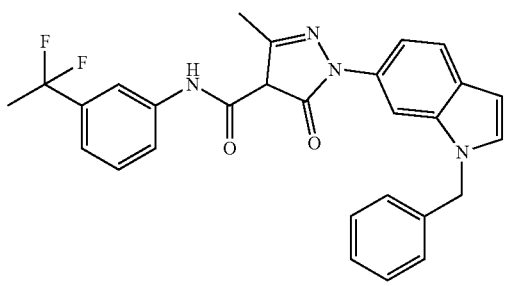 [SMILES: CC1=NN(c2ccc3ccn(Cc4ccccc4)c3c2)C(=O)C1C(=O)Nc1cccc(C(C)(F)F)c1] |
| 368 | 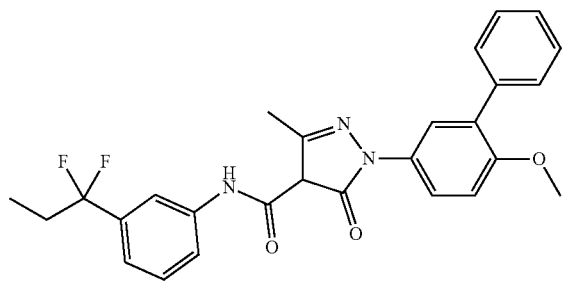 [SMILES: CCC(F)(F)c1cccc(NC(=O)C2C(=O)N(c3ccc(OC)c(-c4ccccc4)c3)N=C2C)c1] |
| 369 | 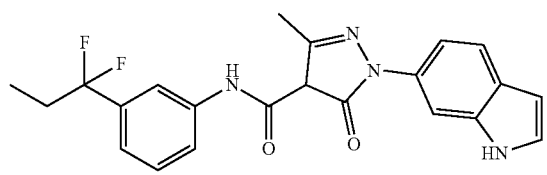 [SMILES: CCC(F)(F)c1cccc(NC(=O)C2C(=O)N(c3ccc4cc[nH]c4c3)N=C2C)c1] |

370 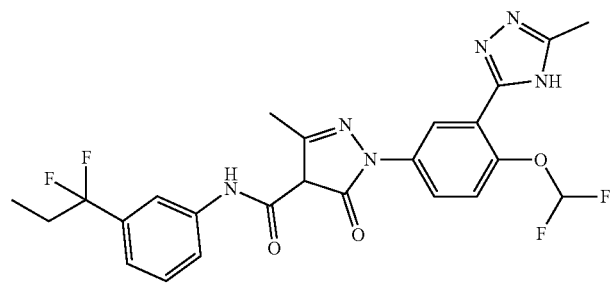 [SMILES: CCC(F)(F)c1cccc(NC(=O)C2C(=O)N(c3ccc(OC(F)F)c(-c4nnc(C)[nH]4)c3)N=C2C)c1]
371 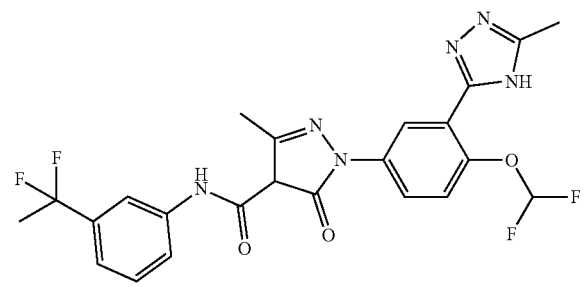 [SMILES: CC1=NN(c2ccc(OC(F)F)c(-c3nnc(C)[nH]3)c2)C(=O)C1C(=O)Nc1cccc(C(C)(F)F)c1]
372 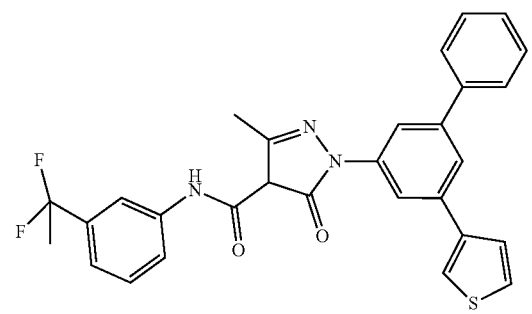 [SMILES: CC1=NN(c2cc(-c3ccccc3)cc(-c3ccsc3)c2)C(=O)C1C(=O)Nc1cccc(C(C)(F)F)c1]
373 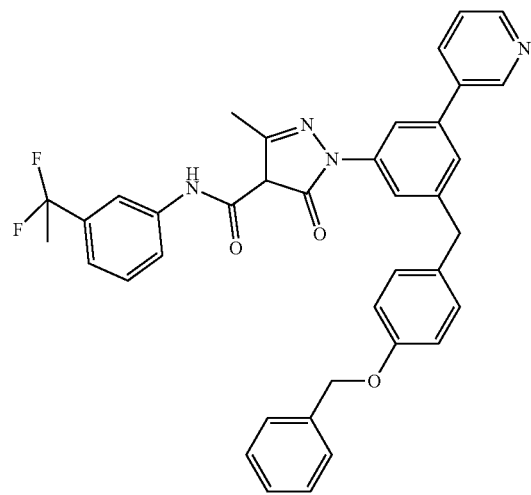 [SMILES: CC1=NN(c2cc(Cc3ccc(OCc4ccccc4)cc3)cc(-c3cccnc3)c2)C(=O)C1C(=O)Nc1cccc(C(C)(F)F)c1]

374 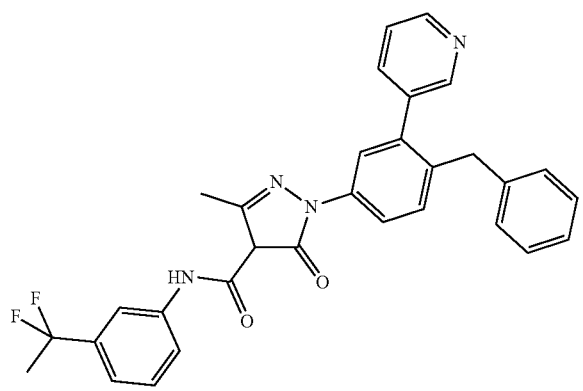 [SMILES: CC1=NN(c2ccc(Cc3ccccc3)c(-c3cccnc3)c2)C(=O)C1C(=O)Nc1cccc(C(C)(F)F)c1]
375 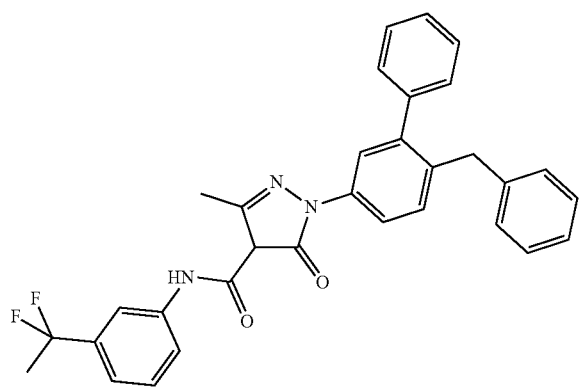 [SMILES: CC1=NN(c2ccc(Cc3ccccc3)c(-c3ccccc3)c2)C(=O)C1C(=O)Nc1cccc(C(C)(F)F)c1]
376 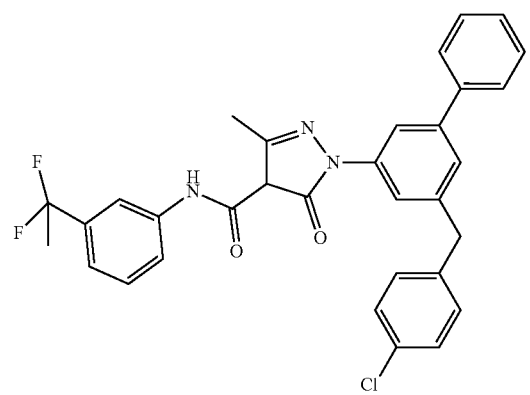 [SMILES: CC1=NN(c2cc(Cc3ccc(Cl)cc3)cc(-c3ccccc3)c2)C(=O)C1C(=O)Nc1cccc(C(C)(F)F)c1]
377 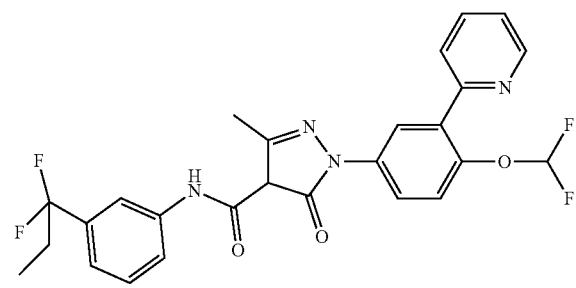 [SMILES: CCC(F)(F)c1cccc(NC(=O)C2C(=O)N(c3ccc(OC(F)F)c(-c4ccccn4)c3)N=C2C)c1]

378
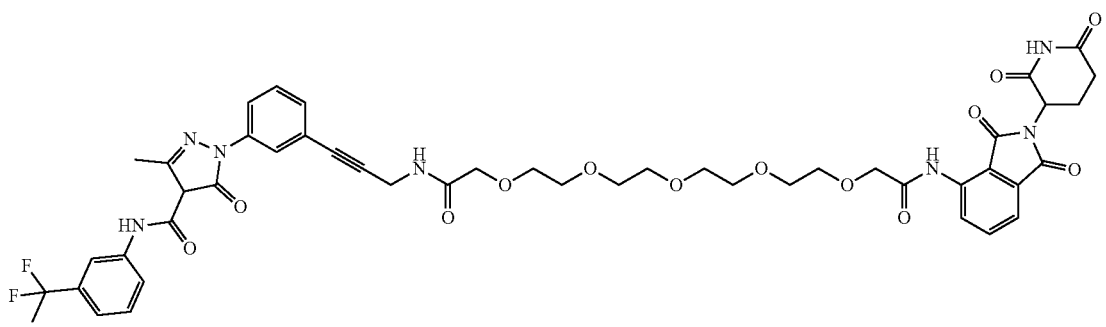 [SMILES: CC1=NN(c2cccc(C#CCNC(=O)COCCOCCOCCOCCOCC(=O)Nc3cccc4c3C(=O)N(C3CCC(=O)NC3=O)C4=O)c2)C(=O)C1C(=O)Nc1cccc(C(C)(F)F)c1]
379
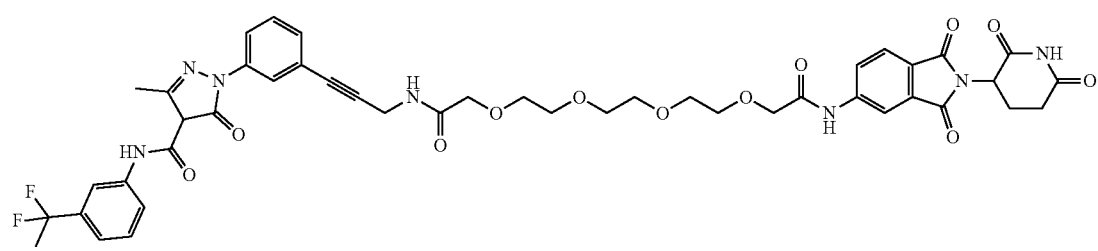 [SMILES: CC1=NN(c2cccc(C#CCNC(=O)COCCOCCOCCOCC(=O)Nc3ccc4c(c3)C(=O)N(C3CCC(=O)NC3=O)C4=O)c2)C(=O)C1C(=O)Nc1cccc(C(C)(F)F)c1]
380
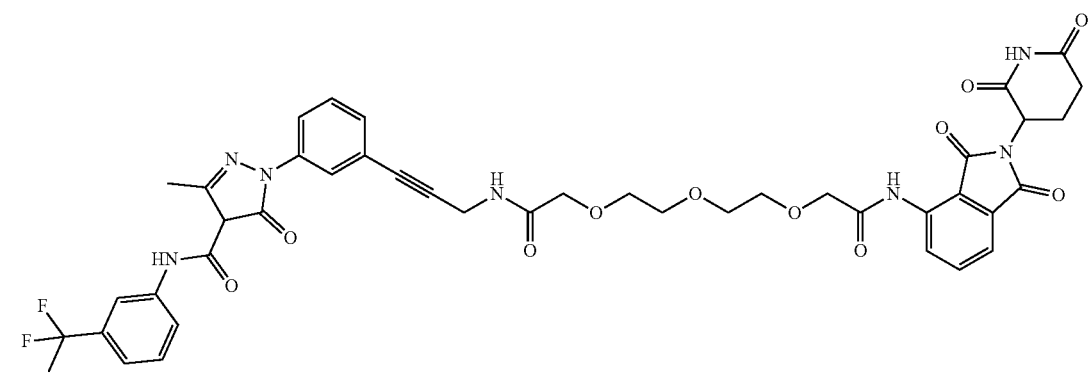 [SMILES: CC1=NN(c2cccc(C#CCNC(=O)COCCOCCOCC(=O)Nc3cccc4c3C(=O)N(C3CCC(=O)NC3=O)C4=O)c2)C(=O)C1C(=O)Nc1cccc(C(C)(F)F)c1]
381
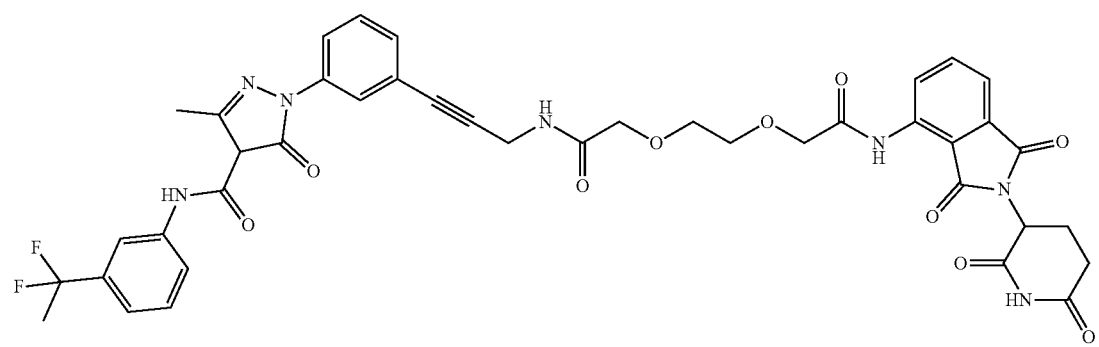 [SMILES: CC1=NN(c2cccc(C#CCNC(=O)COCCOCC(=O)Nc3cccc4c3C(=O)N(C3CCC(=O)NC3=O)C4=O)c2)C(=O)C1C(=O)Nc1cccc(C(C)(F)F)c1]

382 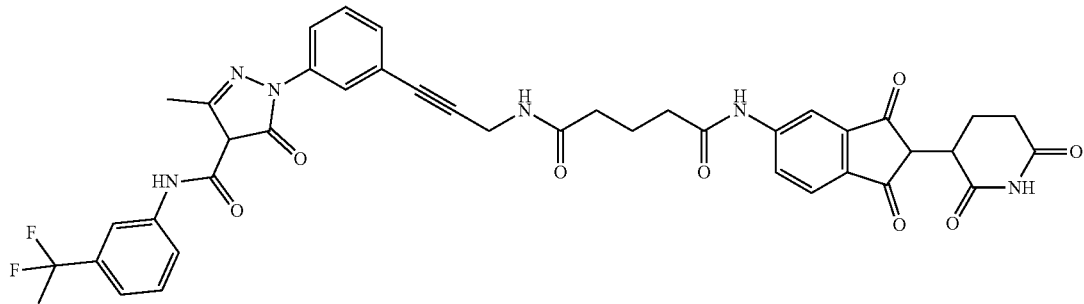 [SMILES: CC1=NN(c2cccc(C#CCNC(=O)CCCC(=O)Nc3ccc4c(c3)C(=O)C(C3CCC(=O)NC3=O)C4=O)c2)C(=O)C1C(=O)Nc1cccc(C(C)(F)F)c1]
383 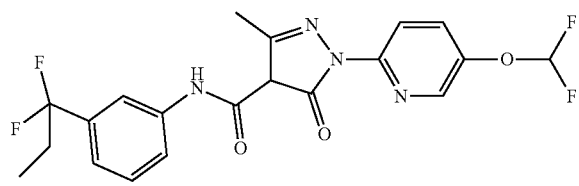 [SMILES: CCC(F)(F)c1cccc(NC(=O)C2C(=O)N(c3ccc(OC(F)F)cn3)N=C2C)c1]
384 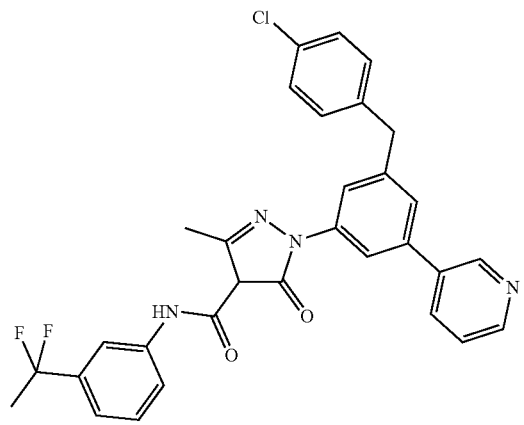 [SMILES: CC1=NN(c2cc(Cc3ccc(Cl)cc3)cc(-c3cccnc3)c2)C(=O)C1C(=O)Nc1cccc(C(C)(F)F)c1]
385 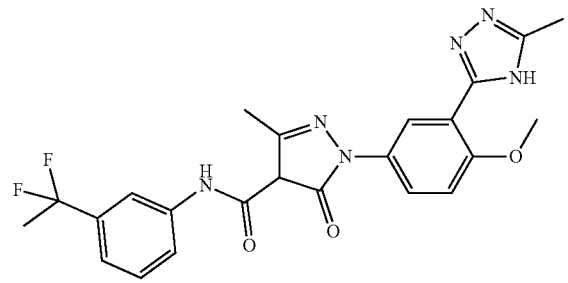 [SMILES: COc1ccc(N2N=C(C)C(C(=O)Nc3cccc(C(C)(F)F)c3)C2=O)cc1-c1nnc(C)[nH]1]
386 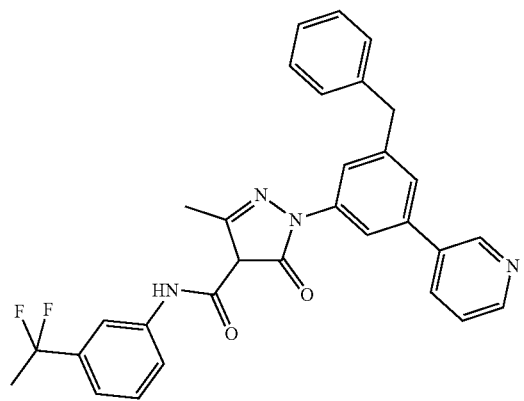 [SMILES: CC1=NN(c2cc(Cc3ccccc3)cc(-c3cccnc3)c2)C(=O)C1C(=O)Nc1cccc(C(C)(F)F)c1]

387 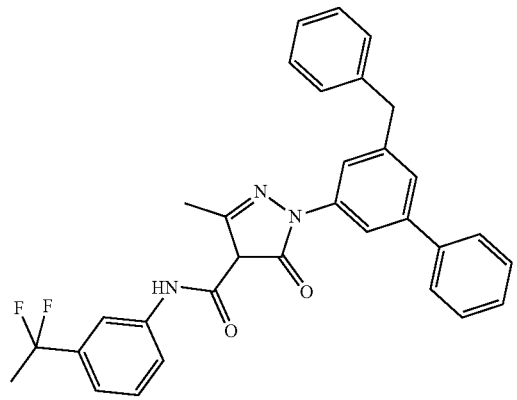 [SMILES: CC1=NN(c2cc(Cc3ccccc3)cc(-c3ccccc3)c2)C(=O)C1C(=O)Nc1cccc(C(C)(F)F)c1]
388 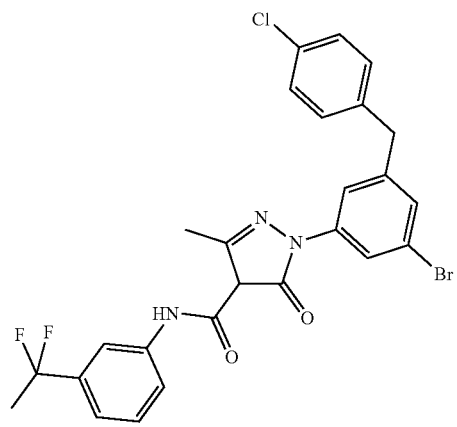 [SMILES: CC1=NN(c2cc(Br)cc(Cc3ccc(Cl)cc3)c2)C(=O)C1C(=O)Nc1cccc(C(C)(F)F)c1]
389 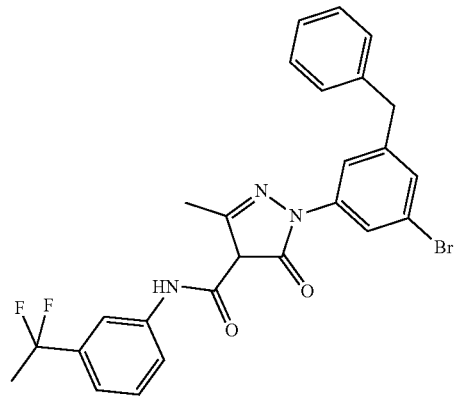 [SMILES: CC1=NN(c2cc(Br)cc(Cc3ccccc3)c2)C(=O)C1C(=O)Nc1cccc(C(C)(F)F)c1]
390 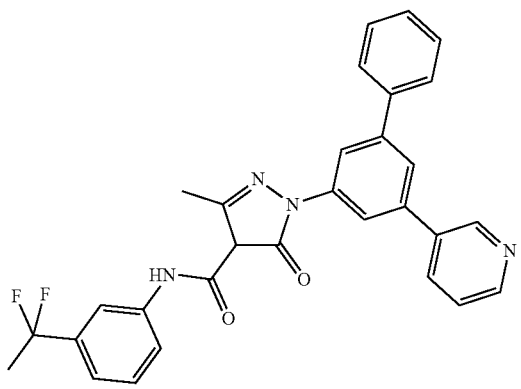 [SMILES: CC1=NN(c2cc(-c3ccccc3)cc(-c3cccnc3)c2)C(=O)C1C(=O)Nc1cccc(C(C)(F)F)c1]

391 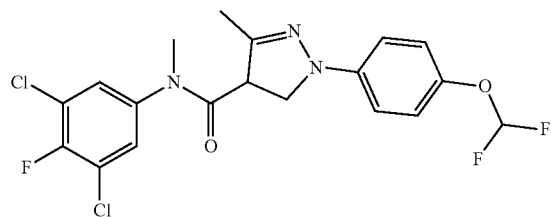 [SMILES: CC1=NN(c2ccc(OC(F)F)cc2)CC1C(=O)N(C)c1cc(Cl)c(F)c(Cl)c1]
392 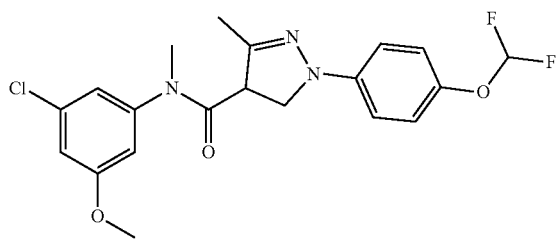 [SMILES: COc1cc(Cl)cc(N(C)C(=O)C2CN(c3ccc(OC(F)F)cc3)N=C2C)c1]
393 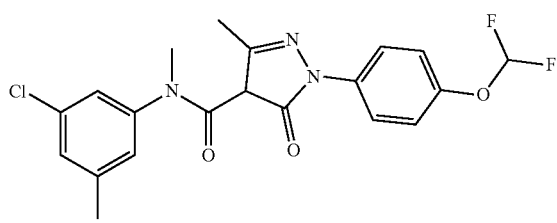 [SMILES: CC1=NN(c2ccc(OC(F)F)cc2)C(=O)C1C(=O)N(C)c1cc(C)cc(Cl)c1]
394 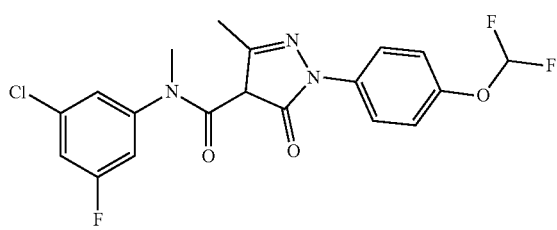 [SMILES: CC1=NN(c2ccc(OC(F)F)cc2)C(=O)C1C(=O)N(C)c1cc(F)cc(Cl)c1]
395 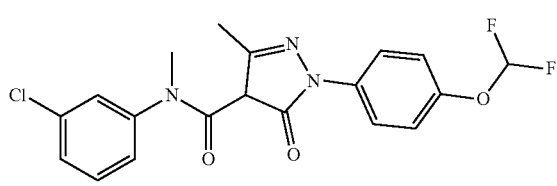 [SMILES: CC1=NN(c2ccc(OC(F)F)cc2)C(=O)C1C(=O)N(C)c1cccc(Cl)c1]
396 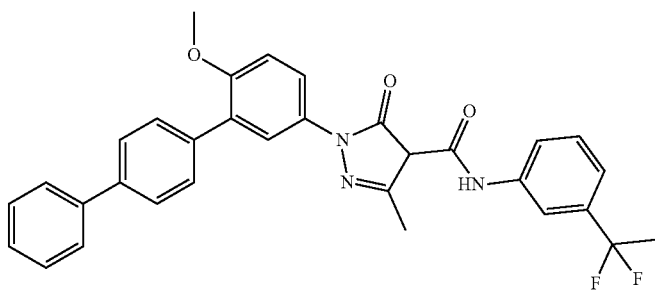 [SMILES: COc1ccc(N2N=C(C)C(C(=O)Nc3cccc(C(C)(F)F)c3)C2=O)cc1-c1ccc(-c2ccccc2)cc1]
397 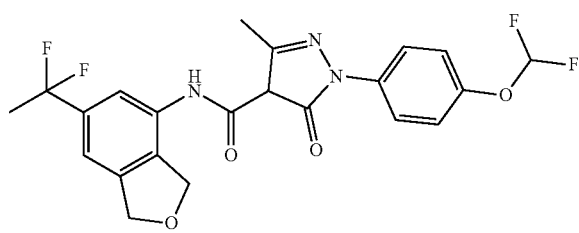 [SMILES: CC1=NN(c2ccc(OC(F)F)cc2)C(=O)C1C(=O)Nc1cc(C(C)(F)F)cc2c1COC2]

| | |
|---|---|
| 398 | 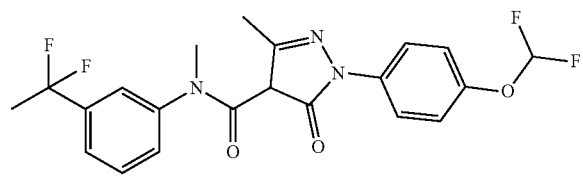 [SMILES: CC1=NN(c2ccc(OC(F)F)cc2)C(=O)C1C(=O)N(C)c1cccc(C(C)(F)F)c1] |
| 399 | 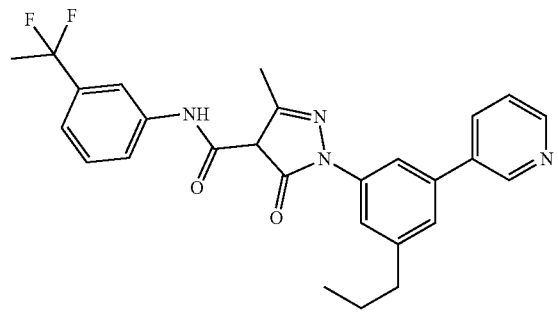 [SMILES: CCCc1cc(-c2cccnc2)cc(N2N=C(C)C(C(=O)Nc3cccc(C(C)(F)F)c3)C2=O)c1] |
| 400 | 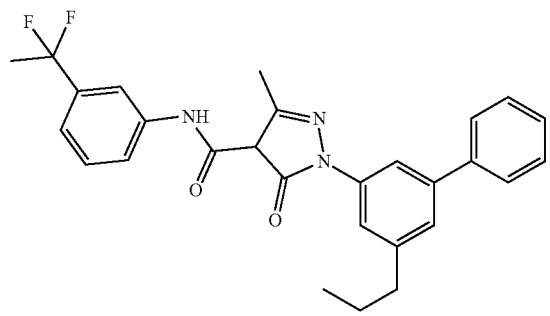 [SMILES: CCCc1cc(-c2ccccc2)cc(N2N=C(C)C(C(=O)Nc3cccc(C(C)(F)F)c3)C2=O)c1] |
| 401 | 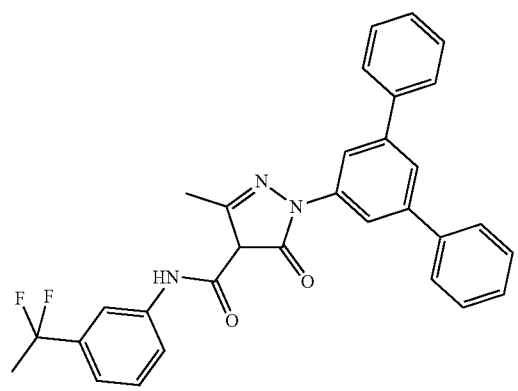 [SMILES: CC1=NN(c2cc(-c3ccccc3)cc(-c3ccccc3)c2)C(=O)C1C(=O)Nc1cccc(C(C)(F)F)c1] |
| 402 | 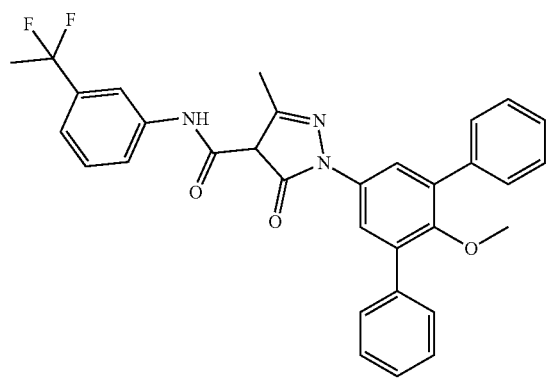 [SMILES: COc1c(-c2ccccc2)cc(N2N=C(C)C(C(=O)Nc3cccc(C(C)(F)F)c3)C2=O)cc1-c1ccccc1] |

-continued
| | |
|---|---|
| 403 | 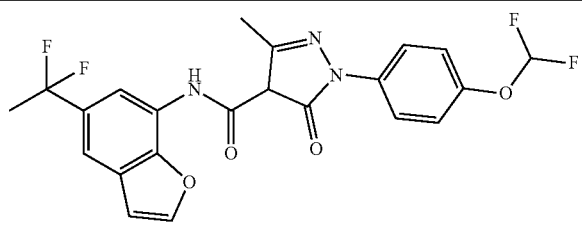 |
| 404 | 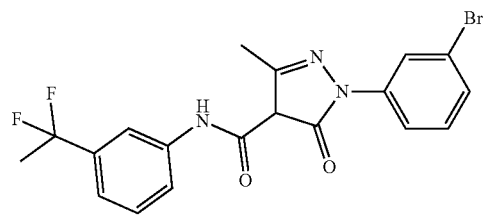 [SMILES: CC1=NN(c2cccc(Br)c2)C(=O)C1C(=O)Nc1cccc(C(C)(F)F)c1] |
| 405 | 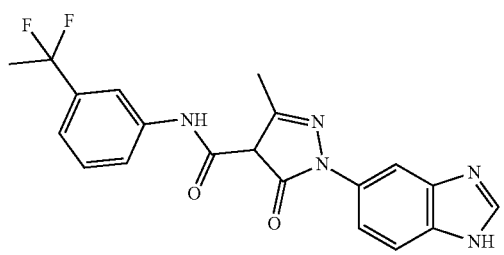 [SMILES: CC1=NN(c2ccc3[nH]cnc3c2)C(=O)C1C(=O)Nc1cccc(C(C)(F)F)c1] |
| 406 | 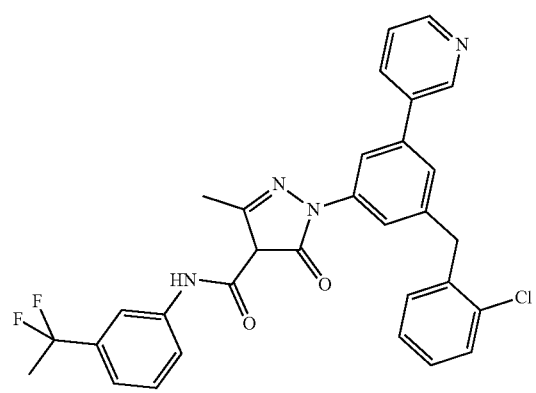 [SMILES: CC1=NN(c2cc(Cc3ccccc3Cl)cc(-c3cccnc3)c2)C(=O)C1C(=O)Nc1cccc(C(C)(F)F)c1] |
| 407 | 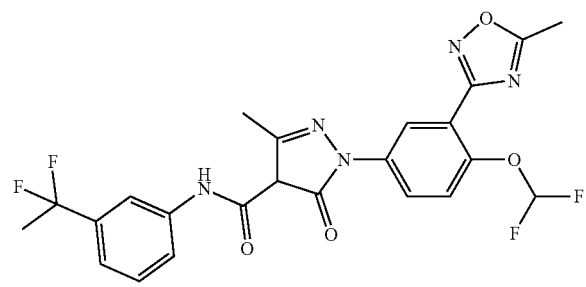 [SMILES: CC1=NN(c2ccc(OC(F)F)c(-c3noc(C)n3)c2)C(=O)C1C(=O)Nc1cccc(C(C)(F)F)c1] |
| 408 | 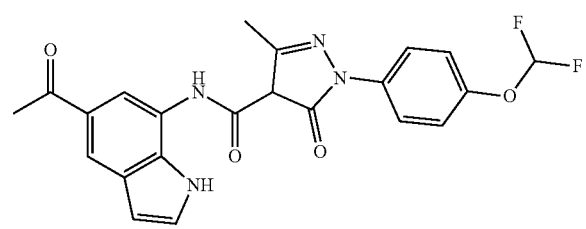 [SMILES: CC(=O)c1cc(NC(=O)C2C(=O)N(c3ccc(OC(F)F)cc3)N=C2C)c2[nH]ccc2c1] |

-continued
| | |
|---|---|
| 409 | 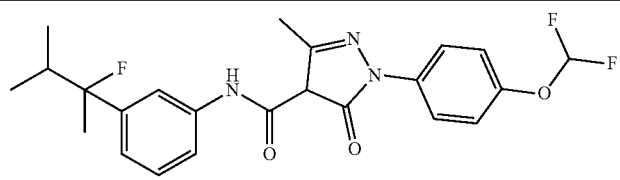 |
| 410 | 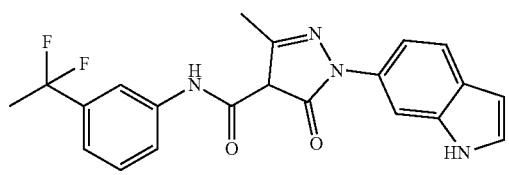 [SMILES: CC1=NN(c2ccc3cc[nH]c3c2)C(=O)C1C(=O)Nc1cccc(C(C)(F)F)c1] |
| 461 | 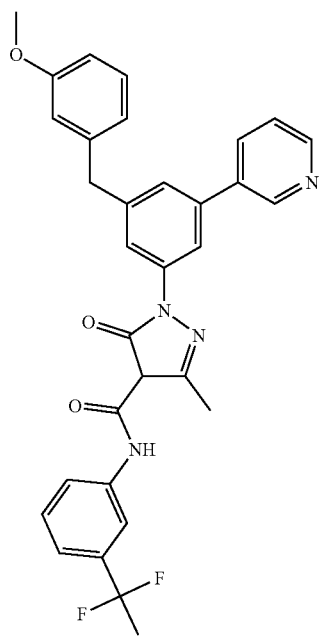 [SMILES: COc1cccc(Cc2cc(-c3cccnc3)cc(N3N=C(C)C(C(=O)Nc4cccc(C(C)(F)F)c4)C3=O)c2)c1] |
| 462 | 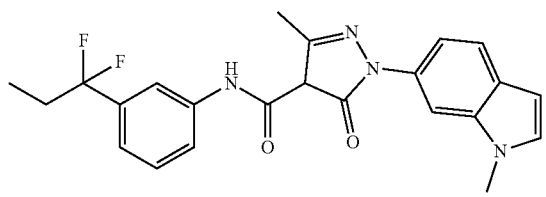 [SMILES: CCC(F)(F)c1cccc(NC(=O)C2C(=O)N(c3ccc4ccn(C)c4c3)N=C2C)c1] |
| 463 | 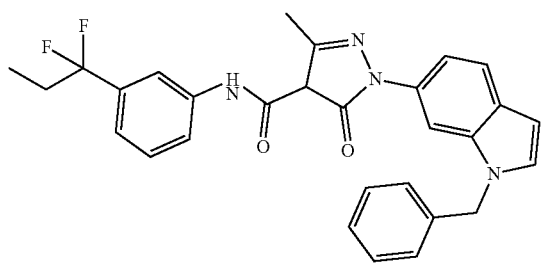 [SMILES: CCC(F)(F)c1cccc(NC(=O)C2C(=O)N(c3ccc4ccn(Cc5ccccc5)c4c3)N=C2C)c1] |
| 464 | 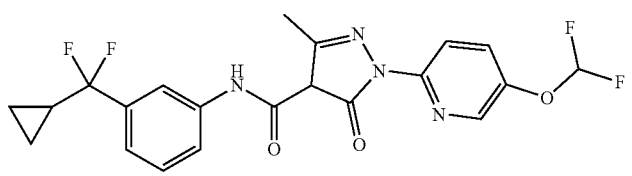 [SMILES: CC1=NN(c2ccc(OC(F)F)cn2)C(=O)C1C(=O)Nc1cccc(C(F)(F)C2CC2)c1] |

465
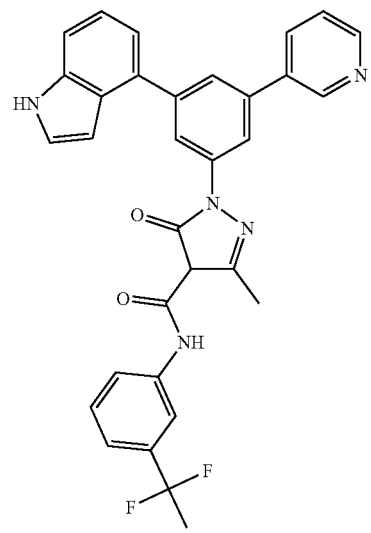 [SMILES: CC1=NN(c2cc(-c3cccnc3)cc(-c3cccc4[nH]ccc34)c2)C(=O)C1C(=O)Nc1cccc(C(C)(F)F)c1]
466
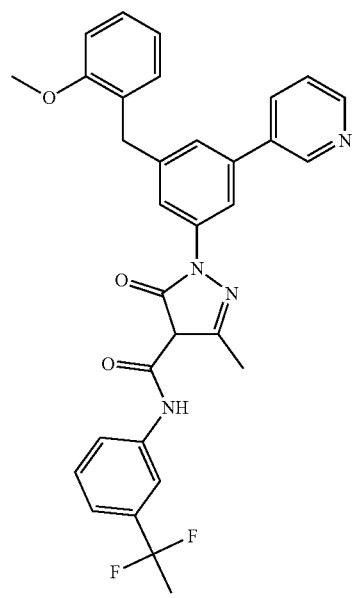 [SMILES: COc1ccccc1Cc1cc(-c2cccnc2)cc(N2N=C(C)C(C(=O)Nc3cccc(C(C)(F)F)c3)C2=O)c1]

467 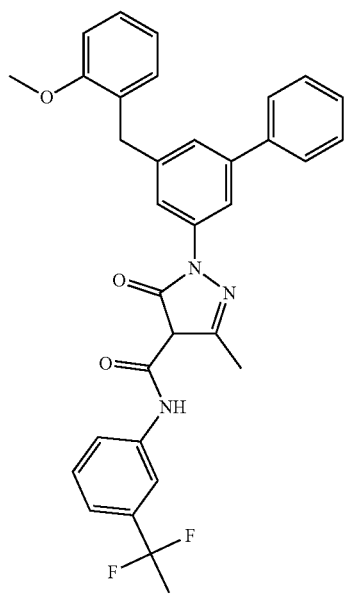 [SMILES: COc1ccccc1Cc1cc(-c2ccccc2)cc(N2N=C(C)C(C(=O)Nc3cccc(C(C)(F)F)c3)C2=O)c1]
468 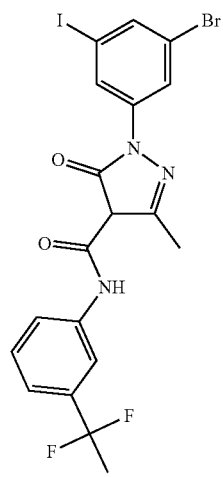 [SMILES: CC1=NN(c2cc(Br)cc(I)c2)C(=O)C1C(=O)Nc1cccc(C(C)(F)F)c1]
470 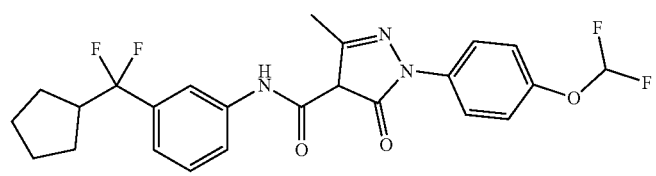 [SMILES: CC1=NN(c2ccc(OC(F)F)cc2)C(=O)C1C(=O)Nc1cccc(C(F)(F)C2CCCC2)c1]
471 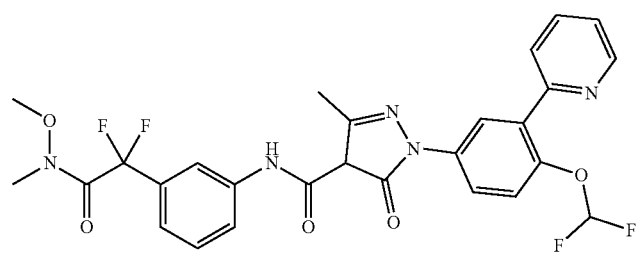 [SMILES: CON(C)C(=O)C(F)(F)c1cccc(NC(=O)C2C(=O)N(c3ccc(OC(F)F)c(-c4ccccn4)c3)N=C2C)c1]

-continued
| 472 | 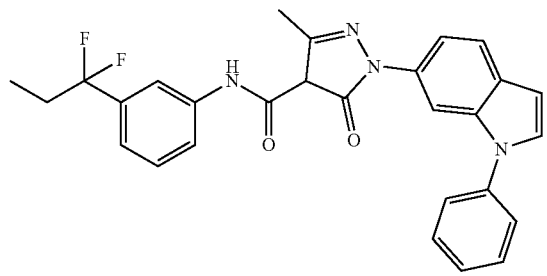 [SMILES: CCC(F)(F)c1cccc(NC(=O)C2C(=O)N(c3ccc4ccn(-c5ccccc5)c4c3)N=C2C)c1] |
| 473 | 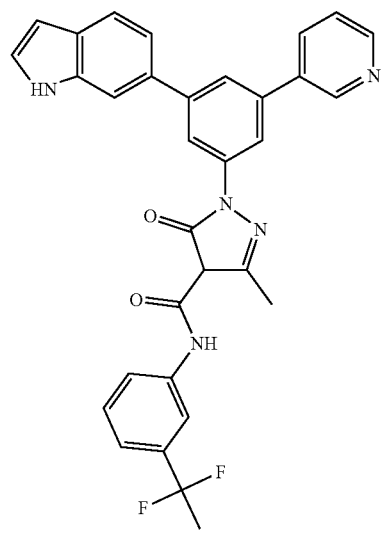 [SMILES: CC1=NN(c2cc(-c3cccnc3)cc(-c3ccc4cc[nH]c4c3)c2)C(=O)C1C(=O)Nc1cccc(C(C)(F)F)c1] |
| 474 | 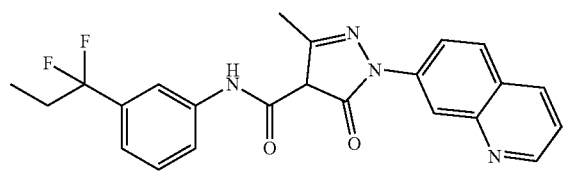 [SMILES: CCC(F)(F)c1cccc(NC(=O)C2C(=O)N(c3ccc4cccnc4c3)N=C2C)c1] |
| 475 | 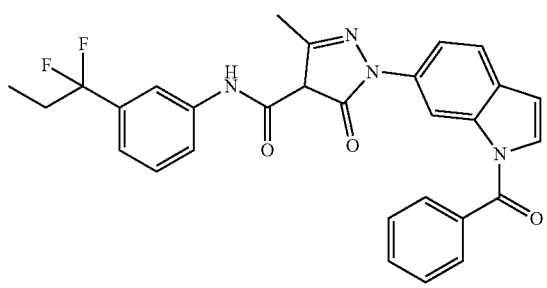 [SMILES: CCC(F)(F)c1cccc(NC(=O)C2C(=O)N(c3ccc4ccn(C(=O)c5ccccc5)c4c3)N=C2C)c1] |
| 476 | 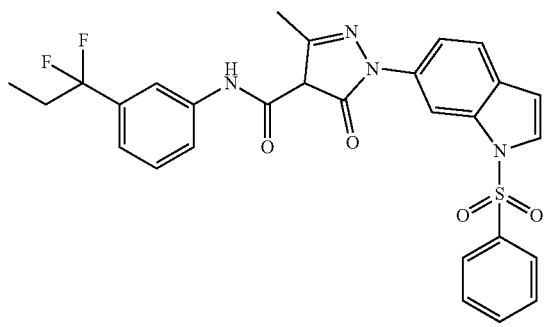 [SMILES: CCC(F)(F)c1cccc(NC(=O)C2C(=O)N(c3ccc4ccn(S(=O)(=O)c5ccccc5)c4c3)N=C2C)c1] |

US 12,133,852 B2
| 477 | 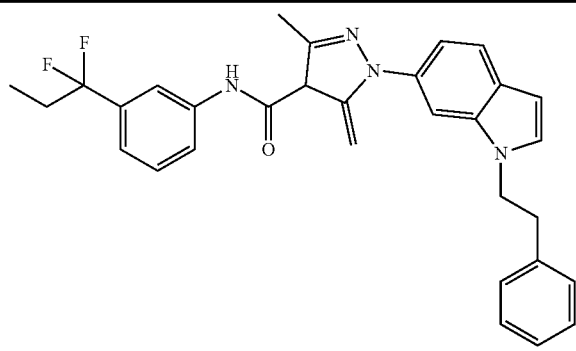 |
| 478 | 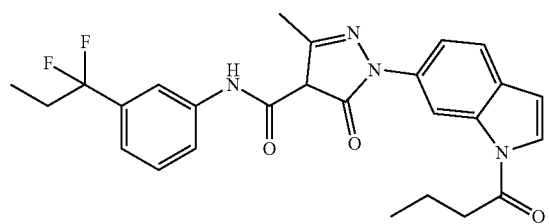 [SMILES: CCCC(=O)n1ccc2ccc(N3N=C(C)C(C(=O)Nc4cccc(C(F)(F)CC)c4)C3=O)cc21] |
| 479 | 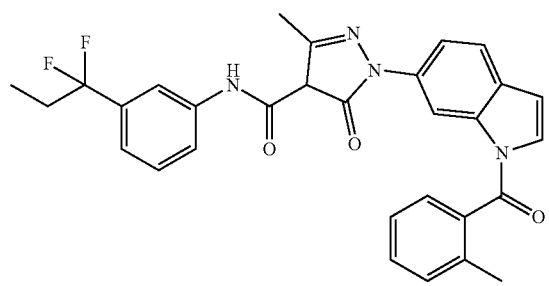 [SMILES: CCC(F)(F)c1cccc(NC(=O)C2C(=O)N(c3ccc4ccn(C(=O)c5ccccc5C)c4c3)N=C2C)c1] |
| 480 | 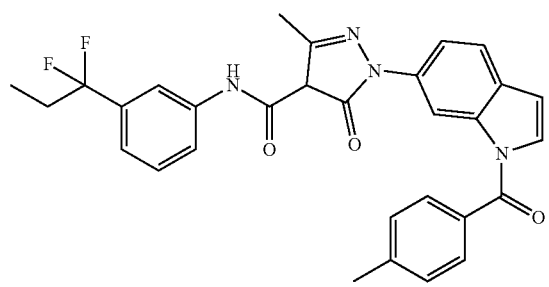 [SMILES: CCC(F)(F)c1cccc(NC(=O)C2C(=O)N(c3ccc4ccn(C(=O)c5ccc(C)cc5)c4c3)N=C2C)c1] |
| 481 | 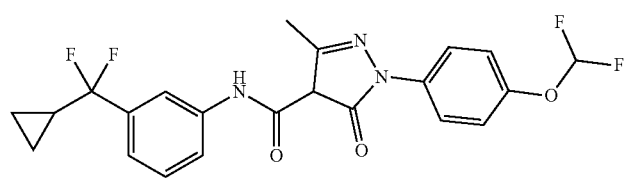 [SMILES: CC1=NN(c2ccc(OC(F)F)cc2)C(=O)C1C(=O)Nc1cccc(C(F)(F)C2CC2)c1] |
| 482 | 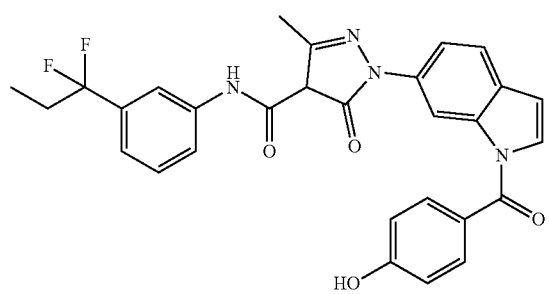 [SMILES: CCC(F)(F)c1cccc(NC(=O)C2C(=O)N(c3ccc4ccn(C(=O)c5ccc(O)cc5)c4c3)N=C2C)c1] |

| 483 | 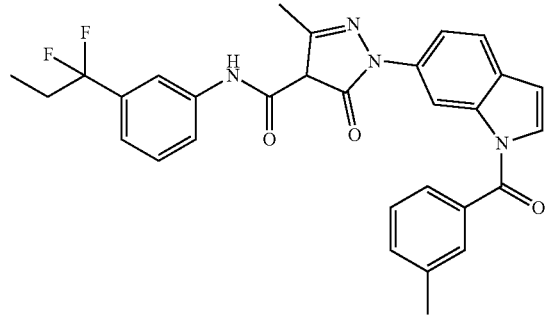 [SMILES: CCC(F)(F)c1cccc(NC(=O)C2C(=O)N(c3ccc4ccn(C(=O)c5cccc(C)c5)c4c3)N=C2C)c1] |
| 484 | 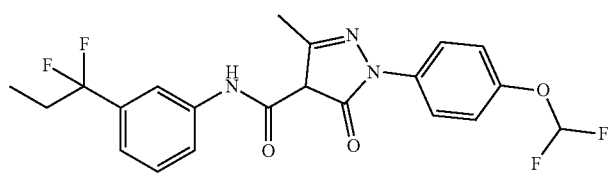 [SMILES: CCC(F)(F)c1cccc(NC(=O)C2C(=O)N(c3ccc(OC(F)F)cc3)N=C2C)c1] |
| 485 | 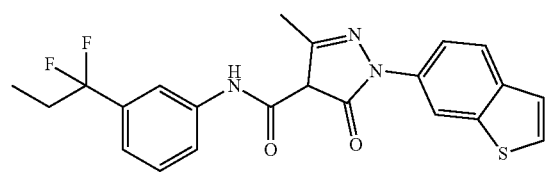 |
| 486 | 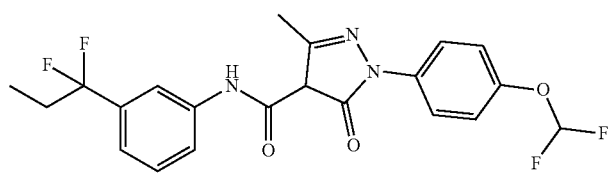 [SMILES: CCC(F)(F)c1cccc(NC(=O)C2C(=O)N(c3ccc(OC(F)F)cc3)N=C2C)c1] |
| 487 | 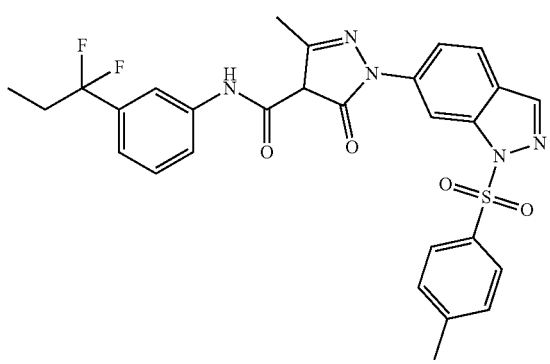 [SMILES: CCC(F)(F)c1cccc(NC(=O)C2C(=O)N(c3ccc4cnn(S(=O)(=O)c5ccc(C)cc5)c4c3)N=C2C)c1] |
| 488 | 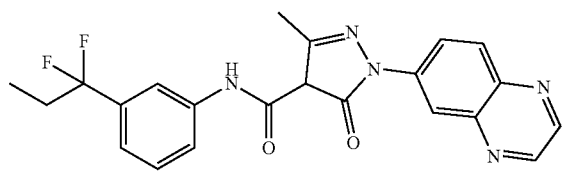 [SMILES: CCC(F)(F)c1cccc(NC(=O)C2C(=O)N(c3ccc4nccnc4c3)N=C2C)c1] |
| 489 | 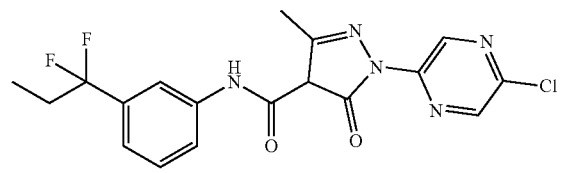 [SMILES: CCC(F)(F)c1cccc(NC(=O)C2C(=O)N(c3cnc(Cl)cn3)N=C2C)c1] |

| | |
|---|---|
| 490 | 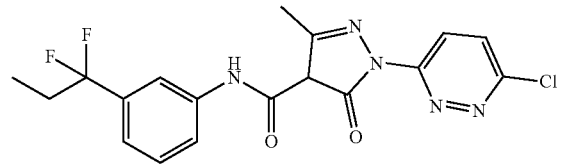 [SMILES: CCC(F)(F)c1cccc(NC(=O)C2C(=O)N(c3ccc(Cl)nn3)N=C2C)c1] |
| 491 | 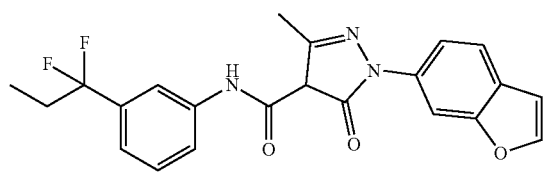 [SMILES: CCC(F)(F)c1cccc(NC(=O)C2C(=O)N(c3ccc4ccoc4c3)N=C2C)c1] |
| 492 | 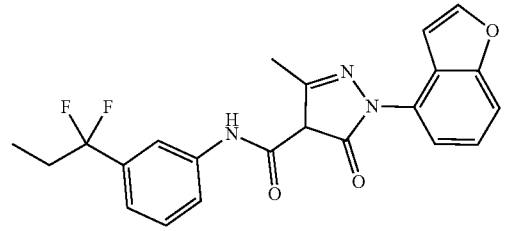 [SMILES: CCC(F)(F)c1cccc(NC(=O)C2C(=O)N(c3cccc4occc34)N=C2C)c1] |
| 493 | 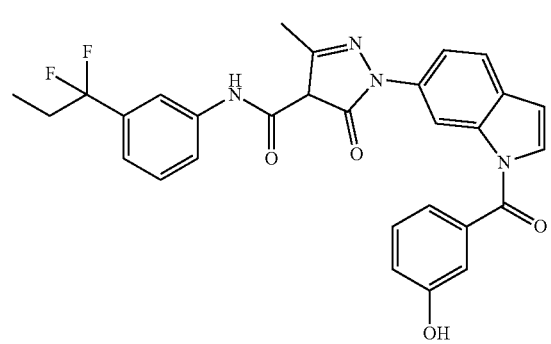 [SMILES: CCC(F)(F)c1cccc(NC(=O)C2C(=O)N(c3ccc4ccn(C(=O)c5cccc(O)c5)c4c3)N=C2C)c1] |
| 494 | 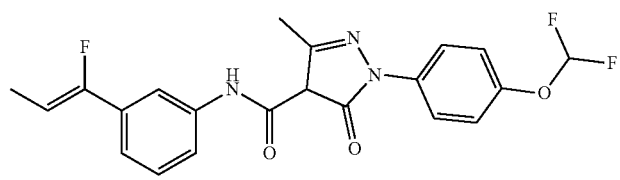 [SMILES: C/C=C(\F)c1cccc(NC(=O)C2C(=O)N(c3ccc(OC(F)F)cc3)N=C2C)c1] |
| 495 | 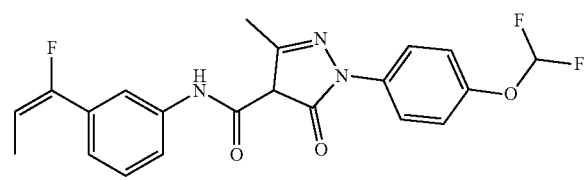 [SMILES: C/C=C(/F)c1cccc(NC(=O)C2C(=O)N(c3ccc(OC(F)F)cc3)N=C2C)c1] |
| 496 | 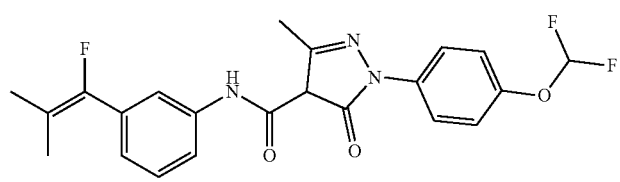 [SMILES: CC1=NN(c2ccc(OC(F)F)cc2)C(=O)C1C(=O)Nc1cccc(C(F)=C(C)C)c1] |

-continued
| 497 | 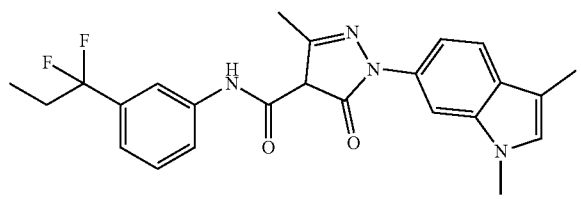 [SMILES: CCC(F)(F)c1cccc(NC(=O)C2C(=O)N(c3ccc4c(C)cn(C)c4c3)N=C2C)c1] |
| 498 | 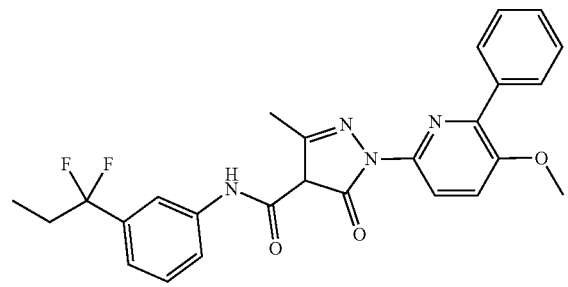 [SMILES: CCC(F)(F)c1cccc(NC(=O)C2C(=O)N(c3ccc(OC)c(-c4ccccc4)n3)N=C2C)c1] |
| 499 | 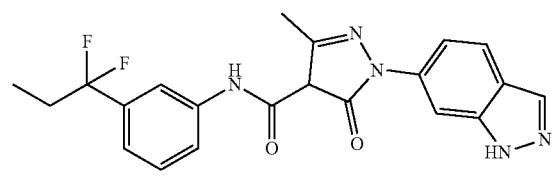 [SMILES: CCC(F)(F)c1cccc(NC(=O)C2C(=O)N(c3ccc4cn[nH]c4c3)N=C2C)c1] |
| 500 | 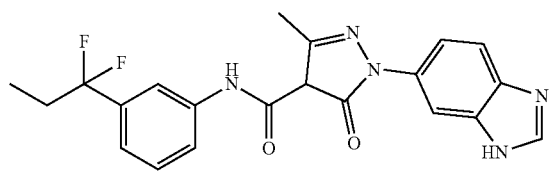 |
| 501 | 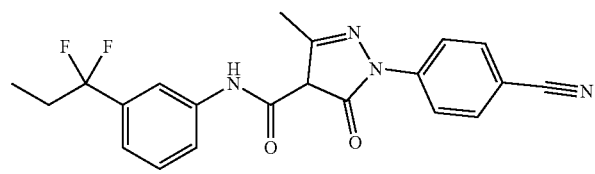 [SMILES: CCC(F)(F)c1cccc(NC(=O)C2C(=O)N(c3ccc(C#N)cc3)N=C2C)c1] |
| 502 | 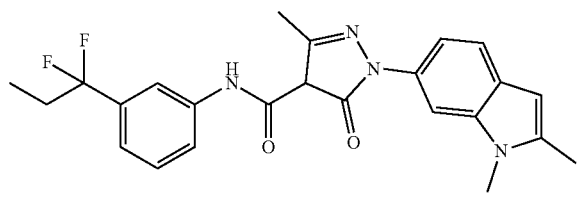 [SMILES: CCC(F)(F)c1cccc(NC(=O)C2C(=O)N(c3ccc4cc(C)n(C)c4c3)N=C2C)c1] |
| 503 | 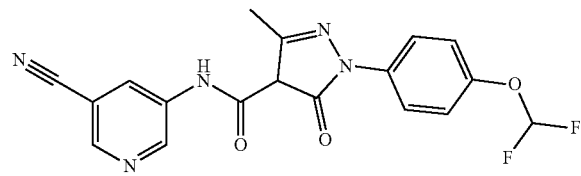 [SMILES: CC1=NN(c2ccc(OC(F)F)cc2)C(=O)C1C(=O)Nc1cncc(C#N)c1] |
| 504 | 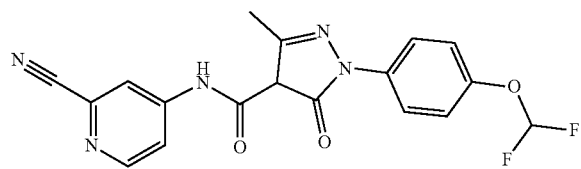 [SMILES: CC1=NN(c2ccc(OC(F)F)cc2)C(=O)C1C(=O)Nc1ccnc(C#N)c1] |

| 505 | 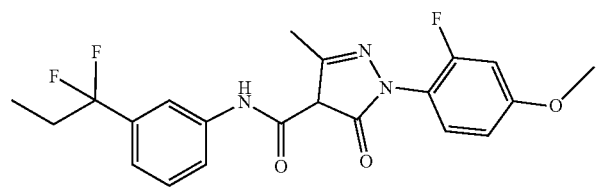 [SMILES: CCC(F)(F)c1cccc(NC(=O)C2C(=O)N(c3ccc(OC)cc3F)N=C2C)c1] |
| --- | --- |
| 506 | 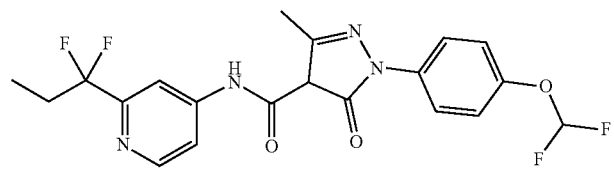 [SMILES: CCC(F)(F)c1cc(NC(=O)C2C(=O)N(c3ccc(OC(F)F)cc3)N=C2C)ccn1] |
| 507 | 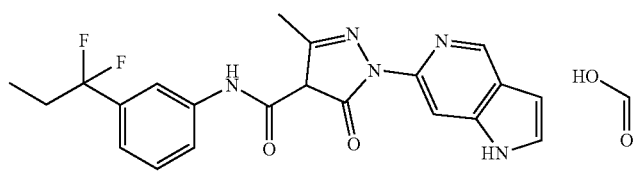 |
| 508 | 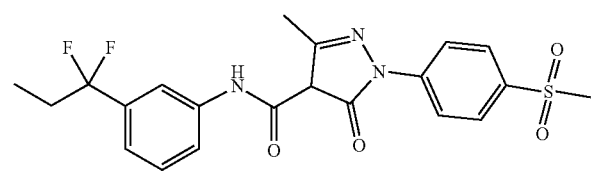 [SMILES: CCC(F)(F)c1cccc(NC(=O)C2C(=O)N(c3ccc(S(C)(=O)=O)cc3)N=C2C)c1] |
| 509 | 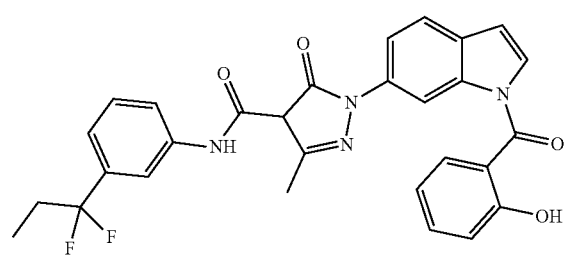 [SMILES: CCC(F)(F)c1cccc(NC(=O)C2C(=O)N(c3ccc4ccn(C(=O)c5ccccc5O)c4c3)N=C2C)c1] |
| 510 | 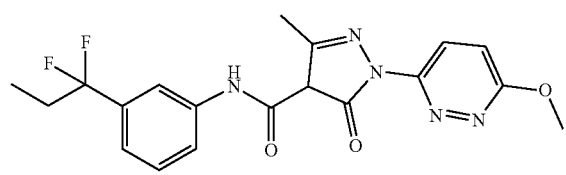 [SMILES: CCC(F)(F)c1cccc(NC(=O)C2C(=O)N(c3ccc(OC)nn3)N=C2C)c1] |
| 511 | 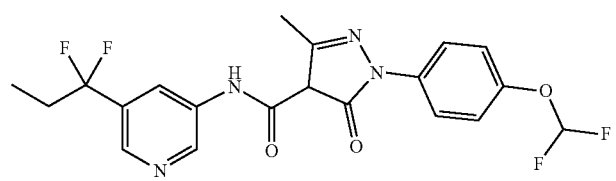 [SMILES: CCC(F)(F)c1cncc(NC(=O)C2C(=O)N(c3ccc(OC(F)F)cc3)N=C2C)c1] |
| 512 | 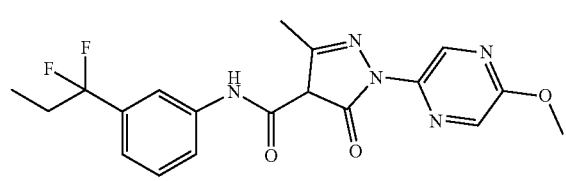 [SMILES: CCC(F)(F)c1cccc(NC(=O)C2C(=O)N(c3cnc(OC)cn3)N=C2C)c1] |

516 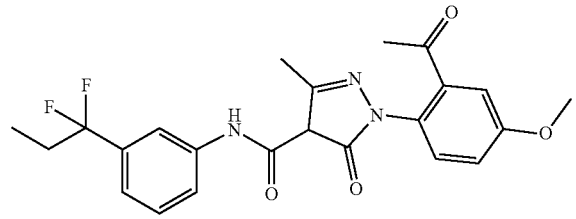 [SMILES: CCC(F)(F)c1cccc(NC(=O)C2C(=O)N(c3ccc(OC)cc3C(C)=O)N=C2C)c1]
524 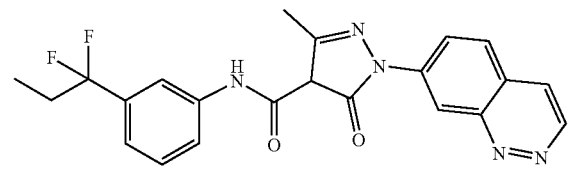 [SMILES: CCC(F)(F)c1cccc(NC(=O)C2C(=O)N(c3ccc4ccnnc4c3)N=C2C)c1]
529 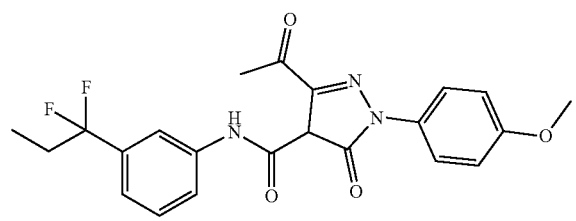 [SMILES: CCC(F)(F)c1cccc(NC(=O)C2C(=O)N(c3ccc(OC)cc3)N=C2C(C)=O)c1]
530 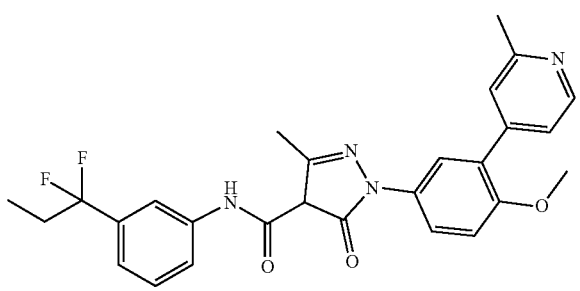 [SMILES: CCC(F)(F)c1cccc(NC(=O)C2C(=O)N(c3ccc(OC)c(-c4ccnc(C)c4)c3)N=C2C)c1]
531 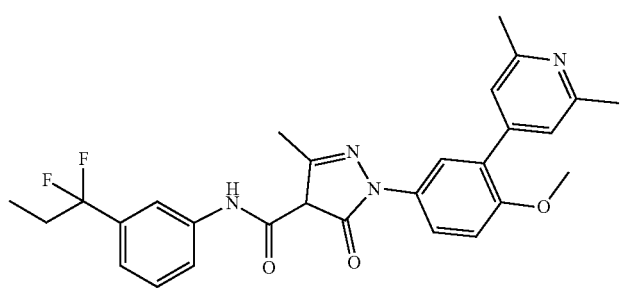 [SMILES: CCC(F)(F)c1cccc(NC(=O)C2C(=O)N(c3ccc(OC)c(-c4cc(C)nc(C)c4)c3)N=C2C)c1]
532 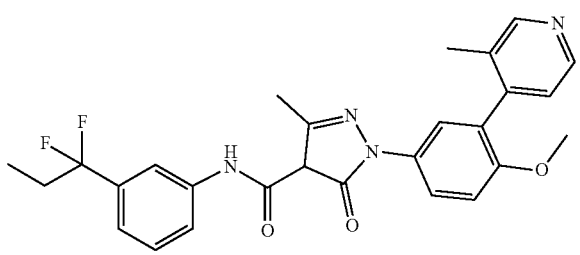 [SMILES: CCC(F)(F)c1cccc(NC(=O)C2C(=O)N(c3ccc(OC)c(-c4ccncc4C)c3)N=C2C)c1]

534
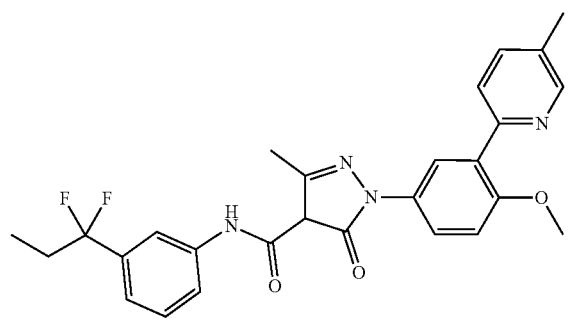 [SMILES: CCC(F)(F)c1cccc(NC(=O)C2C(=O)N(c3ccc(OC)c(-c4ccc(C)cn4)c3)N=C2C)c1]
535
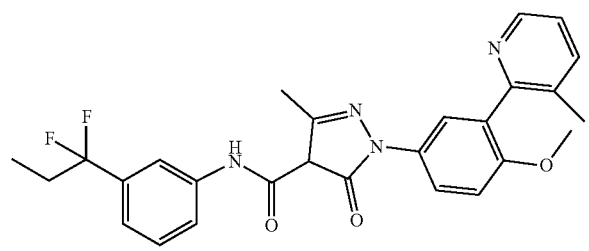 [SMILES: CCC(F)(F)c1cccc(NC(=O)C2C(=O)N(c3ccc(OC)c(-c4ncccc4C)c3)N=C2C)c1]
536
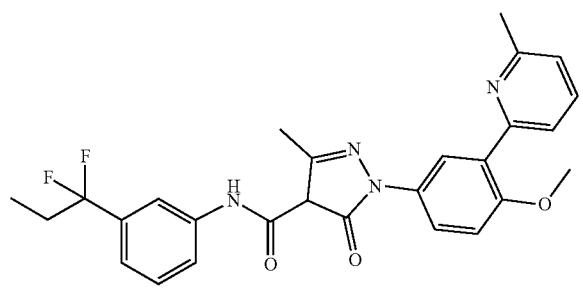 [SMILES: CCC(F)(F)c1cccc(NC(=O)C2C(=O)N(c3ccc(OC)c(-c4cccc(C)n4)c3)N=C2C)c1]
537
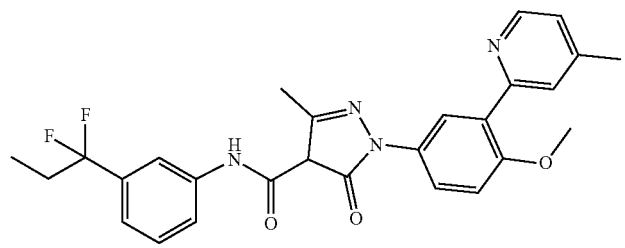 [SMILES: CCC(F)(F)c1cccc(NC(=O)C2C(=O)N(c3ccc(OC)c(-c4cc(C)ccn4)c3)N=C2C)c1]
538
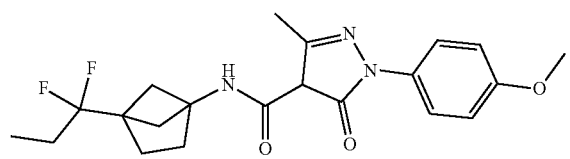 [SMILES: CCC(F)(F)C12CCC(NC(=O)C3C(=O)N(c4ccc(OC)cc4)N=C3C)(C1)C2]
539
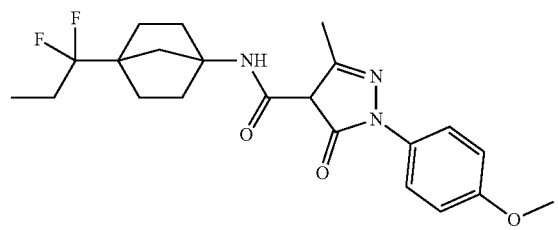 [SMILES: CCC(F)(F)C12CCC(NC(=O)C3C(=O)N(c4ccc(OC)cc4)N=C3C)(CC1)C2]

-continued
| | |
|---|---|
| 540 | 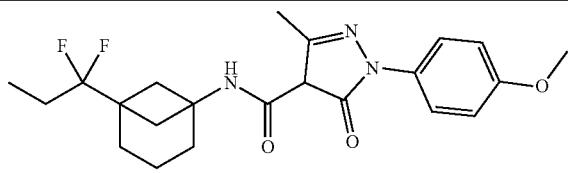 |
| 541 | 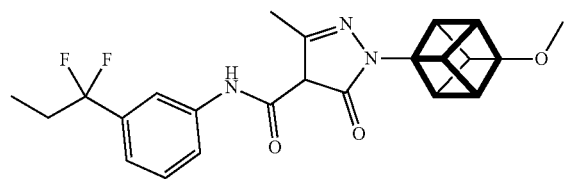 |
| 542 | 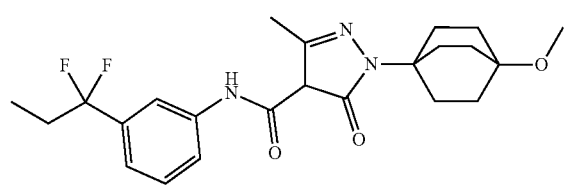 [SMILES: CCC(F)(F)c1cccc(NC(=O)C2C(=O)N(C34CCC(OC)(CC3)CC4)N=C2C)c1] |
| 543 | 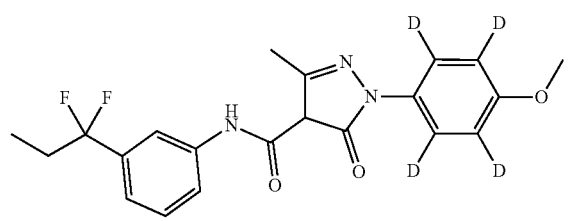 [SMILES: [2H]c1c([2H])c(N2N=C(C)C(C(=O)Nc3cccc(C(F)(F)CC)c3)C2=O)c([2H])c([2H])c1OC] |
| 544 | 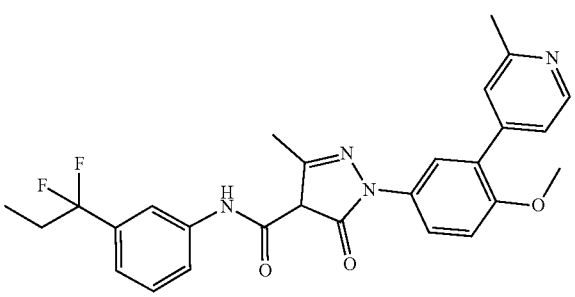 [SMILES: CCC(F)(F)c1cccc(NC(=O)C2C(=O)N(c3ccc(OC)c(-c4ccnc(C)c4)c3)N=C2C)c1] |
| 545 | 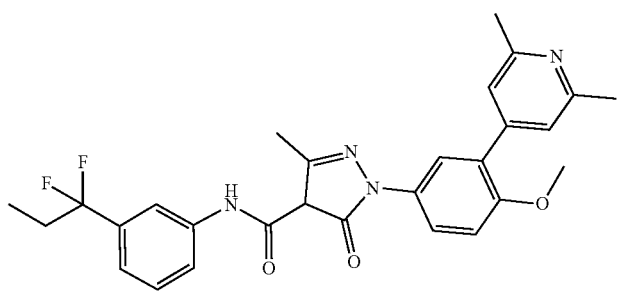 [SMILES: CCC(F)(F)c1cccc(NC(=O)C2C(=O)N(c3ccc(OC)c(-c4cc(C)nc(C)c4)c3)N=C2C)c1] |
| 546 | 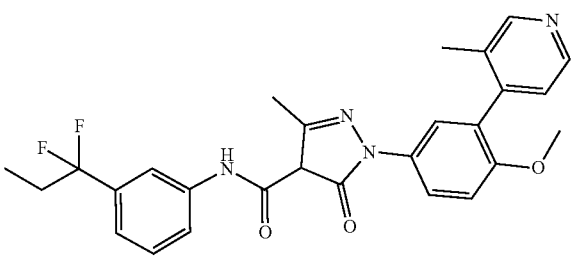 [SMILES: CCC(F)(F)c1cccc(NC(=O)C2C(=O)N(c3ccc(OC)c(-c4ccncc4C)c3)N=C2C)c1] |

547 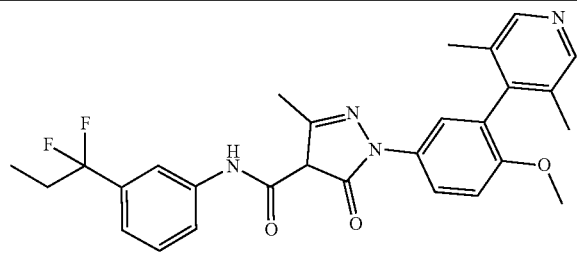
548 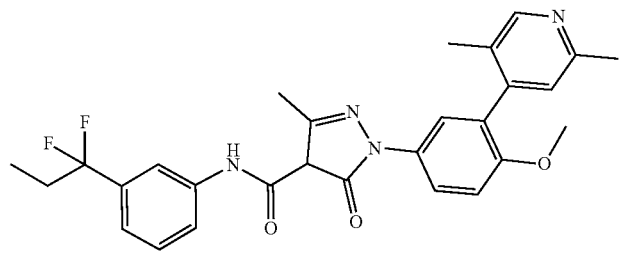 [SMILES: CCC(F)(F)c1cccc(NC(=O)C2C(=O)N(c3ccc(OC)c(-c4cc(C)ncc4C)c3)N=C2C)c1]
549 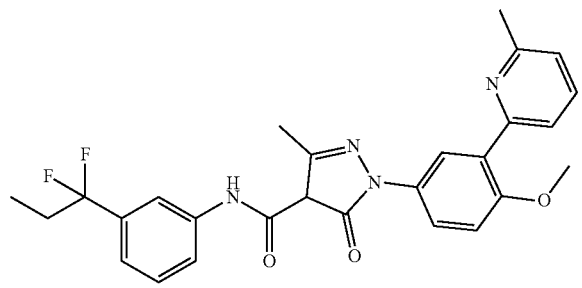 [SMILES: CCC(F)(F)c1cccc(NC(=O)C2C(=O)N(c3ccc(OC)c(-c4cccc(C)n4)c3)N=C2C)c1]
550 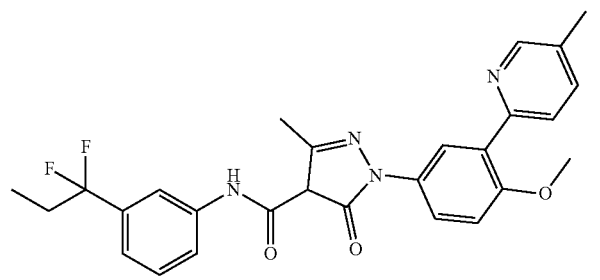 [SMILES: CCC(F)(F)c1cccc(NC(=O)C2C(=O)N(c3ccc(OC)c(-c4ccc(C)cn4)c3)N=C2C)c1]
551 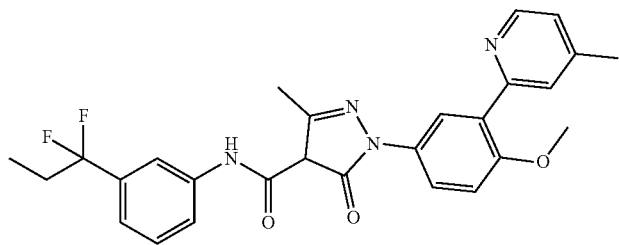 [SMILES: CCC(F)(F)c1cccc(NC(=O)C2C(=O)N(c3ccc(OC)c(-c4cc(C)ccn4)c3)N=C2C)c1]
552 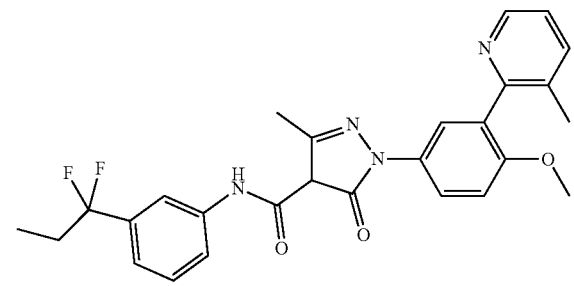 [SMILES: CCC(F)(F)c1cccc(NC(=O)C2C(=O)N(c3ccc(OC)c(-c4ncccc4C)c3)N=C2C)c1]

553 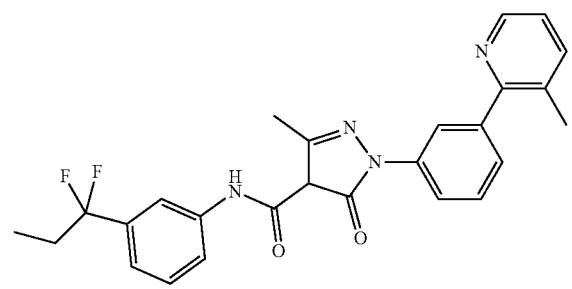 [SMILES: CCC(F)(F)c1cccc(NC(=O)C2C(=O)N(c3cccc(-c4ncccc4C)c3)N=C2C)c1]
554 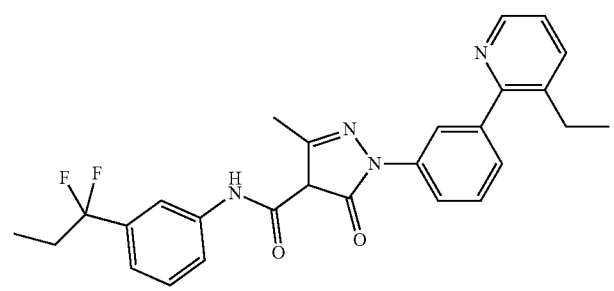 [SMILES: CCc1cccnc1-c1cccc(N2N=C(C)C(C(=O)Nc3cccc(C(F)(F)CC)c3)C2=O)c1]
555 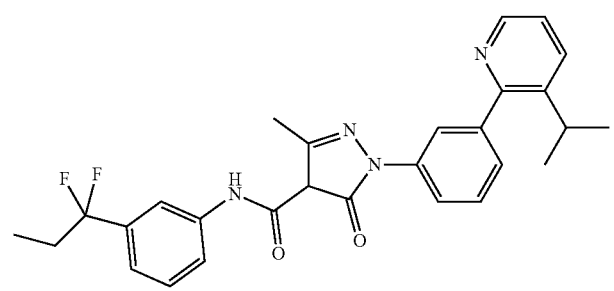 [SMILES: CCC(F)(F)c1cccc(NC(=O)C2C(=O)N(c3cccc(-c4ncccc4C(C)C)c3)N=C2C)c1]
556 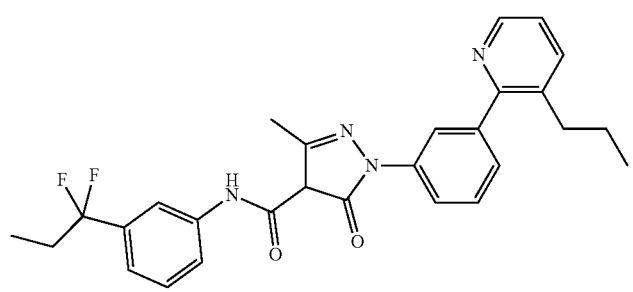 [SMILES: CCCc1cccnc1-c1cccc(N2N=C(C)C(C(=O)Nc3cccc(C(F)(F)CC)c3)C2=O)c1]
557 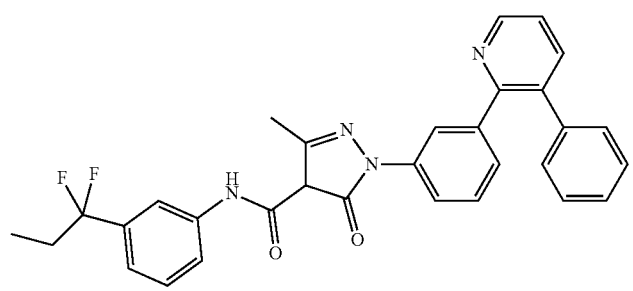 [SMILES: CCC(F)(F)c1cccc(NC(=O)C2C(=O)N(c3cccc(-c4ncccc4-c4ccccc4)c3)N=C2C)c1]

| | |
|---|---|
| 558 | 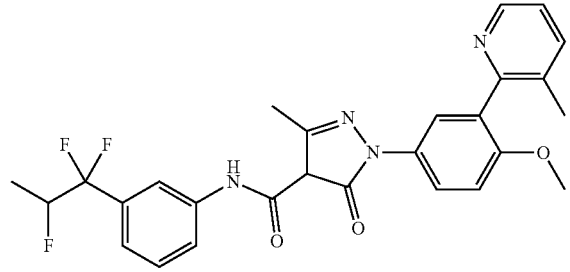 [SMILES: COc1ccc(N2N=C(C)C(C(=O)Nc3cccc(C(F)(F)C(C)F)c3)C2=O)cc1-c1ncccc1C] |
| 559 | 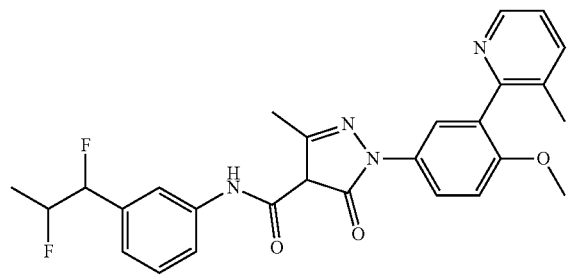 [SMILES: COc1ccc(N2N=C(C)C(C(=O)Nc3cccc(C(F)C(C)F)c3)C2=O)cc1-c1ncccc1C] |
| 560 | 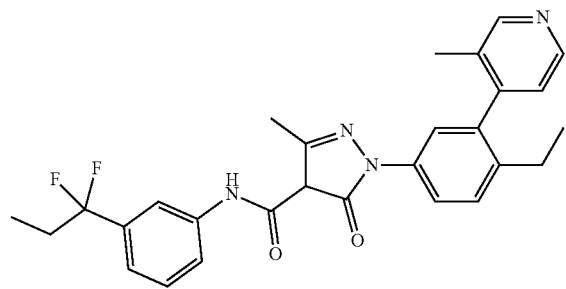 [SMILES: CCc1ccc(N2N=C(C)C(C(=O)Nc3cccc(C(F)(F)CC)c3)C2=O)cc1-c1ccncc1C] |
| 561 | 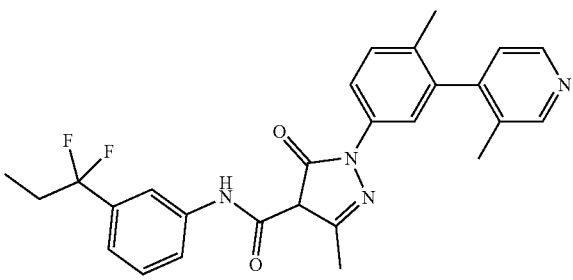 [SMILES: CCC(F)(F)c1cccc(NC(=O)C2C(=O)N(c3ccc(C)c(-c4ccncc4C)c3)N=C2C)c1] |
| 562 | 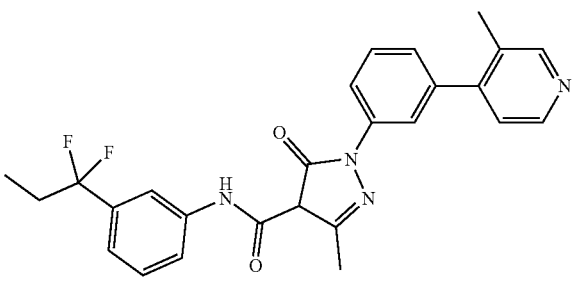 [SMILES: CCC(F)(F)c1cccc(NC(=O)C2C(=O)N(c3cccc(-c4ccncc4C)c3)N=C2C)c1] |

563 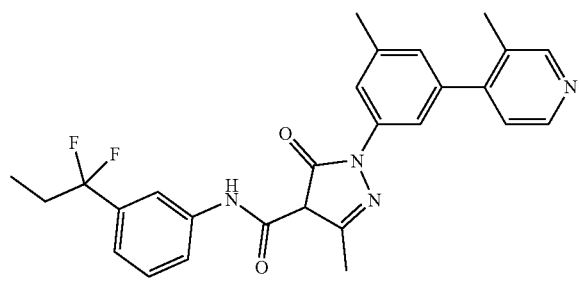 [SMILES: CCC(F)(F)c1cccc(NC(=O)C2C(=O)N(c3cc(C)cc(-c4ccncc4C)c3)N=C2C)c1]
564 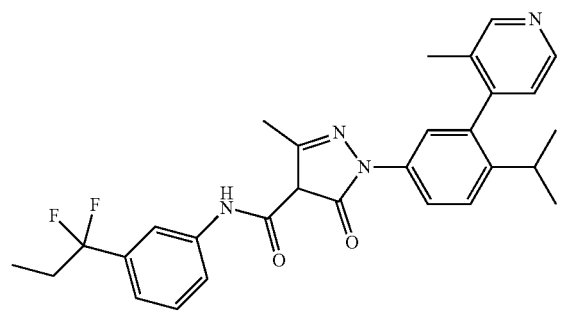 [SMILES: CCC(F)(F)c1cccc(NC(=O)C2C(=O)N(c3ccc(C(C)C)c(-c4ccncc4C)c3)N=C2C)c1]
565 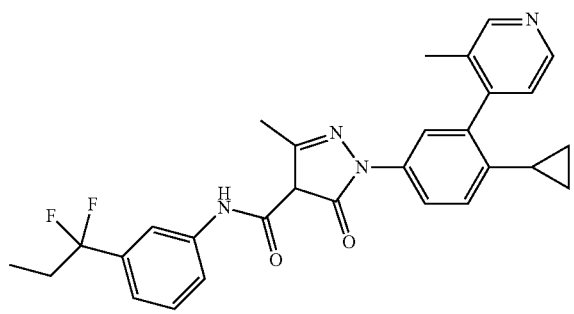 [SMILES: CCC(F)(F)c1cccc(NC(=O)C2C(=O)N(c3ccc(C4CC4)c(-c4ccncc4C)c3)N=C2C)c1]
566 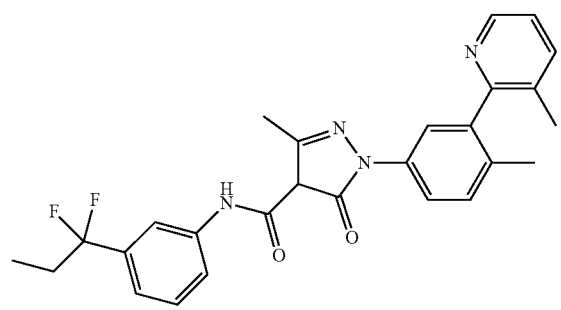 [SMILES: CCC(F)(F)c1cccc(NC(=O)C2C(=O)N(c3ccc(C)c(-c4ncccc4C)c3)N=C2C)c1]
567 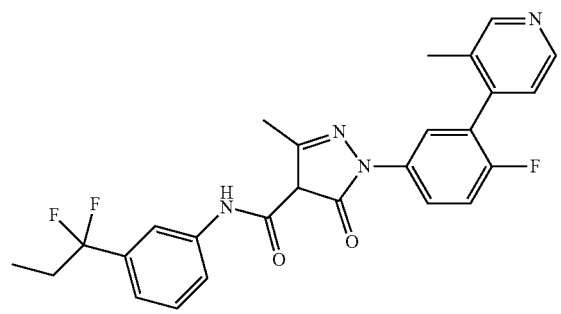 [SMILES: CCC(F)(F)c1cccc(NC(=O)C2C(=O)N(c3ccc(F)c(-c4ccncc4C)c3)N=C2C)c1]

568 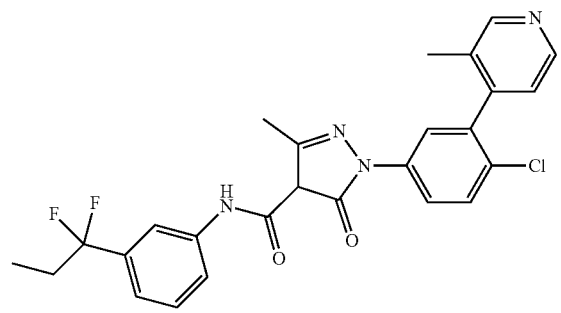
569 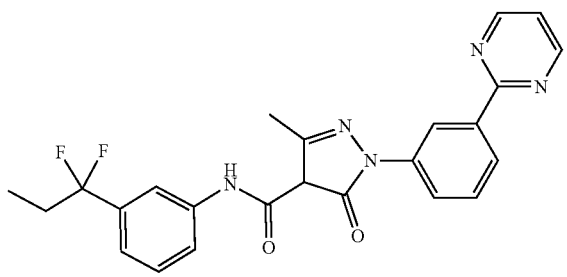 [SMILES: CCC(F)(F)c1cccc(NC(=O)C2C(=O)N(c3cccc(-c4ncccn4)c3)N=C2C)c1]
570 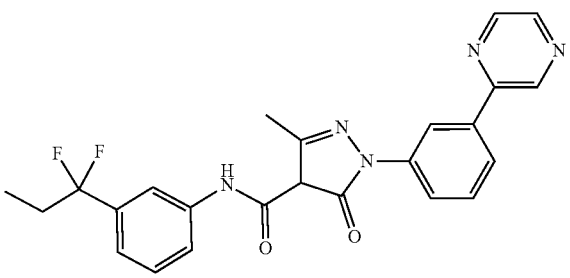 [SMILES: CCC(F)(F)c1cccc(NC(=O)C2C(=O)N(c3cccc(-c4cnccn4)c3)N=C2C)c1]
571 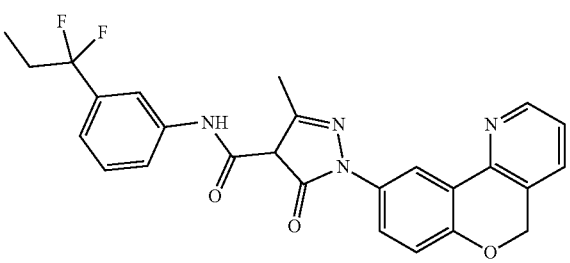 [SMILES: CCC(F)(F)c1cccc(NC(=O)C2C(=O)N(c3ccc4c(c3)-c3ncccc3CO4)N=C2C)c1]
572 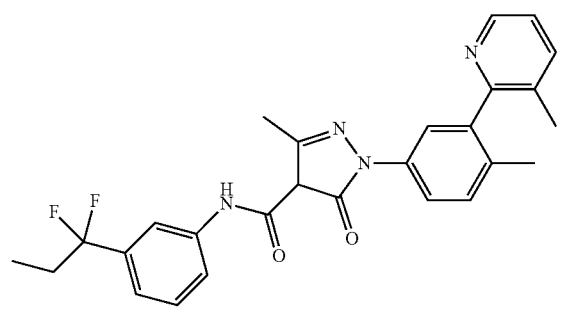 [SMILES: CCC(F)(F)c1cccc(NC(=O)C2C(=O)N(c3ccc(C)c(-c4ncccc4C)c3)N=C2C)c1]

| | |
|---|---|
| 573 | 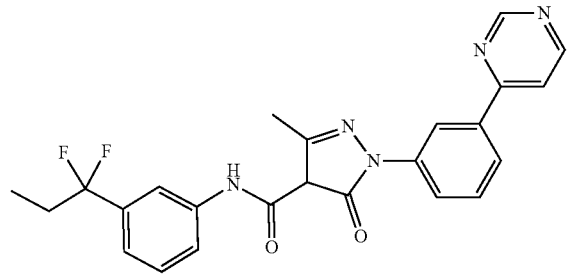 [SMILES: CCC(F)(F)c1cccc(NC(=O)C2C(=O)N(c3cccc(-c4ccncn4)c3)N=C2C)c1] |
| 574 | 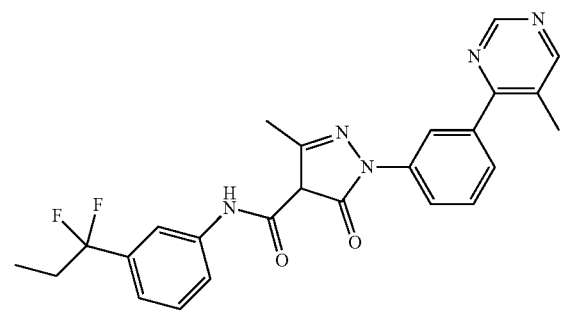 [SMILES: CCC(F)(F)c1cccc(NC(=O)C2C(=O)N(c3cccc(-c4ncncc4C)c3)N=C2C)c1] |
| 575 | 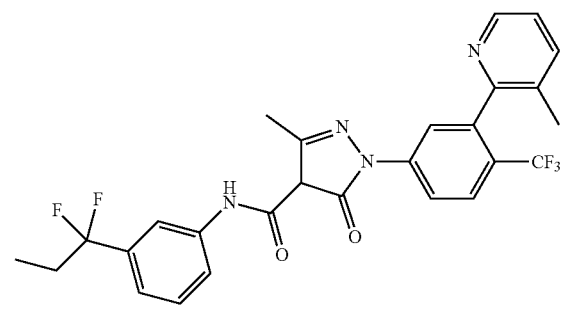 [SMILES: CCC(F)(F)c1cccc(NC(=O)C2C(=O)N(c3ccc(C(F)(F)F)c(-c4ncccc4C)c3)N=C2C)c1] |
| 576 | 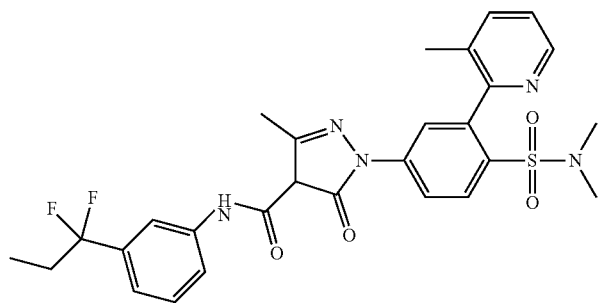 [SMILES: CCC(F)(F)c1cccc(NC(=O)C2C(=O)N(c3ccc(S(=O)(=O)N(C)C)c(-c4ncccc4C)c3)N=C2C)c1] |
| 577 | 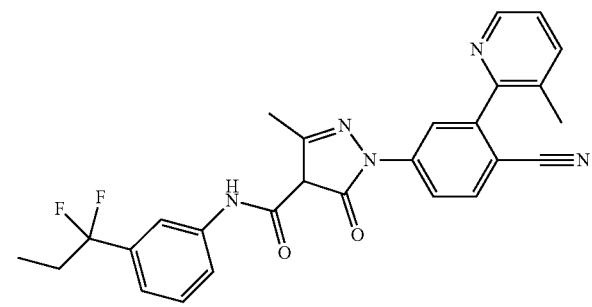 [SMILES: CCC(F)(F)c1cccc(NC(=O)C2C(=O)N(c3ccc(C#N)c(-c4ncccc4C)c3)N=C2C)c1] |

578 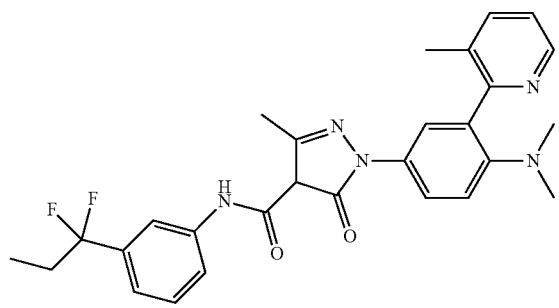 [SMILES: CCC(F)(F)c1cccc(NC(=O)C2C(=O)N(c3ccc(N(C)C)c(-c4ncccc4C)c3)N=C2C)c1]
579 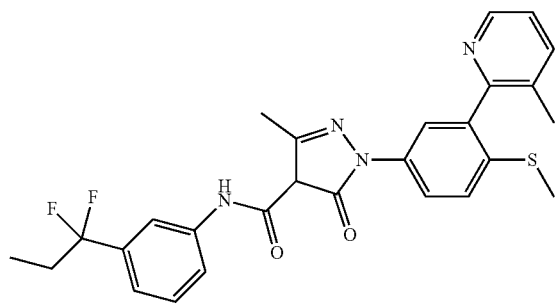 [SMILES: CCC(F)(F)c1cccc(NC(=O)C2C(=O)N(c3ccc(SC)c(-c4ncccc4C)c3)N=C2C)c1]
580 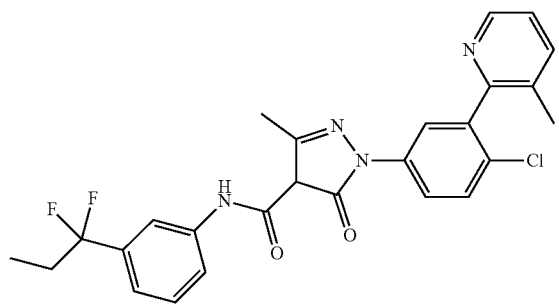 [SMILES: CCC(F)(F)c1cccc(NC(=O)C2C(=O)N(c3ccc(Cl)c(-c4ncccc4C)c3)N=C2C)c1]
581 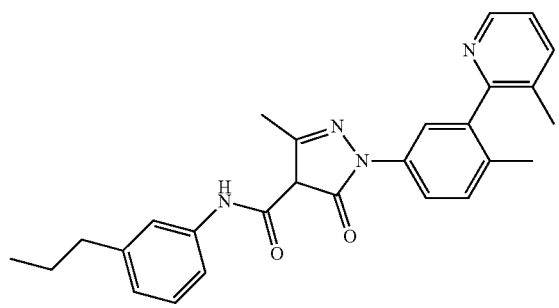 [SMILES: CCCc1cccc(NC(=O)C2C(=O)N(c3ccc(C)c(-c4ncccc4C)c3)N=C2C)c1]
582 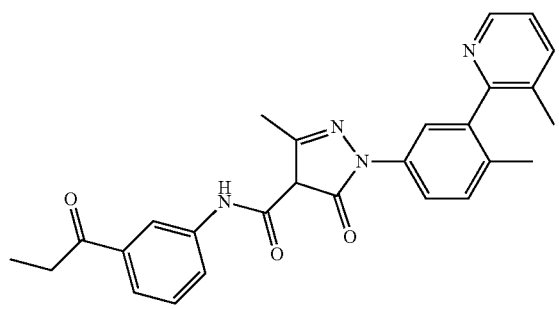 [SMILES: CCC(=O)c1cccc(NC(=O)C2C(=O)N(c3ccc(C)c(-c4ncccc4C)c3)N=C2C)c1]

-continued
583 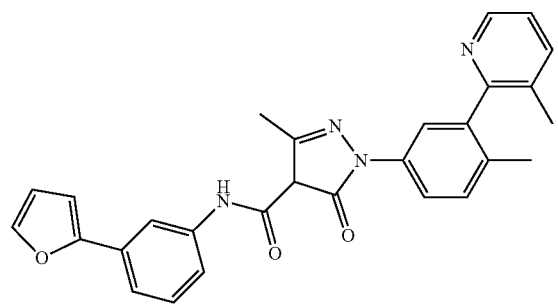
584 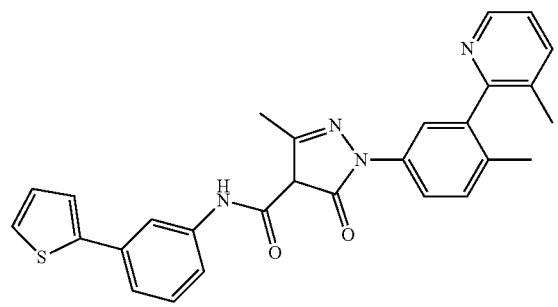 [SMILES: CC1=NN(c2ccc(C)c(-c3ncccc3C)c2)C(=O)C1C(=O)Nc1cccc(-c2ccco2)c1]
585 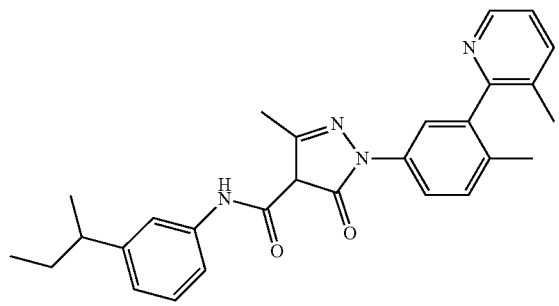 [SMILES: CCC(C)c1cccc(NC(=O)C2C(=O)N(c3ccc(C)c(-c4ncccc4C)c3)N=C2C)c1]
586 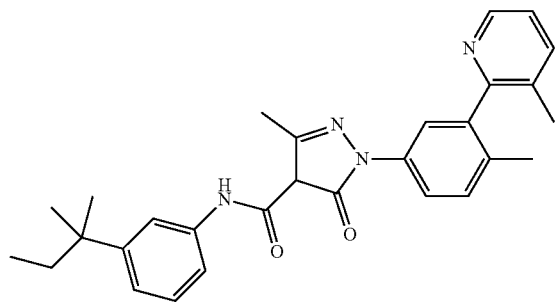 [SMILES: CCC(C)(C)c1cccc(NC(=O)C2C(=O)N(c3ccc(C)c(-c4ncccc4C)c3)N=C2C)c1]
587 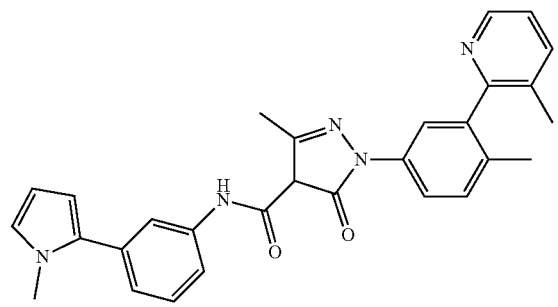 [SMILES: CC1=NN(c2ccc(C)c(-c3ncccc3C)c2)C(=O)C1C(=O)Nc1cccc(-c2cccn2C)c1]

588 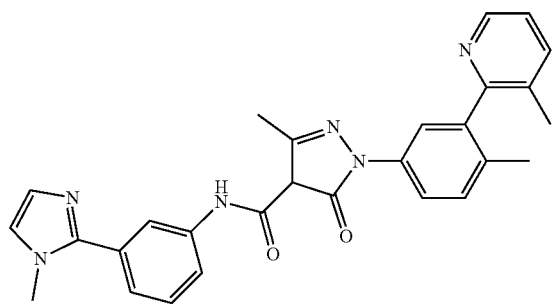 [SMILES: CC1=NN(c2ccc(C)c(-c3ncccc3C)c2)C(=O)C1C(=O)Nc1cccc(-c2nccn2C)c1]
589 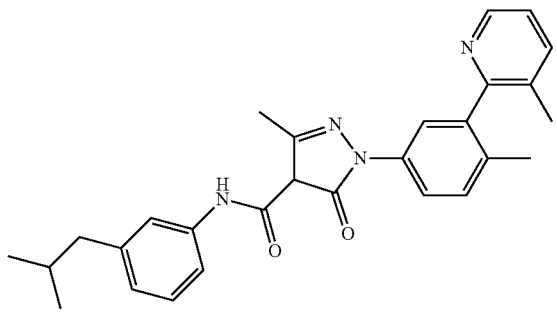 [SMILES: CC1=NN(c2ccc(C)c(-c3ncccc3C)c2)C(=O)C1C(=O)Nc1cccc(CC(C)C)c1]
590 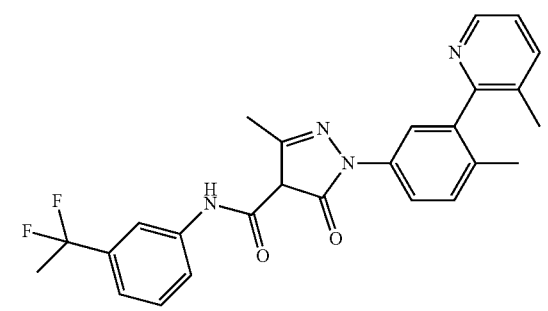 [SMILES: CC1=NN(c2ccc(C)c(-c3ncccc3C)c2)C(=O)C1C(=O)Nc1cccc(C(C)(F)F)c1]
591 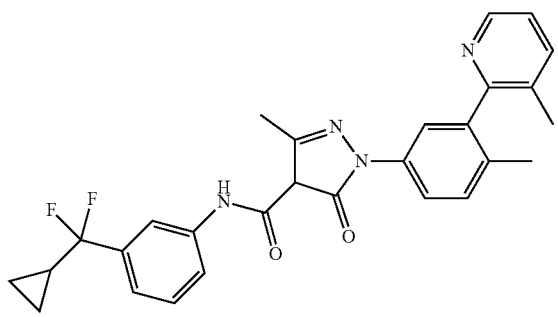 [SMILES: CC1=NN(c2ccc(C)c(-c3ncccc3C)c2)C(=O)C1C(=O)Nc1cccc(C(F)(F)C2CC2)c1]
592 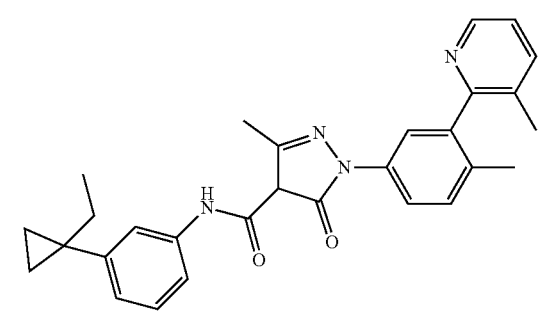 [SMILES: CCC1(c2cccc(NC(=O)C3C(=O)N(c4ccc(C)c(-c5ncccc5C)c4)N=C3C)c2)CC1]

10. The method of claim 1, wherein the subject has been previously treated with chemotherapy, immunotherapy, radiotherapy, biological therapy, surgical intervention, or any combination thereof.

11. The method of claim 1, wherein the subject has BRAF mutant melanoma.

12. The method of claim 1, wherein the subject has invasive ductal carcinoma of the breast or triple-negative breast cancer.

13. The method of claim 6, wherein the subject has a cancer selected from the list of:
hepatocellular carcinoma, melanoma, glioblastoma, breast cancer, prostate cancer, liver cancer, brain cancer, ovarian cancer, lung cancer, Lewis lung carcinoma (LLC), colon carcinoma, pancreatic cancer, renal cell carcinoma and mammary carcinoma.

14. The method of claim 6, wherein the subject has been previously treated with chemotherapy, immunotherapy, radiotherapy, biological therapy, surgical intervention, or any combination thereof.

15. The method of claim 6, wherein the subject has BRAF mutant melanoma.

16. The method of claim 6, wherein the subject has invasive ductal carcinoma of the breast or triple-negative breast cancer.

17. The method of claim 1, wherein the subject has a cancer selected from the list of: hepatocellular carcinoma, melanoma, glioblastoma, breast cancer, prostate cancer, liver cancer, brain cancer, ovarian cancer, lung cancer, Lewis lung carcinoma (LLC), colon carcinoma, pancreatic cancer, renal cell carcinoma and mammary carcinoma.

* * * * *